United States Patent
Zheng et al.

(10) Patent No.: US 12,097,261 B2
(45) Date of Patent: Sep. 24, 2024

(54) CDK2 DEGRADERS AND USES THEREOF

(71) Applicant: Kymera Therapeutics, Inc., Watertown, MA (US)

(72) Inventors: Xiaozhang Zheng, Lexington, MA (US); Yi Zhang, Belmont, MA (US); Robert Aversa, Watertown, MA (US); Xiao Zhu, Winchester, MA (US); Philip Collier, Watertown, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/738,556

(22) Filed: May 6, 2022

(65) Prior Publication Data

US 2023/0110180 A1 Apr. 13, 2023

Related U.S. Application Data

(60) Provisional application No. 63/185,929, filed on May 7, 2021.

(51) Int. Cl.
A61K 47/55 (2017.01)

(52) U.S. Cl.
CPC .................................. A61K 47/55 (2017.08)

(58) Field of Classification Search
CPC ..................................................... A61K 47/55
USPC ........................................................ 514/157
See application file for complete search history.

(56) References Cited

U.S. PATENT DOCUMENTS

| | | |
|---|---|---|
| 4,323,469 A | 4/1982 | Lugosi et al. |
| 4,650,750 A | 3/1987 | Giese |
| 4,709,016 A | 11/1987 | Giese |
| 5,217,866 A | 6/1993 | Summerton et al. |
| 5,360,811 A | 11/1994 | Tegeler et al. |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 5,721,246 A | 2/1998 | Yoshino et al. |
| 6,306,663 B1 | 10/2001 | Kenten et al. |
| 6,552,065 B2 | 4/2003 | Remiszewski et al. |
| 6,559,280 B2 | 5/2003 | Kenten et al. |
| 6,627,754 B2 | 9/2003 | Blumenkopf et al. |
| 6,720,427 B2 | 4/2004 | Sanner et al. |
| 6,949,537 B2 | 9/2005 | Garlich et al. |
| 7,041,298 B2 | 5/2006 | Deshaies et al. |
| 7,071,189 B2 | 7/2006 | Kawashima et al. |
| 7,074,620 B2 | 7/2006 | Kenten et al. |
| 7,173,015 B2 | 2/2007 | Schreiber et al. |
| 7,208,157 B2 | 4/2007 | Dashaies et al. |
| 7,273,920 B2 | 9/2007 | Kenten et al. |
| 7,307,077 B2 | 12/2007 | Kawashima et al. |
| 7,390,799 B2 | 6/2008 | Bruncko et al. |
| 7,402,325 B2 | 7/2008 | Addington |
| 7,449,458 B2 | 11/2008 | Bhamidipati et al. |
| 7,501,496 B1 | 3/2009 | Endl et al. |
| 7,514,444 B2 | 4/2009 | Honigberg et al. |
| 7,528,143 B2 | 5/2009 | Noronha et al. |
| 7,557,210 B2 | 7/2009 | Singh et al. |
| 7,598,257 B2 | 10/2009 | Rodgers et al. |
| 7,622,496 B2 | 11/2009 | Larsen et al. |
| 7,667,039 B2 | 2/2010 | Garcia-Echeverria et al. |
| 7,713,943 B2 | 5/2010 | Klippel-Giese et al. |
| 7,781,433 B2 | 8/2010 | Chuckowree et al. |
| 7,932,260 B2 | 4/2011 | Fowler et al. |
| 7,989,622 B2 | 8/2011 | Bajjalieh et al. |
| 8,138,347 B2 | 3/2012 | Knight et al. |
| 8,185,616 B2 | 5/2012 | Nagata et al. |
| 8,217,035 B2 | 7/2012 | Burger et al. |
| 8,338,439 B2 | 12/2012 | Singh et al. |
| 8,486,941 B2 | 7/2013 | Burns et al. |
| 8,906,682 B2 | 12/2014 | June et al. |
| 9,500,653 B2 | 11/2016 | Crews et al. |
| 9,632,089 B2 | 4/2017 | Crews et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 9,969,710 B2 | 5/2018 | Jorand-Lebrun et al. |
| 10,125,114 B2 | 11/2018 | Bradner et al. |
| 10,233,188 B2 | 3/2019 | Freeman-Cook et al. |
| 10,336,744 B2 | 7/2019 | Harling et al. |
| 10,874,743 B2 | 12/2020 | Mainolfi et al. |
| 11,066,404 B2 | 7/2021 | Sokolsky et al. |
| 11,292,792 B2 | 4/2022 | Ji et al. |
| 11,358,948 B2 | 6/2022 | Mainolf et al. |
| 11,512,080 B2 | 11/2022 | Mainolf et al. |

(Continued)

FOREIGN PATENT DOCUMENTS

| | | |
|---|---|---|
| CN | 104606197 A | 5/2013 |
| CN | 104003988 A | 8/2014 |

(Continued)

OTHER PUBLICATIONS

Adams et al., "Big opportunities for small molecules in immuno-oncology," Nat Rev Drug Discov. 2015;14(9):603-22.

Aruri et al., "Metal-free Cross-Dehydrogenative Coupling of HN-azoles with a-C(sp3)-H Amides via C—H Activation and Its Mechanistic and Application Studies," J Org Chem. 2017;82(2):1000-1012.

Balasubramanian et al., "Abstract 3646: Novel IRAK-4 inhibitors exhibit highly potent anti-proliferative activity in DLBCL cell lines with activating MYD88 L265P mutation," AACR 106th Annual Meeting 2015; Apr. 18-22, 2015; Philadelphia, PA.

Berge et al., "Pharmaceutical salts," J Pharm Sci. Jan. 1977;66(1):1-19.

Berndsen et al., "New insights into ubiquitin E3 ligase mechanism," Nat Struct Mol Biol. 2014;21(4):301-7.

(Continued)

*Primary Examiner* — Kristin A Vajda
(74) *Attorney, Agent, or Firm* — Dechert LLP; Andrea L. C. Reid; Matthew C Stevens

(57) ABSTRACT

The present invention provides compounds, compositions thereof, and methods of using the same.

12 Claims, No Drawings

(56) References Cited

U.S. PATENT DOCUMENTS

| | | |
|---|---|---|
| 11,744,896 B2 | 9/2023 | Zuo et al. |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2004/0029902 A1 | 2/2004 | Singh et al. |
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | McElroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0256468 A1 | 9/2016 | Schafer et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Kelley et al. |
| 2016/0326151 A1 | 11/2016 | Gummadi et al. |
| 2016/0340366 A1 | 11/2016 | Gummadi et al. |
| 2017/0001990 A1 | 1/2017 | Chen et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0152263 A1 | 6/2017 | Gummadi et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 5/2018 | Harling et al. |
| 2018/0134684 A1 | 5/2018 | Bradner et al. |
| 2018/0147202 A1 | 5/2018 | Crew et al. |
| 2018/0186799 A1 | 7/2018 | Gardner et al. |
| 2018/0194724 A1 | 7/2018 | Kemp et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2019/0054097 A1 | 2/2019 | Zhou et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0127387 A1 | 5/2019 | Wang et al. |
| 2019/0151457 A1 | 5/2019 | Bradner et al. |
| 2019/0192668 A1 | 6/2019 | Mainolfi et al. |
| 2019/0276474 A1 | 9/2019 | Chan et al. |
| 2020/0010468 A1 | 1/2020 | Ji et al. |
| 2020/0199106 A1 | 6/2020 | Shu |
| 2020/0247784 A1* | 8/2020 | Behenna .............. C07D 471/04 |
| 2020/0306273 A1 | 10/2020 | Yang et al. |
| 2020/0316064 A1 | 10/2020 | Ye et al. |
| 2020/0347045 A1 | 11/2020 | Mainolfi et al. |
| 2020/0347066 A1 | 11/2020 | Ye et al. |
| 2020/0347067 A1 | 11/2020 | Ye et al. |
| 2020/0377469 A1 | 12/2020 | Mainolfi et al. |
| 2020/0392139 A1 | 12/2020 | Sokolsky et al. |
| 2020/0392142 A1 | 12/2020 | Behenna et al. |
| 2020/0399273 A1 | 12/2020 | Sokolsky et al. |
| 2021/0002296 A1 | 1/2021 | Mainolfi et al. |
| 2021/0017156 A1 | 1/2021 | Hummel et al. |
| 2021/0107901 A1 | 4/2021 | Ye et al. |
| 2022/0096642 A1 | 3/2022 | Zuo et al. |
| 2022/0112191 A1 | 4/2022 | Gray et al. |

(56) References Cited

U.S. PATENT DOCUMENTS

| | | |
|---|---|---|
| 2022/0117982 A1 | 4/2022 | Yang et al. |
| 2022/0281831 A1 | 9/2022 | Ji et al. |
| 2022/0306631 A1 | 9/2022 | Ji et al. |
| 2022/0340579 A1 | 10/2022 | Hummel et al. |
| 2022/0356185 A1 | 11/2022 | Ji et al. |
| 2023/0002376 A1 | 1/2023 | Hummel et al. |
| 2023/0038512 A1 | 2/2023 | Mainolf et al. |
| 2023/0158152 A1 | 5/2023 | Lei et al. |
| 2023/0183250 A1 | 6/2023 | Hummel et al. |
| 2023/0192706 A1 | 6/2023 | Hummel et al. |
| 2023/0210999 A1 | 7/2023 | Cao et al. |
| 2023/0234936 A1 | 7/2023 | Feng et al. |
| 2023/0234950 A1 | 7/2023 | Mainolf et al. |
| 2023/0242510 A1 | 8/2023 | Lu et al. |
| 2023/0279004 A1 | 9/2023 | Sclafani et al. |
| 2023/0303509 A1 | 9/2023 | Lou et al. |
| 2024/0002339 A1 | 1/2024 | Georg et al. |

FOREIGN PATENT DOCUMENTS

| | | |
|---|---|---|
| CN | 105878244 A | 8/2016 |
| CN | 105085620 B | 5/2018 |
| CN | 107903256 B | 11/2019 |
| CN | 110684015 A | 1/2020 |
| CN | 108484606 B | 3/2020 |
| CN | 107987054 B | 5/2020 |
| CN | 108484613 B | 7/2020 |
| CN | 112898271 | 6/2021 |
| CN | 110256465 B | 8/2021 |
| CN | 113387931 A | 9/2021 |
| CN | 113527329 A | 10/2021 |
| CN | 111777604 B | 12/2021 |
| CN | 113912589 B | 1/2022 |
| CN | 110204543 B | 3/2022 |
| CN | 114262321 A | 4/2022 |
| CN | 114591213 A | 6/2022 |
| CN | 115010711 A | 9/2022 |
| CN | 115304606 A | 11/2022 |
| CN | 114380822 B | 2/2023 |
| CN | 115703760 A | 2/2023 |
| CN | 115650968 B | 3/2023 |
| CN | 115745979 A | 3/2023 |
| CN | 115806551 A | 3/2023 |
| CN | 115845068 A | 3/2023 |
| CN | 116003418 A | 4/2023 |
| CN | 113999210 B | 5/2023 |
| CN | 114349738 B | 5/2023 |
| CN | 115160298 B | 5/2023 |
| CN | 116143766 A | 5/2023 |
| CN | 113698391 B | 6/2023 |
| CN | 114853672 B | 6/2023 |
| CN | 116283915 A | 6/2023 |
| CN | 114163444 B | 7/2023 |
| CN | 116440139 A | 7/2023 |
| CN | 116554126 A | 8/2023 |
| CN | 116675731 A | 9/2023 |
| CN | 116813621 A | 9/2023 |
| CN | 117143093 A | 12/2023 |
| CN | 117263957 A | 12/2023 |
| CN | 114685507 B | 1/2024 |
| KR | 20000055080 A | 9/2000 |
| KR | 100368515 B1 | 1/2003 |
| WO | WO-1996007655 A1 | 3/1996 |
| WO | WO9943675 A1 | 9/1999 |
| WO | WO9962503 A2 | 12/1999 |
| WO | WO0012496 A1 | 3/2000 |
| WO | WO0035908 A1 | 6/2000 |
| WO | WO0035920 A2 | 6/2000 |
| WO | WO0064900 A1 | 11/2000 |
| WO | WO0110832 A1 | 2/2001 |
| WO | WO0114375 A1 | 3/2001 |
| WO | WO-2001042246 A2 | 6/2001 |
| WO | WO0164653 A1 | 9/2001 |
| WO | WO0172717 A1 | 10/2001 |
| WO | WO0202551 A1 | 1/2002 |
| WO | WO0210141 A1 | 2/2002 |
| WO | WO0218346 A1 | 3/2002 |
| WO | WO-2002020740 A2 | 3/2002 |
| WO | WO02059109 A2 | 8/2002 |
| WO | WO02079193 A1 | 10/2002 |
| WO | WO-2002088112 A1 | 11/2002 |
| WO | WO-2003063794 A2 | 8/2003 |
| WO | WO03101989 A1 | 12/2003 |
| WO | WO-2004019973 A1 | 3/2004 |
| WO | WO2004022561 A1 | 3/2004 |
| WO | WO2004031158 A1 | 4/2004 |
| WO | WO2004032882 A2 | 4/2004 |
| WO | WO2004037814 A1 | 5/2004 |
| WO | WO2004046130 A1 | 6/2004 |
| WO | WO2005075461 A1 | 8/2004 |
| WO | WO2004076414 A2 | 9/2004 |
| WO | WO2004078682 A2 | 9/2004 |
| WO | WO-2004089925 A1 | 10/2004 |
| WO | WO2004101549 A1 | 11/2004 |
| WO | WO-2004106328 A1 | 12/2004 |
| WO | WO2004108136 A1 | 12/2004 |
| WO | WO-2005007623 A2 | 1/2005 |
| WO | 2005009539 A2 | 2/2005 |
| WO | WO2005082903 A1 | 9/2005 |
| WO | WO2005085231 A1 | 9/2005 |
| WO | WO2005111019 A1 | 11/2005 |
| WO | WO-2005113554 A2 | 12/2005 |
| WO | WO2005121107 A1 | 12/2005 |
| WO | WO-2006029879 A2 | 3/2006 |
| WO | WO2006040036 A1 | 4/2006 |
| WO | WO2006040049 A1 | 4/2006 |
| WO | WO2006064251 A1 | 6/2006 |
| WO | WO2006077419 A1 | 7/2006 |
| WO | WO-2006078846 A1 | 7/2006 |
| WO | WO-2006105021 A2 | 10/2006 |
| WO | WO2006105386 A1 | 10/2006 |
| WO | WO-2006122806 A2 | 11/2006 |
| WO | WO-2007005874 A2 | 1/2007 |
| WO | WO-2007016176 A2 | 2/2007 |
| WO | WO-2007044729 A2 | 4/2007 |
| WO | WO-2007053452 A1 | 5/2007 |
| WO | WO2007060110 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO2007138268 A1 | 12/2007 |
| WO | WO2008015139 A3 | 4/2008 |
| WO | WO-2008039218 A2 | 4/2008 |
| WO | WO2008079933 A2 | 7/2008 |
| WO | WO-2008109943 A1 | 9/2008 |
| WO | WO-2008118802 A1 | 10/2008 |
| WO | WO2008122767 A2 | 10/2008 |
| WO | WO-2008132601 A1 | 11/2008 |
| WO | WO-2009009116 A2 | 1/2009 |
| WO | WO-2009044273 A2 | 4/2009 |
| WO | WO-2009073620 A2 | 6/2009 |
| WO | WO-2009114512 A1 | 9/2009 |
| WO | WO-2009132238 A3 | 10/2009 |
| WO | WO-2010019570 A2 | 2/2010 |
| WO | WO-2010077634 A1 | 7/2010 |
| WO | WO-2011028683 A1 | 3/2011 |
| WO | WO-2011043371 A1 | 4/2011 |
| WO | WO-2011056652 A1 | 5/2011 |
| WO | WO-2011070024 A1 | 6/2011 |
| WO | WO-2011090760 A1 | 7/2011 |
| WO | WO-2011107553 A1 | 9/2011 |
| WO | WO-2011109400 A2 | 9/2011 |
| WO | WO-2011131407 A1 | 10/2011 |
| WO | WO-2011140249 A2 | 11/2011 |
| WO | WO-2012003281 A3 | 1/2012 |
| WO | WO-2012007375 A1 | 1/2012 |
| WO | WO-2012032433 A1 | 3/2012 |
| WO | WO-2012068546 A1 | 5/2012 |
| WO | WO-2012078559 A2 | 6/2012 |
| WO | WO-2012084704 A1 | 6/2012 |
| WO | WO-2012097013 A1 | 7/2012 |
| WO | WO-2012129258 | 9/2012 |
| WO | WO-2012142237 A1 | 10/2012 |
| WO | WO-2012145493 A1 | 10/2012 |

(56) References Cited

FOREIGN PATENT DOCUMENTS

| | | |
|---|---|---|
| WO | WO-2013042137 A1 | 3/2013 |
| WO | WO-2013066729 A1 | 5/2013 |
| WO | WO-2013079174 A1 | 6/2013 |
| WO | WO-2013087699 A1 | 6/2013 |
| WO | WO-2013106535 A1 | 7/2013 |
| WO | WO-2013106612 A1 | 7/2013 |
| WO | WO-2013106614 A1 | 7/2013 |
| WO | WO-2013106641 A1 | 7/2013 |
| WO | WO-2013106643 A2 | 7/2013 |
| WO | WO-2013106646 A2 | 7/2013 |
| WO | WO-2013119716 A1 | 8/2013 |
| WO | WO-2013132044 A1 | 9/2013 |
| WO | WO-2013169264 A1 | 11/2013 |
| WO | WO-2014008218 A1 | 1/2014 |
| WO | WO-2014008992 A1 | 1/2014 |
| WO | WO-2014011902 A1 | 1/2014 |
| WO | WO-2014011906 A2 | 1/2014 |
| WO | WO-2014011911 A2 | 1/2014 |
| WO | WO-2014036357 A1 | 3/2014 |
| WO | WO-2014044622 A1 | 3/2014 |
| WO | WO-2014058685 A1 | 4/2014 |
| WO | WO-2014058691 A1 | 4/2014 |
| WO | WO-2014063061 A1 | 4/2014 |
| WO | WO-2014074675 A1 | 5/2014 |
| WO | WO-2014108452 A1 | 7/2014 |
| WO | WO-2014121931 A1 | 8/2014 |
| WO | WO-2014121942 A1 | 8/2014 |
| WO | WO-2014143672 A1 | 9/2014 |
| WO | WO-2015048281 A1 | 4/2015 |
| WO | WO-2015068856 A1 | 5/2015 |
| WO | WO-2015071393 A1 | 5/2015 |
| WO | WO-2015091426 A1 | 6/2015 |
| WO | WO-2015103453 A1 | 7/2015 |
| WO | WO-2015104662 A1 | 7/2015 |
| WO | WO-2015104688 A1 | 7/2015 |
| WO | WO-2015116904 A1 | 8/2015 |
| WO | WO2015124941 A1 | 8/2015 |
| WO | WO-2015150995 A1 | 10/2015 |
| WO | WO-2015160845 A3 | 10/2015 |
| WO | WO-2015164374 A1 | 10/2015 |
| WO | WO-2015193846 A1 | 12/2015 |
| WO | WO-2016011390 A1 | 1/2016 |
| WO | WO-2016053769 A1 | 4/2016 |
| WO | WO-2016053770 A1 | 4/2016 |
| WO | WO-2016053771 A1 | 4/2016 |
| WO | WO-2016053772 A1 | 4/2016 |
| WO | WO-2016081679 A1 | 5/2016 |
| WO | WO-2016105518 A1 | 6/2016 |
| WO | WO-2016118666 A1 | 7/2016 |
| WO | WO-2016144844 A1 | 9/2016 |
| WO | WO-2016144846 A1 | 9/2016 |
| WO | WO-2016144847 A1 | 9/2016 |
| WO | WO-2016144848 A1 | 9/2016 |
| WO | WO-2016144849 A1 | 9/2016 |
| WO | WO-2016149668 A1 | 9/2016 |
| WO | WO-2016169989 A1 | 10/2016 |
| WO | WO-2016172560 A1 | 10/2016 |
| WO | WO-2016174183 A1 | 11/2016 |
| WO | WO2016180380 A1 | 11/2016 |
| WO | WO-2016197032 A1 | 12/2016 |
| WO | WO-2016197114 A1 | 12/2016 |
| WO | WO-2016210034 A1 | 12/2016 |
| WO | WO-2017004133 A1 | 1/2017 |
| WO | WO-2017004134 | 1/2017 |
| WO | WO-2017007612 A1 | 1/2017 |
| WO | WO-2017009798 A1 | 1/2017 |
| WO | WO-2017009806 A1 | 1/2017 |
| WO | WO-2017011371 A1 | 1/2017 |
| WO | WO-2017011590 A1 | 1/2017 |
| WO | WO2017024317 A3 | 2/2017 |
| WO | WO2017024318 A1 | 2/2017 |
| WO | WO2017024319 A1 | 2/2017 |
| WO | WO-2017030814 A1 | 2/2017 |
| WO | WO-2017033093 A1 | 3/2017 |
| WO | WO-2017049068 A1 | 3/2017 |
| WO | WO-2017059280 A1 | 4/2017 |
| WO | WO-2017079267 A1 | 5/2017 |
| WO | WO-2017108723 A2 | 6/2017 |
| WO | WO-2017117473 A1 | 7/2017 |
| WO | WO-2017117474 A1 | 7/2017 |
| WO | WO-2017127430 A1 | 7/2017 |
| WO | WO-2017161119 A1 | 9/2017 |
| WO | WO-2017176708 A1 | 10/2017 |
| WO | WO-2017176957 A1 | 10/2017 |
| WO | WO-2017176958 A1 | 10/2017 |
| WO | WO2017184995 A1 | 10/2017 |
| WO | WO-2017197036 A1 | 11/2017 |
| WO | WO-2017197046 A1 | 11/2017 |
| WO | WO-2017197051 A1 | 11/2017 |
| WO | WO-2017197055 A1 | 11/2017 |
| WO | WO-2017197056 A1 | 11/2017 |
| WO | WO-2017201449 A1 | 11/2017 |
| WO | WO-2017205762 A1 | 11/2017 |
| WO | WO-2017205766 A1 | 11/2017 |
| WO | WO-2017207385 A1 | 12/2017 |
| WO | WO-2017211924 A1 | 12/2017 |
| WO | WO-2018033815 A1 | 2/2018 |
| WO | WO-2018052058 A1 | 3/2018 |
| WO | WO2018071606 A1 | 4/2018 |
| WO | WO-2018089736 A1 | 5/2018 |
| WO | WO-2018098367 A1 | 5/2018 |
| WO | WO2018118947 A1 | 6/2018 |
| WO | WO-2018144649 A1 | 8/2018 |
| WO | WO2018148440 A1 | 8/2018 |
| WO | WO2017204445 A3 | 9/2018 |
| WO | WO-2018209012 A1 | 11/2018 |
| WO | WO-2018237026 A1 | 12/2018 |
| WO | WO2019040274 A1 | 2/2019 |
| WO | WO-2019043214 A1 | 3/2019 |
| WO | WO-2019060693 A1 | 3/2019 |
| WO | WO-2019060742 A1 | 3/2019 |
| WO | WO-2019084026 A1 | 5/2019 |
| WO | WO-2019084030 A1 | 5/2019 |
| WO | WO-2019099868 A1 | 5/2019 |
| WO | WO-2019099926 A1 | 5/2019 |
| WO | WO2019113071 A1 | 6/2019 |
| WO | WO-2019133531 A1 | 7/2019 |
| WO | WO-2019140380 A1 | 7/2019 |
| WO | WO-2019140387 A1 | 7/2019 |
| WO | WO-2019165229 A1 | 8/2019 |
| WO | WO2019199816 A1 | 10/2019 |
| WO | WO-2019236483 | 12/2019 |
| WO | WO2020006264 A1 | 1/2020 |
| WO | WO-2020010177 A1 | 1/2020 |
| WO | WO-2020010210 A1 | 1/2020 |
| WO | WO-2020010227 A1 | 1/2020 |
| WO | WO-2020018788 A1 | 1/2020 |
| WO | WO2020023851 A1 | 1/2020 |
| WO | WO2020035049 A1 | 2/2020 |
| WO | WO2020041405 A1 | 2/2020 |
| WO | WO2020041406 A1 | 2/2020 |
| WO | WO2020069106 A1 | 4/2020 |
| WO | WO-2020113233 A1 | 6/2020 |
| WO | WO2020142228 A1 | 7/2020 |
| WO | WO-2020157652 A2 | 8/2020 |
| WO | WO2020167518 A1 | 8/2020 |
| WO | WO-2020168178 A1 | 8/2020 |
| WO | WO-2020168197 A1 | 8/2020 |
| WO | WO-2020180959 A1 | 9/2020 |
| WO | WO2020198711 A1 | 10/2020 |
| WO | WO2020200291 A1 | 10/2020 |
| WO | WO-2020205560 A1 | 10/2020 |
| WO | WO-2020206034 A1 | 10/2020 |
| WO | WO-2020206137 A1 | 10/2020 |
| WO | WO-2020206424 A1 | 10/2020 |
| WO | WO2020210229 A1 | 10/2020 |
| WO | WO2020210630 A1 | 10/2020 |
| WO | WO2020219650 A1 | 10/2020 |
| WO | WO-2020223469 A1 | 11/2020 |
| WO | WO-2020223558 A1 | 11/2020 |
| WO | WO2020264499 A1 | 12/2020 |
| WO | WO-2021011631 A1 | 1/2021 |
| WO | WO2021016521 A1 | 1/2021 |
| WO | WO2021018018 A1 | 2/2021 |

(56) References Cited

FOREIGN PATENT DOCUMENTS

| | | |
|---|---|---|
| WO | WO2021026109 A1 | 2/2021 |
| WO | WO2021030537 A1 | 2/2021 |
| WO | WO2021022163 A3 | 3/2021 |
| WO | WO2021058017 A1 | 4/2021 |
| WO | WO2021066873 A1 | 4/2021 |
| WO | WO-2021072232 A1 | 4/2021 |
| WO | WO2021072475 A1 | 4/2021 |
| WO | WO2021073593 A1 | 4/2021 |
| WO | WO2021113557 A1 | 6/2021 |
| WO | WO2021129653 A1 | 7/2021 |
| WO | WO2021170109 A1 | 9/2021 |
| WO | WO2021173677 A1 | 9/2021 |
| WO | WO2021183994 A1 | 9/2021 |
| WO | WO2021185291 A1 | 9/2021 |
| WO | WO2021190413 A1 | 9/2021 |
| WO | WO2021205363 A1 | 10/2021 |
| WO | WO2021210343 A1 | 10/2021 |
| WO | WO2021216828 A1 | 10/2021 |
| WO | WO2021219070 A1 | 11/2021 |
| WO | WO2021228814 A1 | 11/2021 |
| WO | WO2021236650 A1 | 11/2021 |
| WO | WO2021249258 A1 | 12/2021 |
| WO | WO2021254384 A1 | 12/2021 |
| WO | WO2021257650 A1 | 12/2021 |
| WO | WO2022012623 A1 | 1/2022 |
| WO | WO2022015670 A1 | 1/2022 |
| WO | WO2022018596 A1 | 1/2022 |
| WO | WO2022018667 A1 | 1/2022 |
| WO | WO2022037592 A1 | 2/2022 |
| WO | WO2022051616 A1 | 3/2022 |
| WO | WO2022068933 A1 | 4/2022 |
| WO | WO2022073469 A1 | 4/2022 |
| WO | WO2022081925 A1 | 4/2022 |
| WO | WO2022081928 A1 | 4/2022 |
| WO | WO2022093742 A1 | 5/2022 |
| WO | WO2022098843 A1 | 5/2022 |
| WO | WO2022100710 A1 | 5/2022 |
| WO | WO2022109307 A1 | 5/2022 |
| WO | WO2022109396 A1 | 5/2022 |
| WO | WO2022111526 A1 | 6/2022 |
| WO | WO2022111634 A1 | 6/2022 |
| WO | WO2022113003 A1 | 6/2022 |
| WO | WO2022113621 A1 | 6/2022 |
| WO | WO2022120355 A1 | 6/2022 |
| WO | WO2022131741 A1 | 6/2022 |
| WO | WO2022133184 A1 | 6/2022 |
| WO | WO2022135365 A1 | 6/2022 |
| WO | WO2022135442 A1 | 6/2022 |
| WO | WO2022137106 A1 | 6/2022 |
| WO | WO2022140472 A1 | 6/2022 |
| WO | WO2022143856 A1 | 7/2022 |
| WO | WO2022149057 A1 | 7/2022 |
| WO | WO2022152259 A1 | 7/2022 |
| WO | WO2022155593 A1 | 7/2022 |
| WO | WO2022155941 A1 | 7/2022 |
| WO | WO2022159644 A1 | 7/2022 |
| WO | WO2022159650 A1 | 7/2022 |
| WO | WO2022165185 A1 | 8/2022 |
| WO | WO2022165513 A1 | 8/2022 |
| WO | WO2022166793 A1 | 8/2022 |
| WO | WO2022171123 A1 | 8/2022 |
| WO | WO2022174031 A1 | 8/2022 |
| WO | WO2022187611 A1 | 9/2022 |
| WO | WO2022187693 A1 | 9/2022 |
| WO | WO2022194269 A1 | 9/2022 |
| WO | WO2022206737 A1 | 10/2022 |
| WO | WO2022206888 A1 | 10/2022 |
| WO | WO2022235698 A1 | 11/2022 |
| WO | WO2022236058 A1 | 11/2022 |
| WO | WO2022242725 A1 | 11/2022 |
| WO | WO2022245776 A1 | 11/2022 |
| WO | WO2022246025 A1 | 11/2022 |
| WO | WO2022248682 A1 | 12/2022 |
| WO | WO2022253283 A1 | 12/2022 |
| WO | WO2022258023 A1 | 12/2022 |
| WO | WO2022266190 A1 | 12/2022 |
| WO | WO2022266248 A1 | 12/2022 |
| WO | WO2022268052 A1 | 12/2022 |
| WO | WO2022268229 A1 | 12/2022 |
| WO | WO2022272106 A1 | 12/2022 |
| WO | WO2023274397 A1 | 1/2023 |
| WO | WO2023278325 A1 | 1/2023 |
| WO | WO2023278326 A1 | 1/2023 |
| WO | WO2023281413 A1 | 1/2023 |
| WO | WO2023288305 A1 | 1/2023 |
| WO | WO2023006097 A1 | 2/2023 |
| WO | WO2023011513 A1 | 2/2023 |
| WO | WO2023011533 A1 | 2/2023 |
| WO | WO2023023376 A2 | 2/2023 |
| WO | WO2023023531 A1 | 2/2023 |
| WO | WO2023023664 A1 | 2/2023 |
| WO | WO2023023941 A1 | 3/2023 |
| WO | WO2023025091 A1 | 3/2023 |
| WO | WO2023039405 A1 | 3/2023 |
| WO | WO2023051302 A1 | 4/2023 |
| WO | WO2023056423 A1 | 4/2023 |
| WO | WO2023059609 A1 | 4/2023 |
| WO | WO2023059792 A1 | 4/2023 |
| WO | WO2023060057 A1 | 4/2023 |
| WO | WO2023061440 A1 | 4/2023 |
| WO | WO2023061478 A1 | 4/2023 |
| WO | WO2023069700 A1 | 4/2023 |
| WO | WO2023069720 A1 | 4/2023 |
| WO | WO2023072096 A1 | 5/2023 |
| WO | WO2023076161 A1 | 5/2023 |
| WO | WO2023080652 A1 | 5/2023 |
| WO | WO2023081759 A1 | 5/2023 |
| WO | WO2023083201 A1 | 5/2023 |
| WO | WO2023088385 A1 | 5/2023 |
| WO | WO2023092088 A1 | 5/2023 |
| WO | WO2023092107 A1 | 5/2023 |
| WO | WO2023093845 A1 | 6/2023 |
| WO | WO2023094310 A1 | 6/2023 |
| WO | WO2023098656 A1 | 6/2023 |
| WO | WO2023098831 A1 | 6/2023 |
| WO | WO2023100131 A1 | 6/2023 |
| WO | WO2023100134 A1 | 6/2023 |
| WO | WO2023116884 A1 | 6/2023 |
| WO | WO2023122581 A3 | 6/2023 |
| WO | WO2023122615 A1 | 6/2023 |
| WO | WO2023125907 A1 | 7/2023 |
| WO | WO2023125908 A1 | 7/2023 |
| WO | WO2023129564 A1 | 7/2023 |
| WO | WO2023137225 A1 | 7/2023 |
| WO | WO2023133260 A3 | 8/2023 |
| WO | WO2023141852 A1 | 8/2023 |
| WO | WO2023143482 A1 | 8/2023 |
| WO | WO2023143589 A1 | 8/2023 |
| WO | WO2023150612 A1 | 8/2023 |
| WO | WO2023151635 A1 | 8/2023 |
| WO | WO2023154426 A1 | 8/2023 |
| WO | WO2023160572 A1 | 8/2023 |
| WO | WO2023164175 A3 | 8/2023 |
| WO | WO2023141635 A3 | 9/2023 |
| WO | WO2023172957 A1 | 9/2023 |
| WO | WO2023177451 A1 | 9/2023 |
| WO | WO2023178130 A1 | 9/2023 |
| WO | WO2023178181 A1 | 9/2023 |
| WO | WO2023185920 A1 | 10/2023 |
| WO | WO2023186069 A1 | 10/2023 |
| WO | WO2023192534 A1 | 10/2023 |
| WO | WO2023198180 A1 | 10/2023 |
| WO | WO2023205892 A1 | 11/2023 |
| WO | WO2023220640 A1 | 11/2023 |
| WO | WO2023226920 A1 | 11/2023 |
| WO | WO2023239629 A1 | 12/2023 |
| WO | WO2023240024 A1 | 12/2023 |
| WO | WO2023241598 A1 | 12/2023 |
| WO | WO2023244710 A1 | 12/2023 |
| WO | WO2023249968 A1 | 12/2023 |
| WO | WO2023249970 A1 | 12/2023 |
| WO | WO2023249974 A2 | 12/2023 |

(56) References Cited

FOREIGN PATENT DOCUMENTS

| WO | WO2024008097 A1 | 1/2024 |
|---|---|---|
| WO | WO2024039901 A2 | 2/2024 |
| WO | WO2024039903 A2 | 2/2024 |

OTHER PUBLICATIONS

Boichenko et al., "A FRET-Based Assay for the Identification and Characterization of Cereblon Ligands," J Med Chem. 2016;59(2):770-4.
Buckley et al., "IRAK-4 inhibitors. Part 1: a series of amides," Bioorg Med Chem Lett. 2008;18(11):3211-4.
Buckley et al., "IRAK-4 inhibitors. Part II: a structure-based assessment of imidazo[1,2-a]pyridine binding," Bioorg Med Chem Lett. 2008;18(11):3291-5.
Buckley et al., "IRAK-4 inhibitors. Part III: A series of imidazo[1,2-a]pyridines," Bioorg Med Chem Lett. 2008;18(12):3656-60.
Cameron et al., "Loss of Interleukin Receptor-Associated Kinase 4 Signaling Suppresses Amyloid Pathology and Alters Microglial Phenotype in a Mouse Model of Alzheimer's Disease," J Neurosci. 2012;32(43):15112-23.
Cario, "Therapeutic Impact of Toll-like Receptors on Inflammatory Bowel Diseases: A Multiple-edged Sword," Inflamm Bowel Dis. 2008; 14(3):411-21.
CAS STN Abstract, RN 1787975-60-3 (Pub. Jun. 24, 2015).
CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STN Abstract, RN 779303-42-3 (Pub. Nov. 12, 2004).
Chang et al., "What is the functional role of the thalidomide binding protein cereblon?" Int J Biochem Mol Biol. 2011;2(3):287-94.
Charrier et al., "Desulfonylative radical ring closure onto aromatics. A modular route to benzazepin-2-ones and 5-arylpiperidin-2-ones," Org Lett. 2012;14(8):2018-21.
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem. 2015;58(1):96-110.
Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types," J Immunol. 2011; 186(2):1279-88.
Cohen, "Targeting protein kinases for the development of anti-inflammatory drugs," Curr Opin Cell Biol. 2009;21(2):17-24.
Connolly et al., "Complexities of TGF-beta Targeted Cancer Therapy," Int J Biol Sci. 2012;8(7):964-978.
Contino-Pepin et al., "Preliminary biological evaluations of new thalidomide analogues for multiple sclerosis application," Bioorg Med Chem Lett. 2009; 19(3):878-81.
Crews, "Targeting the Undruggable Proteome: The Small Molecules of My Dreams," Chem Biol. 2010;17(6):551-5.
Cushing et al., "IRAK4 kinase controls Toll-like receptor induced inflammation through the transcription factor IRF5 in primary human monocytes," J Biol Chem. 2017;292(45):18689-18698.
Dalbeth et al., "Hyperuricaemia and gout: state of the art and future perspectives," Ann Rheum Dis. 2014;73(9):1598-600.
Degorce et al., "Optimization of permeability in a series of pyrrolotriazine inhibitors of IRAK4," Bioorg Med Chem. 2018;26(4):913-924.
Deshaies and Joazeiro, "RING domain E3 ubiquitin ligases," Annu Rev Biochem. 2009;78:399-434.
Dinarello, "IL-1: Discoveries, controversies and future directions," Eur J Immunol. 2010;40(3):599-606.
Dinarello, "Interleukin 1 and interleukin 18 as mediators of inflammation and the aging process," Am J Clin Nutr. 2006;83(suppl):447S-55S.
Dinarello, "Interleukin-18 and the Pathogenesis of Inflammatory Diseases," Semin Nephrol. 2007;27(1):98-114.
Dudhgaonkar et al., "Selective IRAK4 Inhibition Attenuates Disease in Murine Lupus Models and Demonstrates Steroid Sparing Activity," J Immunol. 2017; 198(3):1308-1319.
Dunne et al., "IRAK1 and IRAK4 Promote Phosphorylation, Ubiquitation, and Degradation of MyD88 Adaptor-like (Mal)," J Biol Chem. 2010;285(24):18276-82.
Fischer et al., "Structure of the DDB1-CRBN E3 ubiquitin ligase in complex with thalidomide," Nature. 2014;512(7512):49-53.
Flannery et al., "The interleukin-1 receptor-associated kinases: Critical regulators of innate immune signaling," Biochem Pharmacol. 2010;80(12):1981-91.
Gearing, "Targeting toll-like receptors for drug development: a summary of commercial approaches," Immunol Cell Biol. 2007;85(6):490-4.
Geyer and Müller-Ladner, "Actual status of antiinterleukin-1 therapies in rheumatic diseases," Curr Opin Rheumatol. 2010;22(3):246-51.
Gottipati et al., "IRAK1: A critical signaling mediator of innate immunity," Cell Signal. 2008;20(2):269-76.
Hagner et al., "CC-122, a pleiotropic pathway modifier, mimics an interferon response and has antitumor activity in DLBCL," Blood. 2015;126(6):779-89.
Hennessy et al., "Targeting Toll-like receptors: emerging therapeutics?" Nat Rev Drug Discov. 2010;9(4):293-307.
Hines et al., "MDM2-Recruiting PROTAC Offers Superior, Synergistic Antiproliferative Activity via Simultaneous Degradation of BRD4 and Stabilization of p53," Cancer Res. 2019;79(1):251-262.
Hoffman et al., "Efficacy and Safety of Rilonacept (Interleukin-1 Trap) in Patients with Cryopyrin-Associated Periodic Syndromes," Arthritis Rheum. 2008;58(8):2443-5.
Hu et al., "Specific CP110 Phosphorylation Sites Mediate Anaphase Catastrophe after CDK2 Inhibition: Evidence for Cooperation with USP33 Knockdown," Mol Cancer Ther. 2015;14(11):2576-85.
Iannello et al., "Role of Interleukin-18 in the Development and Pathogenesis of AIDS," AIDS Rev. 2009;11(3):115-25.
Iconomou and Saunders, "Systematic approaches to identify E3 ligase substrates," Biochem J. 2016;473(22):4083-4101.
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., "Identification of a primary target of thalidomide teratogenicity," Science. 2010;327(5971):1345-50.
Kelly et al., "Selective interleukin-1 receptor-associated kinase 4 inhibitors for the treatment of autoimmune disorders and lymphoid malignancy," J Exp Med. 2015;212(13):2189-201.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem. 2013;56(20):7788-803.
Kim et al., "A critical role for IRAK4 kinase activity in Toll-like receptor-mediated innate immunity," J Exp Med. 2007;204(5):1025-36.
Kondo et al., "Renoprotective effects of novel interleukin-1 receptor-associated kinase 4 inhibitor AS2444697 through anti-inflammatory action in 5/6 nephrectomized rats," Naunyn Schmiedebergs Arch Pharmacol. 2014;387(10):909-19.
Kou et al., "Effects of RuPeng15 Powder (RPP15) on Monosodium Urate Crystal-Induced Gouty Arthritis in Rats," Evid Based Complement Alternat Med. 2015;2015:527019.
Koziczak-Holbro et al., "IRAK-4 Kinase Activity Is Required for Interleukin-1 (IL-1) Receptor- and Toll-like Receptor 7-mediated Signaling and Gene Expression," J Biol Chem. 2007;282(18):13552-60.
Krönke et al., "Lenalidomide causes selective degradation of IKZF1 and IKZF3 in multiple myeloma cells" Science. 2014;343(6168):301-305.

(56) References Cited

OTHER PUBLICATIONS

Ku et al., "Selective predisposition to bacterial infections in IRAK-4-deficient children: IRAK-4-dependent TLRs are otherwise redundant in protective immunity," J Exp Med. 2007;204(10):2407-2422.
Kubo-Murai et al., "IRAK-4-dependent Degradation of IRAK-1 is a Negative Feedback Signal for TLR-mediated NF-κB Activation," J Biochem. 2008; 143(3):295-302.
Küppers, "IRAK inhibition to shut down TLR signaling in autoimmunity and MyD88-dependent lymphomas," J Exp Med. 2015;212(13):2184.
Lebakken et al., "A Fluorescence Lifetime Based Binding Assay to Characterize Kinase Inhibitors," J Biomol Screen. 2007;12(6):828-41.
Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," J Med Chem. 2017;60(13):5521-5542.
Li et al., "Genome-wide and functional annotation of human E3 ubiquitin ligases identifies MULAN, a mitochondrial E3 that regulates the organelle's dynamics and signaling," PLoS One. 2008;3(1):e1487.
Li et al., "IRAK-4: A novel member of the IRAK family with the properties of an IRAK-kinase," Proc Natl Acad Sci USA. 2002;99(8):5567-72.
Li et al., "Targeting interleukin-1 receptor-associated kinase for human hepatocellular carcinoma," J Exp Clin Cancer Res. 2016;35(1):140.
Li, "IRAK4 in TLR/IL-1R signaling: Possible clinical applications," Eur J Immunol. 2008;38(3):614-8.
Lim et al., "Discovery of 5-Amino-N-(1H-pyrazol-4-yl)pyrazolo[1,5-a]pyrimidine-3-carboxamide Inhibitors of IRAK4," ACS Med Chem Lett. 2015;6(6):683-688.
Lin et al., "Helical assembly in the MyD88-IRAK4-IRAK2 complex in TLR /IL-1R signalling," Nature. 2010:465(7300):885-90.
Lu et al., "Discovery of a Keap1-dependent peptide PROTAC to knockdown Tau by ubiquitination-proteasome degradation pathway," Eur J Med Chem. 2018; 146:251-259.
Lu et al., "Hijacking the E3 Ubiquitin Ligase Cereblon to Efficiently Target BRD4," Chem Biol. 2015;2(6):755-63.
Lu et al., "The myeloma drug lenalidomide promotes the cereblon-dependent destruction of Ikaros proteins," Science. 2014;343(6168):305-309.
Lust et al., "Induction of a Chronic Disease State in patients With Smoldering of Indolent Multiple Myeloma by Targeting Interleukin 1ß-Induced Interleukin 6 Production and the Myeloma Proliferative Component," Mayo Clin Proc. 2009;84(2):114-22.
Martinon et al., "Gout-associated uric acid crystals activate the NALP3 inflammasome," Nature. 2006;440(7081):237-41.
Maschera et al., "Overexpression of an enzymatically inactive interleukin-1-receptor-associated kinase activates nuclear factor-κB," Biochem J. 1999;339(Pt2):227-31.
Matyskiela et al., "A Cereblon Modulator (CC-220) with Improved Degradation of Ikaros and Aiolos," J Med Chem. 2018;61(2):535-542.
McElroy et al., "Discovery and hit-to-lead optimization of 2,6-diaminopyrimidine Inhibitors of interleukin-1 receptor-associated kinase 4," Bioorg Med Chem Lett. 2015;25(9):1836-41.
McElroy et al., "Potent and Selective Amidopyrazole Inhibitors of IRAK4 That Are Efficacious in a Rodent Model of Inflammation," ACS Med Chem Lett. 2015;6(6):677-682.
Molenaar et al., "Inactivation of CDK2 is synthetically lethal to MYCN over-expressing cancer cells," Proc Natl Acad Sci U S A. 2009; 106(31): 12968-12973.
Muller et al., "Amino-Substituted Thalidomide Analogs: Potent Inhibitors of TNF-? Production," Bioorg Med Chem Lett. 1999;9(11):1625-30.
Ngo et al., "Oncogenically active MYD88 mutations in human lymphoma," Nature. 2011;470(7332):115-9.

Ohoka et al., "In Vivo Knockdown of Pathogenic Proteins via Specific and Nongenetic Inhibitor of Apoptosis Protein (IAP)-dependent Protein Erasers (SNIPERs)," J Bio Chem. 2017;292(11):4556-4570.
Okazaki et al., "A rheostat for immune responses: the unique properties of PD-1 and their advantages for clinical application," Nat. Immunol. 2013; 14(12): 1212-1218.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/042105, dated Nov. 20, 2020.
Picard et al., "Clinical features and outcome of patients with IRAK-4 and MyD88 deficiency," Medicine (Baltimore). 2010;89(6):403-425.
Picard et al., "Inherited human IRAK-4 deficiency: an update," Immunol Res. 2007;38(1-3):347-52.
Piya et al., "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood. 2016;126(23): 675-676.
Powers et al., "Discovery and initial SAR of inhibitors of interleukin-1 receptor-associated kinase-4," Bioorg Med Chem Lett. 2006;16(11):2842-5.
Priyadarshini et al., "Copper catalyzed oxidative cross-coupling of aromatic amines with 2-pyrrolidinone: a facile synthesis of N-aryl-r-amino-r-lactams," Tetrahedron. 2014;70(36):6068-6074.
Pubmed Compound Summary for CID 101524675, "(2R)-3-Fluoro-2-(2-methylpropyl)-3-phenyl-1,3-azasilinan-6-one," U.S. National Library of Medicine, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, 3-(5-Amino-2-oxo-3H-benzimidazol-1-yl) piperidine-2,6-dione, U.S. Library of Medicine, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1- yl) piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 17607528, "4-(Carbazol-9-ylmethyl)-1,3-oxazolidin-2-one," U.S. National Library of Medi-

(56) References Cited

OTHER PUBLICATIONS cine, Nov. 13, 2007, https://pubchem.ncbi.nlm.nih.gov/compound/17607528. Date Accessed: Feb. 25, 2020 (6 pages).
Pubmed Compound Summary for CID 63661260, "5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," *U.S. National Library of Medicine*, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-yl)ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," *U.S. National Library of Medicine*, created Oct. 20, 2014, https://pubchem.ncbi.nlm.nih.gov/compound/83543479. Date Accessed: Feb. 25, 2020 (6 pages).
Pubmed Compound Summary for CID 84036945, 1-Piperidin-3-yl-3H-indol-2-one, *U.S. Library of Medicine*, created Oct. 20, 2014, https://pubchem.ncbi.nlm.nih.gov/compound/84036945. Date Accessed: Feb. 25, 2020 (7 pages).
Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.
Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.
Pubmed Compound Summary for CID 99784232, (3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.
Raina et al., "Chemical Inducers of Targeted Protein Degradation," J Biol Chem. 2010;285(15):11057-60.
Ramirez et al., "Defining causative factors contributing in the activiation of hedgehog signaling in diffuse large B-cell lymphoma," Leuk Res. 2012;36(10):1267-73.
Rokosz et al., 2008, "Kinase inhibitors as drugs for chronic inflammatory and immunological diseases: progress and challenges," Expert Opinions on Therapeutic Targets 12(7): 883-903.
Ronnebaum et al., "Synthesis of 1, 2, 3-triazole 'click' analogues of thalidomide," Tetrahedron. 2016;72(40): 6136-6141.
Ross et al., "Bispecific T cell engager (BITE®) antibody constructs can mediate bystander tumor cell killing," PLoS One. 2017; 12(8): e0183390.
Rostovtsev et al., "A Stepwise Huisgen Cycloaddition Process: Copper(I)-Catalyzed Regioselective "Ligation" of Azides and Terminal Alkynes," Angew Chem Int Ed Engl. 2002;41(14):2596-9.
Schnnekloth et al., "Chemical approaches to controlling intracellular protein degradation," Chembiochem. 2005;6(1):40-46.
Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," J Med Chem. 2017;60(24):10071-10091.
Seganish et al., "Discovery and Structure Enabled Synthesis of 2,6-diaminopyrimidine-4-one IRAK4 Inhibitors," ACS Med Chem Lett. 2015;6(8):942-947.

Seganish et al., "Initial optimization and series evolution of diaminopyrimidine inhibitors of interleukin-1 receptor associated kinase 4," Bioorg Med Chem Lett. 2015;25(16):3203-3207.
Seitz et al., "Sulfenylation and Halogenation of Di-and Trianions Derived from Substituted Glutarimides," Synthetic Communications. 1977;7(6):367-374.
Sen et al., "Transcriptional signaling by double-stranded RNA: role of TLR3," Cytokine Growth Factor Rev. 2005;16(1):1-14.
Shanmugasundaram et al., "A modular PROTAC design for target destruction using a degradation signal based on a single amino acid," J Biol Chem. 2019;294(41):15172-15175.
Smith et al., "Identification of quinazoline based inhibitors of IRAK4 for the treatment of inflammation," Bioorg Med Chem Lett. 2017;27(12):2721-2726.
So et al., "A pilot study of IL-1 inhibition by anakinra in acute gout," Arthritis Res Ther. 2007;9(2):R28.
Song et al., "The kinase activities of interleukin-e receptor associated kinase (IRAK)-1 and 4 are redundant in the control of inflammatory cytokine expression in human cells," Mol Immunol. 2009;46(7):1458-66.
Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.
Spratt et al., "RBR E3 ubiquitin ligases: new structures, new insights, new question," Biochem J. 2014;458(3);421-37.
Stewart et al., "Efforts toward elucidating Thalidomide's molecular target: an expedient synthesis of the first Thalidomide biotin analogue," Organic & Biomolecular Chemistry. 2010;8(18): 4059-4062.
Sun et al., "Carbohydrate and protein immobilization onto solid surfaces by sequential Diels-Alder and azide-alkyne cycloadditions," Bioconjug Chem. 2006;17(1):52-7.
Suzuki et al., "IRAK-4 as the central TIR signaling mediator in innate immunity," Trends Immunol. 2002;23(10):503-6.
Suzuki et al., "Severe impairment of interleukin-1 and Toll-like receptor signalling in mice lacking IRAK-4," Nature. 2002;416(6882):750-6.
Swantek et al., "IL-1 Receptor-Associated Kinase Modulates Host Responsiveness to Endotoxin," Journal of Immunology 164: 4301-4306, J Immunol. 2000; 164(8):4301-6.
Takada et al., "FBW7 Loss Promotes Chromosomal Instability and Tumorigenesis via Cyclin E1/CDK2-Mediated Phosphorylation of CENP-A," Cancer Res. 2017;77(18):4881-4893.
Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009;68(10):1613-7.
Terkeltaub, "Update on gout: new therapeutic strategies and options," Nat Rev Rheumatol. 2010;6(1):30-8.
Tong et al., "Targeted Protein Degradation via a Covalent Reversible Degrader Based on Bardoxolone", ChemRxiv 2020.
Toogood, "Small molecule immuno-oncology therapeutic agents," Bioorg. Med. Chem. Lett. 2018;28(3):319-329.
Torres et al., "Hyperalgesia, synovitis and multiple biomarkers of inflammation are suppressed by interleukin 1 inhibition in a novel animal model of gouty arthritis," Ann Rheum Dis. 2009;68(10):1602-8.
Toure and Crews, "Small-Molecule PROTACS: New Approaches to Protein Degradation," Angew Chem Int Ed Engl. 2016;55(6):1966-73.
Treon et al., "Whole genome sequencing reveals a widely expressed mutation (MYD88 L265P) with oncogenic activity in Waldenstrom's Macroglobulinemia" 53rd ASH Annual Meeting, San Diego, California, Dec. 10-13, 2011 [abstract].
Trøseid et al., "The role of interleukin-18 in the metabolic syndrome," Cardiovasc Diabetol. 2010;9:11.
Tumey et al., "Identification and optimization of indolo[2,3-c]quinoline inhibitors of IRAK4," Bioorg Med Chem Lett. 2014;24(9):2066-72.
Uehara et al., "Selective degradation of splicing factor CAPER? by anticancer sulfonamides," Nat Chem Biol. 2017;13(6):675-680.

(56) References Cited

OTHER PUBLICATIONS

Varfolomeev et al., "IAP antagonists induce autoubiquitination of c-IAPs, NF-kappaB activation, and TNFalpha-dependent apoptosis," Cell. 2007;131(4):669-81.
Vollmer et al., "The mechanism of activation of IRAK1 and IRAK4 by interleukin-1 and Toll-like receptor agonists," Biochem J. 2017;474(12):2027-2038.
Wang et al., "Crystal Structure of IRAK-4 Kinase in Complex with Inhibitors: Serine/Threonine Kinase with Tyrosine as a Gatekeeper," Structure. 2006;14(12):1835-44.
Wang et al., "Discovery of potent, selective, and orally bioavailable inhibitors of interleukin-1 receptor-associated kinase 4," Bioorg Med Chem Lett. 2015;25(23):5546-5550.
Wang et al., "IRAK-4 Inhibitors for Inflammation," Curr Top Med Chem. 2009;9(8):724-37.
Wang et al., "Roles of F-box proteins in cancer," Nat Rev Cancer. 2014;14(4):233-47.
Ward et al., "Covalent Ligand Screening Uncovers a RNF4 E3 Ligase Recruiter for Targeted Protein Degradation Applications," bioRxiv.org, https://www.biorxiv.org/content/biorxiv/early/2018/11/16/439125.full.pdf. Date Accessed, Oct. 3, 2019 (24 pages).
Weaver, "Epidemiology of gout," Cleve Clin J Med. 2008;75 Suppl 5:S9-12.
Winter et al., "Selective Target Protein Degradation via Phthalimide Conjugation," Science. 2015;348(6241):1376-1381.
Xia and Chen, "Iron-catalyzed N-alkylation of azoles via cleavage of an sp3 C—H bond adjacent to a nitrogen atom," J Org Chem. 2012;77(20):9366-73.
Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAK1, NK-κB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Yang et al., "Exploiting synthetic lethality for the therapy of ABC diffuse large B cell lymphoma," Cancer Cell. 2012;21(6):723-37.
Zhang et al., "Constitutive IRAK4 Activation Underlies Poor Prognosis and Chemoresistance in Pancreatic Ductal Adenocarcinoma," Clin Cancer Res. 2017;23(7):1748-1759.
Zhang et al., "Electrophilic PROTACs that degrade nuclear proteins by engaging DCAF16," bioRxiv.org, https://www.biorxiv.org/content/biorxiv/early/2018/10/15/443804.full.pdf. Date Accessed, Oct. 3, 2019.
Zhou et al., "Targets of curcumin," Curr Drug Targets. 2011;12(3):332-347.
Zinc 170596280, Date Added Aug. 8, 2015, https://zinc.docking.org/substances/ZINC000170596280/. Date Accessed: Jan. 10, 2022.
Zou et al., "PD-L1 (B7—H1) and PD-1 pathway blockade for cancer therapy: Mechanisms, response biomarkers, and combinations," Sci. Transl. Med. 2016;8(328):328rv4.
"Acute Leukemia," Merck Manual (Online Edition), 2013, 6 pages.
Damasio, "Alzheimer's Disease and related dementias", Cecil Textbook of Medicine, 20th Edition, 1996, vol. 2, pp. 1992-1996.
Gura T., "Systems for identifying new drugs are often faulty," Science, 1997, 278(5340):1041-1042.
Hatcher et al., "Development of Highly Potent and Selective Steroidal Inhibitors and Degraders of CDK8", ACS Med. Chem. Lett. 2018. 9, pp. 540-545, especially: abstract; p. 543, col. 1, para 3.
Johnson et al., "Relationships between drug activity in NCI preclinical in vitro and in vivo models and early clinical trials," British Journal of Cancer, 2001, 84(10):1424-1431.
Layzer, Robert B., "Degenerative diseases of the nervous system", Cecil Textbook of Medicine, 20th Edition, 1996, vol. 2, pp. 2050-2057.
Pearce et al., "Failure modes in anticancer drug discovery and development," Cancer Drug Design and Discovery, Edited by Stephen Neidle, Chapter 18, 2008, pp. 424-435.
Simone, "Oncology: Introduction", Cecil Textbook of Medicine, 20th Edition, 1996, vol. 1, pp. 1004-1010.
PCT International Preliminary Report on Patentability received from PCT/US2018/052181, dated Apr. 2, 2020, 8 pages.
PCT International Preliminary Report on Patentability received from PCT/US2019/013491, dated Jul. 23, 2020, 7 pages.
PCT International Preliminary Report on Patentability received from PCT/US2019/040462 dated Jan. 21, 2021, 6 pages.
PCT International Preliminary Report on Patentability received from PCT/US2020/042105, dated Jan. 27, 2022, 7 pages.
PCT International Preliminary Report on Patentability received from PCT/US2022/028076, dated Nov. 16, 2023, 8 pages.
PCT International Search Report and Written Opinion received from PCT/US2022/028076, dated Sep. 29, 2022, 11 pages.
Chen et al., "Folate-Guided Protein Degradation by Immunomodulatory Imide Drug-Based Molecular Glues and Proteolysis Targeting Chimeras," J Med Chem., Aug. 26, 2021, 64(16):12273-12285.
Donovan et al., "Mapping the Degradable Kinome Provides a Resource for Expedited Degrader Development," Cell., Dec. 10, 2020, 183(6):1714-1731.
Freeman-Cook et al., "Discovery of PF-06873600, a CDK2/4/6 Inhibitor for the Treatment of Cancer", Journal of Medicinal Chemistry, 2021, 64(13):9056-9077.
Gao et al., "Catalytic Degraders Effectively Address Kinase Site Mutations in EML4-Alk Oncogenic Fusions," J. Med. Chem., 2023, 66(8):5524-5535.
Hati et al., "AZD5438-PROTAC: A selective CDK2 degrader that protects against cisplatin- and noise-induced hearing loss," Eur J Med Chem., Dec. 15, 2021, 226:113849.
Jiang et al., "Discovery and resistance mechanism of a selective CDK12 degrader," Nat Chem Biol., Jun. 2021, 17(6):675-683.
Liu et al., "Transcriptional cyclin-dependent kinases: Potential drug targets in cancer therapy," Eur J Med Chem., Feb. 5, 2022, 229:114056.
Powell et al., "Selective Degradation of GSPT1 by Cereblon Modulators Identified via a Focused Combinatorial Library, " ACS Chem Biol., Oct. 16, 2020,15(10): 2722-2730.
Powell et al., "Chemically Induced Degradation of Anaplastic Lymphoma Kinase (ALK)," J Med Chem., May 10, 2018, 61(9):4249-4255.
Pubmed Compound Summary for SID 104834768, AKOS000286345, Created Dec. 14, 2023, from https://pubchem.ncbi.nlm.nih.gov/substance/104834768.
Sokolsky et al., "Discovery of 5,7-Dihydro-6H-pyrrolo[2,3-d]pyrimidin-6-ones as Highly Selective CDK2 Inhibitors", ACS Medicinal Chemistry Letters, Oct. 6, 2022, 13(11):1797-1804.
Teng et al., "Development of CDK2 and CDK5 Dual Degrader TMX-2172," Angew Chem Int Ed Engl., Aug. 10, 2020, 59(33):13865-13870.
Trapotsi et al., "Cell Morphological Profiling Enables High-Throughput Screening for PROteolysis TArgeting Chimera (PROTAC) Phenotypic Signature," ACS Chem Biol., Jul. 15, 2022, 17(7):1733-1744.
Wang et al., "Discovery of a first-in-class CDK2 selective degrader for AML differentiation therapy," Nat Chem Biol., May 2021, 17(5):567-575.
Xie et al., "Development of Alectinib-Based PROTACs as Novel Potent Degraders of Anaplastic Lymphoma Kinase (ALK)," J. Med. Chem., 2021, 64(13):9120-9140.
Yan et al., "Discovery of a PROTAC targeting ALK with in vivo activity, " Eur J Med Chem., Feb. 15, 2021, 212:113150.
Yang et al., "Discovery of a Highly Potent and Selective Dual PROTAC Degrader of CDK12 and CDK13," J Med Chem., Aug. 25, 2022, 65(16):11066-11083.
Zhang et al., "Proteolysis Targeting Chimeras (PROTACs) of Anaplastic Lymphoma Kinase (ALK)," Eur J Med Chem., May 10, 2018, 151: 304-314.
PCT International Search Report and Written Opinion received from PCT/US2023/030721, dated Jan. 31, 2024, 14 pages.

* cited by examiner

CDK2 DEGRADERS AND USES THEREOF

CROSS-REFERENCE TO RELATED APPLICATIONS

This application claims the benefit of priority to U.S. Provisional Appl. No. 63/185,929, filed May 7, 2021, the entirety of which is herein incorporated by reference.

TECHNICAL FIELD OF THE INVENTION

The present invention relates to compounds and methods useful for the modulation of cyclin-dependent kinase 2 ("CDK2") protein via ubiquitination and/or degradation by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer., 2014, 14, 233-347) titled "Roles of F-box proteins in cancer."

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17(6):551-555; Schnnekloth J S Jr., Chembiochem, 2005, 6(1):40-46).

An ongoing need exists in the art for effective treatments for disease, especially cancers. Cyclin-dependent kinases (CDKs) are a family of serine/threonine kinases. Heterodimerized with regulatory subunits known as cyclins, such as cyclin E1 ("CCNE1"), CDKs become fully activated and regulate key cellular processes including cell cycle progression and cell division. Uncontrolled proliferation is a hallmark of cancer cells. The deregulation of the CDK activity is associated with abnormal regulation of cell-cycle, and is detected in virtually all forms of human cancers. As such, small molecule therapeutic agents that leverage UPP mediated protein degradation to target cancer-associated proteins such as cyclin-dependent kinase 2 ("CDK2") or CDK2 and CCNE1 protein hold promise as therapeutic agents. Accordingly, there remains a need to find compounds that are CDK2 or CDK2 and CCNE1 degraders useful as therapeutic agents.

SUMMARY OF THE INVENTION

The present application relates novel bifunctional compounds, which function to recruit CDK2 or CDK2 and CCNE1 protein to E3 ubiquitin ligase for degradation, and methods of preparation and uses thereof. In particular, the present disclosure provides bifunctional compounds, which find utility as modulators of targeted ubiquitination of CDK2 or CDK2 and CCNE1, which is then degraded and/or otherwise inhibited by the bifunctional compounds as described herein. Also provided are monovalent compounds, which find utility as inducers of targeted ubiquitination of CDK2 or CDK2 and CCNE1, which are then degraded and/or otherwise inhibited by the monovalent compounds as described herein. An advantage of the compounds provided herein is that a broad range of pharmacological activities is possible, consistent with the degradation/inhibition of CDK2 or CDK2 and CCNE1. In addition, the description provides methods of using an effective amount of the compounds as described herein for the treatment or amelioration of a disease condition, such those caused by aberrant CDK2 or CDK2 and CCNE1 activity.

The present application further relates to targeted degradation of CDK2 or CDK2 and CCNE1 protein through the use of bifunctional molecules, including bifunctional molecules that link a cereblon-binding moiety to a ligand that binds CDK2 or CDK2 and CCNE1.

It has now been found that compounds of this invention, and pharmaceutically acceptable compositions thereof, are effective as degraders of CDK2 or CDK2 and CCNE1 protein. Such compounds have the general formula I.

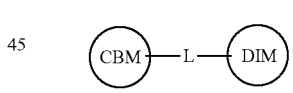

I or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of CDK2 protein. Such diseases, disorders, or conditions include those described herein.

Compounds provided by this invention are also useful for the study of CDK2 protein in biological and pathological phenomena; and the comparative evaluation of new CDK2 inhibitors or CDK2 degraders, in vitro or in vivo.

DETAILED DESCRIPTION OF CERTAIN EMBODIMENTS

1. General Description of Certain Embodiments of the Invention

Compounds of the present invention, and compositions thereof, are useful as degraders and/or inhibitors of CDK protein. In some embodiments, a provided compound degrades and/or inhibits CDK2 protein. In some embodiments, a provided compound degrades and/or inhibits CDK2 and CCNE1 protein.

In certain embodiments, the present invention provides a compound of formula I:

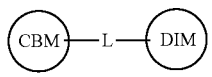

I or a pharmaceutically acceptable salt thereof, wherein:
CBM is a CDK binding moiety capable of binding CDK2 or CDK2 and CCNE1;
L is a bivalent moiety that connects CBM to DIM; and
DIM is a degradation inducing moiety, such as a ligase binding moiety (LBM), lysine mimetic, or hydrogen atom.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic, bicyclic, bridged bicyclic, or spirocyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

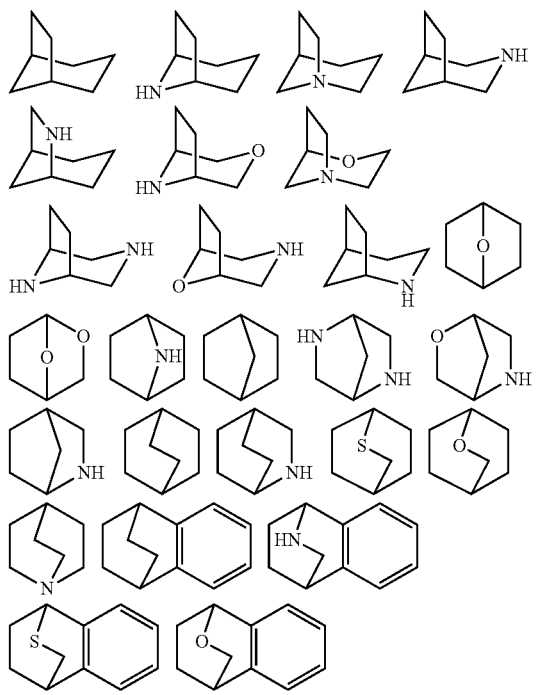

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

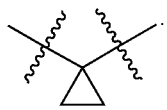 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. A heteroaryl ring may include one or more oxo (═O) or thioxo (═S) substituent. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, bridged bicyclic, or spirocyclic. A heterocyclic ring may include one or more oxo (═O) or thioxo (═S) substituent. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●$$_2$, —NO$_2$, —SiR$^●$$_3$, —OSiR$^●$$_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$)$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●$$_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●$$_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. In some embodiments, the provided compounds are purified in salt form for convenience and/or ease of purification, e.g., using an acidic or basic mobile phase during chromatography. Salts forms of the provided compounds formed during chromatographic purification are contemplated herein and are readily apparent to those having skill in the art.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention As used herein, the term "provided compound" refers to any genus, subgenus, and/or species set forth herein.

As used herein, the term "inhibitor" is defined as a compound that binds to and/or inhibits CDK2 or CDK2 and CCNE1 with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

As used herein, the term "degrader" is defined as a heterobifunctional compound that binds to and/or inhibits both CDK2 or CDK2 and CCNE1, and an E3 ligase with measurable affinity resulting in the ubiquitination and subsequent degradation of the CDK2 or CDK2 and CCNE1. In certain embodiments, a degrader has an $DC_{50}$ of less than about 50 µM, less than about 1 µM, less than about 500 nM, less than about 100 nM, less than about 10 nM, or less than about 1 nM. As used herein, the term "monovalent" refers to a degrader compound without an appended E3 ligase binding moiety.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41:2596-9 and Sun et al., Bioconjugate Chem., 2006, 17:52-7.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in CDK2 or CDK2 and CCNE1 activity between a sample comprising a compound of the present invention, or composition thereof, and CDK2 or CDK2 and CCNE1, and an equivalent sample comprising CDK2 or CDK2 and CCNE1, in the absence of said compound, or composition thereof.

3. Description of Exemplary Embodiments

As described above, in certain embodiments, the present invention provides a compound of formula I.

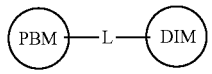

or a pharmaceutically acceptable salt thereof, wherein:
CBM is a CDK binding moiety capable of binding CDK2 or CDK2 and CCNE1;
L is a bivalent moiety that connects CBM to DIM; and
DIM is a degradation inducing moiety, such as a ligase binding moiety (LBM), lysine mimetic, or hydrogen atom.

CDK2 Binding Moiety (CBM)

As defined herein and described above, CBM is a CDK binding moiety capable of binding CDK2 protein. In some embodiments, CBM binds to CDK2 protein which then undergoes ubiquitination thereby marking the CDK2 for degradation via the Ubiquitin-Proteasome Pathway (UPP). In some embodiments, CBM is a CDK binding moiety capable of selectively binding and degrading CDK2 over other CDK proteins (e.g., CDK1, CDK3, CDK4, CDK5, CDK6, CDK7, CDK8, CDK9, etc.). In some embodiments, CBM is a CDK binding moiety capable of selectively binding and degrading CDK2 over one or more of CDK1, CDK4, and CDK9 proteins.

In some embodiments, CBM binds to CDK2 and CCNE1 protein which then undergoes ubiquitination thereby marking the CDK2 and CCNE1 for degradation via the Ubiquitin-Proteasome Pathway (UPP). In some embodiments, a provided compound is a dual CDK2 and CCNE1 degrader.

As defined herein and described below, wherein a formula is depicted using square brackets, e.g.,

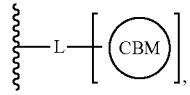

L is attached to a modifiable carbon, oxygen, nitrogen or sulfur atom within CBM including substitution or replacement of a defined group in CBM.

In certain embodiments, the present invention provides a compound of formula I, wherein CBM is a CDK2 or CDK2 and CCNE1 binding moiety thereby forming a compound of formula I-a:

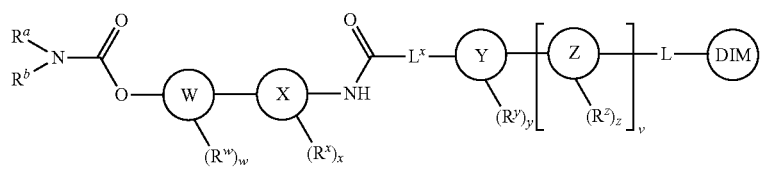

or a pharmaceutically acceptable salt thereof, wherein L and DIM are as defined above and described herein, and wherein:

$R^a$ and $R^b$ are independently hydrogen or $R^4$, or
$R^a$ and $R^b$ are taken together with the nitrogen to which they are attached to form to form a 4-7 membered saturated, partially unsaturated, or heteroaryl ring having 0-3 heteroatoms, in addition to the nitrogen atom to which they are attached, independently selected from nitrogen, oxygen, and sulfur;

each $R^4$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring W, Ring X, and Ring Y are independently a ring selected from phenyl, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur;

Ring Z is phenyl or a 4 to 8-membered saturated or partially unsaturated monocyclic, bicyclic, bridged bicyclic, or spirocyclic carbocyclyl or heterocyclyl with 1-3 heteroatoms independently selected from nitrogen, oxygen, and sulfur;

$R^w$, $R^x$, $R^y$, and $R^z$ are independently selected from hydrogen, $R^4$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)NROR, —CR$_2$NRC(O)R, —CR$_2$NRC(O)NR$_2$, —OC(O)R, —OC(O)NR$_2$, —OP(O)R$_2$, —OP(O)(OR)$_2$, —OP(O)(OR)NR$_2$, —OP(O)(NR$_2$)$_2$—, —NRC(O)OR, —NRC(O)R, —NRC(O)N(R)$_2$, —NRS(O)$_2$R, —NP(O)R$_2$, —NRP(O)(OR)$_2$, —NRP(O)(OR)NR$_2$, —NRP(O)(NR$_2$)$_2$, and —NRS(O)$_2$R;

each R is independently hydrogen, or an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen atom to which they are attached, independently selected from nitrogen, oxygen, and sulfur;

$L^x$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —CF$_2$—, —CRF—, —NR—, —S—, —S(O)—, —S(O)$_2$— or —CR=CR—;

v is 0 or 1; and w, x, y, and z are independently 0, 1, 2, 3, or 4.

In certain embodiments, the present invention provides a compound of formula I, wherein CBM is a CDK2 or CDK2 and CCNE1 binding moiety thereby forming a compound of formula I-b:

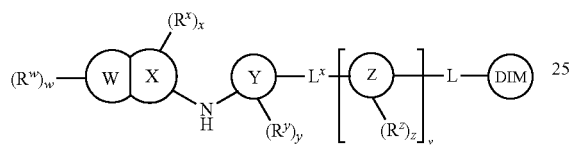

I-b or a pharmaceutically acceptable salt thereof, wherein L and DIM are as defined above and described herein, and wherein:

Ring W and Ring X are independently fused rings selected from benzo, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur;

Ring Y is a ring selected from phenyl, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur;

Ring Z is phenyl or a 4 to 8-membered saturated or partially unsaturated monocyclic, bicyclic, bridged bicyclic, or spirocyclic carbocyclyl or heterocyclyl with 1-3 heteroatoms independently selected from nitrogen, oxygen, and sulfur;

$R^w$, $R^x$, $R^y$, and $R^z$ are independently selected from hydrogen, $R^A$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)NROR, —CR$_2$NRC(O)R, —CR$_2$NRC(O)NR$_2$, —OC(O)R, —OC(O)NR$_2$, —OP(O)R$_2$, —OP(O)(OR)$_2$, —OP(O)(OR)NR$_2$, —OP(O)(NR$_2$)$_2$—, —NRC(O)OR, —NRC(O)R, —NRC(O)N(R)$_2$, —NRS(O)$_2$R, —NP(O)R$_2$, —NRP(O)(OR)$_2$, —NRP(O)(OR)NR$_2$, —NRP(O)(NR$_2$)$_2$, and —NRS(O)$_2$R; or two $R^w$ groups attached to the same carbon atom are optionally taken together to form a spiro fused ring selected from a 3-5 membered saturated or partially unsaturated carbocyclyl and a 3-5 membered saturated or partially unsaturated heterocyclyl having 1-2 heteroatoms independently selected from nitrogen, oxygen, and sulfur;

each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from $C_{1-6}$ aliphatic, phenyl, a 4-7 membered saturated or partially unsaturated carbocylic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen atom to which they are attached, independently selected from nitrogen, oxygen, and sulfur; and $L^x$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —CF$_2$—, —CRF—, —NR—, —S—, —S(O)—, —S(O)$_2$— or —CR=CR—;

v is 0 or 1; and w, x, y, and z are independently 0, 1, 2, 3, or 4.

In certain embodiments, the present invention provides a compound of formula I, wherein CBM is a CDK2 or CDK2 and CCNE1 binding moiety thereby forming a compound of formula I-c:

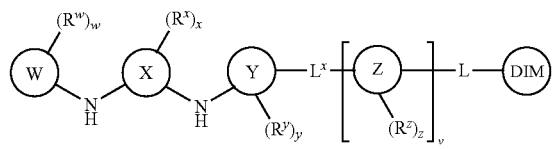

I-c or a pharmaceutically acceptable salt thereof, wherein L and DIM are as defined above and described herein, and wherein:

Ring W, Ring X, and Ring Y are independently a ring selected from phenyl, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur;

Ring Z is phenyl or a 4 to 8-membered saturated or partially unsaturated monocyclic, bicyclic, bridged bicyclic, or spirocyclic carbocyclyl or heterocyclyl with 1-3 heteroatoms independently selected from nitrogen, oxygen, and sulfur;

$R^w$, $R^x$, $R^y$, and $R^z$ are independently selected from hydrogen, $R^A$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)NROR, —CR$_2$NRC(O)R, —CR$_2$NRC(O)NR$_2$, —OC(O)R, —OC(O)NR$_2$, —OP(O)R$_2$, —OP(O)(OR)$_2$, —OP(O)

(OR)NR$_2$, —OP(O)(NR$_2$)$_2$—, —NRC(O)OR, —NRC(O)R, —NRC(O)N(R)$_2$, —NRS(O)$_2$R, —NP(O)R$_2$, —NRP(O)(OR)$_2$, —NRP(O)(OR)NR$_2$, —NRP(O)(NR$_2$)$_2$, and —NRS(O)$_2$R;

each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen atom to which they are attached, independently selected from nitrogen, oxygen, and sulfur;

$L^x$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —CF$_2$—, —CRF—, —NR—, —S—, —S(O)—, —S(O)$_2$— or —CR=CR—;

v is 0 or 1; and w, x, y, and z are independently 0, 1, 2, 3, or 4.

In certain embodiments, the present invention provides a compound of formula I, wherein CBM is a CDK2 or CDK2 and CCNE1 binding moiety thereby forming a compound of formula I-d:

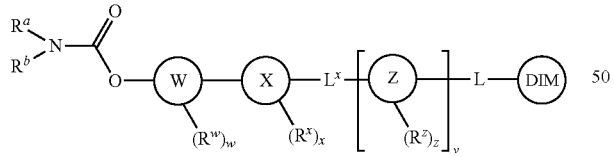

I-d or a pharmaceutically acceptable salt thereof, wherein L and DIM are as defined above and described herein, and wherein:

$R^a$ and $R^b$ are independently hydrogen or $R^A$, or $R^a$ and $R^b$ are taken together with the nitrogen to which they are attached to form to form a 4-7 membered saturated, partially unsaturated, or heteroaryl ring having 0-3 heteroatoms, in addition to the nitrogen atom to which they are attached, independently selected from nitrogen, oxygen, and sulfur;

each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring W is a ring selected from phenyl, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur;

Ring X is a bicyclic ring selected from naphthyl, a 9 to 10-membered saturated or partially unsaturated carbocyclyl or heterocyclyl with 1-4 heteroatoms independently selected from nitrogen, oxygen, and sulfur, and a 9 to 10-membered heteroaryl with 1-4 heteroatoms independently selected from nitrogen, oxygen and sulfur;

Ring Z is phenyl or a 4 to 8-membered saturated or partially unsaturated monocyclic, bicyclic, bridged bicyclic, or spirocyclic carbocyclyl or heterocyclyl with 1-3 heteroatoms independently selected from nitrogen, oxygen, and sulfur;

$R^w$, $R^x$, and $R^z$ are independently selected from hydrogen, $R^A$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)NROR, —CR$_2$NRC(O)R, —CR$_2$NRC(O)NR$_2$, —OC(O)R, —OC(O)NR$_2$, —OP(O)R$_2$, —OP(O)(OR)$_2$, —OP(O)(OR)NR$_2$, —OP(O)(NR$_2$)$_2$—, —NRC(O)OR, —NRC(O)R, —NRC(O)N(R)$_2$, —NRS(O)$_2$R, —NP(O)R$_2$, —NRP(O)(OR)$_2$, —NRP(O)(OR)NR$_2$, —NRP(O)(NR$_2$)$_2$, and —NRS(O)$_2$R;

each R is independently hydrogen, or an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen atom to which they are attached, independently selected from nitrogen, oxygen, and sulfur;

$L^x$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —CF$_2$—, —CRF—, —NR—, —S—, —S(O)—, —S(O)$_2$— or —CR=CR—;

v is 0 or 1; and w, x, and z are independently 0, 1, 2, 3, or 4.

In certain embodiments, the present invention provides a compound of formula I, wherein CBM is a CDK2 or CDK2 and CCNE1 binding moiety thereby forming a compound of formula I-e:

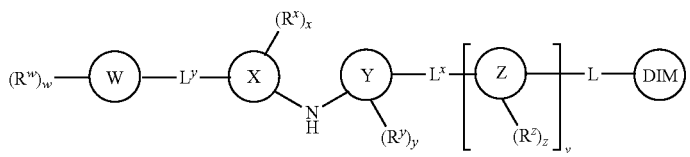

I-e or a pharmaceutically acceptable salt thereof, wherein L and DIM are as defined above and described herein, and wherein:

Ring W and Ring X are independently rings selected from phenyl, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur;

Ring Y is a ring selected from phenyl, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur;

Ring Z is phenyl or a 4 to 8-membered saturated or partially unsaturated monocyclic, bicyclic, bridged bicyclic, or spirocyclic carbocyclyl or heterocyclyl with 1-3 heteroatoms independently selected from nitrogen, oxygen, and sulfur;

$R^w$, $R^x$, $R^y$, and $R^z$ are independently selected from hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —$C(O)NR_2$, —C(O)NROR, —$CR_2NRC(O)R$, —$CR_2NRC(O)NR_2$, —OC(O)R, —$OC(O)NR_2$, —$OP(O)R_2$, —$OP(O)(OR)_2$, —OP(O)(OR)$NR_2$, —$OP(O)(NR_2)_2$—, —NRC(O)OR, —NRC(O)R, —$NRC(O)N(R)_2$, —$NRS(O)_2R$, —$NP(O)R_2$, —$NRP(O)(OR)_2$, —$NRP(O)(OR)NR_2$, —NRP(O)$(NR_2)_2$, and —$NRS(O)_2R$; or two $R^w$ groups attached to the same carbon atom are optionally taken together to form a spiro fused ring selected from a 3-5 membered saturated or partially unsaturated carbocyclyl and a 3-5 membered saturated or partially unsaturated heterocyclyl having 1-2 heteroatoms independently selected from nitrogen, oxygen, and sulfur;

each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen atom to which they are attached, independently selected from nitrogen, oxygen, and sulfur; and $L^x$ and $L^y$ are independently, a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$CF_2$—, —CRF—, —NR—, —S—, —S(O)—, —$S(O)_2$— or —CR=CR—;

v is 0 or 1; and w, x, y, and z are independently 0, 1, 2, 3, or 4.

As defined generally above, $R^a$ and $R^b$ are independently hydrogen or $R^A$, or $R^a$ and $R^b$ are taken together with the nitrogen to which they are attached to form to form a 4-7 membered saturated, partially unsaturated, or heteroaryl ring having 0-3 heteroatoms, in addition to the nitrogen atom to which they are attached, independently selected from nitrogen, oxygen, and sulfur.

In some embodiments, $R^a$ is hydrogen. In some embodiments, $R^a$ is $R^A$. In some embodiments, $R^b$ is hydrogen. In some embodiments, $R^b$ is $R^A$. In some embodiments, $R^a$ and $R^b$ are taken together with the nitrogen to which they are attached to form to form a 4-7 membered saturated, partially unsaturated, or heteroaryl ring having 0-3 heteroatoms, in addition to the nitrogen atom to which they are attached, independently selected from nitrogen, oxygen, and sulfur.

In some embodiments, $R^a$ is isopropyl. In some embodiments, $R^a$ and $R^b$ are taken together to form

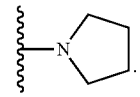

In some embodiments, $R^a$ and $R^b$ are selected from those depicted in Table 1, below.

As defined generally above, each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^A$ is an optionally substituted $C_{1-6}$ aliphatic. In some embodiments, R is $C_{1-6}$ alkyl (e.g., methyl, ethyl, isopropyl, etc.). In some embodiments, R is $C_{1-6}$ haloalkyl (e.g., —$CF_3$, $CHF_2$, etc.). In some embodiments, $R^A$ is an optionally substituted phenyl. In some embodiments, $R^A$ is an optionally substituted 3-7 membered saturated or partially unsaturated carbocyclic ring. In some embodiments, $R^A$ is an optionally substituted heterocyclic ring having 1-2 heteroatoms independently selected from nitrogen, oxygen, and sulfur. In some embodiments, $R^A$ is an optionally substituted 5-6 membered heteroaryl ring having 1-4 heteroatoms independently selected from nitrogen, oxygen, and sulfur.

In some embodiments, each $R^A$ is selected from those depicted in Table 1, below.

As defined generally above, Ring W, Ring X, and Ring Y are independently a ring selected from phenyl, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur.

In some embodiments, one or more of Ring W, Ring X, and Ring Y is a ring selected from phenyl. In some embodiments, one or more of Ring W, Ring X, and Ring Y is a 4 to 7-membered saturated or partially unsaturated carbocyclyl or heterocyclyl with 1-3 heteroatoms independently selected from nitrogen, oxygen, and sulfur. In some embodiments, one or more of Ring W, Ring X, and Ring Y is a 5 to 6-membered heteroaryl with 1-4 heteroatoms independently selected from nitrogen, oxygen and sulfur.

As defined generally above, Ring W and Ring X are independently fused rings selected from benzo, a 4 to 7-membered saturated or partially unsaturated carbocyclyl or heterocyclyl with 1-3 heteroatoms independently selected from nitrogen, oxygen, and sulfur, and a 5 to 6-membered heteroaryl with 1-4 heteroatoms independently selected from nitrogen, oxygen and sulfur.

In some embodiments, one or more of Ring W and Ring X is benzo. In some embodiments, one or more of Ring W and Ring X is a fused 4 to 7-membered saturated or partially unsaturated carbocyclyl or heterocyclyl with 1-3 heteroatoms independently selected from nitrogen, oxygen, and sulfur. In some embodiments, one or more of Ring W and Ring X is a fused 5 to 6-membered heteroaryl with 1-4 heteroatoms independently selected from nitrogen, oxygen and sulfur.

As defined generally above, Ring X is a bicyclic ring selected from naphthyl, a 9 to 10-membered saturated or partially unsaturated carbocyclyl or heterocyclyl with 1-4 heteroatoms independently selected from nitrogen, oxygen, and sulfur, and a 9 to 10-membered heteroaryl with 1-4 heteroatoms independently selected from nitrogen, oxygen and sulfur.

In some embodiments, Ring X is naphthyl. In some embodiments, Ring X is a 9 to 10-membered saturated or partially unsaturated carbocyclyl or heterocyclyl with 1-4 heteroatoms independently selected from nitrogen, oxygen, and sulfur. In some embodiments, Ring X is 9 to 10-membered heteroaryl with 1-4 heteroatoms independently selected from nitrogen, oxygen and sulfur.

In some embodiments, Ring W is cyclopentyl. In some embodiments Ring W is cyclohexyl. In some embodiments, Ring W is

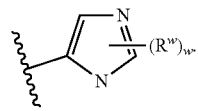

In some embodiments, Ring W is

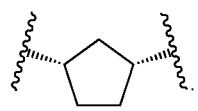

In some embodiments, Ring W is

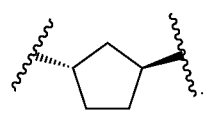

In some embodiments, Ring W is

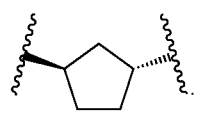

In some embodiments, Ring W is

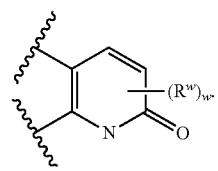

In some embodiments, Ring W is

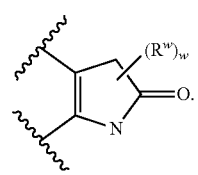

In some embodiments, Ring W is

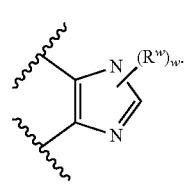

In some embodiments, Ring W is

In some embodiments, Ring W is

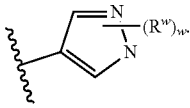

In some embodiments, Ring X is

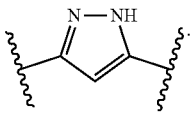 [SMILES: *c1cc(*)[nH]n1]

In some embodiments, Ring X is

In some embodiments, Ring X is

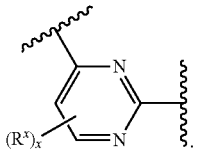

In some embodiments, Ring X is

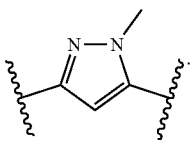 [SMILES: *c1cc(*)n(C)n1]

In some embodiments, Ring X is

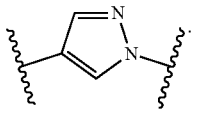

In some embodiments, Ring X is

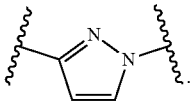

In some embodiments, Ring X is

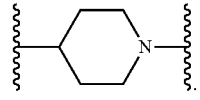

In some embodiments, Ring W, Ring X, and Ring Y are selected from those depicted in Table 1, below.

As defined generally above, Ring Z is phenyl or a 4 to 8-membered saturated or partially unsaturated monocyclic, bicyclic, bridged bicyclic, or spirocyclic carbocyclyl or heterocyclyl with 1-3 heteroatoms independently selected from nitrogen, oxygen, and sulfur.

In some embodiments, Ring Z is phenyl. In some embodiments, Ring Z is a 4 to 8-membered saturated or partially unsaturated monocyclic, bicyclic, bridged bicyclic, or spirocyclic carbocyclyl. In some embodiments, Ring Z is a 4 to 8-membered saturated or partially unsaturated monocyclic, bicyclic, bridged bicyclic, or spirocyclic heterocyclyl with 1-3 heteroatoms independently selected from nitrogen, oxygen, and sulfur.

In some embodiments, Ring Z is cyclohexane.

In some embodiments, Ring Z is selected from those depicted in Table 1, below.

As defined generally above, $R^w$, $R^x$, $R^y$, and $R^z$ are independently selected from hydrogen, $R^A$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)NROR, —CR$_2$NRC(O)R, —CR$_2$NRC(O)NR$_2$, —OC(O)R, —OC(O)NR$_2$, —OP(O)R$_2$, —OP(O)(OR)$_2$, —OP(O)(OR)NR$_2$, —OP(O)(NR$_2$)$_2$—, —NRC(O)OR, —NRC(O)R, —NRC(O)N(R)$_2$, —NRS(O)$_2$R, —NP(O)R$_2$, —NRP(O)(OR)$_2$, —NRP(O)(OR)NR$_2$, —NRP(O)(NR$_2$)$_2$, and —NRS(O)$_2$R, or two $R^w$ groups attached to the same carbon atom are optionally taken together to form a spiro fused ring selected from a 3-5 membered saturated or partially unsaturated carbocyclyl and a 3-5 membered saturated or partially unsaturated heterocyclyl having 1-2 heteroatoms independently selected from nitrogen, oxygen, and sulfur.

In some embodiments, one or more of $R^w$, $R^x$, $R^y$, and $R^z$ is hydrogen. In some embodiments, one or more of $R^w$, $R^x$, $R^y$, and $R^z$ is $R^A$. In some embodiments, one or more of $R^w$, $R^x$, $R^y$, and $R^z$ is halogen. In some embodiments, one or more of $R^w$, $R^x$, $R^y$, and $R^z$ is —CN. In some embodiments, one or more of $R^w$, $R^x$, $R^y$, and $R^z$ is —NO$_2$. In some embodiments, one or more of $R^w$, $R^x$, $R^y$, and $R^z$ is —OR. In some embodiments, one or more of $R^w$, $R^x$, $R^y$, and $R^z$ is —SR. In some embodiments, one or more of $R^w$, $R^x$, $R^y$, and $R^z$ is —NR$_2$. In some embodiments, one or more of $R^w$, $R^x$, $R^y$, and $R^z$ is —SiR$_3$. In some embodiments, one or more of $R^w$, $R^x$, $R^y$, and $R^z$ is —S(O)$_2$R. In some embodiments, one or more of $R^w$, $R^x$, $R^y$, and $R^z$ is —S(O)$_2$NR$_2$. In some embodiments, one or more of $R^w$, $R^x$, $R^y$, and $R^z$ is —S(O)R. In some embodiments, one or more of $R^w$, $R^x$, $R^y$, and $R^z$ is —C(O)R. In some embodiments, one or more of $R^w$, $R^x$, $R^y$, and $R^z$ is —C(O)OR. In some embodiments, one or more of $R^w$, $R^x$, $R^y$, and $R^z$ is —C(O)NR$_2$. In some embodiments, one or more of $R^w$, $R^x$, $R^y$, and $R^z$ is —C(O)NROR. In some embodiments, one or more of $R^w$, $R^x$, $R^y$, and $R^z$ is —CR$_2$NRC(O)R. In some embodiments, one or more of $R^w$, $R^x$, $R^y$, and $R^z$ is —CR$_2$NRC(O)NR$_2$. In some embodiments, one or more of $R^w$, $R^x$, $R^y$, and $R^z$ is —OC(O)R. In some embodiments, one or more of $R^w$, $R^x$, $R^y$, and $R^z$ is —OC(O)NR$_2$. In some embodiments, one or more of $R^w$, $R^x$, $R^y$, and $R^z$ is —OP(O)R$_2$. In some embodiments, one or more of $R^w$, $R^x$, $R^y$, and $R^z$ is —OP(O)(OR)$_2$. In some embodiments, one or more of $R^w$, $R^x$, $R^y$, and $R^z$ is —OP(O)(OR)NR$_2$. In some embodiments, one or more of $R^w$, $R^x$, $R^y$, and $R^z$ is —OP(O)(NR$_2$)$_2$—. In some embodiments, one or more of $R^w$, $R^x$, $R^y$, and $R^z$ is —NRC(O)OR. In some embodiments, one or more of $R^w$, $R^x$, $R^y$, and $R^z$ is —NRC(O)R. In some embodiments, one or more of $R^w$, $R^x$, $R^y$, and $R^z$ is —NRC(O)N(R)$_2$. In some embodiments, one or more of $R^w$, $R^x$, $R^y$, and $R^z$ is —NRS(O)$_2$R. In some embodiments, one or more of $R^w$, $R^x$, $R^y$, and $R^z$ is —NP(O)R$_2$. In some embodiments, one or more of $R^w$, $R^x$, $R^y$, and $R^z$ is —NRP(O)(OR)$_2$. In some embodiments, one or more of $R^w$, $R^x$, $R^y$, and $R^z$ is —NRP(O)(OR)NR$_2$. In some embodiments, one or more of $R^w$, $R^x$, $R^y$, and $R^z$ is —NRP(O)(NR$_2$)$_2$. In some embodiments, one or more of $R^w$, $R^x$, $R^y$, and $R^z$ is —NRS(O)$_2$R. In some embodiments, two $R^w$ groups attached to the same carbon atom are taken together to form a 3-5 membered saturated or partially unsaturated carbocyclic spiro fused ring. In some embodiments, two $R^w$ groups attached to the same carbon atom are optionally taken together to form a 3-5 membered saturated or partially unsaturated heterocyclic spiro fused ring having 1-2 heteroatoms independently selected from nitrogen, oxygen, and sulfur.

In some embodiments, $R^w$ is fluoro. In some embodiments, $R^w$ is chloro. In some embodiments, $R^w$ is bromo. In some embodiments, $R^w$ is methyl. In some embodiments, $R^w$ is isopropyl. In some embodiments, $R^w$ is —CHF$_2$. In some embodiments, $R^w$ is —CF$_3$. In some embodiments, $R^w$ is —CH$_2$CHF$_2$. In some embodiments, $R^w$ is —CH$_2$CF$_3$. In some embodiments, $R^w$ is —CH(Me)CF$_3$. In some embodiments, $R^w$ is —CONH$_2$. In some embodiments, $R^w$ is

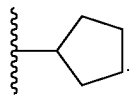

In some embodiments, $R^w$ is

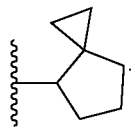

In some embodiments, $R^w$ is

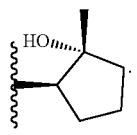

In some embodiments, two $R^w$ cyclize to form cyclopropylenyl.

In some embodiments, $R^x$ is bromo. In some embodiments, $R^x$ is —CF$_3$. In some embodiments, $R^x$ is —O—C$_{1-6}$ cycloalkyl. In some embodiments, $R^x$ is —O-cyclohexyl.

In some embodiments, $R^y$ is methyl.

In some embodiments, $R^w$, $R^x$, $R^y$, and $R^z$ are selected from those depicted in Table 1, below.

As defined generally above, each R is independently hydrogen, or an optionally substituted group selected from C$_{1-6}$ aliphatic, phenyl, a 4-7 membered saturated or partially unsaturated carbocyclic or heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same nitrogen are optionally taken together with their intervening atoms to form a 4-7 membered saturated, partially unsaturated, or heteroaryl ring having 0-3 heteroatoms, in addition to the nitrogen atom to which they are attached, independently selected from nitrogen, oxygen, and sulfur.

In some embodiments, R is hydrogen. In some embodiments, R is an optionally substituted C$_{1-6}$ aliphatic. In some embodiments, R is C$_{1-6}$ alkyl (e.g., methyl, ethyl, isopropyl, etc.). In some embodiments, R is C$_{1-6}$ haloalkyl (e.g., —CF$_3$, CHF$_2$, etc.). In some embodiments, R is an optionally substituted phenyl. In some embodiments, R is an optionally substituted 3-7 membered saturated or partially unsaturated carbocyclic ring. In some embodiments, R is an optionally substituted a 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen atom to which they are attached, independently selected from nitrogen, oxygen, and sulfur.

In some embodiments, R is selected from those depicted in Table 1, below.

As defined generally above, L$^x$ and L$^y$ are independently a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —CF$_2$—, —CRF—, —NR—, —S—, —S(O)—, —S(O)$_2$— or —CR═CR—.

In some embodiments, L$^x$ is a covalent bond. In some embodiments, L$^x$ is a C$_{1-3}$ bivalent straight or branched saturated or unsaturated hydrocarbon chain wherein 1-2 methylene units of the chain are independently and optionally replaced with —O—, —C(O)—, —C(S)—, —CF$_2$—, —CRF—, —NR—, —S—, —S(O)—, —S(O)$_2$— or —CR═CR—.

In some embodiments, L$^y$ is a covalent bond. In some embodiments, L$^y$ is a C$_{1-3}$ bivalent straight or branched saturated or unsaturated hydrocarbon chain wherein 1-2 methylene units of the chain are independently and optionally replaced with —O—, —C(O)—, —C(S)—, —CF$_2$—, —CRF—, —NR—, —S—, —S(O)—, —S(O)$_2$— or —CR═CR—.

In some embodiments, L$^x$ is a —C(O)—. In some embodiments, L$^x$ is a —S(O)$_2$—.

In some embodiments, L$^y$ is a —C(O)—.

In some embodiments, L$^x$ and L are selected from those depicted in Table 1, below.

As defined generally above, v is 0 or 1.

In some embodiments, v is 0. In some embodiments, v is 1.

In some embodiments, v is selected from those depicted in Table 1, below.

As defined generally above, w, x, y, and z are independently 0, 1, 2, 3, or 4.

In some embodiments, one or more of w, x, y, and z is 0. In some embodiments, one or more of w, x, y, and z is 1. In some embodiments, one or more of w, x, y, and z is 2. In some embodiments, one or more of w, x, y, and z is 3. In some embodiments, one or more of w, x, y, and z is 4.

In some embodiments, w, x, y, and z are selected from those depicted in Table 1, below.

In some embodiments, CBM is

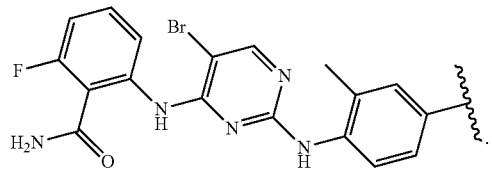 [SMILES: *c1ccc(Nc2ncc(Br)c(Nc3cccc(F)c3C(N)=O)n2)c(C)c1]

In some embodiments, CBM is

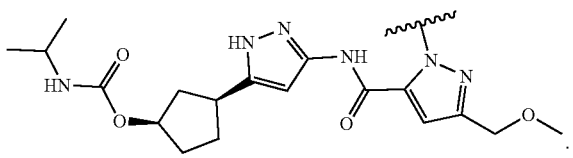 [SMILES: *n1nc(COC)cc1C(=O)Nc1cc([C@H]2CC[C@@H](OC(=O)NC(C)C)C2)[nH]n1]

In some embodiments, CBM is

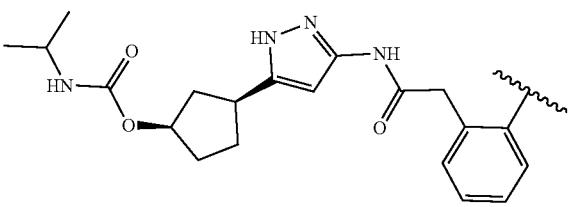 [SMILES: *c1ccccc1CC(=O)Nc1cc([C@H]2CC[C@@H](OC(=O)NC(C)C)C2)[nH]n1]

In some embodiments, CBM is

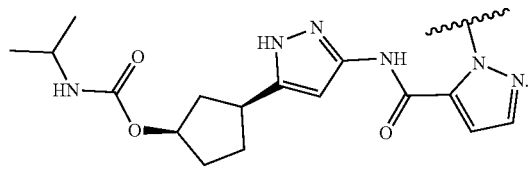 [SMILES: *n1nccc1C(=O)Nc1cc([C@H]2CC[C@@H](OC(=O)NC(C)C)C2)[nH]n1]

In some embodiments, CBM is

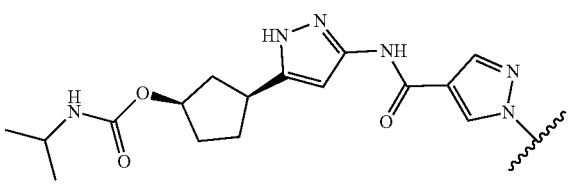 [SMILES: *n1cc(C(=O)Nc2cc([C@H]3CC[C@@H](OC(=O)NC(C)C)C3)[nH]n2)cn1]

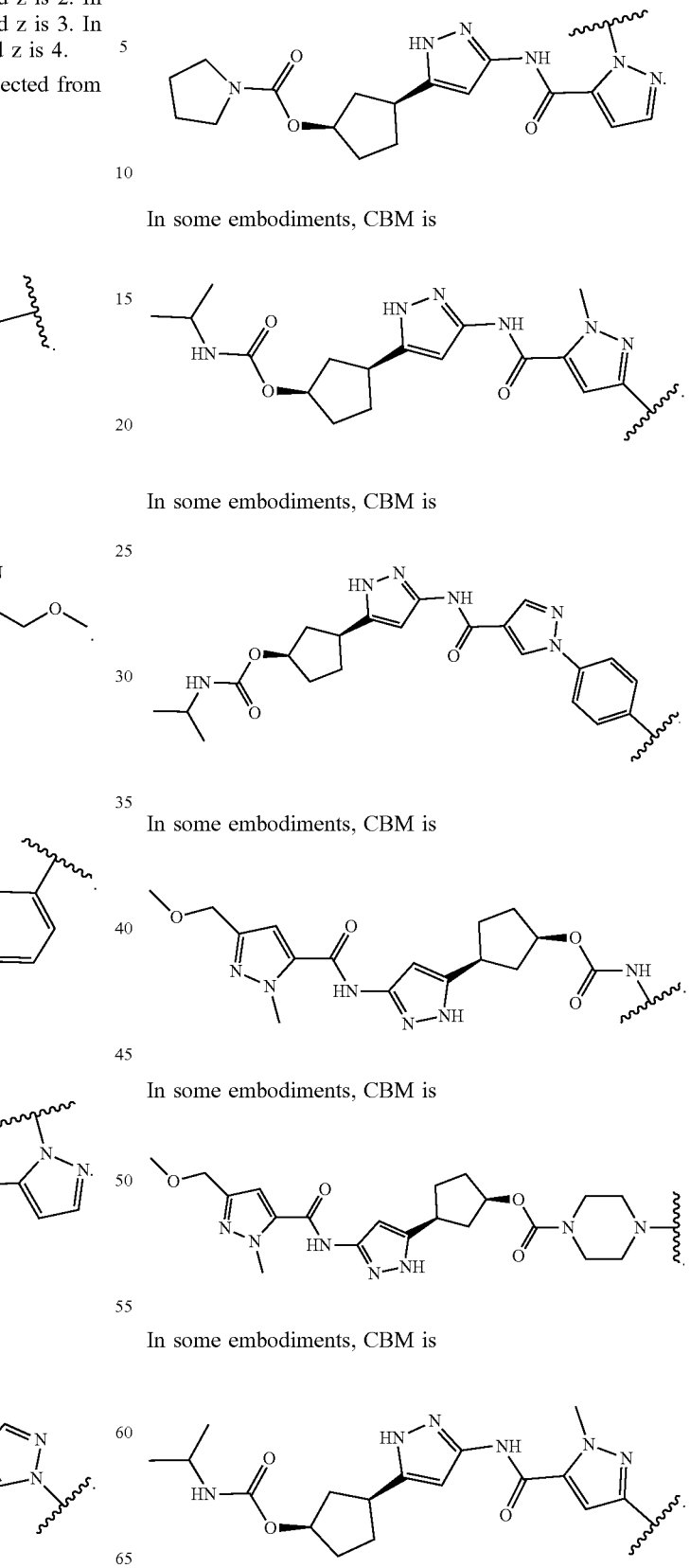

In some embodiments, CBM is
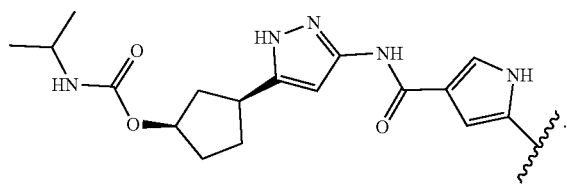 [SMILES: *c1cc(C(=O)Nc2cc([C@H]3CC[C@@H](OC(=O)NC(C)C)C3)[nH]n2)c[nH]1]
In some embodiments, CBM is
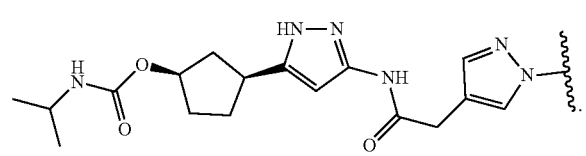 [SMILES: *n1cc(CC(=O)Nc2cc([C@H]3CC[C@@H](OC(=O)NC(C)C)C3)[nH]n2)cn1]
In some embodiments, CBM is
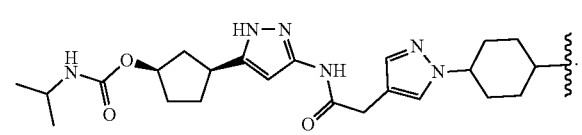 [SMILES: *C1CCC(n2cc(CC(=O)Nc3cc([C@H]4CC[C@@H](OC(=O)NC(C)C)C4)[nH]n3)cn2)CC1]
In some embodiments, CBM is
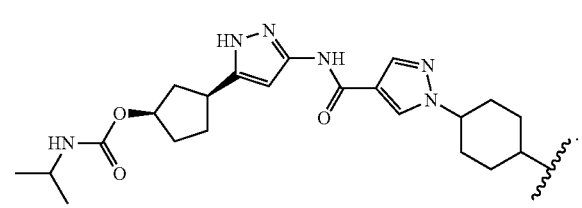 [SMILES: *C1CCC(n2cc(C(=O)Nc3cc([C@H]4CC[C@@H](OC(=O)NC(C)C)C4)[nH]n3)cn2)CC1]
In some embodiments, CBM is
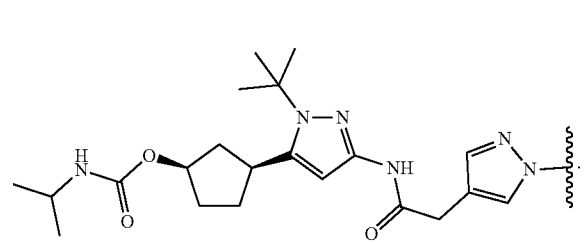 [SMILES: *n1cc(CC(=O)Nc2cc([C@H]3CC[C@@H](OC(=O)NC(C)C)C3)n(C(C)(C)C)n2)cn1]
In some embodiments, CBM is
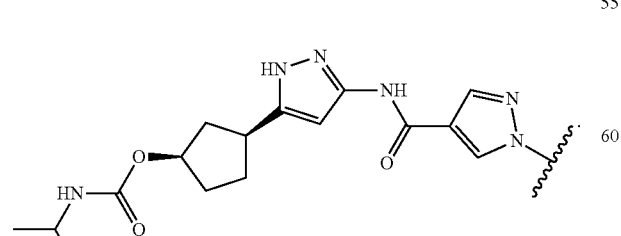
In some embodiments, CBM is
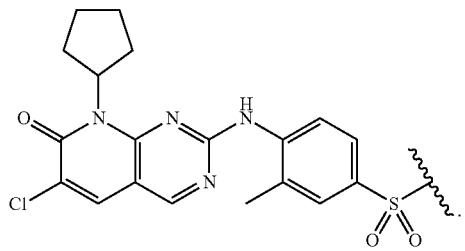 [SMILES: *S(=O)(=O)c1ccc(Nc2ncc3cc(Cl)c(=O)n(C4CCCC4)c3n2)c(C)c1]
In some embodiments, CBM is
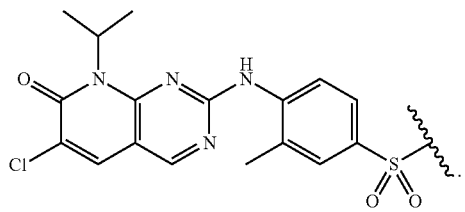 [SMILES: *S(=O)(=O)c1ccc(Nc2ncc3cc(Cl)c(=O)n(C(C)C)c3n2)c(C)c1]
In some embodiments, CBM is
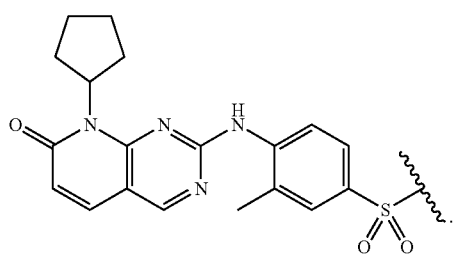 [SMILES: *S(=O)(=O)c1ccc(Nc2ncc3ccc(=O)n(C4CCCC4)c3n2)c(C)c1]
In some embodiments, CBM is
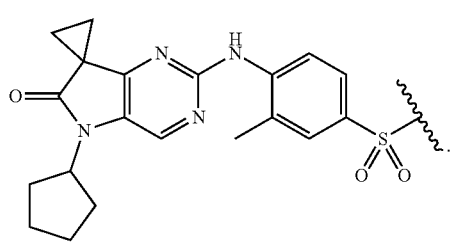 [SMILES: *S(=O)(=O)c1ccc(Nc2ncc3c(n2)C2(CC2)C(=O)N3C2CCCC2)c(C)c1]
In some embodiments, CBM is
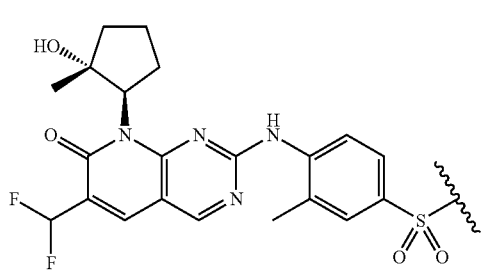

In some embodiments, CBM is
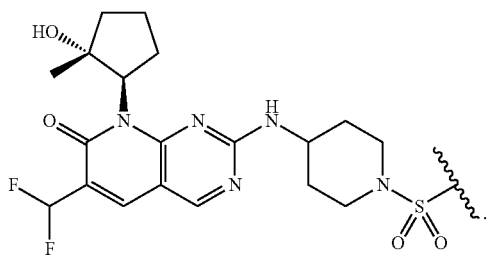 [SMILES: *S(=O)(=O)N1CCC(Nc2ncc3cc(C(F)F)c(=O)n([C@@H]4CCC[C@@]4(C)O)c3n2)CC1]
In some embodiments, CBM is
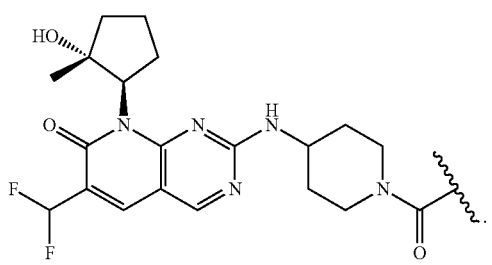 [SMILES: *C(=O)N1CCC(Nc2ncc3cc(C(F)F)c(=O)n([C@@H]4CCC[C@@]4(C)O)c3n2)CC1]
In some embodiments, CBM is
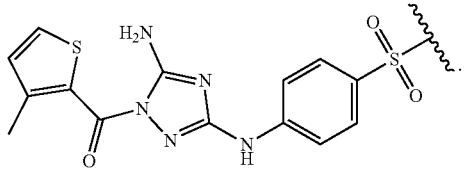 [SMILES: *S(=O)(=O)c1ccc(Nc2nc(N)n(C(=O)c3sccc3C)n2)cc1]
In some embodiments, CBM is
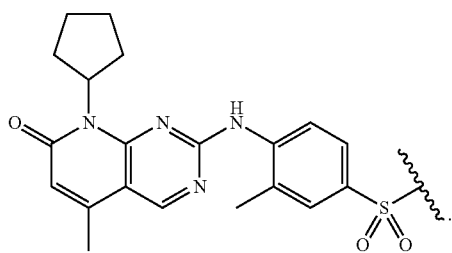 [SMILES: *S(=O)(=O)c1ccc(Nc2ncc3c(C)cc(=O)n(C4CCCC4)c3n2)c(C)c1]
In some embodiments, CBM is
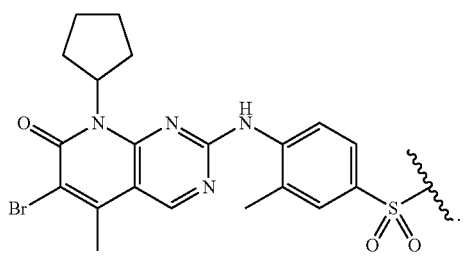
In some embodiments, CBM is
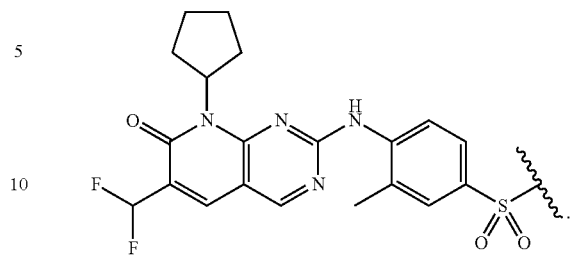
In some embodiments, CBM is

In some embodiments, CBM is
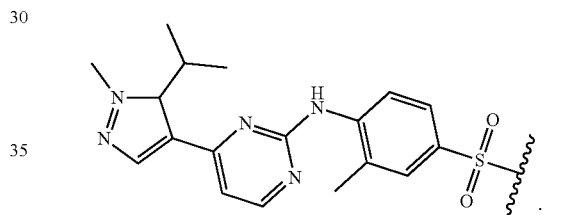
In some embodiments, CBM is
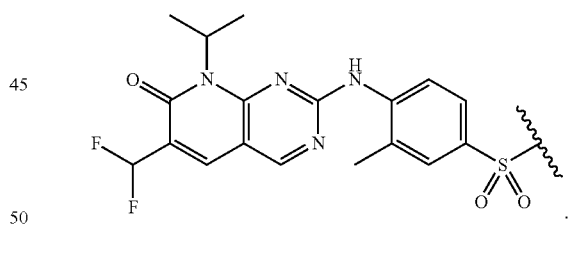
In some embodiments, CBM is
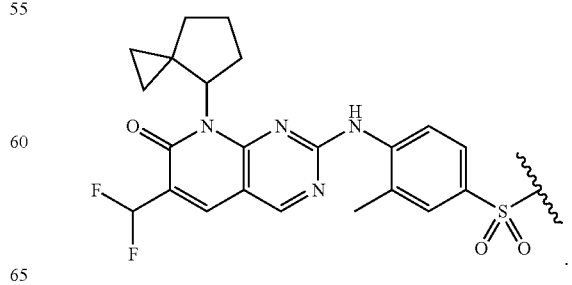

In some embodiments, CBM is

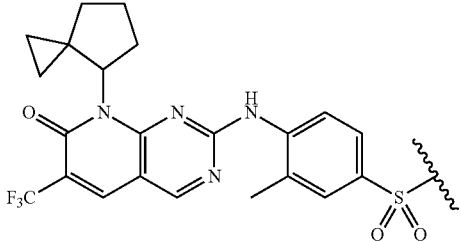

In some embodiments, CBM is

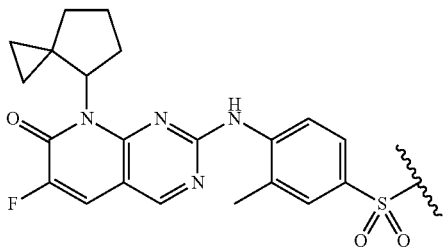

In some embodiments, CBM is

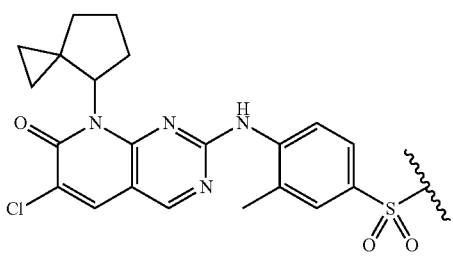

In some embodiments, CBM is

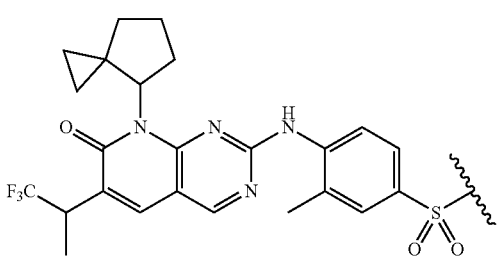

In some embodiments, CBM is

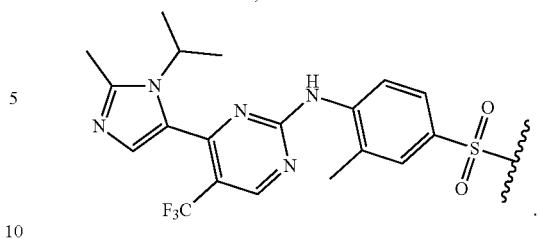

In some embodiments, CBM is

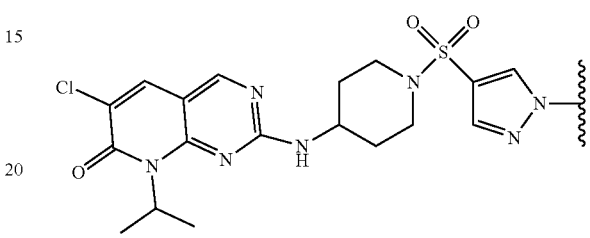

In some embodiments, CBM is

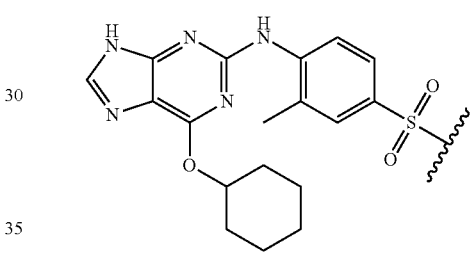

In some embodiments, CBM is

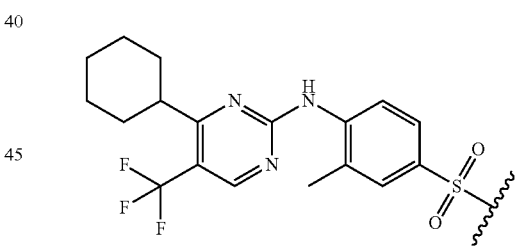

In certain embodiments, the present invention provides a compound of formula I, wherein CBM is a CDK2 binding moiety thereby forming a compound of formula I-e-1:

I-e-1

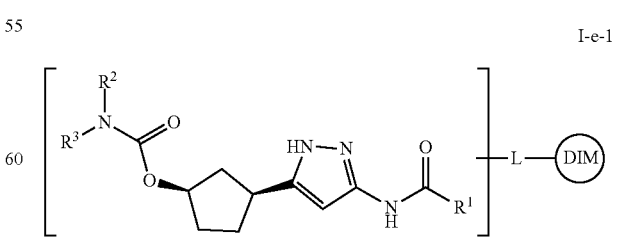

or a pharmaceutically acceptable salt thereof, wherein L and DIM are as defined above and described in embodiments herein, and wherein each of the variables $R^1$, $R^2$, and $R^3$ is as defined and described in WO 2020/157652 and US 2020/247784, the entirety of each of which is herein incorporated by reference.

In certain embodiments, the present invention provides a compound of formula I, wherein CBM is a CDK2 binding moiety thereby forming a compound of formula I-e-2:

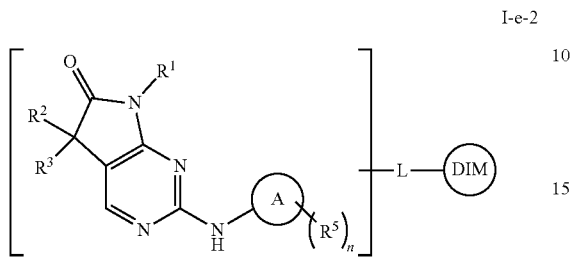

I-e-2 or a pharmaceutically acceptable salt thereof, wherein L and DIM are as defined above and described in embodiments herein, and wherein each of the variables $R^1$, $R^2$, $R^3$, $R^5$, Ring A, and n is as defined and described in WO 2020/168197 and US 2020/392139, the entirety of each of which is herein incorporated by reference.

In certain embodiments, the present invention provides a compound of formula I, wherein CBM is a CDK2 binding moiety thereby forming a compound of formula I-e-3:

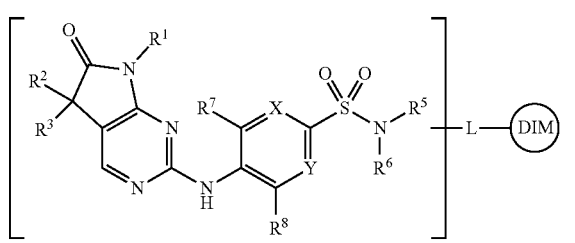

I-e-3 or a pharmaceutically acceptable salt thereof, wherein L and DIM are as defined above and described in embodiments herein, and wherein each of the variables $R^1$, $R^2$, $R^3$, $R^4$, $R^5$, $R^6$, $R^7$, $R^8$, X, and Y is as defined and described in WO 2020/205560 and US 2020/399273, the entirety of each of which is herein incorporated by reference.

In certain embodiments, the present invention provides a compound of formula I, wherein CBM is a CDK2/4/6 binding moiety thereby forming a compound of formula I-e-4:

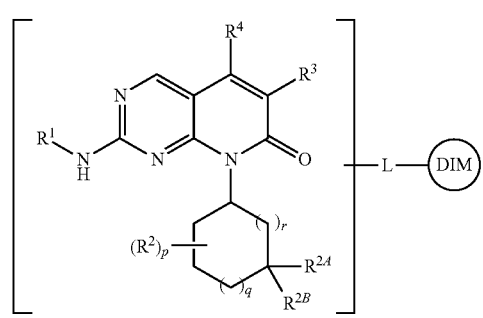

I-e-4 or a pharmaceutically acceptable salt thereof, wherein L and DIM are as defined above and described in embodiments herein, and wherein each of the variables $R^1$, $R^2$, $R^{2A}$, $R^{2B}$, $R^3$, $R^4$, p, q, and r is as defined and described in WO 2018/033815 and U.S. Pat. No. 10,233,188, the entirety of each of which is herein incorporated by reference.

In certain embodiments, the present invention provides a compound of formula I, wherein CBM is a CDK2 binding moiety thereby forming a compound of formula I-e-5:

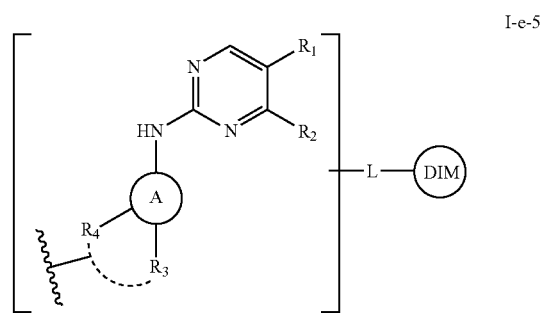

I-e-5 or a pharmaceutically acceptable salt thereof, wherein L and DIM are as defined above and described in embodiments herein, and wherein each of the variables $R^1$, $R^2$, $R^3$, $R^4$ and Ring A is as defined and described in WO 2020/206137, the entirety of each of which is herein incorporated by reference.

In certain embodiments, the present invention provides a compound of formula I, wherein CBM is a CDK2 binding moiety thereby forming a compound of formula I-e-6:

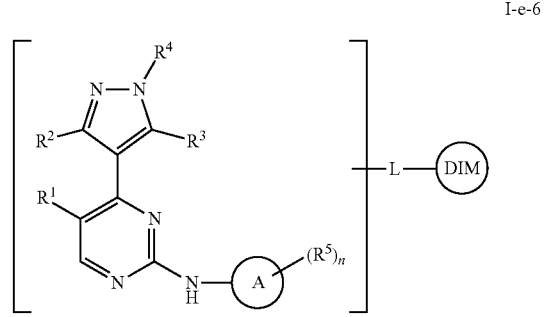

I-e-6 or a pharmaceutically acceptable salt thereof, wherein L and DIM are as defined above and described in embodiments herein, and wherein each of the variables $R^1$, $R^2$, $R^3$, $R^4$, $R^5$, n and Ring A is as defined and described in WO 2020/180959 and US 2021/017156, the entirety of each of which is herein incorporated by reference.

In certain embodiments, the present invention provides a compound of formula I, wherein CBM is a CDK2 binding moiety thereby forming a compound of formula I-e-7:

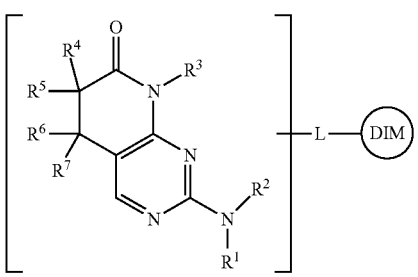

or a pharmaceutically acceptable salt thereof, wherein L and DIM are as defined above and described in embodiments herein, and wherein each of the variables $R^1$, $R^2$, $R^3$, $R^4$, $R^5$, $R^6$, and $R^7$ is as defined and described in WO 2020/168178 and US 2020/316064, the entirety of each of which is herein incorporated by reference.

In certain embodiments, the present invention provides a compound of formula I, wherein CBM is a CDK2 binding moiety thereby forming a compound of formula I-e-8:

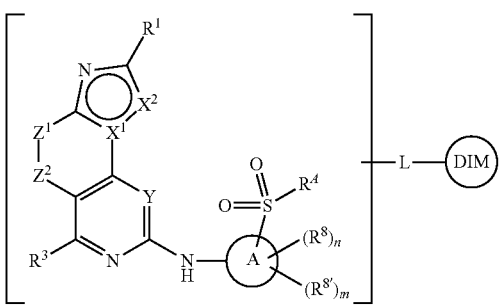

or a pharmaceutically acceptable salt thereof, wherein L and DIM are as defined above and described in embodiments herein, and wherein each of the variables $R^1$, $R^3$, $R^8$, $R^{8'}$, $R^4$, $X^1$, Y, $Z^1$, $Z^2$, n, m, and Ring A is as defined and described in WO 2020/223558 and US 2020/347066, the entirety of each of which is herein incorporated by reference.

In certain embodiments, the present invention provides a compound of formula I, wherein CBM is a CDK2 binding moiety thereby forming a compound of formula I-e-9:

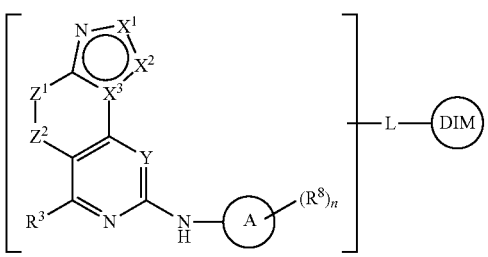

or a pharmaceutically acceptable salt thereof, wherein L and DIM are as defined above and described in embodiments herein, and wherein each of the variables $R^3$, $R^8$, $X^1$, $X^2$, $X^3$, Y, $Z^1$, $Z^2$, n, and Ring A is as defined and described in WO 2020/223469 and US 2020/347067, the entirety of each of which is herein incorporated by reference.

In certain embodiments, the present invention provides a compound of formula I, wherein CBM is a CDK2 binding moiety thereby forming a compound of formula I-e-10:

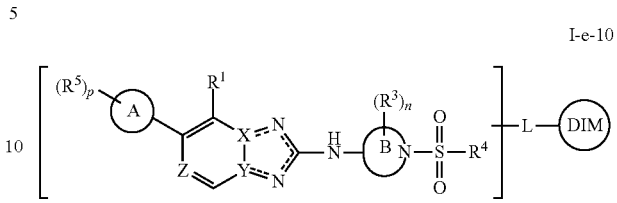

or a pharmaceutically acceptable salt thereof, wherein L and DIM are as defined above and described in embodiments herein, and wherein each of the variables $R^1$, $R^2$, $R^4$, $R^5$, Ring A, Ring B, X, Y, Z, n, and p is as defined and described in WO 2021/072232, the entirety of each of which is herein incorporated by reference.

In certain embodiments, the present invention provides a compound of formula I, wherein CBM is a CDK2 binding moiety selected from any one of formula I, II, III, IV, V, VI, VII, VIII, IX, X, XI, XII, XIII, XIV, XV, XVI, XVII, XVIII, XIX, XX, XX1, XXII, XXIII, and XXIV, or a pharmaceutically acceptable salt thereof, wherein L and DIM are as defined above and described in embodiments herein, and wherein each of the variables $R^1$, $R^3$, $R^{11}$, $R^{14}$, $R^{16}$, $R^{17}$, $R^{18}$, $R^{19}$, $R^{20}$, $R^{31}$, $R^{32}$, $R^{32*}$, $R^x$, $X^1$, $X^2$, $X^3$, $X^4$, $X^5$, $X^6$, $X^7$, $X^8$, $X^9$, $X^{10}$, y and y2 as defined and described in WO 2020/206034, the entirety of each of which is herein incorporated by reference.

Ligase Binding Moiety (LBM)

In some embodiments, DIM is LBM. In some embodiments, LBM is an E3 ligase ligand well known to one of ordinary skill in the art including those described in M. Toure, C. M. Crews, *Angew. Chem. Int. Ed.* 2016, 55, 1966, T. Uehara et al. *Nature Chemical Biology* 2017, 13, 675, WO 2017/176708, US 2017/0281784, WO 2017/161119, WO 2017/176957, WO 2017/176958, WO 2015/160845, US 2015/0291562, WO 2016/197032, WO 2016/105518, US 2018/0009779, WO 2017/007612, 2018/0134684, WO 2013/106643, US 2014/0356322, WO 2002/020740, US 2002/0068063, WO 2012/078559, US 2014/0302523, WO 2012/003281, US 2013/0190340, US 2016/0022642, WO 2014/063061, US 2015/0274738, WO 2016/118666, US 2016/0214972, WO 2016/149668, US 2016/0272639, WO 2016/169989, US 2018/0118733, WO 2016/197114, US 2018/0147202, WO 2017/011371, US 2017/0008904, WO 2017/011590, US 2017/0037004, WO 2017/079267, US 2017/0121321, WO 2017/117473, WO 2017/117474, WO 2013/106646, WO 2014/108452, WO 2017/197036, US 2019/0076540, WO 2017/197046, US 2019/0076542, WO 2017/197051, US 2019/0076539, WO 2017/197055, US 2019/0076541, and WO 2017/197056, the entirety of each of which is herein incorporated by reference.

As defined herein and described below, wherein a formula is depicted using square brackets, e.g.,

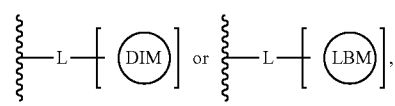

L is attached to a modifiable carbon, oxygen, or nitrogen atom within DIM or LBM including substitution or replacement of a defined group in DIM or LBM.

In certain embodiments, the present invention provides a compound of formula I, wherein LBM is a cereblon E3 ubiquitin ligase binding moiety thereby forming a compound of formula I-aa:

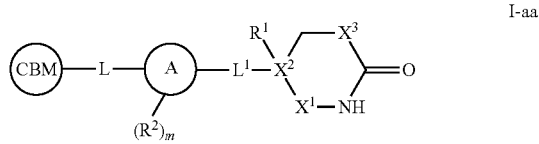

I-aa or a pharmaceutically acceptable salt thereof, wherein L and CBM are as defined above and described herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

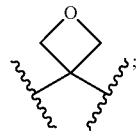 [SMILES: *C1(*)COC1]

$X^2$ is a carbon atom or silicon atom;
$X^3$ is a bivalent moiety selected from —CR$_2$—, —NR—, —O—, —S—, or —Si(R$^2$)—;
$R^1$ is hydrogen, halogen, —CN, —OR, —SR, —S(O)R, —S(O)$_2$R, —N(R)$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;
each $R^2$ is independently hydrogen, —R, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;
Ring A is a bi- or tricyclic ring selected from

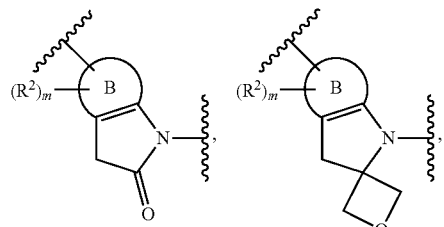

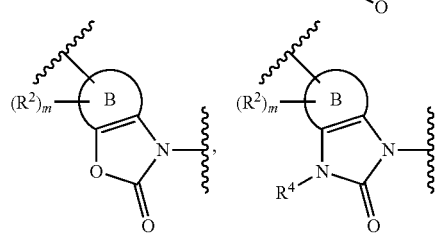

-continued

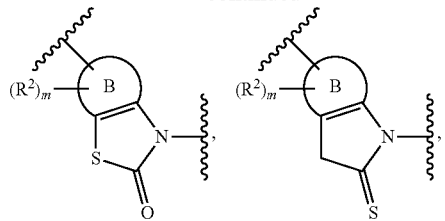

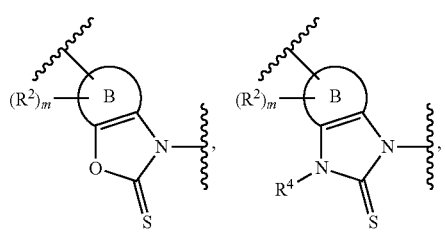

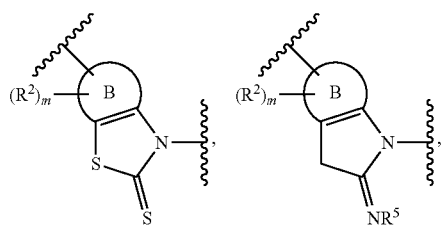

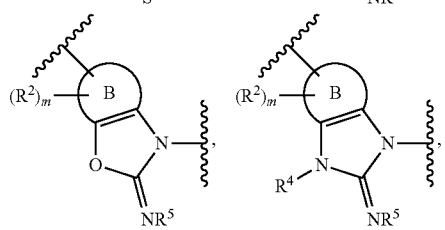

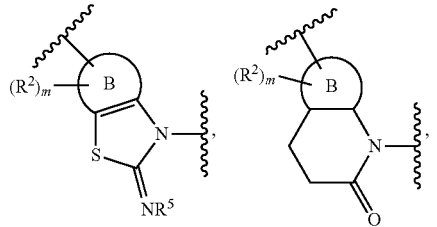

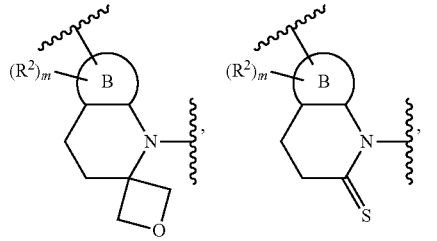

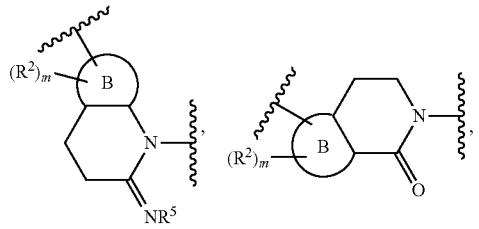

-continued

-continued

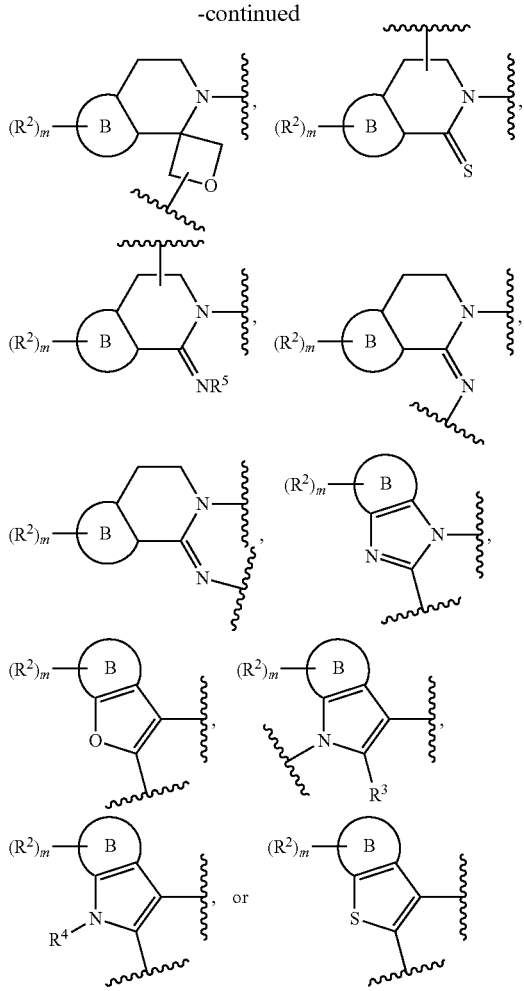

wherein
Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

m is 0, 1, 2, 3 or 4;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_m$ is depicted on Ring B, it is intended, and one of ordinary skill in the art would appreciate, that the point of attachment of —(R$^2$)$_m$ may be on Ring A and may also be at any available carbon or nitrogen atom on Ring A including the ring to which Ring B is fused. Where —R$^2$ is attached to a nitrogen atom bound to $R^4$ or R, $R^4$ or $R^5$ is absent and —R$^2$ takes the place of the $R^4$ or $R^5$ group. Where —R$^2$ is attached to a carbon atom bound to $R^3$, $R^3$ is absent and —R$^2$ takes the place of the $R^3$ group.

In some embodiments, a compound of formula I-aa above is provided as a compound of formula I-aa' or formula I-aa":

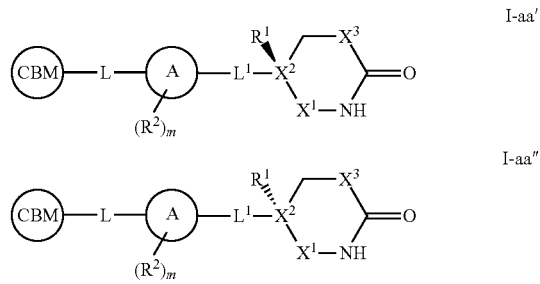

or a pharmaceutically acceptable salt thereof, wherein:
each of CBM, Ring A, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-cc:

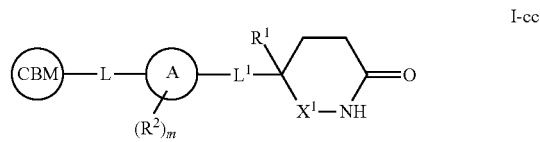

or a pharmaceutically acceptable salt thereof, wherein L and CBM are as defined above and described in embodiments herein, and wherein:

$X^1$ is a bivalent moiety selected from a covalent bond, —CH$_2$—, —C(O)—, —C(S)—, or

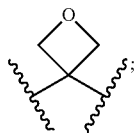 [SMILES: *C1(*)COC1]
R[1] is hydrogen, halogen, —CN, —OR, —SR, —S(O)R, —S(O)$_2$R, —NR$_2$, or an optionally substituted C$_{1-4}$ aliphatic;
each R[2] is independently hydrogen, —R, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
Ring A is a bi- or tricyclic ring selected from
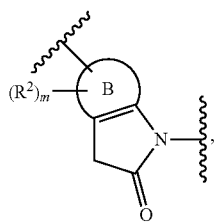 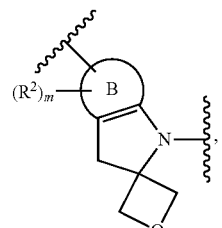
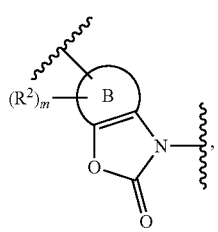 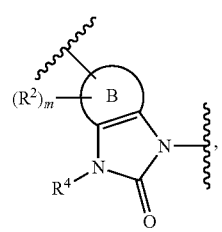
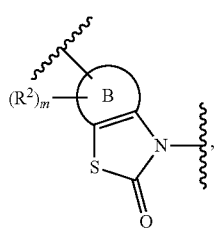 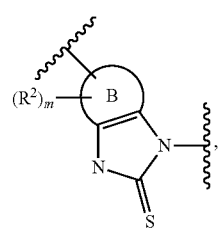
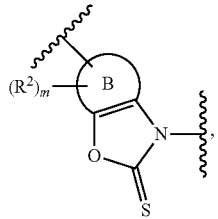 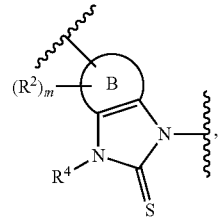
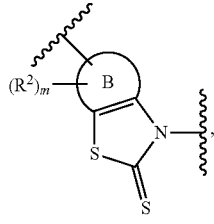 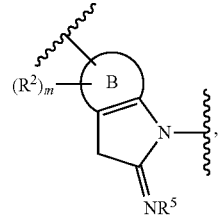
-continued
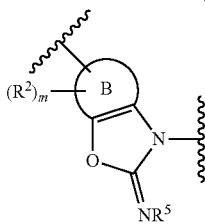 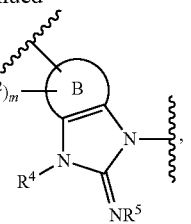
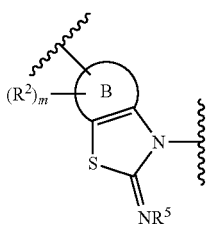 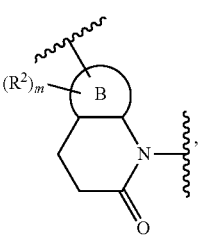
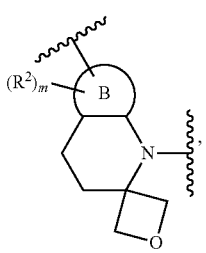 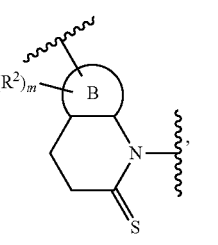
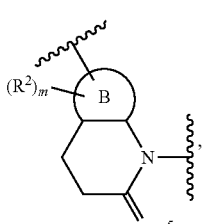 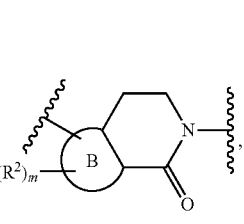
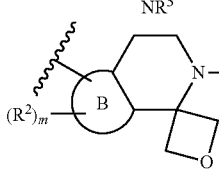 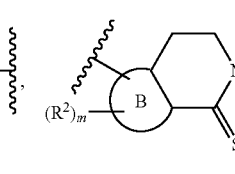
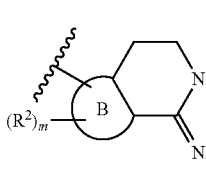 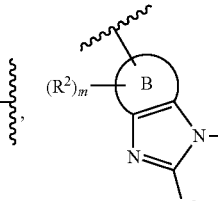
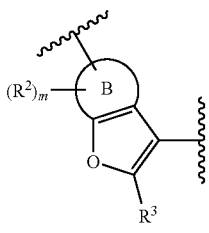 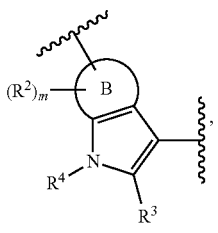

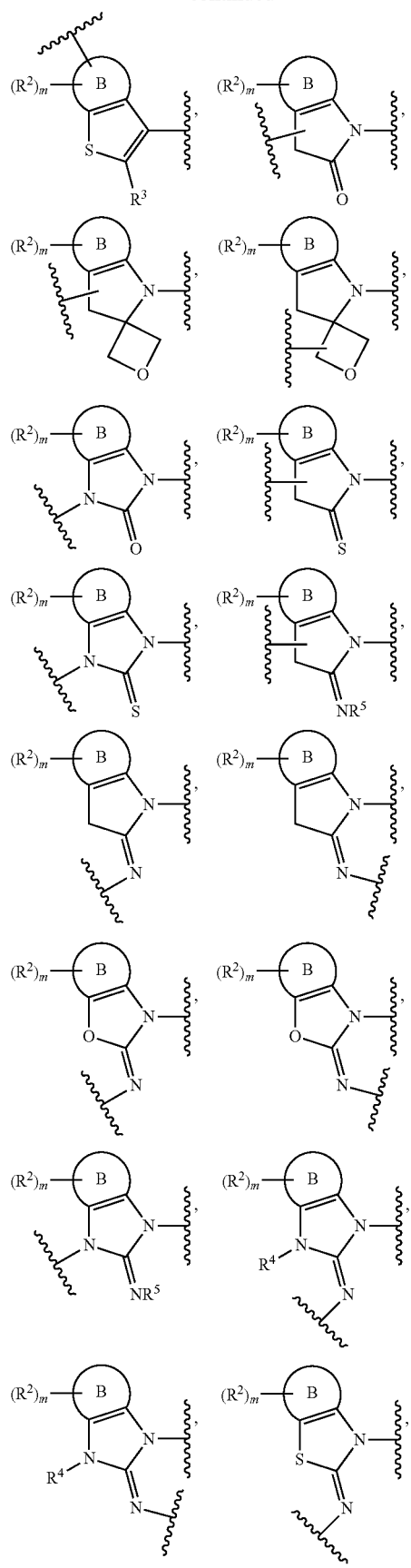
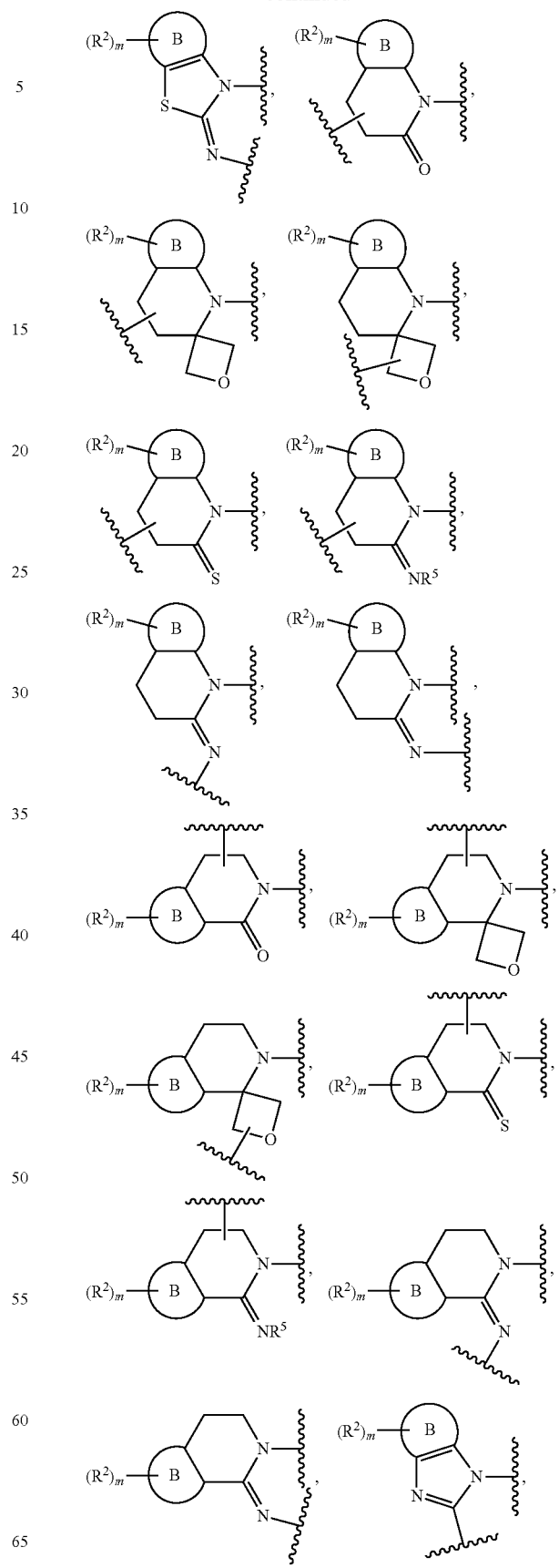

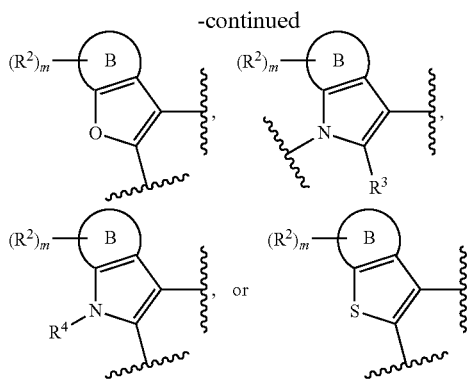

wherein
Ring B is a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —R, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_m$ is depicted on Ring B, it is intended, and one of ordinary skill in the art would appreciate, that the point of attachment of —(R$^2$)$_m$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R group.

In some embodiments, the compound of formula I-cc above is provided as a compound of formula I-cc' or formula I-cc":

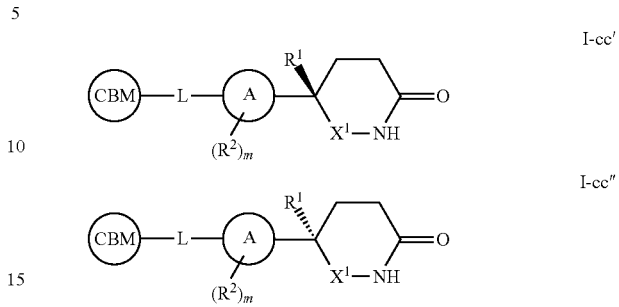

or a pharmaceutically acceptable salt thereof, wherein:
each of CBM, Ring A, L, R$^1$, R$^2$, X$^1$, and m is as defined above.

In certain embodiments, the present invention provides a compound of formula I, wherein LBM is an E3 ubiquitin ligase (cereblon) binding moiety thereby forming a compound of formula I-dd:

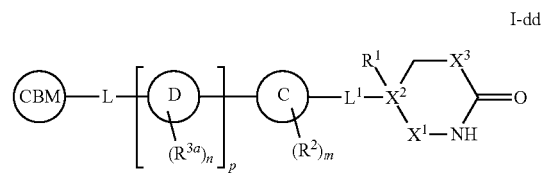

or a pharmaceutically acceptable salt thereof, wherein, L and CBM are as defined above and described in embodiments herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

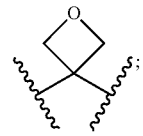

$X^2$ is a carbon atom or silicon atom;
$X^3$ is a bivalent moiety selected from —CR$_2$—, —NR—, —O—, —S—, or —Si(R$^2$)—;
$R^1$ is hydrogen, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted $C_{1-4}$ aliphatic;
Ring C is a mono- or bicyclic ring selected from

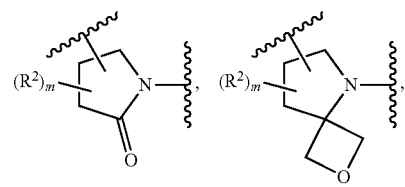

-continued
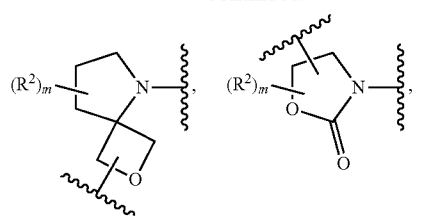
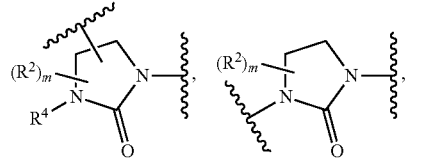
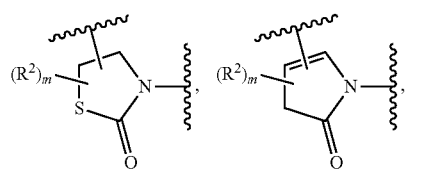
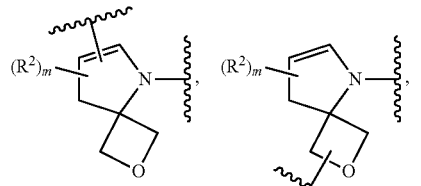
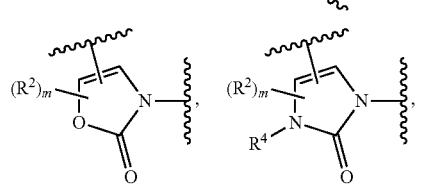
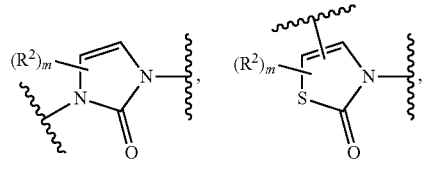
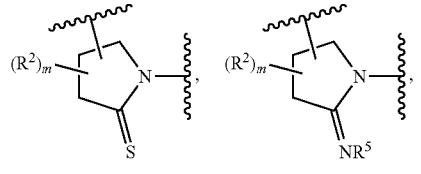
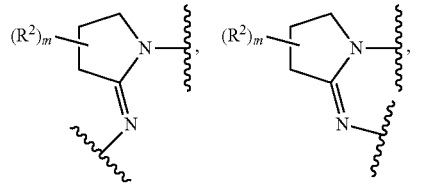
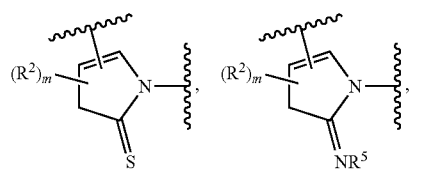
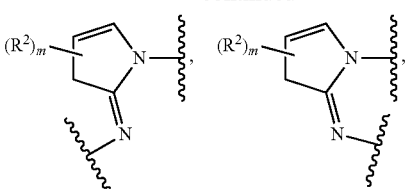
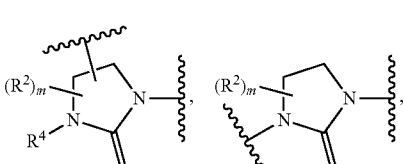
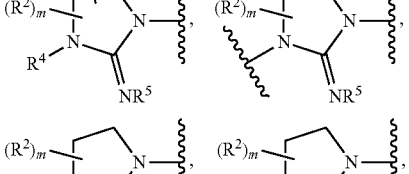
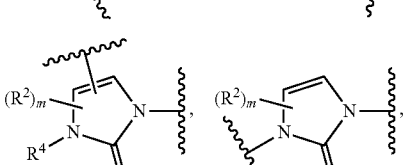
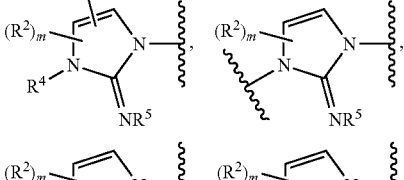
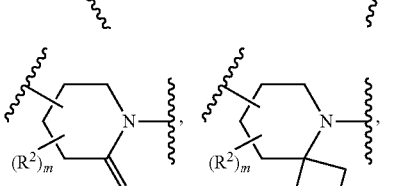
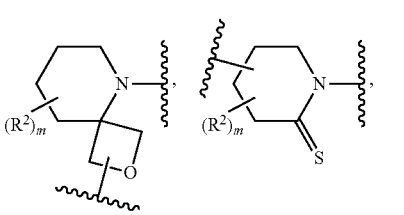

-continued

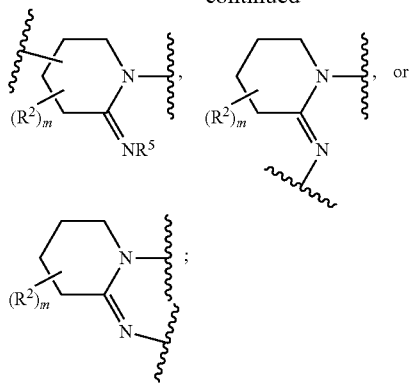

each of $R^2$ and $R^{3a}$ is independently hydrogen, —$R^6$, halogen, —CN, —$NO_2$, —OR, —SR, —$N(R)_2$, —$Si(R)_3$, —$S(O)_2R$, —$S(O)_2N(R)_2$, —$S(O)R$, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —N(R)P(O)(OR)(NR_2), —$N(R)P(O)(NR_2)_2$, or —$N(R)S(O)_2R$;

Ring D is selected from a 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)=CH—;

m is 0, 1, 2, 3 or 4;
n is 0, 1, 2, 3 or 4;
p is 0 or 1, wherein when p is 0, the bond connecting Ring C and Ring D is connected to

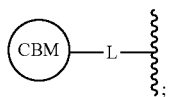

and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-dd above is provided as a compound of formula I-dd' or formula I-dd":

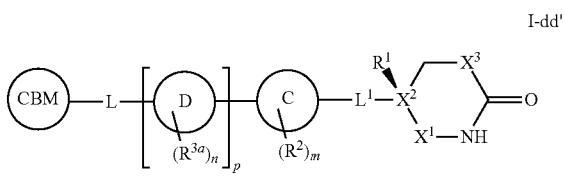

I-dd'

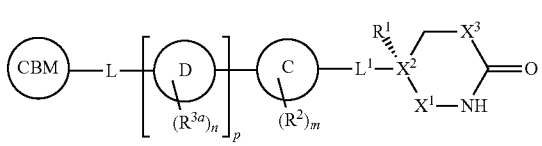

I-dd"

or a pharmaceutically acceptable salt thereof, wherein:
each of CBM, Ring C, Ring D, L, $L^1$, $R^1$, $R^2$, $R^{3a}$, $X^1$, $X^2$, $X^3$, n, m, and p is as defined above.

In certain embodiments, the present invention provides a compound of Formula I, wherein LBM is an E3 ubiquitin ligase (cereblon) binding moiety thereby forming a compound of formula I-ee:

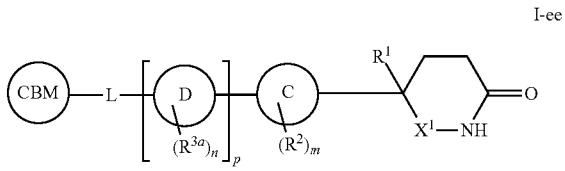

I-ee or a pharmaceutically acceptable salt thereof, wherein L and CBM are as defined above and described in embodiments herein, and wherein:

$X^1$ is a bivalent moiety selected from a covalent bond, —$CH_2$—, —C(O)—, —C(S)—, or

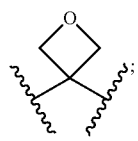

$R^1$ is hydrogen, halogen, —CN, —OR, —SR, —S(O)R, —$S(O)_2R$, —$NR_2$, or an optionally substituted $C_{1-4}$ aliphatic;

Ring C is a mono- or bicyclic ring selected from
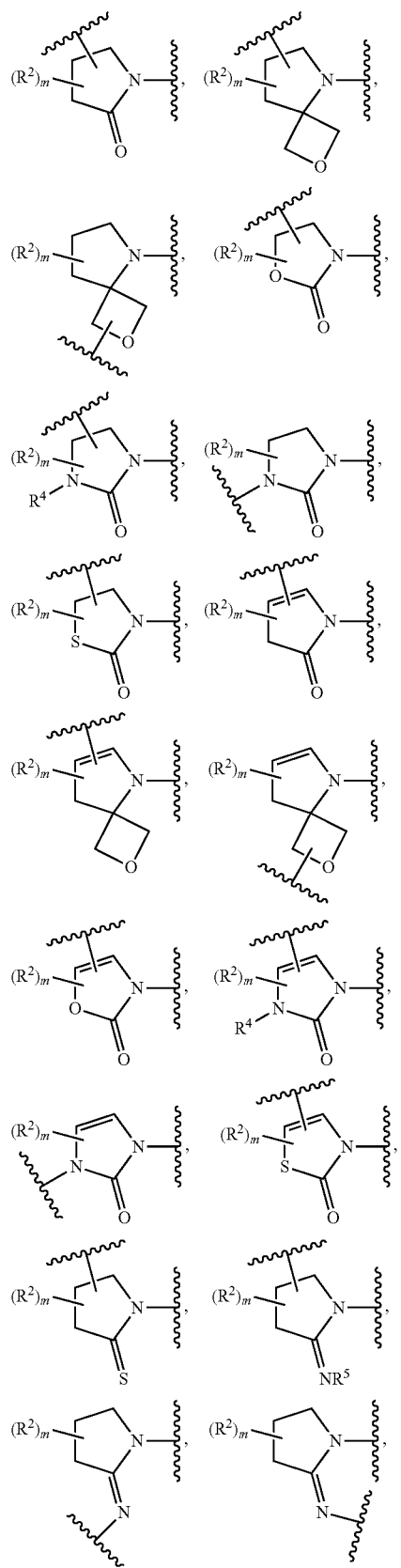
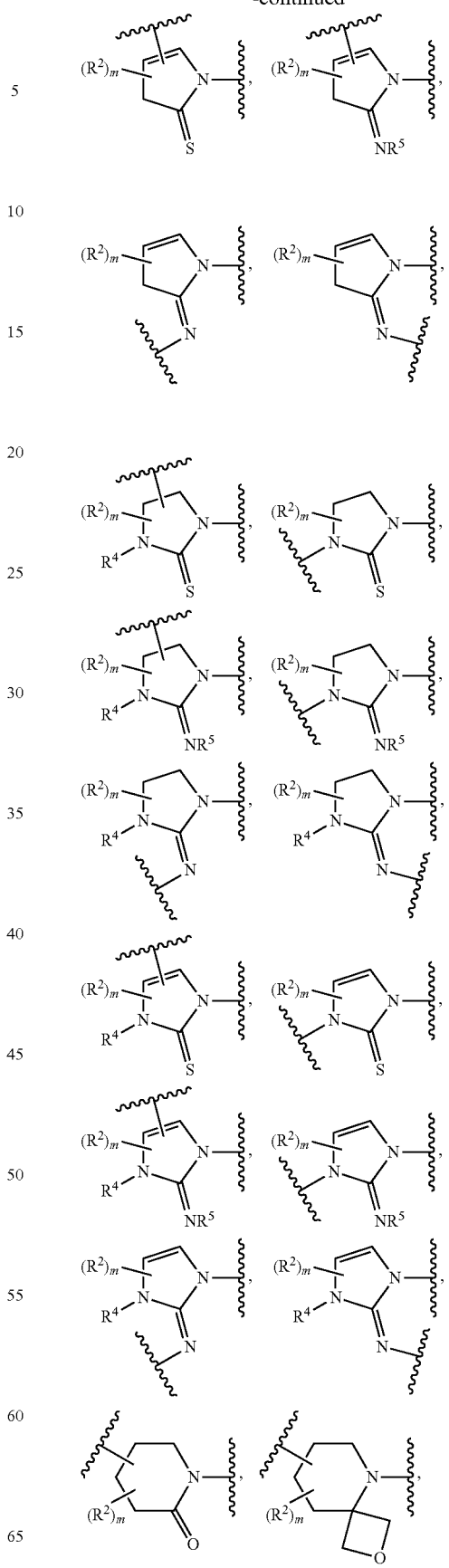
-continued

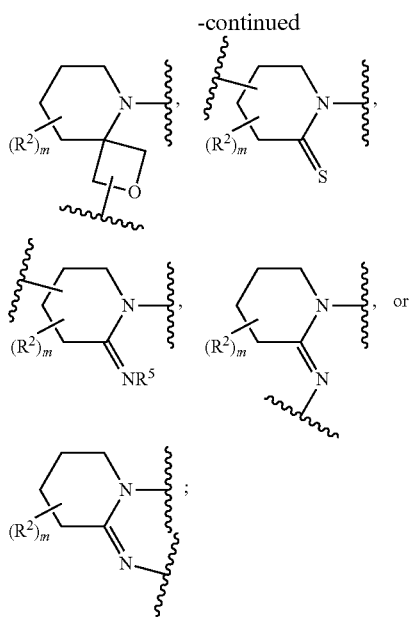

each of $R^2$ and $R^{3a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —OC(O)$NR_2$, —N(R)C(O)OR, —N(R)C(O)R, —N(R)C(O)$NR_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —OC(O)$NR_2$, —N(R)C(O)OR, —N(R)C(O)R, —N(R)C(O)$NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3 or 4;

p is 0 or 1, wherein when p is 0, the bond connecting Ring C and Ring D is connected to

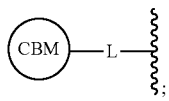

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-ee above is provided as a compound of formula I-ee' or formula I-ee":

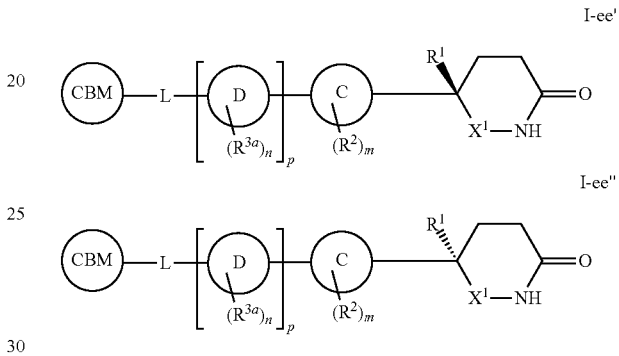

or a pharmaceutically acceptable salt thereof, wherein:
each of CBM, Ring C, Ring D, L, $R^1$, $R^2$, $R^{3a}$, $X^1$, n, m, and p is as defined above.

In certain embodiments, the present invention provides a compound of formula I, wherein LBM is an E3 ubiquitin ligase (cereblon) binding moiety thereby forming a compound of formula I-ff:

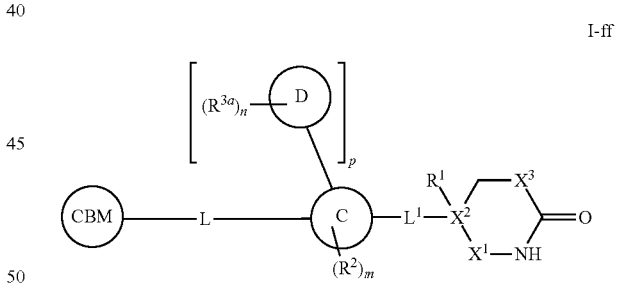

or a pharmaceutically acceptable salt thereof, wherein L and CBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

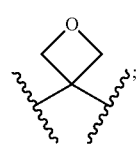

$X^2$ is a carbon atom or silicon atom;
$X^3$ is a bivalent moiety selected from —$CR_2$—, —NR—, —O—, —S—, or —$Si(R^2)$—;
$R^1$ is hydrogen, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)(R)_2$, —$Si(R)_3$, or an optionally substituted $C_{1-4}$ aliphatic;
Ring C is a mono- or bicyclic ring selected from
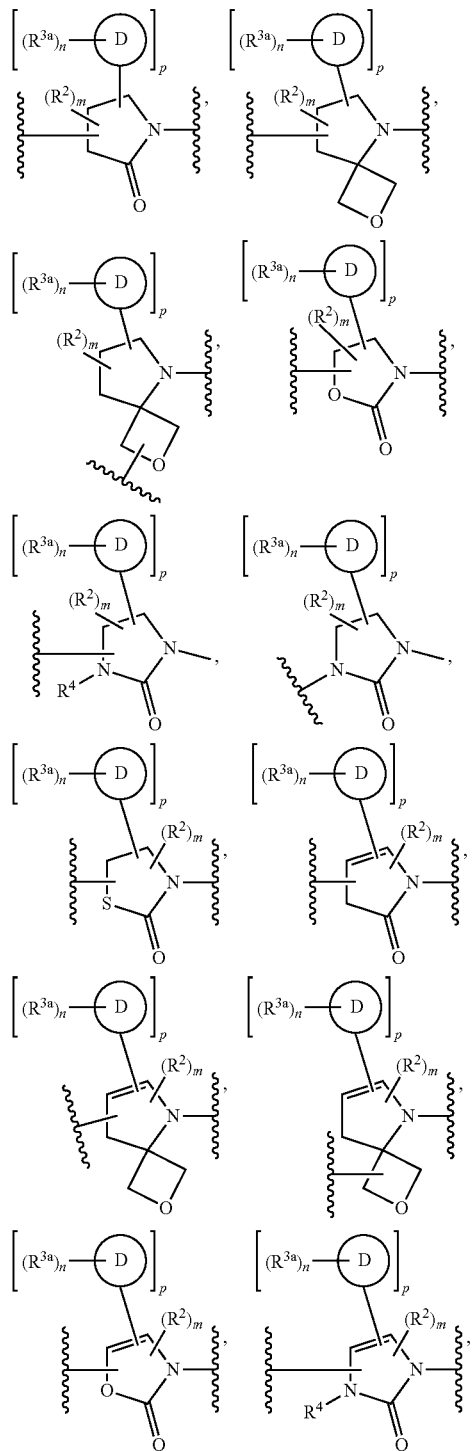
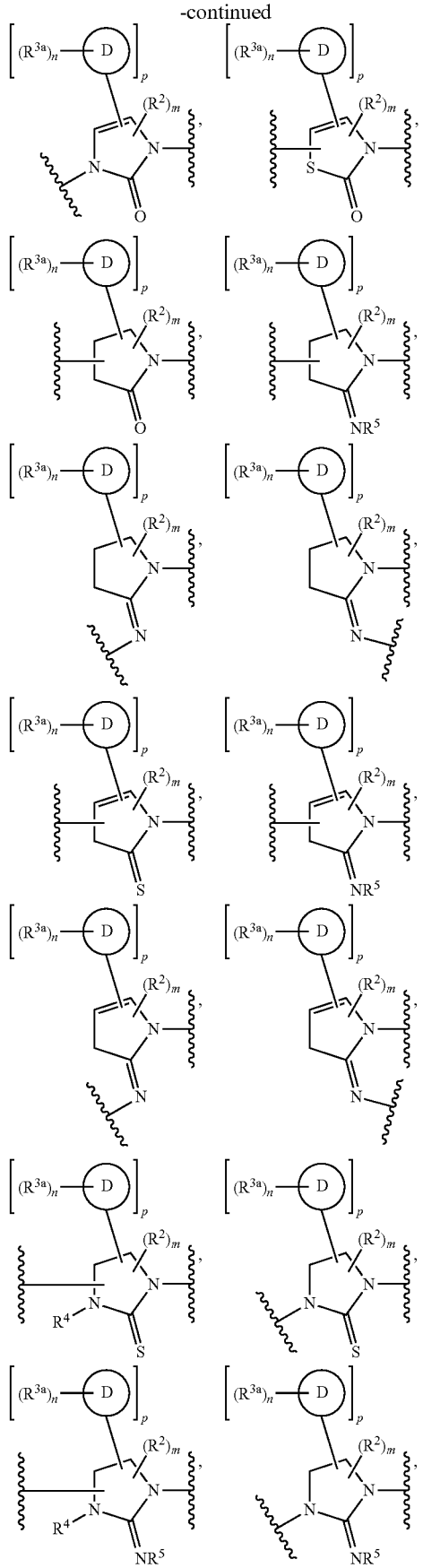

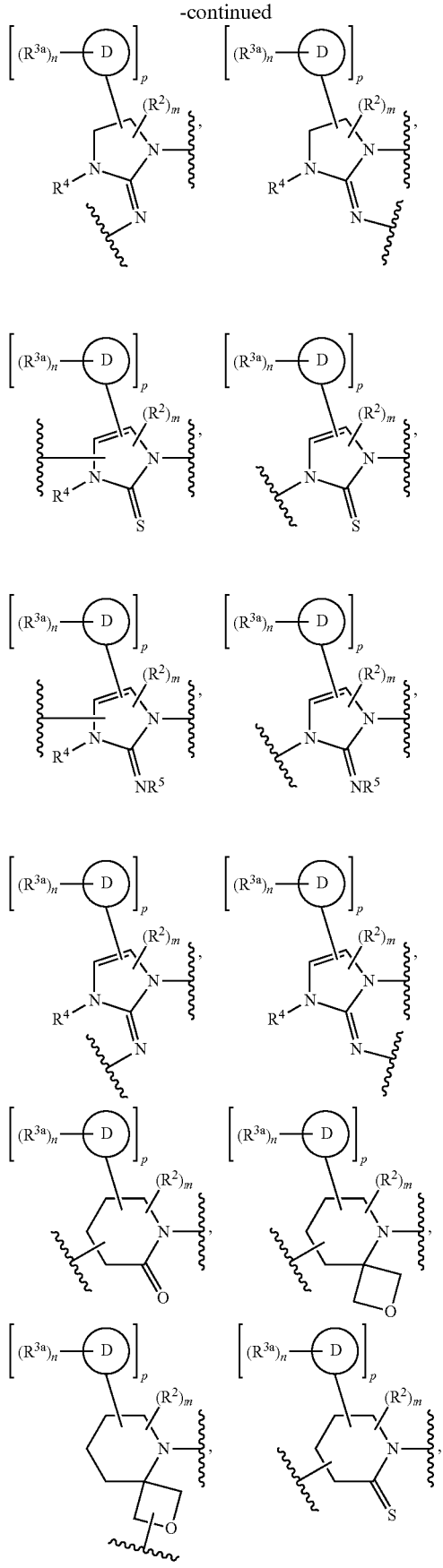
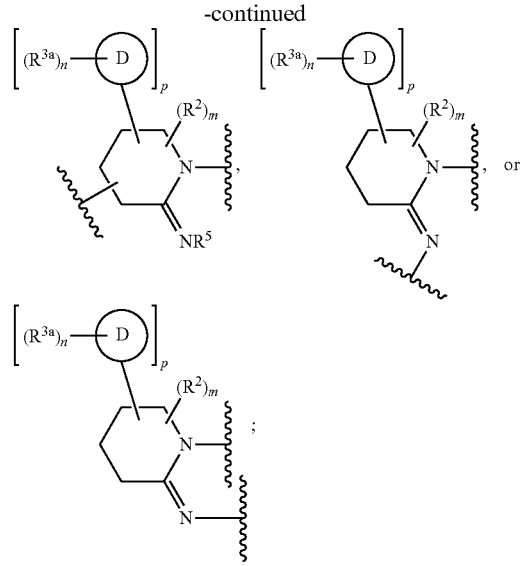

each or $R^2$ and $R^{3a}$ is independently hydrogen, —$R^6$, halogen, —CN, —$NO_2$, —OR, —SR, —$N(R)_2$, —Si$(R)_3$, —$S(O)_2R$, —$S(O)_2N(R)_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —R, halogen, —CN, —$NO_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

m is 0, 1, 2, 3 or 4;

n is 0, 1, 2, 3 or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-ff above is provided as a compound of formula I-ff' or formula I-ff":

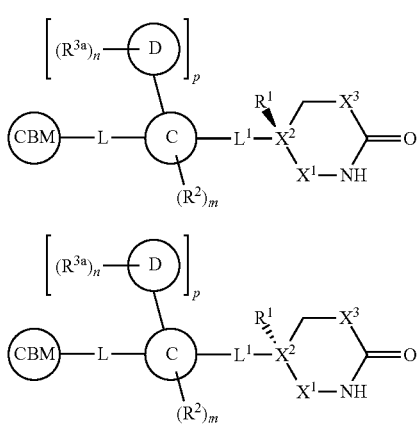

or a pharmaceutically acceptable salt thereof, wherein:
each of CBM, Ring C, Ring D, L, $L^1$, $R^1$, $R^2$, $R^{3a}$, X, $X^2$, $X^3$, m, n, and p is as defined above.

In certain embodiments, the present invention provides a compound of Formula I, wherein LBM is an E3 ubiquitin ligase (cereblon) binding moiety thereby forming a compound of formula I-gg:

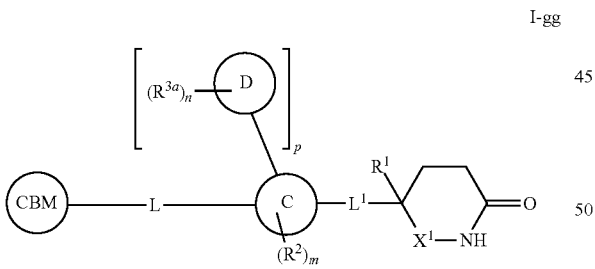

or a pharmaceutically acceptable salt thereof, wherein L and CBM are as defined above and described in embodiments herein, and wherein:

$X^1$ is a bivalent moiety selected from a covalent bond, —CH$_2$—, —C(O)—, —C(S)—, or

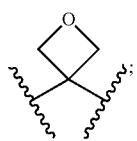 [SMILES: *C1(*)COC1]

$R^1$ is hydrogen, halogen, —CN, —OR, —SR, —S(O)R, —S(O)$_2$R, —NR$_2$, or an optionally substituted $C_{1-4}$ aliphatic;

Ring C is a mono- or bicyclic ring selected from

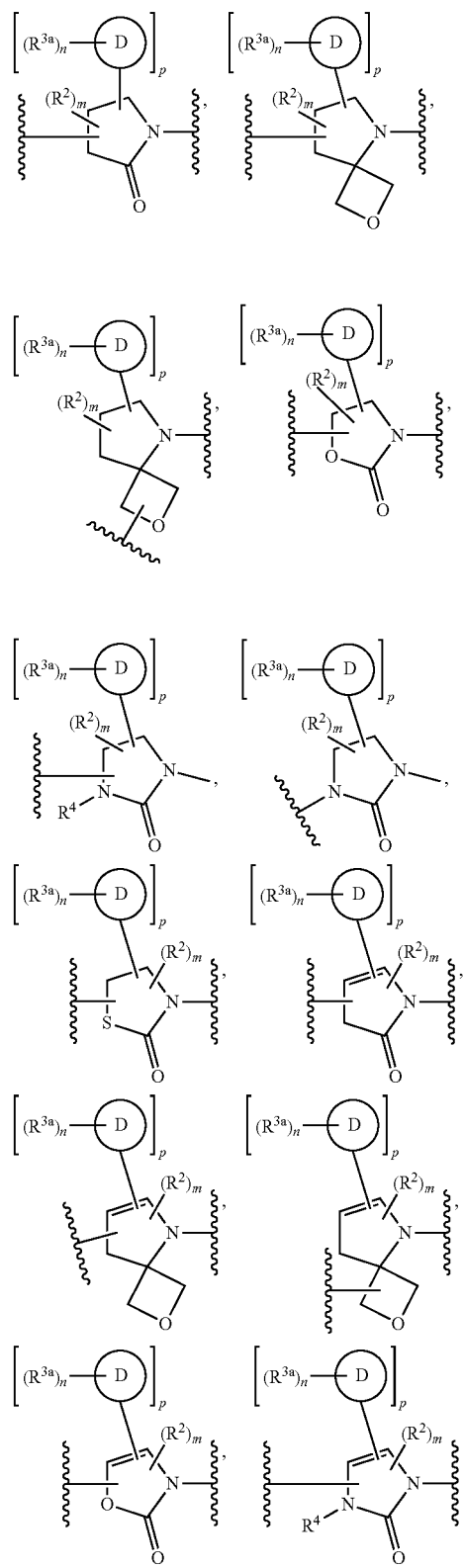

-continued
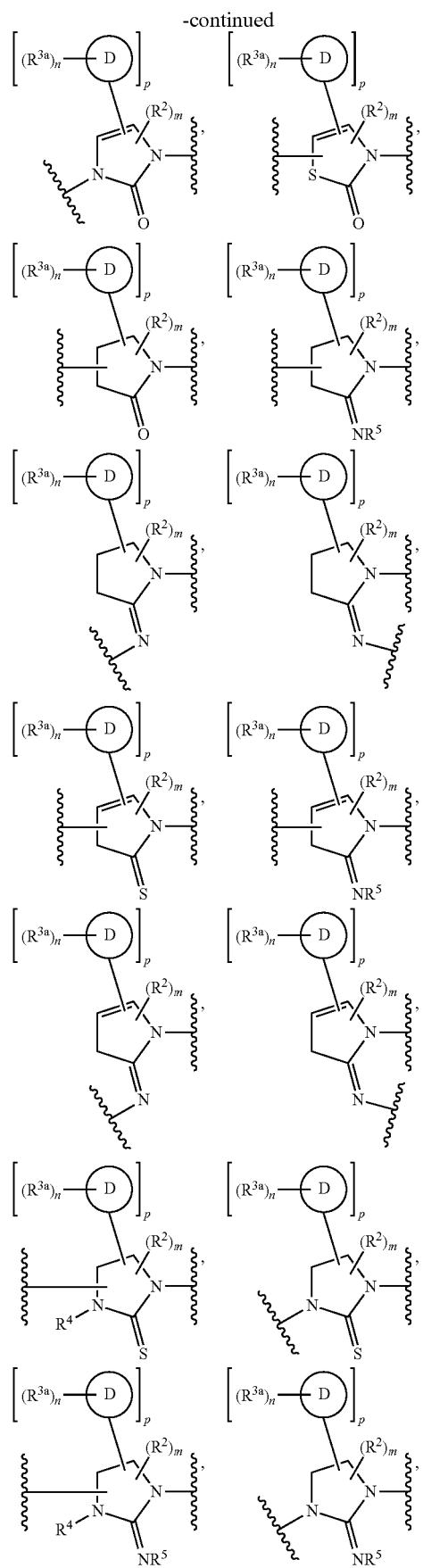
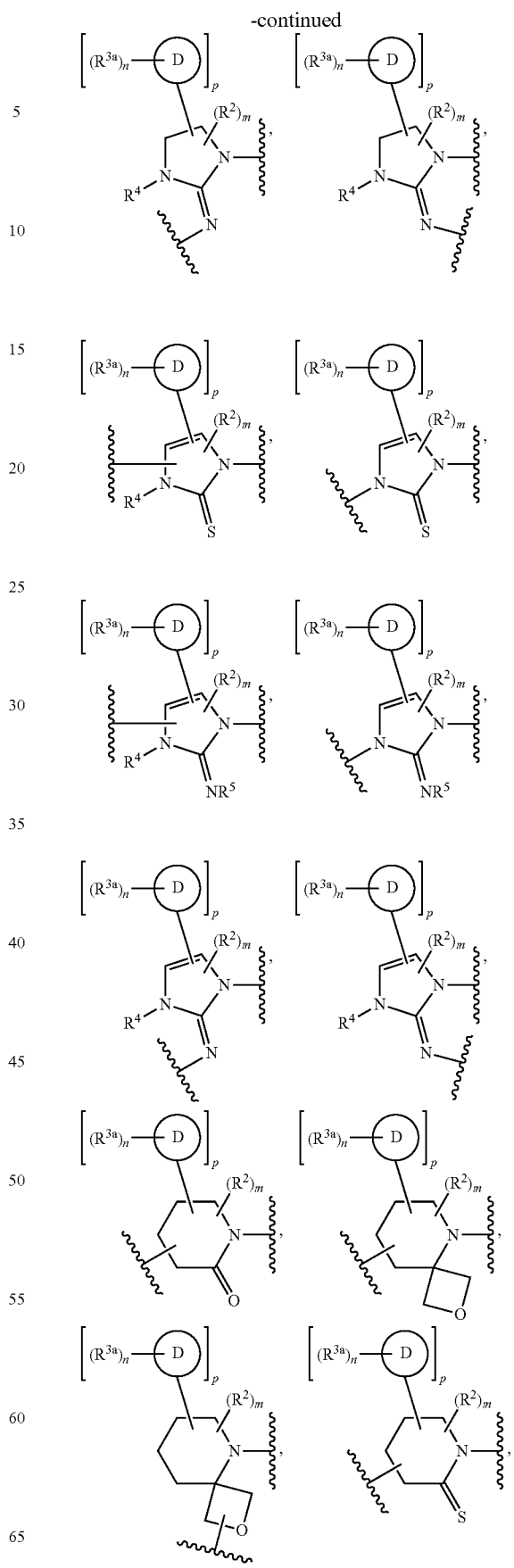

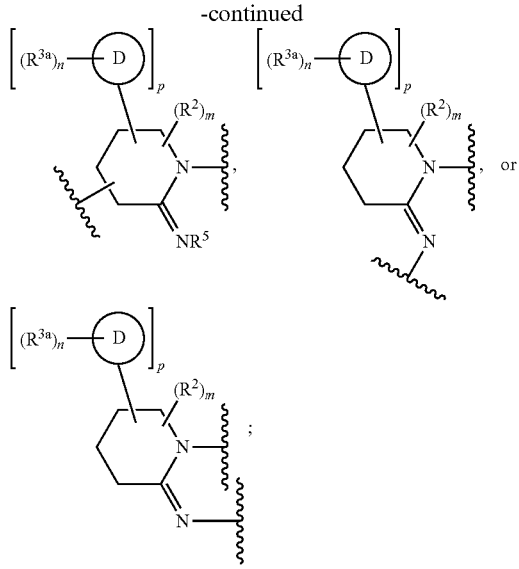

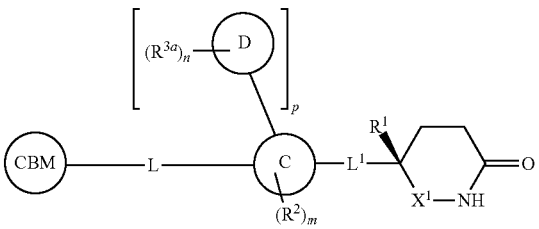

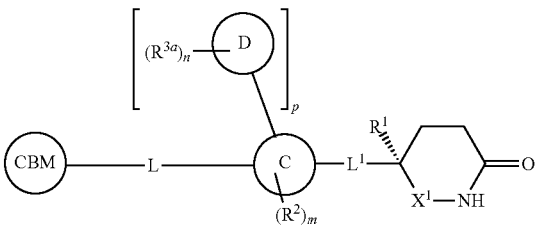

each of R², R³ᵃ, and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-gg above is provided as a compound of formula I-gg' or formula I-gg":

or a pharmaceutically acceptable salt thereof, wherein:
each of CBM, Ring C, Ring D, L, R¹, R², R³ᵃ, X¹, m, n, and p is as defined above.

In certain embodiments, the present invention provides a compound of Formula I, wherein LBM is an E3 ubiquitin ligase (cereblon) binding moiety thereby forming a compound of formula I-hh:

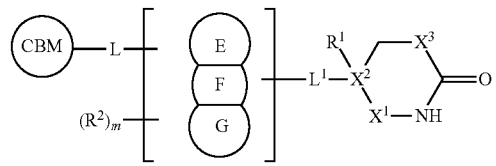

or a pharmaceutically acceptable salt thereof, wherein L and CBM are as defined above and described in embodiments herein, and wherein:

X¹ is a bivalent moiety selected from a covalent bond, —CH₂—, —CHCF₃—, —SO₂—, —S(O)—, —P(O)R—, —P(O)OR—, —P(O)NR₂—, —C(O)—, —C(S)—, or

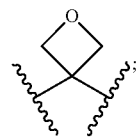 [SMILES: *C1(*)COC1]

X² is a carbon atom, nitrogen atom, or silicon atom;

X³ is a bivalent moiety selected from a covalent bond, —CR₂—, —NR—, —O—, —S—, or —SiR₂—;

R¹ is absent, hydrogen, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)R₂, —SiR₃, or an optionally substituted C₁₋₄ aliphatic;

each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each $R^2$ is independently hydrogen, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)$R_2$, —OP(O)(OR)$_2$, —OP(O)(OR)$NR_2$, —OP(O)(NR$_2$)$_2$—, —N(R)C(O)OR, —N(R)C(O)R, —N(R)C(O)$NR_2$, —N(R)S(O)$_2$R, —NP(O)$R_2$, —N(R)P(O)(OR)$_2$, —N(R)P(O)(OR)$NR_2$, —N(R)P(O)(NR$_2$)$_2$, or —N(R)S(O)$_2$R;
each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups;
$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—; and
m is 0, 1, 2, 3, 4, 5, 6, 7, 8, 9, 10, 11, 12, 13, 14, 15, or 16.

Where a point of attachment of

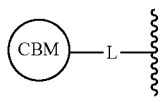

is depicted on Ring E, Ring F, or Ring G, it is intended, and one of ordinary skill in the art would appreciate, that the point of attachment of

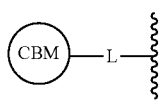

may be on any available carbon or nitrogen atom on Ring E, Ring F, or Ring G, including the ring to which Ring E or Ring G is fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G is fused to Ring F.

Where a point of attachment of

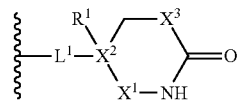

is depicted on Ring E, Ring F, or Ring G, it is intended, and one of ordinary skill in the art would appreciate, that the point of attachment of

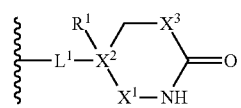

may be on any available carbon or nitrogen atom on Ring E, Ring F, or Ring G, including the carbon atom to which Ring E or Ring G is fused to Ring F.

In some embodiments, a compound of formula I-hh above is provided as a compound of formula I-hh' or formula I-hh":

I-hh'

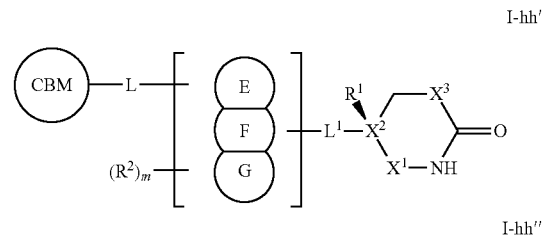

I-hh"

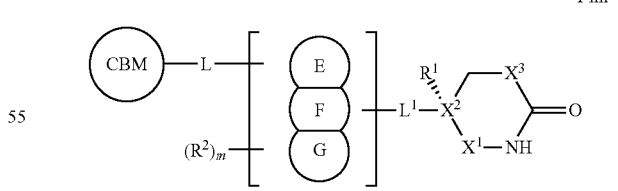

or a pharmaceutically acceptable salt thereof, wherein:
each of CBM, Ring E, Ring F, Ring G, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-hh-1 or I-hh-2:

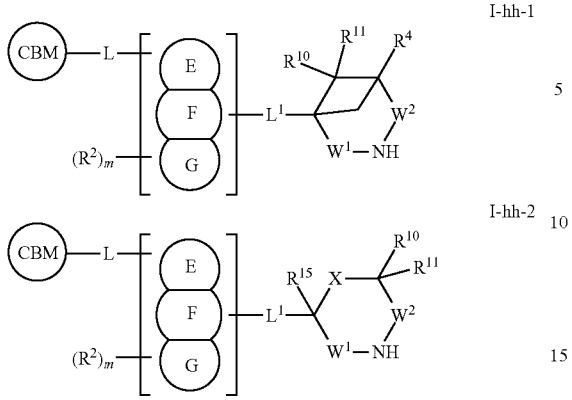

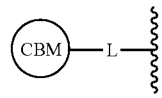

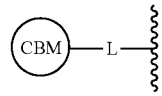

or a pharmaceutically acceptable salt thereof, wherein L and CBM are as defined above and described in embodiments herein, and wherein:

- each $R^2$ is independently hydrogen, $-R^6$, halogen, $-CN$, $-NO_2$, $-OR$, $-SR$, $-NR_2$, $-SiR_3$, $-S(O)_2R$, $-S(O)_2NR_2$, $-S(O)R$, $-C(O)R$, $-C(O)OR$, $-C(O)NR_2$, $-C(O)N(R)OR$, $-C(R)_2N(R)C(O)R$, $-C(R)_2N(R)C(O)N(R)_2$, $-OC(O)R$, $-OC(O)N(R)_2$, $-OP(O)R_2$, $-OP(O)(OR)_2$, $-OP(O)(OR)NR_2$, $-OP(O)(NR_2)_2-$, $-N(R)C(O)OR$, $-N(R)C(O)R$, $-N(R)C(O)NR_2$, $-N(R)S(O)_2R$, $-NP(O)R_2$, $-N(R)P(O)(OR)_2$, $-N(R)P(O)(OR)NR_2$, $-N(R)P(O)(NR_2)_2$, or $-N(R)S(O)_2R$;
- each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
- each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups;
- each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  - two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
- $L^1$ is a covalent bond or a $C_{1-3}$ bivalent straight or branched saturated or unsaturated hydrocarbon chain wherein 1-2 methylene units of the chain are independently and optionally replaced with $-O-$, $-C(O)-$, $-C(S)-$, $-C(R)_2-$, $-CH(R)-$, $-C(F)_2-$, $-N(R)-$, $-S-$, $-S(O)_2-$ or $-(C)=CH-$;
- m is 0, 1, 2, 3, 4, 5, 6, 7, 8, 9, 10, 11, 12, 13, 14, 15, or 16; and
- $R^4$, $R^{10}$, $R^{11}$, $R^1$, $W^1$, $W^2$, and X is as defined in WO 2019/099868, the entirety of each of which is herein incorporated by reference.

Where a point of attachment of

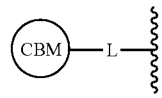

is depicted on Ring E, Ring F, or Ring G, it is intended, and one of ordinary skill in the art would appreciate, that the point of attachment of

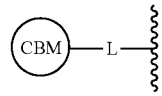

may be on any available carbon or nitrogen atom on Ring E, Ring F, or Ring G, including the ring to which Ring E or Ring G is fused to Ring F.

Where a point of attachment of $-(R^2)_m$ is depicted on Ring E, Ring F, or Ring G, it is intended, and one of ordinary skill in the art would appreciate that the point of attachment of $-(R^2)_m$ may be at any available carbon or nitrogen atom on Ring E, Ring F, or Ring G including the carbon atom to which Ring E or Ring G is fused to Ring F.

Where a point of attachment of

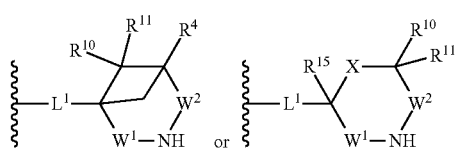

is depicted on Ring E, Ring F, or Ring G, it is intended, and one of ordinary skill in the art would appreciate, that the point of attachment of

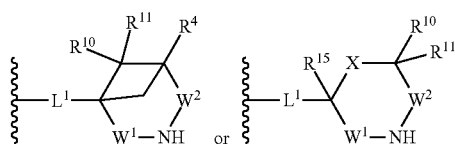

may be on any available carbon or nitrogen atom on Ring E, Ring F, or Ring G, including the carbon atom to which Ring E or Ring G is fused to Ring F.

In certain embodiments, the present invention provides a compound of Formula I, wherein LBM is an E3 ubiquitin ligase (cereblon) binding moiety thereby forming a compound of formula I-ii:

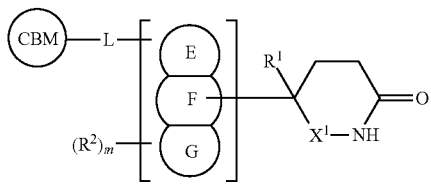

I-ii or a pharmaceutically acceptable salt thereof, wherein L and CBM are as defined above and described in embodiments herein, and wherein:

$X^1$ is a bivalent moiety selected from a covalent bond, —$CH_2$—, —C(O)—, —C(S)—, or

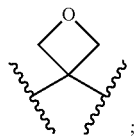
;

$R^1$ is hydrogen, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl containing 0-3 nitrogens, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur, wherein Ring E, Ring F, and Ring G is independently and optionally substituted with 1-2 oxo groups; and m is 0, 1, 2, 3, or 4.

Where a point of attachment of

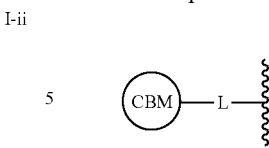

is depicted on Ring E, Ring F, or Ring G, it is intended, and one of ordinary skill in the art would appreciate, that the point of attachment of

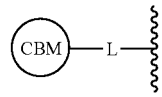

may be on any available carbon or nitrogen atom on Ring E, Ring F, or Ring G, including the ring to which Ring E or Ring G is fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G is fused to Ring F.

In some embodiments, a compound of formula I-ii above is provided as a compound of formula I-ii' or formula I-ii":

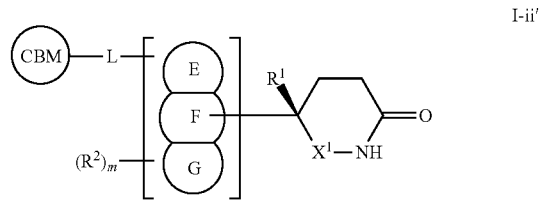

I-ii'

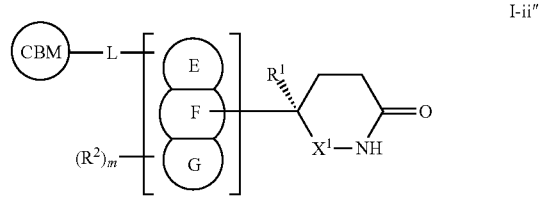

I-ii"

or a pharmaceutically acceptable salt thereof, wherein:
each of CBM, L, Ring E, Ring F, Ring G, L, $R^1$, $R^2$, $X^1$, and m is as defined above.

In certain embodiments, the present invention provides a compound of Formula I, wherein LBM is an E3 ubiquitin ligase (cereblon) binding moiety thereby forming a compound of formula I-jj:

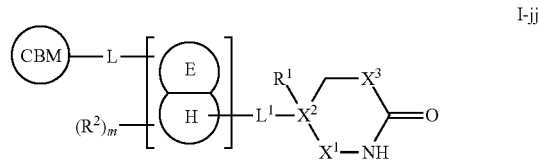

I-jj or a pharmaceutically acceptable salt thereof, wherein L and CBM are as defined above and described in embodiments herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

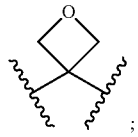 [SMILES: *C1(*)COC1]

;

$X^2$ is a carbon atom, nitrogen atom, or silicon atom;

$X^3$ is a bivalent moiety selected from a covalent bond, —CR$_2$—, —NR—, —O—, —S—, or —SiR$_2$—;

$R^1$ is absent, hydrogen, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)R$_2$, —SiR$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —R$^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;

$L^1$ is a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

m is 0, 1, 2, 3, or 4.

Where a point of attachment of

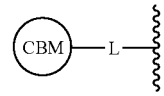

is depicted on Ring E or Ring H, it is intended, and one of ordinary skill in the art would appreciate, that the point of attachment of

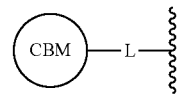

may be on any available carbon or nitrogen atom on Ring E or Ring H including the carbon atom to which Ring E and Ring H are fused.

Where a point of attachment of —(R$^2$)$_m$ is depicted on Ring E and Ring H, it is intended, and one of ordinary skill in the art would appreciate, that the point of attachment of —(R$^2$)$_m$ may be on any available carbon or nitrogen atom on Ring E or Ring H including the carbon atom to which Ring E and Ring H are fused.

Where a point of attachment of

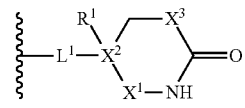

is depicted on Ring E and Ring H, it is intended, and one of ordinary skill in the art would appreciate, that the point of attachment of

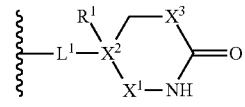

may be on any available carbon or nitrogen atom on Ring E or Ring H including the carbon atom to which Ring E and Ring H are fused.

In some embodiments, a compound of formula I-jj above is provided as a compound of formula I-jj' or formula I-jj":

I-jj'

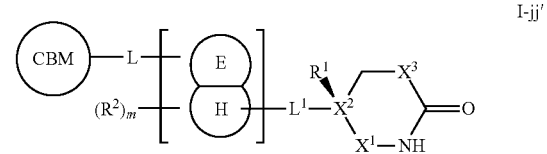

-continued

I-ij″

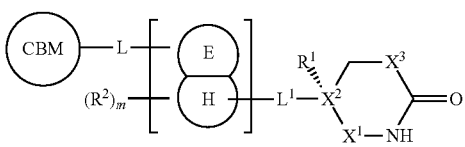

or a pharmaceutically acceptable salt thereof, wherein:
each of CBM, Ring E, Ring H, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-kk:

I-kk

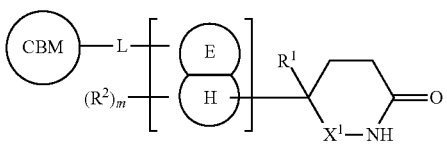

or a pharmaceutically acceptable salt thereof, wherein L and CBM are as defined above and described in embodiments herein, and wherein:

$X^1$ is a bivalent moiety selected from a covalent bond, —$CH_2$—, —C(O)—, —C(S)—, or

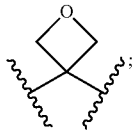 [SMILES: *C1(*)COC1]

$R^1$ is hydrogen, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups; and m is 0, 1, 2, 3, or 4.

Where a point of attachment of

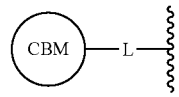

is depicted on Ring E or Ring H, it is intended, and one of ordinary skill in the art would appreciate, that the point of attachment of

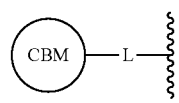

may be on any available carbon or nitrogen atom on Ring E or Ring H including the carbon atom to which Ring E and Ring H are fused.

Where a point of attachment of —$(R^2)_m$ is depicted on Ring E and Ring H, it is intended, and one of ordinary skill in the art would appreciate, that the point of attachment of —$(R^2)_m$ may be on any available carbon or nitrogen atom on Ring E or Ring H including the carbon atom to which Ring E and Ring H are fused.

Where a point of attachment of

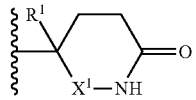

is depicted on Ring E and Ring H, it is intended, and one of ordinary skill in the art would appreciate, that the point of attachment of

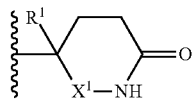

may be on any available carbon or nitrogen atom on Ring E or Ring H including the carbon atom to which Ring E and Ring H are fused.

In some embodiments, a compound of formula I-kk above is provided as a compound of formula I-kk' or formula I-kk":

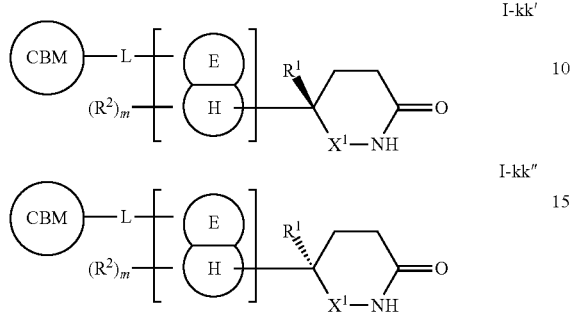

or a pharmaceutically acceptable salt thereof, wherein:
each of CBM, Ring E, Ring H, L, $R^1$, $R^2$, $X^1$, and m is as defined above.

In certain embodiments, the present invention provides a compound of Formula I, wherein LBM is an E3 ubiquitin ligase (cereblon) binding moiety thereby forming a compound of formula I-ll:

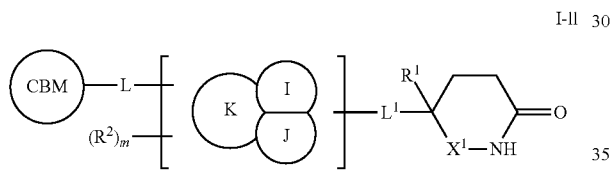

or a pharmaceutically acceptable salt thereof, wherein L and CBM are as defined above and described in embodiments herein, and wherein:

$X^1$ is a bivalent moiety selected from a covalent bond, —$CH_2$—, —$CHCF_3$—, —$SO_2$—, —$S(O)$—, —$P(O)R$—, —$P(O)OR$—, —$P(O)NR_2$—, —$C(O)$—, —$C(S)$—, or

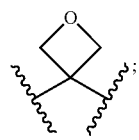 [SMILES: *C1(*)COC1]

$X^2$ is a carbon atom, nitrogen atom, or silicon atom;
$X^3$ is a bivalent moiety selected from a covalent bond, —$CR_2$—, —NR—, —O—, —S—, or —$SiR_2$—;
$R^1$ is absent, hydrogen, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)R_2$, —$SiR_3$, or an optionally substituted $C_{1-4}$ aliphatic;
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)=CH—; and m is 0, 1, 2, 3, or 4.

Where a point of attachment of

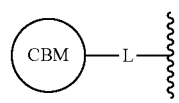

is depicted on Ring I, Ring J, and Ring K, it is intended, and one of ordinary skill in the art would appreciate, that the point of attachment of

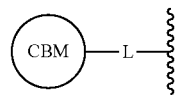

may be on any available carbon or nitrogen atom on Ring I, Ring J, or Ring K, including the carbon atom to which Ring I, Ring J, and Ring K are fused.

Where a point of attachment of —(R²)ₘ is depicted on Ring I, Ring J, and Ring K, it is intended, and one of ordinary skill in the art would appreciate, that the point of attachment of —(R²)ₘ may be on any available carbon or nitrogen atom on Ring I, Ring J, or Ring K, including the carbon atom to which Ring I, Ring J, and Ring K are fused.

Where a point of attachment of

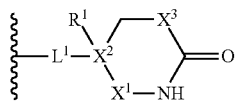

is depicted on Ring I, Ring J, and Ring K, it is intended, and one of ordinary skill in the art would appreciate, that the point of attachment of

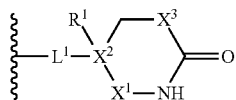

may be on any available carbon or nitrogen atom on Ring I, Ring J, or Ring K, including the carbon atom to which Ring I, Ring J, and Ring K are fused.

In some embodiments, a compound of formula I-ll above is provided as a compound of formula I-ll' or formula I-ll":

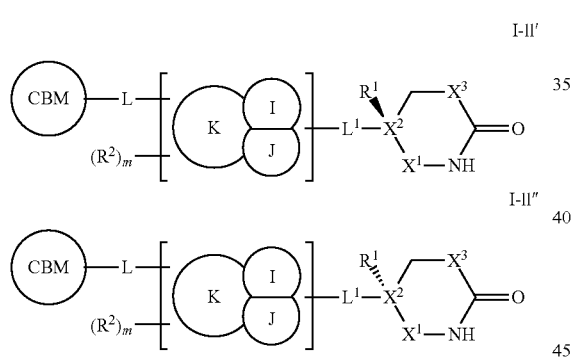

I-ll'

I-ll"

or a pharmaceutically acceptable salt thereof, wherein:
each of CBM, Ring I, Ring J, Ring K, L, L¹, R¹, R², X¹, X², X³, and m is as defined above.

In certain embodiments, the present invention provides a compound of formula I-mm:

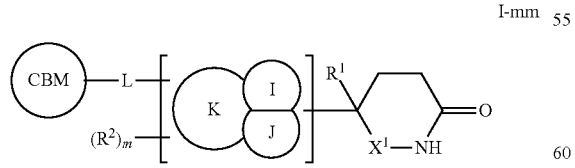

I-mm or a pharmaceutically acceptable salt thereof, wherein L and CBM are as defined above and described in embodiments herein, and wherein:

X¹ is a bivalent moiety selected from a covalent bond, —CH₂—, —C(O)—, —C(S)—, or

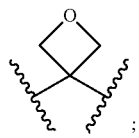 [SMILES: *C1(*)COC1]

R¹ is hydrogen, halogen, —CN, —OR, —SR, —S(O)R, —S(O)₂R, —N(R)₂, —Si(R)₃, or an optionally substituted C₁₋₄ aliphatic;

each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, —R⁶, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups; and m is 0, 1, 2, 3, or 4.

Where a point of attachment of

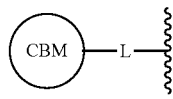

is depicted on Ring I, Ring J, and Ring K, it is intended, and one of ordinary skill in the art would appreciate, that the point of attachment of

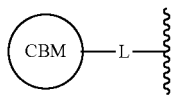

may be on any available carbon or nitrogen atom on Ring I, Ring J, or Ring K, including the carbon atom to which Ring I, Ring J, and Ring K are fused.

Where a point of attachment of —(R)$_m$ is depicted on Ring I, Ring J, and Ring K, it is intended, and one of ordinary skill in the art would appreciate, that the point of attachment of —(R$^2$)$_m$ may be on any available carbon or nitrogen atom on Ring I, Ring J, or Ring K, including the carbon atom to which Ring I, Ring J, and Ring K are fused.

Where a point of attachment of

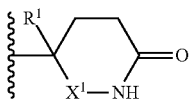

is depicted on Ring I, Ring J, and Ring K, it is intended, and one of ordinary skill in the art would appreciate, that the point of attachment of

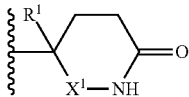

may be on any available carbon or nitrogen atom on Ring I, Ring J, or Ring K, including the carbon atom to which Ring I, Ring J, and Ring K are fused.

In some embodiments, a compound of formula I-mm above is provided as a compound of formula I-mm' or formula I-mm":

I-mm'

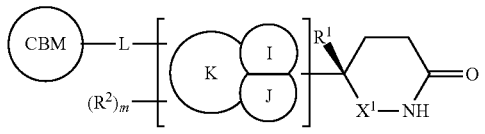

I-mm"

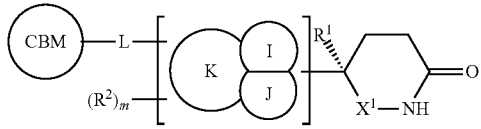

or a pharmaceutically acceptable salt thereof, wherein:
each of CBM, Ring I, Ring J, Ring K, L, R$^1$, R$^2$, X$^1$, and m is as defined above.

As described above, in another aspect, the present invention provides a compound of Formula I-nn:

I-nn

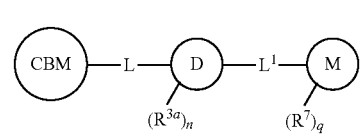

or a pharmaceutically acceptable salt thereof, wherein:
Ring M is selected from

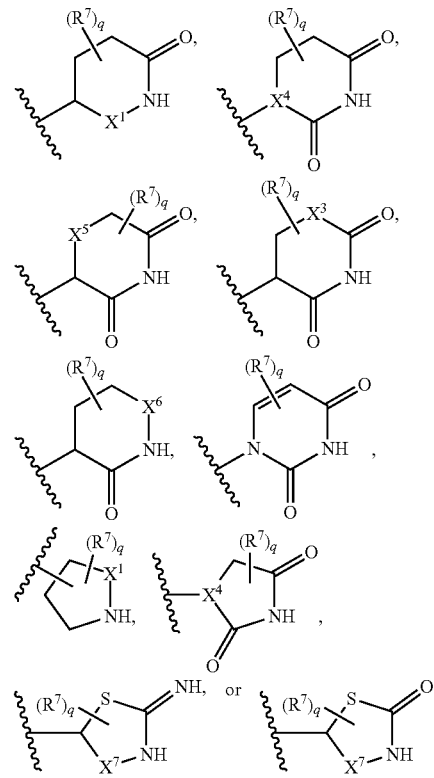

each of X$^1$, X$^6$, and X$^7$ is independently a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

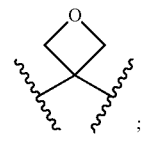

;

each of X$^3$ and X$^5$ is independently a bivalent moiety selected from a covalent bond, —CH$_2$—, —NR—, —O—, —S—, or —SiR$_2$—;
X$^4$ is a trivalent moiety selected from

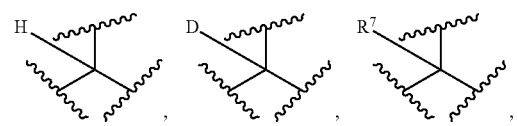

,

-continued

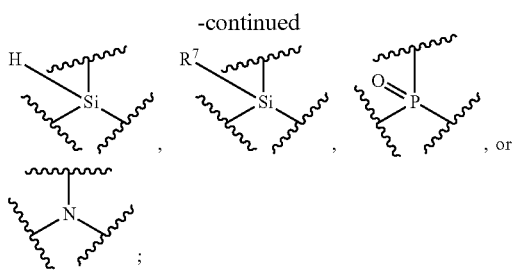

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^{3a}$ is independently hydrogen, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)$R_2$, —OP(O)(OR)$_2$, —OP(O)(OR)$NR_2$, —OP(O)($NR_2$)$_2$—, —N(R)C(O)OR, —N(R)C(O)R, —N(R)C(O)$NR_2$, —N(R)S(O)$_2$R, —NP(O)$R_2$, —N(R)P(O)(OR)$_2$, —N(R)P(O)(OR)$NR_2$, —N(R)P(O)($NR_2$)$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each $R^7$ is independently hydrogen, halogen, —CN, —OR, —SR, —S(O)R, —S(O)$_2$R, —$NR_2$, —P(O)(OR)$_2$, —P(O)($NR_2$)OR, —P(O)($NR_2$)$_2$, —Si(OH)$R_2$, —Si(OH)$_2$R, —$SiR_3$, or an optionally substituted $C_{1-4}$ aliphatic; or $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur;

two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur;

two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur;

Ring D is selected from 6 to 10-membered aryl or heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

n is 0, 1, 2, 3, or 4; and q is 0, 1, 2, 3, or 4.

As defined above and described herein, each of $X^1$, $X^6$, and $X^7$ is independently a bivalent moiety selected from a covalent bond, —$CH_2$—, —C(R)$_2$—, —C(O)—, —C(S)—, —CH(R)—, —CH(CF$_3$)—, —P(O)(OR)—, —P(O)(R)—, —P(O)($NR_2$)—, —S(O)—, —S(O)$_2$—, or

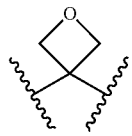

In some embodiments, each of $X^1$, $X^6$, and $X^7$ is independently a covalent bond. In some embodiments, each of $X^1$, $X^6$, and $X^7$ is independently —$CH_2$—. In some embodiments, each of $X^1$, $X^6$, and $X^7$ is independently —$CR_2$—. In some embodiments, each of $X^1$, $X^6$, and $X^7$ is independently —C(O)—. In some embodiments, each of $X^1$, $X^6$, and $X^7$ is independently —C(S)—. In some embodiments, each of $X^1$, $X^6$, and $X^7$ is independently —CH(R)—. In some embodiments, each of $X^1$, $X^6$, and $X^7$ is independently —CH(CF$_3$)—. In some embodiments, each of $X^1$, $X^6$, and $X^7$ is independently —P(O)(OR)—. In some embodiments, each of $X^1$, $X^6$, and $X^7$ is independently —P(O)(R)—. In some embodiments, each of $X^1$, $X^6$, and $X^7$ is independently —P(O)$NR_2$—. In some embodiments, each of $X^1$, $X^6$, and $X^7$ is independently —S(O)—. In some embodiments, each of $X^1$, $X^6$, and $X^7$ is independently —S(O)$_2$—. In some embodiments, each of $X^1$, $X^6$, and $X^7$ is independently

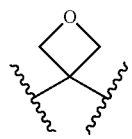

In some embodiments, each of $X^1$, $X^6$, and $X^7$ is independently selected from those depicted in Table 1 below.

As defined above and described herein, $X^2$ is a carbon atom, nitrogen atom, or silicon atom.

In some embodiments, $X^2$ is a carbon atom. In some embodiments, $X^2$ is a nitrogen atom. In some embodiments, $X^2$ is a silicon atom.

In some embodiments, $X^2$ is selected from those depicted in Table 1 below.

As defined above and described herein, $X^3$ is a bivalent moiety selected from —CH$_2$—, —CR$_2$—, —NR—, —CF$_2$—, —CHF—, —S—, —CH(R)—, —SiR$_2$—, or —O—.

In some embodiments, each of $X^3$ and $X^5$ is independently —CH$_2$—. In some embodiments, each of $X^3$ and $X^5$ is independently —CR$_2$—. In some embodiments, each of $X^3$ and $X^5$ is independently —NR—. In some embodiments, each of $X^3$ and $X^5$ is independently —CF$_2$—. In some embodiments, each of $X^3$ and $X^5$ is independently —CHF—. In some embodiments, each of $X^3$ and $X^5$ is independently —S—. In some embodiments, each of $X^3$ and $X^5$ is independently —CH(R)—. In some embodiments, each of $X^3$ and $X^5$ is independently —SiR$_2$—. In some embodiments, each of $X^3$ and $X^5$ is independently —O—.

In some embodiments, each of $X^3$ and $X^5$ is independently selected from those depicted in Table 1 below.

As defined above and described herein, $X^4$ is a trivalent moiety selected from

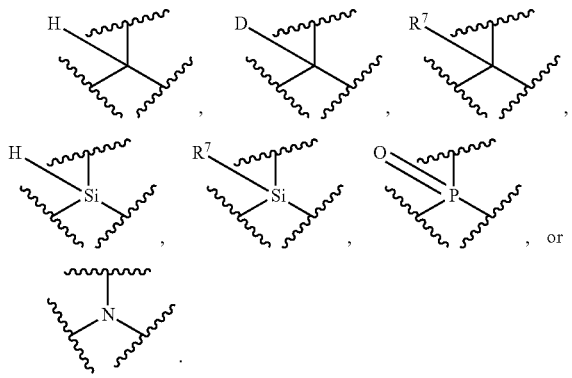

, or

In some embodiments, $X^4$ is

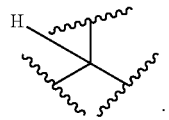

In some embodiments, $X^4$ is

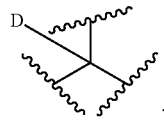 [SMILES: *C(*)(*)[2H]]

In some embodiments, $X^4$ is

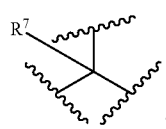

In some embodiments, $X^4$ is

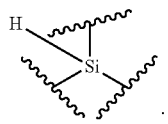

In some embodiments, $X^4$ is

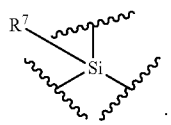

In some embodiments, $X^4$ is

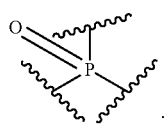 [SMILES: *P(*)(*)=O]

In some embodiments, $X^4$ is

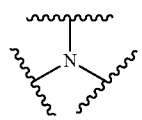

In some embodiments, $X^4$ is selected from those depicted in Table 1 below.

As defined above and described herein, $R^1$ is hydrogen, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)R$_2$, —SiR$_3$, an optionally substituted $C_{1-4}$ aliphatic, or $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is hydrogen. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —S(O)$_2$R. In some embodiments, $R^1$ is —NR$_2$. In some embodiments, $R^1$ is —P(O)(OR)$_2$. In some embodiments, $R^1$ is —P(O)(NR$_2$)OR. In some embodiments, $R^1$ is —P(O)(NR$_2$)$_2$. In some embodiments, $R^1$ is —Si(OH)$_2$R. In some embodiments, $R^1$ is —Si(OH)R$_2$. In some embodiments, $R^1$ is —SiR$_3$. In some embodiments, $R^1$ is an optionally substituted $C_{1-4}$ aliphatic. In some embodiments, $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is selected from those depicted in Table 1 below.

As defined above and described herein, each R is independently hydrogen, or an optionally substituted group selected from $C_{1-6}$ aliphatic, phenyl, a 4-7 membered saturated or partially unsaturated heterocyclic having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is hydrogen. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-3 heteroatoms independently selected from boron, nitrogen, oxygen, silicon, and sulfur. In some embodiments, R is optionally substituted 5-6 membered heteroaryl ring having 1-4 heteroatoms independently selected from boron, nitrogen, oxygen, silicon, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is selected from those depicted in Table 1 below.

As defined above and described herein, each of $R^2$ and $R^{3a}$ is independently hydrogen, —R, halogen, —CN, —NO$_2$, —OR, —Si(OH)$_2$R, —Si(OH)R$_2$, —SR, —NR$_2$, —SiR$_3$, —S(O)$_2$R, —S(O)$_2$NR$_2$, —S(O)R, —C(O)R, —C(O)OR, —C(O)NR$_2$, —C(O)N(R)OR, —C(R)$_2$N(R)C(O)R, —C(R)$_2$N(R)C(O)NR$_2$, —OC(O)R, —OC(O)NR$_2$, —OP(O)R$_2$, —OP(O)(OR)$_2$, —OP(O)(OR)NR$_2$, —OP(O)(NR$_2$)$_2$—, —N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R.

In some embodiments, $R^2$ and $R^{3a}$ is independently hydrogen. In some embodiments, $R^2$ and $R^{3a}$ is independently —R$^6$. In some embodiments, $R^2$ and $R^{3a}$ is independently halogen. In some embodiments, $R^2$ and $R^{3a}$ is independently —CN. In some embodiments, $R^2$ and $R^{3a}$ is independently —NO$_2$. In some embodiments, $R^2$ and $R^{3a}$ is independently —OR. In some embodiments, $R^2$ and $R^{3a}$ is independently —Si(OH)$_2$R. In some embodiments, $R^2$ and $R^{3a}$ is independently —Si(OH)R$_2$. In some embodiments, $R^2$ and $R^{3a}$ is independently —SR. In some embodiments, $R^2$ and $R^{3a}$ is independently —NR$_2$. In some embodiments, $R^2$ and $R^{3a}$ is independently —SiR$_3$. In some embodiments, $R^2$ and $R^{3a}$ is independently —S(O)$_2$R. In some embodiments, $R^2$ and $R^{3a}$ is independently —S(O)$_2$NR$_2$. In some embodiments, $R^2$ and $R^{3a}$ is independently —S(O)R. In some embodiments, $R^2$ and $R^{3a}$ is independently —C(O)R. In some embodiments, $R^2$ and $R^{3a}$ is independently —C(O)OR. In some embodiments, $R^2$ and $R^{3a}$ is independently —C(O)NR$_2$. In some embodiments, $R^2$ and $R^{3a}$ is independently —C(O)N(R)OR. In some embodiments, $R^2$ and $R^{3a}$ is independently —C(R)$_2$N(R)C(O)R. In some embodiments, $R^2$ and $R^{3a}$ is independently —C(R)$_2$N(R)C(O)NR$_2$. In some embodiments, $R^2$ and $R^{3a}$ is independently —OC(O)R. In some embodiments, $R^2$ and $R^{3a}$ is independently —OC(O)NR$_2$. In some embodiments, $R^2$ and $R^{3a}$ is independently —OP(O)R$_2$. In some embodiments, $R^2$ and $R^{3a}$ is independently —OP(O)(OR)$_2$. In some embodiments, $R^2$ and $R^{3a}$ is independently —OP(O)(OR)NR$_2$. In some embodiments, $R^2$ and $R^{3a}$ is independently —OP(O)(NR$_2$)$_2$—. In some embodiments, $R^2$ and $R^{3a}$ is independently —N(R)C(O)OR. In some embodiments, $R^2$ and $R^{3a}$ is independently —N(R)C(O)R. In some embodiments, $R^2$ and $R^{3a}$ is independently —N(R)C(O)NR$_2$. In some embodiments, $R^2$ and $R^{3a}$ is independently —NP(O)R$_2$. In some embodiments, $R^2$ and $R^{3a}$ is independently —N(R)P(O)(OR)$_2$. In some embodiments, $R^z$ and $R^{3a}$ is independently —N(R)P(O)(OR)NR$_2$. In some embodiments, $R^2$ and $R^{3a}$ is independently —N(R)P(O)(NR$_2$)$_2$. In some embodiments, $R^2$ and $R^{3a}$ is independently —N(R)S(O)$_2$R.

In some embodiments, $R^2$ and $R^{3a}$ is independently —OH. In some embodiments, $R^2$ and $R^{3a}$ is independently —NH$_2$. In some embodiments, $R^2$ and $R^{3a}$ is independently —CH$_2$NH$_2$. In some embodiments, $R^2$ and $R^{3a}$ is independently —CH$_2$NHCOMe. In some embodiments, $R^2$ and $R^{3a}$ is independently —CH$_2$NHCONHMe. In some embodiments, $R^2$ and $R^{3a}$ is independently —NHCOMe. In some embodiments, $R^2$ and $R^{3a}$ is independently —NHCONHEt. In some embodiments, $R^2$ and $R^{3a}$ is independently —SiMe$_3$. In some embodiments, $R^2$ and $R^{3a}$ is independently —SiMe$_2$OH. In some embodiments, $R^2$ and $R^{3a}$ is independently —SiMe(OH)$_2$. In some embodiments $R^2$ and $R^{3a}$ is independently

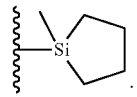

In some embodiments, $R^2$ and $R^{3a}$ is independently Br. In some embodiments, $R^2$ and $R^{3a}$ is independently Cl. In some embodiments, $R^2$ and $R^{3a}$ is independently F. In some embodiments, $R^2$ and $R^{3a}$ is independently Me. In some embodiments, $R^2$ and $R^{3a}$ is independently —NHMe. In some embodiments, $R^2$ and $R^{3a}$ is independently —NMe$_2$. In some embodiments, $R^2$ and $R^{3a}$ is independently —NHCO$_2$Et. In some embodiments, $R^2$ and $R^{3a}$ is independently —CN. In some embodiments, $R^2$ and $R^{3a}$ is independently —CH$_2$Ph. In some embodiments, $R^2$ and $R^{3a}$ is independently —NHCO$_2$tBu. In some embodiments, $R^2$ and $R^{3a}$ is independently —CO$_2$tBu. In some embodiments, $R^2$ and $R^{3a}$ is independently —OMe. In some embodiments, $R^2$ and $R^{3a}$ is independently —CF$_3$.

In some embodiments, $R^2$ or $R^{3a}$ is selected from those depicted in Table 1 below.

As defined above and described herein, $R^3$ is hydrogen, halogen, —CN, —NO$_2$, —OR, —NR$_2$, —SR, —S(O)$_2$R, —S(O)$_2$NR$_2$, —S(O)R, —C(O)R, —C(O)OR, —C(O)NR$_2$, —C(O)NR(OR), —OC(O)R, —OC(O)NR$_2$, —OP(O)(OR)$_2$, —OP(O)(NR$_2$)$_2$, —OP(O)(OR)NR$_2$, —N(R)C(O)R, —N(R)C(O)OR, —N(R)C(O)NR$_2$, —N(R)S(O)$_2$R, —N(R)S(O)$_2$NR$_2$, —N(R)P(O)(OR)$_2$, —N(R)P(O)(OR)NR$_2$, —P(O)(OR)$_2$, —P(O)(NR$_2$)OR, —P(O)(NR$_2$)$_2$, —Si(OH)$_2$R, —Si(OH)(R)$_2$, or —Si(R)$_3$.

In some embodiments, $R^3$ is hydrogen. In some embodiments, $R^3$ is halogen. In some embodiments, $R^3$ is —CN. In some embodiments, $R^3$ is —NO$_2$. In some embodiments, $R^3$ is —OR. In some embodiments, $R^3$ is —NR$_2$. In some embodiments, $R^3$ is —SR. In some embodiments, $R^3$ is —S(O)$_2$R. In some embodiments, $R^3$ is —S(O)$_2$NR$_2$. In some embodiments, $R^3$ is —S(O)R. In some embodiments, $R^3$ is —C(O)R. In some embodiments, $R^3$ is —C(O)OR. In some embodiments, $R^3$ is —C(O)NR$_2$. In some embodiments, $R^3$ is —C(O)NR(OR). In some embodiments, $R^3$ is —OC(O)R. In some embodiments, $R^3$ is —OC(O)NR$_2$. In some embodiments, $R^3$ is —OP(O)(OR)$_2$. In some embodiments, $R^3$ is —OP(O)(NR$_2$)$_2$. In some embodiments, $R^3$ is —OP(O)(OR)NR$_2$. In some embodiments, R$^3$ is —N(R)C(O)R. In some embodiments, R$^3$ is —N(R)C(O)OR. In some embodiments, R$^3$ is —N(R)C(O)NR$_2$. In some embodiments, R$^3$ is —N(R)S(O)$_2$R. In some embodiments, R$^3$ is —N(R)S(O)$_2$NR$_2$. In some embodiments, R$^3$ is —N(R)P(O)(OR)$_2$. In some embodiments, R$^3$ is —N(R)P(O)(OR)NR$_2$. In some embodiments, R$^3$ is —P(O)(OR)$_2$. In some embodiments, R$^3$ is —P(O)(NR$_2$)OR. In some embodiments, R$^3$ is —P(O)(NR$_2$)$_2$. In some embodiments, R$^3$ is —Si(OH)$_2$R. In some embodiments, R$^3$ is —Si(OH)(R)$_2$. In some embodiments, R$^3$ is —Si(R)$_3$.

In some embodiments, R$^3$ is methyl. In some embodiments, R$^3$ is —OCH$_3$. In some embodiments, R$^3$ is chloro.

In some embodiments, R$^3$ is selected from those depicted in Table 1.

As defined above and described herein, each R$^4$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —P(O)(OR)$_2$, —P(O)(NR$_2$)OR, or —P(O)(NR$_2$)$_2$.

In some embodiments, R$^4$ is hydrogen. In some embodiments, R$^4$ is —R$^6$. In some embodiments, R$^4$ is halogen. In some embodiments, R$^4$ is —CN. In some embodiments, R$^4$ is —NO$_2$. In some embodiments, R$^4$ is —OR. In some embodiments, R$^4$ is —SR. In some embodiments, R$^4$ is —NR$_2$. In some embodiments, R$^4$ is —S(O)$_2$R. In some embodiments, R$^4$ is —S(O)$_2$NR$_2$. In some embodiments, R$^4$ is —S(O)R. In some embodiments, R$^4$ is —C(O)R. In some embodiments, R$^4$ is —C(O)OR. In some embodiments, R$^4$ is —C(O)NR$_2$. In some embodiments, R$^4$ is —C(O)N(R)OR. In some embodiments, R$^4$ is —OC(O)R. In some embodiments, R$^4$ is —OC(O)NR$_2$. In some embodiments, R$^4$ is —N(R)C(O)OR. In some embodiments, R$^4$ is —N(R)C(O)R. In some embodiments, R$^4$ is —N(R)C(O)NR$_2$. In some embodiments, R$^4$ is —N(R)S(O)$_2$R. In some embodiments, R$^4$ is —P(O)(OR)$_2$. In some embodiments, R$^4$ is —P(O)(NR$_2$)OR. In some embodiments, R$^4$ is —P(O)(NR$_2$)$_2$.

In some embodiments, R$^4$ is methyl. In some embodiments, R$^4$ is ethyl. In some embodiments, R$^4$ is cyclopropyl.

In some embodiments, R$^4$ is selected from those depicted in Table 1.

As defined above and described herein, R$^5$ is hydrogen, an optionally substitute C$_{1-4}$ aliphatic, or —CN.

In some embodiments, R$^5$ is hydrogen. In some embodiments, R$^5$ is an optionally substituted C$_{1-4}$ aliphatic. In some embodiments, R$^5$ is —CN.

In some embodiments, R$^5$ is selected from those depicted in Table 1.

As defined above and described herein, each R$^6$ is independently an optionally substituted group selected from C$_{1-6}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur.

In some embodiments, R$^6$ is an optionally substituted C$_{1-6}$ aliphatic. In some embodiments, R$^6$ is an optionally substituted phenyl. In some embodiments, R$^6$ is an optionally substituted 4-7 membered saturated or partially unsaturated heterocyclic ring having 1-3 heteroatoms independently selected from boron, nitrogen, oxygen, silicon, and sulfur. In some embodiments, R$^6$ is an optionally substituted 5-6 membered heteroaryl ring having 1-4 heteroatoms independently selected from boron, nitrogen, oxygen, silicon, and sulfur.

In some embodiments, R$^6$ is selected from those depicted in Table 1.

As defined generally above, each R$^7$ is independently hydrogen, halogen, —CN, —OR, —SR, —S(O)R, —S(O)$_2$R, —N(R)$_2$, —P(O)(R)$_2$, —P(O)(OR)$_2$, —P(O)(NR$_2$)OR, —P(O)(NR$_2$)$_2$, —Si(OH)R$_2$, —Si(OH)$_2$R, —SiR$_3$, or an optionally substituted C$_{1-4}$ aliphatic, or R$^1$ and X$^1$ or X$^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur, or two R$^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur, or two R$^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, R$^7$ is hydrogen. In some embodiments, R$^7$ is halogen. In some embodiments, R$^7$ is —CN. In some embodiments, R$^7$ is —OR. In some embodiments, R$^7$ is —SR. In some embodiments, R$^7$ is —S(O)R. In some embodiments, R$^7$ is —S(O)$_2$R. In some embodiments, R$^7$ is —NR$_2$. In some embodiments, R$^7$ is —Si(R)$_3$. In some embodiments, R$^7$ is —P(O)(R)$_2$. In some embodiments, R$^7$ is —P(O)(OR)$_2$. In some embodiments, R$^7$ is —P(O)(NR$_2$)OR. In some embodiments, R$^7$ is —P(O)(NR$_2$)$_2$. In some embodiments, R$^7$ is —Si(OH)R$_2$. In some embodiments, R$^7$ is —Si(OH)$_2$R. In some embodiments, R$^7$ is an optionally substituted C$_{1-4}$ aliphatic. In some embodiments, R$^7$ and X$^1$ or X$^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur. In some embodiments, two R$^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur. In some embodiments, two R$^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur. In some embodiments, two R$^7$ groups on adjacent carbon atoms are optionally taken together with their intervening atoms to form a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, R$^7$ is selected from hydrogen, halogen, —CN, —OR, —NR$_2$, or C$_{1-4}$ alkyl. In some embodiments, R$^7$ is selected from hydrogen, halogen, —CN, or C$_{1-4}$ alkyl. In some embodiments, R$^7$ is fluoro. In some embodiments, two R$^7$ groups on the same carbon are optionally taken together with their intervening atoms to form a 3- or 4-membered spiro fused ring.
In some embodiments, R⁷ is selected from those depicted in Table 1 below.
As defined above and described herein, Ring A is a bi- or tricyclic ring selected from
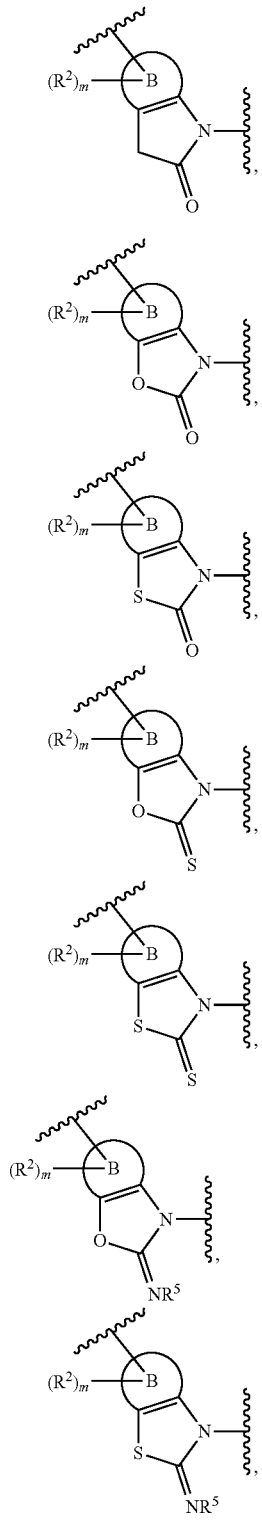
-continued
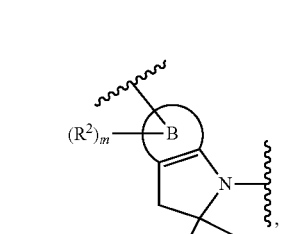
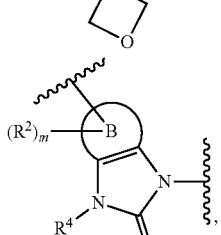
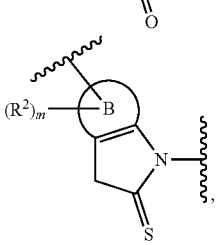
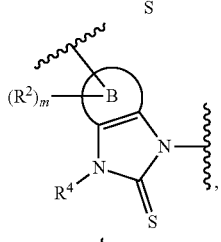
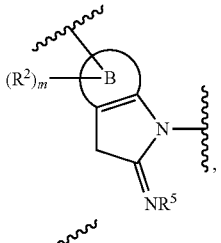
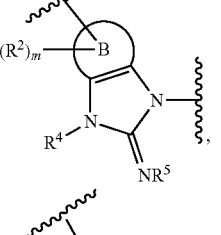
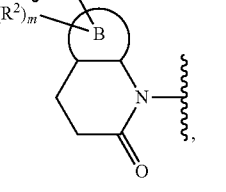
or
In some embodiments, Ring A is

In some embodiments, Ring A is
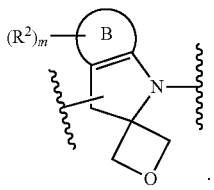
In some embodiments, Ring A is
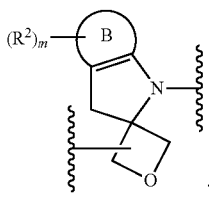
In some embodiments, Ring A is
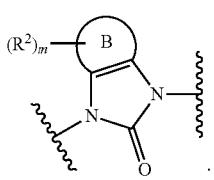
In some embodiments, Ring A is
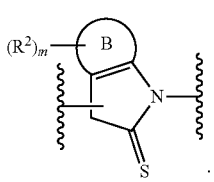
In some embodiments, Ring A is
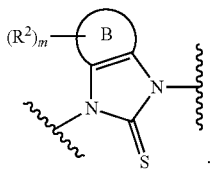
In some embodiments, Ring A is
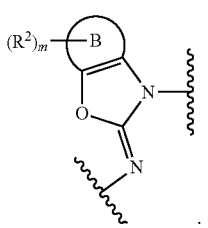
In some embodiments, Ring A is
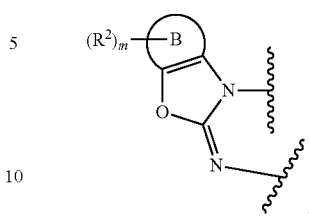
In some embodiments, Ring A is
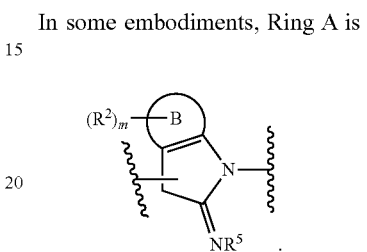
In some embodiments, Ring A is
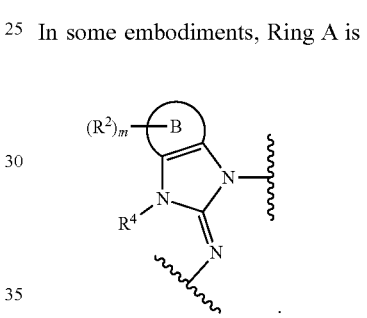
In some embodiments, Ring A is
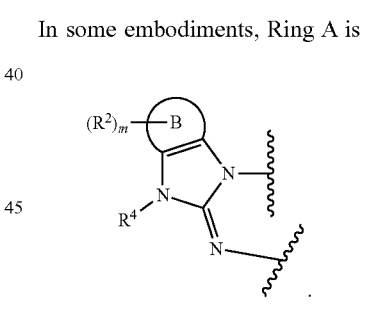
In some embodiments, Ring A
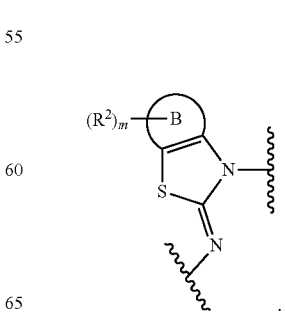

In some embodiments, Ring A is
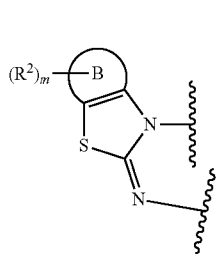
In some embodiments, Ring A is
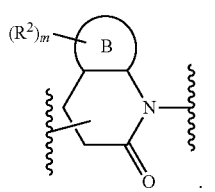
In some embodiments, Ring A is
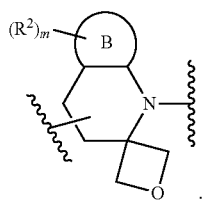
In some embodiments, Ring A is
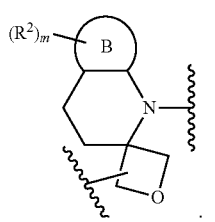
In some embodiments, Ring A is
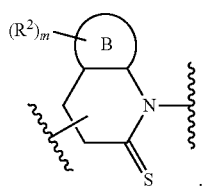
In some embodiments, Ring A is
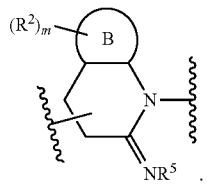
In some embodiments, Ring A is
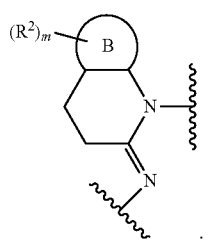
In some embodiments, Ring A is
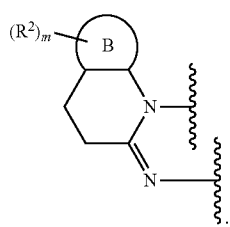
In some embodiments, Ring A is
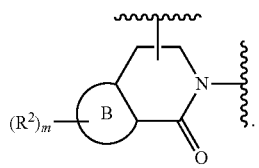
In some embodiments, Ring A is
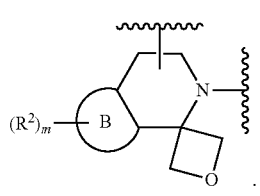

In some embodiments, Ring A is

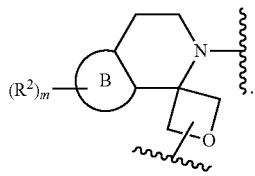

In some embodiments, Ring A is

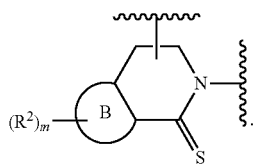

In some embodiments, Ring A is

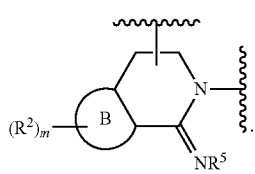

In some embodiments, Ring A is

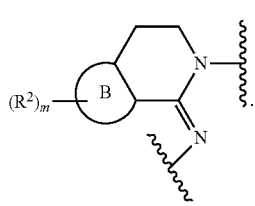

In some embodiments, Ring A is

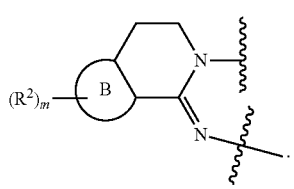

In some embodiments, Ring A is

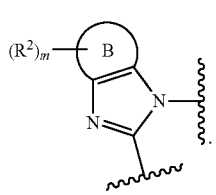

In some embodiments, Ring A is

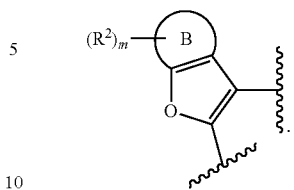

In some embodiments, Ring A is

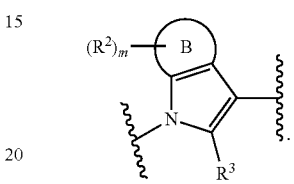

In some embodiments, Ring A is

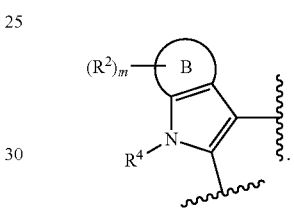

In some embodiments, Ring A is

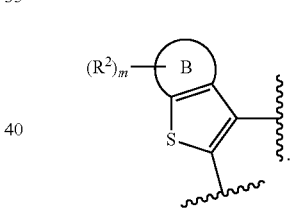

In some embodiments, Ring A is selected from those depicted in Table 1 below.

As defined above and described herein, Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring B is a fused 6-membered aryl. In some embodiments, Ring B is a fused 6-membered heteroaryl containing 1-4 heteroatoms independently selected from nitrogen, oxygen, or sulfur. In some embodiments, Ring B is a fused 5 to 7-membered saturated or partially unsaturated carbocyclyl. In some embodiments, Ring B is fused 5 to 7-membered saturated or partially saturated heterocyclyl with 1-3 heteroatoms independently selected from boron, nitrogen, oxygen, silicon, or sulfur. In some embodiments, Ring B is fused 5-membered heteroaryl with 1-4 heteroatoms independently selected from boron, nitrogen, oxygen, silicon, or sulfur.

In some embodiments, Ring B is
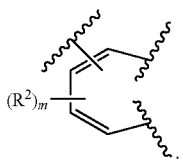
In some embodiments, Ring B is
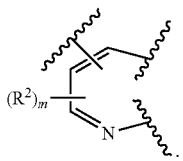
In some embodiments, Ring B is
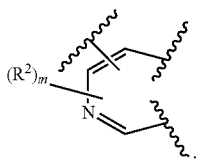
In some embodiments, Ring B is selected from those depicted in Table 1 below.
As defined above and described herein, Ring C is a mono- or bicyclic ring selected from
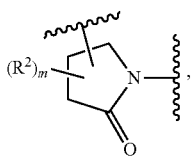
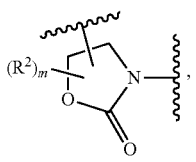
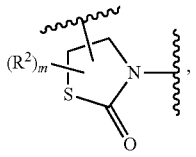
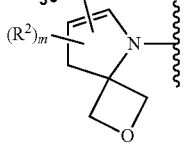
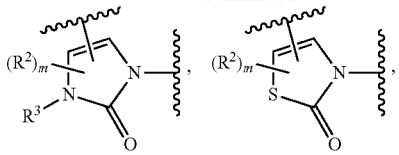
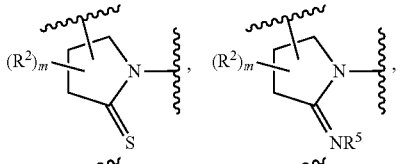

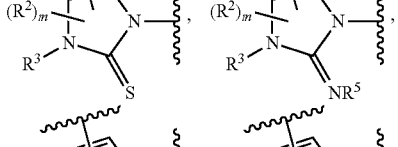

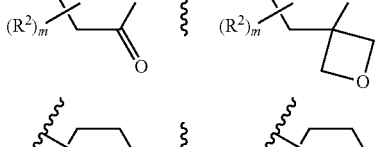
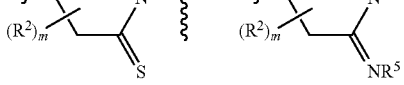
In some embodiments, Ring C is

In some embodiments, Ring C is
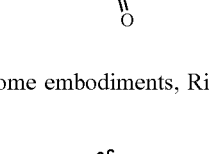

In some embodiments, Ring C is
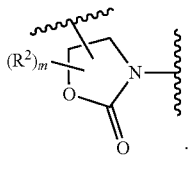
In some embodiments, Ring C is
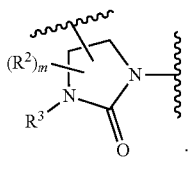
In some embodiments, Ring C is
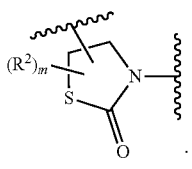
In some embodiments, Ring C is
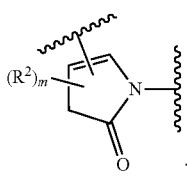
In some embodiments, Ring C is
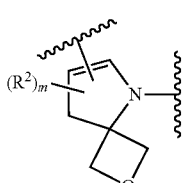
In some embodiments, Ring C is
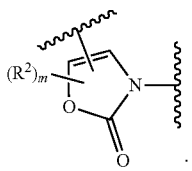
In some embodiments, Ring C is
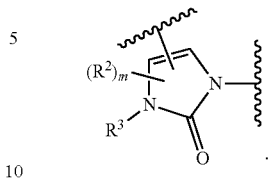
In some embodiments, Ring C is
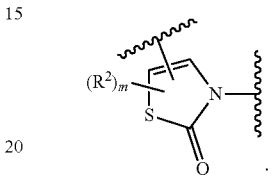
In some embodiments, Ring C is
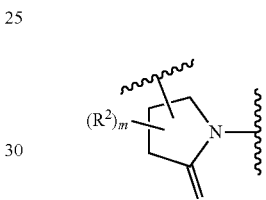
In some embodiments, Ring C is
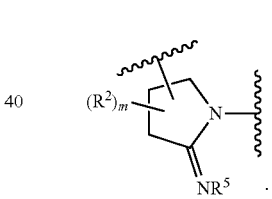
In some embodiments, Ring C is
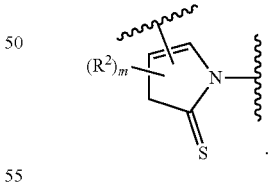
In some embodiments, Ring C is
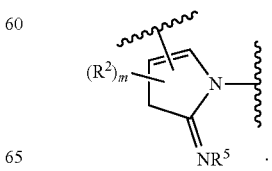

In some embodiments, Ring C is
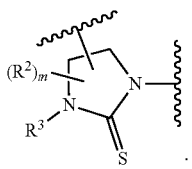
In some embodiments, Ring C is
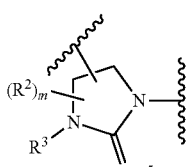
In some embodiments, Ring C is
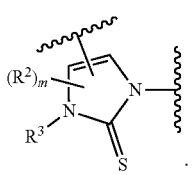
In some embodiments, Ring C is
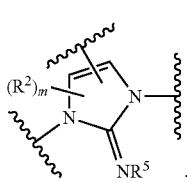
In some embodiments, Ring C is
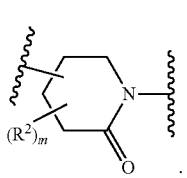
In some embodiments, Ring C is
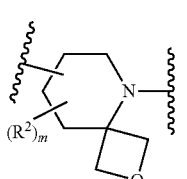
In some embodiments, Ring C is
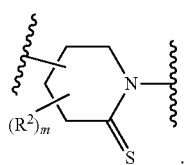
In some embodiments, Ring C is
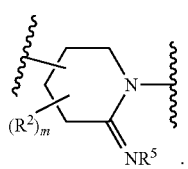
In some embodiments, Ring C is
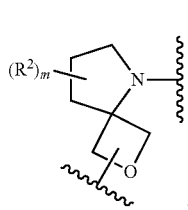
In some embodiments, Ring C is
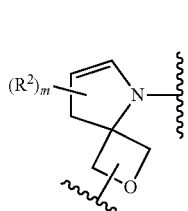
In some embodiments, Ring C is
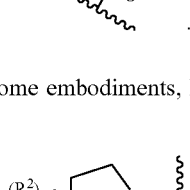
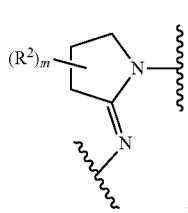
In some embodiments, Ring C is
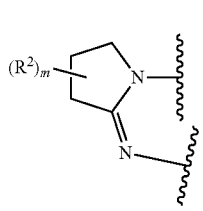

In some embodiments, Ring C is
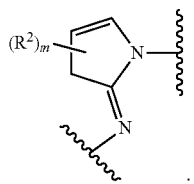
In some embodiments, Ring C is
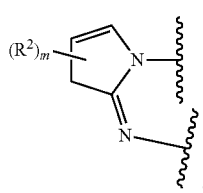
In some embodiments, Ring C is
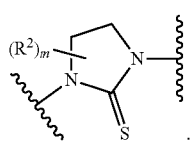
In some embodiments, Ring C is
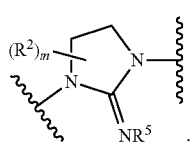
In some embodiments, Ring C is
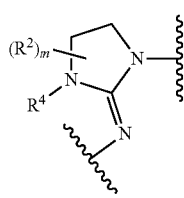
In some embodiments, Ring C is
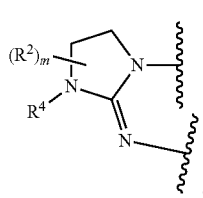
In some embodiments, Ring C is
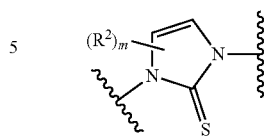
In some embodiments, Ring C is
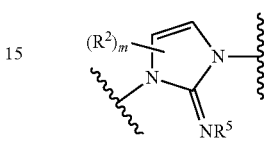
In some embodiments, Ring C is
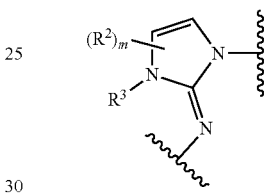
In some embodiments, Ring C is
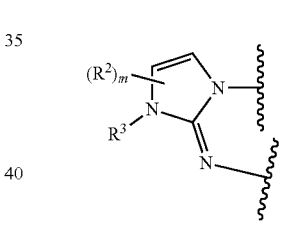
In some embodiments, Ring C is
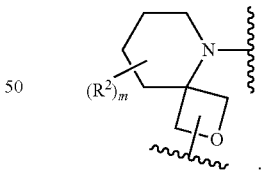
In some embodiments, Ring C is
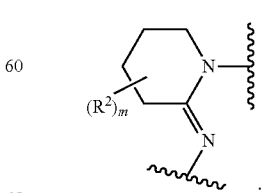

In some embodiments, Ring C is
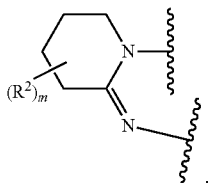
In some embodiments, Ring C is a mono- or bicyclic ring selected from
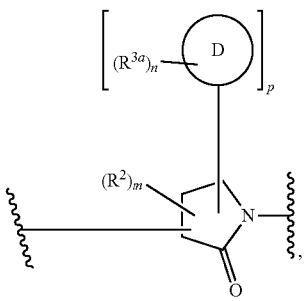
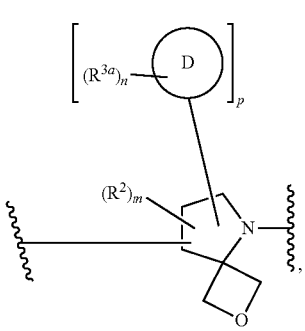
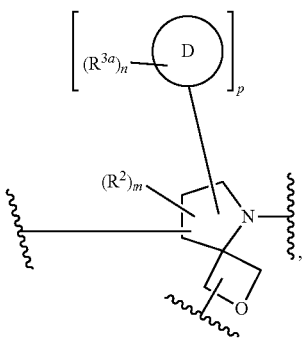
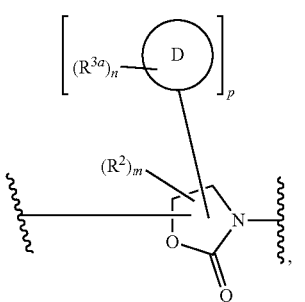
-continued
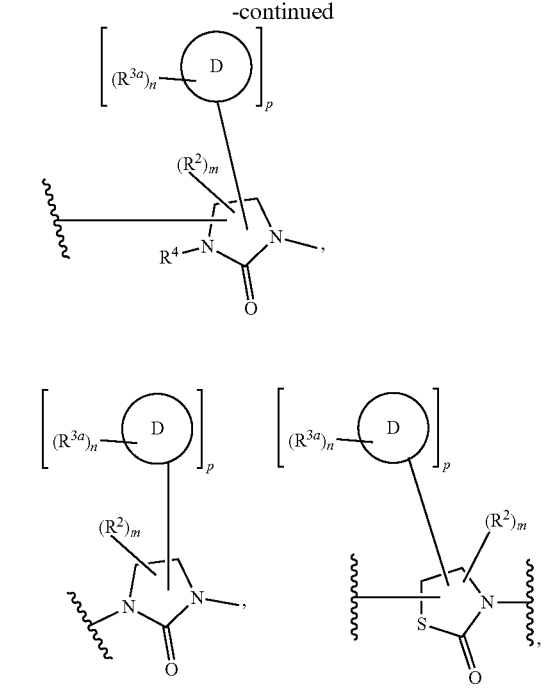
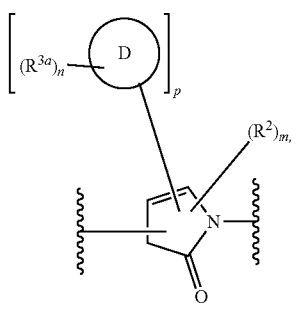
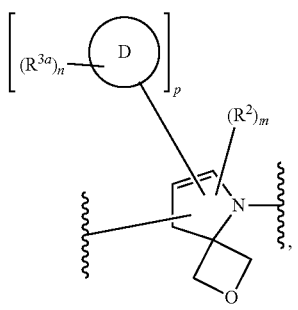
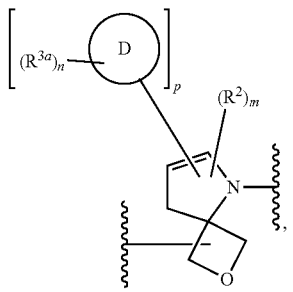

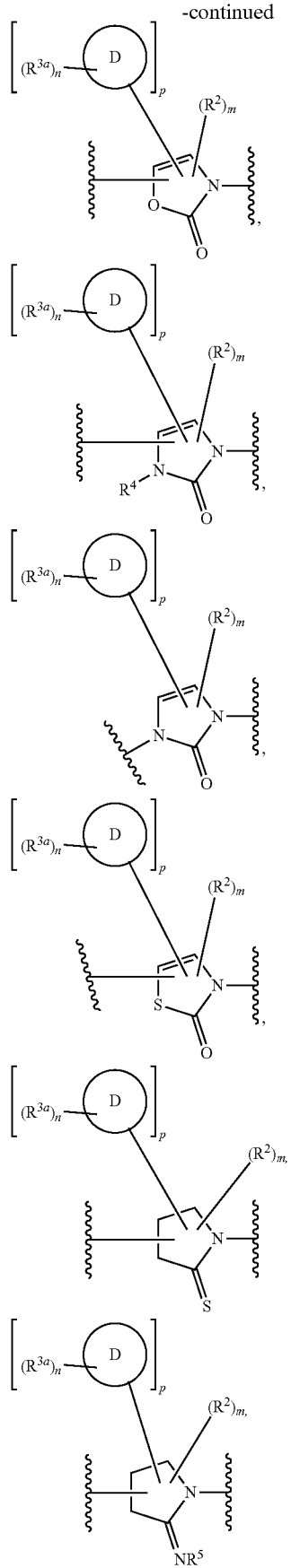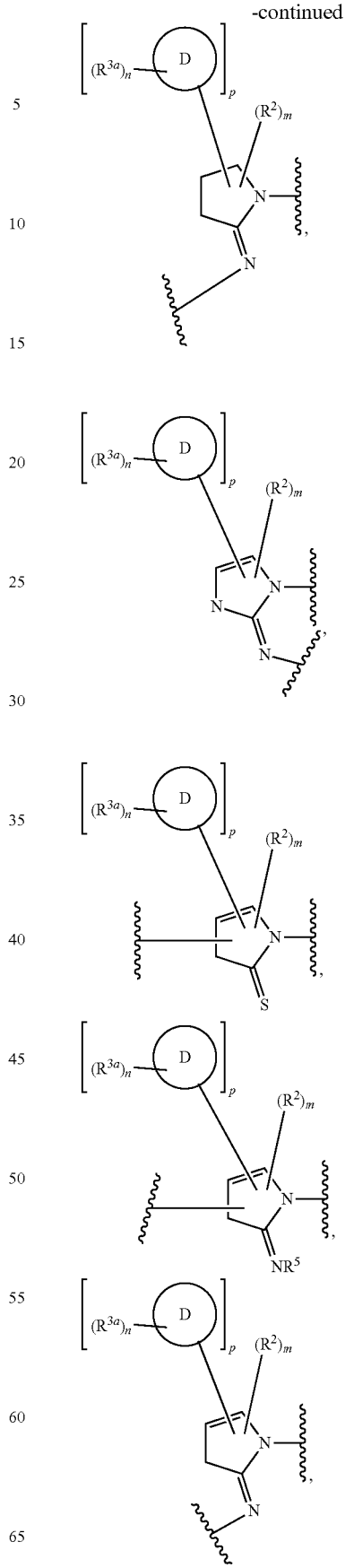

111
-continued
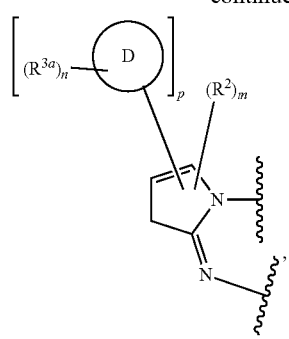
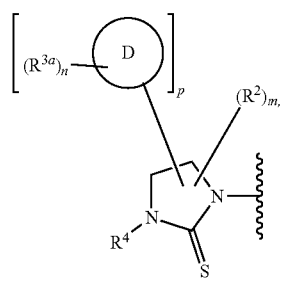
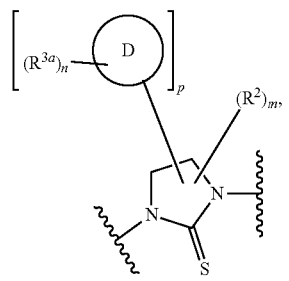
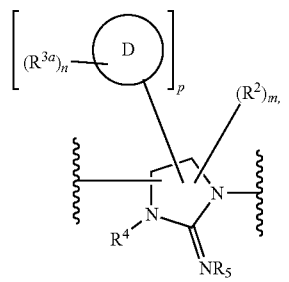
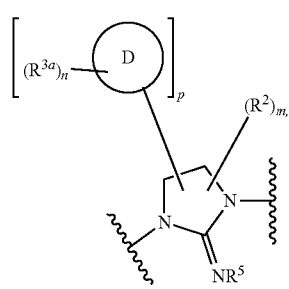
112
-continued
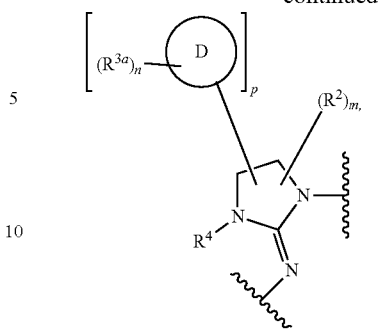
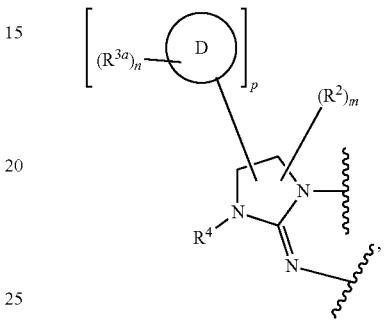
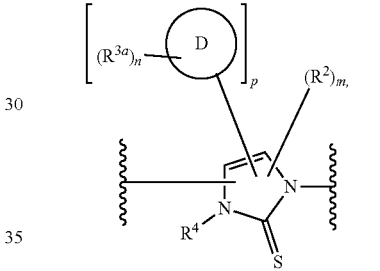
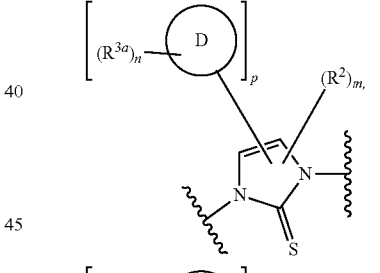

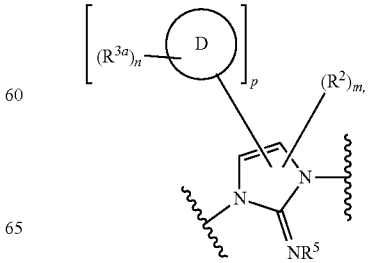

-continued
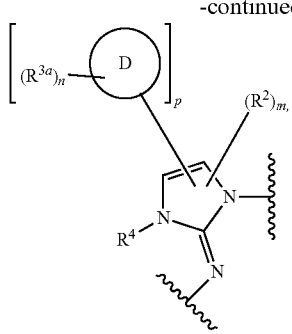
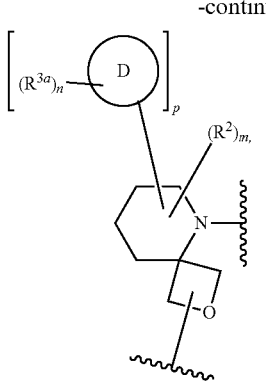
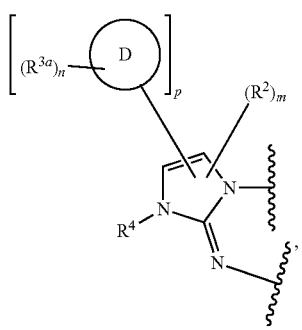
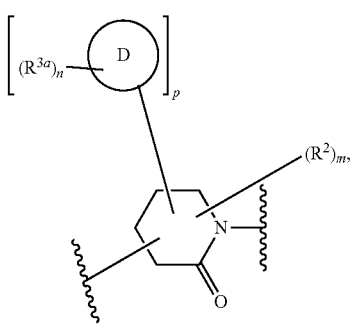
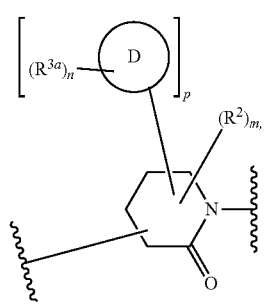
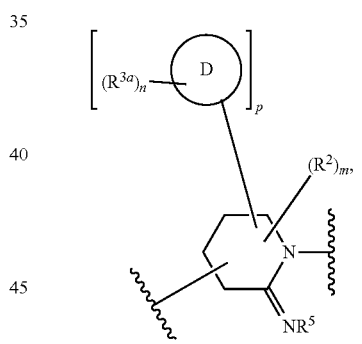
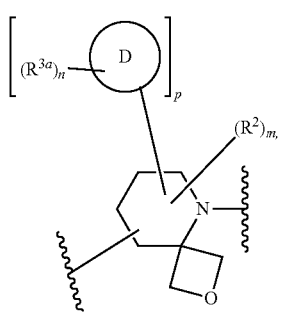
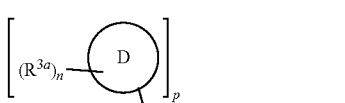
or
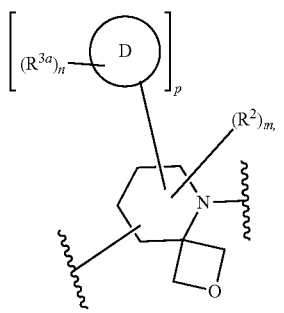
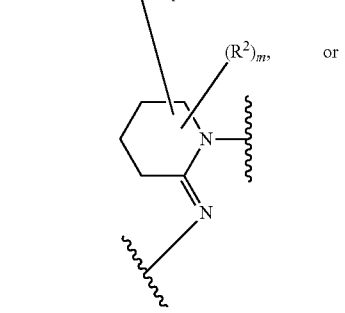

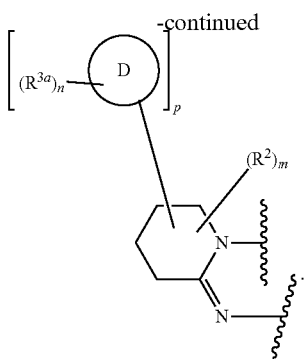

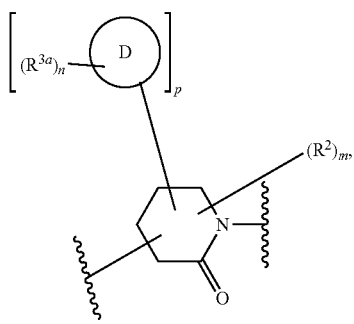

In some embodiments, Ring C is selected from those depicted in Table 1 below.

As defined above and described herein, Ring D is a ring selected from 6 to 10-membered aryl or heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring D is a 6 to 10-membered aryl. In some embodiments, Ring D is a 6 to 10-membered heteroaryl containing 1-4 heteroatoms independently selected from nitrogen, oxygen, or sulfur. In some embodiments, Ring D is a 5 to 7-membered saturated or partially unsaturated carbocyclyl. In some embodiments, Ring D is 5 to 7-membered saturated or partially saturated heterocyclyl with 1-3 heteroatoms independently selected from boron, nitrogen, oxygen, silicon, or sulfur. In some embodiments, Ring D is 5-membered heteroaryl with 1-4 heteroatoms independently selected from boron, nitrogen, oxygen, silicon, or sulfur.

In some embodiments, Ring D phenyl. In some embodiments, Ring D pyridyl. In some embodiments, Ring D is isoquinoline. In some embodiments, Ring D is imidazo[1,2-a]pyridine.

In some embodiments, Ring D is selected from those depicted in Table 1 below.

As defined above and described herein, each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups.

In some embodiments, each of Ring E, Ring F, and Ring G is independently a fused ring selected from 6-membered aryl. In some embodiments, each of Ring E, Ring F, and Ring G is independently a fused ring selected from 6-membered heteroaryl containing 1-4 heteroatoms independently selected from nitrogen, oxygen, or sulfur. In some embodiments, each of Ring E, Ring F, and Ring G is independently a fused ring selected from a 5 to 7-membered saturated or partially unsaturated carbocyclyl. In some embodiments, each of Ring E, Ring F, and Ring G is independently a fused ring selected from a 5 to 7-membered saturated or partially unsaturated heterocyclyl with 1-3 heteroatoms independently selected from boron, nitrogen, oxygen, silicon, or sulfur. In some embodiments, each of Ring E, Ring F, and Ring G is independently a fused ring selected from a 5-membered heteroaryl with 1-4 heteroatoms independently selected from nitrogen, oxygen or sulfur. In some embodiments, Ring E, Ring F, and Ring G is independently and optionally substituted with 1-2 oxo groups.

In some embodiments, Ring F is

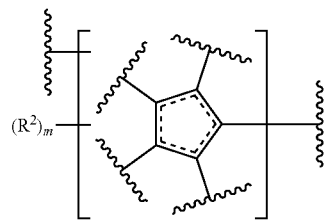

In some embodiments, each of Ring E and Ring G is independently

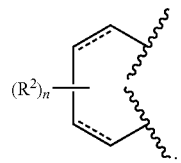

In some embodiments, each of Ring E and Ring G is independently

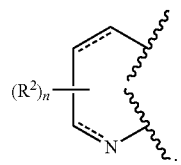

In some embodiments, each of Ring E and Ring G is independently N

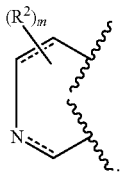

In some embodiments, each of Ring E and Ring G is independently

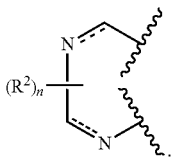

In some embodiments, each of Ring E and Ring G is independently

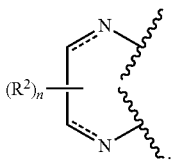

In some embodiments, Ring E, Ring F, and Ring G is

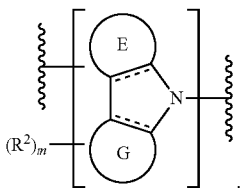

In some embodiments, Ring E, Ring F, and Ring G is

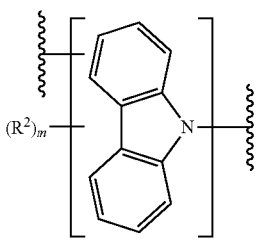

In some embodiments, Ring E, Ring F, and Ring G is

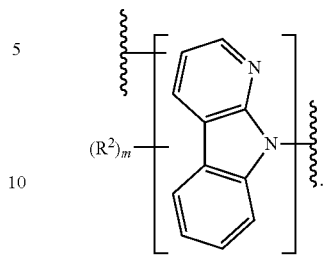

In some embodiments, Ring E, Ring F, and Ring G is selected from those depicted in Table 1, below.

As defined above and described herein, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups.

In some embodiments, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups.

As defined above and described herein, each of Ring I and Ring J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur In some embodiments, each of Ring I and Ring J is independently a 6-membered aryl. In some embodiments, each of Ring I and Ring J is independently a 6-membered heteroaryl containing 1-4 heteroatoms independently selected from nitrogen, oxygen, or sulfur. In some embodiments, each of Ring I and Ring J is independently a 5 to 7-membered saturated or partially unsaturated carbocyclyl. In some embodiments, each of Ring I and Ring J is independently a 5 to 7-membered saturated or partially unsaturated heterocyclyl with 1-3 heteroatoms independently selected from boron, nitrogen, oxygen, silicon, or sulfur. In some embodiments, each of Ring I and Ring J is independently a 5-membered heteroaryl with 1-3 heteroatoms independently selected from nitrogen, oxygen or sulfur.

In some embodiments, Ring I and Ring J is selected from those depicted in Table 1, below.

As defined above and described herein, Ring K is a fused ring selected from a 7-12 membered saturated or partially unsaturated carbocyclyl or heterocyclyl with 1-3 heteroatoms independently selected from boron, nitrogen, oxygen, silicon, or sulfur, wherein Ring H is optionally further substituted with 1-2 oxo groups.

In some embodiments, Ring K is a fused ring selected from a 7-12 membered saturated or partially unsaturated carbocyclyl. In some embodiments, Ring K is a 7-12 membered saturated or partially unsaturated heterocyclyl ring with 1-3 heteroatoms independently selected from boron, nitrogen, oxygen, silicon, or sulfur. In some embodiments, Ring K is optionally further substituted with 1-2 oxo groups.

In some embodiments, Ring K is selected from those depicted in Table 1 below.

As defined above and described herein, Ring M is selected from
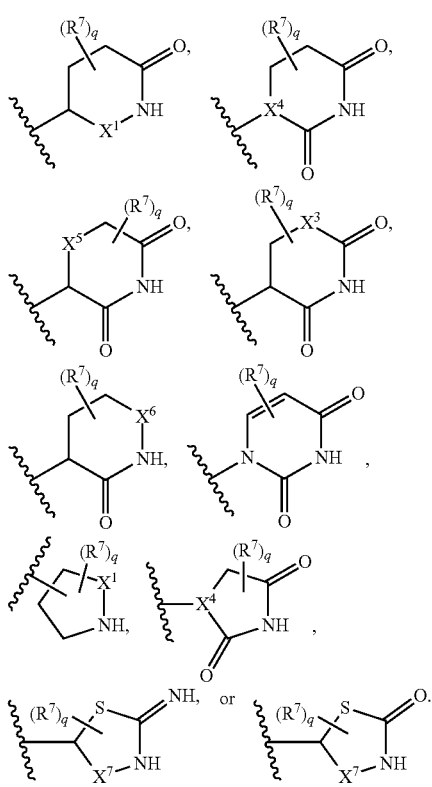
In some embodiments, Ring M is
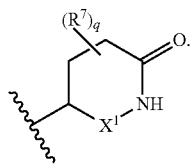
In some embodiments, Ring M is
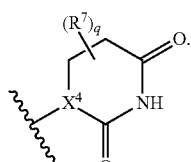
In some embodiments, Ring M is
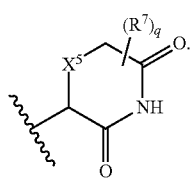
In some embodiments, Ring M is
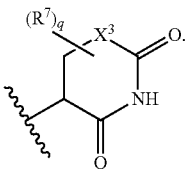
In some embodiments, Ring M is
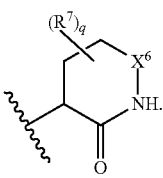
In some embodiments, Ring M is
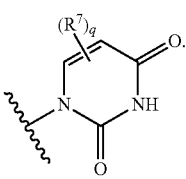
In some embodiments, Ring M is
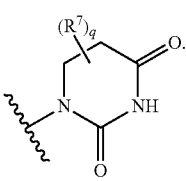
In some embodiments, Ring M is
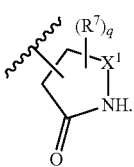
In some embodiments, Ring M is
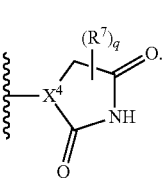

In some embodiments, Ring M is

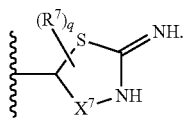

In some embodiments, Ring M is

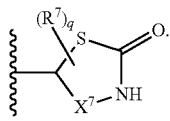

In some embodiments, Ring M is selected from those depicted in Table 1 below.

As defined above and described here, $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

In some embodiments, $L^1$ is a covalent bond. In some embodiments, $L^1$ is a $C_{1-3}$ aliphatic. In some embodiments, $L^1$ is —CH$_2$—. In some embodiments, $L^1$ is —C(D)(H)—. In some embodiments, $L^1$ is —C(D)$_2$-. In some embodiments, $L^1$ is —CH$_2$CH$_2$—. In some embodiments, $L^1$ is —NR—. In some embodiments, $L^1$ is —CH$_2$NR—. In some embodiments, $L^1$ is or —O—. In some embodiments, $L^1$ is —CH$_2$O—. In some embodiments, $L^1$ is —S—. In some embodiments, $L^1$ is —OC(O)—. In some embodiments, $L^1$ is —C(O)O—. In some embodiments, $L^1$ is —C(O)—. In some embodiments, $L^1$ is —S(O)—. In some embodiments, $L^1$ is —S(O)$_2$—. In some embodiments, $L^1$ is —NRS(O)$_2$—. In some embodiments, $L^1$ is —S(O)$_2$NR—. In some embodiments, $L^1$ is —NRC(O)—. In some embodiments, $L^1$ is —C(O)NR—.

In some embodiments, Ring $L^1$ is selected from those depicted in Table 1 below.

As defined above and described herein, === is a single or double bond.

In some embodiments, === is a single bond. In some embodiments, === is a double bond.

In some embodiments, === is selected from those depicted in Table 1 below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1 below.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In some embodiments, n is selected from those depicted in Table 1 below.

As defined above and described herein, p is 0 or 1.

In some embodiments, p is 0. In some embodiments, p is 1.

In some embodiments, p is selected from those depicted in Table 1 below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1 below.

In some embodiments, LBM is

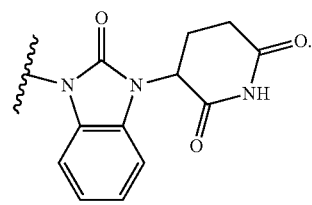 [SMILES: *n1c(=O)n(C2CCC(=O)NC2=O)c2ccccc21]

In some embodiments, LBM is

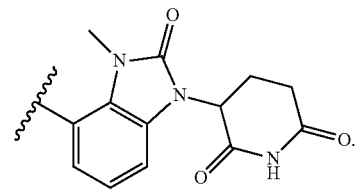 [SMILES: *c1cccc2c1n(C)c(=O)n2C1CCC(=O)NC1=O]

In some embodiments, LBM is

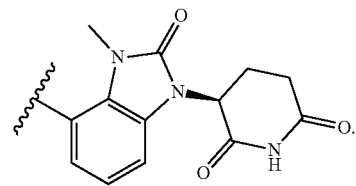 [SMILES: *c1cccc2c1n(C)c(=O)n2[C@H]1CCC(=O)NC1=O]

In some embodiments LBM is

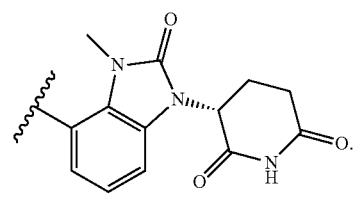

In some embodiments, LBM is
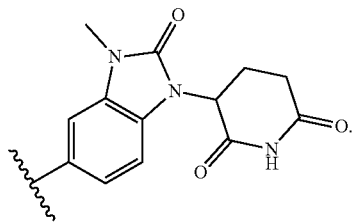 [SMILES: *c1ccc2c(c1)n(C)c(=O)n2C1CCC(=O)NC1=O]
In some embodiments, LBM is
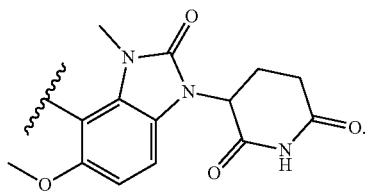 [SMILES: *c1c(OC)ccc2c1n(C)c(=O)n2C1CCC(=O)NC1=O]
In some embodiments, LBM is
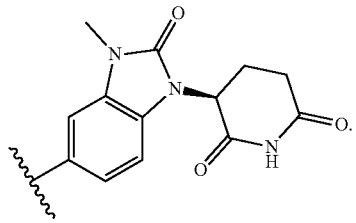 [SMILES: *c1ccc2c(c1)n(C)c(=O)n2[C@H]1CCC(=O)NC1=O]
In some embodiments, LBM is
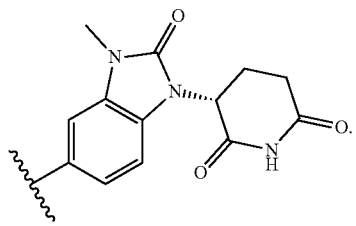 [SMILES: *c1ccc2c(c1)n(C)c(=O)n2[C@@H]1CCC(=O)NC1=O]
In some embodiments, LBM is
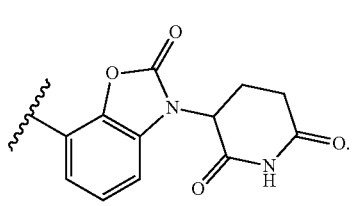 [SMILES: *c1cccc2c1oc(=O)n2C1CCC(=O)NC1=O]
In some embodiments, LBM is
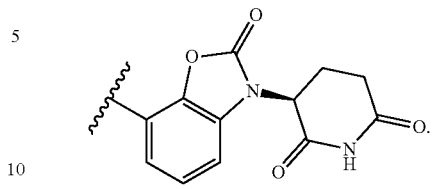
In some embodiments, LBM is
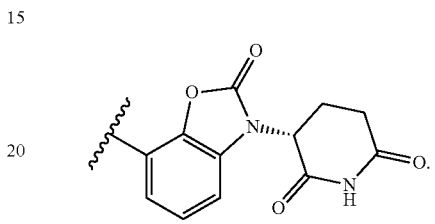
In some embodiments, LBM is
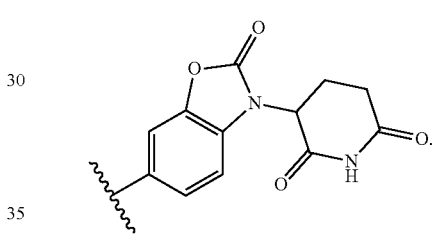
In some embodiments, LBM is
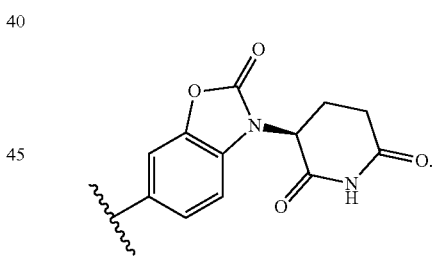
In some embodiments, LBM is
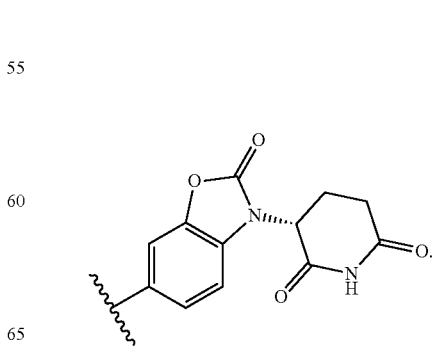

In some embodiments, LBM is
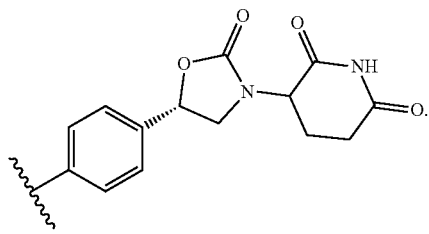 [SMILES: *c1ccc([C@H]2CN(C3CCC(=O)NC3=O)C(=O)O2)cc1]
In some embodiments, LBM is
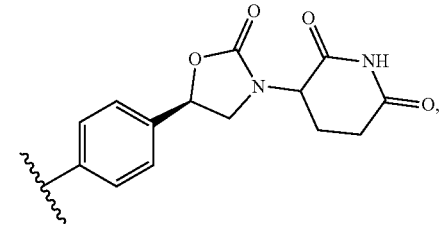
In some embodiments, LBM is
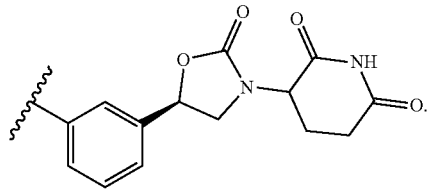 [SMILES: *c1cccc([C@@H]2CN(C3CCC(=O)NC3=O)C(=O)O2)c1]
In some embodiments, LBM is
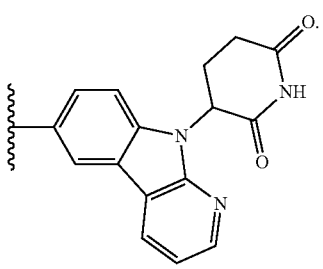 [SMILES: *c1ccc2c(c1)c1cccnc1n2C1CCC(=O)NC1=O]
In some embodiments, LBM is
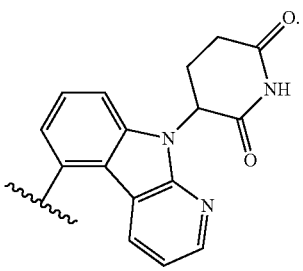 [SMILES: *c1cccc2c1c1cccnc1n2C1CCC(=O)NC1=O]
In some embodiments, LBM is
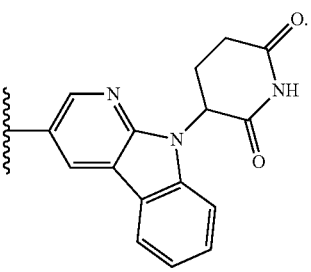 [SMILES: *c1cnc2c(c1)c1ccccc1n2C1CCC(=O)NC1=O]
In some embodiments, LBM is
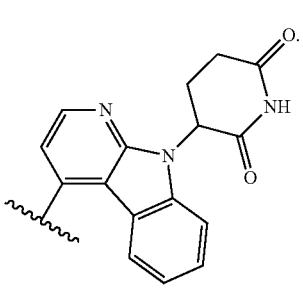 [SMILES: *c1ccnc2c1c1ccccc1n2C1CCC(=O)NC1=O]
In some embodiments, LBM is
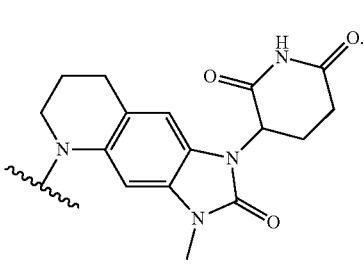 [SMILES: *N1CCCc2cc3c(cc21)n(C)c(=O)n3C1CCC(=O)NC1=O]
In some embodiments, LBM is
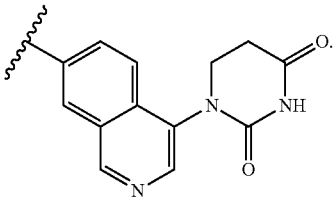 [SMILES: *c1ccc2c(N3CCC(=O)NC3=O)cncc2c1]

In some embodiments, LBM is

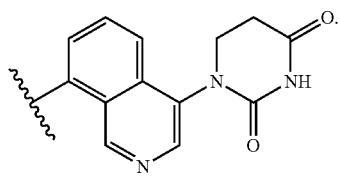 [SMILES: *c1cccc2c(N3CCC(=O)NC3=O)cncc12]

In some embodiments, LBM is

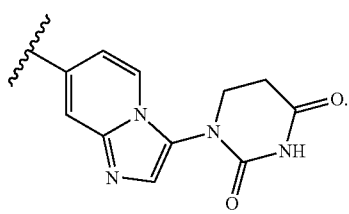 [SMILES: *c1ccn2c(N3CCC(=O)NC3=O)cnc2c1]

In some embodiments, LBM is

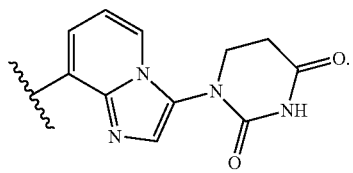 [SMILES: *c1cccn2c(N3CCC(=O)NC3=O)cnc12]

In some embodiments, LBM is

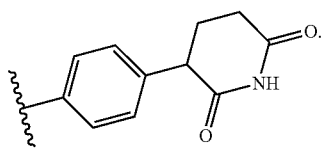 [SMILES: *c1ccc(C2CCC(=O)NC2=O)cc1]

In some embodiments, LBM is

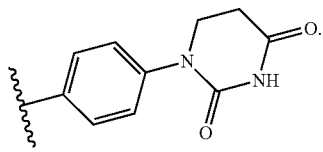 [SMILES: *c1ccc(N2CCC(=O)NC2=O)cc1]

In some embodiments, LBM is

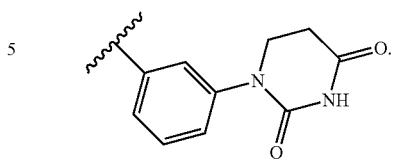

In some embodiments, LBM is

In some embodiments, LBM is


In some embodiments, LBM is

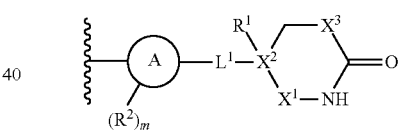

In some embodiments, LBM is selected from those in Table 1 below.

In some embodiments, the present invention provides the compound of formula I-a, wherein LBM is

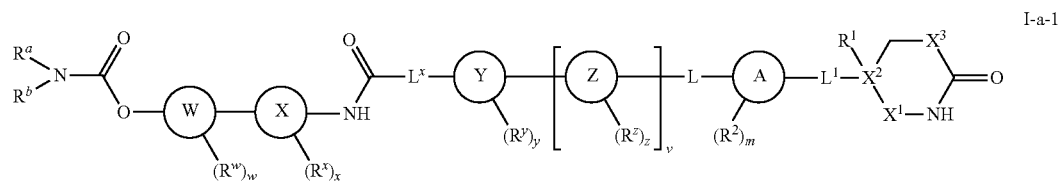

from formula I-aa, to provide a compound of formula I-a-1:

I-a-1 or a pharmaceutically acceptable salt thereof, wherein each of $X^1$, $X^2$, $X^3$, $R^a$, $R^b$, $R^1$, $R^2$, $R^w$, $R^x$, $R^y$, $R^z$, L, $L^1$, $L^x$, Ring A, Ring W, Ring X, Ring Y, Ring Z, m, v, w, x, y, and z is as defined above and described in embodiments herein, both singly and in combination.

In some embodiments, the present invention provides the compound of formula I-a-1, wherein $X^2$ is a carbon atom, $X^3$ is —$CH_2$—, $L^1$ is a covalent bond, Ring W is cyclopentyl, and Ring X is pyrrazolyl as shown, to provide a compound of formula I-a-2:

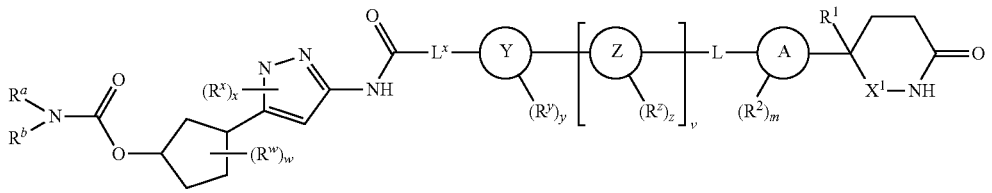

or a pharmaceutically acceptable salt thereof, wherein each of $X^1$, $R^a$, $R^b$, $R^1$, $R^2$, $R^w$, $R^x$, $R^y$, $R^z$, L, $L^x$, Ring A, Ring Y, Ring Z, m, v, w, x, y, and z is as defined above and described in embodiments herein, both singly and in combination.

In some embodiments, the present invention provides the compound of formula I-a, wherein LBM is

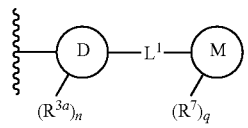

from formula I-nn, to provide a compound of formula I-a-3:

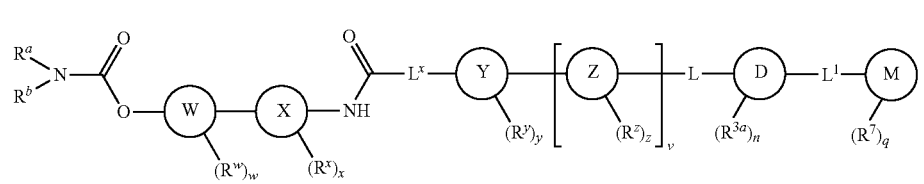

or a pharmaceutically acceptable salt thereof, wherein each of $R^a$, $R^b$, $R^{3a}$, $R^7$, $R^w$, $R^x$, $R^y$, $R^z$, L, $L^1$, $L^x$, Ring D, Ring

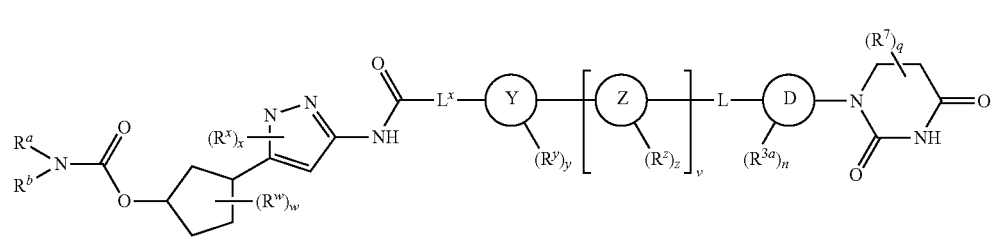

M, Ring W, Ring X, Ring Y, Ring Z, n, q, v, w, x, y, and z is as defined above and described in embodiments herein, both singly and in combination.

In some embodiments, the present invention provides the compound of formula I-a-3, wherein Ring M is

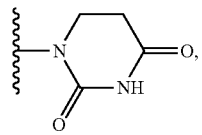

$L^1$ is a covalent bond, Ring W is cyclopentyl, and Ring X is pyrrazolyl as shown, to provide a compound of formula I-a-4:

or a pharmaceutically acceptable salt thereof, wherein each of $R^a$, $R^b$, $R^{3a}$, $R^7$, $R^w$, $R^x$, $R^y$, $R^z$, L, $L^x$, Ring D, Ring Y, Ring Z, n, q, v, w, x, y, and z is as defined above and described in embodiments herein, both singly and in combination.

In some embodiments, the present invention provides the compound of formula I-b, wherein LBM is

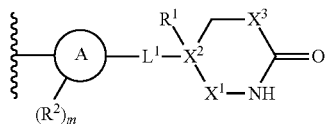

from formula I-aa, to provide a compound of formula I-b-1:

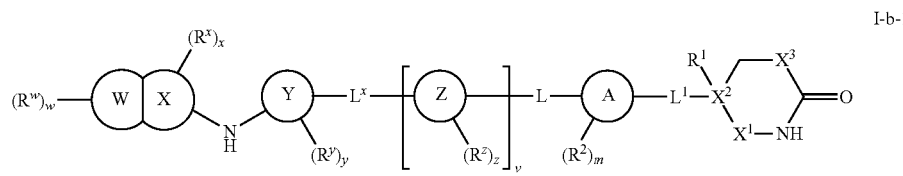

I-b-1 or a pharmaceutically acceptable salt thereof, wherein each of $X^1$, $X^2$, $X^3$, $R^1$, $R^2$, $R^w$, $R^x$, $R^y$, $R^z$, L, $L^1$, $L^x$, Ring A, Ring W, Ring X, Ring Y, Ring Z, m, v, w, x, y, and z is as defined above and described in embodiments herein, both singly and in combination.

In some embodiments, the present invention provides the compound of formula I-b-1, wherein $X^2$ is a carbon atom, $X^3$ is —$CH_2$—, $L^1$ is a covalent bond, and Ring X is pyrimidinyl as shown, to provide a compound of formula I-b-2:

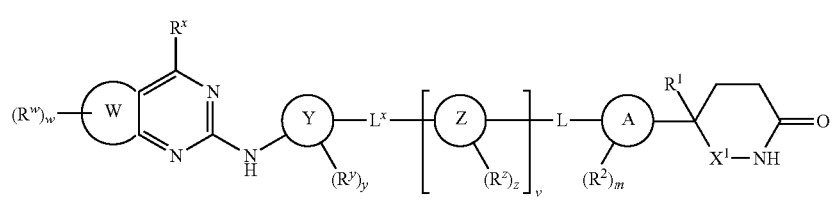

I-b-2 or a pharmaceutically acceptable salt thereof, wherein each of $X^1$, $R^a$, $R^b$, $R^1$, $R^2$, $R^w$, $R^x$, $R^y$, $R^z$, L, $L^x$, Ring A, Ring Y, Ring Z, m, v, w, x, y, and z is as defined above and described in embodiments herein, both singly and in combination.

In some embodiments, the present invention provides the compound of formula I-b-1, wherein $X^2$ is a carbon atom, $X^3$ is —$CH_2$—, $L^1$ is a covalent bond, Ring W is 2-pyrrolidonyl, and Ring X is pyrimidinyl as shown, to provide a compound of formula I-b-3:

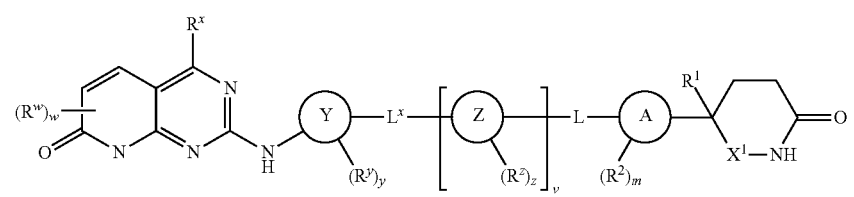

I-b-3 or a pharmaceutically acceptable salt thereof, wherein each of $X^1$, $R^a$, $R^b$, $R^1$, $R^2$, $R^w$, $R^x$, $R^y$, $R^z$, L, $L^x$, Ring A, Ring Y, Ring Z, m, v, w, x, y, and z is as defined above and described in embodiments herein, both singly and in combination.

In some embodiments, the present invention provides the compound of formula I-b-1, wherein $X^2$ is a carbon atom, $X^3$ is —$CH_2$—, $L^1$ is a covalent bond, Ring W is 2-pyrrolidonyl, and Ring X is pyrimidinyl as shown, to provide a compound of formula I-b-4:

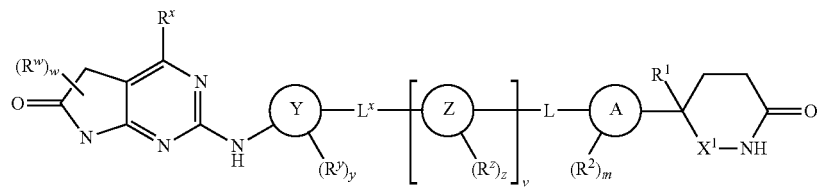

I-b-4 or a pharmaceutically acceptable salt thereof, wherein each of $X^1$, $R^a$, $R^b$, $R^1$, $R^2$, $R^w$, $R^x$, $R^y$, $R^z$, L, $L^x$, Ring A, Ring Y, Ring Z, m, v, w, x, y, and z is as defined above and described in embodiments herein, both singly and in combination.

In some embodiments, the present invention provides the compound of formula I-b, wherein LBM is

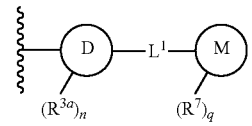

from formula I-nn, to provide a compound of formula I-b-5:

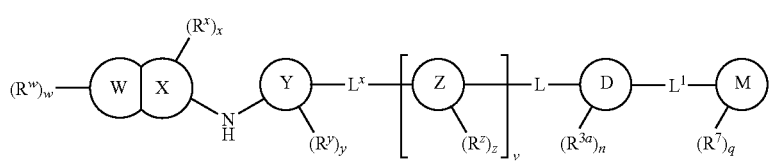

I-b-5 or a pharmaceutically acceptable salt thereof, wherein each of $R^{3a}$, $R^7$, $R^w$, $R^x$, $R^y$, $R^z$, L, $L^1$, $L^x$, Ring D, Ring M, Ring W, Ring X, Ring Y, Ring Z, n, q, v, w, x, y, and z is as defined above and described in embodiments herein, both singly and in combination.

In some embodiments, the present invention provides the compound of formula I-b-5, wherein Ring M is

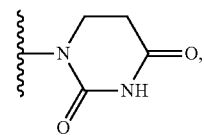 [SMILES: *N1CCC(=O)NC1=O]

$L^1$ is a covalent bond, and Ring X is pyrimidinyl as shown, to provide a compound of formula I-b-6:

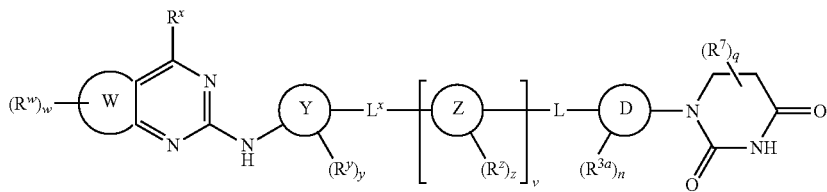

I-b-6 or a pharmaceutically acceptable salt thereof, wherein each of $R^{3a}$, $R^7$, $R^w$, $R^x$, $R^y$, $R^z$, L, $L^x$, Ring D, Ring W, Ring Y, Ring Z, n, q, v, w, x, y, and z is as defined above and described in embodiments herein, both singly and in combination.

In some embodiments, the present invention provides the compound of formula I-b-5, wherein Ring M is

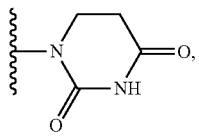 [SMILES: *N1CCC(=O)NC1=O]

$L^1$ is a covalent bond, Ring W is 2-pyridonyl, and Ring X is pyrimidinyl as shown, to provide a compound of formula I-b-7:

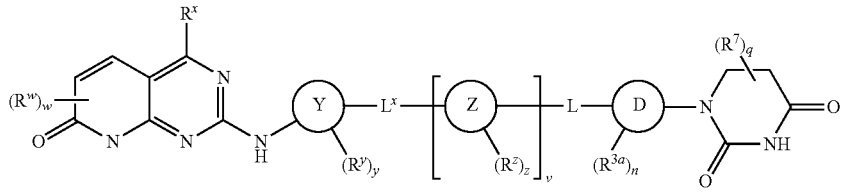

I-b-7 or a pharmaceutically acceptable salt thereof, wherein each of $R^{3a}$, $R^7$, $R^w$, $R^x$, $R^y$, $R^z$, L, $L^x$, Ring D, Ring Y, Ring Z, n, q, v, w, x, y, and z is as defined above and described in embodiments herein, both singly and in combination.

In some embodiments, the present invention provides the compound of formula I-b-5, wherein Ring M is

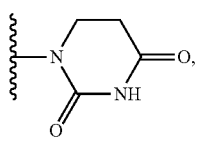 [SMILES: *N1CCC(=O)NC1=O]

$L^1$ is a covalent bond, Ring W is 2-pyrrolidonyl, and Ring X is pyrimidinyl as shown, to provide a compound of formula I-b-8:

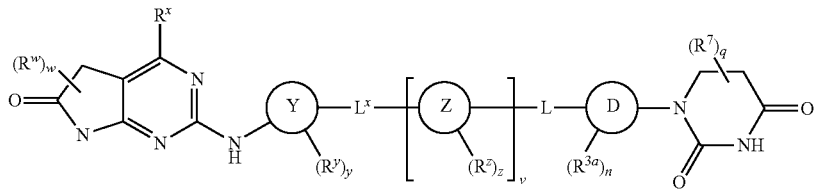

I-b-8 or a pharmaceutically acceptable salt thereof, wherein each of $R^{3a}$, $R^7$, $R^w$, $R^x$, $R^y$, $R^z$, L, $L^x$, Ring D, Ring Y, Ring Z, n, q, v, w, x, y, and z is as defined above and described in embodiments herein, both singly and in combination.

In some embodiments, the present invention provides the compound of formula I-c, wherein LBM is

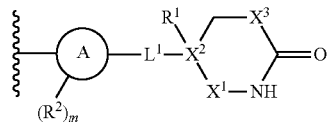

from formula I-aa, to provide a compound of formula I-c-1:

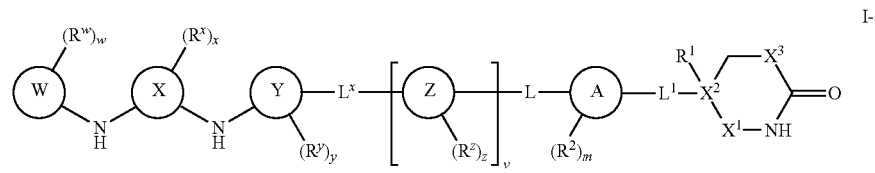

I-c-1 or a pharmaceutically acceptable salt thereof, wherein each of $X^1$, $X^2$, $X^3$, $R^1$, $R^2$, $R^w$, $R^x$, $R^y$, $R^z$, L, $L^1$, $L^x$, Ring A, Ring W, Ring X, Ring Y, Ring Z, m, v, w, x, y, and z is as defined above and described in embodiments herein, both singly and in combination.

In some embodiments, the present invention provides the compound of formula I-c-1, wherein $X^2$ is a carbon atom, $X^3$ is —$CH_2$—, $L^1$ is a covalent bond, Ring W is phenyl, and Ring X is pyrimidinyl as shown, to provide a compound of formula I-c-2:

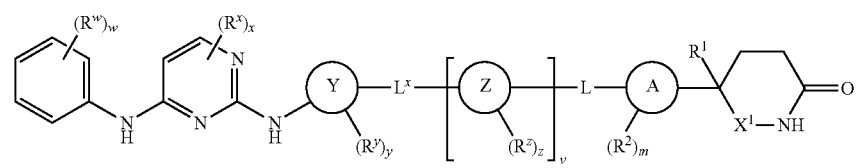

I-c-2 or a pharmaceutically acceptable salt thereof, wherein each of $X^1$, $R^1$, $R^2$, $R^w$, $R^x$, $R^y$, $R^z$, L, $L^x$, Ring A, Ring Y, Ring Z, m, v, w, x, y, and z is as defined above and described in embodiments herein, both singly and in combination.

In some embodiments, the present invention provides the compound of formula I-c, wherein LBM is

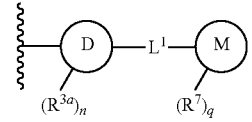

from formula I-nn, to provide a compound of formula I-c-3:

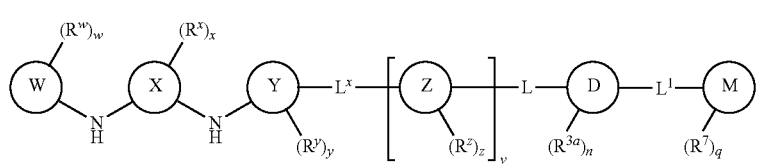

I-c-3 or a pharmaceutically acceptable salt thereof, wherein each of $R^{3a}$, $R^7$, $R^w$, $R^x$, $R^y$, $R^z$, L, $L^1$, $L^x$, Ring D, Ring M, Ring W, Ring X, Ring Y, Ring Z, n, q, v, w, x, y, and z is as defined above and described in embodiments herein, both singly and in combination.

In some embodiments, the present invention provides the compound of formula I-c-3, wherein Ring M is

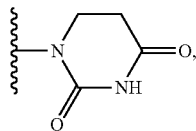

$L^1$ is a covalent bond, Ring W is phenyl, and Ring X is pyrimidinyl as shown, to provide a compound of formula I-c-4:

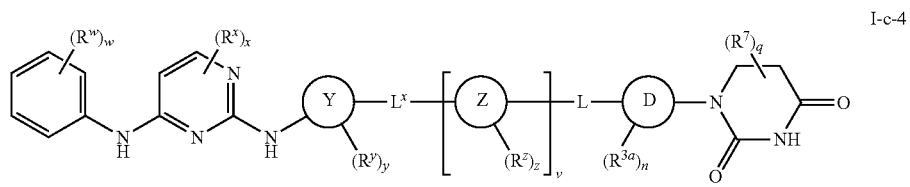

I-c-4 or a pharmaceutically acceptable salt thereof, wherein each of $R^{3a}$, $R^7$, $R^w$, $R^x$, $R^y$, $R^z$, L, $L^x$, Ring D, Ring Y, Ring Z, n, q, v, w, x, y, and z is as defined above and described in embodiments herein, both singly and in combination.

In some embodiments, the present invention provides the compound of formula I-e, wherein LBM is

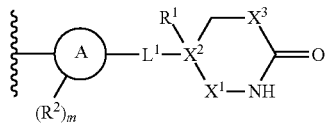

from formula I-aa, to provide a compound of formula I-e-1:

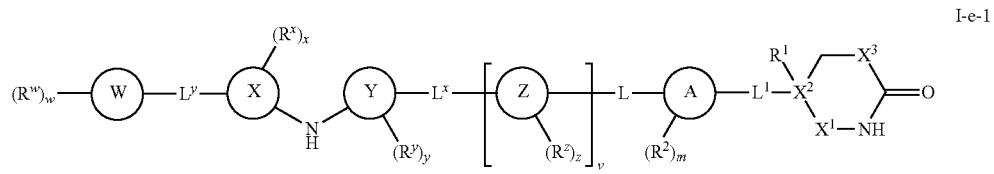

I-e-1 or a pharmaceutically acceptable salt thereof, wherein each of $X^1$, $X^2$, $X^3$, $R^1$, $R^2$, $R^w$, $R^x$, $R^y$, $R^z$, L, $L^1$, $L^x$, L, Ring A, Ring W, Ring X, Ring Y, Ring Z, m, v, w, x, y, and z is as defined above and described in embodiments herein, both singly and in combination.

In some embodiments, the present invention provides the compound of formula I-e-1, wherein $X^2$ is a carbon atom, $X^3$ is —$CH_2$—, $L^1$ is a covalent bond, and Ring X is pyrimidinyl as shown, to provide a compound of formula I-e-2:

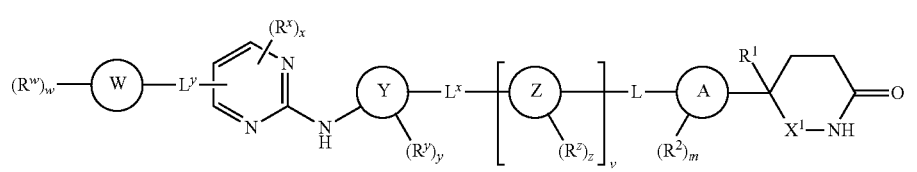

I-e-2 or a pharmaceutically acceptable salt thereof, wherein each of $X^1$, $R^1$, $R^2$, $R^w$, $R^x$, $R^y$, $R^z$, L, $L^x$, $L^y$, Ring A, Ring Y, Ring Z, m, v, w, x, y, and z is as defined above and described in embodiments herein, both singly and in combination.

In some embodiments, the present invention provides the compound of formula I-e, wherein LBM is

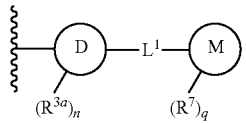

from formula I-nn, to provide a compound of formula I-e-3:

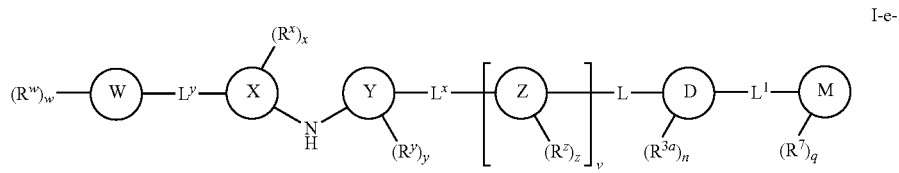

I-e-3 or a pharmaceutically acceptable salt thereof, wherein each of $R^{3a}$, $R^7$, $R^w$, $R^x$, $R^y$, $R^z$, L, L $L^x$, $L^y$, Ring D, Ring M, Ring W, Ring X, Ring Y, Ring Z, n, q, v, w, x, y, and z is as defined above and described in embodiments herein, both singly and in combination.

In some embodiments, the present invention provides the compound of formula I-e-3, wherein Ring M is

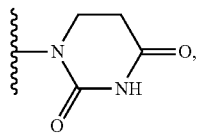

$L^1$ is a covalent bond, and Ring X is pyrimidinyl as shown, to provide a compound of formula I-e-4:

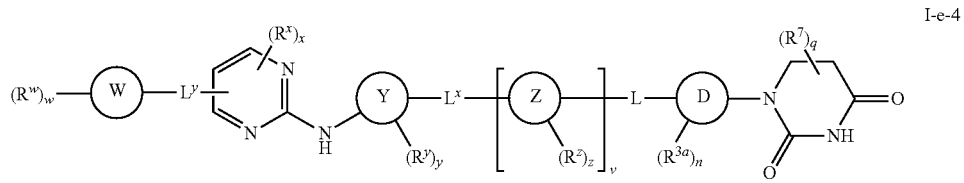

I-e-4 or a pharmaceutically acceptable salt thereof, wherein each of $R^{3a}$, $R^7$, $R^w$, $R^x$, $R^y$, $R^z$, L, LU, L, Ring D, Ring W, Ring Y, Ring Z, n, q, v, w, x, y, and z is as defined above and described in embodiments herein, both singly and in combination.

In certain embodiments, the present invention provides a compound of Formula I, wherein LBM is an E3 ubiquitin ligase (cereblon) binding moiety thereby forming a compound of formula I-oo-1, I-oo-2 I-oo-3, I-oo-4, I-oo-5, I-oo-6, I-oo-7, I-oo-8, I-oo-9, or I-oo-10 respectively:

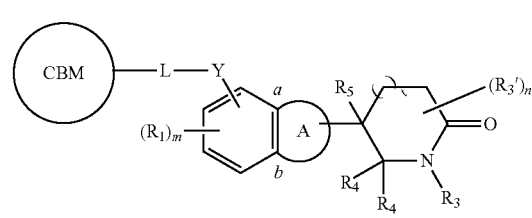

I-oo-1

I-oo-2
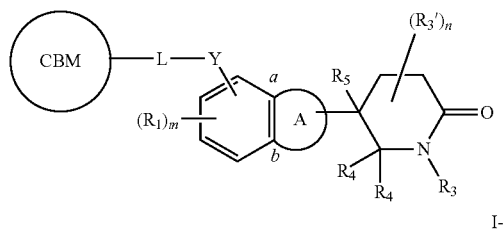
I-oo-3
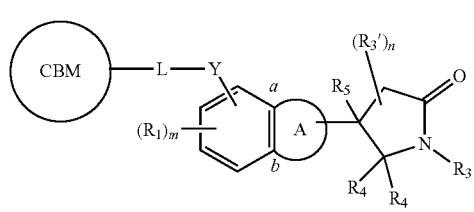
I-oo-4
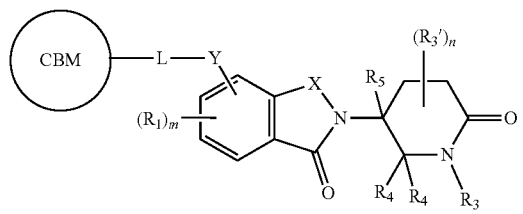
I-oo-5
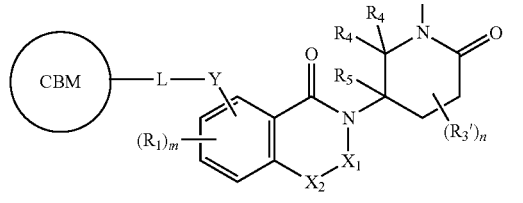
I-oo-6
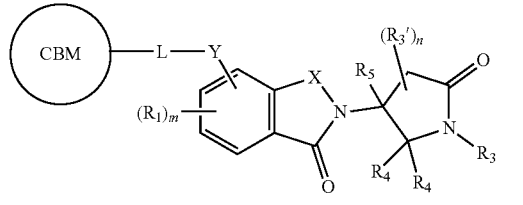
I-oo-7
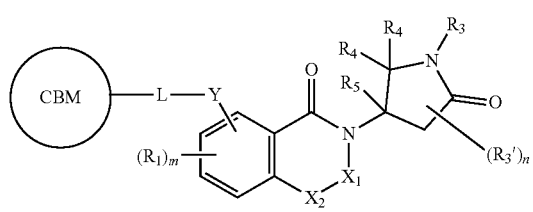
I-oo-8
I-oo-9
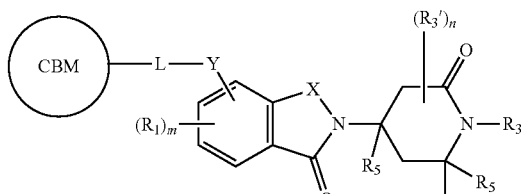
I-oo-10
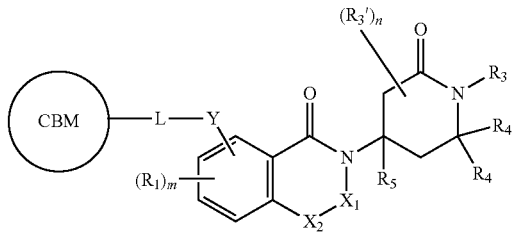
or a compound of formula I-oo'-1, I-oo'-2, I-oo'-3, I-oo'-4, I-oo'-5, I-oo'-6, I-oo'-7, I-oo'-8, I-oo'-9, or I-oo'-10 respectively:
I-oo'-1
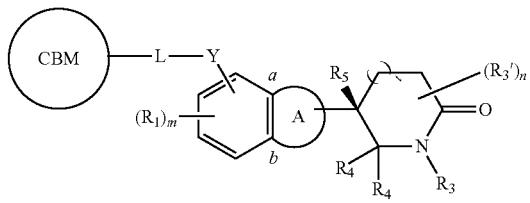
I-oo'-2
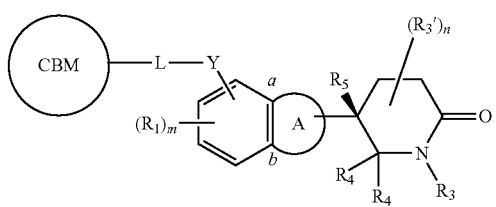
I-oo'-3
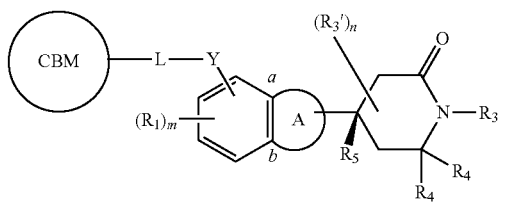
I-oo'-4
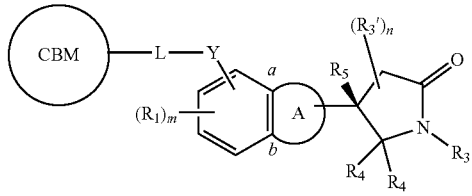

-continued
I-oo′-5
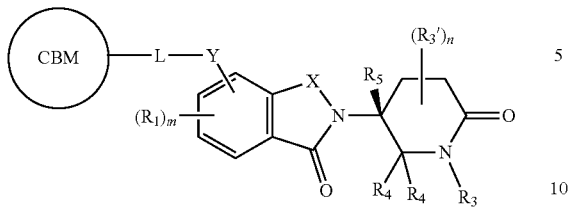
I-oo′-6
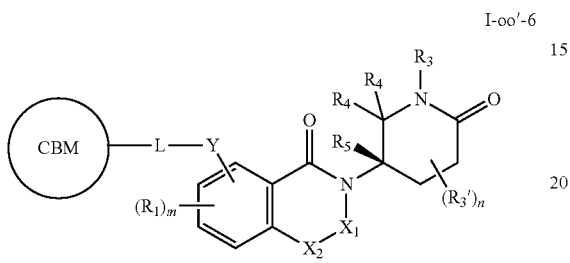
I-oo′-7

I-oo′-8

I-oo′-9
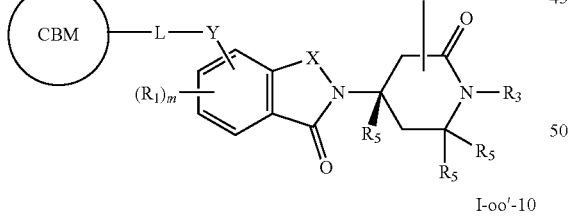
I-oo′-10
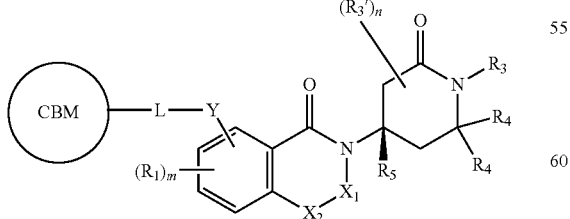
or a compound of formula I-oo″-1, I-oo″-2, I-oo″-3, I-oo″-4, I-oo″-5, I-oo″-6, I-oo″-7, I-oo″-8, I-oo″-9, or I-oo″-10 respectively:
I-oo″-1
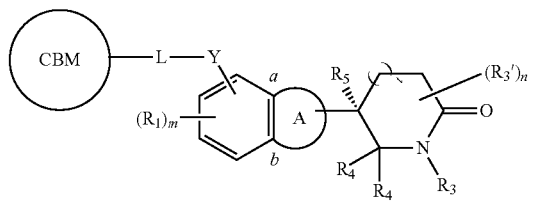
I-oo″-2
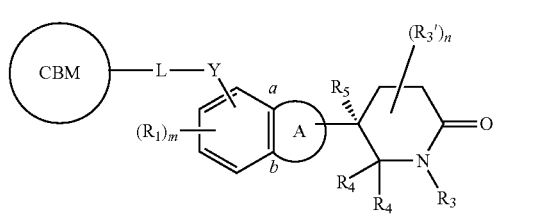
I-oo″-3
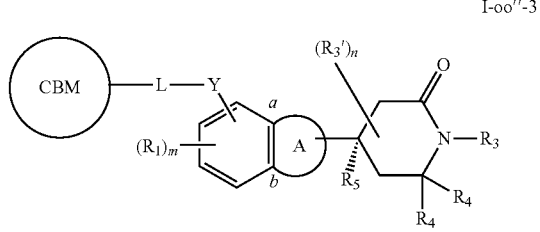
I-oo″-4
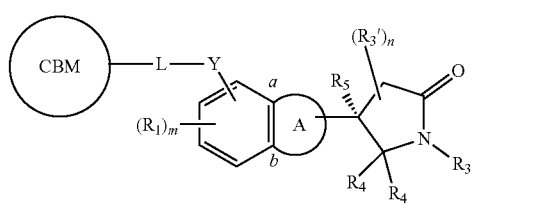
I-oo″-5
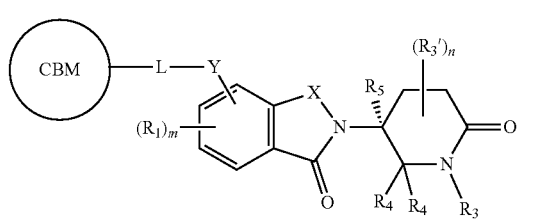
I-oo″-6
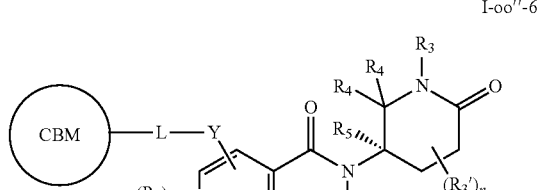
I-oo″-7
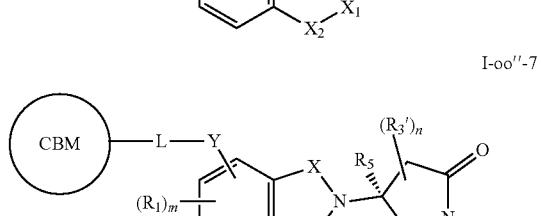

-continued

I-oo''-8

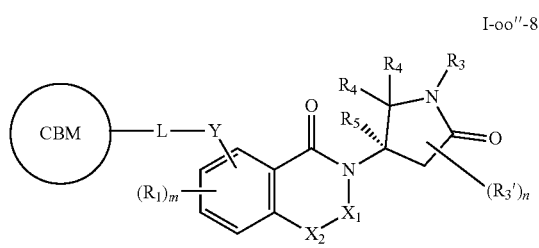

I-oo''-9

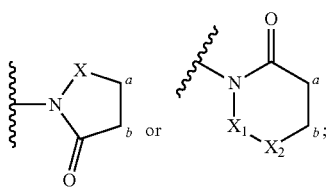

is

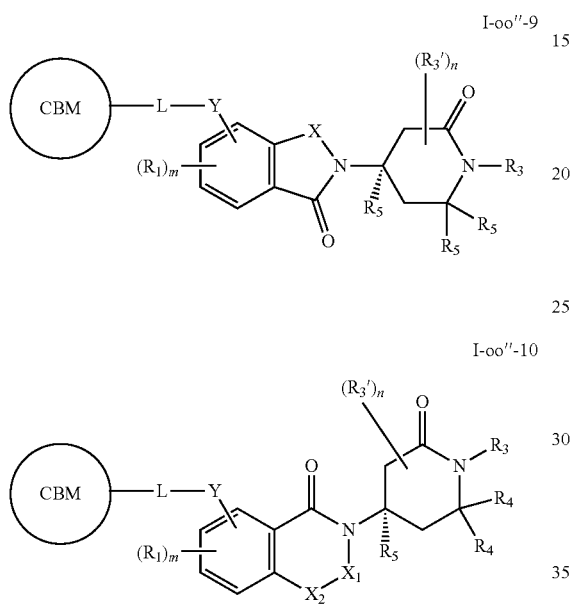

or a pharmaceutically acceptable salt thereof, wherein L and CBM are as defined above and described in embodiments herein, and wherein each of the variables

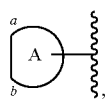

$X, X_1, X_2, Y, R_1, R_3, R_3', R_4, R_5$, t, m and n is as defined and described in WO 2017/007612 and US 2018/0134684, the entirety of each of which is herein incorporated by reference.

Accordingly in some embodiments, the present invention provides a compound of formula I-oo-1, I-oo-2, I-oo-3, I-oo-4, I-oo-5, I-oo-6, I-oo-7, I-oo-8, I-oo-9, I-oo-10, I-oo'-1, I-oo'-2, I-oo'-3, I-oo'-4, I-oo'-5, I-oo'-6, I-oo'-7, I-oo'-8, I-oo'-9, I-oo'-10, I-oo''-1, I-oo''-2, I-oo''-3, I-oo''-4, I-oo''-5, I-oo''-6, I-oo''-7, I-oo''-8, I-oo''-9, or I-oo''-10, or a pharmaceutically acceptable salt thereof, wherein:

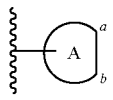

is

Y is a bond, $Y_1$, O, NH, $NR_2$, C(O)O, OC(O), C(O)$NR_2'$, $NR_2'$C(O), $Y_1$—O, $Y_1$—NH, $Y_1$—$NR_2$, $Y_1$—C(O), $Y_1$—C(O)O, $Y_1$—OC(O), $Y_1$—C(O)$NR_2'$, or $Y_1$—$NR_2'$C(O), wherein $Y_1$ is $C_1$-$C_6$ alkylene, $C_2$-$C_6$ alkenylene, or $C_2$-$C_6$ alkynylene;

X is C(O) or C($R^3$)$_2$;

$X_1$—$X_2$ is C($R_3$)=N or C($R^3$)$_2$—C($R^3$)$_2$;

each $R_1$ is independently halogen, nitro, $NH_2$, OH, C(O)OH, $C_1$-$C_6$ alkyl, or $C_1$-$C_6$ alkoxy;

$R_2$ is $C_1$-$C_6$ alkyl, $C_2$-$C_6$ alkenyl, $C_3$-$C_8$ cycloalkyl, 3- to 8-membered heterocycloalkyl, C(O)—$C_1$-$C_6$ alkyl, C(O)—$C_2$-$C_6$ alkenyl, C(O)—$C_3$-$C_8$ cycloalkyl, or C(O)-3- to 8-membered heterocycloalkyl, and $R_2$ is optionally substituted with one or more of halogen, N($R_a$)$_2$, NHC(O)$R_a$, NHC(O)O$R_a$, O$R_b$, $C_3$-$C_8$ cycloalkyl, 3- to 8-membered heterocycloalkyl, $C_6$-$C_{10}$ aryl, or 5- to 10-membered heteroaryl, wherein each of the $C_3$-$C_8$ cycloalkyl, 3- to 8-membered heterocycloalkyl, $C_6$-$C_{10}$ aryl or 5- to 10-membered heteroaryl is optionally further substituted with one or more of halogen, $NH_2$, CN, nitro, OH, C(O)OH, $C_1$-$C_6$ alkyl, $C_1$-$C_6$ haloalkyl, $C_1$-$C_6$ alkoxy, or $C_1$-$C_6$ haloalkoxy;

$R_2'$ is H, $C_1$-$C_6$ alkyl, $C_2$-$C_6$ alkenyl, $C_3$-$C_8$ cycloalkyl, or 3- to 8-membered heterocycloalkyl, and $R_2'$, when not being H, is optionally substituted with one or more of halogen, N($R_a$)$_2$, NHC(O)$R_a$, NHC(O)O$R_a$, O$R_b$, $C_3$-$C_8$ cycloalkyl, 3- to 8-membered heterocycloalkyl, $C_6$-$C_{10}$ aryl, or 5- to 10-membered heteroaryl, wherein each of the $C_3$-$C_8$ cycloalkyl, 3- to 8-membered heterocycloalkyl, $C_6$-$C_{10}$ aryl or 5- to 10-membered heteroaryl is optionally further substituted with one or more of halogen, $NH_2$, CN, nitro, OH, C(O)OH, $C_1$-$C_6$ alkyl, $C_1$-$C_6$ haloalkyl, $C_1$-$C_6$ alkoxy, or $C_1$-$C_6$ haloalkoxy;

each $R_3$ is independently H or $C_1$-$C_3$ alkyl optionally substituted with $C_6$-$C_{10}$ aryl or 5- to 10-membered heteroaryl;

each $R_3'$ is independently $C_1$-$C_3$ alkyl;

each $R_4$ is independently H or $C_1$-$C_3$ alkyl; or two $R_4$, together with the carbon atom to which they are attached, form C(O), a $C_3$-$C_6$ carbocycle, or a 4-, 5-, or 6-membered heterocycle comprising 1 or 2 heteroatoms selected from N and O;

$R_5$ is H, $C_1$-$C_3$ alkyl, F, or Cl;

each $R_a$ independently is H or $C_1$-$C_6$ alkyl;

$R_b$ is H or tosyl;

t is 0 or 1;

m is 0, 1, 2 or 3; and n is 0, 1 or 2.

In certain embodiments, the present invention provides a compound of Formula I, wherein LBM is an E3 ubiquitin ligase (cereblon) binding moiety thereby forming a compound of formula I-pp-1, I-pp-2, I-pp-3, I-pp-4, I-pp-5, or I-pp-6 respectively:

I-pp-1
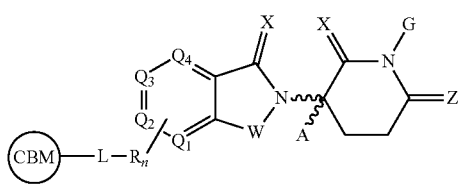

I-pp-2
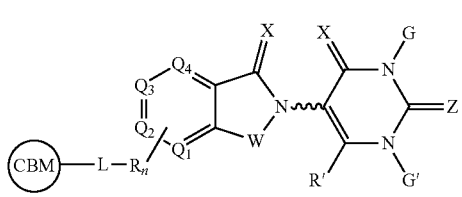

I-pp-3
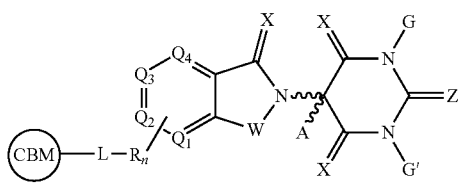

I-pp-4
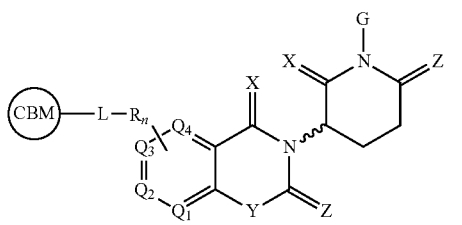

I-pp-5
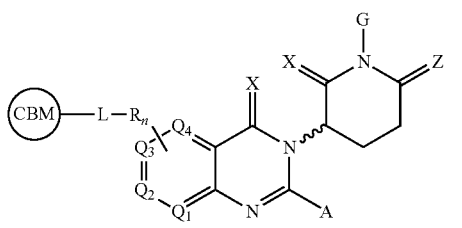

I-pp-6
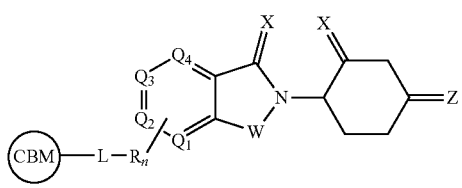

or a pharmaceutically acceptable salt thereof, wherein L and CBM are as defined above and described in embodiments herein, and wherein each of the variables A, G, G', $Q_1$, $Q_2$, $Q_3$, $Q_4$, R, R', W, X, Y, Z, ~~~, and n is as defined and described in WO 2016/197114 and US 2018/0147202, the entirety of each of which is herein incorporated by reference.

In some embodiments, LBM is

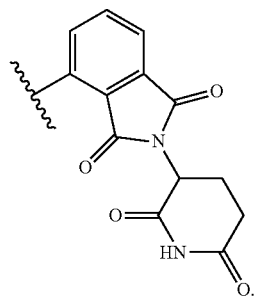 [SMILES: *c1cccc2c1C(=O)N(C1CCC(=O)NC1=O)C2=O]

In some embodiments, LBM is

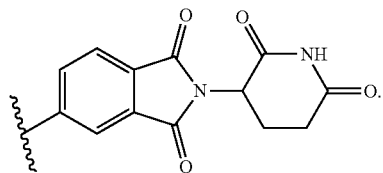 [SMILES: *c1ccc2c(c1)C(=O)N(C1CCC(=O)NC1=O)C2=O]

In some embodiments, LBM is

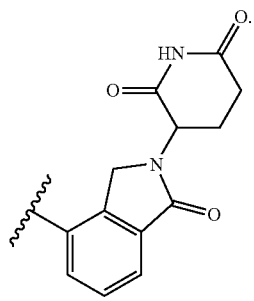 [SMILES: *c1cccc2c1CN(C1CCC(=O)NC1=O)C2=O]

In some embodiments, LBM is

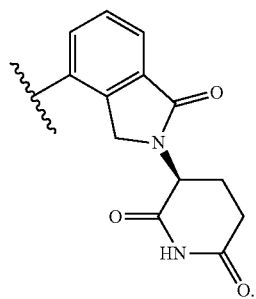 [SMILES: *c1cccc2c1CN([C@H]1CCC(=O)NC1=O)C2=O]

In some embodiments, LBM is

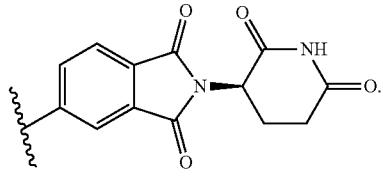 [SMILES: *c1ccc2c(c1)C(=O)N([C@@H]1CCC(=O)NC1=O)C2=O]

In some embodiments, LBM is

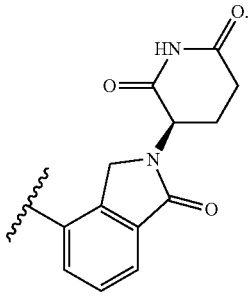 [SMILES: *c1cccc2c1CN([C@@H]1CCC(=O)NC1=O)C2=O]

In some embodiments, LBM is

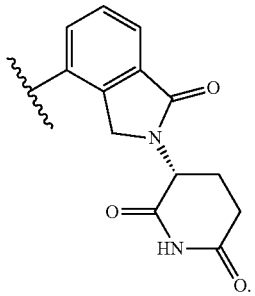 [SMILES: *c1cccc2c1CN([C@@H]1CCC(=O)NC1=O)C2=O]

In some embodiments, LBM is

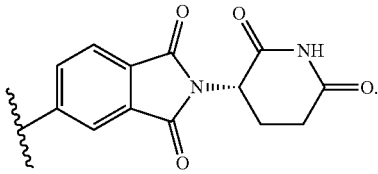 [SMILES: *c1ccc2c(c1)C(=O)N([C@H]1CCC(=O)NC1=O)C2=O]

In some embodiments, LBM is

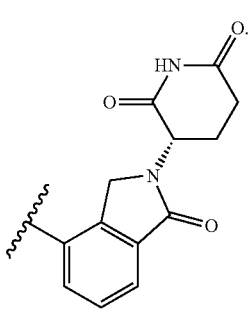 [SMILES: *c1cccc2c1CN([C@H]1CCC(=O)NC1=O)C2=O]

In some embodiments, LBM is selected from those in Table 1 below.

In certain embodiments, the present invention provides a compound of Formula I, wherein LBM is an E3 ubiquitin ligase (cereblon) binding moiety thereby forming a compound of formula I-qq-1, I-qq-2, or I-qq-3 respectively:

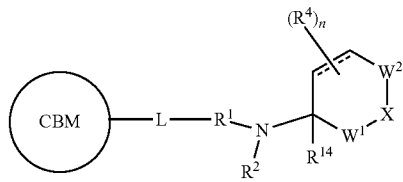

I-qq-1

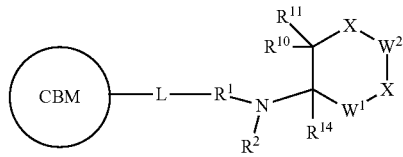

I-qq-2

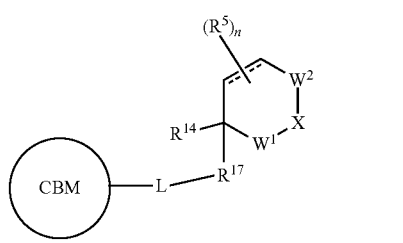

I-qq-3 or a pharmaceutically acceptable salt thereof, wherein L and CBM are as defined above and described herein, and wherein each of the variables $R^1$, $R^2$, $R^4$, $R^5$, $R^{10}$, $R^{11}$, $R^{14}$, $R^{17}$, $W^1$, $W^2$, X, ===, and n is as defined in WO 2017/197051 which is herein incorporated by reference in its entirety and wherein

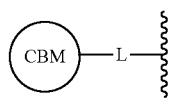

is attached to $R^1$, the ring formed by combining $R^1$ and $R^2$, or $R^{17}$ at the site of attachment of $R^2$ as defined in WO 2017/197051 such that

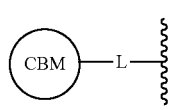

takes the place of the $R^{12}$ substituent.

In some embodiments, the present invention provides a compound of formula I, wherein LBM is an E3 ubiquitin ligase (cereblon) binding moiety thereby forming a compound of formula I-rr-1, I-rr-2, I-rr-3, or I-rr-4, respectively:

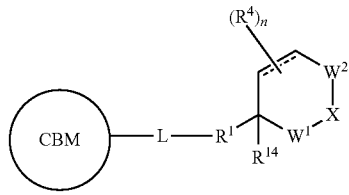

I-rr-1

-continued

I-rr-2

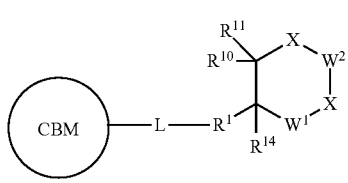

I-rr-3

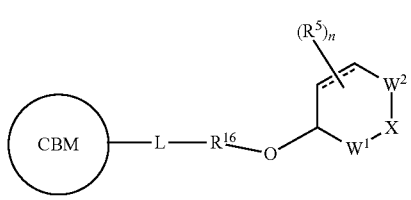

I-rr-4

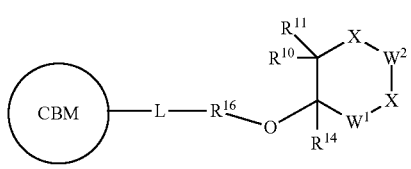

or a pharmaceutically acceptable salt thereof, wherein L and CBM are as defined above and described herein, and wherein each of the variables $R^1$, $R^4$, $R^{10}$, $R^{11}$, $R^{14}$, $R^{16}$, $W^1$, $W^2$, X, ===, and n is as defined in WO 2018/237026, the entirety of each of which is herein incorporated by reference, and wherein


is attached to $R^1$ or $R^{16}$ at the site of attachment of $R^{12}$ as defined in WO 2018/237026, such that


takes the place of the $R^{12}$ substituent.

In some embodiments, the present invention provides a compound of formula I, wherein LBM is an E3 ubiquitin ligase (cereblon) binding moiety thereby forming a compound of formula I-ss-1 or I-ss-3, respectively:

I-ss-1

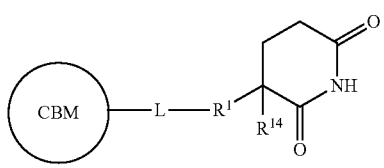

I-ss-3

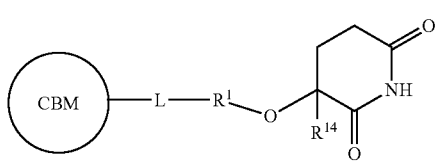

or a pharmaceutically acceptable salt thereof, wherein L and CBM are as defined above and described herein, and wherein each of the variables $R^1$, $R^{14}$, and $R^{16}$ is as defined in WO 2018/237026, the entirety of each of which is herein incorporated by reference, and wherein


is attached to $R^1$ or $R^{16}$ at the site of attachment of $R^{12}$ as defined in WO 2018/237026, such that


takes the place of the $R^{12}$ substituent.

In certain embodiments, the present invention provides a compound of formula I, wherein LBM is an E3 ubiquitin ligase (cereblon) binding moiety thereby forming a compound of formula I-tt-1, I-tt-2, I-tt-3, I-tt-4, I-tt-5, I-tt-6, I-tt-7, or I-tt-8:

I-tt-1

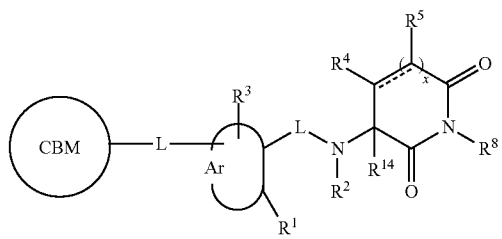

I-tt-2

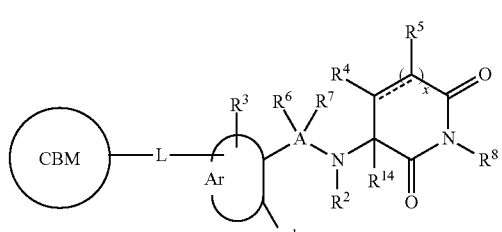

I-tt-3

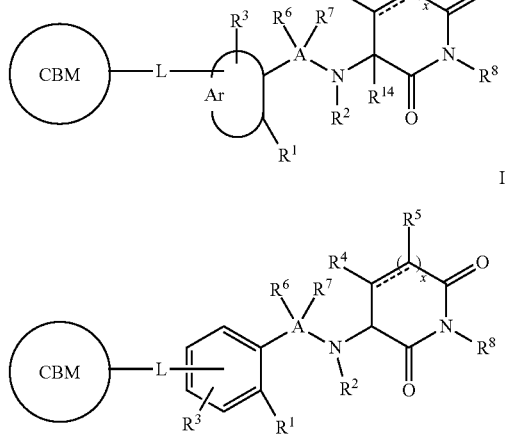

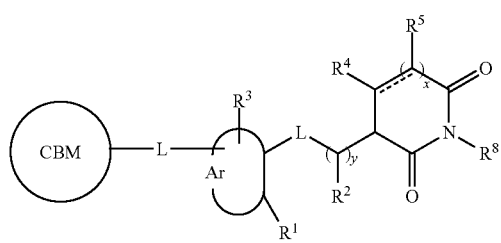

I-tt-4

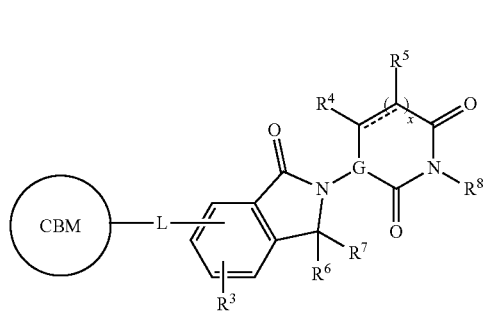

I-tt-5

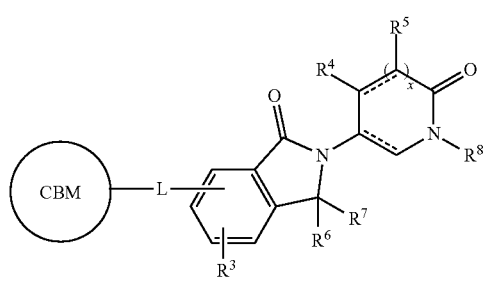

I-tt-6

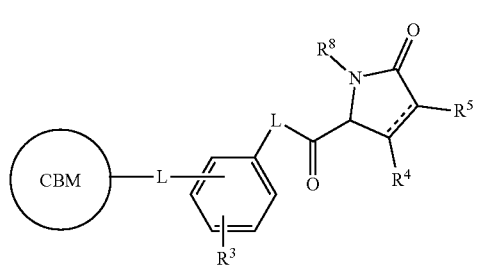

I-tt-7

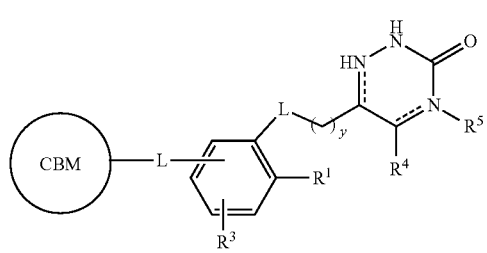

I-tt-8 or a pharmaceutically acceptable salt thereof, wherein L and CBM are as defined above and described in embodiments herein, and wherein each of the variables Ar, $R^1$, $R^2$, $R^3$, $R^4$, $R^5$, $R^6$, $R^7$, $R^8$, A, L, x, y, and ≡ is as described and defined in WO 2017/161119, the entirety of each of which is herein incorporated by reference.

In certain embodiments, the present invention provides a compound of formula I, wherein LBM is an E3 ubiquitin ligase (cereblon) binding moiety thereby forming a compound of formula I-uu:

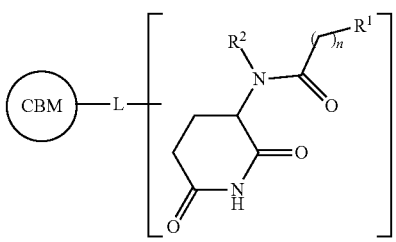

I-uu or a pharmaceutically acceptable salt thereof, wherein L and CBM are as defined above and described in embodiments herein, and wherein each of the variables A, B, C, W, X, Y, and Z is as described and defined in U.S. Pat. No. 5,721,246, the entirety of each of which is herein incorporated by reference.

In certain embodiments, the present invention provides a compound of formula I, wherein LBM is an E3 ubiquitin ligase (cereblon) binding moiety thereby forming a compound of formula I-vv:

I-vv or a pharmaceutically acceptable salt thereof, wherein L and CBM are as defined above and described in embodiments herein, and wherein each of the variables $R_1$, $R_2$, and n is as described and defined in WO 2019/043214, the entirety of each of which is herein incorporated by reference.

In some embodiments, LBM is a IAP E3 Ubiquitin ligase binding moiety recited in Varfolomeev, E. et al., *IAP Antagonists Induce Autoubiquitination of c-IAPs, NF-κB activation, and TNFα-Dependent Apoptosis*, Cell, 2007, 131(4): 669-81, such as, for example:

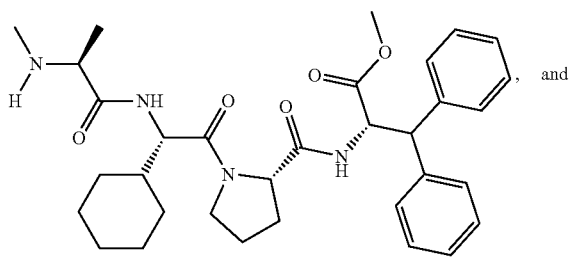
MV1, and
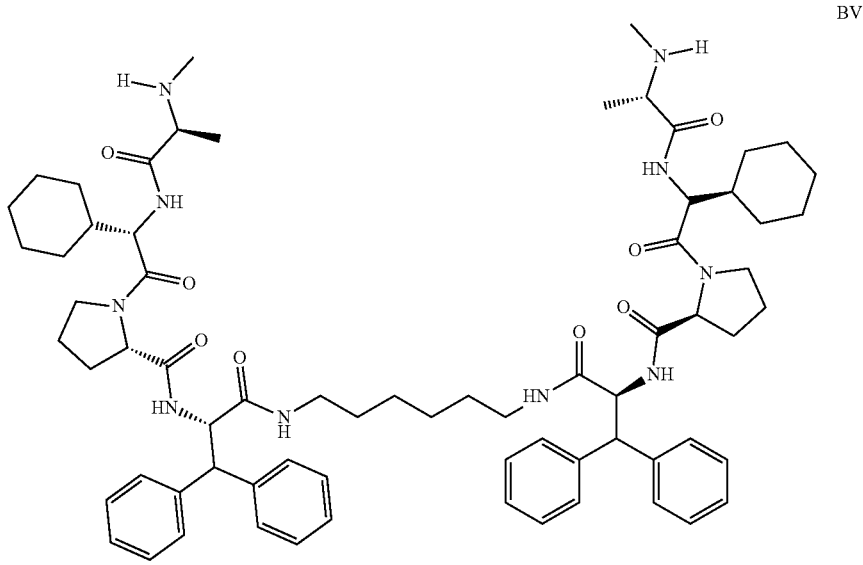
BV6
wherein
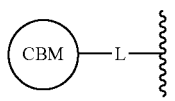
is attached to a modifiable carbon, oxygen, nitrogen or sulfur atom.
In certain embodiments, the present invention provides a compound of Formula I, wherein LBM is a VHL E3 ubiquitin ligase binding moiety thereby forming a compound of formula I-ww-1, I-ww-2, I-ww-3, I-ww-4, or I-ww-5 respectively:
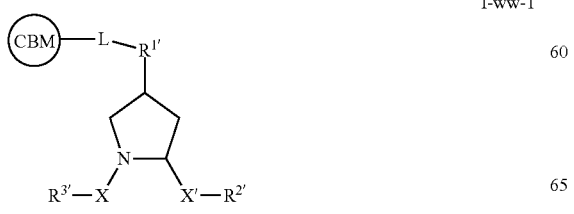
I-ww-1
-continued
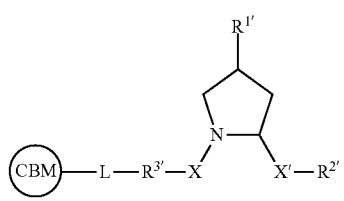
I-ww-2
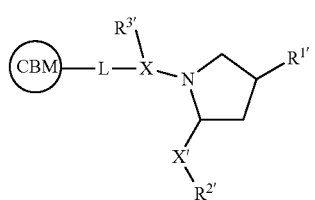
I-ww-3
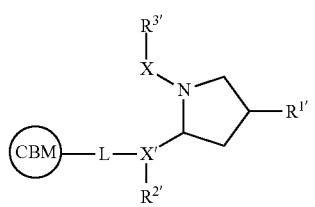
I-ww-4

I-ww-5

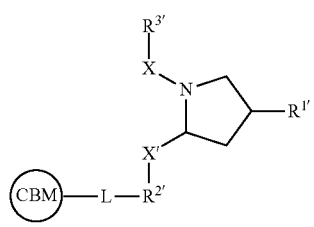

or a pharmaceutically acceptable salt thereof, wherein L and CBM are as defined above and described in embodiments herein, and wherein each of the variables $R^{1'}$, $R^{2'}$, $R^{3'}$, X, and X' is as defined and described in WO 2013/106643 and US 2014/0356322, the entirety of each of which is herein incorporated by reference.

In certain embodiments, the present invention provides a compound of Formula I, wherein LBM is a VHL E3 ubiquitin ligase binding moiety thereby forming a compound of formula I-xx-1, I-xx-2, I-xx-3, I-xx-4, I-xx-5 or I-xx-6 respectively:

I-xx-1

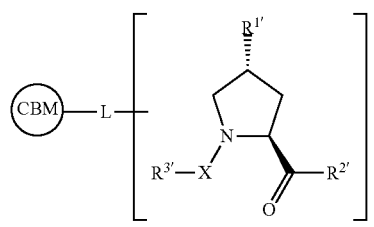

I-xx-2

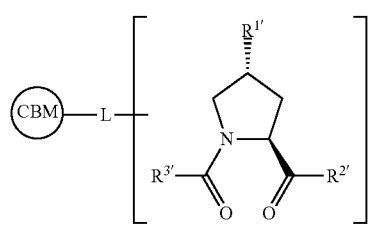

I-xx-3

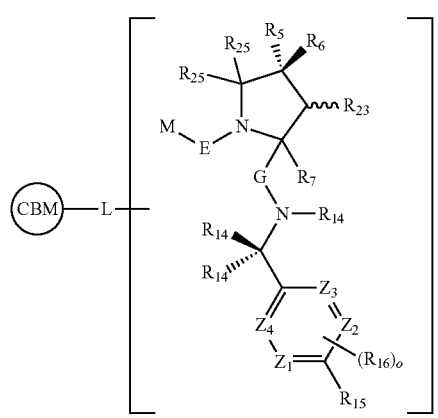

I-xx-4

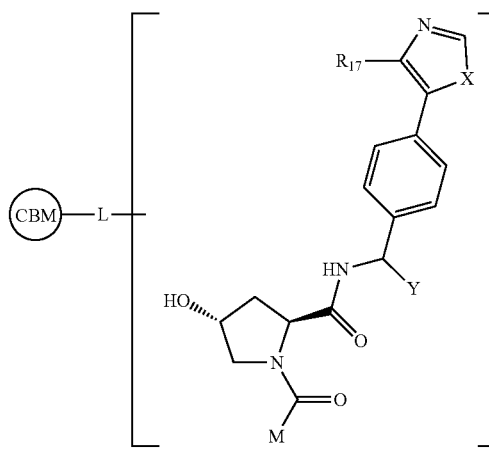

I-xx-5

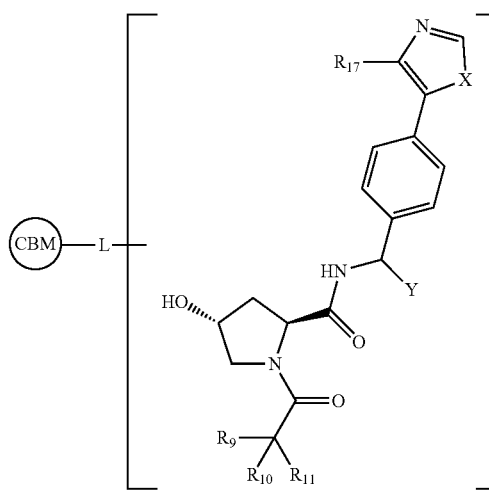

I-xx-6

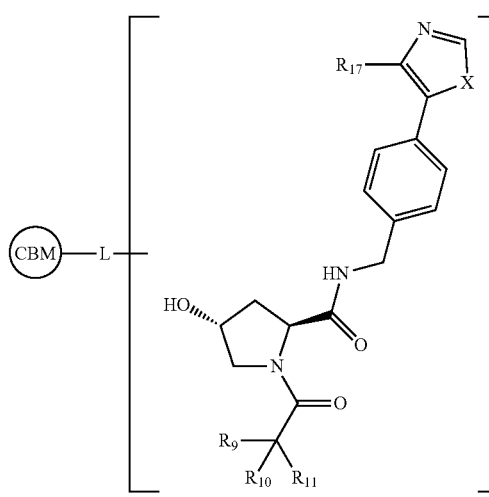

or a pharmaceutically acceptable salt thereof, wherein L and CBM are as defined above and described in embodiments herein, and wherein each of the variables $R^{1'}$, $R^{2'}$, $R^{3'}$, $R_5$, $R_6$, $R_7$, $R_9$, $R_{10}$, $R_{11}$, $R_{14}$, $R_{15}$, $R_{16}$, $R_{17}$, $R_{23}$, $R_{25}$, E, G, M, X, X', Y, $Z_1$, $Z_2$, $Z_3$, $Z_4$, and o is as defined and described in WO 2016/149668 and US 2016/0272639, the entirety of each of which is herein incorporated by reference.

As used herein, depiction of brackets around any LBM

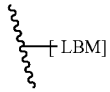

means that the

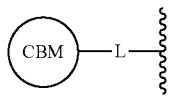

moiety is covalently attached to said LBM at any available modifiable carbon, nitrogen, oxygen, or sulfur atom. For purposes of clarity and by way of example, such available modifiable carbon, nitrogen, oxygen, or sulfur atoms in the following LBM compound structure are depicted below, wherein each wavy bond defines the point of attachment to said

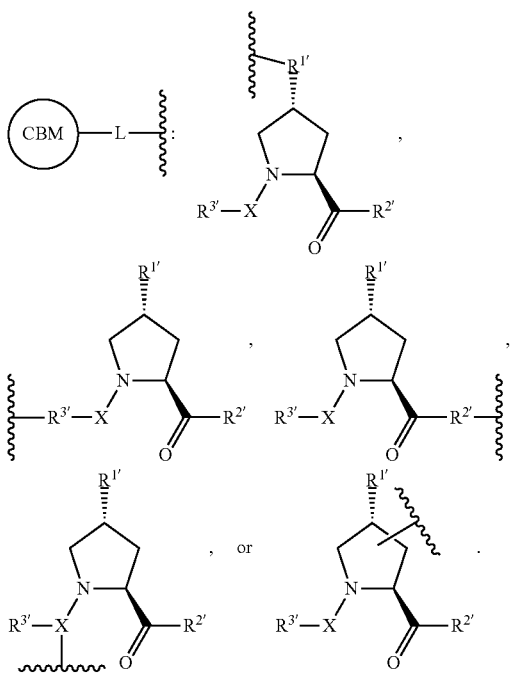

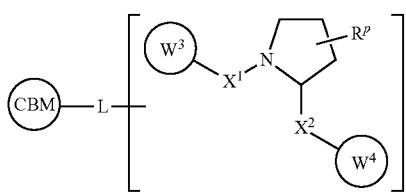

In certain embodiments, the present invention provides a compound of Formula I, wherein LBM is a VHL E3 ubiquitin ligase binding moiety thereby forming a compound of formula I-yy-1, I-yy-2, or I-yy-3 respectively:

I-yy-1

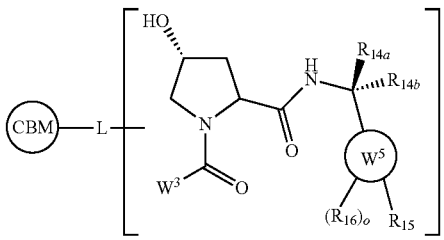

I-yy-2

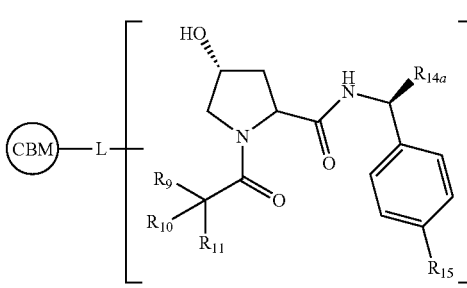

I-yy-3 or a pharmaceutically acceptable salt thereof, wherein L and CBM are as defined above and described in embodiments herein, and wherein each of the variables $R^p$, $R_9$, $R_{10}$, $R_{11}$, $R_{14a}$, $R_{14b}$, $R_{15}$, $R_{16}$, $W^3$, $W^4$, $W^5$, $X^1$, $X^2$, and o is as defined and described in WO 2016/118666 and US 2016/0214972, the entirety of each of which is herein incorporated by reference.

In certain embodiments, the present invention provides a compound of Formula I, wherein LBM is a CRBN or VHL E3 ubiquitin ligase binding moiety thereby forming a compound of formula I-zz-1, I-zz-2, I-zz-3, I-zz-4, I-zz-5, I-zz-6, or I-zz-7 respectively:

I-zz-1

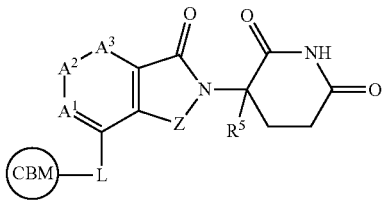

I-zz-2

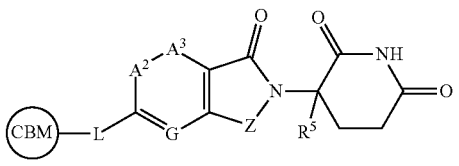

I-zz-3

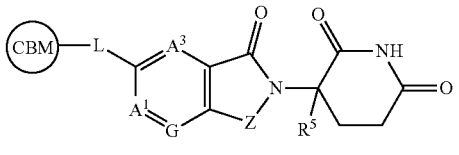

I-zz-4

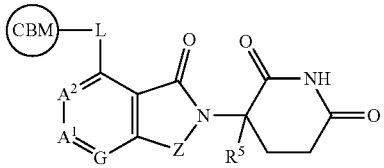

-continued

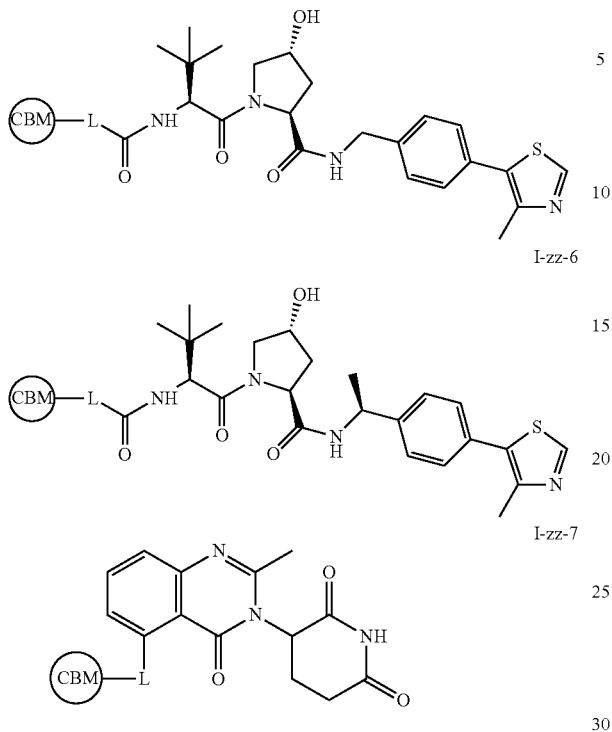

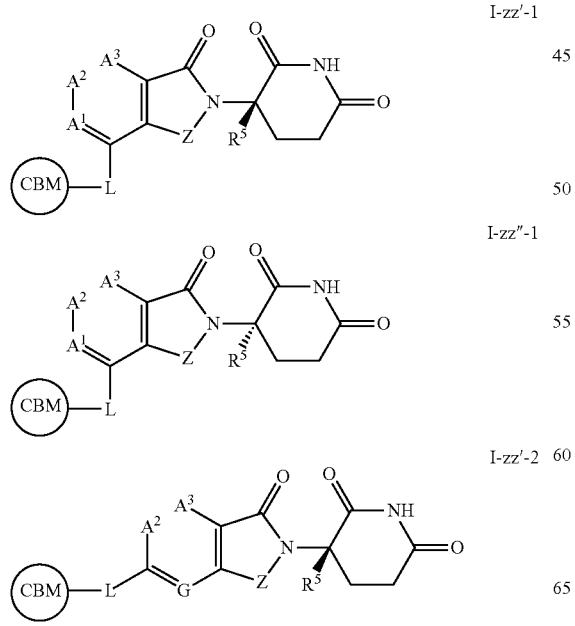

or a pharmaceutically acceptable salt thereof, wherein L and CBM are as defined above and described in embodiments herein, and wherein each of the variables $A^1$, $A^2$, $A^3$, $R^5$, G and Z is as defined and described in WO 2017/176958.

In certain embodiments, the present invention provides a compound of Formula I, wherein LBM is a CRBN E3 ubiquitin ligase binding moiety thereby forming a compound of formula I-zz'-1, I-zz"-1, I-zz'-2, I-zz"-2, I-zz'-3, I-zz"-3, I-zz'-4, I-zz"-4, I-zz'-7 or I-zz"-7 respectively:

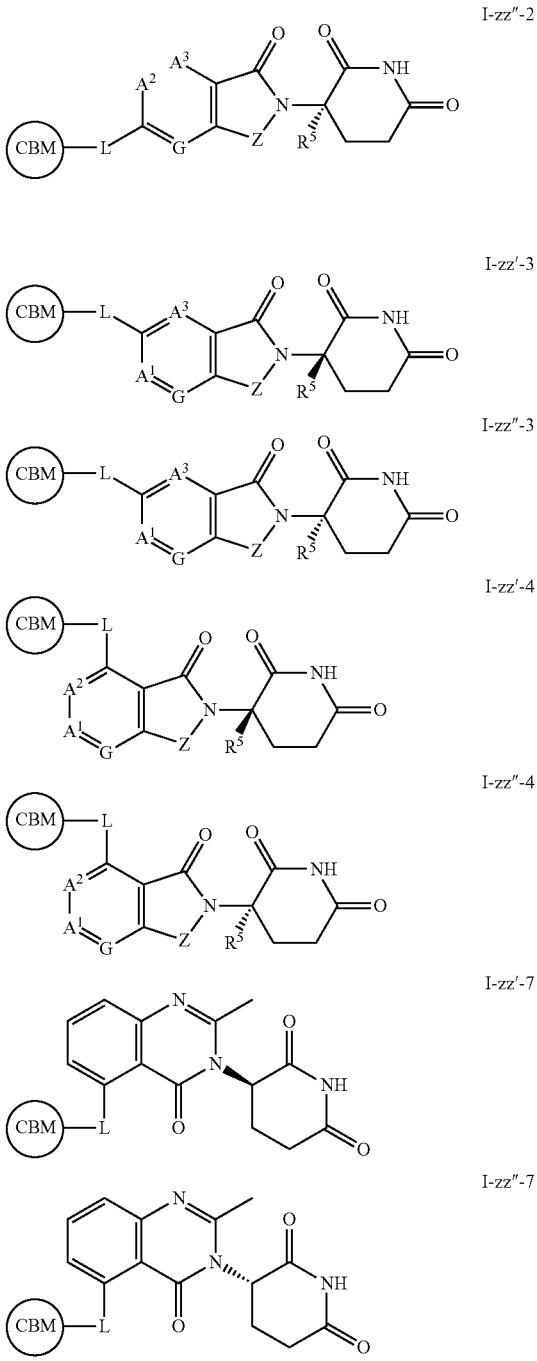

or a pharmaceutically acceptable salt thereof, wherein L and CBM are as defined above and described in embodiments herein, and wherein each of the variables $A^1$, $A^2$, $A^3$, $R^5$, G and Z is as defined and described in WO 2017/176958, the entirety of which is herein incorporated by reference.

In certain embodiments, the present invention provides a compound of Formula I, wherein LBM is a MDM2 (i.e. human double minute 2 or HDM2) E3 ligase binding moiety thereby forming a compound of formula I-aaa-1, I-aaa-2, I-aaa-3, I-aaa-4, I-aaa-5, I-aaa-6, I-aaa-7, I-aaa-8, I-aaa-9, I-aaa-10, I-aaa-11, I-aaa-12, I-aaa-13, I-aaa-14, I-aaa-15, I-aaa-16, I-aaa-17, or I-aaa-18 respectively:

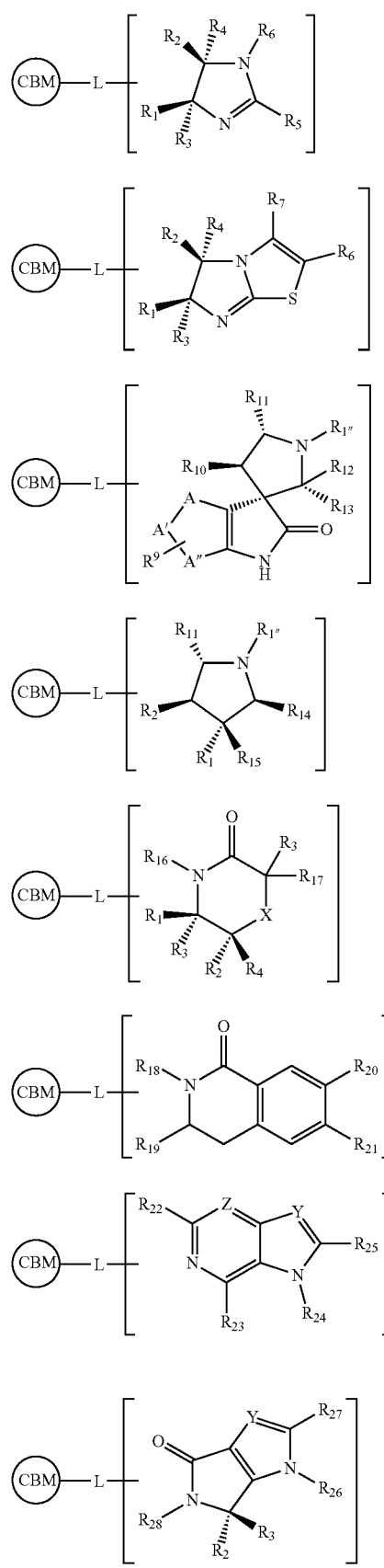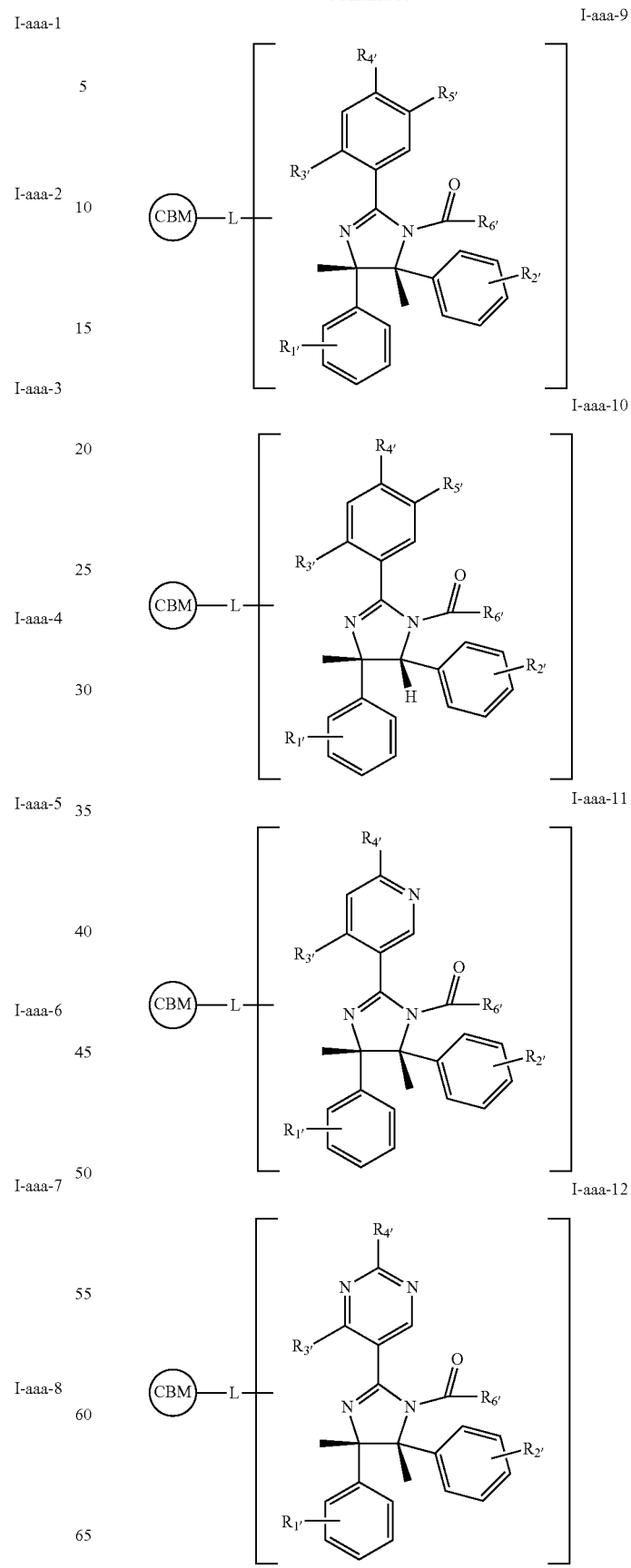

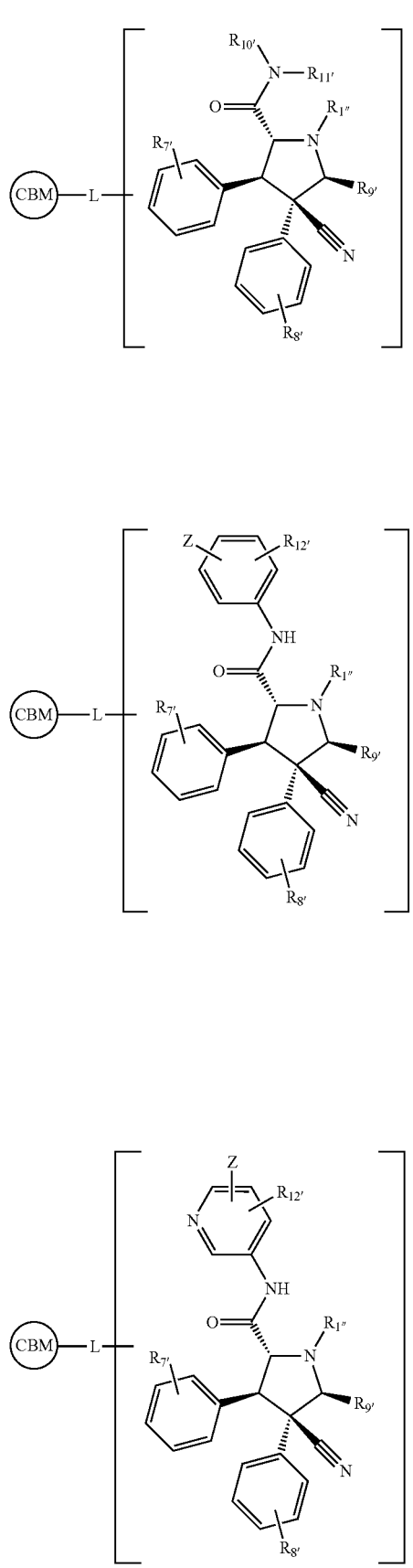

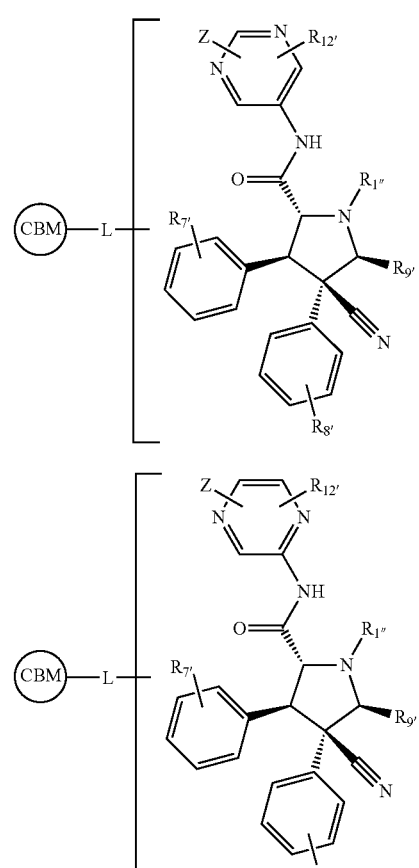

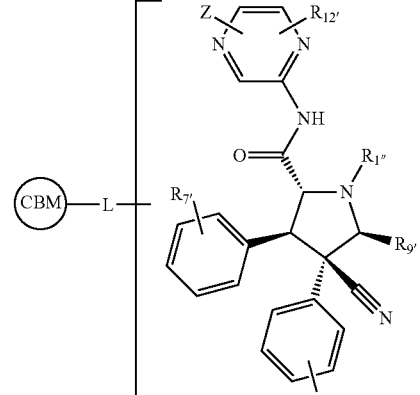

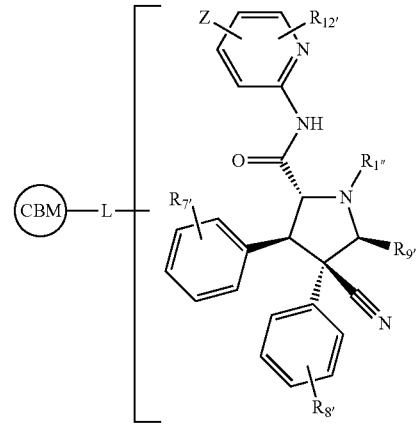

or a pharmaceutically acceptable salt thereof, wherein L and CBM are as defined above and described in embodiments herein, and wherein each of the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{1'}$, $R_{2'}$, $R_{3'}$, $R_{4'}$, $R_{5'}$, $R_{6'}$, $R_{7'}$, $R_{8'}$, $R_{9'}$, $R^{10'}$, $R_{11'}$, $R_{12'}$, $R_{1''}$, A, A', A'', X, Y, and Z is as defined and described in WO 2017/011371 and US 2017/0008904, the entirety of each of which is herein incorporated by reference.

In certain embodiments, the present invention provides a compound of Formula I, wherein LBM is a MDM2 (i.e. human double minute 2 or HDM2) E3 ligase binding moiety thereby forming a compound of formula I-aaa-19, I-aaa-20, or I-aaa-21 respectively

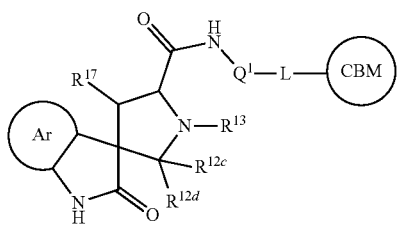

I-aaa-19

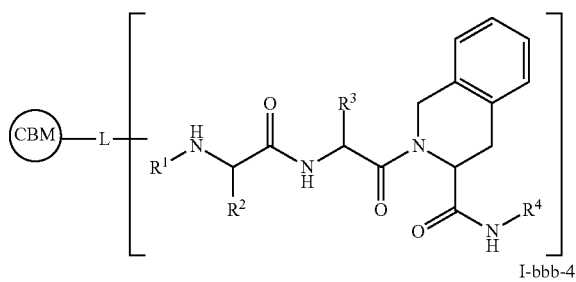

I-bbb-3

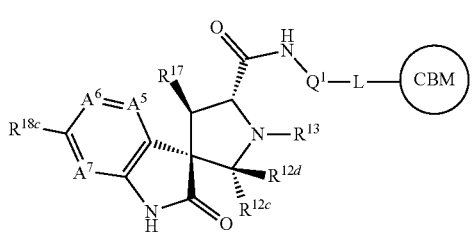

I-aaa-20

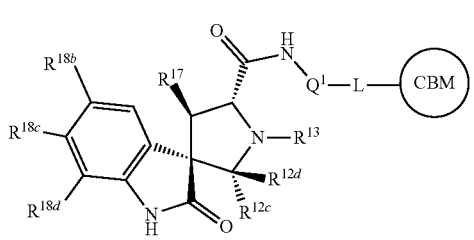

I-aaa-21

I-bbb-4 or a pharmaceutically acceptable salt thereof, wherein L and CBM are as defined above and described in embodiments herein, and wherein each of the variables $R^1$, $R^2$, $R^3$, $R^4$, $R^5$, $R^6$, and $R^7$, is as defined and described in WO 2017/011590 and US 2017/0037004, the entirety of each of which is herein incorporated by reference.

In certain embodiments, the present invention provides a compound of Formula I, wherein LBM is an E3 ubiquitin ligase (cereblon) binding moiety, a DCAF15 E3 ubiquitin ligase binding moiety, or a VHL E3 ubiquitin ligase binding moiety; thereby forming a compound of formula I-ccc-1, I-ccc-2, or I-ccc-3:

or a pharmaceutically acceptable salt thereof, wherein each of the variables $R^{12c}$, $R^{12d}$, $R^{13}$, $R^{17}$, $R^{18b}$, $R^{18c}$, $R^{18d}$, $A^5$, $A^6$, $A^7$, $Q^1$, and Ar is as defined and described in WO 2017/176957 and US2019/127387.

In certain embodiments, the present invention provides a compound of Formula I, wherein LBM is an IAP E3 ubiquitin ligase binding moiety thereby forming a compound of formula I-bbb-1, I-bbb-2, I-bbb-3, or I-bbb-4 respectively:

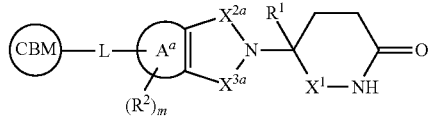

I-ccc-1

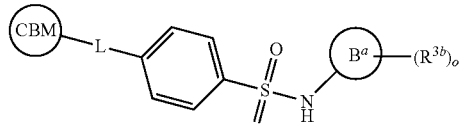

I-ccc-2

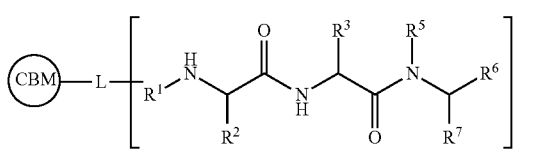

I-bbb-1

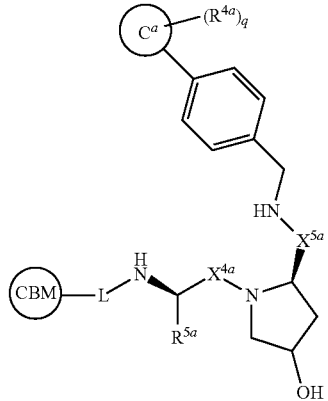

I-ccc-3

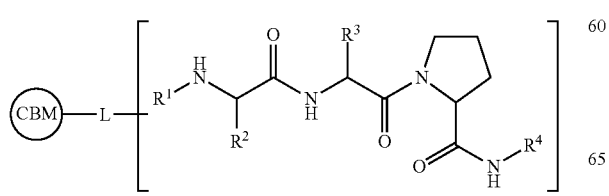

I-bbb-2 or a pharmaceutically acceptable salt thereof, wherein L and CBM is as defined above and described in embodiments herein, and wherein:

each of $X^1$, $X^{2a}$, and $X^{3a}$ is independently a bivalent moiety selected from a covalent bond, —CH$_2$—, —C(O)—, —C(S)—, or;

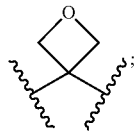 [SMILES: *C1(*)COC1]

each of $X^4a$ and $X^{1a}$ is independently a bivalent moiety selected from —CH$_2$—, —C(O)—, —C(S)—, or

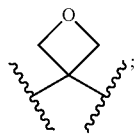 [SMILES: *C1(*)COC1]

$R^1$ is hydrogen, halogen, —CN, —OR, —SR, —S(O)R, —S(O)$_2$R, —NR$_2$, or an optionally substituted C$_{1-4}$ aliphatic;

each of $R^2$, $R^{3b}$, and $R^{4a}$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^{5a}$ is hydrogen or C$_{1-6}$ aliphatic;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring $A^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring $B^a$ is selected from 6-membered aryl containing 0-2 nitrogen atoms or a 8-10 membered bicyclic heteroaryl having 1-5 heteroatoms independently selected from nitrogen, oxygen, or sulfur;

Ring $C^a$ is a selected from 6-membered aryl containing 0-2 nitrogen atoms or a 5-membered heteroaryl with 1-3 heteroatoms independently selected from nitrogen, oxygen or sulfur;

m is 0, 1, 2, 3 or 4;

is 0, 1, 2, 3 or 4;

q is 0, 1, 2, 3 or 4; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I-ccc-1, wherein LBM is an E3 ubiquitin ligase (cereblon) binding moiety thereby forming a compound of formula I-ccc'-1 or I-ccc"-1:

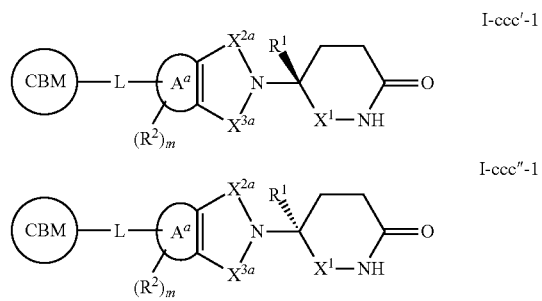

or a pharmaceutically acceptable salt thereof, wherein CBM, L, Ring $A^a$, $X^1$, $X^{2a}$, $X^{3a}$, $R^1$, $R^2$ and m are as described above.

As defined above and described herein, each of $X^1$, $X^{2a}$, and $X^{3a}$ is independently a bivalent moiety selected from a covalent bond, —CH$_2$—, —C(O)—, —C(S)—, or

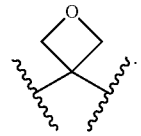

In some embodiments, $X^1$ is a covalent bond, —CH$_2$—, —C(O)—, —C(S)—, or

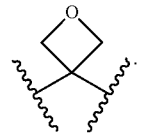

In some embodiments, $X^1$ is selected from those depicted in Table 1, below.

In some embodiments, $X^{2a}$ is a covalent bond, —CH$_2$—, —C(O)—, —C(S)—, or

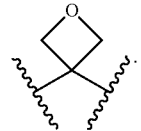

In some embodiments, $X^{2a}$ is selected from those depicted in Table 1, below.

In some embodiments, $X^{3a}$ is a covalent bond, —CH$_2$—, —C(O)—, —C(S)—, or

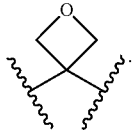 [SMILES: *C1(*)COC1]

In some embodiments, $X^{3a}$ is selected from those depicted in Table 1, below.

As defined above and described herein, each of $X^4$ and $X^5$ is independently a bivalent moiety selected from —CH$_2$—, —C(O)—, —C(S)—, or

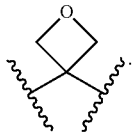 [SMILES: *C1(*)COC1]

In some embodiments, $X^{4a}$ is —CH$_2$—, —C(O)—, —C(S)—, or

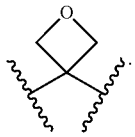

In some embodiments, $X^{4a}$ is selected from those depicted in Table 1, below.

In some embodiments, $X^{5a}$ is —CH$_2$—, —C(O)—, —C(S)—, or

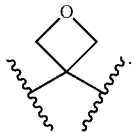 [SMILES: *C1(*)COC1]

In some embodiments, $X^{5a}$ is selected from those depicted in Table 1, below.

As defined above and described herein, $R^1$ is hydrogen, halogen, —CN, —OR, —SR, —S(O)R, —S(O)$_2$R, —NR$_2$, or an optionally substituted C$_{1-4}$ aliphatic.

In some embodiments, $R^1$ is hydrogen, halogen, —CN, —OR, —SR, —S(O)R, —S(O)$_2$R, —NR$_2$, or an optionally substituted C$_{1-4}$ aliphatic.

In some embodiments, $R^1$ is selected from those depicted in Table 1, below.

As defined above and described herein, each of $R^2$, $R^{3b}$, and $R^{4a}$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^2$ is hydrogen, —R, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^2$ is selected from those depicted in Table 1, below.

In some embodiments, $R^{3b}$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^{3b}$ is methyl.

In some embodiments, $R^{3b}$ is selected from those depicted in Table 1, below.

In some embodiments, $R^{4a}$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^{4a}$ is methyl.

In some embodiments, $R^{4a}$ is selected from those depicted in Table 1, below.

As defined above and described herein, $R^a$ is hydrogen or C$_{1-6}$ aliphatic.

In some embodiments, $R^{5a}$ is t-butyl.

In some embodiments, $R^{5a}$ is selected from those depicted in Table 1, below.

As defined above and described herein, each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^6$ is an optionally substituted C$_{1-6}$ aliphatic group. In some embodiments, $R^6$ is an optionally substituted phenyl. In some embodiments, $R^6$ is an optionally substituted 4-7 membered saturated or partially unsaturated heterocyclic ring having 1-2 heteroatoms independently selected from nitrogen, oxygen, and sulfur. In some embodiments, $R^6$ is an optionally substituted 5-6 membered heteroaryl ring having 1-4 heteroatoms independently selected from nitrogen, oxygen, and sulfur.

In some embodiments, $R^6$ is selected from those depicted in Table 1, below.

As defined above and described herein, Ring $A^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur.

In some embodiments Ring $A^a$ is a fused 6-membered aryl containing 0-2 nitrogen atoms. In some embodiments Ring $A^a$ is a fused 5 to 7-membered partially saturated carbocyclyl. In some embodiments Ring $A^a$ is a fused 5 to 7-membered partially saturated heterocyclyl with 1-2 heteroatoms independently selected from nitrogen, oxygen or sulfur. In some embodiments Ring $A^a$ is a fused 5-membered heteroaryl with 1-3 heteroatoms independently selected from nitrogen, oxygen or sulfur.

In some embodiments, Ring $A^a$ is a fused phenyl.

In some embodiments, Ring $A^a$ is selected from those depicted in Table 1, below.

As defined above and described herein, Ring $B^a$ is selected from 6-membered aryl containing 0-2 nitrogen atoms or a 8-10 membered bicyclic heteroaryl having 1-5 heteroatoms independently selected from nitrogen, oxygen, or sulfur.

In some embodiments, Ring $B^a$ is a 6-membered aryl containing 0-2 nitrogen atoms. In some embodiments, Ring $B^a$ is a 8-10 membered bicyclic heteroaryl having 1-5 heteroatoms independently selected from nitrogen, oxygen, or sulfur.

In some embodiments, Ring $B^a$ is

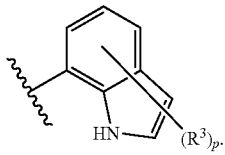

In some embodiments, Ring $B^a$ is selected from those depicted in Table 1, below.

As defined above and described herein, Ring $C^a$ is selected from 6-membered aryl containing 0-2 nitrogen atoms or a 5-membered heteroaryl with 1-3 heteroatoms independently selected from nitrogen, oxygen or sulfur.

In some embodiments, Ring $C^a$ is a 6-membered aryl containing 0-2 nitrogen atoms. In some embodiments, Ring $C^a$ is a 5-membered heteroaryl with 1-3 heteroatoms independently selected from nitrogen, oxygen or sulfur.

In some embodiments, Ring $C^a$ is

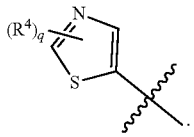

In some embodiments, Ring $C^a$ is selected from those depicted in Table 1, below.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

In some embodiments, o is selected from those depicted in Table 1, below.

As defined above and described herein, o is 0, 1, 2, 3 or 4.

In some embodiments, o is 0. In some embodiments, o is 1. In some embodiments, o is 2. In some embodiments, o is 3. In some embodiments, o is 4.

In some embodiments, o is selected from those depicted in Table 1, below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is phenyl. In some embodiments, R is a 4-7 membered saturated or partially unsaturated heterocyclic having 1-2 heteroatoms independently selected from nitrogen, oxygen, and sulfur. In some embodiments, R is a 5-6 membered heteroaryl ring having 1-4 heteroatoms independently selected from nitrogen, oxygen, and sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

In certain embodiments, the present invention provides a compound of formula I, wherein LBM is a VHL binding moiety thereby forming a compound of formula I-ddd:

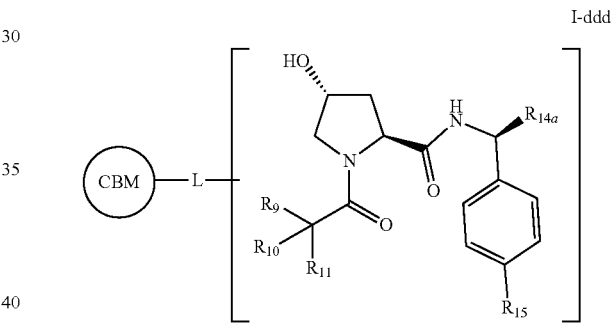

I-ddd or a pharmaceutically acceptable salt thereof, wherein L and CBM are as defined above and described in embodiments herein, and wherein each of the variables $R_9$, $R_{10}$, $R_{11}$, $R_{14a}$, and $R_{15}$ is as described and defined in WO 2017/030814, WO 2016/118666, and US 2017/0327469, the entirety of each of which is herein incorporated by reference.

In certain embodiments, the present invention provides a compound of formula I, wherein LBM is a VHL binding moiety thereby forming a compound of formula I-eee-1 or I-eee-2:

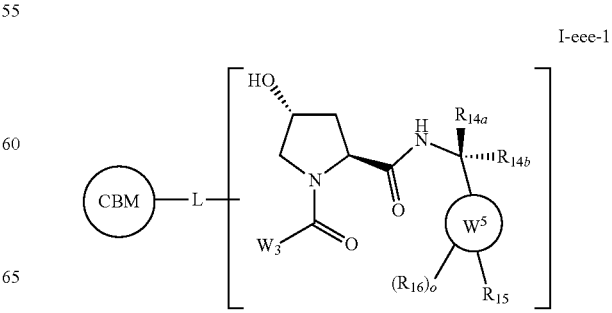

I-eee-1

I-eee-2

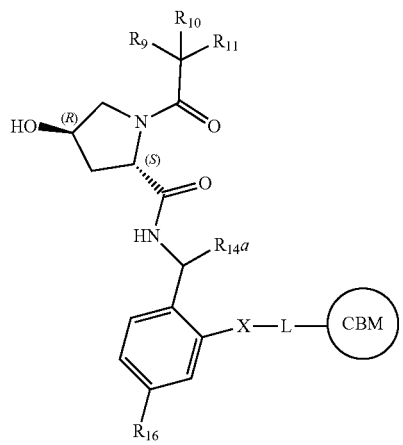

or a pharmaceutically acceptable salt thereof, wherein L and CBM are as defined above and described in embodiments herein, and wherein each of the variables X, W, $R_9$, $R_{10}$, $R_{11}$, $R_{14a}$, and $R_{14b}$, $R_{15}$, $R_{16}$, and o is as described and defined in WO 2017/030814, WO 2016/118666, and US 2017/0327469, the entirety of each of which is herein incorporated by reference.

In certain embodiments, the present invention provides a compound of formula I, wherein LBM is an IAP binding moiety thereby forming a compound of formula I-fff:

I-fff

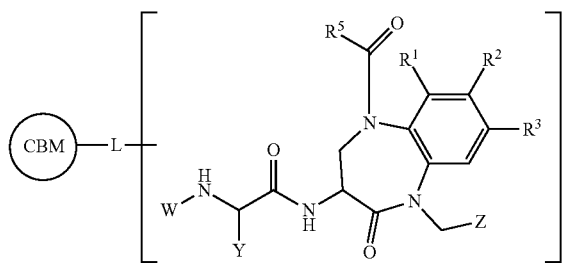

or a pharmaceutically acceptable salt thereof, wherein L and CBM are as defined above and described in embodiments herein, and wherein each of the variables W, Y, Z, $R^1$, $R^2$, $R^3$, $R^4$, and R is as described and defined in WO 2014/044622, US 2015/0225449, WO 2015/071393, and US 2016/0272596, the entirety of each of which is herein incorporated by reference.

In certain embodiments, the present invention provides a compound of formula I, wherein LBM is a MDM2 binding moiety thereby forming a compound of formula I-ggg:

I-ggg

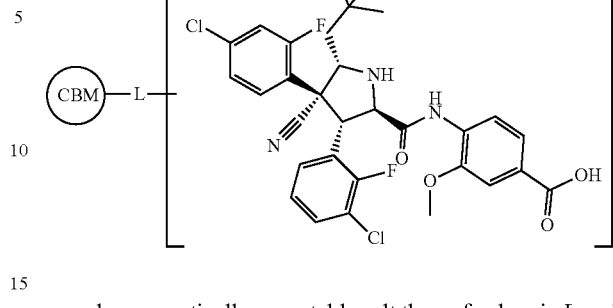

or a pharmaceutically acceptable salt thereof, wherein L and CBM are as defined above and described in embodiments herein, as described and defined in Hines, J. et al., Cancer Res. (DOI: 10.1158/0008-5472.CAN-18-2918), the entirety of each of which is herein incorporated by reference.

In certain embodiments, the present invention provides a compound of formula I, wherein LBM is a DCAF16 binding moiety thereby forming a compound of formula I-hhh:

I-hhh

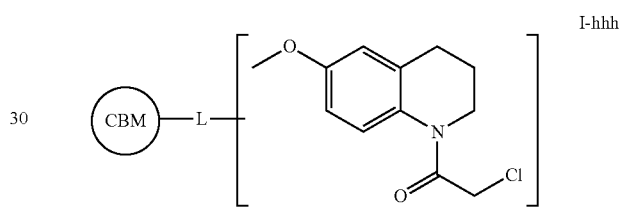

or a pharmaceutically acceptable salt thereof, wherein L and CBM are as defined above and described in embodiments herein, as described and defined in Zhang, X. et al., bioRxiv (doi: https://doi.org/10.1101/443804), the entirety of each of which is herein incorporated by reference.

In certain embodiments, the present invention provides a compound of formula I, wherein LBM is a RNF114 binding moiety thereby forming a compound of formula I-iii:

I-iii

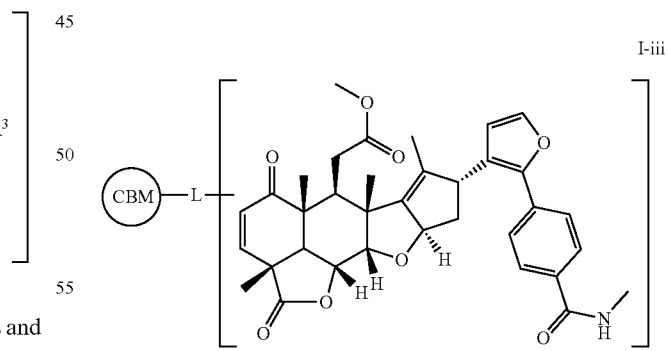

or a pharmaceutically acceptable salt thereof, wherein L and CBM are as defined above and described in embodiments herein, as described and defined in Spradin, J. N. et al., bioRxiv (doi: https://doi.org/10.1101/436998), the entirety of each of which is herein incorporated by reference.

In certain embodiments, the present invention provides a compound of formula I, wherein LBM is a RNF4 binding moiety thereby forming a compound of formula I-jjj:

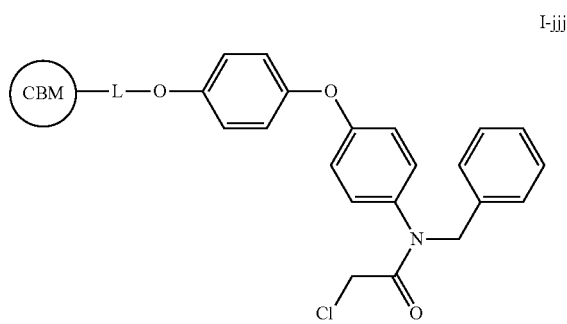

I-jjj or a pharmaceutically acceptable salt thereof, wherein L and CBM are as defined above and described in embodiments herein, as described and defined in Ward, C. C., et al., bioRxiv (doi: https://doi.org %/10.1101/439125), the entirety of each of which is herein incorporated by reference.

In certain embodiments, the present invention provides a compound of formula I, wherein LBM is a VHL binding moiety thereby forming a compound of formula I-nnn-1 or I-nnn-2:

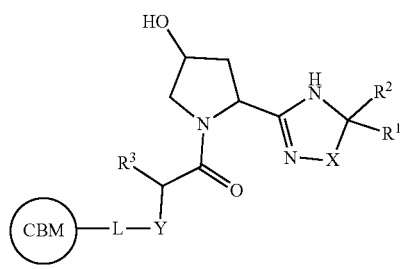

I-nnn-1

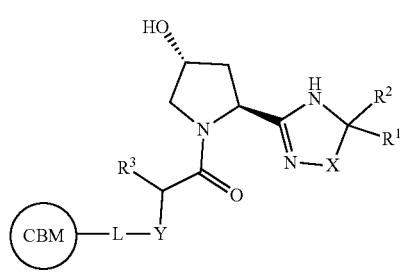

I-nnn-2 or a pharmaceutically acceptable salt thereof, wherein L and CBM are as defined above and described in embodiments herein, and wherein each of the variables $R^1$, $R^2$, $R^3$, X, and Y is as defined and described in WO 2019/084026, the entirety of each of which is herein incorporated by reference.

In certain embodiments, the present invention provides a compound of formula I, wherein LBM is a VHL binding moiety thereby forming a compound of formula I-ooo-1 or I-ooo-2:

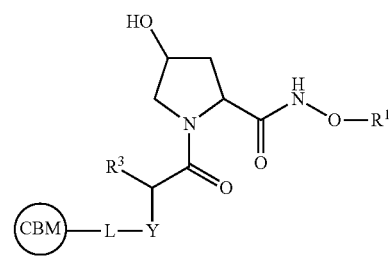

I-ooo-1

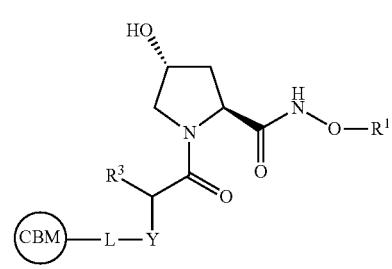

I-ooo-2 or a pharmaceutically acceptable salt thereof, wherein L and CBM are as defined above and described in embodiments herein, and wherein each of the variables $R^1$, $R^3$, and Y is as defined and described in WO 2019/084030, the entirety of each of which is herein incorporated by reference.

In certain embodiments, the present invention provides a compound of formula I, wherein LBM is a E3 ubiquitin ligase (cereblon) binding moiety thereby forming a compound of formula I-ppp-1, I-ppp-2, I-ppp-3, or I-ppp-4:

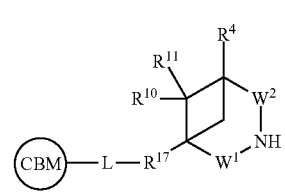

I-ppp-1

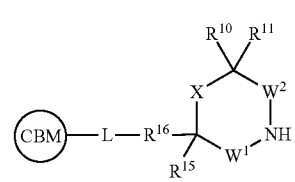

I-ppp-2

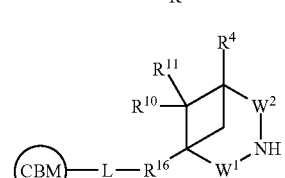

I-ppp-3

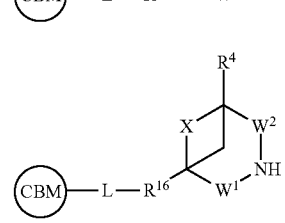

I-ppp-4 or a pharmaceutically acceptable salt thereof, wherein L and CBM are as defined above and described herein, and wherein each of the variables $R^4$, $R^{10}$, $R^{11}$, $R^{15}$, $R^{16}$, $R^{17}$, $W^1$, $W^2$, and X is as defined in WO 2019/099868 which is herein incorporated by reference in its entirety, and wherein

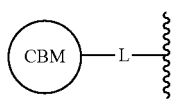

is attached to $R^{17}$ or $R^{16}$ at the site of attachment of $R^{12}$ as defined in WO 2018/237026, such that

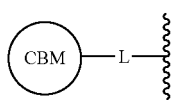

takes the place of the $R^{12}$ substituent.

In some embodiments, LBM is

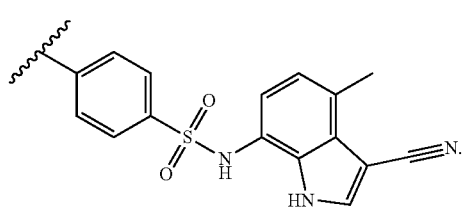 [SMILES: *c1ccc(S(=O)(=O)Nc2ccc(C)c3c(C#N)c[nH]c23)cc1]

In some embodiments LBM is

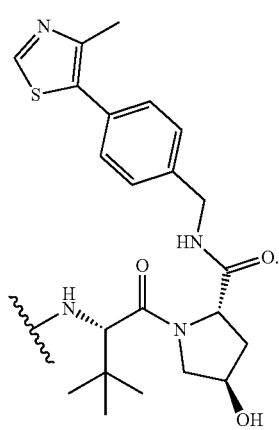 [SMILES: *N[C@H](C(=O)N1C[C@H](O)C[C@H]1C(=O)N[C@@H](C)c1ccc(-c2scnc2C)cc1)C(C)(C)C]

In some embodiments, LBM is

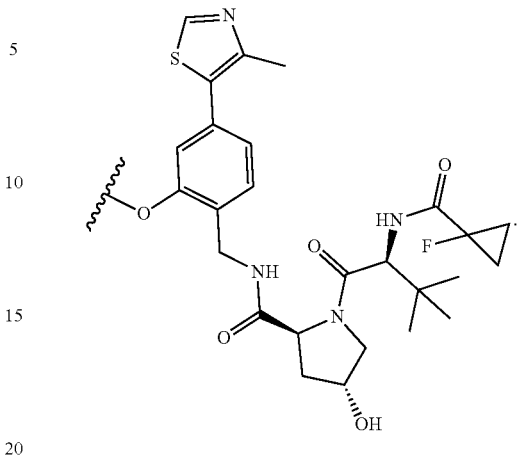

In some embodiments, LBM is

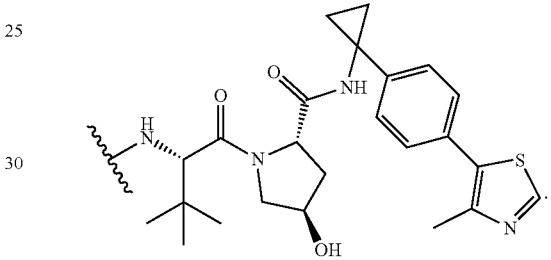

In some embodiments, LBM is

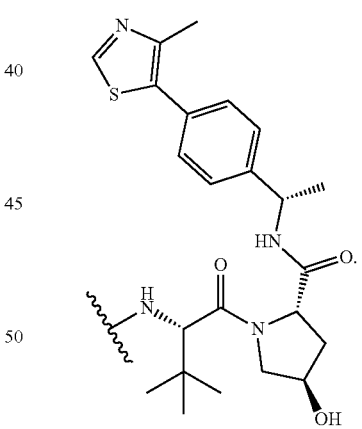

In some embodiments, LBM is

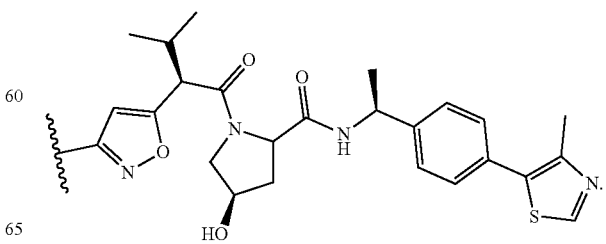

In some embodiments, LBM is
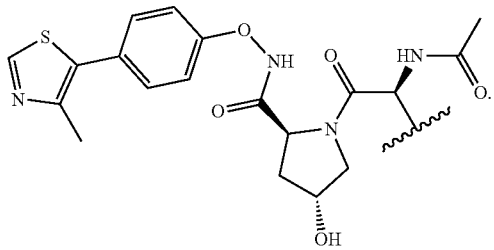 [SMILES: *[C@H](NC(C)=O)C(=O)N1C[C@H](O)C[C@H]1C(=O)NOc1ccc(-c2scnc2C)cc1]
In some embodiments, LBM is
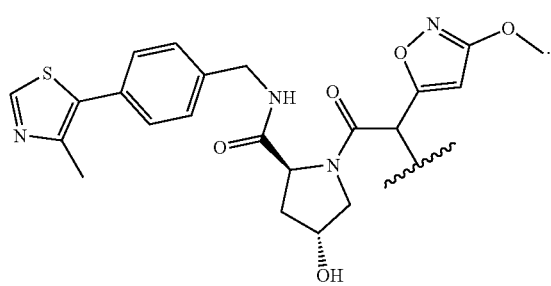 [SMILES: *C(C(=O)N1C[C@H](O)C[C@H]1C(=O)NCc1ccc(-c2scnc2C)cc1)c1cc(OC)no1]
In some embodiments, LBM is
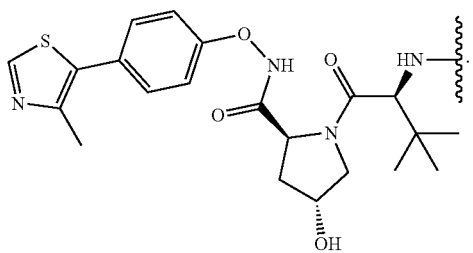 [SMILES: *N[C@H](C(=O)N1C[C@H](O)C[C@H]1C(=O)NOc1ccc(-c2scnc2C)cc1)C(C)(C)C]
In some embodiments, LBM is
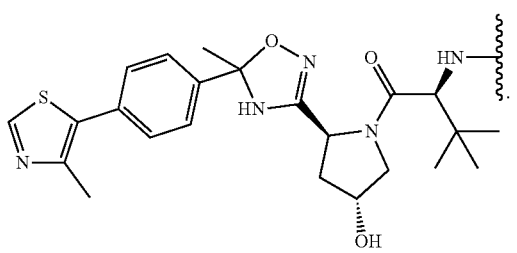 [SMILES: *N[C@H](C(=O)N1C[C@H](O)C[C@H]1C1=NOC(C)(c2ccc(-c3scnc3C)cc2)N1)C(C)(C)C]
In some embodiments, LBM is
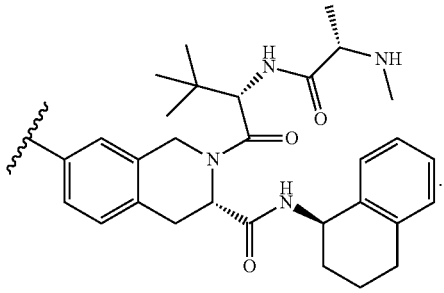 [SMILES: *c1ccc2c(c1)CN(C(=O)[C@@H](NC(=O)[C@H](C)NC)C(C)(C)C)[C@H](C(=O)N[C@@H]1CCCc3ccccc31)C2]
In some embodiments, LBM is
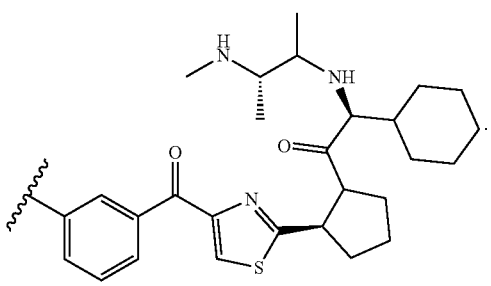 [SMILES: *c1cccc(C(=O)c2csc([C@@H]3CCCC3C(=O)[C@@H](NC(C)[C@H](C)NC)C3CCCCC3)n2)c1]
In some embodiments, LBM is
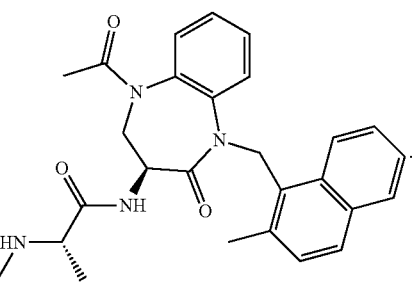 [SMILES: CN[C@@H](C)C(=O)N[C@H]1CN(C(C)=O)c2ccccc2N(Cc2c(C)ccc3ccccc23)C1=O]
In some embodiments, LBM is
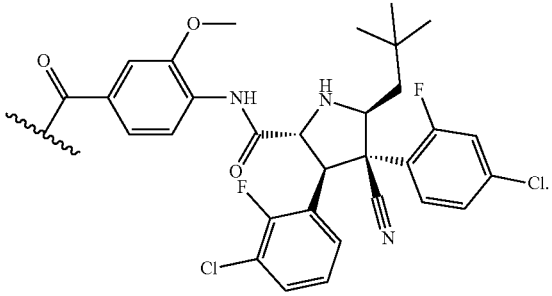 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

In some embodiments, LBM is
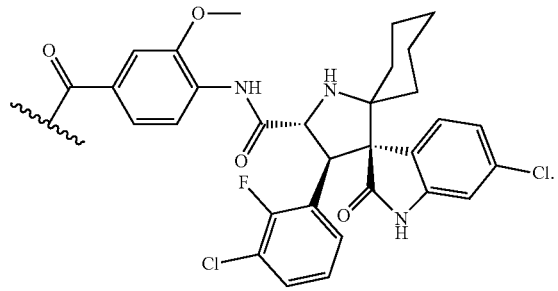 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)c(OC)c1]
In some embodiments, LBM is
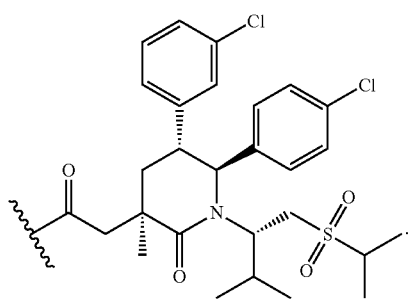 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]
In some embodiments, LBM is
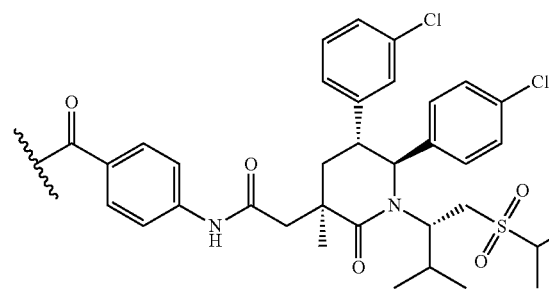
In some embodiments, LBM is
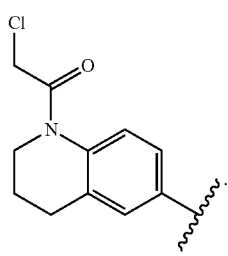 [SMILES: *c1ccc2c(c1)CCCN2C(=O)CCl]
In some embodiments, LBM is
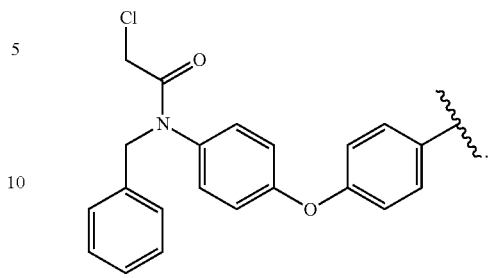
In some embodiments, LBM is
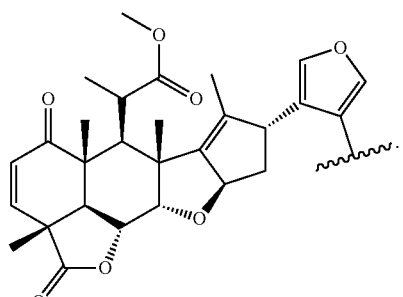
In some embodiments, LBM is
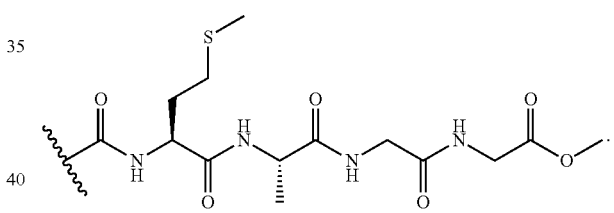
In some embodiments, LBM is
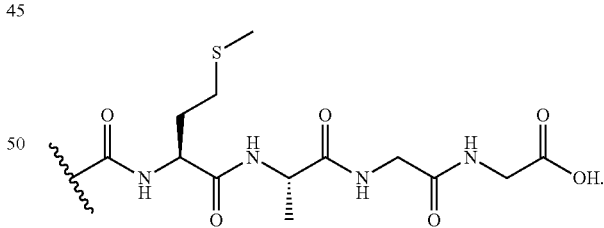
In some embodiments, LBM is
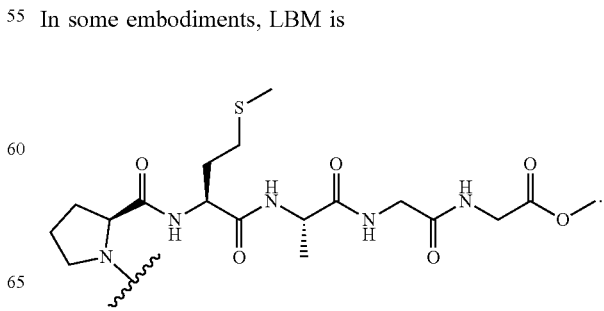

In some embodiments, LBM is

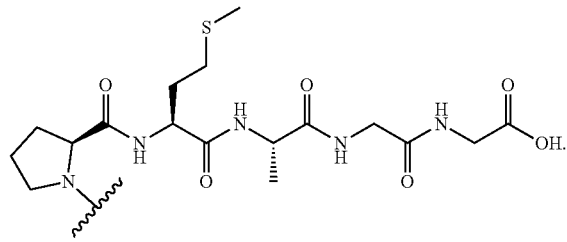 [SMILES: *N1CCC[C@H]1C(=O)N[C@@H](CCSC)C(=O)N[C@@H](C)C(=O)NCC(=O)NCC(=O)O]

In some embodiments, LBM is

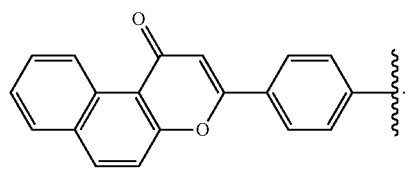 [SMILES: *c1ccc(-c2cc(=O)c3c(ccc4ccccc43)o2)cc1]

In some embodiments, LBM is

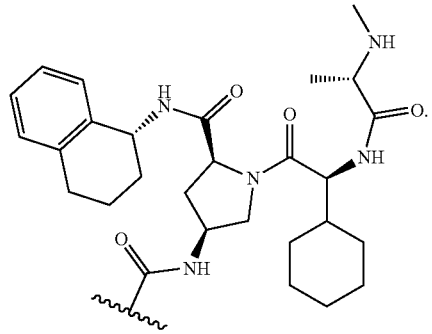 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]

In some embodiments, LBM is

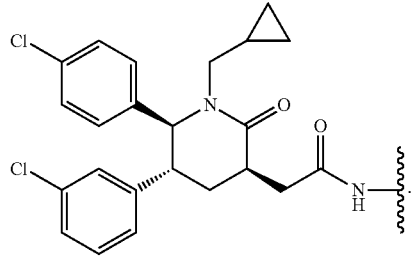 [SMILES: *NC(=O)C[C@H]1C[C@H](c2cccc(Cl)c2)[C@@H](c2ccc(Cl)cc2)N(CC2CC2)C1=O]

In some embodiments, LBM is

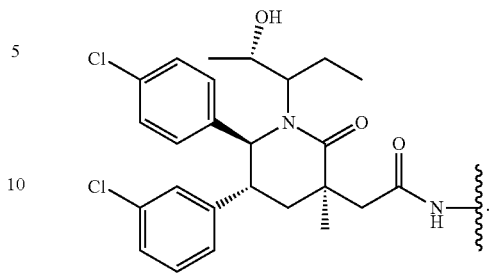

In some embodiments, LBM is

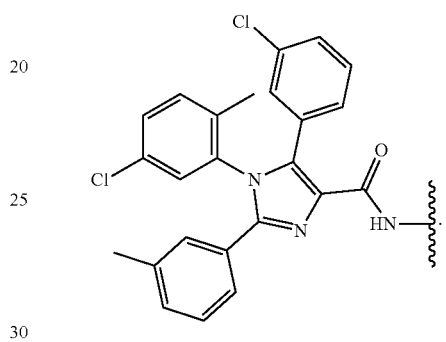

In some embodiments, LBM is

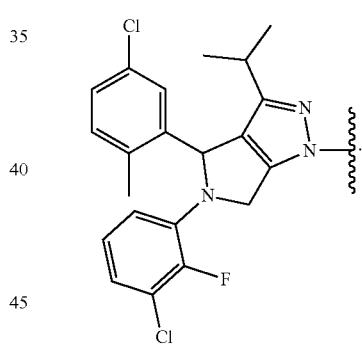

In certain embodiments, the present invention provides a compound of formula I, wherein LBM is a CRBN E3 ubiquitin ligase binding moiety thereby forming a compound of formula I-qqq:

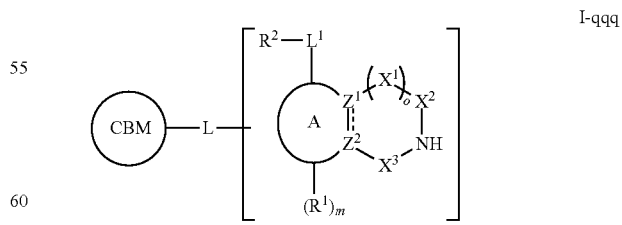

I-qqq or a pharmaceutically acceptable salt thereof, wherein L and CBM are as defined above and described in embodiments herein, wherein:

each $X^1$ is independently —$CH_2$—, —O—, —NR—, —$CF_2$—,

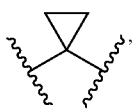 [SMILES: *C1(*)CC1]

—C(O)—, —C(S)—, or

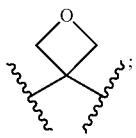

$X^2$ and $X^3$ are independently —CH$_2$—, —C(O)—, —C(S)—, or

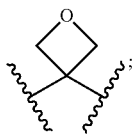 [SMILES: *C1(*)COC1]

$Z^1$ and $Z^2$ are independently a carbon atom or a nitrogen atom;

Ring A is a fused ring selected from benzo, a 4-6 membered saturated or partially unsaturated carbocyclic or heterocyclic ring having 1-3 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —CR$_2$—, —CRF—, —CF$_2$—, —NR—, or —S(O)$_2$—;

each $R^1$ is independently selected from hydrogen, $R^4$, halogen, —CN, —NO$_2$, —OR, —SR, —NR$_2$, —S(O)$_2$R, —S(O)$_2$NR$_2$, —S(O)R, —CF$_2$R, —CR$_2$F, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —Si(OR)R$_2$, and —SiR$_3$; or two $R^1$ groups are optionally taken together to form an optionally substituted 5-8 membered partially unsaturated or aryl fused ring having 0-2 heteroatoms independently selected from nitrogen, oxygen, or sulfur;

each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur;

$R^2$ is selected from

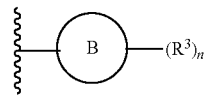

or hydrogen;

Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring B is further optionally substituted with 1-2 oxo groups;

each $R^3$ is independently selected from hydrogen, $R^4$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, and —SiR$_3$;

each $R^4$ is independently selected from an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; === is a single or double bond;

m is 0, 1, 2, 3 or 4;

n is 0, 1, 2, 3 or 4; and is 0, 1, or 2.

As defined above and described herein each $X^1$ is independently a covalent bond, —CH$_2$—, —O—, —NR—, —CF$_2$—,

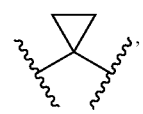 [SMILES: *C1(*)CC1]

C(O)—, —C(S)—, or

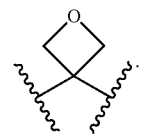 [SMILES: *C1(*)COC1]

In some embodiments, $X^1$ is a covalent bond. In some embodiments, $X^1$ is —CH$_2$—. In some embodiments, $X^1$ is —O—. In some embodiments, $X^1$ is —NR—. In some embodiments, $X^1$ is —CF$_2$—. In some embodiments, $X^1$ is

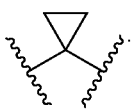 [SMILES: *C1(*)CC1]

In some embodiments, $X^1$ is —C(O)—. In some embodiments, $X^1$ is —C(S)—. In some embodiments, $X^1$ is

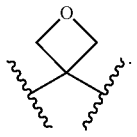 [SMILES: *C1(*)COC1]

In certain embodiments, $X^1$ is selected from those shown in the compounds of Table 1.

As defined above and described herein, $X^2$ and $X^3$ are independently —CH$_2$—, —C(O)—, —C(S)—, or

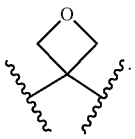 [SMILES: *C1(*)COC1]

In some embodiments, $X^2$ and $X^3$ are independently —CH$_2$—. In some embodiments, $X^2$ and $X^3$ are independently —C(O)—. In some embodiments, $X^2$ and $X^3$ are independently —C(S)—. In some embodiments, $X^2$ and $X^3$ are independently

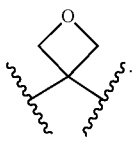

In certain embodiments, $X^2$ and $X^3$ are independently selected from those shown in the compounds of Table 1.

As defined above and described herein, $X^4$ is a covalent bond, —CH$_2$—, —CR$_2$—, —O—, —NR—, —CF$_2$—,

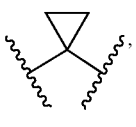 [SMILES: *C1(*)CC1]

—C(O)—, —C(S)—, or

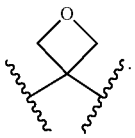 [SMILES: *C1(*)COC1]

As define above and described herein, $Z^1$ and $Z^2$ are independently a carbon atom or a nitrogen atom.

In some embodiments, $Z^1$ and $Z^2$ are independently a carbon atom. In some embodiments, $Z^1$ and $Z^z$ are independently a carbon atom.

In certain embodiments, $Z^1$ and $Z^2$ are independently selected from those shown in the compounds of Table 1.

As defined above and described herein, Ring A is fused ring selected from benzo or a 5-6 membered heteroaryl ring having 1-4 heteroatoms independently selected from nitrogen, oxygen, and sulfur.

In some embodiments, Ring A is benzo. In some embodiments, Ring A is a 5-6 membered heteroaryl ring having 1-4 heteroatoms independently selected from nitrogen, oxygen, and sulfur.

In certain embodiments, Ring A is selected from those shown in the compounds of Table 1.

As defined above and described herein, $L^1$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —CR$_2$—, —CRF—, —CF$_2$—, —NR—, or —S(O)$_2$—

In some embodiments, $L^1$ is a covalent bond. In some embodiments, $L^1$ is a $C_{1-3}$ bivalent straight or branched saturated or unsaturated hydrocarbon chain wherein 1-2 methylene units of the chain are independently and optionally replaced with —O—, —S—, —C(O)—, —C(S)—, —CR$_2$—, —CRF—, —CF$_2$—, —NR—, or —S(O)$_2$—.

In some embodiments, $L^1$ is —C(O)—.

In certain embodiments, $L^1$ is selected from those shown in the compounds of Table 1.

As defined above and described herein, each $R^1$ is independently selected from hydrogen, $R^4$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —Si(OR)R$_2$, and —SiR$_3$, or two $R^1$ groups are optionally taken together to form an optionally substituted 5-8 membered partially unsaturated or aryl fused ring having 0-2 heteroatoms independently selected from nitrogen, oxygen, or sulfur.

In some embodiments, $R^1$ is hydrogen. In some embodiments, $R^1$ is $R^4$. In some embodiments, $R^1$ is halogen. In some embodiments, $R^1$ is —CN. In some embodiments, $R^1$ is —NO$_2$. In some embodiments, $R^1$ is —OR. In some embodiments, $R^1$ is —SR. In some embodiments, $R^1$ is —NR$_2$. In some embodiments, $R^1$ is —S(O)$_2$R. In some embodiments, $R^1$ is —S(O)$_2$NR$_2$. In some embodiments, $R^1$ is —S(O)R. In some embodiments, $R^1$ is —CF$_2$R. In some embodiments, $R^1$ is —CF$_3$. In some embodiments, $R^1$ is —CR$_2$(OR). In some embodiments, $R^1$ is —CR$_2$(NR$_2$). In some embodiments, $R^1$ is —C(O)R. In some embodiments, $R^1$ is —C(O)OR. In some embodiments, $R^1$ is —C(O)NR$_2$. In some embodiments, $R^1$ is —C(O)N(R)OR. In some embodiments, $R^1$ is —OC(O)R. In some embodiments, $R^1$ is —OC(O)NR$_2$. In some embodiments, $R^1$ is —C(S)NR$_2$. In some embodiments, $R^1$ is —N(R)C(O)OR. In some embodiments, $R^1$ is —N(R)C(O)R. In some embodiments, $R^1$ is —N(R)C(O)NR$_2$. In some embodiments, $R^1$ is —N(R)S(O)$_2$R. In some embodiments, $R^1$ is —OP(O)R$_2$. In some embodiments, $R^1$ is —OP(O)(OR)$_2$. In some embodiments, $R^1$ is —OP(O)(OR)NR$_2$. In some embodiments, $R^1$ is —OP(O)(NR$_2$)$_2$. In some embodiments, $R^1$ is —Si(OR)R$_2$. In some embodiments, $R^1$ is —SiR$_3$. In some embodiments, two $R^1$ groups are optionally taken together to form an optionally substituted 5-8 membered partially unsaturated or aryl fused ring having 0-2 heteroatoms independently selected from nitrogen, oxygen, or sulfur.

In certain embodiments, each $R^1$ is independently selected from those shown in the compounds of Table 1.

As defined above and described here, each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In some embodiments, R is hydrogen. In some embodiments, R is an optionally substituted $C_{1-6}$ aliphatic. In some embodiments, R is an optionally substituted phenyl. In some embodiments, R is an optionally substituted 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

As defined above and described herein, $R^2$ is selected from or

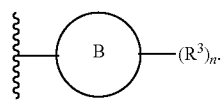

hydrogen.

In some embodiment $R^2$ is

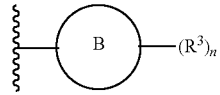

In some embodiments, $R^2$ is hydrogen.

In certain embodiments, $R^2$ is selected from those shown in the compounds of Table 1.

As defined above and described herein, Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring B is further optionally substituted with 1-2 oxo groups.

In some embodiments, Ring B is phenyl. In some embodiments, Ring B is a 4-10 membered saturated or partially unsaturated mono- or bicyclic carbocyclic or heterocyclic ring having 1-3 heteroatoms independently selected from nitrogen, oxygen, and sulfur In some embodiments, Ring B is a 5-6 membered heteroaryl ring having 1-4 heteroatoms independently selected from nitrogen, oxygen, and sulfur. In some embodiments, Ring B is further optionally substituted with 1-2 oxo groups.

In certain embodiments, Ring B is selected from those shown in the compounds of Table 1.

As defined above and described herein, each $R^3$ is independently selected from hydrogen, $R^4$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$OP(O)R_2$, —$OP(O)(OR)_2$, —$OP(O)(OR)NR_2$, —$OP(O)(NR_2)_2$, and —$SiR_3$.

In some embodiments, $R^3$ is hydrogen. In some embodiments, $R^3$ is $R^4$. In some embodiments, $R^3$ is halogen. In some embodiments, $R^3$ is —CN. In some embodiments, $R^3$ is —$NO_2$. In some embodiments, $R^3$ is —OR. In some embodiments, $R^3$ is —SR. In some embodiments, $R^3$ is —$NR_2$. In some embodiments, $R^3$ is —$S(O)_2R$. In some embodiments, $R^3$ is —$S(O)_2NR_2$. In some embodiments, $R^3$ is —S(O)R. In some embodiments, $R^3$ is —$CF_2R$. In some embodiments, $R^3$ is —$CF_3$. In some embodiments, $R^3$ is —$CR_2(OR)$. In some embodiments, $R^3$ is —$CR_2(NR_2)$. In some embodiments, $R^3$ is —C(O)R. In some embodiments, $R^3$ is —C(O)OR. In some embodiments, $R^3$ is —$C(O)NR_2$. In some embodiments, $R^3$ is —C(O)N(R)OR. In some embodiments, $R^3$ is —OC(O)R. In some embodiments, $R^3$ is —$OC(O)NR_2$. In some embodiments, $R^3$ is —N(R)C(O)OR. In some embodiments, $R^3$ is —N(R)C(O)R. In some embodiments, $R^3$ is —$N(R)C(O)NR_2$. In some embodiments, $R^3$ is —$N(R)S(O)_2R$. In some embodiments, $R^3$ is —$OP(O)R_2$. In some embodiments, $R^3$ is —$OP(O)(OR)_2$. In some embodiments, $R^3$ is —$OP(O)(OR)NR_2$. In some embodiments, $R^3$ is —$OP(O)(NR_2)_2$. In some embodiments, $R^3$ is —$SiR_3$.

In certain embodiments, $R^3$ is selected from those shown in the compounds of Table 1.

As defined above and described herein, each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^4$ is an optionally substituted $C_{1-6}$ aliphatic. In some embodiments, $R^4$ is an optionally substituted phenyl. In some embodiments, $R^4$ is an optionally substituted 4-7 membered saturated or partially unsaturated heterocyclic ring having 1-2 heteroatoms independently selected from nitrogen, oxygen, and sulfur. In some embodiments, $R^4$ is an optionally substituted 5-6 membered heteroaryl ring having 1-4 heteroatoms independently selected from nitrogen, oxygen, and sulfur.

In certain embodiments, $R^4$ is selected from those shown in the compounds of Table 1.

As defined above and described herein, === is a single or double bond.

In some embodiments, === is a single bond. In some embodiments, === is a double bond.

In certain embodiments, === is selected from those shown in the compounds of Table 1.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In certain embodiments, m is selected from those shown in the compounds of Table 1.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In certain embodiments, n is selected from those shown in the compounds of Table 1.

As defined above and described herein, o is 0, 1, or 2.

In some embodiments, n is 0. In some embodiments, n is 1. In some embodiments, m is 2.

In certain embodiments, o is selected from those shown in the compounds of Table 1.

In some embodiments, the present invention provides a compound of formula I-qqq, wherein Ring A is benzo, o is 1, $X^1$ is —CH$_2$—, $X^2$ and $X^3$ are —C(O)—, and $Z^1$ and $Z^2$ are carbon atoms as shown, to provide a compound of formula I-qqq-1:

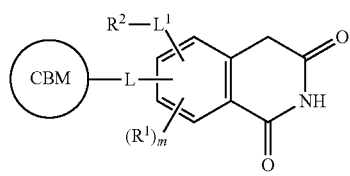

I-qqq-1 or a pharmaceutically acceptable salt thereof, wherein each of CBM, L, $L^1$, $R^1$, $R^2$, and m is as defined above and described in embodiments herein, both singly and in combination.

In some embodiments, the present invention provides a compound of formula I-qqq, wherein Ring A is benzo, o is 1, $X^1$, $X^2$ and $X^3$ are —C(O)—, and $Z^1$ and $Z^2$ are carbon atoms as shown, to provide a compound of formula I-qqq-12:

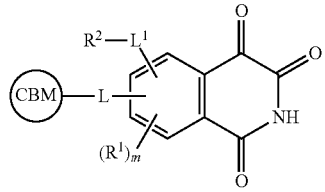

I-qqq-12 or a pharmaceutically acceptable salt thereof, wherein each of CBM, L, $L^1$, $R^1$, $R^2$, and m is as defined above and described in embodiments herein, both singly and in combination.

In some embodiments, LBM is

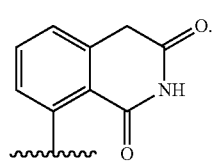 [SMILES: *c1cccc2c1C(=O)NC(=O)C2]

In some embodiments, LBM is

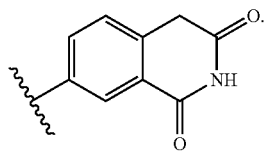 [SMILES: *c1ccc2c(c1)C(=O)NC(=O)C2]

In some embodiments, LBM is

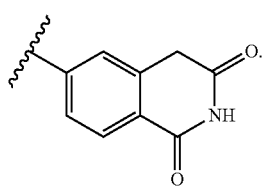 [SMILES: *c1ccc2c(c1)CC(=O)NC2=O]

In some embodiments, LBM is

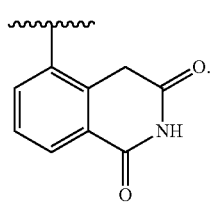 [SMILES: *c1cccc2c1CC(=O)NC2=O]

In some embodiments, LBM is

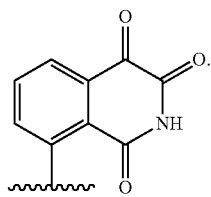 [SMILES: *c1cccc2c1C(=O)NC(=O)C2=O]

In some embodiments, LBM is

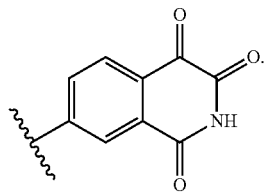 [SMILES: *c1ccc2c(c1)C(=O)NC(=O)C2=O]

In some embodiments, LBM is

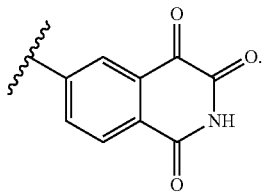 [SMILES: *c1ccc2c(c1)C(=O)C(=O)NC2=O]

In some embodiments, LBM is

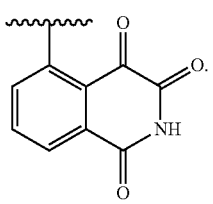 [SMILES: *c1cccc2c1C(=O)C(=O)NC2=O]

In some embodiments, LBM is selected from those in Table 1, below.

In certain embodiments, the present invention provides a compound of formula I, wherein LBM is a RPN13 binding moiety thereby forming a compound of formula I-rrr:

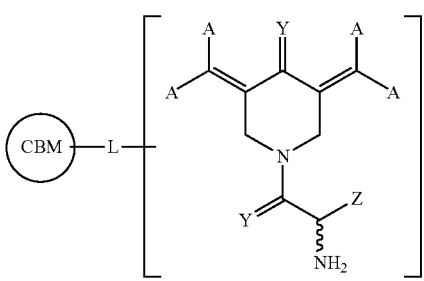

I-rrr or a pharmaceutically acceptable salt thereof, wherein L and CBM are as defined above and described in embodiments herein, and wherein each of the variables A, Y, and Z is as described and defined in WO 2019/165229, the entirety of each of which is herein incorporated by reference.

In certain embodiments, the present invention provides a compound of formula I, wherein LBM is a Ubr1 binding moiety as described in Shanmugasundaram, K. et al, J. Bio. Chem. 2019, doi: 10.1074/jbc.AC119.010790, the entirety of each of which is herein incorporated by reference, thereby forming a compound of formula I-sss-1 or I-sss-2:

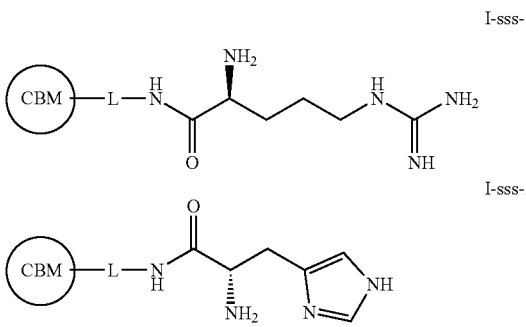

I-sss-1

I-sss-2 or a pharmaceutically acceptable salt thereof, wherein L and CBM are as defined above and described in embodiments herein.

In certain embodiments, the present invention provides a compound of formula I, wherein LBM is a CRBN E3 ubiquitin ligase binding moiety thereby forming a compound of formula I-uuu-1, I-uuu-2, I-uuu-3 or I-uuu-4:

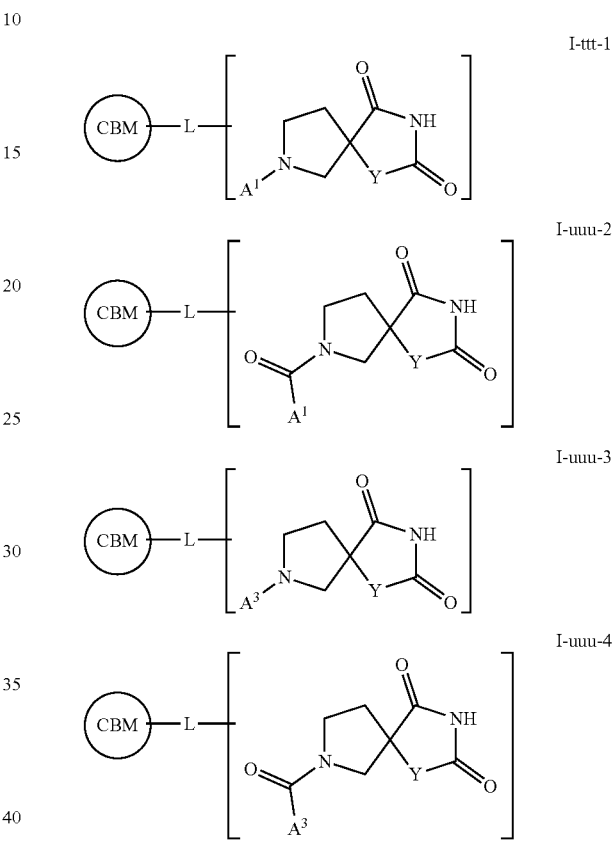

I-ttt-1

I-uuu-2

I-uuu-3

I-uuu-4 or a pharmaceutically acceptable salt thereof, wherein L and CBM are as defined above and described in embodiments herein, and wherein each of the variables Y, $A^1$, and $A^3$ is as described and defined in WO 2019/236483, the entirety of each of which is herein incorporated by reference.

In certain embodiments, the present invention provides a compound of formula I, wherein LBM is human kelch-like ECH-associated protein 1 (KEAP1) thereby forming a compound of formula I-vvv:

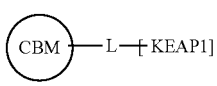

I-vvv or a pharmaceutically acceptable salt thereof, wherein L and CBM are as defined above and described in embodiments herein, both singly and in combination.

In certain embodiments, the present invention provides a compound of formula I, wherein LBM is KEAP1 binding moiety as recited in Lu et al., Euro. J. Med. Chem., 2018, 146:251-9, thereby forming a compound of formula I-www:

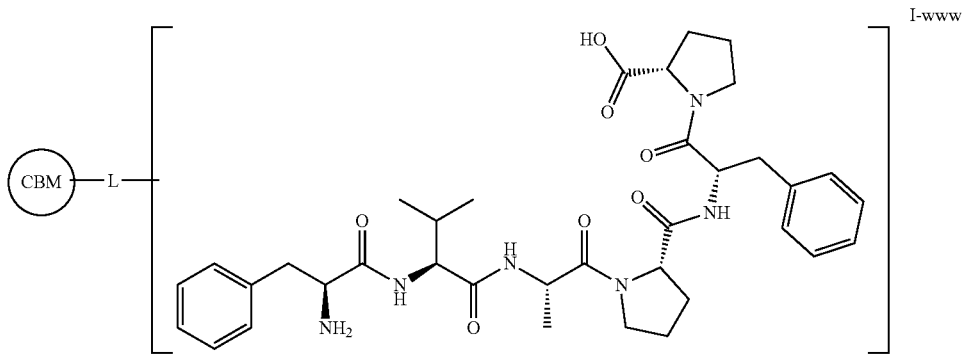

I-www or a pharmaceutically acceptable salt thereof, wherein L and CBM are as defined above and described in embodiments herein, both singly and in combination.

In certain embodiments, the present invention provides a compound of formula I, wherein LBM is KEAP1-NRF2 binding moiety thereby forming a compound of formula I-xxx or I-xxx-2:

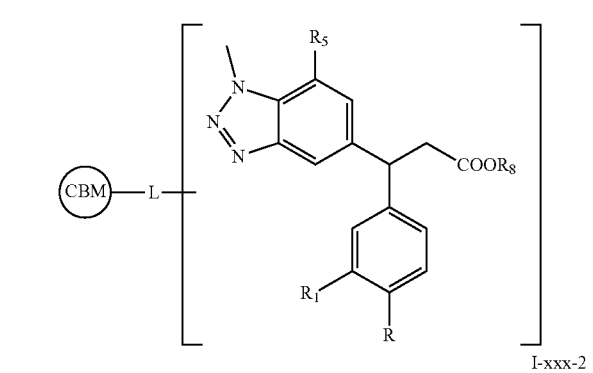

I-xxx-1

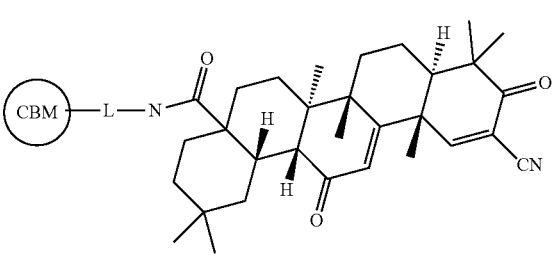

I-yyy-1

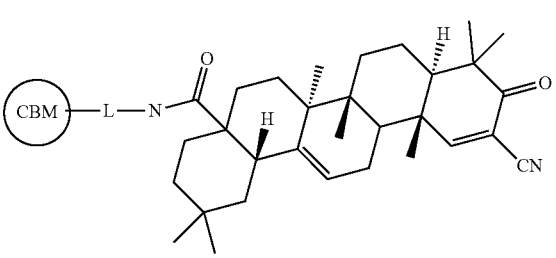

I-yyy-2

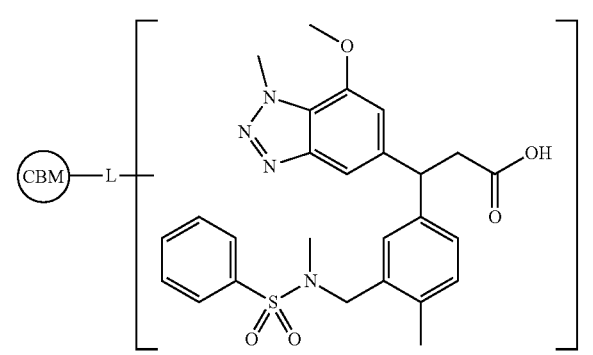

I-xxx-2 or a pharmaceutically acceptable salt thereof, wherein L and CBM are as defined above and described in embodiments herein, both singly and in combination.

In some embodiments, LBM is

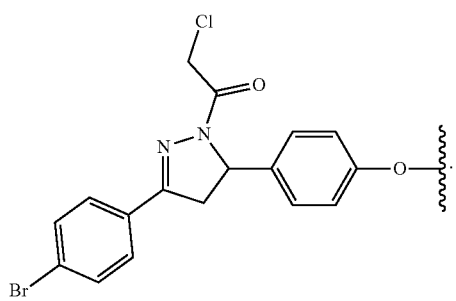 [SMILES: *Oc1ccc(C2CC(c3ccc(Br)cc3)=NN2C(=O)CCl)cc1]

or a pharmaceutically acceptable salt thereof, wherein L and CBM are as defined above and described in embodiments herein, and wherein each of the variables R, $R_1$, $R_5$, and $R_8$ is as described and defined in WO 2020/018788, the entirety of each of which is herein incorporated by reference.

In certain embodiments, the present invention provides a compound of formula I, wherein LBM is KEAP1-NRF2 binding moiety as recited in Tong et al., "Targeted Protein Degradation via a Covalent Reversible Degrader Based on Bardoxolone", ChemRxiv 2020, thereby forming a compound of formula I-yyy-1 or I-yyy-2:

In some embodiments, LBM is

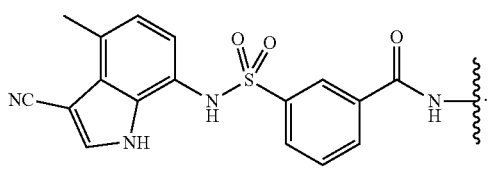 [SMILES: *NC(=O)c1cccc(S(=O)(=O)Nc2ccc(C)c3c(C#N)c[nH]c23)c1]

Degradation Inducing Moiety (DIM)

In certain embodiments, the present invention provides a compound of formula I:

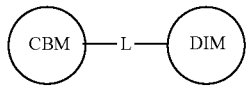

I or a pharmaceutically acceptable salt thereof, wherein L and CBM are as described above and herein, and DIM is a degradation inducing moiety selected from LBM, a lysine mimetic, or a hydrogen atom.

In some embodiments, DIM is LBM as described above and herein. In some embodiments, DIM is a lysine mimetic. In some embodiments, the covalent attachment of ubiquitin to CDK2 protein is achieved through the action of a lysine mimetic. In some embodiments, upon the binding of a compound of formula I to CDK2 protein, the moiety that mimics a lysine undergoes ubiquitination thereby marking CDK2 protein for degradation via the Ubiquitin-Proteasome Pathway (UPP).

In some embodiments, DIM is

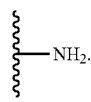

In some embodiments, DIM is

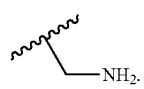

In some embodiments, DIM is

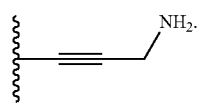

In some embodiments, DIM is selected from those depicted in Table 2, below.

In some embodiments, the present invention provides the compound of formula I as a compound of formula I-aaaa:

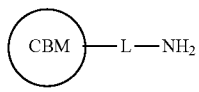

I-aaaa or a pharmaceutically acceptable salt thereof, wherein each of CBM and L is as defined above and described in embodiments herein, both singly and in combination.

In some embodiments, the present invention provides the compound of formula I as a compound of formula I-aaaa-1:

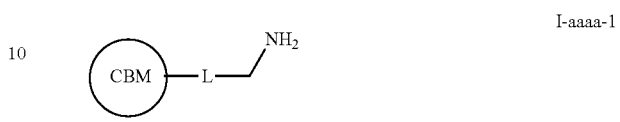

I-aaaa-1 or a pharmaceutically acceptable salt thereof, wherein each of CBM and L is as defined above and described in embodiments herein, both singly and in combination.

In some embodiments, the present invention provides the compound of formula I as a compound of formula I-aaaa-2:

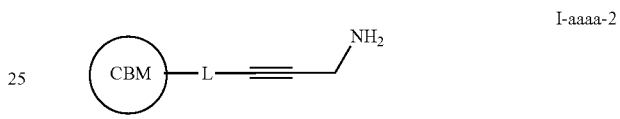

I-aaaa-2 or a pharmaceutically acceptable salt thereof, wherein each of CBM and L is as defined above and described in embodiments herein, both singly and in combination.

In certain embodiments, the present invention provides a compound of Formula I, wherein DIM is a lysine mimetic

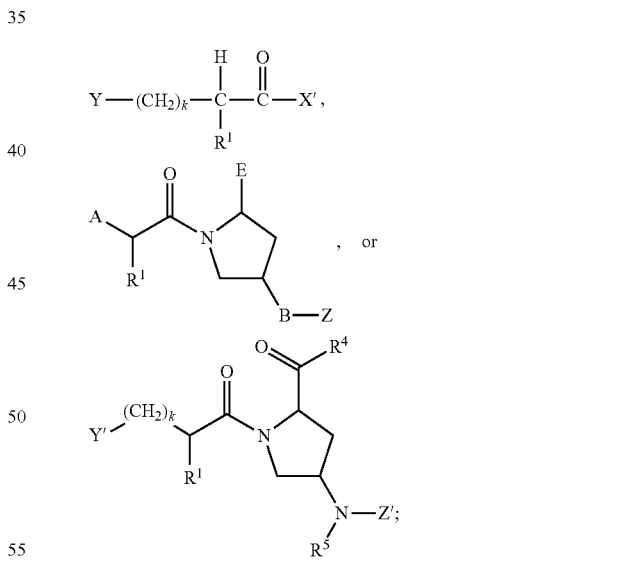

thereby forming a compound of Formulae I-bbbb-1, I-bbbb-2, or I-bbbb-3, respectively:

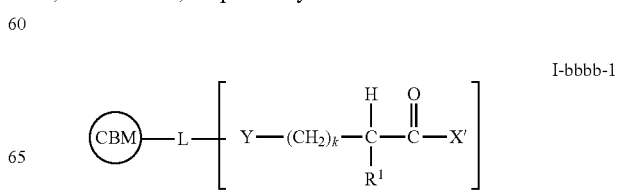

I-bbbb-1

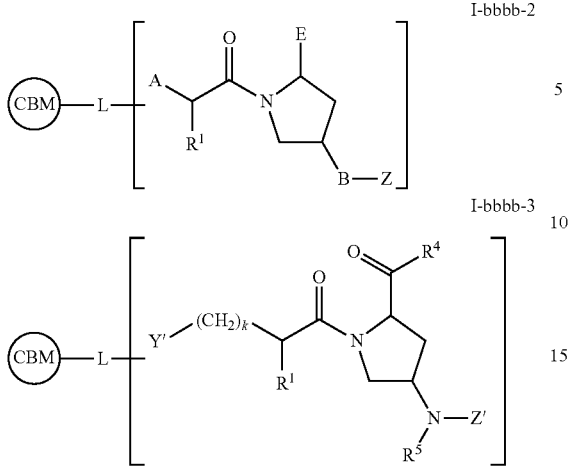

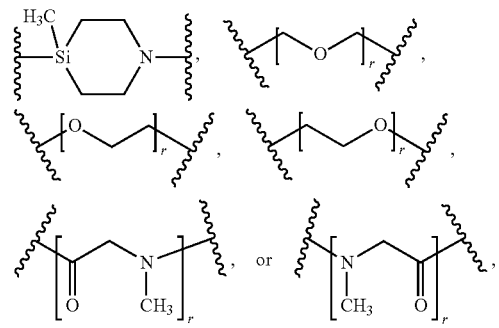

or a pharmaceutically acceptable salt thereof, wherein L and CBM are as defined above and described in embodiments herein, and wherein each of the variables $R^1$, $R^4$, $R^5$, A, B, E, Y, Y', Z, Z', and k are as defined and described in U.S. Pat. No. 7,622,496, the entirety of each of which is herein incorporated by reference.

Hydrogen Atom

In some embodiments, DIM is a hydrogen atom. In some embodiments, the covalent attachment of ubiquitin to CDK2 protein is achieved through a provided compound wherein DIM is a hydrogen atom. In some embodiments, upon the binding of a compound of formula I to CDK2 protein, the moiety being hydrogen effectuates ubiquitination thereby marking CDK2 protein for degradation via the Ubiquitin-Proteasome Pathway (UPP).

In some embodiments, DIM is selected from those depicted in Table 2, below.

In some embodiments, the present invention provides the compound of formula I wherein DIM is a hydrogen atom, thereby forming a compound of formula I-cccc:

or a pharmaceutically acceptable salt thereof, wherein each of CBM and L is as defined above and described in embodiments herein, both singly and in combination.

Linker (L)

As defined above and described herein, L is a bivalent moiety that connects CBM to LBM or CBM to DIM.

In some embodiments, L is a bivalent moiety that connects CBM to LBM. In some embodiments, L is a bivalent moiety that connects CBM to DIM. In some embodiments, L is a bivalent moiety that connects CBM to a lysine mimetic.

In some embodiments, L is a covalent bond or a bivalent, saturated or partially unsaturated, straight or branched $C_{1-50}$ hydrocarbon chain, wherein 0-6 methylene units of L are independently replaced by -Cy-, —O—, —NR—, —SiR$_2$—, —Si(OH)R—, —Si(OH)$_2$—, —P(O)OR—, —P(O)R—, —P(O)NR$_2$—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—, wherein:
each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, and sulfur, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur, and;

r is 0, 1, 2, 3, 4, 5, 6, 7, 8, 9, or 10.

In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-7 membered saturated or partially unsaturated carbocyclylenyl. In some embodiments, each -Cy- is independently an optionally substituted 4-11 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy- is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-11 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, and sulfur.

In some embodiments, -Cy- is

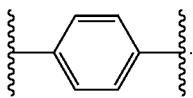 [SMILES: *c1ccc(*)cc1]

In some embodiments, -Cy- is

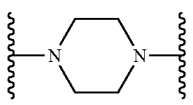

In some embodiments, -Cy- is

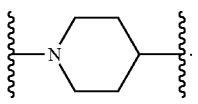

In some embodiments, -Cy- is

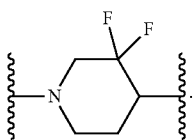 [SMILES: *C1CCN(*)CC1(F)F]

In some embodiments, -Cy- is

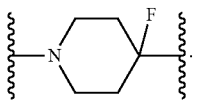

In some embodiments, -Cy- is

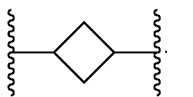 [SMILES: *C1CC(*)C1]

In some embodiments, -Cy- is

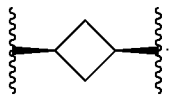 [SMILES: *[C@H]1C[C@@H](*)C1]

In some embodiments, -Cy- is

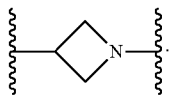

In some embodiments, -Cy- is

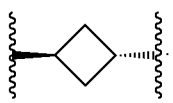 [SMILES: *[C@H]1C[C@H](*)C1]

In some embodiments, -Cy- is

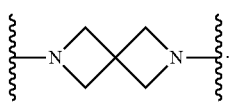 [SMILES: *N1CC2(C1)CN(*)C2]

In some embodiments, -Cy- is

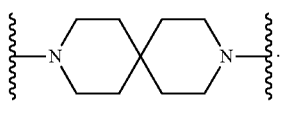

In some embodiments, -Cy- is

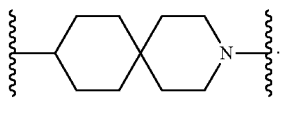

In some embodiments, -Cy- is

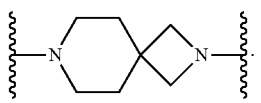

In some embodiments, -Cy- is

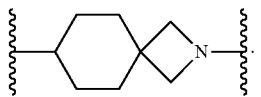

In some embodiments, -Cy- is

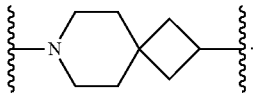

In some embodiments, -Cy- is

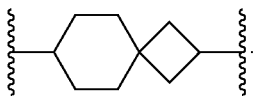

In some embodiments, -Cy- is

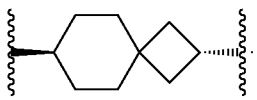

In some embodiments -Cy- is

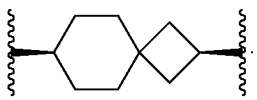

In some embodiments, -Cy- is

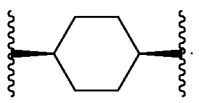

In some embodiments, Cy is

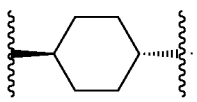

In some embodiments, -Cy- is

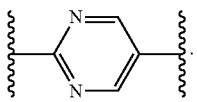

In some embodiments, -Cy- is

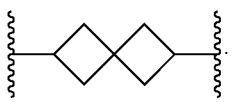 [SMILES: *C1CC2(C1)CC(*)C2]

In some embodiments, -Cy- is

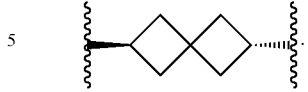

In some embodiments, -Cy- is

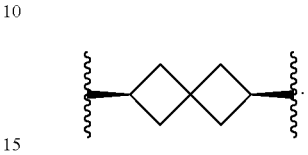

In some embodiments, -Cy- is optionally substituted with one or more fluoro atoms.

In some embodiments, -Cy- is selected from those depicted in Table 2, below.

In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, r is selected from those depicted in Table 2, below.

In some embodiments, L is —NR—($C_{1-10}$ aliphatic)-. In some embodiments, L is —($C_{1-10}$ aliphatic)-NR—($C_{1-10}$ aliphatic)-. In some embodiments, L is —($C_{1-10}$ aliphatic)-NR—($CH_2CH_2O)_{1-10}CH_2CH_2$—. In some embodiments, L is -Cy-NR—($C_{1-10}$ aliphatic)-. In some embodiments, L is -Cy-($C_{1-10}$ aliphatic)-NR—. In some embodiments, L is -Cy-($C_{1-10}$ aliphatic)-NR—($C_{1-10}$ aliphatic)-. In some embodiments, L is —($C_{1-10}$ aliphatic)-Cy-NR—($C_{1-10}$ aliphatic)-. In some embodiments, L is —($C_{1-10}$ aliphatic)-Cy-($C_{1-10}$ aliphatic)-NR—. In some embodiments, L is —($C_{1-10}$ aliphatic)-Cy-($C_{1-10}$ aliphatic)-NR—($C_{1-10}$ aliphatic)-. In some embodiments, L is -Cy-($C_{1-10}$ aliphatic)-Cy-NR—. In some embodiments, L is -Cy-($C_{1-10}$ aliphatic)-NR-Cy-. In some embodiments, L is -Cy-($C_{1-10}$ aliphatic)-Cy-NR—($C_{1-10}$ aliphatic)-. In some embodiments, L is -Cy-($C_{1-10}$ aliphatic)-NR-Cy-($C_{1-10}$ aliphatic)-.

In some embodiments, L is —CONR—($C_{1-10}$ aliphatic)-. In some embodiments, L is —($C_{1-10}$ aliphatic)-CONR—($C_{1-10}$ aliphatic)-. In some embodiments, L is —($C_{1-10}$ aliphatic)-CONR—($CH_2CH_2O)_{1-10}CH_2CH_2$—. In some embodiments, L is -Cy-CONR—($C_{1-10}$ aliphatic)-. In some embodiments, L is -Cy-($C_{1-10}$ aliphatic)-CONR—. In some embodiments, L is -Cy-($C_{1-10}$ aliphatic)-CONR—($C_{1-10}$ aliphatic)-. In some embodiments, L is —($C_{1-10}$ aliphatic)-Cy-CONR—($C_{1-10}$ aliphatic)-. In some embodiments, L is —($C_{1-10}$ aliphatic)-Cy-($C_{1-10}$ aliphatic)-CONR—. In some embodiments, L is —($C_{1-10}$ aliphatic)-Cy-($C_{1-10}$ aliphatic)-CONR—($C_{1-10}$ aliphatic)-. In some embodiments, L is -Cy-($C_{1-10}$ aliphatic)-Cy-CONR—. In some embodiments, L is -Cy-($C_{1-10}$ aliphatic)-CONR-Cy-. In some embodiments, L is -Cy-($C_{1-10}$ aliphatic)-Cy-CONR—($C_{1-10}$ aliphatic)-. In some embodiments, L is -Cy-($C_{1-10}$ aliphatic)-CONR-Cy-($C_{1-10}$ aliphatic)-.

In some embodiments, L is —NRCO—($C_{1-10}$ aliphatic)-. In some embodiments, L is —($C_{1-10}$ aliphatic)-NRCO—($C_{1-10}$ aliphatic)-. In some embodiments, L is —($C_{1-10}$ aliphatic)-NRCO—($CH_2CH_2O)_{1-10}CH_2CH_2$—. In some embodiments, L is -Cy-NRCO—($C_{1-10}$ aliphatic)-. In some embodiments, L is -Cy-($C_{1-10}$ aliphatic)-NRCO—. In some embodiments, L is -Cy-($C_{1-10}$ aliphatic)-NRCO—($C_{1-10}$ aliphatic)-. In some embodiments, L is —($C_{1-10}$ aliphatic)-Cy-NRCO—($C_{1-10}$ aliphatic)-. In some embodiments, L is —($C_{1-10}$ aliphatic)-Cy-($C_{1-10}$ aliphatic)-NRCO—. In some embodiments, L is —($C_{1-10}$ aliphatic)-Cy-($C_{1-10}$ aliphatic)-NRCO—($C_{1-10}$ aliphatic)-. In some embodiments, L is -Cy-($C_{1-10}$ aliphatic)-Cy-NRCO—. In some embodiments, L is -Cy-($C_{1-10}$ aliphatic)-NRCO-Cy-. In some embodiments, L is -Cy-($C_{1-10}$ aliphatic)-Cy-NRCO—($C_{1-10}$ aliphatic)-. In some embodiments, L is -Cy-($C_{1-10}$ aliphatic)-NRCO-Cy-($C_{1-10}$ aliphatic)-.

In some embodiments, L is —O—($C_{1-10}$ aliphatic)-. In some embodiments, L is —($C_{1-10}$ aliphatic)-O—($C_{1-10}$ aliphatic)-. In some embodiments, L is —($C_{1-10}$ aliphatic)-O—($CH_2CH_2O)_{1-10}CH_2CH_2$—. In some embodiments, L is -Cy-O—($C_{1-10}$ aliphatic)-. In some embodiments, L is -Cy-($C_{1-10}$ aliphatic)-O—. In some embodiments, L is -Cy-($C_{1-10}$ aliphatic)-O—($C_{1-10}$ aliphatic)-. In some embodiments, L is —($C_{1-10}$ aliphatic)-Cy-O—($C_{1-10}$ aliphatic)-. In some embodiments, L is —($C_{1-10}$ aliphatic)-Cy-($C_{1-10}$ aliphatic)-O—. In some embodiments, L is —($C_{1-10}$ aliphatic)-Cy-($C_{1-10}$ aliphatic)-O—($C_{1-10}$ aliphatic)-. In some embodiments, L is -Cy-($C_{1-10}$ aliphatic)-Cy-O—. In some embodiments, L is -Cy-($C_{1-10}$ aliphatic)-O-Cy-. In some embodiments, L is -Cy-($C_{1-10}$ aliphatic)-Cy-O—($C_{1-10}$ aliphatic)-. In some embodiments, L is -Cy-($C_{1-10}$ aliphatic)-O-Cy-($C_{1-10}$ aliphatic)-.

In some embodiments, L is -Cy-($C_{1-10}$ aliphatic)-. In some embodiments, L is —($C_{1-10}$ aliphatic)-Cy-($C_{1-10}$ aliphatic)-. In some embodiments, L is —($C_{1-10}$ aliphatic)-Cy-($CH_2CH_2O)_{1-10}CH_2CH_2$—. In some embodiments, L is -Cy-($C_{1-10}$ aliphatic)-Cy-. In some embodiments, L is -Cy-($C_{1-10}$ aliphatic)-Cy-($C_{1-10}$aliphatic)-. In some embodiments, L is -Cy-($C_{1-10}$ aliphatic)-Cy-($C_{1-10}$ aliphatic)-Cy-. In some embodiments, L is —($C_{1-10}$ aliphatic)-Cy-($C_{1-10}$ aliphatic)-Cy-($C_{1-10}$ aliphatic)-.

In some embodiments, L is —NR—$(CH_2)_{1-10}$—. In some embodiments, L is —$(CH_2)_{1-10}$—NR—$(CH_2)_{1-10}$—. In some embodiments, L is —$(CH_2)_{1-10}$—NR—$(CH_2CH_2O)_{1-10}CH_2CH_2$—. In some embodiments, L is -Cy-NR—$(CH_2)_{1-10}$—. In some embodiments, L is -Cy-$(CH_2)_{1-10}$—NR—. In some embodiments, L is -Cy-$(CH_2)_{1-10}$—NR—$(CH_2)_{1-10}$—. In some embodiments, L is —$(CH_2)_{1-10}$-Cy-NR—$(CH_2)_{1-10}$—. In some embodiments, L is —$(CH_2)_{1-10}$-Cy-$(CH_2)_{1-10}$—NR—. In some embodiments, L is —$(CH_2)_{1-10}$-Cy-$(CH_2)_{1-10}$—NR—$(CH_2)_{1-10}$—. In some embodiments, L is -Cy-$(CH_2)_{1-10}$-Cy-NR—. In some embodiments, L is -Cy-$(CH_2)_{1-10}$—NR-Cy-. In some embodiments, L is -Cy-$(CH_2)_{1-10}$-Cy-NR—$(CH_2)_{1-10}$—. In some embodiments, L is -Cy-$(CH_2)_{1-10}$—NR-Cy-$(CH_2)_{1-10}$—.

In some embodiments, L is —CONR—$(CH_2)_{1-10}$—. In some embodiments, L is —$(CH_2)_{1-10}$—CONR—$(CH_2)_{1-10}$—. In some embodiments, L is —$(CH_2)_{1-10}$—CONR—$(CH_2CH_2O)_{1-10}CH_2CH_2$—. In some embodiments, L is -Cy-CONR—$(CH_2)_{1-10}$—. In some embodiments, L is -Cy-$(CH_2)_{1-10}$—CONR—. In some embodiments, L is -Cy-$(CH_2)_{1-10}$—CONR—$(CH_2)_{1-10}$—. In some embodiments, L is —$(CH_2)_{1-10}$-Cy-CONR—$(CH_2)_{1-10}$—. In some embodiments, L is —$(CH_2)_{1-10}$-Cy-$(CH_2)_{1-10}$—CONR—. In some embodiments, L is —$(CH_2)_{1-10}$-Cy-$(CH_2)_{1-10}$—CONR—$(CH_2)_{1-10}$—. In some embodiments, L is -Cy-$(CH_2)_{1-10}$-Cy-CONR—. In some embodiments, L is -Cy-$(CH_2)_{1-10}$—CONR-Cy-. In some embodiments, L is -Cy-$(CH_2)_{1-10}$-Cy-CONR—$(CH_2)_{1-10}$—. In some embodiments, L is -Cy-$(CH_2)_{1-10}$—CONR-Cy-$(CH_2)_{1-10}$—.

In some embodiments, L is —NRCO—$(CH_2)_{1-10}$—. In some embodiments, L is —$(CH_2)_{1-10}$—NRCO—$(CH_2)_{1-10}$—. In some embodiments, L is —$(CH_2)_{1-10}$—NRCO—$(CH_2CH_2O)_{1-10}CH_2CH_2$—. In some embodiments, L is -Cy-NRCO—$(CH_2)_{1-10}$—. In some embodiments, L is -Cy-$(CH_2)_{1-10}$—NRCO—. In some embodiments, L is -Cy-$(CH_2)_{1-10}$—NRCO—$(CH_2)_{1-10}$—. In some embodiments, L is —$(CH_2)_{1-10}$-Cy-NRCO—$(CH_2)_{1-10}$—. In some embodiments, L is —$(CH_2)_{1-10}$-Cy-$(CH_2)_{1-10}$—NRCO—. In some embodiments, L is —$(CH_2)_{1-10}$-Cy-$(CH_2)_{1-10}$—NRCO—$(CH_2)_{1-10}$—. In some embodiments, L is -Cy-$(CH_2)_{1-10}$-Cy-NRCO—. In some embodiments, L is -Cy-$(CH_2)_{1-10}$—NRCO-Cy-. In some embodiments, L is -Cy-$(CH_2)_{1-10}$-Cy-NRCO—$(CH_2)_{1-10}$—. In some embodiments, L is -Cy-$(CH_2)_{1-10}$—NRCO-Cy-$(CH_2)_{1-10}$—.

In some embodiments, L is —O—$(CH_2)_{1-10}$—. In some embodiments, L is —$(CH_2)_{1-10}$—O—$(CH_2)_{1-10}$—. In some embodiments, L is —$(CH_2)_{1-10}$—O—$(CH_2CH_2O)_{1-10}CH_2CH_2$—. In some embodiments, L is -Cy-O—$(CH_2)_{1-10}$—. In some embodiments, L is -Cy-$(CH_2)_{1-10}$—O—. In some embodiments, L is -Cy-$(CH_2)_{1-10}$—O—$(CH_2)_{1-10}$—. In some embodiments, L is —$(CH_2)_{1-10}$-Cy-O—$(CH_2)_{1-10}$—. In some embodiments, L is —$(CH_2)_{1-10}$-Cy-$(CH_2)_{1-10}$—O—. In some embodiments, L is —$(CH_2)_{1-10}$-Cy-$(CH_2)_{1-10}$—O—$(CH_2)_{1-10}$—. In some embodiments, L is -Cy-$(CH_2)_{1-10}$-Cy-O—. In some embodiments, L is -Cy-$(CH_2)_{1-10}$—O-Cy-. In some embodiments, L is -Cy-$(CH_2)_{1-10}$-Cy-O—$(CH_2)_{1-10}$—. In some embodiments, L is -Cy-$(CH_2)_{1-10}$—O-Cy-$(CH_2)_{1-10}$—.

In some embodiments, L is -Cy-$(CH_2)_{1-10}$—. In some embodiments, L is —$(CH_2)_{1-10}$-Cy-$(CH_2)_{1-10}$—. In some embodiments, L is —$(CH_2)_{1-10}$-Cy-$(CH_2CH_2O)_{1-10}CH_2CH_2$—. In some embodiments, L is -Cy-$(CH_2)_{1-10}$-Cy-. In some embodiments, L is -Cy-$(CH_2)_{1-10}$-Cy-$(CH_2)_{1-10}$—. In some embodiments, L is -Cy-$(CH_2)_{1-10}$-Cy-$(CH_2)_{1-10}$-Cy-. In some embodiments, L is —$(CH_2)_{1-10}$-Cy-$(CH_2)_{1-10}$-Cy-$(CH_2)_{1-10}$—.

In some embodiments, L is

[chemical structure: HN-CH₂CH₂-O-CH₂CH₂-O-CH₂CH₂-O-CH₂CH₂CH₂-]

In some embodiments, L is

[chemical structure: -O-CH₂CH₂-O-CH₂CH₂-O-CH₂CH₂-O-CH₂CH₂CH₂-]

In some embodiments, L is

[chemical structure: -CH₂CH₂-O-CH₂CH₂-O-CH₂CH₂-O-CH₂CH₂CH₂-]

In some embodiments, L is

[chemical structure: HN-CH₂CH₂-O-CH₂CH₂-O-CH₂CH₂-O-CH₂CH₂-O-CH₂CH₂CH₂-]

211

In some embodiments, L is

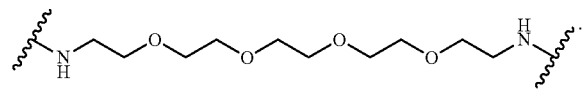 [SMILES: *NCCOCCOCCOCCOCCN*]

In some embodiments, L is

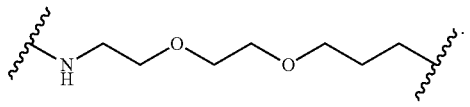 [SMILES: *CCCOCCOCCN*]

In some embodiments, L is

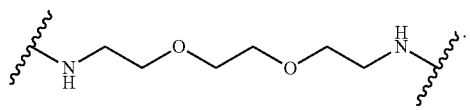 [SMILES: *NCCOCCOCCN*]

In some embodiments, L is

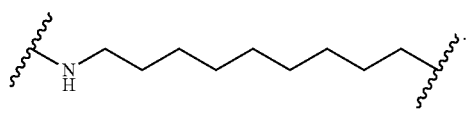 [SMILES: *CCCCCCCCCN*]

In some embodiments, L is

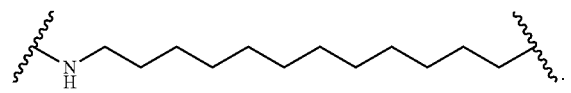 [SMILES: *CCCCCCCCCCCCN*]

In some embodiments, L is

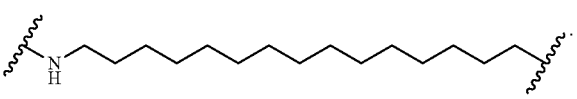 [SMILES: *CCCCCCCCCCCCCCCN*]

In some embodiments, L is

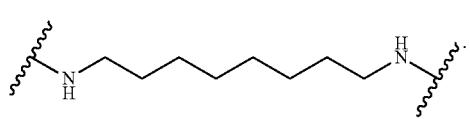 [SMILES: *NCCCCCCCCN*]

In some embodiments, L is

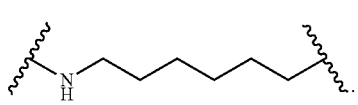 [SMILES: *CCCCCCN*]

212

In some embodiments, L is

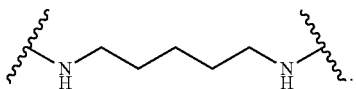 [SMILES: *NCCCCCN*]

In some embodiments, L is

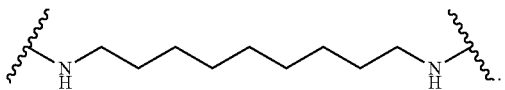 [SMILES: *NCCCCCCCCCN*]

In some embodiments, L is

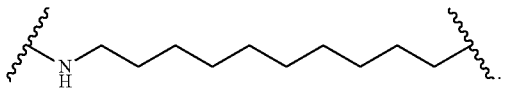 [SMILES: *CCCCCCCCCCN*]

In some embodiments, L is

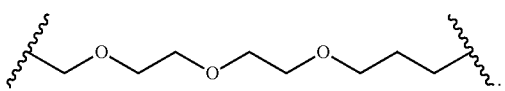 [SMILES: *CCCOCCOCCOC*]

In some embodiments, L is

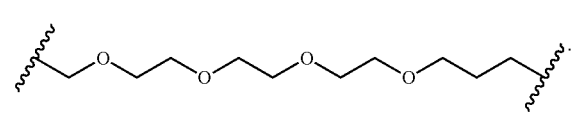 [SMILES: *CCCOCCOCCOCCOC*]

In some embodiments, L is

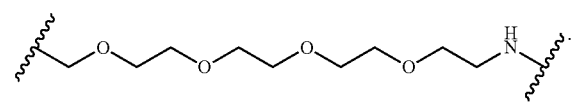 [SMILES: *COCCOCCOCCOCCN*]

In some embodiments, L is

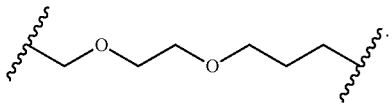 [SMILES: *CCCOCCOC*]

In some embodiments L is

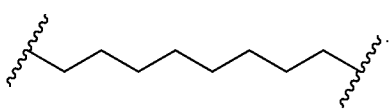 [SMILES: *CCCCCCCC*]

In some embodiments, L is

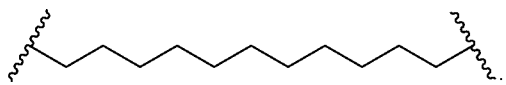 [SMILES: *CCCCCCCCCCC*]

In some embodiments, L is

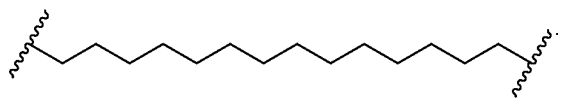 [SMILES: *CCCCCCCCCCCCCC*]

In some embodiments, L is

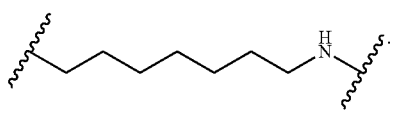 [SMILES: *CCCCCCCN*]

In some embodiments, L is

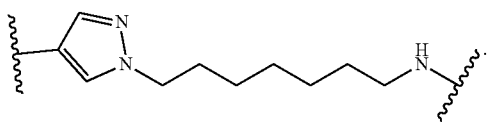 [SMILES: *NCCCCCCCn1cc(*)cn1]

In some embodiments, L is

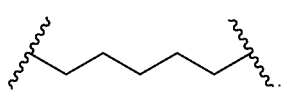

In some embodiments, L is

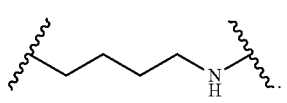 [SMILES: *CCCCN*]

In some embodiments, L is

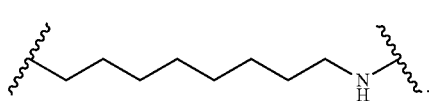 [SMILES: *CCCCCCCCN*]

In some embodiments, L is

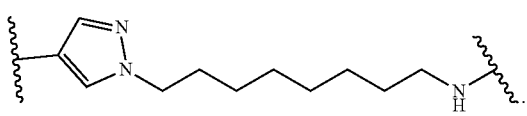 [SMILES: *NCCCCCCCCn1cc(*)cn1]

In some embodiments, L is

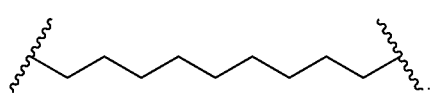 [SMILES: *CCCCCCCCC*]

In some embodiments, L is

In some embodiments, L is

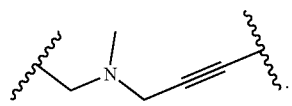 [SMILES: *C#CCN(C)C*]

In some embodiments, L is

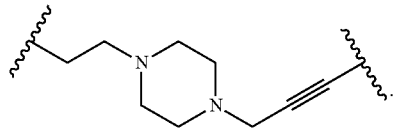 [SMILES: *C#CCN1CCN(CC*)CC1]

In some embodiments L is

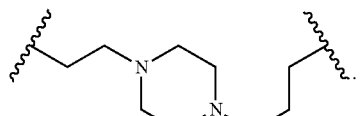

In some embodiments, L is

In some embodiments, L is

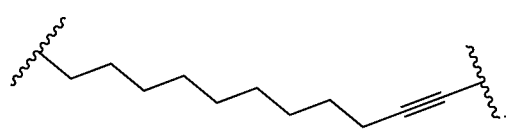 [SMILES: *C#CCCCCCCCCC*]

In some embodiments L is
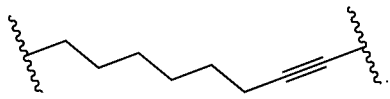 [SMILES: *C#CCCCCCC*]
In some embodiments, L is
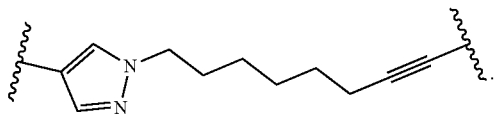 [SMILES: *C#CCCCCCCn1cc(*)cn1]
In some embodiments, L is
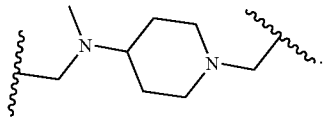 [SMILES: *CN1CCC(N(C)C*)CC1]
In some embodiments, L is
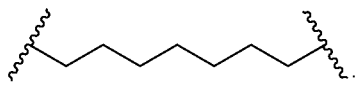 [SMILES: *CCCCCCC*]
In some embodiments, L is
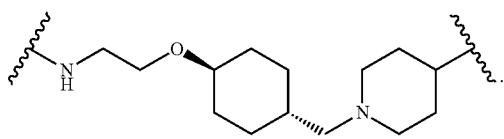 [SMILES: *NCCO[C@H]1CC[C@H](CN2CCC(*)CC2)CC1]
In some embodiments, L is
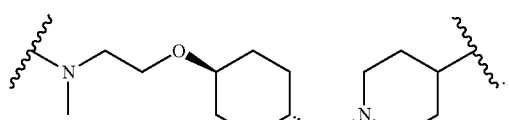
In some embodiments, L is
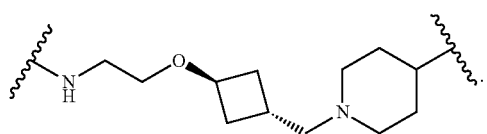 [SMILES: *NCCO[C@H]1C[C@H](CN2CCC(*)CC2)C1]
In some embodiments, L is
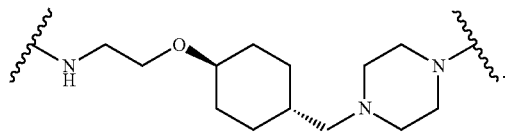 [SMILES: *NCCO[C@H]1CC[C@H](CN2CCN(*)CC2)CC1]
In some embodiments, L is
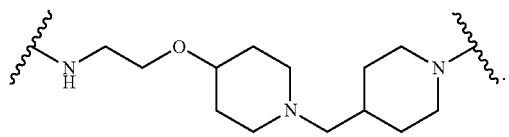 [SMILES: *NCCOC1CCN(CC2CCN(*)CC2)CC1]
In some embodiments, L is
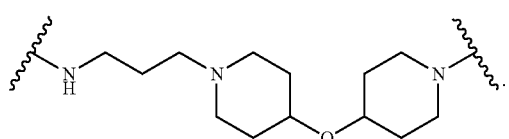
In some embodiments, L is
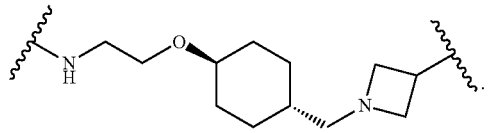 [SMILES: *NCCO[C@H]1CC[C@H](CN2CC(*)C2)CC1]
In some embodiments, L is
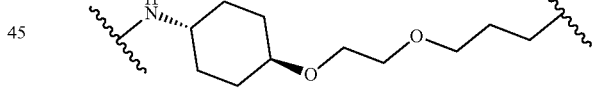
In some embodiments, L is
In some embodiments, L is
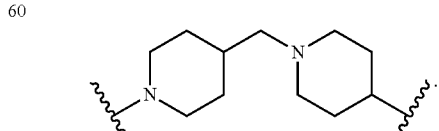

In some embodiments, L is
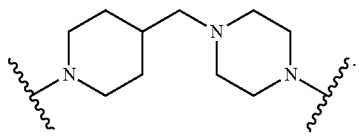 [SMILES: *N1CCC(CN2CCN(*)CC2)CC1]
In some embodiments, L is
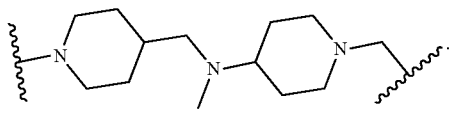 [SMILES: *CN1CCC(N(C)CC2CCN(*)CC2)CC1]
In some embodiments, L is
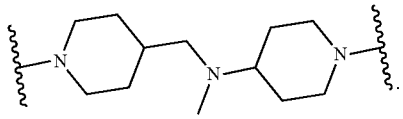 [SMILES: *N1CCC(CN(C)C2CCN(*)CC2)CC1]
In some embodiments, L is
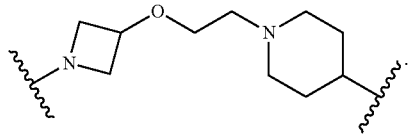 [SMILES: *C1CCN(CCOC2CN(*)C2)CC1]
In some embodiments, L is
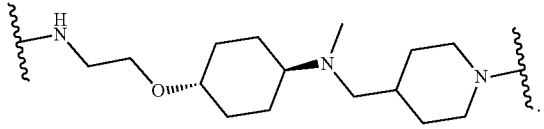 [SMILES: *NCCO[C@H]1CC[C@H](N(C)CC2CCN(*)CC2)CC1]
In some embodiments, L is
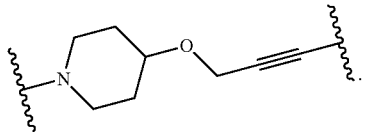 [SMILES: *C#CCOC1CCN(*)CC1]
In some embodiments, L is
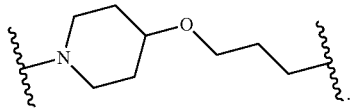 [SMILES: *CCCOC1CCN(*)CC1]
In some embodiments, L is
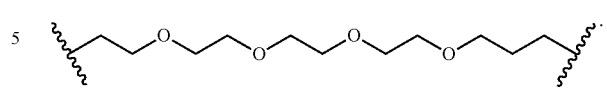
In some embodiments, L is
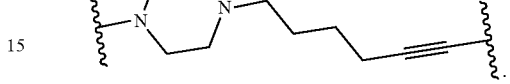
In some embodiments, L is
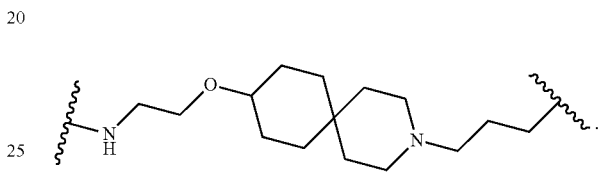
In some embodiments, L is
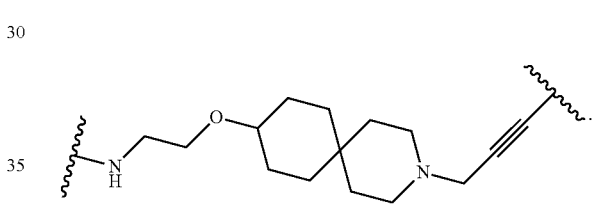
In some embodiments, L is
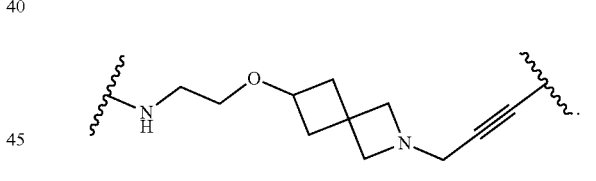
In some embodiments, L is
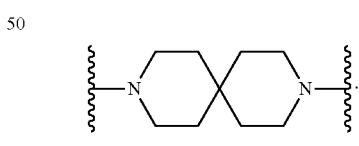
In some embodiments, L is
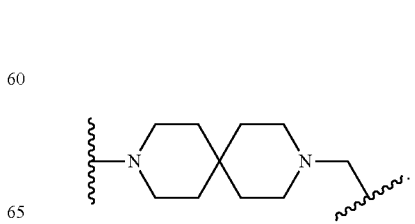

In some embodiments, L is

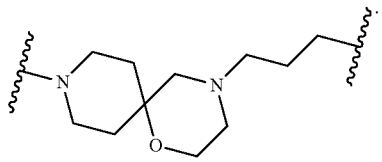 [SMILES: *CCCN1CCOC2(CCN(*)CC2)C1]

In some embodiments, L is

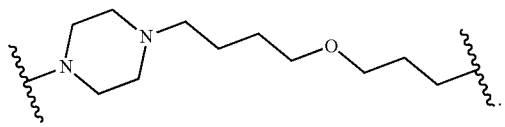 [SMILES: *CCCOCCCCN1CCN(*)CC1]

In some embodiments, L is

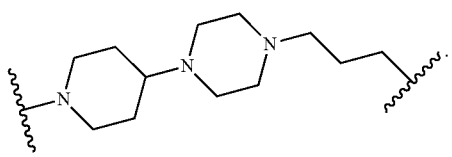 [SMILES: *CCCN1CCN(C2CCN(*)CC2)CC1]

In some embodiments, L is

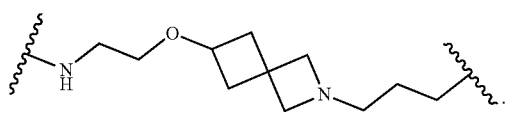 [SMILES: *CCCN1CC2(CC(OCCN*)C2)C1]

In some embodiments, L is

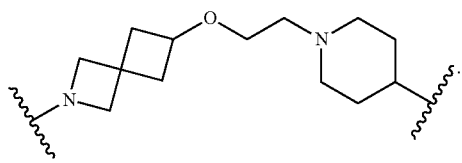 [SMILES: *C1CCN(CCOC2CC3(C2)CN(*)C3)CC1]

In some embodiments, L is

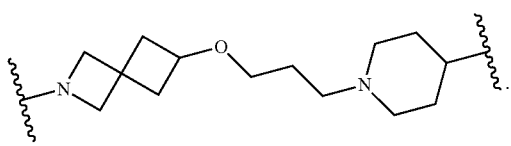 [SMILES: *C1CCN(CCCOC2CC3(C2)CN(*)C3)CC1]

In some embodiments, L is

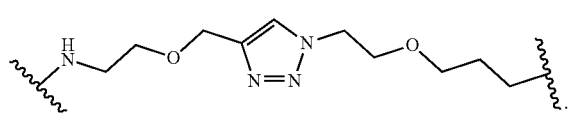 [SMILES: *CCCOCCn1cc(COCCN*)nn1]

In some embodiments, L is

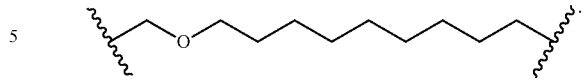

In some embodiments, L is

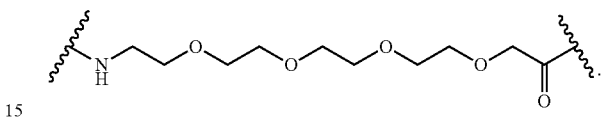

In some embodiments, L is

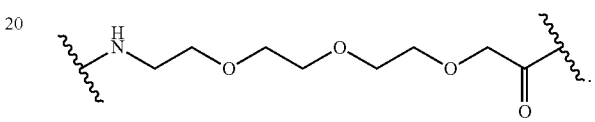

In some embodiments, L is

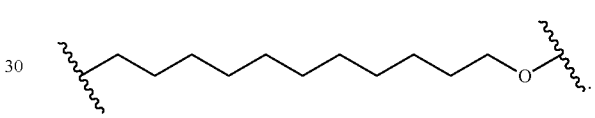

In some embodiments, L is

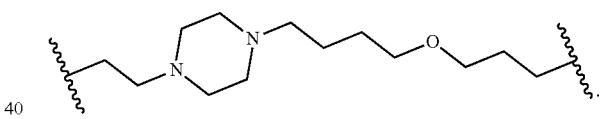

In some embodiments, L is

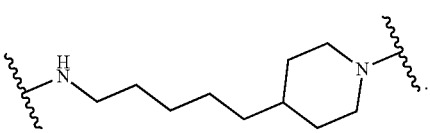 [SMILES: *NCCCCCC1CCN(*)CC1]

In some embodiments, L is

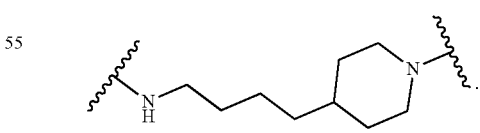

In some embodiments, L is

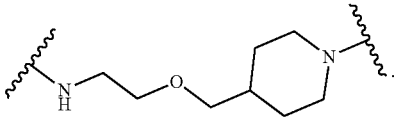 [SMILES: *NCCOCC1CCN(*)CC1]

In some embodiments, L is
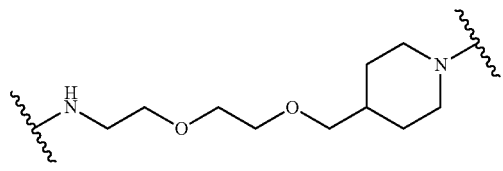
In some embodiments, L is
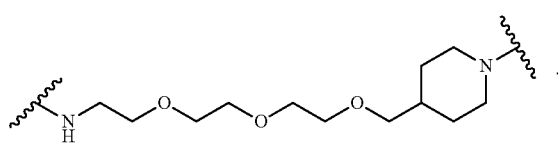 [SMILES: *NCCOCCOCCOCC1CCN(*)CC1]
In some embodiments, L is
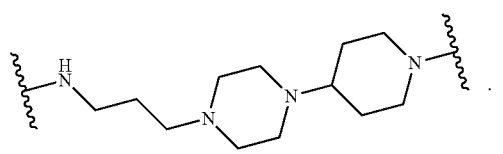 [SMILES: *NCCCN1CCN(C2CCN(*)CC2)CC1]
In some embodiments, L is
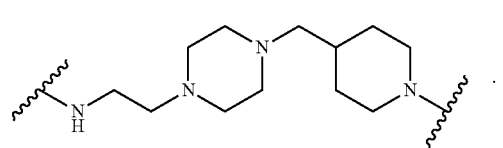 [SMILES: *NCCN1CCN(CC2CCN(*)CC2)CC1]
In some embodiments, L is
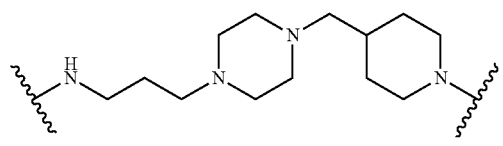
In some embodiments, L is
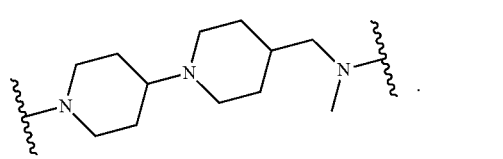 [SMILES: *N(C)CC1CCN(C2CCN(*)CC2)CC1]
In some embodiments, L is
In some embodiments, L is
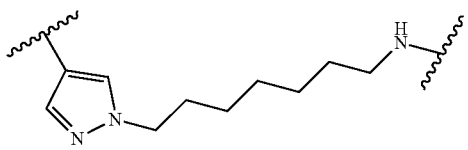
In some embodiments, L is
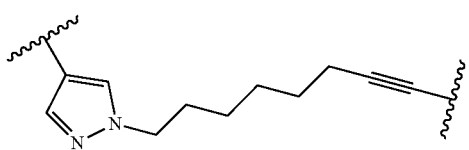
In some embodiments, L is
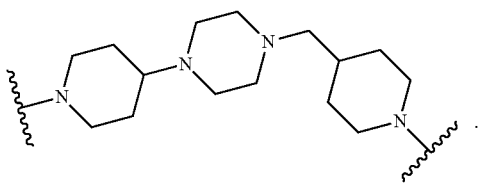 [SMILES: *N1CCC(CN2CCN(C3CCN(*)CC3)CC2)CC1]
In some embodiments, L is
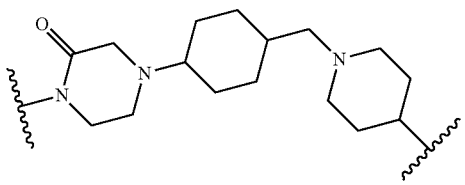
In some embodiments, L is
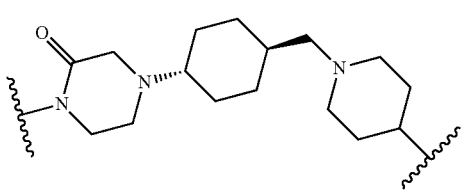

In some embodiments, L is
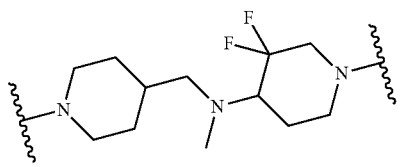
In some embodiments, L is
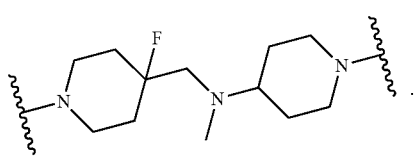 [SMILES: *N1CCC(N(C)CC2(F)CCN(*)CC2)CC1]
In some embodiments, L is
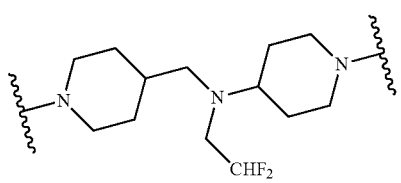
In some embodiments, L is
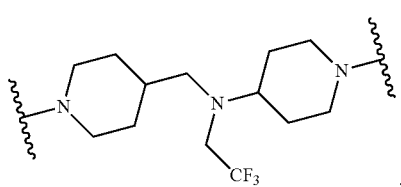 [SMILES: *N1CCC(CN(CC(F)(F)F)C2CCN(*)CC2)CC1]
In some embodiments, L is
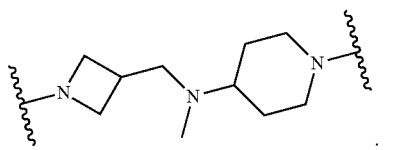 [SMILES: *N1CCC(N(C)CC2CN(*)C2)CC1]
In some embodiments, L is
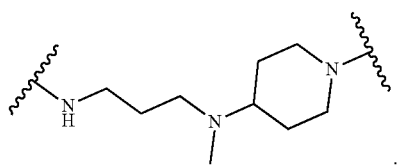 [SMILES: *NCCCN(C)C1CCN(*)CC1]
In some embodiments, L is
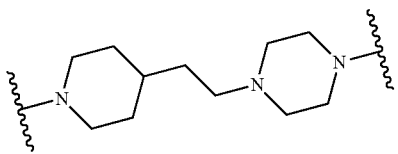
In some embodiments, L is
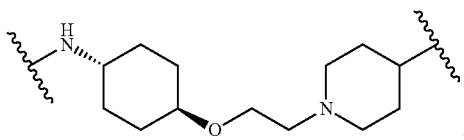
In some embodiments, L is
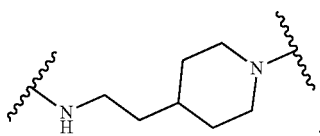 [SMILES: *NCCC1CCN(*)CC1]
In some embodiments, L is
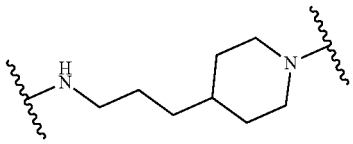
In some embodiments, L is
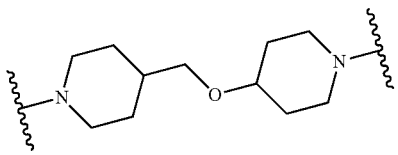
In some embodiments, L is
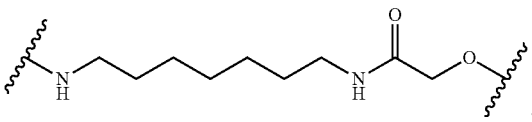
In some embodiments, L is
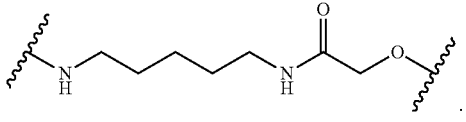 [SMILES: *NCCCCCNC(=O)CO*]

In some embodiments, L is

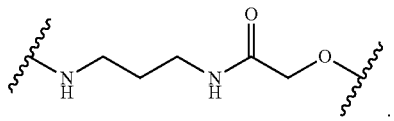 [SMILES: *NCCCNC(=O)CO*]

In some embodiments, L is

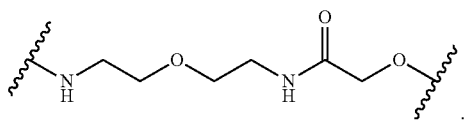 [SMILES: *NCCOCCNC(=O)CO*]

In some embodiments, L is

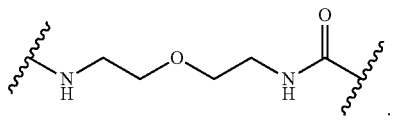 [SMILES: *NCCOCCNC(*)=O]

In some embodiments, L is

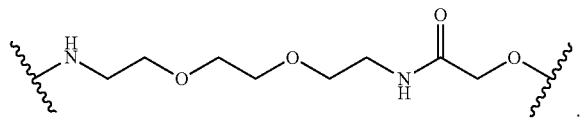 [SMILES: *NCCOCCOCCNC(=O)CO*]

In some embodiments, L is

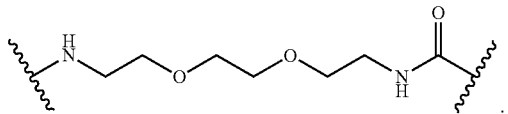 [SMILES: *NCCOCCOCCNC(*)=O]

In some embodiments, L is

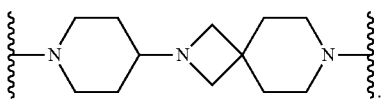

In some embodiments, L is

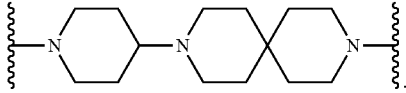

In some embodiments, L is

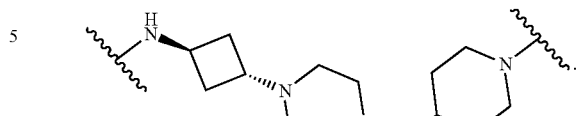

In some embodiments, L is

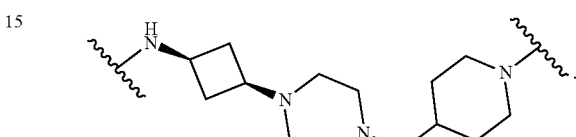

In some embodiments L is

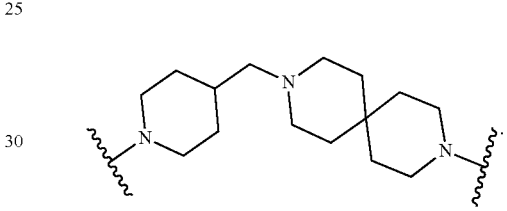

In some embodiment, L is also selected from those depicted in Table B, below.

In some embodiments, L is selected from those depicted in Table 1, below.

Without limitation, the point of attachment of L to CBM and DIM can be, for example when L is

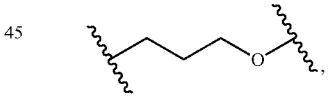

either

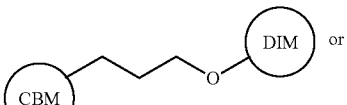

or

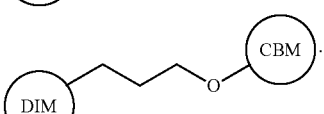

In some embodiments, a provided compound or pharmaceutically acceptable salt thereof, is selected from those wherein CBM is

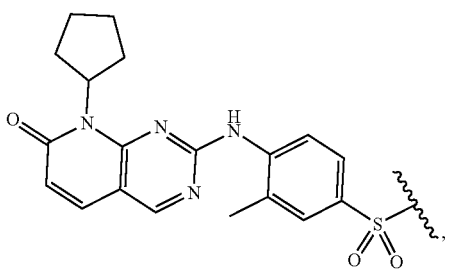 [SMILES: *S(=O)(=O)c1ccc(Nc2ncc3ccc(=O)n(C4CCCC4)c3n2)c(C)c1]

LBM is selected from any of those in Table A below, and L is selected from any of those in Table B below.

In some embodiments, a provided compound or pharmaceutically acceptable salt thereof, is selected from those wherein CBM is

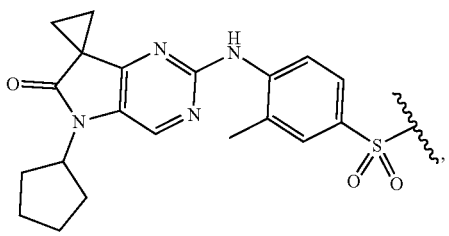 [SMILES: *S(=O)(=O)c1ccc(Nc2ncc3c(n2)C2(CC2)C(=O)N3C2CCCC2)c(C)c1]

LBM is selected from any of those in Table A below, and L is selected from any of those in Table B below.

In some embodiments, a provided compound or pharmaceutically acceptable salt thereof, is selected from those wherein CBM is

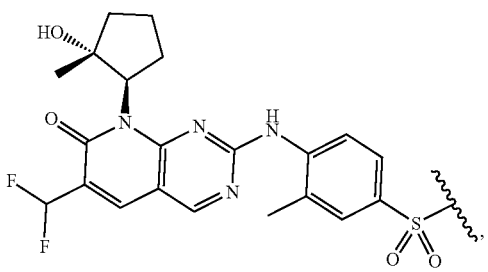 [SMILES: *S(=O)(=O)c1ccc(Nc2ncc3cc(C(F)F)c(=O)n([C@@H]4CCC[C@@]4(C)O)c3n2)c(C)c1]

LBM is selected from any of those in Table A below, and L is selected from any of those in Table B below.

In some embodiments, a provided compound or pharmaceutically acceptable salt thereof, is selected from those wherein CBM is

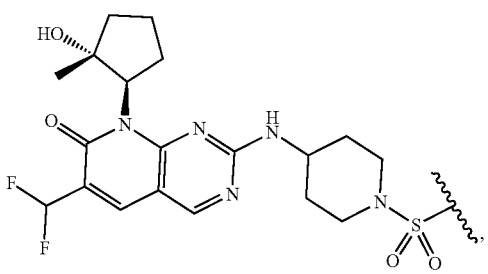 [SMILES: *S(=O)(=O)N1CCC(Nc2ncc3cc(C(F)F)c(=O)n([C@@H]4CCC[C@@]4(C)O)c3n2)CC1]

LBM is selected from any of those in Table A below, and L is selected from any of those in Table B below.

In some embodiments, a provided compound or pharmaceutically acceptable salt thereof, is selected from those wherein CBM is

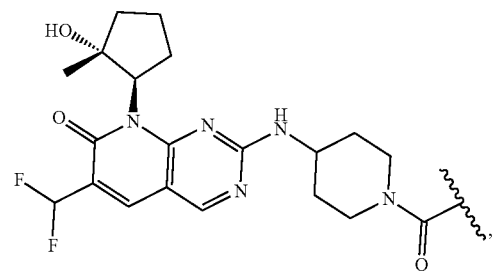 [SMILES: *C(=O)N1CCC(Nc2ncc3cc(C(F)F)c(=O)n([C@@H]4CCC[C@@]4(C)O)c3n2)CC1]

LBM is selected from any of those in Table A below, and L is selected from any of those in Table B below.

In some embodiments, a provided compound or pharmaceutically acceptable salt thereof, is selected from those wherein CBM is

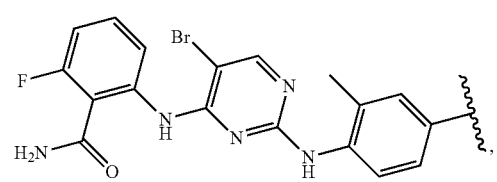 [SMILES: *c1ccc(Nc2ncc(Br)c(Nc3cccc(F)c3C(N)=O)n2)c(C)c1]

LBM is selected from any of those in Table A below, and L is selected from any of those in Table B below.

In some embodiments, a provided compound or pharmaceutically acceptable salt thereof, is selected from those wherein CBM is

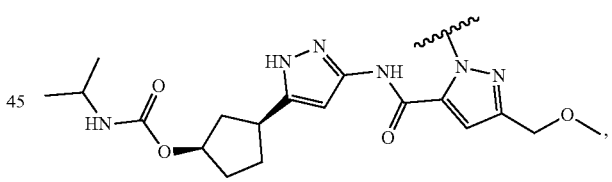

LBM is selected from any of those in Table A below, and L is selected from any of those in Table B below.

In some embodiments, a provided compound or pharmaceutically acceptable salt thereof, is selected from those wherein CBM is

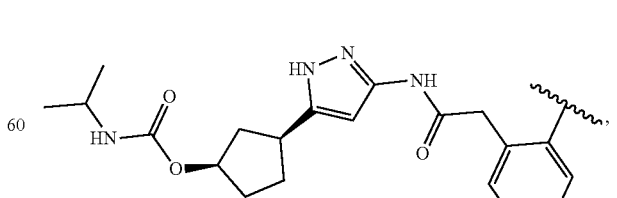

LBM is selected from any of those in Table A below, and L is selected from any of those in Table B below.

In some embodiments, a provided compound or pharmaceutically acceptable salt thereof, is selected from those wherein CBM is

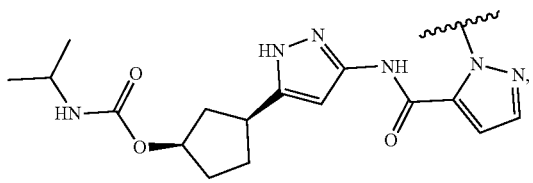 [SMILES: *n1nccc1C(=O)Nc1cc([C@H]2CC[C@@H](OC(=O)NC(C)C)C2)[nH]n1]

LBM is selected from any of those in Table A below, and L is selected from any of those in Table B below.

In some embodiments, a provided compound or pharmaceutically acceptable salt thereof, is selected from those wherein CBM is

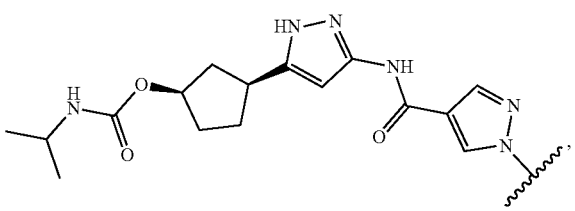 [SMILES: *n1cc(C(=O)Nc2cc([C@H]3CC[C@@H](OC(=O)NC(C)C)C3)[nH]n2)cn1]

LBM is selected from any of those in Table A below, and L is selected from any of those in Table B below.

In some embodiments, a provided compound or pharmaceutically acceptable salt thereof, is selected from those wherein CBM is

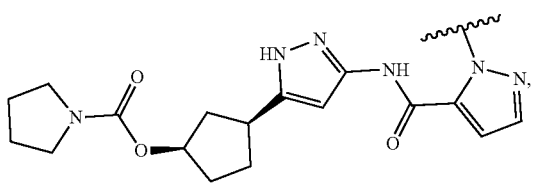 [SMILES: *n1nccc1C(=O)Nc1cc([C@H]2CC[C@@H](OC(=O)N3CCCC3)C2)[nH]n1]

LBM is selected from any of those in Table A below, and L is selected from any of those in Table B below.

In some embodiments, a provided compound or pharmaceutically acceptable salt thereof, is selected from those wherein CBM is

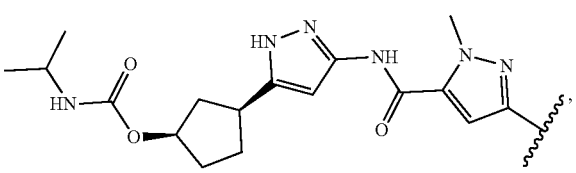 [SMILES: *c1cc(C(=O)Nc2cc([C@H]3CC[C@@H](OC(=O)NC(C)C)C3)[nH]n2)n(C)n1]

LBM is selected from any of those in Table A below, and L is selected from any of those in Table B below.

In some embodiments, a provided compound or pharmaceutically acceptable salt thereof, is selected from those wherein CBM is

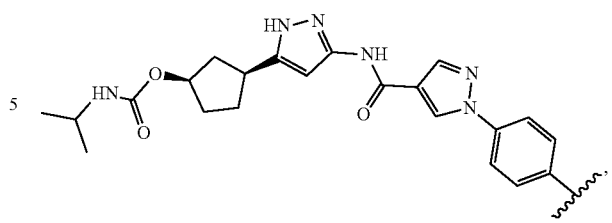

LBM is selected from any of those in Table A below, and L is selected from any of those in Table B below.

In some embodiments, a provided compound or pharmaceutically acceptable salt thereof, is selected from those wherein CBM is

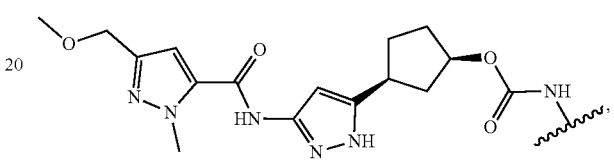

LBM is selected from any of those in Table A below, and L is selected from any of those in Table B below.

In some embodiments, a provided compound or pharmaceutically acceptable salt thereof, is selected from those wherein CBM is

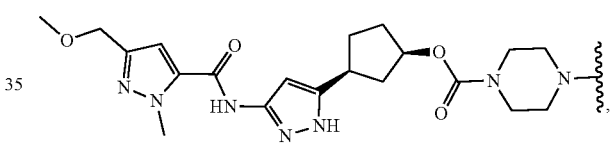

In some embodiments, a provided compound or pharmaceutically acceptable salt thereof, is selected from those wherein CBM is

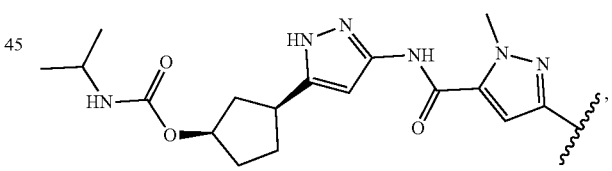

LBM is selected from any of those in Table A below, and L is selected from any of those in Table B below.

In some embodiments, a provided compound or pharmaceutically acceptable salt thereof, is selected from those wherein CBM is

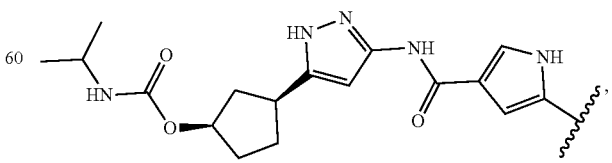

LBM is selected from any of those in Table A below, and L is selected from any of those in Table B below.

In some embodiments, a provided compound or pharmaceutically acceptable salt thereof, is selected from those wherein CBM is

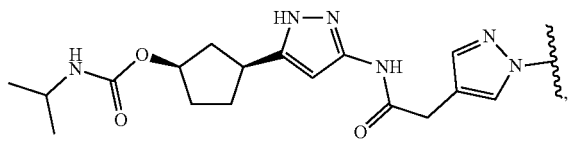 [SMILES: *n1cc(CC(=O)Nc2cc([C@H]3CC[C@@H](OC(=O)NC(C)C)C3)[nH]n2)cn1]

LBM is selected from any of those in Table A below, and L is selected from any of those in Table B below.

In some embodiments, a provided compound or pharmaceutically acceptable salt thereof, is selected from those wherein CBM is

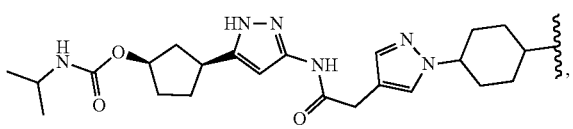 [SMILES: *C1CCC(n2cc(CC(=O)Nc3cc([C@H]4CC[C@@H](OC(=O)NC(C)C)C4)[nH]n3)cn2)CC1]

LBM is selected from any of those in Table A below, and L is selected from any of those in Table B below.

In some embodiments, a provided compound or pharmaceutically acceptable salt thereof, is selected from those wherein CBM is

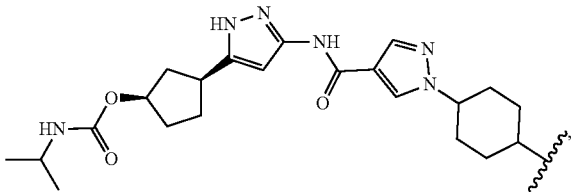 [SMILES: *C1CCC(n2cc(C(=O)Nc3cc([C@H]4CC[C@@H](OC(=O)NC(C)C)C4)[nH]n3)cn2)CC1]

LBM is selected from any of those in Table A below, and L is selected from any of those in Table B below.

In some embodiments, a provided compound or pharmaceutically acceptable salt thereof, is selected from those wherein CBM is

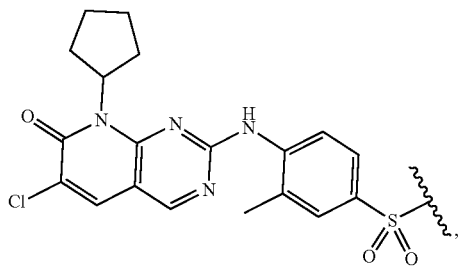 [SMILES: *S(=O)(=O)c1ccc(Nc2ncc3cc(Cl)c(=O)n(C4CCCC4)c3n2)c(C)c1]

LBM is selected from any of those in Table A below, and L is selected from any of those in Table B below.

In some embodiments, a provided compound or pharmaceutically acceptable salt thereof, is selected from those wherein CBM is

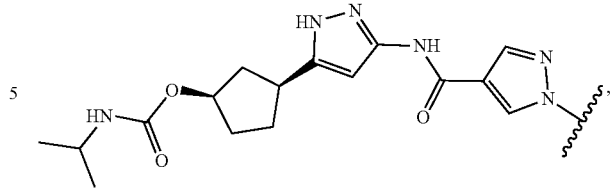

LBM is selected from any of those in Table A below, and L is selected from any of those in Table B below.

In some embodiments, a provided compound or pharmaceutically acceptable salt thereof, is selected from those wherein CBM is

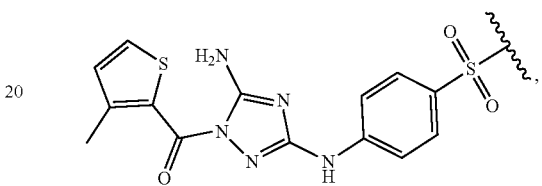

LBM is selected from any of those in Table A below, and L is selected from any of those in Table B below.

In some embodiments, a provided compound or pharmaceutically acceptable salt thereof, is selected from those wherein CBM is

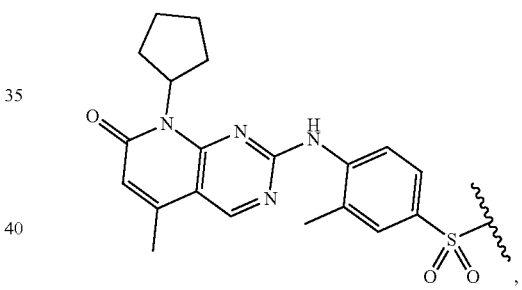

LBM is selected from any of those in Table A below, and L is selected from any of those in Table B below.

In some embodiments, a provided compound or pharmaceutically acceptable salt thereof, is selected from those wherein CBM is

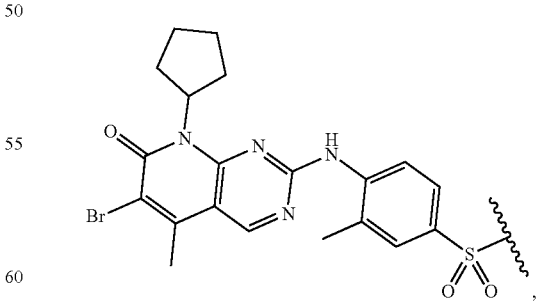

LBM is selected from any of those in Table A below, and L is selected from any of those in Table B below.

In some embodiments, a provided compound or pharmaceutically acceptable salt thereof, is selected from those wherein CBM is

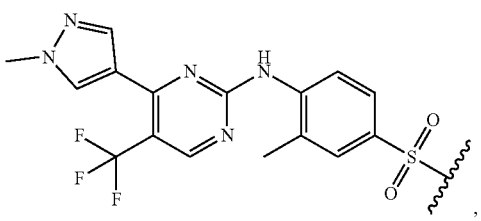 [SMILES: *S(=O)(=O)c1ccc(Nc2ncc(C(F)(F)F)c(-c3cnn(C)c3)n2)c(C)c1]

LBM is selected from any of those in Table A below, and L is selected from any of those in Table B below.

In some embodiments, a provided compound or pharmaceutically acceptable salt thereof, is selected from those wherein CBM is

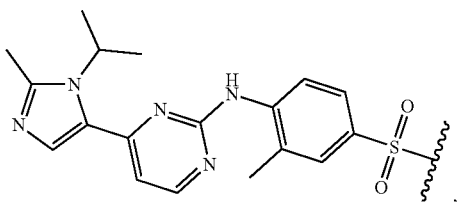

LBM is selected from any of those in Table A below, and L is selected from any of those in Table B below.

In some embodiments, a provided compound or pharmaceutically acceptable salt thereof, is selected from those wherein CBM is

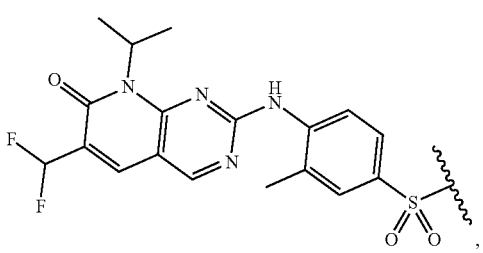 [SMILES: *S(=O)(=O)c1ccc(Nc2ncc3cc(C(F)F)c(=O)n(C(C)C)c3n2)c(C)c1]

LBM is selected from any of those in Table A below, and L is selected from any of those in Table B below.

In some embodiments, a provided compound or pharmaceutically acceptable salt thereof, is selected from those wherein CBM is

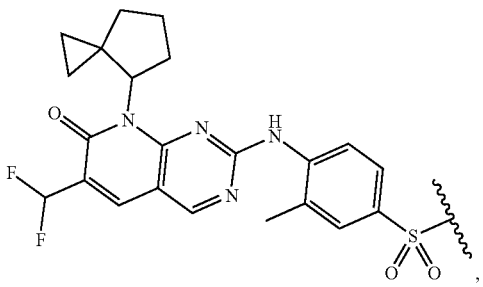 [SMILES: *S(=O)(=O)c1ccc(Nc2ncc3cc(C(F)F)c(=O)n(C4CCCC45CC5)c3n2)c(C)c1]

LBM is selected from any of those in Table A below, and L is selected from any of those in Table B below.

In some embodiments, a provided compound or pharmaceutically acceptable salt thereof, is selected from those wherein CBM is

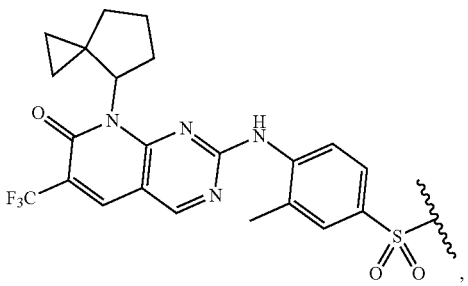 [SMILES: *S(=O)(=O)c1ccc(Nc2ncc3cc(C(F)(F)F)c(=O)n(C4CCCC45CC5)c3n2)c(C)c1]

LBM is selected from any of those in Table A below, and L is selected from any of those in Table B below.

In some embodiments, a provided compound or pharmaceutically acceptable salt thereof, is selected from those wherein CBM is

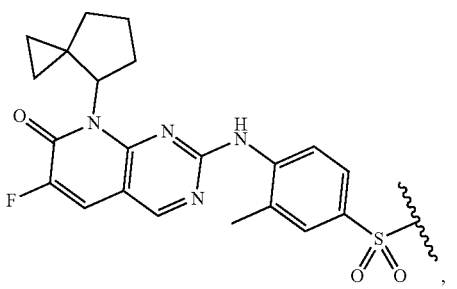 [SMILES: *S(=O)(=O)c1ccc(Nc2ncc3cc(F)c(=O)n(C4CCCC45CC5)c3n2)c(C)c1]

LBM is selected from any of those in Table A below, and L is selected from any of those in Table B below.

In some embodiments, a provided compound or pharmaceutically acceptable salt thereof, is selected from those wherein CBM is

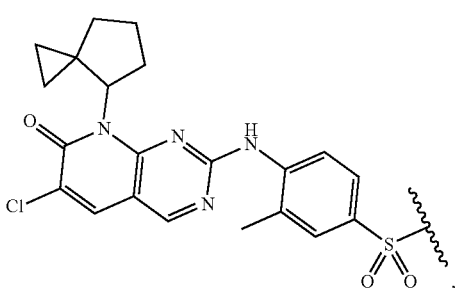 [SMILES: *S(=O)(=O)c1ccc(Nc2ncc3cc(Cl)c(=O)n(C4CCCC45CC5)c3n2)c(C)c1]

LBM is selected from any of those in Table A below, and L is selected from any of those in Table B below.

In some embodiments, a provided compound or pharmaceutically acceptable salt thereof, is selected from those wherein CBM is

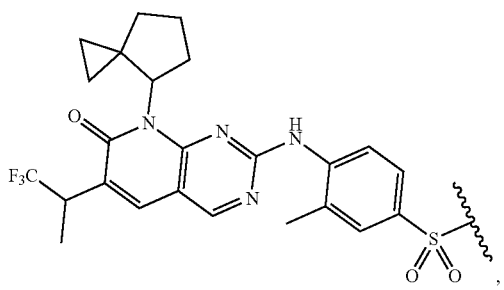 [SMILES: *S(=O)(=O)c1ccc(Nc2ncc3cc(C(C)C(F)(F)F)c(=O)n(C4CCCC45CC5)c3n2)c(C)c1]

LBM is selected from any of those in Table A below, and L is selected from any of those in Table B below.

In some embodiments, a provided compound or pharmaceutically acceptable salt thereof, is selected from those wherein CBM is

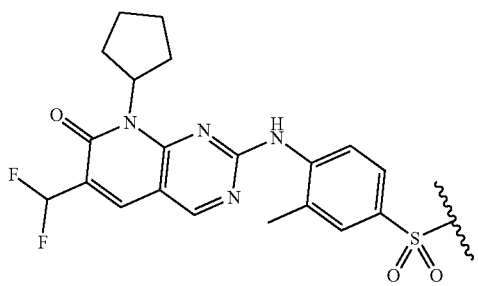

LBM is selected from any of those in Table A below, and L is selected from any of those in Table B below.

In some embodiments, a provided compound or pharmaceutically acceptable salt thereof, is selected from those wherein CBM is

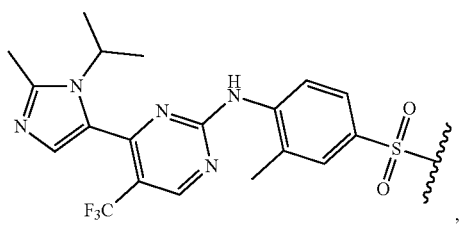 [SMILES: *S(=O)(=O)c1ccc(Nc2ncc(C(F)(F)F)c(-c3cnc(C)n3C(C)C)n2)c(C)c1]

LBM is selected from any of those in Table A below, and L is selected from any of those in Table B below.

In some embodiments, a provided compound or pharmaceutically acceptable salt thereof, is selected from those wherein CBM is

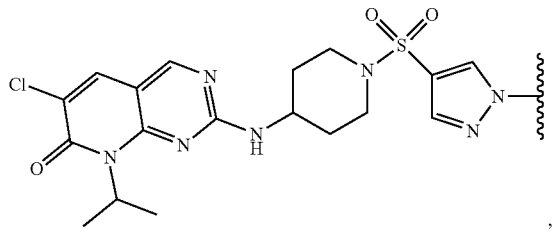 [SMILES: *n1cc(S(=O)(=O)N2CCC(Nc3ncc4cc(Cl)c(=O)n(C(C)C)c4n3)CC2)cn1]

LBM is selected from any of those in Table A below, and L is selected from any of those in Table B below.

In some embodiments, a provided compound or pharmaceutically acceptable salt thereof, is selected from those wherein CBM is

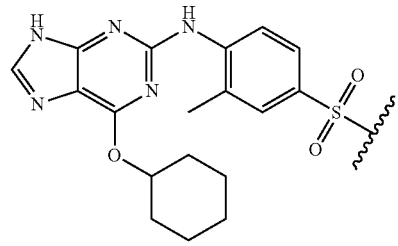

LBM is selected from any of those in Table A below, and L is selected from any of those in Table B below.

In some embodiments, a provided compound or pharmaceutically acceptable salt thereof, is selected from those wherein CBM is

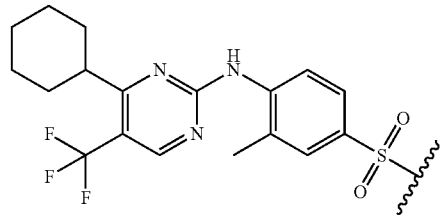

LBM is selected from any of those in Table A below, and L is selected from any of those in Table B below. Table A. Exemplified E3 Ligase Binding Moiety (LBM)

TABLE A

Exemplified E3 Ligase Binding Moiety (LBM)

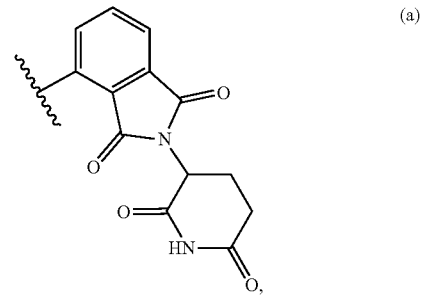

(a)

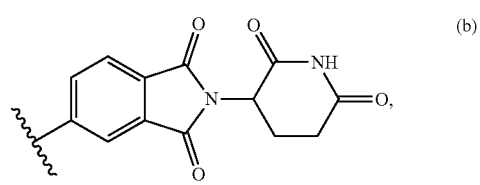

(b)

TABLE A-continued
Exemplified E3 Ligase Binding Moiety (LBM)
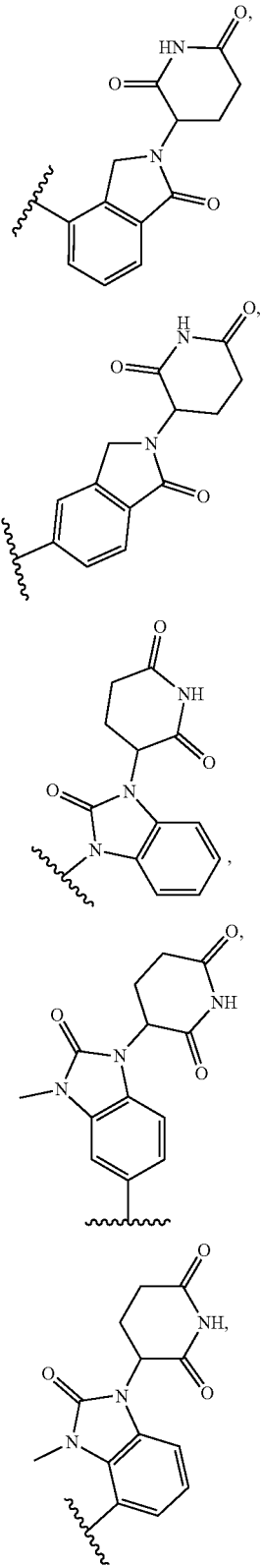
(c)
(d)
(e)
(f)
(g)
TABLE A-continued
Exemplified E3 Ligase Binding Moiety (LBM)
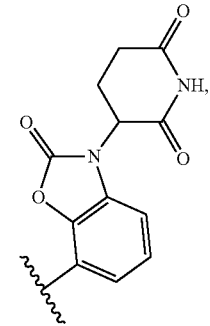 [SMILES: *c1cccc2c1oc(=O)n2C1CCC(=O)NC1=O]
(h)
(i)
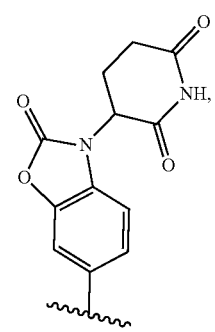 [SMILES: *c1ccc2c(c1)oc(=O)n2C1CCC(=O)NC1=O]
(j)
(k)

TABLE A-continued
Exemplified E3 Ligase Binding Moiety (LBM)
(l)
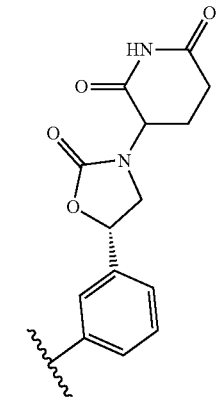
(m)
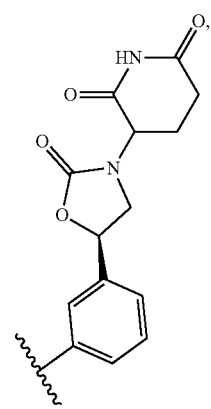 [SMILES: *c1cccc([C@@H]2CN(C3CCC(=O)NC3=O)C(=O)O2)c1]
(n)
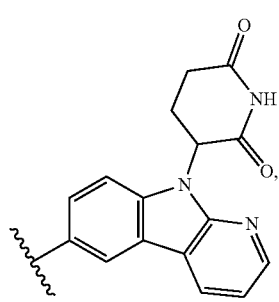 [SMILES: *c1ccc2c(c1)c1cccnc1n2C1CCC(=O)NC1=O]
(o)
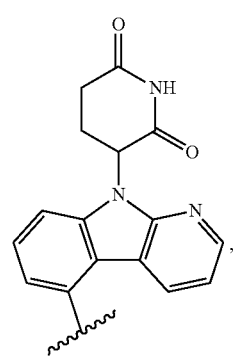 [SMILES: *c1cccc2c1c1cccnc1n2C1CCC(=O)NC1=O]
TABLE A-continued
Exemplified E3 Ligase Binding Moiety (LBM)
(p)
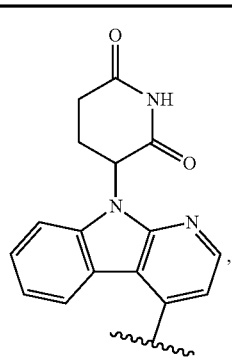
(q)
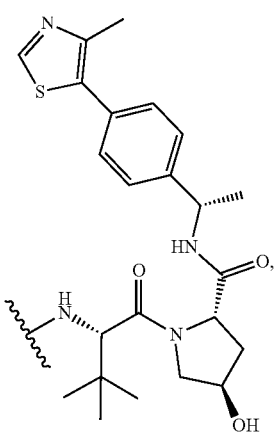
(r)
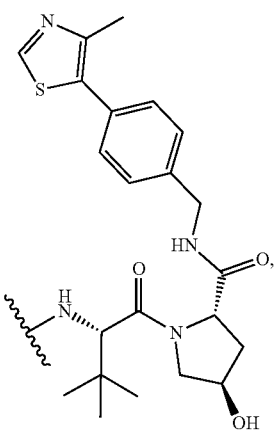 [SMILES: *N[C@H](C(=O)N1C[C@H](O)C[C@H]1C(=O)NCc1ccc(-c2scnc2C)cc1)C(C)(C)C]
(s)
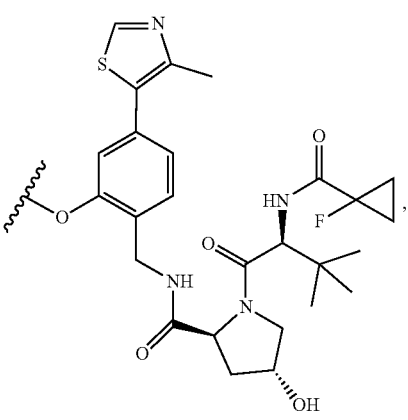 [SMILES: *Oc1cc(-c2scnc2C)ccc1CNC(=O)[C@@H]1C[C@@H](O)CN1C(=O)[C@@H](NC(=O)C1(F)CC1)C(C)(C)C]

TABLE A-continued
Exemplified E3 Ligase Binding Moiety (LBM)
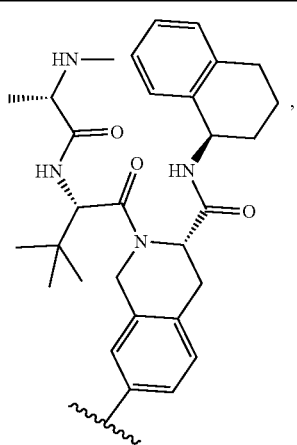 (t)
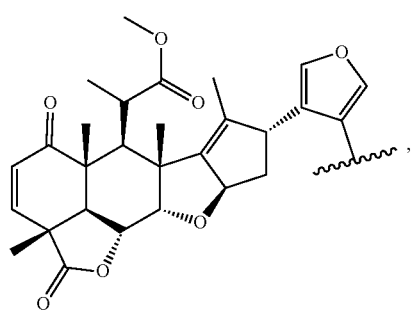 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45] (u)
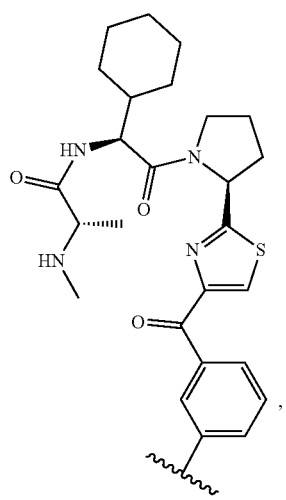 [SMILES: *c1cccc(C(=O)c2csc([C@@H]3CCCN3C(=O)[C@@H](NC(=O)[C@H](C)NC)C3CCCCC3)n2)c1] (v)
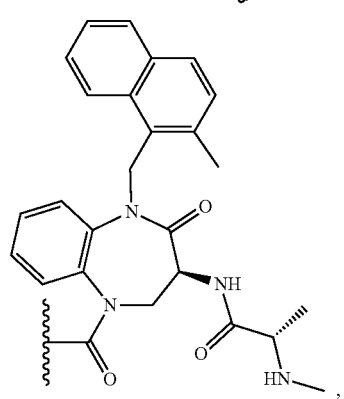 (w)
TABLE A-continued
Exemplified E3 Ligase Binding Moiety (LBM)
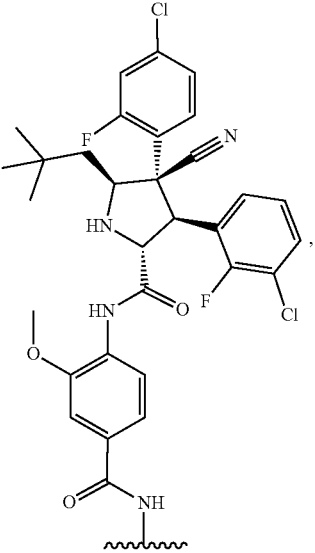 [SMILES: *NC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1] (x)
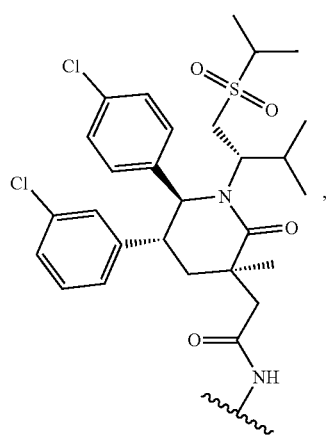 [SMILES: *NC(=O)C[C@@]1(C)C[C@H](c2cccc(Cl)c2)[C@@H](c2ccc(Cl)cc2)N([C@H](CS(=O)(=O)C(C)C)C(C)C)C1=O] (y)
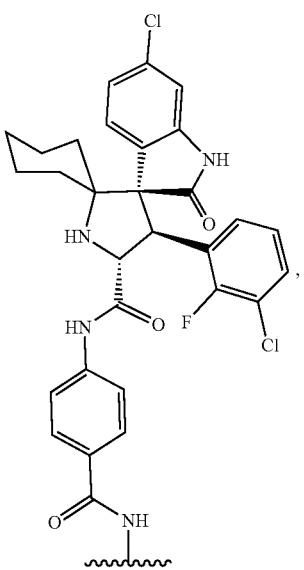 [SMILES: *NC(=O)c1ccc(NC(=O)[C@@H]2NC3(CCCCC3)[C@@]3(C(=O)Nc4cc(Cl)ccc43)[C@H]2c2cccc(Cl)c2F)cc1] (z)

TABLE A-continued

Exemplified E3 Ligase Binding Moiety (LBM)

(aa)

(bb)

(cc)

(dd)

(ee)

(ff)

(gg)

(hh)

(ii)

(jj)

(kk)

(ll)

(mm)

(nn)

TABLE A-continued

Exemplified E3 Ligase Binding Moiety (LBM)

(oo), (pp), (qq), (rr), (ss), (tt), (uu), (vv), (ww), (xx), (yy), (zz), (aaa)

TABLE A-continued
Exemplified E3 Ligase Binding Moiety (LBM)
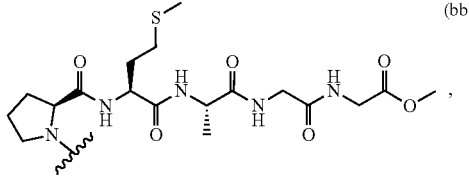 (bbb)
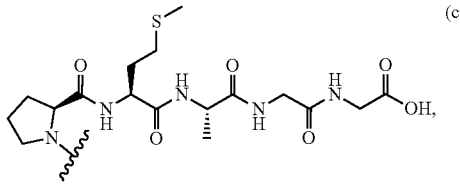 (ccc)
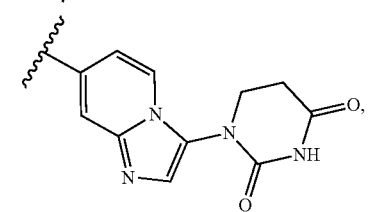 (ddd)
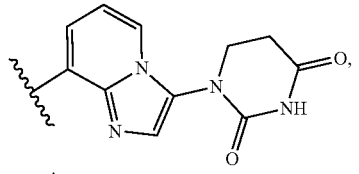 (eee)
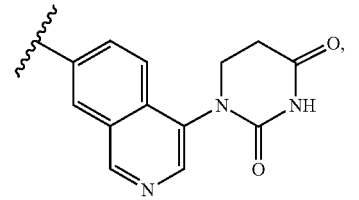 [SMILES: *c1ccc2c(N3CCC(=O)NC3=O)cncc2c1] (fff)
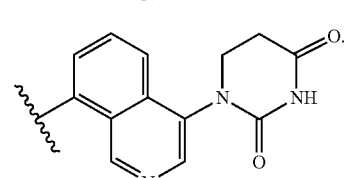 (ggg)
TABLE B
Exemplified Linkers (L)
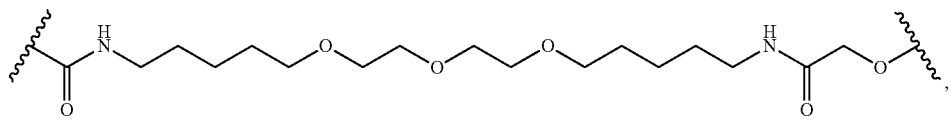 [SMILES: *OCC(=O)NCCCCCOCCOCCOCCCCCNC(*)=O] (1)
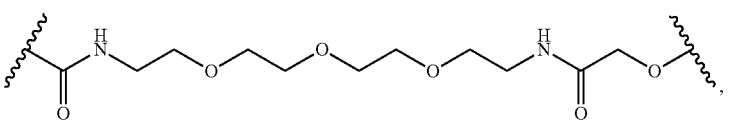 [SMILES: *OCC(=O)NCCOCCOCCOCCNC(*)=O] (2)
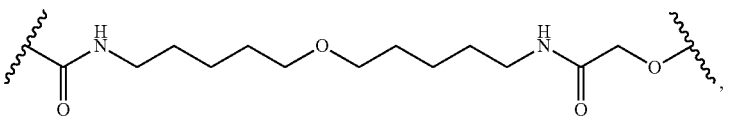 [SMILES: *OCC(=O)NCCCCCOCCCCCNC(*)=O] (3)
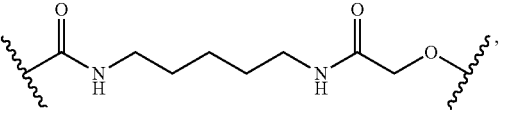 [SMILES: *OCC(=O)NCCCCCNC(*)=O] (4)
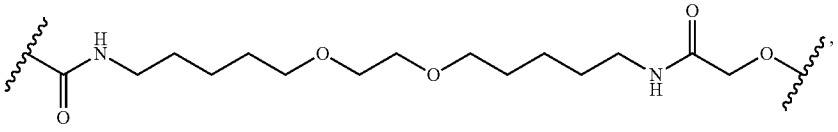 [SMILES: *OCC(=O)NCCCCCOCCOCCCCCNC(*)=O] (5)
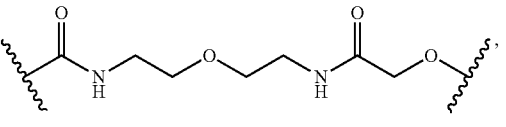 [SMILES: *OCC(=O)NCCOCCNC(*)=O] (6)

TABLE B-continued
Exemplified Linkers (L)
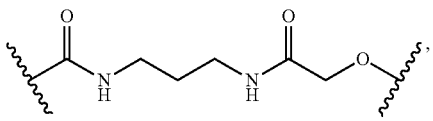 [SMILES: *OCC(=O)NCCCNC(*)=O]
(7)
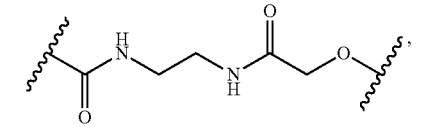 [SMILES: *OCC(=O)NCCNC(*)=O]
(8)
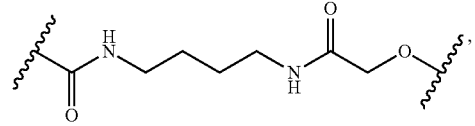 [SMILES: *OCC(=O)NCCCCNC(*)=O]
(9)
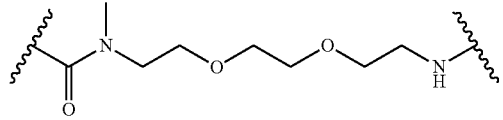
(10)
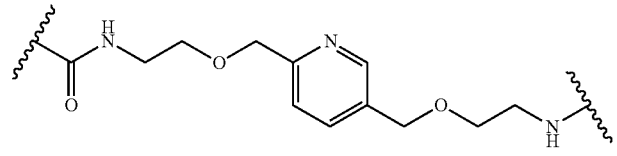
(11)
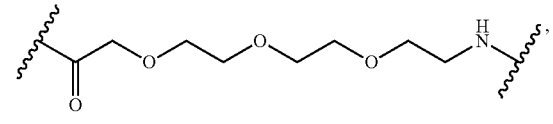 [SMILES: *NCCOCCOCCOCC(*)=O]
(12)
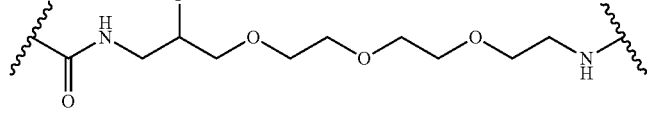
(13)
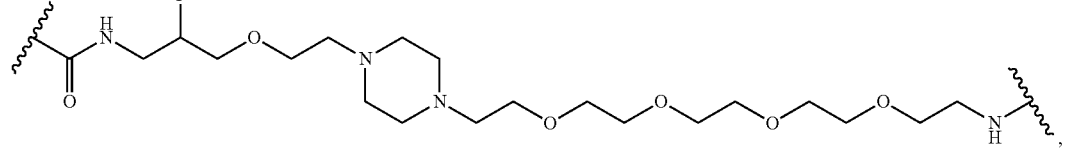
(14)
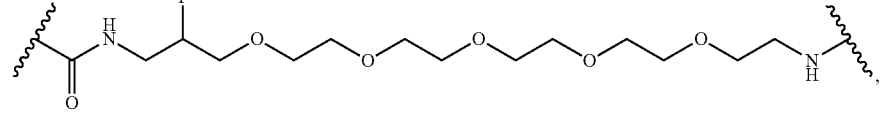
(15)
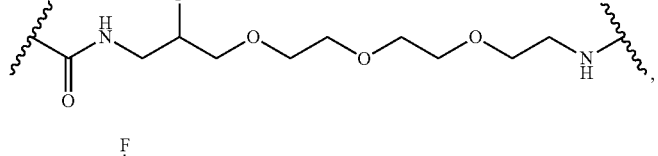
(16)
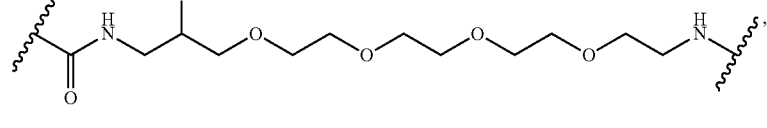
(17)

TABLE B-continued
Exemplified Linkers (L)
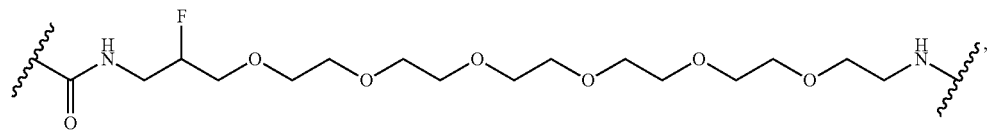 [SMILES: *NCCOCCOCCOCCOCCOCCOCC(F)CNC(*)=O] (18)
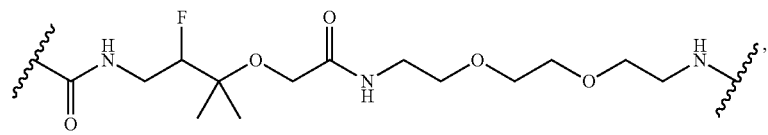 (19)
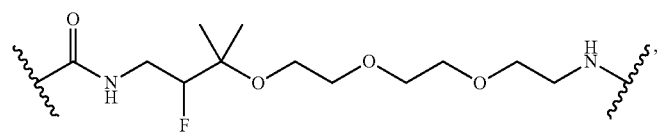 [SMILES: *NCCOCCOCCOC(C)(C)C(F)CNC(*)=O] (20)
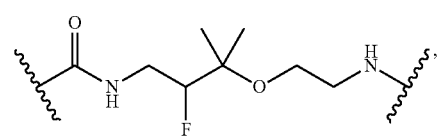 [SMILES: *NCCOC(C)(C)C(F)CNC(*)=O] (21)
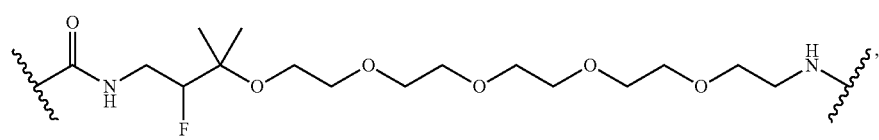 [SMILES: *NCCOCCOCCOCCOCCOC(C)(C)C(F)CNC(*)=O] (22)
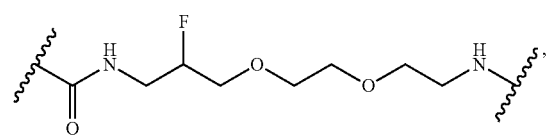 [SMILES: *NCCOCCOCC(F)CNC(*)=O] (23)
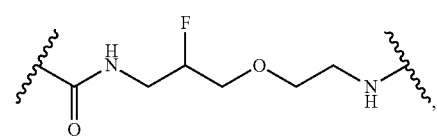 [SMILES: *NCCOCC(F)CNC(*)=O] (24)
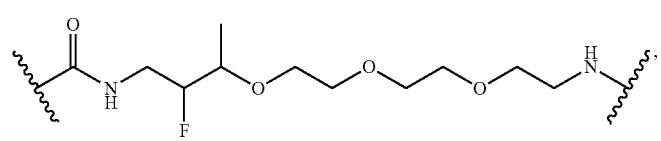 [SMILES: *NCCOCCOCCOC(C)C(F)CNC(*)=O] (25)
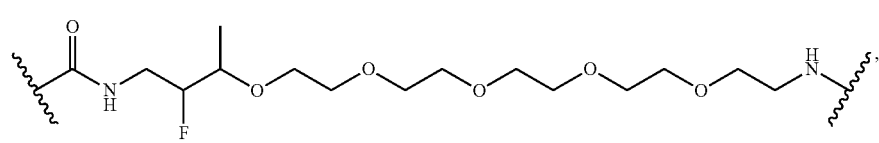 [SMILES: *NCCOCCOCCOCCOCCOC(C)C(F)CNC(*)=O] (26)
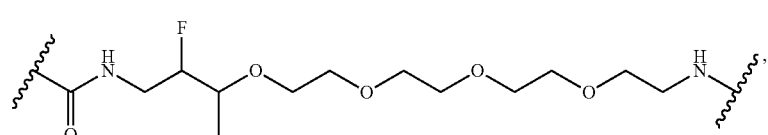 (27)
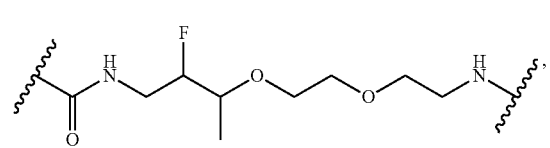 [SMILES: *NCCOCCOC(C)C(F)CNC(*)=O] (28)

TABLE B-continued
Exemplified Linkers (L)
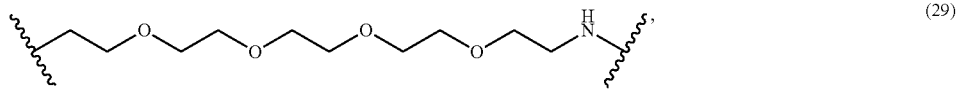 (29)
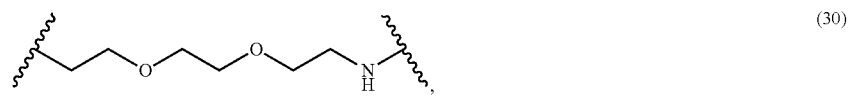 (30)
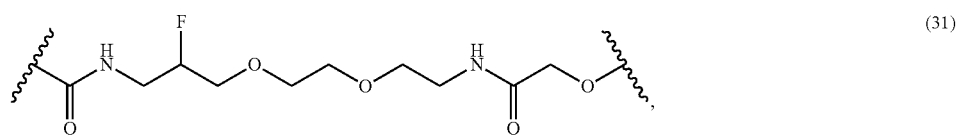 (31)
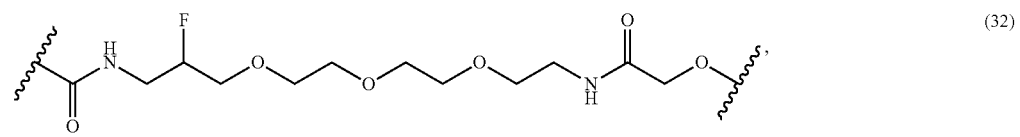 (32)
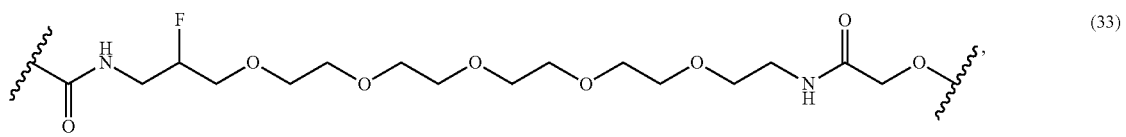 (33)
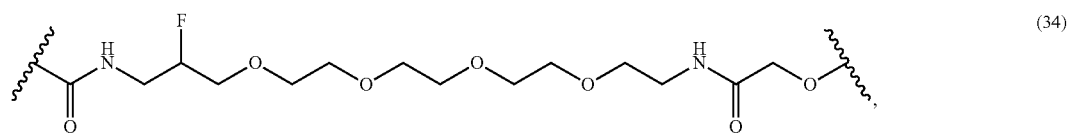 (34)
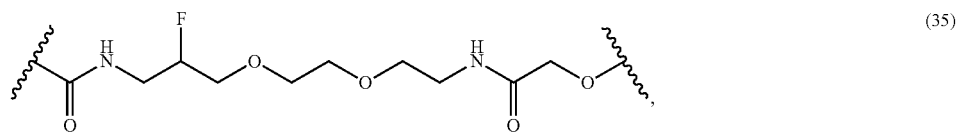 (35)
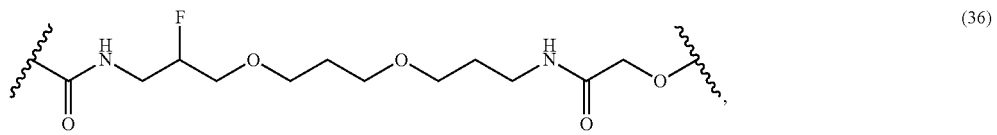 (36)
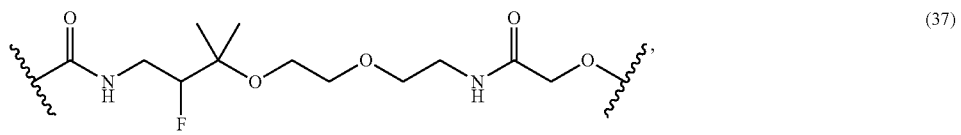 (37)
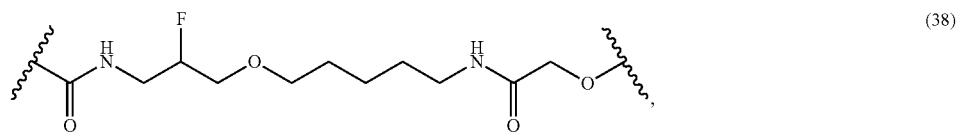 (38)
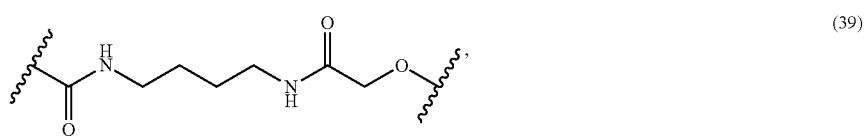 (39)

TABLE B-continued

Exemplified Linkers (L)

(40)

(41)

(42)

(43)

(44)

(45)

(46)

(47)

(49)

(50)

(51)

(52)

TABLE B-continued
Exemplified Linkers (L)
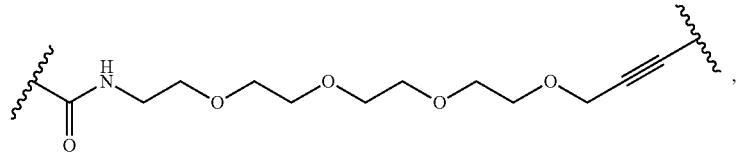 [SMILES: *C#CCOCCOCCOCCOCCNC(*)=O]
(53)
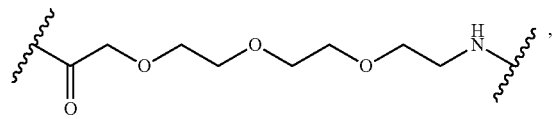 [SMILES: *NCCOCCOCCOCC(*)=O]
(54)
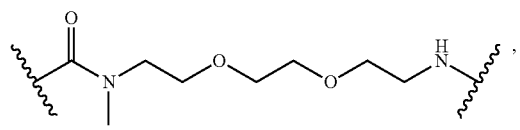 [SMILES: *NCCOCCOCCN(C)C(*)=O]
(55)
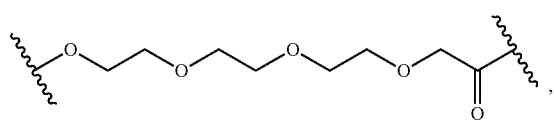 [SMILES: *OCCOCCOCCOCC(*)=O]
(56)
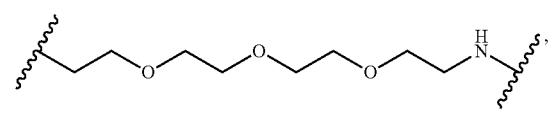 [SMILES: *CCOCCOCCOCCN*]
(57)
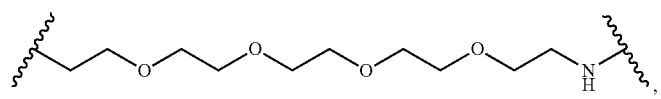 [SMILES: *CCOCCOCCOCCOCCN*]
(58)
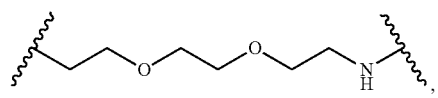 [SMILES: *CCOCCOCCN*]
(59)
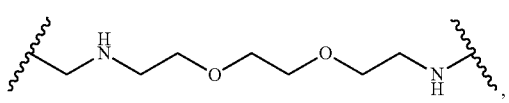 [SMILES: *CNCCOCCOCCN*]
(60)
(61)
(62)
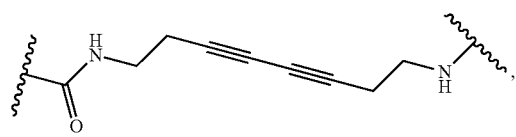 [SMILES: *NCCC#CC#CCCNC(*)=O]
(63)
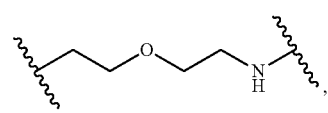 [SMILES: *CCOCCN*]
(64)

TABLE B-continued
Exemplified Linkers (L)
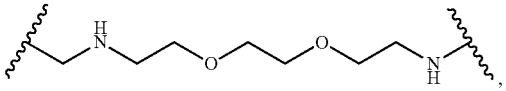 [SMILES: *CNCCOCCOCCN*] (65)
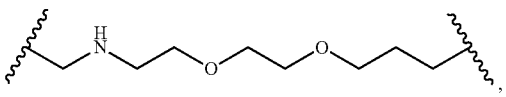 [SMILES: *CCCOCCOCCNC*] (66)
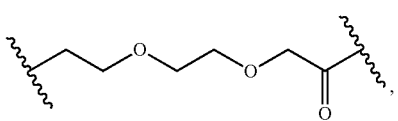 [SMILES: *CCOCCOCC(*)=O] (67)
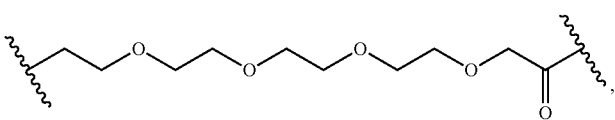 [SMILES: *CCOCCOCCOCCOCC(*)=O] (68)
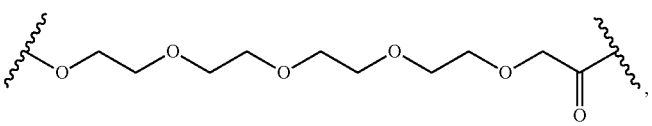 [SMILES: *OCCOCCOCCOCCOCC(*)=O] (69)
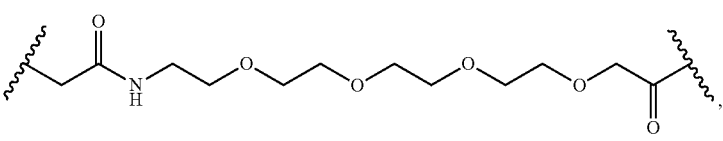 [SMILES: *CC(=O)NCCOCCOCCOCCOCC(*)=O] (70)
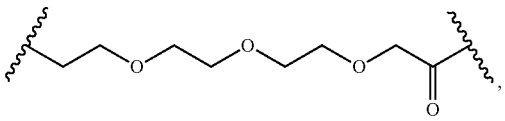 [SMILES: *CCOCCOCCOCC(*)=O] (71)
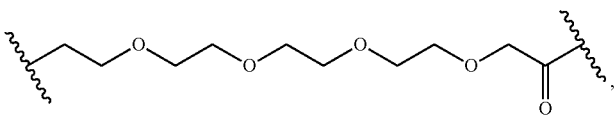 [SMILES: *CCOCCOCCOCCOCC(*)=O] (72)
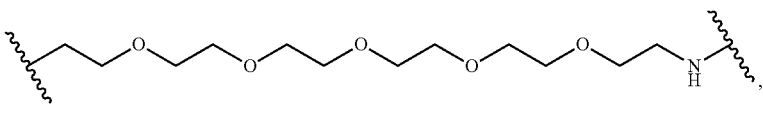 [SMILES: *CCOCCOCCOCCOCCOCCN*] (73)
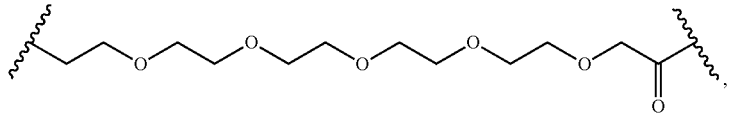 [SMILES: *CCOCCOCCOCCOCCOCC(*)=O] (74)
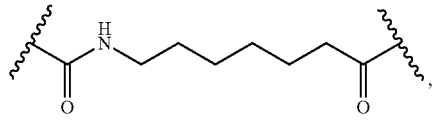 [SMILES: *C(=O)CCCCCCNC(*)=O] (75)
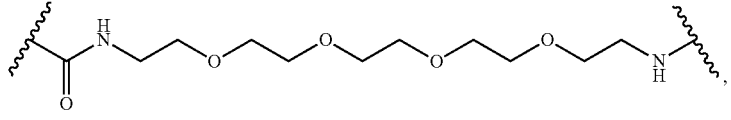 [SMILES: *NCCOCCOCCOCCOCCNC(*)=O] (76)

TABLE B-continued
Exemplified Linkers (L)
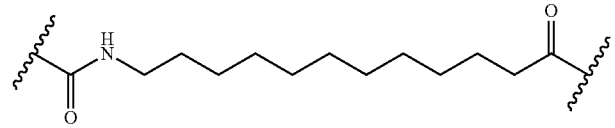
(77)
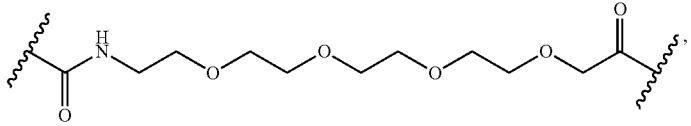 [SMILES: *C(=O)COCCOCCOCCOCCNC(*)=O]
(78)
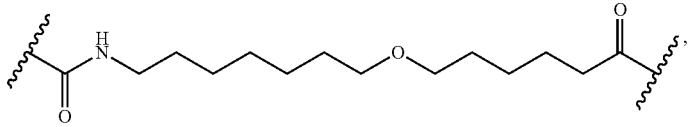 [SMILES: *C(=O)CCCCCOCCCCCCCNC(*)=O]
(79)
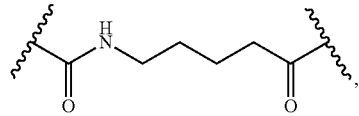 [SMILES: *C(=O)CCCCNC(*)=O]
(80)
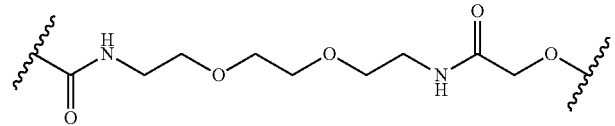
(81)
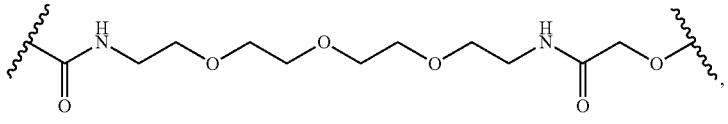 [SMILES: *OCC(=O)NCCOCCOCCOCCNC(*)=O]
(82)
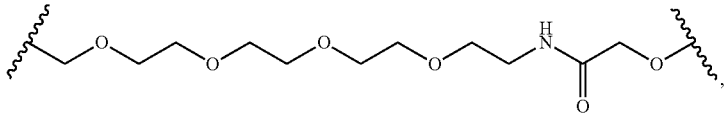 [SMILES: *COCCOCCOCCOCCNC(=O)CO*]
(83)
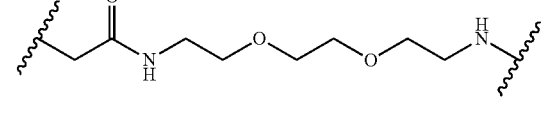
(84)
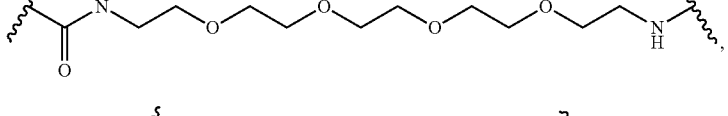
(85)
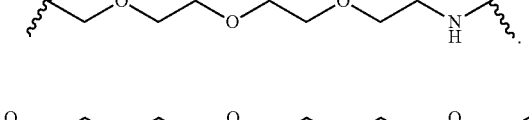
(86)
(87)
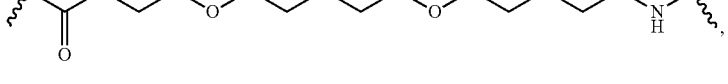
(88)

TABLE B-continued

Exemplified Linkers (L)

(89) — (99) [chemical structures]

TABLE B-continued
Exemplified Linkers (L)
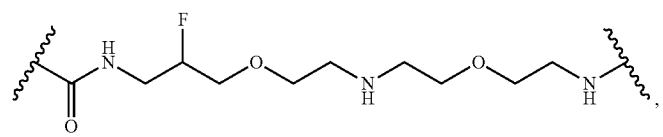 [SMILES: *NCCOCCNCCOCC(F)CNC(*)=O] (100)
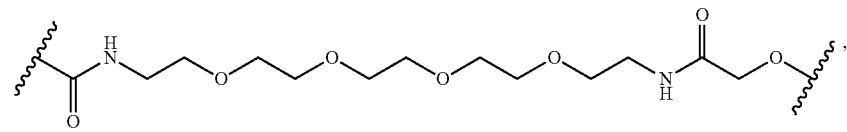 [SMILES: *OCC(=O)NCCOCCOCCOCCOCCNC(*)=O] (101)
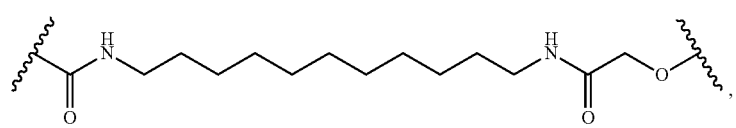 [SMILES: *OCC(=O)NCCCCCCCCCCCNC(*)=O] (102)
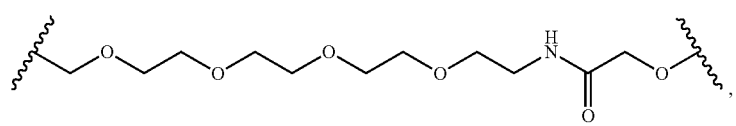 [SMILES: *COCCOCCOCCOCCNC(=O)CO*] (103)
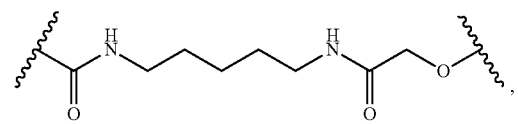 [SMILES: *OCC(=O)NCCCCCNC(*)=O] (104)
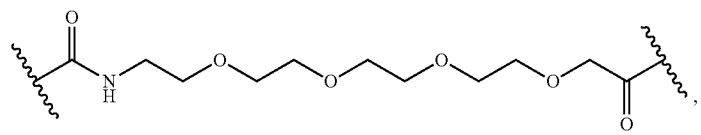 [SMILES: *C(=O)COCCOCCOCCOCCNC(*)=O] (105)
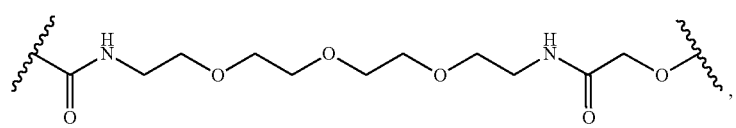 [SMILES: *OCC(=O)NCCOCCOCCOCCNC(*)=O] (106)
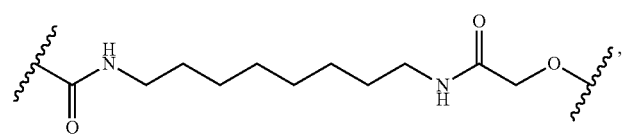 [SMILES: *OCC(=O)NCCCCCCCCNC(*)=O] (107)
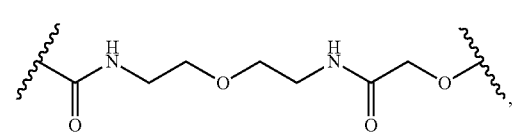 [SMILES: *OCC(=O)NCCOCCNC(*)=O] (108)
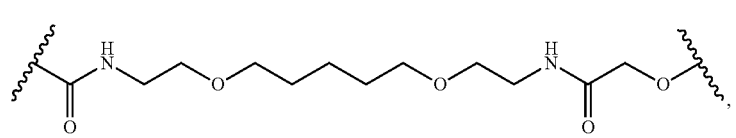 [SMILES: *OCC(=O)NCCOCCCCCOCCNC(*)=O] (109)
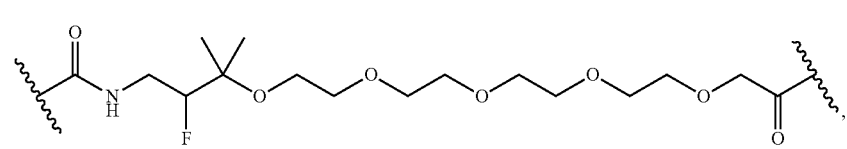 [SMILES: *C(=O)COCCOCCOCCOCCOC(C)(C)C(F)CNC(*)=O] (110)

TABLE B-continued
Exemplified Linkers (L)
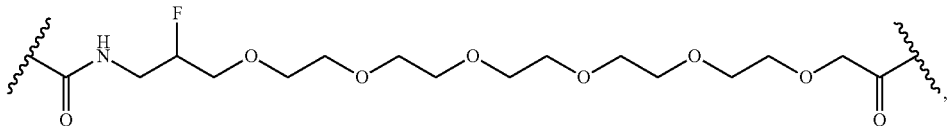 [SMILES: *C(=O)COCCOCCOCCOCCOCCOCC(F)CNC(*)=O] (111)
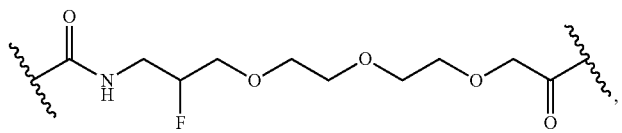 [SMILES: *C(=O)COCCOCCOCC(F)CNC(*)=O] (112)
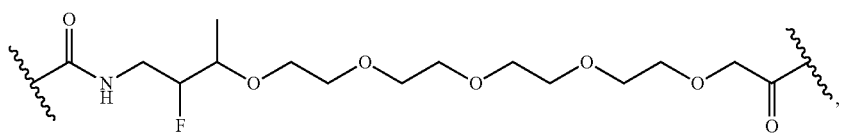 [SMILES: *C(=O)COCCOCCOCCOCCOC(C)C(F)CNC(*)=O] (113)
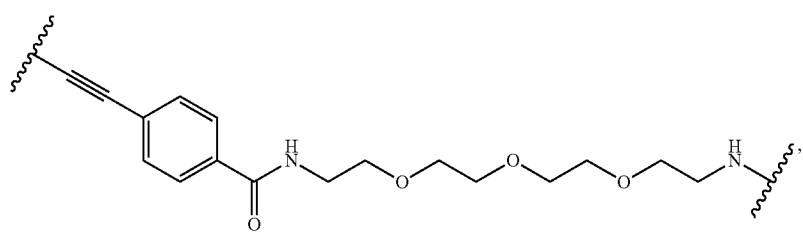 [SMILES: *C#Cc1ccc(C(=O)NCCOCCOCCOCCN*)cc1] (114)
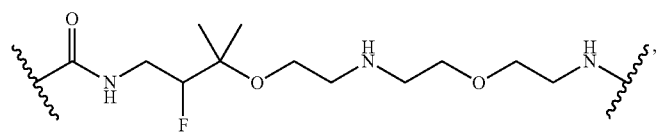 [SMILES: *NCCOCCNCCOC(C)(C)C(F)CNC(*)=O] (115)
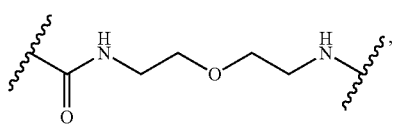 [SMILES: *NCCOCCNC(*)=O] (116)
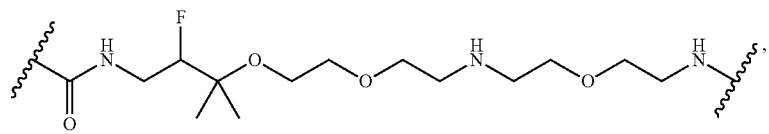 [SMILES: *NCCOCCNCCOCCOC(C)(C)C(F)CNC(*)=O] (117)
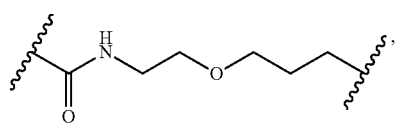 [SMILES: *CCCOCCNC(*)=O] (118)
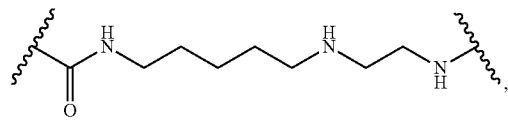 [SMILES: *NCCNCCCCCNC(*)=O] (119)
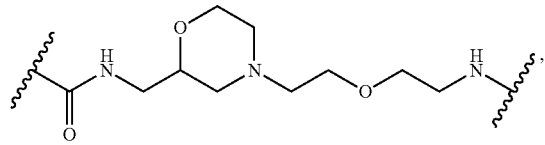 [SMILES: *NCCOCCN1CCOC(CNC(*)=O)C1]

TABLE B-continued

Exemplified Linkers (L)

(120)

(121)

(122)

(123)

(124)

(125)

(126)

(127)

(128)

TABLE B-continued

Exemplified Linkers (L)

TABLE B-continued
Exemplified Linkers (L)
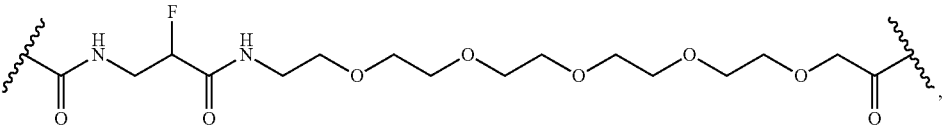 [SMILES: *C(=O)COCCOCCOCCOCCOCCNC(=O)C(F)CNC(*)=O] (140)
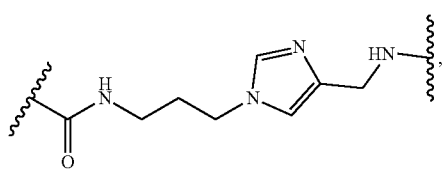 [SMILES: *NCc1cn(CCCNC(*)=O)cn1] (141)
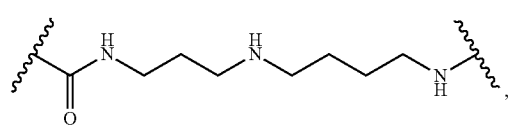 [SMILES: *NCCCCNCCCNC(*)=O] (142)
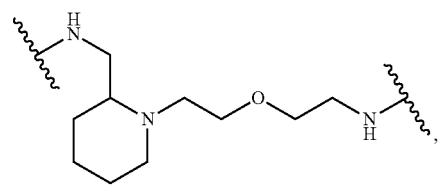 [SMILES: *NCCOCCN1CCCCC1CN*] (143)
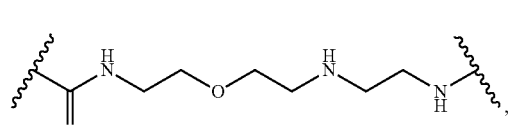 (144)
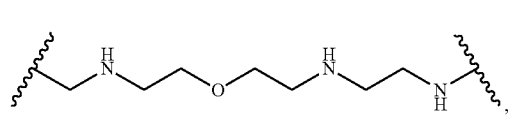 (145)
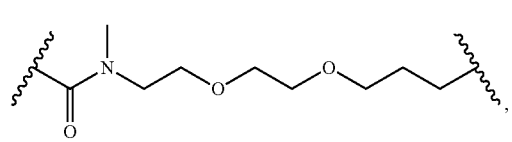 [SMILES: *CCCOCCOCCN(C)C(*)=O] (146)
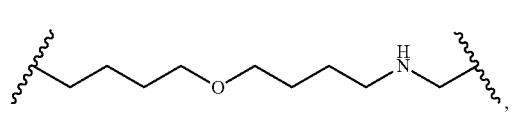 [SMILES: *CCCCOCCCCNC*] (147)
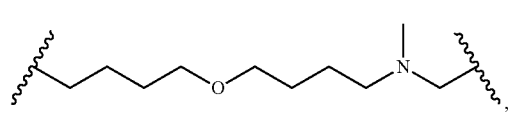 [SMILES: *CCCCOCCCCN(C)C*] (148)
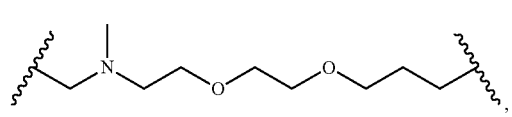 (149)
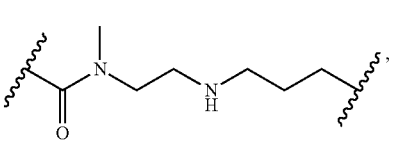 [SMILES: *CCCNCCN(C)C(*)=O] (150)

TABLE B-continued
Exemplified Linkers (L)
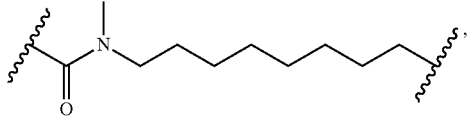 [SMILES: *CCCCCCCCN(C)C(*)=O] (151)
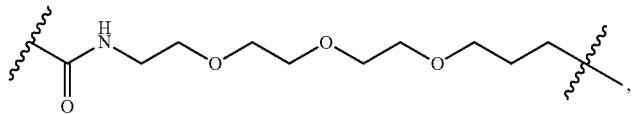 [SMILES: *CCCOCCOCCOCCNC(*)=O] (152)
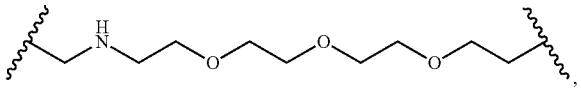 [SMILES: *CCOCCOCCOCCNC*] (153)
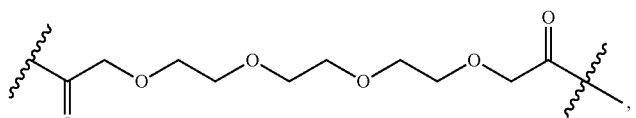 (154)
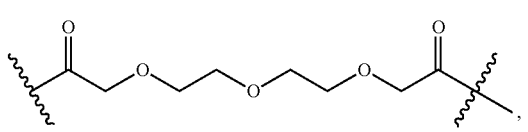 [SMILES: *C(=O)COCCOCCOCC(*)=O] (155)
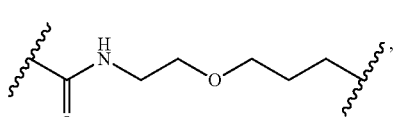 (156)
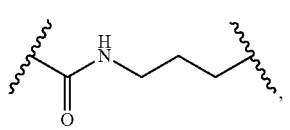 [SMILES: *CCCNC(*)=O] (157)
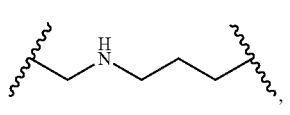 [SMILES: *CCCNC*] (158)
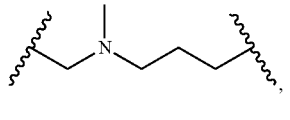 [SMILES: *CCCN(C)C*] (159)
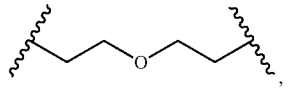 [SMILES: *CCOCC*] (160)
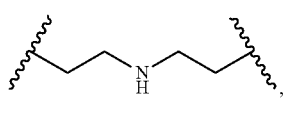 (161)
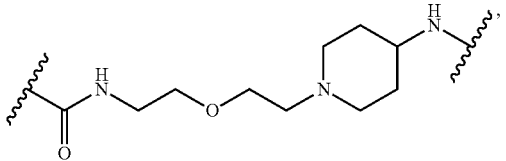 [SMILES: *NC1CCN(CCOCCNC(*)=O)CC1] (162)

TABLE B-continued
Exemplified Linkers (L)
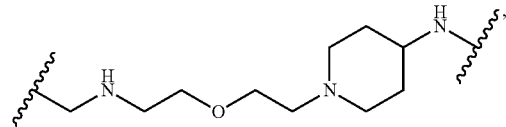 [SMILES: *CNCCOCCN1CCC(N*)CC1] (163)
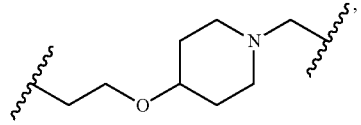 (164)
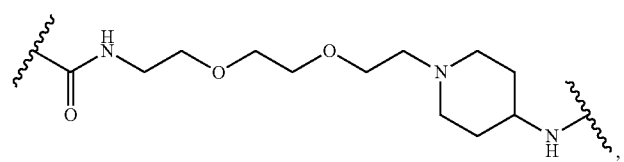 [SMILES: *NC1CCN(CCOCCOCCNC(*)=O)CC1] (165)
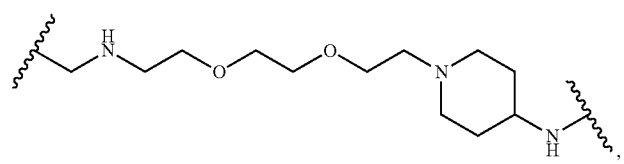 [SMILES: *CNCCOCCOCCN1CCC(N*)CC1] (166)
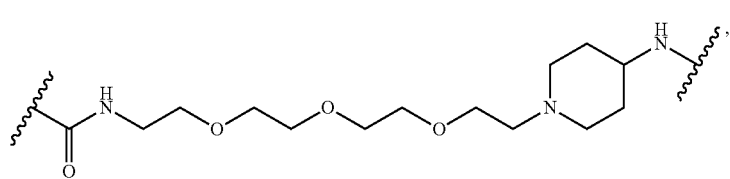 [SMILES: *NC1CCN(CCOCCOCCOCCNC(*)=O)CC1] (167)
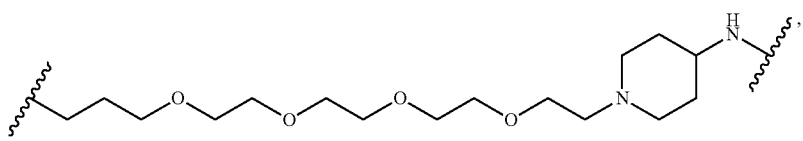 [SMILES: *CCCOCCOCCOCCOCCN1CCC(N*)CC1] (168)
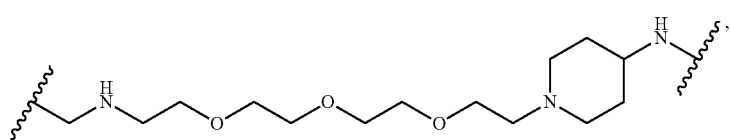 [SMILES: *CNCCOCCOCCOCCN1CCC(N*)CC1] (169)
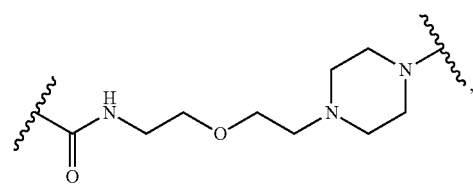 [SMILES: *C(=O)NCCOCCN1CCN(*)CC1] (170)
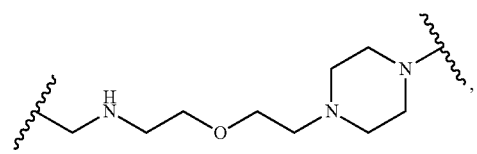 [SMILES: *CNCCOCCN1CCN(*)CC1] (171)

TABLE B-continued

Exemplified Linkers (L)

(172) — (182) [chemical structures]

TABLE B-continued

Exemplified Linkers (L)

(183) — (195) [chemical structures]

TABLE B-continued
Exemplified Linkers (L)
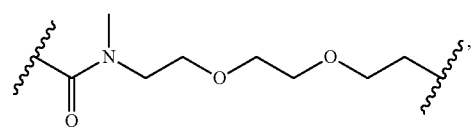 [SMILES: *CCOCCOCCN(C)C(*)=O]
(196)
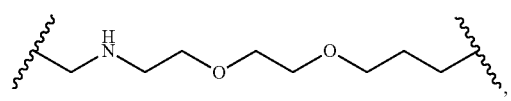 [SMILES: *CCCOCCOCCNC*]
(197)
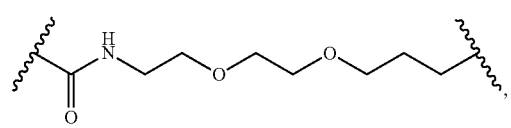 [SMILES: *CCCOCCOCCNC(*)=O]
(198)
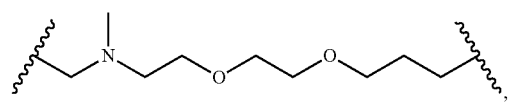 [SMILES: *CCCOCCOCCN(C)C*]
(199)
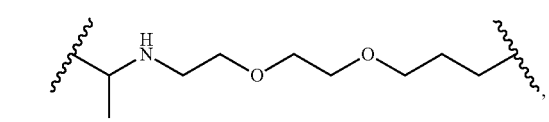 [SMILES: *CCCOCCOCCNC(*)C]
(200)
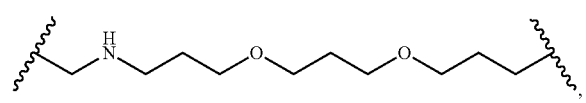 [SMILES: *CCCOCCCOCCCNC*]
(201)
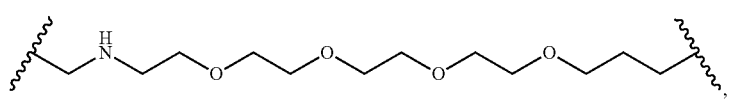
(202)
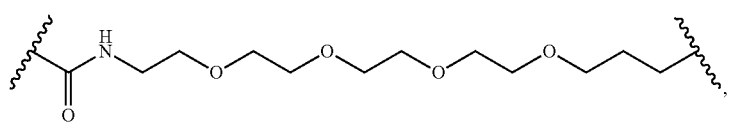 [SMILES: *CCCOCCOCCOCCOCCNC(*)=O]
(203)
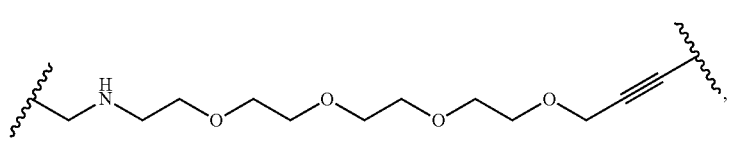 [SMILES: *C#CCOCCOCCOCCOCCNC*]
(204)
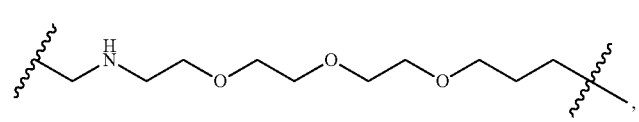 [SMILES: *CCCOCCOCCOCCNC*]
(205)
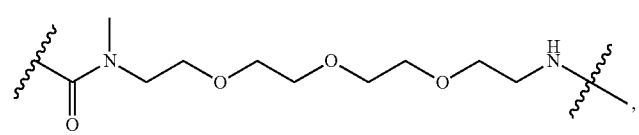 [SMILES: *NCCOCCOCCOCCN(C)C(*)=O]
(206)
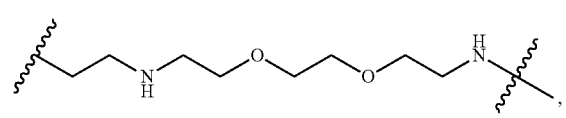 [SMILES: *CCNCCOCCOCCN*]
(207)

TABLE B-continued
Exemplified Linkers (L)
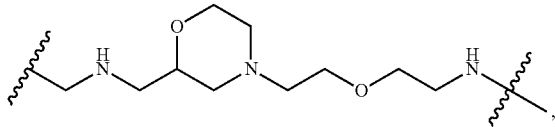 [SMILES: *CNCC1CN(CCOCCN*)CCO1] (208)
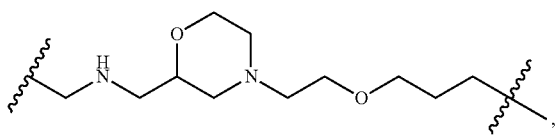 [SMILES: *CCCOCCN1CCOC(CNC*)C1] (209)
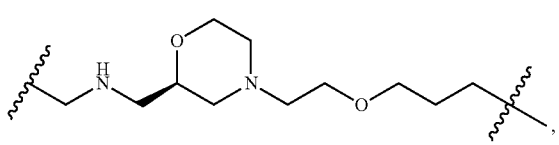 [SMILES: *CCCOCCN1CCO[C@H](CNC*)C1] (210)
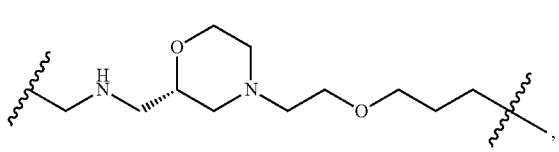 [SMILES: *CCCOCCN1CCO[C@@H](CNC*)C1] (211)
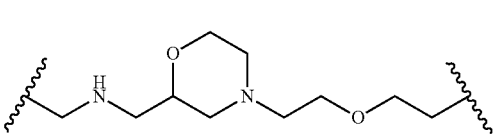 (212)
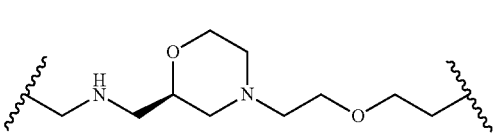 (213)
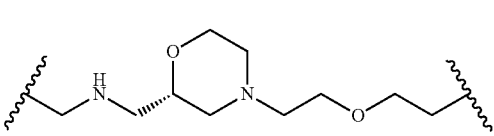 (214)
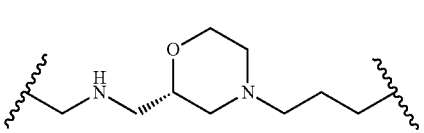 (215)
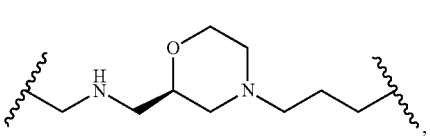 [SMILES: *CCCN1CCO[C@H](CNC*)C1] (216)
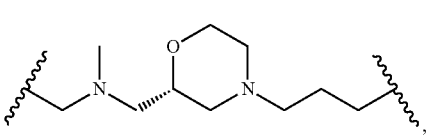 (217)
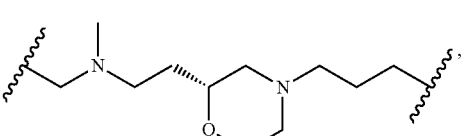 (218)

TABLE B-continued
Exemplified Linkers (L)
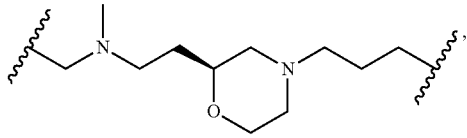 [SMILES: *CCCN1CCO[C@@H](CCN(C)C*)C1] (219)
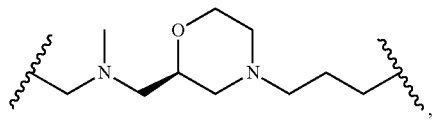 [SMILES: *CCCN1CCO[C@H](CN(C)C*)C1] (220)
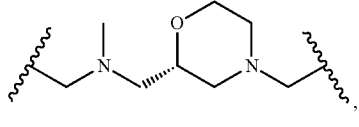 [SMILES: *CN(C)C[C@H]1CN(C*)CCO1] (221)
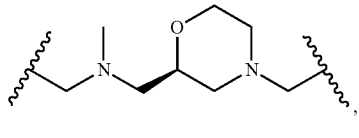 [SMILES: *CN(C)C[C@@H]1CN(C*)CCO1] (222)
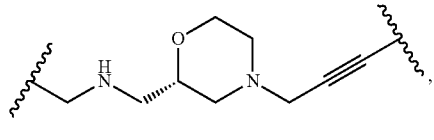 [SMILES: *C#CCN1CCO[C@@H](CNC*)C1] (223)
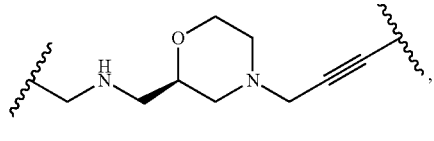 [SMILES: *C#CCN1CCO[C@H](CNC*)C1] (224)
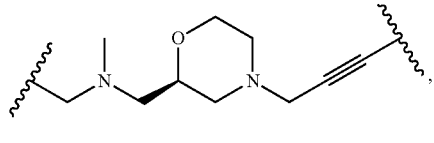 [SMILES: *C#CCN1CCO[C@H](CN(C)C*)C1] (225)
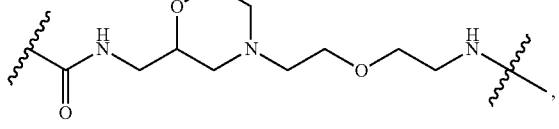 (226)
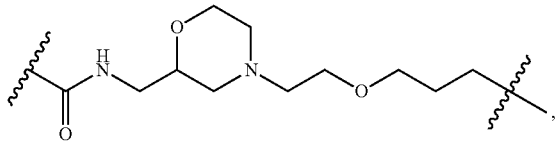 [SMILES: *CCCOCCN1CCOC(CNC(*)=O)C1] (227)
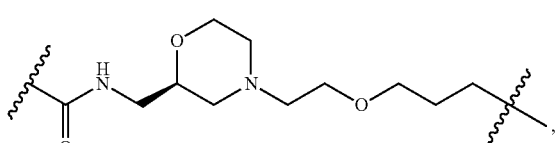 (228)
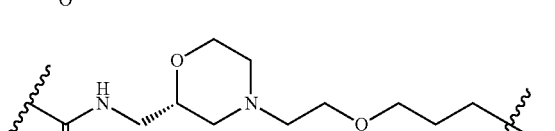 (229)

TABLE B-continued
Exemplified Linkers (L)
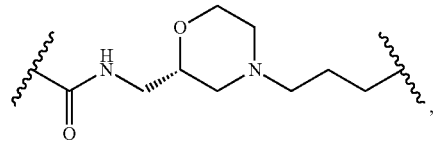 [SMILES: *CCCN1CCO[C@@H](CNC(*)=O)C1] (230)
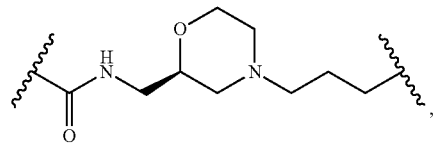 [SMILES: *CCCN1CCO[C@H](CNC(*)=O)C1] (231)
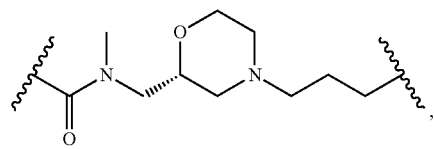 [SMILES: *CCCN1CCO[C@@H](CN(C)C(*)=O)C1] (232)
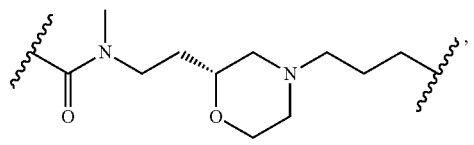 [SMILES: *CCCN1CCO[C@H](CCN(C)C(*)=O)C1] (233)
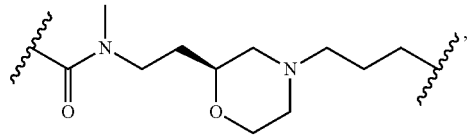 [SMILES: *CCCN1CCO[C@@H](CCN(C)C(*)=O)C1] (234)
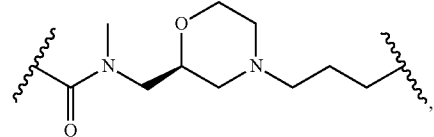 [SMILES: *CCCN1CCO[C@H](CN(C)C(*)=O)C1] (235)
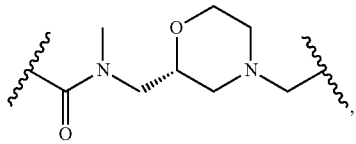 [SMILES: *CN1CCO[C@@H](CN(C)C(*)=O)C1] (236)
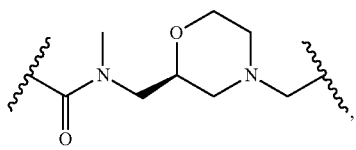 [SMILES: *CN1CCO[C@H](CN(C)C(*)=O)C1] (237)
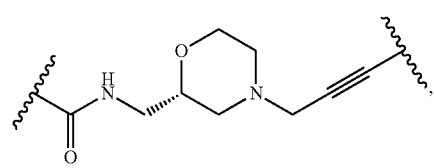 [SMILES: *C#CCN1CCO[C@@H](CNC(*)=O)C1] (238)
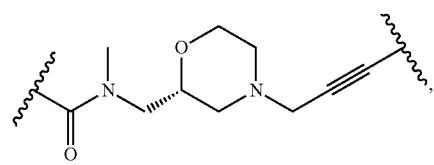 [SMILES: *C#CCN1CCO[C@@H](CN(C)C(*)=O)C1] (239)

TABLE B-continued
Exemplified Linkers (L)
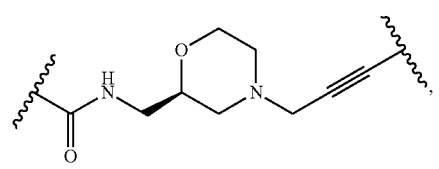 [SMILES: *C#CCN1CCO[C@H](CNC(*)=O)C1]
(240)
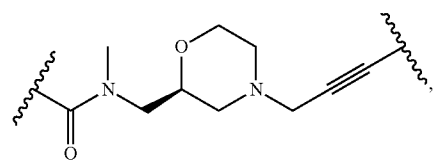 [SMILES: *C#CCN1CCO[C@H](CN(C)C(*)=O)C1]
(241)
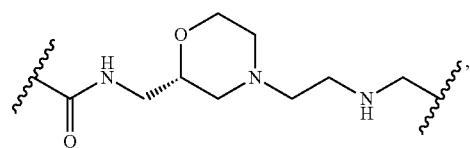 [SMILES: *CNCCN1CCO[C@@H](CNC(*)=O)C1]
(242)
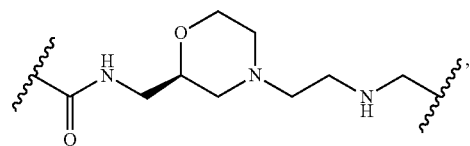 [SMILES: *CNCCN1CCO[C@H](CNC(*)=O)C1]
(243)
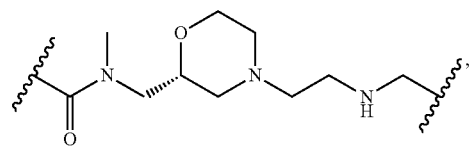 [SMILES: *CNCCN1CCO[C@@H](CN(C)C(*)=O)C1]
(244)
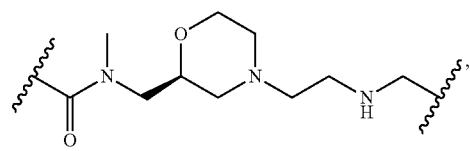 [SMILES: *CNCCN1CCO[C@H](CN(C)C(*)=O)C1]
(245)
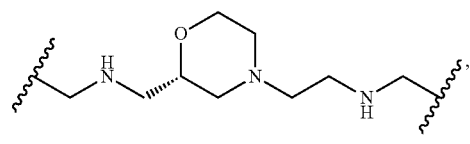 [SMILES: *CNCCN1CCO[C@@H](CNC*)C1]
(246)
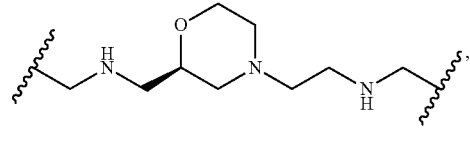
(247)
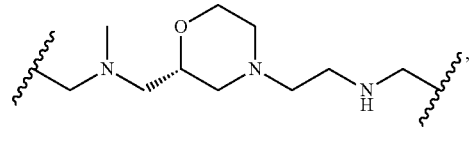 [SMILES: *CNCCN1CCO[C@@H](CN(C)C*)C1]
(248)
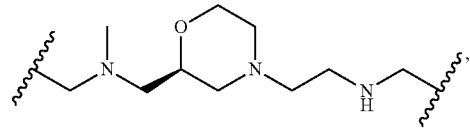 [SMILES: *CNCCN1CCO[C@H](CN(C)C*)C1]
(249)

TABLE B-continued

Exemplified Linkers (L)

(250) [structure]

(251) [structure]

(253) [structure]

(254) [structure]

(255) [structure]

(256) [structure]

(257) [structure]

(258) [structure]

(259) [structure]

(260) [structure]

TABLE B-continued

Exemplified Linkers (L)

(261) [structure]

(262) [structure]

(263) [structure]

(264) [structure]

(265) [structure]

(266) [structure]

(267) [structure]

(268) [structure]

(269) [structure]

(270) [structure]

(271) [structure]

(272) [structure]

TABLE B-continued
Exemplified Linkers (L)
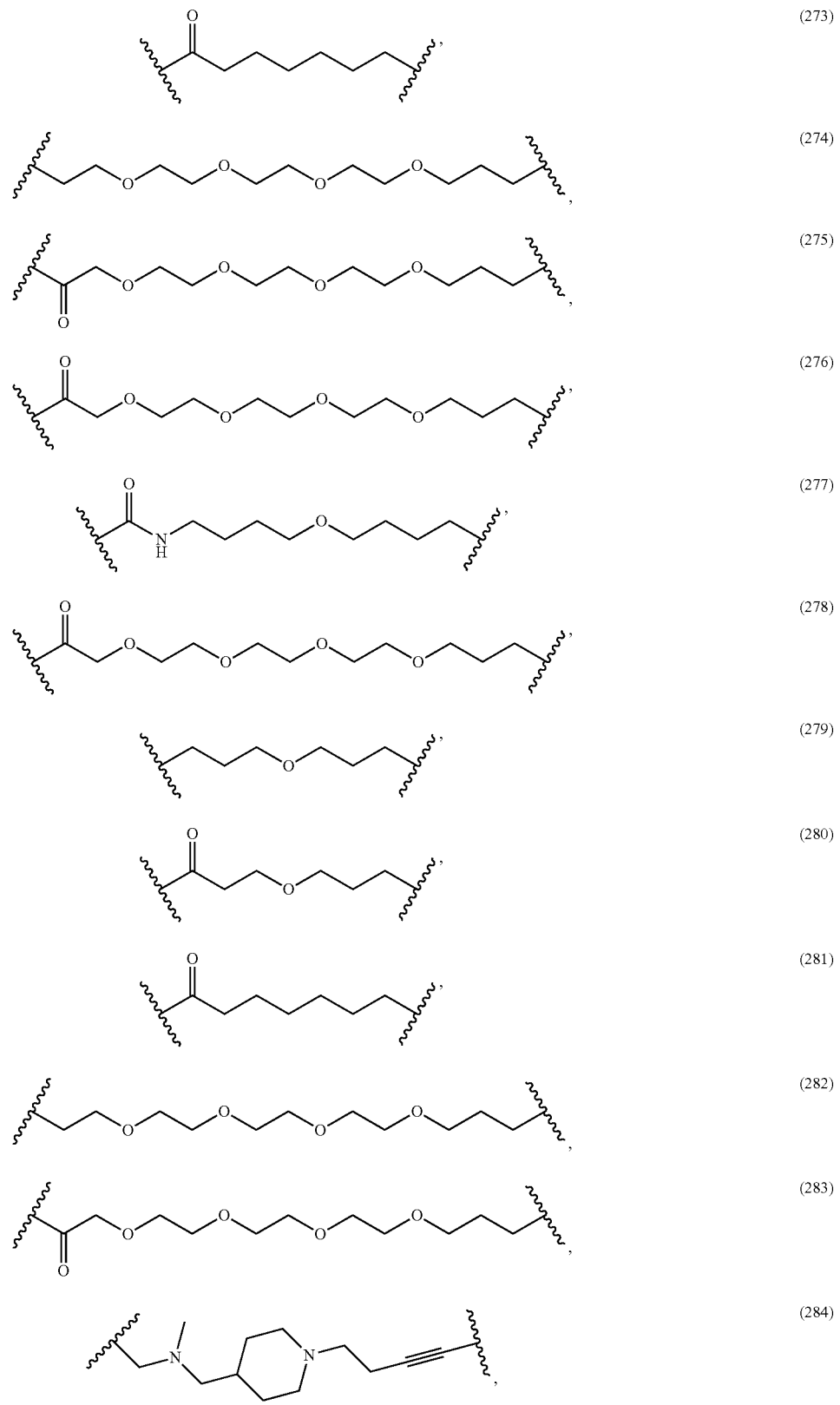

TABLE B-continued
Exemplified Linkers (L)
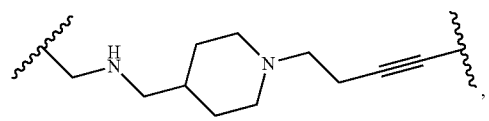 [SMILES: *C#CCCN1CCC(CNC*)CC1] (285)
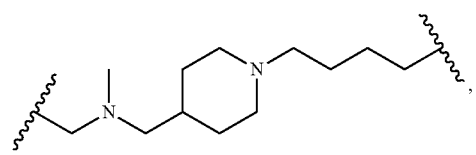 [SMILES: *CCCCN1CCC(CN(C)C*)CC1] (286)
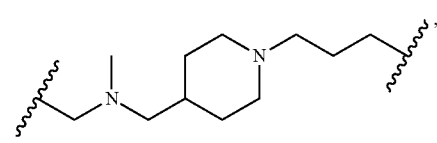 [SMILES: *CCCN1CCC(CN(C)C*)CC1] (287)
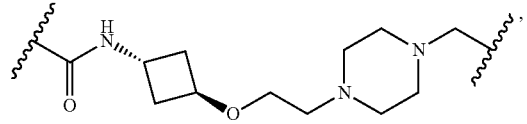 [SMILES: *CN1CCN(CCO[C@H]2C[C@H](NC(*)=O)C2)CC1] (288)
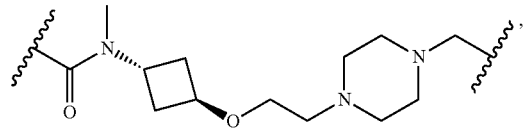 [SMILES: *CN1CCN(CCO[C@H]2C[C@H](N(C)C(*)=O)C2)CC1] (289)
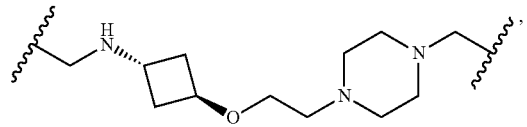 [SMILES: *CN[C@H]1C[C@H](OCCN2CCN(C*)CC2)C1] (290)
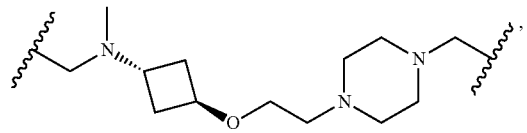 [SMILES: *CN1CCN(CCO[C@H]2C[C@H](N(C)C*)C2)CC1] (291)
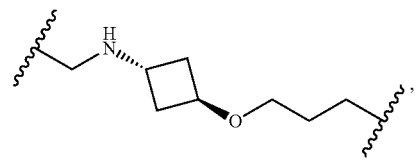 [SMILES: *CCCO[C@H]1C[C@H](NC*)C1] (292)
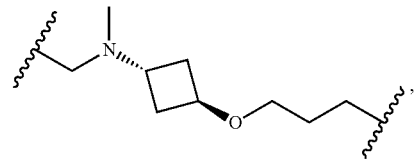 [SMILES: *CCCO[C@H]1C[C@H](N(C)C*)C1] (293)
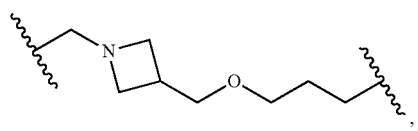 [SMILES: *CCCOCC1CN(C*)C1] (294)

TABLE B-continued
Exemplified Linkers (L)
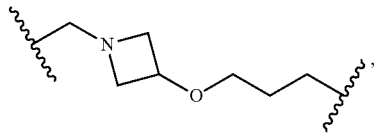 [SMILES: *CCCOC1CN(C*)C1]
(295)
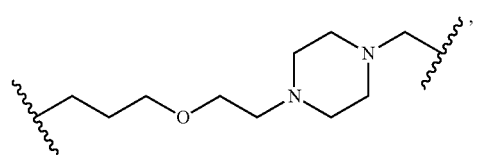 [SMILES: *CCCOCCN1CCN(C*)CC1]
(296)
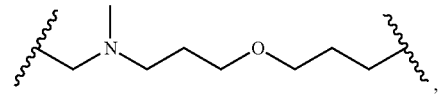 [SMILES: *CCCOCCCN(C)C*]
(297)
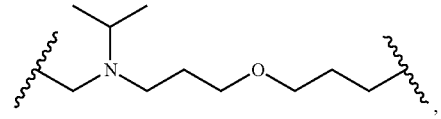 [SMILES: *CCCOCCCN(C*)C(C)C]
(298)
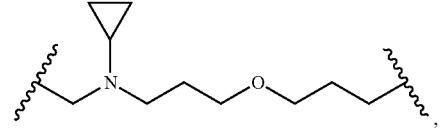 [SMILES: *CCCOCCCN(C*)C1CC1]
(299)
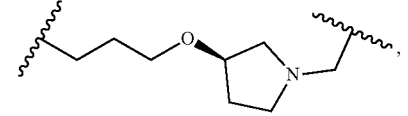 [SMILES: *CCCO[C@@H]1CCN(C*)C1]
(300)
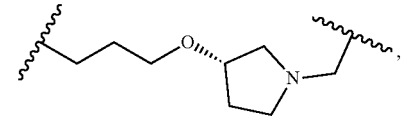 [SMILES: *CCCO[C@H]1CCN(C*)C1]
(301)
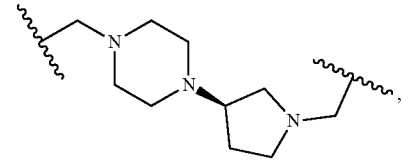 [SMILES: *CN1CCN([C@@H]2CCN(C*)C2)CC1]
(302)
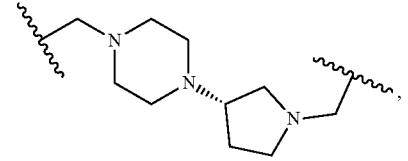 [SMILES: *CN1CCN([C@H]2CCN(C*)C2)CC1]
(303)
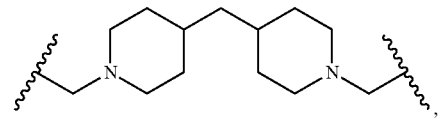 [SMILES: *CN1CCC(CC2CCN(C*)CC2)CC1]
(304)

TABLE B-continued
Exemplified Linkers (L)
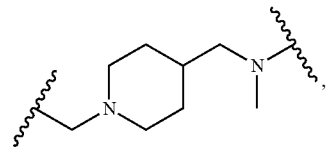 [SMILES: *CN1CCC(CN(*)C)CC1]
(305)
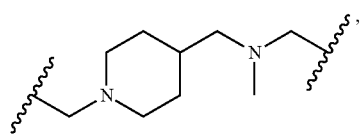 [SMILES: *CN(C)CC1CCN(C*)CC1]
(306)
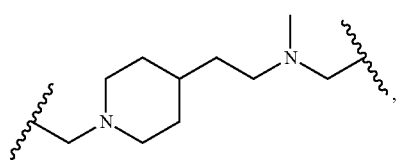 [SMILES: *CN(C)CCC1CCN(C*)CC1]
(307)
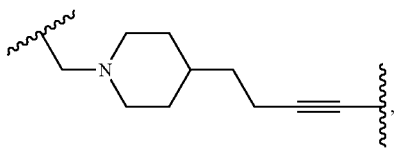 [SMILES: *C#CCCC1CCN(C*)CC1]
(308)
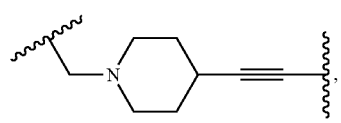 [SMILES: *C#CC1CCN(C*)CC1]
(309)
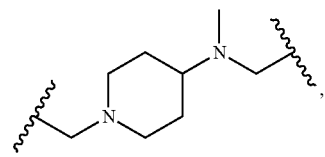 [SMILES: *CN1CCC(N(C)C*)CC1]
(310)
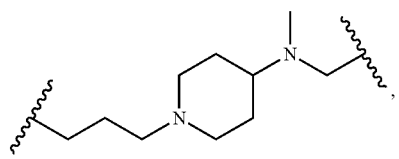 [SMILES: *CCCN1CCC(N(C)C*)CC1]
(311)
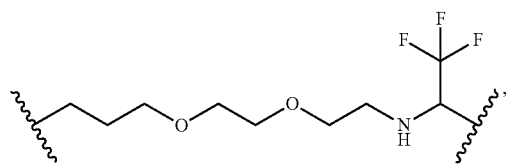 [SMILES: *CCCOCCOCCNC(*)C(F)(F)F]
(312)
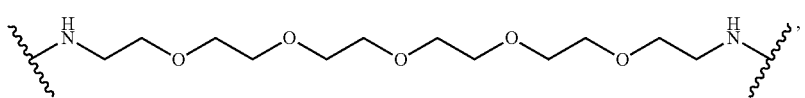 [SMILES: *NCCOCCOCCOCCOCCOCCN*]
(313)
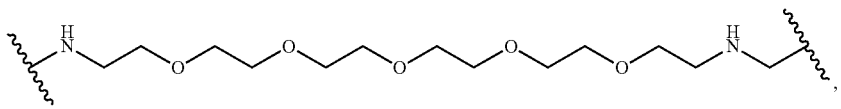 [SMILES: *CNCCOCCOCCOCCOCCOCCN*]
(314)

TABLE B-continued

Exemplified Linkers (L)

(315)

(316)

(317)

(318)

(319)

(320)

(321)

(322)

(323)

(324)

(325)

TABLE B-continued
Exemplified Linkers (L)
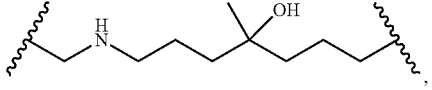 (326)
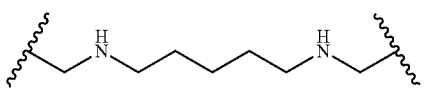 (327)
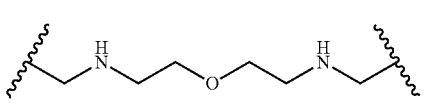 (328)
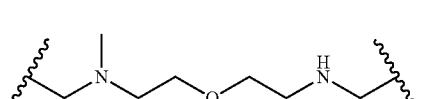 (329)
 (330)
 (331)
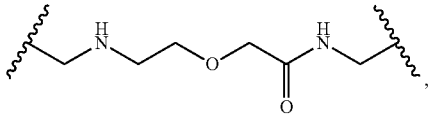 [SMILES: *CNCCOCC(=O)NC*] (332)
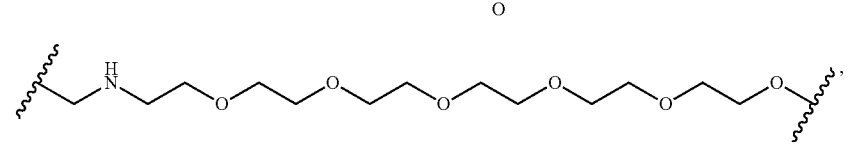 (333)
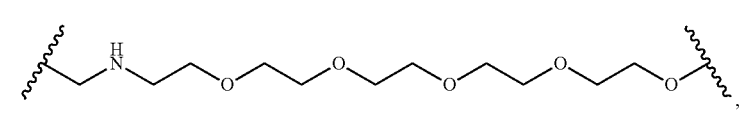 [SMILES: *CNCCOCCOCCOCCOCCO*] (334)
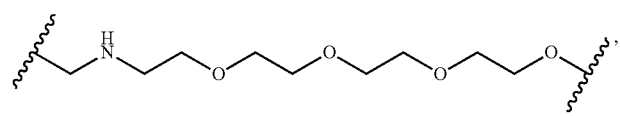 [SMILES: *CNCCOCCOCCOCCO*] (335)
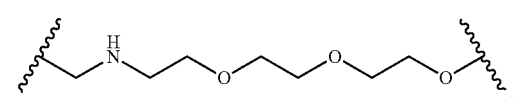 (336)
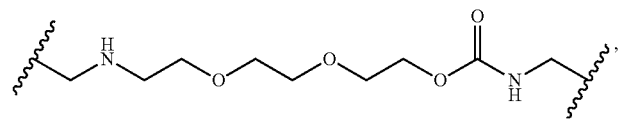 [SMILES: *CNCCOCCOCCOC(=O)NC*] (337)
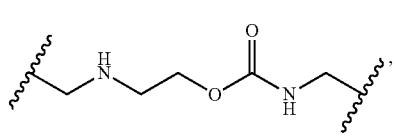 [SMILES: *CNCCOC(=O)NC*] (338)

TABLE B-continued
Exemplified Linkers (L)
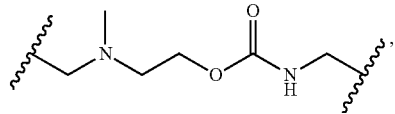 [SMILES: *CNC(=O)OCCN(C)C*]
(339)
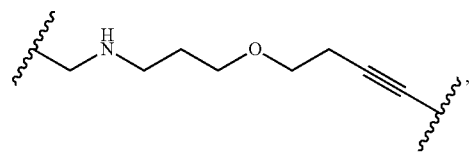 [SMILES: *C#CCCOCCCNC*]
(340)
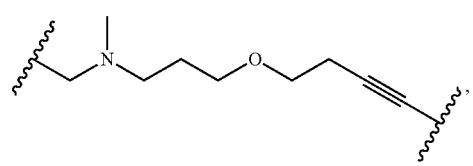 [SMILES: *C#CCCOCCCN(C)C*]
(341)
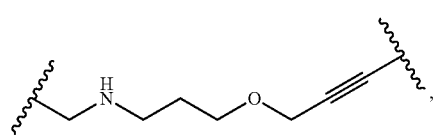 [SMILES: *C#CCOCCCNC*]
(342)
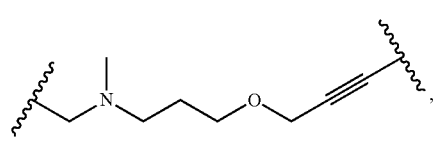 [SMILES: *C#CCOCCCN(C)C*]
(343)
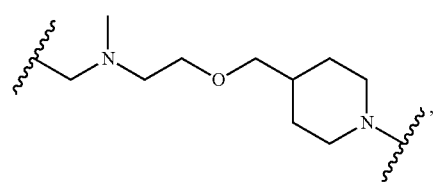 [SMILES: *CN(C)CCOCC1CCN(*)CC1]
(344)
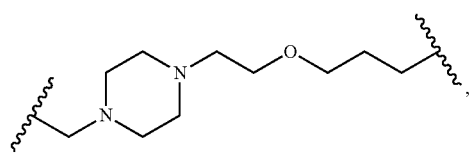 [SMILES: *CCCOCCN1CCN(C*)CC1]
(345)
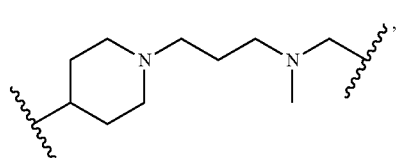 [SMILES: *CN(C)CCCN1CCC(*)CC1]
(346)
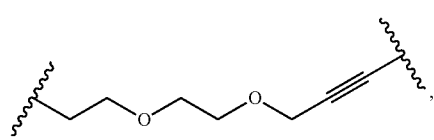 [SMILES: *C#CCOCCOCC*]
(347)

TABLE B-continued
Exemplified Linkers (L)
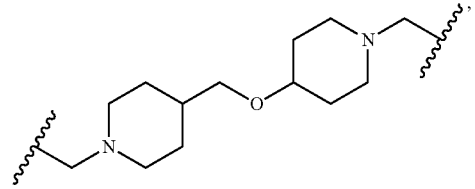 [SMILES: *CN1CCC(COC2CCN(C*)CC2)CC1]
(348)
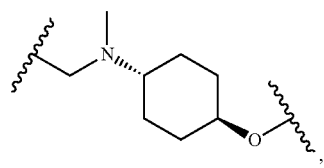 [SMILES: *CN(C)[C@H]1CC[C@H](O*)CC1]
(349)
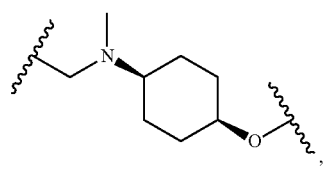
(350)
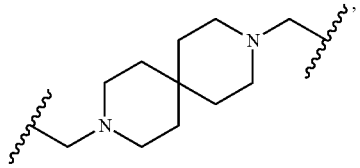 [SMILES: *CN1CCC2(CC1)CCN(C*)CC2]
(351)
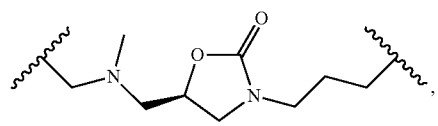 [SMILES: *CCCN1C[C@@H](CN(C)C*)OC1=O]
(352)
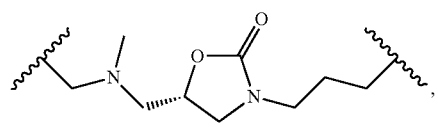 [SMILES: *CCCN1C[C@H](CN(C)C*)OC1=O]
(353)
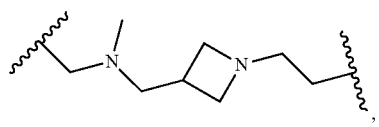 [SMILES: *CCN1CC(CN(C)C*)C1]
(354)
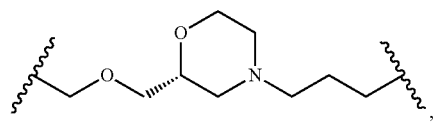 [SMILES: *CCCN1CCO[C@@H](COC*)C1]
(355)
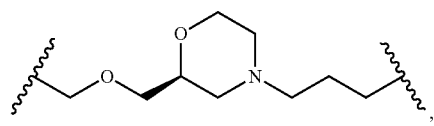 [SMILES: *CCCN1CCO[C@H](COC*)C1]
(356)

TABLE B-continued
Exemplified Linkers (L)
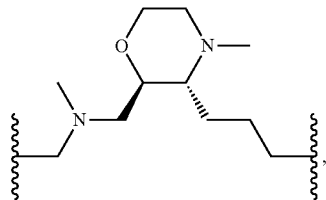 [SMILES: *CCC[C@@H]1[C@@H](CN(C)C*)OCCN1C]
(357)
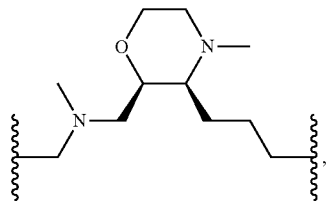 [SMILES: *CCC[C@H]1[C@@H](CN(C)C*)OCCN1C]
(358)
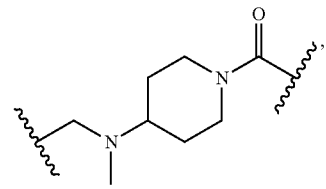 [SMILES: *CN(C)C1CCN(C(*)=O)CC1]
(359)
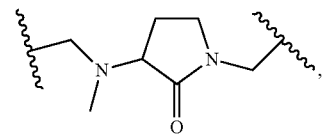 [SMILES: *CN1CCC(N(C)C*)C1=O]
(360)
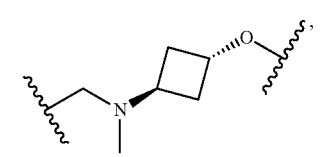 [SMILES: *CN(C)[C@H]1C[C@H](O*)C1]
(361)
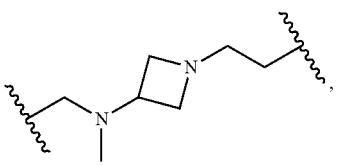 [SMILES: *CCN1CC(N(C)C*)C1]
(362)
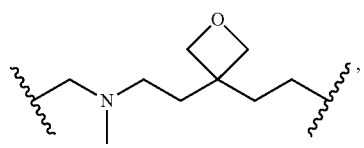 [SMILES: *CCC1(CCN(C)C*)COC1]
(363)
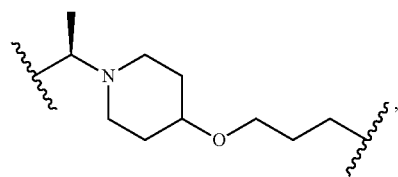
(364)

TABLE B-continued
Exemplified Linkers (L)
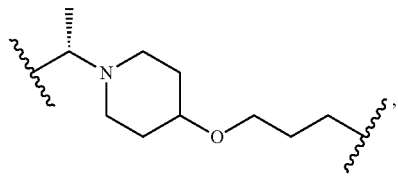 [SMILES: *CCCOC1CCN([C@H](*)C)CC1] (365)
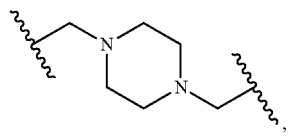 [SMILES: *CN1CCN(C*)CC1] (366)
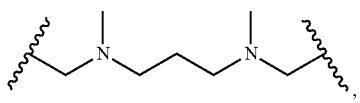 [SMILES: *CN(C)CCCN(C)C*] (367)
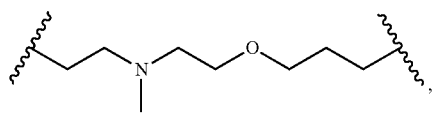 [SMILES: *CCCOCCN(C)CC*] (368)
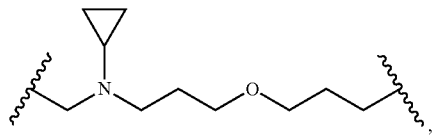 (369)
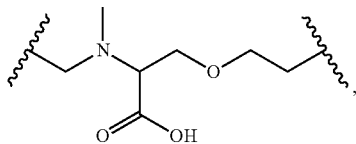 [SMILES: *CCOCC(C(=O)O)N(C)C*] (370)
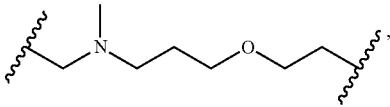 [SMILES: *CCOCCCN(C)C*] (371)
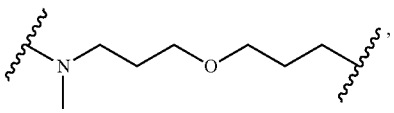 [SMILES: *CCCOCCCN(*)C] (372)
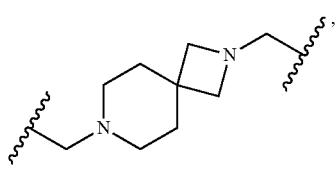 [SMILES: *CN1CCC2(CC1)CN(C*)C2] (373)
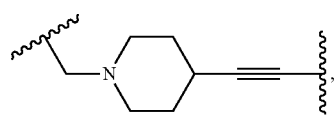 (374)

TABLE B-continued
Exemplified Linkers (L)
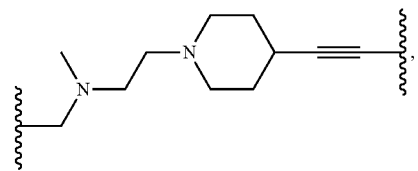 [SMILES: *C#CC1CCN(CCN(C)C*)CC1] (375)
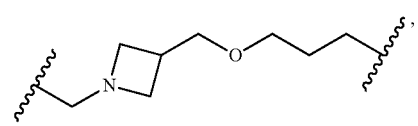 [SMILES: *CCCOCC1CN(C*)C1] (376)
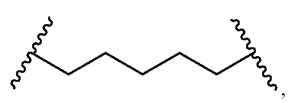 (377)
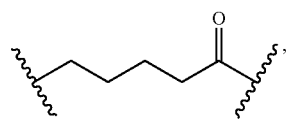 [SMILES: *CCCCC(*)=O] (378)
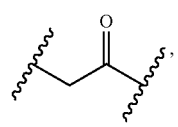 [SMILES: *CC(*)=O] (379)
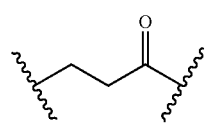 (380)
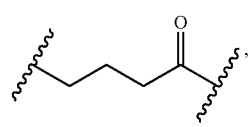 [SMILES: *CCCC(*)=O] (381)
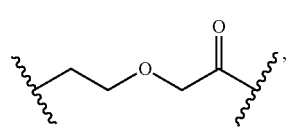 [SMILES: *CCOCC(*)=O] (382)
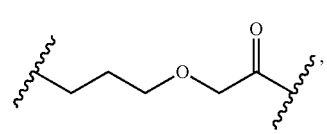 [SMILES: *CCCOCC(*)=O] (383)
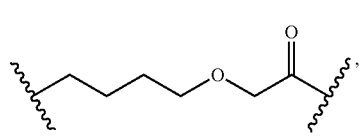 [SMILES: *CCCCOCC(*)=O] (384)
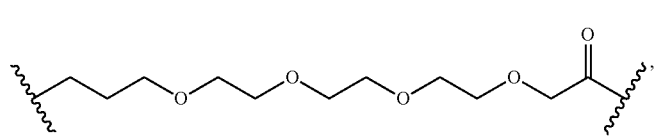 [SMILES: *CCCOCCOCCOCCOCC(*)=O] (385)

TABLE B-continued

Exemplified Linkers (L)

(386) — (398) chemical linker structures.

TABLE B-continued

Exemplified Linkers (L)

TABLE B-continued
Exemplified Linkers (L)
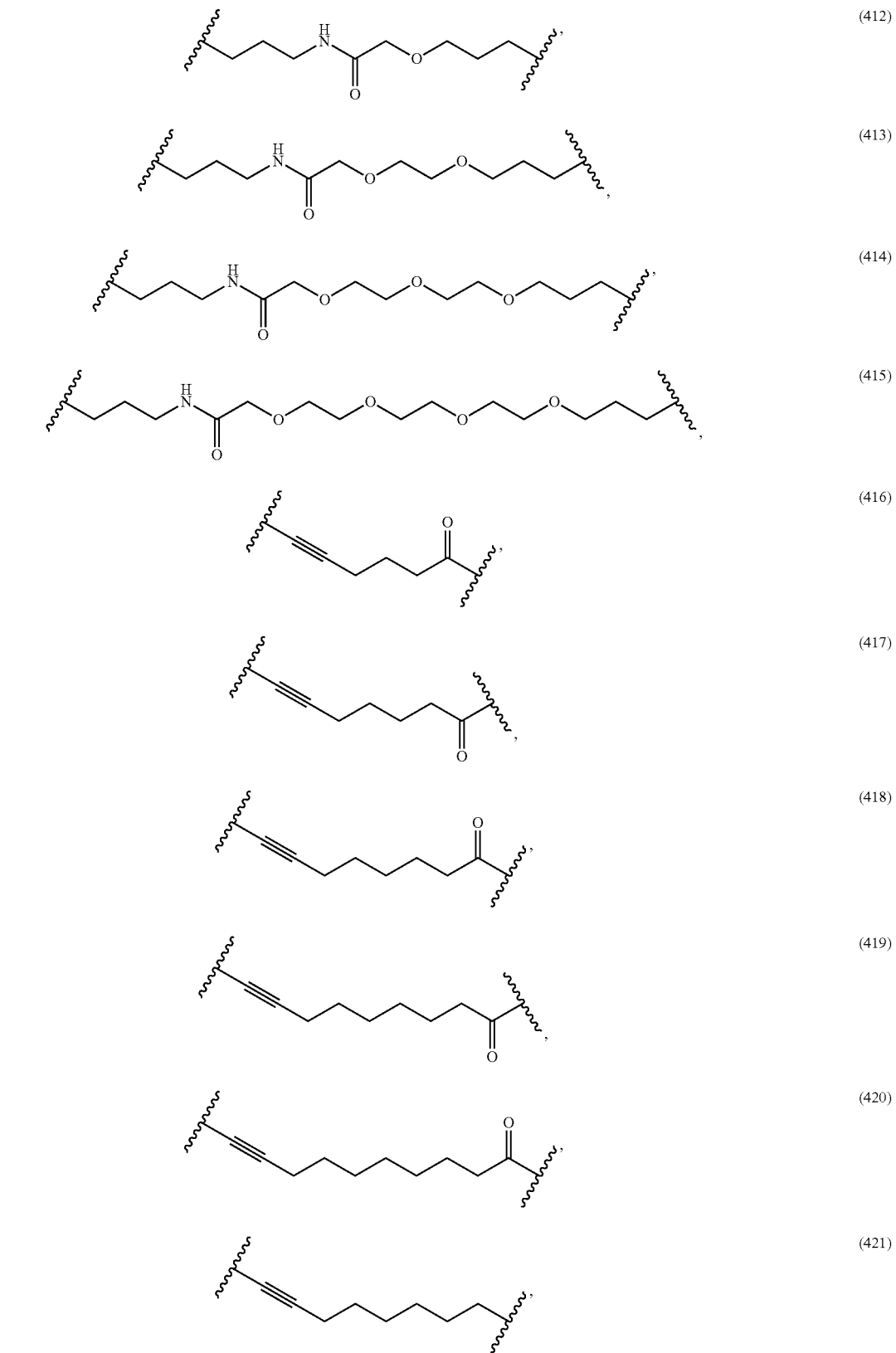

TABLE B-continued

Exemplified Linkers (L)

(422) — (431): structures not transcribed.

TABLE B-continued
Exemplified Linkers (L)
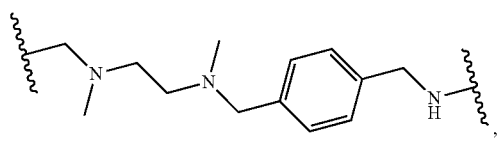 [SMILES: *CN(C)CCN(C)Cc1ccc(CN*)cc1]
(432)
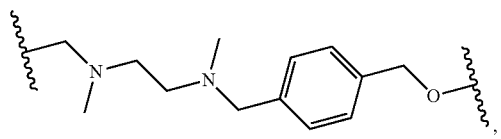 [SMILES: *CN(C)CCN(C)Cc1ccc(CO*)cc1]
(433)
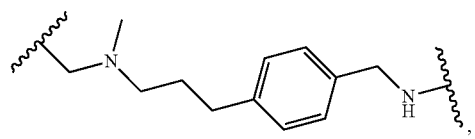 [SMILES: *CN(C)CCCc1ccc(CN*)cc1]
(434)
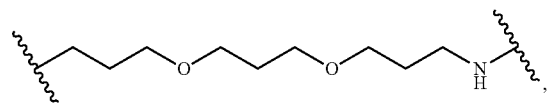 [SMILES: *CCCOCCCOCCCN*]
(435)
(436)
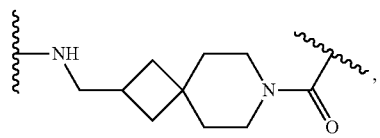 [SMILES: *NCC1CC2(CCN(C(*)=O)CC2)C1]
(437)
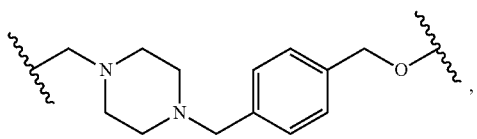 [SMILES: *CN1CCN(Cc2ccc(CO*)cc2)CC1]
(438)
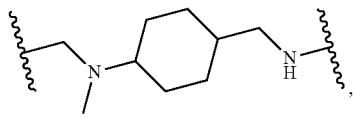 [SMILES: *CN(C)C1CCC(CN*)CC1]
(438)
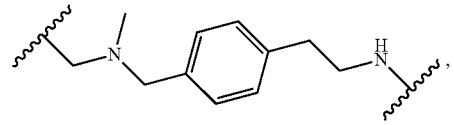 [SMILES: *CN(C)Cc1ccc(CCN*)cc1]
(439)
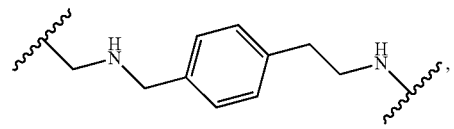 [SMILES: *CNCc1ccc(CCN*)cc1]
(440)
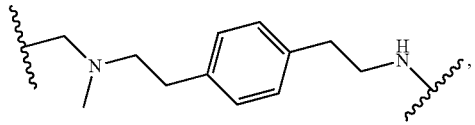 [SMILES: *CN(C)CCc1ccc(CCN*)cc1]
(441)

TABLE B-continued
Exemplified Linkers (L)
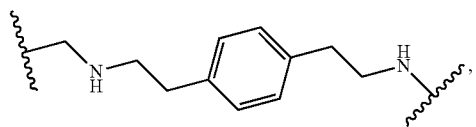 [SMILES: *CNCCc1ccc(CCN*)cc1] (442)
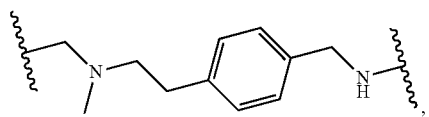 (443)
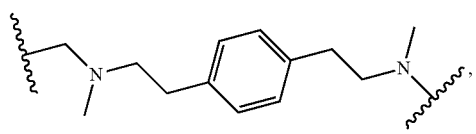 [SMILES: *CN(C)CCc1ccc(CCN(*)C)cc1] (444)
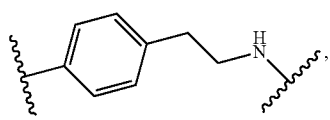 [SMILES: *NCCc1ccc(*)cc1] (445)
 (446)
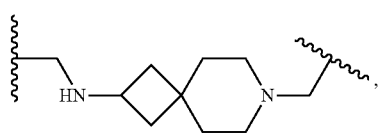 [SMILES: *CNC1CC2(CCN(C*)CC2)C1] (447)
 (448)
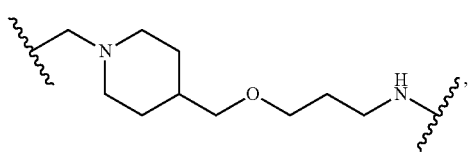 [SMILES: *CN1CCC(COCCCN*)CC1] (449)
 (450)
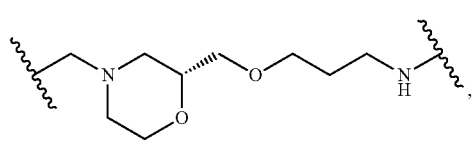 [SMILES: *CN1CCO[C@@H](COCCCN*)C1] (451)
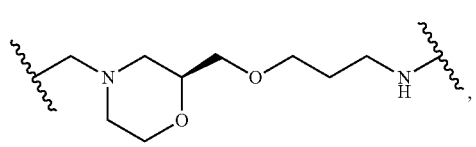 [SMILES: *CN1CCO[C@H](COCCCN*)C1] (452)

TABLE B-continued
Exemplified Linkers (L)
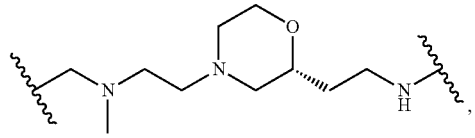 [SMILES: *CN(C)CCN1CCO[C@H](CCN*)C1]
(453)
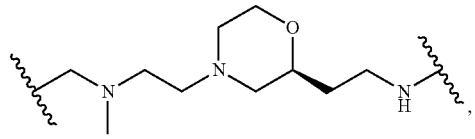 [SMILES: *CN(C)CCN1CCO[C@@H](CCN*)C1]
(454)
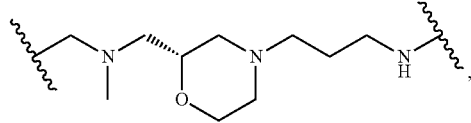 [SMILES: *CN(C)C[C@@H]1CN(CCCN*)CCO1]
(455)
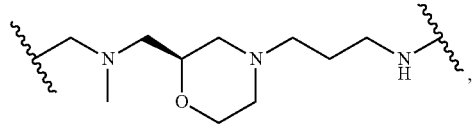 [SMILES: *CN(C)C[C@H]1CN(CCCN*)CCO1]
(456)
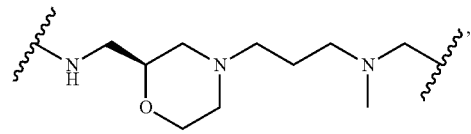 [SMILES: *CN(C)CCCN1CCO[C@@H](CN*)C1]
(457)
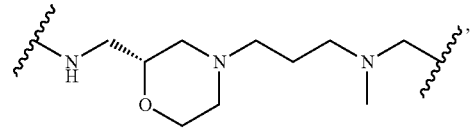 [SMILES: *CN(C)CCCN1CCO[C@H](CN*)C1]
(458)
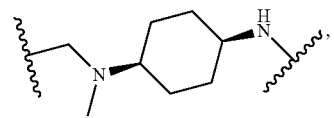 [SMILES: *CN(C)[C@H]1CC[C@@H](N*)CC1]
(459)
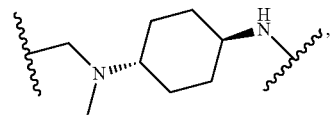 [SMILES: *CN(C)[C@H]1CC[C@H](N*)CC1]
(460)
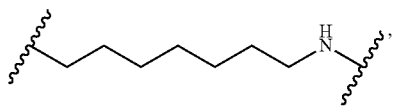 [SMILES: *CCCCCCCN*]
(461)
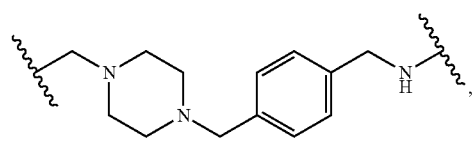 [SMILES: *CN1CCN(Cc2ccc(CN*)cc2)CC1]
(462)
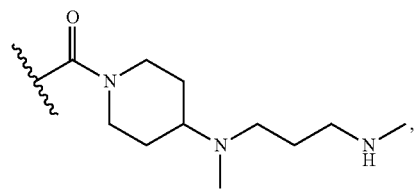 [SMILES: *C(=O)N1CCC(N(C)CCCNC)CC1]
(463)

TABLE B-continued
Exemplified Linkers (L)
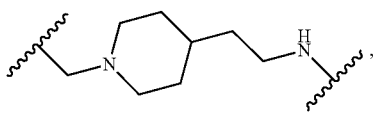 [SMILES: *CN1CCC(CCN*)CC1] (464)
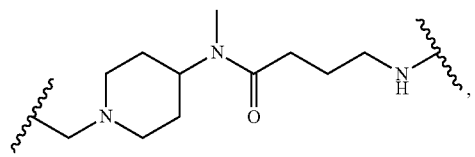 [SMILES: *CN1CCC(N(C)C(=O)CCCN*)CC1] (465)
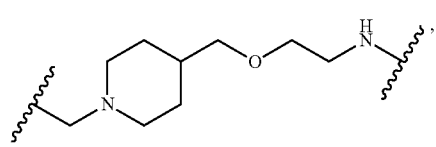 [SMILES: *CN1CCC(COCCN*)CC1] (466)
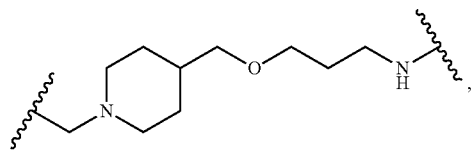 [SMILES: *CN1CCC(COCCCN*)CC1] (467)
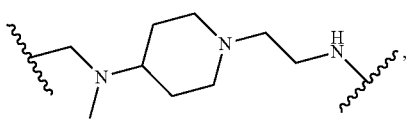 [SMILES: *CN(C)C1CCN(CCN*)CC1] (468)
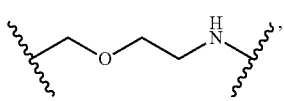 [SMILES: *COCCN*] (469)
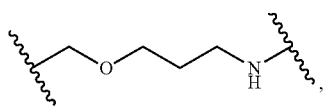 [SMILES: *COCCCN*] (470)
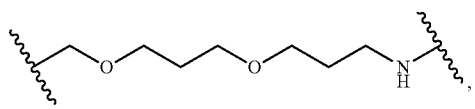 [SMILES: *COCCCOCCCN*] (471)
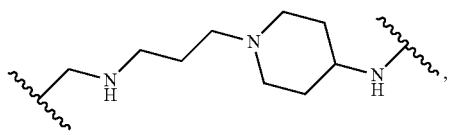 [SMILES: *CNCCCN1CCC(N*)CC1] (472)
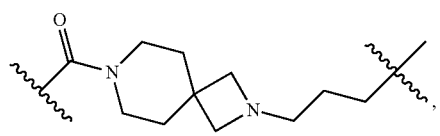 [SMILES: *CCCN1CC2(CCN(C(*)=O)CC2)C1] (473)
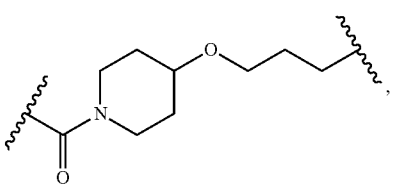 [SMILES: *CCCOC1CCN(C(*)=O)CC1] (474)

TABLE B-continued
Exemplified Linkers (L)
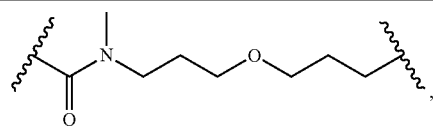 (475)
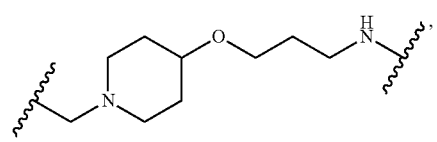 [SMILES: *CN1CCC(OCCCN*)CC1] (475)
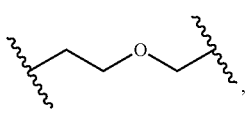 [SMILES: *CCOC*] (476)
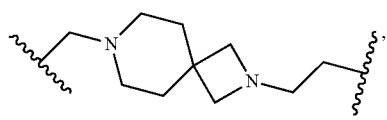 [SMILES: *CCN1CC2(CCN(C*)CC2)C1] (477)
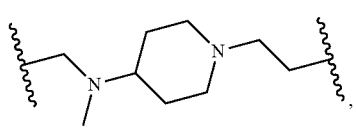 [SMILES: *CCN1CCC(N(C)C*)CC1] (478)
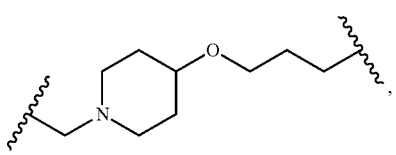 [SMILES: *CCCOC1CCN(C*)CC1] (479)
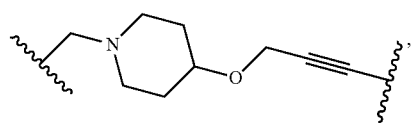 [SMILES: *C#CCOC1CCN(C*)CC1] (480)
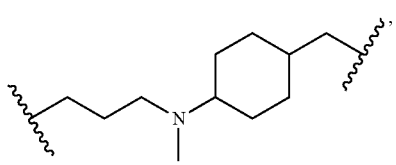 [SMILES: *CCCN(C)C1CCC(C*)CC1] (481)
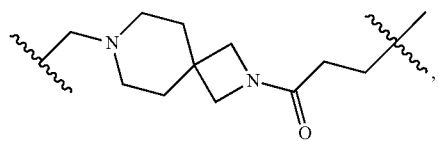 [SMILES: *CCC(=O)N1CC2(CCN(C*)CC2)C1] (482)
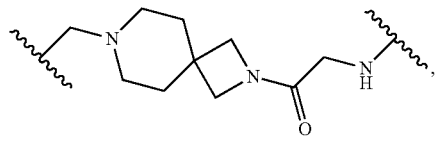 [SMILES: *CN1CCC2(CC1)CN(C(=O)CN*)C2] (483)
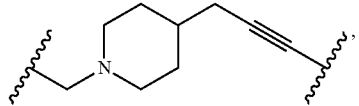 [SMILES: *C#CCC1CCN(C*)CC1] (484)

TABLE B-continued
Exemplified Linkers (L)
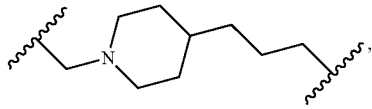 [SMILES: *CCCC1CCN(C*)CC1] (485)
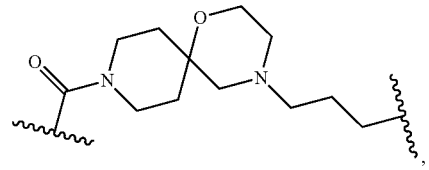 [SMILES: *CCCN1CCOC2(CCN(C(*)=O)CC2)C1] (486)
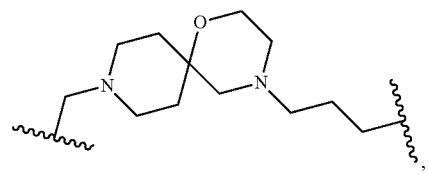 [SMILES: *CCCN1CCOC2(CCN(C*)CC2)C1] (487)
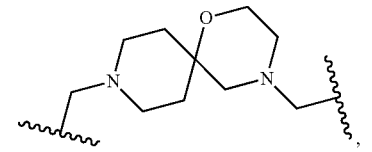 [SMILES: *CN1CCC2(CC1)CN(C*)CCO2] (488)
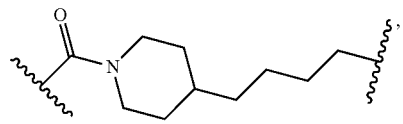 [SMILES: *CCCCC1CCN(C(*)=O)CC1] (489)
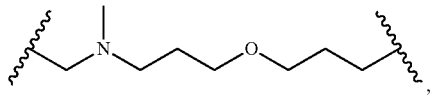 [SMILES: *CCCOCCCN(C)C*] (490)
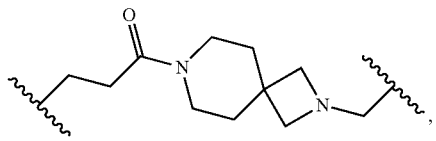 [SMILES: *CCC(=O)N1CCC2(CC1)CN(C*)C2] (491)
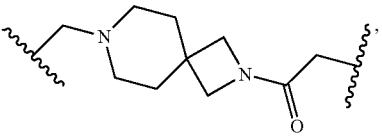 [SMILES: *CC(=O)N1CC2(CCN(C*)CC2)C1] (492)
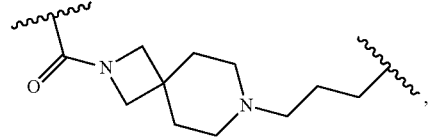 [SMILES: *CCCN1CCC2(CC1)CN(C(*)=O)C2] (493)
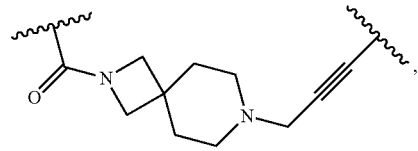 [SMILES: *C#CCN1CCC2(CC1)CN(C(*)=O)C2] (494)

TABLE B-continued
Exemplified Linkers (L)
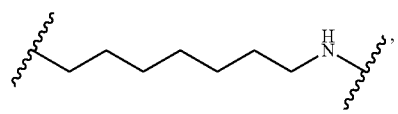 [SMILES: *CCCCCCCN*]
(495)
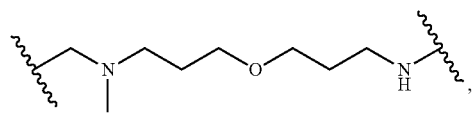 [SMILES: *CN(C)CCCOCCCN*]
(496)
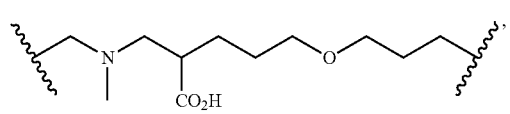 [SMILES: *CCCOCCCC(CN(C)C*)C(=O)O]
(497)
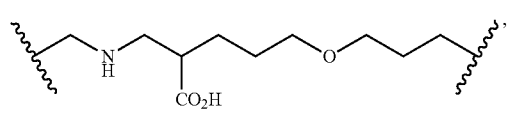 [SMILES: *CCCOCCCC(CNC*)C(=O)O]
(498)
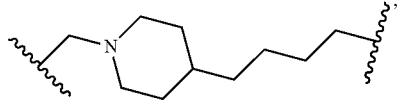 [SMILES: *CCCCC1CCN(C*)CC1]
(499)
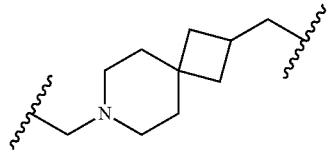
(500)
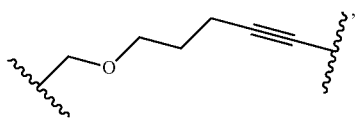 [SMILES: *C#CCCCOC*]
(501)
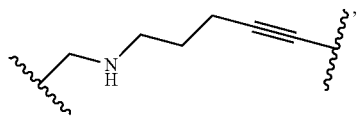 [SMILES: *C#CCCCNC*]
(502)
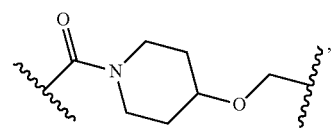 [SMILES: *COC1CCN(C(*)=O)CC1]
(503)
(504)
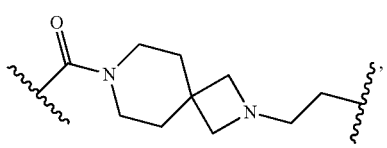 [SMILES: *CCN1CC2(CCN(C(*)=O)CC2)C1]
(505)

TABLE B-continued

Exemplified Linkers (L)

(506)

(507)

(508)

(509)

(510)

(511)

(512)

(513)

(514)

(515)

(516)

(517)

TABLE B-continued
Exemplified Linkers (L)
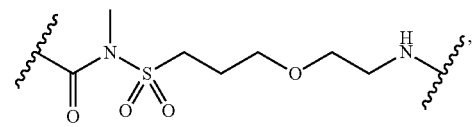 [SMILES: *NCCOCCCS(=O)(=O)N(C)C(*)=O] (518)
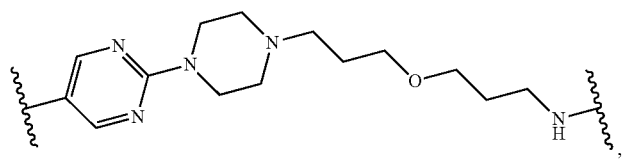 [SMILES: *NCCCOCCCN1CCN(c2ncc(*)cn2)CC1] (519)
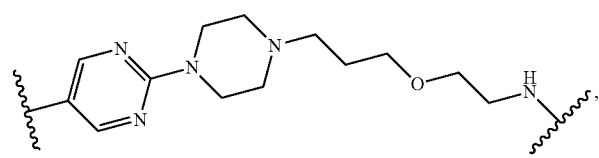 [SMILES: *NCCOCCCN1CCN(c2ncc(*)cn2)CC1] (520)
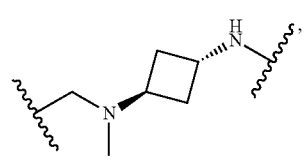 [SMILES: *CN(C)[C@H]1C[C@H](N*)C1] (521)
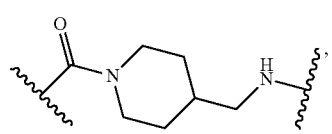 [SMILES: *NCC1CCN(C(*)=O)CC1] (522)
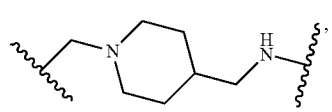 [SMILES: *CN1CCC(CN*)CC1] (523)
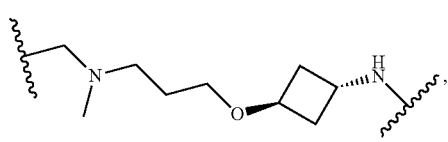 [SMILES: *CN(C)CCCO[C@H]1C[C@H](N*)C1] (524)
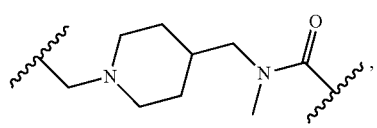 [SMILES: *CN1CCC(CN(C)C(*)=O)CC1] (525)
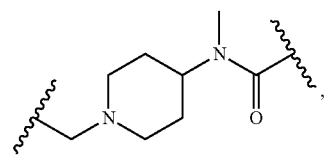 [SMILES: *CN1CCC(N(C)C(*)=O)CC1] (526)
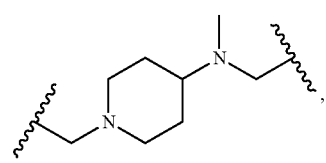 [SMILES: *CN1CCC(N(C)C*)CC1] (527)

TABLE B-continued
Exemplified Linkers (L)
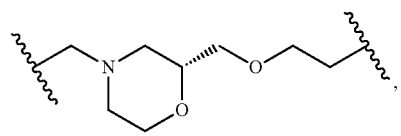 [SMILES: *CCOC[C@H]1CN(C*)CCO1] (528)
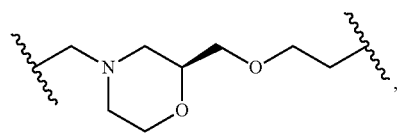 [SMILES: *CCOC[C@@H]1CN(C*)CCO1] (529)
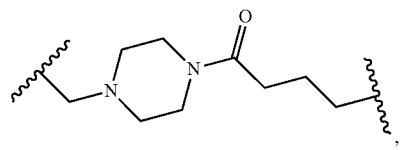 [SMILES: *CCCC(=O)N1CCN(C*)CC1] (530)
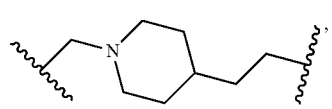 [SMILES: *CCC1CCN(C*)CC1] (531)
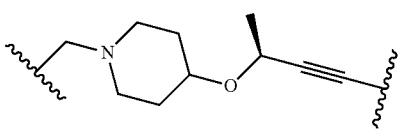 (532)
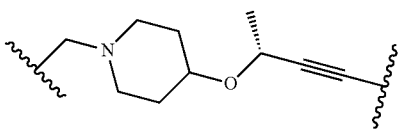 (533)
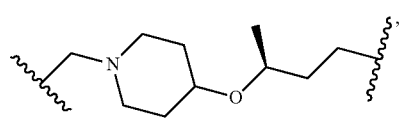 [SMILES: *CC[C@H](C)OC1CCN(C*)CC1] (534)
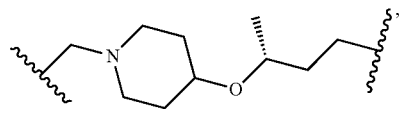 [SMILES: *CC[C@@H](C)OC1CCN(C*)CC1] (535)
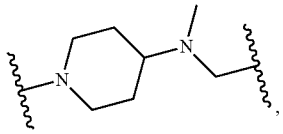 [SMILES: *CN(C)C1CCN(*)CC1] (536)
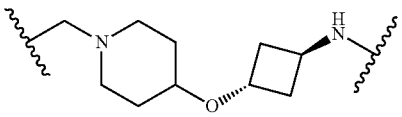 (537)
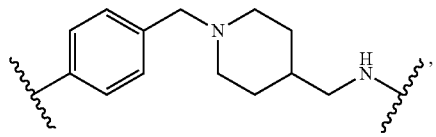 [SMILES: *NCC1CCN(Cc2ccc(*)cc2)CC1] (538)

TABLE B-continued
Exemplified Linkers (L)
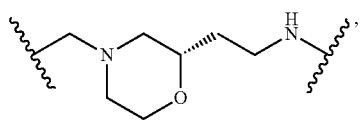 [SMILES: *CN1CCO[C@@H](CCN*)C1] (539)
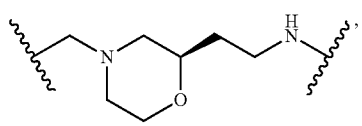 [SMILES: *CN1CCO[C@H](CCN*)C1] (540)
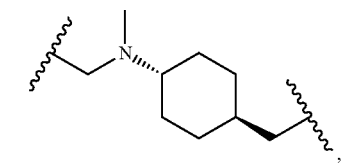 [SMILES: *CN(C)[C@H]1CC[C@H](C*)CC1] (541)
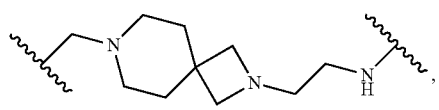 [SMILES: *CN1CCC2(CC1)CN(CCN*)C2] (542)
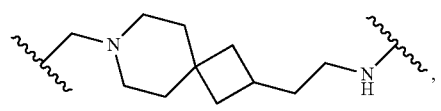 [SMILES: *CN1CCC2(CC1)CC(CCN*)C2] (543)
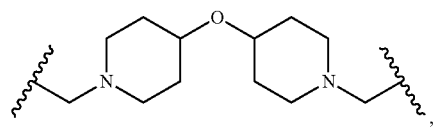 [SMILES: *CN1CCC(OC2CCN(C*)CC2)CC1] (544)
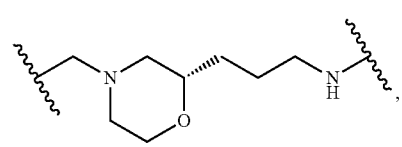 [SMILES: *CN1CCO[C@@H](CCCN*)C1] (545)
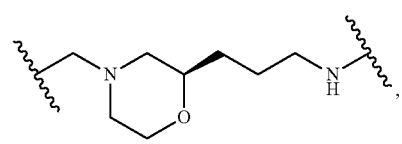 [SMILES: *CN1CCO[C@H](CCCN*)C1] (546)
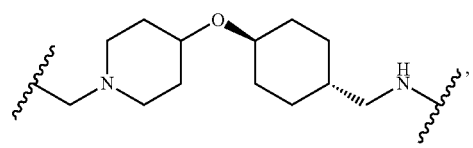 [SMILES: *CN1CCC(O[C@H]2CC[C@H](CN*)CC2)CC1] (547)
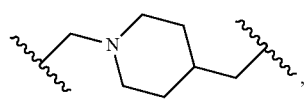 [SMILES: *CC1CCN(C*)CC1] (548)
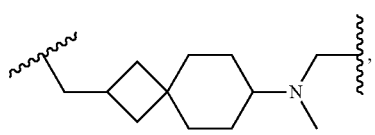 [SMILES: *CC1CC2(CCC(N(C)C*)CC2)C1] (549)

TABLE B-continued
Exemplified Linkers (L)
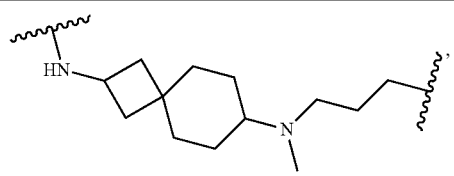
(550)
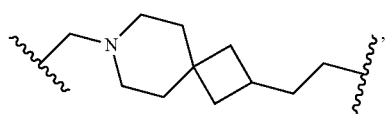
(551)
(552)
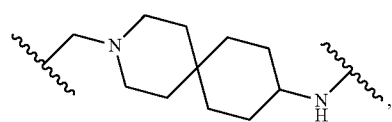 [SMILES: *CN1CCC2(CCC(N*)CC2)CC1]
(553)
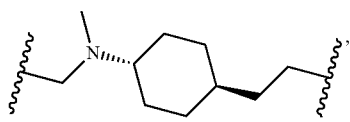 [SMILES: *CC[C@H]1CC[C@H](N(C)C*)CC1]
(554)
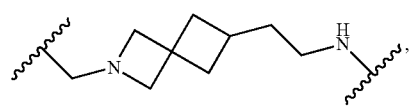 [SMILES: *CN1CC2(CC(CCN*)C2)C1]
(555)
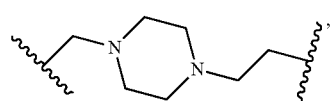 [SMILES: *CCN1CCN(C*)CC1]
(556)
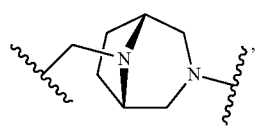 [SMILES: *CN1[C@@H]2CC[C@H]1CN(*)C2]
(557)
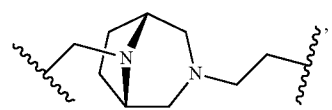 [SMILES: *CCN1C[C@H]2CC[C@@H](C1)N2C*]
(558)
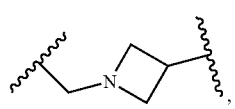 [SMILES: *CN1CC(*)C1]
(559)
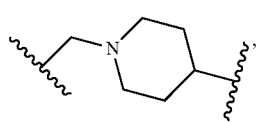 [SMILES: *CN1CCC(*)CC1]
(560)
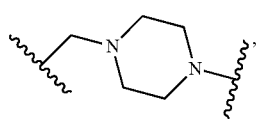 [SMILES: *CN1CCN(*)CC1]
(561)

TABLE B-continued

Exemplified Linkers (L)

TABLE B-continued
Exemplified Linkers (L)
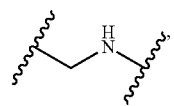 (574)
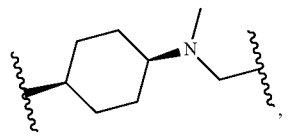 [SMILES: *CN(C)[C@H]1CC[C@@H](*)CC1] (575)
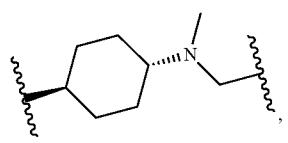 [SMILES: *CN(C)[C@H]1CC[C@H](*)CC1] (576)
 (577)
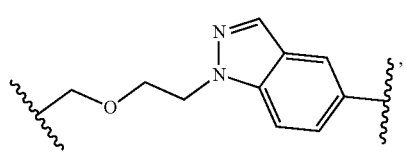 [SMILES: *COCCn1ncc2cc(*)ccc21] (578)
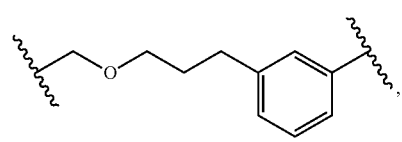 [SMILES: *COCCCc1cccc(*)c1] (579)
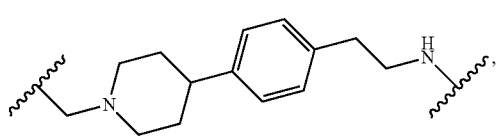 [SMILES: *CN1CCC(c2ccc(CCN*)cc2)CC1] (580)
 (581)
 (582)
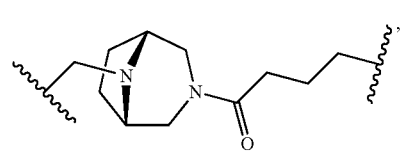 [SMILES: *CCCC(=O)N1C[C@H]2CC[C@@H](C1)N2C*] (583)
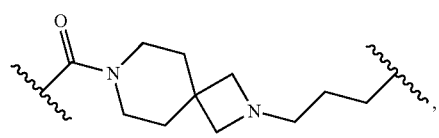 [SMILES: *CCCN1CC2(CCN(C(*)=O)CC2)C1] (584)

TABLE B-continued
Exemplified Linkers (L)
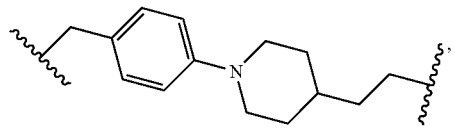 [SMILES: *CCC1CCN(c2ccc(C*)cc2)CC1] (585)
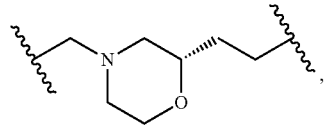 [SMILES: *CC[C@H]1CN(C*)CCO1] (586)
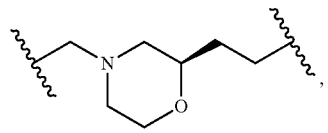 [SMILES: *CC[C@@H]1CN(C*)CCO1] (587)
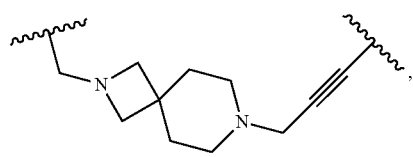 [SMILES: *C#CCN1CCC2(CC1)CN(C*)C2] (588)
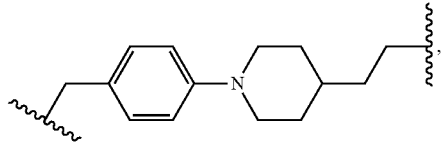 [SMILES: *CCC1CCN(c2ccc(C*)cc2)CC1] (589)
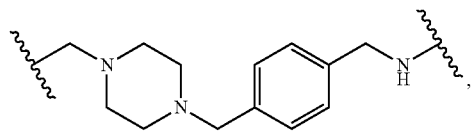 [SMILES: *CN1CCN(Cc2ccc(CN*)cc2)CC1] (590)
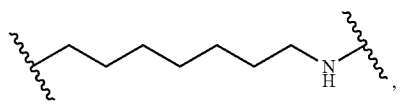 [SMILES: *CCCCCCCN*] (591)
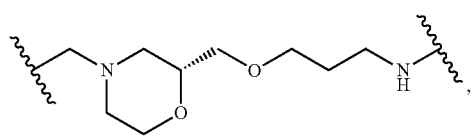 [SMILES: *CN1CCO[C@@H](COCCCN*)C1] (592)
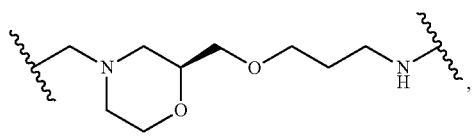 [SMILES: *CN1CCO[C@H](COCCCN*)C1] (593)
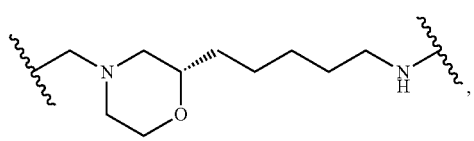 [SMILES: *CN1CCO[C@@H](CCCCCN*)C1] (594)
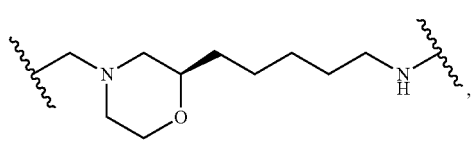 [SMILES: *CN1CCO[C@H](CCCCCN*)C1] (595)

TABLE B-continued
Exemplified Linkers (L)
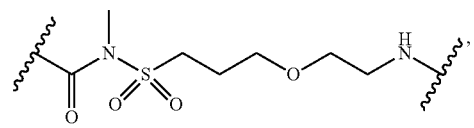 [SMILES: *NCCOCCCS(=O)(=O)N(C)C(*)=O] (596)
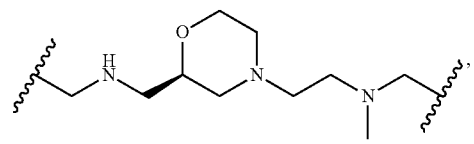 [SMILES: *CNC[C@@H]1CN(CCN(C)C*)CCO1] (597)
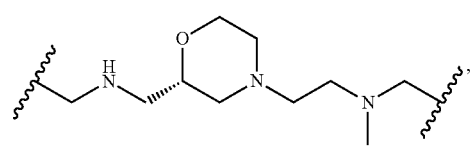 [SMILES: *CNC[C@H]1CN(CCN(C)C*)CCO1] (598)
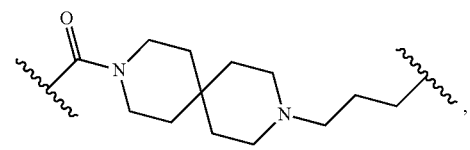 [SMILES: *CCCN1CCC2(CC1)CCN(C(*)=O)CC2] (599)
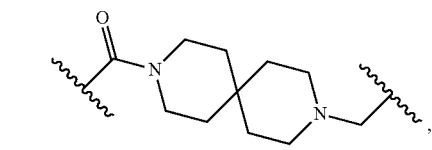 [SMILES: *CN1CCC2(CC1)CCN(C(*)=O)CC2] (600)
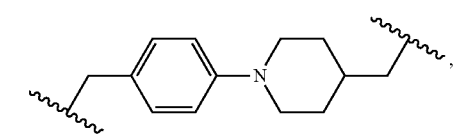 (601)
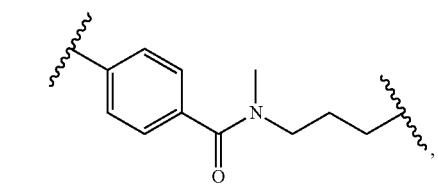 [SMILES: *CCCN(C)C(=O)c1ccc(*)cc1] (602)
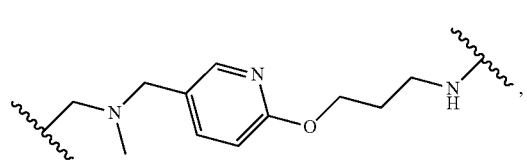 [SMILES: *CN(C)Cc1ccc(OCCCN*)nc1] (603)
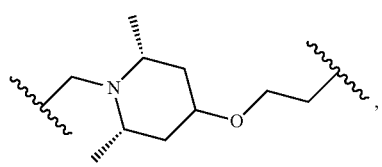 [SMILES: *CCOC1C[C@@H](C)N(C*)[C@@H](C)C1] (604)
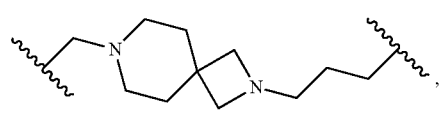 [SMILES: *CCCN1CC2(CCN(C*)CC2)C1] (605)

TABLE B-continued

Exemplified Linkers (L)

(606)

(607)

(608)

(609)

(610)

(611)

(612)

(613)

(614)

(615)

(616)

(617)

TABLE B-continued
Exemplified Linkers (L)
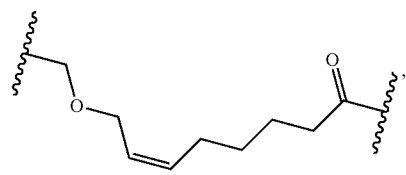 [SMILES: *COC/C=C\CCCCC(*)=O] (618)
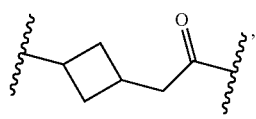 [SMILES: *C(=O)CC1CC(*)C1] (619)
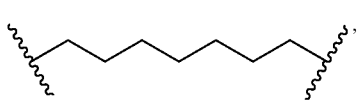 [SMILES: *CCCCCCC*] (620)
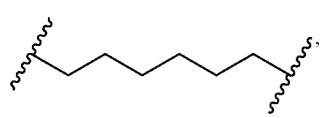 [SMILES: *CCCCCC*] (621)
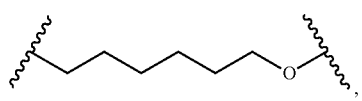 (622)
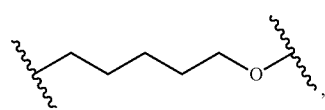 [SMILES: *CCCCCO*] (623)
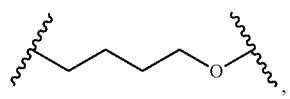 [SMILES: *CCCCO*] (624)
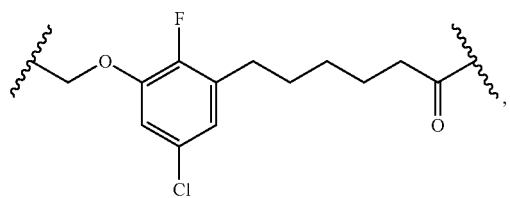 [SMILES: *COc1cc(Cl)cc(CCCCCC(*)=O)c1F] (625)
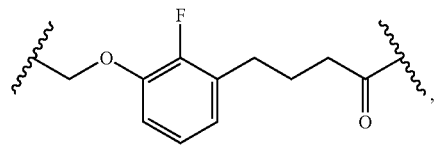 (626)
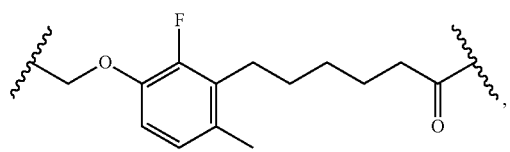 (627)
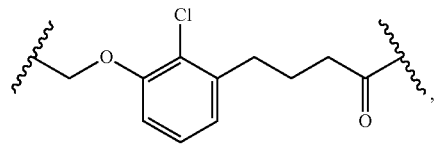 [SMILES: *COc1cccc(CCCC(*)=O)c1F] (628)

TABLE B-continued
Exemplified Linkers (L)
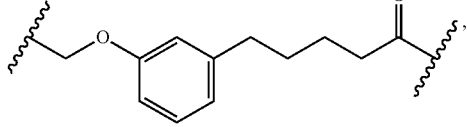 (629)
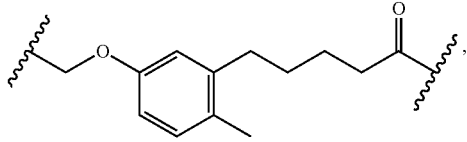 [SMILES: *COc1ccc(C)c(CCCCC(*)=O)c1] (630)
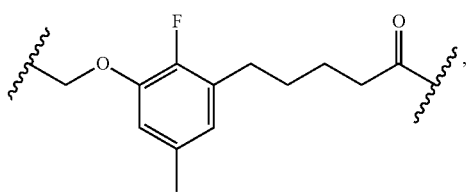 [SMILES: *COc1cc(C)cc(CCCCC(*)=O)c1F] (631)
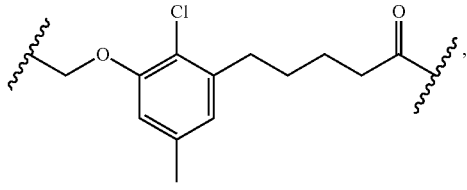 [SMILES: *COc1cc(C)cc(CCCCC(*)=O)c1Cl] (632)
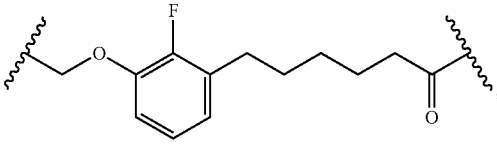 (633)
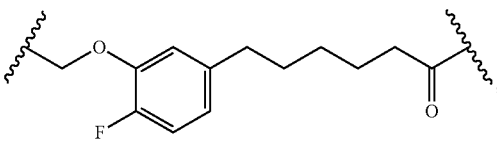 (634)
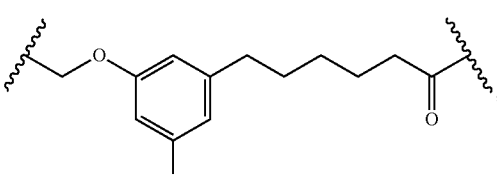 (635)
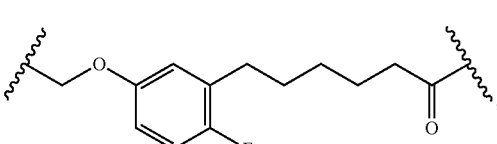 (636)
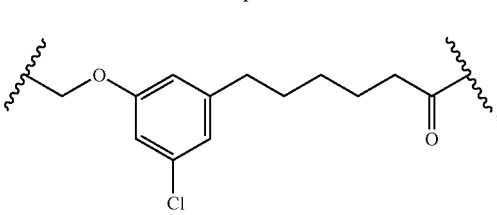 (637)

TABLE B-continued

Exemplified Linkers (L)

(638)

(639)

(640)

(641)

(642)

(643)

(644)

(645)

(646)

(647)

TABLE B-continued
Exemplified Linkers (L)
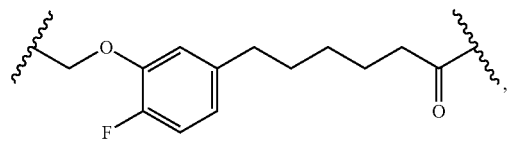 [SMILES: *COc1cc(CCCCCC(*)=O)ccc1F]
(648)
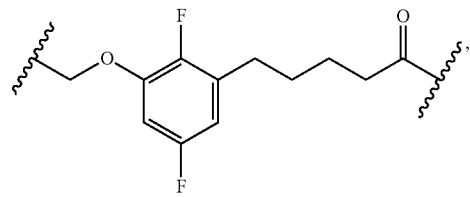 [SMILES: *COc1cc(F)cc(CCCCC(*)=O)c1F]
(649)
(650)
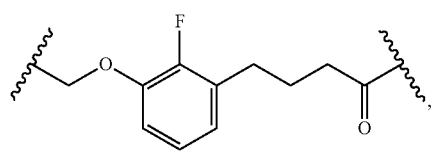 [SMILES: *COc1cccc(CCCC(*)=O)c1F]
(651)
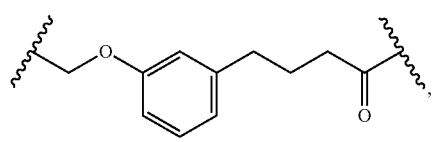 [SMILES: *COc1cccc(CCCC(*)=O)c1]
(652)
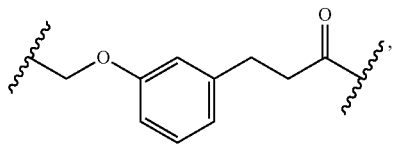 [SMILES: *COc1cccc(CCC(*)=O)c1]
(653)
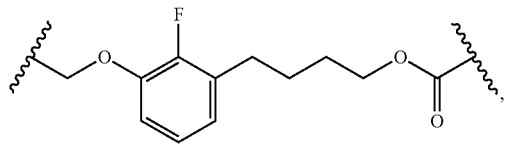 [SMILES: *COc1cccc(CCCCOC(*)=O)c1F]
(654)
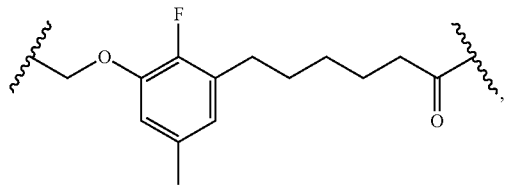 [SMILES: *COc1cc(C)cc(CCCCCC(*)=O)c1F]
(655)
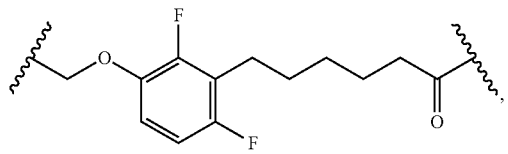 [SMILES: *COc1ccc(F)c(CCCCCC(*)=O)c1F]
(656)

TABLE B-continued
Exemplified Linkers (L)
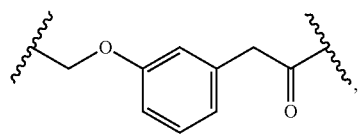 [SMILES: *COc1cccc(CC(*)=O)c1] (657)
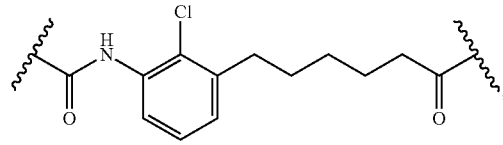 (658)
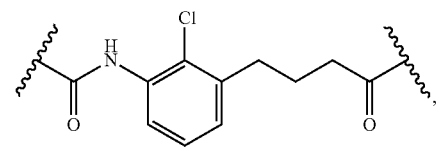 [SMILES: *C(=O)CCCc1cccc(NC(*)=O)c1Cl] (659)
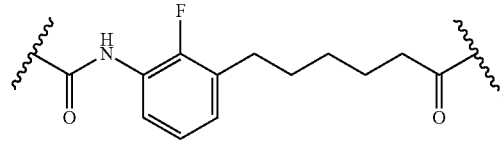 (660)
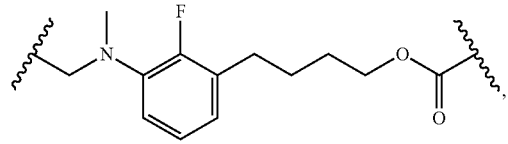 [SMILES: *CN(C)c1cccc(CCCCOC(*)=O)c1F] (661)
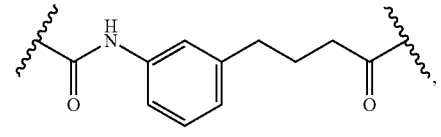 [SMILES: *C(=O)CCCc1cccc(NC(*)=O)c1] (662)
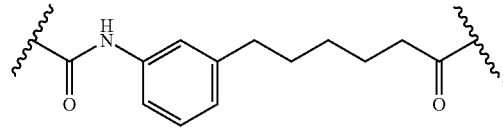 (663)
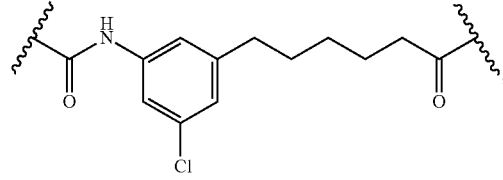 (664)
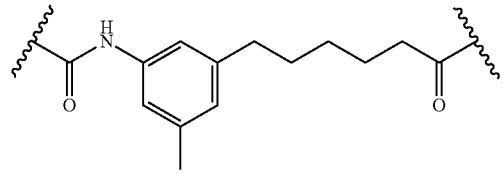 (665)
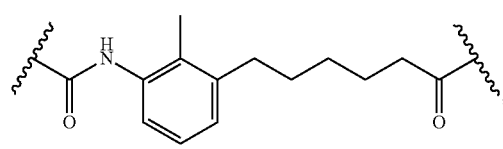 (666)

TABLE B-continued
Exemplified Linkers (L)
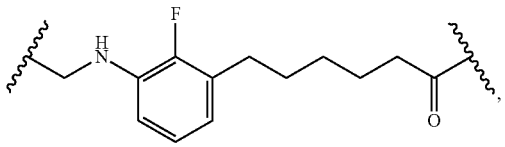 [SMILES: *CNc1cccc(CCCCCC(*)=O)c1F]
(667)
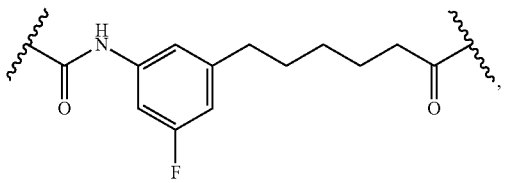 [SMILES: *C(=O)CCCCCc1cc(F)cc(NC(*)=O)c1]
(668)
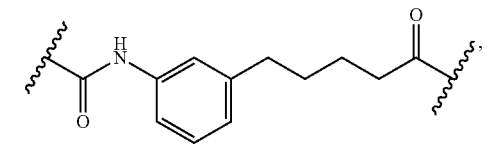 [SMILES: *C(=O)CCCCc1cccc(NC(*)=O)c1]
(669)
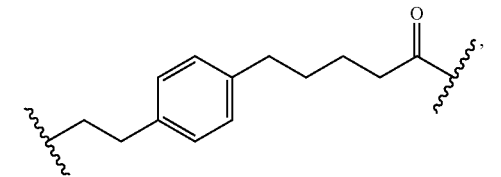 [SMILES: *CCc1ccc(CCCCC(*)=O)cc1]
(670)
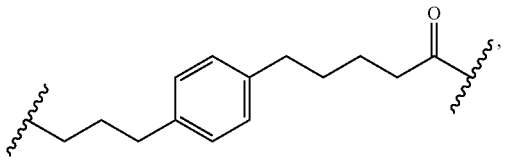 [SMILES: *CCCc1ccc(CCCCC(*)=O)cc1]
(671)
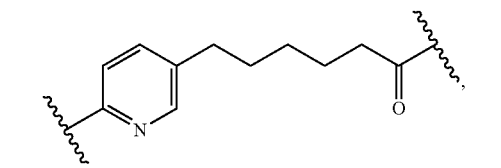 [SMILES: *C(=O)CCCCCc1ccc(*)nc1]
(672)
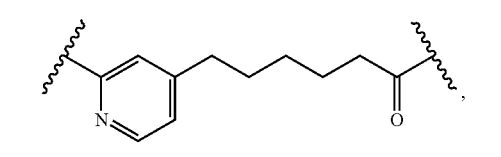 [SMILES: *C(=O)CCCCCc1ccnc(*)c1]
(673)
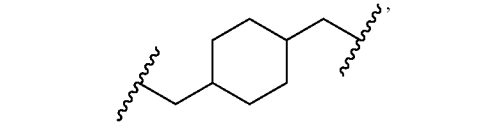 [SMILES: *CC1CCC(C*)CC1]
(674)
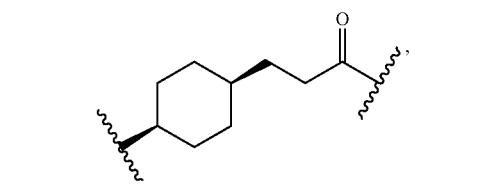 [SMILES: *C(=O)CC[C@H]1CC[C@@H](*)CC1]
(675)

TABLE B-continued

Exemplified Linkers (L)

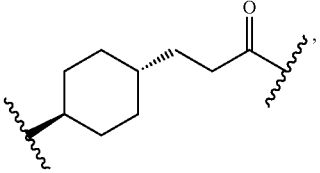 [SMILES: *C(=O)CC[C@H]1CC[C@H](*)CC1] (676)

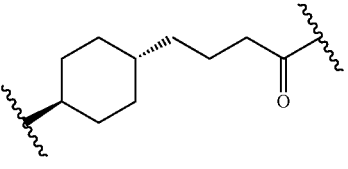 (677)

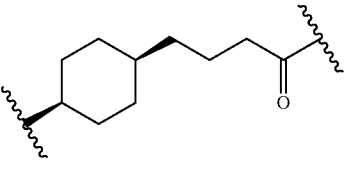 (678)

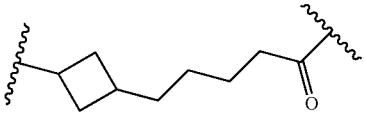 (679)

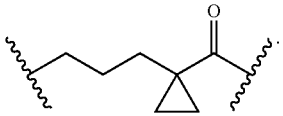 [SMILES: *CCCC1(C(*)=O)CC1] (680)

In some embodiments, the present invention provides a compound having CBM described and disclosed herein, LBM set forth in Table A above, and a linker set forth in Table B above, or a pharmaceutically acceptable salt thereof.

Exemplary compounds of the invention are set forth in Table 1, below.

TABLE 1

Exemplary Compounds

| I-# | Structure |
|---|---|
| I-1 | 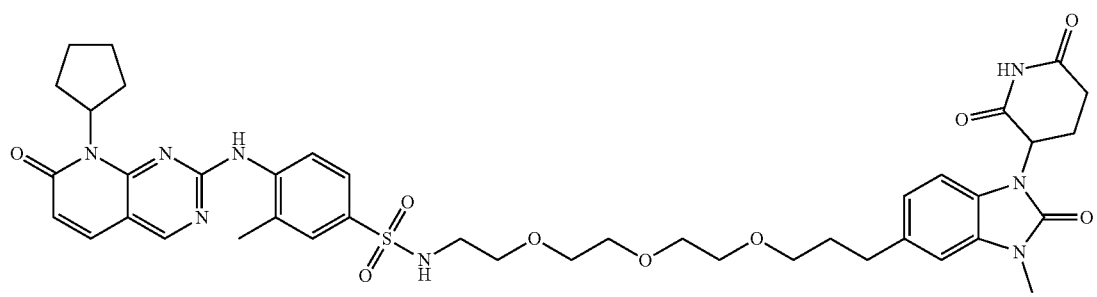 [SMILES: Cc1cc(S(=O)(=O)NCCOCCOCCOCCCc2ccc3c(c2)n(C)c(=O)n3C2CCC(=O)NC2=O)ccc1Nc1ncc2ccc(=O)n(C3CCCC3)c2n1] |

TABLE 1-continued
Exemplary Compounds
| I-# | Structure |
|---|---|
| I-2 | 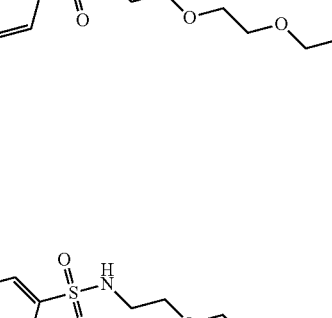 |
| I-3 | 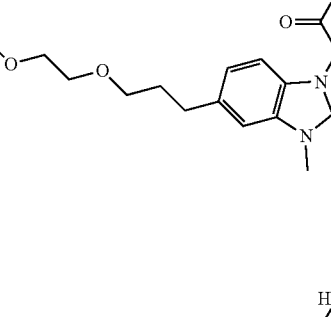 |
| I-4 | 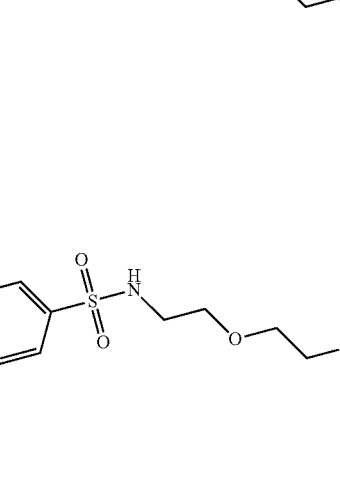 |
| I-5 | 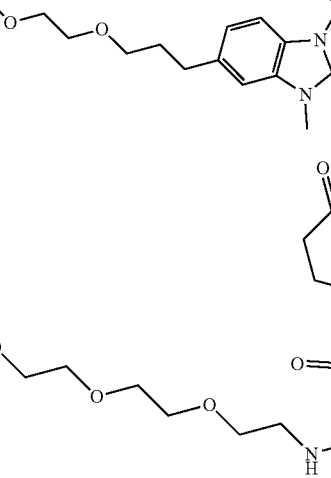 |
| I-6 | 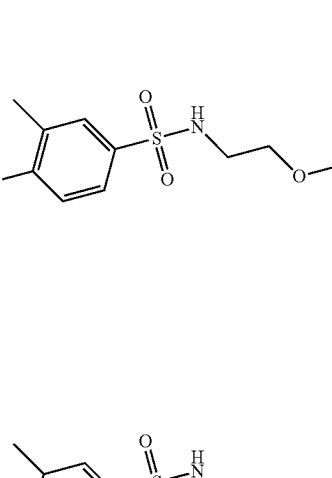 |

TABLE 1-continued

Exemplary Compounds

| I-# | Structure |
|---|---|
| I-7 | 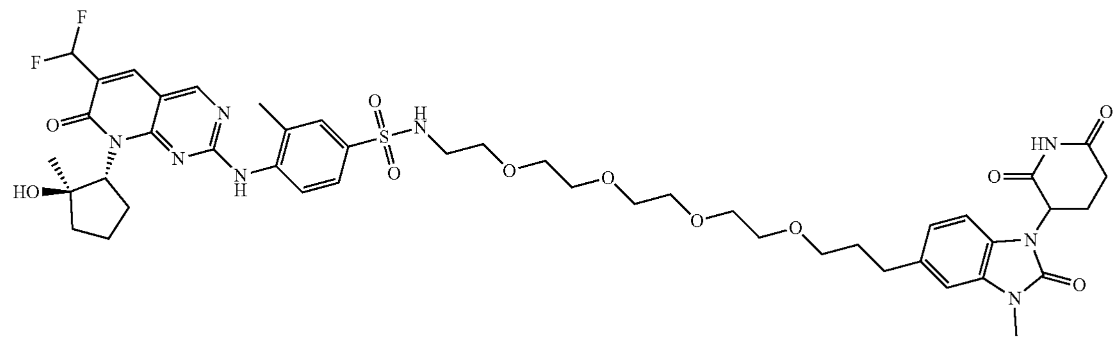 [SMILES: Cc1cc(S(=O)(=O)NCCOCCOCCOCCOCCCc2ccc3c(c2)n(C)c(=O)n3C2CCC(=O)NC2=O)ccc1Nc1ncc2cc(C(F)F)c(=O)n([C@@H]3CCC[C@@]3(C)O)c2n1] |
| I-8 | 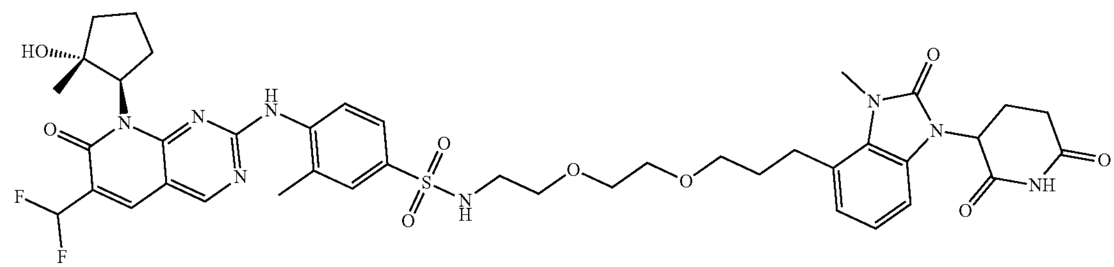 [SMILES: Cc1cc(S(=O)(=O)NCCOCCOCCCc2cccc3c2n(C)c(=O)n3C2CCC(=O)NC2=O)ccc1Nc1ncc2cc(C(F)F)c(=O)n([C@@H]3CCC[C@@]3(C)O)c2n1] |
| I-9 | 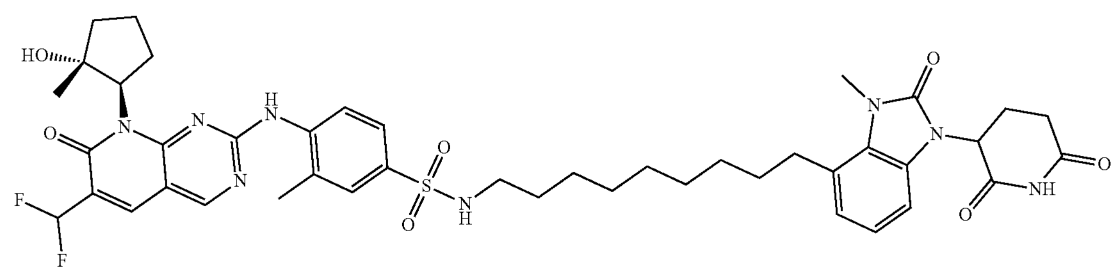 [SMILES: Cc1cc(S(=O)(=O)NCCCCCCCCCc2cccc3c2n(C)c(=O)n3C2CCC(=O)NC2=O)ccc1Nc1ncc2cc(C(F)F)c(=O)n([C@@H]3CCC[C@@]3(C)O)c2n1] |
| I-10 | 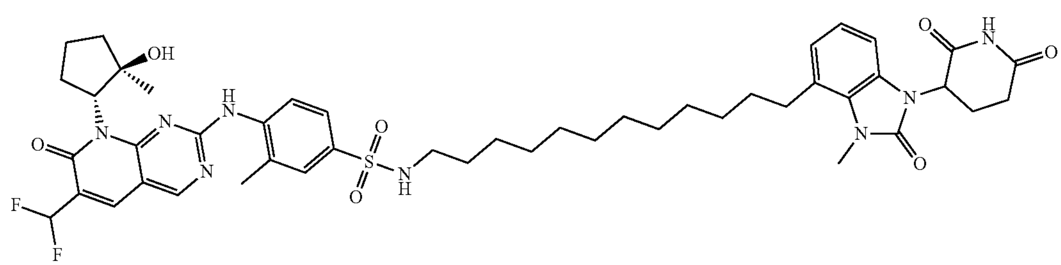 [SMILES: Cc1cc(S(=O)(=O)NCCCCCCCCCCCCc2cccc3c2n(C)c(=O)n3C2CCC(=O)NC2=O)ccc1Nc1ncc2cc(C(F)F)c(=O)n([C@@H]3CCC[C@@]3(C)O)c2n1] |
| I-11 | 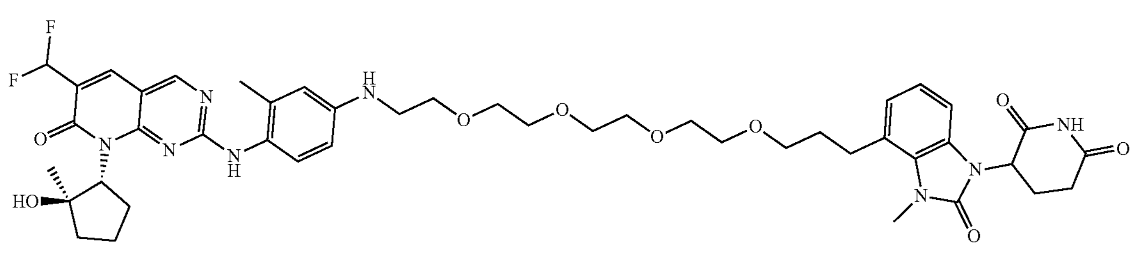 [SMILES: Cc1cc(NCCOCCOCCOCCOCCCc2cccc3c2n(C)c(=O)n3C2CCC(=O)NC2=O)ccc1Nc1ncc2cc(C(F)F)c(=O)n([C@@H]3CCC[C@@]3(C)O)c2n1] |

TABLE 1-continued

Exemplary Compounds

| I-# | Structure |
|---|---|
| I-12 | 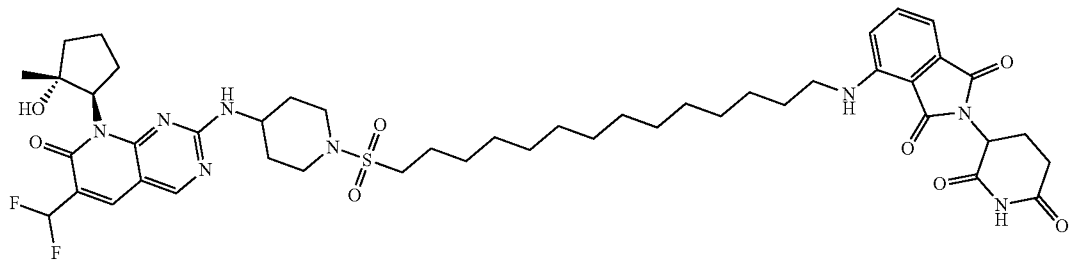 [SMILES: C[C@@]1(O)CCC[C@H]1n1c(=O)c(C(F)F)cc2cnc(NC3CCN(S(=O)(=O)CCCCCCCCCCCCCCNc4cccc5c4C(=O)N(C4CCC(=O)NC4=O)C5=O)CC3)nc21] |
| I-13 | 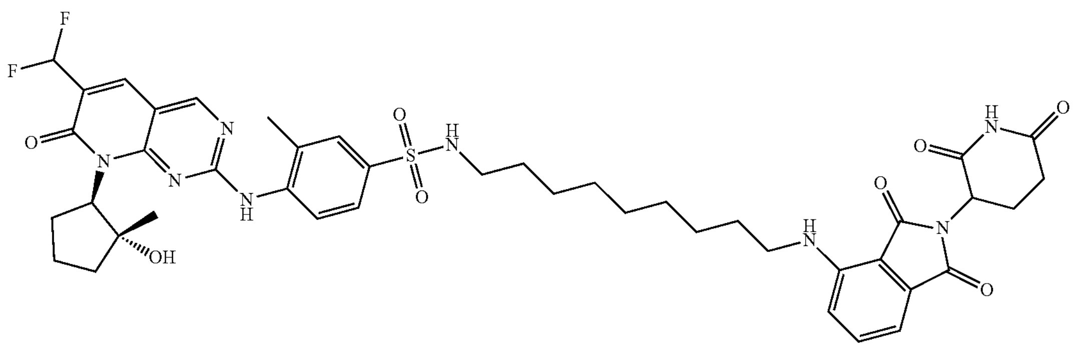 [SMILES: Cc1cc(S(=O)(=O)NCCCCCCCCCNc2cccc3c2C(=O)N(C2CCC(=O)NC2=O)C3=O)ccc1Nc1ncc2cc(C(F)F)c(=O)n([C@@H]3CCC[C@@]3(C)O)c2n1] |
| I-14 | 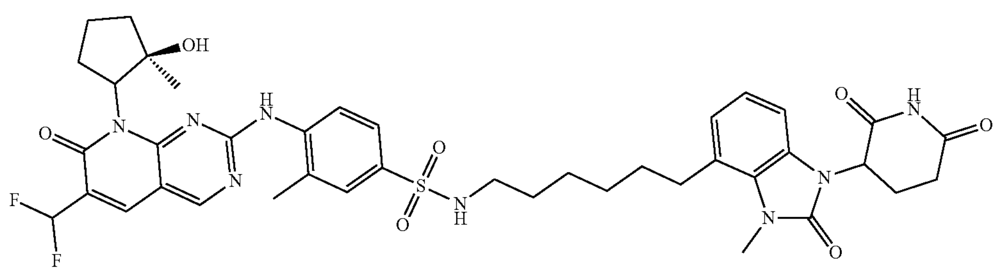 [SMILES: Cc1cc(S(=O)(=O)NCCCCCCc2cccc3c2n(C)c(=O)n3C2CCC(=O)NC2=O)ccc1Nc1ncc2cc(C(F)F)c(=O)n(C3CCC[C@@]3(C)O)c2n1] |
| I-15 | 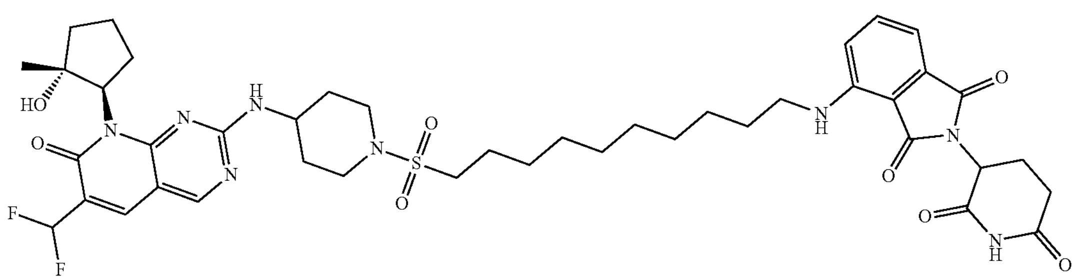 [SMILES: C[C@@]1(O)CCC[C@H]1n1c(=O)c(C(F)F)cc2cnc(NC3CCN(S(=O)(=O)CCCCCCCCCCNc4cccc5c4C(=O)N(C4CCC(=O)NC4=O)C5=O)CC3)nc21] |
| I-16 | 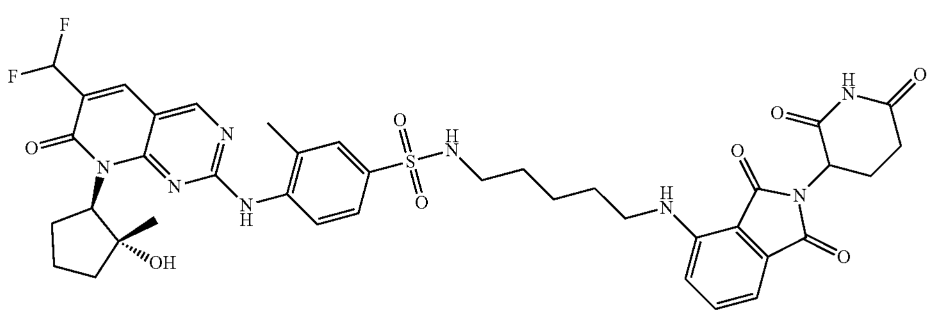 [SMILES: Cc1cc(S(=O)(=O)NCCCCCNc2cccc3c2C(=O)N(C2CCC(=O)NC2=O)C3=O)ccc1Nc1ncc2cc(C(F)F)c(=O)n([C@@H]3CCC[C@@]3(C)O)c2n1] |

TABLE 1-continued
Exemplary Compounds
| I-# | Structure |
|---|---|
| I-17 | 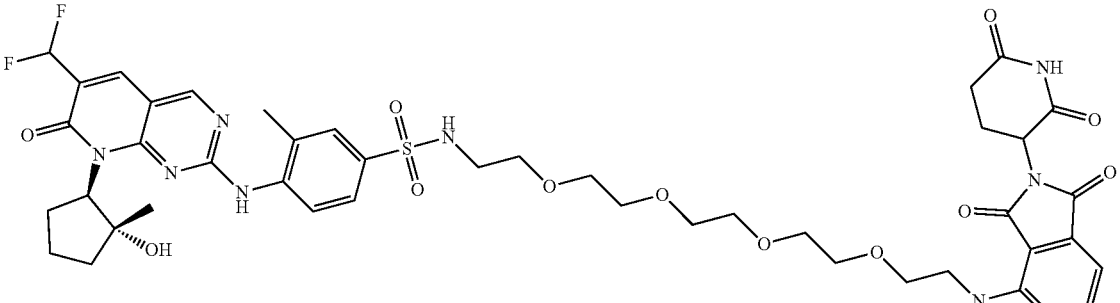 |
| I-18 | 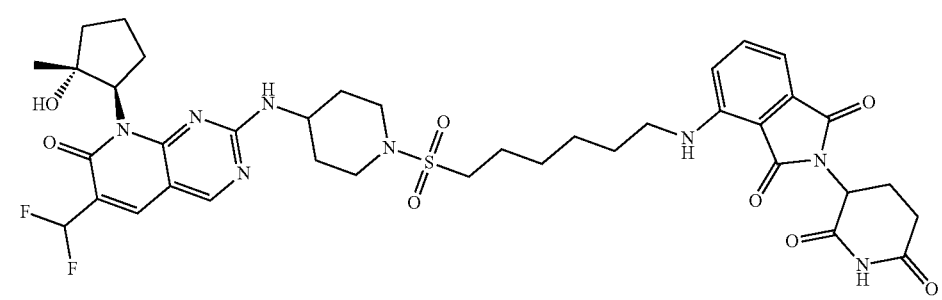 [SMILES: C[C@@]1(O)CCC[C@H]1n1c(=O)c(C(F)F)cc2cnc(NC3CCN(S(=O)(=O)CCCCCCNc4cccc5c4C(=O)N(C4CCC(=O)NC4=O)C5=O)CC3)nc21] |
| I-19 | 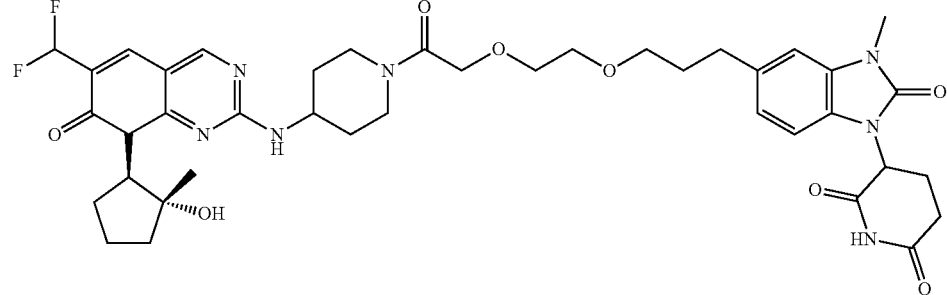 [SMILES: Cn1c(=O)n(C2CCC(=O)NC2=O)c2ccc(CCCOCCOCC(=O)N3CCC(Nc4ncc5c(n4)C([C@@H]4CCC[C@@]4(C)O)C(=O)C(C(F)F)=C5)CC3)cc21] |
| I-20 | 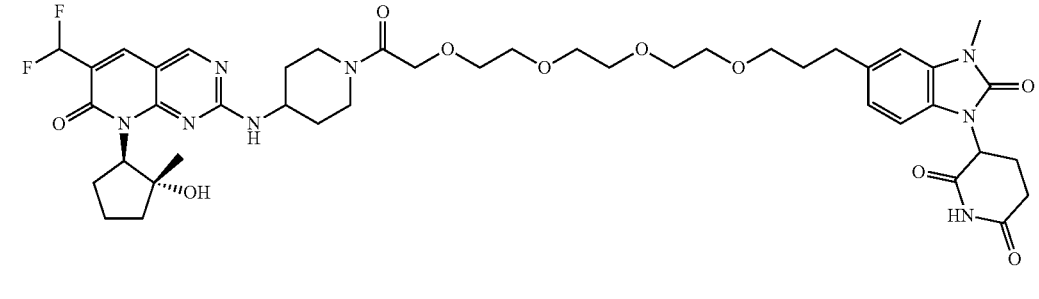 [SMILES: Cn1c(=O)n(C2CCC(=O)NC2=O)c2ccc(CCCOCCOCCOCCOCC(=O)N3CCC(Nc4ncc5cc(C(F)F)c(=O)n([C@@H]6CCC[C@@]6(C)O)c5n4)CC3)cc21] |
| I-21 | 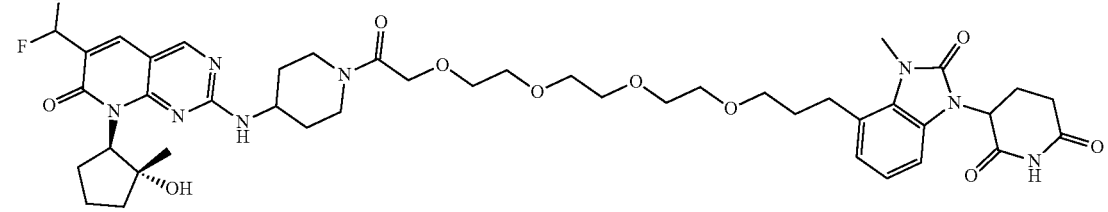 |

TABLE 1-continued

Exemplary Compounds

| I-# | Structure |
|---|---|
| I-22 | 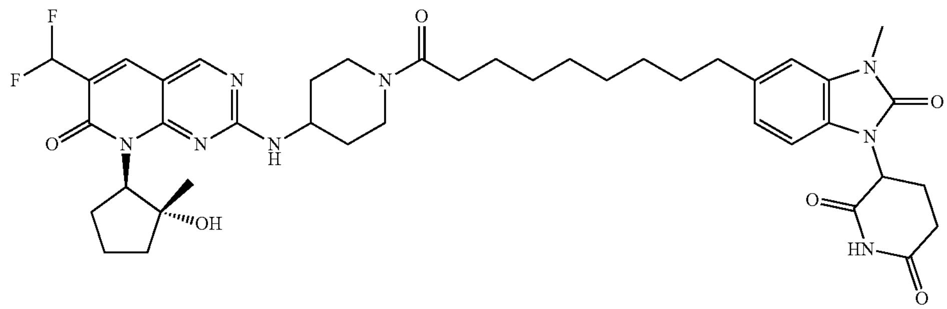 [SMILES: Cn1c(=O)n(C2CCC(=O)NC2=O)c2ccc(CCCCCCCCC(=O)N3CCC(Nc4ncc5cc(C(F)F)c(=O)n([C@@H]6CCC[C@@]6(C)O)c5n4)CC3)cc21] |
| I-23 | 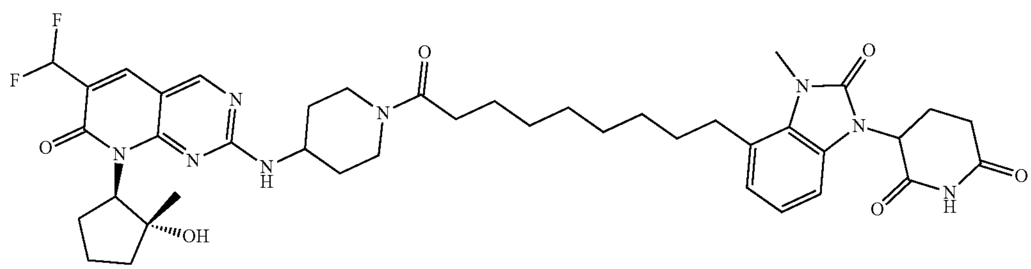 [SMILES: Cn1c(=O)n(C2CCC(=O)NC2=O)c2cccc(CCCCCCCCC(=O)N3CCC(Nc4ncc5cc(C(F)F)c(=O)n([C@@H]6CCC[C@@]6(C)O)c5n4)CC3)c21] |
| I-24 | 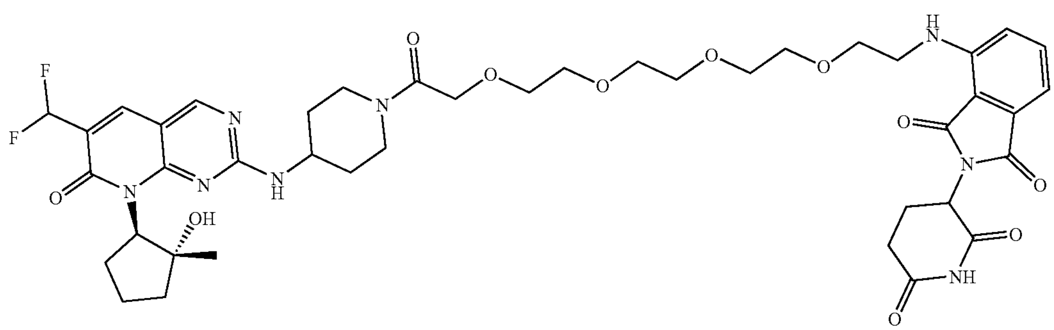 [SMILES: C[C@@]1(O)CCC[C@H]1n1c(=O)c(C(F)F)cc2cnc(NC3CCN(C(=O)COCCOCCOCCOCCNc4cccc5c4C(=O)N(C4CCC(=O)NC4=O)C5=O)CC3)nc21] |
| I-25 | 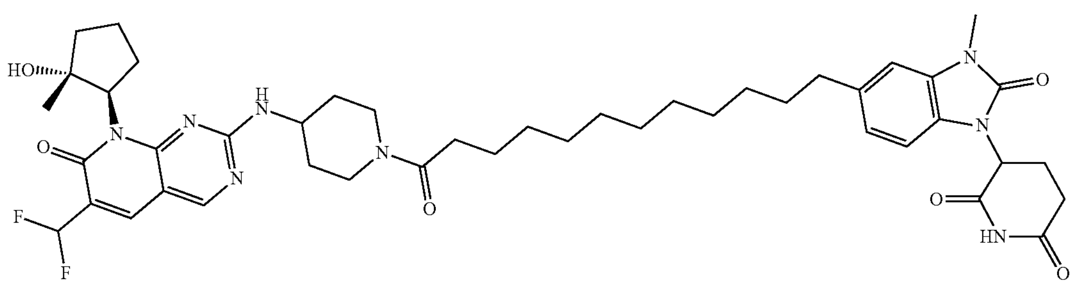 [SMILES: Cn1c(=O)n(C2CCC(=O)NC2=O)c2ccc(CCCCCCCCCCCC(=O)N3CCC(Nc4ncc5cc(C(F)F)c(=O)n([C@@H]6CCC[C@@]6(C)O)c5n4)CC3)cc21] |
| I-26 | 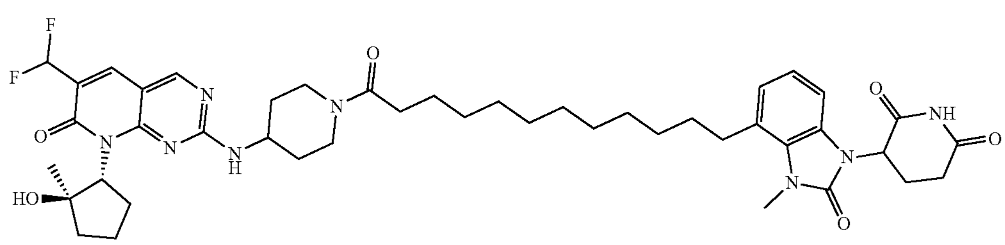 [SMILES: Cn1c(=O)n(C2CCC(=O)NC2=O)c2cccc(CCCCCCCCCCCC(=O)N3CCC(Nc4ncc5cc(C(F)F)c(=O)n([C@@H]6CCC[C@@]6(C)O)c5n4)CC3)c21] |

TABLE 1-continued
Exemplary Compounds
| I-# | Structure |
|---|---|
| I-27 | 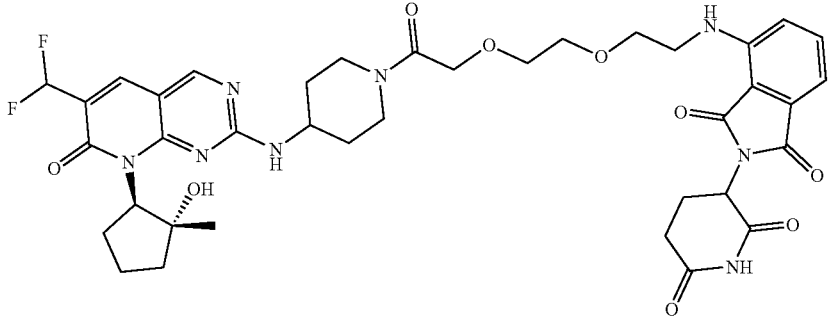 [SMILES: C[C@@]1(O)CCC[C@H]1n1c(=O)c(C(F)F)cc2cnc(NC3CCN(C(=O)COCCOCCNc4cccc5c4C(=O)N(C4CCC(=O)NC4=O)C5=O)CC3)nc21] |
| I-28 | 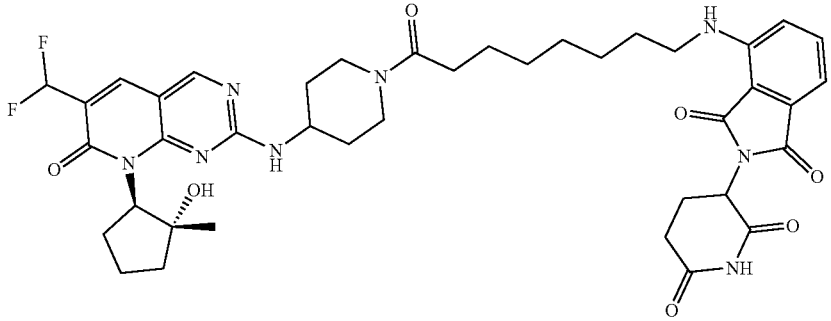 [SMILES: C[C@@]1(O)CCC[C@H]1n1c(=O)c(C(F)F)cc2cnc(NC3CCN(C(=O)CCCCCCCNc4cccc5c4C(=O)N(C4CCC(=O)NC4=O)C5=O)CC3)nc21] |
| I-29 | 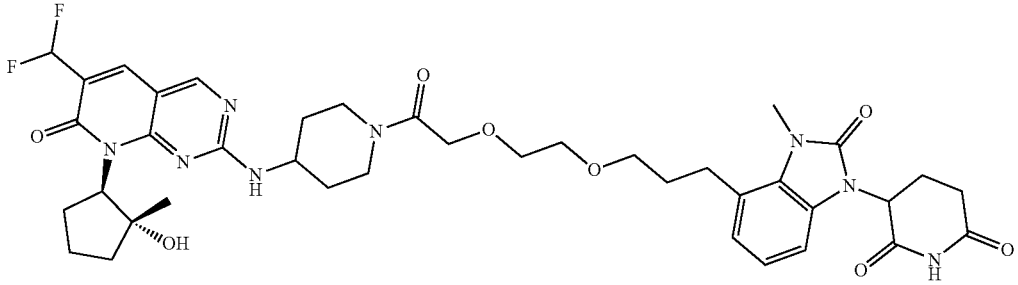 [SMILES: Cn1c(=O)n(C2CCC(=O)NC2=O)c2cccc(CCCOCCOCC(=O)N3CCC(Nc4ncc5cc(C(F)F)c(=O)n([C@@H]6CCC[C@@]6(C)O)c5n4)CC3)c21] |
| I-30 | 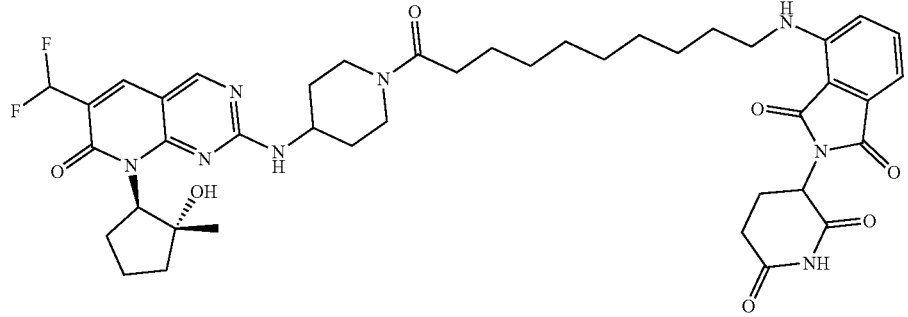 [SMILES: C[C@@]1(O)CCC[C@H]1n1c(=O)c(C(F)F)cc2cnc(NC3CCN(C(=O)CCCCCCCCCNc4cccc5c4C(=O)N(C4CCC(=O)NC4=O)C5=O)CC3)nc21] |

TABLE 1-continued

Exemplary Compounds

| I-# | Structure |
|---|---|
| I-31 | 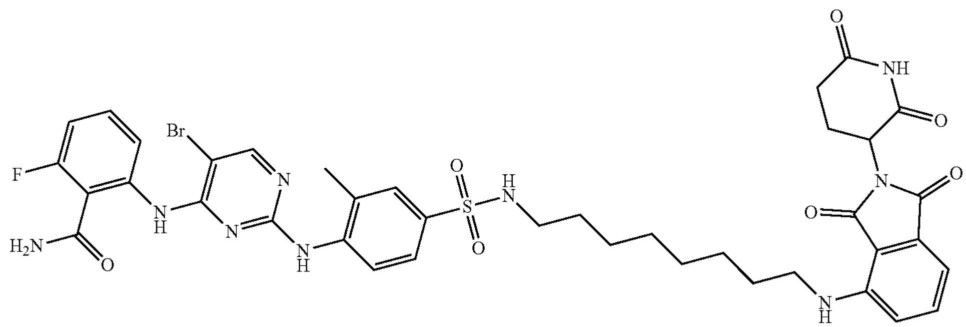 [SMILES: Cc1cc(S(=O)(=O)NCCCCCCCCNc2cccc3c2C(=O)N(C2CCC(=O)NC2=O)C3=O)ccc1Nc1ncc(Br)c(Nc2cccc(F)c2C(N)=O)n1] |
| I-32 | 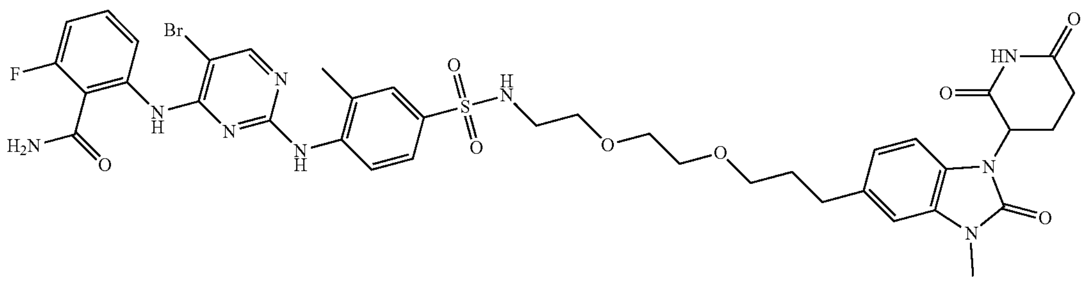 [SMILES: Cc1cc(S(=O)(=O)NCCOCCOCCCc2ccc3c(c2)n(C)c(=O)n3C2CCC(=O)NC2=O)ccc1Nc1ncc(Br)c(Nc2cccc(F)c2C(N)=O)n1] |
| I-34 | 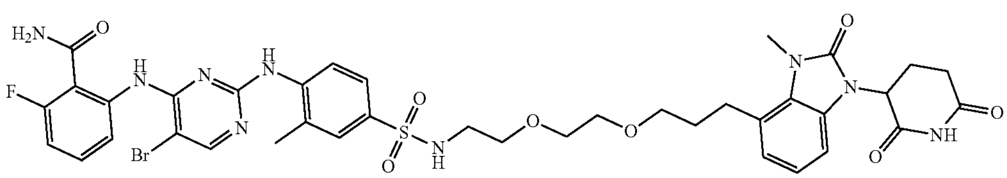 [SMILES: Cc1cc(S(=O)(=O)NCCOCCOCCCc2cccc3c2n(C)c(=O)n3C2CCC(=O)NC2=O)ccc1Nc1ncc(Br)c(Nc2cccc(F)c2C(N)=O)n1] |
| I-35 | 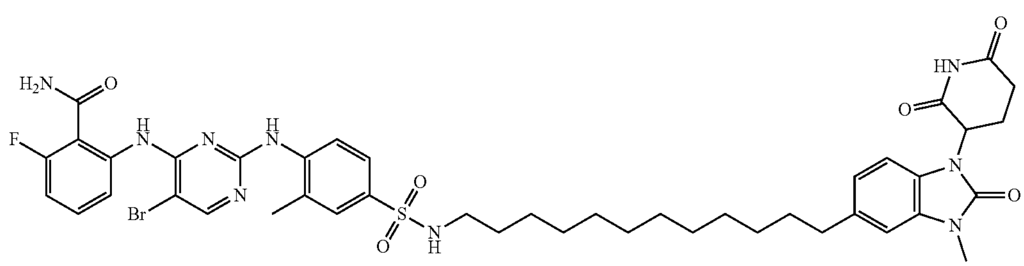 [SMILES: Cc1cc(S(=O)(=O)NCCCCCCCCCCCCc2ccc3c(c2)n(C)c(=O)n3C2CCC(=O)NC2=O)ccc1Nc1ncc(Br)c(Nc2cccc(F)c2C(N)=O)n1] |
| I-36 | 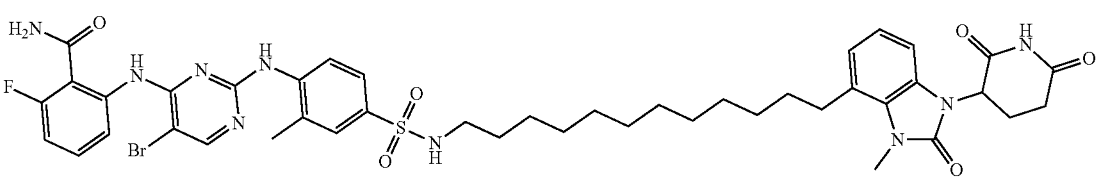 [SMILES: Cc1cc(S(=O)(=O)NCCCCCCCCCCCCc2cccc3c2n(C)c(=O)n3C2CCC(=O)NC2=O)ccc1Nc1ncc(Br)c(Nc2cccc(F)c2C(N)=O)n1] |
| I-37 | 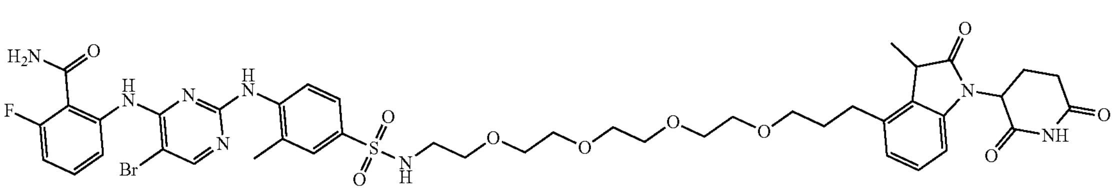 [SMILES: Cc1cc(S(=O)(=O)NCCOCCOCCOCCOCCCc2cccc3c2C(C)C(=O)N3C2CCC(=O)NC2=O)ccc1Nc1ncc(Br)c(Nc2cccc(F)c2C(N)=O)n1] |

TABLE 1-continued
Exemplary Compounds
| I-# | Structure |
|---|---|
| I-38 | 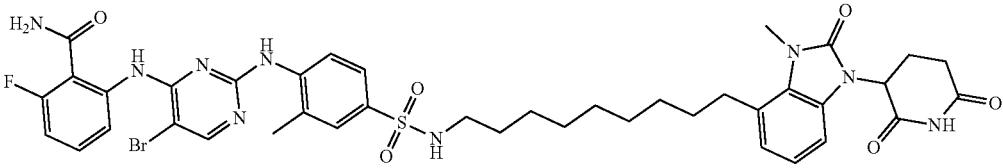 [SMILES: Cc1cc(S(=O)(=O)NCCCCCCCCCc2cccc3c2n(C)c(=O)n3C2CCC(=O)NC2=O)ccc1Nc1ncc(Br)c(Nc2cccc(F)c2C(N)=O)n1] |
| I-39 | 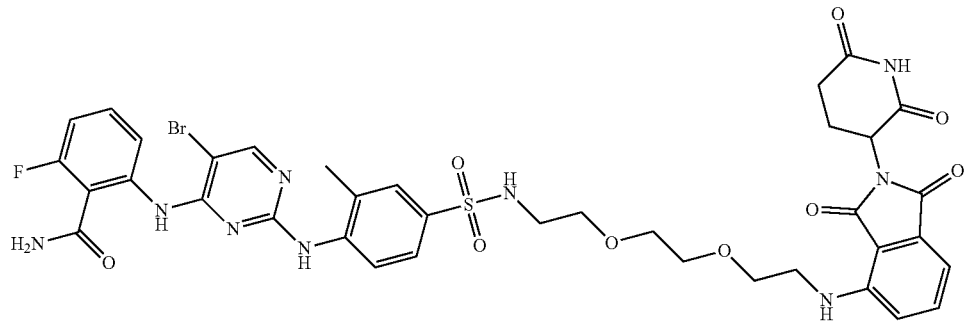 [SMILES: Cc1cc(S(=O)(=O)NCCOCCOCCNc2cccc3c2C(=O)N(C2CCC(=O)NC2=O)C3=O)ccc1Nc1ncc(Br)c(Nc2cccc(F)c2C(N)=O)n1] |
| I-40 | 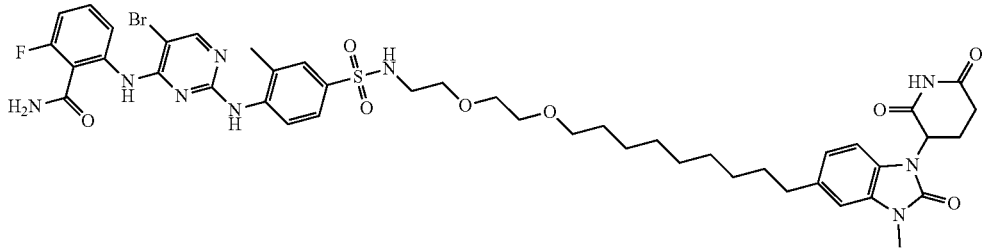 [SMILES: Cc1cc(S(=O)(=O)NCCOCCOCCCCCCCCCc2ccc3c(c2)n(C)c(=O)n3C2CCC(=O)NC2=O)ccc1Nc1ncc(Br)c(Nc2cccc(F)c2C(N)=O)n1] |
| I-41 | 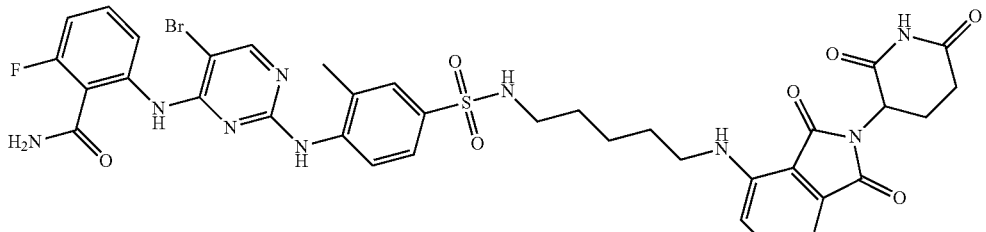 |
| I-42 | 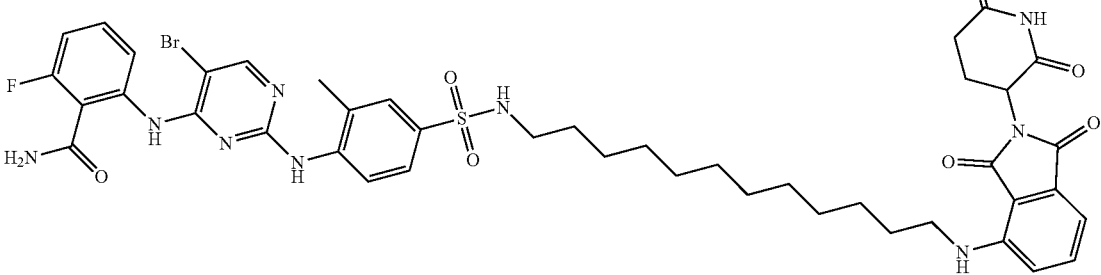 |

TABLE 1-continued

Exemplary Compounds

| I-# | Structure |
|---|---|
| I-43 | 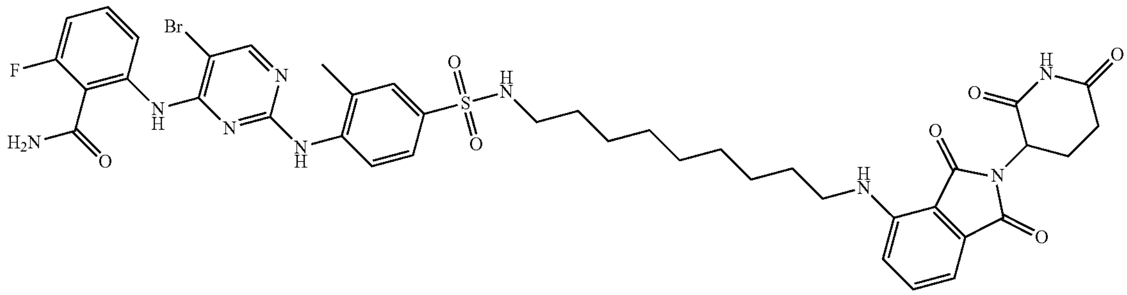 [SMILES: Cc1cc(S(=O)(=O)NCCCCCCCCCNc2cccc3c2C(=O)N(C2CCC(=O)NC2=O)C3=O)ccc1Nc1ncc(Br)c(Nc2cccc(F)c2C(N)=O)n1] |
| I-44 | 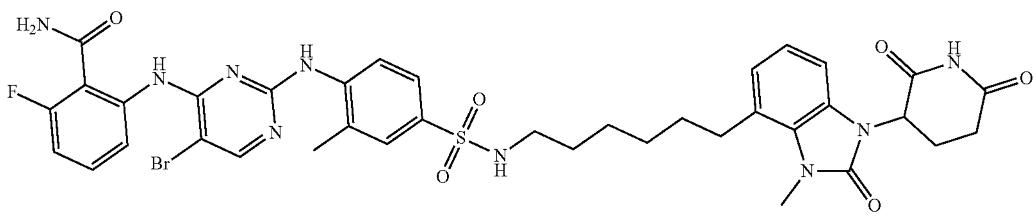 [SMILES: Cc1cc(S(=O)(=O)NCCCCCCc2cccc3c2n(C)c(=O)n3C2CCC(=O)NC2=O)ccc1Nc1ncc(Br)c(Nc2cccc(F)c2C(N)=O)n1] |
| I-45 | 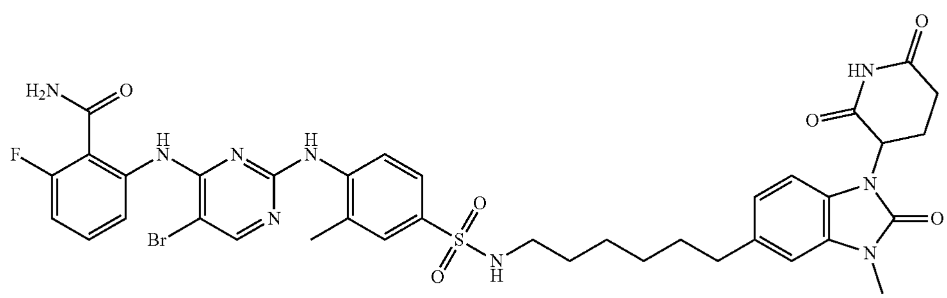 [SMILES: Cc1cc(S(=O)(=O)NCCCCCCc2ccc3c(c2)n(C)c(=O)n3C2CCC(=O)NC2=O)ccc1Nc1ncc(Br)c(Nc2cccc(F)c2C(N)=O)n1] |
| I-46 | 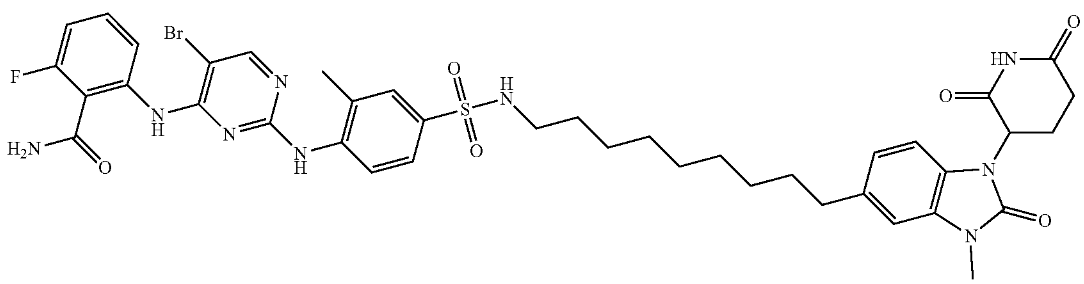 [SMILES: Cc1cc(S(=O)(=O)NCCCCCCCCCc2ccc3c(c2)n(C)c(=O)n3C2CCC(=O)NC2=O)ccc1Nc1ncc(Br)c(Nc2cccc(F)c2C(N)=O)n1] |
| I-47 | 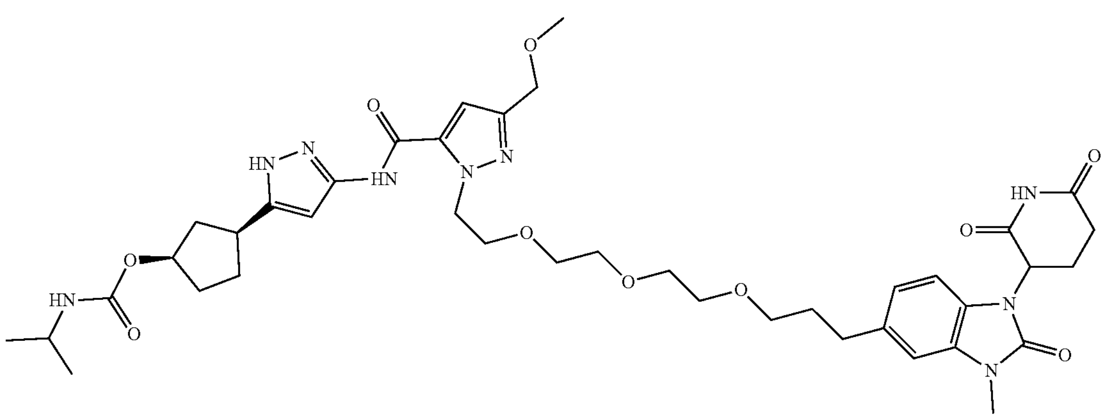 [SMILES: COCc1cc(C(=O)Nc2cc([C@H]3CC[C@@H](OC(=O)NC(C)C)C3)[nH]n2)n(CCOCCOCCOCCCc2ccc3c(c2)n(C)c(=O)n3C2CCC(=O)NC2=O)n1] |

393

TABLE 1-continued

Exemplary Compounds

| I-# | Structure |
|---|---|
| I-48 | 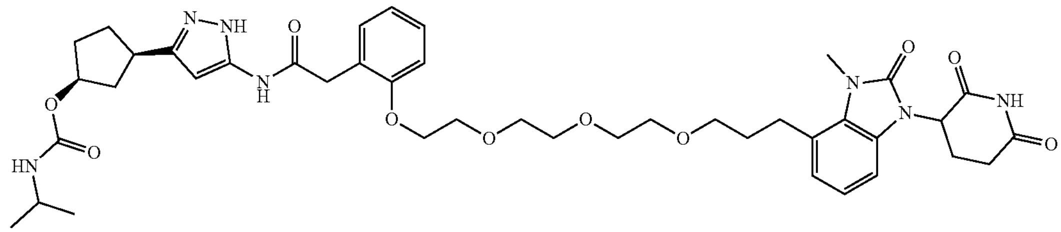 [SMILES: CC(C)NC(=O)O[C@H]1CC[C@@H](c2cc(NC(=O)Cc3ccccc3OCCOCCOCCOCCCc3cccc4c3n(C)c(=O)n4C3CCC(=O)NC3=O)[nH]n2)C1] |
| I-49 | 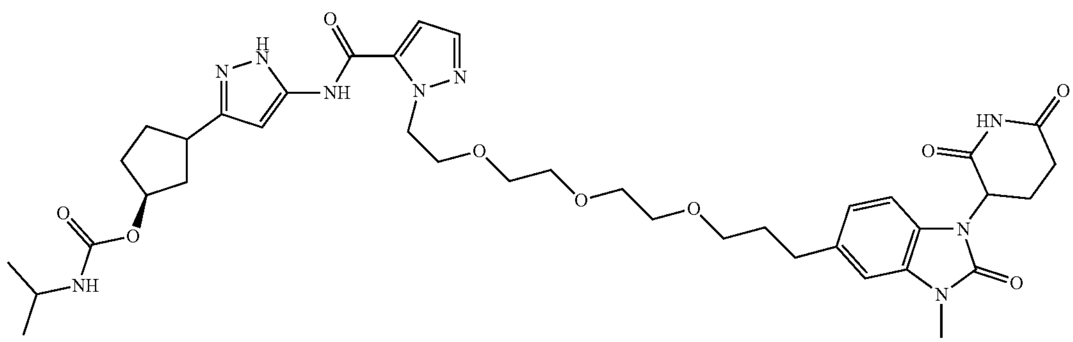 [SMILES: CC(C)NC(=O)O[C@H]1CCC(c2cc(NC(=O)c3ccnn3CCOCCOCCOCCCc3ccc4c(c3)n(C)c(=O)n4C3CCC(=O)NC3=O)[nH]n2)C1] |
| I-50 | 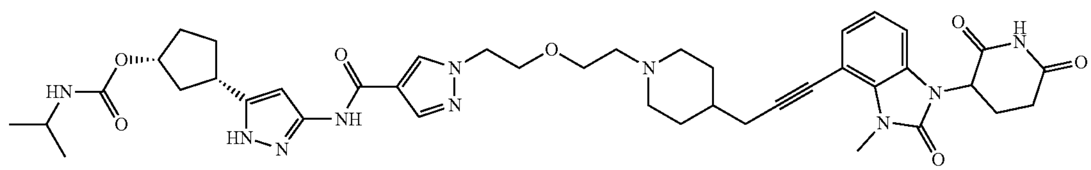 [SMILES: CC(C)NC(=O)O[C@@H]1CC[C@H](c2cc(NC(=O)c3cnn(CCOCCN4CCC(CC#Cc5cccc6c5n(C)c(=O)n6C5CCC(=O)NC5=O)CC4)c3)n[nH]2)C1] |
| I-51 | 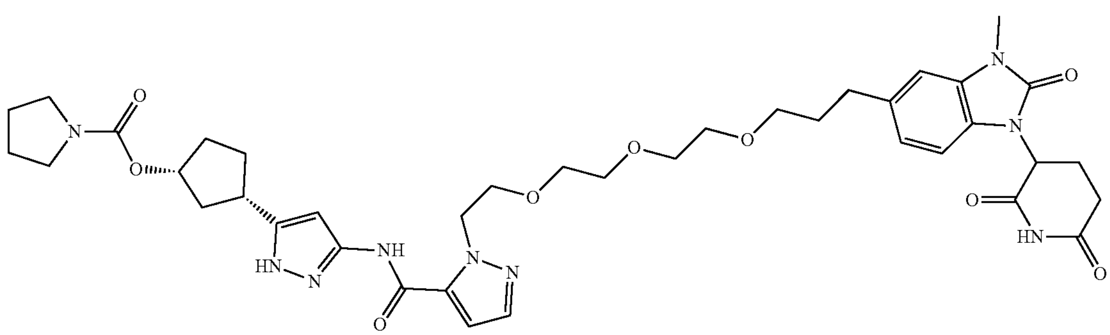 [SMILES: Cn1c(=O)n(C2CCC(=O)NC2=O)c2ccc(CCCOCCOCCOCCn3nccc3C(=O)Nc3cc([C@H]4CC[C@@H](OC(=O)N5CCCC5)C4)[nH]n3)cc21] |
| I-52 | 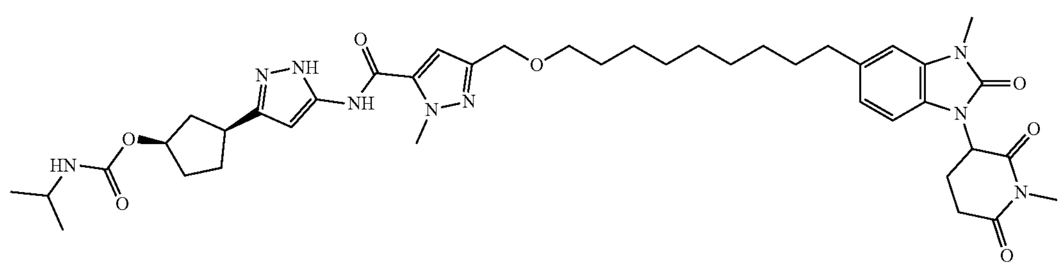 [SMILES: CC(C)NC(=O)O[C@@H]1CC[C@H](c2cc(NC(=O)c3cc(COCCCCCCCCCc4ccc5c(c4)n(C)c(=O)n5C4CCC(=O)N(C)C4=O)nn3C)[nH]n2)C1] |

TABLE 1-continued
Exemplary Compounds
| I-# | Structure |
|---|---|
| I-53 | 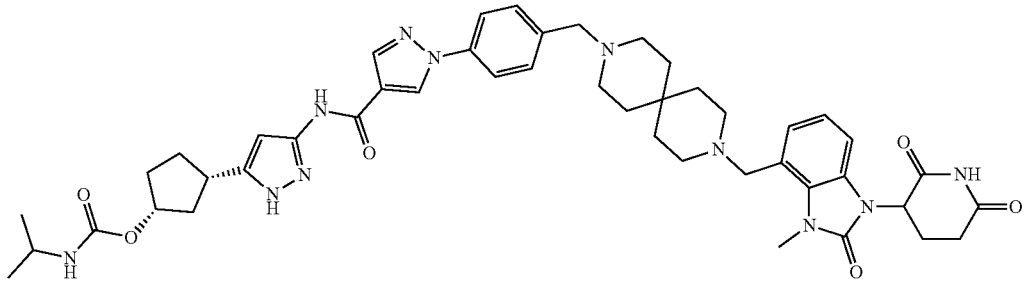 [SMILES: CC(C)NC(=O)O[C@@H]1CC[C@H](c2cc(NC(=O)c3cnn(-c4ccc(CN5CCC6(CC5)CCN(Cc5cccc7c5n(C)c(=O)n7C5CCC(=O)NC5=O)CC6)cc4)c3)n[nH]2)C1] |
| I-54 | 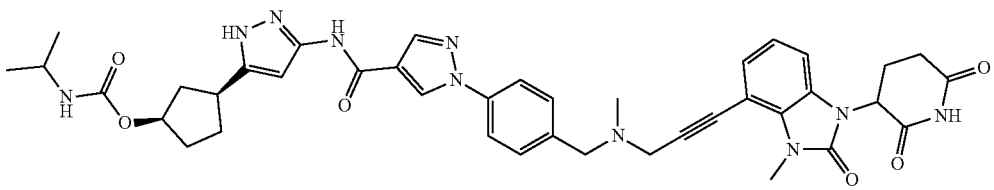 [SMILES: CC(C)NC(=O)O[C@@H]1CC[C@H](c2cc(NC(=O)c3cnn(-c4ccc(CN(C)CC#Cc5cccc6c5n(C)c(=O)n6C5CCC(=O)NC5=O)cc4)c3)n[nH]2)C1] |
| I-55 | 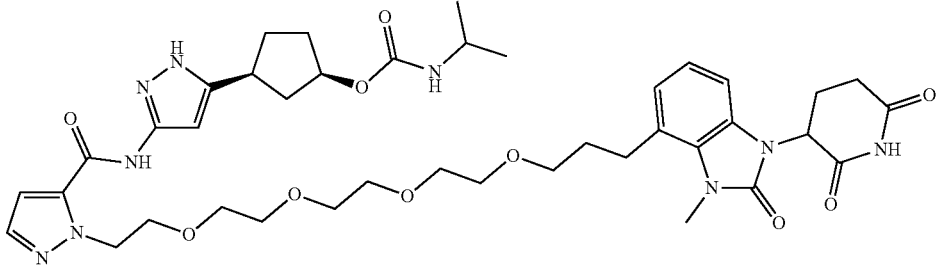 [SMILES: CC(C)NC(=O)O[C@@H]1CC[C@H](c2cc(NC(=O)c3ccnn3CCOCCOCCOCCOCCCc3cccc4c3n(C)c(=O)n4C3CCC(=O)NC3=O)n[nH]2)C1] |
| I-56 | 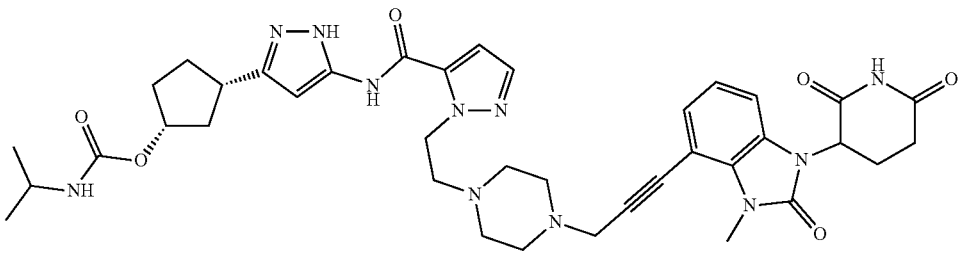 [SMILES: CC(C)NC(=O)O[C@@H]1CC[C@H](c2cc(NC(=O)c3ccnn3CCN3CCN(CC#Cc4cccc5c4n(C)c(=O)n5C4CCC(=O)NC4=O)CC3)[nH]n2)C1] |
| I-57 | 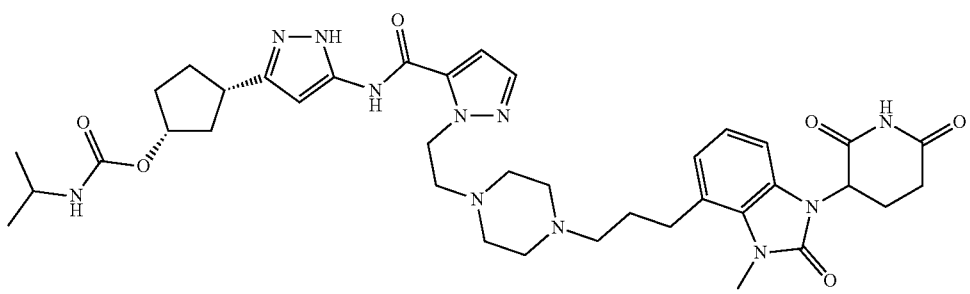 [SMILES: CC(C)NC(=O)O[C@@H]1CC[C@H](c2cc(NC(=O)c3ccnn3CCN3CCN(CCCc4cccc5c4n(C)c(=O)n5C4CCC(=O)NC4=O)CC3)[nH]n2)C1] |

TABLE 1-continued

Exemplary Compounds

| I-# | Structure |
|---|---|
| I-58 | 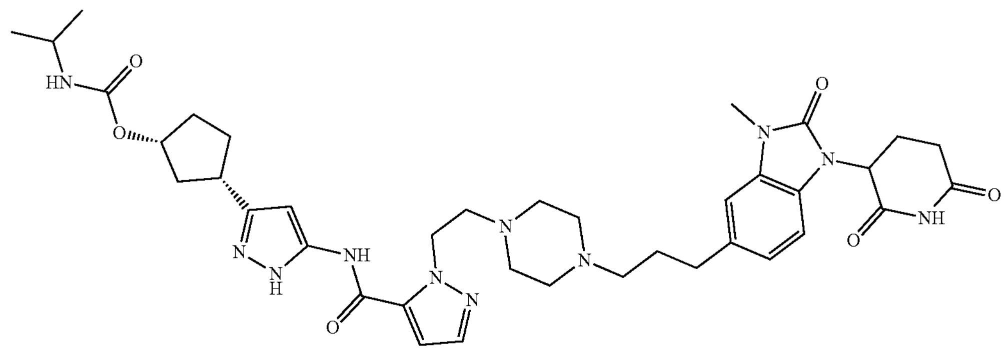 [SMILES: CC(C)NC(=O)O[C@@H]1CC[C@H](c2cc(NC(=O)c3ccnn3CCN3CCN(CCCc4ccc5c(c4)n(C)c(=O)n5C4CCC(=O)NC4=O)CC3)[nH]n2)C1] |
| I-59 | 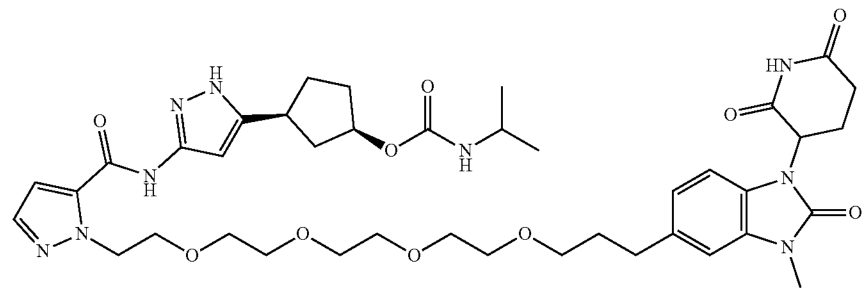 [SMILES: CC(C)NC(=O)O[C@@H]1CC[C@H](c2cc(NC(=O)c3ccnn3CCOCCOCCOCCOCCCc3ccc4c(c3)n(C)c(=O)n4C3CCC(=O)NC3=O)n[nH]2)C1] |
| I-60 | 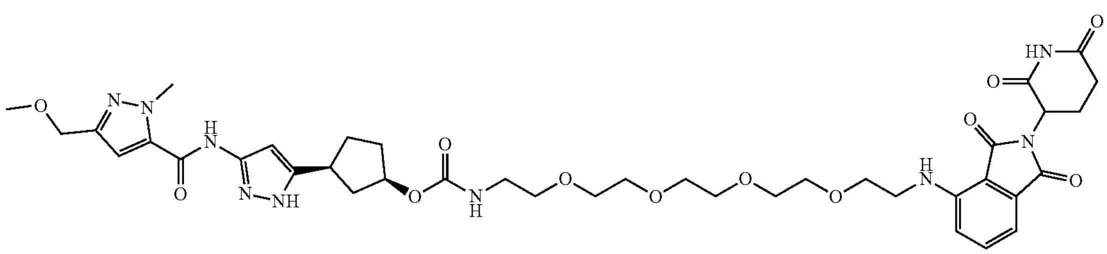 [SMILES: COCc1cc(C(=O)Nc2cc([C@H]3CC[C@@H](OC(=O)NCCOCCOCCOCCOCCNc4cccc5c4C(=O)N(C4CCC(=O)NC4=O)C5=O)C3)[nH]n2)n(C)n1] |
| I-61 | 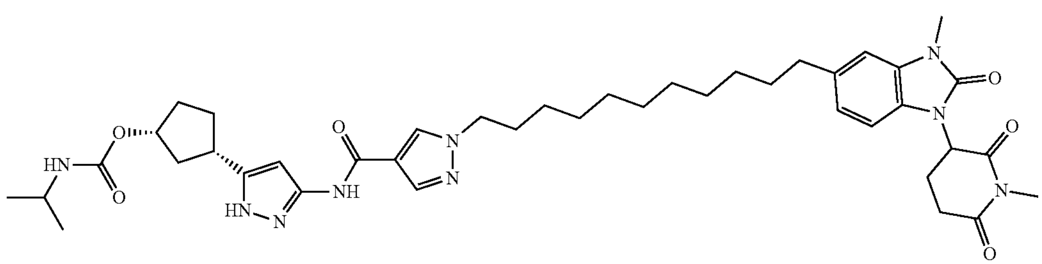 [SMILES: CC(C)NC(=O)O[C@@H]1CC[C@H](c2cc(NC(=O)c3cnn(CCCCCCCCCCCc4ccc5c(c4)n(C)c(=O)n5C4CCC(=O)N(C)C4=O)c3)n[nH]2)C1] |
| I-62 | 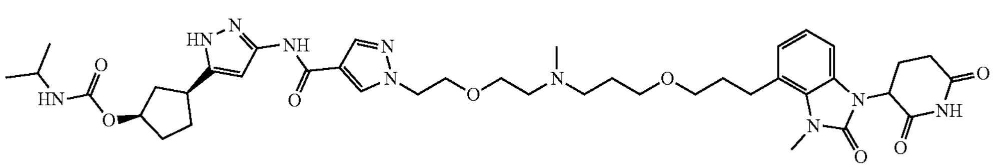 [SMILES: CC(C)NC(=O)O[C@@H]1CC[C@H](c2cc(NC(=O)c3cnn(CCOCCN(C)CCCOCCCc4cccc5c4n(C)c(=O)n5C4CCC(=O)NC4=O)c3)n[nH]2)C1] |
| I-63 | 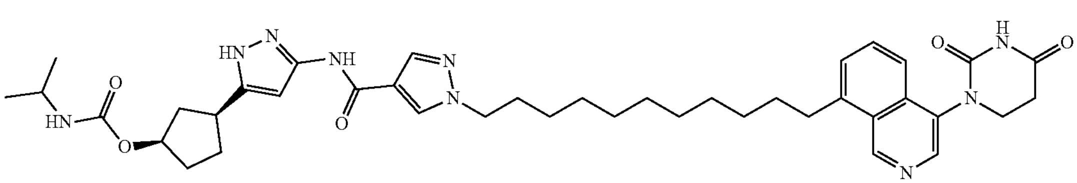 [SMILES: CC(C)NC(=O)O[C@@H]1CC[C@H](c2cc(NC(=O)c3cnn(CCCCCCCCCCCc4cccc5c(N6CCC(=O)NC6=O)cncc45)c3)n[nH]2)C1] |

TABLE 1-continued

Exemplary Compounds

| I-# | Structure |
|---|---|
| I-64 | 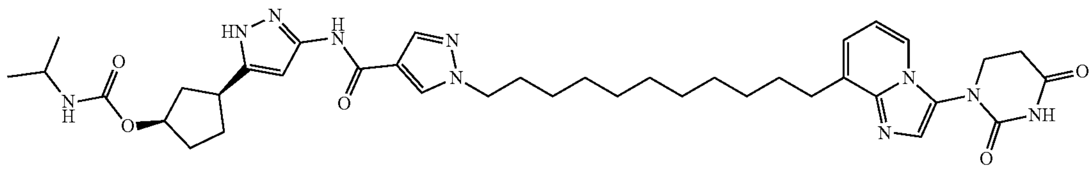 [SMILES: CC(C)NC(=O)O[C@@H]1CC[C@H](c2cc(NC(=O)c3cnn(CCCCCCCCCCCc4cccn5c(N6CCC(=O)NC6=O)cnc45)c3)n[nH]2)C1] |
| I-65 | 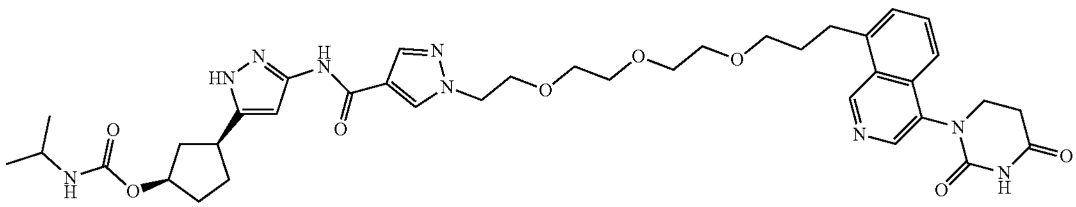 [SMILES: CC(C)NC(=O)O[C@@H]1CC[C@H](c2cc(NC(=O)c3cnn(CCOCCOCCOCCCc4cccc5c(N6CCC(=O)NC6=O)cncc45)c3)n[nH]2)C1] |
| I-66 | 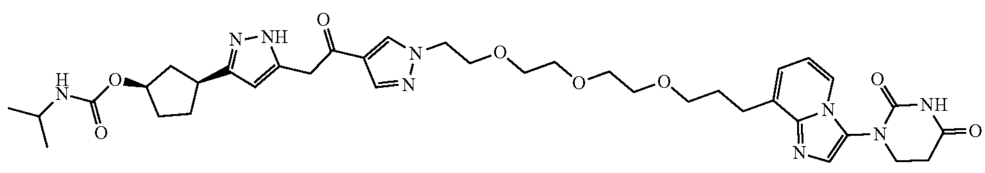 [SMILES: CC(C)NC(=O)O[C@@H]1CC[C@H](c2cc(CC(=O)c3cnn(CCOCCOCCOCCCc4cccn5c(N6CCC(=O)NC6=O)cnc45)c3)[nH]n2)C1] |
| I-67 | 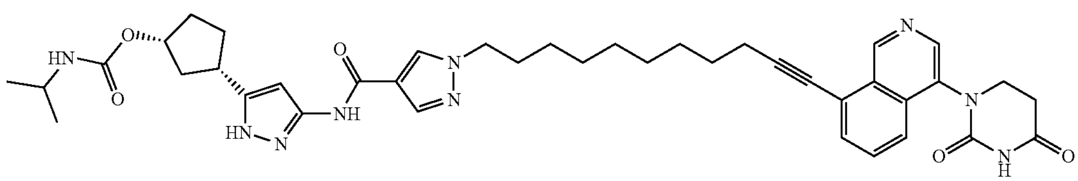 [SMILES: CC(C)NC(=O)O[C@@H]1CC[C@H](c2cc(NC(=O)c3cnn(CCCCCCCCCC#Cc4cccc5c(N6CCC(=O)NC6=O)cncc45)c3)n[nH]2)C1] |
| I-68 | 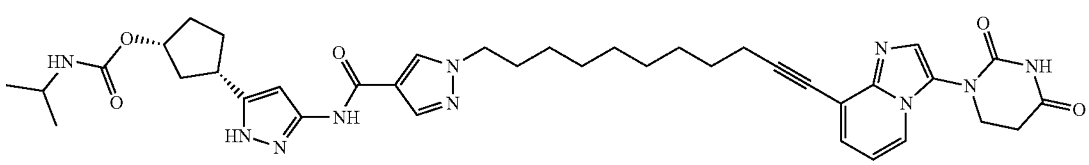 [SMILES: CC(C)NC(=O)O[C@@H]1CC[C@H](c2cc(NC(=O)c3cnn(CCCCCCCCCC#Cc4cccn5c(N6CCC(=O)NC6=O)cnc45)c3)n[nH]2)C1] |
| I-69 | 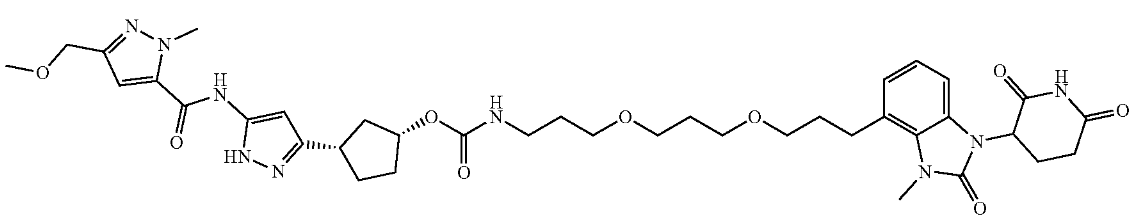 [SMILES: COCc1cc(C(=O)Nc2cc([C@H]3CC[C@@H](OC(=O)NCCCOCCCOCCCc4cccc5c4n(C)c(=O)n5C4CCC(=O)NC4=O)C3)n[nH]2)n(C)n1] |
| I-70 | 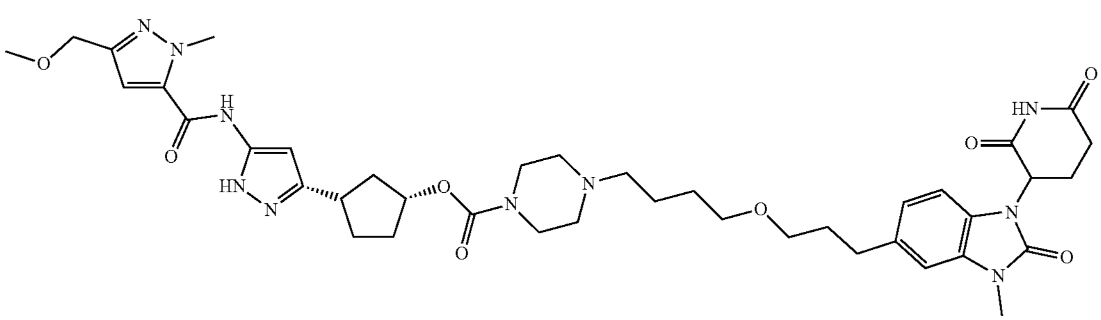 |

TABLE 1-continued

Exemplary Compounds

| I-# | Structure |
|---|---|
| I-71 | 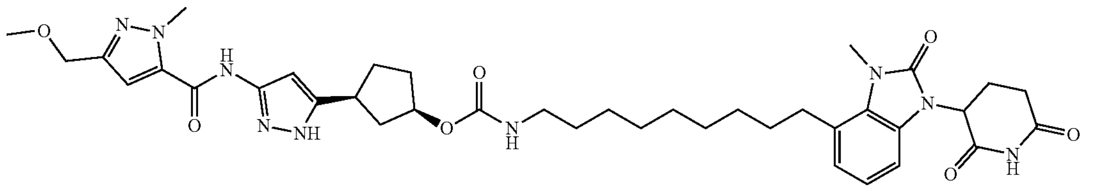 [SMILES: COCc1cc(C(=O)Nc2cc([C@H]3CC[C@@H](OC(=O)NCCCCCCCCCc4cccc5c4n(C)c(=O)n5C4CCC(=O)NC4=O)C3)[nH]n2)n(C)n1] |
| I-72 | 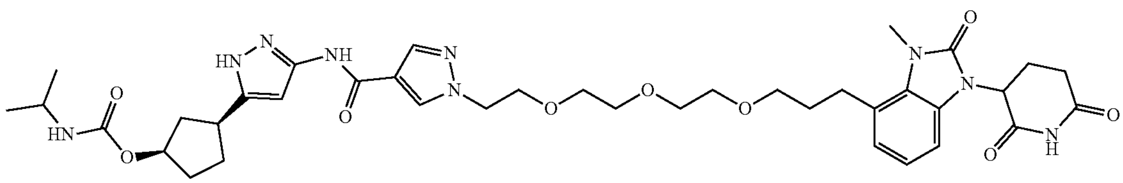 [SMILES: CC(C)NC(=O)O[C@@H]1CC[C@H](c2cc(NC(=O)c3cnn(CCOCCOCCOCCCc4cccc5c4n(C)c(=O)n5C4CCC(=O)NC4=O)c3)n[nH]2)C1] |
| I-73 | 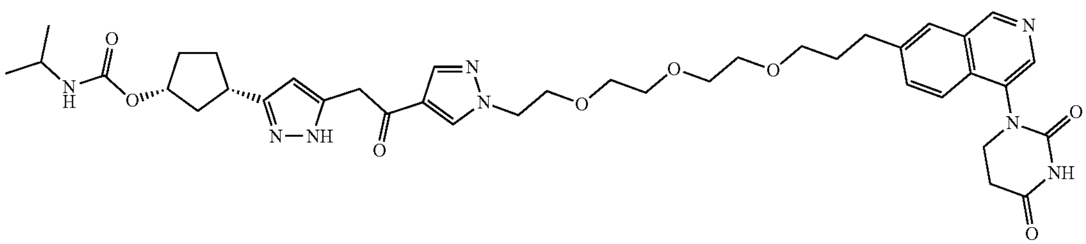 [SMILES: CC(C)NC(=O)O[C@@H]1CC[C@H](c2cc(CC(=O)c3cnn(CCOCCOCCOCCCc4ccc5c(N6CCC(=O)NC6=O)cncc5c4)c3)[nH]n2)C1] |
| I-74 | 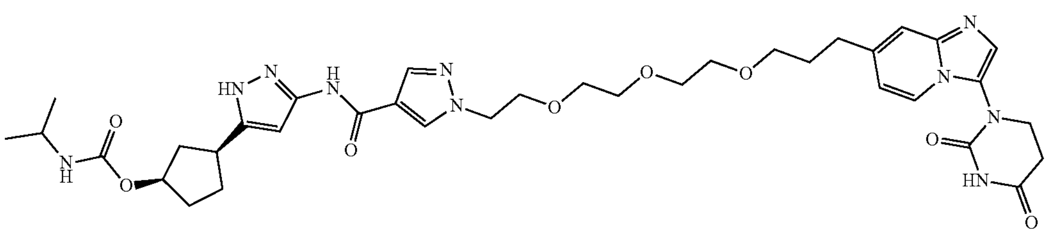 [SMILES: CC(C)NC(=O)O[C@@H]1CC[C@H](c2cc(NC(=O)c3cnn(CCOCCOCCOCCCc4ccn5c(N6CCC(=O)NC6=O)cnc5c4)c3)n[nH]2)C1] |
| I-75 | 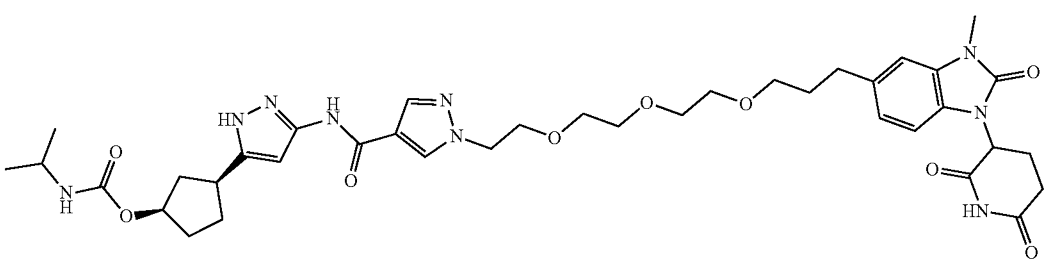 [SMILES: CC(C)NC(=O)O[C@@H]1CC[C@H](c2cc(NC(=O)c3cnn(CCOCCOCCOCCCc4ccc5c(c4)n(C)c(=O)n5C4CCC(=O)NC4=O)c3)n[nH]2)C1] |
| I-76 | 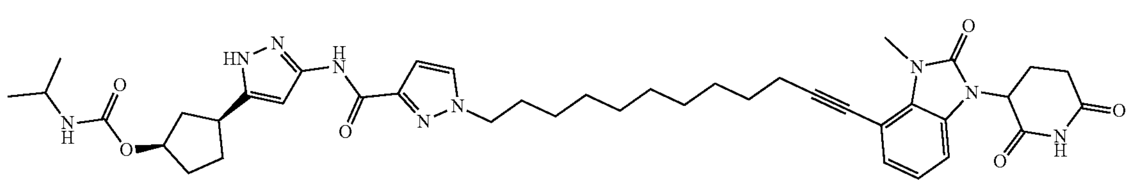 [SMILES: CC(C)NC(=O)O[C@@H]1CC[C@H](c2cc(NC(=O)c3ccn(CCCCCCCCCCC#Cc4cccc5c4n(C)c(=O)n5C4CCC(=O)NC4=O)n3)n[nH]2)C1] |
| I-77 | 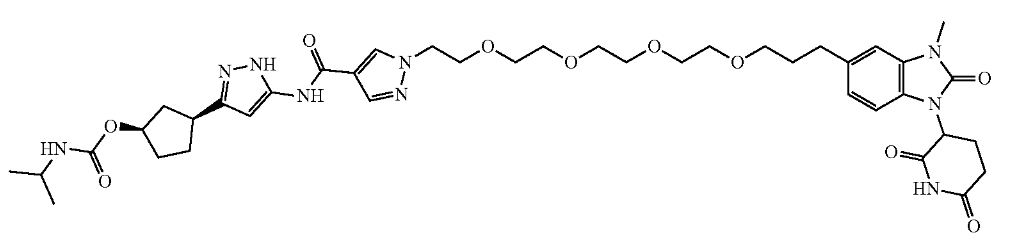 [SMILES: CC(C)NC(=O)O[C@@H]1CC[C@H](c2cc(NC(=O)c3cnn(CCOCCOCCOCCOCCCc4ccc5c(c4)n(C)c(=O)n5C4CCC(=O)NC4=O)c3)[nH]n2)C1] |

403
404
TABLE 1-continued
Exemplary Compounds
| I-# | Structure |
|---|---|
| I-78 | 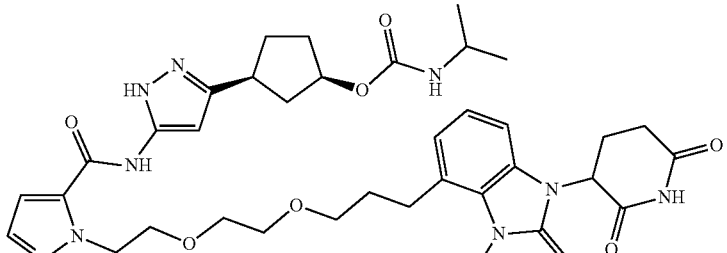 |
| I-79 | 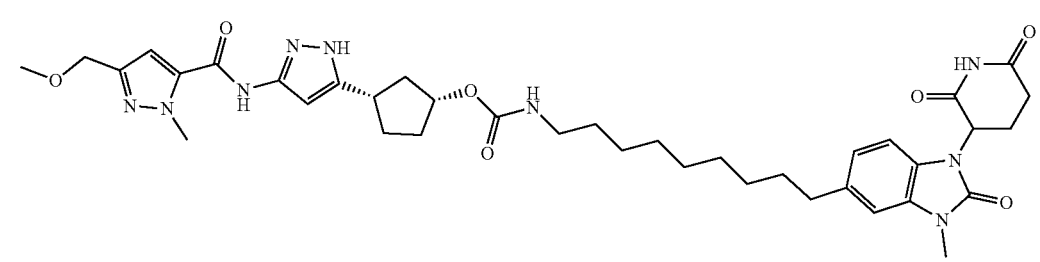 [SMILES: COCc1cc(C(=O)Nc2cc([C@H]3CC[C@@H](OC(=O)NCCCCCCCCCc4ccc5c(c4)n(C)c(=O)n5C4CCC(=O)NC4=O)C3)[nH]n2)n(C)n1] |
| I-81 | 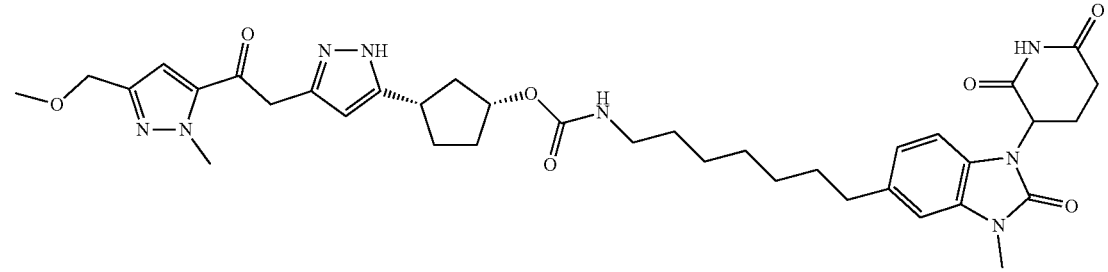 [SMILES: COCc1cc(C(=O)Cc2cc([C@H]3CC[C@@H](OC(=O)NCCCCCCCc4ccc5c(c4)n(C)c(=O)n5C4CCC(=O)NC4=O)C3)[nH]n2)n(C)n1] |
| I-82 | 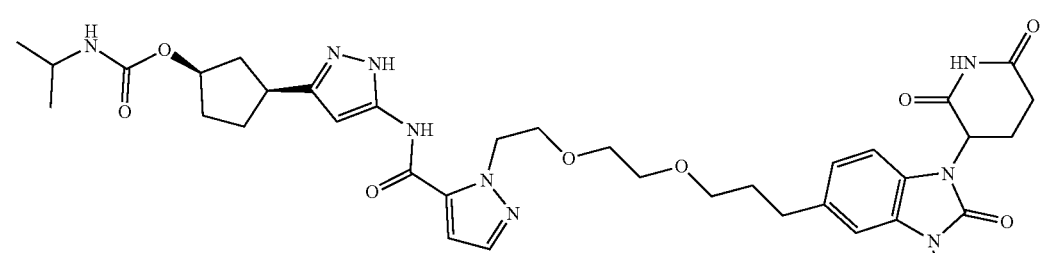 |
| I-83 | 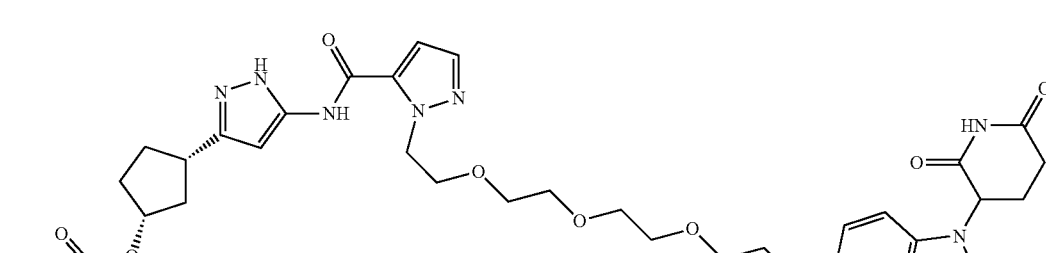 |

TABLE 1-continued

Exemplary Compounds

| I-# | Structure |
|---|---|
| I-84 | 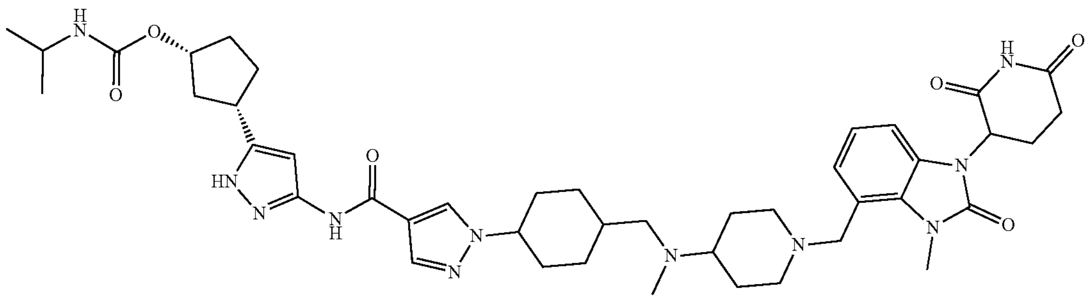 [SMILES: CC(C)NC(=O)O[C@@H]1CC[C@H](c2cc(NC(=O)c3cnn(C4CCC(CN(C)C5CCN(Cc6cccc7c6n(C)c(=O)n7C6CCC(=O)NC6=O)CC5)CC4)c3)n[nH]2)C1] |
| I-85 | 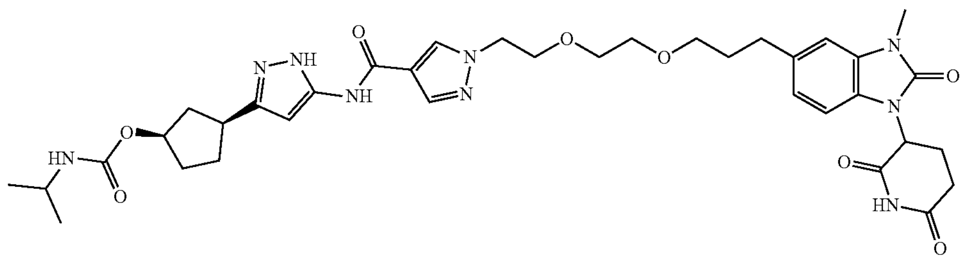 [SMILES: CC(C)NC(=O)O[C@@H]1CC[C@H](c2cc(NC(=O)c3cnn(CCOCCOCCCc4ccc5c(c4)n(C)c(=O)n5C4CCC(=O)NC4=O)c3)[nH]n2)C1] |
| I-86 | 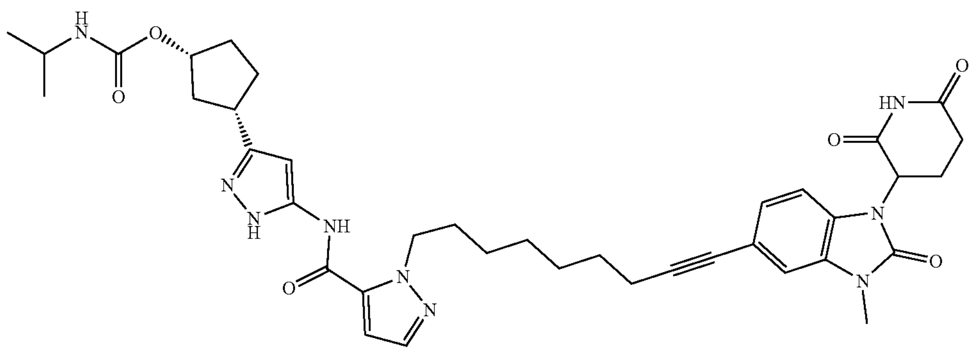 [SMILES: CC(C)NC(=O)O[C@@H]1CC[C@H](c2cc(NC(=O)c3ccnn3CCCCCCCC#Cc3ccc4c(c3)n(C)c(=O)n4C3CCC(=O)NC3=O)[nH]n2)C1] |
| I-87 | 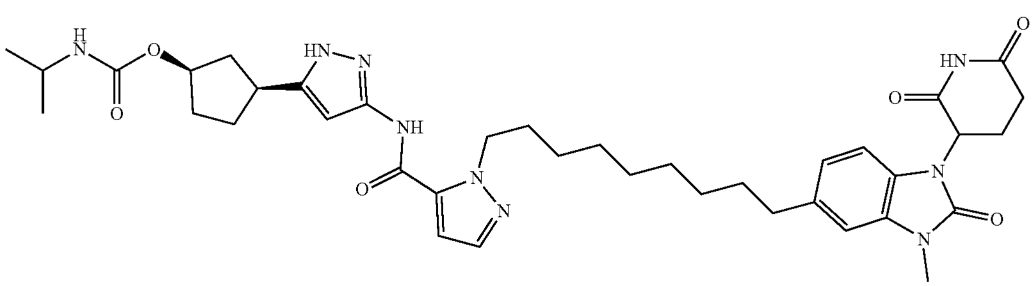 [SMILES: CC(C)NC(=O)O[C@@H]1CC[C@H](c2cc(NC(=O)c3ccnn3CCCCCCCCCc3ccc4c(c3)n(C)c(=O)n4C3CCC(=O)NC3=O)n[nH]2)C1] |
| I-88 | 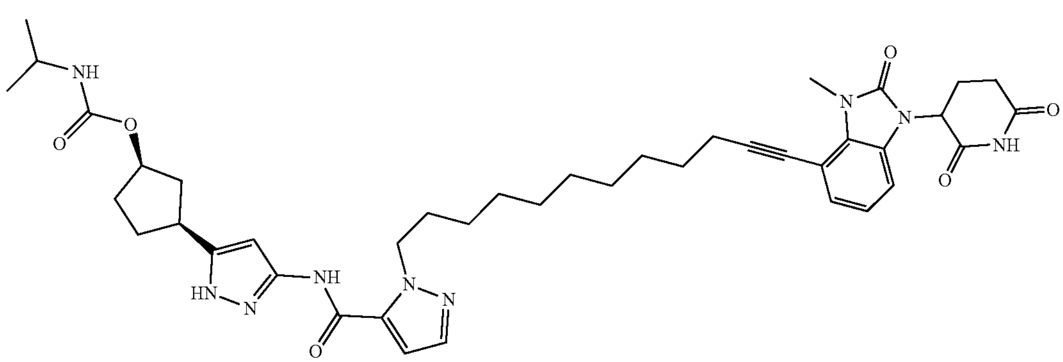 [SMILES: CC(C)NC(=O)O[C@@H]1CC[C@H](c2cc(NC(=O)c3ccnn3CCCCCCCCCCC#Cc3cccc4c3n(C)c(=O)n4C3CCC(=O)NC3=O)n[nH]2)C1] |

TABLE 1-continued

Exemplary Compounds

| I-# | Structure |
|---|---|
| I-89 | 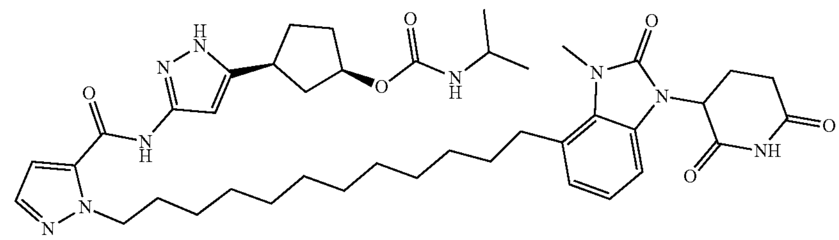 [SMILES: CC(C)NC(=O)O[C@@H]1CC[C@H](c2cc(NC(=O)c3ccnn3CCCCCCCCCCCCc3cccc4c3n(C)c(=O)n4C3CCC(=O)NC3=O)n[nH]2)C1] |
| I-90 | 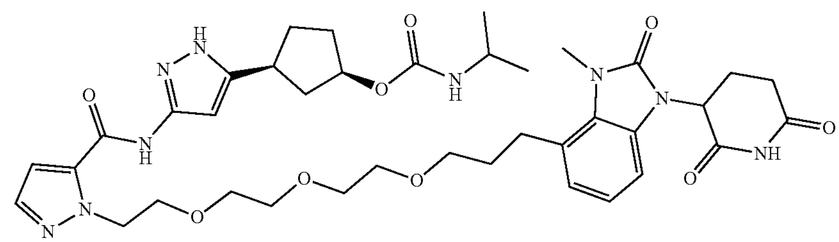 [SMILES: CC(C)NC(=O)O[C@@H]1CC[C@H](c2cc(NC(=O)c3ccnn3CCOCCOCCOCCCc3cccc4c3n(C)c(=O)n4C3CCC(=O)NC3=O)n[nH]2)C1] |
| I-91 | 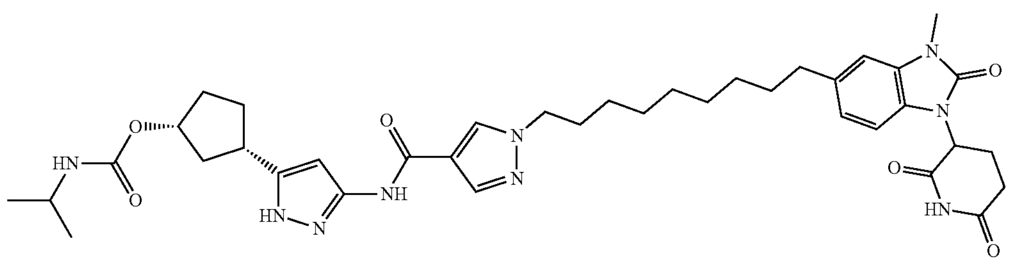 [SMILES: CC(C)NC(=O)O[C@@H]1CC[C@H](c2cc(NC(=O)c3cnn(CCCCCCCCCc4ccc5c(c4)n(C)c(=O)n5C4CCC(=O)NC4=O)c3)n[nH]2)C1] |
| I-92 | 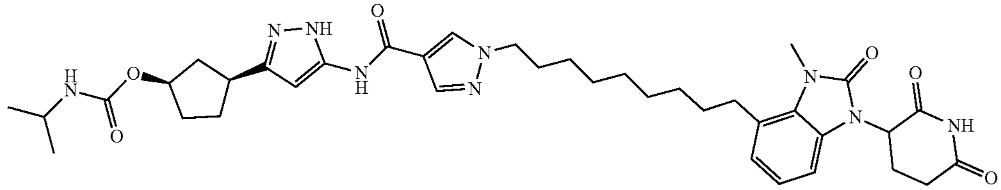 [SMILES: CC(C)NC(=O)O[C@@H]1CC[C@H](c2cc(NC(=O)c3cnn(CCCCCCCCCc4cccc5c4n(C)c(=O)n5C4CCC(=O)NC4=O)c3)[nH]n2)C1] |
| I-93 | 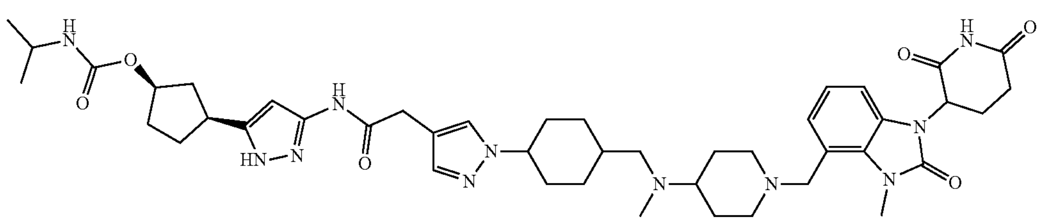 [SMILES: CC(C)NC(=O)O[C@@H]1CC[C@H](c2cc(NC(=O)Cc3cnn(C4CCC(CN(C)C5CCN(Cc6cccc7c6n(C)c(=O)n7C6CCC(=O)NC6=O)CC5)CC4)c3)n[nH]2)C1] |
| I-94 | 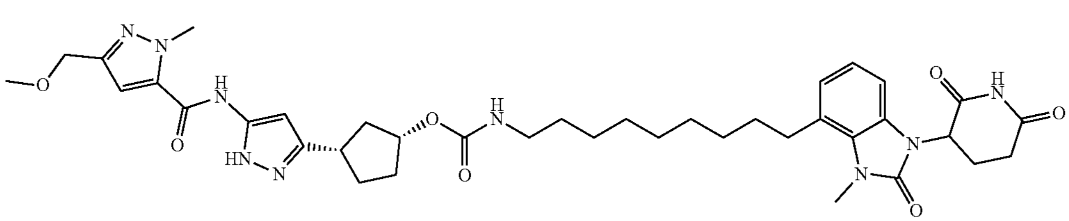 [SMILES: COCc1cc(C(=O)Nc2cc([C@H]3CC[C@@H](OC(=O)NCCCCCCCCCc4cccc5c4n(C)c(=O)n5C4CCC(=O)NC4=O)C3)n[nH]2)n(C)n1] |

TABLE 1-continued

Exemplary Compounds

| I-# | Structure |
|---|---|
| I-95 | 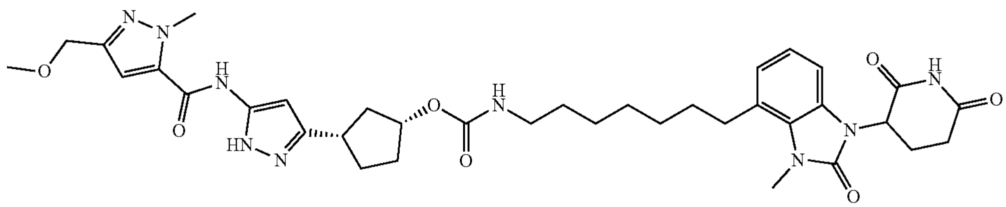 [SMILES: COCc1cc(C(=O)Nc2cc([C@H]3CC[C@@H](OC(=O)NCCCCCCCc4cccc5c4n(C)c(=O)n5C4CCC(=O)NC4=O)C3)n[nH]2)n(C)n1] |
| I-96 | 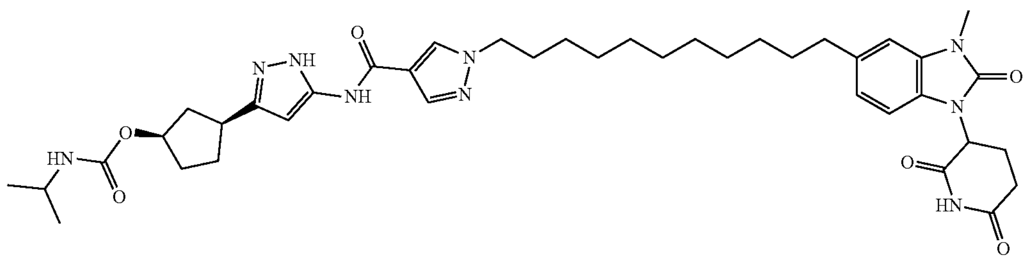 [SMILES: CC(C)NC(=O)O[C@@H]1CC[C@H](c2cc(NC(=O)c3cnn(CCCCCCCCCCCc4ccc5c(c4)n(C)c(=O)n5C4CCC(=O)NC4=O)c3)[nH]n2)C1] |
| I-97 | 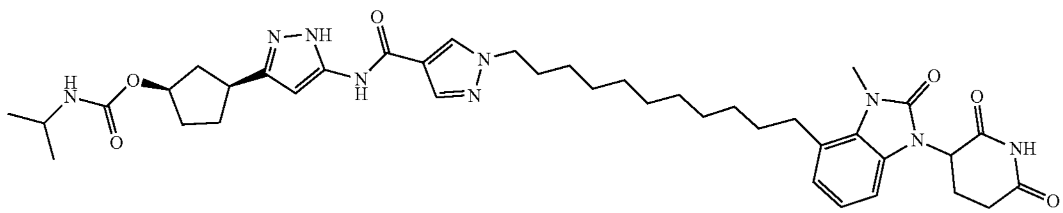 [SMILES: CC(C)NC(=O)O[C@@H]1CC[C@H](c2cc(NC(=O)c3cnn(CCCCCCCCCCCc4cccc5c4n(C)c(=O)n5C4CCC(=O)NC4=O)c3)[nH]n2)C1] |
| I-98 | 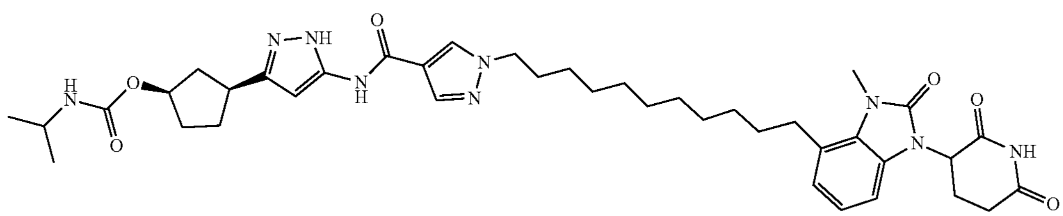 [SMILES: CC(C)NC(=O)O[C@@H]1CC[C@H](c2cc(NC(=O)c3cnn(CCCCCCCCCCCc4cccc5c4n(C)c(=O)n5C4CCC(=O)NC4=O)c3)[nH]n2)C1] |
| I-99 | 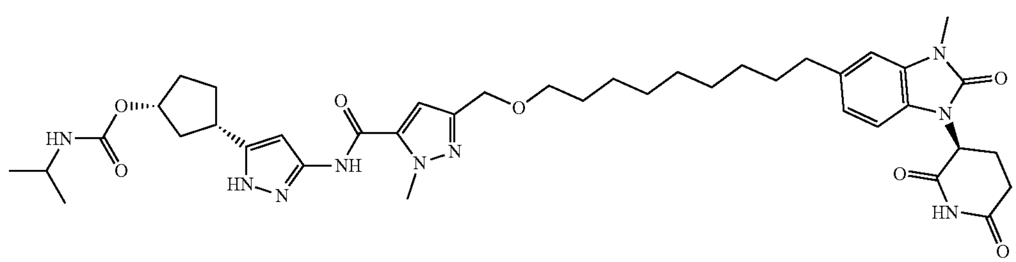 [SMILES: CC(C)NC(=O)O[C@@H]1CC[C@H](c2cc(NC(=O)c3cc(COCCCCCCCCCc4ccc5c(c4)n(C)c(=O)n5[C@H]4CCC(=O)NC4=O)nn3C)n[nH]2)C1] |
| I-100 | 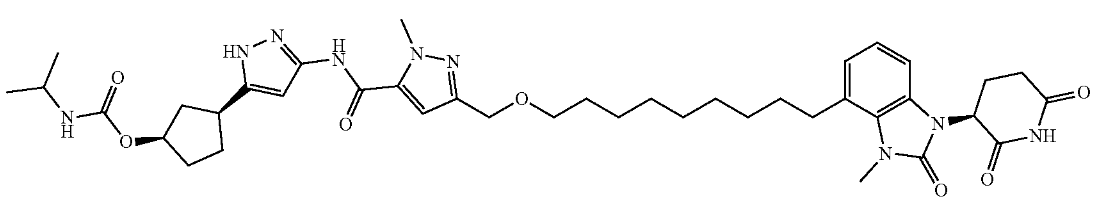 [SMILES: CC(C)NC(=O)O[C@@H]1CC[C@H](c2cc(NC(=O)c3cc(COCCCCCCCCCc4cccc5c4n(C)c(=O)n5[C@H]4CCC(=O)NC4=O)nn3C)n[nH]2)C1] |
| I-101 | 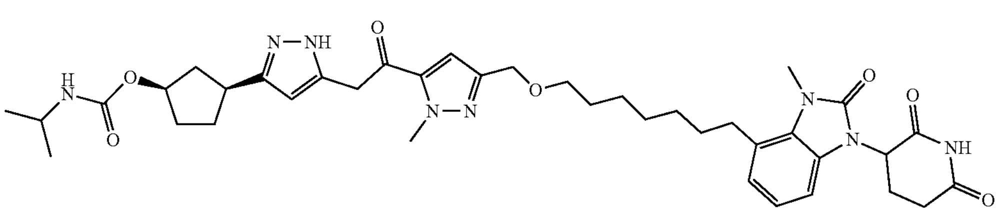 [SMILES: CC(C)NC(=O)O[C@@H]1CC[C@H](c2cc(CC(=O)c3cc(COCCCCCCCc4cccc5c4n(C)c(=O)n5C4CCC(=O)NC4=O)nn3C)[nH]n2)C1] |

TABLE 1-continued

Exemplary Compounds

| I-# | Structure |
|---|---|
| I-102 | 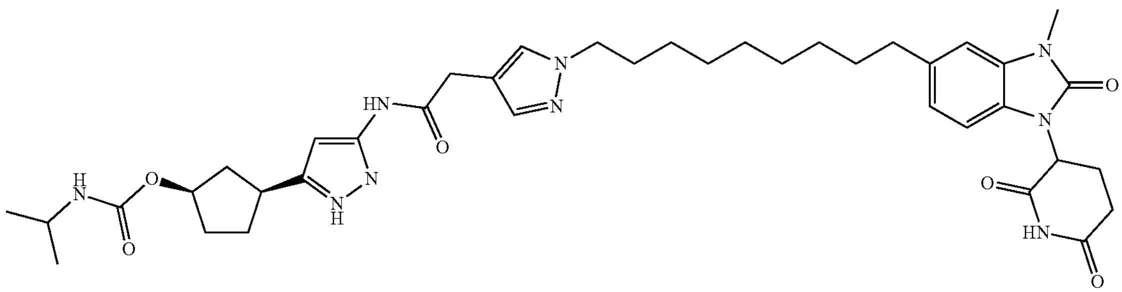 [SMILES: CC(C)NC(=O)O[C@@H]1CC[C@H](c2cc(NC(=O)Cc3cnn(CCCCCCCCCc4ccc5c(c4)n(C)c(=O)n5C4CCC(=O)NC4=O)c3)[nH]n2)C1] |
| I-103 | 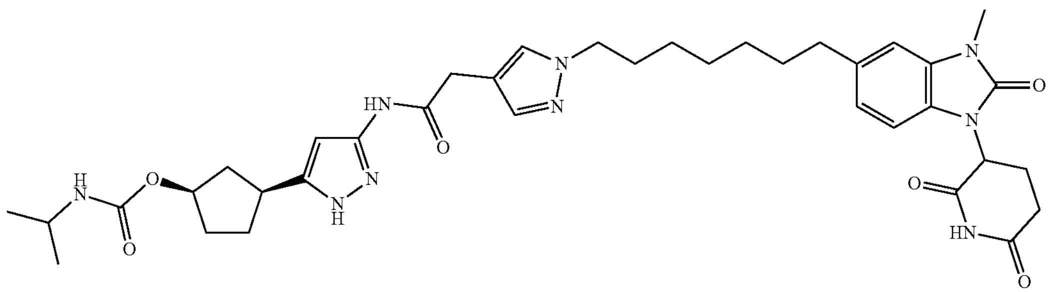 [SMILES: CC(C)NC(=O)O[C@@H]1CC[C@H](c2cc(NC(=O)Cc3cnn(CCCCCCCc4ccc5c(c4)n(C)c(=O)n5C4CCC(=O)NC4=O)c3)n[nH]2)C1] |
| I-104 | 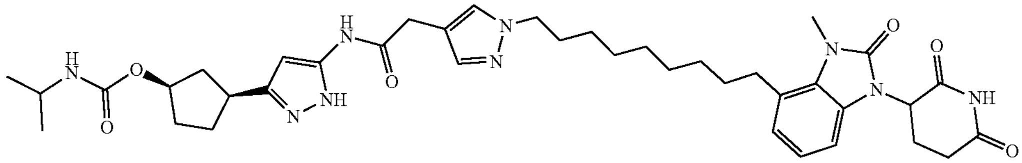 [SMILES: CC(C)NC(=O)O[C@@H]1CC[C@H](c2cc(NC(=O)Cc3cnn(CCCCCCCCCc4cccc5c4n(C)c(=O)n5C4CCC(=O)NC4=O)c3)[nH]n2)C1] |
| I-105 | 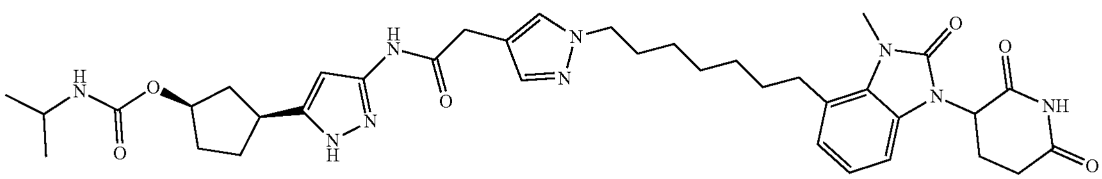 [SMILES: CC(C)NC(=O)O[C@@H]1CC[C@H](c2cc(NC(=O)Cc3cnn(CCCCCCCc4cccc5c4n(C)c(=O)n5C4CCC(=O)NC4=O)c3)n[nH]2)C1] |
| I-106 | 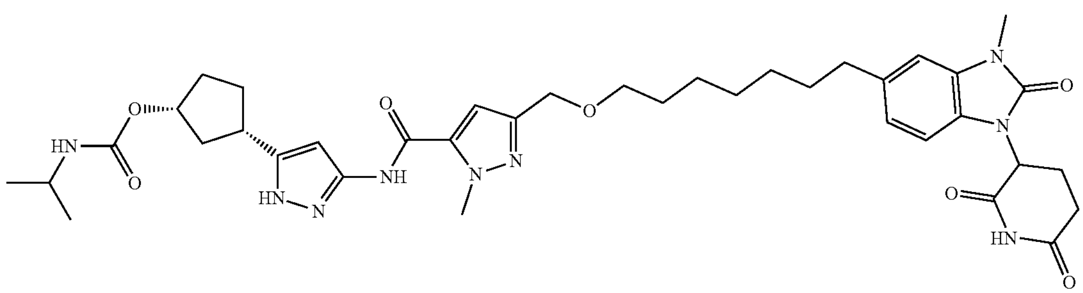 [SMILES: CC(C)NC(=O)O[C@@H]1CC[C@H](c2cc(NC(=O)c3cc(COCCCCCCCc4ccc5c(c4)n(C)c(=O)n5C4CCC(=O)NC4=O)nn3C)n[nH]2)C1] |
| I-107 | 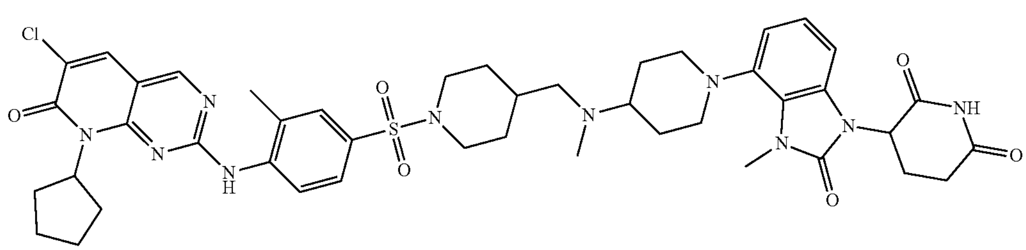 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2cc(Cl)c(=O)n(C3CCCC3)c2n1] |

TABLE 1-continued
Exemplary Compounds
| I-# | Structure |
|---|---|
| I-108 | 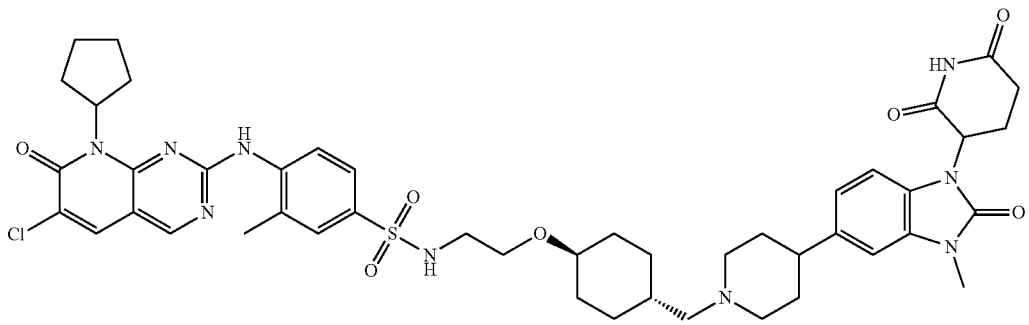 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc2cc(Cl)c(=O)n(C3CCCC3)c2n1] |
| I-109 | 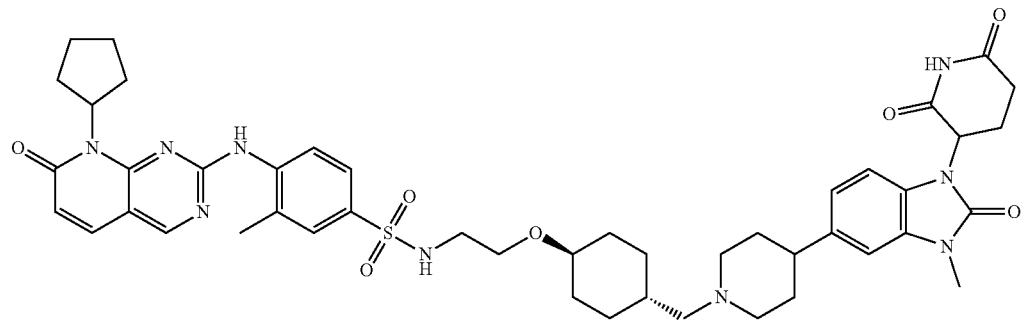 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc2ccc(=O)n(C3CCCC3)c2n1] |
| I-110 | 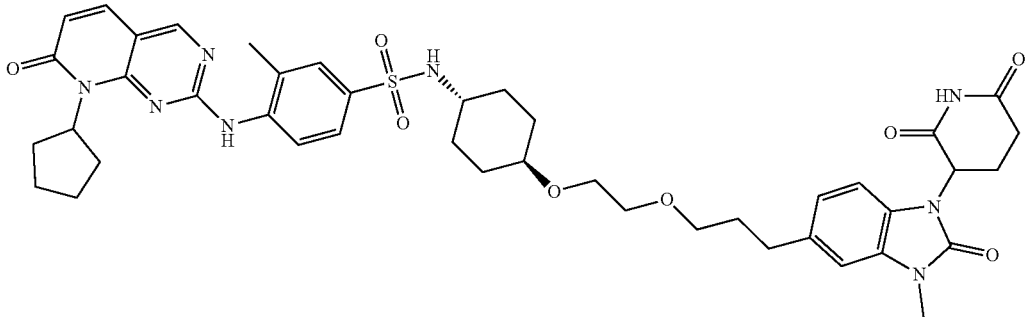 [SMILES: Cc1cc(S(=O)(=O)N[C@H]2CC[C@H](OCCOCCCc3ccc4c(c3)n(C)c(=O)n4C3CCC(=O)NC3=O)CC2)ccc1Nc1ncc2ccc(=O)n(C3CCCC3)c2n1] |
| I-111 | 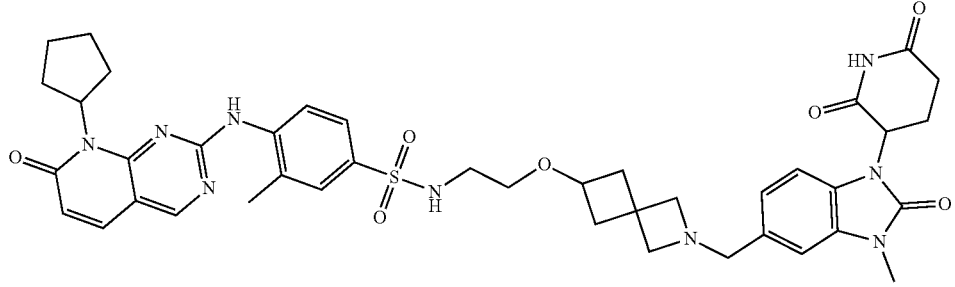 [SMILES: Cc1cc(S(=O)(=O)NCCOC2CC3(C2)CN(Cc2ccc4c(c2)n(C)c(=O)n4C2CCC(=O)NC2=O)C3)ccc1Nc1ncc2ccc(=O)n(C3CCCC3)c2n1] |

TABLE 1-continued

Exemplary Compounds

| I-# | Structure |
|---|---|
| I-112 | 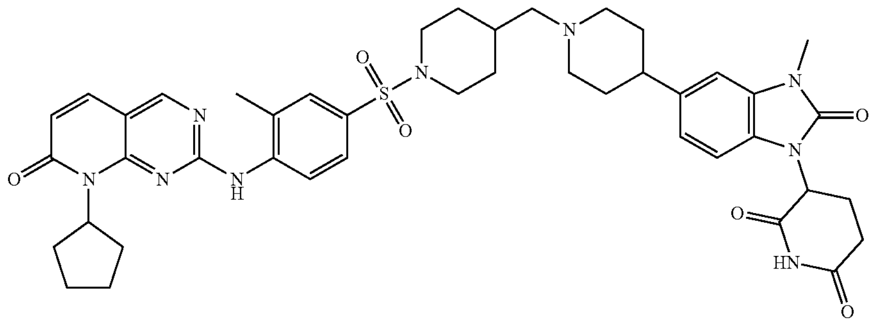 [SMILES: Cc1cc(S(=O)(=O)N2CCC(CN3CCC(c4ccc5c(c4)n(C)c(=O)n5C4CCC(=O)NC4=O)CC3)CC2)ccc1Nc1ncc2ccc(=O)n(C3CCCC3)c2n1] |
| I-113 | 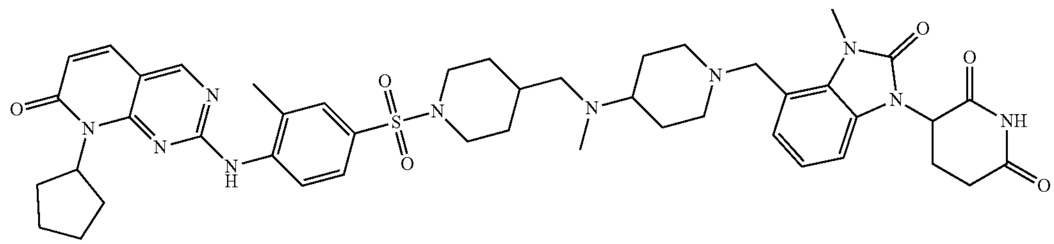 [SMILES: Cc1cc(S(=O)(=O)N2CCC(CN(C)C3CCN(Cc4cccc5c4n(C)c(=O)n5C4CCC(=O)NC4=O)CC3)CC2)ccc1Nc1ncc2ccc(=O)n(C3CCCC3)c2n1] |
| I-114 | 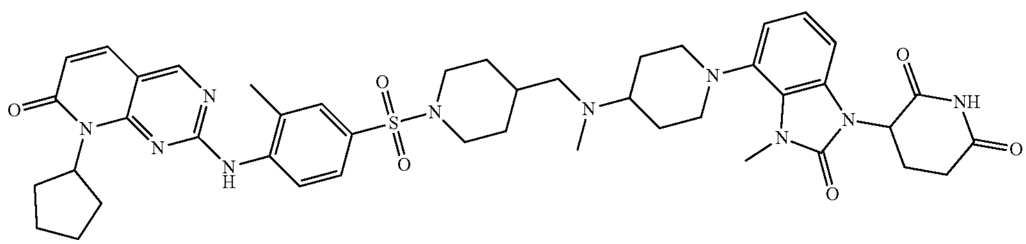 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2ccc(=O)n(C3CCCC3)c2n1] |
| I-115 | 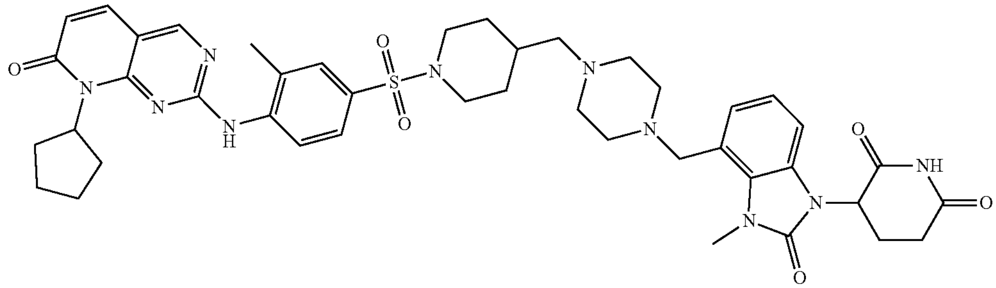 [SMILES: Cc1cc(S(=O)(=O)N2CCC(CN3CCN(Cc4cccc5c4n(C)c(=O)n5C4CCC(=O)NC4=O)CC3)CC2)ccc1Nc1ncc2ccc(=O)n(C3CCCC3)c2n1] |
| I-116 | 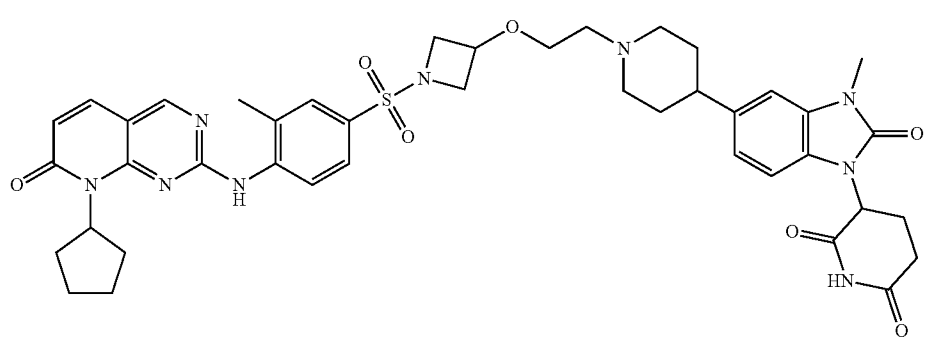 [SMILES: Cc1cc(S(=O)(=O)N2CC(OCCN3CCC(c4ccc5c(c4)n(C)c(=O)n5C4CCC(=O)NC4=O)CC3)C2)ccc1Nc1ncc2ccc(=O)n(C3CCCC3)c2n1] |

TABLE 1-continued

Exemplary Compounds

| I-# | Structure |
|---|---|
| I-117 | 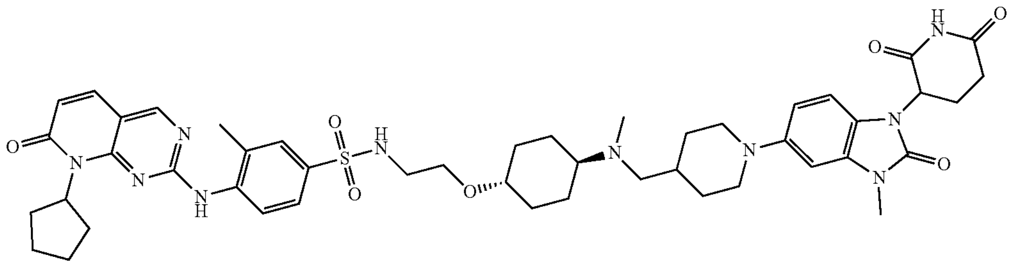 [SMILES: Cc1cc(S(=O)(=O)NCCO[C@H]2CC[C@H](N(C)CC3CCN(c4ccc5c(c4)n(C)c(=O)n5C4CCC(=O)NC4=O)CC3)CC2)ccc1Nc1ncc2ccc(=O)n(C3CCCC3)c2n1] |
| I-118 | 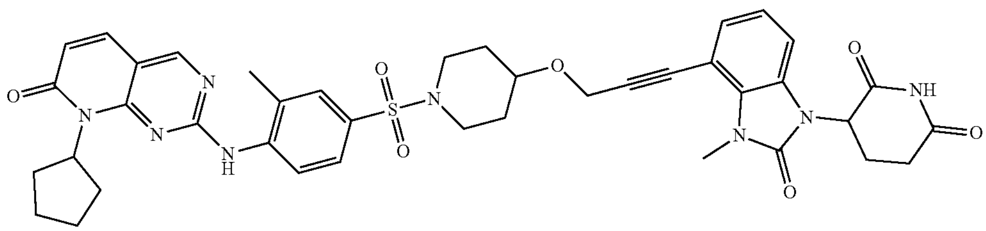 [SMILES: Cc1cc(S(=O)(=O)N2CCC(OCC#Cc3cccc4c3n(C)c(=O)n4C3CCC(=O)NC3=O)CC2)ccc1Nc1ncc2ccc(=O)n(C3CCCC3)c2n1] |
| I-119 | 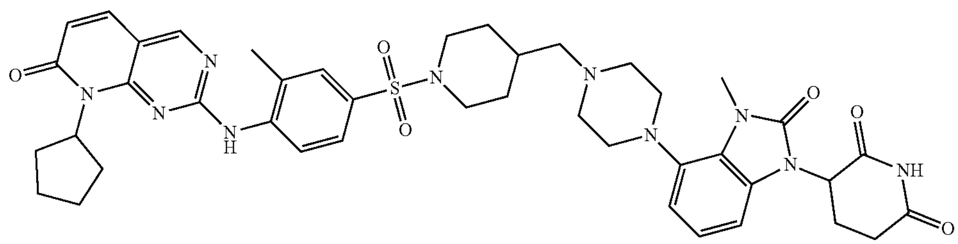 [SMILES: Cc1cc(S(=O)(=O)N2CCC(CN3CCN(c4cccc5c4n(C)c(=O)n5C4CCC(=O)NC4=O)CC3)CC2)ccc1Nc1ncc2ccc(=O)n(C3CCCC3)c2n1] |
| I-120 | 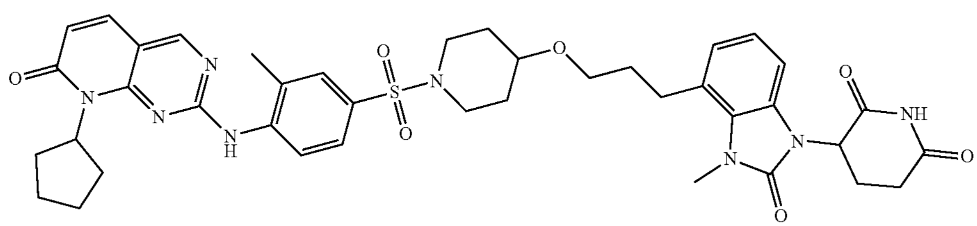 [SMILES: Cc1cc(S(=O)(=O)N2CCC(OCCCc3cccc4c3n(C)c(=O)n4C3CCC(=O)NC3=O)CC2)ccc1Nc1ncc2ccc(=O)n(C3CCCC3)c2n1] |
| I-121 | 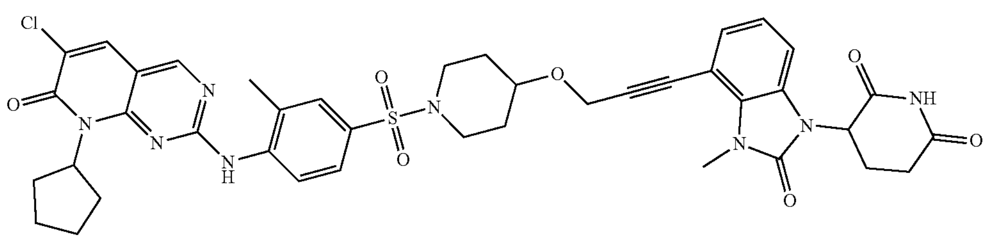 [SMILES: Cc1cc(S(=O)(=O)N2CCC(OCC#Cc3cccc4c3n(C)c(=O)n4C3CCC(=O)NC3=O)CC2)ccc1Nc1ncc2cc(Cl)c(=O)n(C3CCCC3)c2n1] |
| I-122 | 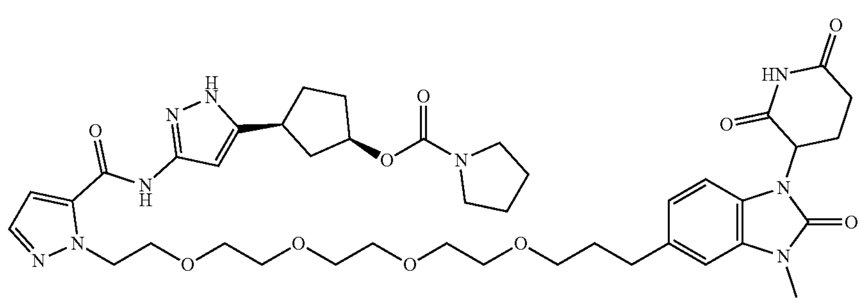 [SMILES: Cn1c(=O)n(C2CCC(=O)NC2=O)c2ccc(CCCOCCOCCOCCOCCn3nccc3C(=O)Nc3cc([C@H]4CC[C@@H](OC(=O)N5CCCC5)C4)[nH]n3)cc21] |

TABLE 1-continued

Exemplary Compounds

| I-# | Structure |
| --- | --- |
| I-123 | 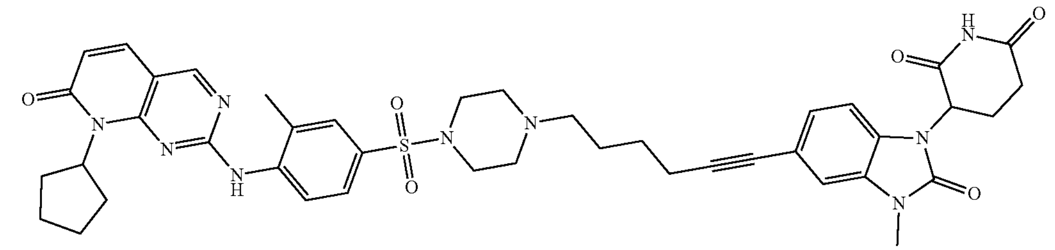 [SMILES: Cc1cc(S(=O)(=O)N2CCN(CCCCC#Cc3ccc4c(c3)n(C)c(=O)n4C3CCC(=O)NC3=O)CC2)ccc1Nc1ncc2ccc(=O)n(C3CCCC3)c2n1] |
| I-124 | 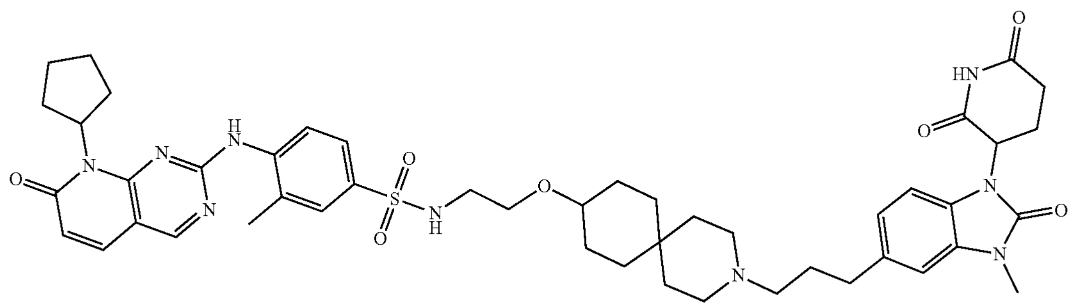 [SMILES: Cc1cc(S(=O)(=O)NCCOC2CCC3(CC2)CCN(CCCc2ccc4c(c2)n(C)c(=O)n4C2CCC(=O)NC2=O)CC3)ccc1Nc1ncc2ccc(=O)n(C3CCCC3)c2n1] |
| I-125 | 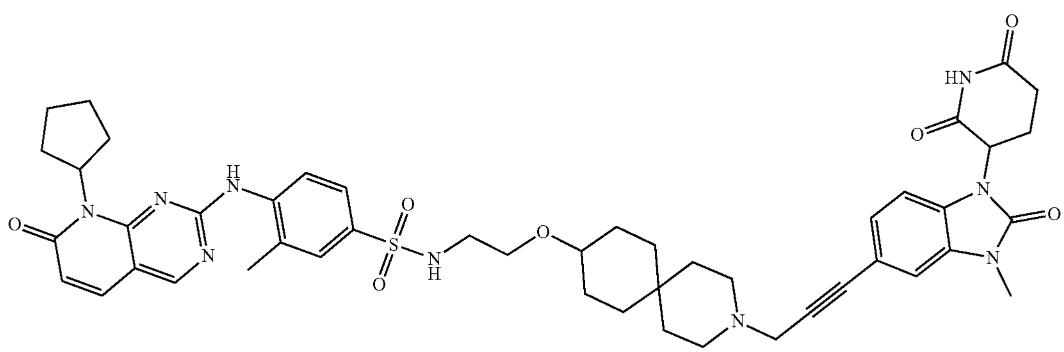 [SMILES: Cc1cc(S(=O)(=O)NCCOC2CCC3(CC2)CCN(CC#Cc2ccc4c(c2)n(C)c(=O)n4C2CCC(=O)NC2=O)CC3)ccc1Nc1ncc2ccc(=O)n(C3CCCC3)c2n1] |
| I-126 | 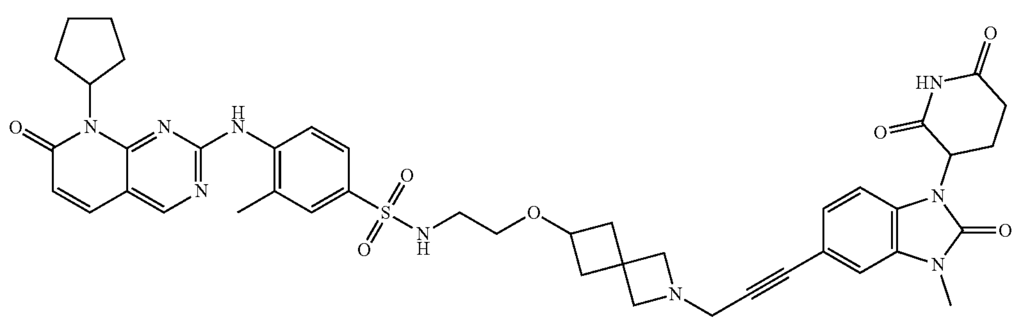 [SMILES: Cc1cc(S(=O)(=O)NCCOC2CC3(C2)CN(CC#Cc2ccc4c(c2)n(C)c(=O)n4C2CCC(=O)NC2=O)C3)ccc1Nc1ncc2ccc(=O)n(C3CCCC3)c2n1] |
| I-127 | 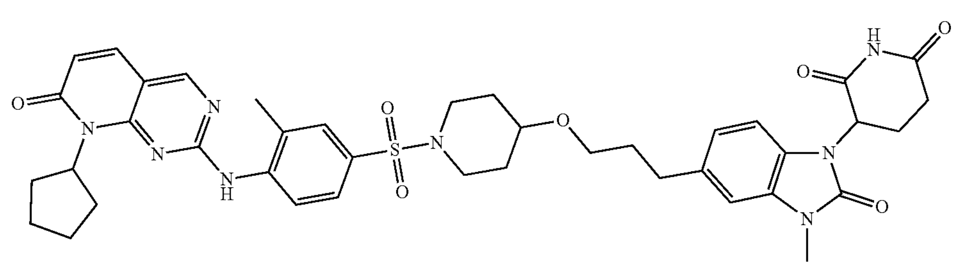 [SMILES: Cc1cc(S(=O)(=O)N2CCC(OCCCc3ccc4c(c3)n(C)c(=O)n4C3CCC(=O)NC3=O)CC2)ccc1Nc1ncc2ccc(=O)n(C3CCCC3)c2n1] |

TABLE 1-continued

Exemplary Compounds

| I-# | Structure |
|---|---|
| I-128 | 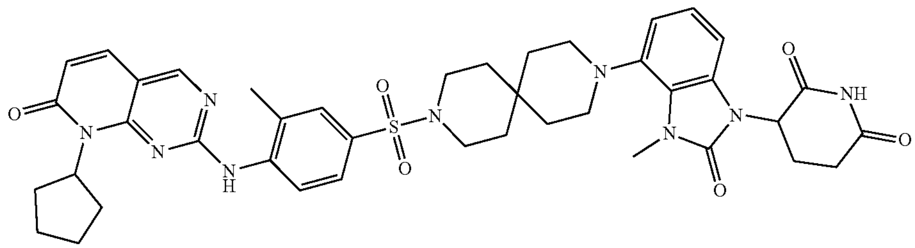 [SMILES: Cc1cc(S(=O)(=O)N2CCC3(CCN(c4cccc5c4n(C)c(=O)n5C4CCC(=O)NC4=O)CC3)CC2)ccc1Nc1ncc2ccc(=O)n(C3CCCC3)c2n1] |
| I-129 | 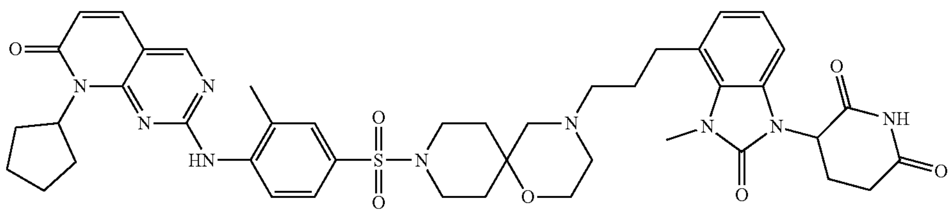 [SMILES: Cc1cc(S(=O)(=O)N2CCC3(CC2)CN(CCCc2cccc4c2n(C)c(=O)n4C2CCC(=O)NC2=O)CCO3)ccc1Nc1ncc2ccc(=O)n(C3CCCC3)c2n1] |
| I-130 | 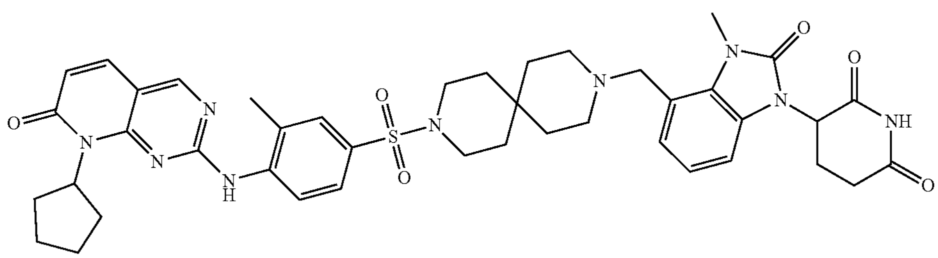 [SMILES: Cc1cc(S(=O)(=O)N2CCC3(CCN(Cc4cccc5c4n(C)c(=O)n5C4CCC(=O)NC4=O)CC3)CC2)ccc1Nc1ncc2ccc(=O)n(C3CCCC3)c2n1] |
| I-131 | 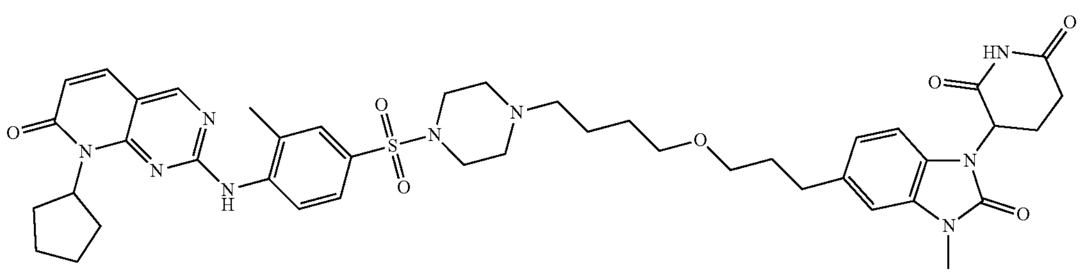 [SMILES: Cc1cc(S(=O)(=O)N2CCN(CCCCOCCCc3ccc4c(c3)n(C)c(=O)n4C3CCC(=O)NC3=O)CC2)ccc1Nc1ncc2ccc(=O)n(C3CCCC3)c2n1] |
| I-132 | 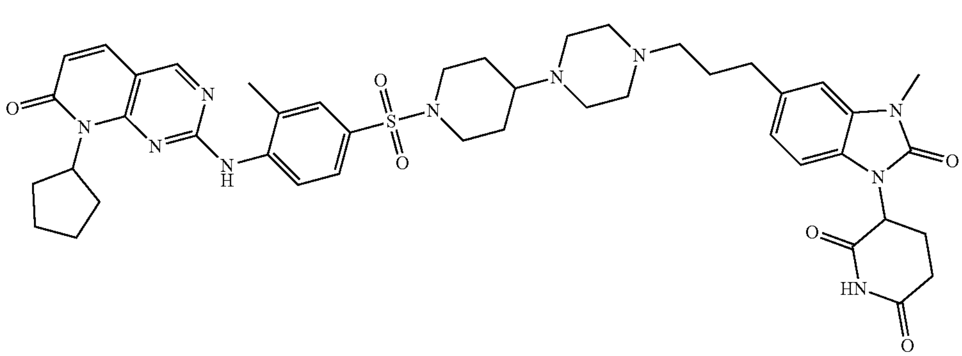 [SMILES: Cc1cc(S(=O)(=O)N2CCC(N3CCN(CCCc4ccc5c(c4)n(C)c(=O)n5C4CCC(=O)NC4=O)CC3)CC2)ccc1Nc1ncc2ccc(=O)n(C3CCCC3)c2n1] |

TABLE 1-continued

Exemplary Compounds

| I-# | Structure |
|---|---|
| I-133 | 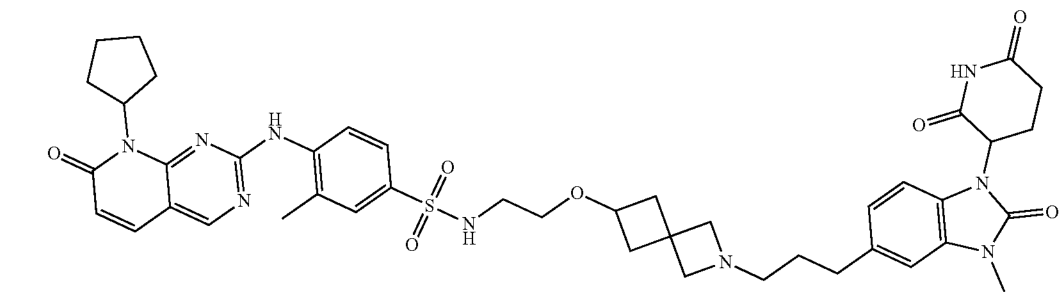 [SMILES: Cc1cc(S(=O)(=O)NCCOC2CC3(C2)CN(CCCc2ccc4c(c2)n(C)c(=O)n4C2CCC(=O)NC2=O)C3)ccc1Nc1ncc2ccc(=O)n(C3CCCC3)c2n1] |
| I-134 | 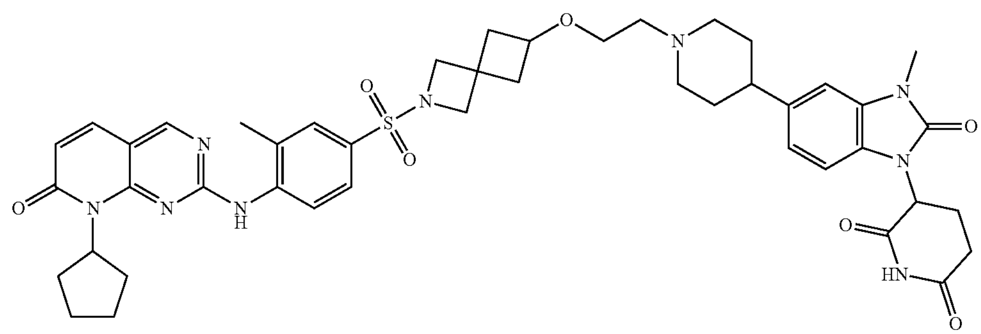 [SMILES: Cc1cc(S(=O)(=O)N2CC3(CC(OCCN4CCC(c5ccc6c(c5)n(C)c(=O)n6C5CCC(=O)NC5=O)CC4)C3)C2)ccc1Nc1ncc2ccc(=O)n(C3CCCC3)c2n1] |
| I-135 | 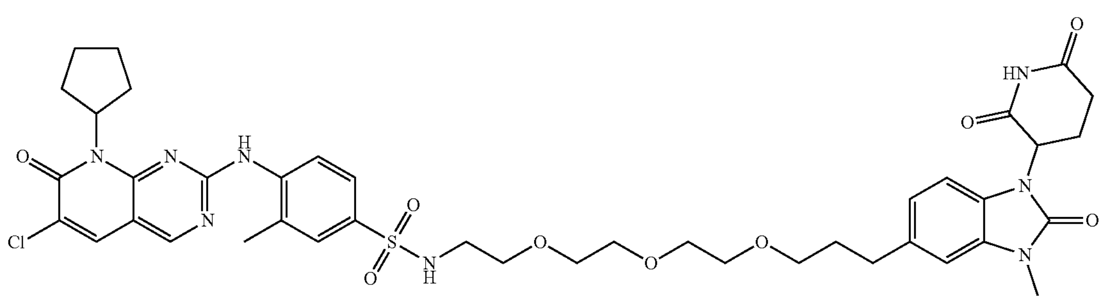 [SMILES: Cc1cc(S(=O)(=O)NCCOCCOCCOCCCc2ccc3c(c2)n(C)c(=O)n3C2CCC(=O)NC2=O)ccc1Nc1ncc2cc(Cl)c(=O)n(C3CCCC3)c2n1] |
| I-136 | 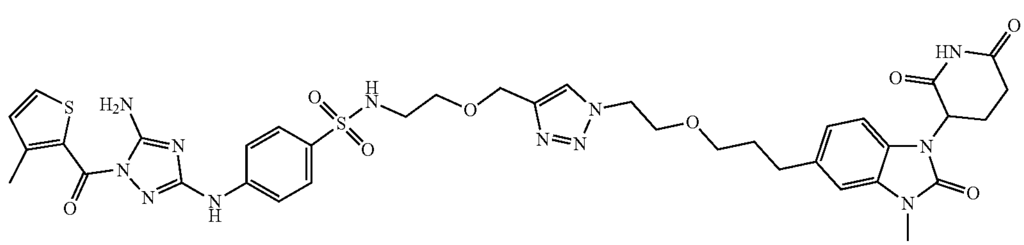 [SMILES: Cc1ccsc1C(=O)n1nc(Nc2ccc(S(=O)(=O)NCCOCc3cn(CCOCCCc4ccc5c(c4)n(C)c(=O)n5C4CCC(=O)NC4=O)nn3)cc2)nc1N] |
| I-137 | 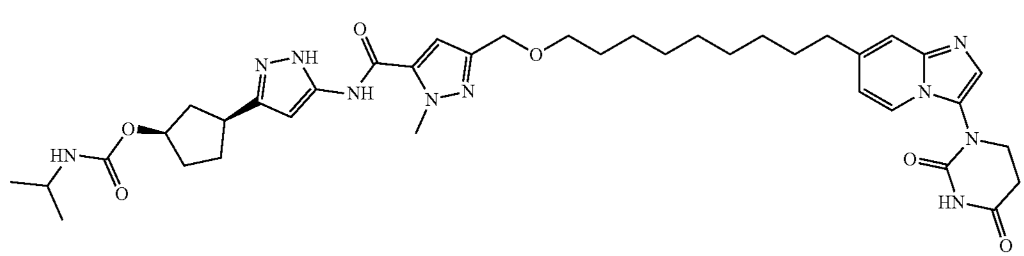 [SMILES: CC(C)NC(=O)O[C@@H]1CC[C@H](c2cc(NC(=O)c3cc(COCCCCCCCCCc4ccn5c(N6CCC(=O)NC6=O)cnc5c4)nn3C)[nH]n2)C1] |

TABLE 1-continued

Exemplary Compounds

| I-# | Structure |
|---|---|
| I-138 | 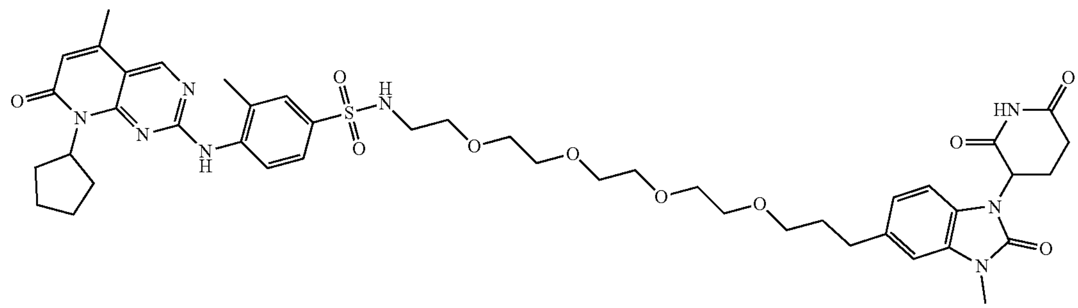 [SMILES: Cc1cc(S(=O)(=O)NCCOCCOCCOCCOCCCc2ccc3c(c2)n(C)c(=O)n3C2CCC(=O)NC2=O)ccc1Nc1ncc2c(C)cc(=O)n(C3CCCC3)c2n1] |
| I-139 | 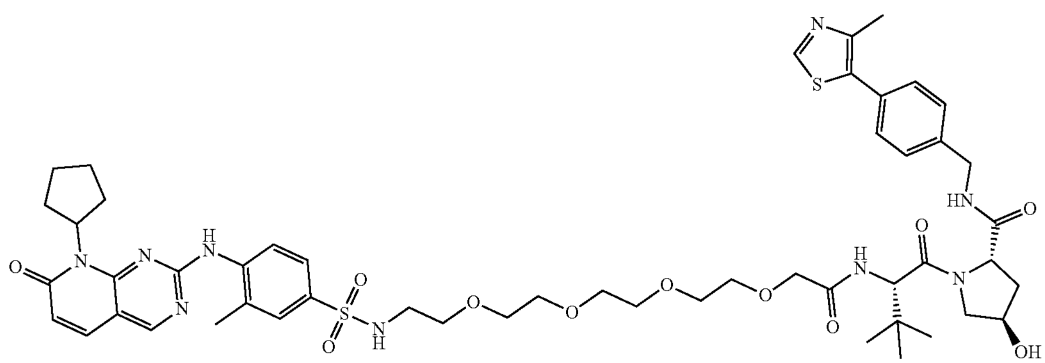 [SMILES: Cc1cc(S(=O)(=O)NCCOCCOCCOCCOCC(=O)N[C@H](C(=O)N2C[C@H](O)C[C@H]2C(=O)NCc2ccc(-c3scnc3C)cc2)C(C)(C)C)ccc1Nc1ncc2ccc(=O)n(C3CCCC3)c2n1] |
| I-140 | 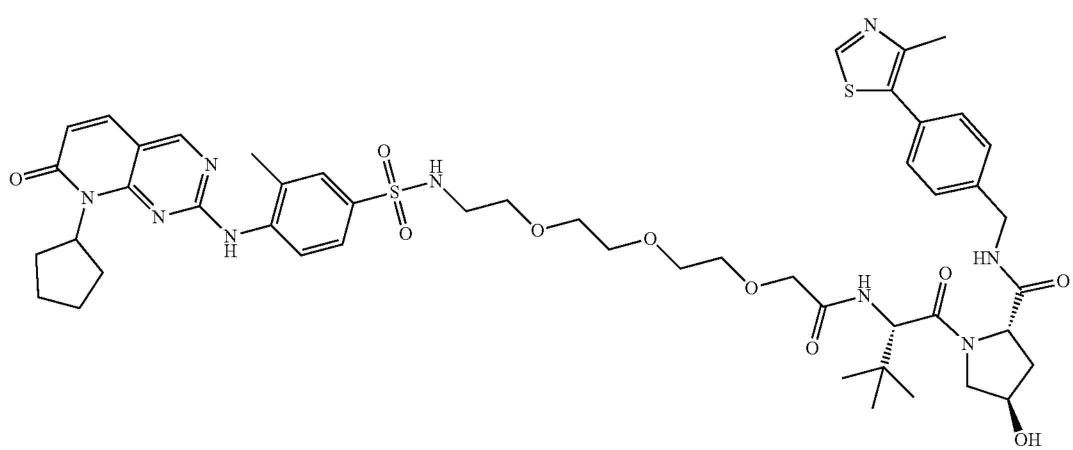 [SMILES: Cc1cc(S(=O)(=O)NCCOCCOCCOCC(=O)N[C@H](C(=O)N2C[C@H](O)C[C@H]2C(=O)NCc2ccc(-c3scnc3C)cc2)C(C)(C)C)ccc1Nc1ncc2ccc(=O)n(C3CCCC3)c2n1] |
| I-141 | 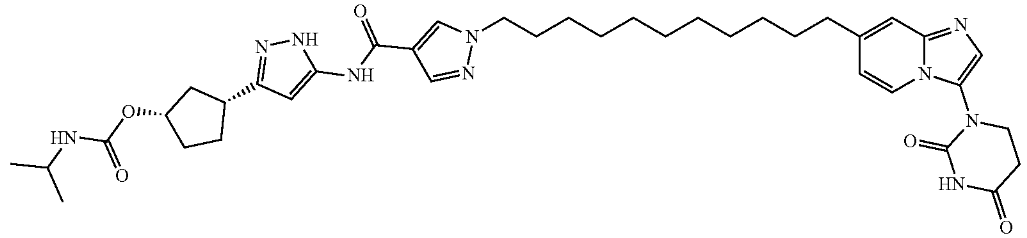 [SMILES: CC(C)NC(=O)O[C@H]1CC[C@@H](c2cc(NC(=O)c3cnn(CCCCCCCCCCCc4ccn5c(N6CCC(=O)NC6=O)cnc5c4)c3)[nH]n2)C1] |

TABLE 1-continued

Exemplary Compounds

| I-# | Structure |
|---|---|
| I-142 | 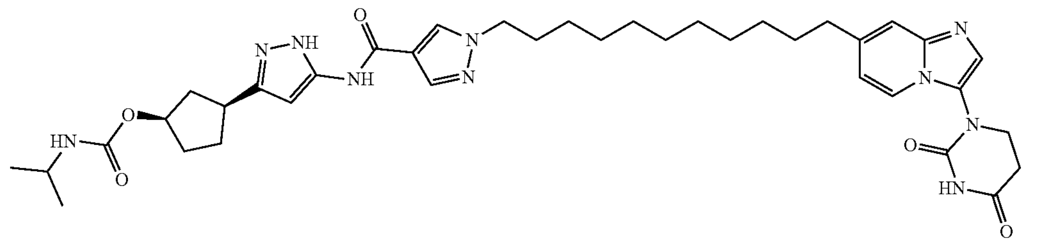 [SMILES: CC(C)NC(=O)O[C@@H]1CC[C@H](c2cc(NC(=O)c3cnn(CCCCCCCCCCCc4ccn5c(N6CCC(=O)NC6=O)cnc5c4)c3)[nH]n2)C1] |
| I-143 | 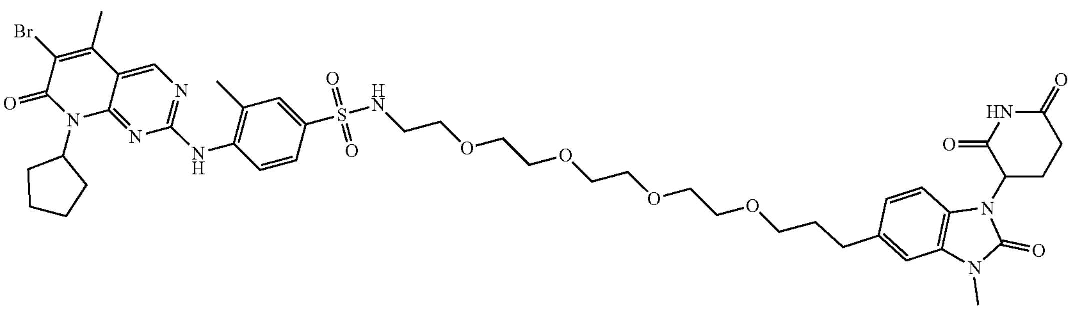 [SMILES: Cc1cc(S(=O)(=O)NCCOCCOCCOCCOCCCc2ccc3c(c2)n(C)c(=O)n3C2CCC(=O)NC2=O)ccc1Nc1ncc2c(C)c(Br)c(=O)n(C3CCCC3)c2n1] |
| I-144 | 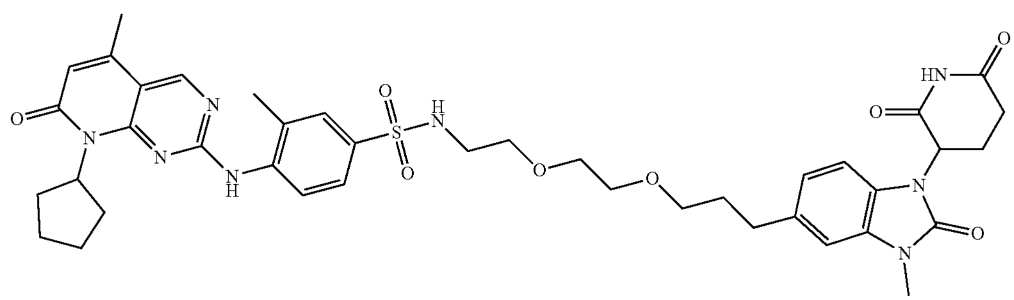 [SMILES: Cc1cc(S(=O)(=O)NCCOCCOCCCc2ccc3c(c2)n(C)c(=O)n3C2CCC(=O)NC2=O)ccc1Nc1ncc2c(C)cc(=O)n(C3CCCC3)c2n1] |
| I-145 | 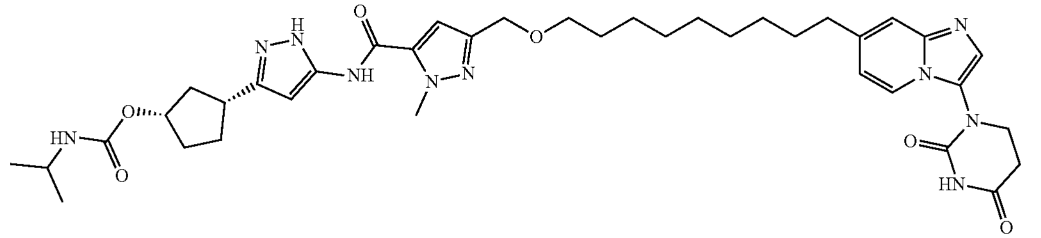 [SMILES: CC(C)NC(=O)O[C@H]1CC[C@@H](c2cc(NC(=O)c3cc(COCCCCCCCCCc4ccn5c(N6CCC(=O)NC6=O)cnc5c4)nn3C)[nH]n2)C1] |
| I-146 | 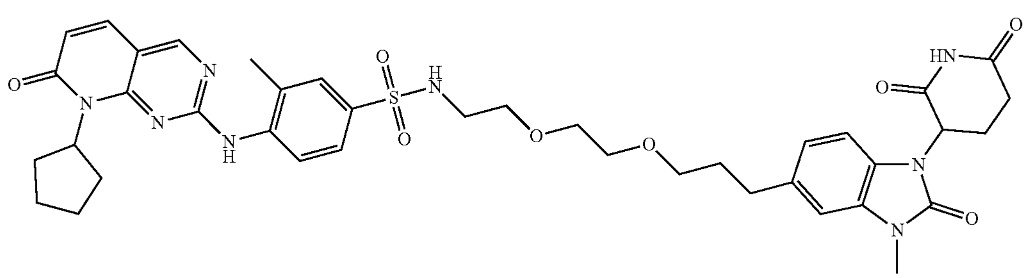 [SMILES: Cc1cc(S(=O)(=O)NCCOCCOCCCc2ccc3c(c2)n(C)c(=O)n3C2CCC(=O)NC2=O)ccc1Nc1ncc2ccc(=O)n(C3CCCC3)c2n1] |

TABLE 1-continued

Exemplary Compounds

| I-# | Structure |
|---|---|
| I-147 | 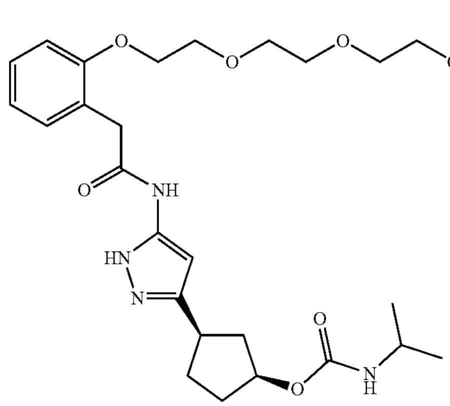 |
| I-148 | 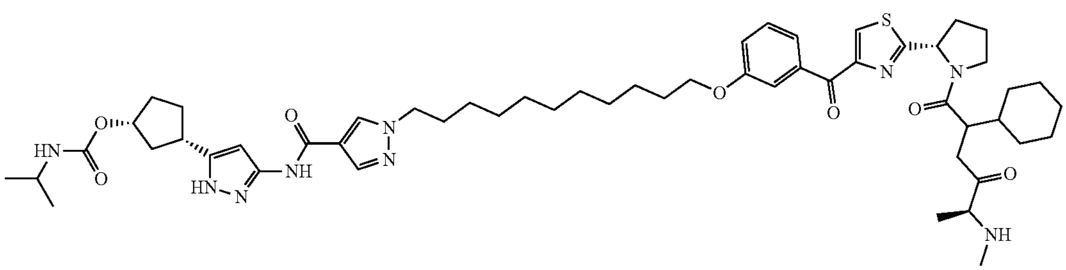 [SMILES: CN[C@@H](C)C(=O)CC(C(=O)N1CCC[C@H]1c1nc(C(=O)c2cccc(OCCCCCCCCCCCn3cc(C(=O)Nc4cc([C@H]5CC[C@@H](OC(=O)NC(C)C)C5)[nH]n4)cn3)c2)cs1)C1CCCCC1] |
| I-149 | 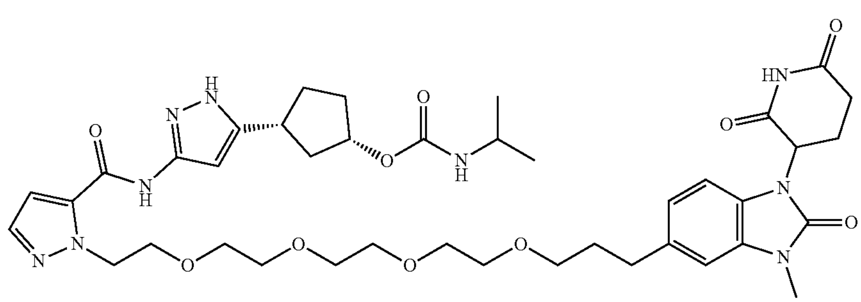 [SMILES: CC(C)NC(=O)O[C@H]1CC[C@@H](c2cc(NC(=O)c3ccnn3CCOCCOCCOCCOCCCc3ccc4c(c3)n(C)c(=O)n4C3CCC(=O)NC3=O)n[nH]2)C1] |
| I-150 | 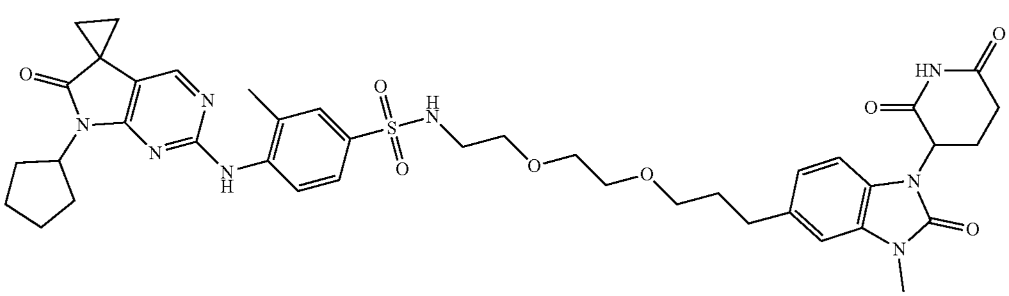 [SMILES: Cc1cc(S(=O)(=O)NCCOCCOCCCc2ccc3c(c2)n(C)c(=O)n3C2CCC(=O)NC2=O)ccc1Nc1ncc2c(n1)N(C1CCCC1)C(=O)C21CC1] |

TABLE 1-continued
Exemplary Compounds
| I-# | Structure |
|---|---|
| I-151 | 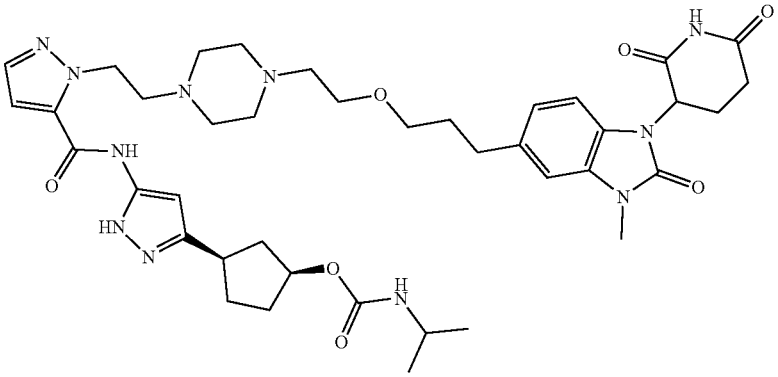 [SMILES: CC(C)NC(=O)O[C@H]1CC[C@@H](c2cc(NC(=O)c3ccnn3CCN3CCN(CCOCCCc4ccc5c(c4)n(C)c(=O)n5C4CCC(=O)NC4=O)CC3)[nH]n2)C1] |
| I-152 | 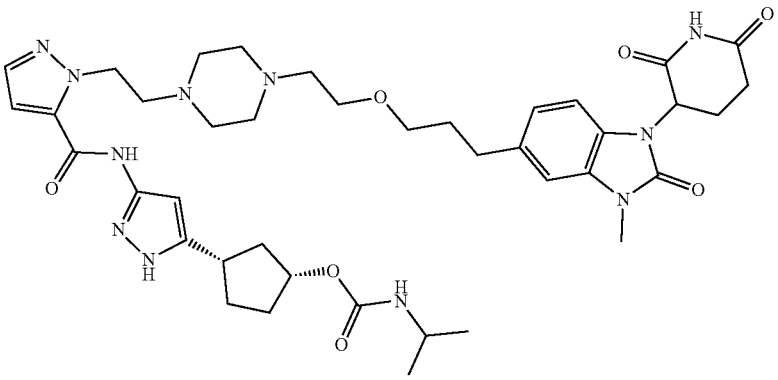 [SMILES: CC(C)NC(=O)O[C@@H]1CC[C@H](c2cc(NC(=O)c3ccnn3CCN3CCN(CCOCCCc4ccc5c(c4)n(C)c(=O)n5C4CCC(=O)NC4=O)CC3)n[nH]2)C1] |
| I-153 | 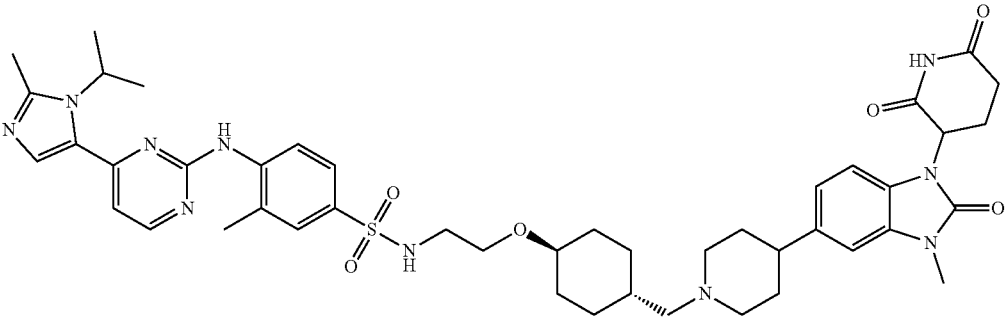 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1nccc(-c2cnc(C)n2C(C)C)n1] |
| I-154 | 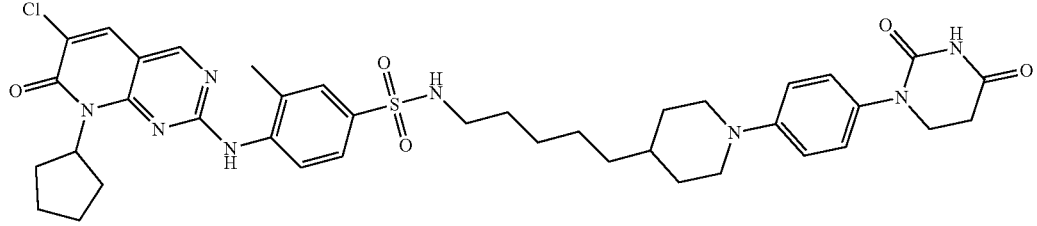 [SMILES: Cc1cc(S(=O)(=O)NCCCCCC2CCN(c3ccc(N4CCC(=O)NC4=O)cc3)CC2)ccc1Nc1ncc2cc(Cl)c(=O)n(C3CCCC3)c2n1] |

//
TABLE 1-continued
Exemplary Compounds
| I-# | Structure |
|---|---|
| I-155 | 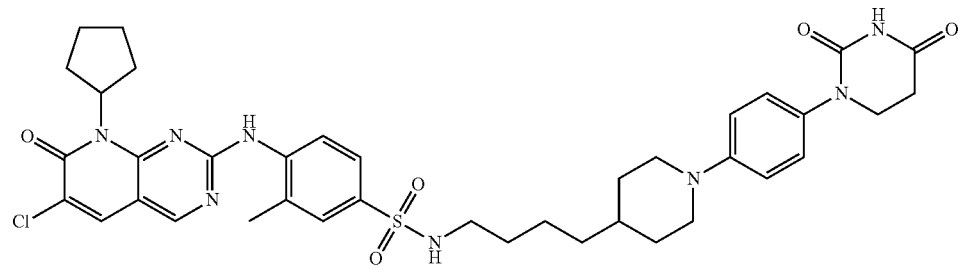 |
| I-156 | 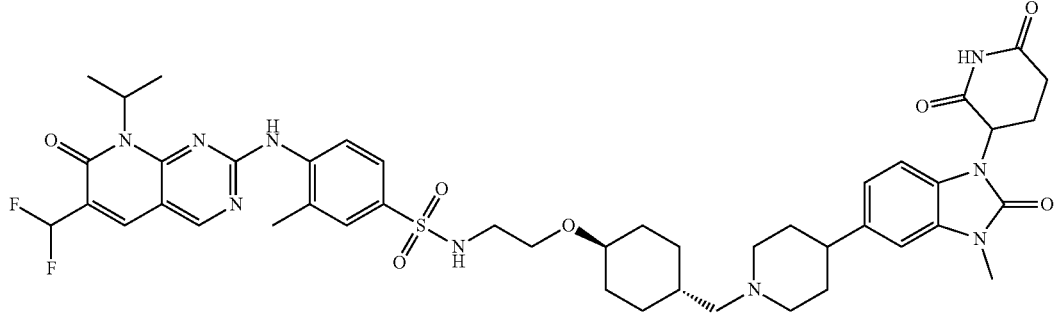 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc2cc(C(F)F)c(=O)n(C(C)C)c2n1] |
| I-157 | 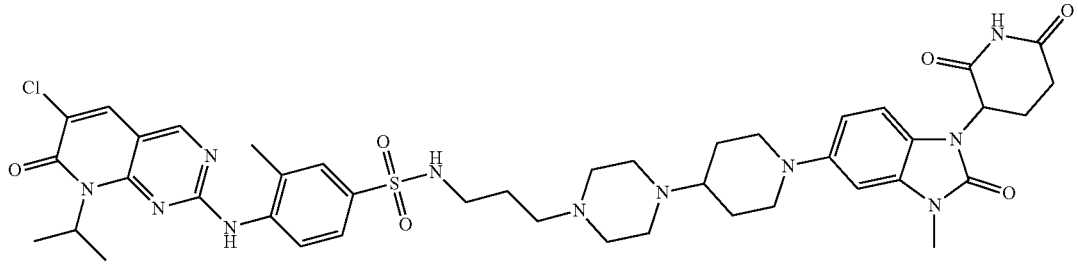 [SMILES: Cc1cc(S(=O)(=O)NCCCN2CCN(C3CCN(c4ccc5c(c4)n(C)c(=O)n5C4CCC(=O)NC4=O)CC3)CC2)ccc1Nc1ncc2cc(Cl)c(=O)n(C(C)C)c2n1] |
| I-158 | 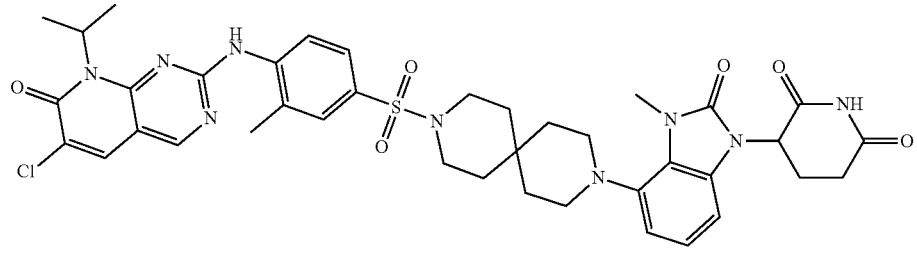 [SMILES: Cc1cc(S(=O)(=O)N2CCC3(CCN(c4cccc5c4n(C)c(=O)n5C4CCC(=O)NC4=O)CC3)CC2)ccc1Nc1ncc2cc(Cl)c(=O)n(C(C)C)c2n1] |
| I-159 | 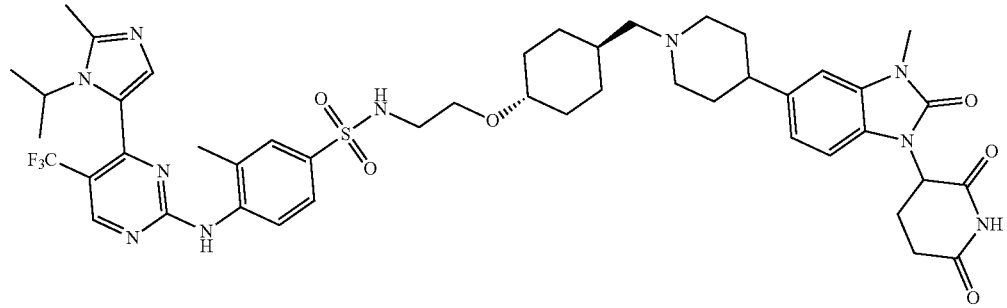 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc(C(F)(F)F)c(-c2cnc(C)n2C(C)C)n1] |

TABLE 1-continued

Exemplary Compounds

| I-# | Structure |
|---|---|
| I-160 | 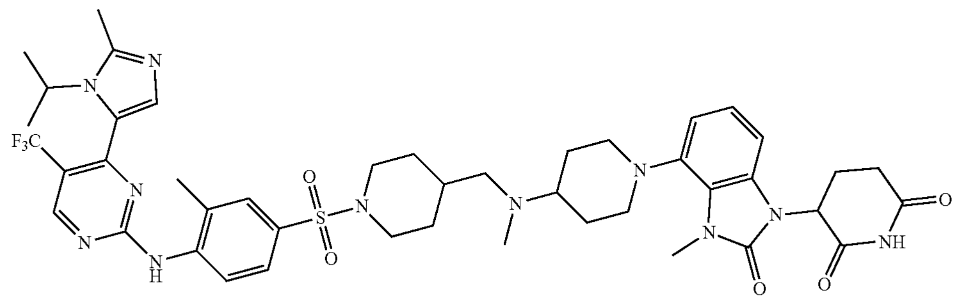 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc(C(F)(F)F)c(-c2cnc(C)n2C(C)C)n1] |
| I-161 | 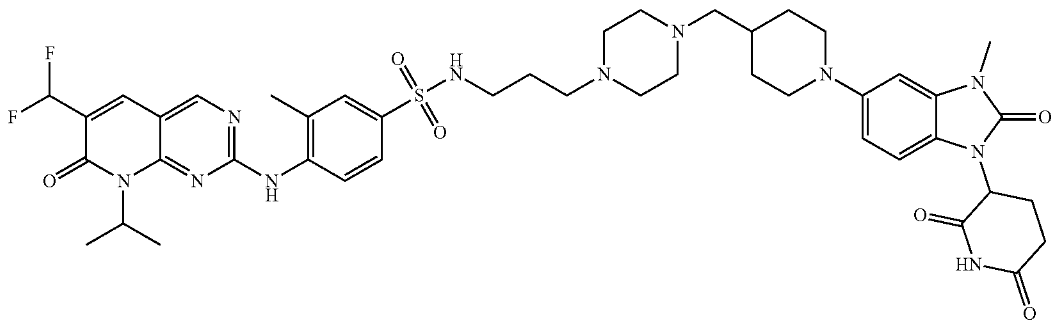 [SMILES: Cc1cc(S(=O)(=O)NCCCN2CCN(CC3CCN(c4ccc5c(c4)n(C)c(=O)n5C4CCC(=O)NC4=O)CC3)CC2)ccc1Nc1ncc2cc(C(F)F)c(=O)n(C(C)C)c2n1] |
| I-162 | 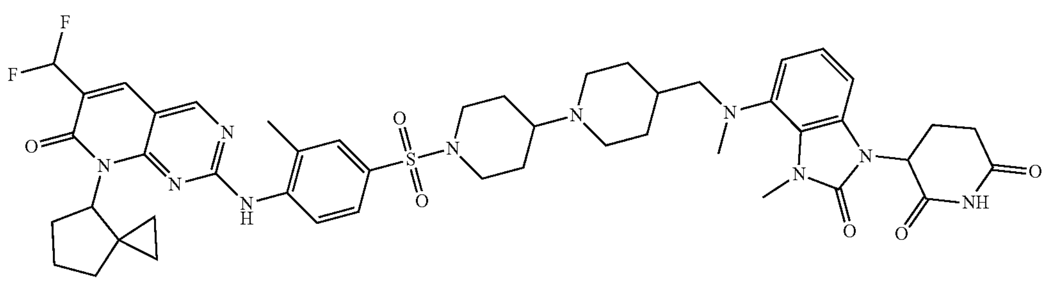 [SMILES: Cc1cc(S(=O)(=O)N2CCC(N3CCC(CN(C)c4cccc5c4n(C)c(=O)n5C4CCC(=O)NC4=O)CC3)CC2)ccc1Nc1ncc2cc(C(F)F)c(=O)n(C3CCCC34CC4)c2n1] |
| I-163 | 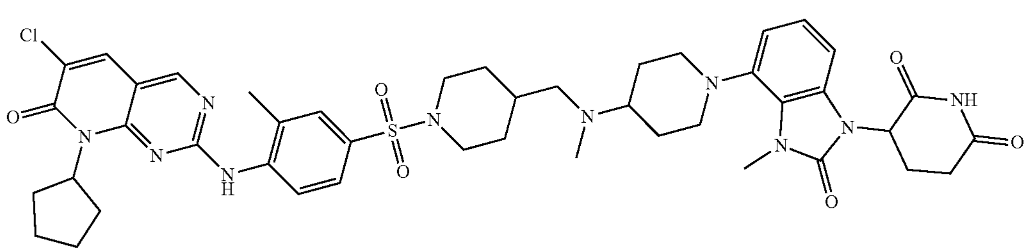 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2cc(Cl)c(=O)n(C3CCCC3)c2n1] |
| I-164 | 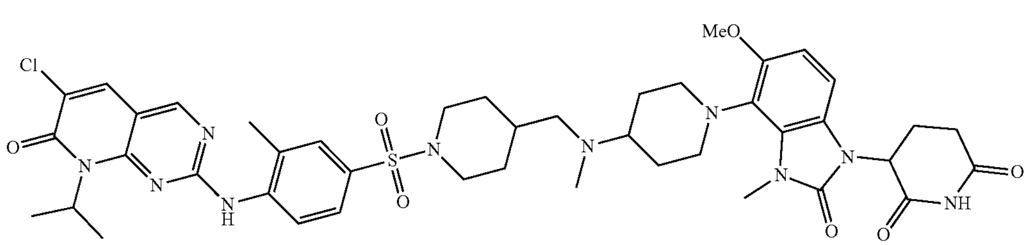 [SMILES: COc1ccc2c(c1N1CCC(N(C)CC3CCN(S(=O)(=O)c4ccc(Nc5ncc6cc(Cl)c(=O)n(C(C)C)c6n5)c(C)c4)CC3)CC1)n(C)c(=O)n2C1CCC(=O)NC1=O] |

TABLE 1-continued

Exemplary Compounds

| I-# | Structure |
|---|---|
| I-165 | 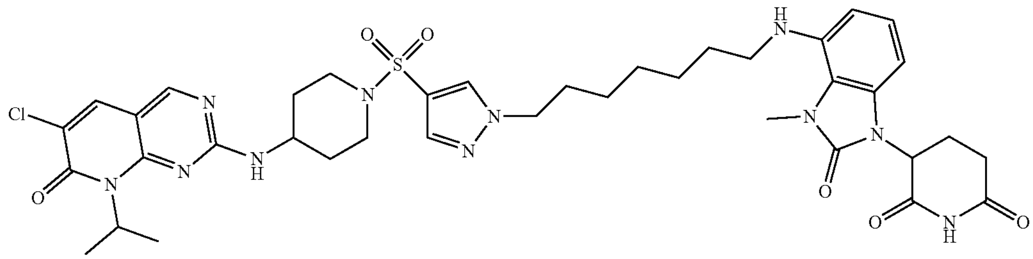 [SMILES: CC(C)n1c(=O)c(Cl)cc2cnc(NC3CCN(S(=O)(=O)c4cnn(CCCCCCCNc5cccc6c5n(C)c(=O)n6C5CCC(=O)NC5=O)c4)CC3)nc21] |
| I-166 | 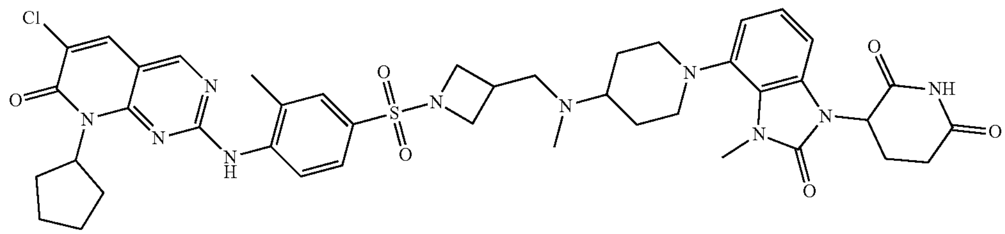 [SMILES: Cc1cc(S(=O)(=O)N2CC(CN(C)C3CCN(c4cccc5c4n(C)c(=O)n5C4CCC(=O)NC4=O)CC3)C2)ccc1Nc1ncc2cc(Cl)c(=O)n(C3CCCC3)c2n1] |
| I-167 | 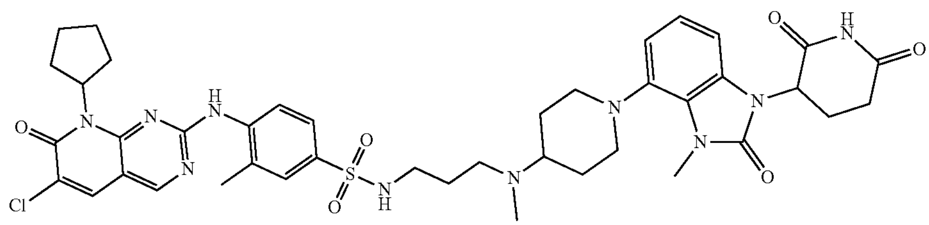 [SMILES: Cc1cc(S(=O)(=O)NCCCN(C)C2CCN(c3cccc4c3n(C)c(=O)n4C3CCC(=O)NC3=O)CC2)ccc1Nc1ncc2cc(Cl)c(=O)n(C3CCCC3)c2n1] |
| I-168 | 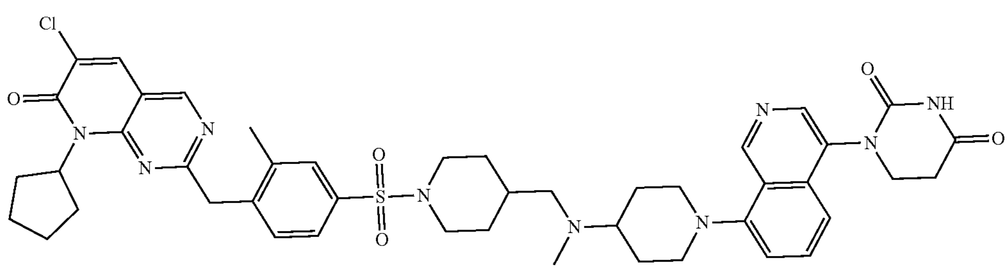 [SMILES: Cc1cc(S(=O)(=O)N2CCC(CN(C)C3CCN(c4cccc5c(N6CCC(=O)NC6=O)cncc45)CC3)CC2)ccc1Cc1ncc2cc(Cl)c(=O)n(C3CCCC3)c2n1] |
| I-169 | 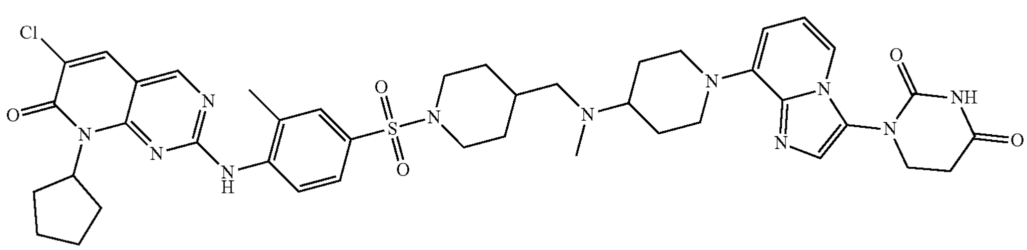 [SMILES: Cc1cc(S(=O)(=O)N2CCC(CN(C)C3CCN(c4cccn5c(N6CCC(=O)NC6=O)cnc45)CC3)CC2)ccc1Nc1ncc2cc(Cl)c(=O)n(C3CCCC3)c2n1] |
| I-170 | 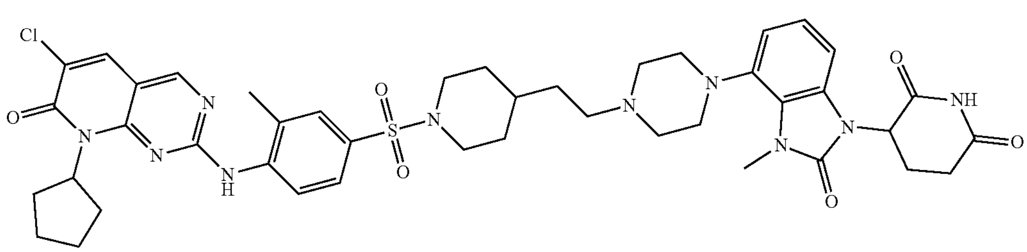 [SMILES: Cc1cc(S(=O)(=O)N2CCC(CCN3CCN(c4cccc5c4n(C)c(=O)n5C4CCC(=O)NC4=O)CC3)CC2)ccc1Nc1ncc2cc(Cl)c(=O)n(C3CCCC3)c2n1] |

TABLE 1-continued

Exemplary Compounds

| I-# | Structure |
| --- | --- |
| I-171 | 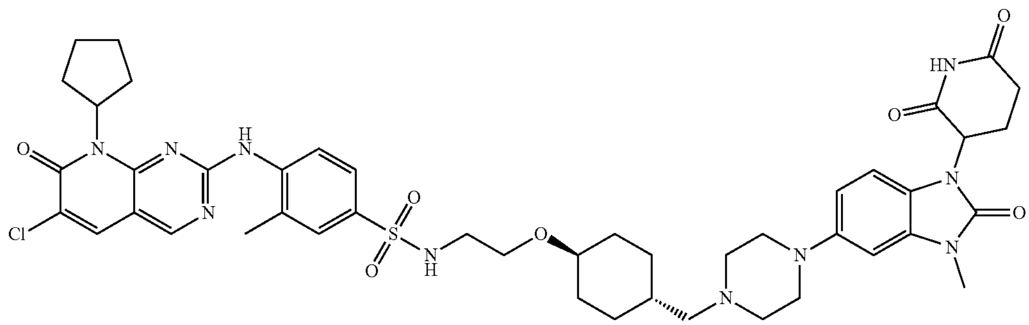 [SMILES: Cc1cc(S(=O)(=O)NCCO[C@H]2CC[C@H](CN3CCN(c4ccc5c(c4)n(C)c(=O)n5C4CCC(=O)NC4=O)CC3)CC2)ccc1Nc1ncc2cc(Cl)c(=O)n(C3CCCC3)c2n1] |
| I-172 | 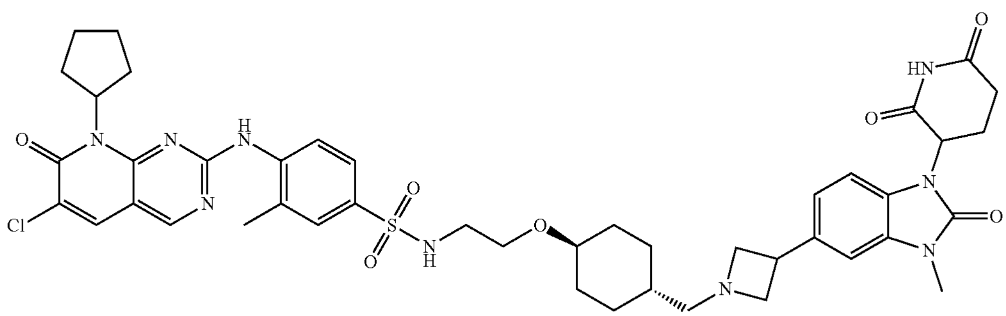 [SMILES: Cc1cc(S(=O)(=O)NCCO[C@H]2CC[C@H](CN3CC(c4ccc5c(c4)n(C)c(=O)n5C4CCC(=O)NC4=O)C3)CC2)ccc1Nc1ncc2cc(Cl)c(=O)n(C3CCCC3)c2n1] |
| I-173 | 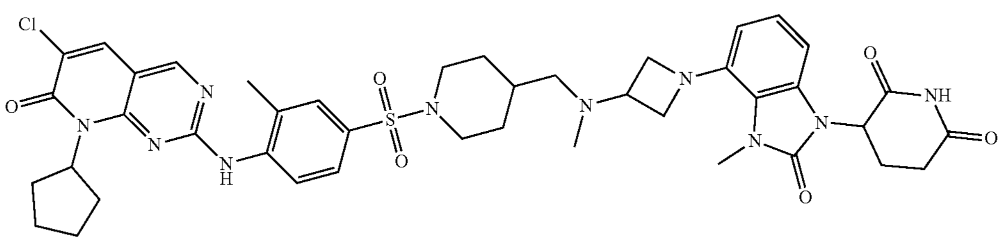 [SMILES: Cc1cc(S(=O)(=O)N2CCC(CN(C)C3CN(c4cccc5c4n(C)c(=O)n5C4CCC(=O)NC4=O)C3)CC2)ccc1Nc1ncc2cc(Cl)c(=O)n(C3CCCC3)c2n1] |
| I-174 | 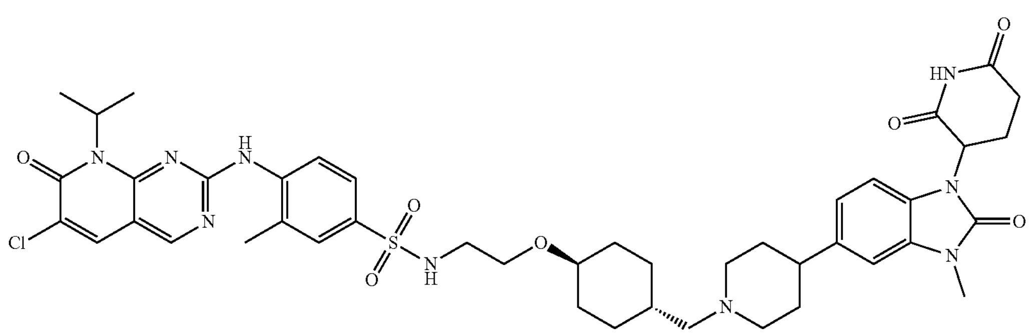 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc2cc(Cl)c(=O)n(C(C)C)c2n1] |
| I-175 | 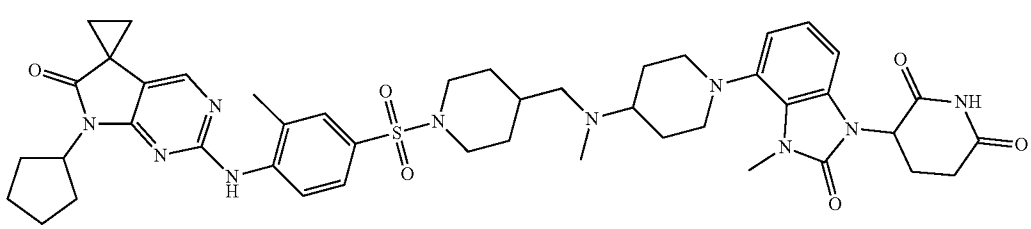 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2c(n1)N(C1CCCC1)C(=O)C21CC1] |

TABLE 1-continued

Exemplary Compounds

| I-# | Structure |
|---|---|
| I-176 | 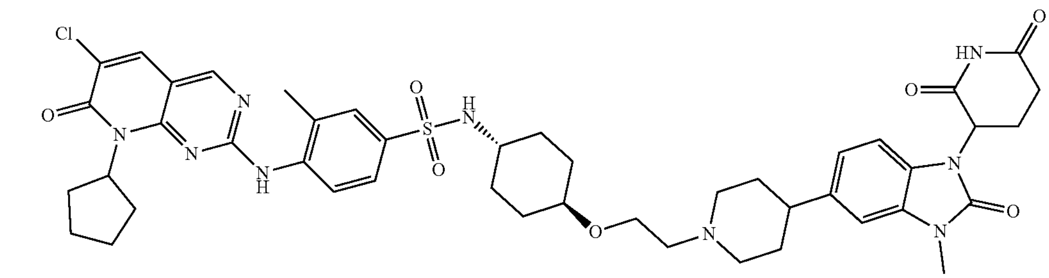 [SMILES: Cc1cc(S(=O)(=O)N[C@H]2CC[C@H](OCCN3CCC(c4ccc5c(c4)n(C)c(=O)n5C4CCC(=O)NC4=O)CC3)CC2)ccc1Nc1ncc2cc(Cl)c(=O)n(C3CCCC3)c2n1] |
| I-177 | 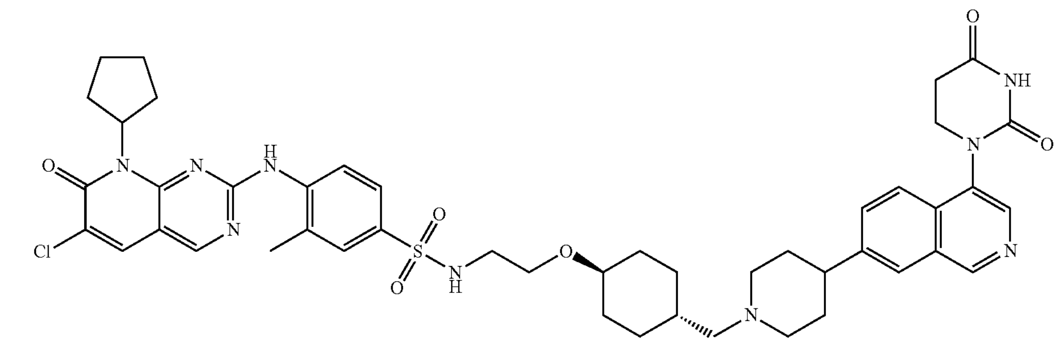 [SMILES: Cc1cc(S(=O)(=O)NCCO[C@H]2CC[C@H](CN3CCC(c4ccc5c(N6CCC(=O)NC6=O)cncc5c4)CC3)CC2)ccc1Nc1ncc2cc(Cl)c(=O)n(C3CCCC3)c2n1] |
| I-178 | 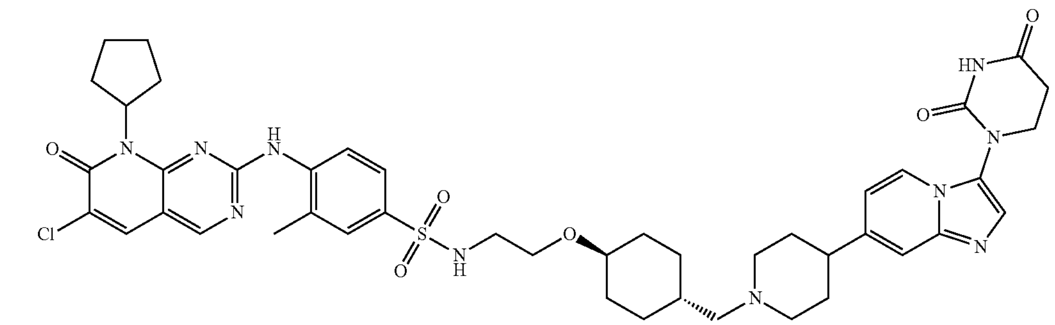 [SMILES: Cc1cc(S(=O)(=O)NCCO[C@H]2CC[C@H](CN3CCC(c4ccn5c(N6CCC(=O)NC6=O)cnc5c4)CC3)CC2)ccc1Nc1ncc2cc(Cl)c(=O)n(C3CCCC3)c2n1] |
| I-179 | 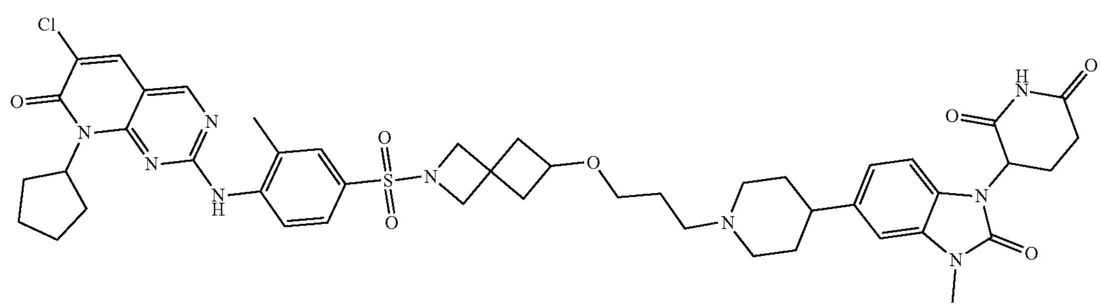 [SMILES: Cc1cc(S(=O)(=O)N2CC3(CC(OCCCN4CCC(c5ccc6c(c5)n(C)c(=O)n6C5CCC(=O)NC5=O)CC4)C3)C2)ccc1Nc1ncc2cc(Cl)c(=O)n(C3CCCC3)c2n1] |
| I-180 | 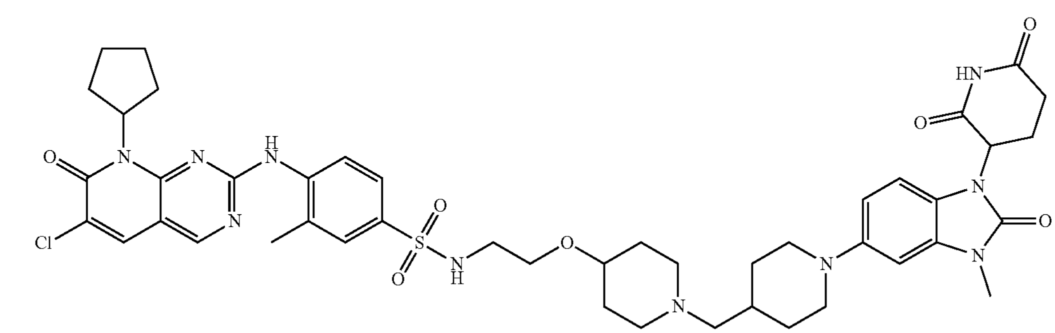 [SMILES: Cc1cc(S(=O)(=O)NCCOC2CCN(CC3CCN(c4ccc5c(c4)n(C)c(=O)n5C4CCC(=O)NC4=O)CC3)CC2)ccc1Nc1ncc2cc(Cl)c(=O)n(C3CCCC3)c2n1] |

TABLE 1-continued

Exemplary Compounds

| I-# | Structure |
|---|---|
| I-181 | 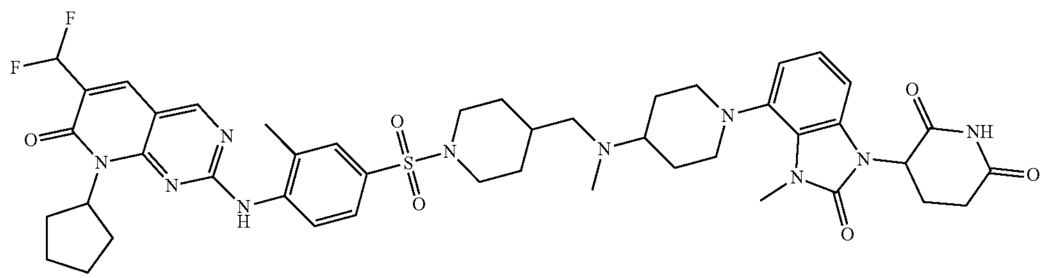 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2cc(C(F)F)c(=O)n(C3CCCC3)c2n1] |
| I-182 | 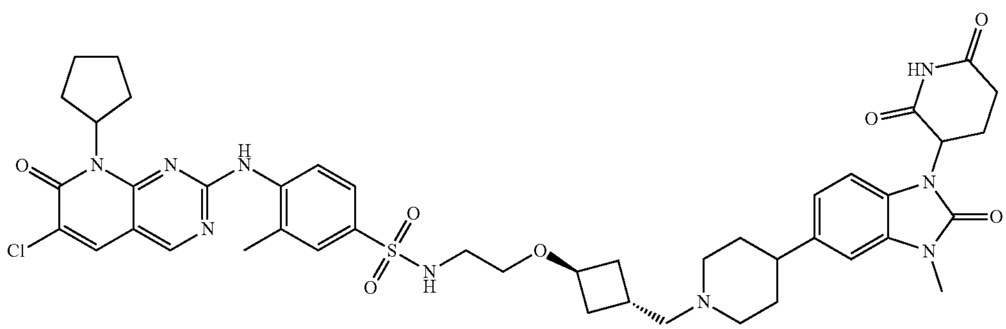 [SMILES: Cc1cc(S(=O)(=O)NCCO[C@H]2C[C@H](CN3CCC(c4ccc5c(c4)n(C)c(=O)n5C4CCC(=O)NC4=O)CC3)C2)ccc1Nc1ncc2cc(Cl)c(=O)n(C3CCCC3)c2n1] |
| I-183 | 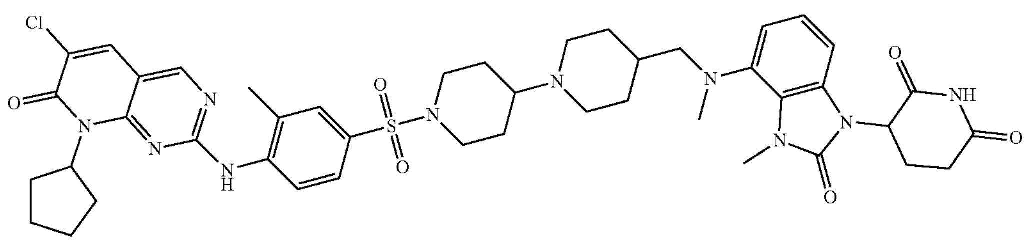 [SMILES: Cc1cc(S(=O)(=O)N2CCC(N3CCC(CN(C)c4cccc5c4n(C)c(=O)n5C4CCC(=O)NC4=O)CC3)CC2)ccc1Nc1ncc2cc(Cl)c(=O)n(C3CCCC3)c2n1] |
| I-184 | 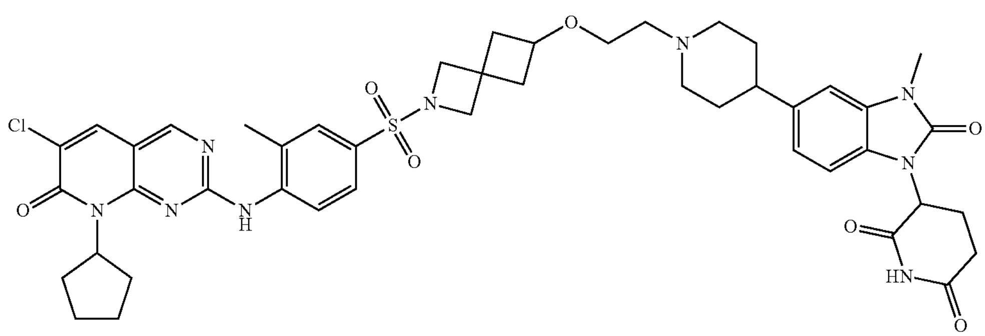 [SMILES: Cc1cc(S(=O)(=O)N2CC3(CC(OCCN4CCC(c5ccc6c(c5)n(C)c(=O)n6C5CCC(=O)NC5=O)CC4)C3)C2)ccc1Nc1ncc2cc(Cl)c(=O)n(C3CCCC3)c2n1] |
| I-185 | 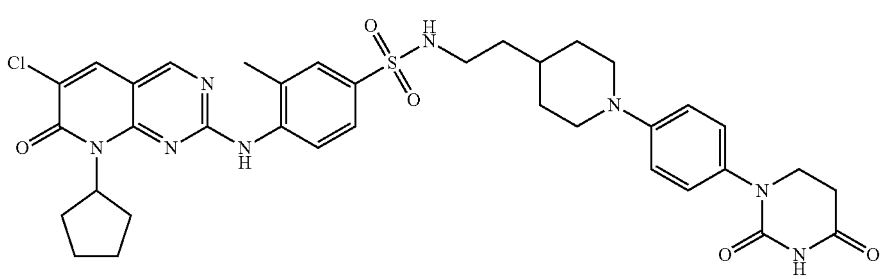 [SMILES: Cc1cc(S(=O)(=O)NCCC2CCN(c3ccc(N4CCC(=O)NC4=O)cc3)CC2)ccc1Nc1ncc2cc(Cl)c(=O)n(C3CCCC3)c2n1] |

TABLE 1-continued

Exemplary Compounds

| I-# | Structure |
|---|---|
| I-186 | 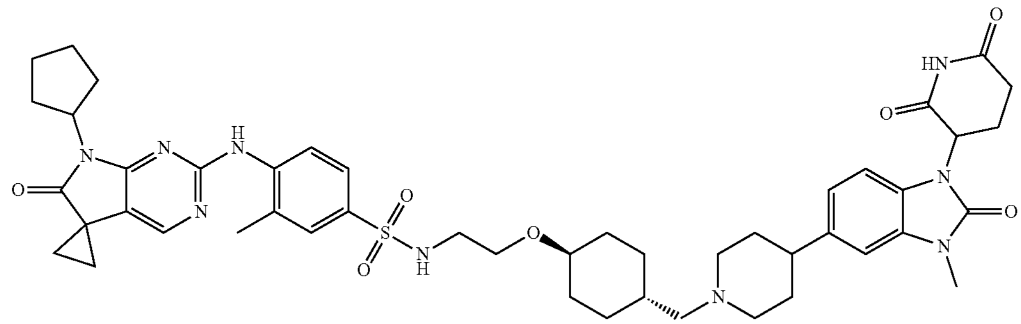 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc2c(n1)N(C1CCCC1)C(=O)C21CC1] |
| I-187 | 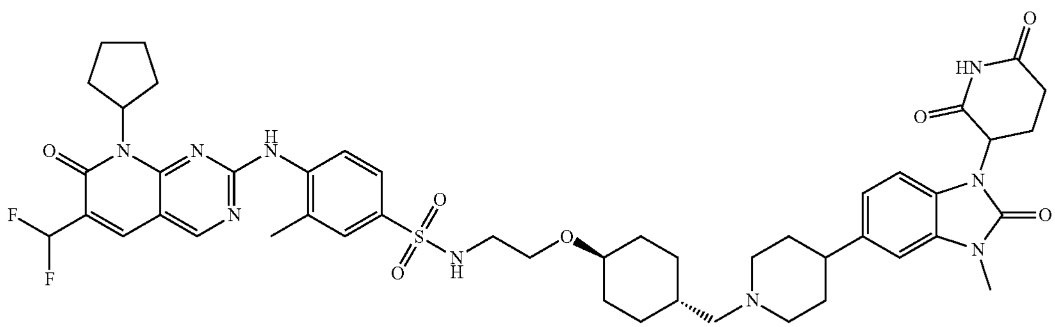 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc2cc(C(F)F)c(=O)n(C3CCCC3)c2n1] |
| I-188 | 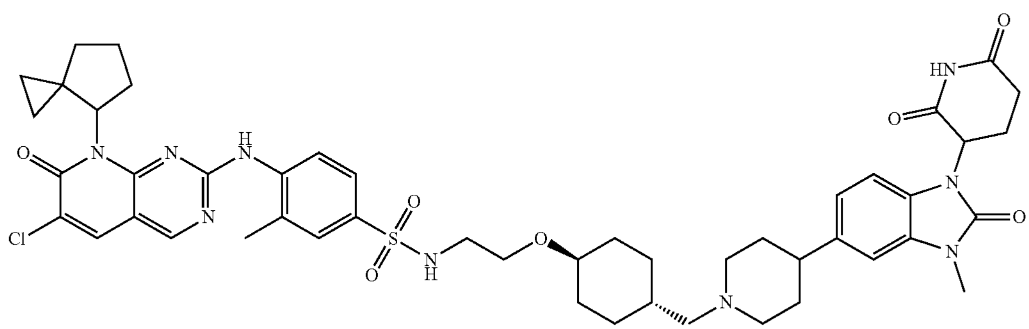 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc2cc(Cl)c(=O)n(C3CCCC34CC4)c2n1] |
| I-189 | 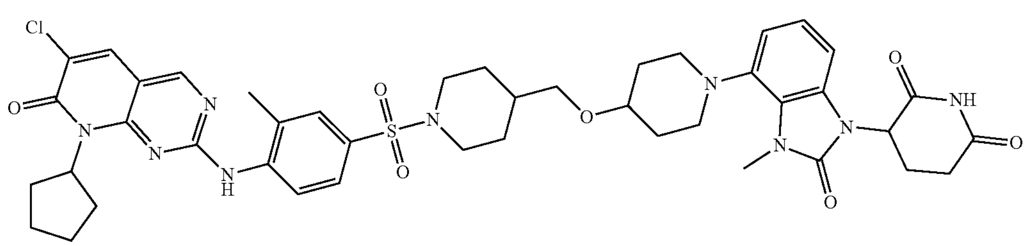 [SMILES: Cc1cc(S(=O)(=O)N2CCC(COC3CCN(c4cccc5c4n(C)c(=O)n5C4CCC(=O)NC4=O)CC3)CC2)ccc1Nc1ncc2cc(Cl)c(=O)n(C3CCCC3)c2n1] |
| I-190 | 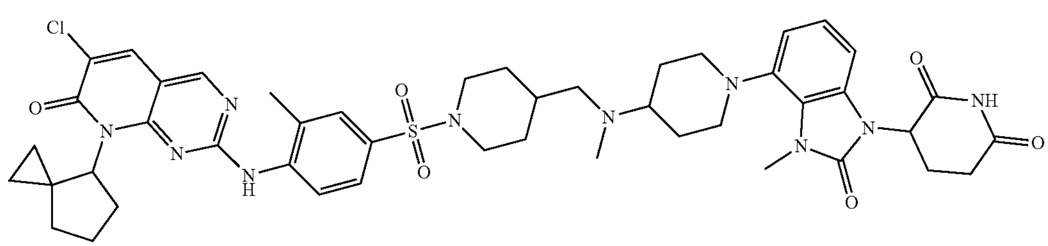 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2cc(Cl)c(=O)n(C3CCCC34CC4)c2n1] |

TABLE 1-continued

Exemplary Compounds

| I-# | Structure |
|---|---|
| I-191 | 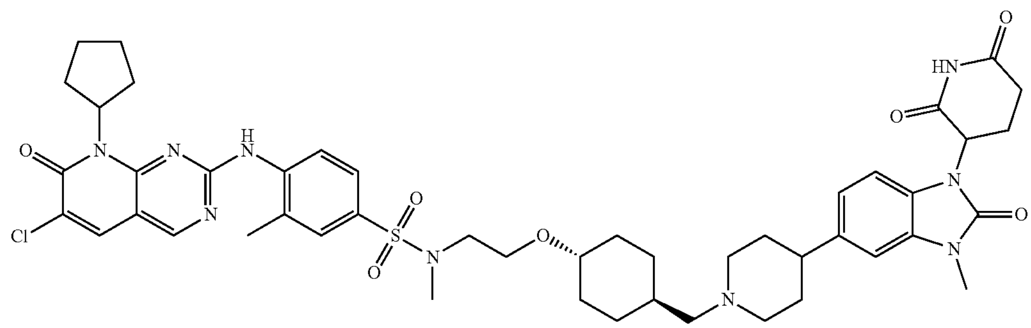 [SMILES: Cc1cc(S(=O)(=O)N(C)CCO[C@H]2CC[C@H](CN3CCC(c4ccc5c(c4)n(C)c(=O)n5C4CCC(=O)NC4=O)CC3)CC2)ccc1Nc1ncc2cc(Cl)c(=O)n(C3CCCC3)c2n1] |
| I-192 | 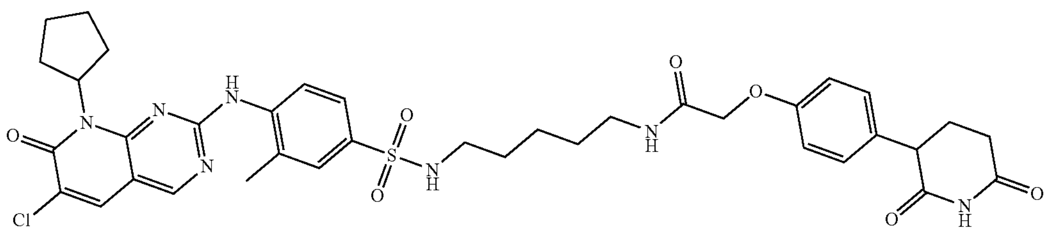 [SMILES: Cc1cc(S(=O)(=O)NCCCCCNC(=O)COc2ccc(C3CCC(=O)NC3=O)cc2)ccc1Nc1ncc2cc(Cl)c(=O)n(C3CCCC3)c2n1] |
| I-193 | 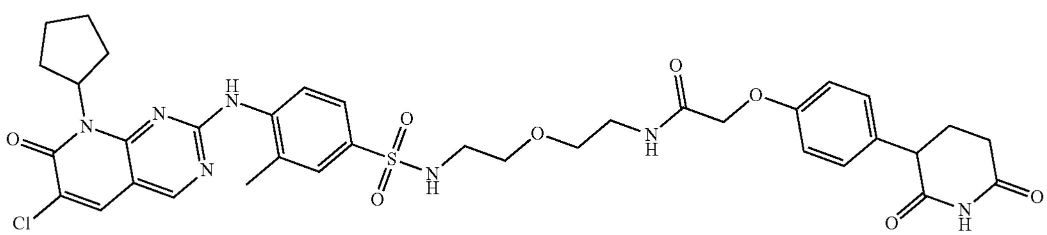 [SMILES: Cc1cc(S(=O)(=O)NCCOCCNC(=O)COc2ccc(C3CCC(=O)NC3=O)cc2)ccc1Nc1ncc2cc(Cl)c(=O)n(C3CCCC3)c2n1] |
| I-194 | 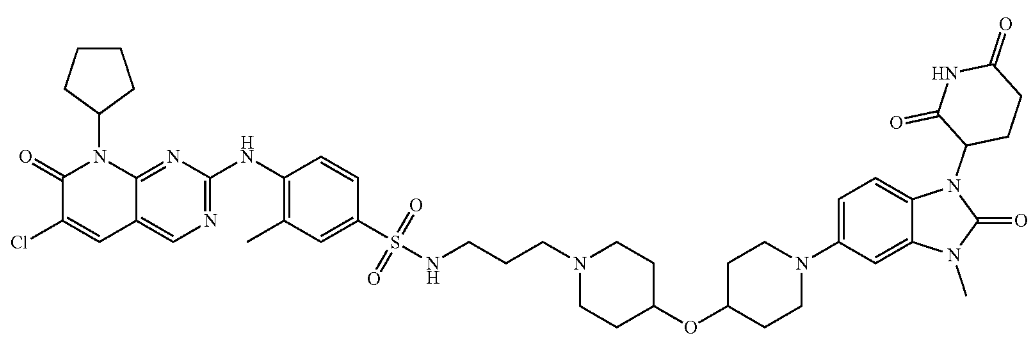 [SMILES: Cc1cc(S(=O)(=O)NCCCN2CCC(OC3CCN(c4ccc5c(c4)n(C)c(=O)n5C4CCC(=O)NC4=O)CC3)CC2)ccc1Nc1ncc2cc(Cl)c(=O)n(C3CCCC3)c2n1] |
| I-195 | 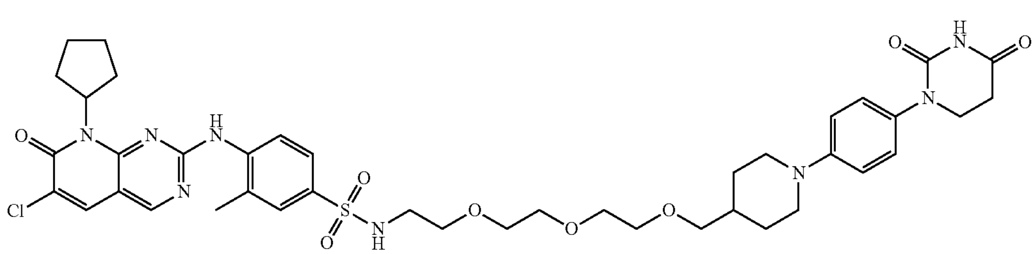 [SMILES: Cc1cc(S(=O)(=O)NCCOCCOCCOCC2CCN(c3ccc(N4CCC(=O)NC4=O)cc3)CC2)ccc1Nc1ncc2cc(Cl)c(=O)n(C3CCCC3)c2n1] |

TABLE 1-continued

Exemplary Compounds

| I-# | Structure |
|---|---|
| I-196 | 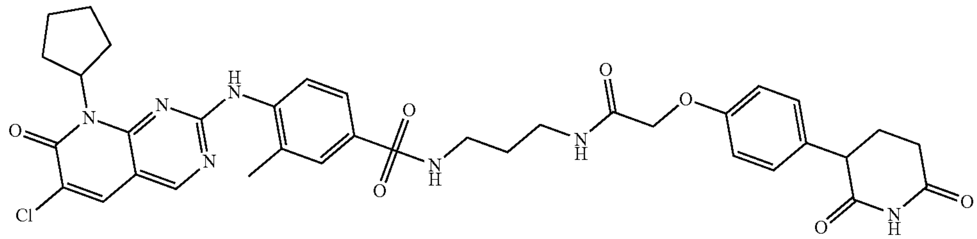 |
| I-197 | 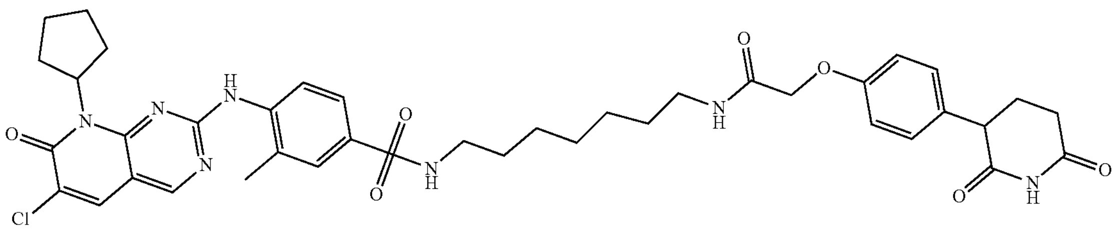 |
| I-198 | 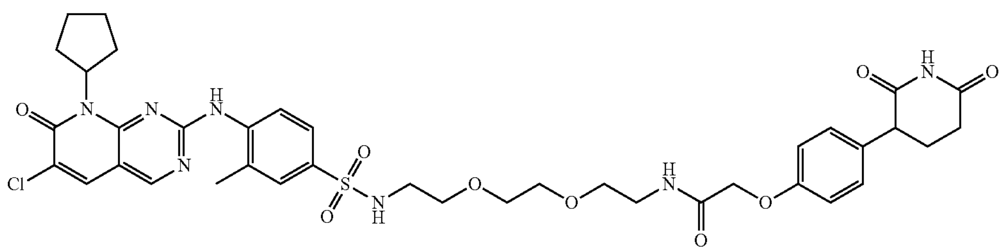 [SMILES: Cc1cc(S(=O)(=O)NCCOCCOCCNC(=O)COc2ccc(C3CCC(=O)NC3=O)cc2)ccc1Nc1ncc2cc(Cl)c(=O)n(C3CCCC3)c2n1] |
| I-199 | 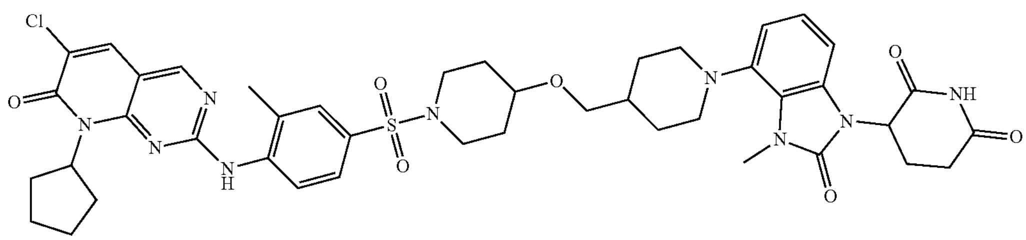 [SMILES: Cc1cc(S(=O)(=O)N2CCC(OCC3CCN(c4cccc5c4n(C)c(=O)n5C4CCC(=O)NC4=O)CC3)CC2)ccc1Nc1ncc2cc(Cl)c(=O)n(C3CCCC3)c2n1] |
| I-200 | 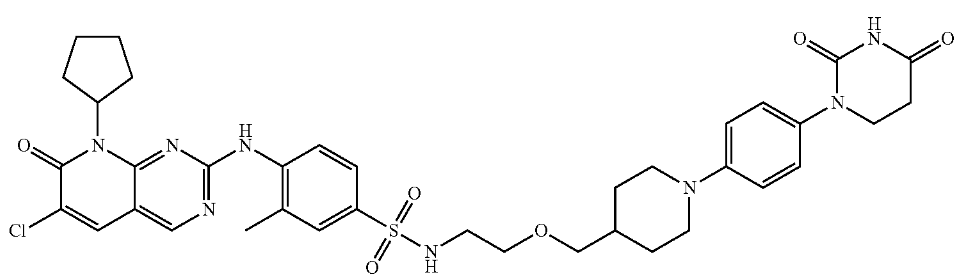 [SMILES: Cc1cc(S(=O)(=O)NCCOCC2CCN(c3ccc(N4CCC(=O)NC4=O)cc3)CC2)ccc1Nc1ncc2cc(Cl)c(=O)n(C3CCCC3)c2n1] |
| I-201 | 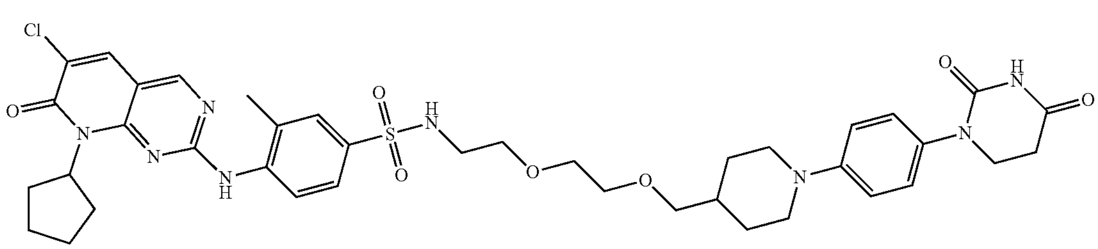 [SMILES: Cc1cc(S(=O)(=O)NCCOCCOCC2CCN(c3ccc(N4CCC(=O)NC4=O)cc3)CC2)ccc1Nc1ncc2cc(Cl)c(=O)n(C3CCCC3)c2n1] |

TABLE 1-continued

Exemplary Compounds

| I-# | Structure |
|---|---|
| I-202 | 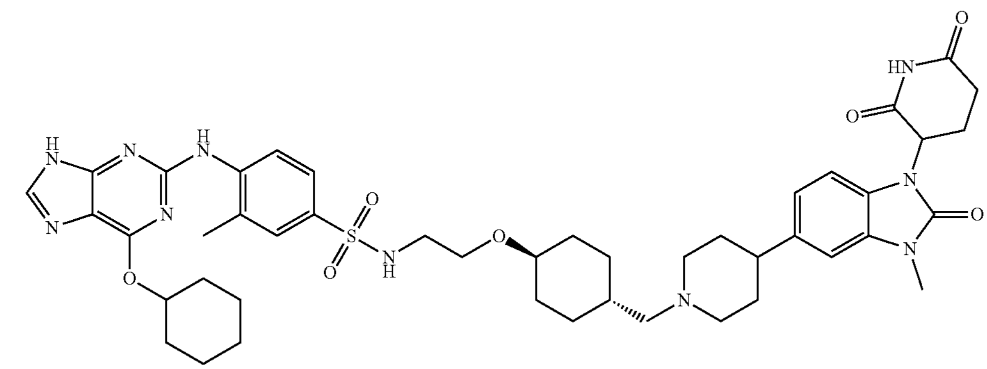 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1nc(OC2CCCCC2)c2nc[nH]c2n1] |
| I-203 | 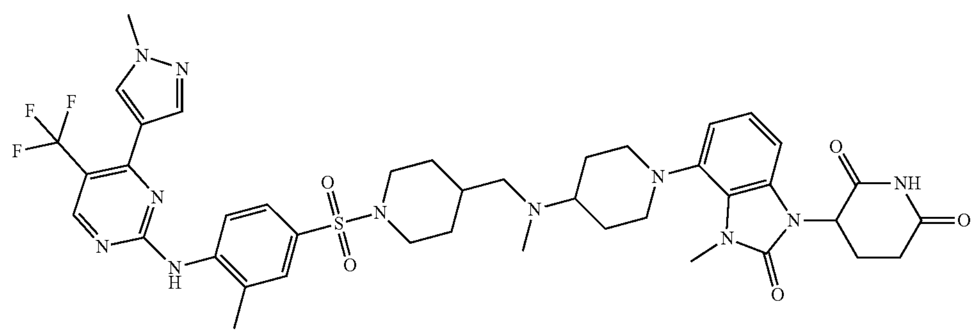 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc(C(F)(F)F)c(-c2cnn(C)c2)n1] |
| I-204 | 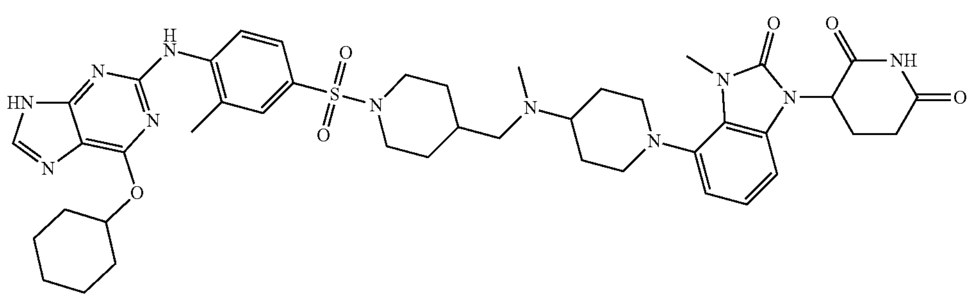 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1nc(OC2CCCCC2)c2nc[nH]c2n1] |
| I-205 | 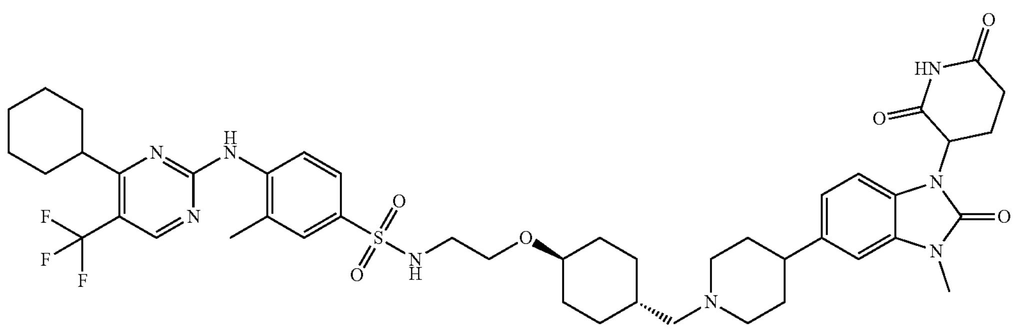 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc(C(F)(F)F)c(C2CCCCC2)n1] |

TABLE 1-continued

Exemplary Compounds

| I-# | Structure |
| --- | --- |
| I-206 | 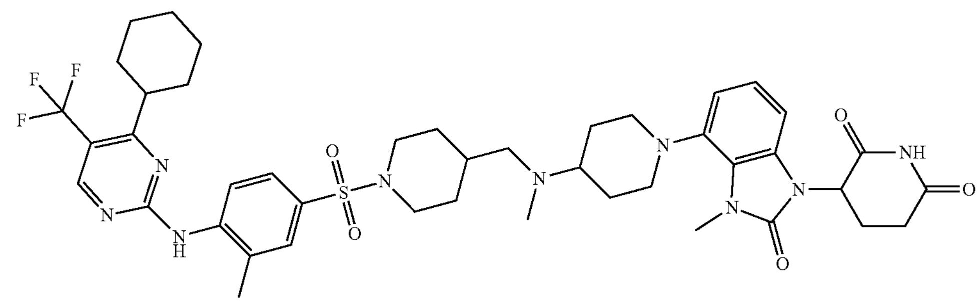 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc(C(F)(F)F)c(C2CCCCC2)n1] |
| I-207 | 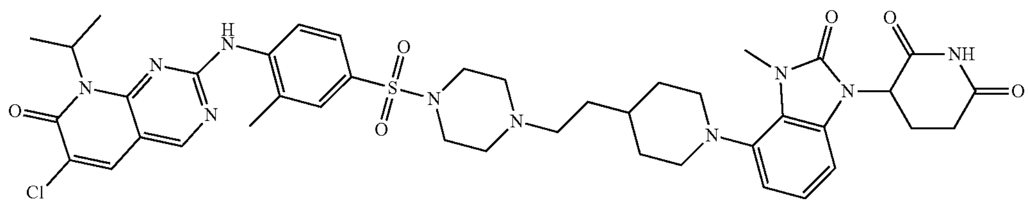 [SMILES: Cc1cc(S(=O)(=O)N2CCN(CCC3CCN(c4cccc5c4n(C)c(=O)n5C4CCC(=O)NC4=O)CC3)CC2)ccc1Nc1ncc2cc(Cl)c(=O)n(C(C)C)c2n1] |
| I-208 | 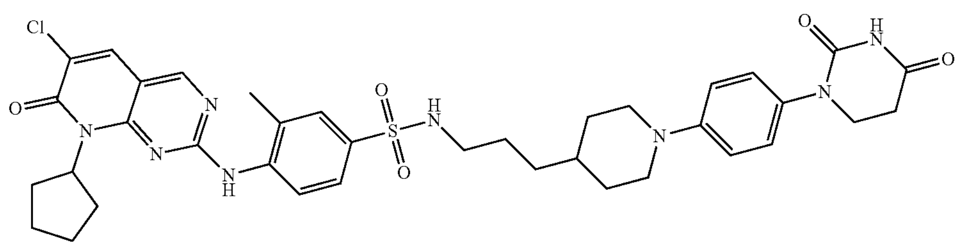 [SMILES: Cc1cc(S(=O)(=O)NCCCC2CCN(c3ccc(N4CCC(=O)NC4=O)cc3)CC2)ccc1Nc1ncc2cc(Cl)c(=O)n(C3CCCC3)c2n1] |
| I-209 | 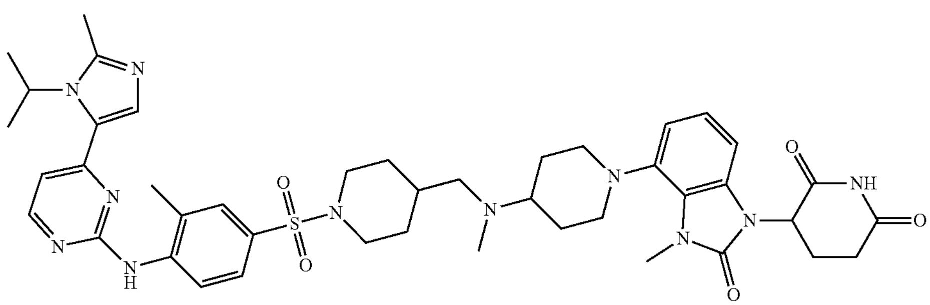 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1nccc(-c2cnc(C)n2C(C)C)n1] |
| I-210 | 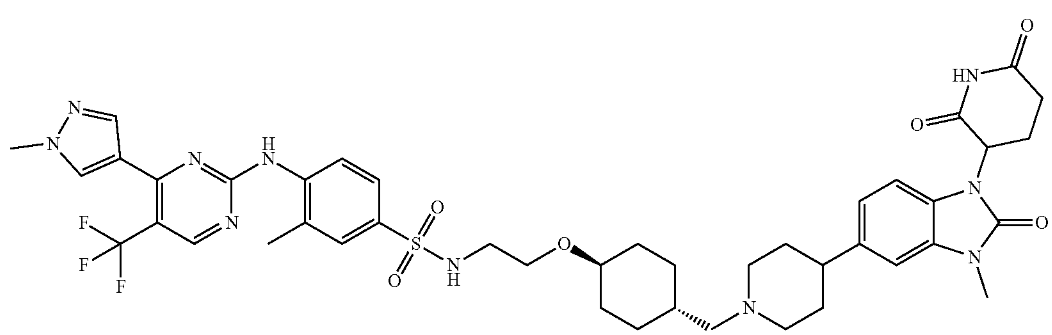 [SMILES: Cc1cc(S(=O)(=O)NCCO[C@H]2CC[C@H](CN3CCC(c4ccc5c(c4)n(C)c(=O)n5C4CCC(=O)NC4=O)CC3)CC2)ccc1Nc1ncc(C(F)(F)F)c(-c2cnn(C)c2)n1] |

TABLE 1-continued

Exemplary Compounds

| I-# | Structure |
|---|---|
| I-211 | 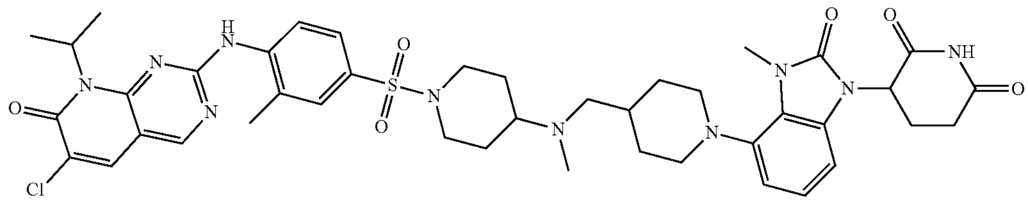 [SMILES: Cc1cc(S(=O)(=O)N2CCC(N(C)CC3CCN(c4cccc5c4n(C)c(=O)n5C4CCC(=O)NC4=O)CC3)CC2)ccc1Nc1ncc2cc(Cl)c(=O)n(C(C)C)c2n1] |
| I-212 | 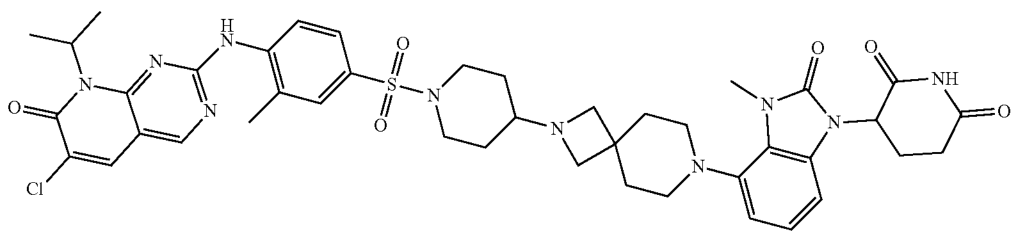 [SMILES: Cc1cc(S(=O)(=O)N2CCC(N3CC4(CCN(c5cccc6c5n(C)c(=O)n6C5CCC(=O)NC5=O)CC4)C3)CC2)ccc1Nc1ncc2cc(Cl)c(=O)n(C(C)C)c2n1] |
| I-213 | 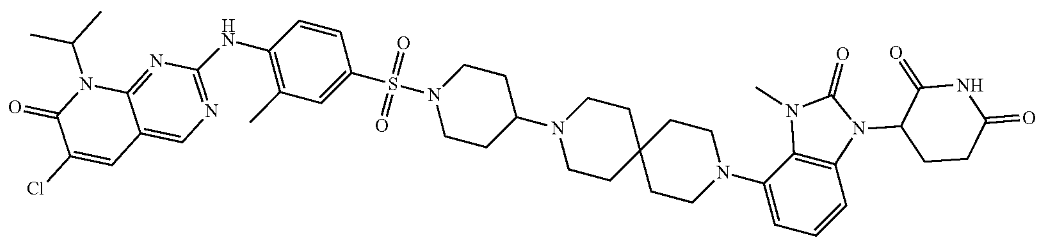 [SMILES: Cc1cc(S(=O)(=O)N2CCC(N3CCC4(CCN(c5cccc6c5n(C)c(=O)n6C5CCC(=O)NC5=O)CC4)CC3)CC2)ccc1Nc1ncc2cc(Cl)c(=O)n(C(C)C)c2n1] |
| I-214 | 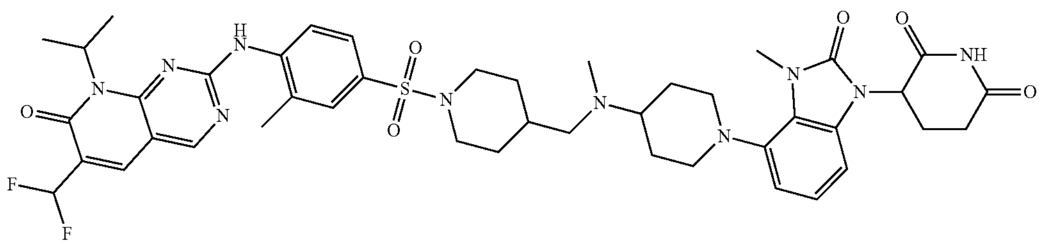 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2cc(C(F)F)c(=O)n(C(C)C)c2n1] |
| I-215 | 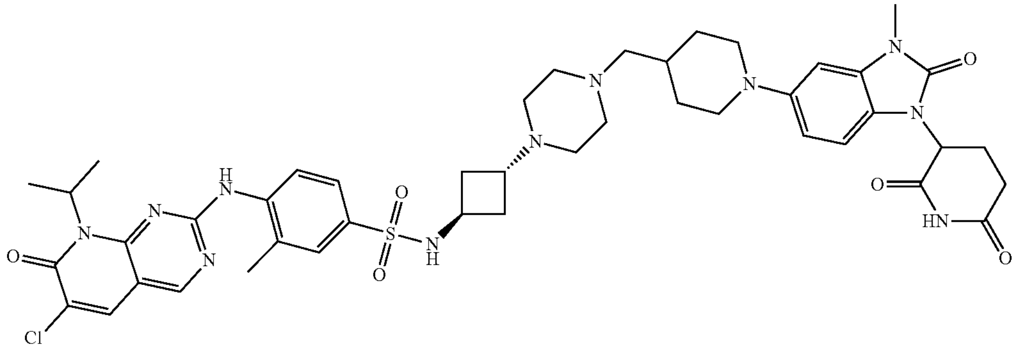 [SMILES: Cc1cc(S(=O)(=O)N[C@H]2C[C@H](N3CCN(CC4CCN(c5ccc6c(c5)n(C)c(=O)n6C5CCC(=O)NC5=O)CC4)CC3)C2)ccc1Nc1ncc2cc(Cl)c(=O)n(C(C)C)c2n1] |

TABLE 1-continued

Exemplary Compounds

| I-# | Structure |
|---|---|
| I-216 | 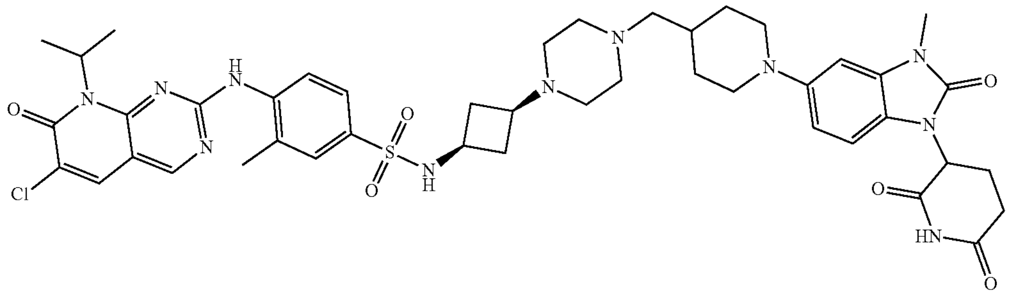 [SMILES: Cc1cc(S(=O)(=O)N[C@H]2C[C@@H](N3CCN(CC4CCN(c5ccc6c(c5)n(C)c(=O)n6C5CCC(=O)NC5=O)CC4)CC3)C2)ccc1Nc1ncc2cc(Cl)c(=O)n(C(C)C)c2n1] |
| I-217 | 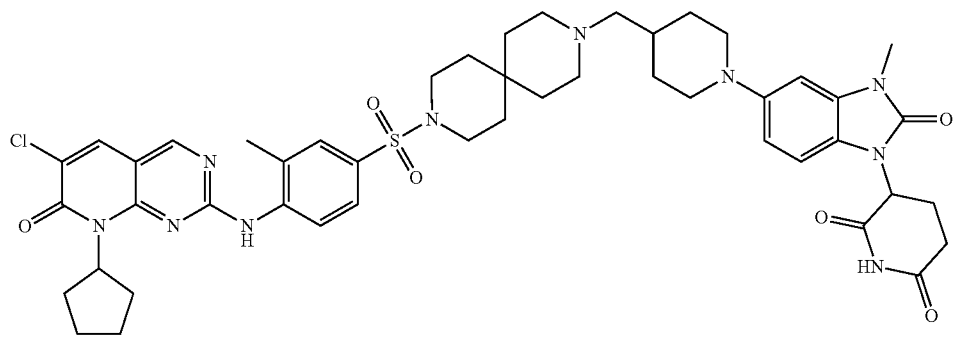 [SMILES: Cc1cc(S(=O)(=O)N2CCC3(CCN(CC4CCN(c5ccc6c(c5)n(C)c(=O)n6C5CCC(=O)NC5=O)CC4)CC3)CC2)ccc1Nc1ncc2cc(Cl)c(=O)n(C3CCCC3)c2n1] |
| I-218 | 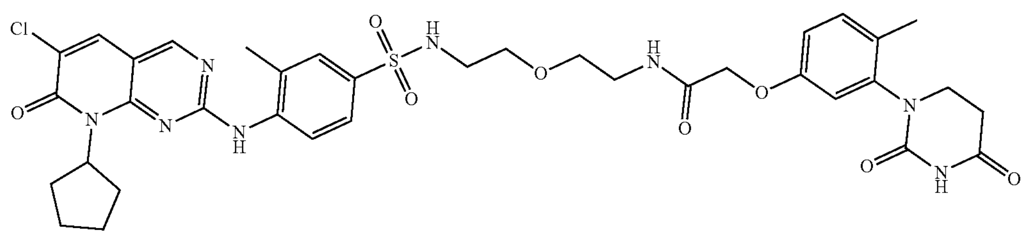 [SMILES: Cc1cc(S(=O)(=O)NCCOCCNC(=O)COc2ccc(C)c(N3CCC(=O)NC3=O)c2)ccc1Nc1ncc2cc(Cl)c(=O)n(C3CCCC3)c2n1] |
| I-219 | 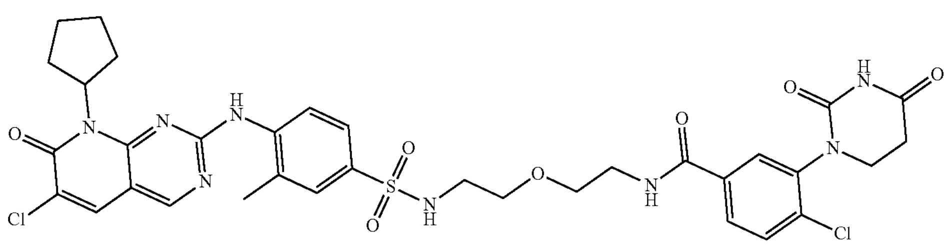 [SMILES: Cc1cc(S(=O)(=O)NCCOCCNC(=O)c2ccc(Cl)c(N3CCC(=O)NC3=O)c2)ccc1Nc1ncc2cc(Cl)c(=O)n(C3CCCC3)c2n1] |
| I-220 | 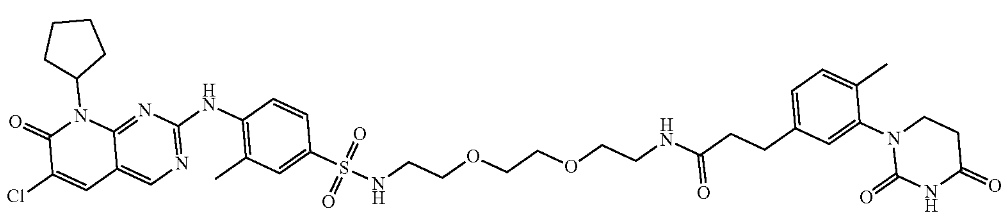 [SMILES: Cc1cc(S(=O)(=O)NCCOCCOCCNC(=O)CCc2ccc(C)c(N3CCC(=O)NC3=O)c2)ccc1Nc1ncc2cc(Cl)c(=O)n(C3CCCC3)c2n1] |
| I-221 | 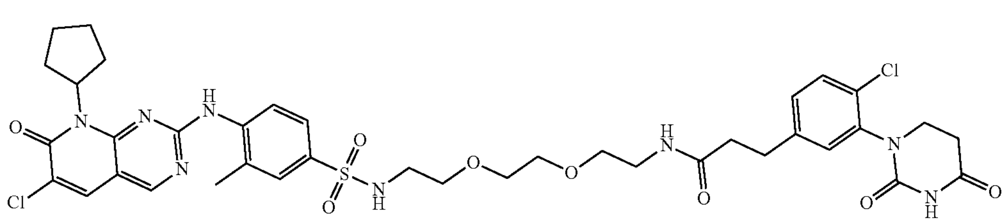 [SMILES: Cc1cc(S(=O)(=O)NCCOCCOCCNC(=O)CCc2ccc(Cl)c(N3CCC(=O)NC3=O)c2)ccc1Nc1ncc2cc(Cl)c(=O)n(C3CCCC3)c2n1] |

TABLE 1-continued

Exemplary Compounds

| I-# | Structure |
|---|---|
| I-222 | 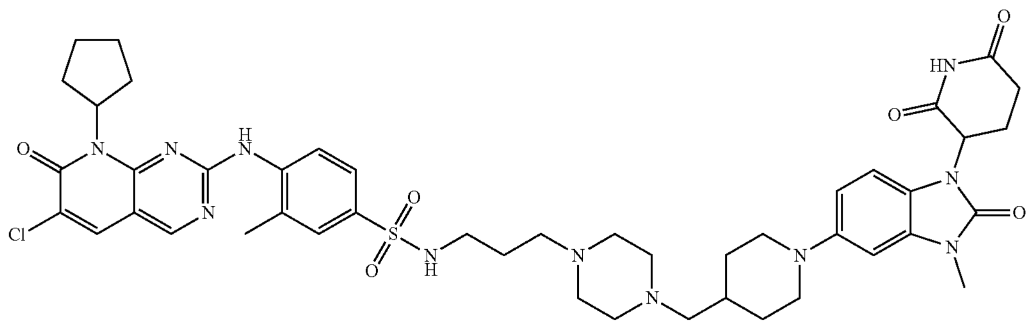 [SMILES: Cc1cc(S(=O)(=O)NCCCN2CCN(CC3CCN(c4ccc5c(c4)n(C)c(=O)n5C4CCC(=O)NC4=O)CC3)CC2)ccc1Nc1ncc2cc(Cl)c(=O)n(C3CCCC3)c2n1] |
| I-223 | 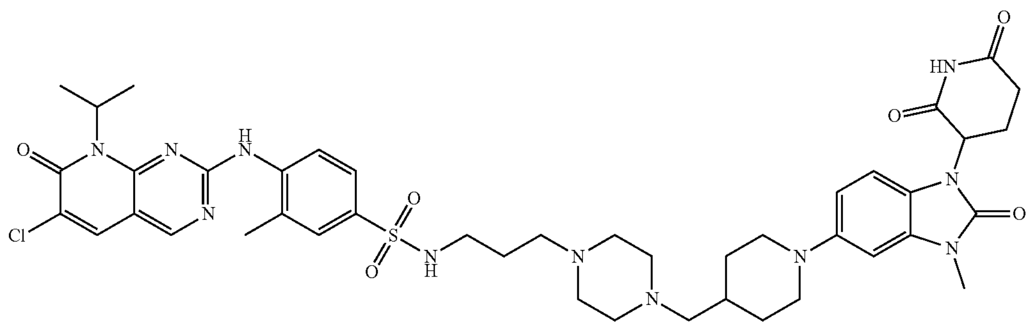 [SMILES: Cc1cc(S(=O)(=O)NCCCN2CCN(CC3CCN(c4ccc5c(c4)n(C)c(=O)n5C4CCC(=O)NC4=O)CC3)CC2)ccc1Nc1ncc2cc(Cl)c(=O)n(C(C)C)c2n1] |
| I-224 | 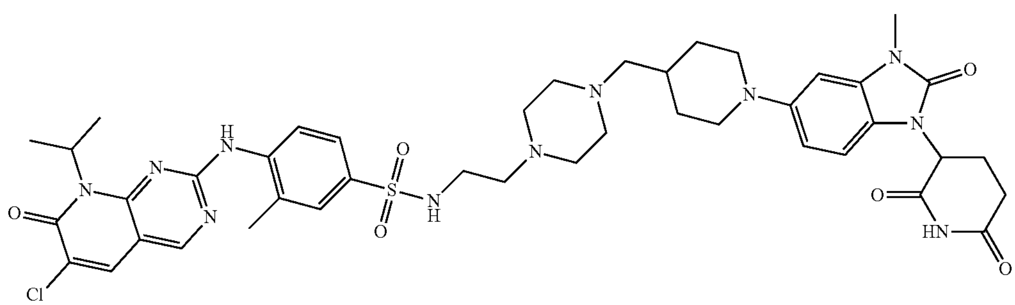 [SMILES: Cc1cc(S(=O)(=O)NCCN2CCN(CC3CCN(c4ccc5c(c4)n(C)c(=O)n5C4CCC(=O)NC4=O)CC3)CC2)ccc1Nc1ncc2cc(Cl)c(=O)n(C(C)C)c2n1] |
| I-225 | 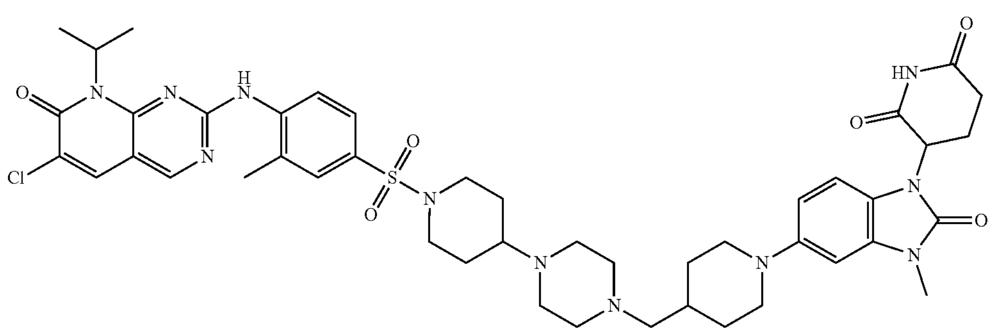 [SMILES: Cc1cc(S(=O)(=O)N2CCC(N3CCN(CC4CCN(c5ccc6c(c5)n(C)c(=O)n6C5CCC(=O)NC5=O)CC4)CC3)CC2)ccc1Nc1ncc2cc(Cl)c(=O)n(C(C)C)c2n1] |
| I-226 | 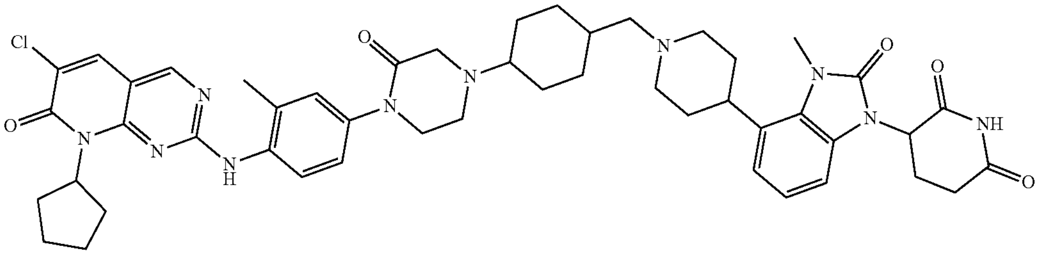 [SMILES: Cc1cc(N2CCN(C3CCC(CN4CCC(c5cccc6c5n(C)c(=O)n6C5CCC(=O)NC5=O)CC4)CC3)CC2=O)ccc1Nc1ncc2cc(Cl)c(=O)n(C3CCCC3)c2n1] |

TABLE 1-continued
Exemplary Compounds
| I-# | Structure |
|---|---|
| I-227 | 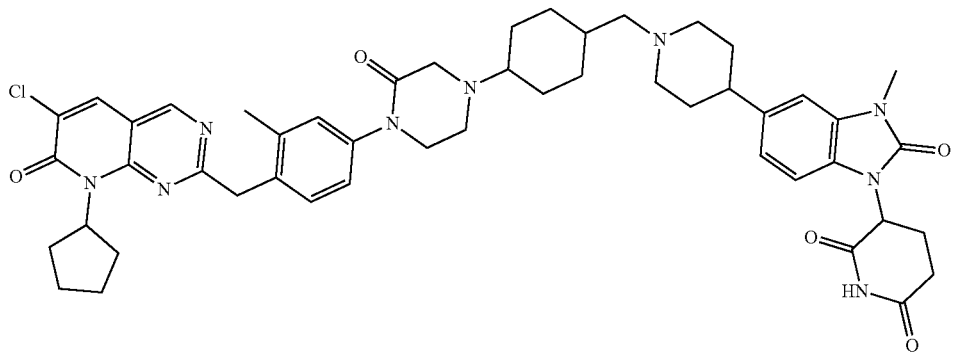 [SMILES: Cc1cc(N2CCN(C3CCC(CN4CCC(c5ccc6c(c5)n(C)c(=O)n6C5CCC(=O)NC5=O)CC4)CC3)CC2=O)ccc1Cc1ncc2cc(Cl)c(=O)n(C3CCCC3)c2n1] |
| I-228 | 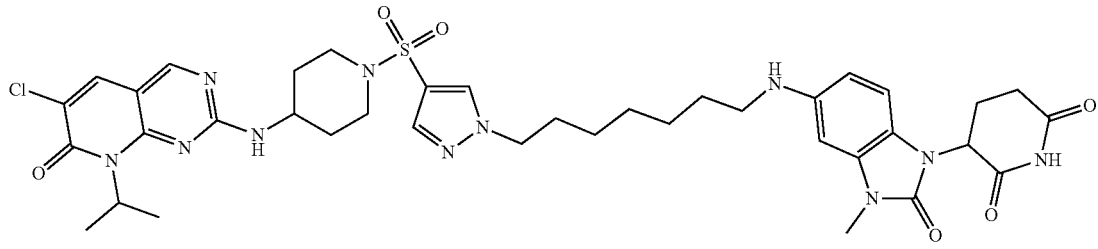 [SMILES: CC(C)n1c(=O)c(Cl)cc2cnc(NC3CCN(S(=O)(=O)c4cnn(CCCCCCCNc5ccc6c(c5)n(C)c(=O)n6C5CCC(=O)NC5=O)c4)CC3)nc21] |
| I-229 | 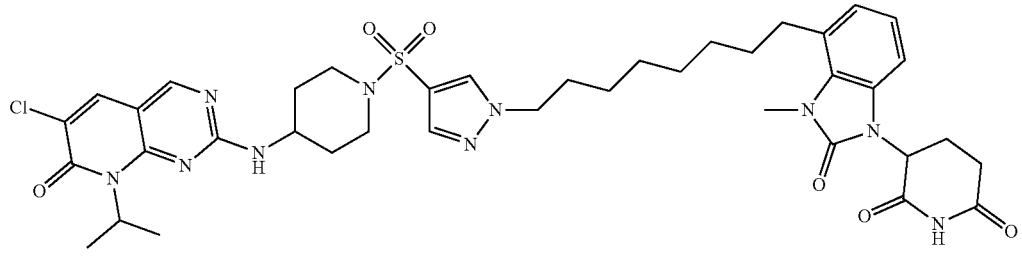 [SMILES: CC(C)n1c(=O)c(Cl)cc2cnc(NC3CCN(S(=O)(=O)c4cnn(CCCCCCCCc5cccc6c5n(C)c(=O)n6C5CCC(=O)NC5=O)c4)CC3)nc21] |
| I-230 | 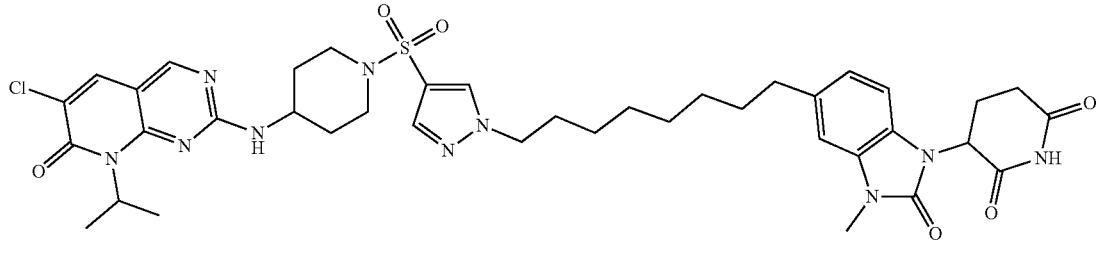 [SMILES: CC(C)n1c(=O)c(Cl)cc2cnc(NC3CCN(S(=O)(=O)c4cnn(CCCCCCCCc5ccc6c(c5)n(C)c(=O)n6C5CCC(=O)NC5=O)c4)CC3)nc21] |
| I-231 | 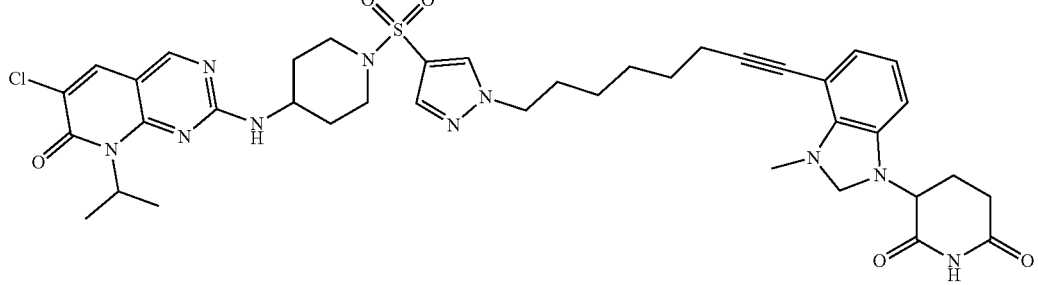 |

TABLE 1-continued

Exemplary Compounds

| I-# | Structure |
|---|---|
| I-232 | 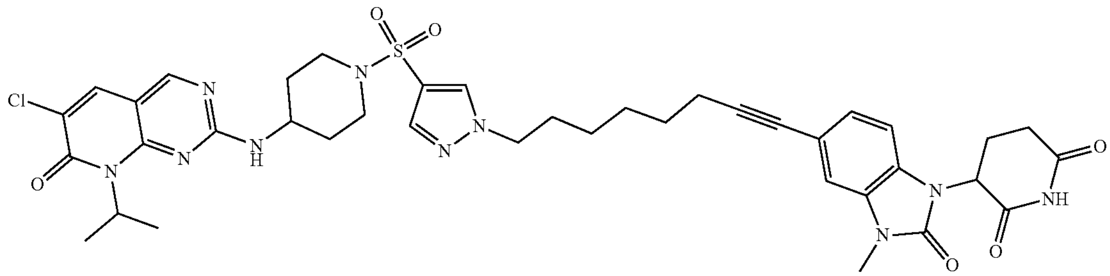 [SMILES: CC(C)n1c(=O)c(Cl)cc2cnc(NC3CCN(S(=O)(=O)c4cnn(CCCCCCC#Cc5ccc6c(c5)n(C)c(=O)n6C5CCC(=O)NC5=O)c4)CC3)nc21] |
| I-233 | 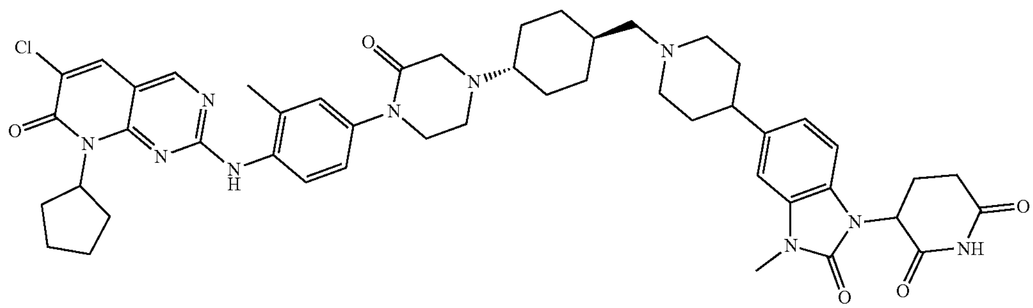 [SMILES: Cc1cc(N2CCN([C@H]3CC[C@H](CN4CCC(c5ccc6c(c5)n(C)c(=O)n6C5CCC(=O)NC5=O)CC4)CC3)CC2=O)ccc1Nc1ncc2cc(Cl)c(=O)n(C3CCCC3)c2n1] |
| I-234 | 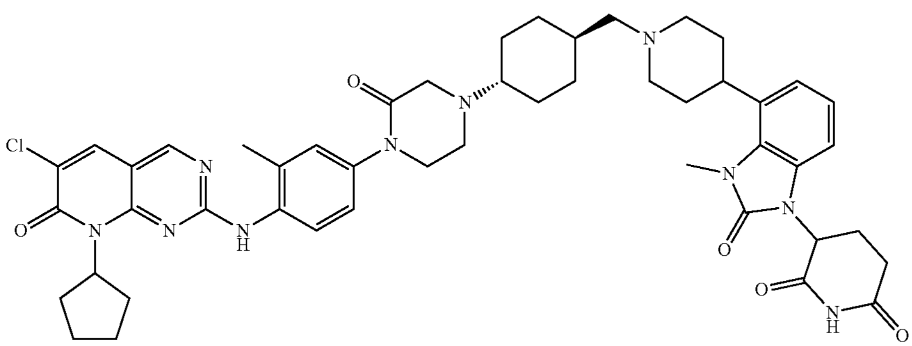 [SMILES: Cc1cc(N2CCN([C@H]3CC[C@H](CN4CCC(c5cccc6c5n(C)c(=O)n6C5CCC(=O)NC5=O)CC4)CC3)CC2=O)ccc1Nc1ncc2cc(Cl)c(=O)n(C3CCCC3)c2n1] |
| I-235 | 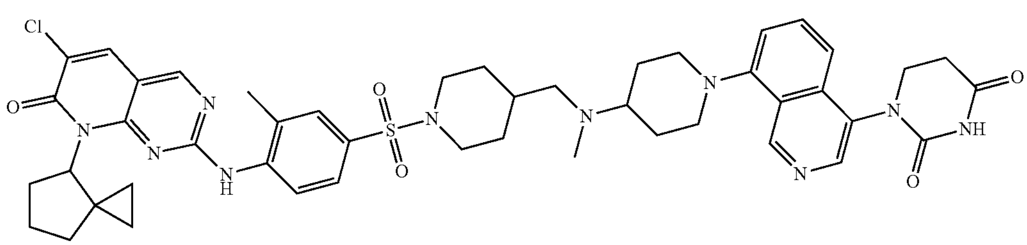 [SMILES: Cc1cc(S(=O)(=O)N2CCC(CN(C)C3CCN(c4cccc5c(N6CCC(=O)NC6=O)cncc45)CC3)CC2)ccc1Nc1ncc2cc(Cl)c(=O)n(C3CCCC34CC4)c2n1] |
| I-236 | 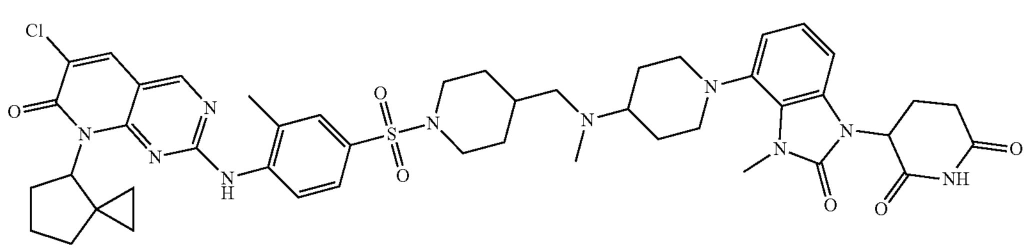 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2cc(Cl)c(=O)n(C3CCCC34CC4)c2n1] |

TABLE 1-continued

Exemplary Compounds

| I-# | Structure |
|---|---|
| I-237 | 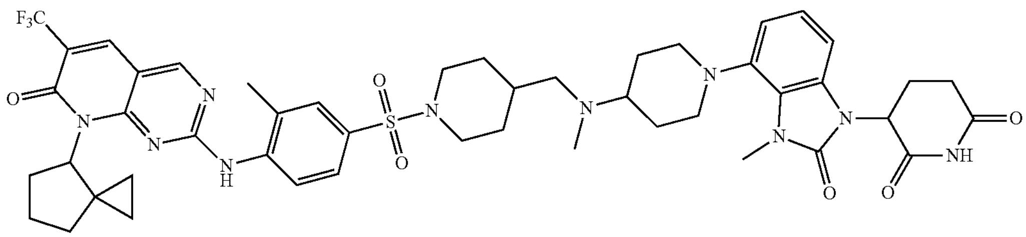 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2cc(C(F)(F)F)c(=O)n(C3CCCC34CC4)c2n1] |
| I-238 | 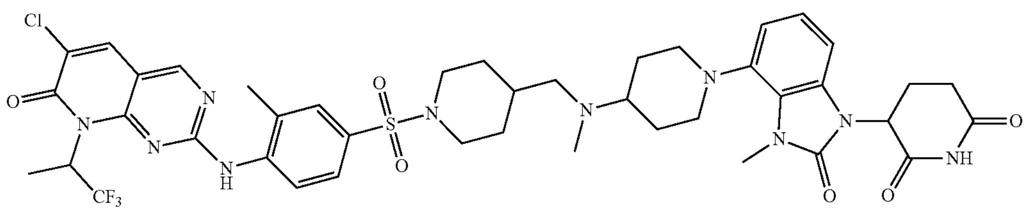 [SMILES: Cc1cc(S(=O)(=O)N2CCC(CN(C)C3CCN(c4cccc5c4n(C)c(=O)n5C4CCC(=O)NC4=O)CC3)CC2)ccc1Nc1ncc2cc(Cl)c(=O)n(C(C)C(F)(F)F)c2n1] |
| I-239 | 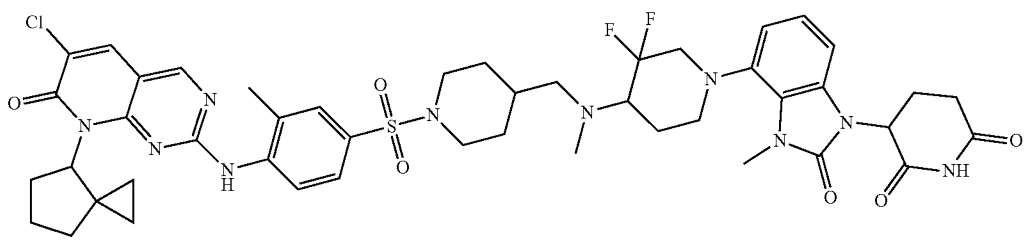 [SMILES: Cc1cc(S(=O)(=O)N2CCC(CN(C)C3CCN(c4cccc5c4n(C)c(=O)n5C4CCC(=O)NC4=O)CC3(F)F)CC2)ccc1Nc1ncc2cc(Cl)c(=O)n(C3CCCC34CC4)c2n1] |
| I-240 | 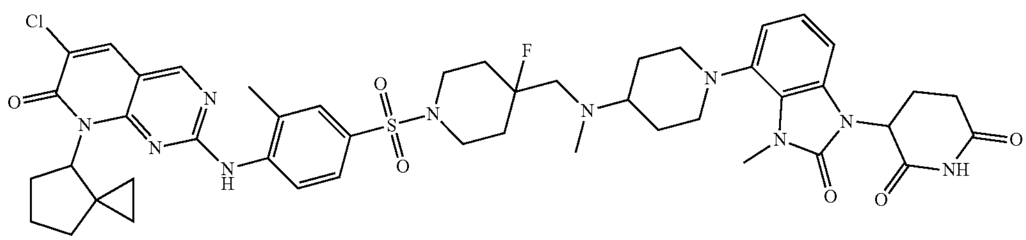 [SMILES: Cc1cc(S(=O)(=O)N2CCC(F)(CN(C)C3CCN(c4cccc5c4n(C)c(=O)n5C4CCC(=O)NC4=O)CC3)CC2)ccc1Nc1ncc2cc(Cl)c(=O)n(C3CCCC34CC4)c2n1] |
| I-241 | 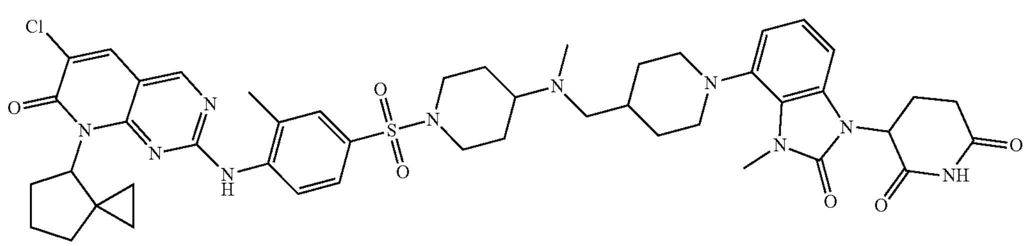 [SMILES: Cc1cc(S(=O)(=O)N2CCC(N(C)CC3CCN(c4cccc5c4n(C)c(=O)n5C4CCC(=O)NC4=O)CC3)CC2)ccc1Nc1ncc2cc(Cl)c(=O)n(C3CCCC34CC4)c2n1] |
| I-242 | 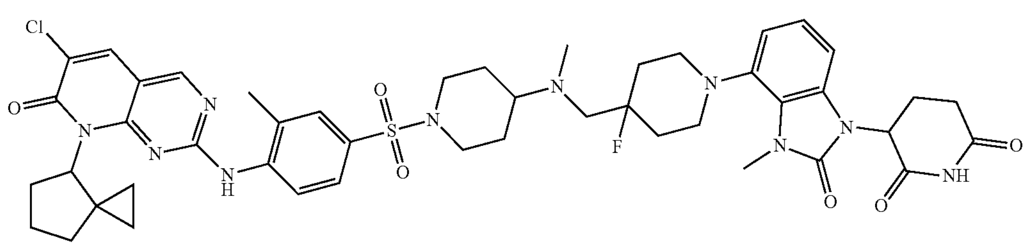 [SMILES: Cc1cc(S(=O)(=O)N2CCC(N(C)CC3(F)CCN(c4cccc5c4n(C)c(=O)n5C4CCC(=O)NC4=O)CC3)CC2)ccc1Nc1ncc2cc(Cl)c(=O)n(C3CCCC34CC4)c2n1] |

TABLE 1-continued

Exemplary Compounds

| I-# | Structure |
|---|---|
| I-243 | 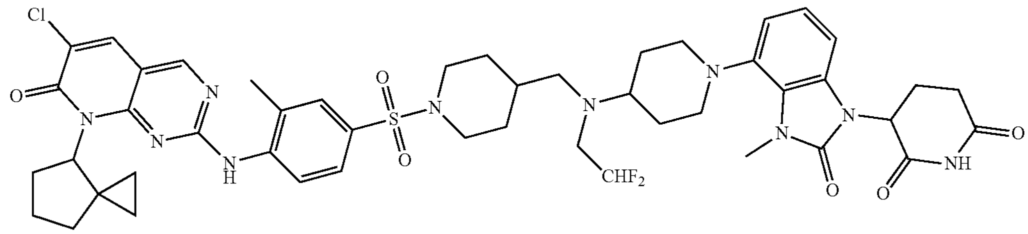 [SMILES: Cc1cc(S(=O)(=O)N2CCC(CN(CC(F)F)C3CCN(c4cccc5c4n(C)c(=O)n5C4CCC(=O)NC4=O)CC3)CC2)ccc1Nc1ncc2cc(Cl)c(=O)n(C3CCCC34CC4)c2n1] |
| I-244 | 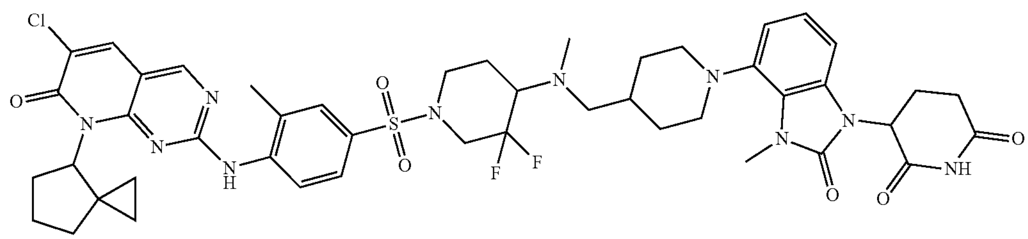 [SMILES: Cc1cc(S(=O)(=O)N2CCC(N(C)CC3CCN(c4cccc5c4n(C)c(=O)n5C4CCC(=O)NC4=O)CC3)C(F)(F)C2)ccc1Nc1ncc2cc(Cl)c(=O)n(C3CCCC34CC4)c2n1] |
| I-245 | 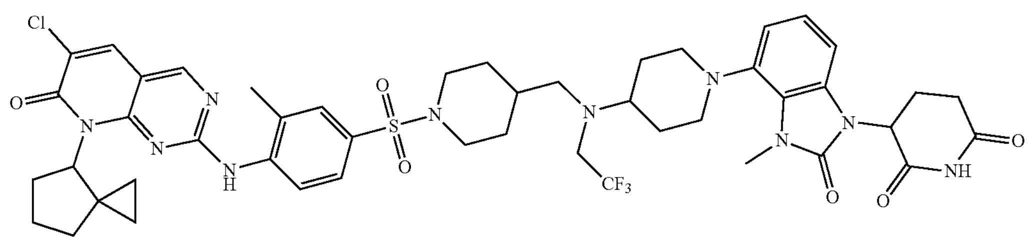 [SMILES: Cc1cc(S(=O)(=O)N2CCC(CN(CC(F)(F)F)C3CCN(c4cccc5c4n(C)c(=O)n5C4CCC(=O)NC4=O)CC3)CC2)ccc1Nc1ncc2cc(Cl)c(=O)n(C3CCCC34CC4)c2n1] |
| I-246 | 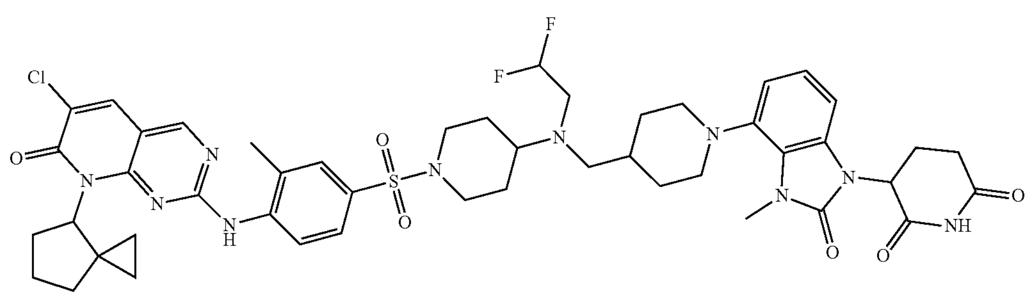 [SMILES: Cc1cc(S(=O)(=O)N2CCC(N(CC(F)F)CC3CCN(c4cccc5c4n(C)c(=O)n5C4CCC(=O)NC4=O)CC3)CC2)ccc1Nc1ncc2cc(Cl)c(=O)n(C3CCCC34CC4)c2n1] |
| I-247 | 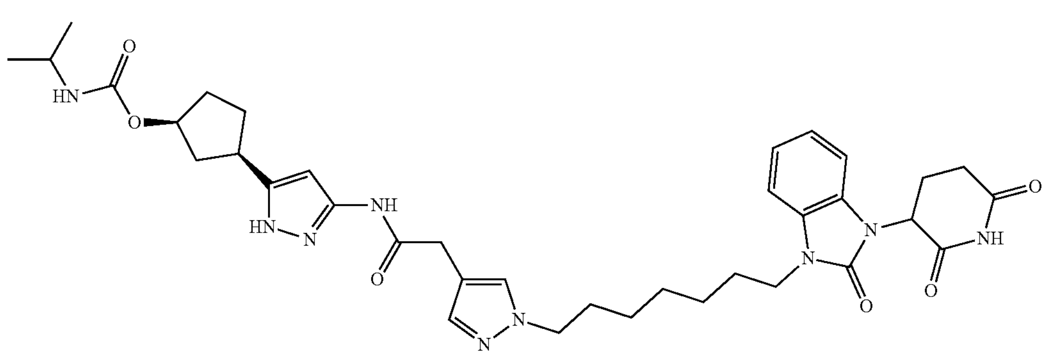 [SMILES: CC(C)NC(=O)O[C@H]1CC[C@@H](c2cc(NC(=O)Cc3cnn(CCCCCCCn4c(=O)n(C5CCC(=O)NC5=O)c5ccccc54)c3)n[nH]2)C1] |

In some embodiments, the present invention provides a compound set forth in Table 2, above, or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, Comprehensive Organic Transformations, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of each of which is herein incorporated by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of each of which is herein incorporated by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In the schemes below, where a provided compound is formed having a reactive moiety (e.g., amine, alcohol, etc.), it is not shown but it is generally appreciated and well known by those having ordinary skill in the art that the reactivity of said reactive moiety may be masked by employing a suitable protecting group that can thereafter be removed in situ or during a separate synthetic step.

In certain embodiments, compounds of the present invention are generally prepared according to Scheme 1 set forth below:

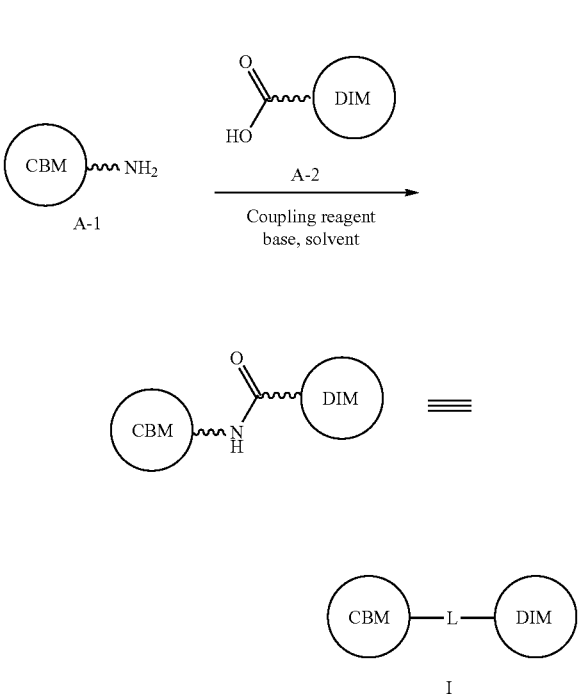

Scheme 1
Synthesis of Compounds of Formula I

As depicted in Scheme 1, above, amine A-1 is coupled to acid A-2 using the a coupling reagent in the presence of the base (e.g., DIPEA) in a solvent (e.g., DMF) to form a compound of formula I with a linker comprising an amide bond. The squiggly bond, ∿∿∿, represents the portion of the linker between CBM and the terminal amino group of A-1 or the portion of the linker between DIM and the terminal carboxyl group of A-2, respectively. The amide bond can be formed using coupling reagents known in the art such as, but not limited to DCC, DIC, EDC, HATU, HBTU, HCTU, PyAOP, PyBOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2
Synthesis of Compounds
of Formula I

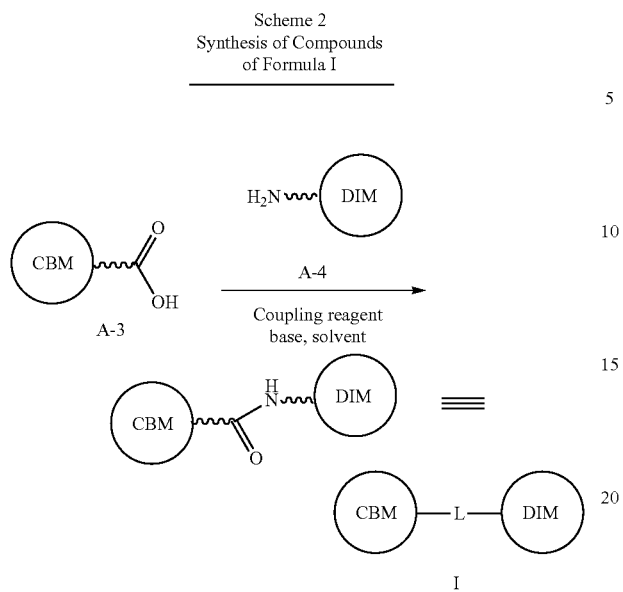

As depicted in Scheme 2, above, acid A-3 is coupled to amine A-4 using a coupling reagent in the presence of the base (e.g., DIPEA) in a solvent (e.g., DMF) to form a compound of formula I with a linker comprising an amide bond. The squiggly bond, ∼∼∼∼, represents the portion of the linker between CBM and the terminal carboxyl group of A-3 or the portion of the linker between DIM and the terminal amino group of A-4, respectively. The amide bond can be formed using coupling reagents known in the art such as, but not limited to DCC, DIC, EDC, HATU, HBTU, HCTU, PyAOP, PyBOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of Formula I

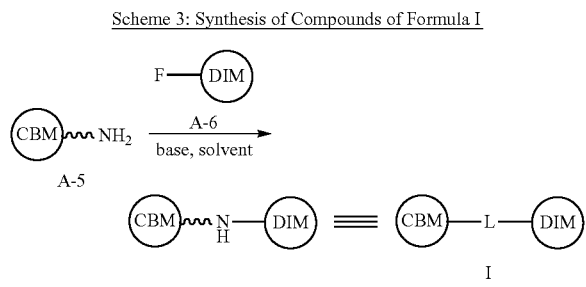

As depicted in Scheme 3, above, an $S_N Ar$ displacement of fluoride A-6 by amine A-5 is effected in the presence of the base (e.g., DIPEA) in a solvent (e.g., DMF) to form a compound of formula I with a linker comprising a secondary amine. The squiggly bond, ∼∼∼∼ represents the portion of the linker between CBM and the terminal amino group of A-5.

In certain embodiments, compounds of the present invention are generally prepared according to Scheme 4 set forth below:

Scheme 4
Synthesis of Compounds
of Formula I

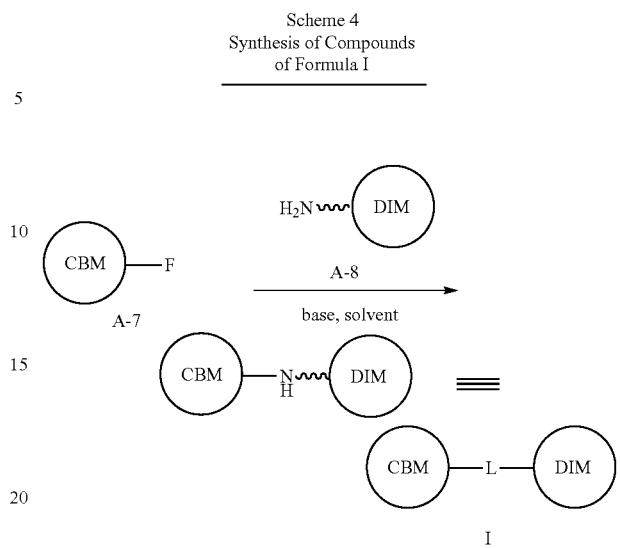

As depicted in Scheme 4, above, an $S_N Ar$ displacement of fluoride A-7 by amine A-8 is effected in the presence of the base (e.g., DIPEA) in a solvent (e.g., DMF) to form a compound of formula I with a linker comprising a secondary amine. The squiggly bond, ∼∼∼∼, represents the portion of the linker between DIM and the terminal amino group of A-8.

Scheme 5
Synthesis of Compounds
of Formula I

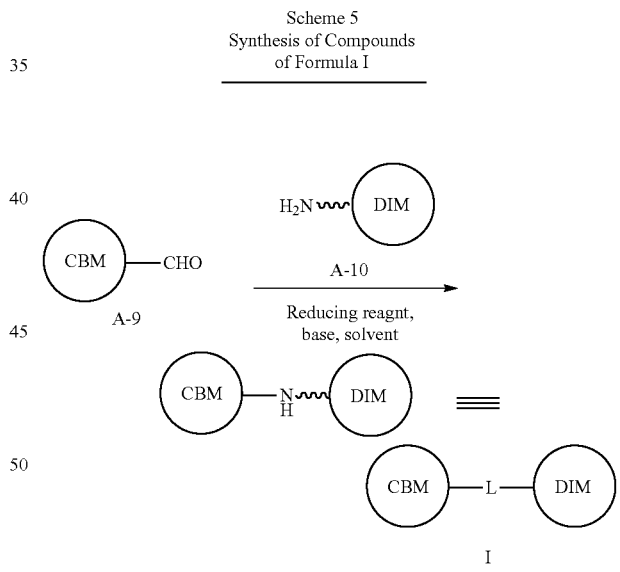

As depicted in Scheme 7, above, reductive amination of the mixture of aldehyde A-9 and amine A-10 is effected in the presence of a reducing agent (e.g., $NaHB(OAc)_3$) and base (e.g., KOAc) in a solvent (e.g., DMF/THF) to form a compound of formula I with a linker comprising a secondary amine. The squiggly bond, ∼∼∼∼, represents the portion of the linker between DIM and the terminal amino group of A-8.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that it is effective to measurably degrade and/or inhibit an CDK protein, or a mutant thereof, in a biological sample or in a patient. In certain embodiments, the amount of compound in compositions of this invention is such that it is effective to measurably degrade and/or inhibit an CDK protein, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of an CDK protein, or a mutant thereof.

As used herein, the term "degratorily active metabolite or residue thereof" means that a metabolite or residue thereof is also a degrader of an CDK protein, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of kinase activity of one or more enzymes.

As used herein, the terms "CDK1-mediated", "CDK2-mediated", "CDK4-mediated", "CDK6-mediated", "CDK7-mediated", "CDK8-mediated", and/or "CDK9-mediated" disorders, diseases, and/or conditions as used herein means any disease or other deleterious condition in which one or more of CDK1, CDK2, CDK4, CDK6, CDK7, CDK8, CDK9 or a mutant thereof, are known to play a role. Accordingly, another embodiment of the present invention relates to treating or lessening the severity of one or more diseases in which one or more of CDK1, CDK2, CDK4, CDK6, CDK7, CDK8, and/or CDK9 or a mutant thereof, are known to play a role. In some embodiments, the term "CDK2-mediated" also includes treating or lessening the severity of one or more diseases in which CCNE (e.g., CCNE1) or a mutant thereof, are known to play a role.

Compounds of the present disclosure can degrade CDK2 or CDK2 and CCNE1 and therefore are useful for treating diseases wherein the underlying pathology is, wholly or partially, mediated by CDK2. Such diseases include cancer and other diseases with proliferation disorder. In some embodiments, the present disclosure provides treatment of an individual or a patient in vivo using a provided compound or a pharmaceutically acceptable salt thereof such that growth of cancerous tumors is inhibited. A provided compound or a pharmaceutically acceptable salt thereof can be used to inhibit the growth of cancerous tumors with aberrations that activate CDK2 activity. These include, but not limited to, disease (e.g., cancers) that are characterized by amplification or overexpression of CCNE1 such as ovarian cancer, uterine carcinosarcoma and breast cancer and p27 inactivation such as breast cancer and melanomas. Accordingly, in some embodiments of the methods, the patient has been previously determined to have an amplification of the CCNE1 gene and/or an expression level of CCNE1 in a biological sample obtained from the human subject that is higher than a control expression level of CCNE1. Alternatively, a provided compound or a pharmaceutically acceptable salt thereof can be used in conjunction with other agents or standard cancer treatments, as described below. In one embodiment, the present disclosure provides a method for inhibiting growth of tumor cells in vitro. The method includes contacting the tumor cells in vitro with a provided compound or a pharmaceutically acceptable salt thereof. In another embodiment, the present disclosure provides a method for inhibiting growth of tumor cells with CCNE1 amplification and overexpression in an individual or a patient. The method includes administering to the individual or patient in need thereof a therapeutically effective amount of a provided compound or a pharmaceutically acceptable salt thereof.

In some embodiments, provided herein is a method of inhibiting CDK2, comprising contacting the CDK2 with a provided compound or a pharmaceutically acceptable salt thereof. In some embodiments, provided herein is a method of inhibiting CDK2 in a patient, comprising administering to the patient a provided compound or a pharmaceutically acceptable salt thereof.

In some embodiments, provided herein is a method of inhibiting CDK2 and CCNE1, comprising contacting the CDK2 and CCNE1 with a provided compound or a pharmaceutically acceptable salt thereof. In some embodiments, provided herein is a method of inhibiting CDK2 and CCNE1 in a patient, comprising administering to the patient a provided compound or a pharmaceutically acceptable salt thereof.

In some embodiments, provided herein is a method of degrading CDK2, comprising contacting the CDK2 with a provided compound or a pharmaceutically acceptable salt thereof. In some embodiments, provided herein is a method of degrading CDK2 in a patient, comprising administering to the patient a provided compound or a pharmaceutically acceptable salt thereof.

In some embodiments, provided herein is a method of degrading CDK2 and inhibiting CCNE1, comprising contacting the CDK2 and CCNE1 with a provided compound or a pharmaceutically acceptable salt thereof. In some embodiments, provided herein is a method of degrading CDK2 and inhibiting CCNE1 in a patient, comprising administering to the patient a provided compound or a pharmaceutically acceptable salt thereof.

In some embodiments, provided herein is a method of degrading CDK2 and CCNE1, comprising contacting the CDK2 and CCNE1 with a provided compound or a pharmaceutically acceptable salt thereof. In some embodiments, provided herein is a method of degrading CDK2 and CCNE1 in a patient, comprising administering to the patient a provided compound or a pharmaceutically acceptable salt thereof.

In some embodiments, provided herein is a method for treating cancer. The method includes administering to a patient (in need thereof), a therapeutically effective amount of a provided compound or a pharmaceutically acceptable salt thereof. In another embodiment, the cancer is characterized by amplification or overexpression of CCNE1. In some embodiments, the cancer is ovarian cancer or breast cancer, characterized by amplification or overexpression of CCNE1.

In some embodiments, provided herein is a method of treating a disease or disorder associated with CDK2 in a patient, comprising administering to the patient a therapeutically effective amount of a provided compound or a pharmaceutically acceptable salt thereof. In some embodiments, the disease or disorder associated with CDK2 is associated with an amplification of the CCNE1 gene and/or overexpression of CCNE1.

In some embodiments, the disease or disorder associated with CDK2 is N-myc amplified neuroblastoma cells (see Molenaar et al., Proc. Natl. Acad. Sci. USA, 2009, 106(31): 12968-12973), K-Ras mutant lung cancers (see Hu, S., et al., Mol. Cancer Ther., 2015, 14(11):2576-85), and cancers with FBW7 mutation and CCNE1 overexpression (see Takada et al., Cancer Res., 2017, 77(18):4881-4893).

In some embodiments, the disease or disorder associated with CDK2 is lung squamous cell carcinoma, lung adenocarcinoma, pancreatic adenocarcinoma, breast invasive carcinoma, uterine carcinosarcoma, ovarian serous cystadenocarcinoma, stomach adenocarcinoma, esophageal carcinoma, bladder urothelial carcinoma, mesothelioma, or sarcoma.

In some embodiments, the disease or disorder associated with CDK2 is lung adenocarcinoma, breast invasive carcinoma, uterine carcinosarcoma, ovarian serous cystadenocarcinoma, or stomach adenocarcinoma.

In some embodiments, the disease or disorder associated with CDK2 is an adenocarcinoma, carcinoma, or cystadenocarcinoma.

In some embodiments, the disease or disorder associated with CDK2 is uterine cancer, ovarian cancer, stomach cancer, esophageal cancer, lung cancer, bladder cancer, pancreatic cancer, or breast cancer.

In some embodiments, the disease or disorder associated with CDK2 is a cancer.

In some embodiments, the cancer is characterized by amplification or overexpression of CCNE1. In some embodiments, the cancer is ovarian cancer or breast cancer, characterized by amplification or overexpression of CCNE1.

In some embodiments, the breast cancer is chemotherapy or radiotherapy resistant breast cancer, endocrine resistant breast cancer, trastuzumab resistant breast cancer, or breast cancer demonstrating primary or acquired resistance to CDK4/6 inhibition. In some embodiments, the breast cancer is advanced or metastatic breast cancer.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include melanoma (e.g., metastatic malignant melanoma, BRAF and HSP90 inhibition-resistant melanoma), renal cancer (e.g., clear cell carcinoma), prostate cancer (e.g., hormone refractory prostate adenocarcinoma), breast cancer, colon cancer, lung cancer (e.g., non-small cell lung cancer and small cell lung cancer), squamous cell head and neck cancer, urothelial cancer (e.g., bladder) and cancers with high microsatellite instability (MSI$^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer (SCLC), bronchogenic carcinoma, squamous cell, undifferentiated small cell, undifferentiated large cell, adenocarcinoma, alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, Merkel cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

It is believed that a provided compound or a pharmaceutically acceptable salt thereof may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Co-Administration with One or More Other Therapeutic Agent(s)

Depending upon the particular condition, or disease, to be treated, additional therapeutic agents that are normally administered to treat that condition, can also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention can also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides, or in addition, be administered especially for tumor therapy in combination with chemotherapy, radiotherapy, immunotherapy, phototherapy, surgical intervention, or a combination of these. Long-term therapy is equally possible, as is adjuvant therapy in the context of other treatment strategies, as described above. Other possible treatments are therapy to maintain the patient's status after tumor regression, or even chemopreventive therapy, for example in patients at risk.

One or more other therapeutic agent(s) can be administered separately from a compound or composition of the invention, as part of a multiple dosage regimen. Alternatively, one or more other therapeutic agent(s) may be part of a single dosage form, mixed together with a compound of this invention in a single composition. If administered as a multiple dosage regime, one or more other therapeutic agent(s) and a compound or composition of the invention can be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent(s) and a compound or composition of the invention are administered as a multiple dosage regimen within greater than 24 hours apart.

As used herein, the term "combination," "combined," and related terms refers to the simultaneous or sequential administration of therapeutic agents in accordance with this invention. For example, a compound of the present invention can be administered with one or more other therapeutic agent(s) simultaneously or sequentially in separate unit dosage forms or together in a single unit dosage form. Accordingly, the present invention provides a single unit dosage form comprising a compound of the current invention, one or more other therapeutic agent(s), and a pharmaceutically acceptable carrier, adjuvant, or vehicle.

The amount of a compound of the invention and one or more other therapeutic agent(s) (in those compositions which comprise an additional therapeutic agent as described above) that can be combined with the carrier materials to produce a single dosage form varies depending upon the host treated and the particular mode of administration. Preferably, a composition of the invention should be formulated so that a dosage of between 0.01-100 mg/kg body weight/day of a compound of the invention can be administered.

In those compositions which comprise one or more other therapeutic agent(s), the one or more other therapeutic agent(s) and a compound of the invention can act synergistically. Therefore, the amount of the one or more other therapeutic agent(s) in such compositions may be less than that required in a monotherapy utilizing only that therapeutic agent. In such compositions a dosage of between 0.01-1,000 g/kg body weight/day of the one or more other therapeutic agent(s) can be administered.

The amount of one or more other therapeutic agent(s) present in the compositions of this invention may be no more than the amount that would normally be administered in a composition comprising that therapeutic agent as the only active agent. Preferably the amount of one or more other therapeutic agent(s) in the presently disclosed compositions ranges from about 50% to 100% of the amount normally present in a composition comprising that agent as the only therapeutically active agent. In some embodiments, one or more other therapeutic agent(s) is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is provided for dosing per the FDA label insert.

The compounds of this invention, or pharmaceutical compositions thereof, can also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Other Therapeutic Agents

In some embodiments, one or more other therapeutic agent is a Poly ADP ribose polymerase (PARP) inhibitor. In some embodiments, a PARP inhibitor is selected from olaparib (LYNPARZA®, AstraZeneca); rucaparib (RUBRACA®, Clovis Oncology); niraparib (ZEJULA®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (ZOLINZA®, Merck); romidepsin (ISTODAX®, Celgene); panobinostat (FARYDAK®, Novartis); belinostat (BELEODAQ®, Spectrum Pharmaceuticals); entinostat (SNDX-275, Syndax Pharmaceuticals) (NCT00866333); and chidamide (EPIDAZA®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (IBRANCE®, Pfizer); ribociclib (KISQALI®, Novartis); abemaciclib (Ly2835219, Eli Lilly); and trilaciclib (G1T28, G1 Therapeutics).

In some embodiments, one or more other therapeutic agent is a phosphatidylinositol 3 kinase (PI3K) inhibitor. In some embodiments, a PI3K inhibitor is selected from idelalisib (ZYDELIG®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly Rp5230, TG Therapeutics).

In some embodiments, one or more other therapeutic agent is a platinum-based therapeutic, also referred to as platins. Platins cause cross-linking of DNA, such that they inhibit DNA repair and/or DNA synthesis, mostly in rapidly reproducing cells, such as cancer cells. In some embodiments, a platinum-based therapeutic is selected from cisplatin (PLATINOL®, Bristol-Myers Squibb); carboplatin (PARAPLATIN®, Bristol-Myers Squibb; also, Teva; Pfizer); oxaliplatin (ELOXITIN® Sanofi-Aventis); nedaplatin (AQUPLA®, Shionogi), picoplatin (Poniard Pharmaceuticals); and satraplatin (JM-216, Agennix).

In some embodiments, one or more other therapeutic agent is a taxane compound, which causes disruption of microtubules, which are essential for cell division. In some embodiments, a taxane compound is selected from paclitaxel (TAXOL®, Bristol-Myers Squibb), docetaxel (TAXOTERE®, Sanofi-Aventis; DOCEFREZ®, Sun Pharmaceutical), albumin-bound paclitaxel (ABRAXANE®; Abraxis/Celgene), cabazitaxel (JEVTANA®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, YONDELIS®, Janssen Oncology), mechlorethamine (alkylating agent, VALCHLOR®, Aktelion Pharmaceuticals); vincristine (ONCOVIN®, Eli Lilly; VINCASAR®, Teva Pharmaceuticals; MARQIBO®, Talon Therapeutics); temozolomide (prodrug to alkylating agent 5-(3-methyltriazen-1-yl)-imidazole-4-carboxamide (MTIC) TEMODAR®, Merck); cytarabine injection (ara-C, antimetabolic cytidine analog, Pfizer); lomustine (alkylating agent, CEENU®, Bristol-Myers Squibb; GLEOSTINE®, NextSource Biotechnology); azacitidine (pyrimidine nucleoside analog of cytidine, VIDAZA®, Celgene); omacetaxine mepesuccinate (cephalotaxine ester) (protein synthesis inhibitor, SYNRIBO®; Teva Pharmaceuticals); asparaginase Erwinia chrysanthemi (enzyme for depletion of asparagine, ELSPAR®, Lundbeck; ERWINAZE®, EUSA Pharma); eribulin mesylate (microtubule inhibitor, tubulin-based antimitotic, HALAVEN®, Eisai); cabazitaxel (microtubule inhibitor, tubulin-based antimitotic, JEVTANA®, Sanofi-Aventis); capacetrine (thymidylate synthase inhibitor, XELODA®, Genentech); bendamustine (bifunctional mechlorethamine derivative, believed to form interstrand DNA cross-links, TREANDA®, Cephalon/Teva); ixabepilone (semi-synthetic analog of epothilone B, microtubule inhibitor, tubulin-based antimitotic, IXEMPRA®, Bristol-Myers Squibb); nelarabine (prodrug of deoxyguanosine analog, nucleoside metabolic inhibitor, ARRANON®, Novartis); clorafabine (prodrug of ribonucleotide reductase inhibitor, competitive inhibitor of deoxycytidine, CLOLAR®, Sanofi-Aventis); and trifluridine and tipiracil (thymidine-based nucleoside analog and thymidine phosphorylase inhibitor, LONSURF®, Taiho Oncology).

In some embodiments, one or more other therapeutic agent is a kinase inhibitor or VEGF-R antagonist. Approved VEGF inhibitors and kinase inhibitors useful in the present invention include: bevacizumab (AVASTIN®, Genentech/Roche) an anti-VEGF monoclonal antibody; ramucirumab (CYRAMZA®, Eli Lilly), an anti-VEGFR-2 antibody and ziv-aflibercept, also known as VEGF Trap (ZALTRAP®; Regeneron/Sanofi). VEGFR inhibitors, such as regorafenib (STIVARGA®, Bayer); vandetanib (CAPRELSA®, AstraZeneca); axitinib (INLYTA®, Pfizer); and lenvatinib (LENVIMA®, Eisai); Raf inhibitors, such as sorafenib (NEXAVAR®, Bayer AG and Onyx); dabrafenib (TAFINLAR®, Novartis); and vemurafenib (ZELBORAF®, Genentech/Roche); MEK inhibitors, such as cobimetanib (COTELLIC®, Exelexis/Genentech/Roche); trametinib (MEKINIST®, Novartis); Bcr-Abl tyrosine kinase inhibitors, such as imatinib (GLEEVEC®, Novartis); nilotinib (TASIGNA®, Novartis); dasatinib (SPRYCEL®, BristolMyersSquibb); bosutinib (BOSULIF®, Pfizer); and ponatinib (INCLUSIG®, Ariad Pharmaceuticals); Her2 and EGFR inhibitors, such as gefitinib (IRESSA®, AstraZeneca); erlotinib (TARCEEVA®, Genentech/Roche/Astellas); lapatinib (TYKERB®, Novartis); afatinib (GILOTRIF®, Boehringer Ingelheim); osimertinib (targeting activated EGFR, TAGRISSO®, AstraZeneca); and brigatinib (ALUNBRIG®, Ariad Pharmaceuticals); c-Met and VEGFR2 inhibitors, such as cabozanitib (COMETRIQ®, Exelexis); and multikinase inhibitors, such as sunitinib (SUTENT®, Pfizer); pazopanib (VOTRIENT®, Novartis); ALK inhibitors, such as crizotinib (XALKORI®, Pfizer); ceritinib (ZYKADIA®, Novartis); and alectinib (ALECENZa®, Genentech/Roche); Bruton's tyrosine kinase inhibitors, such as ibrutinib (IMBRUVICA®, Pharmacyclics/Janssen); and Flt3 receptor inhibitors, such as midostaurin (RYDAPT®, Novartis).

Other kinase inhibitors and VEGF-R antagonists that are in development and may be used in the present invention include tivozanib (Aveo Pharmaecuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (SUPECT®, IY5511, Il-Yang Pharmaceuticals, S. Korea); ruxolitinib (JAKAFI®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In some embodiments, one or more other therapeutic agent is an mTOR inhibitor, which inhibits cell proliferation, angiogenesis and glucose uptake. In some embodiments, an mTOR inhibitor is everolimus (AFINITOR®, Novartis); temsirolimus (TORISEL®, Pfizer); and sirolimus (RAPAMUNE®, Pfizer).

In some embodiments, one or more other therapeutic agent is a proteasome inhibitor. Approved proteasome inhibitors useful in the present invention include bortezomib (VELCADE®, Takeda); carfilzomib (KYPROLIS®, Amgen); and ixazomib (NINLARO®, Takeda).

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (LARTRUVO®; Eli Lilly). Approved EGFR antagonists which may be used in the present invention include cetuximab (ERBITUX®, Eli Lilly); necitumumab (PORTRAZZA®, Eli Lilly), panitumumab (VECTIBIX®, Amgen); and osimertinib (targeting activated EGFR, TAGRISSO®, AstraZeneca).

In some embodiments, one or more other therapeutic agent is an aromatase inhibitor. In some embodiments, an aromatase inhibitor is selected from exemestane (AROMASIN®, Pfizer); anastazole (ARIMIDEX®, AstraZeneca) and letrozole (FEMARA®, Novartis).

In some embodiments, one or more other therapeutic agent is an antagonist of the hedgehog pathway. Approved hedgehog pathway inhibitors which may be used in the present invention include sonidegib (ODOMZO®, Sun Pharmaceuticals); and vismodegib (ERIVEDGE®, Genentech), both for treatment of basal cell carcinoma.

In some embodiments, one or more other therapeutic agent is a folic acid inhibitor. Approved folic acid inhibitors useful in the present invention include pemetrexed (ALIMTA®, Eli Lilly).

In some embodiments, one or more other therapeutic agent is a CC chemokine receptor 4 (CCR4) inhibitor. CCR4 inhibitors being studied that may be useful in the present invention include mogamulizumab (POTELIGEO®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (RITUXAN®, Genentech/BiogenIdec); ofatumumab (anti-CD20, ARZERRA®, GlaxoSmithKline); obinutuzumab (anti-CD20, GAZYVA®, Genentech), ibritumomab (anti-CD20 and Yttrium-90, ZEVALIN®, Spectrum Pharmaceuticals); daratumumab (anti-CD38, DARZALEX®, Janssen Biotech), dinutuximab (anti-glycolipid GD2, UNITUXIN®, United Therapeutics); trastuzumab (anti-HER2, HERCEPTIN®, Genentech); ado-trastuzumab emtansine (anti-HER2, fused to emtansine, KADCYLA®, Genentech); and pertuzumab (anti-HER2, PERJETA®, Genentech); and brentuximab vedotin (anti-CD30-drug conjugate, ADCETRIS®, Seattle Genetics).

In some embodiments, one or more other therapeutic agent is a topoisomerase inhibitor. Approved topoisomerase inhibitors useful in the present invention include irinotecan (ONIVYDE®, Merrimack Pharmaceuticals); topotecan (HYCAMTIN®, GlaxoSmithKline). Topoisomerase inhibitors being studied which may be used in the present invention include pixantrone (PIXUVRI®, CTI Biopharma).

In some embodiments, one or more other therapeutic agent is an inhibitor of anti-apoptotic proteins, such as BCL-2. Approved anti-apoptotics which may be used in the present invention include venetoclax (VENCLEXTA®, AbbVie/Genentech); and blinatumomab (BLINCYTO®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (XTANDI®, Astellas/Medivation); approved inhibitors of androgen synthesis include abiraterone (ZYTIGA®, Centocor/Ortho); approved antagonist of gonadotropin-releasing hormone (GnRH) receptor (degaralix, FIRMAGON®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (EVISTA®, Eli Lilly).

In some embodiments, one or more other therapeutic agent is an inhibitor of bone resorption. An approved therapeutic which inhibits bone resorption is Denosumab (XGEVA®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (ZOMETA®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGF-β trap compound (NCT02699515); and (NCT02517398). M7824 is comprised of a fully human IgG1 antibody against PD-L1 fused to the extracellular domain of human TGF-beta receptor II, which functions as a TGF-β "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agents is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, TEMODAL CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name AROMASIN™. Formestane is marketed under the trade name LENTARON™. Fadrozole is marketed under the trade name AFEMA™. Anastrozole is marketed under the trade name ARIMIDEX™. Letrozole is marketed under the trade names FEMARA™ or FEMAr™. Aminoglutethimide is marketed under the trade name ORIMETEN™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name NOLVADEX™ Raloxifene hydrochloride is marketed under the trade name EVISTA™. Fulvestrant can be administered under the trade name FASLODEX™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (CASODEX™). The term "gonadorelin agonist" as used herein includes, but is not limited to abarelix, goserelin, and goserelin acetate. Goserelin can be administered under the trade name ZOLADEX™

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g., under the trademark CAMPTOSAR™. Topotecan is marketed under the trade name HYCAMPTIN™

The term "topoisomerase II inhibitor" as used herein includes, but is not limited to the anthracyclines such as doxorubicin (including liposomal formulation, such as CAELYX™), daunorubicin, epirubicin, idarubicin and nemorubicin, the anthraquinones mitoxantrone and losoxantrone, and the podophillotoxines etoposide and teniposide. Etoposide is marketed under the trade name ETOPOPHOS™ Teniposide is marketed under the trade name VM 26-Bristol Doxorubicin is marketed under the trade name ACRIBLASTIN™ or ADRIAMYCIN™. Epirubicin is marketed under the trade name FARMORUBICIN™. Idarubicin is marketed. under the trade name ZAVEDOS™. Mitoxantrone is marketed under the trade name NOVANTRON™

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name TAXOL™. Docetaxel is marketed under the trade name TAXOTERE™. Vinblastine sulfate is marketed under the trade name VINBLASTIN R.P™. Vincristine sulfate is marketed under the trade name FARMISTIN™

The term "alkylating agent" as used herein includes, but is not limited to, cyclophosphamide, ifosfamide, melphalan or nitrosourea (BCNU or Gliadel). Cyclophosphamide is marketed under the trade name CYCLOSTIN™. Ifosfamide is marketed under the trade name HOLOXAN™

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name XELODA™. Gemcitabine is marketed under the trade name GEMZAR™

The term "platin compound" as used herein includes, but is not limited to, carboplatin, cisplatin, cisplatinum and oxaliplatin. Carboplatin can be administered, e.g., in the form as it is marketed, e.g., under the trademark CARBO- PLAT™. Oxaliplatin can be administered, e.g., in the form as it is marketed, e.g. under the trademark ELOXATIN™

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporne derivatives, such as midostaurin; examples of further compounds include UCN-01, safingol, BAY 43-9006, Bryostatin 1, Perifosine; llmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR₁ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (HERCEPTIN™), cetuximab (ERBITUX™), Iressa, Tarceva, OSI-774, Cl-1033, EKB-569, GW-2016, ELI, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-a, p85-0, p55-y, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof, see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g., unrelated to protein or lipid kinase inhibition e.g., thalidomide (THALOMID™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2- arylaminophenylacetic acid, such as 5-methyl-2-(2'-chloro-6'-fluoroanilino) phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name DIDRONEL™. Clodronic acid is marketed under the trade name BONEFOS™ Tiludronic acid is marketed under the trade name Skelid™. Pamidronic acid is marketed under the trade name AREDIA™. Alendronic acid is marketed under the trade name FOSAMAX™. Ibandronic acid is marketed under the trade name BONDRANAT™. Risedronic acid is marketed under the trade name ACTONEL™. Zoledronic acid is marketed under the trade name ZOMETA™. The term "mTOR inhibitors" relates to compounds which inhibit the mammalian target of rapamycin (mTOR) and which possess antiproliferative activity such as sirolimus (RAPAMUNE®), everolimus (CERTICAN™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (ZARNESTRA™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (VELCADE™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (HERCEPTIN™), Trastuzumab-DM1, erbitux, bevacizumab (AVASTIN™), rituximab (RITUXAN®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; ANGIOSTATIN™; ENDOSTATIN™; anthranilic acid amides; ZD4190; Zd$_6$474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (AVASTIN™).

Photodynamic therapy as used herein refers to therapy which uses certain chemicals known as photosensitizing compounds to treat or prevent cancers. Examples of photodynamic therapy include treatment with compounds, such as VISUDYNE™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g., Patents International (e.g., IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTOR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonist of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YER-VOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MED14736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO®, Bristol-Myers Squibb, also known as ONO-4538, MDX1106 and BMS-936558), has shown potential to improve the overall survival inpatients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (IMLYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al.; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that can be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those described in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiments, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the checkpoint inhibitor is a biologic therapeutic or a small molecule. In some embodiments, the checkpoint inhibitor is a monoclonal antibody, a humanized antibody, a fully human antibody, a fusion protein or a combination thereof. In some embodiments, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor is an immunostimulatory agent, a T cell growth factor, an interleukin, an antibody, a vaccine or a combination thereof. In some embodiments, the interleukin is IL-7 or IL-15. In some embodiments, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors can include small molecule inhibitors or can include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+(αβ) T cells), CD160 (also referred to as BY55), CGEN-15049, CHK 1 and CHK2 kinases, A2aR, and various B-7 family ligands. B7 family ligands include, but are not limited to, B7- 1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-H1; MED14736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca); and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that can be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MED16469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that can be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that can be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that can be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that can be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that can be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that can be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that can be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that can be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that can be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Abbreviations

Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis (pinacolato)diboron-4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
"BuOH: n-butanol
CDI: carbonyldiimidazole
COD: cyclooctadiene
d: days
DABCO: 1,4-diazabicyclo[2.2.2]octane
DAST: diethylaminosulfur trifluoride
dba: dibenzylideneacetone
DBU: 1,8-diazabicyclo[5.4.0]undec-7-ene
DCE: 1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
MeI: iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
nBuLi: n-butyllithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N-methylmorpholine N-oxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or $Tf_2O$: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials can be confirmed by standard analytical methods, e.g., microanalysis and spectroscopic characteristics, e.g., MS, IR, NMR, such as those exemplified below. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1$H NMR) was conducted in deuterated solvent. In certain compounds disclosed herein, one or more $^1$H shifts overlap with residual proteo solvent signals; these signals have not been reported in the experimental provided hereinafter.

TABLE 3

| Analytical instruments | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give MH$^+$] and equipped with Chromolith Flash R$^P$-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column can be a BEH C18 50*2.1 mm, 1.7 micron. Column flow is 0.55 ml/min and mobile phase used may include (A)

2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give MH⁺] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % $NH_3 \cdot H_2O$ in water (solvent A) and acetonitrile (solvent B).

HPLC Analytical Method: HPLC was carried out on X Bridge C18 150*4.6 mm, 5 micron. Column flow may be 1.0 ml/min and the mobile phase can include (A) 0.1% Ammonia in water and (B) 0.1% Ammonia in Acetonitrile.

Prep HPLC Analytical Method: In some instances, the compounds were purified on Shimadzu LC-20AP and UV detector. The column used may include an X-BRIDGE C18 (250*19)mm, 5. Column flow can be 16.0 ml/min and the Mobile phase can include (A) 0.1% Formic Acid in Water and (B) Acetonitrile Basic method used (A) 5 mM ammonium bicarbonate and 0.1% NH3 in Water and (B) Acetonitrile or (A) 0.1% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO) or equivalent. The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Intermediates 15-(1-(2,6-dioxopiperidin-3-yl)-3-methyl-2-oxo-2,3-dihydro-1H-benzo[d]imidazol-4-yl)-3,6,9,12-tetraoxapentadecanoic acid (Intermediate A1)

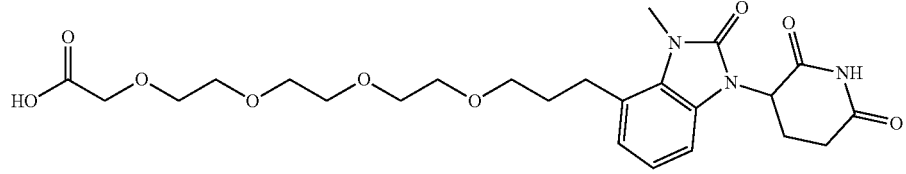

This intermediate was synthesized as previously described in WO 2020/113233 & US 2019/192668.

12-(1-(2,6-dioxopiperidin-3-yl)-3-methyl-2-oxo-2,3-dihydro-1H-benzo[d]imidazol-4-yl)dodecanoic acid (Intermediate A2)

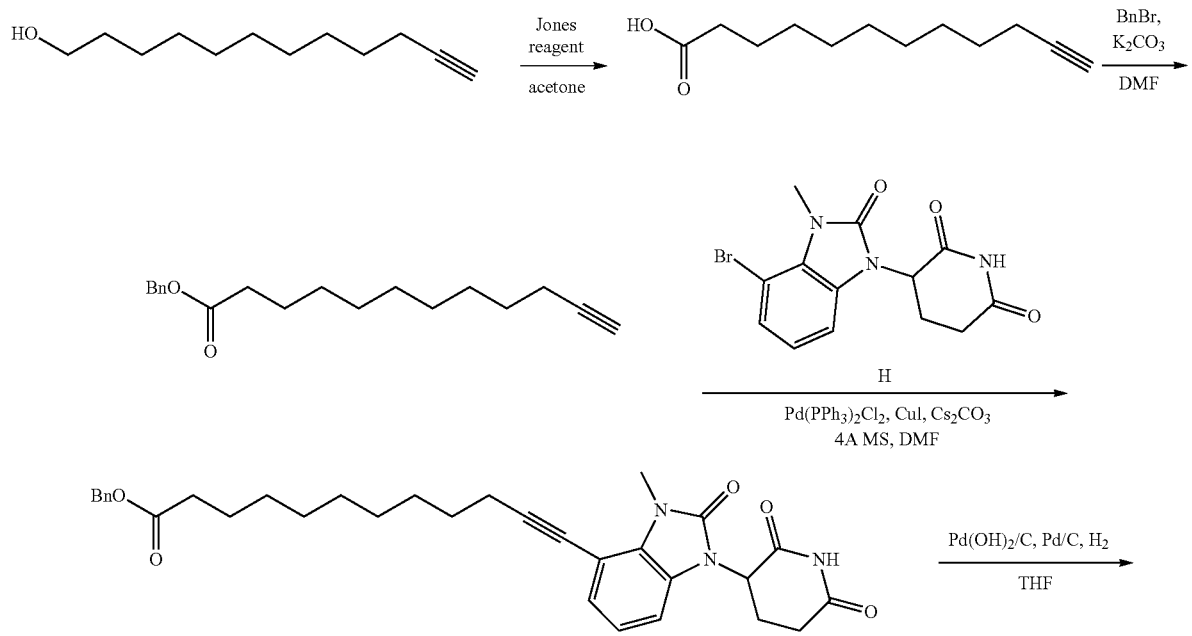

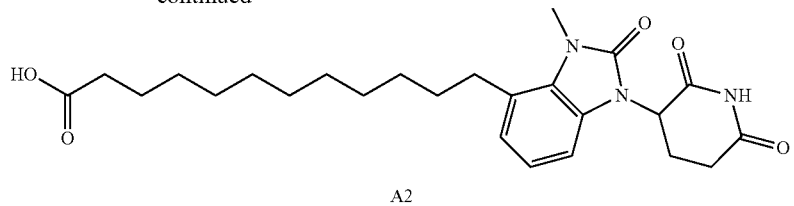

A2

Step 1—Dodec-11-ynoic acid. To a solution of dodec-11-yn-1-ol (700 mg, 3.84 mmol, CAS #18202-10-3) in acetone (10 mL) at 0° C. was added Jones reagent (3.7 mL, 9.6 mmol). The mixture was then stirred at 0° C. for 2 h. On completion, the reaction mixture was diluted with water (50 mL) and extracted with EtOAc (80 mL×3). The combined organic layers were washed with brine, dried over $Na_2SO_4$ and concentrated under reduced pressure to afford the title compound (500 mg, 66%) as a colorless oil. $^1$H NMR (400 MHz, DMSO-$d_6$) δ 12.0 (br s, 1H), 2.72 (t, J=2.6 Hz, 1H), 2.22-2.10 (m, 4H), 1.52-1.38 (m, 4H), 1.35-1.33 (m, 2H), 1.28-1.21 (m, 8H).

Step 2—Benzyl dodec-11-ynoate. To a solution of dodec-11-ynoic acid (500 mg, 2.55 mmol) in DMF (10 mL) at 0° C. was added $K_2CO_3$ (529 mg, 33.8 mmol) and BnBr (523 mg, 3.06 mmol). The mixture was stirred at rt overnight. On completion, the reaction mixture was diluted with water (50 mL) and extracted with EtOAc (60 mL×3). The combined organic layers were washed with brine, dried over $Na_2SO_4$ and concentrated under reduced pressure. The residue was purified by silica gel chromatography (Petroleum ether/EtOAc=10/1, v/v) to afford the title compound (600 mg, 82%) as a colorless oil. $^1$H NMR: (400 MHz, DMSO-$d_6$) δ 7.44-7.25 (m, 5H), 5.08 (s, 2H), 2.72 (t, J=2.6 Hz, 1H), 2.34 (t, J=7.4 Hz, 2H), 2.13 (td, J=6.8, 2.8 Hz, 2H), 1.57-1.49 (m, 2H), 1.48-1.38 (m, 2H), 1.37-1.29 (m, 2H), 1.25-1.20 (m, 8H).

Step 3—Benzyl 12-(1-(2,6-dioxopiperidin-3-yl)-3-methyl-2-oxo-2,3-dihydro-1H-benzo[d]imidazol-4-yl)dodec-11-ynoate. A mixture of benzyl dodec-11-ynoate (170 mg, 0.6 mmol), 3-(4-bromo-3-methyl-2-oxo-2,3-dihydro-1H-benzo[d]imidazol-1-yl)piperidine-2,6-dione (101 mg, 0.3 mmol, Intermediate H), $Pd(PPh_3)_2Cl_2$ (42 mg, 0.06 mmol), CuI (12 mg, 0.06 mmol), $Cs_2CO_3$ (488 mg, 1.5 mmol) and 4A molecular sieves (150 mg) in dry DMF (5 mL) was heated at 85° C. under microwave irradiation for 40 min. On completion, the mixture was poured into water (50 mL), and extracted with EtOAc (20 mL×3). The combined organic phases washed with brine, dried over $Na_2SO_4$ and concentrated under reduced pressure. The residue was purified by prep-TLC (Pet.ether/EtOAc=1/2, v/v) to afford the title compound (80 mg, 44%) as a yellow solid. LCMS m/z=544.4 [M+H]$^+$; $^1$H NMR: (400 MHz, DMSO-$d_6$) δ 11.1 (s, 1H), 7.43-7.28 (m, 5H), 7.10 (dd, J=7.7, 1.3 Hz, 1H), 7.04 (dd, J=7.9, 1.2 Hz, 1H), 6.98 (t, J=7.8 Hz, 1H). 5.38 (dd, J=12.8, 5.4 Hz, 1H), 5.07 (s, 2H), 3.63 (s, 3H), 2.95-2.81 (m, 1H), 2.77-2.58 (m, 2H), 2.49 (t, J=7.2 Hz, 2H), 2.33 (t, J=7.2 Hz, 2H), 2.05-1.98 (m, 1H), 1.60-1.48 (m, 4H), 1.45-1.35 (m, 2H), 1.33-1.21 (m, 8H).

Step 4—12-(1-(2,6-Dioxopiperidin-3-yl)-3-methyl-2-oxo-2,3-dihydro-1H-benzo[d]imidazol-4-yl)dodecanoic acid. To a solution of benzyl 12-(1-(2,6-dioxopiperidin-3-yl)-3-methyl-2-oxo-2,3-dihydro-1H-benzo[d]imidazol-4-yl)dodec-11-ynoate (80 mg, 0.15 mmol) in THF (5 mL) was added 10% Pd(OH)$_2$/C (16 mg) and 10% Pd/C (16 mg). The mixture was stirred at 35° C. under H$_2$ (1 atm) overnight. On completion, the reaction mixture was filtered and the filtrate was concentrated under reduced pressure to afford the title compound (60 mg, 90%) as a white solid. LCMS m/z=458.4 [M+H]$^+$. $^1$H NMR: (400 MHz, DMSO-$d_6$) δ 11.1 (s, 1H), 7.01-6.82 (m, 3H), 5.35 (dd, J=12.6, 5.4 Hz, 1H), 3.54 (s, 3H), 2.95-2.82 (m, 3H), 2.76-2.58 (m, 2H), 2.18 (t, J=7.3 Hz, 2H), 2.05-1.94 (m, 1H), 1.64-1.53 (m, 2H), 1.53-1.42 (m, 2H), 1.42-1.70 (m, 14H).

9-(1-(2,6-dioxopiperidin-3-yl)-3-methyl-2-oxo-2,3-dihydro-1H-benzo[d]imidazol-4-yl)nonanoic acid
(Intermediate A3)

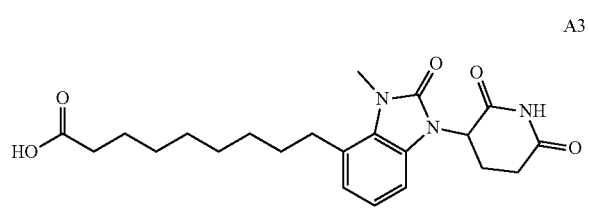 [SMILES: Cn1c(=O)n(C2CCC(=O)NC2=O)c2cccc(CCCCCCCCC(=O)O)c21]

A3

This intermediate was synthesized as previously described in WO 2020/206424.

2-(2-(3-(1-(2,6-dioxopiperidin-3-yl)-3-methyl-2-oxo-2,3-dihydro-1H-benzo[d]imidazol-4-yl)propoxy)ethoxy)acetic acid (Intermediate A4)

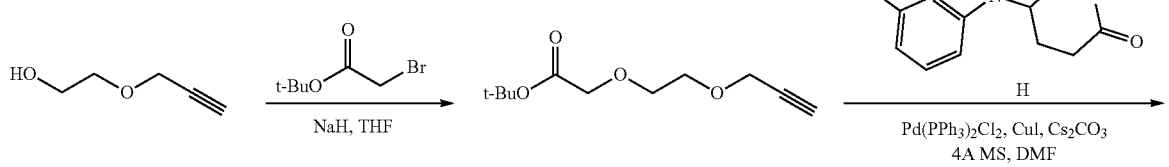

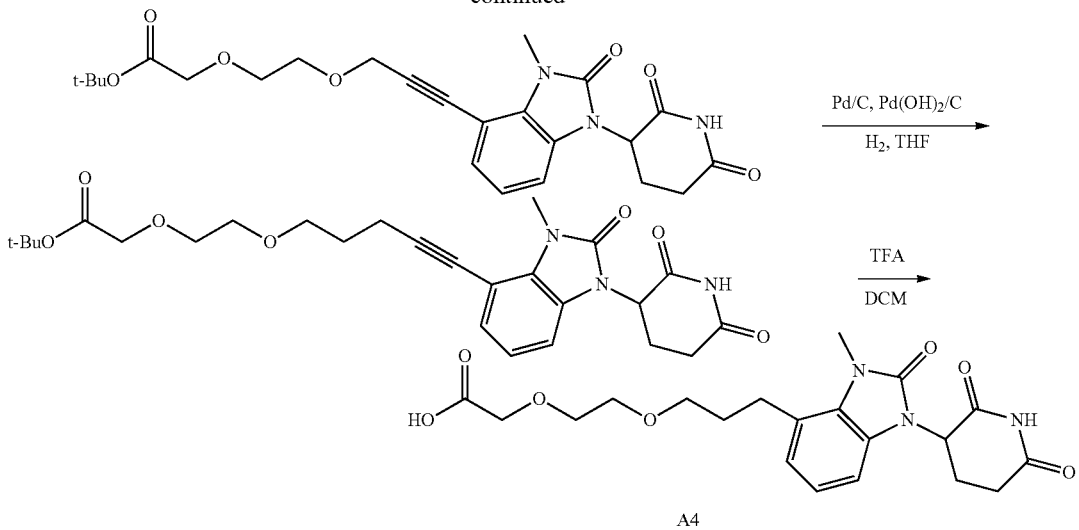

A4

Step 1—Tert-butyl 2-(2-(prop-2-yn-1-yloxy)ethoxy)acetate. To a solution of 2-(prop-2-yn-1-yloxy)ethan-1-ol (500 mg, 4.99 mmol, CAS #3973-18-0) in dry THF (8 mL) at 0° C. under $N_2$ was added NaH (60% w/w dispersion in oil, 339.6 mg, 8.49 mmol) portion-wise and the mixture was stirred at 0° C. for 1 h. Next, tert-Butyl 2-bromoacetate (974.1 mg, 4.99 mmol) was added and the mixture was stirred at rt overnight. On completion, the reaction was quenched with a sat. aq. $NH_4Cl$ solution and the mixture extracted with EtOAc (20 mL×4). The combined organic phases were washed with brine, dried over $Na_2SO_4$ and concentrated under reduced pressure. The residue was purified by silica gel chromatography (Petroleum Ether/EtOAc=50/1 to 20/1, v/v) to give the title compound (220 mg, 21%) as a light-yellow oil. $^1$H NMR (400 MHz, $CDCl_3$) δ 4.21 (d, J=2.4 Hz, 2H), 4.02 (s, 2H), 3.74 (s, 4H), 2.42 (t, J=2.4 Hz, 1H), 1.47 (s, 9H).

Step 2—Tert-butyl 2-(2-((3-(1-(2,6-dioxopiperidin-3-yl)-3-methyl-2-oxo-2,3-dihydro-1H-benzo[d]imidazol-4-yl)prop-2-yn-1-yl)oxy)ethoxy)acetate. A mixture of tert-butyl 2-(2-(prop-2-yn-1-yloxy)ethoxy)acetate (126.4 mg, 0.59 mmol), 3-(4-bromo-3-methyl-2-oxo-2,3-dihydro-1H-benzo[d]imidazol-1-yl)piperidine-2,6-dione (100 mg, 0.30 mmol, Intermediate H), $Pd(PPh_3)Cl_2$ (41.4 mg, 0.059 mmol), CuI (11.2 mg, 0.059 mmol), $Cs_2CO_3$ (479.4 mg, 1.48 g) and 4A molecular sieves (150 mg) in dry DMF (8 mL) was heated at 85° C. under microwave irradiation for 40 min. On completion, the mixture was poured into water, and extracted with EtOAc (20 mL×4). The combined organic phases washed with water, brine, dried over $Na_2SO_4$ and concentrated under reduced pressure. The residue was purified by prep-TLC (Petroleum Ether/EtOAc=1/2, v/v) to give the title compound (110 mg, 79%) as a yellow solid. LCMS m/z=470.1 [M–H]$^-$.

Step 3—Tert-butyl 2-(2-(3-(1-(2,6-dioxopiperidin-3-yl)-3-methyl-2-oxo-2,3-dihydro-1H-benzo[d]imidazol-4-yl)propoxy)ethoxy)acetate. To a solution of tert-butyl 2-(2-((3-(1-(2,6-dioxopiperidin-3-yl)-3-methyl-2-oxo-2,3-dihydro-1H-benzo[d]imidazol-4-yl)prop-2-yn-1-yl)oxy)ethoxy)acetate (110 mg, 0.23 mmol) in THF (4 mL) was added 10% Pd/C (10 mg) and 10% Pd(OH)$_2$/C (10 mg). The mixture was stirred at 35° C. under $H_2$ (1 atm) overnight. On completion, the reaction mixture was filtered and the filtrate was concentrated under reduced pressure to give the title compound (90 mg, 81%) as a yellow oil. LCMS m/z=474.2 [M–H]$^-$.

Step 4—2-(2-(3-(1-(2,6-Dioxopiperidin-3-yl)-3-methyl-2-oxo-2,3-dihydro-1H-benzo[d]imidazol-4-yl)propoxy)ethoxy)acetic acid. To a solution of tert-butyl 2-(2-(3-(1-(2,6-dioxopiperidin-3-yl)-3-methyl-2-oxo-2,3-dihydro-1H-benzo[d]imidazol-4-yl)propoxy)ethoxy)acetate (90 mg) in DCM (3 mL) was added TFA (0.5 mL) and the mixture was stirred at rt under $N_2$ for 6 h. On completion, the mixture was concentrated under reduced pressure and the residue was triturated with $Et_2O$ to give the title compound (80 mg, 100%) as a brown solid. LCMS m/z=418.2 [M–H]$^-$.

15-(1-(2,6-dioxopiperidin-3-yl)-3-methyl-2-oxo-2,3-dihydro-1H-benzo[d]imidazol-5-yl)-3,6,9,12-tetraoxapentadecanoic acid (Intermediate B1)

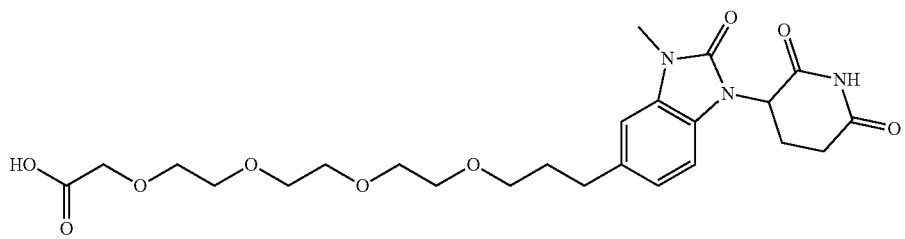

B1

This intermediate was synthesized as previously described in WO 2020/206424, WO 2020/113233, and US 2019/0192668.

12-(1-(2,6-dioxopiperidin-3-yl)-3-methyl-2-oxo-2,3-dihydro-1H-benzo[d]imidazol-5-yl)dodecanoic acid (Intermediate B2)

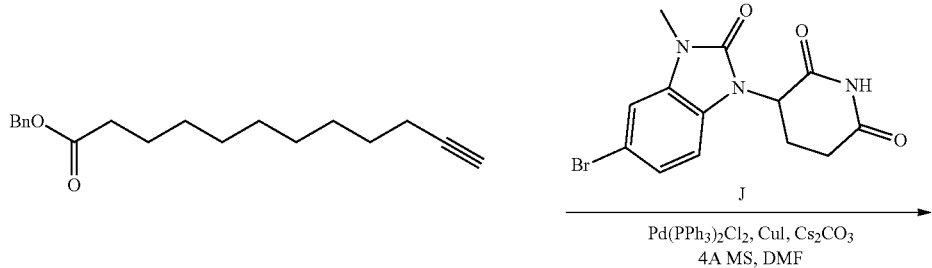

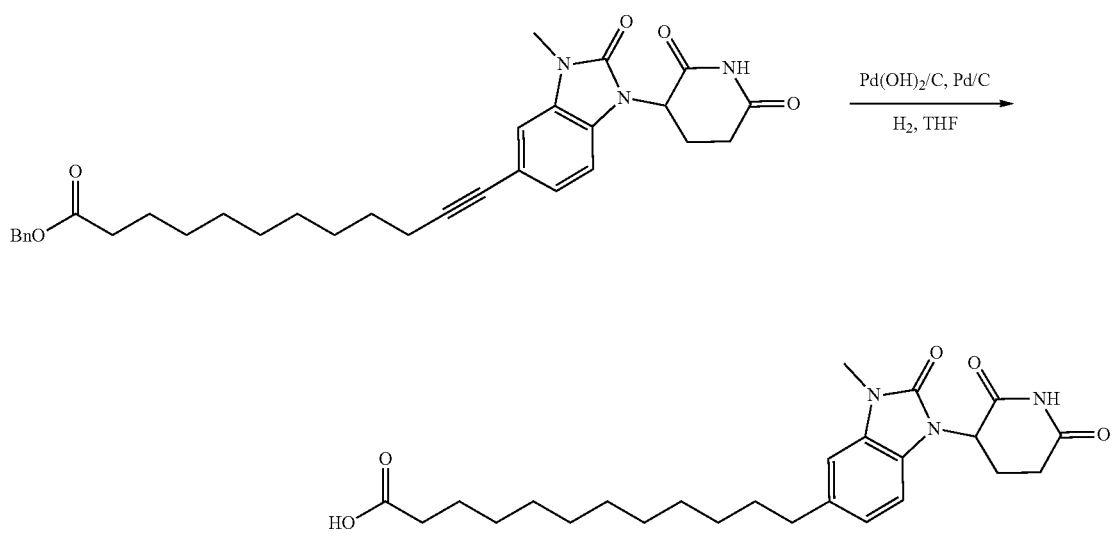

Step 1—Benzyl 12-(1-(2,6-dioxopiperidin-3-yl)-3-methyl-2-oxo-2,3-dihydro-1H-benzo[d]imidazol-5-yl)dodec-11-ynoate. A mixture of benzyl dodec-11-ynoate A2-2 (226 mg, 0.79 mmol, synthesized via Steps 1-2 of Intermediate A2), 3-(5-bromo-3-methyl-2-oxo-2,3-dihydro-1H-benzo[d]imidazol-1-yl)piperidine-2,6-dione (150 mg, 0.44 mmol, Intermediate J), Pd(PPh$_3$)$_2$Cl$_2$ (63 mg, 0.09 mmol), CuI (17 mg, 0.09 mmol), Cs$_2$CO$_3$ (716 mg, 2.2 mmol) and 4A molecular sieves (150 mg) in dry DMF (5 mL) was heated at 85° C. under microwave irradiation for 40 min. On completion, the mixture was poured into water (50 mL), and extracted with EtOAc (20 mL×3). The combined organic phases were washed with brine, dried over Na$_2$SO$_4$ and concentrated under reduced pressure. The residue was purified by prep-TLC (Petroleum ether/EtOAc=1/2, v/v) to afford the title compound (130 mg, 54%) as a yellow solid. LCMS m/z=566.4 [M+Na]$^+$, $^1$H NMR: (400 MHz, DMSO-d$_6$) δ 11.1 (s, 1H), 7.38-7.28 (m, 5H), 7.21 (s, 1H), 7.08-7.06 (m, 2H), 5.35 (dd, J=12.8, 5.4 Hz, 1H), 5.07 (s, 2H), 3.32 (s, 3H), 2.95-2.81 (m, 1H), 2.75-2.56 (m, 2H), 2.39 (t, J=7.2 Hz, 2H), 2.33 (t, J=7.2 Hz, 2H), 2.03-1.96 (m, 1H), 1.58-1.47 (m, 4H), 1.43-1.34 (m, 2H), 1.32-1.18 (m, 8H).

Step 2—12-(1-(2,6-Dioxopiperidin-3-yl)-3-methyl-2-oxo-2,3-dihydro-1H-benzo[d]imidazol-5-yl)dodecanoic acid. To a solution of benzyl 12-(1-(2,6-dioxopiperidin-3-yl)-3-methyl-2-oxo-2,3-dihydro-1H-benzo[d]imidazol-5-yl)dodec-11-ynoate (130 mg, 0.24 mmol) in THF (5 mL) was added 10% Pd(OH)$_2$/C (26 mg) and 10% Pd/C (26 mg). The mixture was stirred at 35° C. under H$_2$ (1 atm) overnight. On completion, the reaction mixture was filtered and the filtrate was concentrated under reduced pressure to afford the title compound (100 mg, 92%) as a white solid. LCMS: m/z=458.4 [M+H]$^+$.

9-(1-(2,6-Dioxopiperidin-3-yl)-3-methyl-2-oxo-2,3-dihydro-1H-benzo[d]imidazol-5-yl)nonanoic acid
(Intermediate B3)

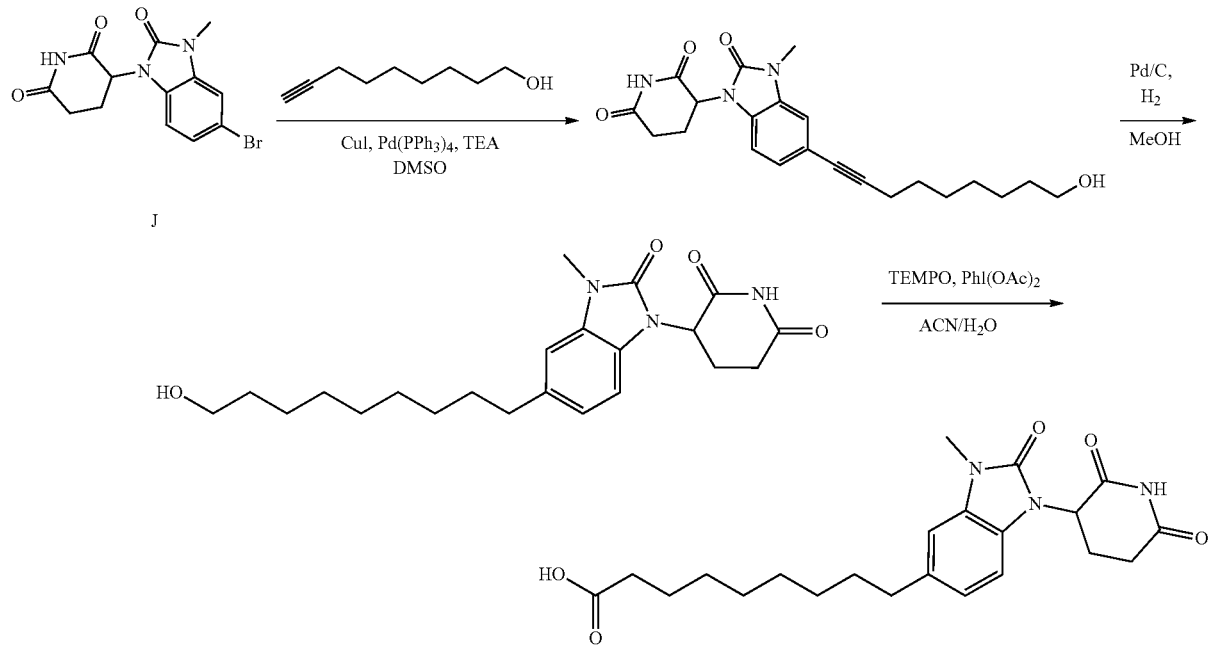

Step 1—3-[5-(9-hydroxynon-1-yn-1-yl)-3-methyl-2-oxo-1,3-benzodiazol-1-yl]piperidine-2,6-dione. To a solution of 3-(5-bromo-3-methyl-2-oxo-1,3-benzodiazol-1-yl)piperidine-2,6-dione (12 g, 36 mmol, Intermediate J) and non-8-yn-1-ol (14.93 g, 106.5 mmol, CAS #10160-28-8) in TEA (30.00 mL, 215.8 mmol) and DMSO (60.00 mL, 844.7 mmol) were added CuI (675.83 mg, 3.549 mmol) and Pd(PPh$_3$)$_4$ (4.10 g, 3.55 mmol). After stirring for 3 h at 85° C. under a nitrogen atmosphere, the reaction mixture was concentrated under reduced pressure. The residue was purified by reverse phase flash chromatography (Column: Spherical C18, 20-40 um, 330 g; Mobile Phase A: Water (plus 10 mM FA); Mobile Phase B: ACN; Flow rate: 80 mL/min; Gradient: 5%-5% B, 10 min, 30% B—45% B gradient in 20 min; Detector: 254 nm; the fractions containing the desired product were collected at 36% B) and concentrated under reduced pressure to afford the title compound (9 g, 64% yield) as a yellow solid. $^1$H NMR (400 MHz, DMSO-d$_6$) δ 11.11 (s, 1H), 7.23 (s, 1H), 7.11-7.07 (m, 2H), 5.38 (dd, J=12.8, 5.3 Hz, 1H), 4.35-4.31 (m, 1H), 3.42-3.35 (m, 2H), 3.34 (s, 3H), 2.92-3.88 (m, 1H), 2.77-2.57 (m, 2H), 2.41 (t, J=7.1 Hz, 2H), 2.09-1.98 (m, 1H), 1.57-1.53 (m, 2H), 1.48-1.23 (m, 8H). LC/MS (ESI, m/z): [(M−1)]$^-$=396.2.

Step 2—3-[5-(9-hydroxynonyl)-3-methyl-2-oxo-1,3-benzodiazol-1-yl]piperidine-2,6-dione. To a stirred solution of 3-[5-(9-hydroxynon-1-yn-1-yl)-3-methyl-2-oxo-1,3-benzodiazol-1-yl]piperidine-2,6-dione (9.00 g, 22.6 mmol) in MeOH (1.00 L) was added Pd/C (2.00 g, 1.88 mmol, 10 wt %) at rt. The reaction mixture was purged with hydrogen 3 times and was stirred for 3 h at rt under hydrogen atmosphere. On completion, the reaction mixture was filtered through a celite pad and concentrated under reduced pressure to give the title compound (9 g, 99% yield) as a yellow solid. $^1$H NMR (400 MHz, DMSO-d$_6$) δ 11.09 (s, 1H), 7.02-6.99 (m, 2H), 6.86 (d, J=8.0 Hz, 1H), 5.34 (dd, J=12.7, 5.4 Hz, 1H), 4.35-4.30 (m, 1H), 3.39-3.35 (m, 2H), 3.32 (s, 3H), 2.95-2.84 (m, 1H), 2.73-2.58 (m, 4H), 2.02-1.98 (m, 1H), 1.62-1.57 (m, 2H), 1.39-1.27 (m, 12H). LC/MS (ESI, m/z): [(M+1)]$^+$=402.3.

Step 3—9-(1-(2,6-Dioxopiperidin-3-yl)-3-methyl-2-oxo-2,3-dihydro-1H-benzo[d]imidazol-5-yl)nonanoic acid. To a solution of 3-(5-(9-hydroxynonyl)-3-methyl-2-oxo-2,3-dihydro-1H-benzo[d]imidazol-1-yl)piperidine-2,6-dione (100 mg, 249 μmol) in MeCN/H$_2$O (10/1, 5.0 mL) were added PIDA (401 mg, 1.25 mmol) and TEMPO (7.78 mg, 49.8 μmol) and the mixture was stirred at rt overnight. On completion, the reaction mixture was poured into water and extracted with EtOAc (10 mL×3). The combined organic layers were dried over Na$_2$SO$_4$ and concentrated under reduced pressure. The residue was purified by prep-TLC (DCM/MeOH=15/1, v/v) to afford the title compound (92 mg, 89%) as a pink solid. LCMS: m/z=416.2 [M+H]$^+$. $^1$H NMR (400 MHz, DMSO-d$_6$) δ 12.0 (br s, 1H), 11.1 (s, 1H), 6.97-6.93 (m, 2H), 6.87-6.83 (m, 1H), 5.37 (dd, J=12.5, 5.4 Hz, 1H), 3.54 (s, 3H), 2.92-2.83 (m, 3H), 2.75-2.57 (m, 2H), 2.18 (t, J=7.4 Hz, 2H), 2.04-1.92 (m, 1H), 1.63-1.53 (m, 2H), 1.53-1.43 (m, 2H), 1.41-1.21 (m, 8H).

2-(2-(3-(1-(2,6-dioxopiperidin-3-yl)-3-methyl-2-oxo-2,3-dihydro-1H-benzo[d]imidazol-5-yl)propoxy)ethoxy)acetic acid (Intermediate B4)

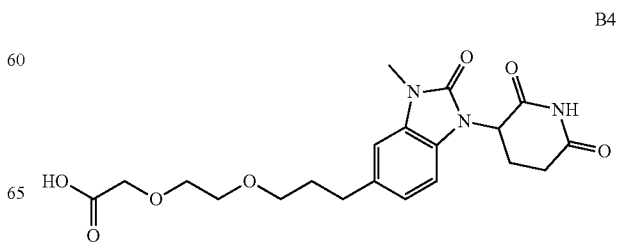

This intermediate was synthesized as previously described in WO 2020/206424 and US 2019/192668.

14-((2-(2,6-dioxopiperidin-3-yl)-1,3-dioxoisoindo-lin-4-yl)amino)-3,6,9,12-tetraoxatetradecanoic acid (Intermediate C1)

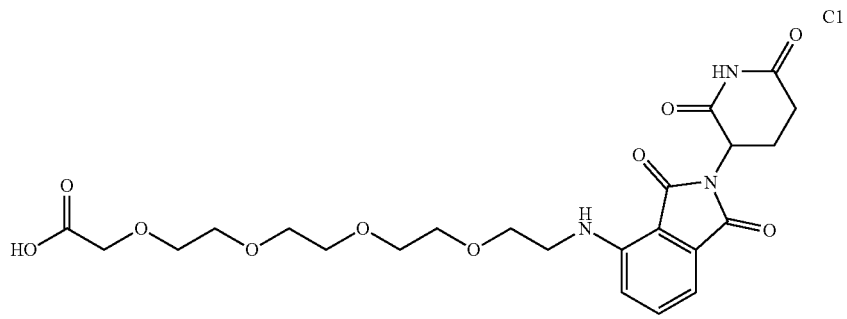 [SMILES: O=C(O)COCCOCCOCCOCCNc1cccc2c1C(=O)N(C1CCC(=O)NC1=O)C2=O]

This intermediate was synthesized as previously described in WO 2020/113233 and US 2019/192668.

12-((2-(2,6-Dioxopiperidin-3-yl)-1,3-dioxoisoindo-lin-4-yl)amino)dodecanoic acid (Intermediate C2)

8-((2-(2,6-Dioxopiperidin-3-yl)-1,3-dioxoisoindolin-4-yl)amino)octanoic acid (Intermediate C3)

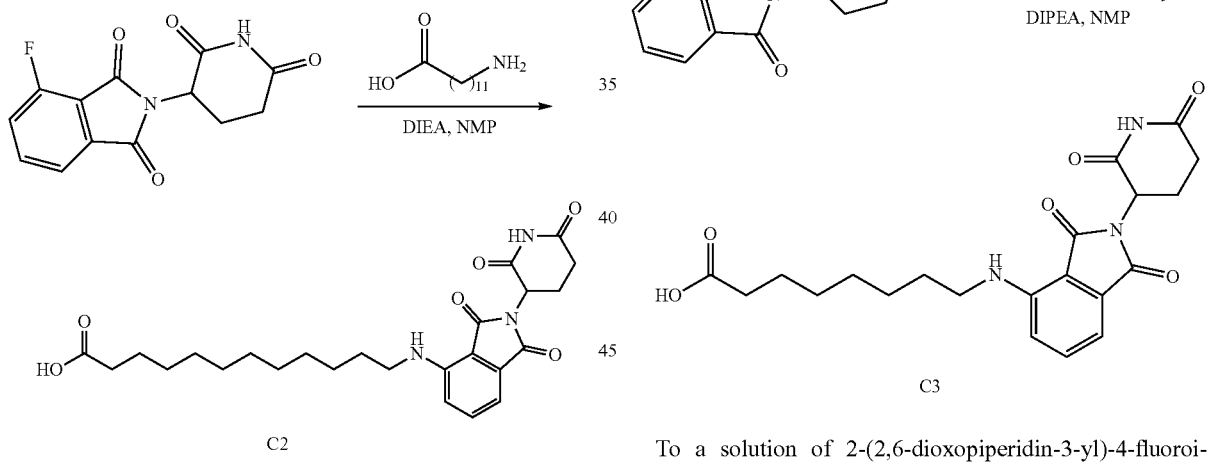

To a solution of 2-(2,6-dioxopiperidin-3-yl)-4-fluoroisoindoline-1,3-dione (1.87 g, 8.7 mmol, CAS #835616-60-9) in NMP (20 mL) was added 12-aminododecanoic acid (2.0 g, 7.2 mmol, CAS #693-57-2) and DIEA (1.87 g, 14.5 mmol). The mixture was heated at 90° C. overnight. On completion, the reaction mixture was allowed to cool to rt and purified directly by C18 reverse phase chromatography (Biotage, MeCN/H$_2$O, 40/60, v/v, 0.1% HCOOH) to give the title compound (1.4 g, 41%) as a yellow solid. LCMS: m/z=472.4 [M+H]$^+$; $^1$H NMR (400 MHz, DMSO-d$_6$) δ 12.2 (br s, 1H), 11.1 (s, 1H), 7.57 (dd, J=8.4, 7.2 Hz, 1H), 7.08 (d, J=8.6 Hz, 1H), 7.01 (d, J=7.0 Hz, 1H), 6.51 (t, J=5.8 Hz, 1H), 5.04 (dd, J=12.9, 5.4 Hz, 1H), 3.31-3.23 (m, 3H), 2.95-2.82 (m, 1H), 2.63-2.53 (m, 1H), 2.17 (t, J=7.4 Hz, 2H), 2.10-1.96 (m, 1H), 1.65-1.41 (m, 4H), 1.41-1.20 (m, 14H).

To a solution of 2-(2,6-dioxopiperidin-3-yl)-4-fluoroisoindoline-1,3-dione (1.00 g, 3.62 mmol, CAS #835616-60-9) in NMP (18 mL) was added 8-aminooctanoic acid (0.69 g, 4.34 mmol, CAS #1002-57-9) and DIEA (1.40 g, 10.9 mmol). The mixture was heated at 90° C. overnight. On completion, the reaction mixture was allowed to cool to rt, diluted with water (100 mL) and extracted with EtOAc (30 mL×3). The combined organic layers were washed with brine, dried over Na$_2$SO$_4$ and concentrated under reduced pressure. The residue was purified by C18 reverse phase chromatography (Biotage, MeCN/H$_2$O, 40/60, v/v, 0.1% HCOOH) to give the title compound (0.8 g, 53%) as a light green solid. LCMS: m/z=416.2 [M+H]$^+$; $^1$H NMR (400 MHz, DMSO-d$_6$) δ 11.1 (s, 1H), 7.57 (dd, J=8.5, 7.1 Hz, 1H), 7.08 (d, J=8.6 Hz, 1H), 7.01 (d, J=7.0 Hz, 1H), 6.51 (t, J=5.8 Hz, 1H), 5.04 (dd, J=12.8, 5.4 Hz, 1H), 3.31-3.23 (m, 3H), 2.95-2.81 (m, 1H), 2.64-2.50 (m, 1H), 2.18 (t, J=7.2 Hz, 2H), 2.08-1.95 (m, 1H), 1.62-1.40 (m, 4H), 1.37-1.08 (m, 6H).

519

2-(2-(2-((2-(2,6-dioxopiperidin-3-yl)-1,3-dioxoisoindolin-4-yl)amino)ethoxy)ethoxy)acetic acid (Intermediate C4)

520

3-(4-(1-amino-3,6,9,12-tetraoxapentadecan-15-yl)-3-methyl-2-oxo-2,3-dihydro-1H-benzo[d]imidazol-1-yl)piperidine-2,6-dione (Intermediate D1)

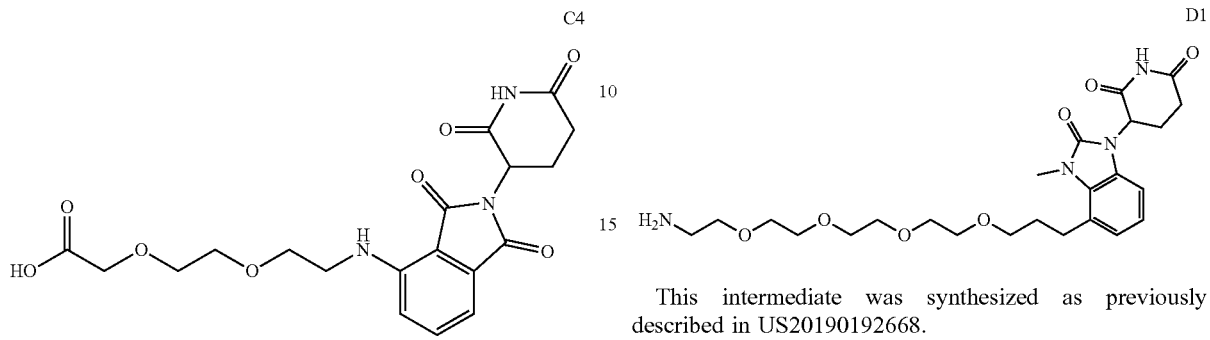

This intermediate was synthesized as previously described in US 2019/0192668.

This intermediate was synthesized as previously described in US20190192668.

3-(4-(12-aminododecyl)-3-methyl-2-oxo-2,3-dihydro-1H-benzo[d]imidazol-1-yl)piperidine-2,6-dione (Intermediate D2)

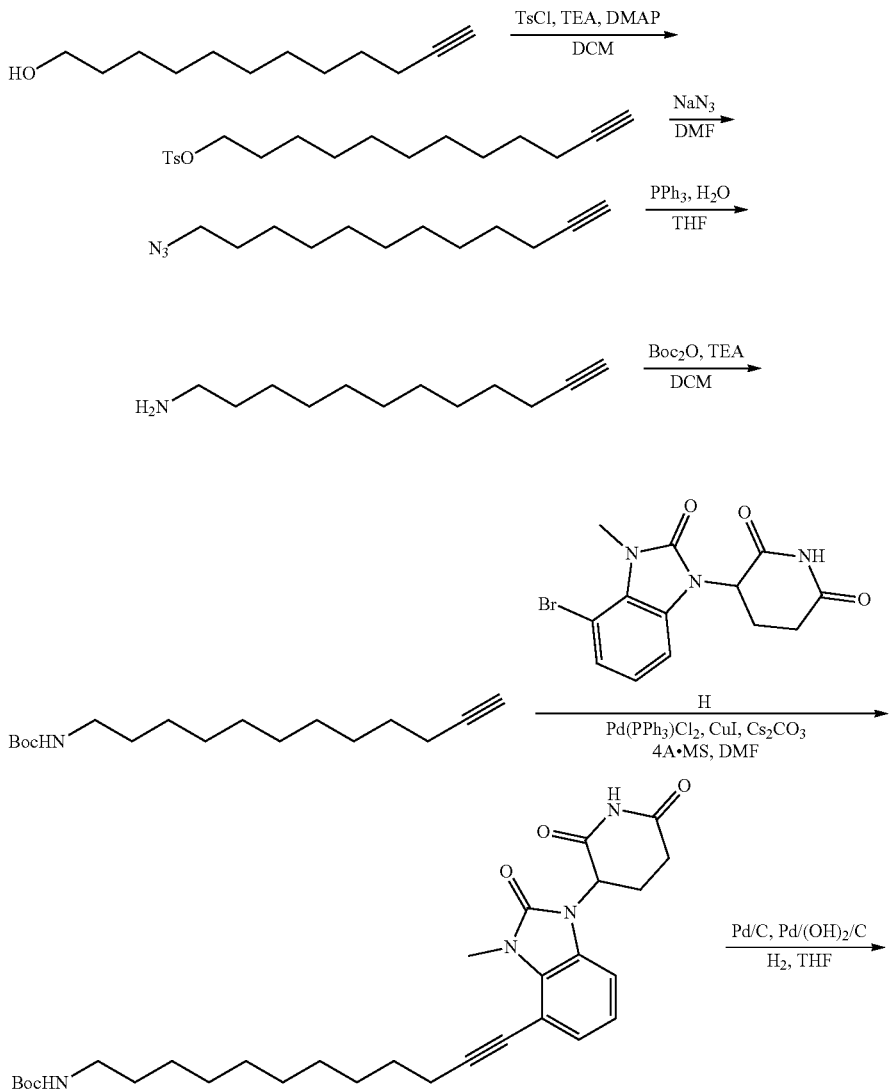

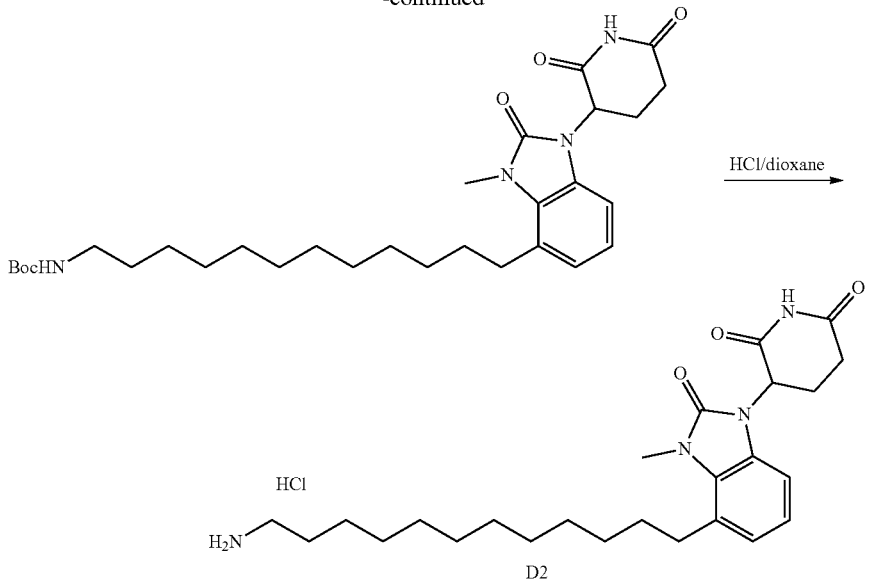

Step 1—Dodec-11-yn-1-yl 4-methylbenzenesulfonate. To a solution of dodec-11-yn-1-ol (200 mg, 517 μmol, CAS #18202-10-3) and TsCl (416 mg, 2.19 mmol) in DCM (5 mL) was added TEA (333 mg, 3.29 mmol) and DMAP (13.4 mg, 110 μmol). The mixture was stirred at rt under $N_2$ for 2 h. On completion, the reaction was concentrated under reduced pressure and the residue purified by silica gel chromatography (Petroleum Ether/EtOAc=50/1, v/v) to afford the title compound (200 mg, 54%) as a yellow oil. $^1$H NMR (400 MHz, CDCl$_3$) δ 7.79 (d, J=8.4 Hz, 2H), 7.34 (d, J=8.4 Hz, 2H), 4.01 (t, J=6.5 Hz, 2H), 2.45 (s, 3H), 2.17 (td, J=7.1, 2.6 Hz, 2H), 1.93 (t, J=2.6 Hz, 1H), 1.68-1.57 (m, 2H), 1.55-1.46 (m, 2H), 1.42-1.32 (m, 2H), 1.31-1.18 (m, 10H).

Step 2—12-Azidododec-1-yne. To a solution of dodec-11-yn-1-yl 4-methylbenzenesulfonate (2.4 g, 7.1 mmol) in DMF (40 mL) was added NaN$_3$ (696 mg, 10.7 mmol) and the mixture was heated at 45° C. overnight. On completion, the mixture was diluted with water (50 mL), and extracted with EtOAc (100 mL×2). The combined organic layers were washed with brine, dried over Na$_2$SO$_4$ and concentrated under reduced pressure to afford the title compound (1.2 g, 81%) as colorless oil. $^1$H NMR (400 MHz, CDCl$_3$) δ 3.25 (t, J=7.0 Hz, 2H), 2.18 (td, J=7.2, 2.6 Hz, 2H), 1.94 (t, J=2.6 Hz, 1H), 1.65-1.47 (m, 6H), 1.44-1.23 (m, 10H).

Step 3—Dodec-11-yn-1-amine. To a solution of 12-Azidododec-1-yne (1.2 g, 5.79 mmol) in THF (30 mL) was added PPh$_3$ (1.82 g, 6.95 mmol) and H$_2$O (104 mg, 5.79 mmol) and the mixture was stirred at rt overnight. On completion, the reaction was concentrated under reduced pressure and the residue triturated with petroleum ether and filtered. The filtrate was concentrated under reduced pressure to afford the title compound (1.0 g, 96%) as a colorless oil.

Step 4—Tert-butyl dodec-11-yn-1-ylcarbamate. To a solution of dodec-11-yn-1-amine (1.0 g, 5.52 mmol) in DCM (30 mL) was added Boc$_2$O (1.44 g, 6.62 mmol) and TEA (1.11 g, 11.1 mmol) and the mixture was stirred at rt overnight. On completion, the solvent was removed under reduced pressure and the residue purified by silica gel chromatography (Pet. Ether/EtOAc=30/1, v/v) to afford the title compound (1.2 g, 77%) as a colorless oil. $^1$H NMR (400 MHz, DMSO-d$_6$) δ 6.74 (t, J=5.2 Hz, 1H), 2.92-2.84 (m, 2H), 2.71 (t, J=2.6 Hz, 1H), 2.13 (td, J=6.8, 2.6 Hz, 2H), 1.45-1.29 (m, 16H), 1.23 (s, 9H).

Step 5—Tert-butyl (12-(1-(2,6-dioxopiperidin-3-yl)-3-methyl-2-oxo-2,3-dihydro-1H-benzo[d]imidazole-4-yl)dodec-11-yn-1-yl)carbamate. A mixture of tert-butyl dodec-11-yn-1-ylcarbamate (249 mg, 887 μmol), 3-(4-bromo-3-methyl-2-oxo-2,3-dihydro-1H-benzo[d]imidazol-1-yl) piperidine-2,6-dione (150 mg, 443 μmol, Intermediate H), Pd(PPh$_3$)$_2$Cl$_2$ (32.3 g, 88.7 umol), CuI (16.8 mg, 88.7 μmol), Cs$_2$CO$_3$ (719 mg, 2.21 mmol) and 4A molecular sieves (200 mg) in dry DMF (8.0 mL) was heated at 85° C. under microwave irradiation for 1 h. On completion, the mixture was diluted with water (50 mL), and extracted with EtOAc (100 mL×2). The combined organic layers were washed with brine, dried over Na$_2$SO$_4$ and concentrated under reduced pressure. The residue was purified by prep-TLC (DCM/MeOH=15/1, v/v) to afford the title compound (90 mg, 38%) as a colorless oil. LCMS m/z=539.3 [M+H]$^+$; $^1$H NMR (400 MHz, DMSO-d$_6$) δ 11.1 (s, 1H), 7.10 (dd, J=7.7, 1.3 Hz, 1H), 7.07-7.02 (m, 1H), 6.98 (t, J=7.8 Hz, 1H), 6.72 (t, J=5.6 Hz, 1H), 5.37 (dd, J=12.8, 5.2 Hz, 1H), 3.63 (s, 3H), 2.91-2.84 (m, 3H), 2.73-2.59 (m, 2H), 2.47 (t, J=7.2 Hz, 2H), 2.05-1.98 (m, 1H), 1.61-1.53 (m, 2H), 1.46-1.39 (m, 2H), 1.36-1.26 (m, 12H), 1.24 (s, 9H).

Step 6—Tert-butyl (12-(1-(2,6-dioxopiperidin-3-yl)-3-methyl-2-oxo-2,3-dihydro-1H-benzo[d]imidazole-4-yl)dodecyl)carbamate. To a solution of tert-butyl (12-(1-(2,6-dioxopiperidin-3-yl)-3-methyl-2-oxo-2,3-dihydro-1H-benzo[d]imidazole-4-yl)dodec-11-yn-1-yl)carbamate (249 mg, 887 μmol) in THF (10.0 mL) was added 10% Pd/C (20 mg) and 10% Pd(OH)$_2$/C (20 mg). The mixture was stirred at 35° C. under H$_2$ (1 atm) for 20 h. On completion, the reaction mixture was filtered and the filtrate concentrated under reduced pressure to afford the title compound (60 mg, 66%) as a white solid. LCMS m/z=543.3 [M+H]$^+$; $^1$H NMR (400 MHz, CDCl$_3$) δ 8.24 (br s, 1H), 6.97 (t, J=7.6 Hz, 1H), 6.88 (d, J=7.7 Hz, 1H), 6.65 (d, J=7.8 Hz, 1H), 5.20 (dd, J=12.3, 5.4 Hz, 1H), 3.66 (s, 3H), 3.16-3.04 (m, 2H), 2.93-2.83 (m, 3H), 2.32-2.16 (m, 2H), 2.08-1.82 (m, 3H), 1.66-1.59 (m, 4H), 1.51-1.24 (m, 23H).

Step 7—3-(4-(12-Aminododecyl)-3-methyl-2-oxo-2,3-dihydro-1H-benzo[d]imidazol-1-yl)piperidine-2,6-dione hydrochloride. A mixture of tert-butyl (12-(1-(2,6-dioxopiperidin-3-yl)-3-methyl-2-oxo-2,3-dihydro-1H-benzo[d]imidazole-4-yl)dodecyl)carbamate (60 mg, 110 umol) and a 4 M HCl in dioxane solution (10.0 mL) was stirred at rt for 3 h. On completion, the mixture was concentrated under reduced pressure to afford the title compound (50 mg, 96%) as a white solid. LCMS m/z=443.2 [M+H]$^+$.

3-(4-(9-aminononyl)-3-methyl-2-oxo-2,3-dihydro-1H-benzo[d]imidazol-1-yl)piperidine-2,6-dione (Intermediate D3)

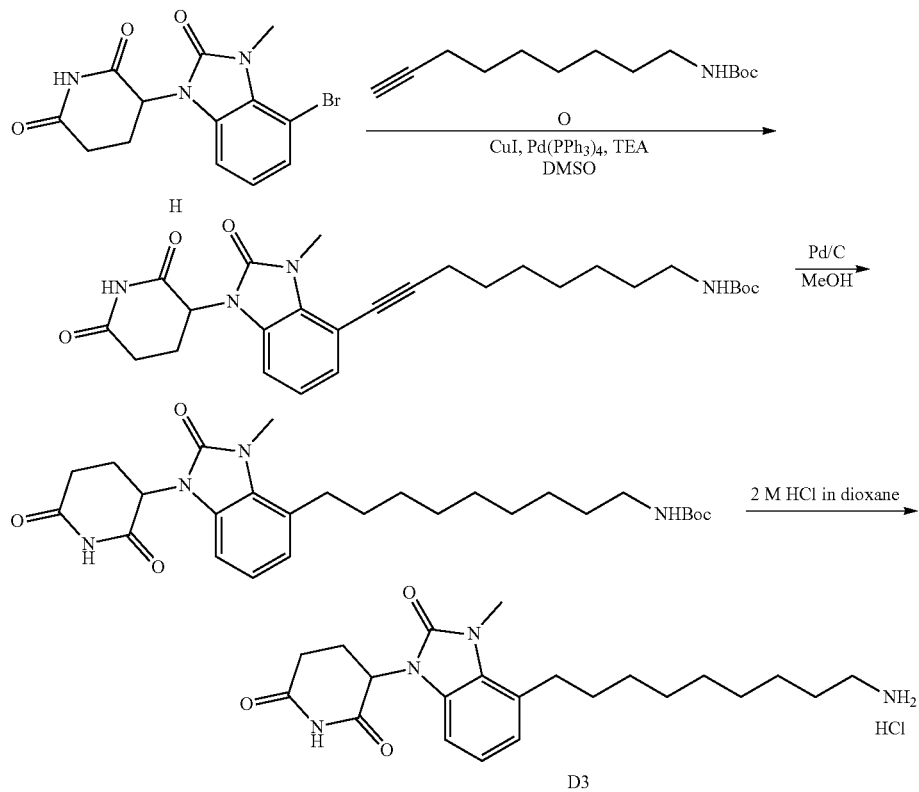

D3

Step 1—Tert-butyl N-[9-[1-(2,6-dioxopiperidin-3-yl)-3-methyl-2-oxo-1,3-benzodiazol-4-yl]non-8-yn-1-yl]carbamate. To a stirred mixture of 3-(4-bromo-3-methyl-2-oxo-1,3-benzodiazol-1-yl)piperidine-2,6-dione (8.00 g, 23.7 mmol, Intermediate H) and tert-butyl N-(non-8-yn-1-yl)carbamate (8.49 g, 35.5 mmol, Intermediate O) in DMA (40.0 mL) and TEA (20.0 mL) were added Pd(PPh$_3$)$_4$ (2.73 g, 2.37 mmol) in portions at rt under nitrogen atmosphere. The resulting mixture was stirred for 3 h at 80° C. under nitrogen atmosphere. On completion, the resulting mixture was diluted with water (100 mL) and extracted with EtOAc (3×75 mL). The combined organic layers were washed with brine (3×50 mL), and dried over anhydrous Na$_2$SO$_4$. After filtration, the filtrate was concentrated under reduced pressure. The residue product was purified by reverse phase flash (Column: Spherical C18, 20~40 um, 330 g; Mobile Phase A: Water (0.05% FA), Mobile Phase B: ACN; Flow rate: 45 mL/min; Gradient (B %): 5%~5%, 8 min; 40%~60%, 30 min; 60%~95%; 0 min; 95%, 5 min; Detector: 254 nm; Rt: 23.4 min.) to afford the title compound (6.4 g, 55% yield) as a yellow solid. $^1$H NMR (400 MHz, DMSO-d$_6$) δ 11.12 (s, 1H), 7.11 (dd, J=7.8, 1.3 Hz, 1H), 7.05 (dd, J=7.9, 1.2 Hz, 1H), 6.99 (t, J=7.8 Hz, 1H), 6.77 (t, J=5.8 Hz, 1H), 5.39 (dd, J=12.7, 5.4 Hz, 1H), 3.64 (s, 3H), 2.98-2.78 (m, 3H), 2.74-2.59 (m, 2H), 2.52-2.46 (m, 2H), 2.06-1.96 (m, 1H), 1.61-1.54 (m, 2H), 1.45-1.34 (m, 13H), 1.33-1.19 (m, 4H). LC/MS (ESI, m/z): [(M+1)]$^+$=497.3.

Step 2—Tert-butyl N-[9-[1-(2,6-dioxopiperidin-3-yl)-3-methyl-2-oxo-1,3-benzodiazol-4-yl]nonyl]carbamate. To a stirred mixture of tert-butyl N-[9-[1-(2,6-dioxopiperidin-3-yl)-3-methyl-2-oxo-1,3-benzodiazol-4-yl]non-8-yn-1-yl]carbamate (6.40 g, 12.9 mmol) in MeOH (500 mL) was added Pd/C (1371.48 mg, 12.887 mmol) in portions at rt under nitrogen atmosphere. The resulting mixture was stirred for 4 h at rt under hydrogen atmosphere. On completion the reaction mixture was filtered and the filter cake was washed with MeOH (3×100 mL). The filtrate was concentrated under reduced pressure to give the title compound (6.0 g) as a white solid. $^1$H NMR (400 MHz, DMSO-d$_6$) δ 11.10 (s, 1H), 7.02-6.91 (m, 2H), 6.88-6.85 (m, 1H), 6.75 (t, J=5.7 Hz, 1H), 5.37 (dd, J=12.6, 5.4 Hz, 1H), 3.55 (s, 3H), 2.90-2.87 (m, 3H), 2.78-2.56 (m, 2H), 2.04-1.94 (m, 1H), 1.61-1.56 (m, 2H), 1.38-1.32 (m, 15H), 1.29-1.19 (m, 8H). LC/MS (ESI, m/z): [(M+1)]$^+$=501.3.

Step 3—3-[4-(9-aminononyl)-3-methyl-2-oxo-1,3-benzodiazol-1-yl]piperidine-2,6-dione hydrochloride. To a stirred solution of tert-butyl N-[9-[1-(2,6-dioxopiperidin-3-yl)-3-methyl-2-oxo-1,3-benzodiazol-4-yl]nonyl]carbamate (6.00 g, 12 mmol) in DCM (20.0 mL) was added HCl (4 M) in 1,4-dioxane (20.0 mL) at rt under nitrogen atmosphere and the solution was stirred for 4 h at rt. On completion, the reaction mixture was concentrated under reduced pressure to give the title compound (3.9 g, 91% yield) as a white solid. $^1$H NMR (400 MHz, DMSO-d$_6$) δ 11.11 (s, 1H), 8.03 (broad, 3H), 7.03-6.91 (m, 2H), 6.89-6.86 (m, 1H), 5.40 (dd, J=12.6, 5.4 Hz, 1H), 3.57 (s, 3H), 2.94-2.85 (m, 3H), 2.81-2.57 (m, 4H), 2.03-1.97 (m, 1H), 1.64-1.53 (m, 4H), 1.41-1.26 (m, 10H). LC/MS (ESI, m/z): [(M+1)]$^+$=401.3.

3-(4-(3-(2-(2-aminoethoxy)ethoxy)propyl)-3-methyl-2-oxo-2,3-dihydro-1H-benzo[d]imidazol-1-yl)piperidine-2,6-dione (Intermediate D4)

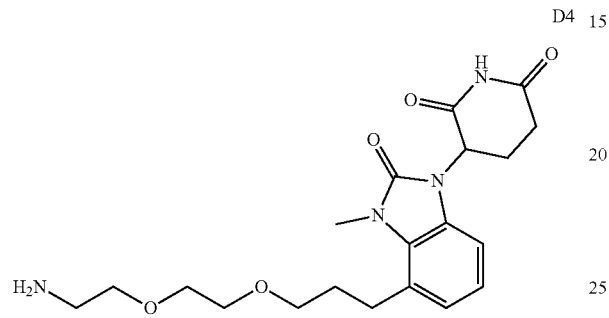

This intermediate was synthesized as previously described in WO 2020/113233 and US 2019/192668.

3-(4-(6-aminohexyl)-3-methyl-2-oxo-2,3-dihydro-1H-benzo[d]imidazol-1-yl)piperidine-2,6-dione (Intermediate D5)

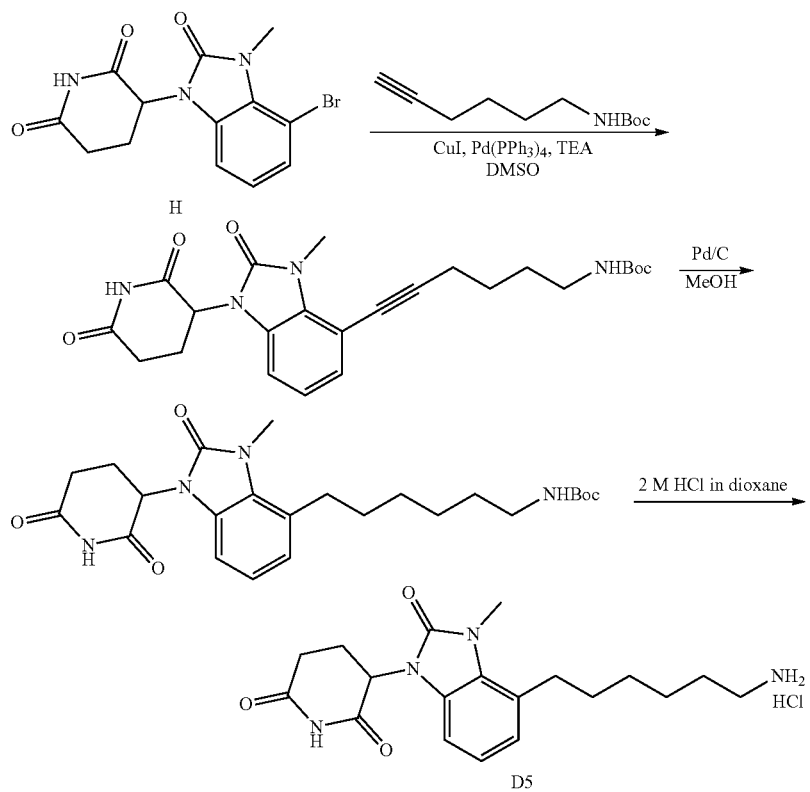

Step 1—Tert-butyl N-[6-[1-(2,6-dioxopiperidin-3-yl)-3-methyl-2-oxo-1,3-benzodiazol-4-yl]hex-5-yn-1-yl]carbamate. To a stirred mixture of 3-(4-bromo-3-methyl-2-oxo-1,3-benzodiazol-1-yl)piperidine-2,6-dione (8.00 g, 23.7 mmol, Intermediate H) and tert-butyl N-(hex-5-yn-1-yl) carbamate (7.00 g, 35.5 mmol) in DMA (40.00 mL) and TEA (20.00 mL) were added Pd(PPh$_3$)$_4$ (2.73 g, 2.37 mmol) in portions at rt under nitrogen atmosphere. The resulting mixture was stirred for 3 h at 80° C. under nitrogen atmosphere. On completion, the reaction mixture was diluted with water (100 mL) and extracted with EtOAc (3×75 mL). The combined organic layers were washed with brine (3×50 mL), and dried over anhydrous Na$_2$SO$_4$. After filtration, the filtrate was concentrated under reduced pressure. The residue product was purified by reverse phase flash with the following conditions (Column: Spherical C18, 20-40 um, 330 g; Mobile Phase A: Water (0.05% FA), Mobile Phase B: ACN; Flow rate: 45 mL/min; Gradient (B %): 5%~5%, 8 min; 40%~60%, 30 min; 60%~95%; 0 min; 95%, 5 min; Detector: 254 nm; Rt: 23.4 min.) to afford the title compound (4.5 g, 42% yield) as a yellow solid. $^1$H NMR (400 MHz, DMSO-d$_6$) δ 11.12 (s, 1H), 7.12 (d, J=7.7 Hz, 1H), 7.06 (dd, J=7.9, 1.2 Hz, 1H), 6.99 (t, J=7.8 Hz, 1H), 6.85 (t, J=5.7 Hz, 1H), 5.39 (dd, J=12.7, 5.3 Hz, 1H), 3.64 (s, 3H), 2.99-2.93 (m, 2H), 2.92-2.84 (m, 1H), 2.81-2.59 (m, 2H), 2.52-2.47 (m, 2H), 2.05-1.99 (m, 1H), 1.57-1.51 (m, 4H), 1.38 (s, 9H). LC/MS (ESI, m/z): [(M+1)]$^+$=455.3.

Step 2—Tert-butyl N-[6-[1-(2,6-dioxopiperidin-3-yl)-3-methyl-2-oxo-1,3-benzodiazol-4-yl]hexyl]carbamate. To a stirred mixture of tert-butyl N-[6-[1-(2,6-dioxopiperidin-3-yl)-3-methyl-2-oxo-1,3-benzodiazol-4-yl]hex-5-yn-1-yl] carbamate (5.50 g, 12.1 mmol) in MeOH (500.00 mL) was added Pd/C (1.29 g, 12.1 mmol) in portions at rt under nitrogen atmosphere. The resulting mixture was stirred for 4 h at rt under hydrogen atmosphere. On completion, the reaction mixture was filtered and the filter cake was washed with MeOH (3×100 mL). The filtrate was concentrated under reduced pressure to give the title compound (5 g, 90% yield) as a white solid. $^1$H NMR (400 MHz, DMSO-d$_6$) δ 11.10 (s, 1H), 6.99-6.92 (m, 2H), 6.86 (dd, J=5.5, 3.5 Hz, 1H), 6.77 (t, J=5.6 Hz, 1H), 5.37 (dd, J=12.6, 5.4 Hz, 1H), 3.55 (s, 3H), 2.92-2.85 (m, 5H), 2.79-2.56 (m, 2H), 2.03-1.99 (m, 1H), 1.61-1.56 (m, 2H), 1.37 (s, 13H), 1.34-1.29 (m, 2H). LC/MS (ESI, m/z): [(M+1)]$^+$=459.3.

Step 3—3-[4-(6-aminohexyl)-3-methyl-2-oxo-1,3-benzodiazol-1-yl]piperidine-2,6-dione hydrochloride. To a stirred solution of tert-butyl N-[6-[1-(2,6-dioxopiperidin-3-yl)-3-methyl-2-oxo-1,3-benzodiazol-4-yl]hexyl]carbamate (5.00 g, 10.9 mmol) in DCM (20.0 mL) was added HCl (4M) in 1,4-dioxane (20.0 mL) at rt under nitrogen atmosphere. The solution was stirred for 4 h at rt. On completion, the reaction mixture was concentrated under reduced pressure to give the title compound (3.9 g, 91% yield) as a white solid. $^1$H NMR (400 MHz, DMSO-d$_6$) δ 11.11 (s, 1H), 8.04 (broad, 3H), 7.08-6.91 (m, 2H), 6.90-6.86 (m, 1H), 5.40 (dd, J=12.6, 5.4 Hz, 1H), 3.57 (s, 3H), 2.98-2.84 (m, 3H), 2.80-2.73 (m, 2H), 2.71-2.57 (m, 2H), 2.04-1.98 (m, 1H), 1.63-1.56 (m, 4H), 1.49-1.32 (m, 4H). LC/MS (ESI, m/z): [(M+1)]$^+$=359.3.

3-(5-(1-amino-3,6,9,12-tetraoxapentadecan-15-yl)-3-methyl-2-oxo-2,3-dihydro-1H-benzo[d]imidazol-1-yl)piperidine-2,6-dione (Intermediate E1)

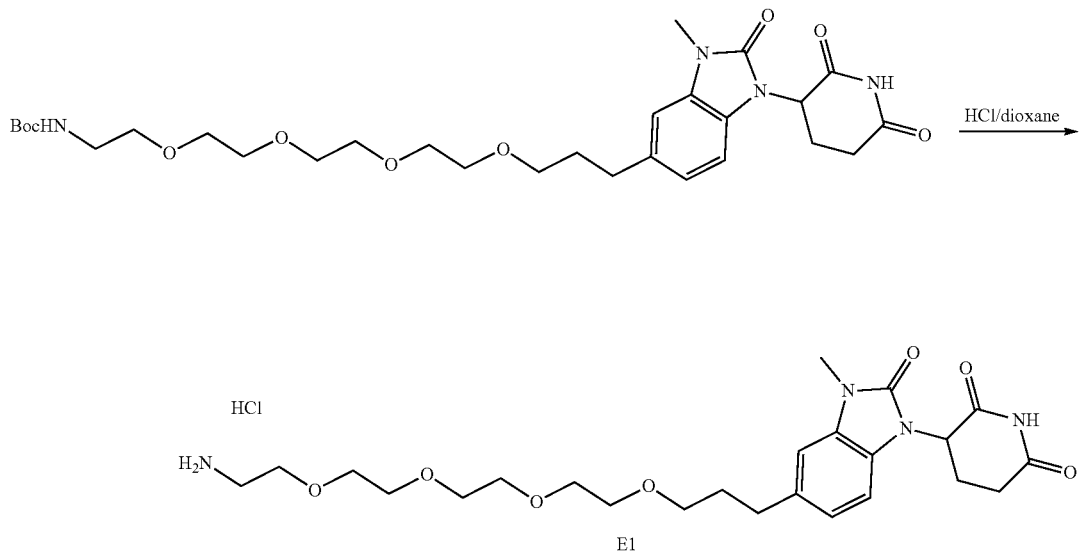

E1

A mixture of tert-butyl (15-(1-(2,6-dioxopiperidin-3-yl)-3-methyl-2-oxo-2,3-dihydro-1H-benzo[d]imidazol-5-yl)-3,6,9,12-tetraoxapentadecyl)carbamate (50 mg, 84 μmol, synthesized as described in WO2019060693) and a 4 M HCl in dioxane solution (10.0 mL) was stirred at rt for 3 h. On completion, the mixture was concentrated under reduced pressure to afford the title compound (60 mg, >100%) as a yellow solid. LCMS m/z=493.4 [M+H]$^+$.

3-(5-(12-aminododecyl)-3-methyl-2-oxo-2,3-di-hydro-1H-benzo[d]imidazol-1-yl)piperidine-2,6-dione (Intermediate E2)

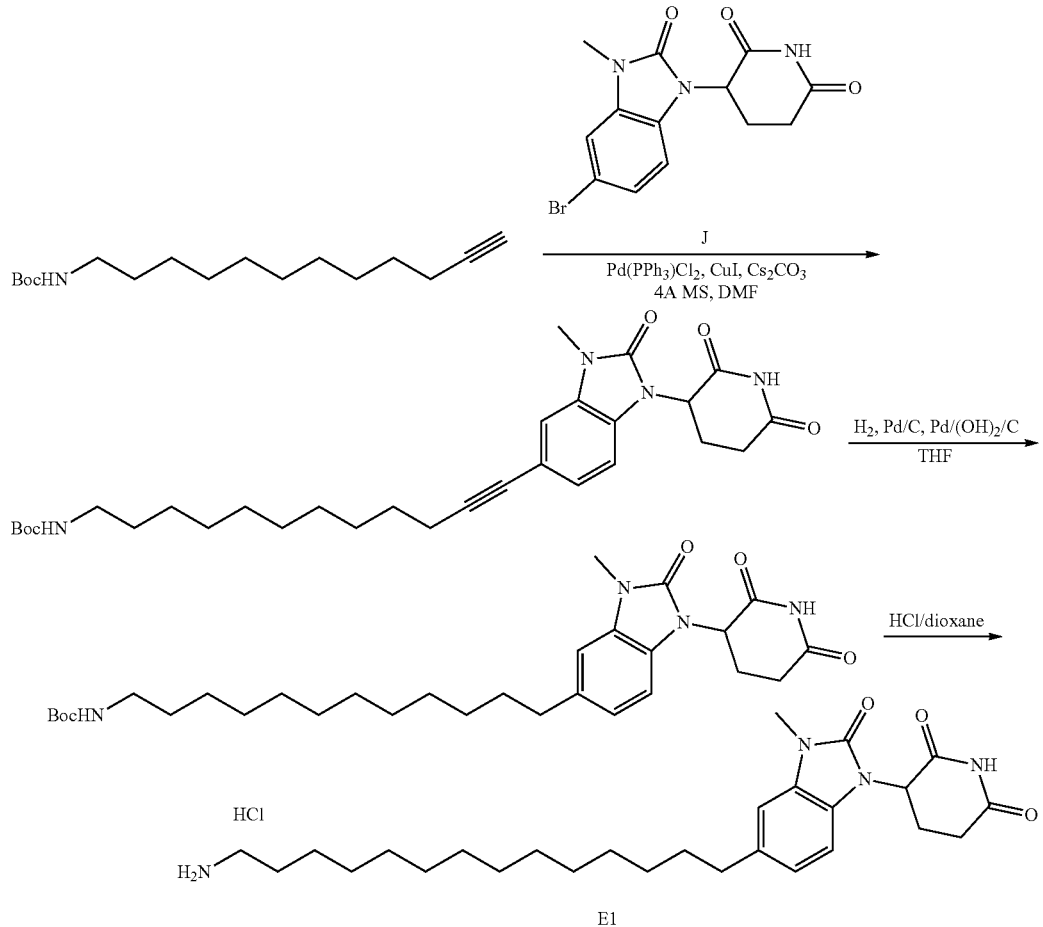

Step 1—Tert-butyl (12-(1-(2,6-dioxopiperidin-3-yl)-3-methyl-2-oxo-2,3-dihydro-1H-benzo[d]imidazol-5-yl)dodec-11-yn-1-yl)carbamate. A mixture of 3-(5-bromo-3-methyl-2-oxo-2,3-dihydro-1H-benzo[d]imidazol-1-yl)piperidine-2,6-dione (100 mg, 295 μmol, Intermediate J), tert-butyl dodec-11-yn-1-ylcarbamate (141 mg, 502 μmol, synthesized via Steps 1-4 of Intermediate D2), Pd(PPh$_3$)$_2$Cl$_2$ (41.5 mg, 59 μmol), CuI (11.2 mg, 59 μmol), Cs$_2$CO$_3$ (479 mg, 1.4 mmol) and 4A molecular sieves (200 mg) in dry DMF (8.0 mL) was heated at 85° C. under microwave irradiation for 1 h. On completion, the mixture was diluted with water (50 mL), and extracted with EtOAc (100 mL×2). The combined organic layers were washed with brine, dried over Na$_2$SO$_4$ and concentrated under reduced pressure. The residue was purified by prep-TLC (DCM/MeOH=15/1, v/v) to afford the title compound (65 mg, 41%) as a colorless oil. LCMS m/z=539.3 [M+H]; $^1$H NMR (400 MHz, DMSO-d$_6$) δ 11.1 (s, 1H), 7.22 (s, 1H), 7.10-7.05 (m, 2H), 6.73 (t, J=5.2 Hz, 1H), 5.36 (dd, J=12.8, 5.4 Hz, 1H), 3.34 (s, 3H), 2.92-2.84 (m, 3H), 2.74-2.59 (m, 2H), 2.40 (t, J=7.0 Hz, 2H), 2.07-1.97 (m, 1H), 1.58-1.49 (m, 2H), 1.45-1.19 (m, 23H).

Step 2—Tert-butyl (12-(1-(2,6-dioxopiperidin-3-yl)-3-methyl-2-oxo-2,3-dihydro-1H-benzo[d]imidazol-5-yl)dodecyl)carbamate. To a solution of tert-butyl (12-(1-(2,6-dioxopiperidin-3-yl)-3-methyl-2-oxo-2,3-dihydro-1H-benzo[d]imidazol-5-yl)dodec-11-yn-1-yl)carbamate (100 mg, 185 μmol) in THF (10.0 mL) was added 10% Pd/C (20 mg) and 10% Pd(OH)$_2$/C (20 mg). The mixture was stirred at 35° C. under H$_2$ (1 atm) for 20 h. On completion, the reaction was filtered and the filtrate was concentrated under reduced pressure to afford the title compound (60 mg, 59%) as a white solid. LCMS m/z=543.2 [M+H]$^+$; $^1$H NMR (400 MHz, CDCl$_3$) δ 8.13 (br s, 1H), 6.88 (dd, J=8.1, 1.5 Hz, 1H), 6.84 (d, J=1.4 Hz, 1H), 6.70 (d, J=8.0 Hz, 1H), 5.20 (dd, J=12.5, 5.3 Hz, 1H), 3.42 (s, 3H), 3.15-3.01 (m, 2H), 2.99-2.68 (m, 3H), 2.67-2.60 (m, 2H), 2.29-2.18 (m, 1H), 1.64-1.59 (m, 2H), 1.44 (s, 12H), 1.36-1.23 (m, 15H).

Step 3—3-(5-(12-Aminododecyl)-3-methyl-2-oxo-2,3-dihydro-1H-benzo[d]imidazol-1-yl)piperidine-2,6-dione hydrochloride. A mixture of tert-butyl (12-(1-(2,6-dioxopiperidin-3-yl)-3-methyl-2-oxo-2,3-dihydro-1H-benzo[d]imidazol-5-yl)dodecyl)carbamate (60 mg, 110 μmol) and a 4 M HCl in dioxane solution (10.0 mL) was stirred at rt for 3 h. On completion, the mixture was concentrated under reduced pressure to afford the title compound (60 mg, >100%) as a yellow solid. LCMS m/z=443.3 [M+H]$^+$.

3-(5-(9-aminononyl)-3-methyl-2-oxo-2,3-dihydro-1H-benzo[d]imidazol-1-yl)piperidine-2,6-dione (Intermediate E3)

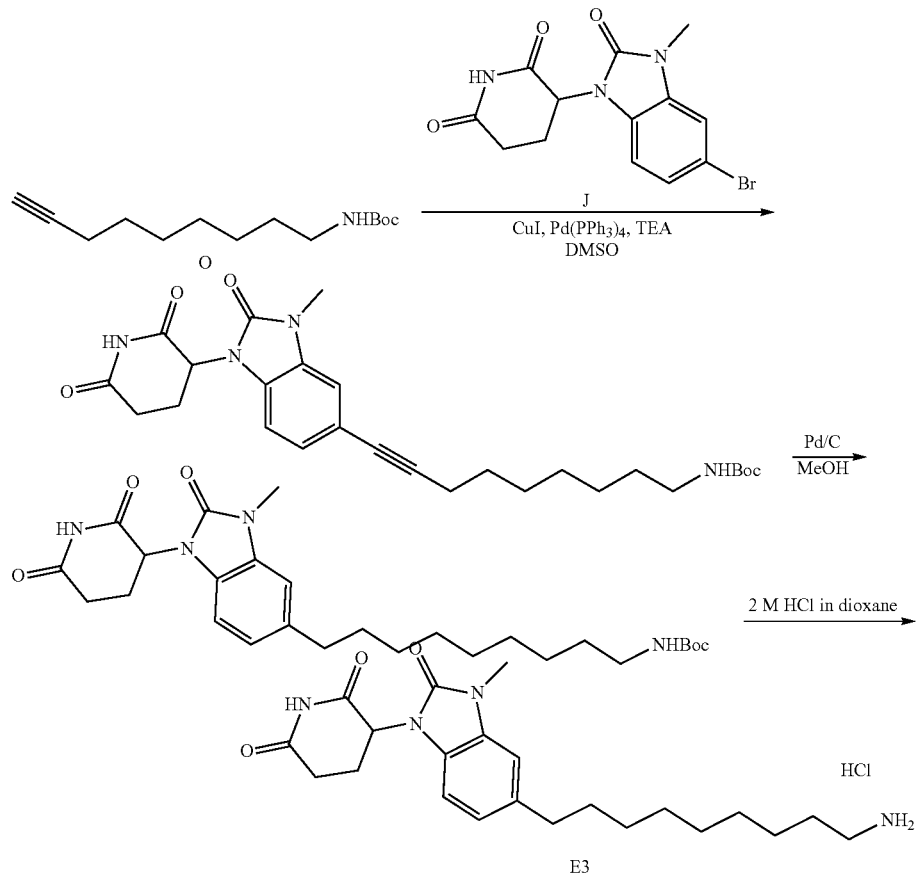

Step 1—Tert-butyl N-[6-[1-(2,6-dioxopiperidin-3-yl)-3-methyl-2-oxo-1,3-benzodiazol-5-yl]hex-5-yn-1-yl]carbamate. To a stirred solution of 3-(5-bromo-3-methyl-2-oxo-1,3-benzodiazol-1-yl)piperidine-2,6-dione (8.00 g, 23.7 mmol, Intermediate J) and tert-butyl non-8-yn-1-ylcarbamate (9.33 g, 47.3 mmol, Intermediate O) in DMSO (40.00 mL) and TEA (20.00 mL) were added Pd(PPh₃)₄ (2.73 g, 2.37 mmol) and CuI (450.55 mg, 2.366 mmol) in portions at rt under nitrogen atmosphere. The resulting mixture was stirred for 3 h at 80° C. under nitrogen atmosphere. On completion, the reaction mixture was diluted with EtOAc (800 mL). The resulting mixture was washed with 4×400 mL of water. The resulting mixture was concentrated under reduced pressure. The residue was purified by silica gel column chromatography, eluted with PE/EtOAc (1:2), to afford the title compound (7.2 g, 67% yield) as a yellow solid. $^1$H NMR (400 MHz, DMSO-$d_6$) δ 11.09 (s, 1H), 7.23-7.21 (m, 1H), 7.10-7.06 (m, 2H), 6.75-6.72 (m, 1H), 5.36 (dd, J=12.8, 5.3 Hz, 1H), 3.30 (s, 3H), 2.92-2.83 (m, 3H), 2.75-2.55 (m, 2H), 2.40 (t, J=7.0 Hz, 2H), 2.06-1.98 (m, 1H), 1.57-1.50 (m, 2H), 1.43-1.34 (m, 13H), 1.31-1.23 (m, 4H). LC/MS (ESI, m/z): [(M+1-56)]$^+$=497.3.

Step 2—Tert-butyl N-[9-[1-(2,6-dioxopiperidin-3-yl)-3-methyl-2-oxo-1,3-benzodiazol-5-yl]nonyl]carbamate. To a stirred solution of tert-butyl N-[9-[1-(2,6-dioxopiperidin-3-yl)-3-methyl-2-oxo-1,3-benzodiazol-5-yl]non-8-yn-1-yl]carbamate (7.00 g, 14.1 mmol) in MeOH (500.0 mL) was added Pd/C (2.00 g, 1.88 mmol, 10 wt %) in portions at rt under nitrogen atmosphere. The resulting mixture was stirred for 24 h at rt under hydrogen atmosphere. On completion, the reaction mixture was filtered and the filter cake was washed with MeOH (3×100 mL). The filtrate was concentrated under reduced pressure. The residue was purified by reverse flash chromatography (Column, C18 silica gel; mobile phase, ACN in water, 60% to 80% gradient in 25 min; detector, UV 254 nm) to afford the title compound (7 g) as a white solid. $^1$H NMR (400 MHz, DMSO-$d_6$) δ 11.07 (s, 1H), 7.05-6.96 (m, 2H), 6.87-6.84 (m, 1H), 6.78-6.69 (m, 1H), 5.34 (dd, J=12.7, 5.4 Hz, 1H), 3.32 (s, 3H), 2.92-2.87 (m, 3H), 2.77-2.63 (m, 2H), 2.62-2.58 (m, 2H), 2.05-1.95 (m, 1H), 1.61-1.55 (m, 2H), 1.39-1.34 (s, 11H), 1.31-1.20 (m, 10H). LC/MS (ESI, m/z): [(M+1-56)]$^+$=501.3.

Step 3—3-[5-(9-aminononyl)-3-methyl-2-oxo-1,3-benzodiazol-1-yl]piperidine-2,6-dione hydrochloride. To a stirred solution of tert-butyl N-[9-[1-(2,6-dioxopiperidin-3-yl)-3-methyl-2-oxo-1,3-benzodiazol-5-yl]nonyl]carbamate (6.00 g, 12.0 mmol) in DCM (15.00 mL) was added 4 M HCl (gas) in 1,4-dioxane (15.00 mL) dropwise at rt under nitrogen atmosphere. The resulting mixture was stirred for 4 h at rt under nitrogen atmosphere. On completion, the reaction mixture was concentrated under reduced pressure. The residue was triturated with Et₂O to afford the title compound (5 g, 96% yield) as an off-white solid. $^1$H NMR (400 MHz, Methanol-$d_4$) δ 7.06-7.00 (m, 2H), 6.97-6.94 (m, 1H), 5.33 (dd, J=12.3, 5.4 Hz, 1H), 3.43 (s, 3H), 2.98-2.87 (m, 3H), 2.86-2.75 (m, 2H), 2.70 (t, J=7.6 Hz, 2H), 2.21-2.15 (m, 1H), 1.75-1.59 (m, 4H), 1.45-1.30 (m, 10H). LC/MS (ESI, m/z): [(M+1-56)]$^+$=401.3.

3-(5-(3-(2-(2-aminoethoxy)ethoxy)propyl)-3-methyl-2-oxo-2,3-dihydro-1H-benzo[d]imidazol-1-yl)piperidine-2,6-dione (Intermediate E4)

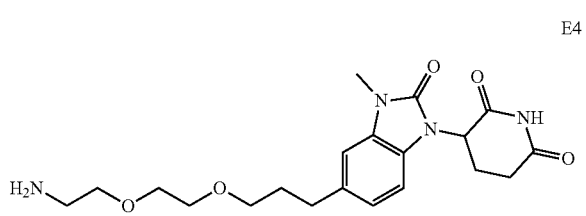 [SMILES: Cn1c(=O)n(C2CCC(=O)NC2=O)c2ccc(CCCOCCOCCN)cc21]

This intermediate was synthesized as previously described in US 2019/192668 and WO 2020/010210.

3-(5-(6-aminohexyl)-3-methyl-2-oxo-2,3-dihydro-1H-benzo[d]imidazol-1-yl)piperidine-2,6-dione (Intermediate E5)

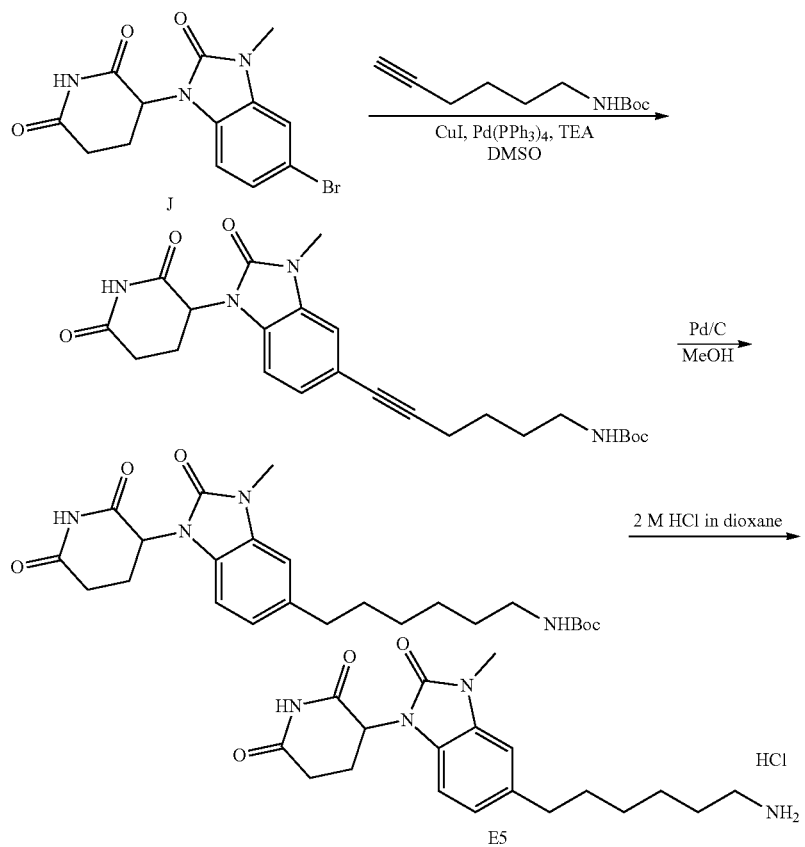

Step 1—tert-butyl N-[6-[1-(2,6-dioxopiperidin-3-yl)-3-methyl-2-oxo-1,3-benzodiazol-5-yl]hex-5-yn-1-yl]carbamate. To a stirred solution of 3-(5-bromo-3-methyl-2-oxo-1,3-benzodiazol-1-yl)piperidine-2,6-dione (8.00 g, 23.7 mmol, Intermediate J) and tert-butyl N-(hex-5-yn-1-yl)carbamate (9.33 g, 47.3 mmol, CAS #151978-58-4) in DMSO (40.0 mL) and TEA (20.0 mL) were added Pd(PPh$_3$)$_4$ (2.73 g, 2.37 mmol) and CuI (450.55 mg, 2.366 mmol) in portions at rt under nitrogen atmosphere. The resulting mixture was stirred for 3 h at 80° C. under nitrogen atmosphere. On completion, the reaction mixture was diluted with EtOAc (800 mL) and washed with 4×400 mL of water. The resulting mixture was concentrated under reduced pressure. The residue was purified by silica gel column chromatography, eluted with PE/EtOAc (1:2), to afford the title compound (7.2 g, 67% yield) as a yellow solid. $^1$H NMR (400 MHz, DMSO-d$_6$) δ 11.10 (s, 1H), 7.24 (d, J=1.2 Hz, 1H), 7.09 (d, J=1.2 Hz, 2H), 6.83 (t, J=5.7 Hz, 1H), 5.38 (dd, J=12.7, 5.4 Hz, 1H), 3.34 (s, 3H), 2.97 (d, J=5.1 Hz, 2H), 2.91-2.83 (m, 1H), 2.77-2.57 (m, 2H), 2.44-2.37 (m, 2H), 2.06-2.00 (m, 1H), 1.56-1.50 (m, 4H), 1.38 (s, 9H); LC/MS (ESI, m/z): [(M+1)]$^+$=355.3.

Step 2—tert-butyl N-[6-[1-(2,6-dioxopiperidin-3-yl)-3-methyl-2-oxo-1,3-benzodiazol-5-yl]hexyl]carbamate. To a stirred solution of tert-butyl N-[6-[1-(2,6-dioxopiperidin-3-yl)-3-methyl-2-oxo-1,3-benzodiazol-5-yl]hex-5-yn-1-yl] carbamate (6.00 g, 13.2 mmol) in MeOH (500 mL) was added Pd/C (1.97 g, 1.85 mmol, 10 wt %) in portions at rt under nitrogen atmosphere. The resulting mixture was stirred for 48 h at rt under hydrogen atmosphere. On completion, the reaction mixture was filtered and the filter cake was washed with MeOH (3×100 mL). The filtrate was concentrated under reduced pressure. The residue was purified by reverse flash chromatography (Column, C18 silica gel; mobile phase, ACN in water, 60% to 80% gradient in 25 min; detector, UV 254 nm) to afford the title compound (5 g, 83%) as a white solid. $^1$H NMR (400 MHz, DMSO-d6) δ 11.07 (s, 1H), 7.05-6.96 (m, 2H), 6.86 (m, 1H), 6.76-6.73 (m, 1H), 5.36-5.31 (m, 1H), 3.18 (d, J=5.2 Hz, 1H), 2.92-2.86 (m, 3H), 2.72 (m, 1H), 2.67-2.62 (m, 1H), 2.62-2.57 (m, 2H), 2.03-1.98 (m, 1H), 1.57 (d, J=7.5 Hz, 2H), 1.39-1.34 (m, 13H), 1.32-1.25 (m, 4H). LC/MS (ESI, m/z): [(M+1)]$^+$=359.2.

Step 3—3-[5-(6-aminohexyl)-3-methyl-2-oxo-1,3-benzodiazol-1-yl]piperidine-2,6-dione hydrochloride. To a stirred solution of tert-butyl N-[6-[1-(2,6-dioxopiperidin-3-yl)-3-methyl-2-oxo-1,3-benzodiazol-5-yl]hexyl]carbamate (4.8 g) in DCM (20 mL) was added 4 M HCl (gas) in 1,4-dioxane (20 mL) dropwise at rt under nitrogen atmosphere. On completion, the reaction mixture was concentrated under reduced pressure. The residue was triturated with Et$_2$O to afford the title compound (4 g, 97% yield) as a yellow solid. $^1$H NMR (400 MHz, DMSO-d$_6$) δ 11.08 (s, 1H), 8.01 (broad, 3H), 7.07-6.97 (m, 2H), 6.88-6.85 (m, 1H), 5.36 (dd, J=12.7, 5.4 Hz, 1H), 3.50-3.36 (m, 2H), 3.32 (s, 3H), 3.00-2.82 (m, 1H), 2.77-2.71 (m, 2H), 2.66-2.60 (m 2H), 2.05-1.94 (m, 1H), 1.62-1.51 (m, 4H), 1.42-1.18 (m, 4H).

4-((12-aminododecyl)amino)-2-(2,6-dioxopiperidin-3-yl)isoindoline-1,3-dione (Intermediate F2)

Step 1—Tert-butyl (12-((2-(2,6-dioxopiperidin-3-yl)-1,3-dioxoisoindolin-4-yl)amino)dodecyl)carbamate. To a solution of tert-butyl (12-aminododecyl)carbamate (900 mg, 333 μmol, CAS #109792-60-1) and 2-(2,6-dioxopiperidin-3-yl)-4-fluoroisoindoline-1,3-dione (993 mg, 399 μmol, CAS #835616-60-9) in DMF (15.0 mL) was added DIPEA (774 mg, 666 μmol) and the mixture was heated at 90° C. under N$_2$ overnight. On completion, the mixture was poured into water, and extracted with DCM (10 mL×3). The combined organic phases dried over Na$_2$SO$_4$ and concentrated under reduced pressure. The residue was purified by C18 reverse phase chromatography (Biotage, MeCN/H$_2$O, 60/40, v/v, 0.1% HCOOH) to afford the title compound (586 mg, 54%) as a yellow-green semi-solid. LCMS m/z=557.3 [M+H]$^+$. $^1$H NMR (400 MHz, CDCl$_3$) δ 8.20 (br s, 1H), 7.48 (dd, J=8.5, 7.1 Hz, 1H), 7.08 (d, J=7.1 Hz, 1H), 6.87 (d, J=8.6 Hz, 1H), 6.22 (t, J=5.6 Hz, 1H), 4.91 (dd, J=12.1, 5.3 Hz, 1H), 4.51 (br s, 1H), 3.27-3.23 (m, 2H), 3.15-3.03 (m, 2H), 2.92-2.67 (m, 3H), 2.18-2.08 (m, 1H), 1.69-1.65 (m, 2H), 1.44 (s, 12H), 1.33-1.23 (m, 15H).

Step 2—4-((12-Aminododecyl)amino)-2-(2,6-dioxopiperidin-3-yl)isoindoline-1,3-dione hydrochloride. A mixture of tert-butyl (12-((2-(2,6-dioxopiperidin-3-yl)-1,3-dioxoisoindolin-4-yl)amino)dodecyl)carbamate (140 mg, 252 umol) and a 4 M HCl in dioxane solution (14.0 mL) was stirred at rt for 2 h. On completion, the mixture was concentrated under reduced pressure to afford the title compound (118 mg, 96%) as a yellow oil. LCMS m/z=457.3 [M+H]$^+$.

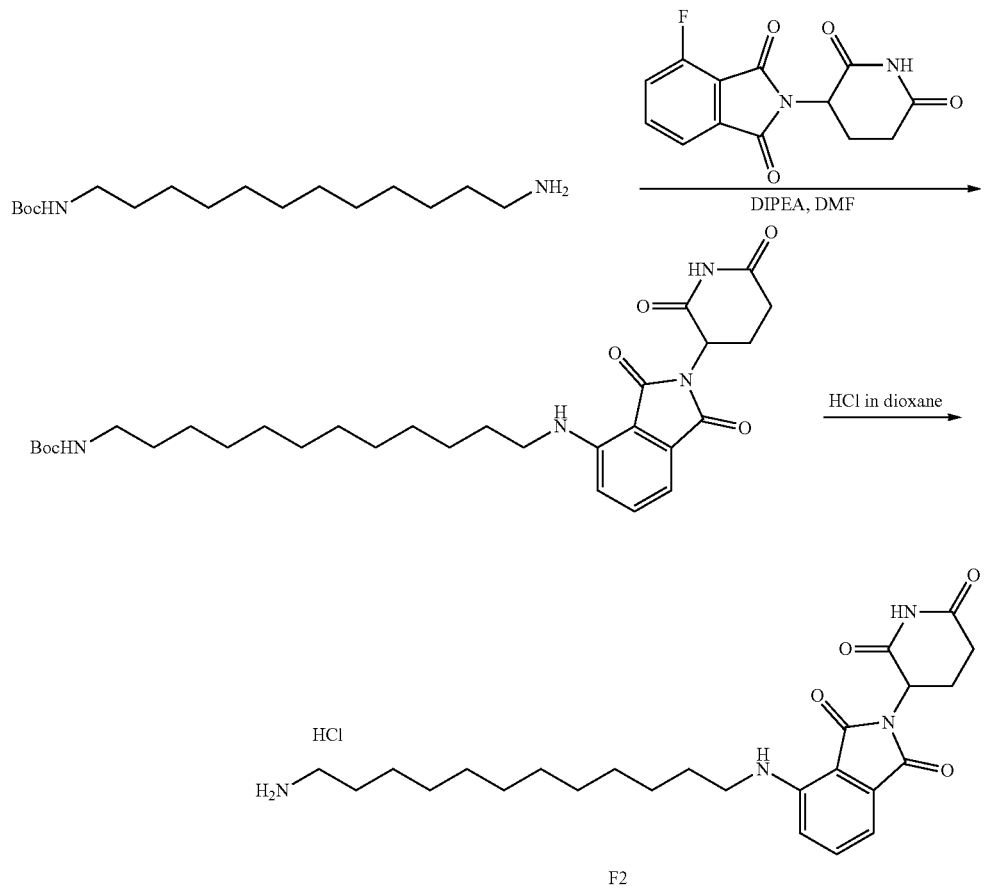

F2

4-((2-(2-(2-aminoethoxy)ethoxy)ethyl)amino)-2-(2,6-dioxopiperidin-3-yl)isoindoline-1,3-dione (Intermediate F3)

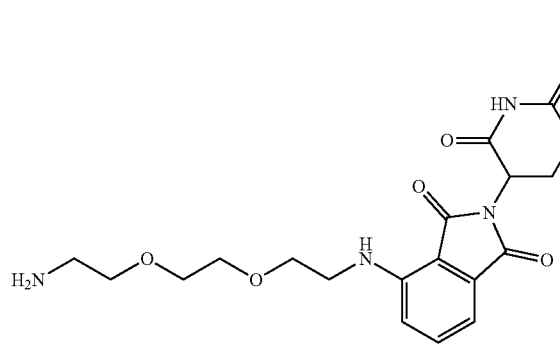

This intermediate was synthesized as previously described in US 2019/192668.

4-((8-aminooctyl)amino)-2-(2,6-dioxopiperidin-3-yl)isoindoline-1,3-dione (Intermediate F4)

Step 1—Tert-Butyl (8-((2-(2,6-dioxopiperidin-3-yl)-1,3-dioxoisoindolin-4-yl)amino)octyl)carbamate. To a solution of tert-butyl (8-aminooctyl)carbamate (450 mg, 1.85 mmol, CAS #88829-82-7) and 2-(2,6-dioxopiperidin-3-yl)-4-fluoroisoindoline-1,3-dione (612 mg, 2.21 mmol, CAS #835616-60-9) in DMF (8 mL) was added DIPEA (476.9 mg, 3.69 mmol) and the mixture was heated at 90° C. under $N_2$ overnight. On completion, the mixture was diluted with water (80 mL) and extracted with EtOAc (3×30 mL). The combined organic layers were washed with brine, dried over $Na_2SO_4$ and concentrated under reduced pressure. The residue was purified by C18 reverse phase chromatography (Biotage, MeCN/$H_2O$, 40/60, v/v, 0.1% HCOOH) to give the title compound (350 mg, 38% yield) as a green solid. LCMS: m/z=501.25 [M+H]$^+$. $^1$H NMR (400 MHz, DMSO-$d_6$) δ 11.1 (s, 1H), 7.60-7.55 (m, 1H), 7.08 (d, J=8.6 Hz, 1H), 7.01 (d, J=7.0 Hz, 1H), 6.74 (t, J=5.2 Hz, 1H), 6.52 (t, J=6.0 Hz, 1H), 5.05 (dd, J=12.8, 5.4 Hz, 1H), 3.30-3.26 (m, 2H), 2.97-2.79 (m, 4H), 2.63-2.52 (m, 2H), 1.41-1.27 (m, 21H).

Step 2—4-((8-Aminooctyl)amino)-2-(2,6-dioxopiperidin-3-yl)isoindoline-1,3-dione hydrochloride. A mixture of tert-butyl (8-((2-(2,6-dioxopiperidin-3-yl)-1,3-dioxoisoindolin-4-yl)amino)octyl)carbamate (350 mg, 0.70 mmol) and a 4 M HCl in dioxane solution (8 mL) was stirred at rt for 1 h. On completion, the mixture was concentrated under reduced pressure to obtain the title compound (300 mg, 98% yield) as a green solid. LCMS: m/z=401.20 [M+H]$^+$.

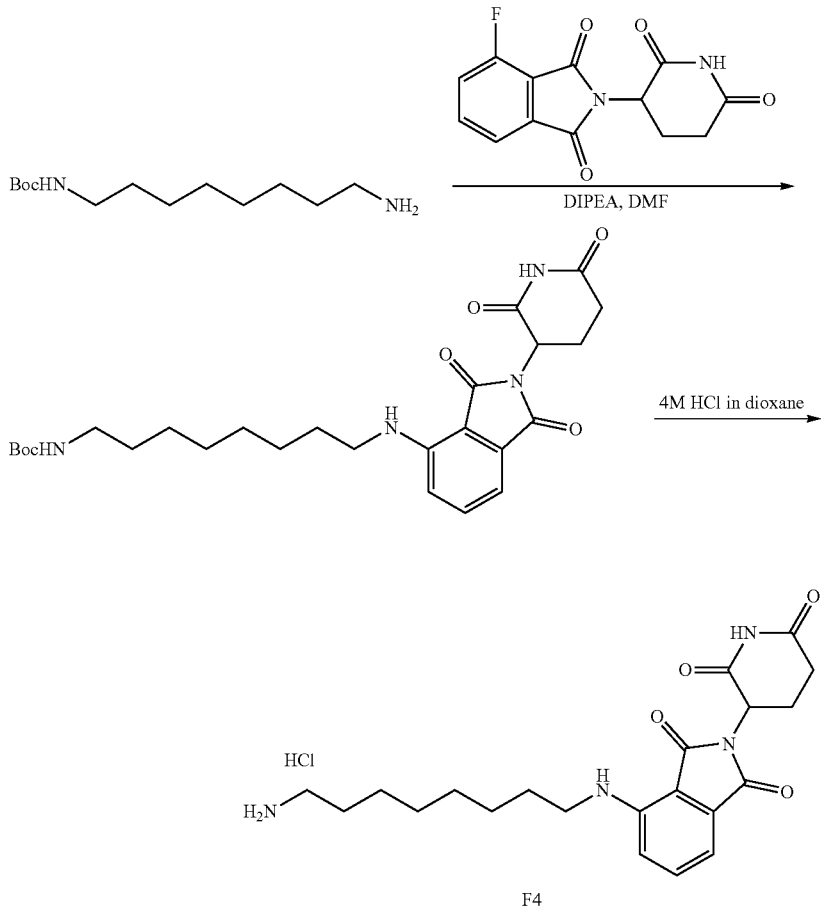

4-((9-aminononyl)amino)-2-(2,6-dioxopiperidin-3-yl)isoindoline-1,3-dione (Intermediate F5)

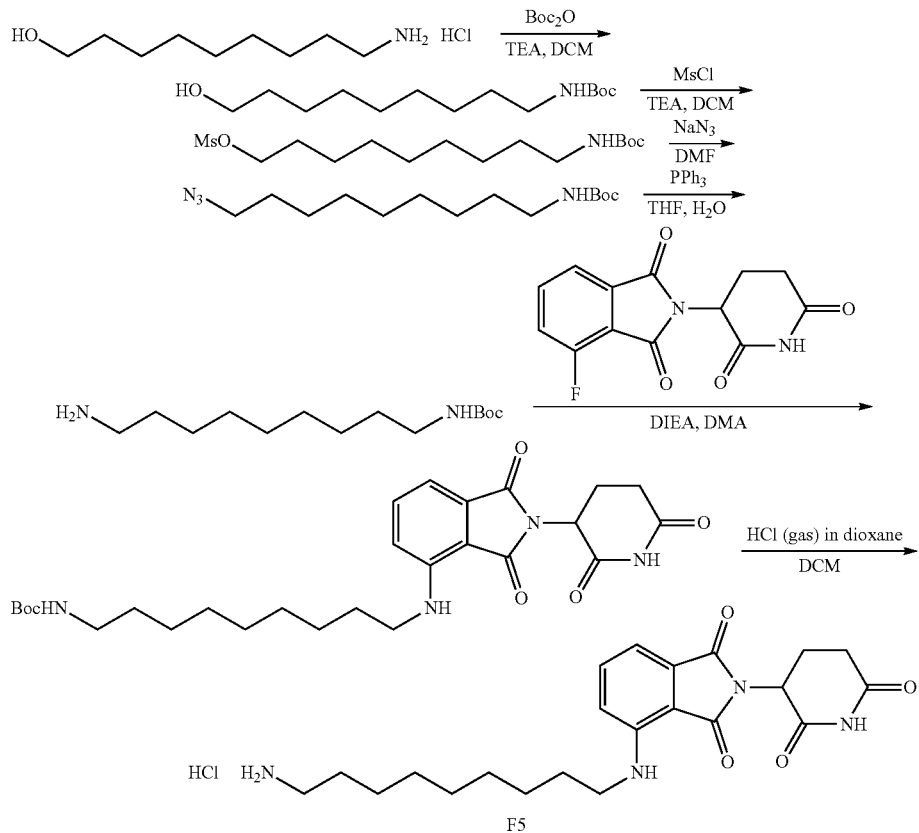

F5

Step 1—Tert-butyl N-(9-hydroxynonyl)carbamate. To a stirred solution of 9-aminononan-1-ol hydrochloride (42.00 g, 214.6 mmol) and TEA (59.5 mL, 429 mmol) in DCM (500.00 mL) was added Boc$_2$O (56.20 g, 257.5 mmol) in portions at 0° C. The resulting mixture was stirred overnight at rt under nitrogen atmosphere. On completion, the resulting mixture was diluted with water (300 mL) and the aqueous layer was extracted with CH$_2$Cl$_2$ (300 mL×3). The combined organic layers were dried over anhydrous Na$_2$SO$_4$. After filtration, the filtrate was concentrated under reduced pressure. The residue was purified by silica gel column chromatography, eluted with PE/EtOAc (3:1) to afford the title compound (53 g, 95% yield) as a colorless oil. $^1$H NMR (400 MHz, Chloroform-d) δ 4.58 (broad, 1H), 3.64-3.56 (m, 2H), 3.07 (t, J=6.9 Hz, 2H), 1.54 (p, J=7.6, 6.2 Hz, 2H), 1.46 (s, 9H), 1.34-1.24 (m, 12H); LC/MS (ESI, m/z): [(M−1)]$^+$=258.3.

Step 2—Tert-butyl N-[9-(methanesulfonyloxy)nonyl]carbamate. To a stirred solution of tert-butyl N-(9-hydroxynonyl)carbamate (50.00 g, 192.8 mmol) and TEA (54.54 mL, 385.5 mmol) in DCM (1.00 L) was added MsCl (33.12 g, 289.1 mmol) dropwise at 0° C. under nitrogen atmosphere. The resulting solution was stirred for 3 h at rt under nitrogen atmosphere. On completion, the resulting solution was diluted with water (500 mL) and the aqueous layer was extracted with CH$_2$Cl$_2$ (200 mL×3). The combined organic layers were dried over anhydrous Na$_2$SO$_4$. After filtration, the filtrate was concentrated under reduced pressure to afford the title compound (66 g) as a yellow solid. $^1$H NMR (400 MHz, Chloroform-d) δ 4.52 (broad, 1H), 4.24 (t, J=6.6 Hz, 2H), 3.17-3.05 (m, 2H), 3.02 (s, 3H), 1.82-1.69 (m, 2H), 1.53-1.39 (m, 14H), 1.33-1.24 (m, 8H); LC/MS (ESI, m/z): [(M−1)]$^+$=336.1.

Step 3—Tert-butyl N-(9-azidononyl)carbamate. A mixture of tert-butyl N-[9-(methanesulfonyloxy)nonyl]carbamate (66.00 g, 195.6 mmol) and NaN$_3$ (22.88 g, 352.0 mmol) in DMF (400.0 mL) was stirred for 4 h at 40° C. under nitrogen atmosphere. On completion, the resulting mixture was allowed to cooled down to rt and diluted with water (800 mL). The resulting mixture was extracted with co-solvent (PE:EA=2:1) (2×1.5 L). The combined organic layers were washed with brine (1 L), dried over anhydrous Na$_2$SO$_4$. After filtration, the filtrate was concentrated under reduced pressure. The residue was purified by silica gel column chromatography, eluted with PE/EtOAc (5:1) to afford the title compound (50.8 g, 91% yield) as a light yellow oil. $^1$H NMR (400 MHz, DMSO-d$_6$) δ 6.71 (t, J=5.6 Hz, 1H), 3.31 (t, J=6.9 Hz, 2H), 2.90 (q, J=6.6 Hz, 2H), 1.53 (p, J=6.9 Hz, 2H), 1.40-1.36 (m, 11H), 1.29-1.24 (m, 10H).

Step 4—Tert-butyl N-(9-aminononyl)carbamate. A solution of tert-butyl N-(9-azidononyl)carbamate (47.00 g, 165.3 mmol) and PPh$_3$ (47.68 g, 181.8 mmol) in THF (500.00 mL) and H$_2$O (50.00 mL) was stirred overnight at 55° C. under nitrogen atmosphere. On completion, the solution was cooled to rt and concentrated under reduced pressure to afford the title compound (100 g) as a white solid.

Step 5—Tert-butyl N-(9-[[2-(2,6-dioxopiperidin-3-yl)-1,3-dioxoisoindol-4-yl]amino]nonyl)carbamate. To a solution of 2-(2,6-dioxopiperidin-3-yl)-4-fluoroisoindole-1,3-dione (481.03 mg, 1.741 mmol, CAS #835616-60-9) and tert-butyl N-(9-aminononyl)carbamate (450.00 mg, 1.741 mmol) in DMA (8.00 mL) was added DIEA (450.14 mg, 3.483 mmol) dropwise. The resulting mixture was stirred for 3 h at 80° C. under nitrogen atmosphere. On completion, the mixture was cooled to rt. The resulting mixture was diluted with water (800 mL) and extracted with EtOAc (2×1 L). The combined organic layers were washed with brine (500 mL), dried over anhydrous $Na_2SO_4$. After filtration, the filtrate was concentrated under reduced pressure. The residue was purified by silica gel column chromatography, eluted with PE/EtOAc (2:1) to afford the title compound (50 g, 18% yield) as a green solid. $^1$H NMR (400 MHz, DMSO-$d_6$) δ 11.10 (s, 1H), 7.55-7.52 (m, 1H), 7.09 (d, J=8.6 Hz, 1H), 7.02 (d, J=7.0 Hz, 1H), 6.75 (t, J=5.7 Hz, 1H), 6.52 (t, J=5.9 Hz, 1H), 5.06 (dd, J=12.9, 5.4 Hz, 1H), 3.29 (q, J=6.7 Hz, 2H), 2.93-2.87 (m, 3H), 2.68-2.53 (m, 2H), 2.14-2.01 (m, 1H), 1.61-1.54 (m, 2H), 1.38-1.24 (m, 21H). LC/MS (ESI, m/z): [(M+1)]=515.4.

Step 6—4-[(9-Aminononyl)amino]-2-(2,6-dioxopiperidin-3-yl)isoindole-1,3-dione hydrochloride. To a stirred solution of tert-butyl N-(9-[[2-(2,6-dioxopiperidin-3-yl)-1,3-dioxoisoindol-4-yl]amino]nonyl)carbamate (57.00 g, 111 mmol) in DCM (150 mL) was added 4 M HCl (gas) in 1,4-dioxane (150 mL) dropwise at rt under nitrogen atmosphere. The resulting mixture was stirred overnight at rt under nitrogen atmosphere. On completion, the resulting mixture was concentrated under reduced pressure. The residue was diluted with EtOAc (400 mL) and stirred overnight at rt under nitrogen atmosphere. The precipitated solids were collected by filtration and dried under vacuum to afford the title compound (13 g, 26% yield) as a yellow solid. $^1$H NMR (400 MHz, DMSO-$d_6$) δ 11.10 (s, 1H), 7.94 (broad, 3H), 7.61-7.57 (m, 1H), 7.10 (d, J=8.6 Hz, 1H), 7.03 (d, J=7.0 Hz, 1H), 6.53 (t, J=5.9 Hz, 1H), 5.06 (dd, J=12.8, 5.4 Hz, 1H), 3.30 (q, J=6.6 Hz, 2H), 2.92-2.88 (m, 1H), 2.75 (q, J=7.3, 6.8 Hz, 2H), 2.62 (t, J=3.6 Hz, 1H), 2.59-2.56 (m, 1H), 2.10-1.97 (m, 1H), 1.59-1.55 (m, 4H), 1.39-1.24 (m, 11H); LC/MS (ESI, m/z): [(M+1)]=415.2.

4-((5-aminopentyl)amino)-2-(2,6-dioxopiperidin-3-yl)isoindoline-1,3-dione (Intermediate F6)

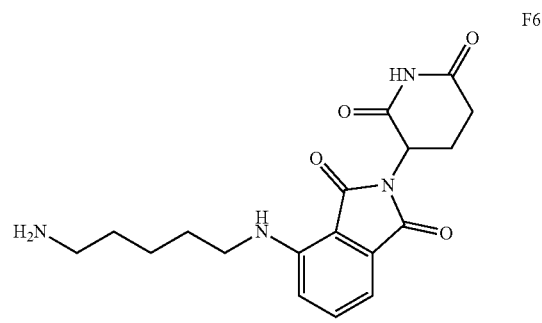 [SMILES: NCCCCCNc1cccc2c1C(=O)N(C1CCC(=O)NC1=O)C2=O]

This intermediate was synthesized as previously described in US 2019/192668.

4-((6-((4-aminopiperidin-1-yl)sulfonyl)hexyl)amino)-2-(2,6-dioxopiperidin-3-yl)isoindoline-1,3-dione (Intermediate G1)

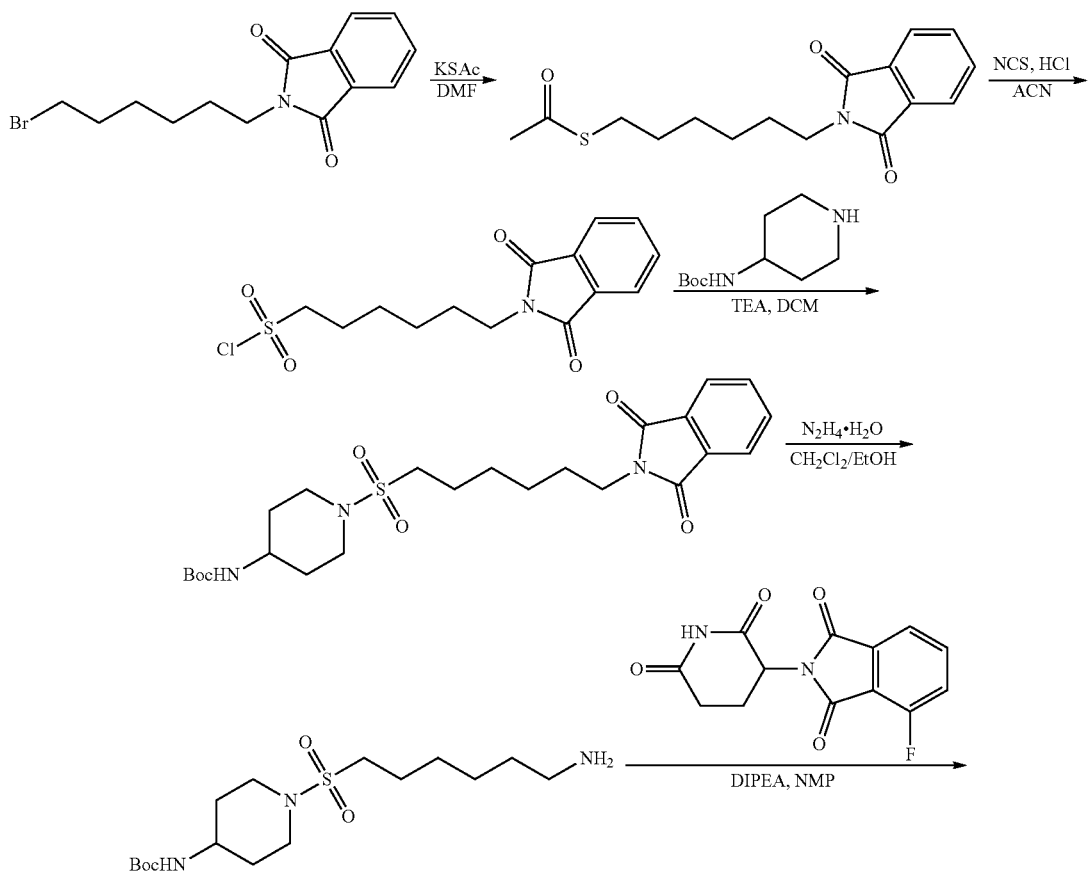

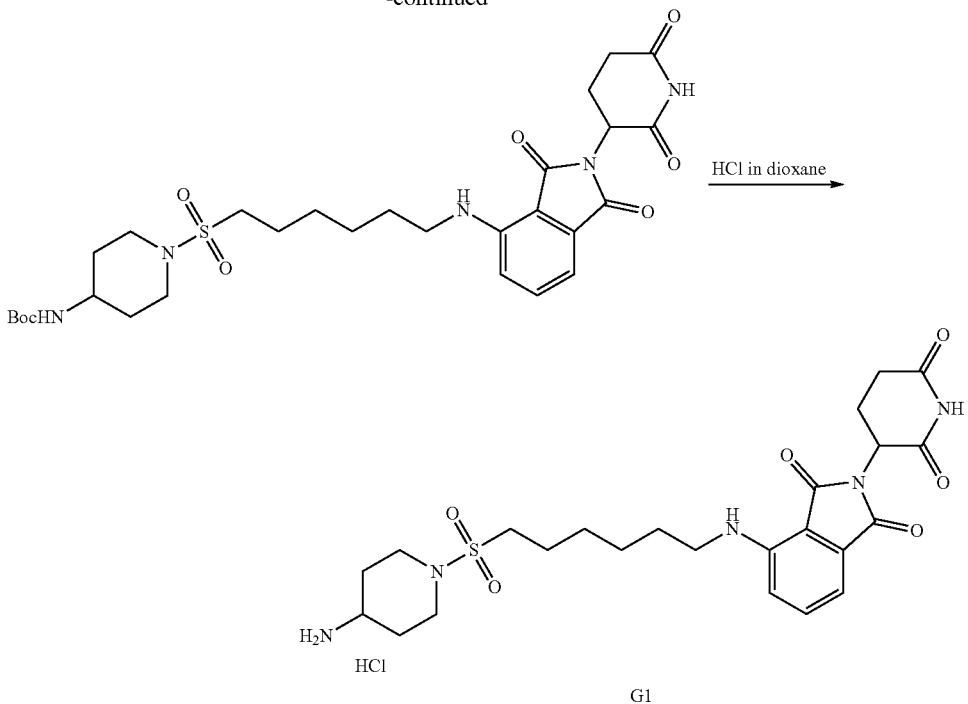

Step 1—S—(6-(1,3-Dioxoisoindolin-2-yl)hexyl) ethanethioate. To a solution of 2-(6-bromohexyl)isoindoline-1,3-dione (3.0 g, 9.68 mmol, CAS #24566-79-8) in DMF (90 mL) was added KSAc (3.31 g, 29.04 mmol) and the mixture was stirred at rt under $N_2$ for 2 h. On completion, the mixture was diluted with water (50 mL), and extracted with EtOAc (50 mL×3). The combined organic layers were dried over $Na_2SO_4$ and concentrated under reduced pressure to afford the title compound (2.3 g, 75% yield) as a white solid. $^1$H NMR (400 MHz, CDCl$_3$) δ 7.86-7.80 (m, 2H), 7.73-7.67 (m, 2H), 3.67 (t, J=7.2 Hz, 2H), 2.85 (t, J=7.3 Hz, 2H), 2.30 (s, 3H), 1.73-1.65 (m, 2H), 1.58-1.51 (m, 2H), 1.38 (m, 4H).

Step 2—6-(1,3-Dioxoisoindolin-2-yl)hexane-1-sulfonyl chloride. To a solution of S—(6-(1,3-dioxoisoindolin-2-yl)hexyl)ethanethioate (1.0 g, 3.28 mmol) and 2 M aqueous HCl (2 mL) in MeCN (25.0 mL) at 0° C. was added NCS (1.18 g, 8.81 mmol) portion-wise and the mixture was allowed to warm to rt and stirred for 1 h. On completion, the mixture was diluted with ice-cold water (30 mL) and extracted with EtOAc (50 mL×3). The combined organic layers were dried over $Na_2SO_4$ and concentrated under reduced pressure to afford the title compound (1.1 g, 80% yield) as an off-white solid. LCMS: m/z=330.2 [M+H]$^+$.

Step 3—Tert-butyl (1-((6-(1,3-dioxoisoindolin-2-yl)hexyl)sulfonyl)piperidin-4-yl)carbamate. To a solution of 6-(1,3-dioxoisoindolin-2-yl)hexane-1-sulfonyl chloride (1.1 g, 3.34 mmol) and tert-butyl piperidin-4-ylcarbamate (668 mg, 3.34 mmol, CAS #73874-95-0) in DCM (20.0 mL) was added TEA (675 mg, 6.67 mmol) and the mixture was stirred at rt overnight. On completion, the solid was collected by filtration to afford the title compound (630 mg, 38% yield) as a white solid. The filtrate was diluted with water (30 mL), extracted with DCM (50 mL×3) and the combined organic layers were dried over $Na_2SO_4$ and concentrated under reduced pressure. The residue was purified by C18 reverse phase chromatography (Biotage, MeCN/H$_2$O, 65/35, v/v, 0.1% HCOOH) to afford a further aliquot of the title compound title compound (500 mg, 30% yield) as a white solid. LCMS: m/z=494.2 [M+H]$^+$; $^1$H NMR (400 MHz, CDCl$_3$) δ 7.87-7.82 (m, 2H), 7.74-7.69 (m, 2H), 4.58 (br s, 1H), 3.77-3.63 (m, 4H), 3.58 (br s, 1H), 2.94-2.83 (m, 4H), 2.08-1.95 (m, 2H), 1.83-1.66 (m, 4H), 1.53-1.32 (m 15H).

Step 4—Tert-butyl (1-((6-aminohexyl)sulfonyl)piperidin-4-yl)carbamate. To a solution of tert-butyl (1-((6-(1,3-dioxoisoindolin-2-yl)hexyl)sulfonyl)piperidin-4-yl)carbamate (900 mg, 1.82 mmol) in DCM/EtOH (2/1, 54.0 mL) was added $N_2H_4·H_2O$ (98%, 365 mg, 7.29 mmol) and the mixture was heated at 50° C. overnight. On completion, the mixture was filtered and the filtrate was diluted with water (20 mL) and extracted with DCM (50 mL×3). The combined organic layers were dried over $Na_2SO_4$ and concentrated under reduced pressure. The residue was triturated with MeCN to afford the title compound (400 mg, 60%) as a white solid. LCMS: m/z=364.2 [M+H]$^+$; $^1$H NMR (400 MHz, CDCl$_3$) δ 4.51 (br s, 1H), 3.74 (d, J=12.4 Hz, 2H), 3.56 (br s, 1H), 2.92-2.84 (m, 4H), 2.69 (t, J=6.8 Hz, 2H), 2.04-1.97 (m, 2H), 1.83-1.76 (m, 2H), 1.52-1.33 (m, 17H).

Step 5—Tert-butyl (1-((6-((2-(2,6-Dioxopiperidin-3-yl)-1,3-dioxoisoindolin-4-yl)amino)hexyl)sulfonyl)piperidin-4-yl)carbamate. To a solution of tert-butyl (1-((6-aminohexyl)sulfonyl)piperidin-4-yl)carbamate (236 mg, 651.6 μmol) and 2-(2,6-dioxopiperidin-3-yl)-4-fluoroisoindoline-1,3-dione (120 mg, 434.4 μmol, CAS #835616-60-9) in NMP (5.0 mL) was added DIPEA (112.3 mg, 868.8 μmol) and the mixture was heated at 90° C. overnight. On completion, the mixture was purified directly by C18 reverse phase chromatography (Biotage, MeCN/H$_2$O, 65/35, v/v, 0.1% HCOOH) to afford the title compound (190 mg, 75%) as a yellow semi-solid. LCMS: m/z=620.2 [M+H]$^+$.

Step 6—4-((6-((4-Aminopiperidin-1-yl)sulfonyl)hexyl)amino)-2-(2,6-dioxopiperidin-3-yl)isoindoline-1,3-dione hydrochloride. A mixture of tert-butyl (1-((6-((2-(2,6-dioxopiperidin-3-yl)-1,3-dioxoisoindolin-4-yl)amino)hexyl)sulfonyl)piperidin-4-yl)carbamate (100 mg, 161.4 μmol) and a 4 M HCl in dioxane solution (6.0 mL) was stirred at rt for 5 h. On completion, the mixture was concentrated under reduced pressure to afford the title compound (100 mg, >100%) as yellow oil. LCMS: m/z=520.2 [M+H]$^+$.

4-((10-((4-aminopiperidin-1-yl)sulfonyl)decyl)amino)-2-(2,6-dioxopiperidin-3-yl)isoindoline-1,3-dione (Intermediate G2)
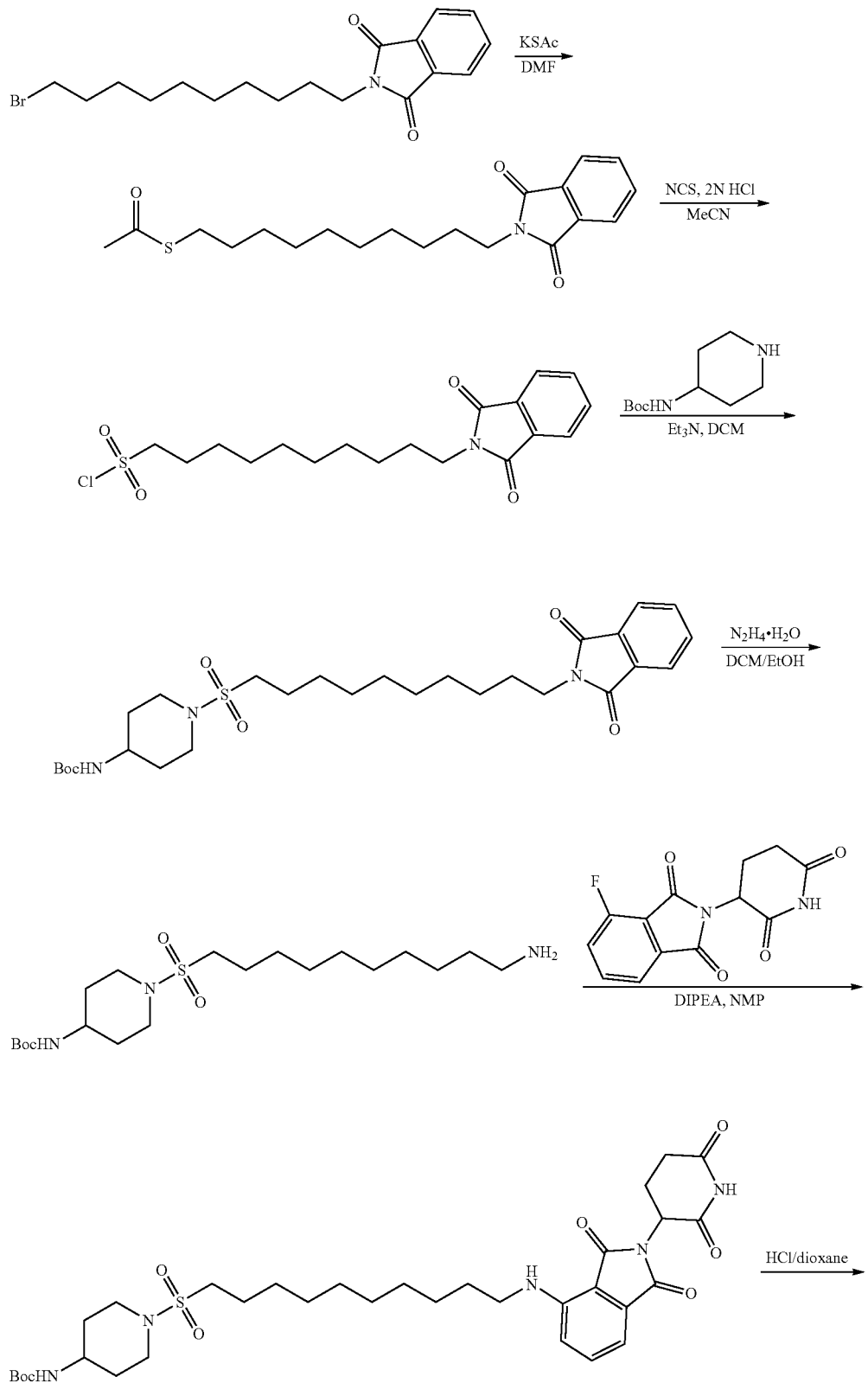

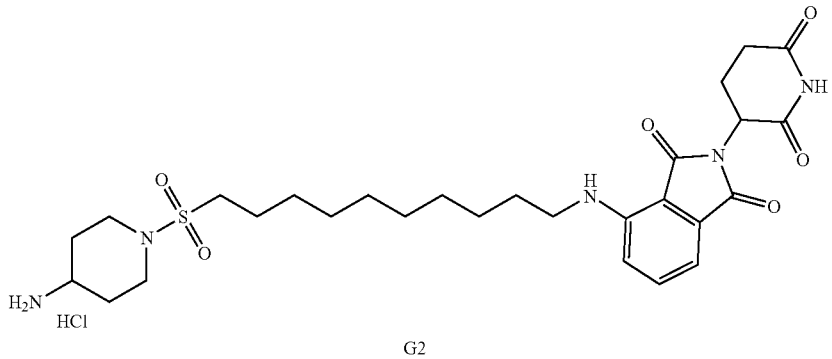

G2

Step 1—S—(10-(1,3-Dioxoisoindolin-2-yl)decyl) ethanethioate. To a solution of 2-(10-bromodecyl)isoindoline-1,3-dione (2.0 g, 5.46 mmol, CAS #24566-80-1) in DMF (20.0 mL) was added KSAc (686 mg, 6.01 mmol) and the mixture was stirred at rt for 2 h under $N_2$. On completion, the mixture was poured into water and extracted with EtOAc (30 mL×3). The combined organic phases were dried over $Na_2SO_4$ and concentrated under reduced pressure to afford the title compound (2.0 g, 100% yield) as a white solid. $^1$H NMR (400 MHz, CDCl$_3$) δ 7.84 (dd, J=5.4, 3.2 Hz, 2H), 7.70 (dd, J=5.6, 3.0 Hz, 2H), 3.67 (t, J=7.2 Hz, 2H), 2.85 (t, J=7.2 Hz, 2H), 2.31 (s, 3H), 1.70-1.60 (m, 2H), 1.59-1.50 (m, 2H), 1.35-1.25 (m, 12H).

Step 2—10-(1,3-Dioxoisoindolin-2-yl)decane-1-sulfonyl chloride. To a solution of S—(10-(1,3-dioxoisoindolin-2-yl)hexyl)ethanethioate (200 mg, 0.55 mmol) and 2 M aqueous HCl (0.15 mL) in MeCN (5.0 mL) at 0° C. was added NCS (295.5 mg, 2.21 mmol) portion-wise and the mixture was allowed to warm to rt and stirred for 1 h. On completion, the mixture was poured into ice-cold water and extracted with EtOAc (10 mL×3). The combined organic layers were dried over $Na_2SO_4$ and concentrated under reduced pressure to afford the title compound (280 mg) as an off-white solid. LCMS: m/z=386.1 [M+H]$^+$.

Step 3—Tert-butyl (1-((10-(1,3-dioxoisoindolin-2-yl)hexyl)sulfonyl)piperidin-4-yl)carbamate. To solution of tert-butyl piperidin-4-ylcarbamate (110.8 mg, 0.55 mmol, CAS #73874-95-0) and Et$_3$N (675.0 mg, 6.67 mmol) in DCM (5.0 mL) at 0° C. was added a solution of 10-(1,3-dioxoisoindolin-2-yl)hexane-1-sulfonyl chloride (280 mg, assumed 0.55 mmol). The mixture was allowed to warm to rt and stirred overnight. On completion, the mixture was concentrated under reduced pressure, the residue was triturated with MeOH. The solid was collected by filtration to afford the title compound (40 mg, 13% over two steps) as a white solid. LCMS: m/z=450.2 [M-Boc+H]$^+$; $^1$H NMR (400 MHz, CDCl$_3$) δ 7.84 (dd, J=5.4, 3.2 Hz, 2H), 7.70 (dd, J=5.6, 3.2 Hz, 2H), 4.46 (br s, 1H), 3.79-3.71 (m, 2H), 3.67 (t, J=7.2 Hz, 2H), 3.63-3.50 (m, 1H), 2.94-2.83 (m, 4H), 2.05-1.97 (m, 2H), 1.81-1.74 (m, 2H), 1.71-1.61 (m, 2H), 1.52-1.24 (m, 23H).

Step 4—Tert-butyl (1-((10-aminohexyl)sulfonyl)piperidin-4-yl)carbamate. To a solution of tert-butyl (1-((10-(1,3-dioxoisoindolin-2-yl)hexyl)sulfonyl)piperidin-4-yl)carbamate (350 mg, 0.64 mmol) in DCM/EtOH (2/1, 15.0 mL) was added $N_2H_4H_2O$ (98%, 127.5 mg, 2.55 mmol) and the mixture was heated at 50° C. overnight. On completion, the mixture was filtered and the filtrate poured into a 1 M aqueous NaOH solution and extracted with DCM (10 mL×3). The combined organic layers were dried over $Na_2SO_4$ and concentrated under reduced pressure. The residue was triturated with MeCN, filtered and the filtrate was concentrated under reduced pressure to afford the title compound (160 mg, 60%) as a white solid. LCMS: m/z=420.3 [M+H]$^+$.

Step 5—Tert-butyl (1-((10-((2-(2,6-dioxopiperidin-3-yl)-1,3-dioxoisoindolin-4-yl)amino)hexyl)sulfonyl)piperidin-4-yl)carbamate. To a solution of tert-butyl (1-((10-aminohexyl)sulfonyl)piperidin-4-yl)carbamate (160 mg, 0.38 mmol) and 2-(2,6-dioxopiperidin-3-yl)-4-fluoroisoindoline-1,3-dione (105.3 mg, 0.38 mmol, CAS #835616-60-9) in NMP (3.0 mL) was added DIPEA (98.4 mg, 0.76 mmol) and the mixture was heated at 90° C. overnight. On completion, the mixture was allowed to cool to rt and purified directly C18 reverse phase chromatography (Biotage, MeCN/H$_2$O, 90/10, v/v, 0.1% HCOOH) to afford the title compound (40 mg, 16%) as a yellow solid. LCMS: m/z=576.3 [M-Boc+H]$^+$; $^1$H NMR (400 MHz, CDCl$_3$) δ 8.13 (br s, 1H), 7.49 (dd, J=8.4, 7.2 Hz, 1H), 7.08 (d, J=7.0 Hz, 1H), 6.88 (d, J=8.2 Hz, 1H), 6.22 (br s, 1H), 4.93 (d, J=12.0, 5.3 Hz, 1H), 4.49 (br s, 1H), 3.81-3.68 (m, 2H), 3.63-3.50 (m, 1H), 3.26 (t, J=7.0 Hz, 2H), 2.92-2.68 (m, 6H), 2.03-1.98 (m, 2H), 1.83-1.76 (m, 2H), 1.69-1.64 (m, 2H), 1.53-1.27 (m, 25H).

Step 6—4-((10-((4-Aminopiperidin-1-yl)sulfonyl)hexyl)amino)-2-(2,6-dioxopiperidin-3-yl)isoindoline-1,3-dione hydrochloride. A mixture of tert-butyl (1-((10-((2-(2,6-dioxopiperidin-3-yl)-1,3-dioxoisoindolin-4-yl)amino)hexyl)sulfonyl)piperidin-4-yl)carbamate (36 mg, 0.053 mmol) and a 4 M HCl in dioxane solution (6.0 mL) was stirred at rt for 2 h. The mixture was concentrated under reduced pressure to afford the title compound (30 mg, 94%) as a yellow oil. LCMS: m/z=576.3 [M+H]$^+$.

4-((14-((4-Aminopiperidin-1-yl)sulfonyl)tetradecyl)amino)-2-(2,6-dioxopiperidin-3-yl)isoindoline-1,3-dione Intermediate G3)
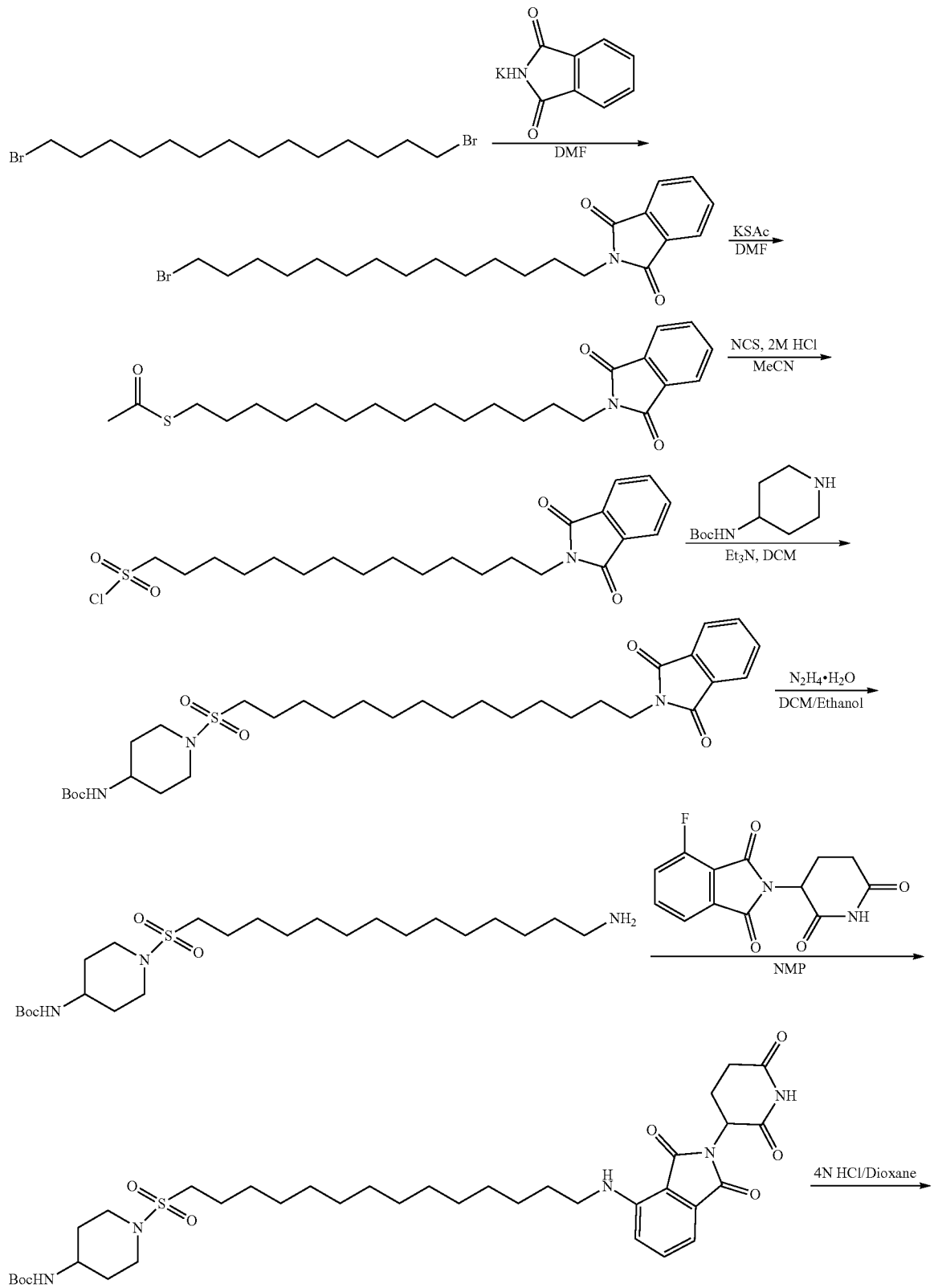

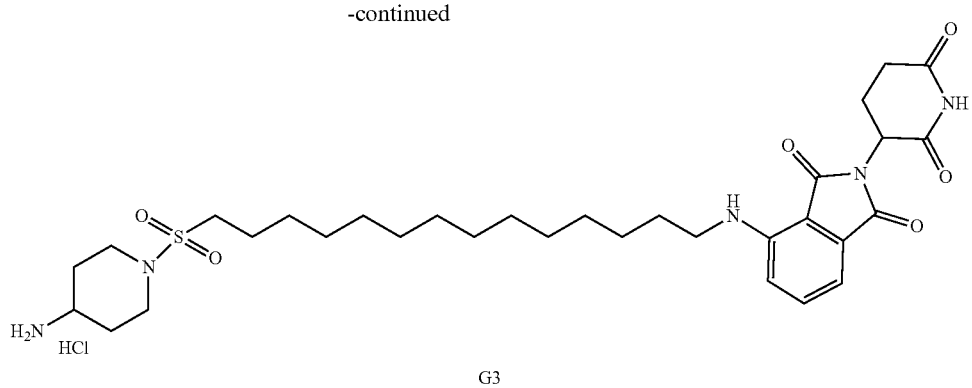

G3

Step 1—2-(14-Bromotetradecyl)isoindoline-1,3-dione. To a solution of 1,14-dibromotetradecane (900 mg, 2.53 mmol, CAS #37688-96-3) in DMF (20 mL) at rt was added potassium phthalimide (471 mg, 2.53 mmol, CAS #1074-82-4) and the mixture was stirred at 30° C. overnight. On completion, the mixture was poured into water (100 mL) and extracted with EtOAc (30 mL×3). The combined organic phases were dried over $Na_2SO_4$ and concentrated under reduced pressure. The residue was purified by silica gel chromatography (Pet. ether/EtOAc=10/1, v/v) to afford the title compound (600 mg, 56% yield) as a white solid. $^1$H NMR (400 MHz, DMSO-$d_6$) δ 7.92-7.77 (m, 4H), 3.59-3.47 (m, 6H), 1.85-1.70 (m, 4H), 1.62-1.53 (m, 2H), 1.40-1.31 (m, 4H), 1.28-1.24 (m, 12H).

Step 2—S—(14-(1,3-Dioxoisoindolin-2-yl)tetradecyl) ethanethioate. To a solution of 2-(14-bromotetradecyl)isoindoline-1,3-dione (600 mg, 1.42 mmol) in DMF (20 mL) was added KSAc (485 mg, 4.26 mmol) and the mixture was stirred at rt for 2 h. On completion, the mixture was poured into water (100 mL) and extracted with EtOAc (30 mL×3). The combined organic phases were dried over $Na_2SO_4$ and concentrated under reduced pressure to afford the title compound (550 mg, 93% yield) as a yellow solid. LCMS: m/z=440.2 [M+Na]$^+$.

Step 3—14-(1,3-Dioxoisoindolin-2-yl)tetradecane-1-sulfonyl chloride. To a solution of S—(14-(1,3-dioxoisoindolin-2-yl)tetradecyl) ethanethioate (550 mg, 1.32 mmol) in MeCN (20 mL) at 0° C. was added 2 M aqueous HCl (2 mL) and NCS (705 mg, 5.28 mmol) and the mixture was stirred at rt for 2 h. The mixture was poured into water (50 mL) and extracted with EtOAc (20 mL×3). The combined organic phases were washed with a saturated aqueous $NaHCO_3$ solution (40 mL), dried over $Na_2SO_4$ and concentrated under reduced pressure to afford the title compound (500 mg, 86% yield) as a yellow solid. LCMS: m/z=442.2 [M+H]$^+$.

Step 4—Tert-butyl(1-((14-(1,3-dioxoisoindolin-2-yl)tetradecyl)sulfonyl)piperidin-4-yl)carbamate. To a solution of 14-(1,3-dioxoisoindolin-2-yl)tetradecane-1-sulfonyl chloride (500 mg, 1.13 mmol) in DCM (10 mL) was added tert-butyl piperidin-4-ylcarbamate (272 mg, 1.36 mmol, CAS #73874-95-0) and Et$_3$N (229 mg, 2.26 mmol) and the mixture was stirred at rt for 2 h. On completion, the solvent was removed under reduced pressure and the residue was triturated with MeOH (20 mL), filtered and the filtrate was concentrated under reduced pressure to afford the title compound (300 mg, 44% yield) as a white solid. LCMS: m/z=506.3 [M-Boc+H]$^+$. H NMR (400 MHz, DMSO-$d_6$) δ 7.89-7.80 (m, 4H), 6.88 (d, J=8.0 Hz, 1H), 3.55 (t, J=7.2 Hz, 2H), 3.52-3.45 (m, 3H), 3.00-2.93 (m, 2H), 2.89-2.80 (m, 2H), 1.82-1.71 (m, 2H), 1.69-1.51 (m, 4H), 1.46-1.18 (m, 31H).

Step 5—tert-Butyl (1-((14-aminotetradecyl)sulfonyl)piperidin-4-yl)carbamate. To a solution of tert-butyl(1-((14-(1,3-dioxoisoindolin-2-yl)tetradecyl)sulfonyl)piperidin-4-yl) carbamate (300 mg, 0.50 mmol) in DCM/Ethanol (5 mL/2.5 mL) was added $N_2H_4H_2O$ (98%, 250 mg, 5.0 mmol) and the mixture was heated at 50° C. for 2 days. On completion, the mixture was filtered and the filtrate was poured into water (50 mL) and extracted with DCM (20 mL×3). The combined organic phases were washed with a saturated aqueous $NaHCO_3$ solution (40 mL), dried over $Na_2SO_4$ and concentrated under reduced pressure to afford the title compound (200 mg, 85% yield) as a white solid. LCMS: m/z=476.4 [M+H]$^+$.

Step 6—Tert-butyl(1-((14-((2-(2,6-dioxopiperidin-3-yl)-1,3-dioxoisoindolin-4-yl)amino)tetradecyl)sulfonyl)piperidin-4-yl)carbamate. To a solution of tert-butyl(1-((14-(1,3-dioxoisoindolin-2-yl)tetradecyl)sulfonyl)piperidin-4-yl) carbamate (200 mg, 0.42 mmol) in NMP (5 mL) was added 2-(2,6-dioxopiperidin-3-yl)-4-fluoroisoindoline-1,3-dione (116 mg, 0.42 mmol, CAS #835616-60-9) and DIPEA (108 mg, 0.84 mmol) and the mixture was heated at 90° C. overnight. On completion, the mixture was allowed to cool to rt and purified directly by C18 reverse phase chromatography (Biotage, MeCN/H$_2$O, 92/8, v/v, 0.1% HCOOH) to afford the title compound (140 mg, 46% yield) as a yellow solid. LCMS: m/z=732.3 [M+H]$^+$. $^1$H NMR (400 MHz, DMSO-$d_6$) δ 11.1 (s, 1H), 7.62-7.53 (m, 1H), 7.08 (d, J=8.6 Hz, 1H), 7.01 (d, J=7.0 Hz, 1H), 6.91-6.85 (m, 1H), 6.51 (t, J=6.4 Hz, 1H), 5.04 (dd, J=13.0, 5.2 Hz, 1H), 3.52-3.44 (m, 2H), 3.43-3.33 (m, 1H), 3.33-3.24 (m, 2H), 3.01-2.94 (m, 2H), 2.89-2.80 (m, 3H), 2.62-2.51 (m, 1H), 2.17 (t, J=8.2 Hz, 2H), 1.95-1.86 (m, 2H), 1.80-1.73 (m, 2H), 1.67-1.52 (m, 5H), 1.41-1.20 (m, 28H).

Step 7—4-((14-((4-Aminopiperidin-1-yl)sulfonyl)tetradecyl)amino)-2-(2,6-dioxopiperidin-3-yl)isoindoline-1,3-dione hydrochloride. To a solution of tert-butyl(1-((14-((2-(2,6-dioxopiperidin-3-yl)-1,3-dioxoisoindolin-4-yl)amino) tetradecyl)sulfonyl)piperidin-4-yl)carbamate (140 mg, 0.19 mmol) in dioxane (2 mL) was added a 4 M HCl in dioxane solution (4 mL) and the mixture was stirred at rt for 2 h. On completion, the mixture was concentrated under reduced pressure to afford the title compound (110 mg, 88% yield) as a yellow solid. LCMS: m/z=632.3 [M+H]$^+$.

6-(Difluoromethyl)-8-((1R,2R)-2-hydroxy-2-methylcyclopentyl)-2-(piperidin-4-ylamino)pyrido[2,3-d]pyrimidin-7(8H)-one (Intermediate L1)

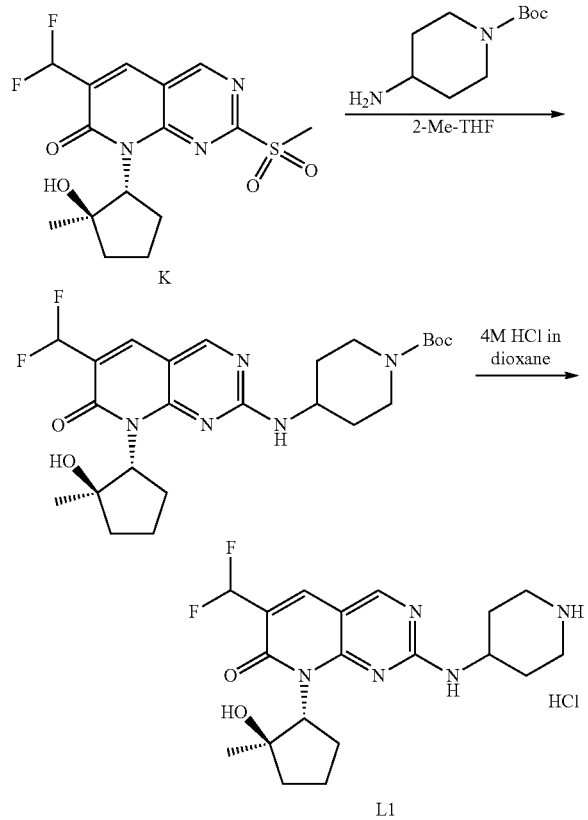

Step 1—Tert-butyl 4-((6-(difluoromethyl)-8-((1R,2R)-2-hydroxy-2-methylcyclopentyl)-7-oxo-7,8-dihydropyrido[2,3-d]pyrimidin-2-yl)amino)piperidine-1-carboxylate. To a solution of 6-(difluoromethyl)-8-((1R,2R)-2-hydroxy-2-methylcyclopentyl)-2-(methylsulfonyl)pyrido[2,3-d]pyrimidin-7(8H)-one (65 mg, 0.17 mmol, Intermediate K) in 2-Me-THF (5 mL) was added tert-butyl 4-aminopiperidine-1-carboxylate (69.7 mg, 0.35 mmol, CAS #87120-72-7) and the mixture was stirred at 30° C. overnight. On completion, the mixture was diluted with water and extracted with EtOAc (30 mL×3). The combined organic layers washed with brine, dried over Na$_2$SO$_4$ and concentrated under reduced pressure. The residue was purified by prep-TLC (Pet. Ether/EtOAc=1/1, v/v) to give the title compound (40 mg, 47% yield) as a white solid. LCMS m/z=492.2 [M−H]$^−$ and 476.2 [M−H$_2$O+H]$^+$; $^1$H NMR (400 MHz, DMSO-d$_6$) δ 8.72 (s, 1H), 8.05 (s, 2H), 6.85 (t, J=55.4 Hz, 1H), 5.90-5.81 (m, 1H), 4.26 (br s, 1H), 4.08-3.87 (m, 2H), 3.23-3.17 (m, 1H), 2.94-2.81 (m, 2H), 2.26-2.14 (m, 1H), 2.07-1.79 (m, 6H), 1.76-1.63 (m, 1H), 1.54-1.38 (m, 11H), 1.00 (s, 3H).

Step 2—6-(Difluoromethyl)-8-((1R,2R)-2-hydroxy-2-methylcyclopentyl)-2-(piperidin-4-ylamino)pyrido[2,3-d]pyrimidin-7(8H)-one hydrochloride. A mixture of tert-butyl 4-((6-(difluoromethyl)-8-((1R,2R)-2-hydroxy-2-methylcyclopentyl)-7-oxo-7,8-dihydropyrido[2,3-d]pyrimidin-2-yl)amino)piperidine-1-carboxylate (160 mg, 0.32 mmol) and a 4 M HCl in dioxane solution (5 mL) was stirred at rt for 1 h. On completion, the mixture was concentrated under reduced pressure and the residue was triturated with diethyl ether to afford the title compound (126 mg, 92%) as a yellow solid. LCMS m/z=376.3 [M−H$_2$O+H]$^+$.

4-((6-(difluoromethyl)-8-((1R,2R)-2-hydroxy-2-methylcyclopentyl)-7-oxo-7,8-dihydropyrido[2,3-d]pyrimidin-2-yl)amino)-3-methylbenzenesulfonyl chloride (Intermediate L2)

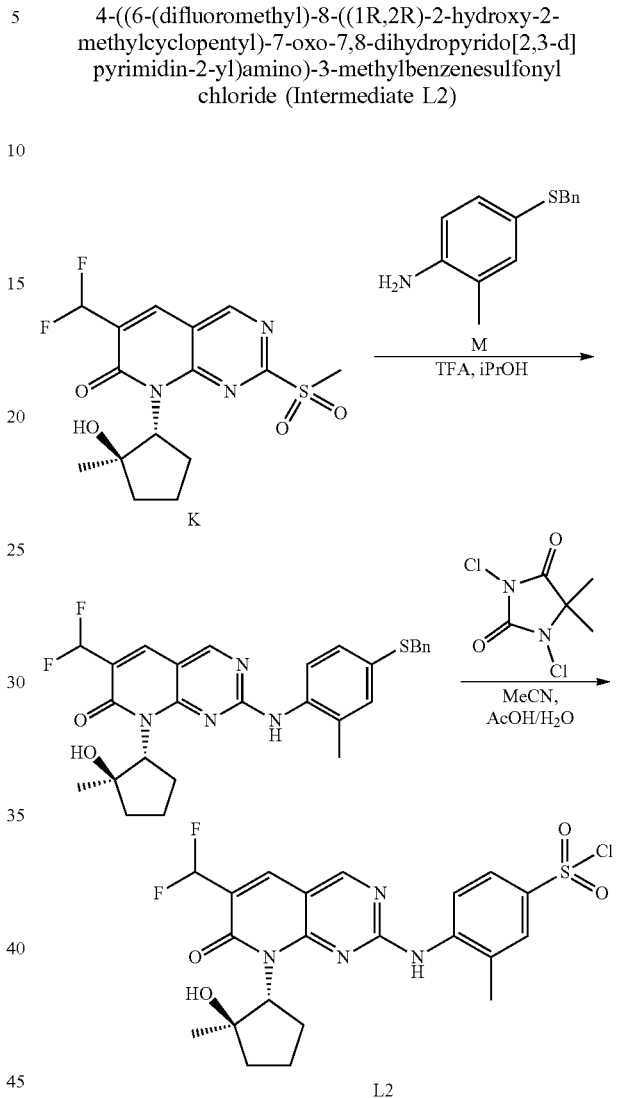

Step 1—2-((4-(Benzylthio)-2-methylphenyl)amino)-6-(difluoromethyl)-8-((1R,2R)-2-hydroxy-2-methylcyclopentyl)pyrido[2,3-d]pyrimidin-7(8H)-one. A mixture of 4-(benzylthio)-2-methylaniline (590 mg, 2.6 mmol, Intermediate M), 6-(difluoromethyl)-8-((1R,2R)-2-hydroxy-2-methylcyclopentyl)-2-(methylsulfonyl)pyrido[2,3-d]pyrimidin-7(8H)-one (500 mg, 1.3 mmol, Intermediate K) and TFA (1.48 g, 13 mmol) in isopropanol (20 mL) was heated at reflux for 6 h. On completion, the mixture was allowed to cool to rt, poured into water (100 mL), and extracted with EtOAc (30 mL×3). The combined organic phases were washed with brine (50 mL), dried over Na$_2$SO$_4$ and concentrated under reduced pressure. The residue was purified by prep-TLC (Pet. ether/EtOAc=3/1, v/v) to afford the title compound (200 mg, 29% yield) as a brown solid. LCMS m/z=523.3 [M+H]$^+$; $^1$H NMR (400 MHz, DMSO-d$_6$) δ 9.49 (s, 1H), 8.83 (s, 1H), 8.13 (s, 1H), 7.40-7.15 (m, 8H), 6.89 (t, J=55.2 Hz, 1H), 5.74-5.63 (m, 1H), 4.29 (s, 1H), 4.23 (s, 2H), 2.43-2.31 (m, 1H), 2.19 (s, 3H), 2.05-1.94 (m, 1H), 1.92-1.60 (m, 3H), 1.53-1.41 (m, 1H), 0.93 (s, 3H).

Step 2—4-((6-(Difluoromethyl)-8-((1R,2R)-2-hydroxy-2-methylcyclopentyl)-7-oxo-7,8-dihydropyrido[2,3-d]pyrimidin-2-yl)amino)-3-methylbenzenesulfonyl chloride. To a solution of 2-((4-(benzylthio)-2-methylphenyl)amino)-6-(difluoromethyl)-8-((1R,2R)-2-hydroxy-2-methylcyclopentyl)pyrido[2,3-d]pyrimidin-7(8H)-one (200 mg, 0.38 mmol) in MeCN (5 mL) at 0° C. was added AcOH/water (0.4 mL/0.8 mL) and the mixture was stirred at 0° C. for 5 min. Next, 1,3-dichloro-5,5-dimethylimidazolidine-2,4-dione (150 mg, 0.76 mmol, CAS #118-52-5) was added and the mixture was stirred at 0° C. for a further 30 min. On completion, the reaction mixture was poured into water (100 mL) and extracted with EtOAc (30 mL×3). The combined organic phases washed with a saturated aqueous NaHCO₃ solution (50 mL), dried over Na₂SO₄ and concentrated under reduced pressure to afford the title compound (180 mg, 94% yield) as a brown solid. LCMS m/z=499.1 [M+H]⁺. 1H NMR (400 MHz, DMSO-d₆) δ 9.50 (s, 1H), 8.84 (s, 1H), 8.14 (s, 1H), 7.49-7.41 (m, 2H), 7.26-7.21 (m, 1H), 6.89 (t, J=55.2 Hz, 1H), 5.82-5.68 (m, 1H), 2.44-2.31 (m, 1H), 2.31-2.18 (m, 1H), 2.25 (s, 3H), 1.58-1.47 (m, 4H), 0.97 (s, 3H).

4-((5-bromo-4-((2-carbamoyl-3-fluorophenyl)amino)pyrimidin-2-yl)amino)-3-methylbenzenesulfonyl chloride (Intermediate L3)

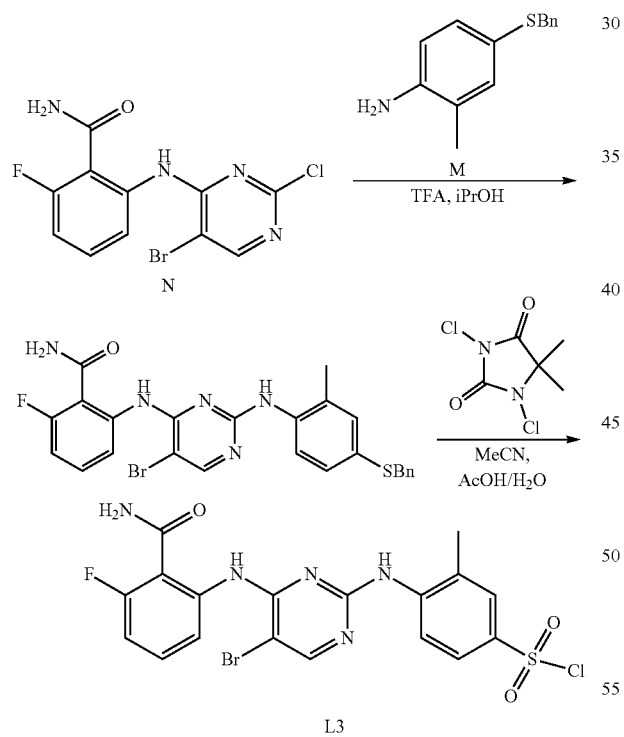

Step 1—2-((2-((4-(Benzylthio)-2-methylphenyl)amino)-5-bromopyrimidin-4-yl)amino)-6-fluorobenzamide. A mixture of 4-(benzylthio)-2-methylaniline (2.0 g, 8.7 mmol, Intermediate M), 2-((5-bromo-2-chloropyrimidin-4-yl)amino)-6-fluorobenzamide (3.0 g, 8.7 mmol, Intermediate N) and TFA (19.8 g, 87 mmol) in isopropanol (50 mL) was heated at reflux overnight. On completion, the mixture was allowed to cool to rt and poured into water (200 mL). The resulting precipitate collected by filtration and washed with ether (20 mL×3) to afford the title compound (1.8 g, 38% yield) as a white solid. LCMS m/z=538.2, 540.2 [M+H]⁺; ¹H NMR (400 MHz, DMSO-d₆) δ 10.2 (s, 1H), 8.78 (s, 1H), 8.20 (s, 1H), 8.16-8.04 (m, 3H), 7.42-7.28 (m, 5H), 7.28-7.20 (m, 2H), 7.16 (dd, J=8.4, 2.4 Hz, 1H), 7.13-7.02 (m, 1H), 6.92 (t, J=9.2 Hz, 1H), 4.23 (s, 2H), 2.14 (s, 3H).

Step 2—4-((5-Bromo-4-((2-carbamoyl-3-fluorophenyl)amino)pyrimidin-2-yl)amino)-3-methylbenzenesulfonyl chloride. To a solution of 2-((2-((4-(benzylthio)-2-methylphenyl)amino)-5-bromopyrimidin-4-yl)amino)-6-fluorobenzamide (1.0 g, 1.86 mmol) in MeCN (20 mL) at 0° C. was added AcOH/H₂O (4 mL/8 mL) and the mixture was stirred at 0° C. for 5 min. Next, 1,3-dichloro-5,5-dimethylimidazolidine-2,4-dione (733 mg, 3.72 mmol, CAS #118-52-5) was added and the mixture was stirred at 0° C. for a further 30 min. On completion, the mixture was diluted with EtOAc (200 mL), washed with brine, dried over Na₂SO₄ and concentrated under reduced pressure. The residue was triturated with ether (10 mL×3) to afford the title compound (500 mg, 52% yield) as a white solid. LCMS m/z=514.1, 516.1 [M+H]⁺; ¹H NMR (400 MHz, DMSO-d₆) δ 10.9 (s, 1H), 9.86 (s, 1H), 8.35 (s, 1H), 8.22 (s, 1H), 8.14 (s, 1H), 7.54 (d, J=2.0 Hz, 1H), 7.48 (dd, J=8.1, 2.0 Hz, 1H), 7.38-7.27 (m, 3H), 7.07 (t, J=9.2 Hz, 1H), 2.20 (s, 3H).

[1-[(4-Methoxyphenyl) methyl]-2,6-dioxo-3-piperidyl] trifluoromethanesulfonate (Intermediate G)

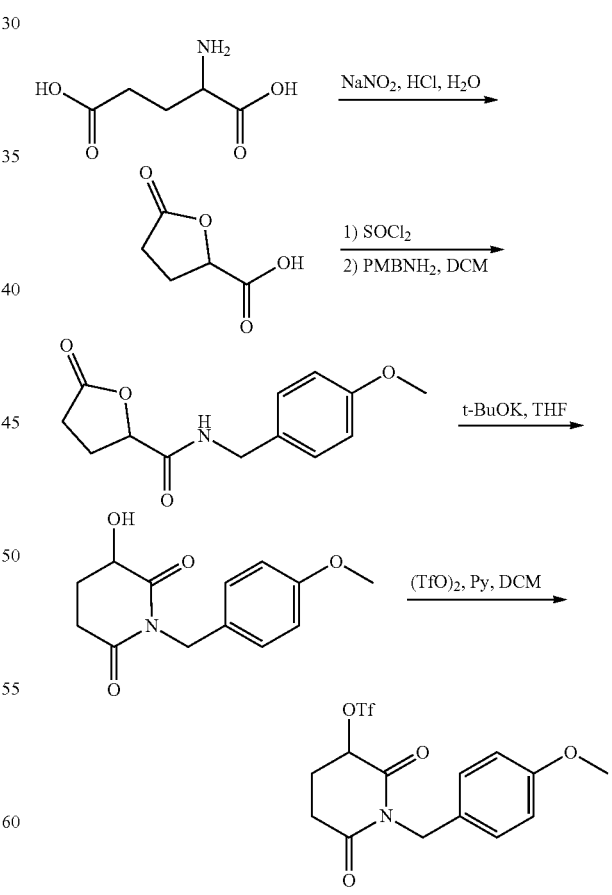

Step 1—5-Oxotetrahydrofuran-2-carboxylic acid. To a solution of 2-aminopentanedioic acid (210 g, 1.43 mol, CAS

617-65-2) in H$_2$O (800 mL) and HCl (12 M, 210 mL) was added a solution of NaNO$_2$ (147 g, 2.13 mol) in H$_2$O (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over Na$_2$SO$_4$, filtered and concentrated in vacuo to give the title compound (200 g, crude) as yellow oil. $^1$H NMR (400 MHz, CDCl$_3$) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide. To 5-oxotetrahydrofuran-2-carboxylic acid (120 g, 922 mmol) was added SOCl$_2$ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under N$_2$. After that a solution of Et$_3$N (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1$H NMR (400 MHz, CDCl$_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS (ESI$^+$) m/z 272.0 (M+Na)$^+$.

Step 3—3-Hydroxy-1-[(4-methoxyphenyl)methyl]piperidine-2,6-dione. A solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated NH$_4$Cl solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. $^1$H NMR (400 MHz, CDCl$_3$) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl) methyl]-2,6-dioxo-3-piperidyl] trifluoromethanesulfonate. To a solution of 3-hydroxy-1-[(4-methoxyphenyl) methyl] piperidine-2, 6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under N$_2$. On completion, the mixture was concentrated in vacuo. The residue was purified by column chromatography on silica gel (PE:EA=20:1/8:1) to give the title compound (45.0 g, 68% yield) as light yellow gum. $^1$H NMR (400 MHz, CDCl$_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

3-(4-bromo-3-methyl-2-oxo-2,3-dihydro-1H-benzo[d]imidazol-1-yl)piperidine-2,6-dione (Intermediate H)

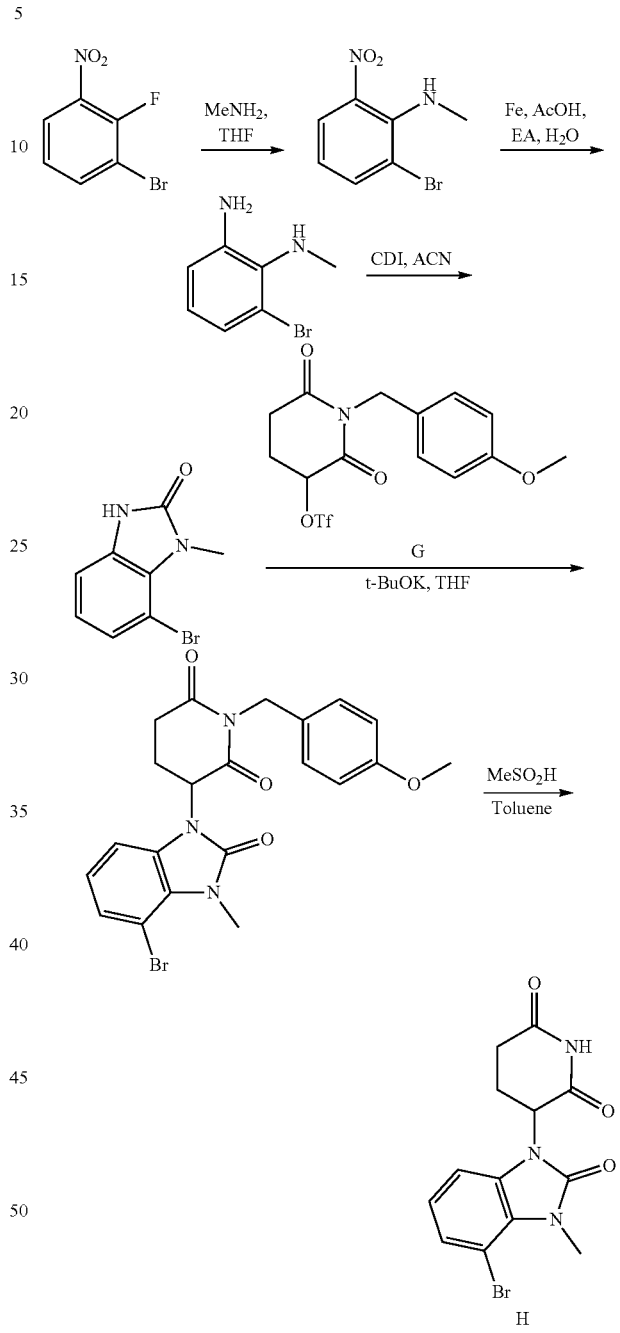

Step 1—2-Bromo-N-methyl-6-nitro-aniline. To a solution of 1-bromo-2-fluoro-3-nitro-benzene (40.0 g, 181 mmol, CAS #58534-94-4) in THF (40 mL) was added MeNH$_2$ (2 M, 400 mL). The reaction mixture was stirred at 60° C. for 12 hours. On completion, the reaction mixture was poured into sat. NaHCO$_3$ (30 mL) and extracted with EA (3×200 mL). The combined organic layers were washed with brine (2×200 mL), dried with anhydrous Na$_2$SO$_4$, filtered and concentrated in vacuo to give the title compound (40.0 g, 95% yield) as red oil. LC-MS (ESI$^+$) m/z 230.9 (M+H)$^+$.

Step 2—3-Bromo-N2-methyl-benzene-1,2-diamine. To a mixture of 2-bromo-N-methyl-6-nitro-aniline (23.0 g, 99.5 mmol) in EA (300 mL) and H$_2$O (10 mL) was added AcOH (100 mL). The mixture was warmed to 50° C. Then Fe (22.2 g, 398 mmol) was added to the reaction mixture and the mixture was heated to 80° C. about 4 hours. On completion, the reaction mixture was filtered and concentrated in vacuo. The residue was diluted with water (100 mL) and extracted with EA (3×200 mL). The combined organic layers was dried over Na$_2$SO$_4$, filtered and concentrated in vacuo to give the title compound (20.0 g, 99% yield) as red oil. $^1$H NMR (400 MHz, DMSO-d$_6$) δ 6.73-6.70 (m, 1H), 6.68-6.60 (m, 2H), 5.02 (s, 2H), 3.67 (s, 1H), 2.58 (s, 3H).

Step 3—4-Bromo-3-methyl-1H-benzimidazol-2-one. To a mixture of 3-bromo-N2-methyl-benzene-1,2-diamine (20.0 g, 99.4 mmol) in ACN (300 mL) was added CDI (32.2 g, 198 mmol). The reaction mixture was stirred at 85° C. for 12 hours under N$_2$ atmosphere. On completion, the reaction mixture was concentrated in vacuo. The reaction mixture was diluted with water (200 mL), where a solid precipitate was formed, which was filtered off. The solid was washed with water (1 L) and dried in vacuo to give the title compound (20.0 g, 88% yield) as white solid. $^1$H NMR (400 MHz, DMSO-d$_6$) δ 11.17 (s, 1H), 7.14 (dd, J=1.2, 8.0 Hz, 1H), 7.00-6.95 (m, 1H), 6.93-6.87 (m, 1H), 3.55 (s, 3H).

Step 4—3-(4-Bromo-3-methyl-2-oxo-benzimidazol-1-yl)-1-[(4-methoxyphenyl)methyl]piperidine-2,6-dione. To a solution of 4-bromo-3-methyl-1H-benzimidazol-2-one (12.0 g, 52.8 mmol) in THF (300 mL) was added t-BuOK (7.12 g, 63.4 mmol). The reaction mixture was stirred at 0° C. for 0.5 hr. Subsequently, [1-[(4-methoxyphenyl)methyl]-2,6-dioxo-3-piperidyl]trifluoromethanesulfonate (20.1 g, 52.8 mmol, Intermediate G) in a solution of THF (100 mL) was added dropwise. The resulting reaction mixture was stirred at 20° C. for 0.5 hr under N$_2$. On completion, the reaction mixture was quenched with saturated NH$_4$Cl (100 mL), and extracted with ethyl acetate (200 mL). The combined organic layers were washed with brine (2×100 mL), dried over anhydrous sodium sulfate, filtered, the filtrate was concentrated in vacuo. The crude product was purified by reversed-phase HPLC (0.1% FA condition) to give the title compound (13.3 g, 55% yield) as a yellow solid. $^1$H NMR (400 MHz, CDCl$_3$) δ 7.38 (d, J=8.8 Hz, 2H), 7.22 (d, J=8.0 Hz, 1H), 6.84 (d, J=8.8 Hz, 2H), 6.80 (t, J=8.0 Hz, 1H), 6.48-6.40 (d, J=8.0 Hz, 1H), 5.22 (dd, J=5.2, 12.8 Hz, 1H), 5.04-4.93 (m, 2H), 3.81 (s, 3H), 3.80 (s, 3H), 3.12-2.98 (m, 1H), 2.93-2.77 (m, 1H), 2.62 (dq, J=4.4, 13.2 Hz, 1H), 2.20-2.17 (m, 1H).

Step 5—3-(4-bromo-3-methyl-2-oxo-2,3-dihydro-1H-benzo[d]imidazol-1-yl)piperidine-2,6-dione. A mixture of 3-(4-bromo-3-methyl-2-oxo-benzimidazol-1-yl)-1-[(4-methoxyphenyl)methyl]piperidine-2,6-dione (13.3 g, 29.0 mmol) in a mixed solvent of Tol. (80 mL) and methane sulfonic acid (40 mL) was degassed and purged with N$_2$ for 3 times, and then the mixture was stirred at 120° C. for 2 hrs under N$_2$ atmosphere. On completion, the reaction mixture was concentrated in vacuo to remove toluene. The residue was added 200 mL of ice water, and then white solid precipitate formed. The mixture was filtered and the filtered cake was collected and dried over in vacuo to give the title compound (7.30 g, 74% yield) as white solid. $^1$H NMR (400 MHz, DMSO-d$_6$) δ 11.13 (s, 1H), 7.25 (d, J=8.0 Hz, 1H), 7.17 (d, J=8.0 Hz, 1H), 7.05-6.93 (m, 1H), 5.41 (dd, J=5.2, 12.8 Hz, 1H), 3.64 (s, 3H), 2.96-2.83 (m, 1H), 2.78-2.59 (m, 2H), 2.08-2.00 (m, 1H).

5-Bromo-3-methyl-1H-benzimidazol-2-one
(Intermediate I)

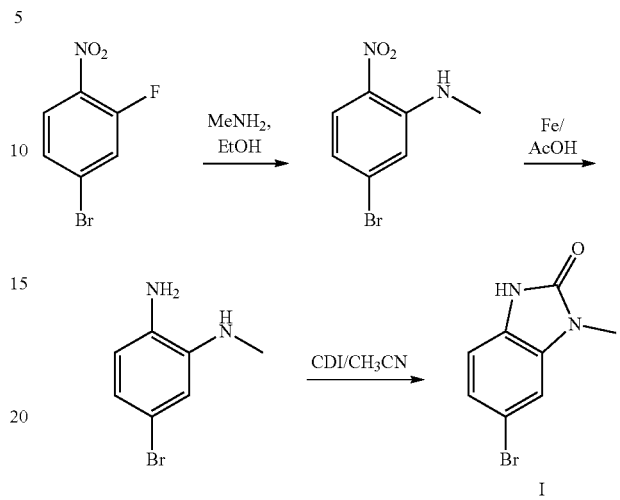

Step 1—5-Bromo-N-methyl-2-nitro-aniline. 4-bromo-2-fluoro-1-nitro-benzene (230 g, 1.05 mol, CAS #321-23-3) was added to a solution of methylamine in tetrahydrofuran (2 M, 1.51 L). The mixture was stirred at 15° C. for 10 minutes. On completion, the mixture was diluted with H$_2$O (250 mL) and extracted with EtOAc (3×300 mL). The combined organic layers were washed with brine (300 mL), dried over Na$_2$SO$_4$, filtered and concentrated in vacuo to give the title compound (200 g, 83% yield) as a yellow solid. $^1$H NMR (400 MHz, DMSO-d$_6$) δ 8.22 (s, 1H), 7.98 (d, J=9.2 Hz, 1H), 7.16 (d, J=1.6 Hz, 1H), 6.82 (dd, J=8.4, 1.6 Hz, 1H), 2.95 (d, J=4.8 Hz, 3H).

Step 2—4-Bromo-N2-methyl-benzene-1,2-diamine. To a mixture of 5-bromo-N-methyl-2-nitro-aniline (200 g, 865 mmol) in EtOAc (1 L) and H$_2$O (500 mL) was added AcOH (1.00 L). The mixture was warmed to 50° C., and then Fe (174 g, 3.11 mol) was added to the reaction mixture. After that, the reaction mixture was stirred at 80° C. for 6 hours. On completion, the reaction mixture was filtered through celite. The filtrate was concentrated in vacuo and the residue was diluted with H$_2$O (250 mL) and extracted with EtOAc (3×300 mL). The combined organic layers were washed with aq. NaHCO$_3$ and brine (300 mL), dried over Na$_2$SO$_4$, filtered and concentrated in vacuo. The residue was purified by flash silica gel chromatography to give the title compound (130 g, 75% yield) as black oil. $^1$H NMR (400 MHz, DMSO-d$_6$) δ 6.55-6.52 (m, 1H), 6.48-6.45 (m, 1H), 6.43-6.42 (m, 1H), 4.89-4.88 (m, 1H), 4.61 (s, 2H), 2.70 (d, J=4.0 Hz, 3H).

Step 3—5-Bromo-3-methyl-1H-benzimidazol-2-one. To a solution of 4-bromo-N2-methyl-benzene-1,2-diamine (110 g, 547 mmol) in CH$_3$CN (1.3 L) was added CDI (177 g, 1.09 mol). The mixture was stirred at 80° C. for 6 hours under N$_2$. On completion, the mixture was concentrated in vacuo. The mixture was diluted with H$_2$O (1.0 L) and filtered. The filter cake was washed with water (3×200 mL) and dried in vacuo to give the title compound (106 g, 85% yield) as a white solid. $^1$H NMR (400 MHz, DMSO-d$_6$) δ 11.00 (s, 1H), 7.33 (s, 1H), 7.13 (d, J=8.0 Hz, 1H), 6.92 (d, J=8.0 Hz, 1H), 3.27 (s, 3H).

3-(5-bromo-3-methyl-2-oxo-benzimidazol-1-yl)piperidine-2,6-dione (Intermediate J)

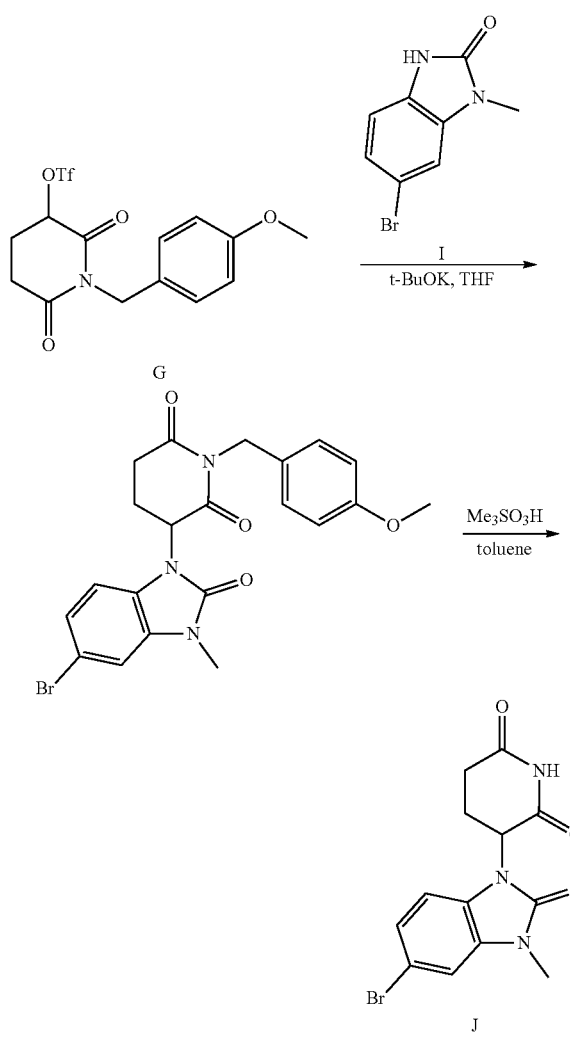

Step 1—3-(5-Bromo-3-methyl-2-oxo-benzimidazol-1-yl)-1-[(4-methoxyphenyl)methyl]piperidine-2,6-dione. To a solution of 5-bromo-3-methyl-1H-benzimidazol-2-one (4.90 g, 21.6 mmol, Intermediate I) in THF (300 mL) was added t-BuOK (3.63 g, 32.3 mmol) at 0° C. The mixture was stirred at 0-10° C. for 1 hour under $N_2$. Then a solution of [1-[(4-methoxyphenyl) methyl]-2, 6-dioxo-3-piperidyl] trifluoromethanesulfonate (9.87 g, 25.9 mmol, Intermediate G) in THF (100 mL) was added to the reaction mixture at 0-10° C. during 30 minutes. The mixture was stirred at 0-10° C. for 30 minutes under $N_2$. An additional solution of [1-[(4-methoxyphenyl) methyl]-2, 6-dioxo-3-piperidyl]trifluoromethanesulfonate (2.47 g, 6.47 mmol) in THF (20 mL) was added to the reaction mixture at 0-10° C. dropwise. The mixture was then stirred at 0-10° C. for another 30 minutes under $N_2$. On completion, the reaction was quenched water (400 mL) and extracted with EA (3×200 mL). The combined organic layer was concentrated in vacuo. The residue was triturated with EA (80 mL) and filtered. The filter cake was collected and dried in vacuo to give the title compound (6.70 g, 67% yield) as light yellow solid. The filtrate was also concentrated in vacuo and the residue was purified by column chromatography to give another batch title compound (1.80 g, 18% yield) as light yellow solid. $^1$H NMR (400 MHz, DMSO-$d_6$) δ 7.47 (d, J=1.6 Hz, 1H), 7.21-7.16 (m, 3H), 7.01 (d, J=8.0 Hz, 1H), 6.85 (d, J=8.8 Hz, 2H), 5.55-5.51 (m, 1H), 4.84-4.73 (m, 2H), 3.72 (s, 3H), 3.33 (s, 3H), 3.04-3.00 (m, 1H), 2.83-2.67 (m, 2H), 2.07-2.05 (m, 1H).

Step 2—3-(5-Bromo-3-methyl-2-oxo-benzimidazol-1-yl)piperidine-2,6-dione. To a mixture of 3-(5-bromo-3-methyl-2-oxo-benzimidazol-1-yl)-1-[(4-methoxyphenyl)methyl]piperidine-2,6-dione (8.50 g, 18.6 mmol) in toluene (50 mL) was added methanesulfonic acid (33.8 g, 351 mmol, 25 mL) at room temperature (15° C.). The mixture was stirred at 120° C. for 2 hours. On completion, the reaction mixture was cooled to room temperature and concentrated in vacuo. The residue was poured into ice/water (200 mL), and extracted with EA (3×100 mL). The combined organic layer was washed with brine (50 mL), dried over $Na_2SO_4$, filtered and concentrated in vacuo. The residue was triturated with EA (80 mL) and filtered. The filtrate cake was collected and dried in vacuo to give the title compound (4.20 g, 67% yield) as off-white solid. $^1$H NMR (400 MHz, DMSO-$d_6$) δ 11.12 (s, 1H), 7.47 (d, J=2.0 Hz, 1H), 7.22 (d, J=8.4 Hz, 1H), 7.10 (d, J=8.4 Hz, 1H), 5.40-5.35 (m, 1H), 2.34 (s, 3H), 2.92-2.88 (m, 1H), 2.71-2.60 (m, 2H), 2.03-1.99 (m, 1H).

6-(Difluoromethyl)-8-((1R,2R)-2-hydroxy-2-methylcyclopentyl)-2-(methylsulfonyl)pyrido[2,3-d]pyrimidin-7(8H)-one (Intermediate K)

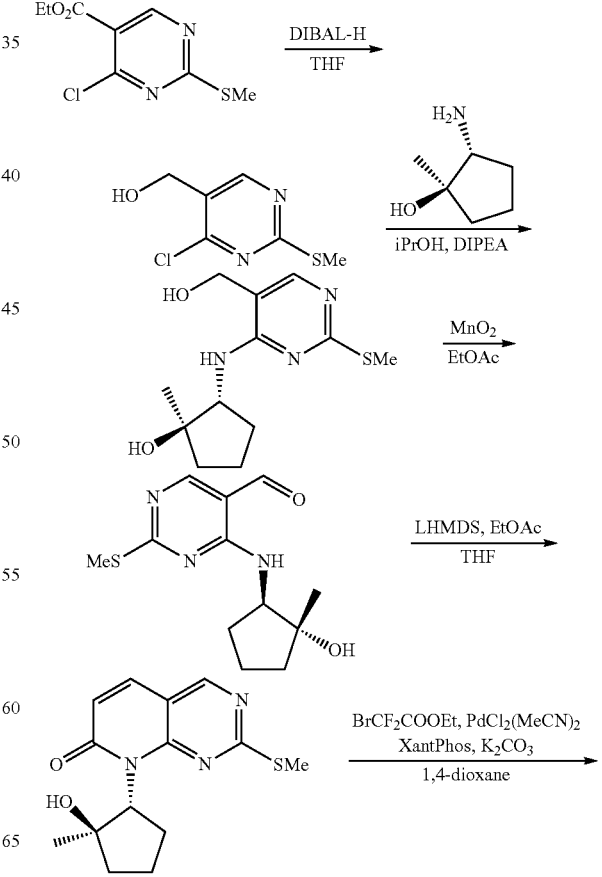

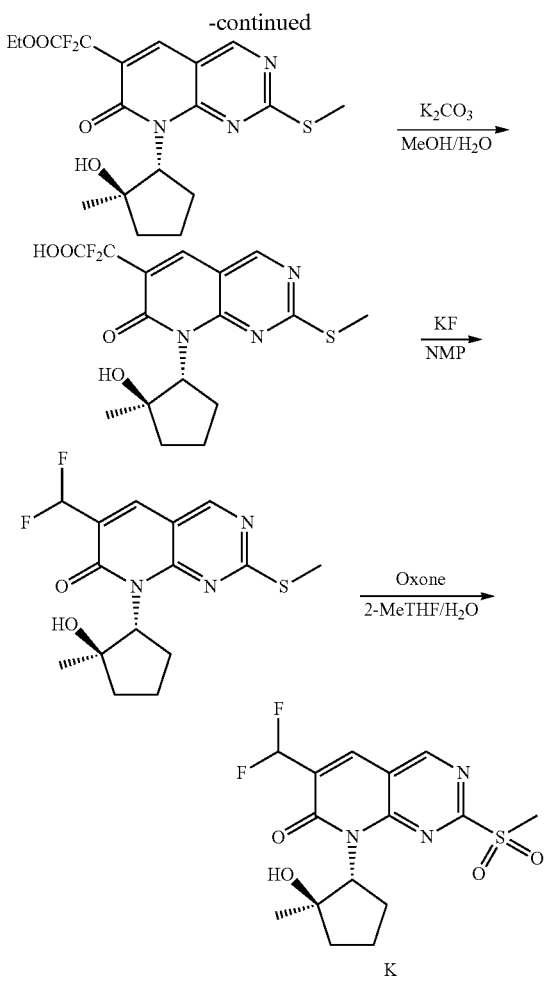

Step 1—(4-Chloro-2-(methylthio)pyrimidin-5-yl)methanol. To a solution of ethyl 4-chloro-2-(methylthio)pyrimidine-5-carboxylate (40.0 g, 172 mmol, CAS #5909-24-0) in THF (600 mL) at −78° C. under $N_2$ was added DIBAL-H (1 M in THF, 517 mL, 517 mmol) and the mixture was allowed to warm to rt and stirred for 0.5 h. On completion, the reaction was quenched with saturated aqueous $NH_4Cl$ (1000 mL) and extracted with EtOAc (1000 mL×2). The combined organic layers were washed with brine, dried over $Na_2SO_4$ and concentrated under reduced pressure. The residue was triturated with Pet. Ether to afford the title compound (28.5 g, 87% yield) as a white solid. LCMS: m/z=191.1 [M+H]; $^1$H NMR (400 MHz, DMSO-$d_6$) δ 8.61 (s, 1H), 4.50 (s, 2H), 2.52 (s, 3H).

Step 2—(1R,2R)-2-((5-(Hydroxymethyl)-2-(methylthio)pyrimidin-4-yl)amino)-1-methylcyclopentan-1-ol. To a solution of (4-chloro-2-(methylthio)pyrimidin-5-yl)methanol (12.0 g, 63.0 mmol) in i-PrOH (200 mL) was added (1R,2R)-2-amino-1-methylcyclopentan-1-ol (7.96 g, 69.4 mmol, CAS #1400689-45-3) and DIPEA (24.0 g, 189 mmol) and the mixture was heated at 90° C. under $N_2$ overnight. On completion, the mixture was concentrated under reduced pressure and the residue was purified by silica gel chromatography (Pet. Ether/EtOAc=5/1, v/v) to afford the title compound (11.0 g, 65% yield) as a white solid. LCMS: m/z=270.2 [M+H]; $^1$H NMR (400 MHz, DMSO-$d_6$) δ 7.82 (s, 1H), 6.33 (d, J=8.0 Hz, 1H), 5.29 (t, J=5.3 Hz, 1H), 4.68 (s, 1H), 4.36 (d, J=5.4 Hz, 2H), 4.33-4.23 (m, 1H), 2.42 (s, 3H), 2.19-2.10 (m, 1H), 1.72-1.55 (m, 4H), 1.52-1.41 (m, 1H), 1.09 (s, 3H).

Step 3—4-(((1R,2R)-2-Hydroxy-2-methylcyclopentyl)amino)-2-(methylthio)pyrimidine-5-carbaldehyde. To a solution of (1R,2R)-2-((5-(hydroxymethyl)-2-(methylthio)pyrimidin-4-yl)amino)-1-methylcyclopentan-1-ol (2.7 g, 10 mmol) in EtOAc (70 mL) was added $MnO_2$ (13.1 g, 150 mmol) and the mixture was heated at 50° C. under $N_2$ overnight. On completion, the mixture was filtered and the filtrate was concentrated under reduced pressure to afford the title compound (2.3 g, 86% yield) as a white solid. LCMS: m/z=268.0 [M+H]$^+$; $^1$H NMR (400 MHz, DMSO-$d_6$) δ 9.75 (s, 1H), 8.65 (d, J=8.6 Hz, 1H), 8.54 (s, 1H), 4.76 (s, 1H), 4.42-4.34 (m, 1H), 2.52 (s, 3H), 2.28-2.15 (m, 1H), 1.77-1.57 (m, 4H), 1.48-1.37 (m, 1H), 1.16 (s, 3H).

Step 4—8-((1R,2R)-2-Hydroxy-2-methylcyclopentyl)-2-(methylthio)pyrido[2,3-d]pyrimidin-7(8H)-one. To a solution of 4-(((1R,2R)-2-hydroxy-2-methylcyclopentyl)amino)-2-(methylthio)pyrimidine-5-carbaldehyde (2.3 g, 8.6 mmol) and EtOAc (2.27 g, 25.8 mmol) in dry THF (25 mL) at −10° C. under $N_2$ was added LiHMDS (1 M in THF, 25.8 mL, 25.8 mmol) dropwise. The mixture was allowed to warm to rt and stirred overnight. On completion, the reaction was quenched with a saturated aqueous $NH_4Cl$ solution and extracted with EtOAc (50 mL×3). The combined organic phases were washed with brine, dried over $Na_2SO_4$ and concentrated under reduced pressure. The residue was purified by silica gel chromatography (Pet. Ether/EtOAc=5/1, v/v) to give the title compound (2.1 g, 84% yield) as a yellow solid. LCMS: m/z=291.9 [M+H]$^+$; $^1$H NMR (400 MHz, DMSO-$d_6$) δ 8.88 (s, 1H), 7.89 (d, J=9.4 Hz, 1H), 6.57 (d, J=9.4 Hz, 1H), 5.93-5.84 (m, 1H), 4.53 (s, 1H), 2.60 (s, 3H), 2.45-2.34 (m, 1H), 2.26-2.15 (m, 1H), 2.04-1.94 (m, 1H), 1.91-1.82 (m, 2H), 1.71-1.64 (m, 1H), 0.95 (s, 3H).

Step 5—Ethyl 2,2-difluoro-2-(8-((1R,2R)-2-hydroxy-2-methylcyclopentyl)-2-(methylthio)-7-oxo-7,8-dihydropyrido[2,3-d]pyrimidin-6-yl)acetate. To a solution of 8-((1R,2R)-2-hydroxy-2-methylcyclopentyl)-2-(methylthio)pyrido[2,3-d]pyrimidin-7(8H)-one (100 mg, 0.34 mmol) in dry dioxane (5 mL) under $N_2$ was added $BrCF_2COOEt$ (139.3 mg, 0.69 mmol, CAS #667-27-6), Pd(MeCN)$_2$Cl$_2$ (8.9 mg, 0.034 mmol), Xantphos (39.7 mg, 0.069 mmol) and $K_2CO_3$ (94.9 mg, 0.69 mmol) and the mixture was heated at reflux overnight. On completion, the mixture was allowed to cool to rt, poured into water, and extracted with EtOAc (30 mL×3). The combined organic phases were washed with brine, dried over $Na_2SO_4$ and concentrated under reduced pressure. The residue was purified by prep-TLC (Pet. Ether/EtOAc=2/1, v/v) to give the title compound (70 mg, 49% yield) as a white solid. LCMS: m/z=414.1 [M+H]$^+$; $^1$H NMR (400 MHz, CDCl$_3$) δ 8.73 (s, 1H), 8.03 (s, 1H), 5.91-5.85 (m, 1H), 4.41-4.31 (m, 2H), 2.79-2.68 (m, 1H), 2.65 (s, 3H), 2.29-2.19 (m, 1H), 2.11-1.88 (m, 3H), 1.85-1.78 (m, 1H), 1.31 (t, J=7.2 Hz, 3H), 1.12 (s, 3H).

Step 6—2,2-Difluoro-2-(8-((1R,2R)-2-hydroxy-2-methylcyclopentyl)-2-(methylthio)-7-oxo-7,8-dihydropyrido[2,3-d]pyrimidin-6-yl)acetic acid. To a solution of ethyl 2,2-difluoro-2-(8-((1R,2R)-2-hydroxy-2-methylcyclopentyl)-2-(methylthio)-7-oxo-7,8-dihydropyrido[2,3-d]pyrimidin-6-yl)acetate (65 mg, 0.16 mmol) in MeOH/H$_2$O (4 mL/1 mL) was added $K_2CO_3$ (43.5 mg, 0.31 mmol) and the mixture was stirred at rt for 2 h. On completion, the mixture was adjusted to pH 3 with 1 M aqueous HCl and extracted with EtOAc (30 mL×4). The combined organic phases were dried over $Na_2SO_4$ and concentrated under reduced pressure to afford the title compound (50 mg, 82% yield) as a yellow solid. LCMS: m/z=386.1 [M+H]$^+$.

Step 7—6-(Difluoromethyl)-8-((1R,2R)-2-hydroxy-2-methylcyclopentyl)-2-(methylthio)pyrido[2,3-d]pyrimidin-7(8H)-one. To a solution of 2,2-difluoro-2-(8-((1R,2R)-2-hydroxy-2-methylcyclopentyl)-2-(methylthio)-7-oxo-7,8-dihydropyrido[2,3-d]pyrimidin-6-yl)acetic acid (330 mg, 0.86 mmol) in NMP (10 mL) was added KF (248.5 mg, 4.28 mmol) and the mixture was heated at 150° C. for 2.5 h. On completion, the mixture was allowed to cool to rt, poured into water (50 mL), and extracted with EtOAc (50 mL×4). The combined organic phases were washed with brine, dried over Na$_2$SO$_4$ and concentrated under reduced pressure. The residue was purified by silica gel chromatography (Pet. Ether/EtOAc=5/1, v/v) to give the title compound (110 mg, 38% yield) as a white solid. LCMS: m/z=342.1 [M+H]$^+$; $^1$H NMR (400 MHz, CDCl$_3$) δ 8.71 (s, 1H), 7.94 (s, 1H), 6.80 (t, J=54.8 Hz, 1H), 5.92-5.85 (m, 1H), 2.82-2.73 (m, 1H), 2.65 (s, 3H), 2.32-2.22 (m, 1H), 2.13-2.01 (m, 2H), 2.00-1.91 (m, 1H), 1.90-1.82 (m, 1H), 1.15 (s, 3H).

Step 8—6-(Difluoromethyl)-8-((1R,2R)-2-hydroxy-2-methylcyclopentyl)-2-(methylsulfonyl)pyrido[2,3-d]pyrimidin-7(8H)-one. To a solution of 6-(difluoromethyl)-8-((1R,2R)-2-hydroxy-2-methylcyclopentyl)-2-(methylthio)pyrido[2,3-d]pyrimidin-7(8H)-one (110 mg, 0.32 mmol) in 2-Me-THF/H$_2$O (5 mL/1 mL) was added oxone (495.2 mg, 0.81 mmol) and the mixture was stirred at 30° C. for 3 h. The mixture was poured into water (20 mL), and extracted with EtOAc (20 mL×4). The combined organic layers were washed with brine, dried over Na$_2$SO$_4$ and concentrated under reduced pressure. The residue was purified by prep-TLC (Pet. Ether/EtOAc=1/1, v/v) to give the title compound (60 mg, 50% yield) as a white solid. LCMS: m/z=356.1 [M−H$_2$O+H]$^+$; H NMR (400 MHz, CDCl$_3$) δ 9.08 (s, 1H), 8.10 (s, 1H), 6.84 (t, J=54.4 Hz, 1H), 5.85-5.76 (m, 1H), 3.41 (s, 3H), 2.82-2.72 (m, 1H), 2.35-2.24 (m, 1H), 2.18-2.07 (m, 2H), 2.02-1.88 (m, 2H), 1.13 (s, 3H).

4-(Benzylthio)-2-methylaniline (Intermediate M)

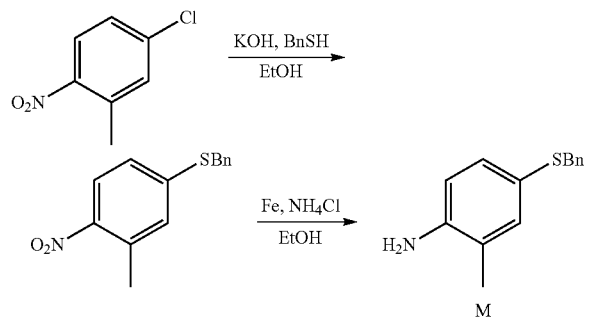

Step 1—Benzyl(3-methyl-4-nitrophenyl)sulfane. To a solution of 4-chloro-2-methyl-1-nitrobenzene (10 g, 58 mmol, CAS #5367-28-2) in ethanol (200 mL) was added KOH (3.6 g, 64 mmol) and BnSH (7.9 g, 64 mmol, CAS #100-53-8) and the mixture was heated at 70° C. overnight. On completion, the mixture was concentrated under reduced pressure and the residue purified by silica gel chromatography (Pet. Ether/EtOAc=10/1, v/v) to afford the title compound (10 g, 67% yield) as a yellow solid. $^1$H NMR (400 MHz, DMSO-d$_6$) δ 7.93 (d, J=8.6 Hz, 1H), 7.46-7.23 (m, 7H), 4.39 (s, 2H), 2.50 (s, 3H).

Step 2—4-(Benzylthio)-2-methylaniline. To a solution of benzyl(3-methyl-4-nitrophenyl)sulfane (9.0 g, 34.7 mmol) in ethanol (100 mL) was added Fe (1.9 g, 347 mmol) and saturated aqueous NH$_4$Cl (50 mL) and the mixture was heated at 70° C. for 2 h. On completion, the mixture was filtered and the filtrate concentrated under reduced pressure to afford the title compound (7.0 g, 89% yield) as a brown solid. LCMS m/z=230.2 [M+H]$^+$; $^1$H NMR (400 MHz, DMSO-d$_6$) δ 7.30-7.16 (m, 5H), 6.95 (d, J=2.2 Hz, 1H), 6.89 (dd, J=8.2, 2.2 Hz, 1H), 6.52 (d, J=8.2 Hz, 1H), 4.97 (s, 2H), 3.94 (s, 2H), 1.99 (s, 3H).

2-((5-Bromo-2-chloropyrimidin-4-yl)amino)-6-fluorobenzamide (Intermediate N)

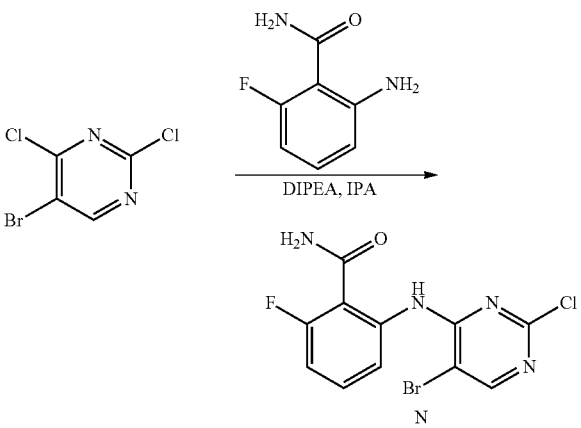

To a solution of 5-bromo-2,4-dichloropyrimidine (8.25 g, 36.2 mmol, CAS #36082-50-5) in isopropanol (50 mL) was added 2-amino-6-fluorobenzamide (5.02 g, 32.5 mmol, CAS #115643-59-9) and DIPEA (21.1 g, 162.9 mmol) and the mixture was heated at reflux under N$_2$ for 18 h. On completion, the mixture was allowed to cooled to rt, dried over Na$_2$SO$_4$ and concentrated under reduced pressure. The residue was purified by silica gel chromatography (Pet. Ether/EtOAc=10/1 to 3/1, v/v) to give the title compound (5.9 g, 48% yield) as a white solid. LCMS m/z=345.0, 347.0 [M+H]$^+$; $^1$H NMR (400 MHz, DMSO-d$_6$) δ 10.6 (s, 1H), 8.57 (s, 1H), 8.21 (s, 1H), 8.16 (s, 1H), 8.09 (d, J=8.2 Hz, 1H), 7.62-7.53 (m, 1H), 7.17-7.08 (m, 1H).

Tert-butyl non-8-yn-1-ylcarbamate (Intermediate O)

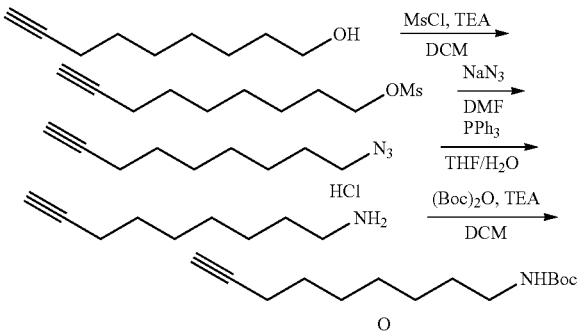

Step 1—Non-8-yn-1-yl methanesulfonate. To a stirred solution of non-8-yn-1-ol (20.00 g, 142.6 mmol) and TEA (39.54 mL, 285.3 mmol) in DCM (200.0 mL) was added MsCl (24.51 g, 213.9 mmol) at 0° C. under nitrogen atmosphere. The mixture was stirred for 1 h at rt. On completion, the reaction was quenched with water (150 mL) at rt. The resulting mixture was extracted with $CH_2Cl_2$ (2×50 mL). The combined organic layers were washed with NaCl aq (1×100 mL), and dried over anhydrous $Na_2SO_4$. After filtration, the filtrate was concentrated under reduced pressure to give the title compound (30 g, 96% yield) as a light yellow oil. $^1H$ NMR (400 MHz, DMSO-$d_6$) δ 4.19 (t, J=6.5 Hz, 2H), 3.16 (s, 3H), 2.73 (t, J=2.7 Hz, 1H), 2.16 (td, J=6.9, 2.7 Hz, 2H), 1.70-1.62 (m, 2H), 1.49-1.42 (m, 2H), 1.40-1.26 (m, 6H).

Step 2—9-Azidonon-1-yne. To a stirred solution of non-8-yn-1-yl methanesulfonate (30.00 g, 137.4 mmol) in DMF (100.00 mL) was added $NaN_3$ (17.87 g, 274.8 mmol) at rt under nitrogen atmosphere. The mixture was stirred for 16 h at 55° C. On completion, the reaction was quenched with water at rt. The resulting mixture was extracted with EtOAc (3×200 mL). The combined organic layers were washed with brine (1×100 mL), and dried over anhydrous $Na_2SO_4$. After filtration, the filtrate was concentrated under reduced pressure. The residue was purified by silica gel column chromatography, eluted with PE/EtOAc (30:1) to afford 9-azidonon-1-yne (21 g, 92% yield) as a colorless oil. $^1H$ NMR (400 MHz, DMSO-$d_6$) δ 3.37-3.27 (m, 2H), 2.73 (t, J=2.8 Hz, 1H), 2.14 (td, J=6.9, 2.6 Hz, 2H), 1.56-1.49 (m, 2H), 1.47-1.40 (m, 2H), 1.39-1.24 (m, 6H).

Step 3—Non-8-yn-1-amine hydrochloride. To a stirred solution of 9-azidonon-1-yne (32.00 g, 193.7 mmol) in THF (300.0 mL)/$H_2O$ (30.00 mL) was added $PPh_3$ (76.19 g, 290.5 mmol) in portions at 0° C. under nitrogen atmosphere. The solution was stirred for 4 h at 55° C. On completion, the solution was concentrated under reduced pressure and diluted with DCM (300 mL). The mixture was acidified to pH 1 with HCl (2 M aq.). The aqueous layer was extracted with DCM (3×100 mL). The aqueous layer was concentrated under reduced pressure to give the title compound (27 g, 79% yield) as a white solid. $^1H$ NMR (400 MHz, DMSO-$d_6$) δ 8.04 (s, 3H), 2.81-2.68 (m, 3H), 2.15 (td, J=6.9, 2.7 Hz, 2H), 1.59-1.51 (m, 2H), 1.50-1.39 (m, 2H), 1.39-1.23 (m, 6H). LC/MS (ESI, m/z): $[(M+1)]^+$=140.2.

Step 4—Tert-butyl N-(non-8-yn-1-yl)carbamate. To a stirred mixture of non-8-yn-1-amine hydrochloride (27.00 g, 153.7 mmol) in DCM (300.0 mL) was added TEA (106.5 mL, 768.4 mmol) dropwise at 0° C. under nitrogen atmosphere. Then $Boc_2O$ (50.31 g, 230.5 mmol) was added dropwise at 0° C. under nitrogen atmosphere. The mixture was stirred for 16 h at rt. On completion, the reaction was quenched with water (200 mL) at rt. The resulting mixture was extracted with $CH_2Cl_2$ (2×100 mL) and the combined organic layers were dried over anhydrous $Na_2SO_4$. After filtration, the filtrate was concentrated under reduced pressure. The residue was purified by silica gel column chromatography, eluted with PE/EtOAc (3:1) to afford the title compound (20 g, 54% yield) as a colorless oil. $^1H$ NMR (400 MHz, DMSO-$d_6$) δ 6.76 (t, J=5.7 Hz, 1H), 2.90 (q, J=6.6 Hz, 2H), 2.73 (t, J=2.6 Hz, 1H), 2.15 (td, J=7.0, 2.7 Hz, 2H), 1.48-1.41 (m, 2H), 1.41-1.32 (m, 13H), 1.30-1.17 (m, 4H). LC/MS (ESI, m/z): $[(M+1-56)]^+$=184.2.

(1R,3S)-3-(1-(tert-butyl)-5-(3-(methoxymethyl)-1-methyl-1H-pyrazole-5-carboxamido)-1H-pyrazol-3-yl)cyclopentyl phenyl carbonate (Intermediate P)

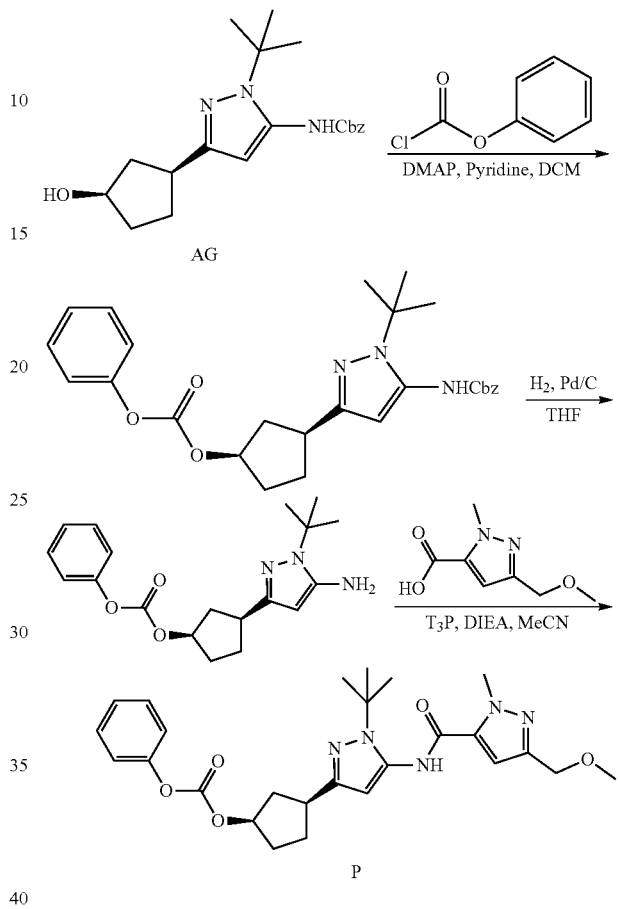

Step 1—Benzyl (1-(tert-butyl)-3-((1S,3R)-3-((phenoxycarbonyl)oxy)cyclopentyl)-1H-pyrazol-5-yl)carbamate. To a solution of benzyl N-[2-tert-butyl-5-[(1S,3R)-3-hydroxycyclopentyl]pyrazol-3-yl]carbamate (1 g, 2.80 mmol, Intermediate AG) and phenyl carbonochloridate (394 mg, 2.52 mmol) in DCM (14 mL) was added DMAP (34.2 mg, 279 umol) and pyridine (663 mg, 8.39 mmol), then the mixture was stirred at 25° C. for 12 h. On completion, the mixture was quenched with sat. $NH_4Cl$ (20 mL), diluted with DCM (20 mL), then washed with water (20 mL×3) and brine (20 mL×3). The solution was then dried over $Na_2SO_4$ and concentrated in vacuo. The residue was purified by column chromatography ($SiO_2$, Petroleum ether/Ethyl acetate=3/1 to 0/1) to give the title compound (1.2 g, 85% yield) as a colorless oil. $^1H$ NMR (400 MHz, $CDCl_3$) δ=7.48-7.29 (m, 7H), 7.27-7.15 (m, 3H), 6.13 (br s, 1H), 5.29-5.22 (m, 1H), 5.21 (s, 2H), 3.17-3.06 (m, 1H), 2.66-2.55 (m, 1H), 2.14-2.07 (m, 1H), 2.04-1.85 (m, 4H), 1.59 (s, 9H).

Step 2—(1R,3S)-3-(5-amino-1-(tert-butyl)-1H-pyrazol-3-yl)cyclopentyl phenyl carbonate. To a solution of benzyl (1-(tert-butyl)-3-((1S,3R)-3-((phenoxycarbonyl)oxy)cyclopentyl)-1H-pyrazol-5-yl)carbamate (1 g, 2.09 mmol) in THF (25 mL) was added Pd/C (1.00 g, 943 umol, 10 wt %) and the reaction mixture was placed under $H_2$ atmosphere. The mixture was stirred at 25° C. for 2 h. On completion, the mixture was filtered and the filtrate was concentrated in vacuo to give the title compound (0.7 g, 98% yield) as a colorless gum. LCMS: tR=0.417 min., (ES⁺) m/z (M+H)⁺ =344.2

Step 3—(1R,3S)-3-(1-(tert-butyl)-5-(3-(methoxymethyl)-1-methyl-1H-pyrazole-5-carboxamido)-1H-pyrazol-3-yl) cyclopentyl phenyl carbonate. A solution of (1R,3S)-3-(5-amino-1-(tert-butyl)-1H-pyrazol-3-yl)cyclopentyl phenyl carbonate (0.7 g, 2.04 mmol), 5-(methoxymethyl)-2-methyl-pyrazole-3-carboxylic acid (416 mg, 2.45 mmol, Intermediate A1), T₃P (3.89 g, 6.11 mmol, 50% solution in DMF), and DIEA (1.32 g, 10.2 mmol) in MeCN (8 mL) was stirred at 60° C. for 12 h. On completion, the mixture was quenched with sat. NH₄Cl (10 mL), and extracted with EtOAc (15 mL×2). The organic layer was washed with brine (10 mL×3), dried over Na₂SO₄, and concentrated in vacuo. The residue was purified by column chromatography (SiO₂, Petroleum ether/Ethyl acetate=5/1 to 0/1) to give the title compound (0.7 g, 62% yield) as a brown oil. ¹H NMR (400 MHz, CDCl₃) δ=7.44 (br s, 1H), 7.40-7.36 (m, 2H), 7.26-7.22 (m, 1H), 7.20-7.17 (m, 2H), 6.63 (br s, 1H), 6.30 (s, 1H), 5.27-5.22 (m, 1H), 4.49 (s, 2H), 4.20 (s, 3H), 3.44 (s, 3H), 3.20-3.11 (m, 1H), 2.66-2.58 (m, 1H), 2.17-2.07 (m, 2H), 2.04 (br s, 1H), 2.02-1.88 (m, 3H), 1.65 (s, 9H).

1-(4-((2,2,2-trifluoroacetoxy)methyl)cyclohexyl)-1H-pyrazole-4-carboxylic acid (Intermediate Q)

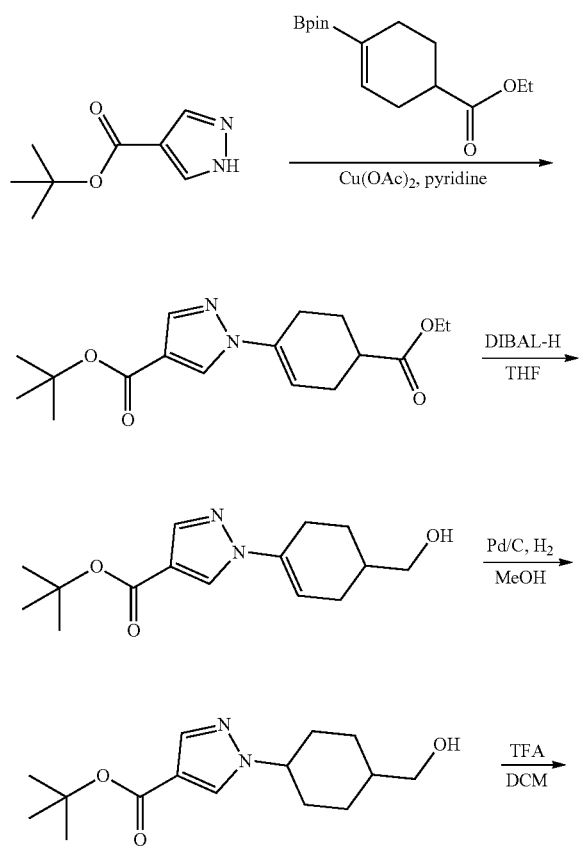

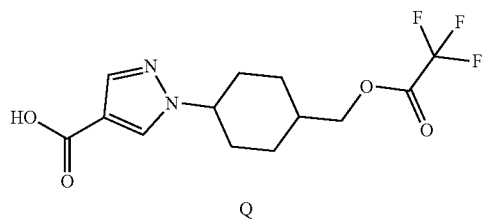

Q

Step 1—Tert-butyl 1-(4-(ethoxycarbonyl)cyclohex-1-en-1-yl)-1H-pyrazole-4-carboxylate. To a solution of tert-butyl 1H-pyrazole-4-carboxylate (900 mg, 5.3 mmol, CAS #611239-23-7) and ethyl 4-(4,4,5,5-tetramethyl-1,3,2-dioxaborolan-2-yl)cyclohex-3-ene-1-carboxylate (1 g, 3.57 mmol, CAS #1049004-32-1) in pyridine (10 mL) was added Cu(OAc)₂ (1.30 g, 7.14 mmol) at 20° C. under nitrogen atmosphere. Then the reaction was stirred at 100° C. for 10 h. On completion, the reaction was poured into ice water (20 mL) and extracted with ethyl acetate (2×20 mL). The combined organic phase was washed with brine (2×10 mL), and dried over sodium sulfate. The solution was then filtered and the filtrate was concentrated to give a residue. The residue was purified by column chromatography on silica gel (eluted with petroleum ether:ethyl acetate=100:1 to 100:7) to give the title compound (0.8 g, 69% yield) as white solid. ¹H NMR (400 MHz, CDCl₃-d) δ=7.99 (s, 1H), 7.90 (s, 1H), 6.29-6.28 (m, 1H), 6.29-6.17 (m, 1H), 4.24-4.12 (m, 2H), 2.81-2.31 (m, 5H), 2.28-2.17 (m, 1H), 2.11-1.86 (m, 1H), 1.56 (s, 8H), 1.29 (t, J=7.2 Hz, 3H).

Step 2—tert-butyl 1-(4-(hydroxymethyl)cyclohex-1-en-1-yl)-1H-pyrazole-4-carboxylate. To a solution of tert-butyl 1-(4-ethoxycarbonylcyclohexen-1-yl)pyrazole-4-carboxylate (750 mg, 2.3 mmol) in THF (17 mL) was added DIBAL-H (1 M, 4.68 mL) at −20° C. under nitrogen atmosphere. Then the reaction was stirred at −20° C. for 0.5 h under nitrogen atmosphere. On completion, the reaction was quenched with 5 mL of methanol, and then stirred at 0° C. for 30 min. Then the reaction was dried over sodium sulfate, filtered, and the filtrate was concentrated to give a residue. The title compound (0.6 g, 92% yield) was obtained as yellow oil. ¹H NMR (400 MHz, CDCl₃-d) δ=7.99 (s, 1H), 7.90 (s, 1H), 6.30-6.12 (m, 1H), 3.68-3.55 (m, 2H), 2.77-2.63 (m, 1H), 2.61-2.47 (m, 1H), 2.43-2.32 (m, 1H), 2.14-1.84 (m, 4H), 1.56 (s, 10H).

Step 3—tert-butyl 1-(4-(hydroxymethyl)cyclohexyl)-1H-pyrazole-4-carboxylate. To a solution of Pd/C (1.90 g, 1.80 mmol, 10 wt %) in MeOH (20 mL) was added tert-butyl 1-[4-(hydroxymethyl)cyclohexen-1-yl]pyrazole-4-carboxylate (0.5 g, 1.8 mmol) under N₂. The suspension was degassed under vacuum and purged with H₂ several times. The mixture was stirred under H₂ (15 psi) at 20° C. for 10 h. On completion, the reaction was filtered to get the filtrate and concentrated to give the title compound (0.55 g) as colorless oil. LC-MS (ESI⁺) m/z 281.2 (M+H)⁺.

Step 4—1-(4-((2,2,2-trifluoroacetoxy)methyl)cyclohexyl)-1H-pyrazole-4-carboxylic acid. To a solution of tert-butyl 1-[4-(hydroxymethyl)cyclohexyl]pyrazole-4-carboxylate (0.55 g, 1.96 mmol) in DCM (10 mL) was added TFA (3.08 g, 27.01 mmol) at 0° C. under nitrogen atmosphere. Then the reaction was stirred at 20° C. for 4 h under nitrogen atmosphere. On completion, the reaction was poured into ice water (10 mL) and extracted with dichloromethane (2×15 mL). The combined organic phase is washed with brine (2×10 mL), and dried over sodium sulfate. Then the mixture was filtered and the filtrate was concentrated to give the title compound (0.6 g) as white solid. LC-MS (ESI⁺) m/z 321.0 (M+H)⁺.

(1R,3S)-3-(1-(tert-butyl)-5-(1-(4-(hydroxymethyl)cyclohexyl)-1H-pyrazole-4-carboxamido)-1H-pyrazol-3-yl)cyclopentyl isopropylcarbamate (Intermediate R)

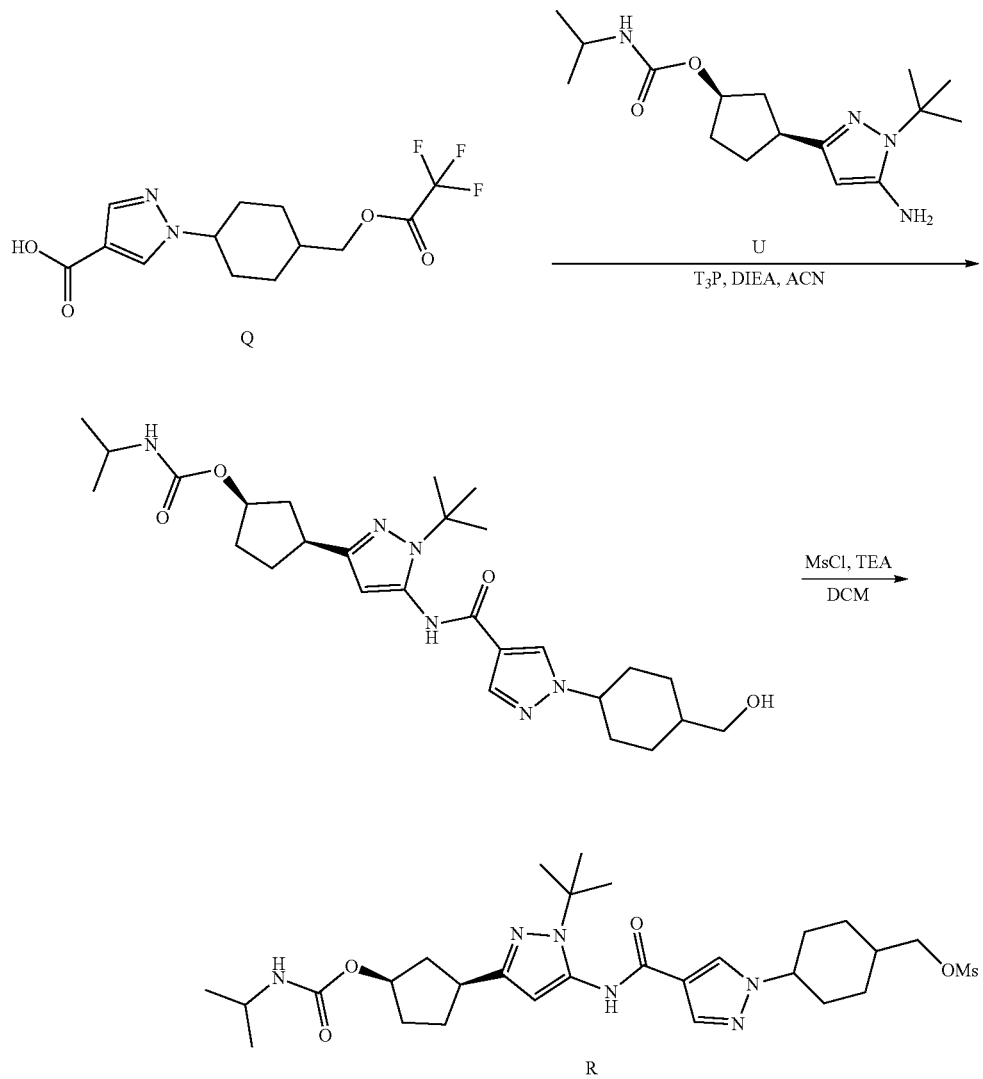

Step 1—(1R,3S)-3-(1-(tert-butyl)-5-(1-(4-(hydroxymethyl)cyclohexyl)-1H-pyrazole-4-carboxamido)-1H-pyrazol-3-yl)cyclopentyl isopropylcarbamate. To a solution of [(1R,3S)-3-(5-amino-1-tert-butyl-pyrazol-3-yl)cyclopentyl] N-isopropylcarbamate (288 mg, 936 umol, Intermediate U) and 1-[4-[(2,2,2-trifluoroacetyl)oxymethyl]cyclohexyl]pyrazole-4-carboxylic acid (300 mg, 936 umol, Intermediate Q) in ACN (6 mL) and was added T$_3$P (1.8 g, 2.8 mmol, 50% solution in DMF) and DIEA (605.3 mg, 4.6 mmol) at 0° C. under nitrogen flow. Then the reaction was stirred at 20° C. for 10 h under nitrogen atmosphere. On completion, the reaction was poured into ice water (10 mL), and extracted with ethyl acetate (2×15 mL). The combined organic phase was washed with brine (2×10 mL), dried over sodium sulfate, filtered and the filtrate was concentrated to give a residue. The residue was purified by prep-TLC (petroleum ether:ethyl acetate=0:1) to give the title compound (60 mg, 10% yield) as colorless oil. LC-MS (ESI$^+$) m/z 515.3 (M+H)$^+$.

Step 2—(1R,3S)-3-(1-(tert-butyl)-5-(1-(4-(hydroxymethyl)cyclohexyl)-1H-pyrazole-4-carboxamido)-1H-pyrazol-3-yl)cyclopentyl isopropylcarbamate. To a solution of [(1R,3S)-3-[1-tert-butyl-5-[[1-[4-(hydroxymethyl)cyclohexyl]pyrazole-4-carbonyl]amino]pyrazol-3-yl]cyclopentyl] N-isopropylcarbamate (60.0 mg, 116.5 umol) and TEA (35.4 mg, 349.7 umol) in DCM (0.6 mL) was added a solution of MsCl (110 mg, 960.27 umol) in DCM (0.6 mL) dropwise slowly at 0° C. under nitrogen flow. Then the reaction was stirred at 0° C. for 2 h under nitrogen atmosphere. On completion, the reaction was poured into saturated sodium bicarbonate aqueous solution (2 mL) at 0° C. and extracted with dichloromethane (2×3 mL). The combined organic phase was washed with brine (2×2 mL), and dried over sodium sulfate. The mixture was filtered and the filtrate was concentrated to give the title compound (60.0 mg) as colorless oil. LC-MS (ESI$^+$) m/z 593.3 (M+H)$^+$.

3-(3-methyl-4-((4-(methylamino)piperidin-1-yl)methyl)-2-oxo-2,3-dihydro-1H-benzo[d]imidazol-1-yl)piperidine-2,6-dione (Intermediate S)

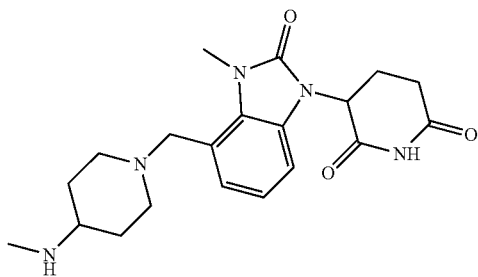 [SMILES: CNC1CCN(Cc2cccc3c2n(C)c(=O)n3C2CCC(=O)NC2=O)CC1]

This intermediate was synthesized as previously described in WO 2020/264499, WO 2020/264490, WO 2020/113233 and US 2019/192668.

2-[2-[2-(2-prop-2-ynoxyethoxy)ethoxy]ethyl]pyrazole-3-carboxylic acid (Intermediate T)

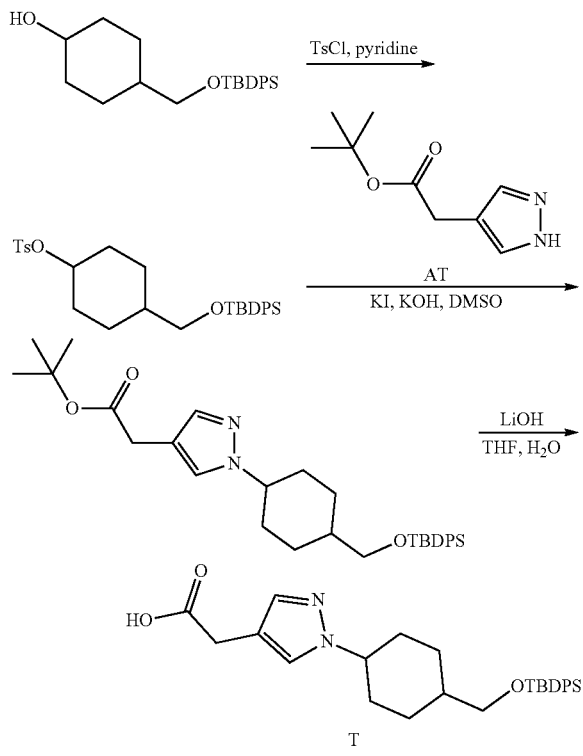

Step 1—[4-[[Tert-butyl(diphenyl)silyl]oxymethyl]cyclohexyl] 4-methylbenzenesulfonate. To a solution of 4-[[tert-butyl(diphenyl)silyl]oxymethyl]cyclohexanol (1 g, 2.71 mmol) and TosCl (517 mg, 2.71 mmol) was added pyridine (10 mL) at 0° C. The mixture was stirred at 0-20° C. for 12 h. The mixture was then stirred at 40° C. for 12 hr. On completion, the mixture was poured into ice water (10 mL) and extracted with ethyl acetate (2×10 mL). The combined organic phase is washed with brine (2×10 mL), and dried over sodium sulfate. Then the solution was filtered and the filtrate was concentrated to give a residue. The residue was purified by column chromatography (SiO$_2$, Petroleum ether/Ethyl acetate=1/0 to 8/1) to give the title compound (1 g, 70% yield) as a white solid. $^1$H NMR (400 MHz, DMSO-d$_6$) δ=7.78 (d, J=8.4 Hz, 2H), 7.59 (dd, J=1.6, 7.5 Hz, 4H), 7.49-7.40 (m, 8H), 4.70 (br s, 1H), 3.46 (d, J=5.8 Hz, 2H), 2.41 (s, 3H), 1.74-1.62 (m, 2H), 1.58-1.44 (m, 5H), 1.33-1.12 (m, 2H), 1.00-0.95 (m, 9H).

Step 2—Tert-butyl 2-[1-[4-[[tert-butyl(diphenyl)silyl]oxymethyl]cyclohexyl]pyrazol-4-yl]acetate. To a solution of tert-butyl 2-(1H-pyrazol-4-yl)acetate (300 mg, 1.65 mmol, Intermediate AT) and [4-[[tert-butyl(diphenyl)silyl]oxymethyl]cyclohexyl] 4-methylbenzenesulfonate (1.72 g, 3.29 mmol) in DMSO (17 mL) was added KI (27.3 mg, 164 umol) and KOH (277 mg, 4.94 mmol) at 20° C. The mixture was stirred at 50° C. for 0.5 h. On completion, the mixture was poured into ice water (5 mL) and extracted with ethyl acetate (2×20 mL). The combined organic phase is washed with brine (2×20 mL), and dried over sodium sulfate. The mixture was then filtered and the filtrate was concentrated to give a residue. The residue was purified by flash silica gel chromatography (ISCO®; 40 g SepaFlash® Silica Flash Column, Eluent of 0~10% Ethyl acetate/Petroleum ether gradient @ 80 mL/min) to give the title compound (180 mg, 20% yield) as a yellow oil. $^1$H NMR (400 MHz, DMSO-d$_6$) δ=7.65-7.57 (m, 5H), 7.49-7.42 (m, 6H), 7.29 (s, 1H), 5.64 (d, J=1.8 Hz, 6H), 4.42 (t, J=5.32 Hz, 3H), 3.70-3.46 (m, 2H), 3.36 (s, 2H), 1.80-1.51 (m, 17H), 1.45-1.38 (m, 9H), 1.03-0.99 (m, 9H).

Step 3—2-[2-[2-(2-prop-2-ynoxyethoxy)ethoxy]ethyl]pyrazole-3-carboxylic acid. To a solution of tert-butyl 2-[1-[4-[[tert-butyl(diphenyl)silyl]oxymethyl]cyclohexyl]pyrazol-4-yl]acetate (180 mg, 337 umol) in THF (1.5 mL) and H$_2$O (0.5 mL) was added LiOH·H$_2$O (70.8 mg, 1.69 mmol). The mixture was then stirred at 20° C. for 12 h. On completion, the mixture was poured into ice water (3 mL) and extracted with ethyl acetate (2×3 mL). The combined organic phase was washed with brine (2×3 mL), dried over sodium sulfate, filtered and the filtrate was concentrated to give a residue. The residue was purified by flash silica gel chromatography (ISCO®; 4 g SepaFlash® Silica Flash Column, Eluent of 0~25% Ethyl acetate/Petroleum ether gradient @ 50 mL/min) to give the title compound (50 mg, 31% yield) as yellow oil. $^1$H NMR (400 MHz, DMSO-d$_6$) δ=12.30-12.09 (m, 1H), 7.65-7.59 (m, 4H), 7.58-7.54 (m, 1H), 7.50-7.40 (m, 6H), 7.29 (s, 1H), 3.63-3.46 (m, 2H), 3.37 (s, 2H), 2.05-1.97 (m, 3H), 1.87 (br d, J=12.0 Hz, 1H), 1.78-1.64 (m, 3H), 1.62-1.53 (m, 2H), 1.20-1.15 (m, 2H), 1.05-0.95 (m, 9H).

(1R,3S)-3-(5-amino-1-(tert-butyl)-1H-pyrazol-3-yl)cyclopentyl isopropylcarbamate (Intermediate U)

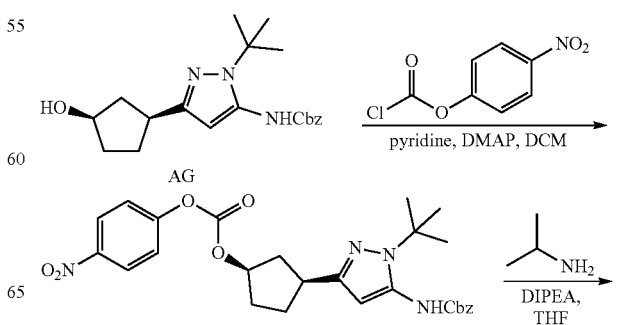

-continued

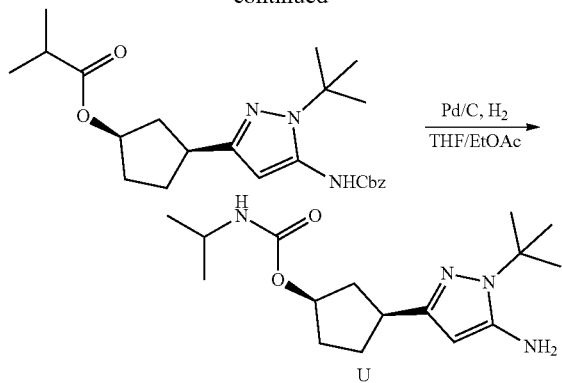

Step 1—Benzyl (1-(tert-butyl)-3-((1S,3R)-3-(((4-nitrophenoxy)carbonyl)oxy)cyclopentyl)-1H-pyrazol-5-yl)carbamate. A solution of benzyl (1-(tert-butyl)-3-((1S,3R)-3-hydroxycyclopentyl)-1H-pyrazol-5-yl)carbamate (300 mg, 839 umol, Intermediate AG) and (4-nitrophenyl) carbonochloridate (254 mg, 1.26 mmol) in anhydrous DCM (5 mL) was treated with pyridine (199 mg, 2.52 mmol, 203 uL) and DMAP (10.3 mg, 83.9 umol) and the reaction mixture was stirred at 20° C. for 16 hr. On completion, the reaction mixture was concentrated in vacuo to give residue. The residue was purified by flash silica gel chromatography (12 g SepaFlash® Silica Flash Column, Ethyl acetate/Petroleum: 0~30%) to give the title compound (223 mg, 50% yield) as yellow oil. LC-MS (ESI+) m/z 523.1 (M+H)+, 1H NMR (400 MHz, CDCl3) δ=8.31-8.24 (m, 2H), 7.42-7.34 (m, 7H), 6.32-6.21 (m, 1H), 6.16 (s, 1H), 5.30-5.23 (m, 1H), 5.21 (s, 2H), 3.22-3.09 (m, 1H), 2.68-2.57 (m, 1H), 2.19-2.09 (m, 1H), 2.09-2.06 (m, 1H), 2.04-1.95 (m, 3H), 1.94-1.86 (m, 1H), 1.60 (s, 9H).

Step 2—(1R,3S)-3-(5-(((benzyloxy)carbonyl)amino)-1-(tert-butyl)-1H-pyrazol-3-yl)cyclopentyl isobutyrate. A solution of [(1R,3S)-3-[5-(benzyloxycarbonylamino)-1-tert-butyl-pyrazol-3-yl]cyclopentyl] (4-nitrophenyl) carbonate (220 mg, 421 umol), propan-2-amine (32.4 mg, 547 umol, 47.0 uL) and DIPEA (272 mg, 2.11 mmol, 367 uL) in THF (3 mL) was stirred at 20° C. for 4 hours. On completion, the reaction mixture was diluted with EA (40 mL) and stirred for 5 min. The organic phase was washed with aq. NaOH (25 mL×4, 1M), brine (30 mL), dried with anhydrous Na2SO4, filtered and concentrated in vacuo to give the title compound (150 mg) as colorless oil. 1H NMR (400 MHz, CDCl3) δ=7.38 (in, 5H), 6.38-5.99 (m, 2H), 5.21-5.19 (m, 2H), 5.15 (m, 1H), 4.55 (br s, 1H), 3.89-3.65 (m, 1H), 3.14-3.00 (m, 1H), 2.51-2.39 (m, 1H), 2.04-1.99 (m, 1H), 1.97-1.75 (m, 5H), 1.58 (s, 9H), 1.20-1.07 (m, 6H).

Step 3—(1R,3S)-3-(5-amino-1-(tert-butyl)-1H-pyrazol-3-yl)cyclopentyl isopropylcarbamate. To a solution of (1R,3S)-3-(5-(((benzyloxy)carbonyl)amino)-1-(tert-butyl)-1H-pyrazol-3-yl)cyclopentyl isobutyrate (150 mg, 339 umol) in THF (2 mL) and EtOAc (4 mL) was added Pd/C (20 mg, 10 wt %) under N2. The suspension was degassed under vacuum and purged with H2 several times. The mixture was stirred under hydrogen balloon (15 psi) at 20° C. for 4 hours. On completion, the reaction mixture was filtered and the filtrate was concentrated in vacuo to give a residue. The residue was purified by flash silica gel chromatography (4 g SepaFlash® Silica Flash Column, Ethyl acetate/Petroleum: 0~40%) to give the title compound (75 mg, 236 umol, 70% yield) as yellow oil. LC-MS (ESI+) m/z 309.1 (M+H)+.

[4-[4-[2-[[2-tert-butyl-5-[(1S,3R)-3-(isopropylcarbamoyloxy)cyclopentyl]pyrazol-3-yl]amino]-2-oxoethyl]pyrazol-1-yl]cyclohexyl]methyl methanesulfonate (Intermediate V)

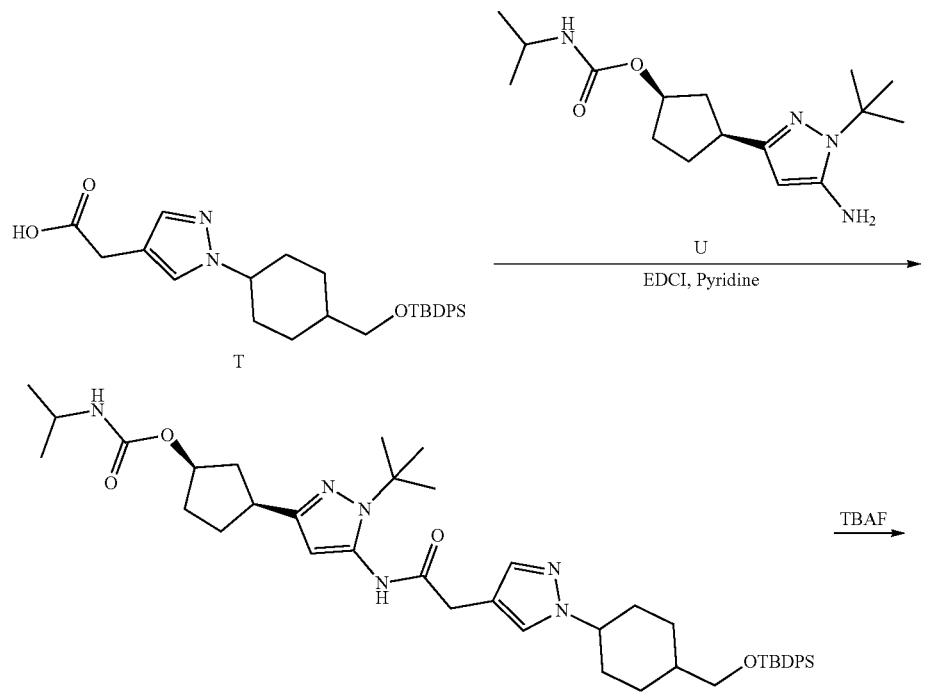

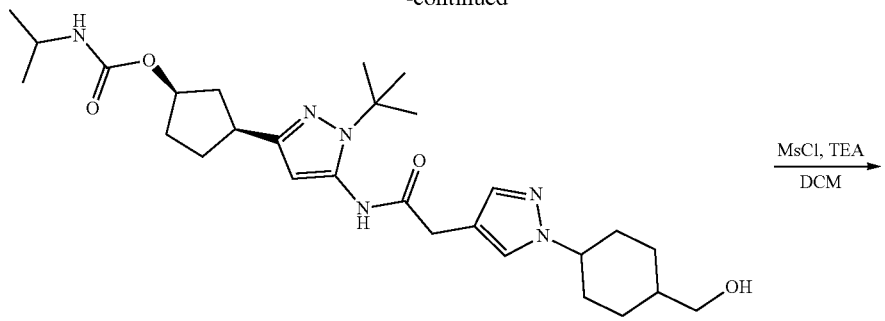

MsCl, TEA
―――→
DCM

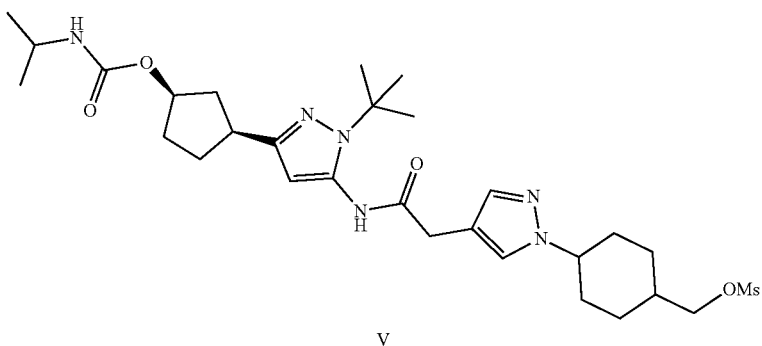

V

Step 1—[(1R,3S)-3-[1-tert-butyl-5-[[2-[2-[2-(2-prop-2-ynoxyethoxy)ethoxy]ethyl]pyrazole-3-carbonyl]amino]pyrazol-3-yl]cyclopentyl] N-isopropylcarbamate. To a solution of [(1R,3S)-3-(5-amino-1-tert-butyl-pyrazol-3-yl)cyclopentyl] N-isopropylcarbamate (64.7 mg, 209 umol, Intermediate U) and 2-[1-[4-[[tert-butyl(diphenyl)silyl]oxymethyl]cyclohexyl]pyrazol-4-yl]acetic acid (100 mg, 209 umol, Intermediate T) in pyridine (1 mL) was added EDCI (120 mg, 629 umol) and DMAP (2.56 mg, 20.9 umol) at 20° C. The mixture was stirred at 50° C. for 12 h. On completion, the reaction was poured into ice water (2 mL) and extracted with ethyl acetate (2×2 mL). The combined organic phase was washed with brine (2×2 mL), dried over sodium sulfate, then filtered and concentrated to give a residue. The residue was purified by prep-TLC (SiO$_2$, EA:PE=4:1) to give the title compound (100 mg, 62% yield) as yellow oil. $^1$H NMR (400 MHz, DMSO-d$_6$) δ=9.41 (s, 1H), 7.63-7.60 (m, 5H), 7.47-7.44 (m, 5H), 7.33 (s, 1H), 6.91 (br d, J=8.0 Hz, 1H), 5.89 (s, 1H), 5.01-4.91 (m, 1H), 4.13-3.98 (m, 3H), 3.55-3.47 (m, 2H), 3.44-3.41 (m, 2H), 3.17 (d, J=5.12 Hz, 1H), 2.34-2.32 (m, 1H), 1.95-1.77 (m, 6H), 1.73-1.57 (m, 8H), 1.26-1.14 (m, 6H), 1.04-1.00 (m, 18H).

Step 2—[(1R,3S)-3-[1-tert-butyl-5-[[2-[1-[4-(hydroxymethyl)cyclohexyl]pyrazol-4-yl]acetyl]amino]pyrazol-3-yl]cyclopentyl] N-isopropylcarbamate. To a solution of [(1R,3S)-3-[1-tert-butyl-5-[[2-[1-[4-[[tert-butyl(diphenyl)silyl]oxymethyl]cyclohexyl]pyrazol-4-yl]acetyl]amino]pyrazol-3-yl]cyclopentyl] N-isopropylcarbamate (100 mg, 130 umol) was added TBAF (1 mL, 1M in THF). The mixture was stirred at 20° C. for 1 h. On completion, the mixture was concentrated to give a residue. The residue was purified by prep-TLC (SiO$_2$, EA:PE=8:1) to give the title compound (47 mg, 51% yield) as yellow oil. LC-MS (ESI$^+$) m/z 529.3 (M+H)$^+$.

Step 3—[4-[4-[2-[[2-tert-butyl-5-[(1S,3R)-3-(isopropylcarbamoyloxy)cyclopentyl]pyrazol-3-yl]amino]-2-oxoethyl]pyrazol-1-yl]cyclohexyl]methyl methanesulfonate. To a solution of [(1R,3S)-3-[1-tert-butyl-5-[[2-[1-[4-(hydroxymethyl)cyclohexyl]pyrazol-4-yl]acetyl]amino]pyrazol-3-yl]cyclopentyl]N-isopropylcarbamate (35 mg, 66.2 umol) and TEA (13.4 mg, 132 umol) in DCM (0.5 mL) was added MsCl (9.10 mg, 79.4 umol) dropwise slowly at 0° C. and the mixture was stirred at 0° C. for 1 h. On completion, the reaction mixture was quenched with NaHCO$_3$ (sat aq, 1 mL) at 0° C. and extracted with DCM (2×2 mL). The combined organic phase was washed with brine (2×2 mL), dried over sodium sulfate. Then the solution was filtered and the filtrate was concentrated to give the title compound (30 mg) as yellow oil. LC-MS (ESI$^+$) m/z 607.2 (M+H)$^+$.

2-[2-(2-prop-2-ynoxyethoxy)ethyl]pyrazole-3-carboxylic acid (Intermediate W)

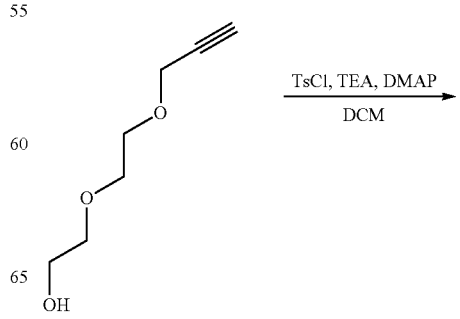

TsCl, TEA, DMAP
―――――→
DCM

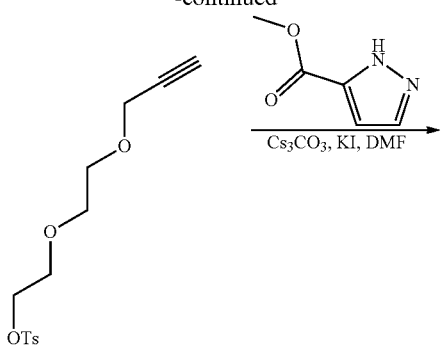

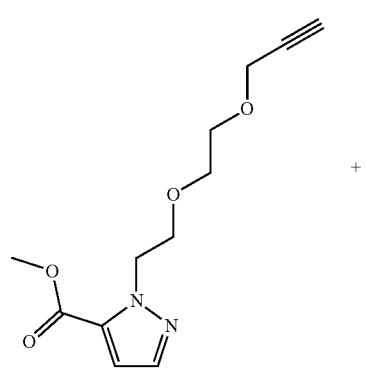

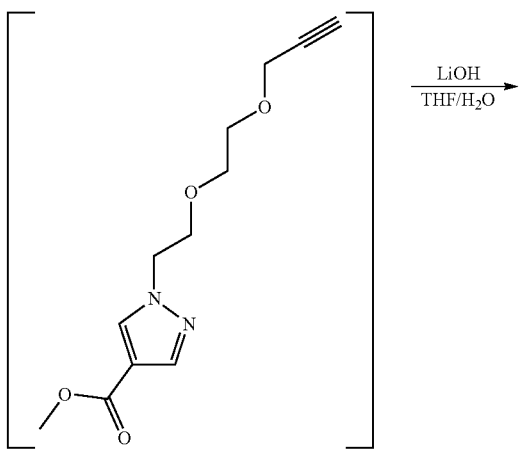

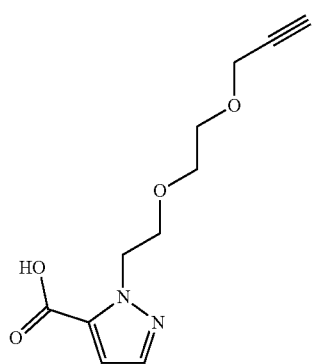

W

Step 1—2-(2-Prop-2-ynoxyethoxy)ethyl 4-methylbenzenesulfonate. To a solution of 2-(2-prop-2-ynoxyethoxy)ethanol (6 g, 41.6 mmol, CAS #7218-43-1) and 4-methylbenzenesulfonyl chloride (15.9 g, 83.2 mmol) in DCM (120 mL) was added TEA (21.1 g, 208 mmol) and DMAP (508 mg, 4.16 mmol). Then the mixture was stirred at 20° C. for 12 h. On completion, the reaction mixture was quenched with $H_2O$ (120 mL) at 25° C., then extracted with EtOAc (120 mL×3). The combined organic layers were washed with EtOAc (120 mL×3), dried over $Na_2SO_4$, filtered and concentrated under reduced pressure to give a residue. The residue was purified by column chromatography ($SiO_2$, Petroleum ether/Ethyl acetate=10/1 to 2/1) to give the title compound (10.9 g, 30.3 mmol, 73% yield) as a orange oil. LCMS: tR=0.546 min., (ES+) m/z $(M+H)^+$=254.3.

Step 2—Methyl 1-(2-(2-(prop-2-yn-1-yloxy)ethoxy)ethyl)-1H-pyrazole-5-carboxylate and methyl 1-(2-(2-(prop-2-yn-1-yloxy)ethoxy)ethyl)-1H-pyrazole-3-carboxylate. To a solution of 2-(2-prop-2-ynoxyethoxy)ethyl 4-methylbenzenesulfonate (5.5 g, 18.4 mmol) and methyl 1H-pyrazole-5-carboxylate (2.79 g, 22.1 mmol) in DMF (55 mL) was added $Cs_2CO_3$ (12.0 g, 36.8 mmol) and KI (306 mg, 1.84 mmol). The mixture was stirred at 70° C. for 1 h. On completion, the reaction mixture was quenched with $H_2O$ (60 mL) at 25° C., then extracted with EtOAc (60 mL×3). The combined organic layers were washed with EtOAc (60 mL×3), dried over $Na_2SO_4$, filtered and concentrated under reduced pressure to give a residue. The residue was purified by prep-HPLC (column: YMC Triart C18 250×50 mm×7 um; mobile phase: [water (10 mM $NH_4HCO_3$)-ACN]; B %: 16%-46%, 17 min) to give methyl 1-(2-(2-(prop-2-yn-1-yloxy)ethoxy)ethyl)-1H-pyrazole-5-carboxylate (1 g, 22% yield) as a orange solid ($^1$H NMR (400 MHz, DMSO-d6) δ=7.58 (d, J=2.0 Hz, 1H), 6.87 (d, J=2.0 Hz, 1H), 4.66 (t, J=5.6 Hz, 2H), 4.07 (d, J=2.4 Hz, 2H), 3.82 (s, 3H), 3.73 (t, J=5.6 Hz, 2H), 3.47 (s, 4H), 3.40 (t, J=2.4 Hz, 1H) and methyl 1-(2-(2-(prop-2-yn-1-yloxy)ethoxy)ethyl)-1H-pyrazole-3-carboxylate (1 g, 3.96 mmol, 22% yield) as an orange solid ($^1$H NMR (400 MHz, DMSO-d6) δ=7.85 (d, J=2.4 Hz, 1H), 6.74 (d, J=2.4 Hz, 1H), 4.35 (t, J=5.4 Hz, 2H), 4.10 (d, J=2.4 Hz, 2H), 3.83-3.76 (m, 5H), 3.56-3.49 (m, 4H), 3.41 (t, J=2.4 Hz, 1H).

Step 3—2-[2-(2-prop-2-ynoxyethoxy)ethyl]pyrazole-3-carboxylic acid. To a solution of methyl 2-[2-(2-prop-2-ynoxyethoxy)ethyl]pyrazole-3-carboxylate (1 g, 3.96 mmol) in THF (10 mL) and $H_2O$ (2 mL) was added LiOH·$H_2O$ (665 mg, 15.8 mmol). The mixture was stirred at 20° C. for 2 h. On completion, the reaction mixture was quenched with $H_2O$ (12 mL) at 25° C. and adjusted to pH less than 5 with HCl (1 M), then the solution was extracted with EtOAc (15 mL×3). The combined organic layer was washed with brine (15 mL×3), dried over $Na_2SO_4$, filtered and concentrated under reduced pressure to give the title compound (850 mg, 77% yield) as a white solid. LCMS: tR=0.337 min., (ES+) m/z $(M+H)^+$=239.0.

[(1R,3S)-3-[1-tert-butyl-5-[[2-[2-(2-prop-2-ynoxy-ethoxy)ethyl]pyrazole-3-carbonyl]amino]pyrazol-3-yl]cyclopentyl] N-isopropylcarbamate (Intermediate X)

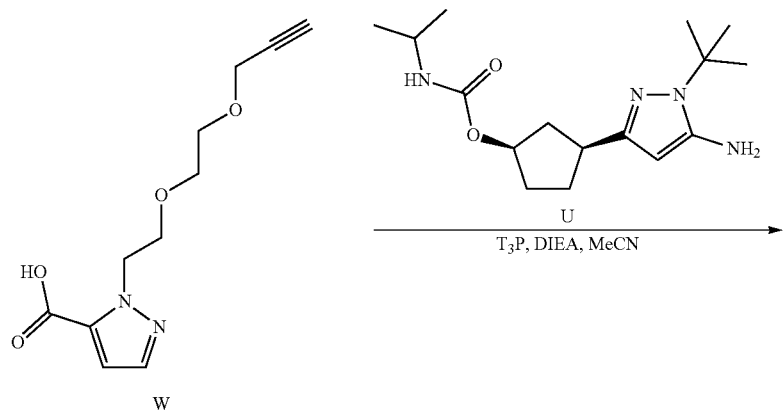

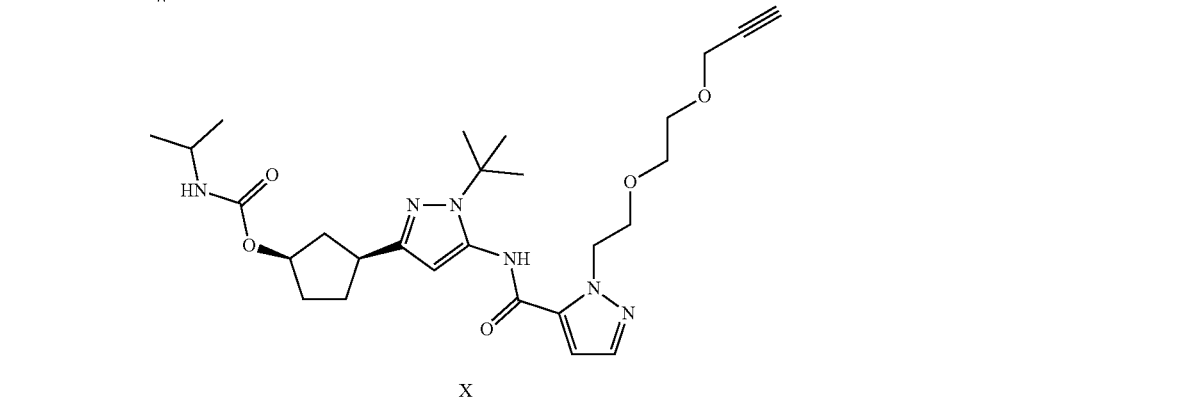

To a solution of 2-[2-(2-prop-2-ynoxyethoxy)ethyl]pyrazole-3-carboxylic acid (840 mg, 3.53 mmol, Intermediate W) and [(1R,3S)-3-(5-amino-1-tert-butyl-pyrazol-3-yl)cyclopentyl] N-isopropylcarbamate (1.20 g, 3.88 mmol, Intermediate U) in MeCN (10 mL) was added T$_3$P (6.73 g, 50% solution in DMF) and DIEA (2.28 g, 17.6 mmol). The mixture was stirred at 80° C. for 12 h. On completion, the reaction mixture was quenched with H$_2$O (10 mL) at 25° C., then extracted with EtOAc (10 mL×3). The combined organic layers was washed with brine (10 mL×3), dried over Na$_2$SO$_4$, filtered and concentrated under reduced pressure to give a residue. The residue was purified by column chromatography (SiO$_2$, Petroleum ether/Ethyl acetate=3/1 to 1/1) to give the title compound (1 g, 53% yield) was obtained as a orange solid. LCMS: tR=0.652 min., (ES+) m/z (M+H)$^+$=529.2.

1-undec-10-ynylpyrazole-4-carboxylic acid (Intermediate Y)

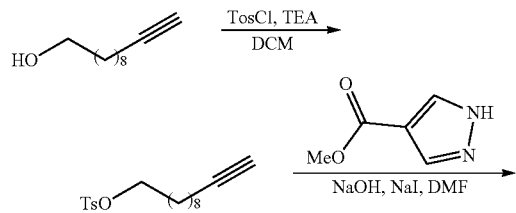

-continued

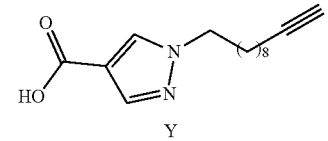

Step 1—Undec-10-ynyl 4-methylbenzenesulfonate. To a solution of undec-10-yn-1-ol (2 g, 11.89 mmol) and TosCl (2.72 g, 14.3 mmol) in DCM (20 mL) was added TEA (3.61 g, 35.7 mmol) at 0° C. Then the mixture was stirred at 20° C. for 12 h. On completion, the mixture was poured into ice water (30 mL) and extracted with ethyl acetate (2×30 mL). The combined organic phase was washed with brine (2×30 mL), dried over sodium sulfate, filtered, then the filtrate was concentrated to give a residue. The residue was purified by flash silica gel chromatography (ISCO®; 40 g SepaFlash® Silica Flash Column, Eluent of 0~5% Ethyl acetate/Petroleum ether gradient @ 100 mL/min) to give the title compound (3.27 g, 85% yield) as a white solid. $^1$H NMR (400 MHz, DMSO-d$_6$) δ=7.78 (d, J=8.4 Hz, 2H), 7.47 (d, J=8.0 Hz, 2H), 4.00 (t, J=6.4 Hz, 2H), 2.71 (t, J=2.6 Hz, 1H), 2.42 (s, 3H), 2.12 (dt, J=2.4, 6.8 Hz, 2H), 1.57-1.49 (m, 2H), 1.45-1.36 (m, 2H), 1.33-1.25 (m, 2H), 1.16 (br d, J=4.4 Hz, 8H).

Step 2—1-Undec-10-ynylpyrazole-4-carboxylic acid. To a solution of undec-10-ynyl 4-methylbenzenesulfonate (3 g, 9.30 mmol) and methyl 1H-pyrazole-4-carboxylate (1.41 g, 11.2 mmol) in DMF (30 mL) was added NaOH (1.12 g, 27.9 mmol) and NaI (139 mg, 930 umol). The mixture was then stirred at 50° C. for 2 h. On completion, the mixture was poured into ice water (30 mL) and extracted with ethyl acetate (2×30 mL). Then the mixture was adjusted to pH=6 with saturated ammonium chloride aqueous solution. The mixture was extracted with ethyl acetate (2×30 mL). The combined organic phase is washed with brine (2×30 mL), dried over sodium sulfate, filtered and the filtrate was concentrated to give a residue. The residue was purified by flash silica gel chromatography (ISCO®; 40 g SepaFlash® Silica Flash Column, Eluent of 0~30% Ethyl acetate/Petroleum ether gradient @ 80 mL/min) to give the title compound (1.6 g, 65% yield) as a white solid. $^1$H NMR (400 MHz, DMSO-d$_6$) δ=12.39-12.11 (m, 1H), 8.24 (s, 1H), 7.78 (s, 1H), 4.11 (t, J=6.8 Hz, 2H), 3.74 (s, 1H), 2.13 (dt, J=2.4, 6.8 Hz, 2H), 1.80-1.70 (m, 2H), 1.47-1.37 (m, 2H), 1.34-1.14 (m, 10H).

[(1R,3S)-3-[1-tert-butyl-5-[(1-undec-10-ynylpyrazole-4-carbonyl)amino]pyrazol-3-yl]cyclopentyl] N-isopropylcarbamate (Intermediate Z)

1-(non-8-yn-1-yl)-1H-pyrazole-5-carboxylic acid (Intermediate AA)

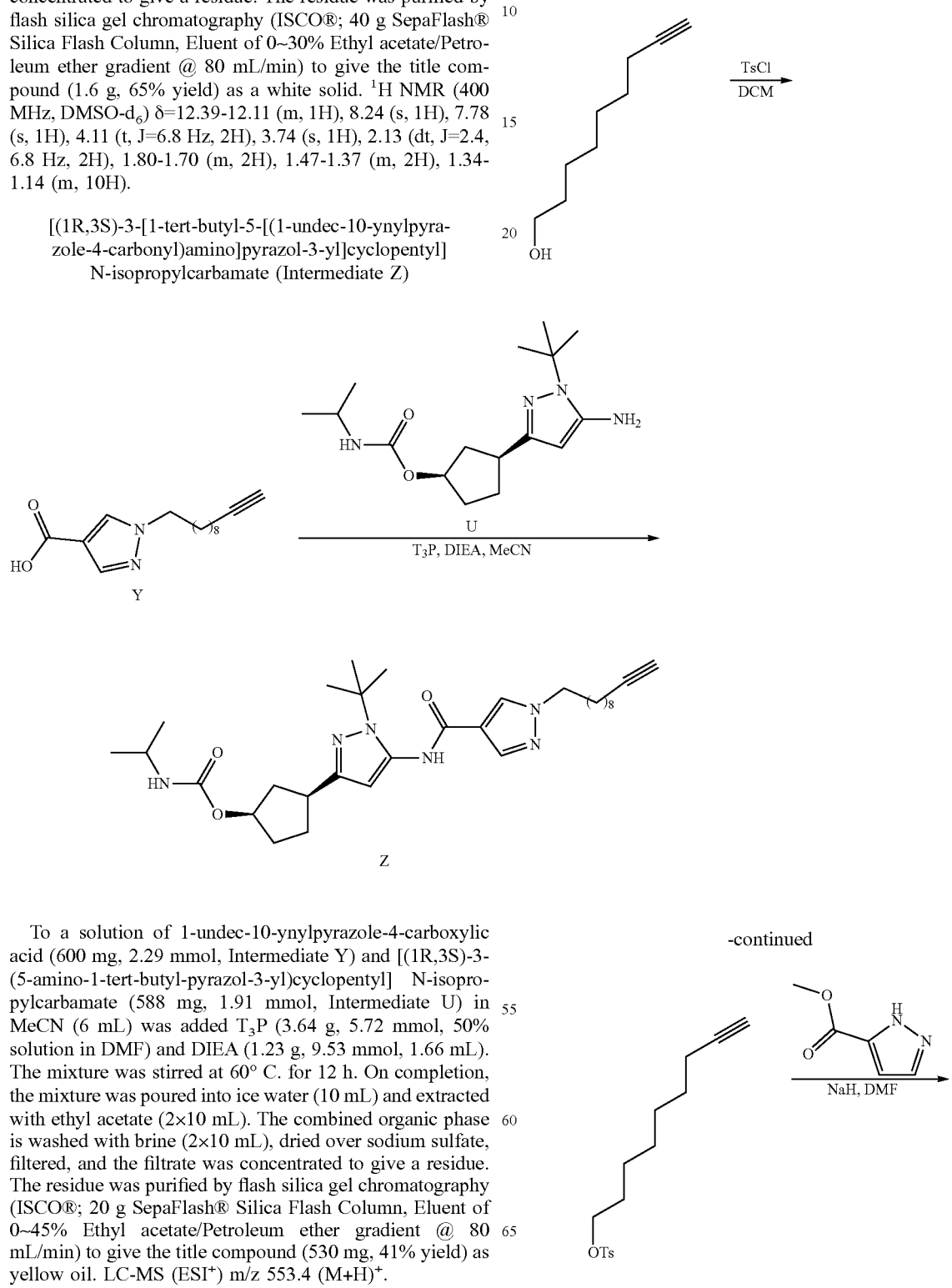

To a solution of 1-undec-10-ynylpyrazole-4-carboxylic acid (600 mg, 2.29 mmol, Intermediate Y) and [(1R,3S)-3-(5-amino-1-tert-butyl-pyrazol-3-yl)cyclopentyl] N-isopropylcarbamate (588 mg, 1.91 mmol, Intermediate U) in MeCN (6 mL) was added T$_3$P (3.64 g, 5.72 mmol, 50% solution in DMF) and DIEA (1.23 g, 9.53 mmol, 1.66 mL). The mixture was stirred at 60° C. for 12 h. On completion, the mixture was poured into ice water (10 mL) and extracted with ethyl acetate (2×10 mL). The combined organic phase is washed with brine (2×10 mL), dried over sodium sulfate, filtered, and the filtrate was concentrated to give a residue. The residue was purified by flash silica gel chromatography (ISCO®; 20 g SepaFlash® Silica Flash Column, Eluent of 0~45% Ethyl acetate/Petroleum ether gradient @ 80 mL/min) to give the title compound (530 mg, 41% yield) as yellow oil. LC-MS (ESI$^+$) m/z 553.4 (M+H)$^+$.

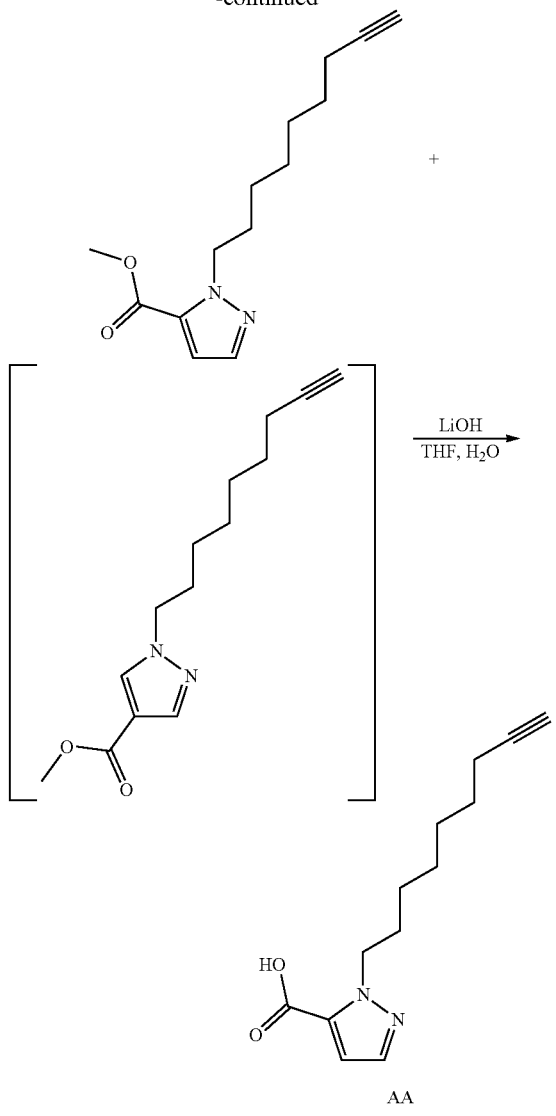

Step 1—non-8-yn-1-yl 4-methylbenzenesulfonate. To a solution of non-8-yn-1-ol (5 g, 35.6 mmol, CAS #10160-28-8) and 4-methylbenzenesulfonyl chloride (8.16 g, 42.7 mmol) in DCM (60 mL) was added TEA (10.8 g, 106 mmol) at 0° C. Then the mixture was stirred at 0-20° C. for 12 h. On completion, the mixture was quenched with sat. NaHCO₃ (80 mL), and diluted with DCM (60 mL). The organic layer was washed with H₂O (60×3 mL) and brine (60×3 mL), then dried with Na₂SO₄, and concentrated in vacuo. The residue was purified by column chromatography (SiO₂, Petroleum ether/Ethyl acetate=15/1 to 10/1) to give the title compound (6.8 g, 62% yield) as colorless oil. ¹H NMR (400 MHz, CDCl₃) δ=7.77 (d, J=8.4 Hz, 2H), 7.33 (d, J=8.2 Hz, 2H), 4.00 (t, J=6.4 Hz, 2H), 2.43 (s, 3H), 2.13 (dt, J=2.4, 7.2 Hz, 2H), 1.92 (t, J=2.4 Hz, 1H), 1.66-1.58 (m, 2H), 1.51-1.40 (m, 2H), 1.36-1.19 (m, 6H).

Step 2—methyl 2-(non-8-yn-1-yl)-1H-pyrazole-5-carboxylate. Sodium hydride (978 mg, 28.5 mmol, 60% dispersion in mineral oil) was added to a solution of methyl 1H-pyrazole-5-carboxylate (1.29 g, 10.1 mmol) in DMF (40 mL) portionwise at 0° C., then the mixture was stirred at 0° C. for 0.5 h. Next, a solution of non-8-ynyl 4-methylbenzenesulfonate (3 g, 10.19 mmol) was added dropwise. The resulting mixture was stirred at 0-20° C. for 12 h. The mixture was quenched with sat. NH₄Cl (40 mL), then extracted with EtOAc (30 mL×3). The combined organic layer was washed with brine (40 mL×3), dried by Na₂SO₄, and concentrated in vacuo. The residue was purified by prep-HPLC (FA condition, column: Phenomenex luna C18 250*50 mm*15 um; mobile phase: [water (0.225% FA)-ACN]; B %: 39%-69%, 25 min) to give the title compound (0.5 g, 19% yield) as colorless oil (¹H NMR (400 MHz, CDCl₃) δ=7.48 (d, J=2.0 Hz, 1H), 6.83 (d, J=2.0 Hz, 1H), 4.62-4.52 (m, 2H), 3.89 (s, 3H), 2.18 (dt, J=2.4, 7.2 Hz, 2H), 1.94 (t, J=2.4 Hz, 1H), 1.84 (quin, J=7.2 Hz, 2H), 1.57-1.48 (m, 2H), 1.43-1.29 (m, 7H)) and methyl 1-non-8-ynylpyrazole-3-carboxylate (1.3 g, 50% yield) as brown oil (¹H NMR (400 MHz, CHLOROFORM-d) δ=7.40 (d, J=2.4 Hz, 1H), 6.82 (d, J=2.4 Hz, 1H), 4.19 (t, J=7.2 Hz, 2H), 3.93 (s, 3H), 2.17 (dt, J=2.4, 7.2 Hz, 2H), 1.96-1.85 (m, 3H), 1.56-1.46 (m, 2H), 1.42-1.29 (m, 6H)).

Step 3—1-(non-8-yn-1-yl)-1H-pyrazole-5-carboxylic acid. To a solution of methyl 2-(non-8-yn-1-yl)-1H-pyrazole-5-carboxylate (0.5 g, 2.01 mmol) in THF (4 mL) was added a solution of LiOH·H₂O (337 mg, 8.05 mmol) in H₂O (1 mL). The mixture was stirred at 25° C. for 12 h. On completion, the solution was diluted with water (10 mL), and extracted with EtOAc (15 mL). The water phase was adjusted to pH<4 by HCl (1 M), then extracted with EtOAc (15 mL×2). The combined organic layer was washed with brine (30 mL×3), dried with Na₂SO₄, and concentrated in vacuo. The residue was purified by column chromatography (SiO₂, Petroleum ether/Ethyl acetate=10/1 to 1/1) to give the title compound (0.33 g, 63% yield) as a white solid. ¹H NMR (400 MHz, CDCl₃) δ=7.54 (s, 1H), 6.98 (s, 1H), 4.59 (t, J=7.2 Hz, 2H), 2.18 (dt, J=2.4, 7.2 Hz, 2H), 1.96-1.82 (m, 4H), 1.52 (td, J=7.2, 14.4 Hz, 3H), 1.45-1.31 (m, 8H).

(1R,3S)-3-(1-(tert-butyl)-5-(1-(non-8-yn-1-yl)-1H-pyrazole-5-carboxamido)-1H-pyrazol-3-yl)cyclopentyl isopropylcarbamate (Intermediate AB)

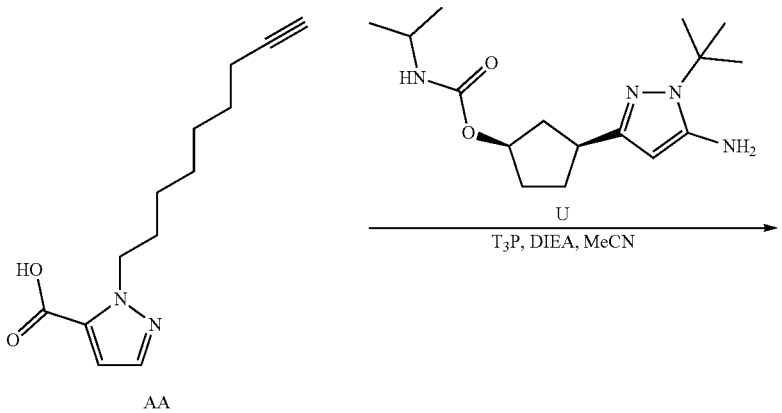

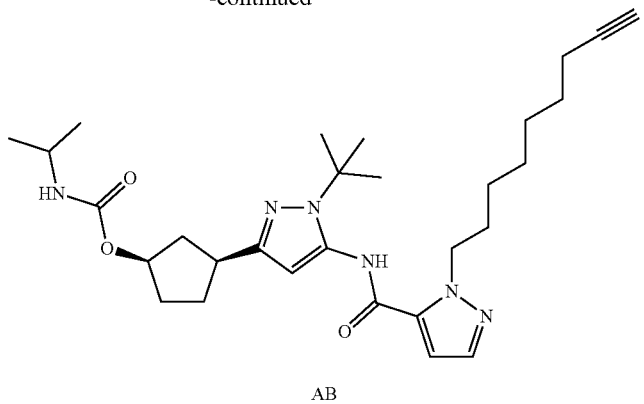

AB

A solution of 1-(non-8-yn-1-yl)-1H-pyrazole-5-carboxylic acid (0.3 g, 1.28 mmol, Intermediate AA), [(1R,3S)-3-(5-amino-1-tert-butyl-pyrazol-3-yl)cyclopentyl] N-isopropylcarbamate (434 mg, 1.41 mmol, Intermediate U), T$_3$P (2.44 g, 3.84 mmol, 50% solution in DMF) and DIEA (330 mg, 2.56 mmol) in MeCN (4 mL) was stirred at 80° C. for 12 h. On completion, the mixture was diluted with EtOAc (10 mL) and quenched with sat. NH$_4$Cl (10 mL). The mixture was extracted with EtOAc (20 mL×3) and the organic layer was washed with brine (20 mL×3), dried by Na$_2$SO$_4$, and concentrated in vacuo. The residue was purified by column chromatography (SiO$_2$, Petroleum ether/Ethyl acetate=5/1 to 1/1) to give the title compound (0.3 g, 36% yield) as a brown solid. $^1$H NMR (400 MHz, CDCl$_3$) δ=7.55 (d, J=2.0 Hz, 1H), 7.47 (br s, 1H), 6.61 (br s, 1H), 6.30 (s, 1H), 5.16 (br s, 1H), 4.60 (t, J=7.3 Hz, 2H), 3.87-3.77 (m, 1H), 3.17-3.05 (m, 1H), 2.53-2.42 (m, 1H), 2.17 (dt, J=2.4, 7.2 Hz, 2H), 2.07-2.04 (m, 1H), 1.94-1.84 (m, 6H), 1.65 (s, 9H), 1.53-1.48 (m, 2H), 1.44-1.30 (m, 7H), 1.27 (t, J=7.2 Hz, 1H), 1.15 (dd, J=2.4, 6.4 Hz, 6H).

1-(dodec-11-yn-1-yl)-1H-pyrazole-3-carboxylic acid (Intermediate AC)

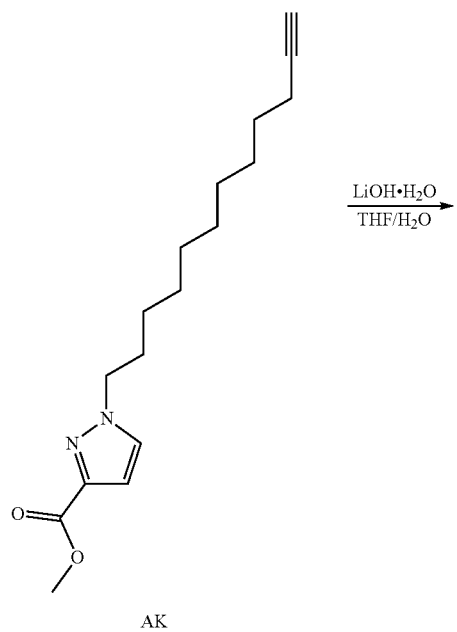

AK

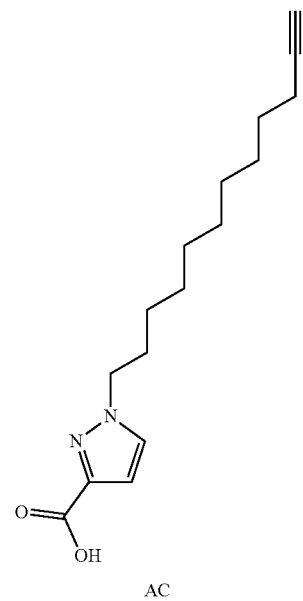

AC

To a solution of methyl 1-dodec-11-ynylpyrazole-3-carboxylate (1.1 g, 3.79 mmol, Intermediate AK) and LiOH·H$_2$O (635 mg, 15.1 mmol) in THF (12 mL) and H$_2$O (3 mL), then the mixture was stirred at 20° C. for 12 hr. On completion, the reaction mixture was quenched with H$_2$O 20 mL at 20° C., and then diluted with EtOAc 10 mL and extracted with EtOAc mL (20 mL×3). Then the aqueous phase was adjusted to pH=3-4, and then extracted with EtOAc mL (20 mL×3). The organic layers were washed with brine (20 mL×2), dried over Na$_2$SO$_4$, filtered and concentrated under reduced pressure to give the title compound (1 g) as yellow solid. This product was used to next step without further purification. LC-MS (ESI$^+$) m/z 567.7 (M+H)$^+$.

[(1R,3S)-3-[1-tert-butyl-5-[(1-dodec-11-ynylpyrazole-3-carbonyl)amino]pyrazol-3-yl]cyclopentyl] N-isopropylcarbamate (Intermediate AD)

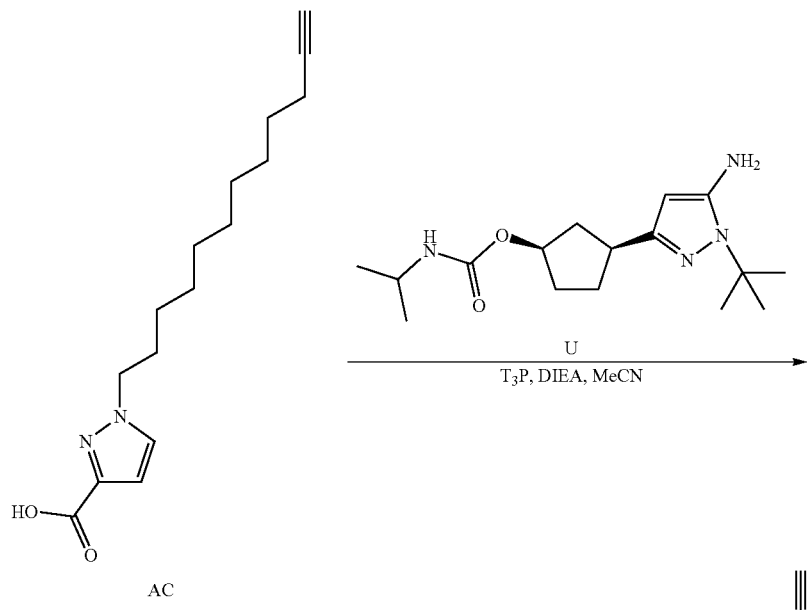

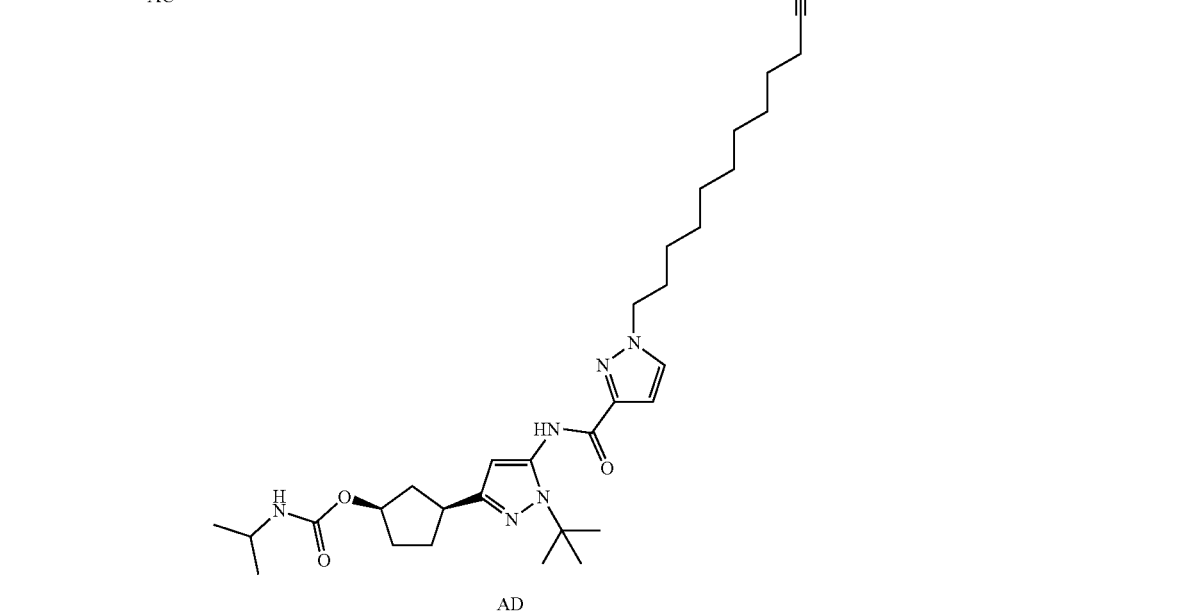

To a solution of 1-dodec-11-ynylpyrazole-3-carboxylic acid (200 mg, 723 umol, Intermediate AC) and (1R,3S)-3-(5-amino-1-tert-butyl-pyrazol-3-yl)cyclopentyl] N-isopropylcarbamate (267 mg, 868 umol, Intermediate U) in MeCN (2 mL) was added T$_3$P (1.38 g, 2.17 mmol, 50% solution in DMF) and DIEA (467.64 mg, 3.62 mmol). The mixture was stirred at 80° C. for 12 h. On completion, the reaction mixture was quenched with H$_2$O (3 mL) at 25° C., and then diluted with EtOAc (5 mL) and extracted with EtOAc (5 mL×3). The combined organic layers were washed with sat. NaCl (5 mL×3), dried over Na$_2$SO$_4$, filtered and concentrated under reduced pressure to give a residue. The residue was purified by column chromatography (SiO$_2$, Petroleum ether/Ethyl acetate=3/1 to 1/1) to give the title compound (250 mg, 61% yield) as a orange solid. LCMS: tR=0.840 min., (ES+) m/z (M+H)$^+$=568.1.

1-(2-(2-(prop-2-yn-1-yloxy)ethoxy)ethyl)-1H-pyrazole-4-carboxylic acid (Intermediate AE)

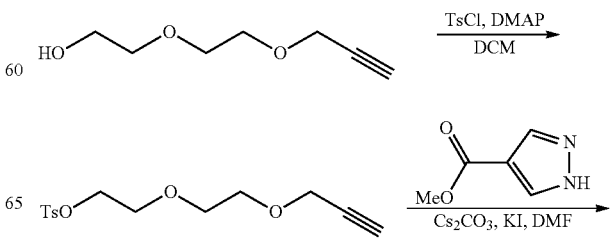

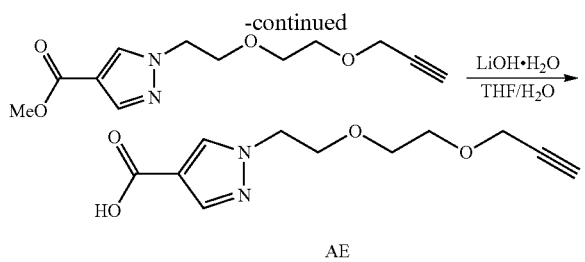

AE

Step 1—2-(2-(Prop-2-yn-1-yloxy)ethoxy)ethyl 4-methylbenzenesulfonate. To a solution of 2-(2-prop-2-ynoxyethoxy)ethanol (2 g, 13.8 mmol) in DCM (60 mL) was added TEA (7.02 g, 69.36 mmol) and DMAP (169 mg, 1.39 mmol) and 4-methylbenzenesulfonyl chloride (5.29 g, 27.7 mmol) at 20° C. under nitrogen atmosphere. Then the reaction was stirred at 20° C. for 10 h under nitrogen atmosphere. On completion, the reaction was poured into ice water (60 mL) and extracted with dichloromethane (50 mL×2). The combined organic phase was washed with brine (2×40 mL), dried over sodium sulfate, filtered and the filtrate was concentrated to give a residue. The residue was purified by column chromatography on silica gel (petroleum ether:ethyl acetate=100:1 to 100:20) to give the title compound (3 g, 72% yield) obtained as yellow oil. $^1$H NMR (400 MHz, CDCl$_3$) δ=7.82 (d, J=8.0 Hz, 2H), 7.36 (d, J=8.0 Hz, 2H), 4.24-4.13 (m, 4H), 3.75-3.69 (m, 2H), 3.68-3.60 (m, 4H), 2.49-2.43 (m, 4H).

Step 2—Methyl 1-(2-(2-(prop-2-yn-1-yloxy)ethoxy)ethyl)-1H-pyrazole-4-carboxylate. To a solution of methyl 1H-pyrazole-4-carboxylate (1.0 g, 8.0 mmol) and 2-(2-prop-2-ynoxyethoxy)ethyl 4-methylbenzenesulfonate (2 g, 6.7 mmol) in DMF (40 mL) was added KI (111 mg, 670 umol) and Cs$_2$CO$_3$ (4.3 g, 13.4 mmol) at 0° C. under nitrogen flow. Then the reaction was stirred at 70° C. for 10 h under nitrogen atmosphere. On completion, the reaction was poured into saturated ammonium chloride aqueous solution (50 mL) and extracted with ethyl acetate (2×40 mL). The combined organic phase is washed with brine (2×20 mL), dried over sodium sulfate, filtered and the filtrate was concentrated to give a residue. The residue was purified by column chromatography on silica gel (eluted with petroleum ether:ethyl acetate=100:1 to 100:40) to give the title compound (1.5 g, 88% yield) as red oil. $^1$H NMR (400 MHz, CDCl$_3$) δ=8.02 (s, 1H), 7.90 (s, 1H), 4.31 (t, J=5.12 Hz, 2H), 4.17 (d, J=2.0 Hz, 2H), 3.86-3.84 (m, 2H), 3.82 (s, 3H), 3.67-3.63 (m, 2H), 3.62-3.57 (m, 2H), 2.45 (t, J=2.12 Hz, 1H).

Step 3—1-(2-(2-(prop-2-yn-1-yloxy)ethoxy)ethyl)-1H-pyrazole-4-carboxylic acid. To a solution of methyl 1-[2-(2-prop-2-ynoxyethoxy)ethyl]pyrazole-4-carboxylate (1.5 g, 5.95 mmol) in THF (24 mL) and H$_2$O (6 mL) was added LiOH·H$_2$O (998 mg, 23.7 mmol) at 20° C. under nitrogen flow. Then the reaction was stirred at 40° C. for 15 h under nitrogen atmosphere. On completion, the reaction was poured into ice water (20 mL) and acidified with 3 N hydrochloride acid to pH=3, then extracted with ethyl acetate (2×30 mL). The combined organic phase is washed with brine (2×20 mL), dried over sodium sulfate, filtered and the filtrate was concentrated to give the title compound as a residue. $^1$H NMR (400 MHz, CDCl$_3$) δ=8.03 (s, 1H), 7.90 (s, 1H), 4.28 (t, J=5.12 Hz, 2H), 4.11 (d, J=2.4 Hz, 2H), 3.80 (t, J=5.12 Hz, 2H), 3.62-3.50 (m, 4H), 2.38 (t, J=2.4 Hz, 1H).

(1R,3S)-3-(1-(tert-butyl)-5-(1-(2-(2-(prop-2-yn-1-yloxy)ethoxy)ethyl)-1H-pyrazole-4-carboxamido)-1H-pyrazol-3-yl)cyclopentyl isopropylcarbamate (Intermediate AF)

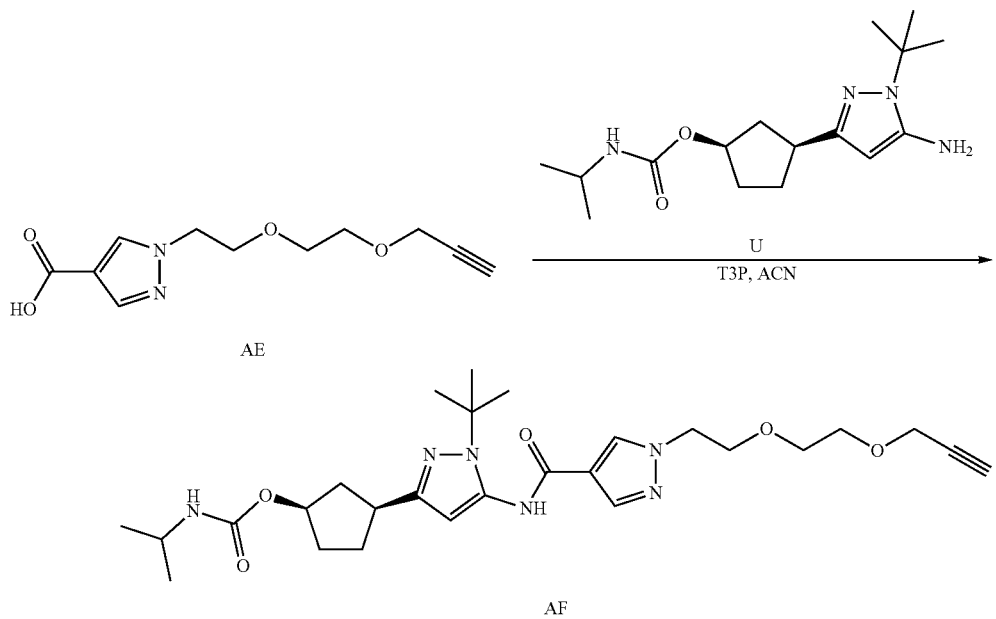

To a solution of 1-[2-(2-prop-2-ynoxyethoxy)ethyl]pyrazole-4-carboxylic acid (668 mg, 2.8 mmol, Intermediate AE) and [(1R,3S)-3-(5-amino-1-tert-butyl-pyrazol-3-yl)cyclopentyl] N-isopropylcarbamate (0.4 g, 1.30 mmol, Intermediate U) in ACN (10 mL) was added T$_3$P (2.68 g, 4.21 mmol, 50% solution in DMF) and DIEA (906 mg, 7.01 mmol, 1.22 mL) at 20° C. under nitrogen flow. Then the reaction was stirred at 60° C. for 10 h under nitrogen atmosphere. On completion, the reaction was poured into ice water (15 mL), and extracted with ethyl acetate (2×20 mL). The combined organic phase was washed with brine (2×10 mL), dried over sodium sulfate, filtered and the filtrate was concentrated to give a residue. The residue was purified by prep-TLC (petroleum ether:ethyl acetate=0:1) to give the title compound (0.25 g, 33% yield) as a colorless oil. $^1$H NMR (400 MHz, CDCl$_3$) δ=8.23-7.56 (m, 2H), 6.19 (br s, 1H), 5.15 (br s, 1H), 4.77-4.60 (m, 1H), 4.33 (br d, J=4.2 Hz, 2H), 4.18 (d, J=2.4 Hz, 1H), 3.87 (br t, J=4.92 Hz, 2H), 3.83-3.72 (m, 1H), 3.69-3.53 (m, 3H), 3.26-2.99 (m, 1H), 2.52-2.45 (m, 1H), 2.44 (t, J=2.4 Hz, 1H), 2.11-2.00 (m, 1H), 1.99-1.74 (m, 5H), 1.63 (s, 9H), 1.18-1.10 (m, 6H).

Benzyl (1-(tert-butyl)-3-((1S,3R)-3-hydroxycyclopentyl)-1H-pyrazol-5-yl)carbamate (Intermediate AG) and Benzyl (1-(tert-butyl)-3-((1R,3S)-3-hydroxycyclopentyl)-1H-pyrazol-5-yl)carbamate (Intermediate AH)

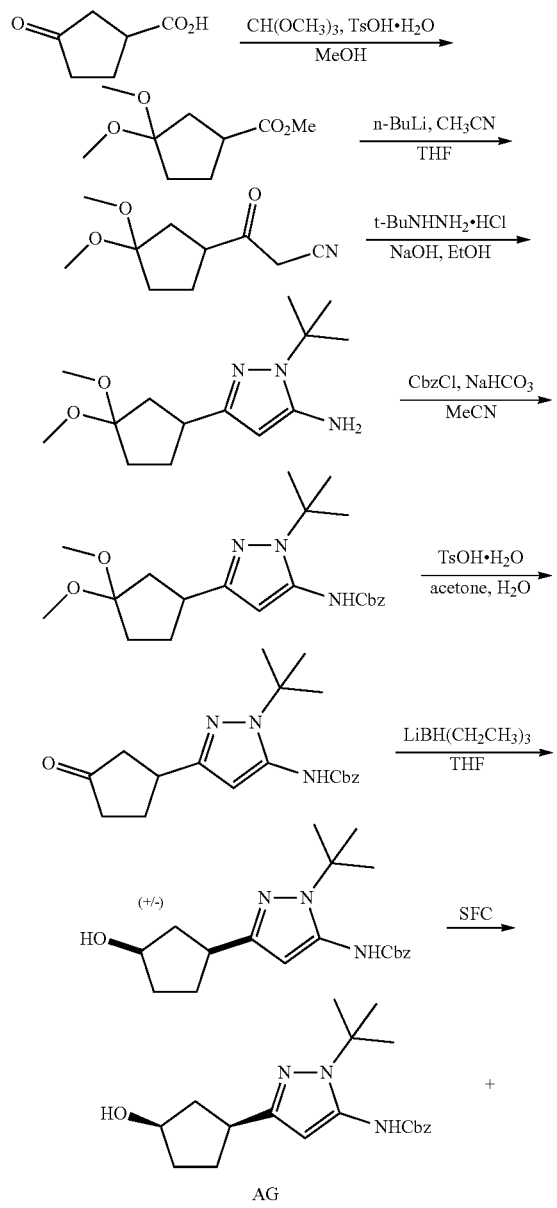

AG

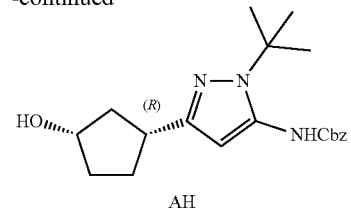

AH

Step 1—Methyl 3,3-dimethoxycyclopentanecarboxylate. To a solution of 3-oxocyclopentanecarboxylic acid (42 g, 328 mmol, CAS #98-78-2) in MeOH (180 mL) was added trimethoxymethane (174 g, 1.64 mol, 180 mL) and TsOH·H$_2$O (12.5 g, 65.6 mmol). The mixture was stirred at 20° C. for 3 hr. Next, to the mixture was added Na$_2$CO$_3$ (80 g) and the mixture was stirred at 20° C. for 11 hour. On completion, the mixture was filtered and the filtrate was concentrated in vacuo. To the mixture was added water (200 mL). The mixture was extracted with EtOAc (200 mL×3). The organic phase was washed with brine (200 mL×2), dried with anhydrous Na$_2$SO$_4$, filtered and concentrated in vacuo to give the title compound (55.2 g, 89% yield) as yellow oil. $^1$H NMR (400 MHz, CDCl$_3$) δ=3.72-3.62 (m, 3H), 3.23-3.15 (m, 6H), 2.93-2.79 (m, 1H), 2.15-2.01 (m, 2H), 2.00-1.84 (m, 3H), 1.83-1.75 (m, 1H).

Step 2—3-(3,3-Dimethoxycyclopentyl)-3-oxopropanenitrile. A solution of n-BuLi (2.5 M, 15.9 mL) was added dropwise to a reactor containing THF (120 mL) at −65° C. Next, anhydrous MeCN (1.64 g, 39.9 mmol, 2.1 mL) was added dropwise, slowly enough to maintain the internal temperature below −65° C. The mixture was stirred for an additional 1 hr at −65° C. Then a solution of methyl 3,3-dimethoxycyclopentanecarboxylate (5 g, 26.6 mmol) in THF (40 mL) was then added dropwise. After addition, the reaction mixture was stirred at −65° C. for 2 hr. On completion, the reaction was quenched with water (60 mL), neutralized with saturated aq NH$_4$Cl to pH=9~10 and extracted with ethyl acetate (60 mL×3). The combined organic layers were washed with sat. aq NaCl (50 mL×2), dried over anhydrous Na$_2$SO$_4$, filtered, and concentrated under vacuum to give the title compound (3.9 g, 19.8 mmol, 74% yield) as yellow oil. $^1$H NMR (400 MHz, CDCl$_3$) δ=3.53-3.50 (m, 2H), 3.21-3.18 (m, 7H), 2.08 (d, J=8.4 Hz, 2H), 1.94-1.81 (m, 4H).

Step 3—2-Tert-butyl-5-(3,3-dimethoxycyclopentyl)pyrazol-3-amine. To a solution of tert-butylhydrazine (2.88 g, 23.1 mmol, HCl) in EtOH (40 mL) was added NaOH (925 mg, 23.1 mmol) 25° C. After addition, the mixture was stirred at 25° C. for 0.5 hr and then 3-(3,3-dimethoxycyclopentyl)-3-oxopropanenitrile (3.8 g, 19.3 mmol) in EtOH (40 mL) was added dropwise. The resulting mixture was stirred at 75° C. for 15.5 hr. On completion, the reaction mixture was filtered and the filtrate was concentrated in vacuo to give residue. The residue was purified by flash silica gel chromatography (20 g SepaFlash® Silica Flash Column, Ethyl acetate/Petroleum: 0~35%) to give the title compound (3.7 g, 72% yield) as yellow oil. $^1$H NMR (400 MHz, CDCl$_3$) δ=5.43 (s, 1H), 5.48-5.35 (m, 1H), 3.56-3.43 (m, 1H), 3.49 (br d, J=1.2 Hz, 1H), 3.23 (d, J=4.0 Hz, 6H), 3.19-3.09 (m, 1H), 2.27 (m, 1H), 2.01-1.93 (m, 1H), 1.88-1.69 (m, 4H), 1.61 (s, 9H).

Step 4—Benzyl (1-(tert-butyl)-3-(3,3-dimethoxycyclopentyl)-1H-pyrazol-5-yl)carbamate. To a solution of 2-tert-butyl-5-(3,3-dimethoxycyclopentyl)pyrazol-3-amine (3.7 g, 13.8 mmol) in MeCN (50 mL) was added NaHCO$_3$ (3.49 g, 41.5 mmol). After addition, the mixture was stirred at 25° C. for 0.5 h and then CbzCl (3.54 g, 20.8 mmol, 2.95 mL) was added dropwise at 0° C. The resulting mixture was stirred at 25° C. for 15.5 h. On completion, the reaction mixture was quenched with H₂O (80 mL), and then diluted with ethyl acetate (50 mL). The aqueous phase was extracted with ethyl acetate (50 mL×3). The combined organic phases were washed with brine (50 mL), dried with anhydrous Na₂SO₄, filtered and concentrated in vacuo to give a residue. The residue was purified by flash silica gel chromatography (20 g SepaFlash® Silica Flash Column, Ethyl acetate/Petroleum: 0~35%) to give the title compound (1.12 g, 21% yield) as a yellow solid. LC-MS (ESI⁺) m/z 356.3 (M+H)⁺; ¹H NMR (400 MHz, CDCl₃) δ=7.48-7.30 (m, 5H), 6.28 (s, 1H), 6.10 (s, 1H), 5.20 (s, 1H), 3.51-3.36 (m, 1H), 2.62-2.53 (m, 1H), 2.50-2.31 (m, 3H), 2.28-2.16 (m, 1H), 2.11-2.05 (m, 1H), 1.58 (s, 9H).

Step 5—Benzyl (1-(tert-butyl)-3-(3-oxocyclopentyl)-1H-pyrazol-5-yl)carbamate. To a solution of benzyl N-[2-tert-butyl-5-(3,3-dimethoxycyclopentyl)pyrazol-3-yl]carbamate (1.12 g, 2.96 mmol) in acetone (10 mL) and H₂O (10 mL) was added TosOH (10.3 g, 59.8 mmol), then the mixture was stirred at 25° C. for 14 h. On completion, the mixture was concentrated and diluted with water (5 mL) and EtOAc (5 mL), then extracted with EtOAc (5 mL×3). The combined organic layers were washed with sat. NaHCO₃ (500 mL×3) and brine (5 mL×3) and dried over Na₂SO₄ and concentrated in vacuo to get the title compound (1.1 g) as a yellow solid. LC-MS (ESI⁺) m/z 356.0 (M+H).

Step 6—Benzyl (1-(tert-butyl)-3-((1S,3R)-3-hydroxycyclopentyl)-1H-pyrazol-5-yl)carbamate. To a solution of benzyl (1-(tert-butyl)-3-(3-oxocyclopentyl)-1H-pyrazol-5-yl) carbamate (1 g, 2.81 mmol) in THF (15 mL) was added dropwise LiBHEt₃ (1 M, 5.63 mL) at −65° C. under N₂. After addition, the mixture was stirred at −65° C. for 2 hr. On completion, the reaction mixture was quenched with sat. aq NaHCO₃ (30 mL) at −40 to −30° C. Next, hydrogen peroxide (30% aqueous, 5 g) was added to the mixture dropwise, while the internal temperature was maintained at −10 to 0° C. Then the mixture was stirred at 10° C. for 1 hour. On completion, the solution was then extracted with ethyl acetate (3×20 mL). The combined organic layers were washed with sat. aq Na₂SO₃ (2×20 mL) and sat. aq NaCl (30 mL). The organic layer was dried over magnesium sulfate, filtered, and concentrated under vacuum to give residue. The residue was purified by flash silica gel chromatography (12 g SepaFlash® Silica Flash Column, Ethyl acetate/Dichloromethane: 0~20%) to give the title compound (708 mg, 68% yield) as a yellow solid. ¹H NMR (400 MHz, DMSO-d₆) δ=9.06 (br s, 1H), 7.46-7.31 (m, 5H), 5.92 (s, 1H), 5.12 (s, 2H), 4.56 (d, J=4.4 Hz, 1H), 4.19-4.11 (m, 1H), 2.89 (m, 1H), 2.25-2.14 (m, 1H), 1.90-1.80 (m, 1H), 1.78-1.68 (m, 2H), 1.61-1.55 (m, 1H), 1.54-1.49 (m, 1H), 1.47 (s, 9H).

Step 7—Benzyl (1-(tert-butyl)-3-((1S,3R)-3-hydroxycyclopentyl)-1H-pyrazol-5-yl)carbamate and Benzyl (1-(tert-butyl)-3-((1R,3S)-3-hydroxycyclopentyl)-1H-pyrazol-5-yl) carbamate. The enantiomers of benzyl (1-(tert-butyl)-3-((1S, 3R)-3-hydroxycyclopentyl)-1H-pyrazol-5-yl)carbamate (700 mg, 1.96 mmol) were separated by chiral SFC (column: DAICEL CHIRALPAK AD (250 mm*30 mm, 10 um); mobile phase: [0.1% NH3H2O MEOH]; B %: 20%-20%, 2.4; 180 min) to give benzyl (1-(tert-butyl)-3-((1S,3R)-3-hydroxycyclopentyl)-1H-pyrazol-5-yl)carbamate (308 mg, 43% yield) as a white solid (LC-MS (ESI⁺) m/z 358.2 (M+H)⁺; SFC (the first-eluting enantiomer peak, 1.076 min); ¹H NMR (400 MHz, DMSO-d₆) δ=9.20-8.85 (m, 1H), 7.50-7.18 (m, 5H), 5.93 (s, 1H), 5.12 (s, 2H), 4.57 (d, J=4.0 Hz, 1H), 4.29-4.10 (m, 1H), 2.90 (m, 1H), 2.32-2.12 (m, 1H), 1.91-1.80 (m, 1H), 1.78-1.67 (m, 2H), 1.66-1.56 (m, 1H), 1.56-1.51 (m, 1H), 1.48 (s, 9H) and benzyl (1-(tert-butyl)-3-((1R,3S)-3-hydroxycyclopentyl)-1H-pyrazol-5-yl) carbamate (308 mg, 43% yield) as a white solid.

3-(methoxymethyl)-1-methyl-1H-pyrazole-5-carboxylic acid (Intermediate AI)

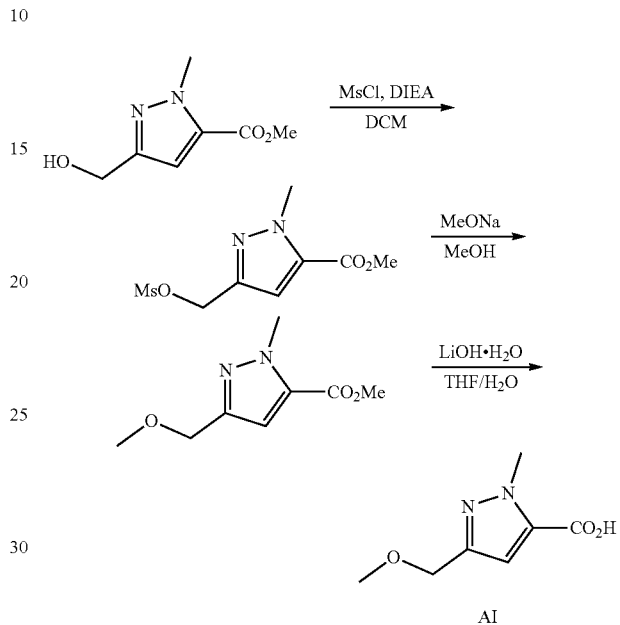

Step 1—Methyl 1-methyl-3-(((methylsulfonyl)oxy) methyl)-1H-pyrazole-5-carboxylate. A solution of methyl 3-(hydroxymethyl)-1-methyl-1H-pyrazole-5-carboxylate (1 g, 5.88 mmol, CAS #1208081-25-7) and DIEA (987 mg, 7.64 mmol, 1.33 mL) in DCM (12 mL) was cooled to 0° C. Then a solution of MsCl (1.08 g, 9.43 mmol, 730 uL) in DCM (3 mL) was added dropwise. The mixture was stirred at 0° C. for 45 minutes then stirred at 20° C. for 1 h 15 min. On completion, the reaction mixture was quenched with sat. NH₄Cl (30 mL) and then extracted with ethyl acetate (30 mL). The organic layer was dried over sodium sulfate, filtered, and concentrated to give the title compound (1.46 g, crude) as a white solid. ¹H NMR (400 MHz, CDCl₃) δ ppm 6.96 (s, 1H) 5.24 (s, 2H) 4.19 (s, 3H) 3.90 (s, 3H) 3.01 (s, 3H).

Step 2—Methyl 3-(methoxymethyl)-1-methyl-1H-pyrazole-5-carboxylate. To a solution of methyl 1-methyl-3-(((methylsulfonyl)oxy)methyl)-1H-pyrazole-5-carboxylate (1.46 g, 5.88 mmol) in MeOH (15 mL) was added NaOMe (635 mg, 11.8 mmol) at 20° C. The mixture was stirred at 70° C. for 30 minutes. On completion, the reaction mixture was poured into 0.5 N HCl (30 mL) with stirring. The pH of the mixture was adjusted to 8 with sodium bicarbonate and then extracted with ethyl acetate, dried over sodium sulfate, filtered, and concentrated to get the product. The crude product was purified by silica gel column chromatography (PE/EA=50/1 to 8/1) to give the title compound (750 mg, 69% yield) as a white solid. ¹H NMR (400 MHz, CDCl₃) δ ppm 6.82 (s, 1H) 4.34 (s, 2H) 4.06 (s, 3H) 3.83 (s, 3H) 3.25 (s, 3H).

Step 3—3-(Methoxymethyl)-1-methyl-1H-pyrazole-5-carboxylic acid. To a solution of methyl 3-(methoxymethyl)-1-methyl-1H-pyrazole-5-carboxylate (740 mg, 4.02 mmol)

in THF (7.6 mL) was added water (2.5 mL) and lithium hydroxide monohydrate (337 mg, 8.04 mmol). The mixture was stirred at 20° C. for 16 hr. On completion, the pH of the mixture reaction was adjusted to 3-4 with aq. HCl (1 M) and then diluted with water 25 mL and extracted with ethyl acetate (20 mL×3). The combined organic layers were dried over Na$_2$SO$_4$, filtered and concentrated under reduced pressure to give the title compound (423 mg, 62% yield) as a yellow solid. $^1$H NMR (400 MHz, DMSO-d$_6$) δ ppm 3.23-3.26 (m, 3H) 4.04 (s, 3H) 4.32 (s, 2H) 6.75 (s, 1H) 13.12-13.51 (m, 1H).

Methyl 1-(dodec-11-yn-1-yl)-1H-pyrazole-5-carboxylate (Intermediate AJ) and methyl 1-(dodec-11-yn-1-yl)-1H-pyrazole-3-carboxylate (Intermediate AK)

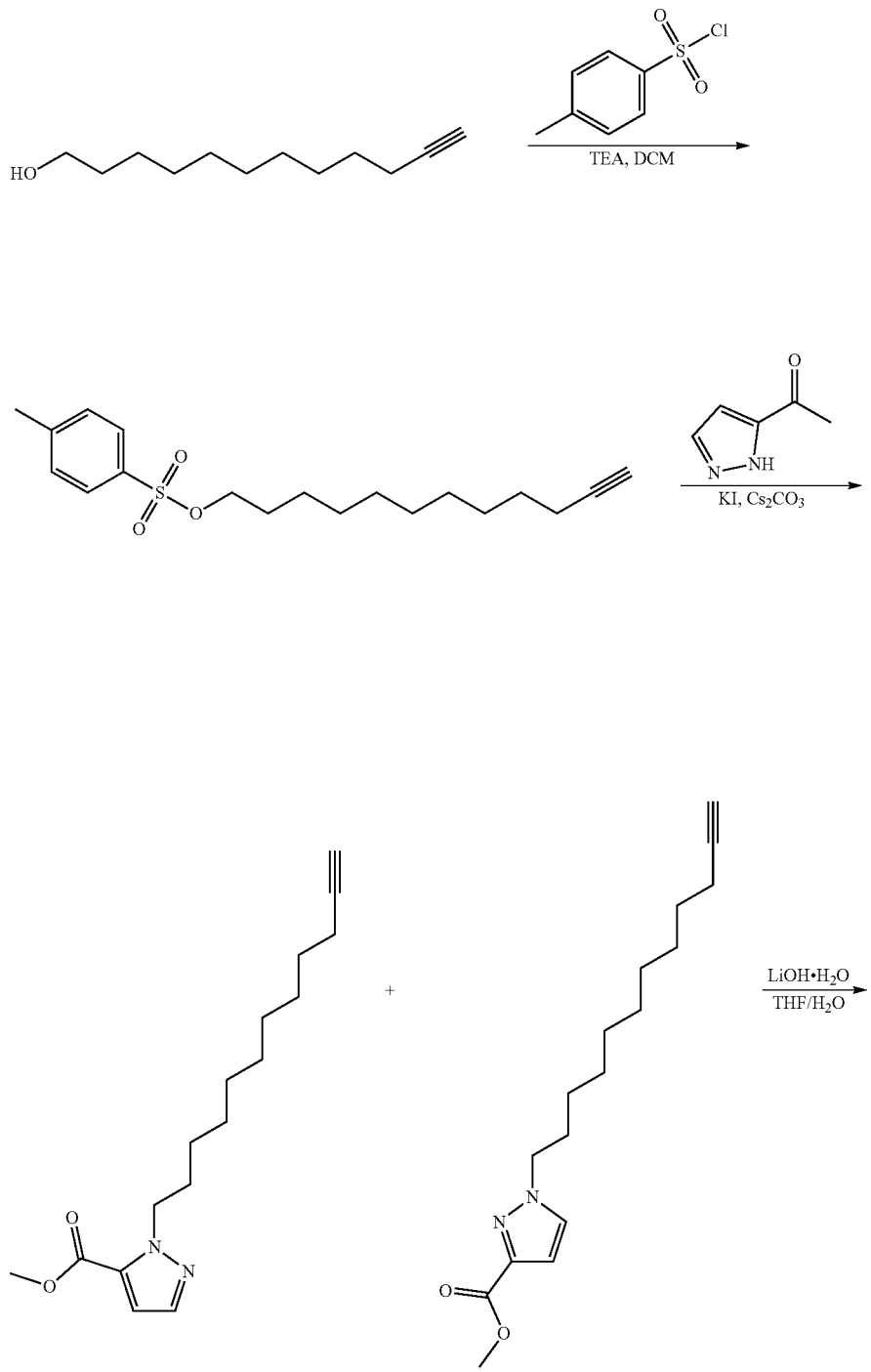

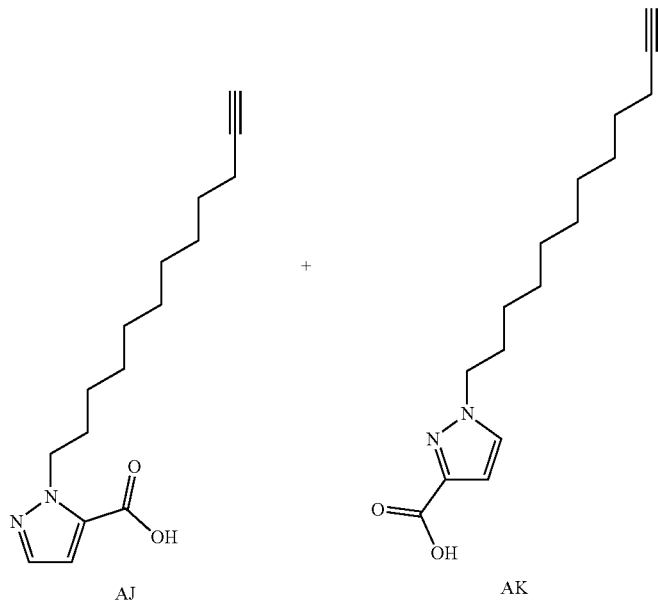

Step 1—Dodec-11-yn-1-yl 4-methylbenzenesulfonate. To a solution of dodec-11-yn-1-ol (3 g, 16.5 mmol, CAS #18202-10-3) and 4-methylbenzenesulfonyl chloride (3.45 g, 18.1 mmol, CAS #98-59-9) in DCM (30 mL) was added TEA (5.00 g, 49.4 mmol) at 0° C., then the mixture was stirred at 0-20° C. for 12 h. On completion, the reaction mixture was quenched by addition $NH_4Cl$ 50 mL at 20° C., and then diluted with EtOAc 20 mL and extracted with EtOAc (20 mL×3). The combined organic layers were washed with brine (20 mL×2), dried over $Na_2SO_4$, filtered and concentrated under reduced pressure to give a residue. The residue was purified by column chromatography ($SiO_2$, Petroleum ether/Ethyl acetate=15/1 to 3/1) to give the title compound (3.6 g, 65% yield) as yellow solid. $^1$H NMR (400 MHz, DMSO-d6) δ=7.78 (d, J=8.4 Hz, 2H), 7.48 (d, J=8.0 Hz, 2H), 4.00 (t, J=6.4 Hz, 2H), 2.73 (t, J=2.8 Hz, 1H), 2.42 (s, 3H), 2.13 (dt, J=2.4, 6.8 Hz, 2H), 1.53 (quin, J=6.8 Hz, 2H), 1.46-1.37 (m, 2H), 1.36-1.27 (m, 2H), 1.24-1.13 (m, 10H).

Step 2—Methyl 1-(dodec-11-yn-1-yl)-1H-pyrazole-5-carboxylate and methyl 1-(dodec-11-yn-1-yl)-1H-pyrazole-3-carboxylate. To a solution of methyl 1H-pyrazole-5-carboxylate (1.19 g, 9.45 mmol, CAS #15366-34-4) and dodec-11-ynyl 4-methylbenzenesulfonate (2.65 g, 7.88 mmol) in DMF (30 mL) was added KI (131 mg, 788 umol) and $Cs_2CO_3$ (5.13 g, 15.8 mmol), then the mixture was stirred at 70° C. for 1 h. On completion, the reaction mixture was quenched with $H_2O$ (30 mL) at 20° C., and then diluted with EtOAc 30 mL and extracted with EtOAc mL (30 mL×3). The combined organic layers were washed with brine (30 mL×2), dried over $Na_2SO_4$, filtered and concentrated under reduced pressure to give a residue. The residue was purified by column chromatography ($SiO_2$, Petroleum ether/Ethyl acetate=5/1 to 1/1) to give methyl 1-(dodec-11-yn-1-yl)-1H-pyrazole-5-carboxylate (1 g, 43.7% yield) as a white solid (1H NMR (400 MHz, DMSO-d6) δ=7.55 (d, J=2.0 Hz, 1H), 6.87 (d, J=2.0 Hz, 1H), 4.47 (t, J=7.2 Hz, 2H), 3.82 (s, 3H), 2.72 (t, J=2.8 Hz, 1H), 2.13 (dt, J=2.4, 6.8 Hz, 2H), 1.72 (quin, J=7.2 Hz, 2H), 1.47-1.37 (m, 2H), 1.36-1.29 (m, 2H), 1.22 (br s, 10H) and methyl 1-(dodec-11-yn-1-yl)-1H-pyrazole-3-carboxylate (1.1 g, 48% yield) as a white solid. $^1$H NMR (400 MHz, DMSO-$d_6$) δ=7.55 (d, J=2.0 Hz, 1H), 6.87 (d, J=2.0 Hz, 1H), 4.47 (t, J=7.2 Hz, 2H), 3.82 (s, 3H), 2.72 (t, J=2.8 Hz, 1H), 2.13 (dt, J=2.8, 6.8 Hz, 2H), 1.72 (q, J=7.1 Hz, 2H), 1.47-1.37 (m, 2H), 1.36-1.29 (m, 2H), 1.22 (br s, 10H).

1-(dodec-11-yn-1-yl)-1H-pyrazole-5-carboxylic acid ((Intermediate AL)

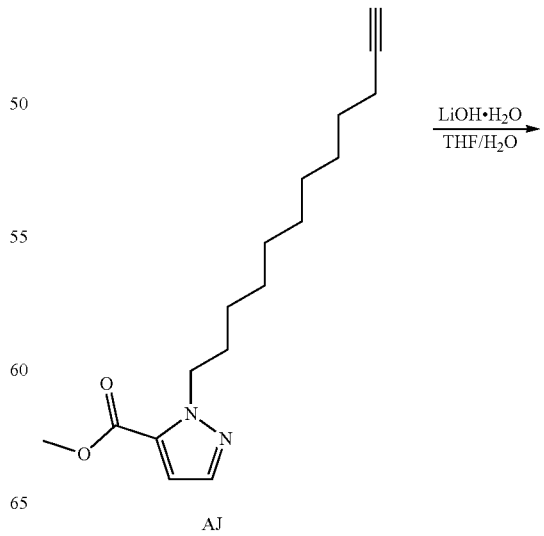

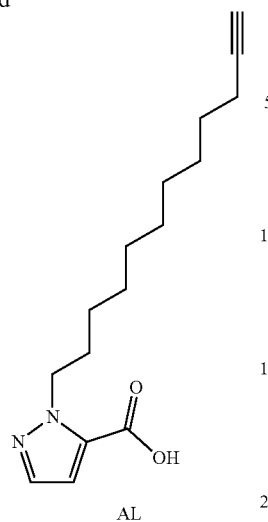

AL

To a solution of methyl 2-dodec-11-ynylpyrazole-3-carboxylate (1 g, 3.44 mmol, Intermediate AJ) and LiOH·H$_2$O (578 mg, 13.8 mmol) in THF (12 mL) and H$_2$O (4 mL), then the mixture was stirred at 20° C. for 12 hr. On completion, the reaction mixture was quenched with H$_2$O 20 mL at 20° C., and then diluted with EtOAc 10 mL and extracted with EtOAc mL (20 mL×3). Then the aqueous phase was adjusted to pH=3-4, and then extracted with EtOAc mL (20 mL×3). The organic layers were washed with brine (20 mL×2), dried over Na$_2$SO$_4$, filtered and concentrated under reduced pressure to give the title compound (930 mg) as a yellow solid. $^1$H NMR (400 MHz, DMSO-d6) δ=13.95-11.71 (m, 1H), 7.50 (d, J=2.0 Hz, 1H), 6.80 (d, J=2.0 Hz, 1H), 4.47 (t, J=7.2 Hz, 2H), 2.71 (t, J=2.4 Hz, 1H), 2.12 (dt, J=2.4, 6.8 Hz, 2H), 1.91 (s, 2H), 1.72 (quin, J=7.2 Hz, 2H), 1.46-1.37 (m, 2H), 1.36-1.27 (m, 2H), 1.22 (br s, 9H)

(1R,3S)-3-(1-(tert-butyl)-5-(1-(dodec-11-yn-1-yl)-1H-pyrazole-5-carboxamido)-1H-pyrazol-3-yl)cyclopentyl isopropylcarbamate (Intermediate AM)

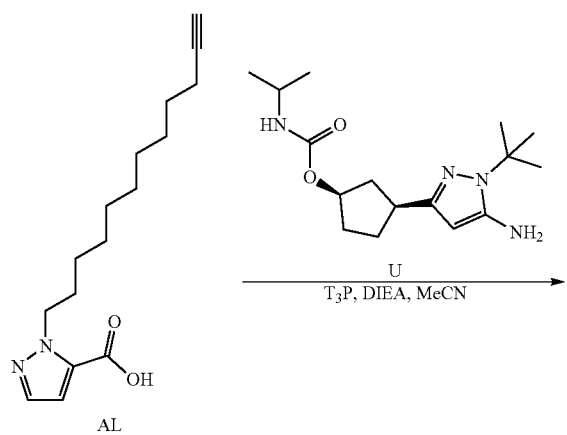

AM

To a solution of 1-(dodec-11-yn-1-yl)-1H-pyrazole-5-carboxylic acid (500 mg, 1.81 mmol, Intermediate AL) and (1R,3S)-3-(5-amino-1-(tert-butyl)-1H-pyrazol-3-yl)cyclopentyl isopropylcarbamate (558 mg, 1.81 mmol, Intermediate U) in MeCN (10 mL) was added DIEA (1.17 g, 9.05 mmol) and T$_3$P (3.45 g, 5.43 mmol, 50% solution), and the mixture was stirred at 60° C. for 2 h. On completion, the reaction mixture was quenched with H$_2$O (10 mL) at 20° C., and then diluted with EtOAc (10 mL) and extracted with EtOAc (10 mL×3). The combined organic layers were washed with brine (10 mL×2), dried over Na$_2$SO$_4$, filtered and concentrated under reduced pressure to give a residue. The residue was purified by column chromatography (SiO$_2$, Petroleum ether/Ethyl acetate=5/1 to 1/1) to give the title compound (300 mg, 529 umol, 29% yield) as a white solid. LC-MS (ESI$^+$) m/z 567.7 (M+H)$^+$.

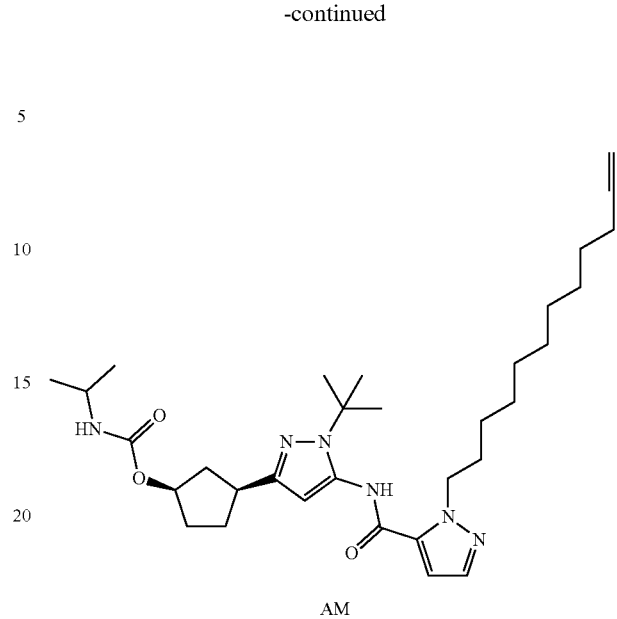

3-[4-(7-aminoheptyl)-3-methyl-2-oxo-benzimidazol-1-yl]piperidine-2,6-dione (Intermediate AN)

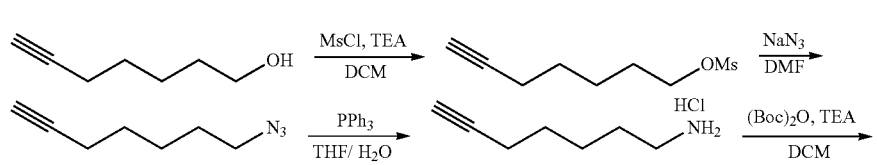

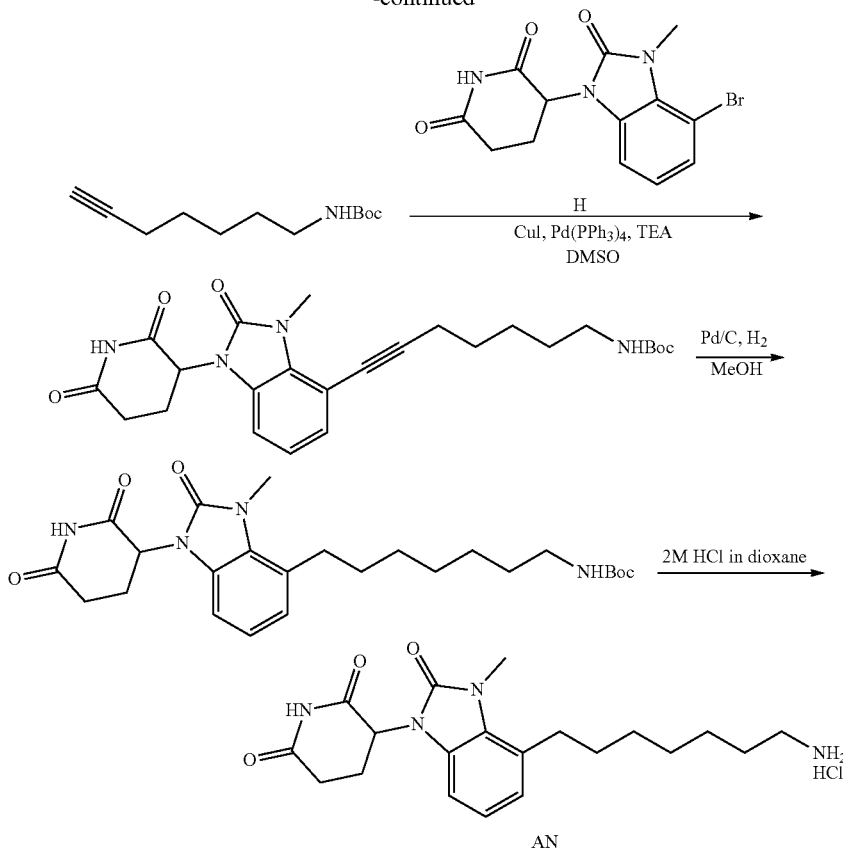

Step 1—Hept-6-yn-1-yl methanesulfonate. To a stirred solution of hept-6-yn-1-ol (30.00 g, 267.5 mmol) in DCM (450.00 mL) were added TEA (92.68 mL, 668.6 mmol) and MsCl (45.95 g, 401.1 mmol) in portions at 0° C. under nitrogen atmosphere. The resulting mixture was then stirred for 2 h at rt under nitrogen atmosphere. On completion, the mixture was diluted with water (250 mL). The resulting mixture was extracted with $CH_2Cl_2$ (3×100 mL). The combined organic layers were washed with brine (1×100 mL), and dried over anhydrous $Na_2SO_4$. After filtration, the filtrate was concentrated under reduced pressure to give the title compound (50 g). $^1$H NMR (400 MHz, $CDCl_3$) δ 4.28-4.24 (m, 2H), 3.03 (s, 3H), 2.27-2.22 (m, 2H), 1.98 (s, 1H), 1.84-1.77 (m, 2H), 1.60-1.52 (m, 6H).

Step 2—7-Azidohept-1-yne. To a stirred solution of hept-6-yn-1-yl methanesulfonate (50.00 g, 262.8 mmol) in DMF (500.0 mL) was added $NaN_3$ (25.63 g, 394.2 mmol) at rt under nitrogen atmosphere. The resulting mixture was stirred overnight at 50° C. under nitrogen atmosphere. On completion, the reaction mixture was diluted with water (1 L). The resulting mixture was extracted with EtOAc (3×200 mL). The combined organic layers were washed with brine (3×100 mL), then dried over anhydrous $Na_2SO_4$. After filtration, the filtrate was concentrated under reduced pressure to give the title compound (36 g) as light oil. $^1$H NMR (400 MHz, Chloroform-d) δ 3.30 (t, J=6.8 Hz, 2H), 2.23 (td, J=6.8, 2.6 Hz, 2H), 1.97 (s, 1H), 1.72-1.41 (m, 6H).

Step 3—Hept-6-yn-1-amine hydrochloride. To a stirred solution of 7-azidohept-1-yne (36.00 g, 262.4 mmol) in THF (400 mL) and $H_2O$ (40.00 mL) was added $PPh_3$ (103.24 g, 393.6 mmol) at 0° C. under nitrogen atmosphere. The resulting mixture was stirred for 2 h at 60° C. under nitrogen atmosphere. On completion, the solution was concentrated under reduced pressure and diluted with DCM (300 mL). The mixture was acidified to pH 1 with HCl (2 M aq.) and the aqueous layer was extracted with DCM (3×100 mL). The aqueous layer was concentrated under reduced pressure to give the title compound (38 g, 98% yield) as a white solid. $^1$H NMR (400 MHz, DMSO-$d_6$) δ 8.09 (broad, 3H), 2.82-2.67 (m, 3H), 2.18-2.14 (m, 2H), 1.61-1.53 (m, 2H), 1.49-1.35 (m, 4H). LC/MS (ESI, m/z): $[(M+1)]^+$=112.2.

Step 4: Tert-butyl N-(hept-6-yn-1-yl)carbamate. To a stirred solution of hept-6-yn-1-amine hydrochloride (28.00 g, 190.5 mmol) in DCM (500.00 mL) were added TEA (144.8 mL, 952.4 mmol) and $Boc_2O$ (62.28 g, 285.7 mmol) in portions at rt under nitrogen atmosphere. The resulting mixture was stirred overnight at rt under nitrogen atmosphere. On completion, the reaction mixture was diluted with water (1 L) and extracted with $CH_2Cl_2$ (3×200 mL). The combined organic layers were washed with brine (2×300 mL), and dried over anhydrous $Na_2SO_4$. After filtration, the filtrate was concentrated under reduced pressure. The residue was purified by silica gel column chromatography, eluted with PE/EtOAc (1:1), to afford the title compound (40 g, 99% yield) as a light yellow solid. $^1$H NMR (400 MHz, Chloroform-d) δ 4.56-4.52 (m, 1H), 3.16-3.12 (m, 2H), 2.21 (td, J=7.0, 2.6 Hz, 2H), 1.96 (t, J=2.7 Hz, 1H), 1.62-1.49 (m, 6H), 1.46 (s, 9H). LC/MS (ESI, m/z): $[(M+1-56)]^+$=156.2.

Step 5—Tert-butyl N-[7-[1-(2,6-dioxopiperidin-3-yl)-3-methyl-2-oxo-1,3-benzodiazol-4-yl]hept-6-yn-1-yl]carbamate. To a stirred mixture of 3-(4-bromo-3-methyl-2-oxo-1, 3-benzodiazol-1-yl)piperidine-2,6-dione (8.00 g, 23.7 mmol, Intermediate H) and tert-butyl N-(hept-6-yn-1-yl) carbamate (10.00 g, 47.32 mmol) in DMA (50.00 mL) and TEA (25.00 mL) were added CuI (450.55 mg, 2.366 mmol) and Pd(PPh₃)₄ (2.73 g, 2.34 mmol) at rt under nitrogen atmosphere. The resulting mixture was stirred for 3 h at 80° C. under nitrogen atmosphere. On completion, the reaction mixture was diluted with water (200 mL) and extracted with EtOAc (3×100 mL). The combined organic layers were washed with brine (3×50 mL), and dried over anhydrous Na₂SO₄. After filtration, the filtrate was concentrated under reduced pressure. The residue product was purified by reverse phase flash (Column: Spherical C18, 20-40 um, 330 g; Mobile Phase A: Water (0.05% FA), Mobile Phase B: ACN; Flow rate: 45 mL/min; Gradient (B %): 5%~5%, 8 min; 40%~70%, 30 min; 70%~95%; 0 min; 95%, 5 min; Detector: 254 nm; Rt: 22.3 min.)) to afford the title compound (6 g, 54% yield) as a light yellow solid. ¹H NMR (400 MHz, DMSO-d₆) δ 11.12 (s, 1H), 7.11 (d, J=7.7 Hz, 1H), 7.06 (d, J=7.6 Hz, 1H), 6.99 (t, J=7.8 Hz, 1H), 6.81 (t, J=5.9 Hz, 1H), 5.39 (dd, J=12.6, 5.4 Hz, 1H), 3.65 (s, 3H), 2.99-2.79 (m, 3H), 2.78-2.56 (m, 2H), 2.51-2.47 (m, 2H), 2.06-1.98 (m, 1H), 1.56 (d, J=6.9 Hz, 2H), 1.43-1.39 (m, 4H), 1.36 (s, 9H). LC/MS (ESI, m/z): [(M+1)]⁺=469.3.

Step 6—Tert-butyl N-[7-[1-(2,6-dioxopiperidin-3-yl)-3-methyl-2-oxo-1,3-benzodiazol-4-yl]heptyl]carbamate. To a stirred solution tert-butyl N-[7-[1-(2,6-dioxopiperidin-3-yl)-3-methyl-2-oxo-1,3-benzodiazol-4-yl]hept-6-yn-1-yl]carbamate (6.50 g, 13.9 mmol) in MeOH (500 mL) was added Pd/C (2.21 g, 20.8 mmol) in portions at rt under nitrogen atmosphere. The resulting mixture was stirred overnight at rt under hydrogen atmosphere. On completion, the resulting mixture was filtered and the filter cake was washed with MeOH (5×100 mL). The filtrate was concentrated under reduced pressure to afford the title compound (6 g, 92% yield) as a white solid. ¹H NMR (400 MHz, DMSO-d₆) δ 11.12 (s, 1H), 6.97-6.93 (m, 2H), 6.88-6.85 (m, 1H), 6.77 (t, J=5.8 Hz, 1H), 5.37 (dd, J=12.6, 5.4 Hz, 1H), 3.55 (s, 3H), 2.95-2.86 (m, 5H), 2.80-2.57 (m, 2H), 2.04-1.96 (m, 1H), 1.563-1.56 (m, 2H), 1.41-1.22 (m, 17H). LC/MS (ESI, m/z): [(M+1)]⁺=473.3.

Step 7—3-(4-(7-Aminoheptyl)-3-methyl-2-oxo-2,3-dihydro-1H-benzo[d]imidazol-1-yl)piperidine-2,6-dione hydrochloride. To a stirred solution of tert-butyl N-[7-[1-(2,6-dioxopiperidin-3-yl)-3-methyl-2-oxo-1,3-benzodiazol-4-yl]heptyl]carbamate (6.00 g, 12.9 mmol) in DCM (50.00 mL) was added HCl (gas) in 1,4-dioxane (20 mL) dropwise at rt under air atmosphere. The resulting mixture was stirred for 2 h at rt under nitrogen atmosphere. On completion, the reaction mixture was concentrated under vacuum. The residue was triturated with Et₂O to afford the title compound (4.5 g, 90% yield) as a white solid. ¹H NMR (300 MHz, DMSO-d₆) δ 11.10 (s, 1H), 7.85 (broad, 3H), 7.01-6.92 (m, 2H), 6.88-6.84 (m, 1H), 5.38 (dd, J=12.7, 5.4 Hz, 1H), 3.56 (s, 3H), 2.97-2.83 (m, 3H), 2.80-2.63 (m, 4H), 2.05-1.91 (m, 1H), 1.64-1.51 (m, 4H), 1.43-1.24 (m, 6H). LC/MS (ESI, m/z): [(M+1)]⁺=373.3.

3-((hept-6-yn-1-yloxy)methyl)-1-methyl-1H-pyrazole-5-carboxylic acid (Intermediate AO)

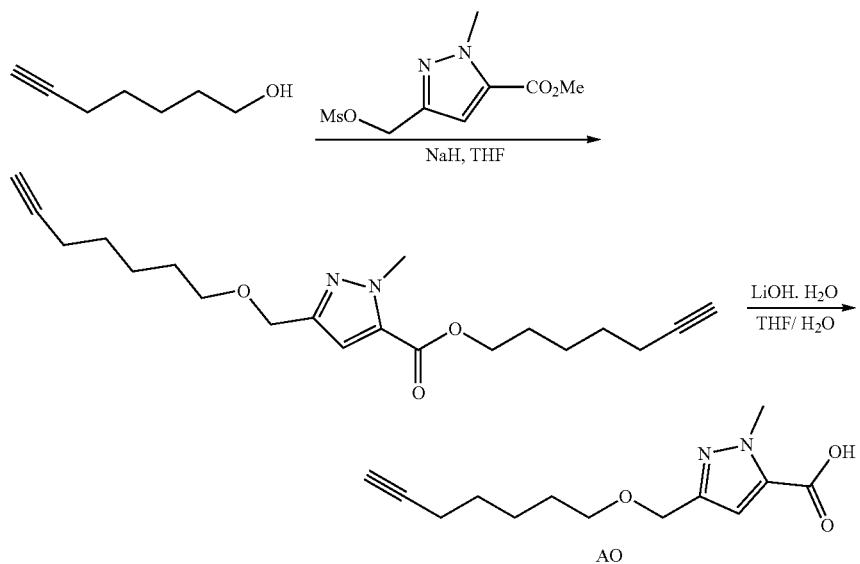

Step 1—Hept-6-yn-1-yl 3-((hept-6-yn-1-yloxy)methyl)-1-methyl-1H-pyrazole-5-carboxylate. Sodium hydride (264 mg, 6.61 mmol, 60% dispersion in mineral oil) was added to the solution of hept-6-yn-1-ol (618 mg, 5.51 mmol, CAS #63478-76-2) in THF (8 mL) at 0° C., the resulting mixture was stirred at 0° C. for 0.5 h. Then a solution of methyl 1-methyl-3-(((methylsulfonyl)oxy)methyl)-1H-pyrazole-5-carboxylate (800 mg, 2.76 mmol, synthesized via Steps 1-2 of Intermediate A1) in THF (2 mL) was added in, and the mixture was stirred at 0° C. for 2 h. On completion, the reaction mixture was quenched with 20 mL H₂O at 20° C. and then extracted with EtOAc (20 mL×3). The combined organic layers were washed with brine (20 mL×2), dried over Na₂SO₄, filtered and concentrated under reduced pressure to give a residue. The residue was purified by column chromatography (SiO₂, Petroleum ether/Ethyl acetate=5/1 to 1/1) to give the title compound (600 mg, 51.84% yield) as brown oil. LC-MS (ESI⁺) m/z 345.2 (M+H)⁺.

Step 2—3-((hept-6-yn-1-yloxy)methyl)-1-methyl-1H-pyrazole-5-carboxylic acid. To a solution of hept-6-yn-1-yl 3-((hept-6-yn-1-yloxy)methyl)-1-methyl-1H-pyrazole-5-carboxylate (600 mg, 1.74 mmol) in H₂O (1 mL) and THF (4 mL) was added LiOH·H₂O (292 mg, 6.97 mmol), then the mixture was stirred at 20° C. for 3 h. On completion, the reaction mixture was filtered and diluted with H₂O (5 mL), then extracted with EtOAc (8 mL×3). Then the aqueous phase was adjusted to pH=3-4, and extracted with EtOAc (8 mL×3). The combined organic layers were washed with brine (5 mL×3), dried over Na₂SO₄, filtered and concentrated in vacuo to give the title compound (400 mg) as yellow solid. $^1$H NMR (400 MHz, DMSO-d6) δ=13.35-13.25 (m, 1H), 6.80-6.66 (m, 1H), 4.38-4.30 (m, 2H), 3.38 (q, J=6.0 Hz, 3H), 3.29 (br s, 3H), 2.74-2.71 (m, 1H), 2.14 (dt, J=2.4, 6.8 Hz, 4H), 1.44-1.34 (m, 9H).

(1R,3S)-3-(1-(tert-butyl)-5-(3-((hept-6-yn-1-yloxy)methyl)-1-methyl-1H-pyrazole-5-carboxamido)-1H-pyrazol-3-yl)cyclopentyl isopropylcarbamate (Intermediate AP)

Tert-butyl 1-methyl-3-(((methylsulfonyl)oxy)methyl)-1H-pyrazole-5-carboxylate (Intermediate AQ)

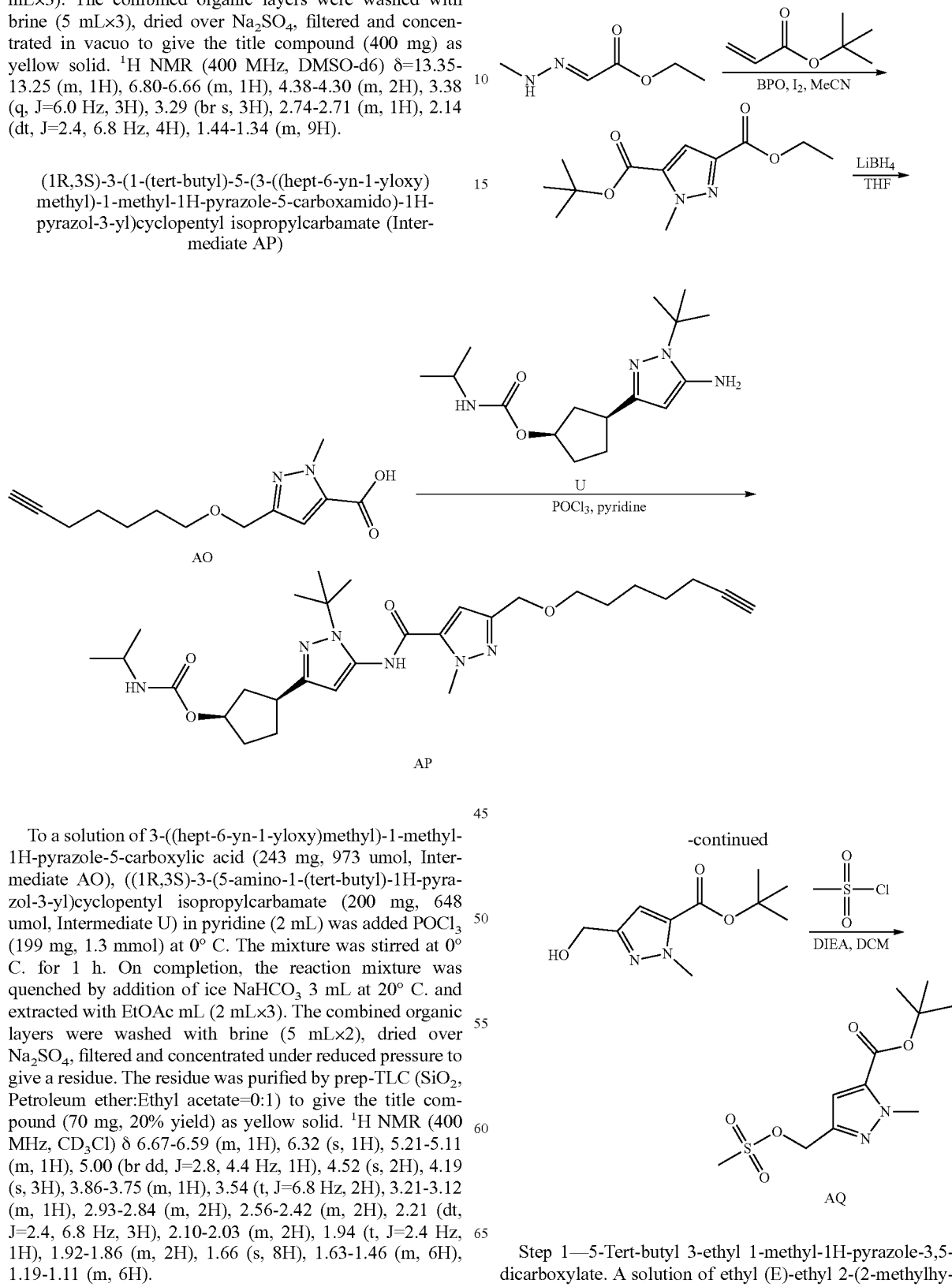

To a solution of 3-((hept-6-yn-1-yloxy)methyl)-1-methyl-1H-pyrazole-5-carboxylic acid (243 mg, 973 umol, Intermediate AO), ((1R,3S)-3-(5-amino-1-(tert-butyl)-1H-pyrazol-3-yl)cyclopentyl isopropylcarbamate (200 mg, 648 umol, Intermediate U) in pyridine (2 mL) was added POCl₃ (199 mg, 1.3 mmol) at 0° C. The mixture was stirred at 0° C. for 1 h. On completion, the reaction mixture was quenched by addition of ice NaHCO₃ 3 mL at 20° C. and extracted with EtOAc mL (2 mL×3). The combined organic layers were washed with brine (5 mL×2), dried over Na₂SO₄, filtered and concentrated under reduced pressure to give a residue. The residue was purified by prep-TLC (SiO₂, Petroleum ether:Ethyl acetate=0:1) to give the title compound (70 mg, 20% yield) as yellow solid. $^1$H NMR (400 MHz, CD₃Cl) δ 6.67-6.59 (m, 1H), 6.32 (s, 1H), 5.21-5.11 (m, 1H), 5.00 (br dd, J=2.8, 4.4 Hz, 1H), 4.52 (s, 2H), 4.19 (s, 3H), 3.86-3.75 (m, 1H), 3.54 (t, J=6.8 Hz, 2H), 3.21-3.12 (m, 1H), 2.93-2.84 (m, 2H), 2.56-2.42 (m, 2H), 2.21 (dt, J=2.4, 6.8 Hz, 3H), 2.10-2.03 (m, 2H), 1.94 (t, J=2.4 Hz, 1H), 1.92-1.86 (m, 2H), 1.66 (s, 8H), 1.63-1.46 (m, 6H), 1.19-1.11 (m, 6H).

Step 1—5-Tert-butyl 3-ethyl 1-methyl-1H-pyrazole-3,5-dicarboxylate. A solution of ethyl (E)-ethyl 2-(2-methylhydrazono)acetate (10 g, 76.8 mmol, MDL #MFCD31391018), tert-butyl acrylate (14.8 g, 115 mmol), I$_2$ (3.9 g, 15.4 mmol, CAS #1663-39-4), and benzoyl peroxide (55.8 g, 230 mmol) in ACN (180 mL) was stirred at 80° C. for 6 h. On completion, the mixture was quenched with Na$_2$SO$_3$ (200 mL), extracted with EtOAc (200 mL×2). The combined organic layer was washed with brine (200 mL×3), dried by Na$_2$SO$_4$, then concentrated in vacuo. The residue was purified by column chromatography (SiO$_2$, Petroleum ether/Ethyl acetate=5/1 to 1/1) to give the title compound (6.5 g, 33% yield) as yellow oil. $^1$H NMR (400 MHz, DMSO-d6) δ=7.15 (s, 1H), 4.28 (q, J=7.2 Hz, 3H), 4.13 (s, 3H), 3.32 (s, 2H), 1.54 (s, 9H), 1.29 (t, J=7.2 Hz, 4H).

Step 2—tert-butyl 3-(hydroxymethyl)-1-methyl-1H-pyrazole-5-carboxylate. To a solution of 5-tert-butyl 3-ethyl 1-methyl-1H-pyrazole-3,5-dicarboxylate (6.5 g, 25.6 mmol) in THF (60 mL) was slowly added LiBH$_4$ (3 g, 138 mmol) at 0° C., then the mixture was stirred for 1 h at the same temperature. On completion, the reaction mixture was quenched by dropwise addition of H$_2$O (60 mL) at 20° C., then the solution was extracted with EtOAc mL (60 mL×3). The combined organic layer was washed with brine (60 mL×2), dried over Na$_2$SO$_4$, filtered and concentrated under reduced pressure to give a residue. The residue was purified by column chromatography (SiO$_2$, Petroleum ether/Ethyl acetate=5/1 to 3/1) to give the title compound (2.5 g, 46% yield) as yellow solid. LC-MS (ESI$^+$) m/z 213.3 (M+H)$^+$.

Step 3—tert-butyl 1-methyl-3-(((methylsulfonyl)oxy) methyl)-1H-pyrazole-5-carboxylate. To a solution of tert-butyl 3-(hydroxymethyl)-1-methyl-1H-pyrazole-5-carboxylate (2.4 g, 11.3 mmol) and DIEA (4.39 g, 33.9 mmol) in DCM (30 mL) was added methanesulfonyl chloride (1.94 g, 16.9 mmol) at 0° C., then the mixture was stirred at 0° C. for 1 h. On completion, the reaction mixture was quenched with NH$_4$Cl (sat. aq, 20 mL) at 20° C. and extracted with EtOAc (20 mL×3). The combined organic layer was washed with brine (20 mL×2), dried over Na$_2$SO$_4$, filtered and concentrated under reduced pressure to give a residue. The residue was purified by column chromatography (SiO$_2$, Petroleum ether/Ethyl acetate=5/1 to 1/1) to give the title compound (1.5 g, 46% yield) as yellow gum. $^1$H NMR (400 MHz, DMSO-d$_6$) δ 6.91 (s, 1H), 5.19 (s, 2H), 4.06 (s, 3H), 3.22 (s, 3H), 1.54 (s, 9H).

1-Methyl-3-((non-8-yn-1-yloxy)methyl)-1H-pyrazole-5-carboxylic acid (Intermediate AR)

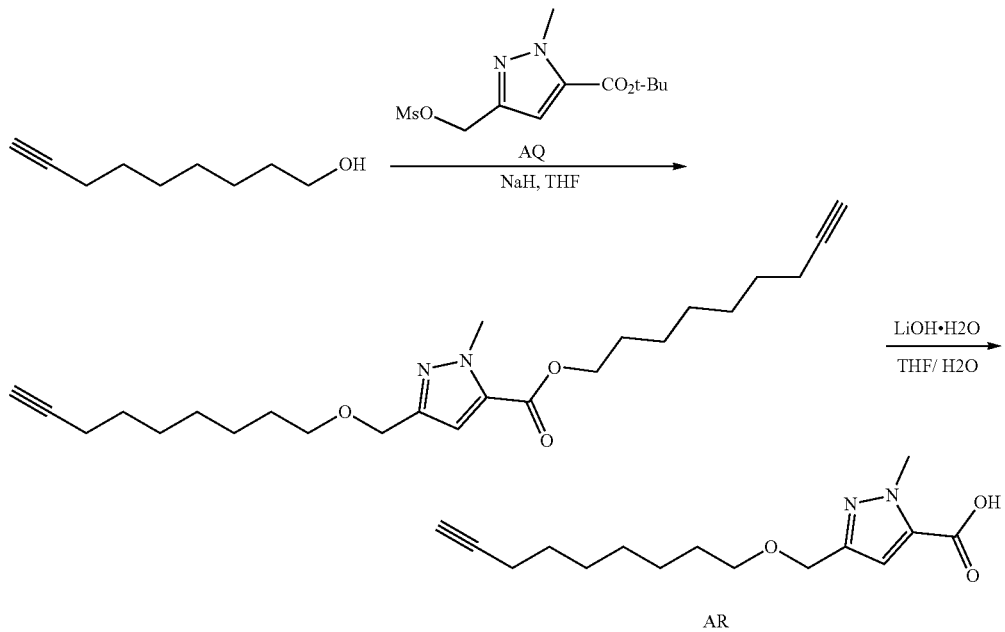

AR

Step 1—Non-8-yn-1-yl 1-methyl-3-((non-8-yn-1-yloxy) methyl)-1H-pyrazole-5-carboxylate. Sodium hydride (248 mg, 6.20 mmol, 60% dispersion in mineral oil) was added to the solution of non-8-yn-1-ol (724 mg, 5.17 mmol, CAS #10160-28-8) in THF (8 mL) at 0° C. by portions, then the mixture was stirred at 0° C. for 0.5 h. Next, the solution of tert-butyl 1-methyl-3-(((methylsulfonyl)oxy)methyl)-1H-pyrazole-5-carboxylate (750 mg, 2.58 mmol, Intermediate AQ) in THF (4 mL) was added in dropwise, and the resulting mixture was stirred at 0° C. for 2 hr. On completion, the reaction mixture was quenched with H$_2$O (10 mL) at 20° C. and extracted with EtOAc (10 mL×3). The combined organic layers were washed with brine (10 mL×2), dried over Na$_2$SO$_4$, filtered and concentrated under reduced pressure to give the title compound (600 mg) as yellow solid. LC-MS (ESI$^+$) m/z 401.3 (M+H)$^+$.

Step 2—1-methyl-3-((non-8-yn-1-yloxy)methyl)-1H-pyrazole-5-carboxylic acid. LiOH·H$_2$O (251 mg, 5.99 mmol) was added to a solution of non-8-yn-1-yl 1-methyl-3-((non-8-yn-1-yloxy)methyl)-1H-pyrazole-5-carboxylate (600 mg, 1.50 mmol) in H$_2$O (2 mL) and THF (8 mL) for one portion, then the resulting mixture was stirred at 25° C. for 12 h. On completion, the reaction mixture was filtered and diluted with H$_2$O (5 mL), and extracted with EtOAc (8 mL×3). Then the aqueous phase was adjusted to pH=3~4, and extracted with EtOAc (8 mL×3). The combined organic layers were washed with brine (5 mL×3), dried over Na$_2$SO$_4$, filtered and concentrated in vacuo to give the title compound (400 mg) as brown oil. LC-MS (ESI$^+$) m/z 279.1 (M+H)$^+$.

(1R,3S)-3-(1-(tert-butyl)-5-(1-methyl-3-((non-8-yn-1-yloxy)methyl)-1H-pyrazole-5-carboxamido)-1H-pyrazol-3-yl)cyclopentyl isopropylcarbamate (Intermediate AS)

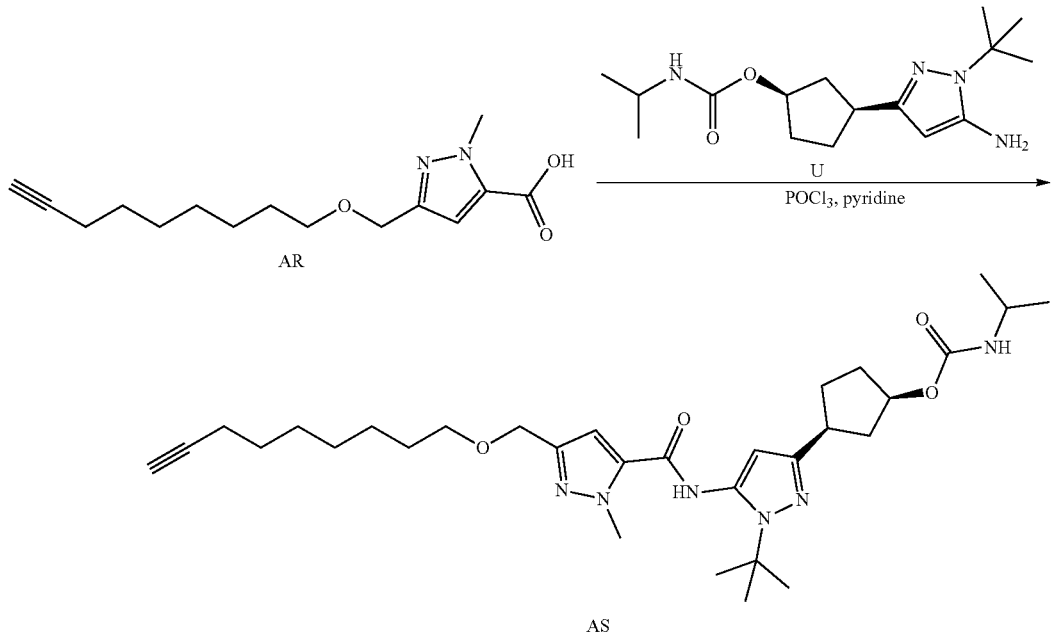

POCl$_3$ (441 mg, 2.87 mmol) was added to a solution of 1-methyl-3-((non-8-yn-1-yloxy)methyl)-1H-pyrazole-5-carboxylic acid (400 mg, 1.44 mmol, Intermediate AR) and (1R,3S)-3-(5-amino-1-(tert-butyl)-1H-pyrazol-3-yl)cyclopentyl isopropylcarbamate (488 mg, 1.58 mmol, Intermediate U) in pydrine (4 mL) dropwise at 0° C., then the resulting mixture was stirred at 0° C. for 2 h. On completion, the reaction mixture was quenched with ice H$_2$O (5 mL) at 20° C. and extracted with EtOAc (10 mL×3). The combined organic layers were washed with brine (10 mL×2), dried over Na$_2$SO$_4$, filtered and concentrated under reduced pressure to give a residue. The residue was purified by silica gel column chromatography (Petroleum ether/Ethyl acetate=10/1 to 1/1) to give the title compound (210 mg, 26% yield) as yellow solid. $^1$H NMR (400 MHz, DMSO-d6) δ 9.92 (s, 1H), 6.99 (s, 1H), 6.91 (br d, J=5.6 Hz, 1H), 6.02 (s, 1H), 5.01-4.96 (m, 1H), 4.39 (s, 2H), 4.02 (s, 3H), 3.45-3.40 (m, 2H), 2.72 (t, J=2.8 Hz, 1H), 2.39 (br dd, J=8.0, 14.4 Hz, 2H), 2.13 (dt, J=2.8, 6.8 Hz, 2H), 1.96 (br d, J=7.2 Hz, 1H), 1.86 (td, J=3.2, 5.6 Hz, 1H), 1.74-1.67 (m, 2H), 1.56 (s, 1H), 1.51 (s, 9H), 1.43-1.27 (m, 8H), 1.03 (s, 3H), 1.01 (s, 3H).

Tert-butyl 2-(1H-pyrazol-4-yl)acetate (AT)

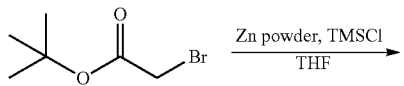

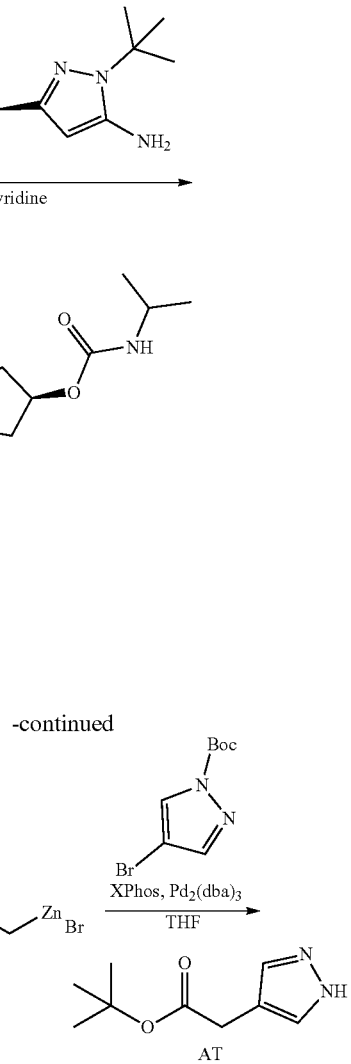

Step 1—(2-(tert-butoxy)-2-oxoethyl)zinc(II) bromide. To a solution of HCl (1 M, 232 mL) was added Zn (40.6 g, 622 mmol, powder) slowly. The mixture was stirred at 20° C. for 5 min. The mixture was filtered and the solid was washed with acetone (100 mL×2). The solid was then dried under vacuum. A mixture of Zn (27 g) and TMSCl (2.23 g, 20.5 mmol) in dry THF (120 mL) was warmed to 60° C. Then a solution of tert-butyl 2-bromoacetate (40 g, 205 mmol, CAS #5292-43-3) in THF (270 mL) was added to the reaction mixture dropwise. The mixture was stirred at 60° C. for 0.5 hour. The mixture was filtered and the filtrate was used into the next step without further purification.

Step 2—Tert-butyl 2-(1H-pyrazol-4-yl)acetate. To a mixture of tert-butyl 4-bromopyrazole-1-carboxylate (25 g, 101 mmol), Pd$_2$(dba)$_3$ (4 g, 4.37 mmol), XPhos (4.5 g, 9.44 mmol) was added the solution of bromo-(2-tert-butoxy-2-oxo-ethyl)zinc (52.7 g, 202 mmol) in THF (380 mL) in one portion under N$_2$. The mixture was stirred at 70° C. for 12 hour under N$_2$. The mixture was concentrated in vacuo and purified by silica gel chromatography (1000 mesh silica gel, Petroleum ether/Ethyl acetate=10/1, 2/1) to give the title compound (5 g, 27.4 mmol, 27% yield). ¹H NMR (400 MHz, CDCl₃) δ=7.57 (s, 2H), 3.47 (s, 2H), 1.48 (s, 9H).

Isopropyl 2-(1-(hept-6-yn-1-yl)-1H-pyrazol-4-yl)acetate (Intermediate AU)

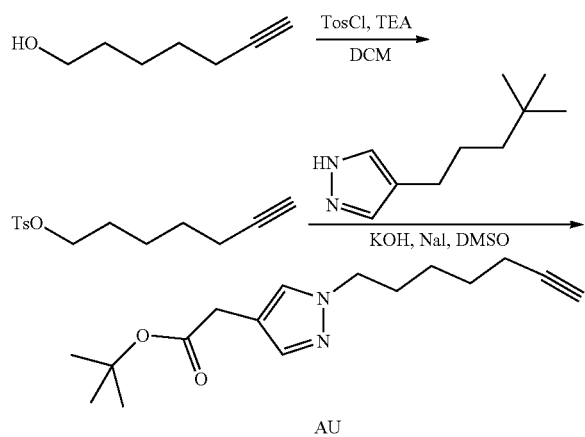

Step 1: Hept-6-yn-1-yl 4-methylbenzenesulfonate. To a solution of hept-6-yn-1-ol (1.00 g, 8.92 mmol, CAS #63478-76-2) and TEA (2.71 g, 26.75 mmol) in DCM (12 mL) was added TosCl (1.87 g, 9.81 mmol) slowly at 0° C. The mixture was stirred at 20° C. for 2 h. On completion, the mixture was diluted with DCM (20 mL) then washed with water (10 mL), dried with anhydrous Na₂SO₄, filtered and concentrated in vacuo. The residue was purified by silica gel chromatography (1000 mesh silica gel, Petroleum ether/Ethyl acetate=20/1) to give the title compound (2.00 g, 84% yield) as a colorless oil. ¹H NMR (400 MHz, CDCl₃) δ=7.80 (d, J=8.0 Hz, 2H), 7.35 (d, J=8.0 Hz, 2H), 4.04 (t, J=6.4 Hz, 2H), 2.46 (s, 3H), 2.15 (dt, J₁=6.8 Hz, J₂=2.4 Hz, 2H), 1.93 (t, J=2.4 Hz, 1H), 1.74-1.62 (m, 2H), 1.50-1.38 (m, 4H).

Step 2—Isopropyl 2-(1-(hept-6-yn-1-yl)-1H-pyrazol-4-yl)acetate. To a solution of tert-butyl 2-(1H-pyrazol-4-yl)acetate (400 mg, 2.20 mmol, Intermediate AT) in DMSO (6 mL) was added KOH (370 mg, 6.59 mmol) and hept-6-ynyl 4-methylbenzenesulfonate (760 mg, 2.85 mmol) in one portion, followed by NaI (33 mg, 0.22 mmol). The mixture was stirred at 50° C. for 2 h. On completion, the residue was poured into ice-water (10 mL). The aqueous phase was extracted with ethyl acetate (15 mL×3). The combined organic phase was washed with brine (10 mL×3), dried with anhydrous Na₂SO₄, filtered and concentrated in vacuo. The residue was purified by silica gel chromatography (1000 mesh silica gel, Petroleum ether/Ethyl acetate=30/1 to 20/1) to give the title compound (350 mg, 48% yield) as a colorless oil. LC-MS (ESI⁺) m/z 277.1 (M+H)⁺.

2-(1-(7-(1-(2,6-dioxopiperidin-3-yl)-3-methyl-2-oxo-2,3-dihydro-1H-benzo[d]imidazol-4-yl)heptyl)-1H-pyrazol-4-yl)acetic acid (Intermediate AV)

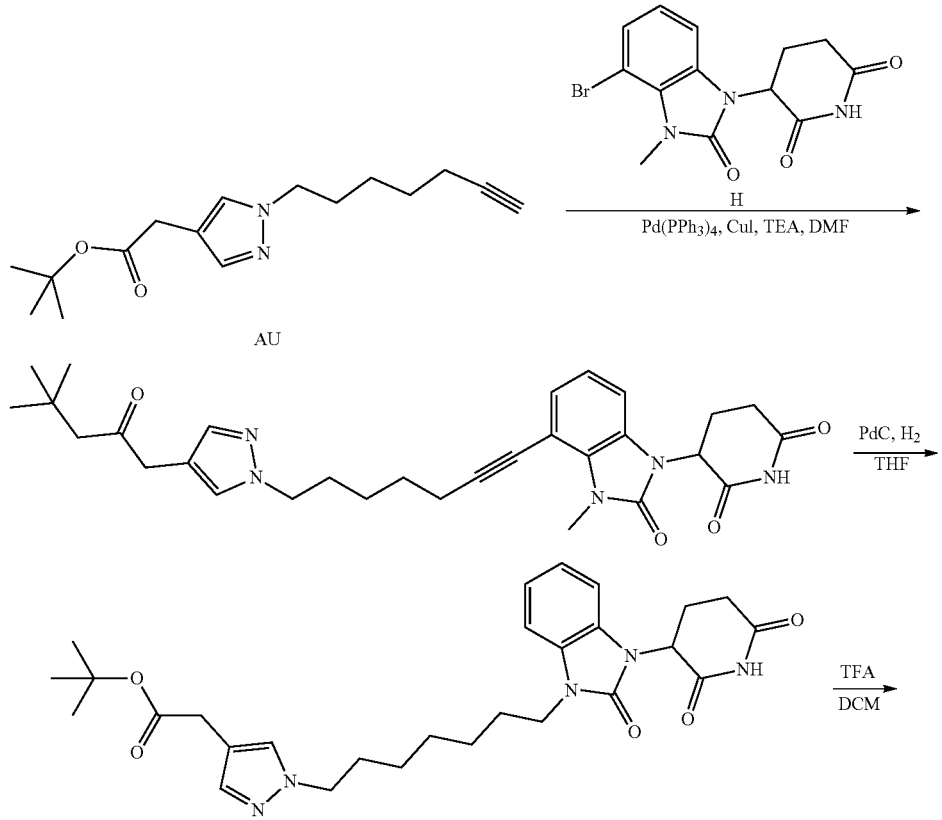

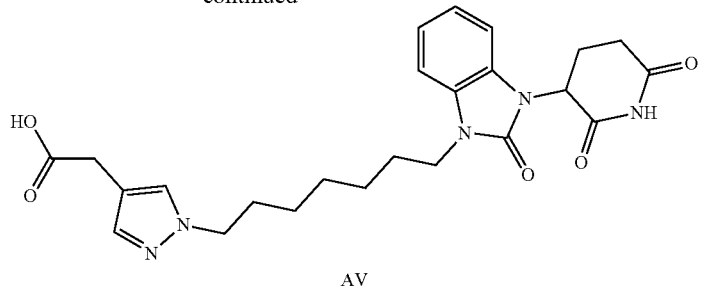

AV

Step 1—Tert-butyl 2-(1-(7-(1-(2,6-dioxopiperidin-3-yl)-3-methyl-2-oxo-2,3-dihydro-1H-benzo[d]imidazol-4-yl)hept-6-yn-1-yl)-1H-pyrazol-4-yl)acetate. To a mixture of 3-(4-bromo-3-methyl-2-oxo-benzimidazol-1-yl)piperidine-2,6-dione (245 mg, 0.72 mmol, Intermediate H), tert-butyl 2-(1-hept-6-ynylpyrazol-4-yl)acetate (200 mg, 0.61 mmol, Intermediate AU), Pd(PPh$_3$)$_2$Cl$_2$ (51 mg, 0.07 mmol) and CuI (14 mg, 0.07 mmol) in DMF (8 mL) was added TEA (110 mg, 1.09 mmol) in one portion. The mixture was stirred at 60° C. for 3 h under N$_2$. On completion, the mixture was concentrated in vacuo and purified by prep-HPLC (column: Phenomenex luna C18 150*25 mm*10 um; mobile phase: [water (0.225% FA)-ACN]; B %: 40%-70%, 11.5 min), then lyophilized to give the title compound (40 mg, 10% yield) as a white solid. LC-MS (ESI$^+$) m/z 534.3 (M+H)$^+$.

Step 2—Tert-butyl 2-(1-(7-(1-(2,6-dioxopiperidin-3-yl)-3-methyl-2-oxo-2,3-dihydro-1H-benzo[d]imidazol-4-yl)heptyl)-1H-pyrazol-4-yl)acetate. To a solution of tert-butyl 2-[1-[7-[1-(2,6-dioxo-3-piperidyl)-3-methyl-2-oxo-benzimidazol-4-yl]hept-6-ynyl]pyrazol-4-yl]acetate (40 mg, 0.07 mmol) in THF (3 mL) was added Pd/C (20 mg, 10 wt %) in one portion. The mixture was stirred at 20° C. for 2 h under H$_2$ (15 psi). On completion, the mixture was filtered and the filtrate was concentrated in vacuo to give the title compound (39 mg, 97% yield) as a colorless oil. LC-MS (ESI$^+$) m/z 538.4 (M+H)$^+$.

Step 3—2-(1-(7-(1-(2,6-Dioxopiperidin-3-yl)-3-methyl-2-oxo-2,3-dihydro-1H-benzo[d]imidazol-4-yl)heptyl)-1H-pyrazol-4-yl)acetic acid. To the solution of tert-butyl 2-[1-[7-[1-(2,6-dioxo-3-piperidyl)-3-methyl-2-oxo-benzimidazol-4-yl]heptyl]pyrazol-4-yl]acetate (39 mg, 0.07 mmol) in DCM (1.5 mL) was added TFA (462 mg, 4.05 mmol) slowly at 0° C. The mixture was stirred at 20° C. for 3 h. On completion, the mixture was concentrated in vacuo to give the title compound (34 mg, 97% yield) as a yellow oil. LC-MS (ESI$^+$) m/z 482.3 (M+H)$^+$.

3-(1-(non-8-yn-1-yl)-1H-pyrazol-4-yl)acetic acid
(Intermediate AW)

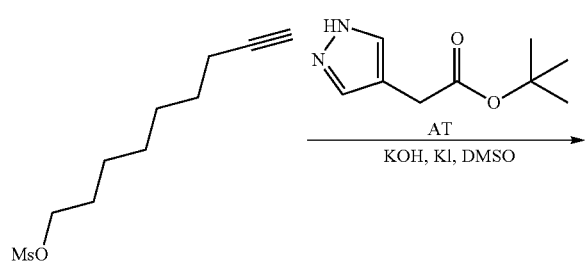

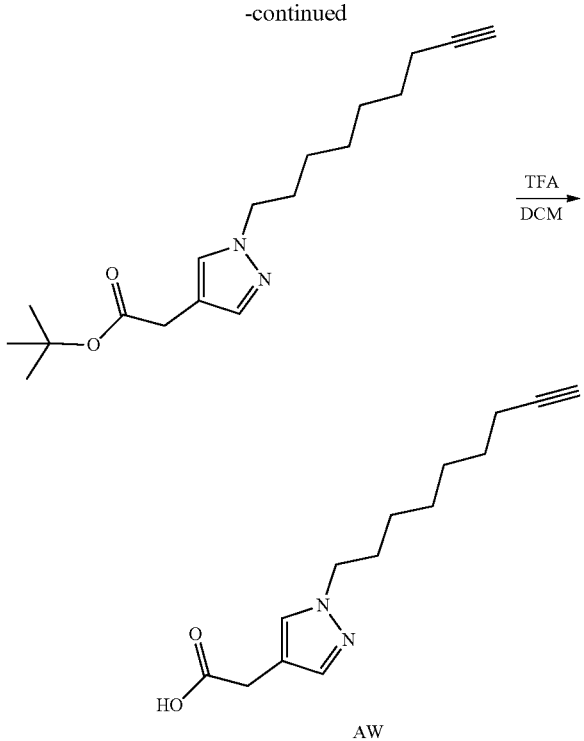

Step 1—Tert-butyl 2-(1-(non-8-yn-1-yl)-1H-pyrazol-4-yl)acetate. To a solution of tert-butyl 2-(1H-pyrazol-4-yl)acetate (667 mg, 3.66 mmol, Intermediate AT) and non-8-yn-1-yl methanesulfonate (1.2 g, 5.50 mmol, synthesized via Step 1 of Intermediate O) in DMSO (14 mL) was added KOH (616 mg, 11.0 mmol) and KI (60.8 mg, 366 umol) at 20° C. under nitrogen flow. Then the reaction was stirred at 50° C. for 10 h under nitrogen atmosphere. On completion, the reaction was poured into ice water (20 mL) and extracted with ethyl acetate (2×25 mL). The combined organic phase was washed with brine (4×10 mL), and dried over sodium sulfate. Then the solution was filtered and the filtrate was concentrated to give a residue. The reaction was purified by column chromatography on silica gel (ethyl acetate=100:1 to 100:30) to give the title compound (0.8 g, 71.7% yield) as colorless oil. $^1$H NMR (400 MHz, CDCl$_3$) δ=7.33 (s, 1H), 7.19 (s, 1H), 4.00 (t, J=7.1 Hz, 2H), 3.32 (s, 2H), 2.10 (dt, J=2.6, 7.1 Hz, 2H), 1.87-1.84 (m, 1H), 1.78 (td, J=7.1, 14.2 Hz, 2H), 1.41-1.22 (m, 18H).

Step 2—3-(1-(Non-8-yn-1-yl)-1H-pyrazol-4-yl)acetic acid. To a solution of tert-butyl 2-(1-(non-8-yn-1-yl)-1H-pyrazol-4-yl)acetate (400 mg, 1.31 mmol) in DCM (5 mL) was added TFA (1.54 g, 13.5 mmol) at 20° C. under nitrogen flow. Then the reaction was stirred at 20° C. for 1 h under nitrogen atmosphere. On completion, the reaction was poured into ice water (8 mL) and extracted with dichloromethane (2×10 mL). The combined organic phase was washed with brine (2×10 mL), and dried over sodium sulfate. Then filtered to get the filtrate and concentrated to give the title compound (370 mg) as colorless oil. $^1$H NMR (400 MHz, CDCl3) δ 7.6 (s, 1H), 7.47 (s, 1H), 4.19 (t, J=7.2 Hz, 2H), 3.59 (s, 2H), 2.21-2.15 (m, 2H), 1.98-1.92 (m, 1H), 1.87 (quin, J=7.2 Hz, 2H), 1.46-1.30 (m, 8H).

(1R,3S)-3-(1-(tert-butyl)-5-(2-(1-(non-8-yn-1-yl)-1H-pyrazol-4-yl)acetamido)-1H-pyrazol-3-yl)cyclopentyl isopropylcarbamate (Intermediate AX)

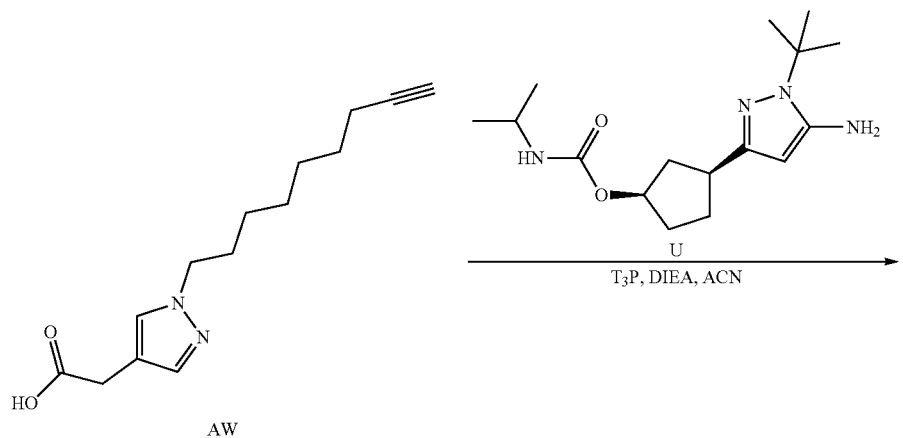

AW

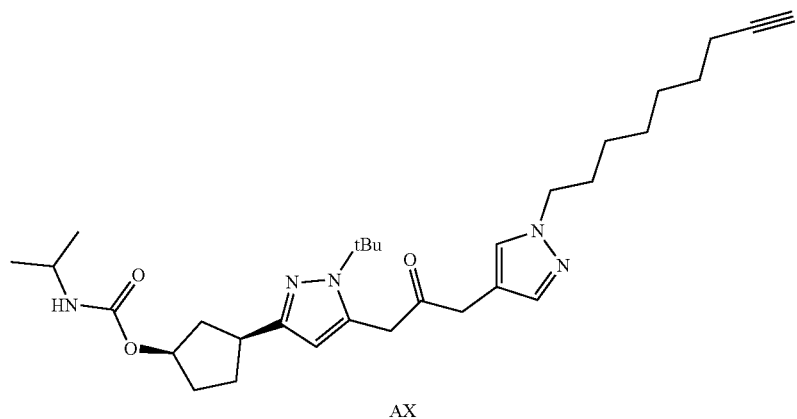

AX

To a solution of (1R,3S)-3-(5-amino-1-(tert-butyl)-1H-pyrazol-3-yl)cyclopentyl isopropylcarbamate (400 mg, 1.30 mmol, Intermediate U) and 2-(1-(non-8-yn-1-yl)-1H-pyrazol-4-yl)acetic acid (611 mg, 2.46 mmol, Intermediate AW) in ACN (4 mL) was added T$_3$P (2.48 g, 3.89 mmol, 50% solution in DMF) and DIEA (838 mg, 6.48 mmol) at 20° C. under nitrogen flow. Then the reaction was stirred at 20° C. for 10 h under nitrogen atmosphere. On completion, the reaction was poured into ice water (10 mL) and extracted with ethyl acetate (2×10 mL). The combined organic phase was washed with brine (2×5 mL), and dried over sodium sulfate. Then filtered to get the filtrate and concentrated to give a residue. The residue was purified by column chromatography on silica gel (petroleum ether:ethyl acetate=100:1 to 100:15) to give the title compound (0.5 g, 928 umol, 72% yield) as colorless oil. $^1$H NMR (400 MHz, CDCl3) δ=7.51 (s, 1H), 7.42 (s, 1H), 7.31 (s, 1H), 6.34 (s, 1H), 5.14 (br s, 1H), 4.64-4.51 (m, 1H), 4.13 (tt, J=3.5, 7.2 Hz, 3H), 3.81 (br d, J=6.6 Hz, 1H), 3.64 (s, 2H), 3.07 (quin, J=8.5 Hz, 1H), 2.44 (td, J=6.9, 13.8 Hz, 1H), 2.24-2.13 (m, 2H), 2.05 (s, 1H), 2.04-1.98 (m, 1H), 1.94 (t, J=2.6 Hz, 1H), 1.92-1.73 (m, 6H), 1.58-1.47 (m, 3H), 1.43 (s, 8H), 1.37-1.30 (m, 4H), 1.18-1.12 (m, 6H).

2-(1-(7-(1-(2,6-dioxopiperidin-3-yl)-3-methyl-2-oxo-2,3-dihydro-1H-benzo[d]imidazol-5-yl)heptyl)-1H-pyrazol-4-yl)acetic acid (Intermediate AY)

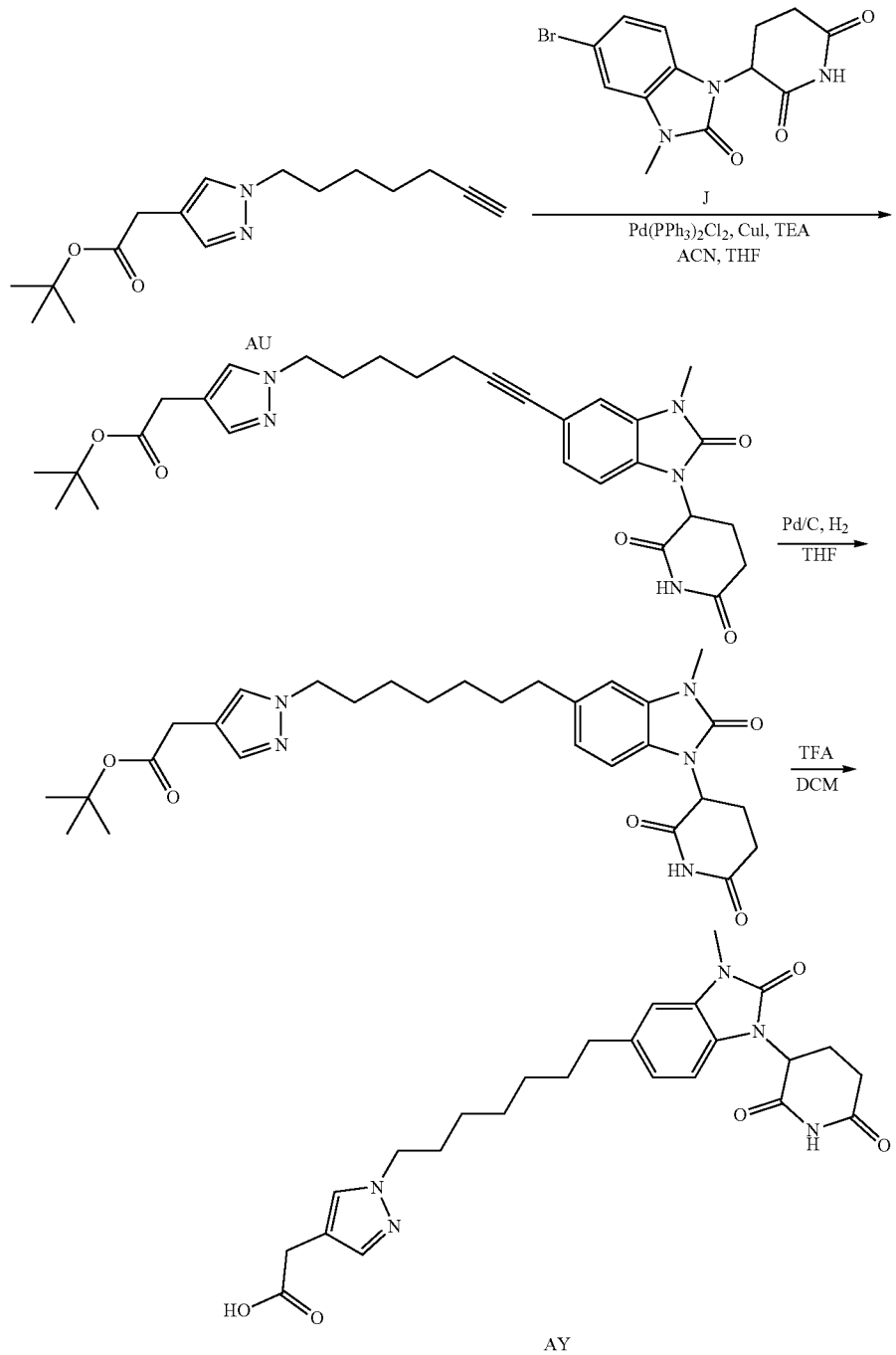

Step 1: tert-butyl 2-(1-(7-(1-(2,6-dioxopiperidin-3-yl)-3-methyl-2-oxo-2,3-dihydro-1H-benzo[d]imidazol-5-yl)hept-6-yn-1-yl)-1H-pyrazol-4-yl)acetate. To a mixture of tert-butyl 2-(1-hept-6-ynylpyrazol-4-yl)acetate (100 mg, 0.30 mmol, Intermediate AU), 3-(5-bromo-3-methyl-2-oxo-benzimidazol-1-yl)piperidine-2,6-dione (122 mg, 0.36 mmol, Intermediate J), Pd(PPh$_3$)$_2$Cl$_2$ (25 mg, 0.04 mmol) and CuI (7 mg, 0.04 mmol) in THF (1.5 mL) and ACN (1.5 mL) was added TEA (55 mg, 0.54 mmol) for one portion. The mixture was stirred at 60° C. for 3 h under N$_2$. On completion, the mixture was filtered and the filtrate was concentrated in vacuo. The mixture was purified by prep-HPLC (column: Phenomenex luna C18 150*25 mm*10 um; mobile phase: [water (0.225% FA)-ACN]; B %: 40%-70%, 11.5 min) and lyophilized to give the title compound (70 mg, 36% yield) as a white solid. LC-MS (ESI$^+$) m/z 534.3 (M+H)$^+$.

Step 2—Tert-butyl 2-(1-(7-(1-(2,6-dioxopiperidin-3-yl)-3-methyl-2-oxo-2,3-dihydro-1H-benzo[d]imidazol-5-yl)heptyl)-1H-pyrazol-4-yl)acetate. To a solution of tert-butyl 2-(1-(7-(1-(2,6-dioxopiperidin-3-yl)-3-methyl-2-oxo-2,3-dihydro-1H-benzo[d]imidazol-5-yl)hept-6-yn-1-yl)-1H-pyrazol-4-yl)acetate (70 mg, 0.13 mmol) in THF (3 mL) was added Pd/C (20 mg, 10 wt %) in one portion. The mixture was stirred at 20° C. for 12 h under H$_2$ atmosphere (15 psi). On completion, the mixture was filtered and the filtrate was concentrated in vacuo to give the title compound (70 mg, 99% yield) as a colorless oil. LC-MS (ESI$^+$) m/z 538.4 (M+H)$^+$.

Step 3—2-(1-(7-(1-(2,6-dioxopiperidin-3-yl)-3-methyl-2-oxo-2,3-dihydro-1H-benzo[d]imidazol-5-yl)heptyl)-1H-pyrazol-4-yl)acetic acid. To a solution of tert-butyl 2-(1-(7-(1-(2,6-dioxopiperidin-3-yl)-3-methyl-2-oxo-2,3-dihydro-1H-benzo[d]imidazol-5-yl)heptyl)-1H-pyrazol-4-yl)acetate (70 mg, 0.13 mmol) in DCM (2 mL) was added TFA (770 mg, 6.75 mmol) slowly at 0° C. The mixture was stirred at 20° C. for 3 h. On completion, the mixture was concentrated in vacuo to give the title compound (62 mg, 99% yield) as a yellow oil. LC-MS (ESI$^+$) m/z 482.3 (M+H)$^+$.

1-(7-bromoimidazo[1,2-a]pyridin-3-yl)hexahydropyrimidine-2,4-dione (Intermediate AZ)

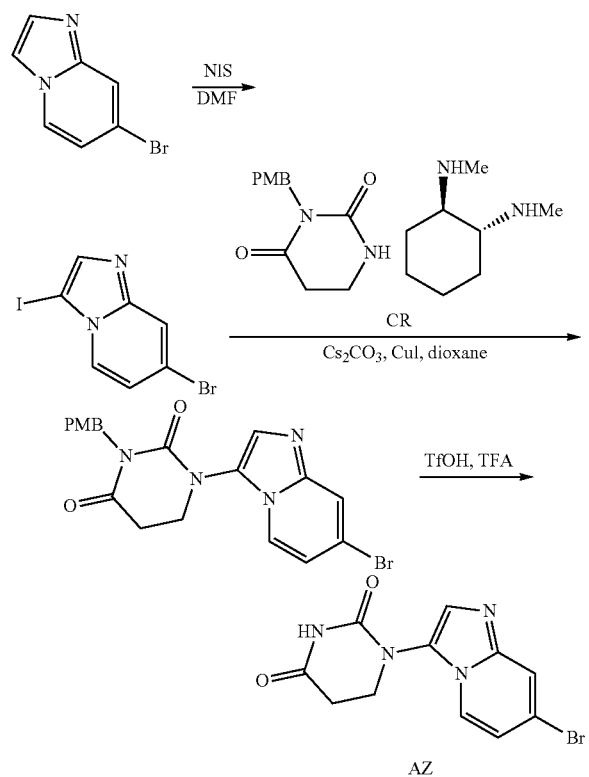

Step 1—7-Bromo-3-iodo-imidazo[1,2-a]pyridine. To a solution of 7-bromoimidazo[1,2-a]pyridine (9.50 g, 48.2 mmol, CAS #808744-34-5) in DMF (150 mL) was added NIS (13.02 g, 57.86 mmol) at 25° C. The mixture was then stirred at 100° C. for 1 hr. On completion, the reaction mixture was poured into 400 mL of water and extracted with EtOAc (200 mL×2). The organic layer was washed by water (200 mL), saturated brine (200 mL), dried over Na$_2$SO$_4$, filtered and concentrated to give the crude product. The crude product was purified by flash silica gel chromatography (ISCO®; 120 g SepaFlash® Silica Flash Column, Eluent of 0~5% Ethyl acetate/Petroleum ether gradient @ 150 mL/min) to give the compound (11.6 g, 74% yield) as black brown solid. $^1$H NMR (400 MHz, CDCl$_3$) δ 8.00 (d, J=7.2 Hz, 1H), 7.82 (d, J=1.2 Hz, 1H), 7.67 (s, 1H), 7.04 (dd, J=2.0, 7.3 Hz, 1H).

Step 2—1-(7-Bromoimidazo[1,2-a]pyridin-3-yl)-3-[(4-methoxyphenyl)methyl]hexahydropyrimidine-2,4-dione. To a solution of 3-[(4-methoxyphenyl)methyl]hexahydropyrimidine-2,4-dione (4.00 g, 17.0 mmol, Intermediate CR), and 7-bromo-3-iodo-imidazo[1,2-a]pyridine (6.62 g, 20.4 mmol) in 1,4-dioxane (80.0 mL) in dioxane was added Cs$_2$CO$_3$ (11.1 g, 34.1 mmol), CuI (650 mg, 3.42 mmol) and (1R,2R)—N1,N2-Dimethyl cyclohexane-1,2-diamine (485 mg, 3.42 mmol) at 25° C. under N$_2$. Then the mixture was stirred at 80° C. for 16 hrs. On completion, the reaction mixture was poured into 200 mL of water and extracted with EtOAc (100 mL×2). The combined organic layers were washed with water (200 mL), saturated brine (200 mL), dried over Na$_2$SO$_4$, filtered and concentrated to give a crude product. The crude product was purified by silica gel chromatography eluted with Petroleum ether/Ethyl acetate=10/1 to 0/1 to give the title compound (2.00 g, 27% yield) as yellow solid. LC-MS (ESI$^+$) m/z 429.0 (M+H)$^+$.

Step 3—1-(7-Bromoimidazo[1,2-a]pyridin-3-yl)hexahydropyrimidine-2,4-dione. A solution of 1-(7-bromoimidazo[1,2-a]pyridin-3-yl)-3-[(4-methoxyphenyl)methyl]hexahydro pyrimidine-2,4-dione (0.90 g, 2.10 mmol) in TFA (10 mL) and TfOH (0.2 mL) was stirred at 60° C. for 4 hours. On completion, the mixture was concentrated to give a residue, then the residue was adjusted pH to 6-7 by TEA at 0° C. The mixture was concentrated to give a residue. The residue was suspended in EtOAc (30 mL) and stirred for 0.5 hr. The suspension was filtered and the filter cake was concentrated in vacuo to give the title compound (485 mg, 73% yield) as yellow solid. $^1$H NMR (400 MHz, DMSO-d$_6$) δ 10.67 (s, 1H), 8.31 (d, J=7.2 Hz, 1H), 7.92 (s, 1H), 7.58 (s, 1H), 7.14 (d, J=6.4 Hz, 1H), 3.80 (t, J=6.4 Hz, 2H), 2.82 (t, J=6.0 Hz, 2H). LC-MS (ESI$^+$) m/z 309.0 (M+H)$^+$.

2-[[5-bromo-2-(2-methyl-4-sulfamoyl-anilino)pyrimidin-4-yl]amino]-6-fluoro-benzamide (Intermediate BA)

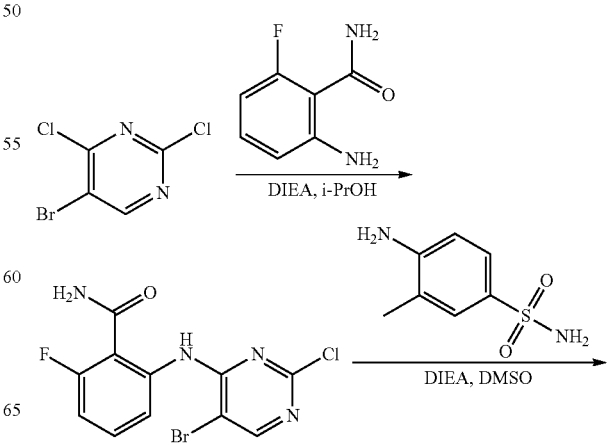

-continued

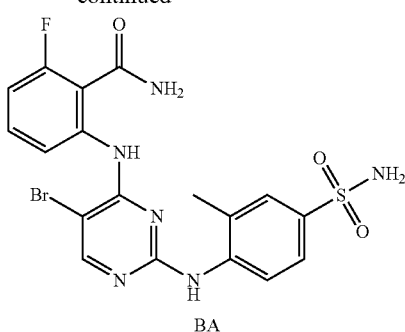

BA

Step 1—2-((5-Bromo-2-chloropyrimidin-4-yl)amino)-6-fluorobenzamide. To a solution of 5-bromo-2,4-dichloropyrimidine (5.00 g, 21.9 mmol, CAS #36082-50-5) and 2-amino-6-fluoro-benzamide (3.72 g, 24.1 mmol, CAS #115463-59-9) in i-PrOH (50 mL) was added DIPEA (5.67 g, 43.8 mmol) in one portion. The resulting mixture was stirred at 90° C. for 24 h to give a yellow solution. On completion, the reaction mixture was filtered through a celite pad and the filtrate was concentrated in vacuo to give the title compound (0.83 g, 72% yield) as a white solid. $^1$H NMR (400 MHz, DMSO-$d_6$) δ=10.64 (s, 1H), 8.57 (s, 1H), 8.23-8.14 (m, 2H), 8.09 (d, J=8.4 Hz, 1H), 7.60-7.54 (m, 1H), 7.15-7.09 (m, 1H); LC/MS (ESI, m/z): [M+1]$^+$=346.7.

Step 2—2-((5-Bromo-2-((2-methyl-4-sulfamoylphenyl) amino)pyrimidin-4-yl)amino)-6-fluorobenzamide. To a solution of 2-((5-bromo-2-chloropyrimidin-4-yl)amino)-6-fluorobenzamide (200 mg, 0.57 mmol) and 4-amino-3-methyl-benzenesulfonamide (108 mg, 0.57 mmol, CAS #53297-70-4) in 2-butanol (3 mL) was added TFA (770 mg, 6.75 mmol) in one portion. The resulting mixture was stirred at 100° C. for 24 h. On completion, the reaction mixture was filtered through a celite pad and the filtrate was concentrated in vacuo. The crude product was triturated with EtOH at 25° C. for 30 min to give the title compound (55 mg, 18% yield) as a purple solid. $^1$H NMR (400 MHz, CDCl$_3$) δ=6.30-6.27 (m, 1H), 6.29-6.27 (m, 1H), 6.22 (s, 1H), 4.46-4.44 (m, 2H), 4.19-4.17 (m, 1H), 4.14-4.12 (m, 3H), 3.9-3.96 (m, 2H), 3.93-3.92 (m, 3H), 2.26 (s, 2H); LC/MS (ESI, m/z): [M+1]$^+$=469.9.

4-((5-bromo-4-((2-carbamoyl-3-fluorophenyl)amino) pyrimidin-2-yl)amino)-3-methylbenzene-1-sulfonyl chloride (Intermediate BB)

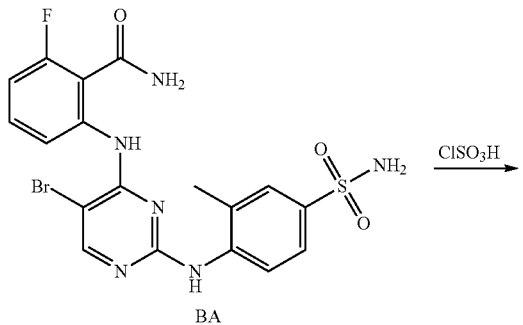

BA

-continued

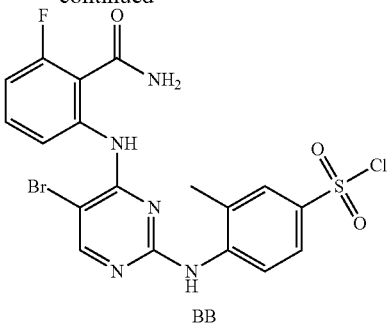

BB

A solution of 2-[[5-bromo-2-(2-methyl-4-sulfamoyl-anilino)pyrimidin-4-yl]amino]-6-fluoro-benzamide (100 mg, 0.20 mmol) in ClSO$_3$H (0.20 mmol, 2 mL) was stirred at 80° C. for 2 h. On completion, the reaction mixture was poured into the ice. The mixture was then extracted with CH$_2$Cl$_2$ (20 mL). The organic phase was separated, dried over Na$_2$SO$_4$, filtered and concentrated under reduced pressure to give the title compound (100 mg, 71% yield) as a yellow solid. LC-MS (ESI$^+$) m/z 515.9 (M+H)$^+$.

1-(Non-8-yn-1-yl)-1H-pyrazole-4-carboxylic acid (Intermediate BC)

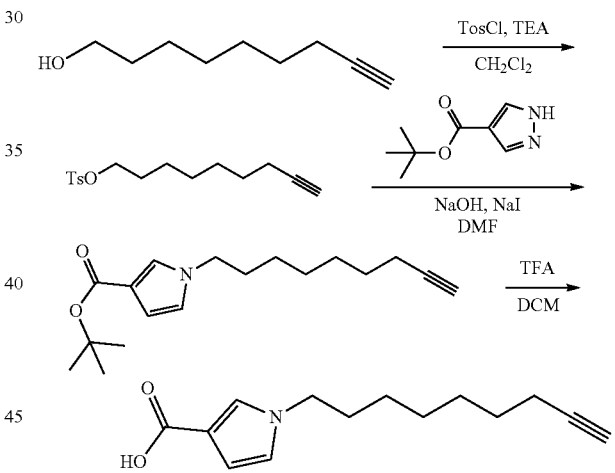

BC

Step 1—Non-8-yn-1-yl 4-methylbenzenesulfonate. To a mixture of non-8-yn-1-ol (1.50 g, 10.7 mmol, CAS #10160-28-8) in DCM (20 mL) was added TosCl (2.65 g, 13.90 mmol) and TEA (3.25 g, 32.10 mmol) at 0° C., then the mixture was stirred at 25° C. for 2 h. The reaction mixture was partitioned between DCM (10 mL) and H$_2$O (5 mL). The organic phase was separated, dried over Na$_2$SO$_4$, filtered and concentrated under reduced pressure to give a residue. The residue was purified by flash silica gel chromatography (ISCO®; 40 g SepaFlash® Silica Flash Column, Eluent of 0~13% Ethyl acetate/Petroleum ether gradient @ 60 mL/min) to give the title compound (2.80 g, 67% yield) as a colorless oil. $^1$H NMR (400 MHz, DMSO-$d_6$) δ=7.78 (d, J=8.4 Hz, 2H), 7.47 (d, J=8.0 Hz, 2H), 4.00 (t, J=6.4 Hz, 2H), 2.69 (t, J=2.8 Hz, 1H), 2.41 (s, 3H), 2.10 (dt, J$_1$=7.2 Hz, J$_2$=2.4 Hz, 2H), 1.58-1.50 (m, 2H), 1.39-1.32 (m, 2H), 1.29-1.13 (m, 6H).

Step 2—Tert-butyl 1-(non-8-yn-1-yl)-1H-pyrazole-4-carboxylate. To a mixture of non-8-ynyl 4-methylbenzenesulfonate (2.80 g, 7.13 mmol), tert-butyl 1H-pyrazole-4-carboxylate (1.00 g, 5.95 mmol, CAS #611239-23-7) and NaOH (713 mg, 17.8 mmol) in DMF (20 mL) was added NaI (89 mg, 0.60 mmol) in one portion, then the mixture was stirred at 50° C. for 1 h. The reaction mixture was partitioned between EtOAc (10 mL) and H$_2$O (10 mL). The organic phase was separated, washed with brine (5 mL×3), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~22% Ethyl acetate/Petroleum ether gradient @ 50 mL/min) to give the title compound (1.30 g, 75% yield) as a colorless oil. LC-MS (ESI$^+$) m/z 292.2 (M+H)$^+$.

Step 3—1-(Non-8-yn-1-yl)-1H-pyrazole-4-carboxylic acid. To a mixture of tert-butyl 1-non-8-ynylpyrazole-4-carboxylate (1.30 g, 4.48 mmol) in DCM (9 mL) was added TFA (4.62 g, 40.5 mmol), then the mixture was stirred at 25° C. for 12 h. On completion, the reaction mixture was filtered. The crude product was purified by reverse phase flash (FA condition) to give the title compound (950 mg, 91% yield) as a light yellow solid. LC-MS (ESI$^+$) m/z 235.4 (M+H)$^+$. $^1$H NMR (400 MHz, DMSO-d$_6$) δ=13.00-11.35 (m, 1H), 8.24 (s, 1H), 7.78 (s, 1H), 4.11 (t, J=6.8 Hz, 2H), 2.72 (t, J=2.8 Hz, 1H), 2.13 (dt, J$_1$=6.8 Hz, J$_2$=2.8 Hz, 2H), 1.79-1.73 (m, 2H), 1.43-1.37 (m, 2H), 1.33-1.25 (m, 4H), 1.21-1.16 (m, 2H).

(1R,3S)-3-(1-(tert-butyl)-5-(1-(non-8-yn-1-yl)-1H-pyrazole-4-carboxamido)-1H-pyrazol-3-yl)cyclopentyl isopropylcarbamate (Intermediate BD)

To a mixture of 1-(non-8-yn-1-yl)-1H-pyrazole-4-carboxylic acid (137 mg, 0.58 mmol, Intermediate BC) and (1R,3S)-3-(5-amino-1-(tert-butyl)-1H-pyrazol-3-yl)cyclopentyl isopropylcarbamate (150 mg, 0.49 mmol, Intermediate U) in MeCN (2 mL) was added T$_3$P (464 mg, 1.46 mmol, 50% solution in DMF) and DIPEA (94 mg, 0.73 mmol) in one portion, then the mixture was stirred at 50° C. for 48 h. On completion, the reaction mixture was concentrated in vacuo. The residue was purified by flash silica gel chromatography (ISCO®; 25 g SepaFlash® Silica Flash Column, Eluent of 0~50% Ethylacetate/Petroleum ether gradient @ 50 mL/min) to give the title compound (150 mg, 56% yield) as a white gum. LC-MS (ESI$^+$) m/z 525.2 (M+H)$^+$.

1-(2-(2-(2-(prop-2-yn-1-yloxy)ethoxy)ethoxy)ethyl)-1H-pyrazole-5-carboxylic acid (Intermediate BE)

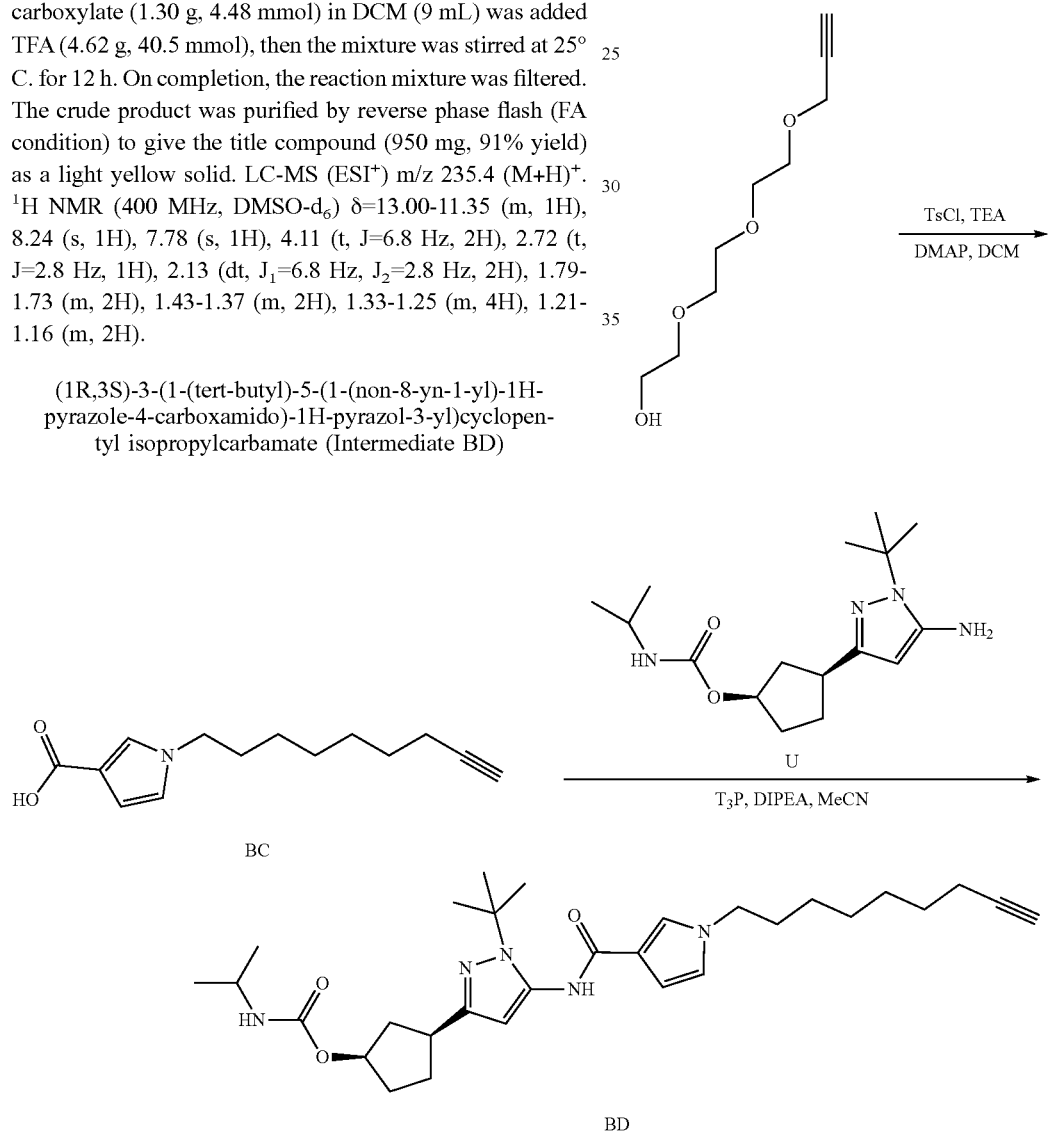

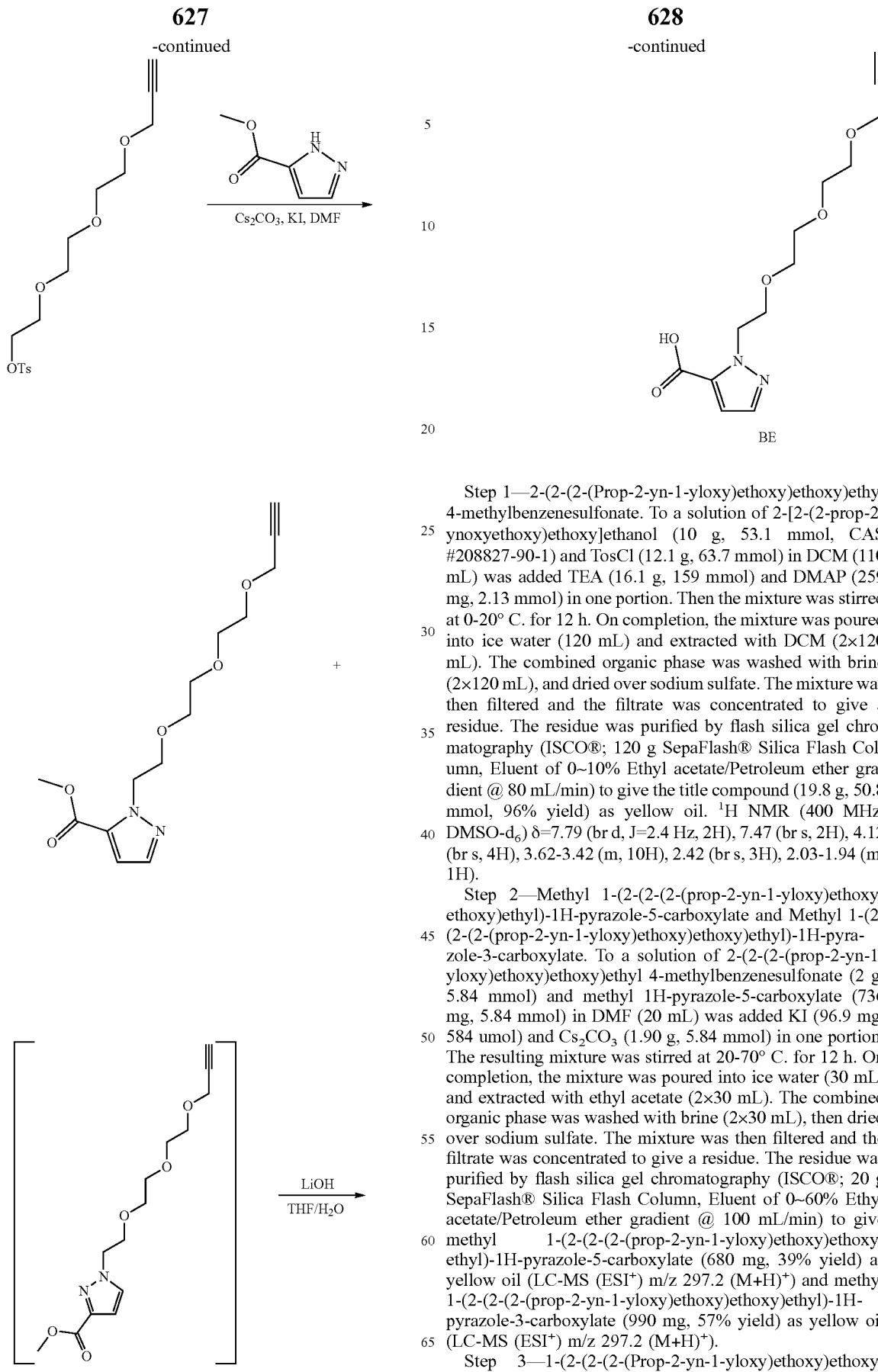

Step 1—2-(2-(2-(Prop-2-yn-1-yloxy)ethoxy)ethoxy)ethyl 4-methylbenzenesulfonate. To a solution of 2-[2-(2-prop-2-ynoxyethoxy)ethoxy]ethanol (10 g, 53.1 mmol, CAS #208827-90-1) and TosCl (12.1 g, 63.7 mmol) in DCM (110 mL) was added TEA (16.1 g, 159 mmol) and DMAP (259 mg, 2.13 mmol) in one portion. Then the mixture was stirred at 0-20° C. for 12 h. On completion, the mixture was poured into ice water (120 mL) and extracted with DCM (2×120 mL). The combined organic phase was washed with brine (2×120 mL), and dried over sodium sulfate. The mixture was then filtered and the filtrate was concentrated to give a residue. The residue was purified by flash silica gel chromatography (ISCO®; 120 g SepaFlash® Silica Flash Column, Eluent of 0~10% Ethyl acetate/Petroleum ether gradient @ 80 mL/min) to give the title compound (19.8 g, 50.8 mmol, 96% yield) as yellow oil. $^1$H NMR (400 MHz, DMSO-$d_6$) δ=7.79 (br d, J=2.4 Hz, 2H), 7.47 (br s, 2H), 4.12 (br s, 4H), 3.62-3.42 (m, 10H), 2.42 (br s, 3H), 2.03-1.94 (m, 1H).

Step 2—Methyl 1-(2-(2-(2-(prop-2-yn-1-yloxy)ethoxy)ethoxy)ethyl)-1H-pyrazole-5-carboxylate and Methyl 1-(2-(2-(2-(prop-2-yn-1-yloxy)ethoxy)ethoxy)ethyl)-1H-pyrazole-3-carboxylate. To a solution of 2-(2-(2-(prop-2-yn-1-yloxy)ethoxy)ethoxy)ethyl 4-methylbenzenesulfonate (2 g, 5.84 mmol) and methyl 1H-pyrazole-5-carboxylate (736 mg, 5.84 mmol) in DMF (20 mL) was added KI (96.9 mg, 584 umol) and $Cs_2CO_3$ (1.90 g, 5.84 mmol) in one portion. The resulting mixture was stirred at 20-70° C. for 12 h. On completion, the mixture was poured into ice water (30 mL) and extracted with ethyl acetate (2×30 mL). The combined organic phase was washed with brine (2×30 mL), then dried over sodium sulfate. The mixture was then filtered and the filtrate was concentrated to give a residue. The residue was purified by flash silica gel chromatography (ISCO®; 20 g SepaFlash® Silica Flash Column, Eluent of 0~60% Ethyl acetate/Petroleum ether gradient @ 100 mL/min) to give methyl 1-(2-(2-(2-(prop-2-yn-1-yloxy)ethoxy)ethoxy)ethyl)-1H-pyrazole-5-carboxylate (680 mg, 39% yield) as yellow oil (LC-MS (ESI$^+$) m/z 297.2 (M+H)$^+$) and methyl 1-(2-(2-(2-(prop-2-yn-1-yloxy)ethoxy)ethoxy)ethyl)-1H-pyrazole-3-carboxylate (990 mg, 57% yield) as yellow oil (LC-MS (ESI$^+$) m/z 297.2 (M+H)$^+$).

Step 3—1-(2-(2-(2-(Prop-2-yn-1-yloxy)ethoxy)ethoxy)ethyl)-1H-pyrazole-5-carboxylic acid. To a solution of methyl 1-(2-(2-(2-(prop-2-yn-1-yloxy)ethoxy)ethoxy)ethyl)-1H-pyrazole-5-carboxylate (326 mg, 1.10 mmol) in THF (3 mL) and H₂O (1 mL) was added LiOH·H₂O (184 mg, 4.40 mmol) at 0° C. The mixture was then stirred at 0-20° C. for 2 h. On completion, the mixture was poured into ice water (4 mL) and extracted with ethyl acetate (2×4 mL). The aqueous phase was acidified with aqueous HCl to pH=2 and extracted with ethyl acetate (2×4 mL). The combined organic phase was washed with brine (2×4 mL), then dried over sodium sulfate. The mixture was filtered and the filtrate was concentrated to give the title compound (280 mg) as yellow oil. LC-MS (ESI⁺) m/z 283.3 (M+H)⁺.

(1R,3S)-3-(1-(tert-butyl)-5-(1-(2-(2-(2-(prop-2-yn-1-yloxy)ethoxy)ethoxy)ethyl)-1H-pyrazole-5-carboxamido)-1H-pyrazol-3-yl)cyclopentyl isopropylcarbamate (Intermediate BF)

To a solution of 2-[2-[2-(2-prop-2-ynoxyethoxy)ethoxy]ethyl]pyrazole-3-carboxylic acid (280 mg, 991.88 umol, Intermediate BE) and (1R,3S)-3-(5-amino-1-(tert-butyl)-1H-pyrazol-3-yl)cyclopentyl isopropylcarbamate (367 mg, 1.19 mmol, Intermediate U) in ACN (5 mL) was added T₃P (1.89 g, 2.98 mmol, 50% solution in DMF) and DIEA (641 mg, 4.96 mmol) in one portion. The resulting mixture was stirred at 20-60° C. for 12 h. On completion, the mixture was poured into ice water (10 mL) and extracted with ethyl acetate (2×10 mL). The combined organic phase was washed with brine (2×10 mL), and dried over sodium sulfate. The mixture was filtered and the filtrate was concentrated to give a residue. The residue was purified by column chromatography (SiO₂, Petroleum ether/Ethyl acetate=1/0 to 1/1) to give the title compound (530 mg, 890 umol, 90% yield) as yellow oil. LC-MS (ESI⁺) m/z 573.3 (M+H)⁺.

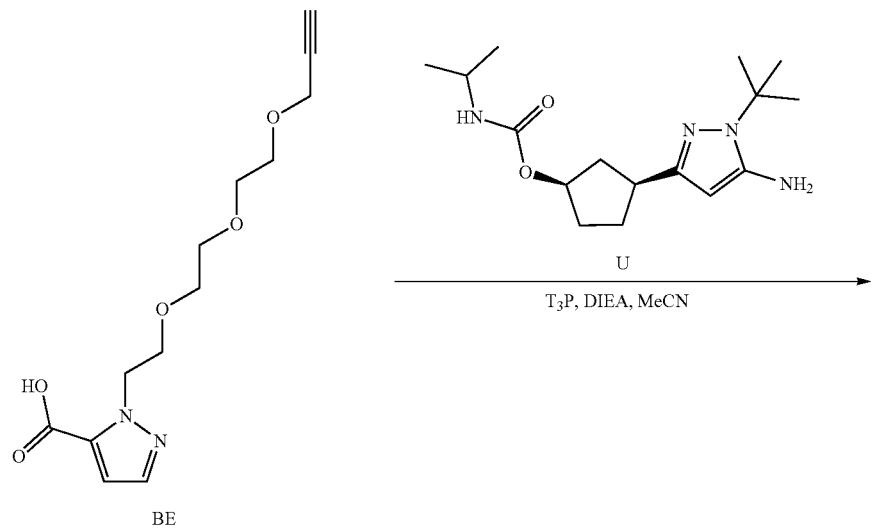

BE

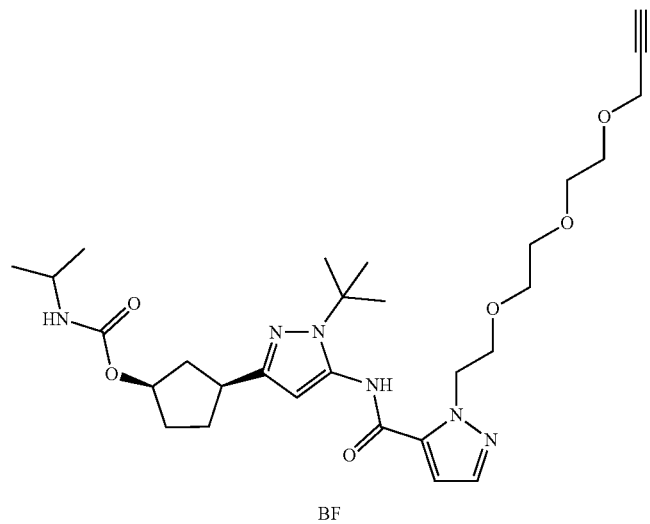

BF 1-(2-(4-(tert-butoxycarbonyl)piperazin-1-yl)ethyl)-1H-pyrazole-5-carboxylic acid (Intermediate BG)

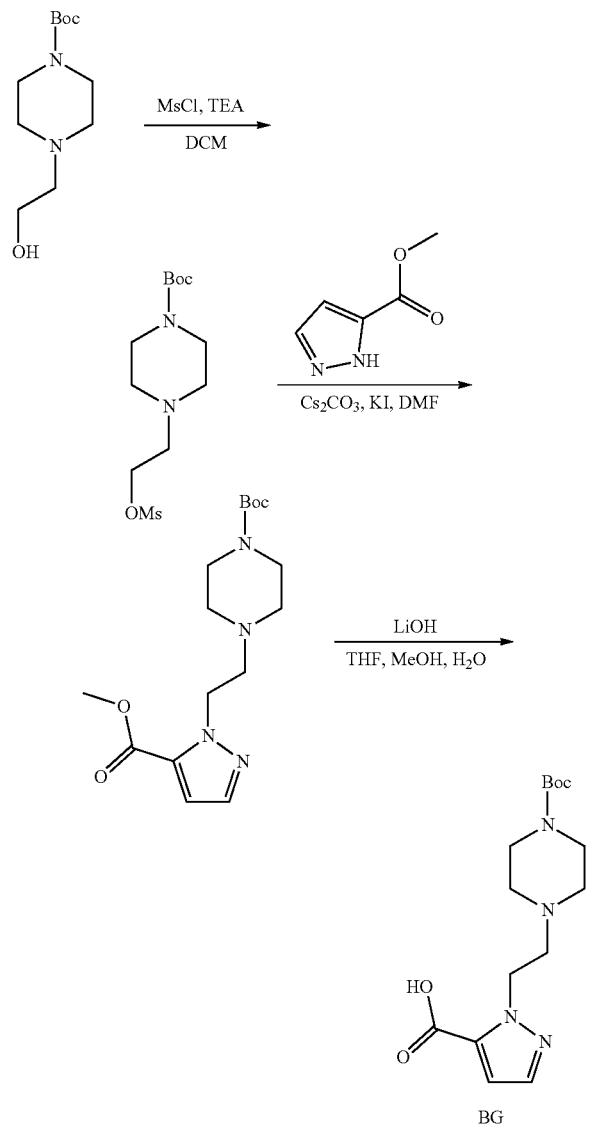

Step 1—Tert-butyl 4-(2-((methylsulfonyl)oxy)ethyl)piperazine-1-carboxylate. To a solution of tert-butyl 4-(2-hydroxyethyl)piperazine-1-carboxylate (2 g, 8.68 mmol, CAS #77279-24-4) and TEA (1.32 g, 13.0 mmol, 1.81 mL) in DCM (30 mL) was added a solution of MsCl (1.19 g, 10.4 mmol) in DCM (10 mL) dropwise slowly at 0° C. under nitrogen flow. Then the reaction was stirred at 20° C. for 2 h under nitrogen atmosphere. On completion, the mixture was poured into saturated NaHCO₃ aqueous solution (50 mL) at 0° C. and extracted with dichloromethane (40 mL×2). The combined organic phase was washed with brine (40 mL×2), and dried over sodium sulfate. The mixture was filtered and the filtrate was concentrated to give the title compound (2.8 g) as a yellow oil.

Step 2—tert-butyl 4-(2-(5-(methoxycarbonyl)-1H-pyrazol-1-yl)ethyl)piperazine-1-carboxylate. To a solution of tert-butyl 4-(2-((methylsulfonyl)oxy)ethyl)piperazine-1-carboxylate (2.8 g, 9.08 mmol) and methyl 1H-pyrazole-5-carboxylate (1.15 g, 9.08 mmol, CAS #15366-34-4) in DMF (40 mL) was added KI (15 mg, 907 umol) and Cs₂CO₃ (14.8 g, 45.4 mmol) at 20° C. under nitrogen flow. Then the reaction was stirred at 70° C. for 10 h under nitrogen atmosphere. On completion, the reaction was poured into ice water (40 mL) and extracted with ethyl acetate (50 mL×2). The combined organic phase is washed with brine (30 mL×2), then dried over sodium sulfate. The mixture was filtered and the filtrate was concentrated to give a residue. The residue was purified by prep-HPLC [column: YMC Triart C18 250*50 mm*7 um; mobile phase: [water (0.05% ammonia hydroxide v/v)-ACN]; B %: 38%-68%, 22 min] to give the title compound (0.55 g, 18% yield) as a colorless oil. ¹H NMR (400 MHz, CDCl₃) δ=7.42 (d, J=2.0 Hz, 1H), 6.72 (d, J=2.0 Hz, 1H), 4.64 (t, J=6.8 Hz, 2H), 3.8 (s, 3H), 3.31 (br s, 4H), 2.72 (br t, J=6.4 Hz, 2H), 2.39 (br s, 4H), 1.38 (s, 9H).

Step 3—1-(2-(4-(tert-butoxycarbonyl)piperazin-1-yl)ethyl)-1H-pyrazole-5-carboxylic acid. To a solution of methyl tert-butyl 4-(2-(5-(methoxycarbonyl)-1H-pyrazol-1-yl)ethyl)piperazine-1-carboxylate (0.16 g, 579 umol) in THF (2 mL), MeOH (1 mL) and H₂O (1 mL) was added LiOH·H₂O (97.2 mg, 2.32 mmol) at 0° C. under nitrogen flow. Then the reaction was stirred at 20° C. for 10 h under nitrogen atmosphere. On completion, the reaction was concentrated to give a residue. The residue was purified by prep-HPLC (column: Phenomenex luna C18 150*25 mm*10 um; mobile phase: [water (0.225% FA)-ACN]; B %: 1%-25%, 11.5 min) and lyophilized to give the title compound (15 mg, 98.7% yield) as colorless oil. ¹H NMR (400 MHz, DMSO-d₆) δ 7.45 (d, J=2.0 Hz, 1H), 6.67 (d, J=0.0 Hz, 1H), 4.62 (t, J=6.4 Hz, 2H), 3.23 (d, J=2.4 Hz, 2H), 2.89 (s, 3H), 2.77-2.70 (m, 5H), 2.43 (br s, 3H).

(1R,3S)-3-(1-(tert-butyl)-5-(1-(2-(4-(prop-2-yn-1-yl)piperazin-1-yl)ethyl)-1H-pyrazole-5-carboxamido)-1H-pyrazol-3-yl)cyclopentyl isopropylcarbamate (Intermediate BH)

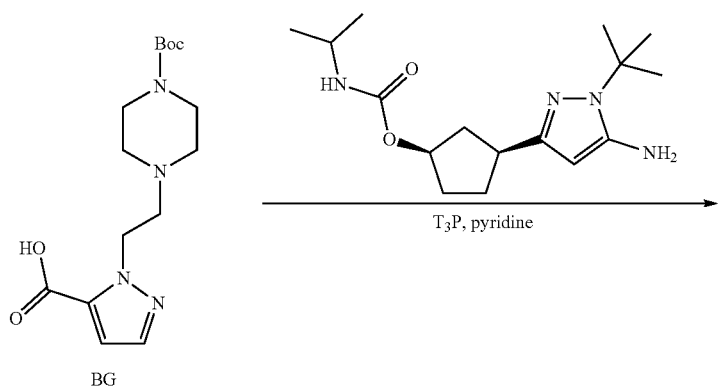

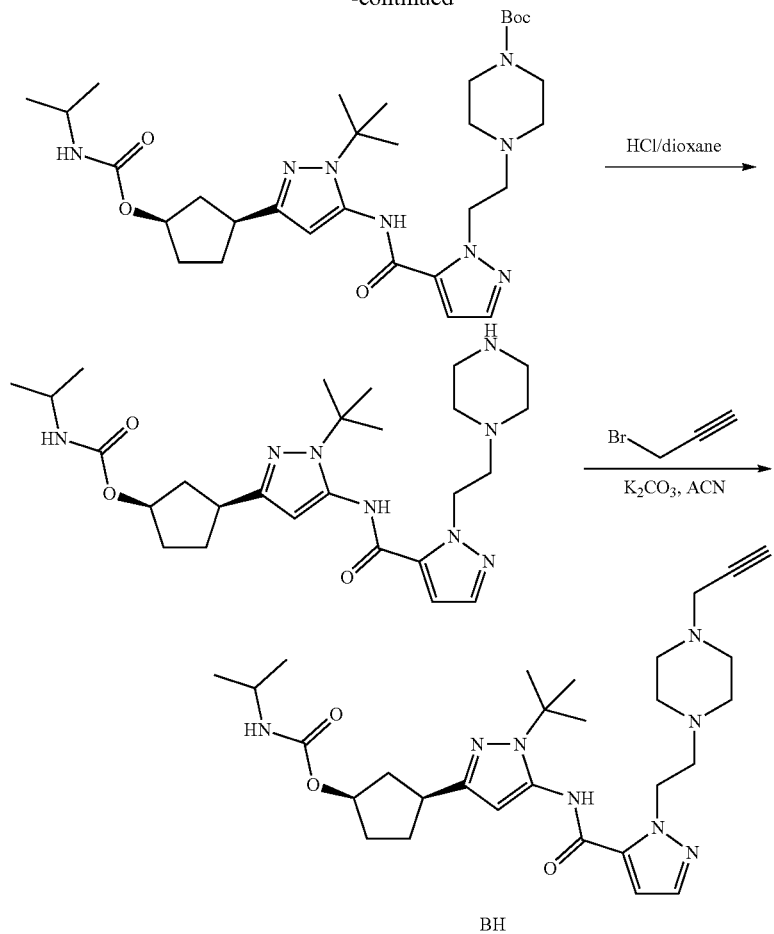

BH

Step 1—Tert-butyl 4-(2-(5-((1-(tert-butyl)-3-((1S,3R)-3-((isopropylcarbamoyl)oxy)cyclopentyl)-1H-pyrazol-5-yl)carbamoyl)-1H-pyrazol-1-yl)ethyl)piperazine-1-carboxylate. To a solution of (1R,3S)-3-(5-amino-1-(tert-butyl)-1H-pyrazol-3-yl)cyclopentyl isopropylcarbamate (1.15 g, 3.73 mmol, Intermediate U) and 1-(2-(4-(tert-butoxycarbonyl)piperazin-1-yl)ethyl)-1H-pyrazole-5-carboxylic acid (1.1 g, 3.39 mmol, Intermediate BG) in ACN (22 mL) was added T$_3$P (6.47 g, 10.17 mmol, 50% solution) and DIEA (2.19 g, 16.96 mmol) at 0° C. under nitrogen flow. Then the reaction was stirred at 20-60° C. for 10 h under nitrogen atmosphere. On completion, the reaction was poured into ice water (30 mL) and extracted with ethyl acetate (30 mL×2). The combined organic phase was washed with brine (30 mL×2), then dried over sodium sulfate. The mixture was filtered and the filtrate was concentrated to give a residue. The residue was purified by column chromatography on silica gel (petroleum ether:ethyl acetate=100:1 to 0:100) to give the title compound (1.1 g, 1.79 mmol, 52.7% yield) as colorless oil. $^1$H NMR (400 MHz, CDCl3) δ=7.54 (d, J=2.0 Hz, 1H), 6.67 (br s, 1H), 6.20 (s, 1H), 5.13 (br s, 1H), 4.74 (t, J=6.4 Hz, 2H), 4.68-4.54 (m, 1H), 3.49-3.27 (m, 4H), 3.16-3.02 (m, 1H), 2.92-2.79 (m, 2H), 2.54-2.37 (m, 5H), 1.89-1.73 (m, 4H), 1.66-1.58 (m, 8H), 1.49-1.39 (m, 11H), 1.19-1.09 (m, 6H).

Step 2—(1R,3S)-3-(1-(tert-butyl)-5-(1-(2-(piperazin-1-yl)ethyl)-1H-pyrazole-5-carboxamido)-1H-pyrazol-3-yl)cyclopentyl isopropylcarbamate. A solution of tert-butyl 4-(2-(5-((1-(tert-butyl)-3-((1S,3R)-3-((isopropylcarbamoyl)oxy)cyclopentyl)-1H-pyrazol-5-yl)carbamoyl)-1H-pyrazol-1-yl)ethyl)piperazine-1-carboxylate (0.6 g, 975 umol) in HCl/dioxane (4 M, 10 mL) was stirred at 20° C. for 1 h. On completion, the reaction was concentrated to give the title compound (502 mg, crude) as colorless oil. LC-MS (ESI$^+$) m/z 645.2 (M+H)$^+$.

Step 3—(1R,3S)-3-(1-(tert-butyl)-5-(1-(2-(4-(prop-2-yn-1-yl)piperazin-1-yl)ethyl)-1H-pyrazole-5-carboxamido)-1H-pyrazol-3-yl)cyclopentyl isopropylcarbamate. To a solution of (1R,3S)-3-(1-(tert-butyl)-5-(1-(2-(piperazin-1-yl)ethyl)-1H-pyrazole-5-carboxamido)-1H-pyrazol-3-yl)cyclopentyl isopropylcarbamate (502 mg, 975 umol) in ACN (10 mL) was added K$_2$CO$_3$ (1.35 g, 9.75 mmol) and 3-bromoprop-1-yne (116 mg, 780 umol, 80% solution) at 0° C. under nitrogen flow. Then the reaction was stirred at 20° C. for 10 h under nitrogen atmosphere. On completion, the reaction was poured into ice water (15 mL) and extracted with ethyl acetate (20 mL×2). The combined organic phase was washed with brine (20 mL×2), then dried over sodium sulfate. The mixture was then filtered and the filtrate was concentrated to give a residue. The residue was purified by column chromatography on silica gel (petroleum ether:ethyl acetate=100:1 to 100:70) to give the title compound (0.45 g, 814 umol, 83.4% yield) as a yellow oil. $^1$H NMR (400 MHz, CDCl3) δ=7.56 (s, 1H), 6.71-6.59 (m, 1H), 6.27 (s, 1H), 5.26-5.08 (m, 1H), 4.91-4.69 (m, 2H), 4.63-4.49 (m, 1H), 3.87-3.69 (m, 3H), 3.40-3.22 (m, 2H), 3.17-2.41 (m, 13H), 2.02-1.74 (m, 7H), 1.66 (s, 9H), 1.64-1.61 (m, 3H), 1.44 (s, 3H), 1.15 (dd, J=2.0, 6.4 Hz, 8H).

1-(2-(2-(2-(prop-2-yn-1-yloxy)ethoxy)ethoxy)ethyl)-1H-pyrazole-4-carboxylic acid (Intermediate BI)

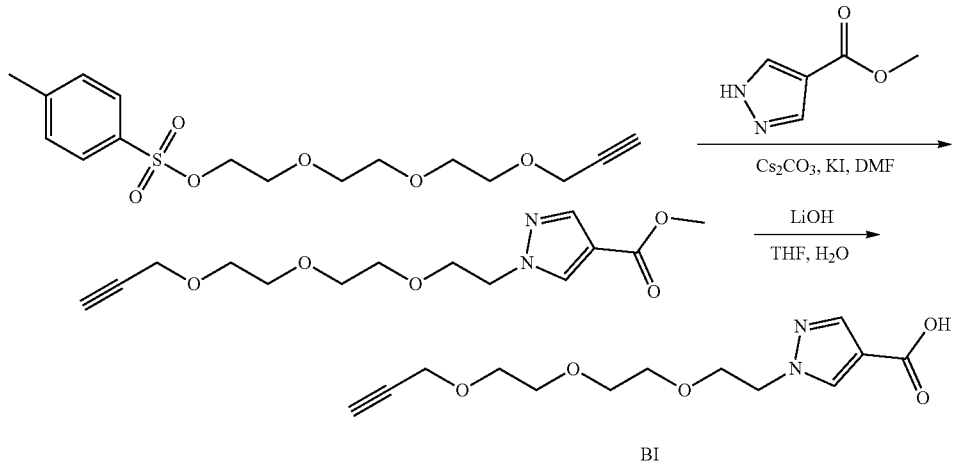

Step 1—Methyl 1-(2-(2-(2-(prop-2-yn-1-yloxy)ethoxy)ethoxy)ethyl)-1H-pyrazole-4-carboxylate. To a solution of 2-(2-(2-(prop-2-yn-1-yloxy)ethoxy)ethoxy)ethyl 4-methylbenzenesulfonate (1.21 g, 3.55 mmol, synthesized via Step 1 of Intermediate BE), KI (58.9 mg, 355 umol) and $Cs_2CO_3$ (3.47 g, 10.6 mmol) in DMF (13 mL) was added methyl 1H-pyrazole-4-carboxylate (537 mg, 4.26 mmol, CAS #181997-36-4) at 25° C., then the mixture was stirred at 70° C. for 2 h. On completion, the mixture was quenched with water (30 mL), and diluted with EtOAc (20 mL×3). The organic layer was washed with brine (20 mL×3) and dried with $Na_2SO_4$, then concentrated in vacuo. The residue was purified by column chromatography ($SiO_2$, Petroleum ether/Ethyl acetate=5/1 to 0/1) to give the title compound (1.10 g, 94% yield) as a colorless solid. $^1$H NMR (400 MHz, $CDCl_3$) δ=8.02 (s, 1H), 7.91 (s, 1H), 4.31 (t, J=5.2 Hz, 2H), 4.20 (d, J=2.4 Hz, 2H), 3.86 (t, J=5.2 Hz, 3H), 3.83 (s, 3H), 3.72-3.63 (m, 5H), 3.62-3.58 (m, 4H). LC-MS ($ESI^+$) m/z 297.2 $(M+H)^+$.

Step 2—1-(2-(2-(2-(prop-2-yn-1-yloxy)ethoxy)ethoxy)ethyl)-1H-pyrazole-4-carboxylic acid. A mixture of methyl methyl 1-(2-(2-(2-(prop-2-yn-1-yloxy)ethoxy)ethoxy)ethyl)-1H-pyrazole-4-carboxylate (1.00 g, 3.37 mmol) and $LiOH·H_2O$ (566 mg, 13.5 mmol) in THF (12 mL) and $H_2O$ (4 mL) was stirred at 25° C. for 12 h. On completion, the mixture was quenched with sat. $NH_4Cl$ (20 mL), diluted with EtOAc (20 mL), and extracted with water (20 mL). Then the water layer was acidified with HCl (1N, 4 mL) to pH<4, and extracted with EtOAc (20 mL×2). The combined organic layer was washed with brine (20 mL×3), dried by $Na_2SO_4$, and concentrated in vacuo. The residue was purified by column chromatography ($SiO_2$, Petroleum ether/Ethyl acetate=5/1 to 0/1) to give the title compound (300 mg, 28%) as a colorless oil. $^1$H NMR (400 MHz, $CDCl_3$) δ=8.11 (s, 1H), 7.97 (s, 1H), 4.35 (t, J=5.2 Hz, 2H), 4.21 (d, J=2.4 Hz, 2H), 3.87 (t, J=5.2 Hz, 2H), 3.72-3.69 (m, 2H), 3.67-3.64 (m, 2H), 2.44 (t, J=2.4 Hz, 1H), 2.12 (s, 1H). LC-MS ($ESI^+$) m/z 283.1 $(M+H)^+$.

(1S,3R)-3-(1-(tert-butyl)-5-(1-(2-(2-(2-(prop-2-yn-1-yloxy)ethoxy)ethoxy)ethyl)-1H-pyrazole-4-carboxamido)-1H-pyrazol-3-yl)cyclopentyl isopropylcarbamate (Intermediate BJ)

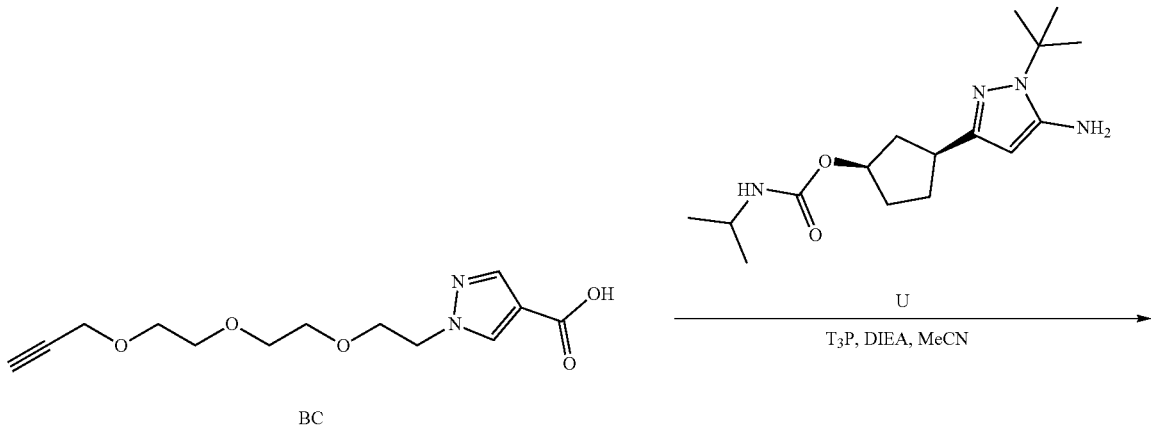

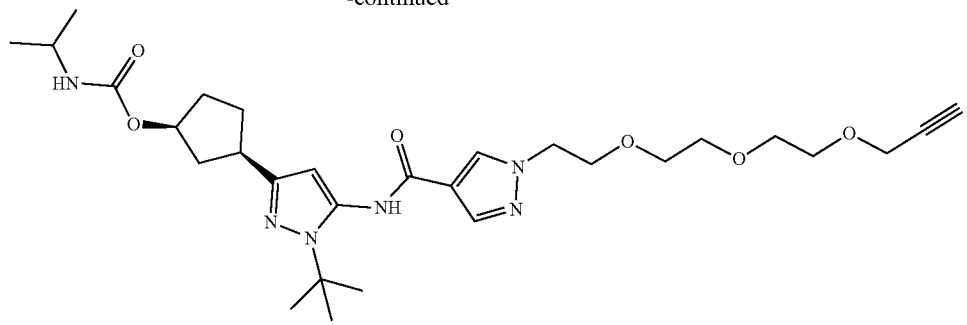

BJ

A solution of 1-(2-(2-(2-(prop-2-yn-1-yloxy)ethoxy)ethoxy)ethyl)-1H-pyrazole-4-carboxylic acid (200 mg, 708 umol, Intermediate BI), (1R,3S)-3-(5-amino-1-(tert-butyl)-1H-pyrazol-3-yl)cyclopentyl isopropylcarbamate (240 mg, 779 umol, Intermediate U), DIEA (183 mg, 1.42 mmol) and T₃P (1.35 g, 2.13 mmol, 50% solution in DMF) in MeCN (8 mL) was stirred at 80° C. for 12 h. On completion, the mixture was quenched with sat. NH₄Cl (10 mL), diluted with EtOAc (20 mL), and extracted with EtOAc (15 mL×3). The organic layer was washed with brine (15 mL×3), dried by Na₂SO₄, and concentrated in vacuo. The residue was purified by column chromatography (SiO₂, Petroleum ether/Ethyl acetate=0/1) to give the title compound (70.0 mg, 14.6% yield) as a white solid. LC-MS (ESI⁺) m/z 573.3 (M+H)⁺.

1-(3,6,9,12-tetraoxapentadec-14-yn-1-yl)-1H-pyrazole-4-carboxylic acid (Intermediate BK)

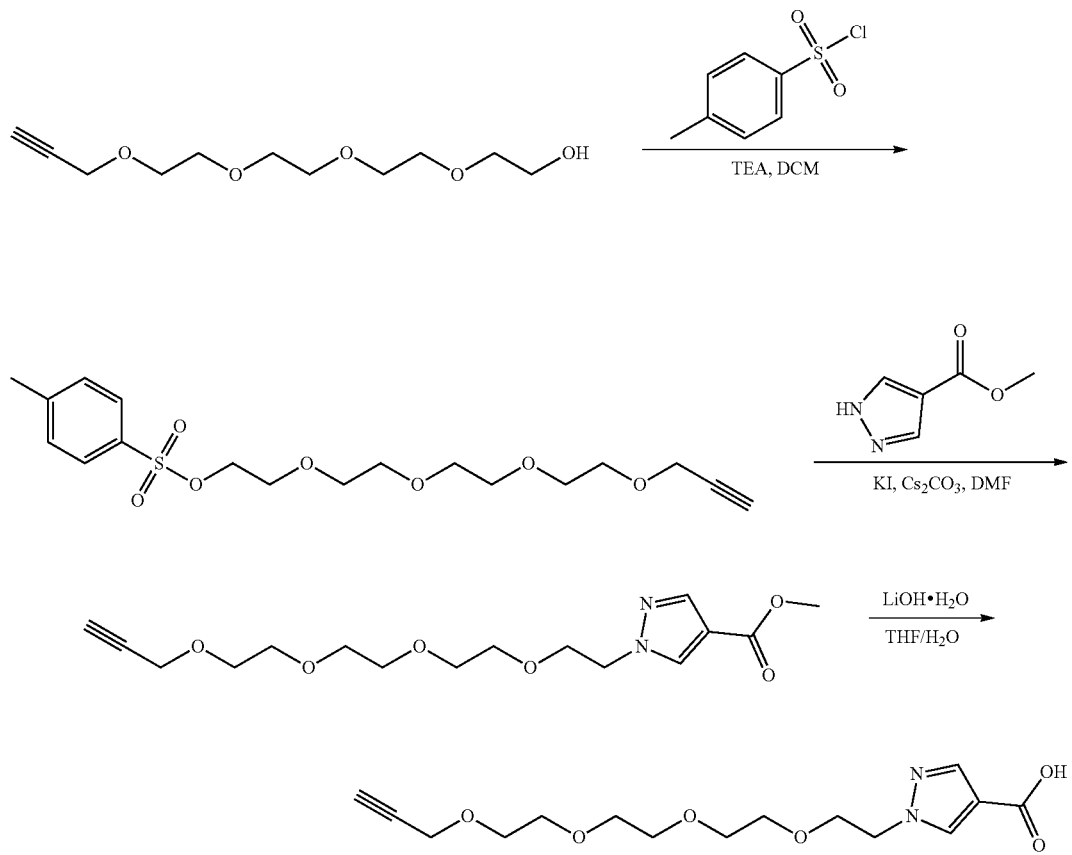

BK

Step 1—3,6,9,12-tetraoxapentadec-14-yn-1-yl 4-methylbenzenesulfonate. To a solution of 3,6,9,12-tetraoxapentadec-14-yn-1-ol (2 g, 8.61 mmol, CAS #87450-10-0) and 4-methylbenzene-1-sulfonyl chloride (1.81 g, 9.47 mmol) in DCM (20 mL) was added TEA (2.61 g, 25.8 mmol) in one portion. The resulting mixture was stirred at 20° C. for 12 h. On completion, the reaction mixture was quenched with H$_2$O (20 mL) at 20° C. and extracted with EtOAc mL (20 mL×3). The combined organic layer was washed with brine (20 mL×2), dried over Na$_2$SO$_4$, filtered and concentrated under reduced pressure to give a residue. The residue was purified by column chromatography (SiO$_2$, Petroleum ether/Ethyl acetate=5/1 to 0/1) to give the title compound (2.5 g, 75% yield) as yellow gum. LC-MS (ESI$^+$) m/z 387.1 (M+H)$^+$.

Step 2—methyl 1-(3,6,9,12-tetraoxapentadec-14-yn-1-yl)-1H-pyrazole-4-carboxylate. A mixture of methyl 1H-pyrazole-4-carboxylate (196 mg, 1.55 mmol, CAS #181997-36-4), 3,6,9,12-tetraoxapentadec-14-yn-1-yl 4-methylbenzenesulfonate (0.5 g, 1.29 mmol), Cs$_2$CO$_3$ (843 mg, 2.59 mmol), KI (21.5 mg, 129 umol) in DMF (5 mL) was stirred at 70° C. for 1 h under N$_2$ atmosphere. On completion, the reaction mixture was quenched with H$_2$O (10 mL) at 20° C. and extracted with EtOAc (10 mL×3). The combined organic layer was washed with brine (10 mL×2), dried over Na$_2$SO$_4$, filtered and concentrated under reduced pressure to give a residue. The residue was purified by column chromatography (SiO$_2$, Petroleum ether/Ethyl acetate=5/1 to 1/1) to give the title compound (410 mg, 93% yield) as yellow gum. $^1$H NMR (400 MHz, DMSO-d6) δ=8.31 (s, 1H), 7.86 (s, 1H), 4.30 (t, J=5.2 Hz, 2H), 4.13 (d, J=2.4 Hz, 2H), 3.78 (t, J=5.2 Hz, 2H), 3.73 (s, 3H), 3.56-3.39 (m, 13H).

Step 3—1-(3,6,9,12-tetraoxapentadec-14-yn-1-yl)-1H-pyrazole-4-carboxylic acid. A solution of methyl 1-(3,6,9,12-tetraoxapentadec-14-yn-1-yl)-1H-pyrazole-4-carboxylate (400 mg, 1.18 mmol) and LiOH·H$_2$O (197 mg, 4.70 mmol) in THF (3 mL) and H$_2$O (1 mL) was stirred at 20° C. for 12 h. On completion, the reaction mixture was quenched with H$_2$O (10 mL) at 20° C. and extracted with EtOAc (10 mL×3). Then the aqueous phase was adjusted to pH=3-4 and extracted with EtOAc (10 mL×3). The organic layer was washed with brine (20 mL×2), dried over Na$_2$SO$_4$, filtered and concentrated under reduced pressure to give the title compound (250 mg, 65% yield) as yellow solid. $^1$H NMR (400 MHz, DMSO-d6) δ=12.32 (br s, 1H), 8.21 (s, 1H), 7.79 (s, 1H), 4.29 (t, J=5.2 Hz, 2H), 4.13 (d, J=2.4 Hz, 2H), 3.77 (t, J=5.4 Hz, 2H), 3.55-3.39 (m, 13H).

(1R,3S)-3-(5-(1-(3,6,9,12-tetraoxapentadec-14-yn-1-yl)-1H-pyrazole-4-carboxamido)-1-(tert-butyl)-1H-pyrazol-3-yl)cyclopentyl isopropylcarbamate (Intermediate BL)

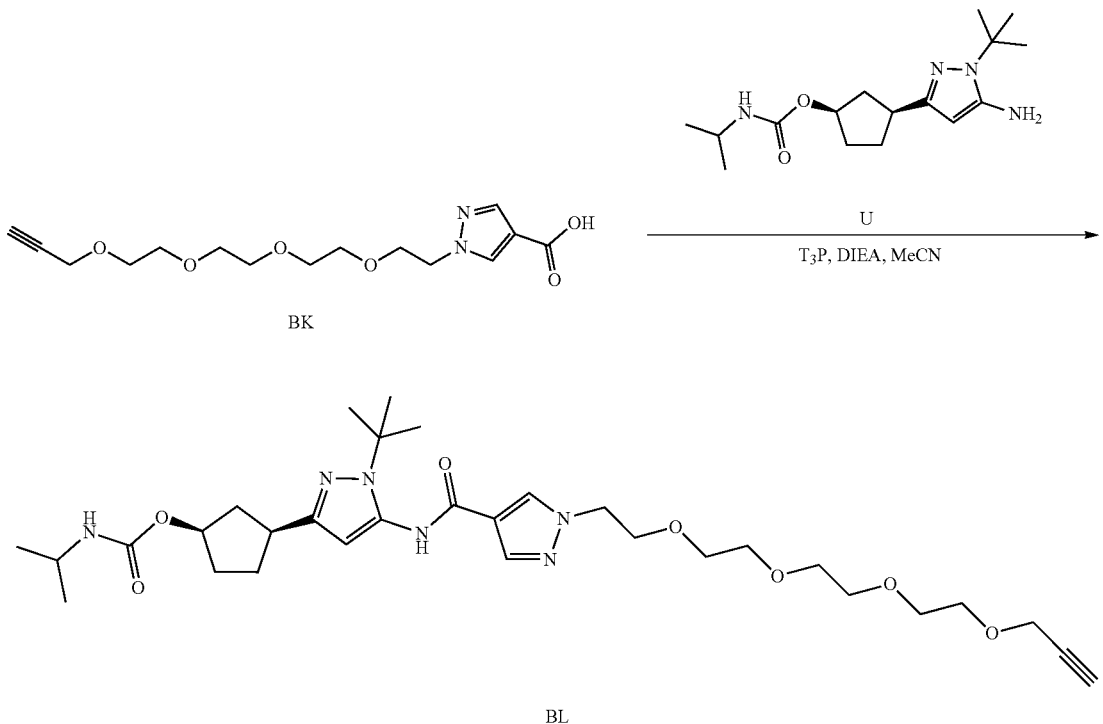

To a solution of 1-(3,6,9,12-tetraoxapentadec-14-yn-1-yl)-1H-pyrazole-4-carboxylic acid (250 mg, 766 umol, Intermediate BK) and (1R,3S)-3-(5-amino-1-(tert-butyl)-1H-pyrazol-3-yl)cyclopentyl isopropylcarbamate (283 mg, 919 umol, Intermediate U) in MeCN (6 mL) was added DIEA (495 mg, 3.83 mmol) and T$_3$P (1.46 g, 2.30 mmol, 50% solution in DMF) in one portion, then the resulting mixture was stirred at 60° C. for 6 h. On completion, the reaction mixture was quenched with H$_2$O (6 mL) at 20° C., and extracted with EtOAc (6 mL×3). The combined organic layer was washed with brine (10 mL×2), dried over Na$_2$SO$_4$, filtered and concentrated under reduced pressure to give a residue. The residue was purified by prep-TLC (SiO$_2$, Ethyl acetate:Petroleum ether=0:1) to give the title compound (153 mg, 32% yield) as colorless gum. LC-MS (ESI$^+$) m/z 617.8 (M+H)$^+$.

1-(7-chloroisoquinolin-4-yl)dihydropyrimidine-2,4 (1H,3H)-dione (Intermediate BM)

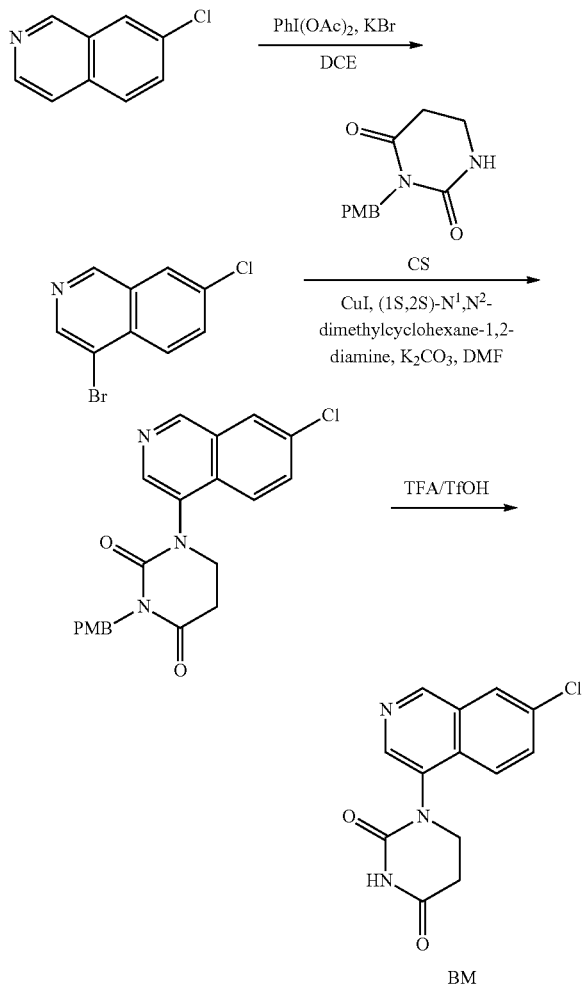

Step 1—4-Bromo-7-chloroisoquinoline. To a solution of 7-chloroisoquinoline (5.00 g, 30.5 mmol, CAS #34784-06-0) in DCE (50 mL) was added PhI(OAc)$_2$ (14.7 g, 45.8 mmol) and KBr (18.1 g, 152 mmol) and the mixture was stirred at 50° C. for 16 hours. On completion, the mixture was poured into water (100 mL), and extracted with EA (300 mL). The organic layer was washed with brine (2×100 mL), dried over anhydrous Na$_2$SO$_4$, filtered and concentrated in vacuo. The mixture was purified by silica gel column to give the title compound (5.50 g, 65% yield) as a white solid. $^1$H NMR (400 MHz, CDCl$_3$) δ 9.13 (s, 1H), 8.74 (s, 1H), 8.13 (d, J=9.2 Hz, 1H), 7.99 (d, J=2.0 Hz, 1H), 7.77 (dd, J=2.0, 9.2 Hz, 1H).

Step 2—1-(7-Chloro-4-isoquinolyl)-3-[(4-methoxyphenyl)methyl]hexahydropyrimidine-2,4-dione. To a solution of 4-bromo-7-chloroisoquinoline (2.00 g, 8.25 mmol) and 3-(4-methoxybenzyl) dihydropyrimidine-2,4(1H,3H)-dione (1.93 g, 8.25 mmol, Intermediate CS) in DMF (20 mL) was added (1S,2S)—N1,N2-dimethylcyclohexane-1,2-diamine (234 mg, 1.65 mmol), CuI (314 mg, 1.65 mmol) and K$_2$CO$_3$ (3.42 g, 24.7 mmol). Then the mixture was stirred at 100° C. for 16 hours under N$_2$. On completion, the reaction solution was diluted with water (100 mL) and then extracted with ethyl acetate (3×100 mL). The combined organic layers were washed with brine (2×100 mL), dried over anhydrous sodium sulfate, filtered and concentrated under vacuum. The mixture was purified by reversed phase flash: (C18, 10% to 40% MeCN in H$_2$O, contained 0.1% FA in H$_2$O) to give the title compound (200 mg, 5% yield) as a light yellow solid. $^1$H NMR (400 MHz, DMSO-d$_6$) δ 9.31 (s, 1H), 8.60 (s, 1H), 8.39 (d, J=2.0 Hz, 1H), 8.00 (d, J=9.2 Hz, 1H), 7.83 (dd, J=2.0, 8.8 Hz, 1H), 7.25 (d, J=8.8 Hz, 2H), 6.90-6.86 (m, 2H), 4.83 (s, 2H), 4.00-3.94 (m, 1H), 3.79-3.76 (m, 1H), 3.73 (s, 3H), 3.19-3.11 (m, 1H), 2.99-2.92 (m, 1H).

Step 3—1-(7-Chloroisoquinolin-4-yl)dihydropyrimidine-2,4(1H,3H)-dione. 1-(7-Chloroisoquinolin-4-yl)-3-(4-methoxybenzyl)dihydropyrimidine-2,4(1H,3H)-dione (50.0 mg, 126 umol) was added into TFA (0.5 mL) and TfOH (0.01 mL) and the mixture was stirred at 60° C. for 2 hours. On completion, the reaction solution was diluted with water (5 mL) and then extracted with ethyl acetate (3×5 mL). The combined organic layers were washed with brine (2×5 mL), dried over anhydrous sodium sulfate, filtered and concentrated in vacuo. The residue was further purified by prep-HPLC (Column: [Phenomenex luna C18, 150 mm*25 mm*10 um]; mobile phase: (water (0.225% FA)-MeCN, MeCN %: 8%-38%); 11 min) to give the title compound (5.18 mg, 14% yield) as a yellow solid. $^1$H NMR (400 MHz, DMSO-d$_6$) δ 10.56 (s, 1H), 9.31 (s, 1H), 8.59 (s, 1H), 8.38 (d, J=2.0 Hz, 1H), 8.06 (d, J=9.2 Hz, 1H), 7.84 (dd, J=2.4, 8.8 Hz, 1H), 4.00-3.93 (m, 1H), 3.75-3.69 (m, 1H), 3.02-2.94 (m, 1H), 2.78-2.71 (m, 1H). LC-MS (ESI$^+$) m/z 275.9 (M+H)$^+$.

1-(8-Bromoimidazo[1,2-a]pyridin-3-yl)hexahydropyrimidine-2,4-dione (Intermediate BN)

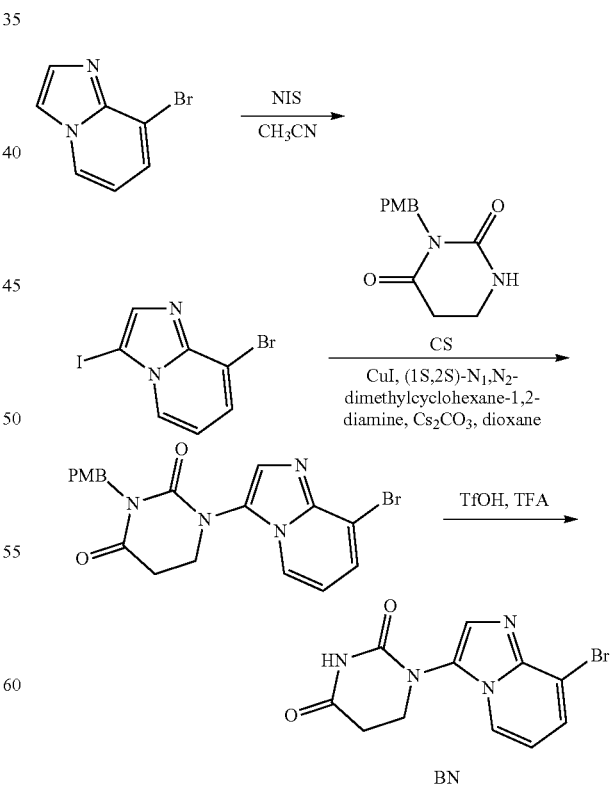

Step 1—8-Bromo-3-iodoimidazo[1,2-a]pyridine. To a solution of 8-bromoimidazo[1,2-a]pyridine (5.00 g, 25.3 mmol, CAS #850349-02-9) in CH$_3$CN (30 mL) was Intermediate CS added NIS (5.71 g, 25.3 mmol) at 25° C. The mixture was stirred at 25° C. for 0.5 hour. On completion, the mixture was concentrated in vacuo. The mixture was purified by silica gel column to give the title compound (7.30 g, 89% yield) as a greenish solid. $^1$H NMR (400 MHz, CDCl$_3$) δ 8.38 (d, J=6.8 Hz, 1H), 7.80 (s, 1H), 7.70 (d, J=7.2 Hz, 1H), 7.00 (t, J=7.2 Hz, 1H).

Step 2—1-(8-Bromoimidazo[1,2-a]pyridin-3-yl)-3-(4-methoxybenzyl)dihydropyrimidine-2,4(1H,3H) dione. A mixture of 8-bromo-3-iodo-imidazo[1,2-a]pyridine (500 mg, 1.55 mmol) and 3-(4-methoxybenzyl) dihydropyrimidine-2,4(1H,3H)-dione (362 mg, 1.55 mmol, Intermediate CS), CuI (58.9 mg, 309 umol), Cs$_2$CO$_3$ (1.01 g, 3.10 mmol), and (1S,2S)—N1,N2-dimethylcyclohexane-1,2-diamine (44.0 mg, 309 umol) in dioxane (10 mL) was stirred at 60° C. for 6 hours under N$_2$. On completion, the mixture was filtered through celite and the filtrate was concentrated in vacuo. The residue was purified by reversed phase flash (120 g Flash Column, Welch Ultimate XB_C18, 20-40 m; 120 A, 5% to 35% MeCN in H$_2$O, 0.5% FA in H$_2$O) and then further purified by prep-HPLC (column: Waters xbridge, 150 mm*25 mm*10 um; mobile phase: [water (10 mM NH$_4$HCO$_3$)-MeCN]; B %: 22%-52%, 10 min) to give the title compound (200 mg, 10% yield) as a yellow solid. $^1$H NMR (400 MHz, DMSO-d$_6$) δ 8.35 (dd, J=0.8, 6.8 Hz, 1H), 7.69-7.67 (m, 1H), 7.67 (s, 1H), 7.24 (d, J=7.6 Hz, 2H), 6.91 (t, J=7.2 Hz, 1H), 6.87-6.84 (m, 2H), 4.81 (s, 2H), 3.84 (t, J=6.4 Hz, 2H), 3.72 (s, 3H), 3.02 (s, 2H).

Step 3—1-(8-Bromoimidazo[1,2-a]pyridin-3-yl)dihydropyrimidine-2,4(1H,3H)-dione. A solution of 1-(8-bromoimidazo[1,2-a]pyridin-3-yl)-3-(4-methoxybenzyl)dihydropyrimidine-2,4 (1H,3H)-dione (50.0 mg, 116 umol) in TFA (0.5 mL) and TfOH (0.01 mL) was stirred at 70° C. for 2.5 hours. On completion, the mixture was concentrated in vacuo. The residue was purified by prep-HPLC (Waters xbridge, 150 mm*25 mm*10 um, water (10 mM NH4HCO$_3$)-MeCN, 1% to 30% MeCN in H$_2$O, 11 min) and then further purified by prep-HPLC (column: Phenomenex Luna C18, 150 mm*25 mm*10 um; mobile phase: [water (0.225% FA)-MeCN]; MeCN %: 0%-20%, 11 min) to give the title compound (3.19 mg, 77% yield) as a white solid. $^1$H NMR (400 MHz, DMSO-d$_6$) δ 10.70 (s, 1H), 8.38 (d, J=6.0 Hz, 1H), 7.67-7.65 (m, 2H), 6.91 (t, J=6.8 Hz, 1H), 3.81 (t, J=6.8 Hz, 2H), 2.84 (t, J=5.2 Hz, 2H); LC-MS (ESI$^+$) m/z 308.9 (M+H)$^+$.

1-(8-Chloro-4-isoquinolyl)hexahydropyrimidine-2,4-dione (Intermediate BO)

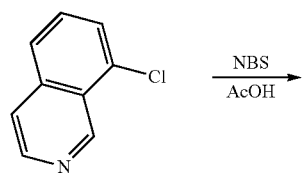

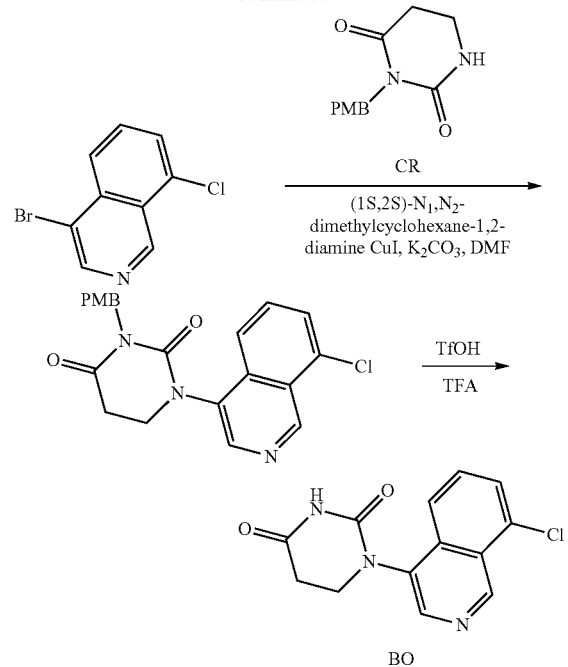

Step 1—4-Bromo-8-chloro-isoquinoline. To a solution of 8-chloroisoquinoline (5.00 g, 30.5 mmol, CAS #34784-07-1) in AcOH (50 mL) was added NBS (7.07 g, 39.7 mmol), then the reaction mixture was stirred at 50° C. for 40 min. On completion, the reaction mixture was diluted with water (100 mL), then extracted with EA (3×80 mL). The combined organic layer was basified with NaHCO$_3$ until the pH=6-7, then the mixture was extracted with EA (2×60 mL). The combined organic layers was dried over Na$_2$SO$_4$, filtered and concentrated in vacuo to give a residue. The residue was purified by column chromatography (SiO$_2$, PE:EA=100:1 to PE:EA=50:1, PE:EA=10:1, P1: R$_f$=0.74) to give the title compound (1.00 g, 37% yield) as yellow solid. $^1$HNMR (400 MHz, CDCl$_3$) δ 9.56 (s, 1H), 8.78 (s, 1H), 8.10-8.03 (m, 1H), 7.73-7.64 (m, 2H). LC-MS (ESI$^+$) m/z 241.9 (M+H)$^+$.

Step 2—1-(8-Chloro-4-isoquinolyl)-3-[(4-methoxyphenyl)methyl]hexahydropyrimidine-2,4-dione. To a solution of 4-bromo-8-chloro-isoquinoline (100 mg, 412 umol) and 3-[(4-methoxyphenyl)methyl]hexahydropyrimidine-2,4-dione (96.6 mg, 412.37 umol, Intermediate CR) in DMF (1 mL) was added CuI (7.85 mg, 41.2 umol), (1S,2S)—N$_1$,N$_2$-dimethylcyclohexane-1,2-diamine (5.87 mg, 41.2 umol) and K$_3$PO$_4$ (175 mg, 824 umol), then the mixture was stirred at 110° C. for 8 hr. On completion, the reaction mixture was filtered and concentrated in vacuo to give the residue. The residue was diluted with water (50 mL) and extracted with EA (5×30 mL). Then the combined organic layers was dried over anhydrous Na$_2$SO$_4$, filtered and concentrated in vacuo to give a residue. The residue was purified by reverse-phase (0.1% FA) to give the title compound (15 mg, 3.06% yield) as yellow solid. $^1$H NMR (400 MHz, DMSO-d$_6$) δ 9.89-9.56 (br s, 1H), 8.59 (br s, 1H), 7.73-7.68 (m, 1H), 7.64 (t, J=8.0 Hz, 1H), 7.60-7.55 (m, 1H), 7.43 (d, J=8.4 Hz, 2H), 6.85 (d, J=8.4 Hz, 2H), 5.00 (s, 2H), 3.95-3.86 (m, 1H), 3.80 (s, 3H), 3.78-3.69 (m, 1H), 3.07-2.99 (m, 2H); LC-MS (ESI$^+$) m/z 396.1 (M+H)$^+$.

Step 3—1-(8-Chloro-4-isoquinolyl)hexahydropyrimidine-2,4-dione. To a solution of 1-(8-chloro-4-isoquinolyl)-3-[(4-methoxyphenyl)methyl]hexahydropyrimidine-2,4-dione (40.0 mg, 101 umol) in TFA (0.49 mL) and TfOH (0.01 mL), then the mixture was stirred at 60° C. for 2 hours. On completion, the mixture was concentrated to give the residue and purified by prep-HPLC (0.1% FA) to give the title compound (3 mg, 10.77% yield) as yellow solid. $^1$H NMR (400 MHz, DMSO-$d_6$) δ=10.59 (s, 1H), 9.56 (s, 1H), 8.71 (s, 1H), 8.03 (d, J=8.4 Hz, 1H), 7.92-7.87 (m, 1H), 7.85-7.78 (m, 1H), 4.00-3.93 (m, 1H), 3.75-3.69 (m 1H), 3.03-2.95 (m, 1H), 2.79-2.72 (m, 1H). LC-MS (ESI$^+$) m/z 276.0 (M+H)$^+$.

3-(3-methyl-4-(3-(3-(methylamino)propoxy)propyl)-2-oxo-2,3-dihydro-1H-benzo[d]imidazol-1-yl)piperidine-2,6-dione (Intermediate BP)

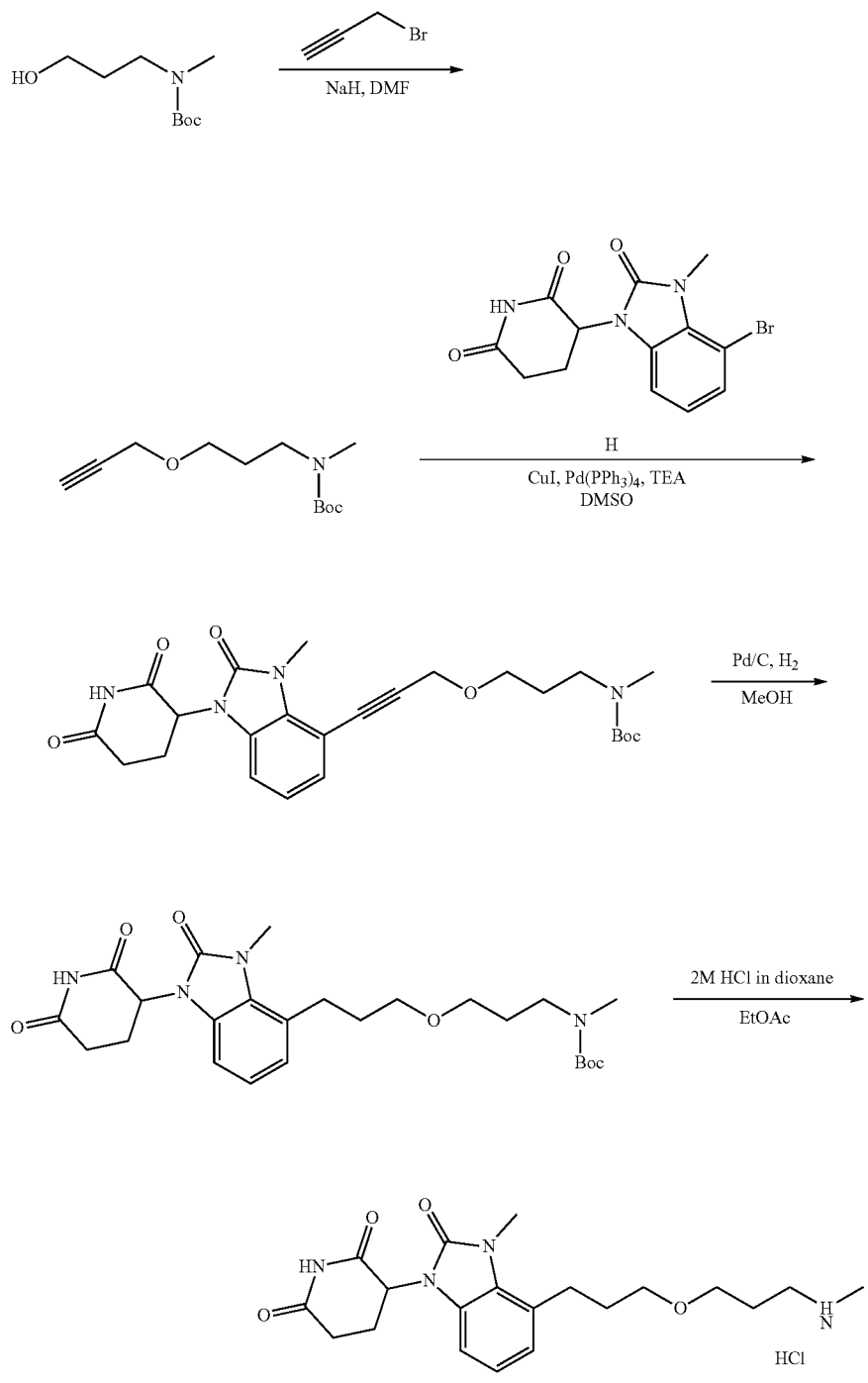

Step 1—Tert-butyl N-methyl-N-[3-(prop-2-yn-1-yloxy)propyl]carbamate. To a stirred solution of tert-butyl N-(3-hydroxypropyl)-N-methylcarbamate (25.00 g, 132.1 mmol) in DMF (200.0 mL) was added NaH (4.76 g, 198 mmol) in portions at 0° C. under nitrogen atmosphere. The above mixture was stirred for 30 min at 0° C. under nitrogen atmosphere. Next propargyl bromide (23.57 g, 198.132 mmol, 1.50 equiv) was added to the mixture dropwise at 0° C. The resulting mixture was stirred for additional 16 h at rt. On completion, the reaction mixture was quenched with water (500 mL) and extracted with EtOAc (3×300 mL). The combined organic layers were washed with brine (500 mL) and dried over anhydrous $Na_2SO_4$. After filtration, the filtrate was concentrated under reduced pressure. The resulting solution was purified on silica gel column chromatography, eluted with PE/EA (30:1), to afford the title compound (47.7 g, 74%) as a yellow oil. $^1$H NMR (400 MHz, Chloroform-d) δ 4.15 (d, J=2.4 Hz, 2H), 3.54 (t, J=6.3 Hz, 2H), 3.31 (t, J=7.0 Hz, 2H), 2.87 (s, 3H), 2.43 (t, J=2.4 Hz, 1H), 1.86-1.80 (m, 2H), 1.47 (s, 9H). LC/MS (ESI, m/z): [(M+1)]$^+$=228.2.

Step 2—Tert-butyl N-(3-[2-[1-(2,6-dioxopiperidin-3-yl)-2-oxo-3H-1,3-benzodiazol-4-ylidyne]ethoxy]propyl)-N-methylcarbamate. To a stirred solution of tert-butyl N-methyl-N-[3-(prop-2-yn-1-yloxy)propyl]carbamate (16.50 g, 72.59 mmol) and 3-(4-bromo-3-methyl-2-oxo-2,3-dihydro-1H-benzo[d]imidazol-1-yl)piperidine-2,6-dione (24.5 g, 72.59 mmol, Intermediate H) in DMSO (140 mL) were added Pd(PPh$_3$)$_4$ (8.39 g, 7.26 mmol) and CuI (392 mg, 7.26 mmol) and TEA (70 mL) dropwise at rt under nitrogen atmosphere. The resulting mixture was stirred for 2 h at 80° C. under nitrogen atmosphere. On completion, the mixture was allowed to cool down to rt. The product was purified by reverse phase flash (Column: Spherical C18, 20-40 um, 330 g; Mobile Phase A: Water (10 mmol/LAcOH), Mobile Phase B: ACN; Flow rate: 80 mL/min; Gradient (B %): 52%~72%, 20 min; Detector: 254/220 nm) desired fractions were collected at 62% B) and concentrated under reduced pressure to afford the title compound (9.22 g, 80% yield) as a dark yellow foam. $^1$H NMR (400 MHz, Chloroform-d) δ 8.20 (s, 1H), 7.19 (dd, J=7.9, 1.0 Hz, 1H), 7.01 (t, J=7.9 Hz, 1H), 6.78 (dd, J=8.0, 1.1 Hz, 1H), 5.22 (dd, J=12.5, 5.3 Hz, 1H), 4.42 (s, 2H), 3.79 (s, 3H), 3.62 (t, J=6.3 Hz, 2H), 3.34 (t, J=7.1 Hz, 2H), 3.03-2.92 (m, 1H), 2.89 (s, 3H), 2.87-2.68 (m, 2H), 2.33-2.20 (m, 1H), 1.92-1.81 (m, 2H), 1.47 (s, 9H). LC/MS (ESI, m/z): [(M+1)]$^+$=485.3.

Step 3—Tert-butyl N-(3-[3-[1-(2,6-dioxopiperidin-3-yl)-3-methyl-2-oxo-1,3-benzodiazol-4-yl]propoxy]propyl)-N-methylcarbamate. Pd/C was added in a mixture of tert-butyl N-[3-([3-[1-(2,6-dioxopiperidin-3-yl)-3-methyl-2-oxo-1,3-benzodiazol-4-yl]prop-2-yn-1-yl]oxy)propyl]-N-methylcarbamate (8.00 g) in THF (200 mL) at rt. The reaction mixture was purged with nitrogen for 3 times and was stirred for 5 h at rt under H$_2$ atmosphere. On completion, the mixture was filtered and the filtrate was concentrated under reduced pressure to afford the title compound (7.96 g, 88% yield) as a white solid. $^1$H NMR (400 MHz, Chloroform-d) δ 8.40 (s, 1H), 7.00 (t, J=7.8 Hz, 1H), 6.92 (d, J=7.7 Hz, 1H), 6.69 (d, J=7.8 Hz, 1H), 5.24 (dd, J=12.5, 5.3 Hz, 1H), 3.70 (s, 3H), 3.50-3.44 (m, 4H), 3.34-3.29 (m, 2H), 3.05-3.01 (m, 2H), 3.00-2.91 (m, 1H), 2.88 (s, 3H), 2.85-2.70 (m, 2H), 2.25-2.20 (m, 1H), 1.97-1.90 (m, 2H), 1.86-1.80 (m, 2H), 1.48 (s, 9H). LC/MS (ESI, m/z): [(M+1)]$^+$=489.3.

Step 4—3-(3-Methyl-4-[3-[3-(methylamino)propoxy]propyl]-2-oxo-1,3-benzodiazol-1-yl)piperidine-2,6-dione hydrochloride. To a stirred mixture of tert-butyl N-(3-[3-[1-(2,6-dioxopiperidin-3-yl)-3-methyl-2-oxo-1,3-benzodiazol-4-yl]propoxy]propyl)-N-methylcarbamate (8.50 g) in EA (200 mL) was added HCl (gas) in 1,4-dioxane (100 mL) in portions at rt nitrogen atmosphere. The resulting mixture was stirred for 4 h at rt under nitrogen atmosphere. On completion, the reaction mixture was concentrated under vacuum. The residue was purified by trituration with EA (100 mL) to give the title compound (7.34 g, 96% yield) as a white solid. $^1$H NMR (400 MHz, DMSO-d$_6$) δ 11.10 (s, 1H), 8.89 (broad, 2H), 7.00-6.96 (m, 2H), 6.90-6.86 (m, 1H), 5.39 (dd, J=12.6, 5.4 Hz, 1H), 3.57 (s, 3H), 3.49-3.43 (m, 5H), 2.98-2.86 (m, 5H), 2.77-2.57 (m, 2H), 2.52-2.48 (m, 2H), 2.05-1.95 (m, 1H), 1.94-1.80 (m, 4H). LC/MS (ESI, m/z): [(M+1)]$^+$=389.3.

1-1-(2-(2-(benzyloxy)ethoxy)ethyl)-1H-pyrazole-4-carboxylic acid (Intermediate BQ)

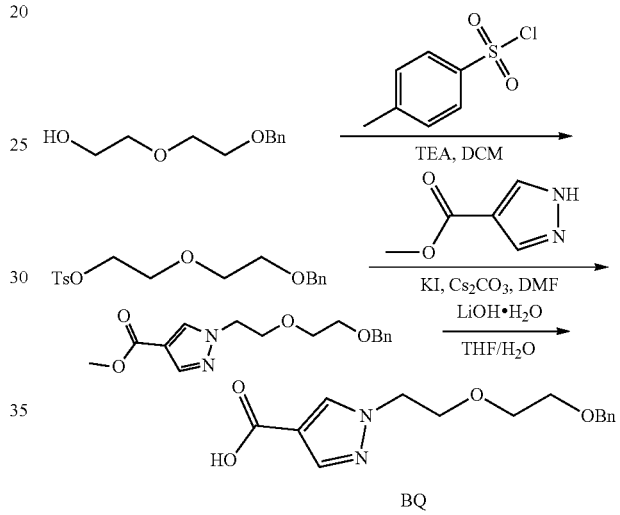

Step 1—2-(2-(benzyloxy)ethoxy)ethyl 4-methylbenzenesulfonate. To a solution of 2-(2-(benzyloxy)ethoxy)ethanol (10 g, 51.0 mmol, CAS #2050-25-1) and 4-methylbenzene-1-sulfonyl chloride (11.7 g, 61.2 mmol, CAS #98-59-9) in DCM (100 mL) was added TEA (15.5 g, 152 mmol) in one portion. The mixture was stirred at 20° C. for 2 h. On completion, the reaction mixture was quenched with H$_2$O (100 mL) at 20° C. and extracted with EtOAc (100 mL×3). The combined organic layer was washed with brine (100 mL×2), dried over Na$_2$SO$_4$, filtered and concentrated under reduced pressure to give a residue. The residue was purified by flash silica gel chromatography (ISCO®; 80 g SepaFlash® Silica Flash Column, Eluent of 0~100% Ethyl acetate/Petroleum ether gradient @ 100 mL/min) to give the title compound (15.3 g, 86% yield) as colorless gum. $^1$H NMR (400 MHz, CD3Cl) δ 7.80 (d, J=8.4 Hz, 2H), 7.38-7.27 (m, 7H), 4.54 (s, 2H), 4.31-4.13 (m, 2H), 3.75-3.66 (m, 2H), 3.64-3.55 (m, 4H), 2.43 (s, 3H).

Step 2—methyl 1-(2-(2-(benzyloxy)ethoxy)ethyl)-1H-pyrazole-4-carboxylate. To a solution of 2-(2-(benzyloxy)ethoxy)ethyl 4-methylbenzenesulfonate (5 g, 14.3 mmol) and methyl 1H-pyrazole-4-carboxylate (2.16 g, 17.1 mmol, CAS #181997-36-4) in DMF (50 mL) was added Cs$_2$CO$_3$ (9.3 g, 28.5 mmol) and KI (237 mg, 1.43 mmol) in one portion. The mixture was stirred at 70° C. for 1 h. On completion, the reaction mixture was quenched with H$_2$O (50 mL) at 20° C. and extracted with EtOAc (50 mL×3). The combined organic layer was washed with brine (50 mL×4), dried over Na$_2$SO$_4$, filtered and concentrated under reduced pressure to give a residue. The residue was purified by column chromatography (SiO$_2$, Petroleum ether/Ethyl acetate=5/1 to 1/1) to give the title compound (4.3 g, 99% yield) as colorless gum. $^1$H NMR (400 MHz, DMSO-d6) δ=8.32 (s, 1H), 7.88 (s, 1H), 7.40-7.21 (m, 5H), 4.43 (s, 2H), 4.32 (t, J=5.2 Hz, 2H), 3.79 (t, J=5.2 Hz, 2H), 3.72 (s, 3H), 3.59-3.47 (m, 4H).

(s, 1H), 7.47-7.13 (m, 5H), 4.44 (s, 2H), 4.30 (t, J=5.2 Hz, 2H), 3.79 (t, J=5.2 Hz, 2H), 3.63-3.45 (m, 4H).

2-(2-(4-((1-(tert-butyl)-3-((1S,3R)-3-((isopropylcarbamoyl)oxy)cyclopentyl)-1H-pyrazol-5-yl)carbamoyl)-1H-pyrazol-1-yl)ethoxy)ethyl methanesulfonate (Intermediate BR)

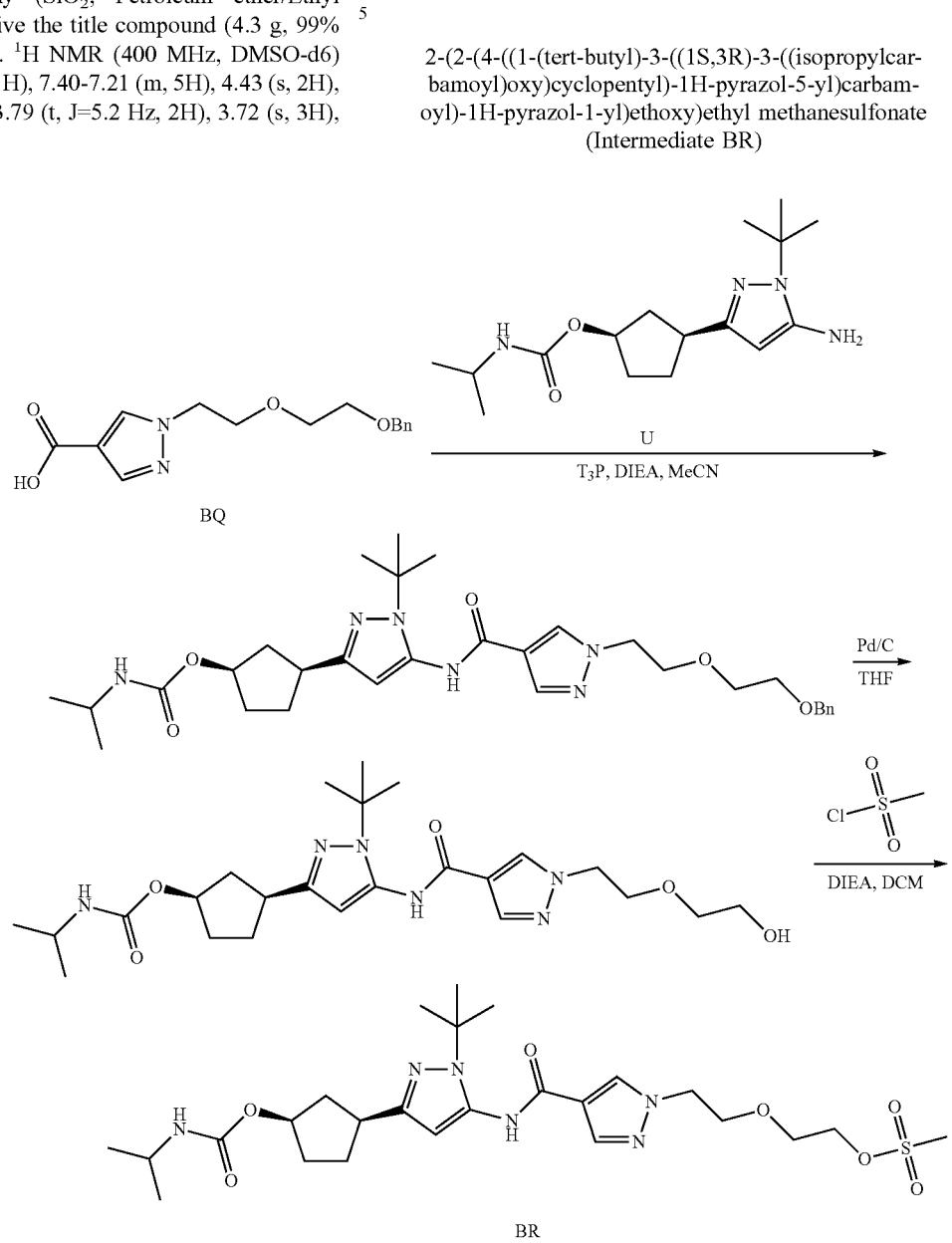

Step 3—1-1-(2-(2-(benzyloxy)ethoxy)ethyl)-1H-pyrazole-4-carboxylic acid. To a solution of methyl methyl 1H-pyrazole-4-carboxylate (2 g, 6.57 mmol) in THF (6 mL) and H$_2$O (3 mL) was added LiOH·H$_2$O (1.10 g, 26.3 mmol) in one portion, then the resulting mixture was stirred at 20° C. for 12 h. On completion, the reaction mixture was quenched with H$_2$O (10 mL) at 20° C. and extracted with EtOAc (10 mL×3). Then the aqueous phase was adjusted to pH=3-4 and extracted with EtOAc (10 mL×3). The organic layer was washed with brine (10 mL×2), dried over Na$_2$SO$_4$, filtered and concentrated under reduced pressure to give the title compound (1.6 g, 84% yield) as white solid. $^1$H NMR (400 MHz, DMSO-d6) δ=12.31 (br s, 1H), 8.23 (s, 1H), 7.80

Step 1—(1R,3S)-3-(5-(1-(2-(2-(benzyloxy)ethoxy)ethyl)-1H-pyrazole-4-carboxamido)-1-(tert-butyl)-1H-pyrazol-3-yl)cyclopentyl isopropylcarbamate. To a solution of 1-(2-(2-(benzyloxy)ethoxy)ethyl)-1H-pyrazole-4-carboxylic acid (0.5 g, 1.72 mmol, Intermediate BQ) and (1R,3S)-3-(5-amino-1-(tert-butyl)-1H-pyrazol-3-yl)cyclopentyl isopropylcarbamate (531 mg, 1.72 mmol, Intermediate U) in MeCN (5 mL) was added DIEA (1.11 g, 8.61 mmol) and T$_3$P (3.29 g, 5.17 mmol, 50% solution in DMF). The resulting mixture was stirred at 60° C. for 12 h. On completion, the reaction mixture was quenched with H$_2$O (5 mL) at 20° C. and extracted with EtOAc (10 mL×3). The combined organic layer was washed with brine (10 mL×2), dried over Na$_2$SO$_4$, filtered and concentrated under reduced pressure to give a residue. The residue was purified by column chromatography (SiO₂, Petroleum ether/Ethyl acetate=1/1 to 0/1) to give the title compound (560 mg, 56% yield) as yellow gum. LC-MS (ESI⁺) m/z 581.3 (M+H)⁺.

Step 2—(1R,3S)-3-(1-(tert-butyl)-5-(1-(2-(2-hydroxyethoxy)ethyl)-1H-pyrazole-4-carboxamido)-1H-pyrazol-3-yl)cyclopentyl isopropylcarbamate. A solution of (1R,3S)-3-(5-(1-(2-(2-(benzyloxy)ethoxy)ethyl)-1H-pyrazole-4-carboxamido)-1-(tert-butyl)-1H-pyrazol-3-yl)cyclopentyl isopropylcarbamate (560 mg, 964 umol) and Pd/C (56.0 mg, 52.8 umol, 10 wt %) in THF (10 mL) was stirred at 20° C. for 1 h under H₂ atmosphere (15 psi). On completion, the mixture was filtered and concentrated in vacuo to give the title compound (393 mg, 83% yield) as white solid. LC-MS (ESI⁺) m/z 491.3 (M+H)⁺.

Step 3—2-(2-(4-((1-(tert-butyl)-3-((1S,3R)-3-((isopropylcarbamoyl)oxy)cyclopentyl)-1H-pyrazol-5-yl)carbamoyl)-1H-pyrazol-1-yl)ethoxy)ethyl methanesulfonate. To a solution of (1R,3S)-3-(1-(tert-butyl)-5-(1-(2-(2-hydroxyethoxy)ethyl)-1H-pyrazole-4-carboxamido)-1H-pyrazol-3-yl)cyclopentyl isopropylcarbamate (150 mg, 305 umol) and DIEA (59.2 mg, 458 umol) in DCM (3 mL) was added MsCl (220 mg, 1.96 mmol, CAS #124-63-0) at 0° C. dropwise, then the mixture was stirred at 0° C. for 2 h. On completion, the reaction mixture was quenched with H₂O (5 mL) at 0° C. and extracted with EtOAc (5 mL×3). The combined organic layer was washed with brine (5 mL×2), dried over Na₂SO₄, filtered and concentrated under reduced pressure to give the title compound (180 mg, 72.47% yield) as yellow gum. LC-MS (ESI⁺) m/z 569.3 (M+H)⁺.

3-(3-methyl-2-oxo-4-(3-(piperidin-4-yl)prop-1-yn-1-yl)-2,3-dihydro-1H-benzo[d]imidazol-1-yl)piperidine-2,6-dione (Intermediate BS)

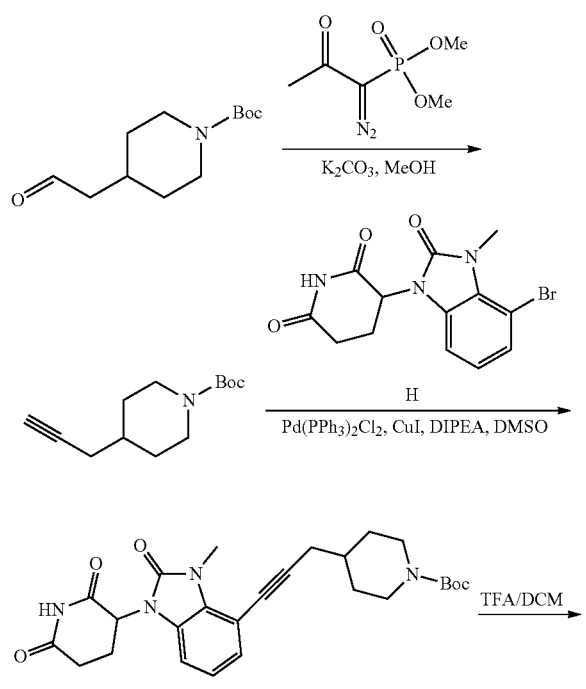

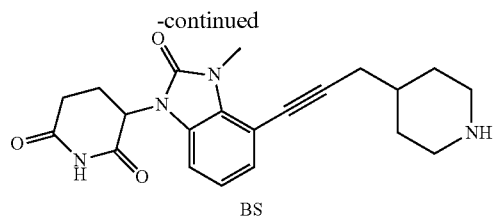

BS

Step 1—Tert-butyl 4-prop-2-ynylpiperidine-1-carboxylate. To a solution of tert-butyl 4-(2-oxoethyl)piperidine-1-carboxylate (500 mg, 2.20 mmol, CAS #142374-19-4), K₂CO₃ (912 mg, 6.60 mmol) in MeOH (15 mL) was added 1-diazo-1-dimethoxyphosphoryl-propan-2-one (507 mg, 2.64 mmol, CAS #90965-06-3) at 0° C. The mixture was stirred at 25° C. for 16 hours. On completion, the mixture was concentrated in vacuo. The mixture was diluted with H₂O (30 mL), then extracted with EA (3×20 mL). The organic layers were washed with brine (2×15 mL), dried over anhydrous Na₂SO₄, filtered and concentrated in vacuo to give the title compound (490 mg, 99% yield) as yellow oil. ¹H NMR (400 MHz, CDCl₃) δ 4.25-4.03 (m, 2H), 2.78-2.65 (m, 2H), 2.22-2.13 (m, 2H), 2.00 (t, J=2.8 Hz, 1H), 1.85-1.72 (m, 2H), 1.72-1.60 (m, 1H), 1.48 (s, 9H), 1.30-1.15 (m, 2H).

Step 2—Tert-butyl 4-[3-[1-(2,6-dioxo-3-piperidyl)-3-methyl-2-oxo-benzimidazol-4-yl]prop-2-ynyl] piperidine-1-carboxylate. To a solution of tert-butyl 4-prop-2-ynylpiperidine-1-carboxylate (390 mg, 1.75 mmol), 3-(4-bromo-3-methyl-2-oxobenzimidazol-1-yl)piperidine-2,6-dione (393 mg, 1.16 mmol, Intermediate H) in DMSO (4 mL) was added Pd(PPh₃)₂Cl₂ (163 mg, 232 umol), CuI (44.3 mg, 232 umol) and DIPEA (752 mg, 5.82 mmol) under N₂. The mixture was stirred at 80° C. for 3 hours. On completion, the mixture was filtered and concentrated in vacuo. The mixture was purified by reverse phase: (0.1% FA) to give the title compound (450 mg, 80% yield) as yellow solid. ¹H NMR (400 MHz, DMSO-d₆) δ 11.12 (s, 1H), 7.17-6.95 (m, 3H), 5.45-5.33 (m, 1H), 4.06-3.89 (m, 2H), 3.63 (s, 3H), 2.98-2.82 (m, 1H), 2.78-2.69 (m, 2H), 2.66-2.59 (m, 1H), 2.56-2.52 (m, 1H), 2.49-2.45 (m, 2H), 2.11-1.97 (m, 1H), 1.82-1.71 (m, 3H), 1.39 (s, 9H), 1.25-1.10 (m, 2H), LC-MS (ESI⁺) m/z 503.3 (M+Na)⁺.

Step 3—3-(3-methyl-2-oxo-4-(3-(piperidin-4-yl)prop-1-yn-1-yl)-2,3-dihydro-1H-benzo[d]imidazol-1-yl)piperidine-2,6-dione. A solution of tert-butyl 4-(3-(1-(2,6-dioxopiperidin-3-yl)-3-methyl-2-oxo-2,3-dihydro-1H-benzo[d]imidazol-4-yl)prop-2-yn-1-yl)piperidine-1-carboxylate (260 mg, 541 umol) in TFA (6 mL) and DCM (6 mL), was stirred at 25° C. for 5 h. On completion, the reaction mixture was quenched with H₂O (5 mL) and extracted with EtOAc (8 mL×2). The pH of aqueous phase was adjusted to 3-4 with 1 N HCl, then extracted with EtOAc (8 mL×4). The combined organic layer was washed with brine (3 mL×3), dried over Na₂SO₄ and evaporated to give the title compound (220 mg) as a white solid. ¹H NMR (400 MHz, DMSO-d₆) δ 7.69 (br dd, J=7.6, 13.2 Hz, 1H), 7.58 (dt, J=3.6, 7.6 Hz, 1H), 7.13 (d, J=7.6 Hz, 1H), 7.09-7.05 (m, 1H), 7.03-6.96 (m, 1H), 5.39 (dd, J=5.2, 12.8 Hz, 1H), 3.64 (s, 3H), 3.12 (br d, J=12.4 Hz, 2H), 2.94-2.83 (m, 1H), 2.77-2.59 (m, 5H), 2.06-1.97 (m, 1H), 1.85-1.72 (m, 3H), 1.39-1.19 (m, 3H), 1.11 (s, 1H).

3-[5-(7-aminoheptyl)-3-methyl-2-oxo-benzimidazol-1-yl]piperidine-2,6-dione (Intermediate BT)

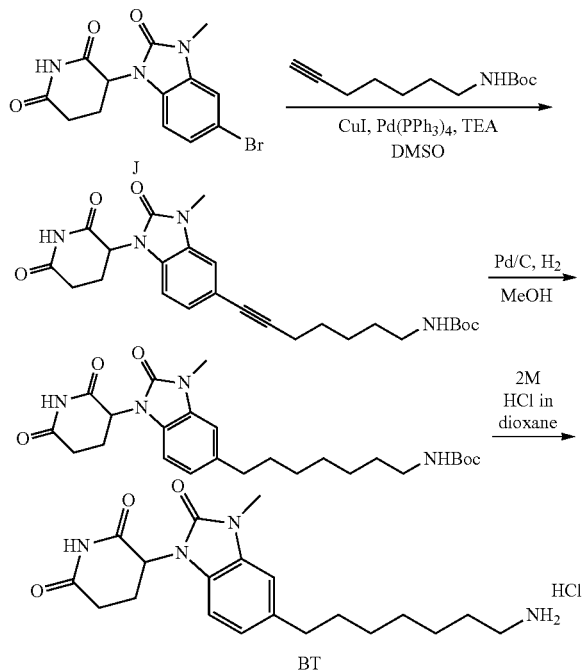

Step 1—Tert-butyl N-[7-[1-(2,6-dioxopiperidin-3-yl)-3-methyl-2-oxo-1,3-benzodiazol-5-yl]hept-6-yn-1-yl]carbamate. To a stirred mixture of 3-(5-bromo-3-methyl-2-oxo-1,3-benzodiazol-1-yl)piperidine-2,6-dione (8.00 g, 23.7 mmol, Intermediate J), tert-butyl N-(hept-6-yn-1-yl)carbamate (10.00 g, 47.32 mmol, synthesized via Steps 1-4 of Intermediate AN) and CuI (0.45 g, 2.37 mmol) in DMSO (40.00 mL)/TEA (20.00 mL) was added Pd(PPh$_3$)$_4$ (2.73 g, 2.37 mmol) at rt under nitrogen atmosphere. The mixture was allowed stirred for 4 h at 85° C. On completion, the mixture was allowed to cool down to rt. The reaction was diluted with water (100 mL) and extracted with EtOAc (3×100 mL). The combined organic layers were washed with brine (2×100 mL), and dried over anhydrous Na$_2$SO$_4$. After filtration, the filtrate was concentrated under reduced pressure. The residue was purified by silica gel column chromatography, eluted with PE/EtOAc (1:2), then further purified by reverse phase flash chromatography (Column: WelFlash™ C18-I, 20-40 ?m, 330 g; Eluent A: Water (plus 10 mmol/L FA); Eluent B: ACN; Gradient: 40%-65% B in 20 min; Flow rate: 80 mL/min; Detector: 220/254 nm; desired fractions were collected at 60% B) and concentrated under reduced pressure to afford the title compound (7.5 g, 68% yield) as a white solid. $^1$H NMR (400 MHz, DMSO-d$_6$) δ 11.13 (s, 1H), 7.25-7.23 (m, 1H), 7.11-7.07 (m, 2H), 6.82 (t, J=5.8 Hz, 1H), 5.38 (dd, J=12.7, 5.3 Hz, 1H), 3.35 (s, 3H), 2.95-2.81 (m, 3H), 2.79-2.56 (m, 2H), 2.41 (t, J=7.0 Hz, 2H), 2.05-1.99 (m, 1H), 1.54 (t, J=7.0 Hz, 2H), 1.41-1.37 (m, 13H). LC/MS (ESI, m/z): [(M+1)]$^+$=469.3.

Step 2—Tert-butyl N-[7-[1-(2,6-dioxopiperidin-3-yl)-3-methyl-2-oxo-1,3-benzodiazol-5-yl]heptyl]carbamate. To a stirred solution of tert-butyl N-[7-[1-(2,6-dioxopiperidin-3-yl)-3-methyl-2-oxo-1,3-benzodiazol-5-yl]hept-6-yn-1-yl]carbamate (8.00 g, 17.0 mmol) in MeOH (200.00 mL)/AcOH (10.00 mL) was added Pd/C (1.00 g, 9.40 mmol) at rt under nitrogen atmosphere. The reaction was purged with H$_2$ three times and stirred for 16 h at t under hydrogen atmosphere. On completion, the reaction mixture was filtered, and the filter cake was washed with CH$_2$Cl$_2$ (3×20 mL). The filtrate was concentrated under reduced pressure to give the title compound (7.5 g, 93% yield) as a white solid. $^1$H NMR (400 MHz, DMSO-d$_6$) δ 11.09 (s, 1H), 7.05-6.96 (m, 2H), 6.88-6.84 (m, 1H), 6.76 (t, J=5.8 Hz, 1H), 5.34 (dd, J=12.7, 5.3 Hz, 1H), 3.35 (s, 3H), 2.91-2.86 (m, 3H), 2.78-2.55 (m, 4H), 2.03-1.98 (m, 1H), 1.58 (t, J=7.4 Hz, 2H), 1.37 (s, 9H), 1.32-1.17 (m, 6H). LC/MS (ESI, m/z): [(M+1)]$^+$=473.3.

Step 3—3-[5-(7-aminoheptyl)-3-methyl-2-oxo-1,3-benzodiazol-1-yl]piperidine-2,6-dione hydrochloride. To a stirred solution of tert-butyl N-[7-[1-(2,6-dioxopiperidin-3-yl)-3-methyl-2-oxo-1,3-benzodiazol-5-yl]heptyl]carbamate (7.50 g, 15.9 mmol) in DCM (20.0 mL) was added HCl (4M) in 1,4-dioxane (20.0 mL) at rt under nitrogen atmosphere. The mixture was stirred for 4 h at rt. On completion, the mixture was concentrated under reduced pressure. The residue was triturated with Et$_2$O to afford the title compound (6.3 g, 97% yield) as an off-white solid. $^1$H NMR (300 MHz, DMSO-d$_6$) δ 11.09 (s, 1H), 7.92 (broad, 3H), 7.07-6.96 (m, 2H), 6.88-6.84 (m, 1H), 5.35 (dd, J=12.8, 5.3 Hz, 1H), 3.32 (s, 3H) 3.02-2.82 (m, 1H), 2.78-2.71 (m, 3H), 2.68-2.56 (m, 3H), 2.06-1.95 (m, 1H), 1.62-1.51 (m, 4H), 1.32-1.27 (m, 6H). LC/MS (ESI, m/z): [(M+1)]$^+$=373.3.

1-(4-(1,3-dioxolan-2-yl)phenyl)-1H-pyrazole-4-carboxylic acid (Intermediate BU)

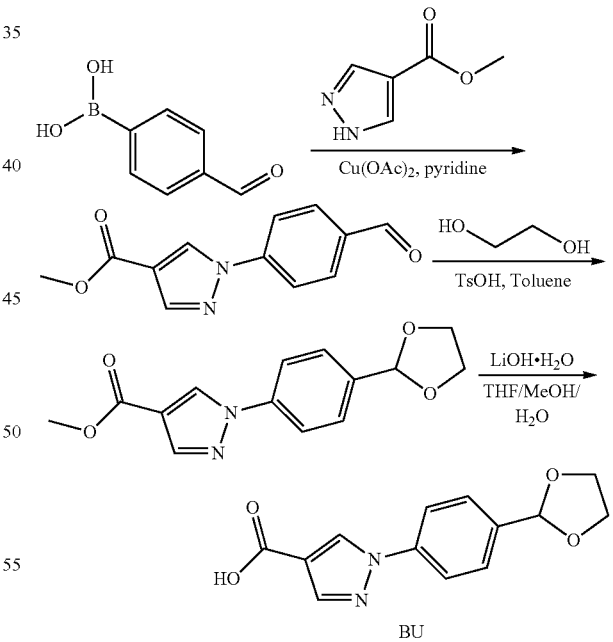

Step 1—Methyl 1-(4-formylphenyl)-1H-pyrazole-4-carboxylate. To a solution of (4-formylphenyl)boronic acid (10 g, 66.7 mmol, CAS #87199-17-5) and methyl 1H-pyrazole-4-carboxylate (12.6 g, 100 mmol, CAS #51105-90-9) in pyridine (100 mL) was added Cu(OAc)$_2$ (24.2 g, 133 mmol). The mixture was stirred at 20 to 100° C. for 12 h. On completion, the mixture was poured into ice water (100 mL) and filtered, then the mixture was extracted with ethyl acetate (2×100 mL). The combined organic phase was washed with brine (2×100 mL), and dried over sodium sulfate. Then filtered to get the filtrate and concentrated to give a residue. The residue was purified by flash silica gel chromatography (ISCO®; 80 g SepaFlash® Silica Flash Column, Eluent of 0~50% Ethyl acetate/Petroleum ether gradient @ 100 mL/min) to give the title compound (1.5 g, 6.52 mmol, 10% yield) as a yellow solid. $^1$H NMR (400 MHz, DMSO-$d_6$) δ=10.59 (br s, 1H), 10.04 (s, 1H), 9.79 (s, 1H), 8.20 (d, J=8.4 Hz, 2H), 8.06 (d, J=8.4 Hz, 2H), 3.82 (s, 3H).

Step 2—Methyl 1-[4-(1,3-dioxolan-2-yl)phenyl]pyrazole-4-carboxylate. To a solution of methyl 1-(4-formylphenyl)-1H-pyrazole-4-carboxylate (1 g, 4.34 mmol) in toluene (10 mL) was added ethylene glycol (808 mg, 13.0 mmol) and 4-methylbenzenesulfonic acid (74.8 mg, 434 umol). The mixture was stirred at 20-130° C. for 4 h. On completion, the mixture was poured into ice water (13 mL) and extracted with ethyl acetate (2×13 mL). The combined organic phase was washed with brine (2×13 mL), then dried over sodium sulfate. Then filtered to get the filtrate and concentrated to give a residue. The residue was purified by flash silica gel chromatography (ISCO®; 12 g SepaFlash® Silica Flash Column, Eluent of 0~18% Ethyl acetate/Petroleum ether gradient @ 40 mL/min) to give the title compound (500 mg, 929 umol, 21% yield) as yellow oil. LC-MS (ESI$^+$) m/z 231.0 (M+H)$^+$.

Step 3—1-(4-(1,3-dioxolan-2-yl)phenyl)-1H-pyrazole-4-carboxylic acid. To a solution of methyl 1-(4-(1,3-dioxolan-2-yl)phenyl)-1H-pyrazole-4-carboxylate (400 mg, 1.46 mmol) in THF (3 mL), H$_2$O (1 mL) and MeOH (1 mL) was added LiOH·H$_2$O (244 mg, 5.83 mmol) in one portion. The mixture was stirred at 20° C. for 10 h. On completion, the mixture was poured into ice water (5 mL) and extracted with ethyl acetate (2×5 mL). The aqueous phase was acidified with aqueous HCl (1 N) to pH=4 and extracted with ethyl acetate (2×5 mL). The combined organic phase was washed with brine (2×5 mL), then dried over sodium sulfate. Then the mixture was filtered and filtrate was concentrated to give the title compound (300 mg) as a white solid. LC-MS (ESI$^+$) m/z 261.1 (M+H)$^+$.

(1R,3S)-3-(1-(tert-butyl)-5-(1-(4-formylphenyl)-1H-pyrazole-4-carboxamido)-1H-pyrazol-3-yl)cyclopentyl isopropylcarbamate (Intermediate BV) and (1R, 3S)-3-(5-(1-(4-formylphenyl)-1H-pyrazole-4-carboxamido)-1H-pyrazol-3-yl)cyclopentyl isopropylcarbamate (Intermediate BW)

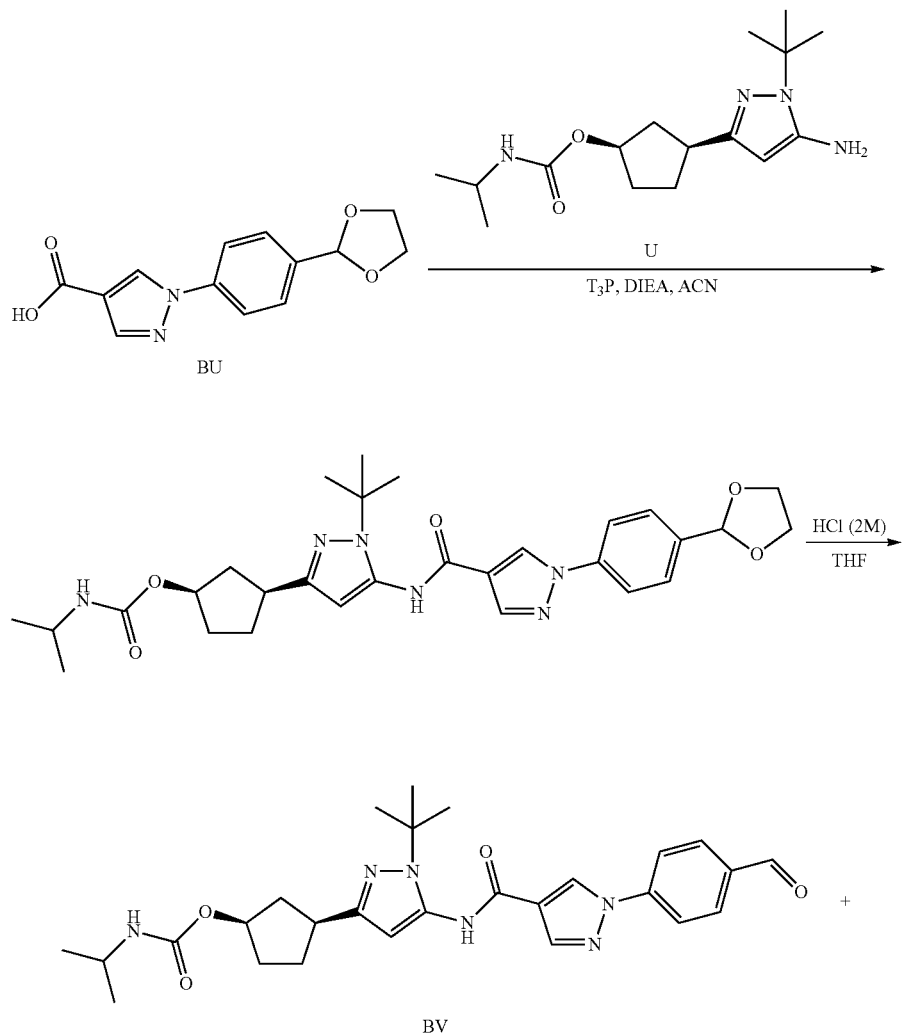

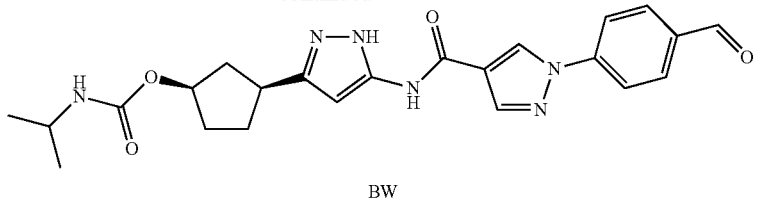

BW

Step 1—(1R,3S)-3-(5-(1-(4-(1,3-dioxolan-2-yl)phenyl)-1H-pyrazole-4-carboxamido)-1-(tert-butyl)-1H-pyrazol-3-yl)cyclopentyl isopropylcarbamate. To a solution of 1-(4-(1,3-dioxolan-2-yl)phenyl)-1H-pyrazole-4-carboxylic acid (300 mg, 1.15 mmol, Intermediate BU) and (1R,3S)-3-(5-amino-1-(tert-butyl)-1H-pyrazol-3-yl)cyclopentyl isopropylcarbamate (355 mg, 1.15 mmol, Intermediate U) in ACN (3 mL) was added $T_3P$ (2.20 g, 3.46 mmol, 50% solution in DMF) and DIEA (745 mg, 5.76 mmol) in one portion. The mixture was stirred at 20-60° C. for 12 h. On completion, the mixture was poured into ice water (5 mL) and extracted with ethyl acetate (2×5 mL). The combined organic phase was washed with brine (2×5 mL), and dried over sodium sulfate. The reaction was then filtered and the filtrate was concentrated to give a residue. The residue was purified by flash silica gel chromatography (ISCO®; 12 g SepaFlash® Silica Flash Column, Eluent of 0~50% Ethyl acetate/Petroleum ether gradient @ 50 mL/min) to give the title compound (420 mg, 541 umol, 47% yield) as yellow oil. LC-MS (ESI⁺) m/z 551.3 (M+H)⁺.

Step 2—(1R,3S)-3-(1-(tert-butyl)-5-(1-(4-formylphenyl)-1H-pyrazole-4-carboxamido)-1H-pyrazol-3-yl)cyclopentyl isopropylcarbamate and (1R,3S)-3-(5-(1-(4-formylphenyl)-1H-pyrazole-4-carboxamido)-1H-pyrazol-3-yl)cyclopentyl isopropylcarbamate. To a solution of (1R,3S)-3-(5-(1-(4-(1,3-dioxolan-2-yl)phenyl)-1H-pyrazole-4-carboxamido)-1-(tert-butyl)-1H-pyrazol-3-yl)cyclopentyl isopropylcarbamate (400 mg, 726 umol) was added HCl (2 M, 2 mL) in THF (2.4 mL). The mixture was stirred at 60° C. for 24 h. The reaction was concentrated to give a residue. The residue was purified by prep-HPLC (column: Phenomenex Luna C18 150*25 mm*10 um; mobile phase: [water (0.225% FA)-ACN]; B %: 39%-69%, 10 min) to give (1R,3S)-3-(1-(tert-butyl)-5-(1-(4-formylphenyl)-1H-pyrazole-4-carboxamido)-1H-pyrazol-3-yl)cyclopentyl isopropylcarbamate (100 mg, 197 umol, 27% yield) as yellow oil (¹H NMR (400 MHz, DMSO-$d_6$) δ=10.04 (s, 1H), 9.79 (s, 1H), 9.22 (s, 1H), 8.37 (s, 1H), 8.18-8.12 (m, 2H), 8.11-8.06 (m, 2H), 6.02 (s, 1H), 5.75 (s, 1H), 5.10-4.92 (m, 1H), 3.62-3.52 (m, 1H), 3.05-2.96 (m, 1H), 2.00-1.82 (m, 3H), 1.75-1.66 (m, 3H), 1.53 (s, 9H), 1.02 (d, J=6.4 Hz, 6H)) and (1R,3S)-3-(5-(1-(4-formylphenyl)-1H-pyrazole-4-carboxamido)-1H-pyrazol-3-yl)cyclopentyl isopropylcarbamate (50 mg, 111 umol, 15% yield) as yellow oil (¹H NMR (400 MHz, DMSO-$d_6$) δ=12.31-12.06 (m, 1H), 10.60 (s, 1H), 10.04 (s, 1H), 9.27 (s, 1H), 8.41 (s, 1H), 8.22-7.90 (m, 4H), 7.06-6.85 (m, 1H), 6.43 (br s, 1H), 5.01 (br d, J=4.4 Hz, 1H), 3.58 (qd, J=6.8, 13.6 Hz, 1H), 3.14-2.99 (m, 1H), 2.10-1.38 (m, 6H), 1.03 (d, J=6.4 Hz, 6H)).

Tert-butyl methyl (prop-2-yn-1-yl)carbamate (Intermediate BX)

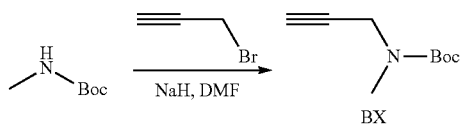

To a solution of tert-butyl N-methylcarbamate (10.0 g, 76.2 mmol, CAS #16066-84-5) in DMF (100 mL) was added NaH (3.66 g, 91.5 mmol) at 0° C. The reaction mixture was stirred at 25° C. for 0.5 h. Then 3-bromoprop-1-yne (13.6 g, 114 mmol, CAS #106-96-7) was added. The mixture was stirred at 25° C. for 2.5 hr. On completion, the reaction mixture was quenched by addition of $H_2O$ (50 mL) and extracted with dichloromethane (3×500 mL). The combined organic layers were washed with brine (3×100 mL) and dried over anhydrous $Na_2SO_4$, filtered and concentrated in vacuo. The residue was purified by column chromatography (Ethyl acetate) give the title compound (4.80 g, 37% yield) as colorless oil. ¹H NMR (400 MHz, DMSO-d6) δ 3.98 (d, J=2.0 Hz, 2H), 3.19 (s, 1H), 2.80 (s, 3H), 1.40 (s, 9H).

3-(3-methyl-4-(3-(methylamino)prop-1-yn-1-yl)-2-oxo-2,3-dihydro-1H-benzo[d]imidazol-1-yl)piperidine-2,6-dione (Intermediate BY)

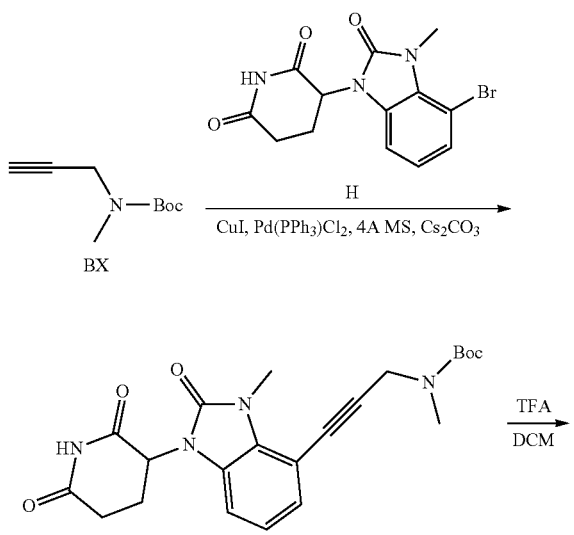

-continued

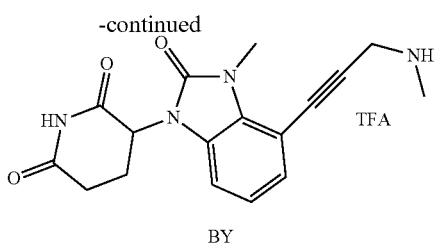

BY

Step 1—Tert-butyl(3-(1-(2,6-dioxopiperidin-3-yl)-3-methyl-2-oxo-2,3-dihydro-1H-benzo[d]imidazol-4-yl)prop-2-yn-1-yl)(methyl)carbamate. To a solution of tert-butyl N-methyl-N-prop-2-ynyl-carbamate (2.00 g, 11.8 mmol, Intermediate BX), 3-(4-bromo-3-methyl-2-oxo-benzimidazol-1-yl)piperidine-2,6-dione (2.66 g, 7.88 mmol, Intermediate H), CuI (150 mg, 787 umol), Pd(PPh$_3$)$_2$Cl$_2$ (553 mg, 787 umol), 4A molecular sieves (1.00 g, 7.88 mmol) and Cs$_2$CO$_3$ (10.2 g, 31.5 mmol) in DMF (50 mL). The mixture was stirred at 80° C. for 16 hr under N$_2$. On completion, the mixture was filtrated and the filtrate was concentrated in vacuo. The crude product was purified by reverse phase flash (0.1% FA condition) to give the title compound (600 mg, 16% yield) as yellow solid. $^1$H NMR (400 MHz, DMSO-d6) δ 11.12 (s, 1H), 7.23-6.90 (m, 3H), 5.44-5.35 (m, 1H), 4.29 (s, 2H), 3.61 (s, 3H), 3.54 (s, 1H), 2.89 (s, 2H), 2.95-2.80 (m, 1H), 2.77-2.59 (m, 2H), 2.07-1.96 (m, 1H), 1.42 (s, 9H).

Step 2—3-(3-Methyl-4-(3-(methylamino)prop-1-yn-1-yl)-2-oxo-2,3-dihydro-1H-benzo[d]imidazol-1-yl)piperidine-2,6-dione. To a solution of tert-butylN-[3-[1-(2,6-dioxo-3-piperidyl)-3-methyl-2-oxo-benzimidazol-4-yl]prop-2-ynyl]-N-methyl-carbamate (100 mg, 234 umol) in DCM (10 mL) was added TFA (1.54 g, 13.5 mmol). The mixture was stirred at 25° C. for 20 min. On completion, the reaction mixture was concentrated in vacuo to give the title compound (750 mg, 95% yield, TFA salt) as yellow oil. LC-MS (ESI$^+$) m/z 349.2 (M+23)$^+$.

1-(2,6-dioxo-3-piperidyl)-3-methyl-2-oxo-benzimidazole-4-carbaldehyde (Intermediate BZ)

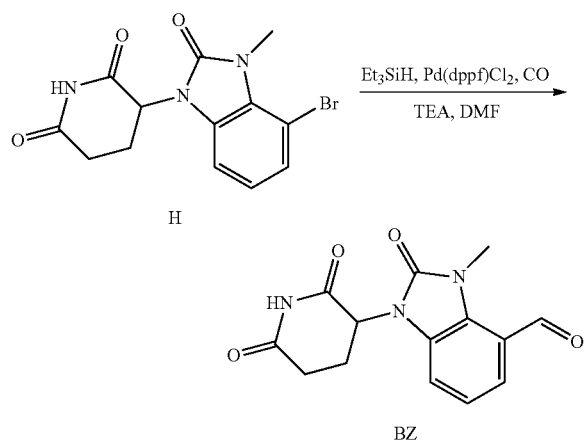

To a solution of 3-(4-bromo-3-methyl-2-oxo-2,3-dihydro-1H-benzo[d]imidazol-1-yl)piperidine-2,6-dione (500 mg, 1.48 mmol, Intermediate H) in DMF (20 mL) was added TEA (448 mg, 4.44 mmol), Pd(dppf)Cl$_2$ (162 mg, 221 umol) and Et$_3$SiH (515 mg, 4.44 mmol). The reaction mixture was stirred at 80° C. for 16 hours under CO (50 Psi). On completion, the reaction mixture was concentrated in vacuo and purified by reverse phase (0.1% FA) to give the title compound (400 mg, 47% yield) as a white solid. LC-MS (ESI$^+$) m/z 288.0 (M+H)$^+$.

3-[4-(3,9-Diazaspiro[5.5]undecan-3-ylmethyl)-3-methyl-2-oxo-benzimidazol-1-yl]piperidine-2,6-dione (Intermediate CA)

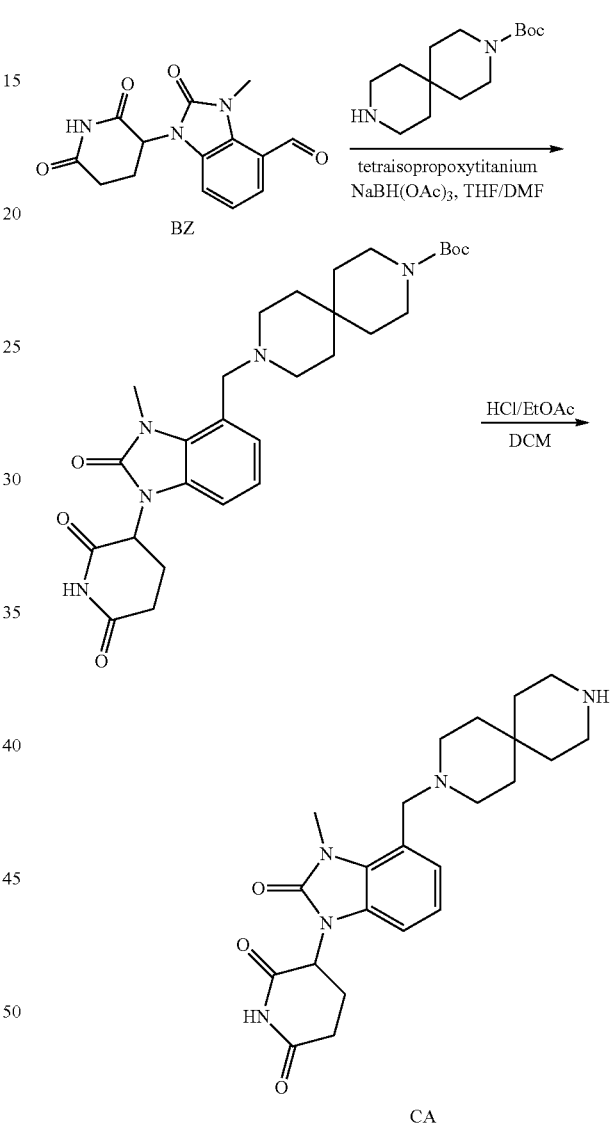

Step 1—Tert-butyl 9-[[1-(2,6-dioxo-3-piperidyl)-3-methyl-2-oxo-benzimidazol-4-yl]methyl]-3,9-diazaspiro[5.5]undecane-3-carboxylate. To a solution of 1-(2,6-dioxo-3-piperidyl)-3-methyl-2-oxo-benzimidazole-4-carbaldehyde (100 mg, 348 umol, Intermediate BZ) and tert-butyl 3,9-diazaspiro[5.5]undecane-3-carboxylate (88.5 mg, 348 umol, CAS #173405-78-2) in THF (3 mL) and DMF (3 mL) was added tetraisopropoxytitanium (296 mg, 1.04 mmol, 308 uL). The mixture was stirred at 80° C. for 2 hrs, then NaBH(OAc)$_3$ (147 mg, 696 umol) was added to the mixture. The reaction mixture was stirred at 20° C. for 16 hrs. On completion, the residue was filtered and the filtrate was concentrated in vacuo to give a residue. The residue was purified by reverse phase (0.1% FA condition) to give the title compound (145 mg, 79% yield) as a white solid. $^1$H NMR (400 MHz, DMSO-$d_6$) δ 11.10 (s, 1H), 7.06 (d, J=8.0 Hz, 1H), 6.95 (t, J=7.6 Hz, 1H), 6.90-6.85 (m, 1H), 5.37 (dd, J=5.2, 12.4 Hz, 1H), 3.66 (s, 3H), 3.65-3.60 (m, 2H), 3.30-3.23 (m, 4H), 2.94-2.84 (m, 1H), 2.77-2.68 (m, 1H), 2.65-2.57 (m, 1H), 2.43-2.34 (m, 4H), 2.05-1.96 (m, 1H), 1.45-1.39 (m, 4H), 1.38 (s, 9H), 1.36-1.30 (m, 4H); LC-MS (ESI$^+$) m/z 526.2 (M+H)$^+$.

Step 2—3-[4-(3,9-Diazaspiro[5.5]undecan-3-ylmethyl)-3-methyl-2-oxo-benzimidazol-1-yl]piperidine-2,6-dione. To a solution of tert-butyl 9-[[1-(2,6-dioxo-3-piperidyl)-3-methyl-2-oxo-benzimidazol-4-yl]methyl]-3,9-diazaspiro[5.5]undecane-3-carboxylate (70.0 mg, 133 umol) in DCM (1.5 mL) was added HCl/EtOAc (4 M, 1.50 mL). The reaction mixture was stirred at 20° C. for 0.5 hr. On completion, the mixture was concentrated in vacuo to give the title compound (60.0 mg, 97% yield, HCl) as a white solid. LC-MS (ESI$^+$) m/z 426.3 (M+H)$^+$.

(1S,3R)-3-(5-amino-1-(tert-butyl)-1H-pyrazol-3-yl)cyclopentyl isopropylcarbamate (Intermediate CB)

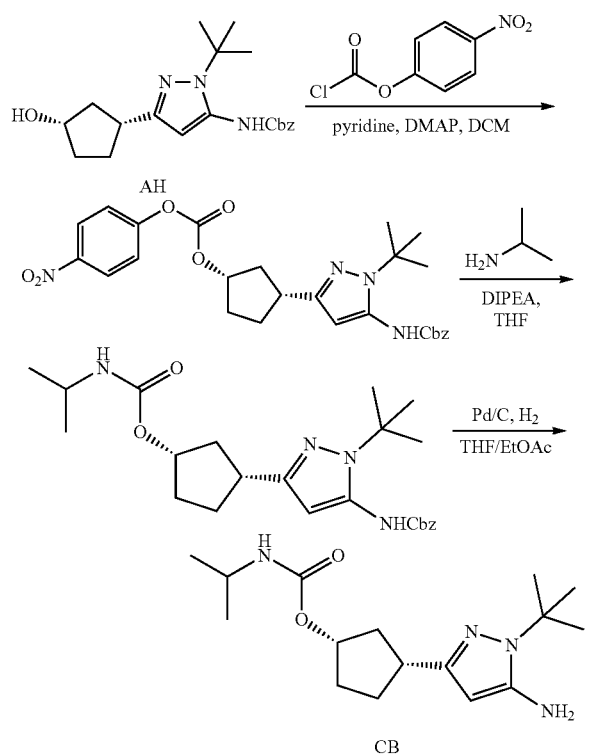

Step 1—Benzyl (1-(tert-butyl)-3-((1R,3S)-3-(((4-nitrophenoxy)carbonyl)oxy)cyclopentyl)-1H-pyrazol-5-yl)carbamate. To a solution of benzyl(1-(tert-butyl)-3-((1R,3S)-3-hydroxycyclopentyl)-1H-pyrazol-5-yl)carbamate (10.0 g, 27.9 mmol, Intermediate AH) and 4-nitrophenyl carbonochloridate (8.46 g, 41.9 mmol, CAS #7693-46-1) in dichloromethane (100 mL) was added DMAP (342 mg, 2.80 mmol) and pyridine (6.64 g, 83.9 mmol). The mixture was stirred at 20° C. for 12 h. On completion, the reaction mixture was quenched with water (100 mL), and extracted with dichloromethane (3×100 mL). The combined organic layers were washed with brine (2×100 mL), dried over sodium sulfate, filtered and concentrated under reduced pressure to give a residue. The crude product was purified by silica gel chromatography (eluted with petroleum ether/ethyl acetate=3:1~1/1) to give the title compound (14 g, 26.7 mmol, 96% yield) as colorless oil. $^1$H NMR (400 MHz, CDCl$_3$) δ=8.22-8.16 (m, 2H), 7.34-7.24 (m, 6H), 6.19-6.02 (m, 2H), 5.23-5.12 (m, 3H), 3.13-3.00 (m, 1H), 2.59-2.48 (m, 1H), 2.08-1.78 (m, 6H), 1.51 (s, 9H).

Step 2—Benzyl (1-(tert-butyl)-3-((1R,3S)-3-((isopropylcarbamoyl)oxy)cyclopentyl)-1H-pyrazol-5-yl)carbamate. To a mixture of benzyl (1-(tert-butyl)-3-((1R,3S)-3-(((4-nitrophenoxy)carbonyl)oxy)cyclopentyl)-1H-pyrazol-5-yl)carbamate (14 g, 26.7 mmol) and propan-2-amine (3.17 g, 53.5 mmol) in THF (140 mL) was added DIEA (17.3 g, 133 mmol) in one portion at 0° C. under N$_2$. The mixture was stirred at 20° C. for 10 h. On completion, the reaction mixture was quenched with water (100 mL), then extracted with dichloromethane (3×140 mL). The combined organic layers were washed with brine (3×100 mL), dried over sodium sulfate, filtered and concentrated under reduced pressure to give a residue. The crude product was purified by silica gel chromatography (eluted with Petroleum ether/Ethyl acetate=3:1~1/1) to give the title compound (10.8 g, 24.5 mmol, 92% yield) as a colorless gum. $^1$H NMR (400 MHz, CDCl$_3$) δ=7.52-7.46 (m, 1H), 7.38 (br s, 4H), 6.32 (br s, 1H), 6.13 (br s, 1H), 5.30 (s, 1H), 5.22-5.18 (m, 2H), 5.09-5.07 (m, 1H), 3.80 (br d, J=5.6 Hz, 1H), 3.10 (br d, J=7.6 Hz, 1H), 2.52-2.37 (m, 1H), 2.04-1.98 (m, 1H), 1.97-1.72 (m, 5H), 1.58 (s, 8H), 1.14 (br d, J=6.4 Hz, 6H).

Step 3—(1S,3R)-3-(5-amino-1-(tert-butyl)-1H-pyrazol-3-yl)cyclopentyl isopropylcarbamate. To a solution of Pd/C (3.24 g, 3.06 mmol, 10 wt %) in ethanol (300 mL) was added benzyl (1-(tert-butyl)-3-((1R,3S)-3-((isopropylcarbamoyl)oxy)cyclopentyl)-1H-pyrazol-5-yl)carbamate (10.8 g, 24.4 mmol) under nitrogen flow. The suspension was degassed under vacuum and purged with hydrogen several times. The mixture was stirred under hydrogen (15 psi) at 20° C. for 10 h. On completion, the reaction was filtered to get the filtrate and concentrated to give the title compound (5.1 g) as a yellow oil. $^1$H NMR (400 MHz, CDCl$_3$) δ=5.2 (br s, 1H), 4.44 (br s, 1H), 3.8 (br d, J=4.4 Hz, 1H), 3.53 (br s, 2H), 3.11-2.94 (m, 1H), 2.55-2.41 (m, 1H), 2.05-1.72 (m, 6H), 1.62 (s, 9H), 1.15 (d, J=6.4 Hz, 6H).

2-(2-(2-(2-(2-(prop-2-yn-1-yloxy)ethoxy)ethoxy)ethoxy)phenyl)acetic acid (Intermediate CC)

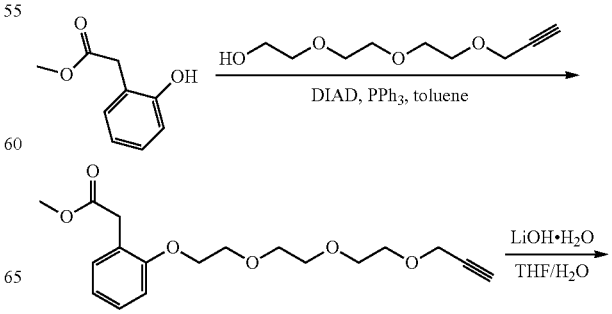

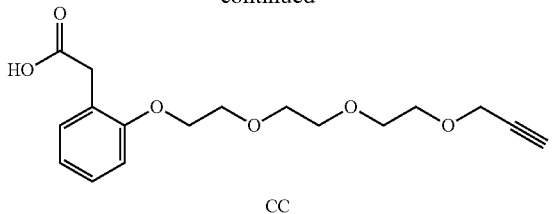

CC

Step 1—Methyl 2-(2-(2-(2-(2-(prop-2-yn-1-yloxy)ethoxy)ethoxy)ethoxy)phenyl)acetate. To a solution of methyl methyl 2-(2-hydroxyphenyl)acetate (993 mg, 5.98 mmol, CAS #22446-37-3), 2-(2-(2-(prop-2-yn-1-yloxy)ethoxy)ethoxy)ethanol (1.35 g, 7.17 mmol, CAS #208827-90-1) and PPh₃ (2.04 g, 7.77 mmol) in toluene (10 mL) was added a solution of DIAD (1.57 g, 7.77 mmol, 1.51 mL) in toluene (10 mL) dropwise slowly at 0° C. Then the reaction was stirred 20° C. for 10 h under nitrogen atmosphere. On completion, the reaction mixture was quenched with water (30 mL) and extracted with ethyl acetate (3×30 mL). The combined organic layers were washed with brine (2×20 mL), dried over sodium sulfate, filtered and concentrated under reduced pressure to give a residue. The residue was purified by column chromatography (SiO₂, Petroleum ether/Ethyl acetate=3/1~1/1) to give the title compound (625 mg, 1.86 mmol, 31% yield) as a colorless gum. ¹H NMR (400 MHz, CDCl₃) δ=7.27-7.22 (m, 1H), 7.19 (d, J=7.2 Hz, 1H), 6.93 (t, J=7.2 Hz, 1H), 6.88 (d, J=8.4 Hz, 1H), 4.21 (d, J=2.4 Hz, 2H), 4.14 (t, J=5.2 Hz, 2H), 3.84 (t, J=5.2 Hz, 2H), 3.76-3.63 (m, 14H), 2.43 (t, J=2.4 Hz, 1H).

Step 2—2-(2-(2-(2-(2-(prop-2-yn-1-yloxy)ethoxy)ethoxy)ethoxy)phenyl)acetic acid. To a solution of methyl methyl 2-(2-(2-(2-(2-(prop-2-yn-1-yloxy)ethoxy)ethoxy)ethoxy)phenyl)acetate (625 mg, 1.86 mmol) in THF (6 mL) and H₂O (2 mL) was added LiOH·H₂O (311 mg, 7.43 mmol) for one portion. The mixture was stirred at 20° C. for 10 h. On completion, the reaction mixture was poured into water (10 mL) and extracted with ethyl acetate (3×20 mL) and the aqueous phase was acidified with 1N HCl to pH=4. The mixture was then extracted with ethyl acetate (3×20 mL), the combined organic layers were washed with brine (3×20 mL), dried over sodium sulfate, filtered and concentrated under reduced pressure to give the title compound (220 mg) as a colorless oil. ¹H NMR (400 MHz, CDCl₃) δ 7.26-7.22 (m, 1H), 7.21-7.18 (m, 1H), 6.95-6.91 (m, 1H), 6.84 (d, J=8.0 Hz, 1H), 4.21 (d, J=2.4 Hz, 2H), 4.19-4.17 (m, 2H), 3.82 (td, J=2.0, 4.4 Hz, 2H), 3.79-3.69 (m, 10H), 3.61 (s, 2H), 2.43 (t, J=2.4 Hz, 1H), 1.29-1.24 (m, 1H).

1S,3R)-3-(1-(tert-butyl)-5-(2-(2-(2-(2-(prop-2-yn-1-yloxy)ethoxy)ethoxy)ethoxy)phenyl)acetamido)-1H-pyrazol-3-yl)cyclopentyl isopropylcarbamate (Intermediate CD)

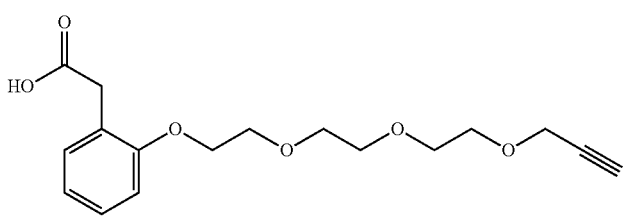 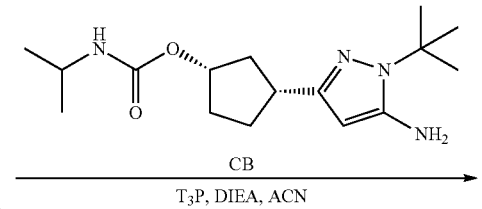

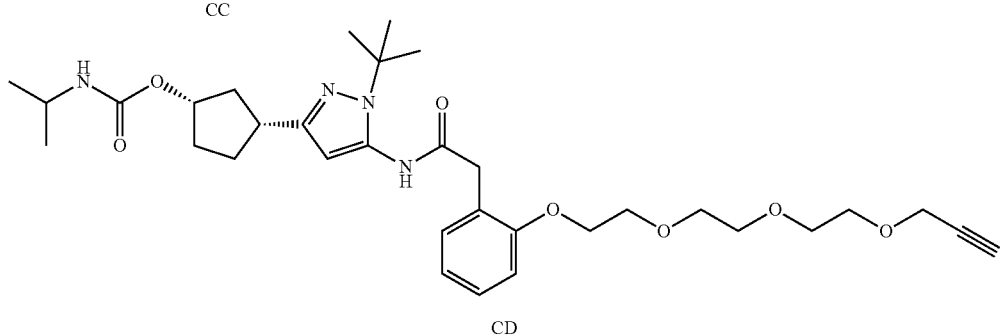

CD

To a solution of (1S,3R)-3-(5-amino-1-(tert-butyl)-1H-pyrazol-3-yl)cyclopentyl isopropylcarbamate (210 mg, 682 umol, Intermediate CB) in ACN (5 mL) was added 2-(2-(2-(2-(2-(prop-2-yn-1-yloxy)ethoxy)ethoxy)ethoxy)phenyl)acetic acid (220 mg, 682 umol, Intermediate CC), DIEA (441 mg, 3.41 mmol) and T₃P (1.30 g, 2.05 mmol, 50% solution in DMF) in one portion. Then the mixture was stirred at 60° C. for 2 h under nitrogen atmosphere. On completion, the reaction mixture was poured into the saturated ammonium chloride solution (10 mL), and extracted with ethyl acetate (3×20 mL). The combined organic layers were washed with brine (3×20 mL), dried over sodium sulfate, filtered and concentrated under reduced pressure to give a residue. The residue was purified by flash silica gel chromatography (ISCO®; 4 g SepaFlash® Silica Flash Column, Eluent of 0~50% Ethyl acetate/Petroleum ether gradient @ 50 mL/min) to give the title compound (95 mg, 154 umol, 23% yield) as a yellow oil. ¹H NMR (400 MHz, CDCl₃) δ=7.26-7.20 (m, 2H), 6.93 (t, J=7.2 Hz, 1H), 6.86 (d, J=8.0 Hz, 1H), 6.09 (s, 1H), 5.06 (br s, 1H), 4.67-4.49 (m, 1H), 4.13-4.10 (m, 4H), 3.82-3.79 (m, 2H), 3.69 (s, 2H), 3.58 (br dd, J=3.6, 5.6 Hz, 4H), 3.53 (dd, J=4.0, 5.6 Hz, 2H), 3.47 (dd, J=3.6, 5.6 Hz, 2H), 3.38-3.31 (m, 2H), 3.07-2.93 (m, 1H), 2.35 (t, J=2.4 Hz, 2H), 1.92-1.66 (m, 6H), 1.23 (s, 9H), 1.07 (dd, J=3.2, 6.4 Hz, 6H).

3-(5-bromo-3-methyl-2-oxo-2,3-dihydro-1H-benzo[d]imidazol-1-yl)-1-methylpiperidine-2,6-dione (Intermediate CE)

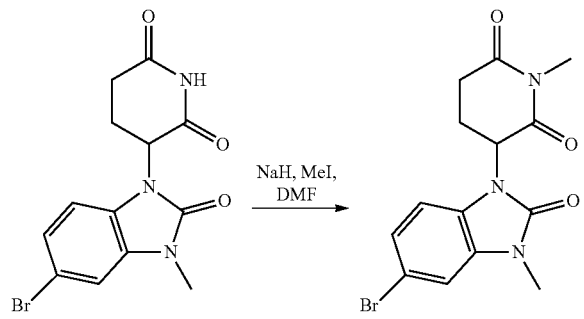

To a solution of 3-(5-bromo-3-methyl-2-oxo-2,3-dihydro-1H-benzo[d]imidazol-1-yl)piperidine-2,6-dione (1 g, 2.96 mmol, Intermediate J) in DMF (16 mL) was added NaH (141 mg, 3.55 mmol, 60% dispersion in mineral oil) portionwise. The mixture was stirred at 0° C. for 30 min under $N_2$ atmosphere. Then MeI (503 mg, 3.55 mmol) was added to the mixture which was then stirred at 25° C. for 12 h. The reaction mixture was quenched with $NH_4Cl$ (sat. aq, 20 mL) at 25° C. and extracted with EtOAc (20 mL×3). The combined organic layer was washed with brine (20 mL×3), dried over $Na_2SO_4$, filtered and concentrated under reduced pressure to give a residue. The residue was purified by column chromatography ($SiO_2$, Petroleum ether/Ethyl acetate=3/1 to 0/1) to give the title compound (850 mg, 2.41 mmol, 82% yield) as a white solid. LC-MS (ESI$^+$) m/z 354.2 (M+H)$^+$.

3-(3-methyl-2-oxo-5-(3-(4-(piperazin-1-yl)butoxy)propyl)-2,3-dihydro-1H-benzo[d]imidazol-1-yl)piperidine-2,6-dione (Intermediate CF)

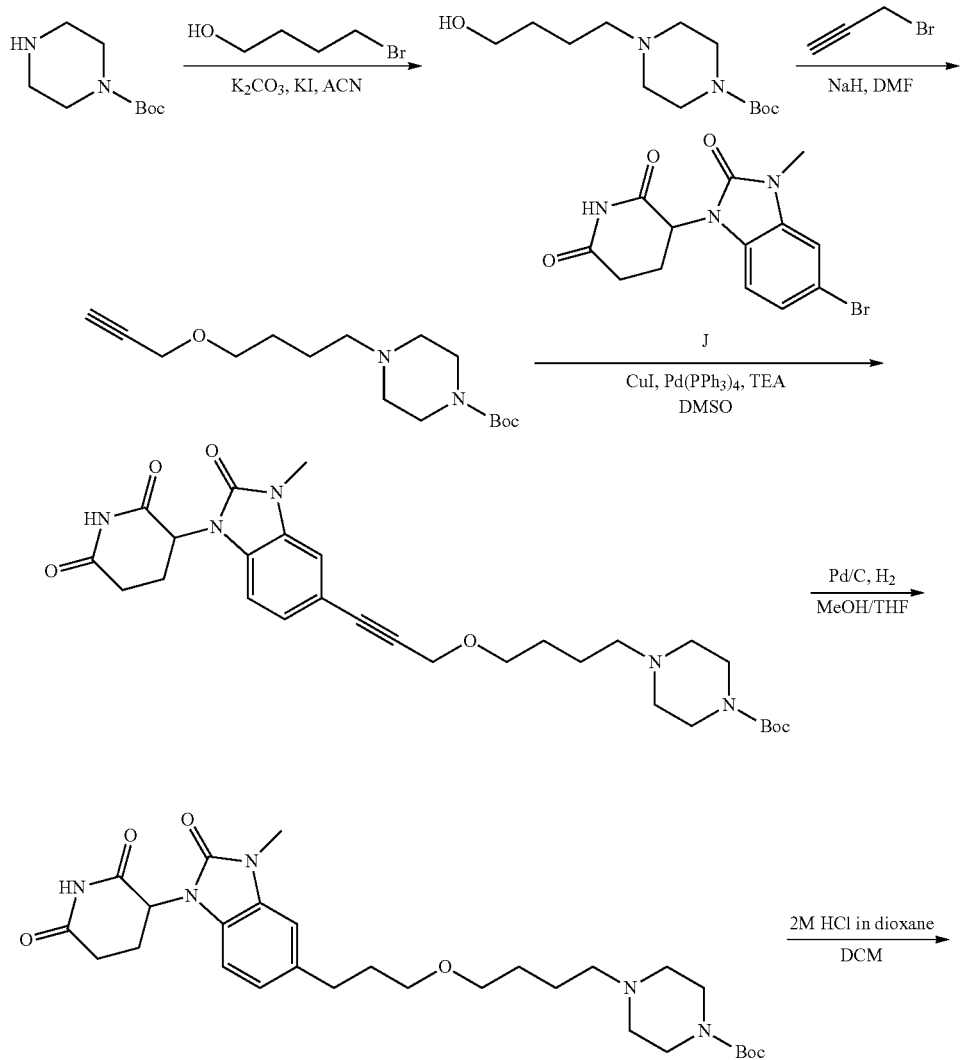

-continued

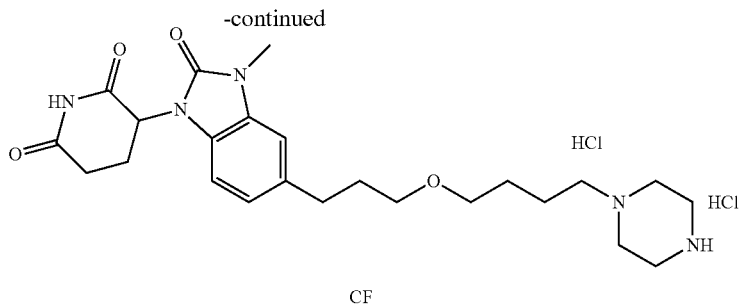

Step 1—Tert-butyl 4-(4-hydroxybutyl)piperazine-1-carboxylate. To a stirred solution of tert-butyl piperazine-1-carboxylate (39.00 g, 209.4 mmol) and 4-bromobutan-1-ol (48.06 g, 314.1 mmol) in ACN (1000 mL) were added $K_2CO_3$ (115.76 g, 837.6 mmol) and KI (17.38 g, 104.7 mmol) in portions at rt under nitrogen atmosphere. The resulting mixture was stirred overnight at 90° C. under nitrogen atmosphere. On completion, the mixture was allowed to cool down to room temperature and was filtered. The filter cake was washed with MeCN (3×50 mL) and the filtrate was concentrated under reduced pressure. The residue was quenched with water and extracted with EtOAc (3×500 mL). The combined organic layers were washed with brine (500 mL), and dried over anhydrous $Na_2SO_4$. After filtration, the filtrate was concentrated under reduced pressure. The residue was purified by silica gel column chromatography, eluted with $CH_2Cl_2$/MeOH (30:1), to afford the title compound (19.7 g, 36% yield) as a light yellow oil. $^1$H NMR (400 MHz, Chloroform-d) δ 5.62-5.57 (m, 1H), 3.57 (t, J=4.9 Hz, 2H), 3.49-3.41 (m, 4H), 2.46-2.42 (m, 4H), 2.42-2.37 (m, 2H), 1.69-1.63 (m, 4H), 1.45 (s, 9H). LC/MS (ESI, m/z): $[(M+1)]^+$=259.3.

Step 2—Tert-butyl 4-[4-(prop-2-yn-1-yloxy)butyl]piperazine-1-carboxylate. To a stirred solution of tert-butyl 4-(4-hydroxybutyl)piperazine-1-carboxylate (31.50 g, 121.9 mmol) in DMF (300.00 mL) was added NaH (5.85 g, 244 mmol, 60% dispersion in mineral oil) in portions at 0° C. under nitrogen atmosphere. The resulting mixture was stirred for 30 min at 0° C. under nitrogen atmosphere. To the above mixture was added a solution of propargyl bromide (29.01 g, 243.9 mmol) in DMF (50.00 mL) dropwise at 0° C. under nitrogen atmosphere. The resulting mixture was stirred overnight at rt under nitrogen atmosphere. On completion, the reaction was quenched with sat. $NH_4Cl$ (aq.) at 0° C. and extracted with EtOAc (3×400 mL). The combined organic layers were washed with brine (500 mL), and dried over anhydrous $Na_2SO_4$. After filtration, the filtrate was concentrated under reduced pressure. The residue was purified by silica gel column chromatography, eluted with PE/EtOAc=5/1 to afford the title compound (19.7 g, 55% yield) as a brown oil. $^1$H NMR (400 MHz, Chloroform-d) δ 4.14 (d, J=2.4 Hz, 2H), 3.54 (t, J=6.1 Hz, 2H), 3.48-3.41 (m, 4H), 2.43 (t, J=2.4 Hz, 1H), 2.42-2.34 (m, 6H), 1.71-1.53 (m, 4H), 1.47 (s, 9H). LC/MS (ESI, m/z): $[(M+1)]^+$=297.3.

Step 3—Tert-butyl 4-[4-([3-[1-(2,6-dioxopiperidin-3-yl)-3-methyl-2-oxo-1,3-benzodiazol-5-yl]prop-2-yn-1-yl]oxy)butyl]piperazine-1-carboxylate. To a stirred solution of 3-(5-bromo-3-methyl-2-oxo-1,3-benzodiazol-1-yl)piperidine-2,6-dione (10.00 g, 29.572 mmol, Intermediate J) and tert-butyl 4-[4-(prop-2-yn-1-yloxy)butyl]piperazine-1-carboxylate (13.19 g, 44.36 mmol) in DMSO (200.00 mL) and TEA 49.20 mL) were added $Pd(PPh_3)_4$ (3.42 g, 2.96 mmol) and CuI (0.56 g, 2.9 mmol) in portions at rt under nitrogen atmosphere. The resulting mixture was purged with nitrogen 3 times. The resulting mixture was stirred for 2 h at 80° C. under nitrogen atmosphere. On completion, the mixture was allowed to cool down to rt and diluted with water (100 mL). The resulting mixture was washed with EA (3×150 mL). The combined organic layer was washed with brine (100 mL), and dried over anhydrous $Na_2SO_4$. The resulting mixture was concentrated under reduced pressure. The residue was purified by silica gel column chromatography, eluted with $CH_2Cl_2$/MeOH (20:1), to afford the title compound (8.3 g, 51% yield) as a yellow oil. $^1$H NMR (400 MHz, Chloroform-d) δ 8.81 (s, 1H), 7.20 (dd, J=8.1, 1.5 Hz, 1H), 7.12 (d, J=1.4 Hz, 1H), 6.76 (d, J=8.1 Hz, 1H), 5.21 (dd, J=12.7, 5.3 Hz, 1H), 4.36 (s, 2H), 3.60 (t, J=6.1 Hz, 2H), 3.46-3.42 (m, 7H), 3.01-2.88 (m, 1H), 2.88-2.66 (m, 2H), 2.42-2.36 (m, 6H), 2.28-2.17 (m, 1H), 1.70-1.59 (m, 4H), 1.47 (s, 9H). LC/MS (ESI, m/z): $[(M+1)]^+$=554.4.

Step 4—Tert-butyl 4-(4-[3-[1-(2,6-dioxopiperidin-3-yl)-3-methyl-2-oxo-1,3-benzodiazol-5-yl]propoxy]butyl)piperazine-1-carboxylate. To a stirred solution of tert-butyl 4-[4-([3-[1-(2,6-dioxopiperidin-3-yl)-3-methyl-2-oxo-1,3-benzodiazol-5-yl]prop-2-yn-1-yl]oxy)butyl]piperazine-1-carboxylate (8.00 g, 14.4 mmol) in $CH_3OH$ (100.00 mL) and THF (10.00 mL) was added Pd/C (4.00 g, 37.6 mmol) at rt. The resulting mixture was purged with hydrogen 3 times and stirred overnight at rt under hydrogen atmosphere. On completion, the resulting mixture was filtered, and the filter cake was washed with THF (3×30 mL). The solution was condensed under reduced pressure to afford the title compound (7.5 g) as a light yellow oil. LC/MS (ESI, m/z): $[(M+1)]^+$=558.4.

Step 5—3-(3-Methyl-2-oxo-5-[3-[4-(piperazin-1-yl)butoxy]propyl]-1,3-benzodiazol-1-yl)piperidine-2,6-dione dihydrochloride. To a stirred solution of tert-butyl 4-(4-[3-[1-(2,6-dioxopiperidin-3-yl)-3-methyl-2-oxo-1,3-benzodiazol-5-yl]propoxy]butyl)piperazine-1-carboxylate (7.50 g, 13.5 mmol) in DCM (100.00 mL) was added 4 M HCl (gas) in 1,4-dioxane (30.00 mL) at rt under nitrogen atmosphere. The resulting mixture was stirred for 1 h at rt under nitrogen atmosphere. On completion, $Et_2O$ (200 mL) was added to the mixture. The precipitated solids were collected by filtration and washed with $Et_2O$ (3×100 mL) to give the title compound (5 g, 70% yield) as a light yellow solid. $^1$H NMR (400 MHz, DMSO-$d_6$) δ 11.56 (broad, 1H), 11.08 (s, 1H), 9.52 (broad, 2H), 7.05 (d, J=1.5 Hz, 1H), 7.01 (d, J=8.1 Hz, 1H), 6.88 (dd, J=8.1, 1.6 Hz, 1H), 5.35 (dd, J=12.7, 5.4 Hz, 1H), 3.68-3.64 (m, 2H), 3.51-3.36 (m, 9H), 3.27-3.11 (m, 4H), 2.99-2.86 (m, 1H), 2.78-2.58 (m, 4H), 2.56-2.53 (m, 2H), 2.03-1.97 (m, 1H), 1.93-1.66 (m, 4H), 1.58-1.53 (m, 2H). LC/MS (ESI, m/z): $[(M+1)]^+$=458.3.

3-(4-(3-(3-(3-aminopropoxy)propoxy)propyl)-3-methyl-2-oxo-2,3-dihydro-1H-benzo[d]imidazol-1-yl)piperidine-2,6-dione (Intermediate CG)

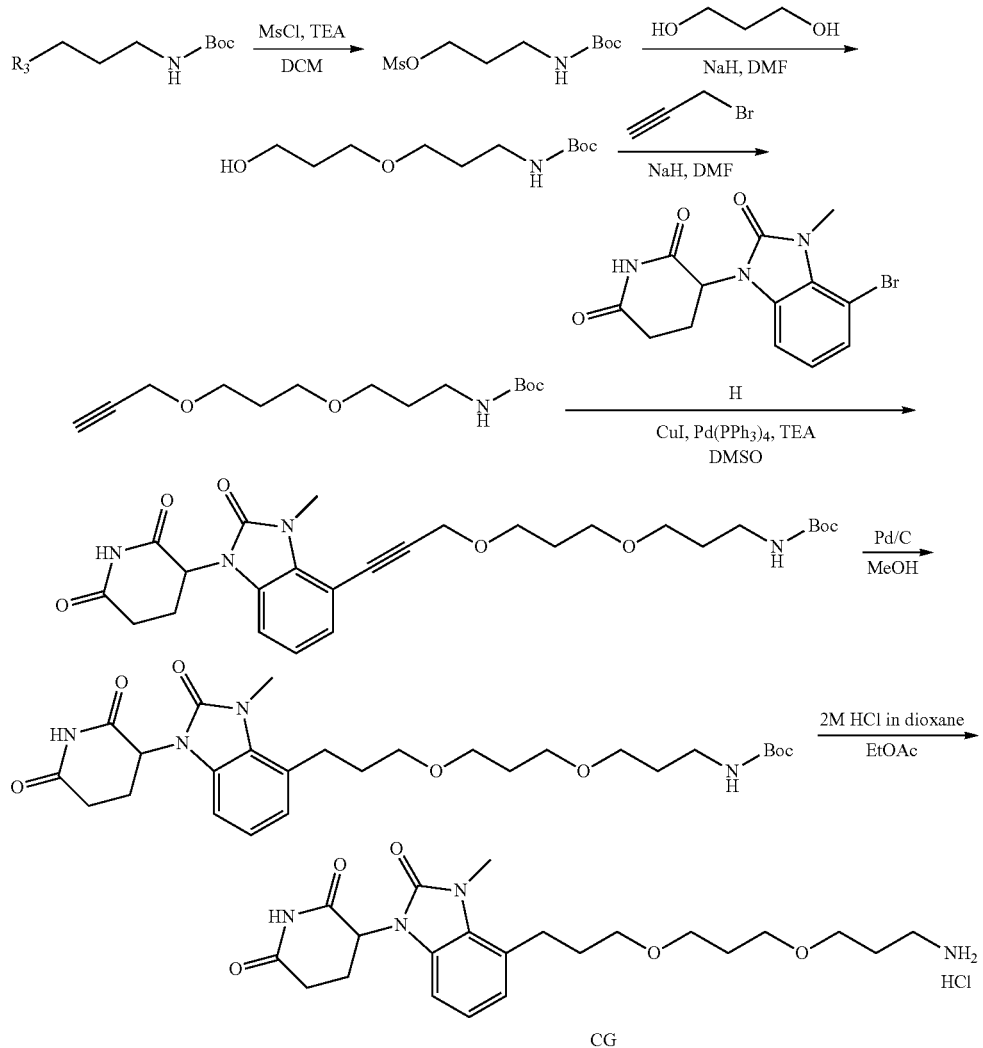

Step 1—Tert-butyl N-[3-(methanesulfonyloxy)propyl]carbamate. To a stirred solution of tert-butyl N-(3-hydroxypropyl)carbamate (92.6 g, 528 mmol) and TEA (109.8 mL, 792.7 mmol) in DCM (800 mL) was added a solution of Ms-Cl (60.5 g, 528 mmol) in DCM (200 mL) dropwise at 0° C. under nitrogen atmosphere. The resulting mixture was stirred for 30 min at rt under nitrogen atmosphere. On completion, the reaction mixture was diluted with water (2 L) and extracted with CH$_2$Cl$_2$ (3×800 mL). The combined organic layers were washed with brine (1.5 L), and dried over anhydrous Na$_2$SO$_4$. After filtration, the filtrate was concentrated under reduced pressure. The residue was purified by silica gel column chromatography, eluted with PE/EtOAc (3:2), to afford the title compound (112 g, 84% yield) as a light brown solid. $^1$H NMR (400 MHz, Chloroform-d) δ 4.93-4.90 (m, 1H), 4.26-4.22 (m, 2H), 3.24-3.19 (m, 2H), 3.01 (s, 3H), 1.94-1.88 (m, 2H), 1.38 (s, 9H). LC/MS (ESI, m/z): [(M+1)]$^+$=254.2.

Step 2—Tert-butyl N-[3-(3-hydroxypropoxy)propyl]carbamate. To a solution of propane-1,3-diol (50 g, 657 mmol) in DMF (500 mL) was added sodium hydride (4.8 g, 200 mmol, 60% dispersion in mineral oil oil) at 0° C. The mixture was stirred for 15 min. To above mixture was added a solution of tert-butyl N-[3-(methanesulfonyloxy)propyl]carbamate (25.3 g, 100 mmol) in DMF (150 mL) at rt. The mixture was stirred for 16 hours at rt. On completion, the reaction was quenched with sat. NH$_4$Cl (aq.) (200 mL) at 0° C. The resulting mixture was concentrated under reduced pressure. The mixture was diluted with brine (1.5 L) and extracted with EtOAc (3×500 mL). The combined organic layers were washed with brine (500 mL), and dried over anhydrous Na$_2$SO$_4$. After filtration, the filtrate was concentrated under reduced pressure. The residue was purified by silica gel column chromatography, eluted with PE/EtOAc (2:1), to afford the title compound (13.7 g, 59% yield) as a light yellow oil. $^1$H NMR (400 MHz, Chloroform-d) δ 5.05-5.02 (m, 1H), 3.69-3.64 (m, 2H), 3.52-3.49 (m, 2H), 3.43-3.40 (m, 2H), 3.15-3.109 (m, 3H), 1.77-1.72 (m, 2H), 1.69-1.64 (m, 2H), 1.37 (s, 9H). LC/MS (ESI, m/z): [(M+1)]$^+$=234.2.

Step 3—Tert-butyl N-[3-[3-(prop-2-yn-1-yloxy)propoxy]propyl]carbamate. To a solution of tert-butyl N-[3-(3-hydroxypropoxy)propyl]carbamate (12.5 g, 53.6 mmol) in THF (300 mL) was added sodium hydride (2.6 g, 110 mmol, 60% dispersion in mineral oil) at 0° C. The mixture was stirred for 15 min. Next, a solution of 3-bromoprop-1-yne (6.4 g, 54 mmol) in THF (50 mL) was added and the mixture was allowed to warm to rt and stirred for 16 hours. On completion, the reaction was quenched with sat. NH$_4$Cl (aq.) (200 mL) at 0° C. The resulting mixture was diluted with brine (500 mL) and extracted with EtOAc (3×300 mL). The combined organic layers were washed with brine (500 mL), and dried over anhydrous Na$_2$SO$_4$. After filtration, the filtrate was concentrated under reduced pressure. The residue was purified by silica gel column chromatography, eluted with PE/EtOAc (3:1), to afford the title compound (9.2 g, 60% yield) as a light yellow solid. $^1$H NMR (400 MHz, Chloroform-d) δ 4.93 (broad, 1H), 4.11 (d, J=2.4 Hz, 2H), 3.57 (t, J=6.3 Hz, 2H), 3.46 (q, J=6.2 Hz, 4H), 3.19 (d, J=7.6 Hz, 2H), 2.42 (t, J=2.4 Hz, 1H), 1.83 (p, J=6.3 Hz, 2H), 1.71 (p, J=6.2 Hz, 2H), 1.41 (s, 9H). LC/MS (ESI, m/z): [(M+1)]$^+$=272.3.

Step 4—Tert-butyl N-[3-[3-([3-[1-(2,6-dioxopiperidin-3-yl)-3-methyl-2-oxo-2,3-dihydro-1H-1,3-benzodiazol-4-yl]prop-2-yn-1-yl]oxy)propoxy]propyl]carbamate. To a stirred solution of 3-(4-bromo-3-methyl-2-oxo-2,3-dihydro-1H-1,3-benzodiazol-1-yl)piperidine-2,6-dione (2 g, 5.9 mmol, Intermediate H), tert-butyl N-[3-[3-(prop-2-yn-1-yloxy)propoxy]propyl]carbamate (3 g, 11 mmol) and TEA (15 mL) in DMA (30 mL) were added CuI (112.64 mg, 0.591 mmol) and Pd(PPh$_3$)$_4$ (683.44 mg, 0.591 mmol) at rt under nitrogen atmosphere. The resulting mixture was stirred for 6 h at 80° C. under nitrogen atmosphere. On completion, the mixture was allowed to cool down to rt then concentrated under reduced pressure. The residue was purified by reverse phase flash chromatography (column, C18 silica gel; mobile phase, ACN in aq. FA (10 mmol/L), 35% to 60% gradient in 15 min; detector, UV 254 nm) to afford the title compound (1.4 g, 45% yield) as a light brown solid. $^1$H NMR (400 MHz, DMSO-d$_6$) δ 11.12 (s, 1H), 7.18 (dd, J=7.9, 1.2 Hz, 1H), 7.13 (dd, J=7.9, 1.2 Hz, 1H), 7.03 (t, J=7.9 Hz, 1H), 6.76-6.72 (m, 1H), 5.41 (dd, J=12.7, 5.4 Hz, 1H), 4.43 (s, 2H), 3.64 (s, 3H), 3.62-3.55 (m, 2H), 3.42 (t, J=6.4 Hz, 2H), 3.35 (d, J=12.6 Hz, 2H), 3.01-2.82 (m, 3H), 2.77-2.56 (m, 2H), 2.06-1.99 (m, 1H), 1.82-1.74 (m, 2H), 1.62-1.55 (m, 2H), 1.37 (s, 9H). LC/MS (ESI, m/z): [(M+1)]$^+$=529.3.

Step 5—Tert-butyl N-[3-(3-[3-[1-(2,6-dioxopiperidin-3-yl)-3-methyl-2-oxo-2,3-dihydro-1H-1,3-benzodiazol-4-yl]propoxy]propoxy)propyl]carbamate. To a stirred solution of tert-butyl N-[3-[3-([3-[1-(2,6-dioxopiperidin-3-yl)-3-methyl-2-oxo-2,3-dihydro-1H-1,3-benzodiazol-4-yl]prop-2-yn-1-yl]oxy)propoxy]propyl]carbamate (600 mg, 1 mmol) in THF (15 mL) was added Pd/C (300 mg, 0.3 mmol, 10 wt %) at rt under nitrogen atmosphere. The resulting mixture was purged with H$_2$ three and stirred for 4 h at rt under hydrogen atmosphere. On completion, the reaction mixture was filtered through a celite pad. The filtrate was concentrated under reduced pressure to afford the title compound (580 mg, 96% yield) as a light brown solid. $^1$H NMR (400 MHz, DMSO-d$_6$) δ 11.10 (s, 1H), 7.00-6.94 (m, 2H), 6.88-6.84 (m, 1H), 6.79-6.76 (m, 1H), 5.37 (dd, J=12.5, 5.4 Hz, 1H), 3.57 (s, 3H), 3.48-3.39 (m, 6H), 3.37-3.34 (m, 2H), 3.01-2.84 (m, 5H), 2.79-2.57 (m, 2H), 2.06-1.95 (m, 1H), 1.86-1.80 (m, 2H), 1.79-1.69 (m, 2H), 1.64-1.57 (m, 2H), 1.37 (s, 9H). LC/MS (ESI, m/z): [(M+1)]$^+$=533.3.

Step 6—3-(4-[3-[3-(3-Aminopropoxy)propoxy]propyl]-3-methyl-2-oxo-2,3-dihydro-1H-1,3-benzodiazol-1-yl)piperidine-2,6-dione hydrochloride. To a stirred solution of tert-butyl N-[3-(3-[3-[1-(2,6-dioxopiperidin-3-yl)-3-methyl-2-oxo-2,3-dihydro-1H-1,3-benzodiazol-4-yl]propoxy]propoxy)propyl]carbamate (580 mg, 1.1 mmol) in 1,4-dioxane (7 mL) was added HCl (4 M in dioxane) (7 mL) dropwise at 0° C. under nitrogen atmosphere. The resulting mixture was stirred for 16 h at rt under nitrogen atmosphere. On completion, the mixture was concentrated under reduced pressure. The residue was dissolved in 1,4-dioxane (10 mL) and re-concentrated under reduced pressure to afford the title compound (489 mg, 96% crude yield) as a light green solid. $^1$H NMR (400 MHz, DMSO-d$_6$) δ 11.11 (s, 1H), 7.81 (broad, 3H), 7.05-6.95 (m, 2H), 6.89-6.85 (m, 1H), 5.38 (dd, J=12.5, 5.4 Hz, 1H), 3.58 (s, 3H), 3.45-3.41 (m, 8H), 3.01-2.78 (m, 5H), 2.78-2.58 (m, 2H), 2.06-1.95 (m, 1H), 1.90-1.69 (m, 6H). LC/MS (ESI, m/z): [(M+1)]$^+$=433.3.

4-[(7'-Cyclopentyl-6'-oxo-spiro[cyclopropane-1,5'-pyrrolo[2,3-d]pyrimidine]-2'-yl)amino]-3-methyl-benzenesulfonyl chloride (Intermediate CH)

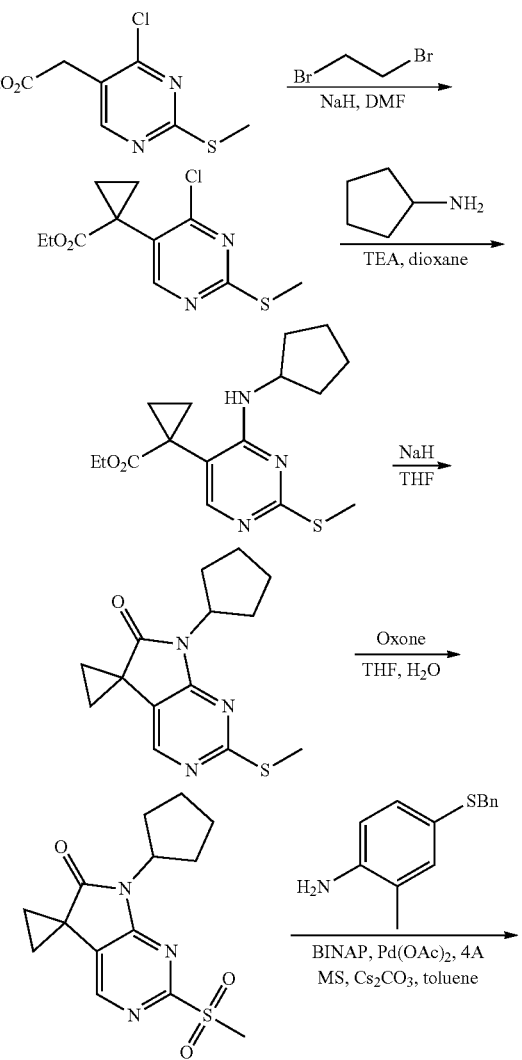

-continued

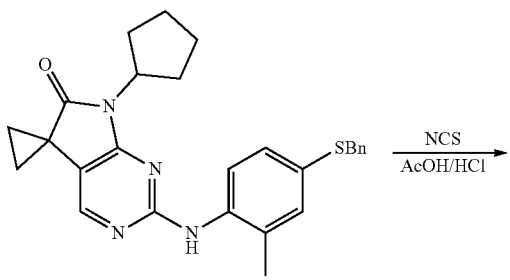

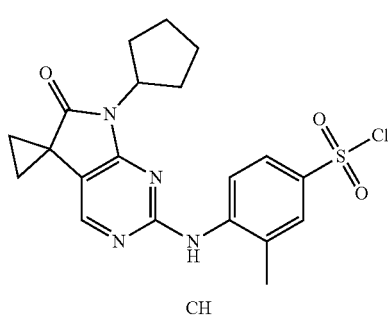

Step 1—Ethyl 1-(4-chloro-2-(methylthio)pyrimidin-5-yl)cyclopropanecarboxylate. To a solution of NaH (2.43 g, 60.8 mmol, 60% dispersion in mineral oil) in DMF (60 mL) at 0° C., and then the solution of ethyl 2-(4-chloro-2-methylsulfanyl-pyrimidin-5-yl)acetate (6 g, 24.3 mmol, CAS #61727-34-2) and 1,2-dibromoethane (6.85 g, 36.5 mmol, CAS #106-93-4) in DMF (60 mL) was added slowly at 0° C. Then the solution was stirred at 25° C. for 0.5 h. On completion, the mixture was poured into sat. $NH_4Cl$ (60 mL) at 0° C. slowly, and the solution was extracted with EtOAc (50 ml×3). The combined organic layer was concentrated under reduced pressure to give the residue. The residue was purified by column chromatography ($SiO_2$, Petroleum ether/Ethyl acetate=15/1 to 10/1) to give the title compound (4.5 g, 63% yield) as a yellow oil. LC-MS (ESI$^+$) m/z 272.9 (M+H)$^+$.

Step 2—Ethyl 1-(4-(cyclopentylamino)-2-(methylthio)pyrimidin-5-yl)cyclopropanecarboxylate. To a solution of ethyl 1-(4-chloro-2-methylsulfanyl-pyrimidin-5-yl)cyclopropanecarboxylate (4.8 g, 17.6 mmol) in dioxane (10 mL) was added TEA (2.67 g, 26.4 mmol) and cyclopentanamine (3.75 g, 44.0 mmol). The mixture was then stirred at 60° C. for 12 h. On completion, the mixture was diluted with water (20 ml), and extracted with $CH_2Cl_2$ (20 ml×3). The organic layers was washed with brine (20 ml×3), then the combined organic layer was concentrated under reduced pressure to give the residue. The residue was purified by column chromatography ($SiO_2$, Petroleum ether/Ethyl acetate=8/1 to 4/1) to give the title compound (5 g, 85% yield) as a red oil. LC-MS (ESI$^+$) m/z 322.0 (M+H)$^+$.

Step 3—7'-Cyclopentyl-2'-(methylthio)spiro[cyclopropane-1,5'-pyrrolo[2,3-d]pyrimidin]-6'(7'H)-one. To a solution of ethyl 1-[4-(cyclopentylamino)-2-methylsulfanyl-pyrimidin-5-yl]cyclopropanecarboxylate (4.8 g, 14.9 mmol) in THF (80 mL) was added NaH (1.19 g, 29.9 mmol, 60% dispersion in mineral oil). Then the mixture was stirred at 0-60° C. for 1 h. On completion, the mixture was quenched with HCl (1 M, 20 ml) at 0° C., and then the solution was extracted with EtOAc (20 ml×3). The combined organic layers was washed with brine (20 ml×3), and the organic layer was concentrated under reduced pressure to give a residue. The residue was purified by column chromatography ($SiO_2$, Petroleum ether/Ethyl acetate=20/1 to 10/1) to give the title compound (3.2 g, 73% yield) as a yellow oil. LC-MS (ESI$^+$) m/z 276.0 (M+H)$^+$.

Step 4—7'-Cyclopentyl-2'-(methylsulfonyl)spiro[cyclopropane-1,5'-pyrrolo[2,3-d]pyrimidin]-6'(7'H)-one. To a solution of 7'-cyclopentyl-2'-methylsulfanyl-spiro[cyclopropane-1,5'-pyrrolo[2,3-d]pyrimidine]-6'-one (1 g, 3.63 mmol) in THF (15 mL) and $H_2O$ (15 mL) was added Oxone (5.58 g, 9.08 mmol). The mixture was then stirred at 30° C. for 4 h. On completion, the reaction mixture was filtered to get a solution. Then the solution was diluted with water (20 ml), and extracted with EtOAc (20 ml×3). The combined organic layers was washed with brine (20 ml×3), and the organic layers was concentrated under reduced pressure to give the residue. The residue was purified by column chromatography ($SiO_2$, Petroleum ether/Ethyl acetate=5/1 to 2/1) to give the title compound (1.1 g, 98% yield) as a white solid. LC-MS (ESI$^+$) m/z 308.0 (M+H)$^+$.

Step 5—2'-((4-(Benzylthio)-2-methylphenyl)amino)-7'-cyclopentylspiro[cyclopropane-1,5'-pyrrolo[2,3-d]pyrimidin]-6'(7'H)-one. To a solution of 7'-cyclopentyl-2'-methylsulfonyl-spiro[cyclopropane-1,5'-pyrrolo[2,3-d]pyrimidine]-6'-one (0.3 g, 976 umol) in toluene (10 mL) was added Pd(OAc)$_2$ (21.9 mg, 97.6 umol) and BINAP (91.2 mg, 146 umol), $Cs_2CO_3$ (954 mg, 2.93 mmol), 4A molecular sieves (300 mg, 976 umol) and 4-benzylsulfanyl-2-methylaniline (224 mg, 976 umol, Intermediate M). The mixture was stirred at 100° C. for 12 h under $N_2$ atmosphere. On completion, the reaction mixture was poured into water (30 ml), and extracted with EtOAc (10 ml×3). The organic layers was dried by $Na_2SO_4$, and the solution was concentrated under reduced pressure to give the residue. The residue was purified by column chromatography ($SiO_2$, Petroleum ether/Ethyl acetate=8/1 to 3/1) and pre-HPLC (FA condition) to give the title compound (74 mg, 13% yield) as a yellow oil. LC-MS (ESI$^+$) m/z 457.0 (M+H)$^+$.

Step 6—4-((7'-Cyclopentyl-6'-oxo-6',7'-dihydrospiro[cyclopropane-1,5'-pyrrolo[2,3-d]pyrimidin]-2'-yl)amino)-3-methylbenzene-1-sulfonyl chloride. To a solution of 2'-(4-benzylsulfanyl-2-methyl-anilino)-7'-cyclopentyl-spiro[cyclopropane-1,5'-pyrrolo[2,3-d]pyrimidine]-6'-one (50 mg, 110 umol) in AcOH (1 mL) and HCl (0.3 mL) was added NCS (58.5 mg, 438 umol) at 0° C. The mixture was then stirred at 0-25° C. for 10 min. On completion, the mixture was diluted with water (5 ml), and extracted with EtOAc (5 ml×3). The organic layers was dried by $Na_2SO_4$, and the organic layers was concentrated under reduced pressure to give the residue (40 mg) as a yellow solid. LC-MS (EST$^+$) m/z 433.1 (M+H)$^+$.

1-(3,6,9,12-tetraoxapentadec-14-yn-1-yl)-1H-pyrazole-5-carboxylic acid (Intermediate CI)

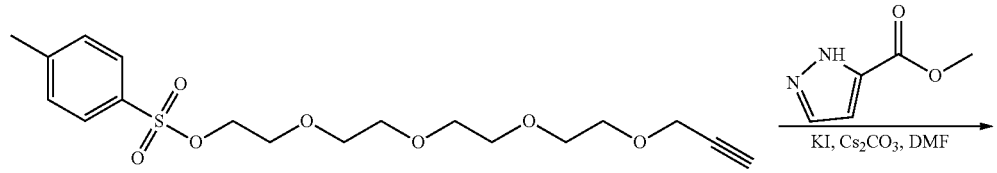

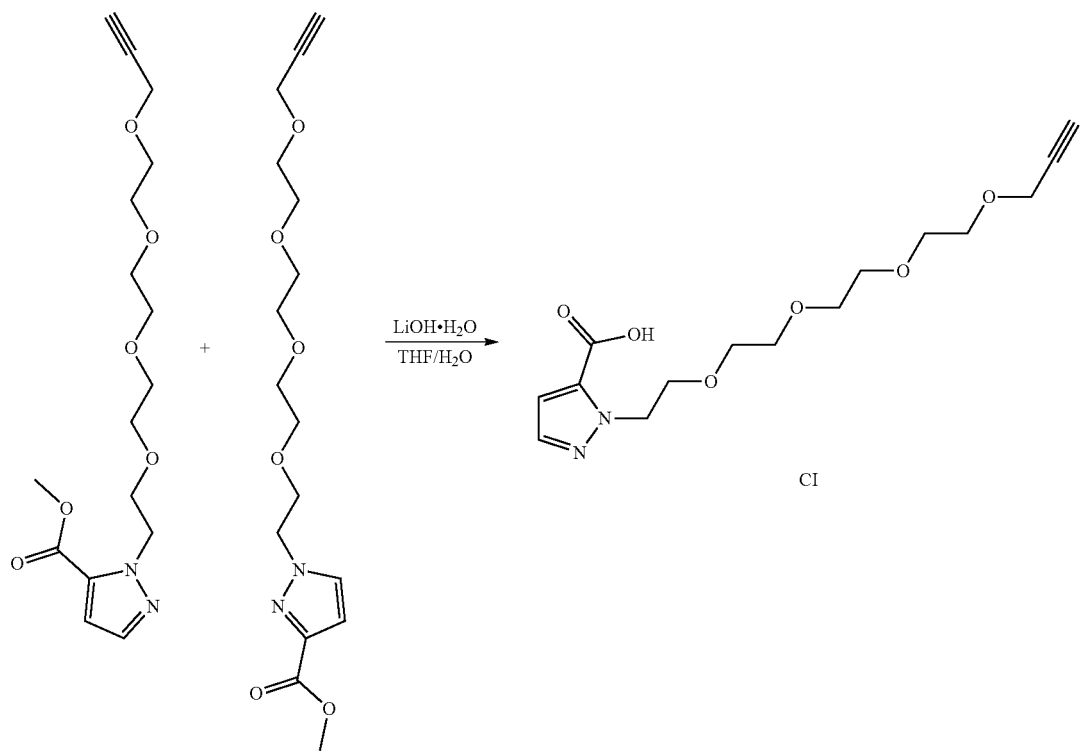

Step 1—Methyl 1-(3,6,9,12-tetraoxapentadec-14-yn-1-yl)-1H-pyrazole-5-carboxylate and methyl 1-(3,6,9,12-tetraoxapentadec-14-yn-1-yl)-1H-pyrazole-3-carboxylate. To a solution of 3,6,9,12-tetraoxapentadec-14-yn-1-yl 4-methylbenzenesulfonate (4.2 g, 10.87 mmol, synthesized via Step 1 of Intermediate BK) and methyl 1H-pyrazole-5-carboxylate (1.37 g, 10.9 mmol) in DMF (60 mL) was added KI (180 mg, 1.09 mmol) and $Cs_2CO_3$ (7.08 g, 21.7 mmol) in one portion. The resulting mixture was stirred at 70° C. for 2 h. On completion, the reaction mixture was quenched with $H_2O$ (60 mL) at 20° C. and extracted with EtOAc (60 mL×3). The combined organic layer was washed with brine (60 mL×2), dried over $Na_2SO_4$, filtered and concentrated under reduced pressure to give a residue. The residue was purified by column chromatography ($SiO_2$, Petroleum ether/Ethyl acetate=5/1 to 1/1) to give methyl 1-(3,6,9,12-tetraoxapentadec-14-yn-1-yl)-1H-pyrazole-5-carboxylate (1.2 g, 32% yield, $^1$H NMR (400 MHz, DMSO-$d_6$) δ=7.58 (d, J=2.0 Hz, 1H), 6.87 (d, J=2.0 Hz, 1H), 4.66 (t, J=5.6 Hz, 2H), 4.13 (d, J=2.4 Hz, 2H), 3.83 (s, 3H), 3.74 (t, J=5.6 Hz, 2H), 3.55-3.50 (m, 4H), 3.47-3.41 (m, 9H)) and methyl 1-(3,6,9,12-tetraoxapentadec-14-yn-1-yl)-1H-pyrazole-3-carboxylate (1.5 g, 41% yield, $^1$H NMR (400 MHz, DMSO-$d_6$) δ=7.02 (d, J=2.4 Hz, 1H), 5.90 (d, J=2.4 Hz, 1H), 3.51 (t, J=5.2 Hz, 2H), 2.99-2.93 (m, 5H), 2.73-2.61 (m, 13H), 2.50 (s, 2H)) as yellow gum.

Step 2—1-(3,6,9,12-tetraoxapentadec-14-yn-1-yl)-1H-pyrazole-5-carboxylic acid. A solution of methyl 1-(3,6,9,12-tetraoxapentadec-14-yn-1-yl)-1H-pyrazole-5-carboxylate (1.2 g, 3.53 mmol) and LiOH·$H_2O$ (591 mg, 14.1 mmol) in THF (10 mL) and $H_2O$ (5 mL) was stirred at 20° C. for 12 h. On completion, the reaction mixture was quenched with $H_2O$ (10 mL) at 20° C. and extracted with EtOAc (20 mL×3). Then the aqueous phase was adjusted to pH=3-4, and extracted with EtOAc mL (20 mL×3). The combined organic layer was washed with brine (20 mL×2), dried over $Na_2SO_4$, filtered and concentrated under reduced pressure to give the title compound (700 mg) as yellow gum. LC-MS (ESI$^+$) m/z 327.2 (M+H)$^+$.

(1R,3S)-3-(5-(1-(3,6,9,12-tetraoxapentadec-14-yn-1-yl)-1H-pyrazole-5-carboxamido)-1-(tert-butyl)-1H-pyrazol-3-yl)cyclopentyl isopropylcarbamate (Intermediate CJ)

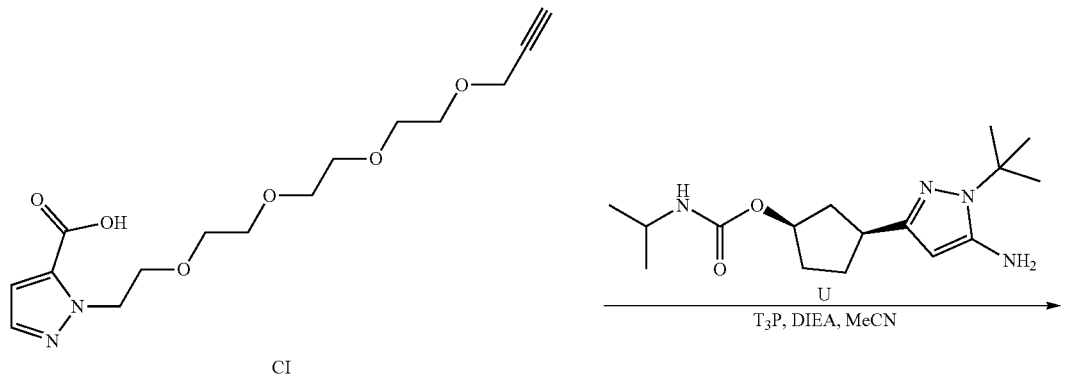

A solution of 1-(3,6,9,12-tetraoxapentadec-14-yn-1-yl)-1H-pyrazole-5-carboxylic acid (0.4 g, 1.23 mmol, Intermediate CI), (1R,3S)-3-(5-amino-1-(tert-butyl)-1H-pyrazol-3-yl)cyclopentyl isopropylcarbamate (455 mg, 1.48 mmol, Intermediate U), DIEA (318 mg, 2.46 mmol), T$_3$P (2.35 g, 3.69 mmol, 50% solution in DMF) in MeCN (10 mL) was stirred at 80° C. for 12 h. On completion, the mixture was quenched with NH$_4$Cl (sat. aq, 10 mL), and extracted with EtOAc (20 mL×2). The combined organic layer was washed with brine (10 mL×3), dried by Na$_2$SO$_4$, concentrated in vacuo. The residue was purified by prep-TLC (SiO$_2$, PE:EtOAc=0:1) to give the title compound (490 mg, 64% yield) as a white solid. LC-MS (ESI$^+$) m/z 617.4 (M+H)$^+$. $^1$H NMR (400 MHz, CDCl$_3$) δ=8.10 (br s, 1H), 7.55 (s, 1H), 6.66 (br s, 1H), 6.21 (s, 1H), 5.15 (br s, 1H), 4.77 (t, J=5.2 Hz, 2H), 4.66-4.52 (m, 1H), 4.17 (d, J=2.4 Hz, 2H), 3.88 (t, J=5.2 Hz, 2H), 3.85-3.76 (m, 1H), 3.68-3.62 (m, 4H), 3.59-3.54 (m, 4H), 3.52-3.47 (m, 4H), 3.17-3.07 (m, 1H), 2.52-2.45 (m, 1H), 2.43 (t, J=2.4 Hz, 1H), 2.10-2.01 (m, 1H), 1.98-1.92 (m, 1H), 1.89-1.84 (m, 2H), 1.65 (s, 9H), 1.62 (br d, J=6.4 Hz, 2H), 1.17-1.13 (m, 6H).

(1R,3S)-3-(5-amino-1-(tert-butyl)-1H-pyrazol-3-yl)cyclopentyl pyrrolidine-1-carboxylate (Intermediate CK)

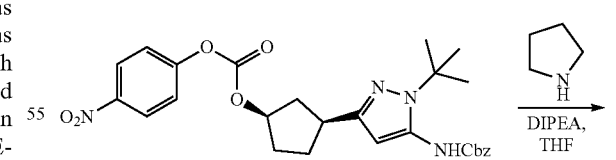

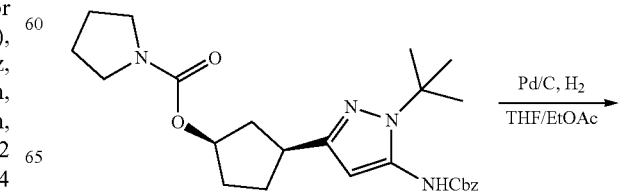

-continued

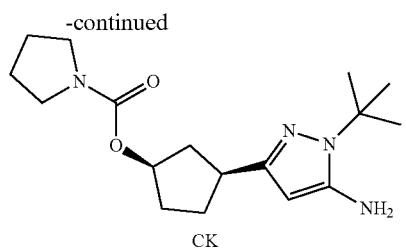

CK

Step 1—(1R,3S)-3-(5-(((benzyloxy)carbonyl)amino)-1-(tert-butyl)-1H-pyrazol-3-yl)cyclopentyl pyrrolidine-1-carboxylate. To a solution of benzyl (1-(tert-butyl)-3-(((1S,3R)-3-(((4-nitrophenoxy)carbonyl)oxy)cyclopentyl)-1H-pyrazol-5-yl)carbamate (500 mg, 956 umol, from synthesized via Step 1 of Intermediate U) and pyrrolidine (136 mg, 1.91 mmol) in THF (5 mL) was added DIEA (618 mg, 4.78 mmol). The mixture was stirred at 20° C. for 12 h. The reaction mixture was quenched with $H_2O$ (8 mL) at 25° C. and extracted with EtOAc (10 mL×3). The combined organic layer was washed with brine (10 mL×3), dried over $Na_2SO_4$, filtered and concentrated under reduced pressure to give a residue. The residue was purified by column chromatography ($SiO_2$, Petroleum ether/Ethyl acetate=3/1 to 2/1) to give the title compound (360 mg, 791 umol, 83% yield) as an orange solid. LC-MS (ESI$^+$) m/z 455.2 (M+H)$^+$.

Step 2—(1R,3S)-3-(5-amino-1-(tert-butyl)-1H-pyrazol-3-yl)cyclopentyl pyrrolidine-1-carboxylate. To a solution of (1R,3S)-3-(5-(((benzyloxy)carbonyl)amino)-1-(tert-butyl)-1H-pyrazol-3-yl)cyclopentyl pyrrolidine-1-carboxylate (360 mg, 791 umol) in THF (4 mL) was added Pd/C (30 mg, 28.3 umol, 10 wt %) in one portion. The mixture was stirred at 25° C. for 4 h under $H_2$ atmosphere (15 psi). The reaction mixture was filtered and concentrated under reduced pressure to give the title compound (250 mg, 780 umol, 99% yield) as an orange solid. LC-MS (ESI$^+$) m/z 321.5 (M+H)$^+$.

(1R,3S)-3-(1-(tert-butyl)-5-(1-(2-(2-(2-(prop-2-yn-1-yloxy)ethoxy)ethoxy)ethyl)-1H-pyrazole-5-carboxamido)-1H-pyrazol-3-yl)cyclopentyl pyrrolidine-1-carboxylate (Intermediate CL)

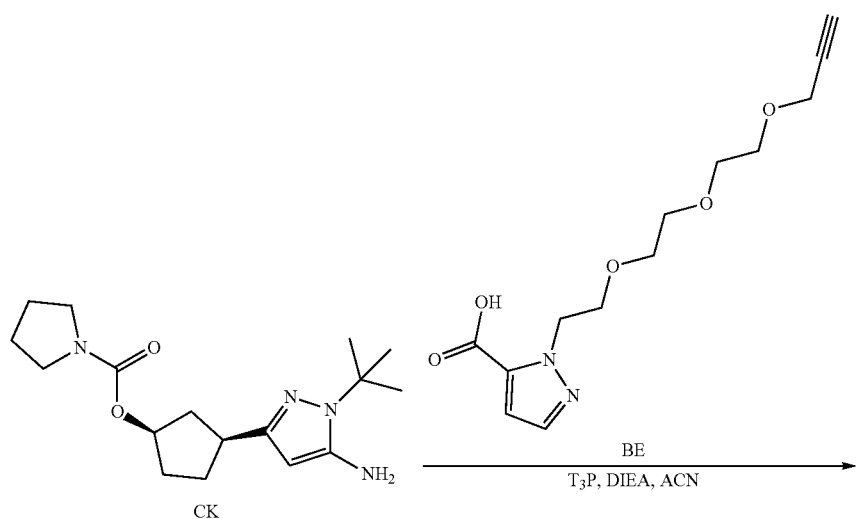

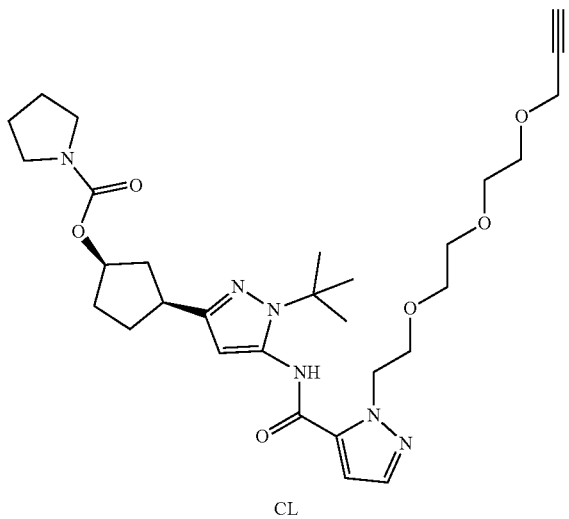

CL

To a solution of (1R,3S)-3-(5-amino-1-(tert-butyl)-1H-pyrazol-3-yl)cyclopentyl pyrrolidine-1-carboxylate (250 mg, 780 umol, Intermediate CK) and 2-[2-[2-(2-prop-2-ynoxyethoxy)ethoxy]ethyl]pyrazole-3-carboxylic acid (210 mg, 743 umol, Intermediate BE) in ACN (2 mL) was added T₃P (1.42 g, 2.23 mmol, 50% solution in DMF) and DIEA (480 mg, 3.72 mmol) in one portion. The mixture was stirred at 60° C. for 12 h. The reaction mixture was quenched with H₂O (3 mL) at 25° C. and extracted with EtOAc (5 mL×3). The combined organic layer was washed with brine (5 mL×3), dried over Na₂SO₄, filtered and concentrated under reduced pressure to give a residue. The residue was purified by flash silica gel chromatography (ISCO®; 4 g SepaFlash® Silica Flash Column, Eluent of 0~100% Ethyl acetate/ Petroleum ether gradient @ 50 mL/min) to give the title compound as an orange solid. LC-MS (ESI⁺) m/z 385.5 (M+H)⁺.

3-(Methoxymethyl)-1-(2-(2-(2-(prop-2-yn-1-yloxy)ethoxy)ethoxy)ethyl)-1H-pyrazole-5-carboxylic acid
(Intermediate CM)

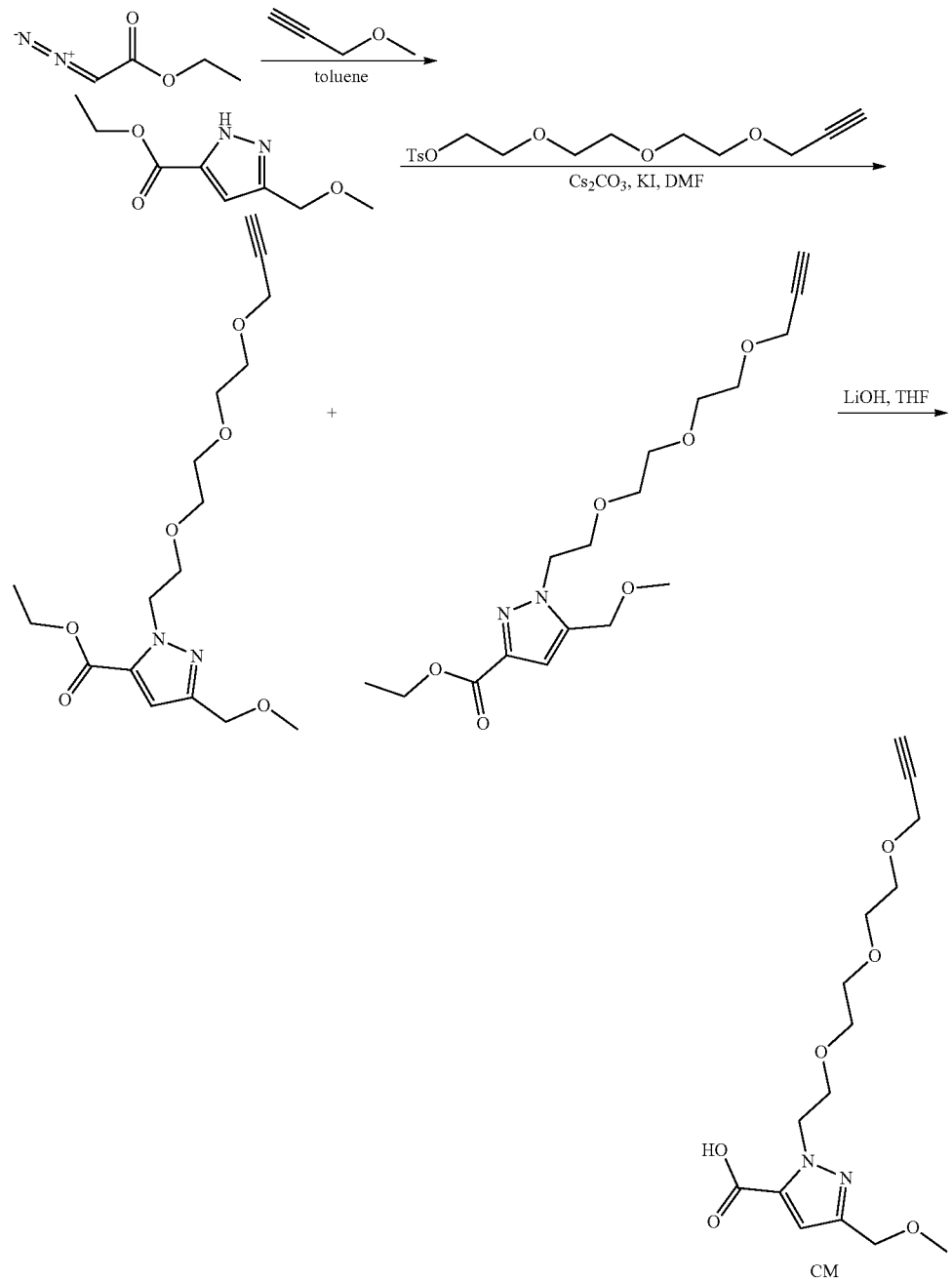

Step 1—Ethyl 3-(methoxymethyl)-1H-pyrazole-5-carboxylate. To a solution of 3-methoxyprop-1-yne (10.2 g, 145 mmol, CAS #627-41-8) in toluene (80 mL) was added ethyl 2-diazoacetate (18.2 g, 160 mmol). The mixture was stirred at 110° C. for 6 h. On completion, the reaction mixture was concentrated in vacuo to give a residue. The residue was purified by column chromatography (SiO$_2$, Petroleum ether/Ethyl acetate=5/1 to 1/1) to give the title compound (10 g, 37% yield) as yellow oil. $^1$H NMR (400 MHz, CDCl$_3$) δ=7.71 (s, 1H), 6.81 (s, 1H), 4.67 (s, 1H), 4.55 (s, 2H), 4.40 (q, J=7.2 Hz, 3H), 3.44 (s, 1H), 3.41 (s, 3H), 1.43 (s, 1H), 1.42-1.38 (m, 3H).

Step 2—Ethyl 3-(methoxymethyl)-1-(2-(2-(2-(prop-2-yn-1-yloxy)ethoxy)ethoxy)ethyl)-1H-pyrazole-5-carboxylate and ethyl 5-(methoxymethyl)-1-(2-(2-(2-(prop-2-yn-1-yloxy)ethoxy)ethoxy)ethyl)-1H-pyrazole-3-carboxylate. A solution of ethyl 3-(methoxymethyl)-1H-pyrazole-5-carboxylate (2.50 g, 13.6 mmol), 2-(2-(2-(prop-2-yn-1-yloxy)ethoxy)ethoxy)ethyl 4-methylbenzenesulfonate (3.87 g, 11.3 mmol, synthesized via Step 1 of Intermediate BE), Cs$_2$CO$_3$ (18.4 g, 56.5 mmol), KI (187 mg, 1.13 mmol) in DMF (80 mL) was stirred at 70° C. for 12 h. On completion, the mixture was quenched with NH$_4$Cl (sat. aq, 80 mL), extracted with EtOAc (8 mL×3). The combined organic layer was washed with brine (80 mL×3), dried by Na$_2$SO$_4$, concentrated in vacuum. The residue was purified by column chromatography (SiO$_2$, Petroleum ether/Ethyl acetate=5/1 to 3/1) to give ethyl 5-(methoxymethyl)-1-(2-(2-(2-(prop-2-yn-1-yloxy)ethoxy)ethoxy)ethyl)-1H-pyrazole-3-carboxylate (1.50 g, 34% yield) as colorless oil ($^1$H NMR (400 MHz, CD$_3$Cl) δ 6.74 (s, 1H), 6.54 (s, 2H), 6.43-6.39 (m, 5H), 4.20 (d, J=2.4 Hz, 2H), 3.87 (t, J=6.0 Hz, 3H), 3.67-3.53 (m, 8H), 3.34 (s, 3H), 2.44 (t, J=2.0 Hz, 1H), 1.39 (t, J=7.2 Hz, 4H); LC-MS (ESI$^+$) m/z 355.2 (M+H)$^+$) and ethyl 3-(methoxymethyl)-1-(2-(2-(2-(prop-2-yn-1-yloxy)ethoxy)ethoxy)ethyl)-1H-pyrazole-5-carboxylate (0.68 g, 15% yield) ($^1$H NMR (400 MHz, CD$_3$Cl) δ 6.84 (s, 1H), 4.75 (t, J=6.0 Hz, 2H), 4.46 (s, 2H), 4.34 (q, J=7.2 Hz, 2H), 4.20 (d, J=2.4 Hz, 2H), 3.86 (t, J=6.0 Hz, 3H), 3.73-3.55 (m, 12H), 3.40 (s, 3H), 2.43 (t, J=2.0 Hz, 1H), 1.37 (t, J=7.2 Hz, 4H); LC-MS (ESI$^+$) m/z 355.2 (M+H)).

Step 3—3-(Methoxymethyl)-1-(2-(2-(2-(prop-2-yn-1-yloxy)ethoxy)ethoxy)ethyl)-1H-pyrazole-5-carboxylic acid. A solution of ethyl 3-(methoxymethyl)-1-(2-(2-(2-(prop-2-yn-1-yloxy)ethoxy)ethoxy)ethyl)-1H-pyrazole-5-carboxylate (1.50 g, 4.23 mmol), LiOH·H$_2$O (888 mg, 21.2 mmol) in THF (10 mL) and H$_2$O (5 mL) was stirred at 40° C. for 4 h. On completion, the mixture was quenched with NH$_4$Cl (sat. aq, 20 mL), then extracted with EtOAc (20 mL×2). The aqueous layer was acidified with HCl/1M (10 mL) to pH<4, then extracted with EtOAc (20 mL×2). The combined organic layer was washed with brine (80 mL×3), dried by Na$_2$SO$_4$, and concentrated in vacuo. $^1$H NMR (400 MHz, CD$_3$Cl) δ=6.90 (s, 1H), 4.77 (t, J=5.6 Hz, 2H), 4.48 (s, 2H), 4.21 (d, J=2.4 Hz, 3H), 3.85 (t, J=5.6 Hz, 3H), 3.72-3.58 (m, 11H), 3.40 (s, 3H); LC-MS (ESI$^+$) m/z 327.2 (M+H)$^+$.

(1R,3S)-3-(1-(tert-butyl)-5-(3-(methoxymethyl)-1-(2-(2-(2-(prop-2-yn-1-yloxy)ethoxy)ethoxy)ethyl)-1H-pyrazole-5-carboxamido)-1H-pyrazol-3-yl)cyclopentyl isopropylcarbamate (Intermediate CN)

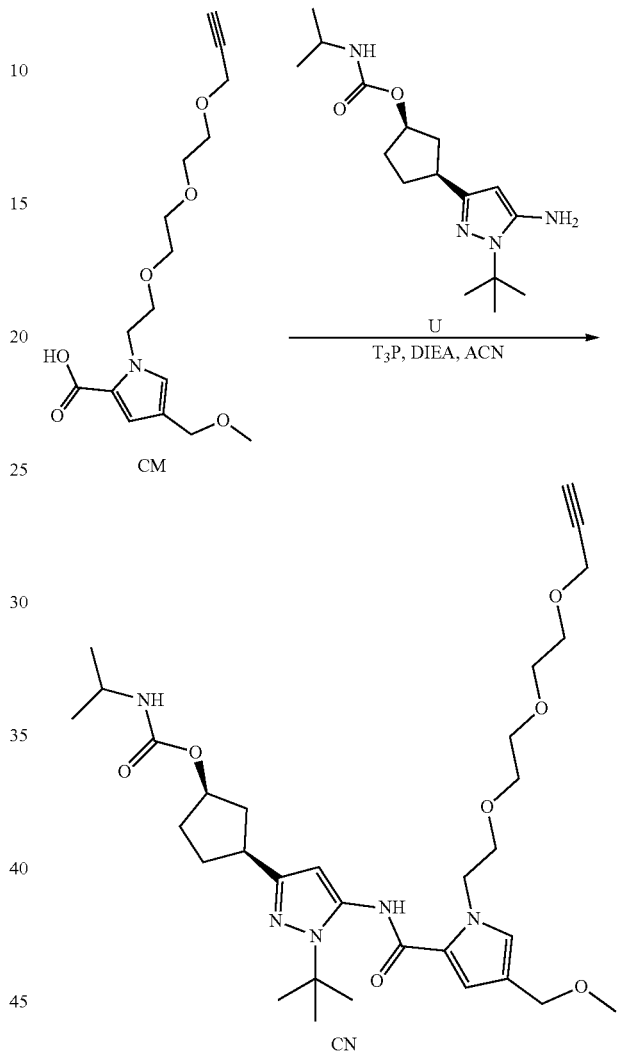

A solution of (1R,3S)-3-(5-amino-1-(tert-butyl)-1H-pyrazol-3-yl)cyclopentyl isopropylcarbamate (472 mg, 1.53 mmol, Intermediate U), 3-(methoxymethyl)-1-(2-(2-(2-(prop-2-yn-1-yloxy)ethoxy) ethoxy)ethyl)-1H-pyrazole-5-carboxylic acid (500 mg, 1.53 mmol, Intermediate CM), T3P (2.92 g, 4.60 mmol, 50% solution in DMF), DIEA (990 mg, 7.66 mmol) in ACN (10 mL) was stirred at 60° C. for 12 h. On completion, the mixture was quenched with H$_2$O (10 mL), then extracted with EtOAc (10 mL×2). The combined organic layer was washed with brine (20 Ml×3), dried by Na$_2$SO$_4$, and concentrated in vacuo. The residue was purified by prep-TLC (SiO$_2$, EtOAc:PE=2:1) to afford the title compound (600 mg, 57% yield) as yellow oil. $^1$H NMR (400 MHz, CD$_3$Cl) δ 8.26-8.19 (m, 1H), 6.65 (s, 1H), 6.32 (s, 1H), 5.19-5.15 (m, 1H), 4.74-4.71 (m, 2H), 4.50 (s, 2H), 4.15 (d, J=1.6 Hz, 2H), 4.14 (br s, 1H), 3.84 (br t, J=4.8 Hz, 2H), 3.59 (br d, J=4.8 Hz, 2H), 3.58-3.53 (m, 3H), 3.49 (br d, J=4.4 Hz, 4H), 3.44 (br s, 1H), 3.44 (s, 3H), 2.44 (br d, J=2.0 Hz, 1H), 2.05 (s, 2H), 1.73 (s, 9H), 1.27 (s, 3H), 1.15 (br d, J=6.4 Hz, 6H). LC-MS (ESI⁺) m/z 617.4 (M+H)⁺.

4-((6-bromo-8-cyclopentyl-7-oxo-7,8-dihydropyrido[2,3-d]pyrimidin-2-yl)amino)-3-methylbenzene-1-sulfonyl chloride (Intermediate CO)

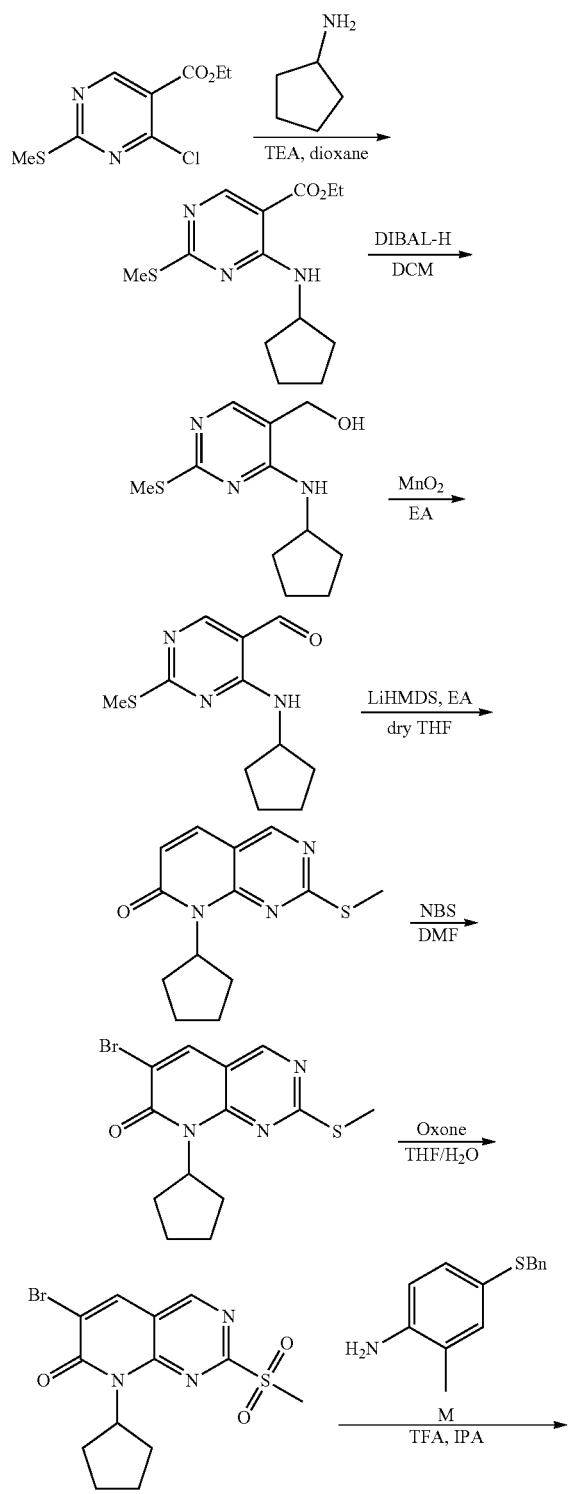

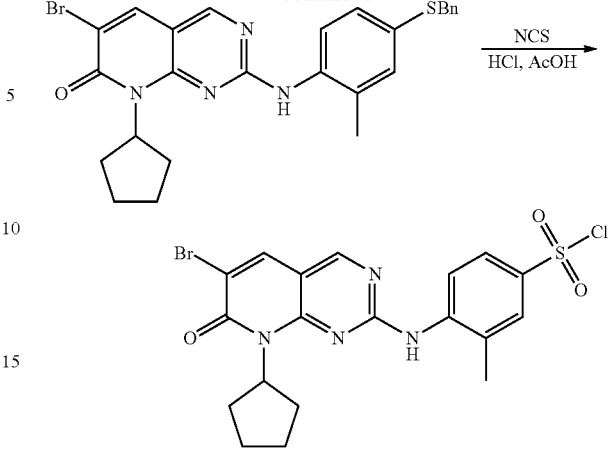

Step 1—Ethyl 4-(cyclopentylamino)-2-(methylthio)pyrimidine-5-carboxylate. To a solution of ethyl 4-chloro-2-methylsulfanyl-pyrimidine-5-carboxylate (10 g, 42.9 mmol, CAS #1074-68-6) in dioxane (100 mL) was added TEA (8.70 g, 85.9 mmol) and cyclopentanamine (4.39 g, 51.5 mmol, CAS #1003-03-08). The mixture was stirred at 25° C. for 16 h. On completion, the reaction mixture was quenched with H₂O (100 mL) at 25° C. and extracted with EtOAc (100 mL×3). The combined organic layer was washed with brine (100 mL×3), dried over Na₂SO₄, filtered and concentrated under reduced pressure to give the title compound (11.5 g, 40.8 mmol, 95% yield) as a orange oil. LC-MS (ESI⁺) m/z 272.2 (M+H)⁺.

Step 2—(4-(Cyclopentylamino)-2-(methylthio)pyrimidin-5-yl)methanol. To a solution of ethyl 4-(cyclopentylamino)-2-(methylthio)pyrimidine-5-carboxylate (11.5 g, 40.8 mmol) in DCM (130 mL) at −65° C. was added DIBAL-H (1 M, 61.31 mL) dropwise and stirred at −50-55° C. for 3 h under N₂ atmosphere. On completion, the reaction mixture was quenched with MeOH (120 mL) at −65° C., and then diluted with DCM (120 mL) and extracted with DCM (120 mL×3). The combined organic layer was washed with brine (120 mL×3), dried over Na₂SO₄, filtered and concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 100 mL/min) to give the title compound (5.5 g, 22.9 mmol, 56% yield) as a white solid. LC-MS (ESI⁺) m/z 240 (M+H)⁺.

Step 3—4-(Cyclopentylamino)-2-(methylthio)pyrimidine-5-carbaldehyde. To a solution of (4-(cyclopentylamino)-2-(methylthio)pyrimidin-5-yl)methanol (2 g, 4.18 mmol) in EtOAc (50 mL) was added MnO₂ (14.5 g, 83.5 mmol). The mixture was stirred at 50° C. for 12 h under N₂ atmosphere. On completion, the reaction mixture was filtered and concentrated under reduced pressure to give the title (1.5 g) as a orange oil. LC-MS (ESI⁺) m/z 238.1 (M+H)⁺.

Step 4—8-Cyclopentyl-2-(methylthio)pyrido[2,3-d]pyrimidin-7(8H)-one. A solution of 4-(cyclopentylamino)-2-(methylthio)pyrimidine-5-carbaldehyde (3.8 g, 16.0 mmol) and ethyl acetate (4.23 g, 48.0 mmol) in THF (45 mL) was purged with nitrogen and cooled in a MeOH-ice bath to −5° C. internal temperature. Then LiHMDS (1 M, 48.04 mL) was added, slowly enough to keep the internal temperature at −5° C. The mixture was then stirred at 0-20° C. for 12 h under N₂ atmosphere. The resulting red solution was cooled in an ice-water bath to −3° C. internal, then EtOH (45 mL) was added via cannula, slowly enough to keep the internal temp at −3° C. internal. The mixture was stirred in the ice bath for 1 h, then the cooling bath was removed, the solution allowed to warm to 20° C. internal, and stirring continued for 1 h. The solvents were evaporated, the residue diluted with water (45 mL) and brine (50 mL×3), and the aqueous layer extracted with EtOAc (20 mL, then 45 mL×2). The residue was purified by column chromatography (SiO$_2$, Petroleum ether/Ethyl acetate=3/1 to 1/1) to give the title compound (3 g, 11.4 mmol, 72% yield) as an orange solid. LC-MS (ESI$^+$) m/z 262.2 (M+H)$^+$.

Step 5—6-Bromo-8-cyclopentyl-2-(methylthio)pyrido[2,3-d]pyrimidin-7(8H)-one. To a solution of 8-cyclopentyl-2-(methylthio)pyrido[2,3-d]pyrimidin-7(8H)-one (3 g, 11.4 mmol) in DMF (30 mL) was added NBS (2.25 g, 12.6 mmol). Then the mixture was stirred at 20° C. for 12 h. The reaction mixture was quenched with water (30 mL) at 25° C., then extracted with EA (50 mL×3). The combined organic layer was washed with brine (50 mL×3), dried over Na$_2$SO$_4$, filtered and concentrated under reduced pressure to give a residue. The residue was purified by column chromatography (SiO$_2$, Petroleum ether/Ethyl acetate=5/1 to 3/1) to give the title compound (1 g, 2.94 mmol, 26% yield) as an orange solid. LC-MS (ESI$^+$) m/z 342.1 (M+H)$^+$.

Step 6—6-bromo-8-cyclopentyl-2-(methylsulfonyl)pyrido[2,3-d]pyrimidin-7(8H)-one. To a solution of 6-bromo-8-cyclopentyl-2-(methylthio)pyrido[2,3-d]pyrimidin-7(8H)-one (1 g, 2.94 mmol) in THF (20 mL) and H$_2$O (20 mL) was added Oxone (4.52 g, 7.35 mmol) in one portion. The mixture was stirred at 30° C. for 3 h. On completion, the reaction mixture was filtered and concentrated under reduced pressure to give the title compound (900 mg) as a orange solid. LC-MS (ESI$^+$) m/z 373.9 (M+H)$^+$.

Step 7—2-((4-(benzylthio)-2-methylphenyl)amino)-6-bromo-8-cyclopentylpyrido[2,3-d]pyrimidin-7(8H)-one. To a solution of 6-bromo-8-cyclopentyl-2-(methylsulfonyl)pyrido[2,3-d]pyrimidin-7(8H)-one (900 mg, 2.42 mmol) and 4-benzylsulfanyl-2-methyl-aniline (554 mg, 2.42 mmol, Intermediate M) in IPA (10 mL) was added TFA (5.51 g, 48.36 mmol). The mixture was stirred at 120° C. for 24 h. On completion, the reaction mixture was quenched with water (10 mL) at 25° C., then extracted with EtOAc (20 mL×3). The combined organic layer was washed with brine (20 mL×3), dried over Na2SO4, filtered and concentrated under reduced pressure to give a residue. The residue was purified by flash silica gel chromatography (ISCO®; 14 g SepaFlash® Silica Flash Column, Eluent of 0~100% Ethyl acetate/Petroleum ether gradient @ 100 mL/min) to give the title compound (300 mg, 575 umol, 24% yield) as an orange solid. LC-MS (ESI$^+$) m/z 523 (M+H)$^+$.

Step 8—4-((6-bromo-8-cyclopentyl-7-oxo-7,8-dihydropyrido[2,3-d]pyrimidin-2-yl)amino)-3-methylbenzene-1-sulfonyl chloride. To a solution of 2-((4-(benzylthio)-2-methylphenyl)amino)-6-bromo-8-cyclopentylpyrido[2,3-d]pyrimidin-7(8H)-one (300 mg, 575 umol) in HCl (1.5 mL) and AcOH (5 mL) was added NCS (307 mg, 2.30 mmol) at 0° C. The mixture was stirred at 0-25° C. for 2 h. On completion, the reaction mixture was quenched with water (10 mL) at 25° C. and extracted with EtOAc (10 mL×3). The combined organic layer was washed with brine (10 mL×3), dried over Na$_2$SO$_4$, filtered and concentrated under reduced pressure to give the title compound (280 mg) as an orange solid. LC-MS (ESI$^+$) m/z 373.9 (M+H)$^+$.

3-(5-(3-(2-(2-(2-aminoethoxy)ethoxy)ethoxy)propyl)-3-methyl-2-oxo-2,3-dihydro-1H-benzo[d]imidazol-1-yl)piperidine-2,6-dione (Intermediate CP)

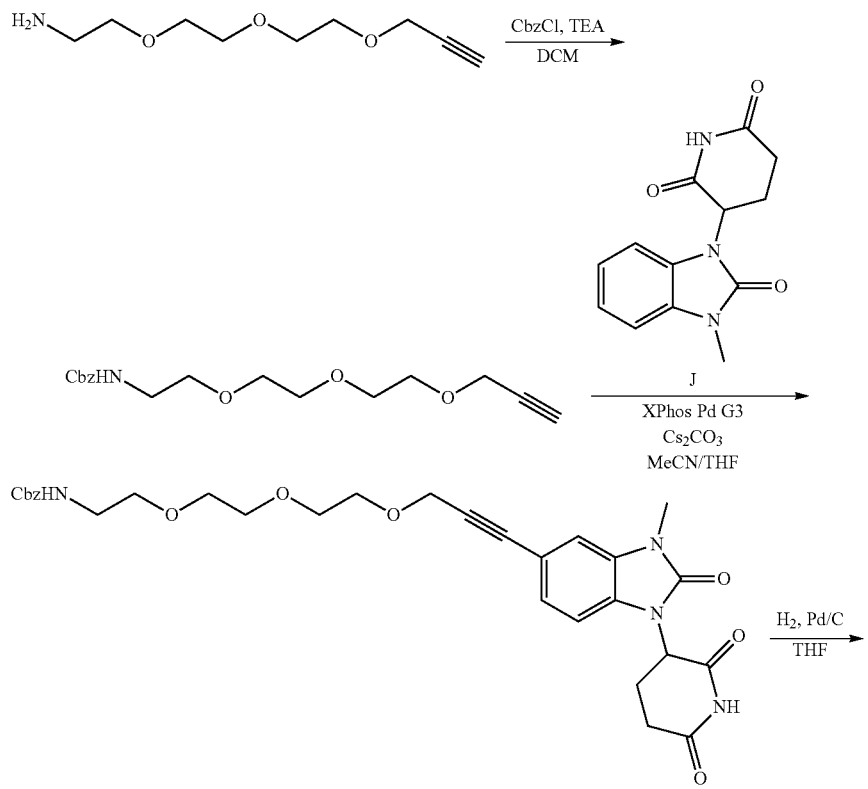

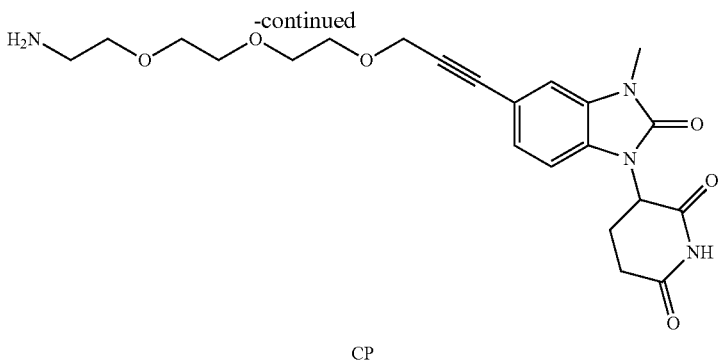

CP

Step 1—Benzyl (2-(2-(2-(prop-2-yn-1-yloxy)ethoxy)ethoxy)ethyl)carbamate. To a solution of 2-(2-(2-(prop-2-yn-1-yloxy)ethoxy)ethoxy)ethanamine (1 g, 5.34 mmol CAS #932741-19-0) in DCM (15 mL) was added TEA (594 mg, 5.87 mmol) in one portion, then benzyl carbonochloridate (1.00 g, 5.87 mmol) was added into the mixture at 0° C. The mixture was stirred at 0-20° C. for 12 h. On completion, the mixture was poured into ice water (20 mL) and extracted with DCM (20 mL×2). The combined organic phase was washed with brine (20 mL×2), dried over sodium sulfate. Then filtered to get the filtrate and concentrated to give a residue. The residue was purified by column chromatography (SiO$_2$, Petroleum ether/Ethyl acetate=1/0 to 1/1) to give the title compound (1.29 g, 3.83 mmol, 72% yield) as yellow oil. LC-MS (ESI$^+$) m/z 322.1 (M+H)$^+$.

Step 2—Benzyl (2-(2-(2-((3-(1-(2,6-dioxopiperidin-3-yl)-3-methyl-2-oxo-2,3-dihydro-1H-benzo[d]imidazol-5-yl)prop-2-yn-1-yl)oxy)ethoxy)ethoxy)ethyl)carbamate. To a solution of 3-(5-bromo-3-methyl-2-oxo-benzimidazol-1-yl)piperidine-2,6-dione (2.04 g, 6.02 mmol, Intermediate J) and benzyl (2-(2-(2-(prop-2-yn-1-yloxy)ethoxy)ethoxy)ethyl)carbamate (1.29 g, 4.01 mmol) in THF (7 mL) and ACN (7 mL) was added Cs$_2$CO$_3$ (7.85 g, 24.08 mmol) and XPhos Pd G3 (1.02 g, 1.20 mmol) in one portion. Then the mixture was degassed with nitrogen and heated to 60° C., then stirred for 10 h. On completion, the mixture was poured into ice water (10 mL) and extracted with EA (2×10 mL). The combined organic phase was washed with brine (2×10 mL) and dried over sodium sulfate. The solution was filtered and the filtrate was concentrated to give a residue. The residue was purified by column chromatography (SiO$_2$, Petroleum ether/Ethyl acetate=1/0 to 1/4) to give the title compound (1.3 g, 2.04 mmol, 51% yield) as yellow oil. LC-MS (ESI$^+$) m/z 840.3 (M+H)$^+$.

Step 3: 3-(5-(3-(2-(2-(2-aminoethoxy)ethoxy)ethoxy)propyl)-3-methyl-2-oxo-2,3-dihydro-1H-benzo[d]imidazol-1-yl)piperidine-2,6-dione. To a solution of benzyl (2-(2-(2-((3-(1-(2,6-dioxopiperidin-3-yl)-3-methyl-2-oxo-2,3-dihydro-1H-benzo[d]imidazol-5-yl)prop-2-yn-1-yl)oxy)ethoxy)ethoxy)ethyl)carbamate (1.3 g, 2.25 mmol) in THF (10 mL) was added Pd/C (0.2 g, 188.68 umol, 10 wt %) at 20° C. The mixture was then stirred at 20° C. for 13 h under hydrogen atmosphere (15 psi). On completion, the mixture was filtered and the filtrate was concentrated to give the title compound (850 mg) as yellow oil. $^1$H NMR (400 MHz, DMSO-d$_6$) δ=7.05-6.98 (m, 2H), 6.89-6.85 (m, 1H), 5.33 (dd, J=5.2, 12.8 Hz, 1H), 3.61-3.59 (m, 1H), 3.55-3.48 (m, 8H), 3.42-3.35 (m, 6H), 3.18-3.05 (m, 1H), 2.95-2.82 (m, 1H), 2.76-2.56 (m, 6H), 1.86-1.72 (m, 4H).

(1S,3R)-3-(1-(tert-butyl)-5-(1-(2-(2-(2-(prop-2-yn-1-yloxy)ethoxy)ethoxy)ethyl)-1H-pyrazole-5-carboxamido)-1H-pyrazol-3-yl)cyclopentyl isopropylcarbamate (Intermediate CQ)

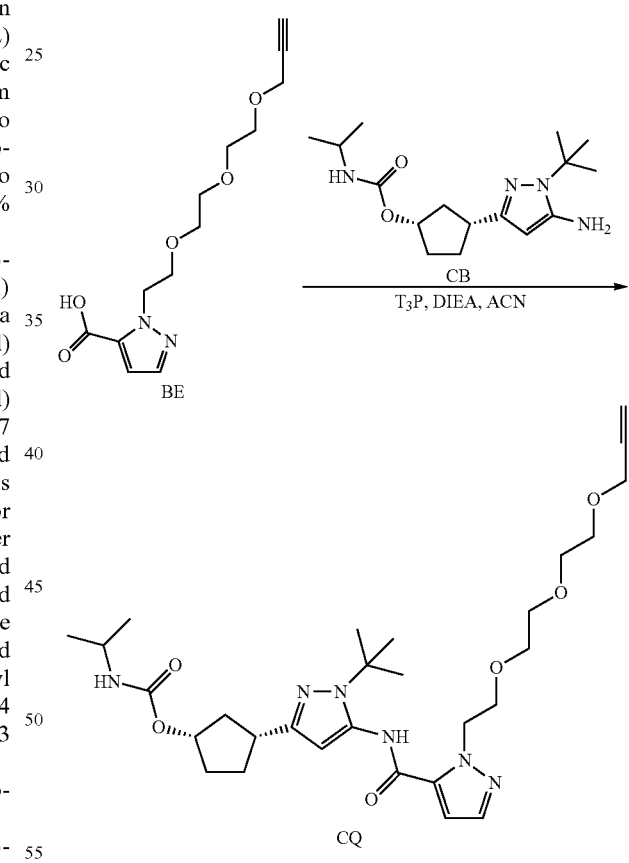

A solution of 1-(2-(2-(2-(prop-2-yn-1-yloxy)ethoxy)ethoxy)ethyl)-1H-pyrazole-5-carboxylic acid (0.4 g, 1.42 mmol, Intermediate BE), (1S,3R)-3-(5-amino-1-(tert-butyl)-1H-pyrazol-3-yl)cyclopentyl isopropylcarbamate (743 mg, 2.41 mmol, Intermediate CB), T$_3$P (2.71 g, 4.25 mmol, 50% solution in DMF), DIEA (366 mg, 2.83 mmol) in ACN (8 mL) was stirred at 60° C. for 16 h. On completion, the mixture was quenched with NH$_4$Cl (sat. aq, 10 mL), then extracted with EtOAc (10 mL×2). The combined organic layer was washed with brine (10 mL×3), dried by Na$_2$SO$_4$, and concentrated in vacuo. The crude product was purified

3-[(4-Methoxyphenyl)methyl]hexahydropyrimidine-2,4-dione (Intermediate CR)

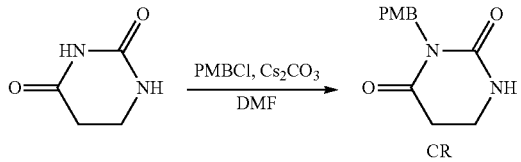

To the solution of hexahydropyrimidine-2,4-dione (3.00 g, 26.2 mmol, CAS #504-07-4) in DMF (60 mL) was added Cs$_2$CO$_3$ (17.13 g, 52.58 mmol) at rt. Then the mixture was warmed up to 50° C., and PMB-Cl (3.71 g, 23.6 mmol) was dropwise added to the mixture very slowly at 50° C. The mixture was stirred at 50° C. for 2 hr. On completion, the reaction was cooled to rt. The reaction was filtered and the filter cake was washed by EA (30 mL×2), the filtrate was poured into water (150 mL) and extracted with EA (100 mL×2). The combined organic layer was washed with water (100 mL) and saturated brine (100 mL), then the organic layer was dried over Na$_2$SO$_4$, filtered and concentrated to give a crude product. The crude product was suspended in EA/PE (1/1, 80 mL) and stirred for 0.5 hr. The suspension was filtered, the filter cake was dried to give the title compound (2.80 g, 45% yield) as white solid. $^1$H NMR (400 MHz, CDCl$_3$) δ 7.42-7.30 (m, 2H), 6.90-6.62 (m, 2H), 6.15 (s, 1H), 4.88 (s, 2H), 3.78 (s, 3H), 3.37 (dt, J=2.4, 6.8 Hz, 2H), 2.71 (t, J=6.8 Hz, 2H).

3-(4-Methoxybenzyl)dihydropyrimidine-2,4(1H,3H)-dione (Intermediate CS)

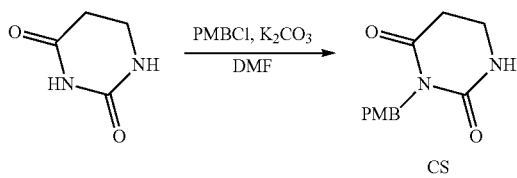

To a mixture of dihydropyrimidine-2,4(1H,3H)-dione (10.0 g, 87.6 mmol, CAS #504-07-4) in DMF (100 mL) was added PMB-Cl (13.7 g, 87.6 mmol, 11.9 mL), Cs$_2$CO$_3$ (28.5 g, 87.6 mmol) at 25° C. The mixture was then stirred at 50° C. for 3 hours. On completion, the reaction mixture was quenched with of water (100 mL), and extracted with EtOAc (3×50 mL). The organic layer was dried over anhydrous Na$_2$SO$_4$, filtered and concentrated in vacuo. The crude product was purified by re-crystallization from EA/PE (20 mL, v/v=1/1) at 25° C. to give the title compound (9.40 g, 45% yield) as a white solid. $^1$H NMR (400 MHz, CDCl$_3$) δ 7.81 (s, 1H), 7.18 (d, J=8.4 Hz, 2H), 6.83 (d, J=8.4 Hz, 2H), 4.72 (s, 2H), 3.72 (s, 3H), 3.23-3.20 (m, 2H), 2.63 (t, J=6.8 Hz, 2H).

by reversed-phase (0.1% FA condition) to give the title compound (100 mg, 12% yield) as a colorless oil. LC-MS (ESI$^+$) m/z 573.8 (M+H)$^+$.

4-[[tert-butyl(diphenyl)silyl]oxymethyl]cyclohexanol (Intermediate CT)

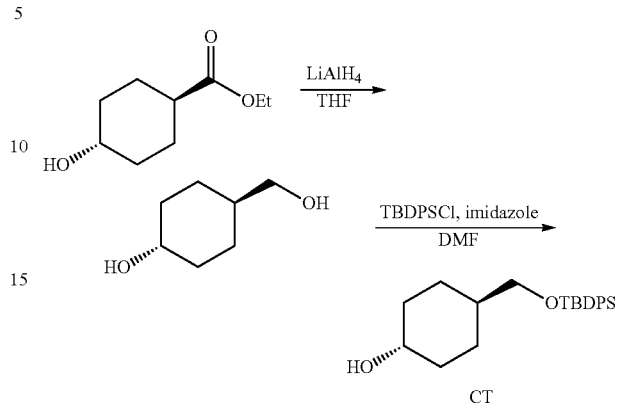

Step 1—4-(Hydroxymethyl)cyclohexanol

To a solution of LiAlH$_4$ (3.31 g, 87.1 mmol) in THF (30 mL), was add ethyl 4-hydroxycyclohexanecarboxylate (10.0 g, 58.0 mmol, CAS #3618-04-0) in THF (100 mL) dropwise at 0° C., then the mixture was stirred at 0° C. for 5 hrs. On completion, the mixture was quenched with H$_2$O (3.3 mL), then a solution of 15% NaOH (3.3 mL) was added dropwise, The mixture was dried with anhydrous Na$_2$SO$_4$, filtered and the filtered liquor was concentrated in vacuo to give the title compound (7.5 g, 99% yield) as yellow solid. $^1$H NMR (400 MHz, DMSO-d$_6$) δ 3.37-3.23 (m, 1H), 3.17 (d, J=6.0 Hz, 2H), 1.85-1.75 (m, 2H), 1.75-1.62 (m, 2H), 1.30-1.16 (m, 1H), 1.14-0.95 (m, 2H), 0.93-0.72 (m, 2H).

Step 2—4-[[Tert-butyl(diphenyl)silyl]oxymethyl]cyclohexanol

To a solution of 4-(hydroxymethyl)cyclohexanol (6.5 g, 49.9 mmol) and imidazole (4.08 g, 59.9 mmol) in DMF (200 mL) was added TBDPSCl (14.4 g, 52.4 mmol) at 0° C. The mixture was stirred at 25° C. for 12 hrs. On completion, the mixture was diluted with H$_2$O (100 mL), and extracted with EA (2×30 mL). The organic layers were washed with brine (2×30 mL), dried over anhydrous Na$_2$SO$_4$, filtered and concentrated in vacuo. The mixture was purified by silica gel column (PE:EA=5:1) to give the title compound (9.10 g, 49% yield) as yellow oil. $^1$H NMR (400 MHz, CDCl$_3$) δ 7.70-7.60 (m, 4H), 7.48-7.31 (m, 6H), 3.63-3.51 (m, 1H), 3.47 (d, J=6.0 Hz, 2H), 2.05-1.95 (m, 2H), 1.89-1.80 (m, 2H), 1.50-1.45 (m, 1H), 1.31-1.22 (m, 2H), 1.10-1.00 (m, 2H), 1.05 (s, 9H).

(4-Allyloxycyclohexyl)methoxy-tert-butyl-diphenyl-silane (Intermediate CU)

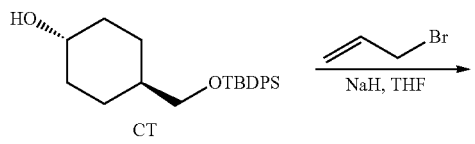

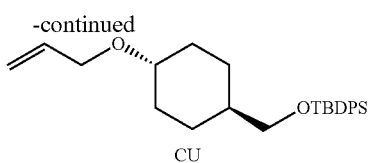

CU

To a solution of 4-[[tert-butyl(diphenyl)silyl]oxymethyl]cyclohexanol (500 mg, 1.36 mmol, Intermediate CT) in THF (5 mL) was added NaH (81.3 mg, 2.03 mmol, 60% dispersion in mineral oil) at 0° C. After addition, the mixture was stirred at this temperature for 30 minutes, then 3-bromoprop-1-ene (656 mg, 5.43 mmol, 0.3 mL, CAS #106-95-6) was added dropwise. The mixture was stirred at 25° C. for 4 hrs. On completion, the mixture was quenched with $H_2O$ (1 mL) at 25° C., diluted with $H_2O$ (10 mL) and extracted with EA (3×10 mL). The combined organic layers were washed with brine (2×5 mL), dried over anhydrous $Na_2SO_4$, filtered and concentrated in vacuo to give a residue. The residue was purified by prep-TLC ($SiO_2$, DCM:MeOH=10:1) to give the title compound (210 mg, 37% yield) as a white solid. $^1$H NMR (400 MHz, $CDCl_3$) δ 7.59-7.55 (m, 4H), 7.33-7.26 (m, 6H), 5.91-5.78 (m, 1H), 5.22-5.13 (m, 1H), 5.10-5.02 (m, 1H), 3.98-3.89 (m, 2H), 3.37 (d, J=6.4 Hz, 2H), 3.18-3.08 (m, 1H), 2.01-1.95 (m, 2H), 1.79-1.73 (m, 2H), 1.45-1.41 (m, 1H), 0.96 (s, 9H), 0.93-0.88 (m, 2H), 0.80-0.76 (m, 2H).

N2-(4-benzylsulfanyl-2-methyl-phenyl)-5-bromo-N4-cyclopentyl-pyrimidine-2,4-diamine (Intermediate CV)

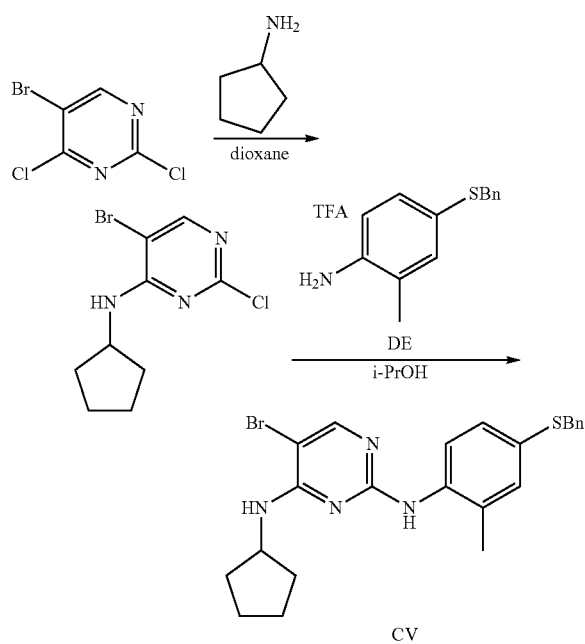

Step 1—5-bromo-2-chloro-N-cyclopentylpyrimidin-4-amine

To a solution of 5-bromo-2,4-dichloro-pyrimidine (10 g, 43.8 mmol, CAS #36082-50-5) in dioxane (100 mL) was added cyclopentanamine (4.48 g, 52.6 mmol, CAS #1003-03-8) at 0° C. under nitrogen flow. Then the reaction was stirred at 20° C. for 6 h under nitrogen atmosphere. On completion, the reaction was poured into ice water (100 mL) then extracted with ethyl acetate (150 mL×2). The combined organic phase is washed with brine (70 mL×2), dried over sodium sulfate, then filtered and the filtrate was concentrated to give a residue. The residue was purified by column chromatography on silica gel (eluted with petroleum ether: ethyl acetate=100:1 to 100:15) to give the title compound (4.7 g, 38% yield) as a yellow solid. $^1$H NMR (400 MHz, $CDCl_3$) δ=8.10 (s, 1H), 5.45 (br s, 1H), 4.57-4.29 (m, 1H), 2.20-2.08 (m, 2H), 1.82-1.57 (m, 4H), 1.48 (qd, J=6.4, 12.8 Hz, 2H).

Step 2: N2-(4-(benzylthio)-2-methylphenyl)-5-bromo-N4-cyclopentylpyrimidine-2,4-diamine To a solution of 5-bromo-2-chloro-N-cyclopentyl-pyrimidin-4-amine (2.65 g, 9.59 mmol) in isopropanol (40 mL) was added 4-benzylsulfanyl-2-methyl-aniline (2 g, 8.72 mmol, Intermediate DE) and TFA (19.8 g, 174 mmol) at 20° C. under nitrogen flow. Then the reaction was stirred at 80° C. for 10 h under nitrogen atmosphere. On completion, the reaction was poured into ice water (40 mL) and extracted with EtOAc (50 mL×2). The combined organic phase is washed with brine (30 mL×2), dried over sodium sulfate, then the mixture was filtered and concentrated to give a residue. The residue was purified by column chromatography on silica gel (eluted with petroleum ether:ethyl acetate=100:1 to 100:15) to give the title compound (3.4 g, 83.0% yield) as a white solid. $^1$H NMR (400 MHz, $CDCl_3$) δ=11.05 (s, 1H), 7.80 (s, 1H), 7.35-7.23 (m, 6H), 7.20 (d, J=1.8 Hz, 1H), 7.13 (dd, J=2.0, 8.3 Hz, 1H), 5.99 (br d, J=6.8 Hz, 1H), 4.18-4.06 (m, 3H), 2.28 (s, 3H), 2.00-1.85 (m, 2H), 1.79-1.56 (m, 4H), 1.52-1.44 (m, 2H).

4-[(6-Chloro-8-cyclopentyl-7-oxo-pyrido[2,3-d]pyrimidin-2-yl)amino]-3-methyl-benzenesulfonyl chloride (Intermediate CW) and 4-((8-cyclopentyl-7-oxo-7,8-dihydropyrido[2,3-d]pyrimidin-2-yl)amino)-3-methylbenzene-1-sulfonyl chloride (Intermediate FX)

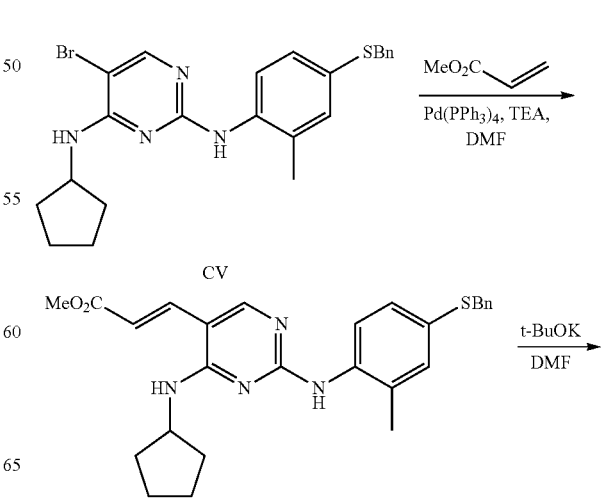

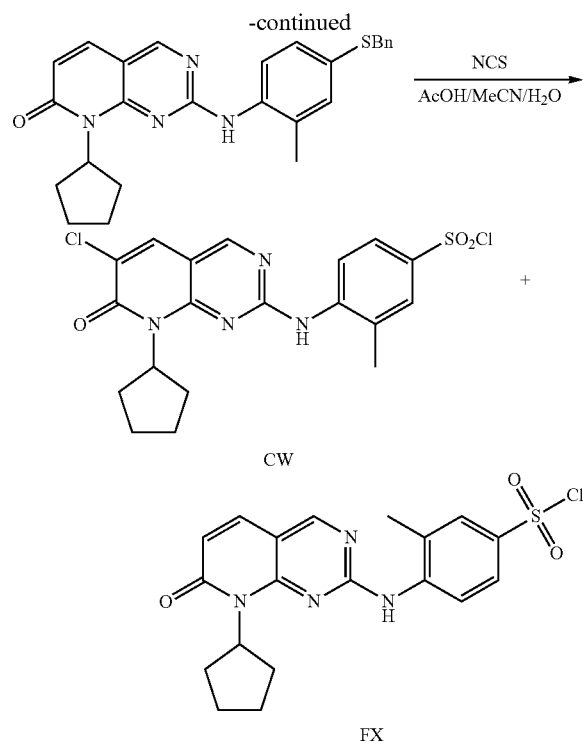

Step 1—Methyl (E)-3-[2-(4-benzylsulfanyl-2-methyl-anilino)-4-(cyclopentylamino) pyrimidin-5-yl]prop-2-enoate A mixture of N2-(4-benzylsulfanyl-2-methyl-phenyl)-5-bromo-N4-cyclopentyl-pyrimidine-2,4-diamine (10 g, 21.3 mmol, Intermediate CV), methyl prop-2-enoate (12.6 g, 146 mmol, CAS #96-33-3), TEA (6.47 g, 63.9 mmol), and Pd(PPh$_3$)$_4$ (2.46 g, 2.13 mmol) in DMF (200 mL) was degassed and purged with N$_2$ three times. Then the mixture was stirred at 90° C. for 36 hours under N$_2$ atmosphere. On completion, the reaction mixture was quenched with H$_2$O (100 mL) at 25° C., and extracted with EA (3×200 mL). The combined organic layers were washed with brine (2×100 mL), dried over with anhydrous Na$_2$SO$_4$, filtered and concentrated in vacuo to give a residue. The residue was purified by prep-HPLC (FA condition) to afford the title compound (15.6 g, 70% yield) $^1$H NMR (400 MHz, DMSO-d$_6$) δ 8.50 (s, 1H), 8.32 (s, 1H), 7.82 (d, J=15.6 Hz, 1H), 7.56 (d, J=8.4 Hz, 1H), 7.34-7.30 (m, 3H), 7.29-7.25 (m, 3H), 7.18 (s, 1H), 7.11 (dd, J=1.6, 8.4 Hz, 1H), 6.31 (d, J=15.6 Hz, 1H), 4.28-4.23 (m, 1H), 4.18 (s, 2H), 3.69 (s, 3H), 2.19 (s, 3H), 1.88-1.82 (m, 2H), 1.70-1.66 (m, 2H), 1.52-1.46 (m, 4H). LC-MS (ESI$^+$) m/z 475.2 (M+H)$^+$.

Step 2—2-(4-Benzylsulfanyl-2-methyl-anilino)-8-cyclopentyl-pyrido[2,3-d]pyrimidin-7-one To a solution of methyl (E)-3-[2-(4-benzylsulfanyl-2-methyl-anilino)-4-(cyclopentylamino) pyrimidin-5-yl]prop-2-enoate (7.8 g, 16.4 mmol) in DMF (80 mL) was added t-BuOK (5.53 g, 49.3 mmol). The mixture was stirred at 25° C. for 30 min. Then the mixture was heated to 120° C. and stirred for 1 hr. On completion, the reaction mixture was quenched with H$_2$O (200 mL) and extracted with EA (2×300 mL). The combined organic layers were washed with brine (2×100 mL), dried over with anhydrous Na$_2$SO$_4$, filtered and concentrated in vacuo. The residue was purified by column chromatography (SiO$_2$, Petroleum ether/Ethyl acetate=40/1 to 10/1, Rf=0.24) to give the title compound (4.60 g, 63% yield) as a yellow solid. LC-MS (ESI$^+$) m/z 443.0 (M+H)$^+$.

Step 3—4-[(6-Chloro-8-cyclopentyl-7-oxo-pyrido [2, 3-d] pyrimidin-2-yl) amino]-3-methyl-benzene-sulfonyl chloride and 4-((8-cyclopentyl-7-oxo-7,8-dihydropyrido[2,3-d]pyrimidin-2-yl)amino)-3-methylbenzene-1-sulfonyl chloride To a solution of 2-(4-benzylsulfanyl-2-methyl-anilino)-8-cyclopentyl-pyrido [2,3-d]pyrimidin-7-one (2 g, 4.52 mmol) in ACN (20 mL), AcOH (2 mL), and H$_2$O (0.5 mL) was added NCS (2.41 g, 18 mmol) in the dark. The mixture was stirred at 25° C. for 0.5 hr in the dark. The reaction mixture was diluted with H$_2$O (50 mL) and extracted with EA (3×50 mL). The combined organic layers were washed with brine (2×60 mL), dried over with anhydrous Na$_2$SO$_4$, filtered and concentrated in vacuo to give a residue. The residue was purified by column chromatography (SiO$_2$, Petroleum ether/Ethyl acetate=40/1 to 10/1, Rf=0.40) to afford 4-[(6-Chloro-8-cyclopentyl-7-oxo-pyrido [2, 3-d] pyrimidin-2-yl) amino]-3-methyl-benzenesulfonyl chloride_(1.49 g, 72% yield) as a yellow solid ($^1$H NMR (400 MHz, DMSO-d$_6$) δ 9.61 (s, 1H), 8.71 (s, 1H), 8.15 (s, 1H), 7.50 (s, 1H), 7.45-7.35 (m, 2H), 5.71 (s, 1H), 2.22 (s, 3H), 2.15-2.04 (m, 2H), 1.69 (s, 4H), 1.44 (s, 2H)) and 4-((8-cyclopentyl-7-oxo-7,8-dihydropyrido[2,3-d]pyrimidin-2-yl)amino)-3-methylbenzene-1-sulfonyl chloride (0.25 g, 12% yield) as a yellowish solid ($^1$H NMR (400 MHz, CDCl3) δ 8.62 (s, 1H), 8.60 (s, 1H), 8.04-7.86 (m, 2H), 7.79 (s, 1H), 7.42 (s, 1H), 5.94 (quin, J=8.7 Hz, 1H), 2.51 (s, 3H), 2.43-2.22 (m, 2H), 2.18-2.06 (m, 2H), 2.00-1.85 (m, 2H), 1.81-1.56 (m, 3H); LC-MS (ESI$^+$) m/z 419.1 (M+H)$^+$).

[1-[(4-Methoxyphenyl) methyl]-2,6-dioxo-3-piperidyl] trifluoromethanesulfonate (Intermediate CY)

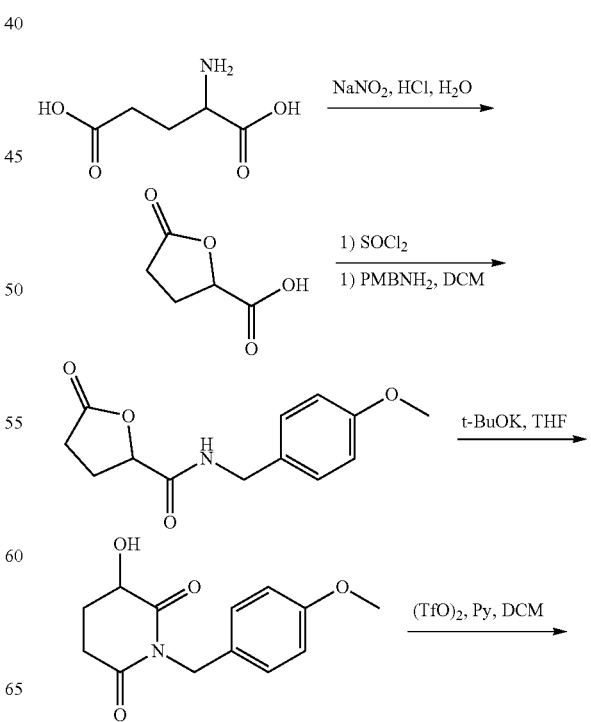

-continued

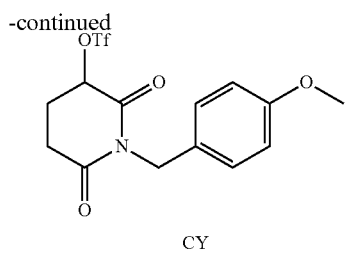

CY

Step 1—5-Oxotetrahydrofuran-2-carboxylic acid

To a solution of 2-aminopentanedioic acid (210 g, 1.43 mol, CAS #617-65-2) in H$_2$O (800 mL) and HCl (12 M, 210 mL) was added a solution of NaNO$_2$ (147 g, 2.13 mol) in H$_2$O (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over Na$_2$SO$_4$, filtered and concentrated in vacuo to give the title compound (200 g, crude) as yellow oil. $^1$H NMR (400 MHz, CDCl$_3$) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide

To 5-oxotetrahydrofuran-2-carboxylic acid (120 g, 922 mmol) was added SOCl$_2$ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under N$_2$. After that a solution of Et$_3$N (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1$H NMR (400 MHz, CDCl$_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS (ESI$^+$) m/z 272.0 (M+Na)$^+$.

Step 3—3-Hydroxy-1-[(4-methoxyphenyl)methyl]piperidine-2,6-dione

A solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated NH$_4$Cl solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. $^1$H NMR (400 MHz, CDCl$_3$) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl) methyl]-2,6-dioxo-3-piperidyl] trifluoromethanesulfonate To a solution of 3-hydroxy-1-[(4-methoxyphenyl)methyl] piperidine-2, 6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under N$_2$. On completion, the mixture was concentrated in vacuo. The residue was purified by column chromatography on silica gel (PE:EA=20:1/8:1) to give the title compound (45.0 g, 68% yield) as light yellow gum. $^1$H NMR (400 MHz, CDCl$_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

5-Bromo-3-methyl-1H-benzimidazol-2-one (Intermediate CZ)

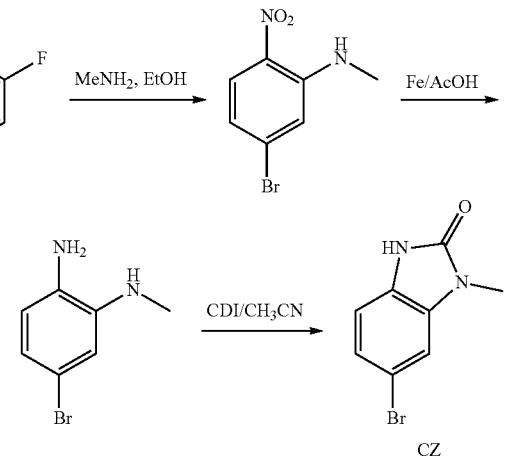

Step 1—5-Bromo-N-methyl-2-nitro-aniline 4-bromo-2-fluoro-1-nitro-benzene (230 g, 1.05 mol, CAS #321-23-3) was added to a solution of methylamine in tetrahydrofuran (2 M, 1.51 L). The mixture was stirred at 15° C. for 10 minutes. On completion, the mixture was diluted with H$_2$O (250 mL) and extracted with EtOAc (3×300 mL). The combined organic layers were washed with brine (300 mL), dried over Na$_2$SO$_4$, filtered and concentrated in vacuo to give the title compound (200 g, 83% yield) as a yellow solid. $^1$H NMR (400 MHz, DMSO-d$_6$) δ 8.22 (s, 1H), 7.98 (d, J=9.2 Hz, 1H), 7.16 (d, J=1.6 Hz, 1H), 6.82 (dd, J=8.4, 1.6 Hz, 1H), 2.95 (d, J=4.8 Hz, 3H).

Step 2—4-Bromo-N2-methyl-benzene-1,2-diamine

To a mixture of 5-bromo-N-methyl-2-nitro-aniline (200 g, 865 mmol) in EtOAc (1 L) and H$_2$O (500 mL) was added AcOH (1.00 L). The mixture was warmed to 50° C., and then Fe (174 g, 3.11 mol) was added to the reaction mixture. After that, the reaction mixture was stirred at 80° C. for 6 hours. On completion, the mixture was filtered through celite. The filtrate was concentrated in vacuo and the residue was diluted with H₂O (250 mL) and extracted with EtOAc (3×300 mL). The combined organic layers were washed with aq. NaHCO₃ and brine (300 mL), dried over Na₂SO₄, filtered and concentrated in vacuo. The residue was purified by flash silica gel chromatography to give the title compound (130 g, 75% yield) as black oil. ¹H NMR (400 MHz, DMSO-d₆) δ 6.55-6.52 (m, 1H), 6.48-6.45 (m, 1H), 6.43-6.42 (m, 1H), 4.89-4.88 (m, 1H), 4.61 (s, 2H), 2.70 (d, J=4.0 Hz, 3H).

Step 3—5-Bromo-3-methyl-1H-benzimidazol-2-one

To a solution of 4-bromo-N2-methyl-benzene-1,2-diamine (110 g, 547 mmol) in CH₃CN (1.3 L) was added CDI (177 g, 1.09 mol). The mixture was stirred at 80° C. for 6 hours under N₂. On completion, the mixture was concentrated in vacuo. The mixture was diluted with H₂O (1.0 L) and filtered. The filter cake was washed with water (3×200 mL) and dried in vacuo to give the title compound (106 g, 85% yield) as a white solid. ¹H NMR (400 MHz, DMSO-d₆) δ 11.00 (s, 1H), 7.33 (s, 1H), 7.13 (d, J=8.0 Hz, 1H), 6.92 (d, J=8.0 Hz, 1H), 3.27 (s, 3H).

3-(5-bromo-3-methyl-2-oxo-benzimidazol-1-yl)piperidine-2,6-dione (Intermediate DA)

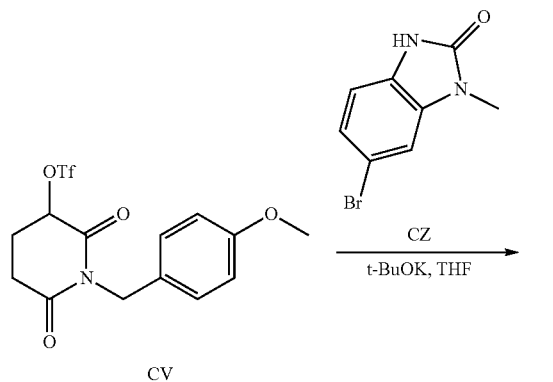

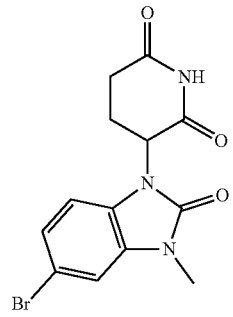

DA

Step 1—3-(5-Bromo-3-methyl-2-oxo-benzimidazol-1-yl)-1-[(4-methoxyphenyl)methyl]piperidine-2,6-dione To a solution of 5-bromo-3-methyl-1H-benzimidazol-2-one (4.90 g, 21.6 mmol, Intermediate CZ) in THF (300 mL) was added t-BuOK (3.63 g, 32.3 mmol) at 0° C. The mixture was stirred at 0-10° C. for 1 hour under N₂. Then a solution of [1-[(4-methoxyphenyl) methyl]-2, 6-dioxo-3-piperidyl] trifluoromethanesulfonate (9.87 g, 25.9 mmol, Intermediate CY) in THF (100 mL) was added to the reaction mixture at 0-10° C. during 30 minutes. The mixture was stirred at 0-10° C. for 30 minutes under N₂. An additional solution of [1-[(4-methoxyphenyl) methyl]-2, 6-dioxo-3-piperidyl] trifluoromethanesulfonate (2.47 g, 6.47 mmol) in THF (20 mL) was added to the reaction mixture at 0-10° C. dropwise. The mixture was then stirred at 0-10° C. for another 30 minutes under N₂. On completion, the reaction was quenched water (400 mL) and extracted with EA (3×200 mL). The combined organic layer was concentrated in vacuo. The residue was triturated with EA (80 mL) and filtered. The filter cake was collected and dried in vacuo to give the title compound (6.70 g, 67% yield) as light yellow solid. The filtrate was also concentrated in vacuo and the residue was purified by column chromatography to give another batch title compound (1.80 g, 18% yield) as light yellow solid. ¹H NMR (400 MHz, DMSO-d₆) δ 7.47 (d, J=1.6 Hz, 1H), 7.21-7.16 (m, 3H), 7.01 (d, J=8.0 Hz, 1H), 6.85 (d, J=8.8 Hz, 2H), 5.55-5.51 (m, 1H), 4.84-4.73 (m, 2H), 3.72 (s, 3H), 3.33 (s, 3H), 3.04-3.00 (m, 1H), 2.83-2.67 (m, 2H), 2.07-2.05 (m, 1H).

Step 2—3-(5-Bromo-3-methyl-2-oxo-benzimidazol-1-yl)piperidine-2,6-dione

To a mixture of 3-(5-bromo-3-methyl-2-oxo-benzimidazol-1-yl)-1-[(4-methoxyphenyl)methyl] piperidine-2,6-dione (8.50 g, 18.6 mmol) in toluene (50 mL) was added methanesulfonic acid (33.8 g, 351 mmol, 25 mL) at room temperature (15° C.). The mixture was stirred at 120° C. for 2 hours. On completion, the reaction mixture was cooled to room temperature and concentrated in vacuo. The residue was poured into ice/water (200 mL), and extracted with EA (3×100 mL). The combined organic layer was washed with brine (50 mL), dried over Na₂SO₄, filtered and concentrated in vacuo. The residue was triturated with EA (80 mL) and filtered. The filtrate cake was collected and dried in vacuo to give the title compound (4.20 g, 67% yield) as off-white solid. ¹H NMR (400 MHz, DMSO-d₆) δ 11.12 (s, 1H), 7.47 (d, J=2.0 Hz, 1H), 7.22 (d, J=8.4 Hz, 1H), 7.10 (d, J=8.4 Hz, 1H), 5.40-5.35 (m, 1H), 2.34 (s, 3H), 2.92-2.88 (m, 1H), 2.71-2.60 (m, 2H), 2.03-1.99 (m, 1H).

3-[3-Methyl-2-oxo-5-(4-piperidyl)benzimidazol-1-yl]piperidine-2,6-dione (Intermediate DB)

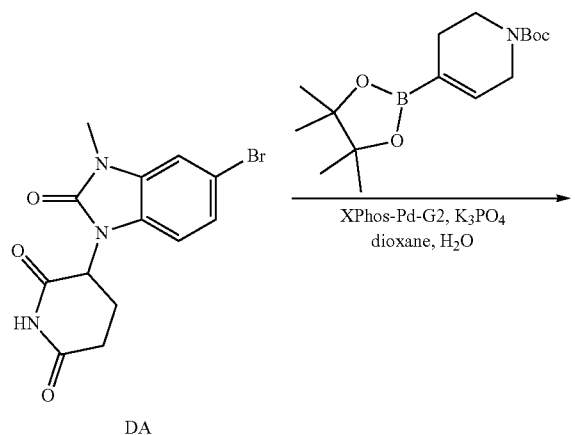

Step 1—Tert-butyl 4-[1-(2,6-dioxo-3-piperidyl)-3-methyl-2-oxo-benzimidazol-4-yl]-3,6-dihydro-2H-pyridine-1-carboxylate To a solution of 3-(5-bromo-3-methyl-2-oxo-benzimidazol-1-yl)piperidine-2,6-dione (5.00 g, 14.8 mmol, Intermediate DA), tert-butyl 4-(4,4,5,5-tetramethyl-1,3,2-dioxaborolan-2-yl)-3,6-dihydro-2H-pyridine-1-carboxylate (5.49 g, 17.7 mmol, CAS #286961-14-6), K₃PO₄ (6.28 g, 29.6 mmol) and [2-(2-aminophenyl)phenyl]-chloro-palladium; dicyclohexyl-[3-(2,4,6-triisopropylphenyl)phenyl]phosphane (1.16 g, 1.48 mmol) in dioxane (100 mL) and H₂O (5.0 mL) was stirred at 80° C. for 4 hrs. On completion, the mixture filtered and the filtrate was concentrated in vacuo. The residue was purified by reversed phase flash (0.1% FA condition) to give the title compound (2.30 g, 53% yield) as white solid. $^1$H NMR (400 MHz, DMSO-$d_6$) δ 11.09 (s, 1H), 7.27 (s, 1H), 7.14-7.04 (m, 2H), 6.11 (s, 1H), 5.36 (dd, J=12.8, 5.2 Hz, 1H), 4.01 (d, J=7.2 Hz, 2H), 3.55 (t, J=5.6 Hz, 2H), 3.35 (s, 3H), 2.95-2.83 (m, 1H), 2.73-2.59 (m, 2H), 2.06-1.95 (m, 2H), 1.46-1.39 (m, 9H), 1.17 (t, J=7.2 Hz, 1H). LC-MS (ESI$^+$) m/z 441.2 (M+H)$^+$.

Step 2—Tert-butyl 4-[1-(2,6-dioxo-3-piperidyl)-3-methyl-2-oxo-benzimidazol-5-yl]piperidine-1-carboxylate To a solution of tert-butyl 4-[1-(2,6-dioxo-3-piperidyl)-3-methyl-2-oxo-benzimidazol-5-yl]-3,6-dihydro-2H-pyridine-1-carboxylate (2.30 g, 5.22 mmol) in THF (150 mL) was added Pd/C (800 mg, 10 wt %) and Pd(OH)₂ (800 mg, 5.70 mmol) at 25° C. The reaction mixture was stirred at 60° C. for 16 hr under H₂ (15 psi). On completion, the reaction mixture was filtered with celite and the filtrate was concentrated in vacuo to give the title compound (2.30 g, 87% yield) as white solid. $^1$H NMR (400 MHz, CDCl₃) δ 8.10 (s, 1H), 7.02-6.87 (m, 2H), 6.76 (d, J=8.0 Hz, 1H), 5.23 (dd, J=5.6, 12.6 Hz, 1H), 4.30-4.25 (m, 2H), 3.45 (s, 3H), 2.99-2.68 (m, 6H), 2.30-2.21 (m, 1H), 1.88-1.81 (m, 2H), 1.51 (s, 9H), 1.48-1.44 (m, 2H). LC-MS (ESI$^+$) m/z 465.2 (M+23)$^+$.

Step 3—3-[3-Methyl-2-oxo-5-(4-piperidyl)benzimidazol-1-yl]piperidine-2,6-dione To a mixture of tert-butyl 4-[1-(2,6-dioxo-3-piperidyl)-3-methyl-2-oxo-benzimidazol-5-yl]piperidine-1-carboxylate (300 mg, 678 umol) in DCM (3.0 mL) was added HCl/dioxane (4 M, 170 uL) in one portion at 25° C. under N₂. The mixture was stirred at 25° C. for 30 min. On completion, the reaction mixture was concentrated in vacuo to give the title compound (250 mg, 910% yield, HCl salt) as white solid. LC-MS (ESI$^+$) m/z 343.1 (M+H)$^+$.

3-(4-Bromo-3-methyl-2-oxo-2,3-dihydro-1H-benzo[d]imidazol-1-yl)piperidine-2,6-dione (Intermediate DC)

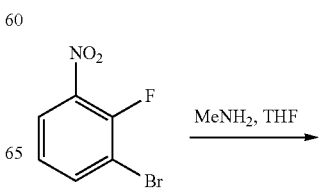

703

-continued

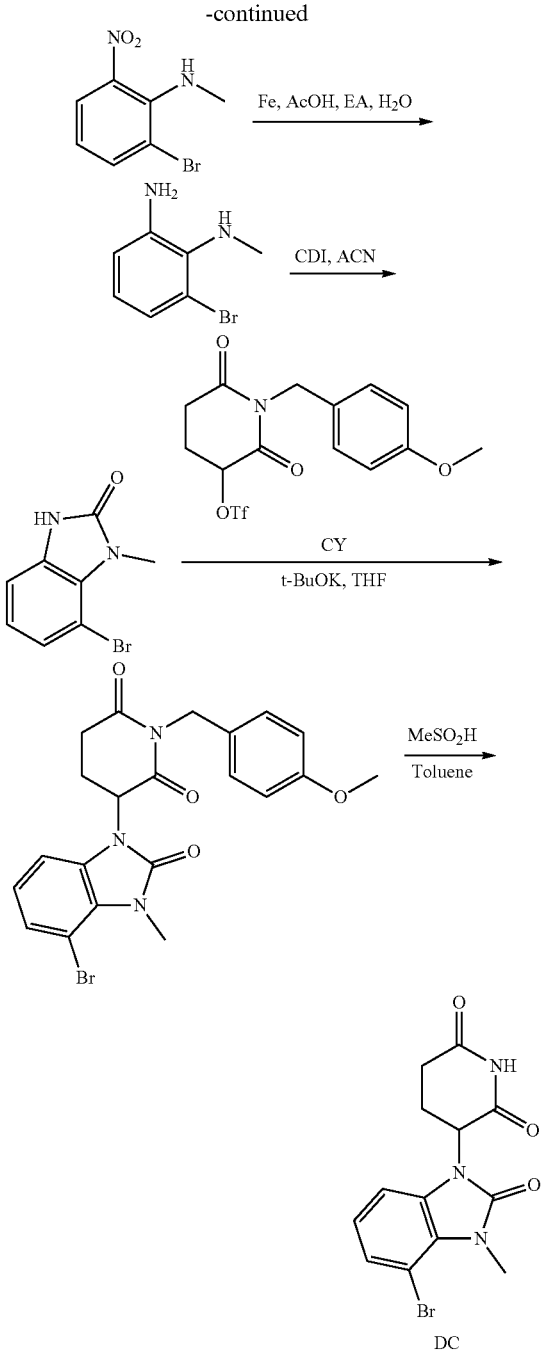

Step 1—2-Bromo-N-methyl-6-nitro-aniline

To a solution of 1-bromo-2-fluoro-3-nitro-benzene (40.0 g, 181 mmol, CAS #58534-94-4) in THF (40 mL) was added MeNH₂ (2 M, 400 mL). The reaction mixture was stirred at 60° C. for 12 hours. On completion, the reaction mixture was poured into sat. NaHCO₃ (30 mL) and extracted with EA (3×200 mL). The combined organic layers were washed with brine (2×200 mL), dried with anhydrous Na₂SO₄, filtered and concentrated in vacuo to give the title compound (40.0 g, 95% yield) as red oil. LC-MS (ESI⁺) m/z 230.9 (M+H)⁺.

704

Step 2—3-Bromo-N2-methyl-benzene-1,2-diamine

To a mixture of 2-bromo-N-methyl-6-nitro-aniline (23.0 g, 99.5 mmol) in EA (300 mL) and H₂O (10 mL) was added AcOH (100 mL). The mixture was warmed to 50° C. Then Fe (22.2 g, 398 mmol) was added to the reaction mixture and the mixture was heated to 80° C. about 4 hours. On completion, the reaction mixture was filtered and concentrated in vacuo. The residue was diluted with water (100 mL) and extracted with EA (3×200 mL). The combined organic layers was dried over Na₂SO₄, filtered and concentrated in vacuo to give the title compound (20.0 g, 99% yield) as red oil. ¹H NMR (400 MHz, DMSO-d₆) δ 6.73-6.70 (m, 1H), 6.68-6.60 (m, 2H), 5.02 (s, 2H), 3.67 (s, 1H), 2.58 (s, 3H).

Step 3—4-Bromo-3-methyl-1H-benzimidazol-2-one

To a mixture of 3-bromo-N2-methyl-benzene-1,2-diamine (20.0 g, 99.4 mmol) in ACN (300 mL) was added CDI (32.2 g, 198 mmol). The reaction mixture was stirred at 85° C. for 12 hours under N₂ atmosphere. On completion, the reaction mixture was concentrated in vacuo. The reaction mixture was diluted with water (200 mL), where a solid precipitate was formed, which was filtered off. The solid was washed with water (1 L) and dried in vacuo to give the title compound (20.0 g, 88% yield) as white solid. ¹H NMR (400 MHz, DMSO-d₆) δ 11.17 (s, 1H), 7.14 (dd, J=1.2, 8.0 Hz, 1H), 7.00-6.95 (m, 1H), 6.93-6.87 (m, 1H), 3.55 (s, 3H).

Step 4—3-(4-Bromo-3-methyl-2-oxo-benzimidazol-1-yl)-1-[(4-methoxyphenyl)methyl]piperidine-2,6-dione To a solution of 4-bromo-3-methyl-1H-benzimidazol-2-one (12.0 g, 52.8 mmol) in THF (300 mL) was added t-BuOK (7.12 g, 63.4 mmol). The reaction mixture was stirred at 0° C. for 0.5 hr. Subsequently, [1-[(4-methoxyphenyl)methyl]-2,6-dioxo-3-piperidyl]trifluoromethanesulfonate (20.1 g, 52.8 mmol, Intermediate CY) in a solution of THF (100 mL) was added dropwise. The resulting reaction mixture was stirred at 20° C. for 0.5 hr under N₂. On completion, the reaction mixture was quenched with saturated NH₄Cl (100 mL), and extracted with ethyl acetate (200 mL). The combined organic layers were washed with brine (2×100 mL), dried over anhydrous sodium sulfate, filtered, the filtrate was concentrated in vacuo. The crude product was purified by reversed-phase HPLC (0.1% FA condition) to give the title compound (13.3 g, 55% yield) as a yellow solid. ¹H NMR (400 MHz, CDCl₃) δ 7.38 (d, J=8.8 Hz, 2H), 7.22 (d, J=8.0 Hz, 1H), 6.84 (d, J=8.8 Hz, 2H), 6.80 (t, J=8.0 Hz, 1H), 6.48-6.40 (d, J=8.0 Hz, 1H), 5.22 (dd, J=5.2, 12.8 Hz, 1H), 5.04-4.93 (m, 2H), 3.81 (s, 3H), 3.80 (s, 3H), 3.12-2.98 (m, 1H), 2.93-2.77 (m, 1H), 2.62 (dq, J=4.4, 13.2 Hz, 1H), 2.20-2.17 (m, 1H).

Step 5—3-(4-bromo-3-methyl-2-oxo-2,3-dihydro-1H-benzo[d]imidazol-1-yl)piperidine-2,6-dione A mixture of 3-(4-bromo-3-methyl-2-oxo-benzimidazol-1-yl)-1-[(4-methoxyphenyl)methyl]piperidine-2,6-dione (13.3 g, 29.0 mmol) in a mixed solvent of Tol. (80 mL) and methane sulfonic acid (40 mL) was degassed and purged with N₂ for 3 times, and then the mixture was stirred at 120° C. for 2 hrs under N₂ atmosphere. On completion, the reaction mixture was concentrated in vacuo to remove toluene. The residue was added 200 mL of ice water, and then white solid precipitate formed. The mixture was filtered and the filtered cake was collected and dried over in vacuo to give the title compound (7.30 g, 74% yield) as white solid. ¹H NMR (400 MHz, DMSO-d₆) δ 11.13 (s, 1H), 7.25 (d, J=8.0 Hz, 1H), 7.17 (d, J=8.0 Hz, 1H), 7.05-6.93 (m, 1H), 5.41 (dd, J=5.2, 12.8 Hz, 1H), 3.64 (s, 3H), 2.96-2.83 (m, 1H), 2.78-2.59 (m, 2H), 2.08-2.00 (m, 1H).

3-[4-(3,9-Diazaspiro[5.5]undecan-3-yl)-3-methyl-2-oxo-benzimidazol-1-yl]piperidine-2,6-dione (Intermediate DD)

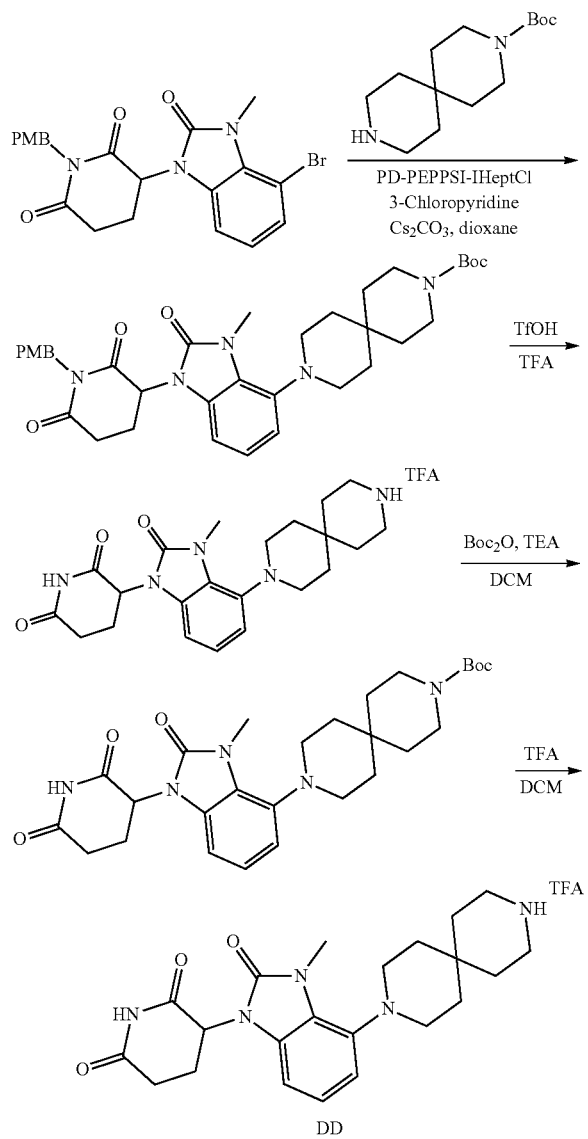

DD

Step 1—3-[4-(3,9-Diazaspiro[5.5]undecan-3-yl)-3-methyl-2-oxo-benzimidazol-1-yl]piperidine-2,6-dione To a solution of 3-(4-bromo-3-methyl-2-oxo-benzimidazol-1-yl)-1-[(4-methoxyphenyl)methyl]piperidine-2,6-dione (1.00 g, 2.18 mmol, synthesized via Steps 1-4 of Intermediate DC) and tert-butyl-3,9-diazaspiro[5.5]undecane-3-carboxylate (666 mg, 2.62 mmol, CAS #173405-78-2) in dioxane (15 mL) was added Pd-PEPPSI-IHEPTCl 3-Chloropyridine (212 mg, 218 umol) and Cs₂CO₃ (1.42 g, 4.36 mmol). Then the mixture was stirred at 100° C. for 10 hours. On completion, the mixture was filtered and concentrated in vacuo to give the residue. The residue was purified by reverse-phase (0.1% FA) to give the title compound (400 mg, 29% yield) as yellow solid. ¹H NMR (400 MHz, CDCl₃-d) δ 7.40-7.35 (m, 2H), 6.93-6.86 (m, 2H), 6.86-6.80 (m, 2H), 6.28 (d, J=7.2 Hz, 1H), 5.21 (dd, J=5.4, 13.0 Hz, 1H), 5.02-4.92 (m, 2H), 3.80 (s, 3H), 3.76 (s, 3H), 3.47-3.39 (m, 4H), 3.04-2.90 (m, 5H), 2.87-2.77 (m, 1H), 2.68-2.55 (m, 1H), 2.18-2.11 (m, 1H), 1.74 (s, 2H), 1.65-1.63 (m, 4H), 1.48 (s, 9H), 1.43 (s, 2H). LC-MS (ESI⁺) m/z 632.4 (M+H)⁺.

Step 2—3-[4-(3,9-Diazaspiro[5.5]undecan-3-yl)-3-methyl-2-oxo-benzimidazol-1-yl]piperidine-2,6-dione To a solution of tert-butyl 9-[1-[1-[(4-methoxyphenyl)methyl]-2,6-dioxo-3-piperidyl]-3-methyl-2-oxo-benzimidazol-4-yl]-3,9-diazaspiro[5.5]undecane-3-carboxylate (200 mg, 316 umol) in TFA (2 mL) was added TfOH (0.2 mL). Then the mixture was stirred at 60° C. for 2 hours. On completion, the mixture was concentrated in vacuo to give the title compound (150 mg, 90% yield, TFA) as a brown solid. LC-MS (ESI⁺) m/z 412.2 (M+H)⁺.

Step 3—Tert-butyl 9-[1-(2,6-dioxo-3-piperidyl)-3-methyl-2-oxo-benzimidazol-4-yl]-3,9-diazaspiro[5.5]undecane-3-carboxylate To a solution of 3-[4-(3,9-diazaspiro[5.5]undecan-3-yl)-3-methyl-2-oxo-benzimidazol-1-yl]piperidine-2,6-dione (150 mg, 285 umol, TFA) in DCM (4 mL) was added TEA (79.4 uL, 570 umol) and Boc₂O (93.4 mg, 428 umol), then the mixture was stirred at 25° C. for 10 hours. On completion, the mixture was diluted with DCM (100 mL) and extracted with water (50 mL×3). The combined organic layer was dried over anhydrous Na₂SO₄, filtered and concentrated in vacuo to give the title compound (140 mg, 96% yield) as a brown solid. ¹H NMR (400 MHz, CDCl₃-d) δ 8.46-8.34 (m, 1H), 7.02-6.92 (m, 2H), 6.57 (d, J=7.2 Hz, 1H), 5.22 (dd, J=5.2, 12.4 Hz, 1H), 3.99-3.90 (m, 1H), 3.77 (s, 3H), 3.46-3.40 (m, 4H), 2.97-2.88 (m, 5H), 2.83 (dd, J=4.8, 13.2 Hz, 1H), 2.77-2.73 (m, J=4.0, 15.2 Hz, 1H), 2.22-2.16 (m, J=2.8, 5.2, 10.8 Hz, 1H), 1.74 (s, 3H), 1.65-1.63 (m, J=8.0 Hz, 4H), 1.48 (s, 9H). LC-MS (ESI⁺) m/z 512.4 (M+H)⁺.

Step 4—3-[4-(3,9-Diazaspiro[5.5]undecan-3-yl)-3-methyl-2-oxo-benzimidazol-1-yl]piperidine-2,6-dione To a solution of tert-butyl 9-[1-(2,6-dioxo-3-piperidyl)-3-methyl-2-oxo-benzimidazol-4-yl]-3,9-diazaspiro[5.5]undecane-3-carboxylate (50.0 mg, 97.7 umol) in DCM (1 mL) was added TFA (1.54 g, 13.5 mmol). The mixture was stirred at 25° C. for 0.5 hr. On completion, the reaction mixture was filtered and concentrated in vacuo to give the title compound (40.0 mg, 99% yield) as colorless oil. LC-MS (ESI⁺) m/z 412.1 (M+H)⁺.

4-Benzylsulfanyl-2-methyl-aniline (Intermediate DE)

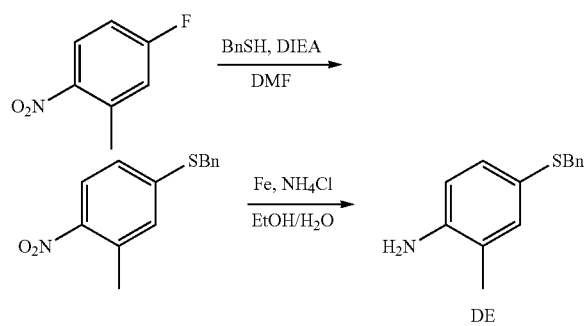

Step-1—4-Benzylsulfanyl-2-methyl-1-nitro-benzene

A mixture of 4-fluoro-2-methyl-1-nitro-benzene (20.0 g, 128 mmol, CAS #446-33-3), BnSH (18.1 mL, 154 mmol), and DIEA (33.3 g, 257 mmol, 44.9 mL) in DMF (200 mL) was degassed and purged with $N_2$ for three times. Then the mixture was stirred at 80° C. for 16 hours under $N_2$ atmosphere. On completion, the reaction mixture was quenched with NaClO (10 mL) at 25° C., and then diluted with $H_2O$ (10 mL) and extracted with EA (10 mL×3). The combined organic layers were washed with brine (10 mL×2), dried over anhydrous $Na_2SO_4$, filtered and concentrated in vacuo to give a residue. Then the residue was purified by column chromatography ($SiO_2$, Petroleum ether/Ethyl acetate=100/1 to 10/1) to give the title compound (26.0 g, 76% yield) as a yellow solid. $^1$H NMR (400 MHz, $CDCl_3$) δ 8.05 (d, J=4.0 Hz, 1H) 7.51-7.37 (m, 5H) 7.30-7.25 (m, 2H) 4.34 (s, 2H) 2.69 (s, 3H). LC-MS (ESI$^+$) m/z 260.0 (M+H)$^+$.

Step-2—4-Benzylsulfanyl-2-methyl-aniline

A mixture of 4-benzylsulfanyl-2-methyl-1-nitro-benzene (18.0 g, 69.4 mmol), Fe (23.2 g, 416 mmol), $NH_4Cl$ (37.1 g, 694 mmol) in EtOH (180 mL) and $H_2O$ (36 mL) was degassed and purged with $N_2$ for three times, and then the mixture was stirred at 80° C. for 1.5 hours under $N_2$ atmosphere. On completion, the reaction mixture was diluted with $H_2O$ 100 mL and extracted with EA (60 mL×3). The combined organic layers were washed with brine (40 mL×2), dried over anhydrous $Na_2SO_4$, filtered and concentrated in vacuo to give a residue. The residue was purified by column chromatography ($SiO_2$, Petroleum ether/Ethyl acetate=100/1 to 10/1) to give the title compound (63 g, 98% yield) as a black oil. $^1$H NMR (400 MHz, DMSO-d$_6$) δ 7.29-7.18 (m, 5H) 6.99 (s, 1H) 6.93 (d, J=1.6 Hz, 1H) 6.57 (d, J=8.0 Hz, 1H) 4.99 (s, 2H) 3.96 (s, 2H) 2.03 (s, 3H).

5-Bromo-2-chloro-N-isopropyl-pyrimidin-4-amine (Intermediate DF)

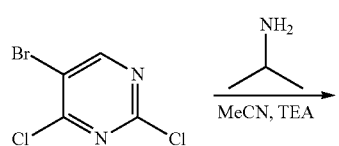

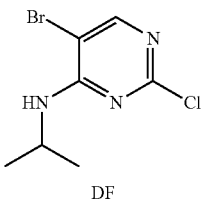

To a solution of 5-bromo-2,4-dichloro-pyrimidine (10.0 g, 43.8 mmol, 5.62 mL, CAS #36082-50-5) in ACN (250 mL) was added TEA (5.77 g, 57.0 mmol, 7.94 mL) and propan-2-amine (3.37 g, 57.0 mmol, 4.90 mL) at 0° C. for 30 min. Then the mixture was stirred for 15.5 hours at 25° C. On completion, the reaction mixture was diluted with $H_2O$ (200 mL) and extracted with EA (3×100 mL). The combined organic layers were washed with brine (2×100 mL), dried over $Na_2SO_4$, filtered and concentrated under reduced pressure to give the title compound (10 g, 90% yield) as a white solid. LC-MS (ESI$^+$) m/z 251.8 (M+H)$^+$.

4-[(6-Chloro-8-isopropyl-7-oxo-pyrido[2,3-d]pyrimidin-2-yl)amino]-3-methyl-benzenesulfonyl chloride (Intermediate DG)

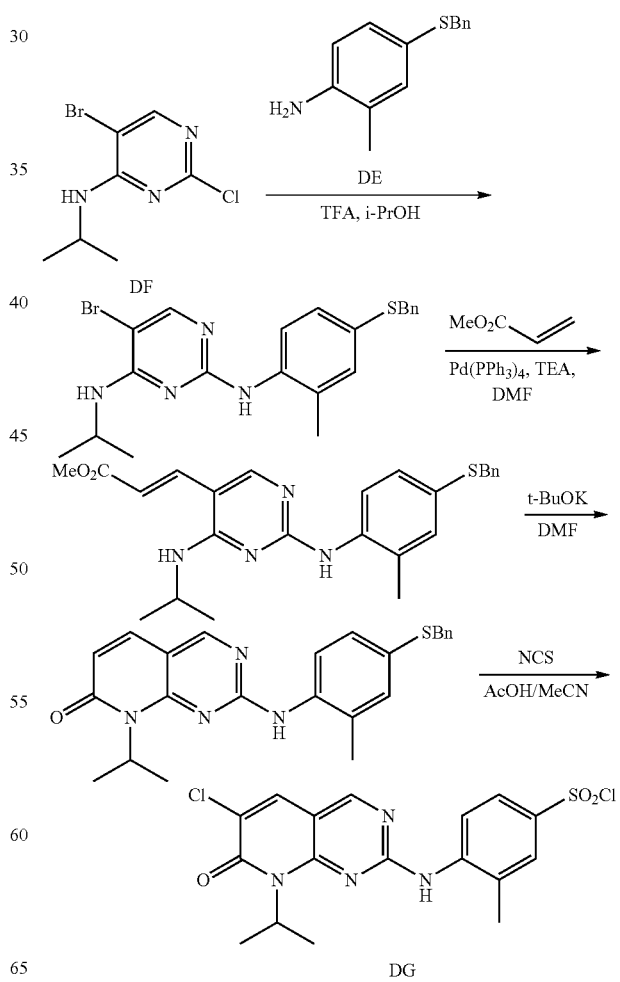

Step 1—N2-(4-benzylsulfanyl-2-methyl-phenyl)-5-bromo-N4-isopropyl-pyrimidine-2,4-diamine To a solution of 4-benzylsulfanyl-2-methyl-aniline (1.00 g, 4.36 mmol, Intermediate DE) in IPA (10 mL) was added 5-bromo-2-chloro-N-isopropyl-pyrimidin-4-amine (1.20 g, 4.80 mmol, Intermediate DF) and TFA (9.94 g, 87.2 mmol, 6.46 mL) at 20° C. under nitrogen flow. Then the reaction was stirred at 80° C. for 20 hrs under nitrogen atmosphere. On completion, the mixture was diluted with $H_2O$ (20 mL), and extracted with EA (30 mL×3). The combined organic layer was washed with $NaHCO_3$ (30 mL), then washed with brine (30 mL×3), dried with anhydrous $Na_2SO_4$, filtered and the filtrate was concentrated in vacuo. The mixture was purified by pre-HPLC (column: Phenomenex luna C18 250*50 mm*15 um; mobile phase: [water(FA)-ACN]; B %: 23%-53%, 20 min) to give the title compound (600 mg, 31% yield) as a black solid. $^1H$ NMR (400 MHz, DMSO-$d_6$) δ 8.25 (s, 1H), 7.91 (s, 1H), 7.47 (d, J=8.4 Hz, 1H), 7.36-7.25 (m, 4H), 7.23 (d, J=6.8 Hz, 1H), 7.16 (s, 1H), 7.09 (d, J=8.4 Hz, 1H), 6.33 (d, J=8.0 Hz, 1H), 4.17 (s, 3H), 2.16 (s, 3H), 1.15 (d, J=6.4 Hz, 6H). LC-MS (ESI$^+$) m/z 444.9 (M+H)$^+$.

Step 2—Methyl (E)-3-[2-(4-benzylsulfanyl-2-methyl-anilino)-4-(isopropylamino)pyrimidin-5-yl]prop-2-enoate A mixture of N2-(4-benzylsulfanyl-2-methyl-phenyl)-5-bromo-N4-isopropyl-pyrimidine-2,4-diamine (2.20 g, 4.96 mmol), TEA (1.51 g, 14.8 mmol, 2.07 mL), and Pd(PPh$_3$)$_4$ (1.15 g, 992 umol) in DMF (25 mL) was added methyl prop-2-enoate (3.11 g, 36.1 mmol, 3.25 mL). The mixture was degassed and purged with $N_2$ three times, and then the mixture was stirred at 90° C. for 16 hours under $N_2$ atmosphere. On completion, the reaction mixture was quenched with $H_2O$ (20 mL) at 25° C., then and extracted with EA (20 mL×3). The combined organic layers were washed with brine (20 mL×3), dried over anhydrous $Na_2SO_4$ filtered and the filtrate was concentrated under reduced pressure to give a residue. The residue was purified by column chromatography (SiO$_2$, Petroleum ether/Ethyl acetate=20/1 to 5/1) (Rf=0.5, PE:EA=2:1) to give the title compound (1.3 g, 58% yield) as a yellow solid. $^1H$ NMR (400 MHz, DMSO-$d_6$) δ 8.50 (s, 1H), 8.31 (s, 1H), 7.78 (d, J=15.6 Hz, 1H), 7.50 (d, J=8.4 Hz, 1H), 7.37-7.08 (m, 9H), 6.31 (d, J=15.2 Hz, 1H), 4.18 (s, 2H), 3.68 (s, 3H), 2.18 (s, 3H), 1.16-1.10 (m, 6H). LC-MS (ESI$^+$) m/z 449.5 (M+H)$^+$.

Step 3—2-(4-Benzylsulfanyl-2-methyl-anilino)-8-isopropyl-pyrido[2,3-d]pyrimidin-7-one To a solution of methyl (E)-3-[2-(4-benzylsulfanyl-2-methyl-anilino)-4-(isopropylamino) pyrimidin-5-yl]prop-2-enoate (110 mg, 245 umol) in DMF (2 mL) was added t-BuOK (82.5 mg, 735 umol). The mixture was stirred at 25° C. for 30 min. Then the mixture was heated to 120° C. and stirred for 1 hr. On completion, the mixture was concentrated in vacuo. The residue was purified by prep-TLC (SiO$_2$, PE:EA=1:1) (Rf=0.5, PE:EA=1:1) to give the title compound (50 mg, 48% yield) as a yellow solid. $^1H$ NMR (400 MHz, DMSO-$d_6$) δ 9.27 (s, 1H), 8.64 (s, 1H), 7.70 (d, J=9.2 Hz, 1H), 7.38-7.16 (m, 8H), 6.25 (d, J=9.2 Hz, 1H), 5.61-5.42 (m, 1H), 4.22 (s, 2H), 2.17 (s, 3H), 1.34 (d, J=5.2 Hz, 6H). LC-MS (ESI$^+$) m/z 867.3 (M+H)$^+$.

Step 4—4-[(6-Chloro-8-isopropyl-7-oxo-pyrido[2,3-d]pyrimidin-2-yl)amino]-3-methyl-benzenesulfonyl chloride To a solution of 2-(4-benzylsulfanyl-2-methyl-anilino)-8-isopropyl-pyrido[2,3-d]pyrimidin-7-one (100 mg, 240 umol) in ACN (1 mL), AcOH (0.1 mL), $H_2O$ (0.01 mL) was added NCS (128 mg, 960 umol). The mixture was stirred at 25° C. for 16 hrs in the dark. On completion, the mixture was quenched with $H_2O$ (5 mL), and extracted with DCM (10 mL×3). The combined organic layer was washed with brine (10 mL×3), dried with anhydrous $Na_2SO_4$, filtered and the filtrate was concentrated in vacuo. The residue was purified by prep-TLC (SiO$_2$, PE:EA=1:1) (Rf=0.56, PE:EA=1:1) to give the title compound (35 mg, 34% yield) as a yellow solid. LC-MS (ESI$^+$) m/z 426.8 (M+H)$^+$.

3-[3-Methyl-2-oxo-5-(4-oxo-1-piperidyl) benzimidazol-1-yl] piperidine-2,6-dione (Intermediate DH)

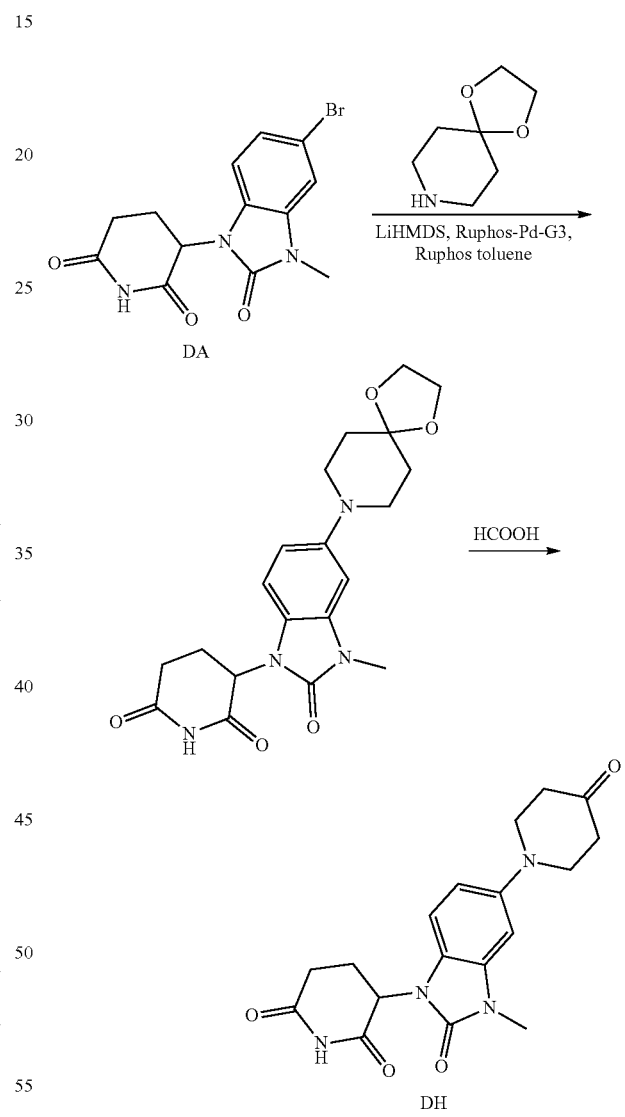

Step 1—3-[5-(1,4-Dioxa-8-azaspiro[4.5]decan-8-yl)-3-methyl-2-oxo-benzimidazol-1-yl]piperidine-2,6-dione To a solution of 1,4-dioxa-8-azaspiro[4.5]decane (635 mg, 4.44 mmol, CAS #177-11-7) in toluene (10 mL) was added LiHMDS (1 M, 17.7 mL), then the mixture was stirred at 110° C. for 30 minutes. Next, 3-(5-bromo-3-methyl-2-oxo-benzimidazol-1-yl)piperidine-2,6-dione (1 g, 2.96 mmol, Intermediate DA), RuPhos Pd G3 (494 mg, 591 umol), and RuPhos (275 mg, 591 umol) was added and the mixture was stirred at 110° C. for 1.5 hrs. On completion, the reaction mixture was filtered and concentrated in vacuo to give a residue. The residue was purified by reverse phase (0.1% FA condition) to give the title compound (500 mg, 42% yield) as gray solid. $^1$H NMR (400 MHz, DMSO-$d_6$) δ 11.05 (s, 1H), 6.96-6.82 (m, 2H), 6.65 (d, J=8.4 Hz, 1H), 3.91 (s, 4H), 3.23-3.14 (m, 5H), 2.95-2.83 (m, 2H), 2.73-2.58 (m, 3H), 2.07 (s, 1H), 2.03-1.94 (m, 1H), 1.78-1.70 (m, 4H). LC-MS (ESI$^+$) m/z 401.0 (M+H)$^+$.

Step 2—3-[3-Methyl-2-oxo-5-(4-oxo-1-piperidyl) benzimidazol-1-yl] piperidine-2,6-dione A mixture of 3-[5-(1,4-dioxa-8-azaspiro[4.5]decan-8-yl)-3-methyl-2-oxo-benzimidazol-1-yl]piperidine-2,6-dione (100 mg, 249 umol) in HCOOH (12.0 mg) was stirred at 80° C. for 12 hrs. On completion, the reaction mixture was concentrated in vacuo to give the title compound (80 mg, 80% yield) as yellow oil. LC-MS (ESI$^+$) m/z 537.1 (M+H)$^+$.

4-[(6-Chloro-8-isopropyl-7-oxo-pyrido[2,3-d]pyrimidin-2-yl)amino]-3-methyl-N-(3-piperazin-1-ylpropyl)benzenesulfonamide (Intermediate DI)

Step 1—Tert-butyl 4-[3-[[4-[(6-chloro-8-isopropyl-7-oxo-pyrido[2,3-d]pyrimidin-2-yl)amino]-3-methyl-phenyl]sulfonylamino]propyl]piperazine-1-carboxylate To a solution of tert-butyl 4-(3-aminopropyl)piperazine-1-carboxylate (68.3 mg, 280 umol, CAS #373608-48-1) in DMF (1 mL) was added DIEA (90.7 mg, 702 umol), then 4-[(6-chloro-8-isopropyl-7-oxo-pyrido[2,3-d]pyrimidin-2-yl)amino]-3-methyl-benzenesulfonyl chloride (100 mg, 234 umol, Intermediate DG) was added. The mixture was stirred at 25° C. for 10 mins. On completion, the reaction mixture was concentrated in vacuo to give the title compound (100 mg, 67% yield) as a gray oil. $^1$H NMR (400 MHz, DMSO-$d_6$) δ 9.65 (s, 1H), 8.81-8.63 (m, 1H), 8.25-8.08 (m, 1H), 7.85-7.71 (m, 3H), 7.69-7.57 (m, 2H), 7.53-7.37 (m, 2H), 2.37-2.33 (m, 3H), 2.07 (d, J=2.0 Hz, 1H), 1.77-1.64 (m, 2H), 1.39 (d, J=1.6 Hz, 9H), 1.27 (s, 6H), LC-MS (ESI$^+$) m/z 633.9 (M+H)$^+$.

Step 2—4-[(6-Chloro-8-isopropyl-7-oxo-pyrido[2,3-d]pyrimidin-2-yl)amino]-3-methyl-N-(3-piperazin-1-ylpropyl)benzenesulfonamide To a solution of tert-butyl 4-[3-[[4-[(6-chloro-8-isopropyl-7-oxo-pyrido [2,3-d]pyrimidin-2-yl)amino]-3-methyl-

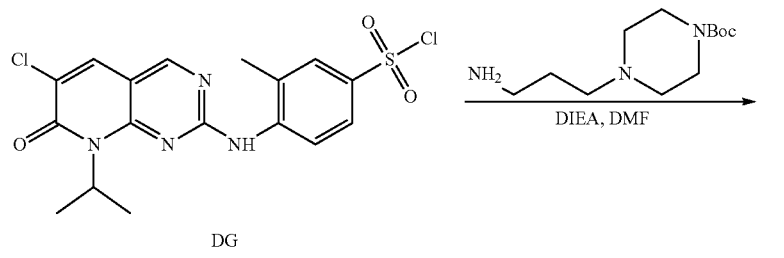

DG

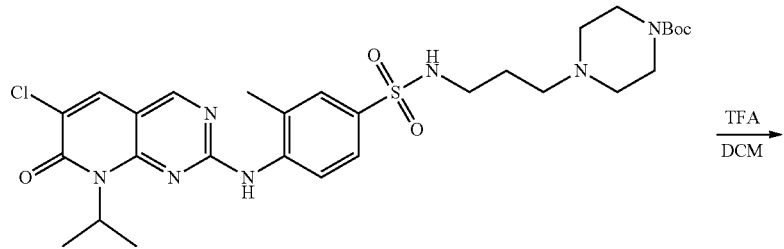

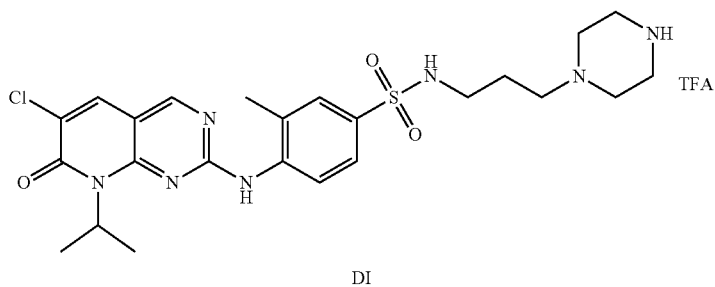

DI phenyl]sulfonylamino]propyl]piperazine-1-carboxylate (50 mg, 78.8 umol) in DCM (1 mL) was added TFA (770 mg), then the mixture was stirred at 25° C. for 1 hour. On completion, the reaction mixture was concentrated in vacuo to give the title compound (50 mg, 97% yield) as a light yellow oil. LC-MS (ESI⁺) m/z 534.1 (M+H)⁺.

Tert-butyl 4-but-3-enylpiperazine-1-carboxylate (Intermediate DJ)

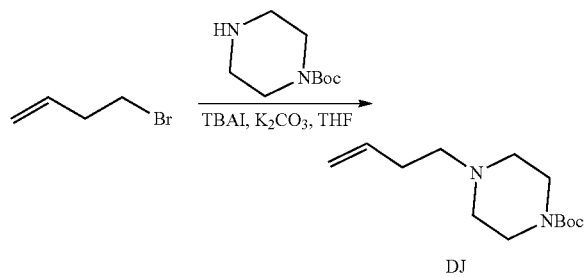

To a solution of 4-bromobut-1-ene (2.83 g, 20.9 mmol, CAS #5162-44-7) and tert-butylpiperazine-1-carboxylate hydrochloride (3.00 g, 13.4 mmol, CAS #57260-71-6) in THF (100 mL) was added $K_2CO_3$ (6.69 g, 48.4 mmol) and TBAI (300 mg, 812 umol). Then the mixture was stirred at 70° C. for 15 hrs. On completion, the mixture was filtered, diluted with water (100 mL) and extracted with EA (30 mL×3). The combined organic layer was dried over anhydrous $Na_2SO_4$, filtered and concentrated in vacuo to give the residue. The residue was purified by column chromatography (SiO₂, PE:EA=15:1 to 1:1) to give the title compound (1.50 g, 46% yield) as yellow oil. ¹H NMR (400 MHz, CDCl₃) δ 5.86-5.76 (m, 1H), 5.09-5.00 (m, 2H), 3.48-3.40 (m, 4H), 2.45-2.39 (m, 6H), 2.28-2.23 (m, 2H), 1.47 (s, 9H). LC-MS (ESI⁺) m/z 241.1 (M+H)⁺.

4-(1,3-dioxolan-2-yl)piperidine (Intermediate DL)

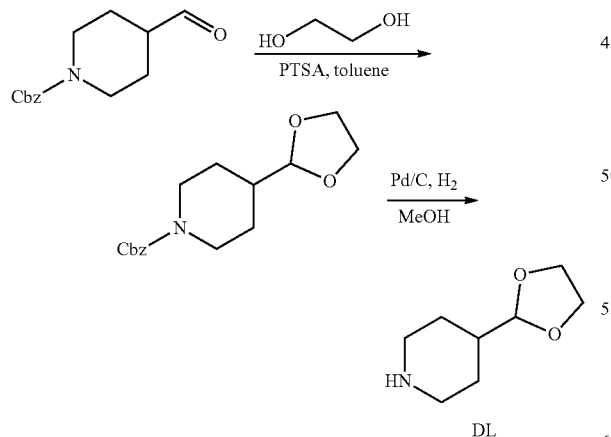

Step 1—Benzyl 4-(1,3-dioxolan-2-yl)piperidine-1-carboxylate

A solution of benzyl 4-formylpiperidine-1-carboxylate (20.0 g, 80.9 mmol, CAS #138163-08-3), PTSA (1.4 g, 8.09 umol) and ethylene glycol (5.52 g, 88.9 mmol, CAS #107-21-1) in toluene (200 mL) was refluxed at 130° C. for 16 hrs. On completion, the reaction mixture was concentrated in vacuo. The residue was purified by column chromatography (SiO₂, Petroleum ether/Ethyl acetate=5/1 to 0/1) to give the title compound (15.0 g, 63% yield). ¹H NMR (400 MHz, CDCl₃) δ 7.43-7.28 (m, 5H), 5.13 (s, 2H), 4.65 (d, J=4.4 Hz, 1H), 4.24 (s, 2H), 3.99-3.82 (m, 4H), 2.77 (s, 2H), 1.85-1.64 (m, 3H), 1.42-1.26 (m, 2H).

Step 2—4-(1,3-Dioxolan-2-yl)piperidine

To a solution of benzyl 4-(1,3-dioxolan-2-yl)piperidine-1-carboxylate (5 g, 20 mmol) in MeOH (100 mL) was added Pd/C (1.5 g, 1.4 mmol, 10 wt %) under N₂. The suspension was degassed in vacuo and purged with H₂ several times. The mixture was stirred at 25° C. for 4 hours under H₂ (15 PSI). On completion, the reaction mixture was filtered and concentrated in vacuo to give the title compound (2.3 g, 85% yield) as yellow solid. ¹H NMR (400 MHz, CDCl₃) δ 4.62 (d, J=4.8 Hz, 1H), 3.98-3.81 (m, 4H), 3.11 (d, J=12.0 Hz, 2H), 2.60 (m, 2H), 1.98 (s, 1H), 1.73 (d, J=14.4 Hz, 2H), 1.69-1.62 (m, 1H), 1.38-1.24 (m, 2H).

1-[1-(2,6-dioxo-3-piperidyl)-3-methyl-2-oxo-benzimidazol-5-yl]piperidine-4-carbaldehyde (Intermediate DM)

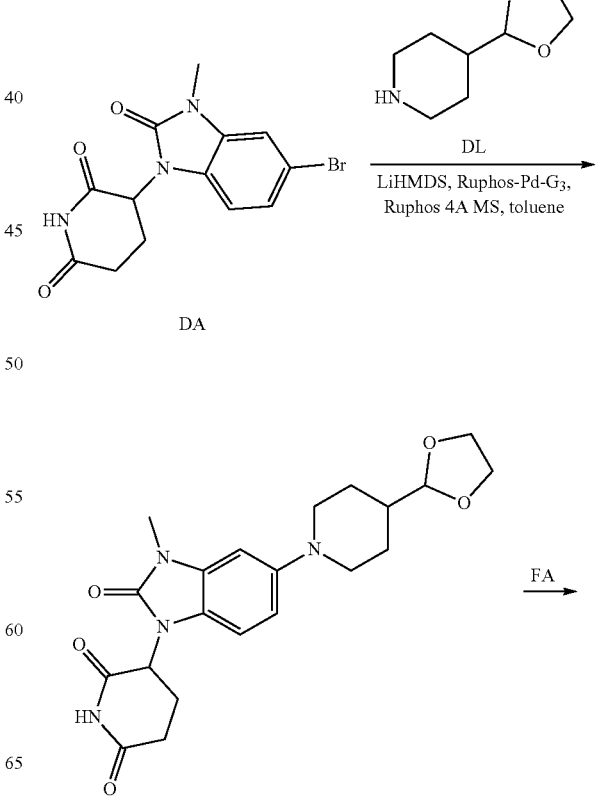

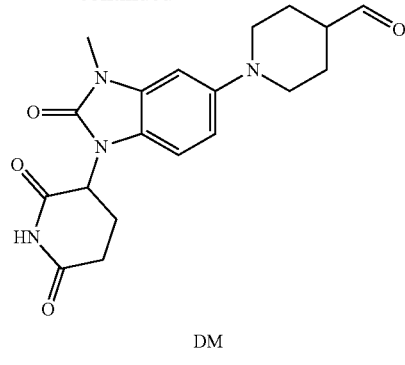

DM

Step 1—3-[5-[4-(1,3-Dioxolan-2-yl)-1-piperidyl]-3-methyl-2-oxo-benzimidazol-1-yl]piperidine-2,6-dione To a solution of 4-(1,3-dioxolan-2-yl)piperidine (500 mg, 3.18 mmol, Intermediate DL) and 3-(5-bromo-3-methyl-2-oxo-benzimidazol-1-yl)piperidine-2,6-dione (1.08 g, 3.18 mmol, Intermediate DA) in toluene (15 mL) was added RuPhos (148 mg, 318 umol), RuPhos Pd $G_3$ (266 mg, 318 umol) and LiHMDS (1 M, 19.0 mL). On completion, the reaction mixture was acidified to pH=7 by HCOOH and concentrated in vacuo. The residue was triturated with PE/EA (3/1), filtered and the filter cake was triturated with water. The solid was filtered and dried in vacuo to give the title compound (1.1 g, 83% yield) as gray solid. $^1$H NMR (400 MHz, DMSO-$d_6$) δ 11.05 (s, 1H), 6.92 (d, J=8.4 Hz, 1H), 6.82 (d, J=2.0 Hz, 1H), 6.63 (dd, J=2.0, 8.4 Hz, 1H), 5.28 (dd, J=5.2, 12.8 Hz, 1H), 4.61 (d, J=5.2 Hz, 1H), 3.93-3.75 (m, 4H), 3.62 (d, J=12.4 Hz, 2H), 3.37-3.30 (m, 3H), 2.95-2.82 (m, 1H), 2.67 (dd, J=4.4, 12.8 Hz, 1H), 2.63-2.55 (m, 3H), 2.02-1.93 (m, 1H), 1.78-1.72 (m, 2H), 1.65-1.56 (m, 1H), 1.50-1.39 (m, 2H).

Step 2—1-[1-(2,6-Dioxo-3-piperidyl)-3-methyl-2-oxo-benzimidazol-5-yl]piperidine-4-carbaldehyde A solution of 3-[5-[4-(1,3-dioxolan-2-yl)-1-piperidyl]-3-methyl-2-oxo-benzimidazol-1-yl]piperidine-2,6-dione (100 mg, 241 umol) in HCOOH (3 mL) was stirred at 50° C. for 3 hrs. On completion, the reaction mixture was concentrated in vacuo to give the title compound (89 mg, 99% yield) as a brown oil. LCMS (ESI$^+$) m/z 371.0 (M+H)$^+$.

8-isopropyl-2-methylsulfanyl-pyrido[2,3-d]pyrimidin-7-one (Intermediate DN)

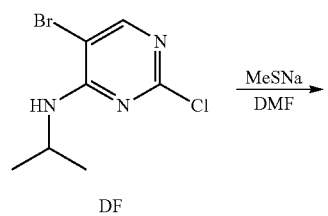

DF

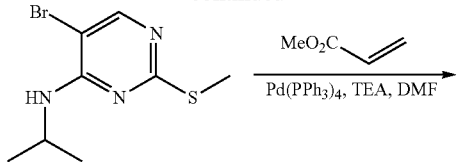

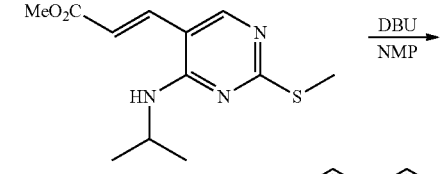

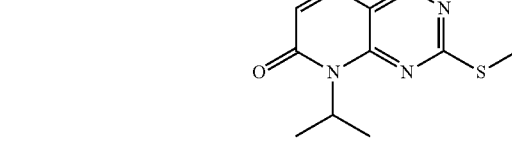

DN

Step 1—5-Bromo-N-isopropyl-2-methylsulfanyl-pyrimidin-4-amine

To a solution of 5-bromo-2-chloro-N-isopropyl-pyrimidin-4-amine (10.0 g, 39.9 mmol, Intermediate DF) in DMF (110 mL) was added NaSMe (7.12 g, 101 mmol, 6.47 mL). The mixture was stirred at 25° C. for 16 hrs under $N_2$. On completion, the reaction mixture was quenched with $H_2O$ (100 mL) at 25° C., and then extracted with EA (100 mL×3). The combined organic layers were washed with brine (100 mL×2), dried over anhydrous $Na_2SO_4$, filtered and concentrated in vacuo to give the title compound (9.50 g, 90% yield) as a yellow solid. $^1$H NMR (400 MHz, DMSO-$d_6$) δ 8.12 (s, 1H), 7.95 (s, 1H), 4.32-4.25 (m, 1H), 2.89 (s, 3H), 2.73 (s, 3H), 2.41 (s, 3H). LC-MS (ESI$^+$) m/z 263.8 (M+H)$^+$.

Step 2—Methyl (E)-3-[4-(isopropylamino)-2-methylsulfanyl-pyrimidin-5-yl]prop-2-enoate A mixture of 5-bromo-N-isopropyl-2-methylsulfanyl-pyrimidin-4-amine (9.50 g, 36.2 mmol), methyl prop-2-enoate (22.3 g, 259 mmol, 23.3 mL, CAS #96-33-3), Pd(PPh$_3$)$_4$ (4.19 g, 3.62 mmol), and TEA (11.0 g, 108 mmol, 15.0 mL) in DMF (100 mL) was degassed and purged with $N_2$ three times. Then the mixture was stirred at 90° C. for 32 hrs under $N_2$ atmosphere. On completion, the reaction mixture was quenched with $H_2O$ (100 mL) at 25° C., and then extracted with EA (100 mL×3). The combined organic layers were washed with brine (100 mL×2), dried over anhydrous $Na_2SO_4$, filtered and concentrated in vacuo to give a residue. The residue was purified by column chromatography (SiO$_2$, Petroleum ether/Ethyl acetate=10/1 to 3/1) (Rf=0.40, PE:EA=1:1) to give the title compound (5.80 g, 59% yield) as a yellow solid. $^1$H NMR (400 MHz, DMSO-$d_6$) δ 8.43-8.30 (m, 1H), 7.79 (d, J=15.6 Hz, 1H), 7.49 (d, J=7.2 Hz, 1H), 6.55-6.43 (m, 1H), 4.35 (d, J=6.8, 13.4 Hz, 1H), 3.71 (s, 3H), 2.44 (s, 3H), 1.19 (d, J=6.4 Hz, 6H). LC-MS (ESI$^+$) m/z 268.1 (M+H)$^+$.

Step 3—8-Isopropyl-2-methylsulfanyl-pyrido[2,3-d]pyrimidin-7-one

A mixture of methyl (E)-3-[4-(isopropylamino)-2-methylsulfanyl-pyrimidin-5-yl]prop-2-enoate (5.73 g, 21.4 mmol), DBU (16.3 g, 107 mmol, 16.1 mL) in NMP (50.0 mL) was degassed and purged with N₂ three times. Then the mixture was stirred at 120° C. for 1 hr under N₂ atmosphere. On completion, the mixture was diluted with H₂O (300 mL), and extracted with DCM (3×100 mL). The combined organic layer was washed with brine (3×100 mL), then dried with anhydrous Na₂SO₄, filtered and the filtrate was concentrated in vacuo. The mixture was purified by reversed phase (0.1% FA) to give the title compound (4.20 g, 83% yield) as a white solid. ¹H NMR (400 MHz, DMSO-d₆) δ 8.84 (s, 1H), 7.86 (d, J=9.6 Hz, 1H), 6.56 (d, J=9.6 Hz, 1H), 5.75-5.56 (m, 1H), 2.59 (s, 3H), 1.53 (d, J=6.8 Hz, 6H). LC-MS (ESI⁺) m/z 236.1 (M+H)⁺.

4-[[6-(Difluoromethyl)-8-isopropyl-7-oxo-pyrido[2,3-d]pyrimidin-2-yl]amino]-3-methyl-benzenesulfonyl chloride (Intermediate DO)

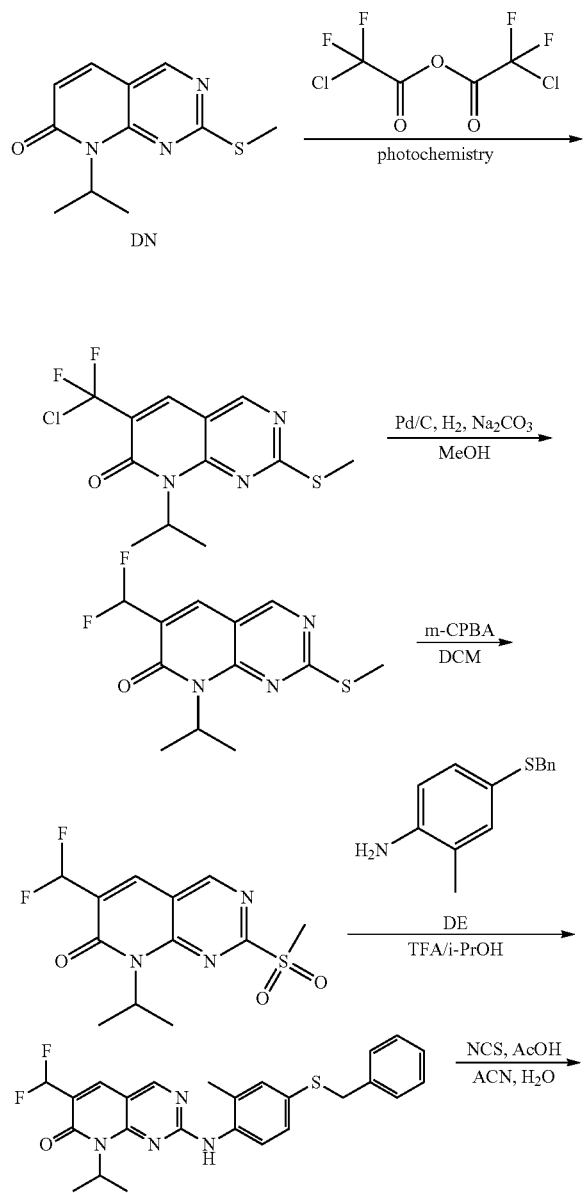

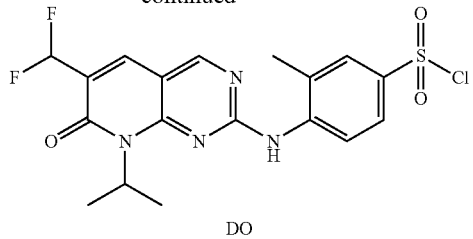

Step 1—6-[Chloro(difluoro)methyl]-8-isopropyl-2-methylsulfanyl-pyrido[2,3-d]pyrimidin-7-one To an 15 mL vial equipped with a stir bar was added 4-phenylpyridine N-Oxide (3.64 g, 21.0 mmol), 8-isopropyl-2-methylsulfanyl-pyrido[2,3-d]pyrimidin-7-one (2.00 g, 8.50 mmol, Intermediate DN), and Ru(bpy)₃Cl₂.6H₂O (63.6 mg, 85.0 umol) in dry ACN (20 mL), then (2-chloro-2,2-difluoro-acetyl) 2-chloro-2,2-difluoro-acetate (5.16 g, 21.0 mmol, CAS #2834-28-3) was added. The vial was sealed and placed under nitrogen was added. The reaction was stirred and irradiated with a 34 W blue LED lamp (2 cm away), with cooling water to keep the reaction temperature at 25° C. for 16 hrs. On completion, the mixture was concentrated in vacuo. The residue was purified by column chromatography (SiO₂, Petroleum ether/Ethyl acetate=20/1 to 10/1) (Rf=0.55, PE:EA=1:1) to give the title compound (1.37 g, 50% yield) as a yellow solid. ¹H NMR (400 MHz, DMSO-d₆) δ 9.02 (s, 1H), 8.50 (s, 1H), 5.82-5.64 (m, 1H), 2.63 (s, 3H), 1.57 (d, J=6.8 Hz, 6H). LC-MS (ESI⁺) m/z 319.6 (M+H)⁺.

Step 2—6-(Difluoromethyl)-8-isopropyl-2-methylsulfanyl-pyrido[2,3-d]pyrimidin-7-one A mixture of 6-[chloro(difluoro)methyl]-8-isopropyl-2-methylsulfanyl-pyrido[2,3-d]pyrimidin-7-one (200 mg, 625 umol), Pd/C (10.0 mg, 6.25 umol, 10 wt %), Na₂CO₃ (99.0 mg, 938 umol) in THF (2 mL) was degassed and purged with H₂ three times. Then the mixture was stirred at 25° C. for 2 hours under H₂ atmosphere. On completion, the mixture was filtered, and the filtrate was concentrated in vacuo. The residue was purified by column chromatography (SiO₂, Petroleum ether/Ethyl acetate=30/1 to 10/1) (Rf=0.70, PE:EA=3:1) to give the title compound (70.0 mg, 39% yield) as a white solid. ¹H NMR (400 MHz, DMSO-d₆) δ 9.00 (s, 1H), 8.28 (s, 1H), 5.87-5.59 (m, 1H), 3.36-3.26 (m, 1H), 2.62 (s, 3H), 1.56 (d, J=6.8 Hz, 6H). LC-MS (ESI⁺) m/z 286.0 (M+H)⁺.

Step 3—6-(Difluoromethyl)-8-isopropyl-2-methylsulfonyl-pyrido[2,3-d]pyrimidin-7-one To a solution of 6-(difluoromethyl)-8-isopropyl-2-methylsulfanyl-pyrido[2,3-d]pyrimidin-7-one (260 mg, 911 umol) in DCM (2 mL) was added m-CPBA (740 mg, 3.65 mmol, 85% solution). The mixture was stirred at 40° C. for 3 hrs. On completion, the mixture was quenched with NaHCO₃ (10 mL), then extracted with EA (3×10 mL). The combined organic layers were washed with brine (3×10 mL), dried with anhydrous Na₂SO₄, filtered and the filtrate was concentrated in vacuo. The residue was purified by column chromatography (SiO₂, Petroleum ether/Ethyl acetate=30/1 to 10/1) to give the title compound (100 mg, 34% yield) as a yellow solid. LC-MS (ESI⁺) m/z 317.9 (M+H)⁺.

Step 4—2-(4-Benzylsulfanyl-2-methyl-anilino)-6-(difluoromethyl)-8-isopropyl-pyrido[2,3-d]pyrimidin-7-one A mixture of 6-(difluoromethyl)-8-isopropyl-2-methylsulfonyl-pyrido[2,3-d]pyrimidin-7-one (70.0 mg, 220 umol), 4-benzylsulfanyl-2-methyl-aniline (151 mg, 661 umol, Intermediate DE), TFA (251 mg, 2.21 mmol, 163 uL) in IPA (2 mL), and then the mixture was stirred at 90° C. for 5 hrs. On completion, the mixture was concentrated in vacuo. The mixture was purified by reversed phase (0.1% FA) to give the title compound (27.0 mg, 26% yield) as a brown oily liquid. ¹H NMR (400 MHz, DMSO-d₆) δ 9.56 (s, 1H), 8.81 (s, 1H), 8.10 (s, 1H), 7.37-7.17 (m, 8H), 6.88 (t, J=56.0 Hz, 1H), 5.59-5.37 (m, 1H), 4.23 (s, 2H), 2.17 (s, 3H), 1.34 (s, 6H). LC-MS (ESI⁺) m/z 467.2 (M+H)⁺.

Step 5—4-[[6-(Difluoromethyl)-8-isopropyl-7-oxo-pyrido[2,3-d]pyrimidin-2-yl]amino]-3-methyl-benzenesulfonyl chloride To a solution of 2-(4-benzylsulfanyl-2-methyl-anilino)-6-(difluoromethyl)-8-isopropyl-pyrido[2,3-d] pyrimidin-7-one (22.0 mg, 47.1 umol) in ACN (1 mL), AcOH (0.1 mL), and H₂O (0.01 mL) was added NCS (16.0 mg, 126 umol). The mixture was stirred at 25° C. for 1 hr in the dark. On completion, the mixture was diluted with H₂O (10 mL), and extracted with EA (3×10 mL). The combined organic layer was washed with brine (3×10 mL), dried with anhydrous Na₂SO₄, filtered and the filtrate was concentrated in vacuo to give the title compound (20.0 mg, 95% yield) as a brown oily liquid. LC-MS (ESI⁺) m/z 442.9 (M+H)⁺.

Tert-butyl N-[2-(4-formylcyclohexoxy)ethyl]carbamate (Intermediate DP)

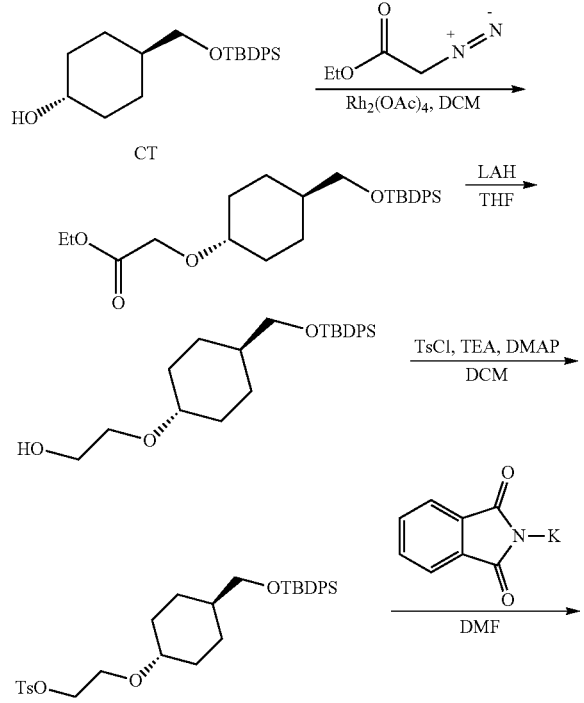

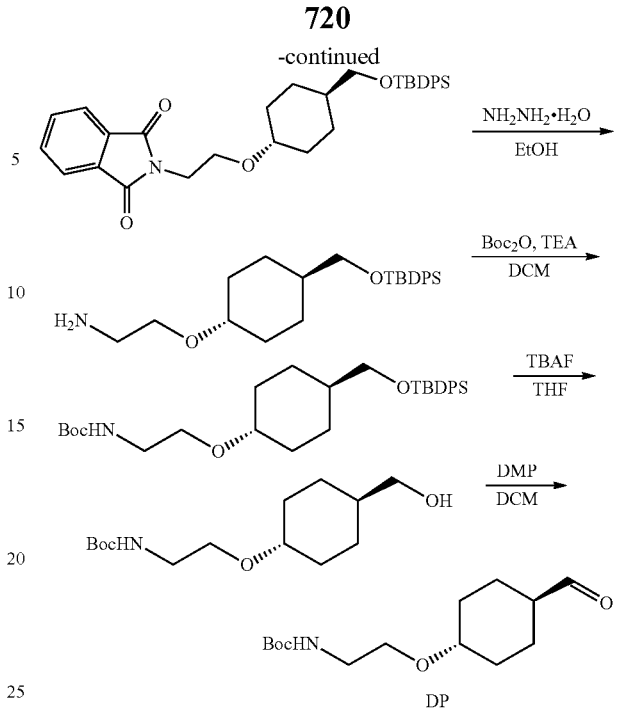

Step 1—Ethyl 2-[4-[[tert-butyl(diphenyl)silyl]oxymethyl]cyclohexoxy]acetate

To a solution of 4-[[tert-butyl (diphenyl)silyl]oxymethyl] cyclohexanol (8.60 g, 23.3 mmol, Intermediate CT) and Rh₂(OAc)₄ (1.03 g, 2.33 mmol) in DCM (40 mL) was added a solution of ethyl 2-diazoacetate (10.6 g, 93.3 mmol) in DCM (40 mL). The mixture was degassed and purged with N₂ three times and the mixture was stirred at 25° C. for 12 hrs under N₂ atmosphere. On completion, the mixture was diluted with DCM (80 mL), the organic layer was washed with H₂O (2×80 mL), brine (2×80 mL), dried over anhydrous Na₂SO₄, filtered and concentrated in vacuo. The mixture was purified by silica gel column (PE:EA=10:1) to give the title compound (10.0 g, 94% yield) as yellow oil. ¹H NMR (400 MHz, CDCl₃) δ 7.72-7.61 (m, 4H), 7.48-7.32 (m, 6H), 4.28-4.25 (m, 2H), 4.12 (s, 2H), 3.46 (d, J=6.0 Hz, 2H), 3.32-3.22 (m, 1H), 2.15-2.04 (m, 2H), 1.91-1.81 (m, 2H), 1.54-1.45 (m, 1H), 1.32-1.28 (m, 5H), 1.09-0.99 (m, 2H), 1.05 (s, 9H).

Step 2—2-[4-[[Tert-butyl(diphenyl)silyl]oxymethyl]cyclohexoxy]ethanol

To a solution of LAH (626 mg, 16.5 mmol) in THF (25 mL) was added a solution of ethyl 2-[4-[[tertbutyl(diphenyl) silyl]oxymethyl]cyclohexoxy]acetate (5.00 g, 11.0 mmol) in THF (25 mL) dropwise at 0° C. The mixture was stirred at 0° C. for 0.5 hr. On completion, the mixture was quenched with H₂O (0.62 mL), then a solution of 15% NaOH (0.62 mL) was added dropwise. The mixture was dried with anhydrous Na₂SO₄, filtered and the filtered liquor was concentrated in vacuo to give the title compound (3.15 g, 69% yield) as yellow oil. ¹H NMR (400 MHz, CDCl₃) δ 7.76-7.61 (m, 4H), 7.49-7.33 (m, 6H), 3.81-3.66 (m, 3H), 3.63-3.57 (m, 2H), 3.50-3.45 (m, 2H), 3.28-3.18 (m, 1H), 2.15-2.04 (m, 2H), 1.88-1.83 (m, 2H), 1.61-1.46 (m, 1H), 1.28-1.20 (m, 2H), 1.10-0.96 (m, 2H), 1.05 (s, 9H).

Step 3—2-[4-[[Tert-butyl(diphenyl)silyl]oxymethyl]cyclohexoxy]ethyl 4-methylbenzenesulfonate To a solution of 2-[4-[[tert-butyl(diphenyl)silyl]oxymethyl]cyclohexoxy]ethanol (3.15 g, 7.63 mmol) in DCM (40 mL) was added TEA (1.13 g, 11.1 mmol), DMAP (170 mg, 1.39 mmol) and TosCl (1.59 g, 8.35 mmol). The mixture was stirred at 25° C. for 16 hrs. On completion, the mixture was concentrated in vacuo. The mixture was purified by silica gel column (PE:EA=10:1) to give the title compound (2.86 g, 90% yield) as colorless oil. $^1$H NMR (400 MHz, CDCl$_3$) δ 7.88-7.76 (m, 2H), 7.68-7.60 (m, 4H), 7.44-7.31 (m, 8H), 4.19-4.12 (m, 2H), 3.72-3.62 (m, 2H), 3.45 (d, J=6.4 Hz, 2H), 3.19-3.06 (m, 1H), 2.45 (s, 3H), 2.00-1.90 (m, 2H), 1.88-1.75 (m, 2H), 1.52-1.42 (m, 1H), 1.20-1.10 (m, 2H), 1.05 (s, 9H), 1.01-0.92 (m, 2H).

Step 4—2-[2-[4-[[Tert-butyl(diphenyl)silyl]oxymethyl]cyclohexoxy]ethyl]isoindoline-1,3-dione To a solution of 2-[4-[[tert-butyl(diphenyl)silyl]oxymethyl]cyclohexoxy]ethyl 4-methylbenzenesulfonate (2.86 g, 5.05 mmol) in DMF (20 mL) was added (1,3-dioxoisoindolin-2-yl) potassium (1.40 g, 7.57 mmol). The mixture was stirred at 50° C. for 5 hrs. On completion, the mixture was diluted with H$_2$O (150 mL), and extracted with EA (3×50 mL). The organic layers were washed with brine (3×40 mL), dried over anhydrous Na$_2$SO$_4$, filtered and concentrated in vacuo to give the title compound (2.7 g, 98% yield) as yellow oil. $^1$H NMR (400 MHz, CDCl$_3$) δ 7.89-7.83 (m, 2H), 7.74-7.69 (m, 2H), 7.68-7.61 (m, 4H), 7.45-7.34 (m, 6H), 3.95-3.82 (m, 2H), 3.77-3.68 (m, 2H), 3.44 (d, J=6.1 Hz, 2H), 3.28-3.15 (m, 1H), 2.03-1.94 (m, 2H), 1.87-1.75 (m, 2H), 1.54-1.40 (m, 1H), 1.22-1.12 (m, 2H), 1.04 (s, 9H), 1.02-0.90 (m, 2H).

Step 5—2-[4-[[Tert-butyl(diphenyl)silyl]oxymethyl]cyclohexoxy]ethanamine

To a solution of 2-[2-[4-[[tert-butyl(diphenyl)silyl]oxymethyl]cyclohexoxy]ethyl] isoindoline-1,3-dione (2.7 g, 4.98 mmol) in EtOH (20 mL) was added NH$_2$NH$_2$·H$_2$O (3.19 g, 54.1 mmol, 3.10 mL, 85% solution). The mixture was stirred at 50° C. for 2 hrs. On completion, the mixture was filtered and the filtrate was concentrated in vacuo. The residue was diluted with DCM (30 mL), and filtered, the filtrate was concentrated in vacuo to give the title compound (2.02 g, 98% yield) as yellow oil. $^1$H NMR (400 MHz, CDCl$_3$) δ 7.70-7.63 (m, 4H), 7.47-7.35 (m, 6H), 3.54 (t, J=4.8 Hz, 2H), 3.47 (d, J=6.0 Hz, 2H), 3.25-3.15 (m, 1H), 2.90 (t, J=5.2 Hz, 2H), 2.33-2.19 (m, 2H), 2.13-2.00 (m, 2H), 1.88-1.78 (m, 2H), 1.56-1.45 (m, 1H), 1.28-1.20 (m, 2H), 1.06 (s, 9H), 1.04-0.94 (m, 2H).

Step 6—Tert-butyl N-[2-[4-[[tert-butyl(diphenyl)silyl]oxymethyl]cyclohexoxy]ethyl]carbamate To a solution of 2-[4-[[tert-butyl(diphenyl)silyl]oxymethyl]cyclohexoxy]ethanamine (2 g, 5 mmol) in DCM (20 mL) was added TEA (983 mg, 9.72 mmol, 1.35 mL) and (Boc)$_2$O (1.27 g, 5.83 mmol, 1.34 mL). The mixture was stirred at 25° C. for 3 hrs. On completion, the mixture was concentrated in vacuo. The mixture was purified by silica gel column (PE:EA=10:1) to give the title compound (1.88 g, 75% yield) as yellow oil. $^1$H NMR (400 MHz, CDCl$_3$) δ 7.77-7.58 (m, 4H), 7.53-7.32 (m, 6H), 5.00-4.79 (m, 1H), 3.53 (t, J=5.2 Hz, 2H), 3.47 (d, J=6.0 Hz, 2H), 3.33-3.25 (m, 2H), 3.22-3.12 (m, 1H), 2.10-1.99 (m, 2H), 1.89-1.80 (m, 2H), 1.54-1.46 (m, 1H), 1.49 (s, 9H), 1.27-1.15 (m, 2H), 1.06 (s, 9H), 1.05-0.93 (m, 2H).

Step 7—Tert-butyl N-[2-[4-(hydroxymethyl)cyclohexoxy]ethyl]carbamate

To a solution of tert-butyl N-[2-[4-[[tert-butyl(diphenyl)silyl]oxymethyl]cyclohexoxy]ethyl]carbamate (1.78 g, 3.48 mmol) in THF (15 mL) was added TBAF (1.00 M, 5.22 mL). The mixture was stirred at 25° C. for 1 hr. On completion, the mixture was concentrated in vacuo, then the mixture was purified by silica gel column (PE:EA=1:1) to give the title compound (950 mg, 99% yield) as yellow oil. $^1$H NMR (400 MHz, CDCl$_3$) δ 5.00-4.75 (m, 1H), 3.53 (t, J=5.2 Hz, 2H), 3.47 (d, J=6.4 Hz, 2H), 3.34-3.26 (m, 2H), 3.25-3.13 (m, 1H), 2.13-2.03 (m, 2H), 1.90-1.80 (m, 2H), 1.56-1.50 (m, 1H), 1.46 (s, 9H), 1.30-1.16 (m, 3H), 1.05-0.91 (m, 2H).

Step 8—Tert-butyl N-[2-(4-formylcyclohexoxy)ethyl]carbamate

To a solution tert-butyl N-[2-[4-(hydroxymethyl)cyclohexoxy]ethyl]carbamate (800 mg, 2.93 mmol) in DCM (20 mL) was added DMP (1.49 g, 3.51 mmol). The mixture was stirred at 25° C. for 0.5 hr. On completion, the mixture was diluted with DCM (100 mL) and quenched with saturated Na$_2$S$_2$O$_3$ (50 mL) and washed with saturated NaHCO$_3$ (3×50 mL). The organic layer was dried over anhydrous Na$_2$SO$_4$, filtered and concentrated in vacuo to give the title compound (790 mg, 99% yield) as yellow oil. $^1$H NMR (400 MHz, CDCl$_3$) δ 9.65 (d, J=1.2 Hz, 1H), 5.05-4.67 (m, 1H), 3.57-3.49 (m, 2H), 3.37-3.17 (m, 3H), 2.17-1.99 (m, 4H), 1.46 (s, 10H), 1.41-1.23 (m, 4H)

3-[5-[1-[[4-(2-Aminoethoxy)cyclohexyl]methyl]-4-piperidyl]-3-methyl-2-oxo-benzimidazol-1-yl]piperidine-2,6-dione (Intermediate DQ)

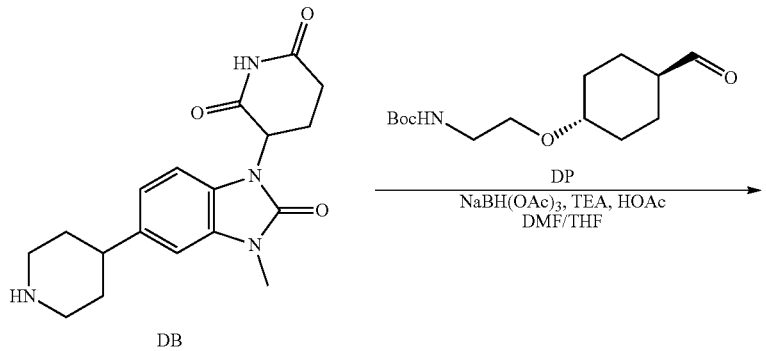

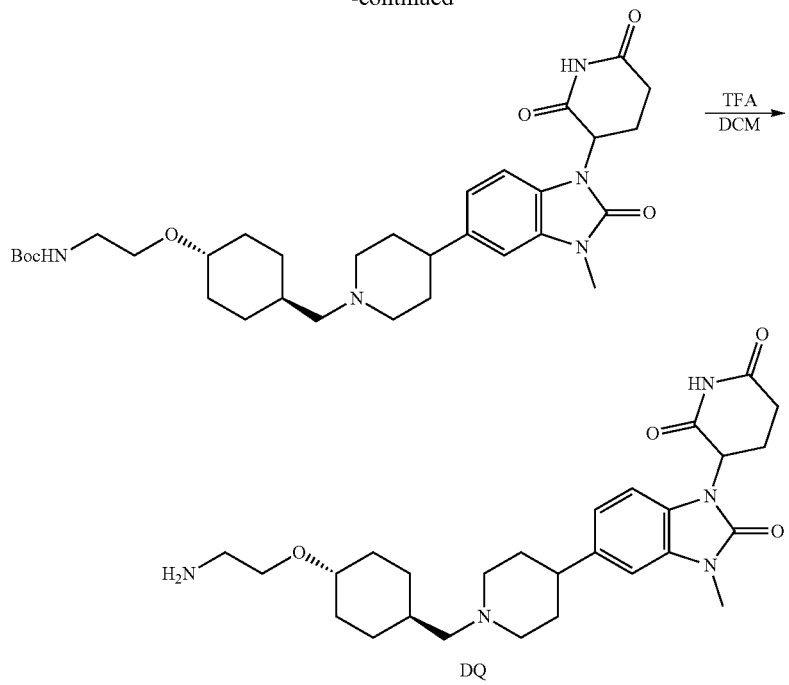

Step 1—Tert-butyl N-[2-[4-[[4-[1-(2,6-dioxo-3-piperidyl)-3-methyl-2-oxo-benzimidazol-5-yl]-1-piperidyl]methyl]cyclohexoxy]ethyl]carbamate To a solution of 3-[3-methyl-2-oxo-5-(4-piperidyl)benzimidazol-1-yl]piperidine-2,6-dione (756 mg, 1.66 mmol, TFA, Intermediate DB), tert-butyl N-[2-(4-formylcyclohexoxy)ethyl]carbamate (500 mg, 1.84 mmol, Intermediate DP) in DMF (4 mL) and THF (16 mL) was added TEA (372 mg, 3.69 mmol). The mixture was stirred at −10° C. for 0.5 hour. Then HOAc (331 mg, 5.53 mmol, 316 uL) was added, and the mixture was stirred at −10° C. for 0.5 hr. Then NaBH(OAc)$_3$ (781 mg, 3.69 mmol) was added and the mixture was stirred at −10° C. for 1 hr. On completion, the mixture was quenched with H$_2$O (0.5 mL) and concentrated in vacuo. The mixture was purified by reverse phase: (0.1% FA) to give the title compound (630 mg, 57% yield) as white solid. $^1$H NMR (400 MHz, DMSO-d$_6$) δ 11.08 (s, 1H), 7.07 (s, 1H), 7.03 (d, J=8.0 Hz, 1H), 6.91 (d, J=8.4 Hz, 1H), 6.79-6.67 (m, 1H), 5.37-3.29 (m, 1H), 3.33 (s, 3H), 3.27-3.12 (m, 7H), 3.05-3.02 (m, 2H), 2.95-2.82 (m, 2H), 2.74-2.66 (m, 2H), 2.64-2.55 (m, 2H), 2.06-1.94 (m, 3H), 1.90-1.70 (m, 6H), 1.67-1.53 (m, 1H), 1.37 (s, 9H), 1.18-1.07 (m, 2H), 1.03-0.86 (m, 2H), LC-MS (ESI$^+$) m/z 598.3 (M+H)$^+$.

Step 2—3-[5-[1-[[4-(2-Aminoethoxy)cyclohexyl]methyl]-4-piperidyl]-3-methyl-2-oxo-benzimidazol-1-yl]piperidine-2,6-dione To a solution of tert-butyl N-[2-[4-[[4-[1-(2,6-dioxo-3-piperidyl)-3-methyl-2-oxo-benzimidazol-5-yl]-1-piperidyl]methyl]cyclohexoxy]ethyl]carbamate (530 mg, 886 umol) in DCM (8 mL) was added TFA (2.04 g, 17.9 mmol, 1.32 mL). The mixture was stirred at 25° C. for 0.5 hr. On completion, the mixture was concentrated in vacuo to give the title compound (530 mg, 97% yield, TFA) as yellow oil. LC-MS (ESI$^+$) m/z 498.2 (M+H)$^+$.

Tert-butyl N-[4-(4-piperidyl)butyl]carbamate (Intermediate DR)

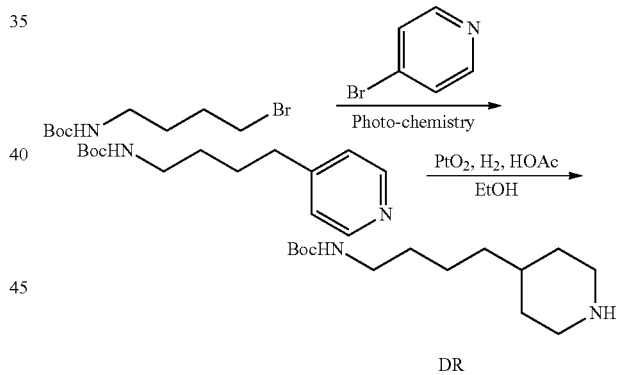

Step 1—Tert-butyl N-[4-(4-pyridyl)butyl]carbamate

A mixture of tert-butyl N-(4-bromobutyl)carbamate (50.4 mg, 0.2 mmol, 41.0 uL, CAS #164365-88-2), and 4-bromopyridine (24.3 mg, 153 umol, CAS #1120-87-2) in ACN (1 mL) was degassed and purged with N$_2$ three times. Then the mixture was stirred at 25° C. for 12 hrs under N$_2$ atmosphere. On completion, the reaction mixture was filtered and concentrated in vacuo to give a residue. The residue was purified by prep-HPLC (column: Phenomenex luna C18 250*50 mm*10 um; mobile phase: [water (FA)-ACN]; B %: 35%-50%, 30 min) to give the title compound (400 mg, 26% yield) as a white solid. $^1$H NMR (400 MHz, CDCl$_3$) δ 8.49 (d, J=4.4 Hz, 2H), 7.12 (d, J=4.0 Hz, 2H), 4.53 (s, 1H), 3.15 (d, J=6.4 Hz, 2H), 2.64 (t, J=7.6 Hz, 2H), 1.72-1.62 (m, 2H), 1.57-1.50 (m, 2H), 1.44 (s, 9H). LC-MS (ESI$^+$) m/z 251.1 (M+H)$^+$.

Step 2—Tert-butyl N-[4-(4-piperidyl)butyl]carbamate

To a solution of tert-butyl N-[4-(4-pyridyl)butyl]carbamate (400 mg, 1.60 mmol) in EtOH (5 mL) was added $PtO_2$ (362 mg, 1.60 mmol) and HOAc (95.9 mg, 1.60 mmol, 92.0 uL) under $N_2$. The suspension was degassed under vacuum and purged with $H_2$ several times. The mixture was stirred under $H_2$ (15 psi) at 25° C. for 12 hrs. On completion, the reaction mixture was filtered and concentrated in vacuo to give the title compound (500 mg, 98% yield, HOAc salt) as yellow oil. $^1$H NMR (400 MHz, $CDCl_3$) δ 4.56 (s, 1H), 3.38 (d, J=12.4 Hz, 2H), 3.11 (d, J=5.6 Hz, 2H), 2.82 (t, J=11.6 Hz, 2H), 1.83 (d, J=11.6 Hz, 2H), 1.44 (s, 15H), 1.32 (s, 4H). LC-MS (ESI$^+$) m/z 257.3 (M+H)$^+$.

1-(4-Bromophenyl)-3-[(4-methoxyphenyl)methyl]hexahydropyrimidine-2,4-dione (Intermediate DS)

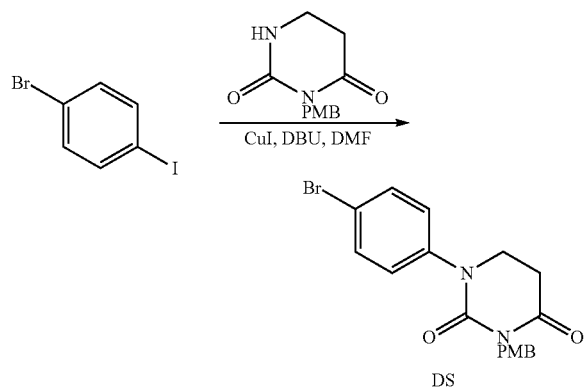

To a solution of 3-[(4-methoxyphenyl)methyl]hexahydropyrimidine-2,4-dione (2 g, 9 mmol, CAS #589-87-8) and 1-bromo-4-iodo-benzene (2.68 g, 9.49 mmol, CAS #504-07-4) in DMF (30 mL) was added DBU (2.89 g, 18.9 mmol) and CuI (1.81 g, 9.49 mmol). The mixture was stirred at 140° C. for 16 hrs. On completion, the reaction mixture was filtered and extracted with ethyl acetate (3×20 mL). The combined organic layers were washed with brine (20 mL), dried over anhydrous sodium sulfate, filtered and the filtrate was concentrated in vacuo. The residue was purified by column chromatography ($SiO_2$, Petroleum ether/Ethylacetate=10/1 to 5/1) to give the title compound (2.5 g, 68% yield) as a yellow solid. LC-MS (ESI$^+$) m/z 390.7 (M+H)$^+$.

1-[4-[4-(4-Aminobutyl)-1-piperidyl]phenyl]hexahydropyrimidine-2,4-dione (Intermediate DT)

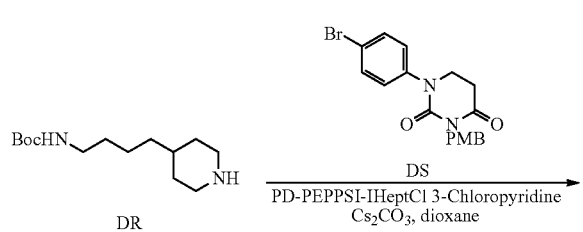

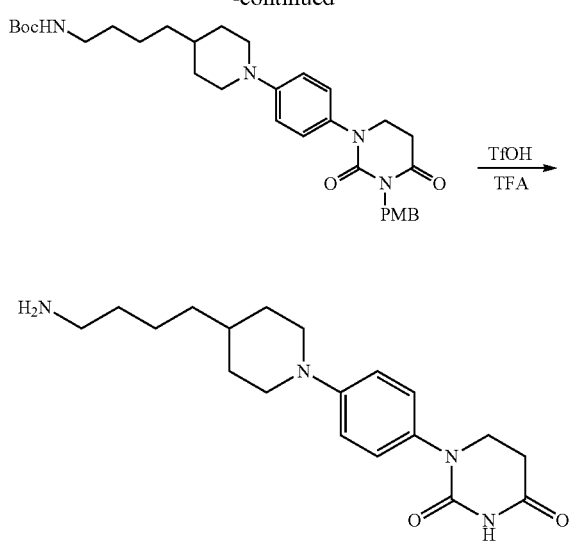

Step 1—Tert-butyl N-[4-[1-[4-[3-[(4-methoxyphenyl)methyl]-2,4-dioxo-hexahydropyrimidin-1-yl]phenyl]-4-piperidyl]butyl]carbamate A mixture of tert-butyl N-[4-(4-piperidyl)butyl]carbamate (280 mg, 1.09 mmol, Intermediate DR), 1-(4-bromophenyl)-3-[(4-methoxyphenyl)methyl]hexahydropyrimidine-2,4-dione (100 mg, 256 umol, Intermediate DS), $Cs_2CO_3$ (502 mg, 1.54 mmol), and 1,3-bis[2,6-bis(1-ethylpropyl)phenyl]-4,5-dichloro-2H-imidazol-1-ium-2-ide 3-chloropyridine;dichloropalladium (22.1 mg, 25.6 umol) in dioxane (1 mL) was degassed and purged with $N_2$ three times. Then the mixture was stirred at 100° C. for 12 hrs under $N_2$ atmosphere. On completion, the reaction mixture was filtered and concentrated in vacuo to give a residue. The residue was purified by prep-HPLC (column: Phenomenex Luna C18 200*40 mm*10 um; mobile phase: [water (FA)-ACN]; B %: 38%-68%, 10 min) to give the title compound (200 mg, 66% yield) as a white solid. $^1$H NMR (400 MHz, $CDCl_3$) δ 7.46-7.38 (m, 2H), 7.16-7.05 (m, 2H), 6.92 (d, J=8.8 Hz, 2H), 6.86-6.79 (m, 2H), 4.95 (s, 2H), 4.54 (s, 1H), 3.78 (s, 3H), 3.71 (t, J=6.8 Hz, 2H), 3.64 (d, J=12.4 Hz, 2H), 3.17-3.07 (m, 2H), 2.84 (t, J=6.8 Hz, 2H), 2.68 (t, J=11.6 Hz, 2H), 1.77 (d, J=10.4 Hz, 2H), 1.53-1.47 (m, 2H), 1.45 (s, 9H), 1.40-1.26 (m, 7H). LC-MS (ESI$^+$) m/z 565.3 (M+H)$^+$.

Step 2—1-[4-[4-(4-Aminobutyl)-1-piperidyl]phenyl]hexahydropyrimidine-2,4-dione A mixture of tert-butyl N-[4-[1-[4-[3-[(4-methoxyphenyl)methyl]-2,4-dioxo-hexahydropyrimidin-1-yl]phenyl]-4-piperidyl]butyl]carbamate (100 mg, 177 umol) and TfOH (26.5 mg, 177 umol, 15.6 uL) in TFA (1.2 mL) was degassed and purged with $N_2$ three times. Then the mixture was stirred at 70° C. for 1 hr under $N_2$ atmosphere. On completion, the mixture was concentrated under reduced pressure to give the title compound (61 mg, 76% yield, TFA salt) as yellow oil. LC-MS (ESI$^+$) m/z 345.0 (M+H)$^+$.

727
Tert-butyl N-[5-(4-piperidyl)pentyl]carbamate
(Intermediate DU)

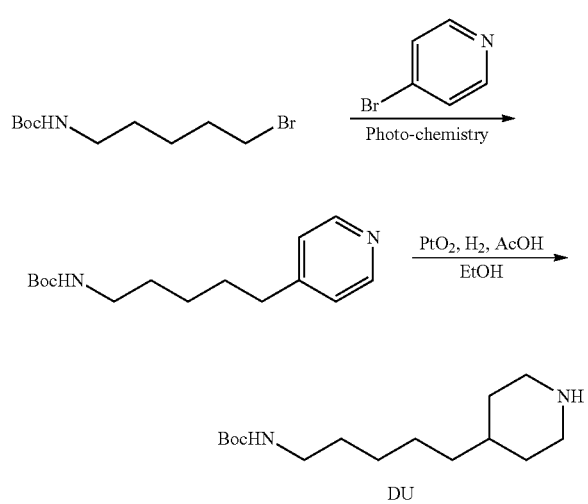

Step 1—Tert-butyl N-[5-(4-pyridyl)pentyl]carbamate

To a vial equipped with a stir bar was added 4-bromopyridine (1.00 g, 6.33 mmol, CAS #1120-87-2), tert-butyl N-(5-bromopentyl)carbamate (2.19 g, 8.23 mmol, CAS #83948-54-3), Ir[dF(CF$_3$)ppy]$_2$ (dtbpy)(PF$_6$) (71.0 mg, 63.2 umol), NiCl$_2$·dtbbpy (37.7 mg, 94.9 umol), TTMSS (1.57 g, 6.33 mmol), and Na$_2$CO$_3$ (1.34 g, 12.6 mmol) in DME (10 mL). The vial was sealed and placed under nitrogen was added. The reaction was stirred and irradiated with a 10 W blue LED lamp (3 cm away), with cooling water to keep the reaction temperature at 25° C. for 14 hours. On completion, the reaction mixture was filtered and concentrated in vacuo to give a residue. The residue was purified by prep-HPLC (column: UniSil 10-120 C18 50×250 mm; mobile phase: [water(FA)-ACN]; B %: 1%-30%, 22 min) to give the title compound (800 mg, 48% yield) as colorless solid. $^1$H NMR (400 MHz, CDCl$_3$) δ 8.46 (d, J=3.2 Hz, 2H) 7.08 (d, J=4.4 Hz, 2H) 4.63 (s, 1H) 3.11-3.06 (m, 2H) 2.58 (t, J=7.6 Hz, 2H) 1.67-1.59 (m, 2H) 1.51-1.46 (m, 2H) 1.42 (s, 9H) 1.37-1.30 (m, 2H). LC-MS (ESI$^+$) m/z 264.9 (M+H)$^+$.

Step 2—Tert-butyl N-[5-(4-piperidyl)pentyl]carbamate

To a solution of tert-butyl N-[5-(4-pyridyl)pentyl]carbamate (800 mg, 3 mmol) in EtOH (8 mL) was added PtO$_2$ (687 mg, 3.03 mmol) and AcOH (363 mg, 6.05 mmol) under N$_2$. The suspension was degassed under vacuum and purged with H$_2$ several times. The mixture was stirred under H$_2$ (15 psi) at 25° C. for 12 hrs. On completion, the reaction mixture was filtered and concentrated in vacuo to give the title compound (775 mg, 95% yield) as yellow oil. $^1$H NMR (400 MHz, CDCl$_3$) δ 4.61 (s, 1H) 3.35 (d, J=12.4 Hz, 2H) 3.10-2.99 (m, 2H) 2.80 (t, J=11.2 Hz, 2H) 1.79 (d, J=11.6 Hz, 2H) 1.41 (s, 15H) 1.26 (s, 6H). LC-MS (ESI$^+$) m/z 271.2 (M+H)$^+$.

728
1-[4-[4-(5-Aminopentyl)-1-piperidyl]phenyl]hexahydropyrimidine-2,4-dione (Intermediate DV)

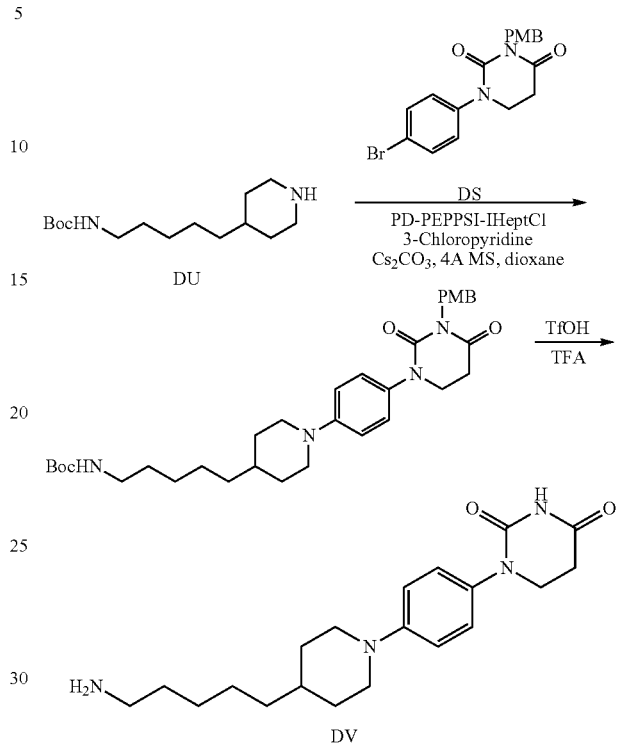

Step 1—Tert-butyl N-[5-[1-[4-[3-[(4-methoxyphenyl)methyl]-2,4-dioxo-hexahydropyrimidin-1-yl]phenyl]-4-piperidyl]pentyl]carbamate A mixture of tert-butyl N-[5-(4-piperidyl)pentyl]carbamate (34.7 mg, 128 umol, Intermediate DU), 1-(4-bromophenyl)-3-[(4-methoxyphenyl)methyl]hexahydropyrimidine-2,4-dione (50.0 mg, 128 umol, Intermediate DS), Cs$_2$CO$_3$ (418 mg, 1.28 mmol), 1,3-bis[2,6-bis(1-propylbutyl)phenyl]-4,5-dichloro-2H-imidazol-1-ium-2-ide;3-chloropyridine;dichloropalladium (12.5 mg, 12.8 umol) and 4A molecular sieves (2.00 mg, 128 umol) in dioxane (1 mL) was degassed and purged with N$_2$ three times. Then the mixture was stirred at 100° C. for 16 hrs under N$_2$ atmosphere. On completion, the reaction mixture was filtered and concentrated in vacuo to give a residue. The residue was purified by prep-HPLC (column: Phenomenex luna C18 150*25 mm*10 um; mobile phase: [water(FA)-ACN]; B %: 43%-73%, 10 min) to give the title compound (50.0 mg, 67% yield) as yellow oil. $^1$H NMR (400 MHz, CDCl$_3$) δ 8.05-8.04 (m, 1H) 7.43 (d, J=8.4 Hz, 2H) 7.12 (d, J=8.8 Hz, 2H) 6.93 (d, J=8.8 Hz, 2H) 6.86-6.78 (m, 2H) 4.95 (s, 2H) 3.78 (s, 3H) 3.72 (t, J=6.4 Hz, 2H) 3.64 (d, J=12.4 Hz, 2H) 3.16-3.06 (m, 2H) 2.85 (t, J=6.8 Hz, 2H) 2.68 (t, J=11.6 Hz, 2H) 1.77 (d, J=10.4 Hz, 2H) 1.53-1.48 (m, 2H) 1.45 (s, 9H) 1.38-1.24 (m, 9H). LC-MS (ESI$^+$) m/z 579.3 (M+H)$^+$.

Step 2—1-[4-[4-(5-Aminopentyl)-1-piperidyl]phenyl]hexahydropyrimidine-2,4-dione To a solution of tert-butyl N-[5-[1-[4-[3-[(4-methoxyphenyl)methyl]-2,4-dioxo-hexahydropyrimidin-1-yl] phenyl]-

4-piperidyl]pentyl]carbamate (50.0 mg, 86.3 umol) in TfOH (0.1 mL) was added TFA (924 mg, 8.10 mmol). The mixture was stirred at 70° C. for 1 hr. On completion, the reaction mixture was filtered and concentrated in vacuo to give the title compound (30.0 mg, 97% yield) as yellow oil. LC-MS (ESI$^+$) m/z 359.1 (M+H)$^+$.

N-isopropylacetamidine (Intermediate DW)

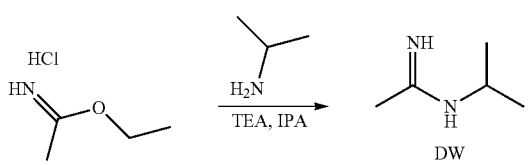

To a solution of ethyl ethanimidate hydrochloride (10.0 g, 80.9 mmol, CAS #2208-07-3) in IPA (60 mL) was added TEA (8.19 g, 80.9 mmol) and propan-2-amine (4.78 g, 80.9 mmol, CAS #4432-77-3). The mixture was stirred at 25° C. for 1 hour. On completion, the reaction mixture was concentrated in vacuo to give the title compound (5.5 g, 67% yield) as a colorless oil.

3-Chloro-4,4-diethoxy-butan-2-one (Intermediate DX)

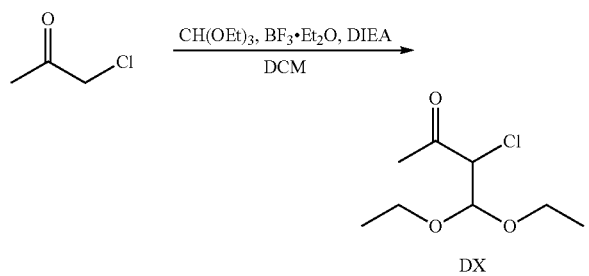

To a stirred solution of diethoxymethoxyethane (16.0 g, 108 mmol, CAS #122-51-0) in DCM (150 mL) was added diethyloxonio(trifluoro)boranuide (32.6 g, 108 mmol, 47% solution) at −30° C. under N$_2$ atmosphere. The reaction mixture was allowed to stir at 25° C. for 1 hr. Then 1-chloropropan-2-one (5.00 g, 54.0 mmol, CAS #78-95-5) was added rapidly at −78° C. followed by DIPEA (20.9 g, 162 mmol). Then the reaction mixture was allowed to stir at −78° C. for 1 hr. The reaction mass was added saturated NaHCO$_3$ (100 mL) and stirred for 15 mins and the layer was separated. The aqueous phase was extracted with DCM (2×100 mL). The combined organic layer was washed with H$_2$SO$_4$:H$_2$O (1:10) ratio followed by water (2×100 mL). The organic layer was dried over anhydrous Na$_2$SO$_4$ and concentrated under reduced pressure to give the title compound (10.0 g, 47% yield) as a red oil.

[4-(3-Isopropyl-2-methyl-imidazol-4-yl)pyrimidin-2-yl] trifluoromethanesulfonate (Intermediate DY)

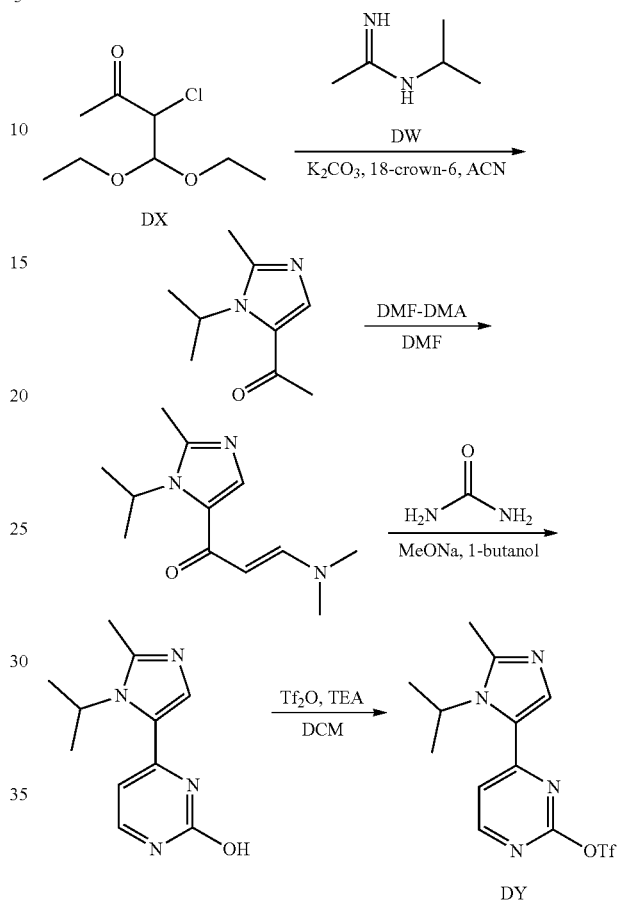

Step 1—1-(3-Isopropyl-2-methyl-imidazol-4-yl)ethanone

A mixture of 3-chloro-4,4-diethoxy-butan-2-one (10.0 g, 51.3 mmol, Intermediate DX), N-isopropylacetamidine (5.15 g, 51.3 mmol, Intermediate DW), K$_2$CO$_3$ (21.3 g, 154 mmol) and 18-CROWN-6 (678 mg, 2.57 mmol) in ACN (100 mL) was degassed and purged with N$_2$ three times. Then the mixture was stirred at 80° C. for 16 hrs under N$_2$ atmosphere. The reaction mixture was partitioned between H$_2$O (100 mL) and EA (2×100 mL). The organic phase was separated, washed with brine (100 mL), dried over anhydrous Na$_2$SO$_4$, filtered and concentrated in vacuo to give a residue. The residue was purified by column chromatography (SiO$_2$, DCM/IPA=100/1 to 10/1) to give the title compound (5.00 g, 58% yield) as a red oil. $^1$H NMR (400 MHz, CDCl$_3$) δ 7.72 (s, 1H), 5.43-5.22 (m, 1H), 2.54 (s, 3H), 2.46 (s, 3H), 1.52 (s, 3H), 1.50 (s, 3H). LCMS (ESI$^+$) m/z 167.1 (M+H)$^+$.

Step 2—(E)-3-(Dimethylamino)-1-(3-isopropyl-2-methyl-imidazol-4-yl)prop-2-en-1-one To a solution of 1-(3-isopropyl-2-methyl-imidazol-4-yl)ethanone (5.00 g, 30.0 mmol) in DMF (30 mL) was added DMF-DMA (3.94 g, 33.0 mmol, CAS #4637-24-5). The mixture was stirred at 130° C. for 16 hrs. The reaction mixture was concentrated in vacuo to remove solvent. The residue was purified by column chromatography (SiO₂, DCM/IPA=100/1 to 10/1) to give the title compound (3.00 g, 45% yield) as a red solid. $^1$H NMR (400 MHz, CDCl₃) δ 7.66 (d, J=12.4 Hz, 1H), 7.48 (s, 1H), 5.49 (d, J=12.4 Hz, 1H), 5.47-5.40 (m, 1H), 3.14-2.87 (m, 6H), 2.60 (s, 3H), 1.56 (s, 3H), 1.54 (s, 3H). LCMS (ESI⁺) m/z 222.2 (M+H)⁺.

Step 3—4-(3-Isopropyl-2-methyl-imidazol-4-yl) pyrimidin-2-ol

To a solution of (E)-3-(dimethylamino)-1-(3-isopropyl-2-methyl-imidazol-4-yl)prop-2-en-1-one (2.00 g, 9.04 mmol), CH₃ONa (1.95 g, 36.1 mmol) and urea (1.36 g, 22.5 mmol, CAS #506-89-8) in 1-butanol (20 mL) was stirred at 140° C. for 16 hrs. On completion, the reaction mixture was concentrated in vacuo to remove the solvent. The residue was purified by prep-HPLC (column: Phenomenex C18 250*50 mm*10 um; mobile phase: [water (ammonia hydroxide v/v)-ACN]; B %: 0%-20%, 8 min) to give the title compound (1.10 g, 55% yield) as a white solid. LCMS (ESI⁺) m/z 219.0 (M+H)⁺.

Step 4—[4-(3-Isopropyl-2-methyl-imidazol-4-yl) pyrimidin-2-yl] trifluoromethanesulfonate To a solution of 4-(3-isopropyl-2-methyl-imidazol-4-yl) pyrimidin-2-ol (550 mg, 2.52 mmol) in DCM (5 mL) was added TEA (509 mg, 5.04 mmol) and Tf₂O (746 mg, 2.65 mmol). The mixture was stirred at 0° C. for 1 hr. On completion, the reaction mixture was partitioned between H₂O (50 mL) and DCM (50 mL). The organic phase was separated, washed with brine (50 mL), dried over anhydrous Na₂SO₄, filtered and concentrated in vacuo to give a residue to give the title compound (780 mg, 88% yield) as a red solid. LCMS (ESI⁺) m/z 350.9 (M+H)⁺.

4-[[4-(3-Isopropyl-2-methyl-imidazol-4-yl)pyrimidin-2-yl]amino]-3-methyl-benzenesulfonyl chloride (Intermediate DZ)

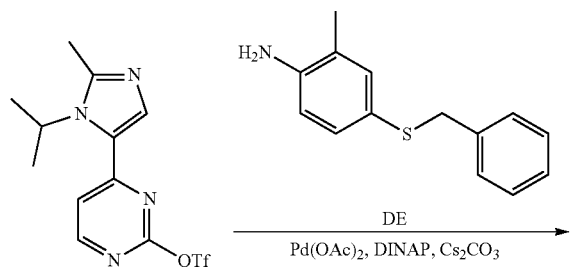

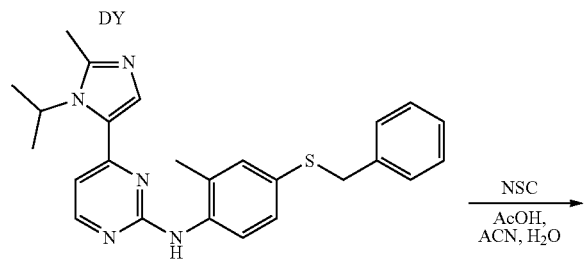

-continued

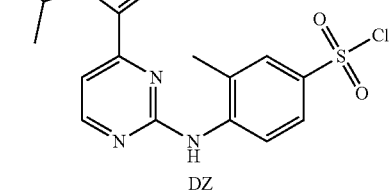

Step 1—N-(4-Benzylsulfanyl-2-methyl-phenyl)-4-(3-isopropyl-2-methyl-imidazol-4-yl) pyrimidin-2-amine A mixture of [4-(3-isopropyl-2-methyl-imidazol-4-yl)pyrimidin-2-yl]trifluoromethanesulfonate (780 mg, 2.23 mmol, Intermediate DY), 4-benzylsulfanyl-2-methyl-aniline (459 mg, 2.00 mmol, Intermediate DE), Pd(OAc)₂ (49.9 mg, 222 umol), BINAP (138 mg, 222 umol) and Cs₂CO₃ (2.18 g, 6.68 mmol) in toluene (10 mL) was degassed and purged with N₂ three times. Then the mixture was stirred at 100° C. for 16 hrs under N₂ atmosphere. The reaction mixture was filtered and concentrated in vacuo to give a residue. The residue was purified by prep-HPLC (column: Phenomenex Luna C18 200*40 mm*10 um; mobile phase: [water(FA)-ACN]; B %: 25%-55%, 10 min) to give the title compound (270 mg, 28% yield) as a yellow solid. LCMS (ESI⁺) m/z 430.4 (M+H)⁺.

Step 2—4-[[4-(3-Isopropyl-2-methyl-imidazol-4-yl) pyrimidin-2-yl]amino]-3-methyl-benzenesulfonyl chloride To a solution of N-(4-benzylsulfanyl-2-methyl-phenyl)-4-(3-isopropyl-2-methyl-imidazol-4-yl) pyrimidin-2-amine (30.0 mg, 69.8 umol) in a mixture solution of ACN (1 mL), AcOH (0.1 mL) and H₂O (0.02 mL) was added NCS (23.3 mg, 174 umol). The mixture was stirred under dark at 25° C. for 1 hrs. The mixture was diluted with water (15 mL), and extracted with EA (3×10 mL). The combined organic layer was washed with brine (30 mL), dried with anhydrous Na₂SO₄, filtered and concentrated in vacuo to give the title compound (28.0 mg, 98% yield) as a yellow solid. LCMS (ESI⁺) m/z 405.7 (M+H)⁺.

N-(4-Benzylsulfanyl-2-methyl-phenyl)-4-chloro-5-(trifluoromethyl)pyrimidin-2-amine (Intermediate EA)

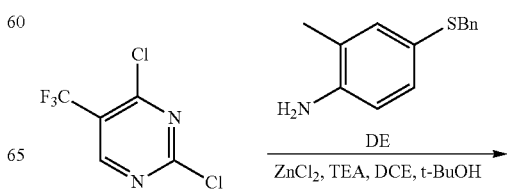

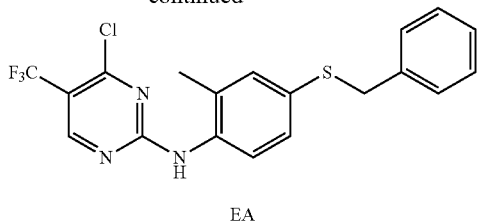

EA

To a solution of 2,4-dichloro-5-(trifluoromethyl)pyrimidine (500 mg, 2.30 mmol, CAS #3932-97-6) in mixture solvent of DCE (6 mL) and t-BuOH (6 mL) was added ZnCl₂ (1 M, 2.77 mL) at 0° C. After 1 hour, a solution of 4-benzylsulfanyl-2-methyl-aniline (528 mg, 2.30 mmol, Intermediate DE) and TEA (256 mg, 2.5 mmol) in mixture solvent of DCE (3 mL) and t-BuOH (3 mL) was added dropwise into the above solution. The mixture was then stirred at 25° C. for 16 hrs. On completion, the mixture was diluted with H₂O (20 mL) and extracted with EA (20 mL×3). The combined organic layers were washed with saturated NaCl (10 mL), dried over anhydrous Na₂SO₄, filtered and concentrated in vacuo to give a residue. The residue was purified by column chromatography (SiO₂, PE:EA=50:1 to 20:1) to give the title compound (600 mg, 63% yield) as a yellow solid. ¹H NMR (400 MHz, DMSO-d₆) δ 10.04 (s, 1H), 8.66-8.60 (m, 1H), 7.40-7.35 (m, 2H), 7.31-7.28 (m, 2H), 7.28-7.21 (m, 3H), 7.20-7.16 (m, 1H), 4.24 (s, 2H), 2.15 (s, 3H). LC-MS (ESI⁺) m/z 410.0 (M+H)⁺.

(1S,3R)-3-(5-amino-1-(tert-butyl)-1H-pyrazol-3-yl)cyclopentyl isopropylcarbamate (Intermediate ED)

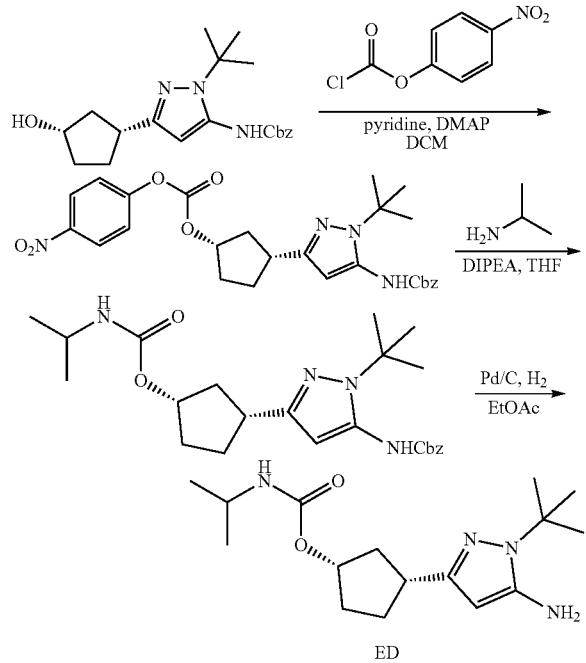

Step 1—Benzyl (1-(tert-butyl)-3-((1S,3S)-3-(((4-nitrophenoxy)carbonyl)oxy)cyclopentyl)-1H-pyrazol-5-yl)carbamate To a mixture of benzyl (1-(tert-butyl)-3-((1R,3S)-3-hydroxycyclopentyl)-1H-pyrazol-5-yl)carbamate (1.00 g, 2.80 mmol, CAS #2460255-81-4) and 4-nitrophenyl carbonochloridate (845 mg, 4.20 mmol, CAS #7693-46-1) in DCM (10 mL) was added DMAP (34.1 mg, 279 umol) and pyridine (663 mg, 8.39 mmol) at 20° C. under N₂ atmosphere. Then the mixture was stirred at 20° C. for 10 h under nitrogen atmosphere. On completion, the reaction mixture was poured into ice water (20 mL) and extracted with DCM (30 mL×2). The combined organic phase is washed with brine (20 mL×2), then dried over Na₂SO₄. The mixture was filtered and the filtrate was concentrated to give a residue. The residue was purified by column chromatography on silica gel (eluted with petroleum ether:ethyl acetate=10:1 to 3:1) to give the title compound (1.4 g, 96% yield) as colorless oil. ¹H NMR (400 MHz, CDCl₃) δ=8.28 (d, J=9.2 Hz, 2H), 7.48-7.31 (m, 6H), 6.31-6.05 (m, 2H), 5.30-5.23 (m, 1H), 5.21 (s, 2H), 3.23-3.09 (m, 1H), 2.62 (ddd, J=7.2, 8.0, 14.8 Hz, 1H), 2.18-2.08 (m, 1H), 2.05-1.95 (m, 3H), 1.94-1.87 (m, 1H), 1.59 (s, 10H).

Step 2—Benzyl (1-(tert-butyl)-3-((1R,3S)-3-((isopropylcarbamoyl)oxy)cyclopentyl)-1H-pyrazol-5-yl)carbamate To a solution of [(1S,3R)-3-[5-(benzyloxycarbonylamino)-1-tert-butyl-pyrazol-3-yl]cyclopentyl] (4-nitrophenyl) carbonate (600 mg, 1.15 mmol) and propan-2-amine (135 mg, 2.30 mmol) in THF (6 mL) was added DIEA (742 mg, 5.74 mmol). The mixture was stirred at 20° C. for 4 h. On completion, the reaction mixture was poured into ice water (6 mL) and extracted with DCM (6 mL×2). The combined organic phase was washed with brine (6 mL×2), and dried over Na₂SO₄. Then the mixture was filtered and filtrate was concentrated to give a residue. The residue was purified by column chromatography on silica gel (eluted with petroleum ether:ethyl acetate=10:1 to 3:1) to give the title compound (350 mg, 69% yield) as colorless oil. LC-MS (ESI⁺) m/z 443.4 (M+H)⁺.

Step 3—(1S,3R)-3-(5-amino-1-(tert-butyl)-1H-pyrazol-3-yl)cyclopentyl isopropylcarbamate To a solution of benzyl N-[2-tert-butyl-5-[(1R,3S)-3-(isopropylcarbamoyloxy)cyclopentyl]pyrazol-3-yl]carbamate (350 mg, 790 umol) in EtOH (20 mL) was added Pd/C (400 mg, 377 umol, 10 wt %). The mixture was stirred at 20° C. for 12 h under H₂ atmosphere (15 psi). On completion, the reaction mixture was filtered and the filter cake was washed with EtOH (10 mL). The mixture was filtered and the filtrate and concentrated to give the title compound (260 mg) as yellow oil. LC-MS (ESI⁺) m/z 309.2 (M+H)⁺.

4-((5-amino-1-(3-methylthiophene-2-carbonyl)-1H-1,2,4-triazol-3-yl)amino)-N-(2-(prop-2-yn-1-yloxy)ethyl)benzenesulfonamide (Intermediate EE)

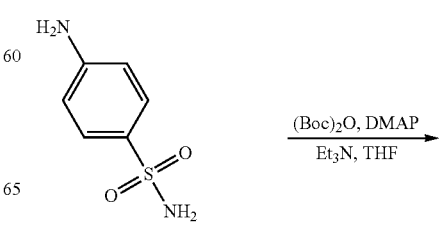

-continued

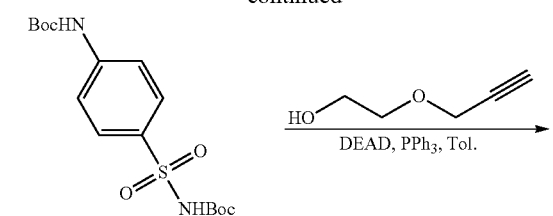

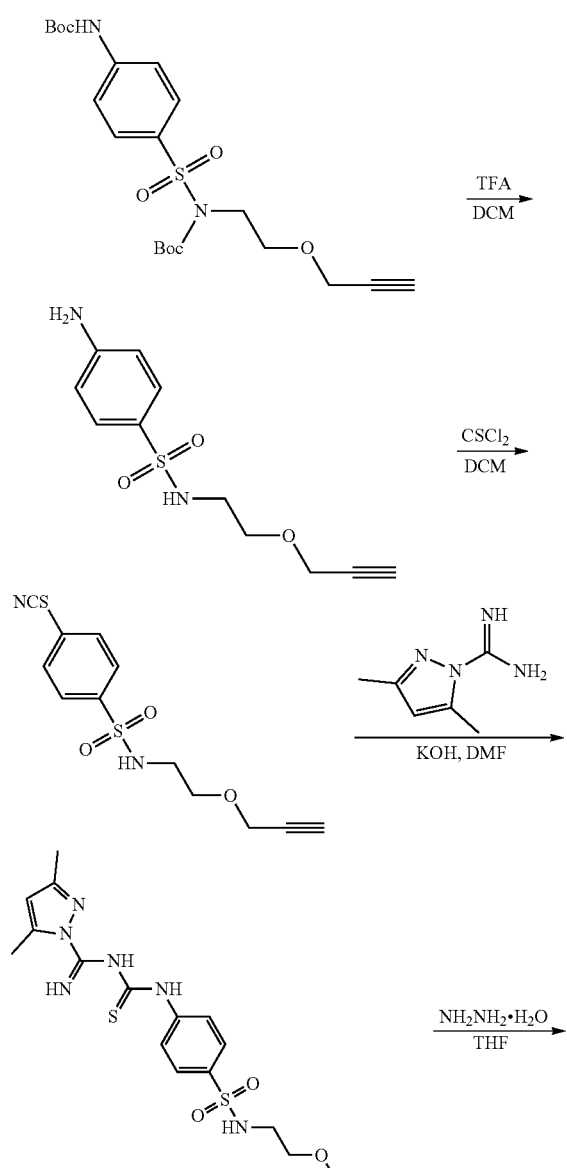

-continued

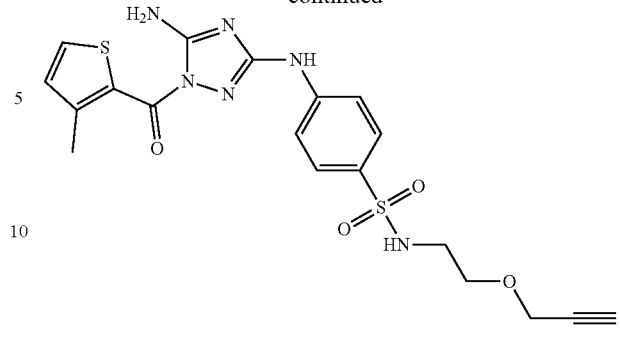

EE

Step 1—Tert-butyl N-[4-(tert-butoxycarbonylamino)phenyl]sulfonylcarbamate

A solution of 4-aminobenzenesulfonamide (50 g, 290 mmol, 50 mL), (Boc)$_2$O (126 g, 580 mmol, 133 mL), DMAP (3.55 g, 29.0 mmol), and Et$_3$N (88.1 g, 871 mmol, 121 mL) in THF (200 mL) was stirred at 20° C. for 8 h. On completion, the reaction mixture was quenched by addition H$_2$O (300 mL) at 20° C., and extracted with EtOAc (200 mL×3). The combined organic layers were washed with brine (200 mL×2), dried over Na$_2$SO$_4$, filtered and concentrated under reduced pressure to give a residue. The residue was purified by column chromatography (SiO$_2$, Dichloromethane:Methanol=1/0 to 50/1) to give the title compound (20 g, 19% yield) as white solid. $^1$H NMR (400 MHz, CDCl$_3$) δ=7.99-7.88 (m, 2H), 7.57-7.46 (m, 2H), 3.50 (s, 1H), 1.53 (s, 9H), 1.41-1.38 (m, 9H)

Step 2—Tert-butyl (4-((tert-butoxycarbonyl)amino)phenyl)sulfonyl(2-(prop-2-yn-1-yloxy)ethyl)carbamate To a solution of tert-butyl N-[4-(tert-butoxycarbonylamino)phenyl]sulfonylcarbamate (10 g, 26.8 mmol), 2-prop-2-ynoxyethanol (3.49 g, 34.9 mmol, CAS #3973-18-0) and PPh$_3$ (9.16 g, 34.91 mmol) in toluene (150 mL) was added a solution of DIAD (7.06 g, 34.9 mmol, 6.79 mL) in toluene (50 mL) dropwise slowly at 0° C. under nitrogen flow. Then the reaction was stirred at 20° C. for 10 h under nitrogen atmosphere. On completion, the reaction was poured into ice water (200 mL) and extracted with ethyl acetate (150 mL×2). The combined organic phase is washed with brine (100 mL×2), and dried over sodium sulfate. Then the mixture was filtered and the filtrate was concentrated to give a residue. The residue was purified by column chromatography on silica gel (eluted with petroleum ether:ethyl acetate=100:1 to 100:15) to give the title compound (17 g) as a yellow oil. LC-MS (ESI$^+$) m/z 448.1 (M−H)$^−$.

Step 3—Tert-butyl (4-((tert-butoxycarbonyl)amino)phenyl)sulfonyl(2-(prop-2-yn-1-yloxy)ethyl) carbamate To a solution of tert-butyl N-[4-(tert-butoxycarbonylamino)phenyl]sulfonyl-N-(2-prop-2-ynoxyethyl)carbamate (17 g, 37.4 mmol) in DCM (300 mL) was added TFA (52.3 g, 459 mmol) at 20° C. under nitrogen flow. Then the reaction was stirred at 20° C. for 10 h under nitrogen atmosphere. On completion, the reaction was concentrated

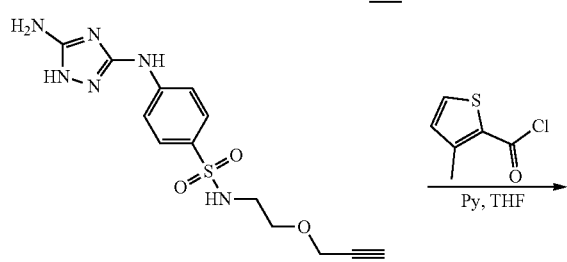

to give a residue. The crude product was purified by reversed-phase HPLC (0.1% NH3·H2O condition) to give the title compound (7 g, 74% yield) as a yellow oil. $^1$H NMR (400 MHz, CDCl$_3$) δ=7.63 (d, J=8.8 Hz, 2H), 6.68 (d, J=8.6 Hz, 2H), 6.40 (br s, 3H), 4.11-3.99 (m, 2H), 3.56 (t, J=5.2 Hz, 2H), 3.19-3.09 (m, 2H), 2.43 (t, J=2.4 Hz, 1H).

Step 4—N-(2-(prop-2-yn-1-yloxy)ethyl)-4-thiocyanatobenzenesulfonamide

To a solution of thiocarbonyl dichloride (3.16 g, 27.5 mmol) in DCM (70 mL) was added a solution of 4-amino-N-(2-prop-2-ynoxyethyl)benzenesulfonamide (7 g, 27.53 mmol) in DCM (70 mL) dropwise slowly at 0° C. Then the reaction was stirred at 20° C. for 10 h under nitrogen atmosphere. On completion, the reaction was poured into water (150 mL) and extracted with dichloromethane (100 mL×2). The combined organic phase is washed with brine (3 mL×2), and dried over sodium sulfate. The mixture was then filtered and the filtrate and concentrated to give the title compound (7 g, 86% yield) as brown solid. $^1$H NMR (400 MHz, CDCl$_3$) δ=7.86 (br d, J=7.8 Hz, 2H), 7.32 (br d, J=8.4 Hz, 2H), 5.31-5.16 (m, 1H), 4.08 (s, 2H), 3.56 (brt, J=4.8 Hz, 2H), 3.18 (br d, J=4.8 Hz, 2H), 2.49-2.41 (m, 1H).

Step 5—3,5-Dimethyl-N-((4-(N-(2-(prop-2-yn-1-yloxy)ethyl)sulfamoyl)phenyl)carbamothioyl)-1H-pyrazole-1-carboximidamide To a solution of 3,5-dimethylpyrazole-1-carboxamidine; nitric acid (9.50 g, 47.2 mmol, CAS #22906-75-8) in DMF (140 mL) was added KOH (2.65 g, 47.24 mmol) and at 0° C. under nitrogen flow. To this, a solution of 3,5-dimethyl-1H-pyrazole-1-carboximidamide (7 g, 23.62 mmol) in DMF (70 mL) was added dropwise slowly at 0° C. Then the reaction was stirred at 60° C. for 10 h under nitrogen atmosphere. On completion, the reaction was poured into saturated ammonium chloride aqueous solution (300 mL) and extracted with ethyl acetate (200 mL×2). The combined organic phase is washed with brine (200 mL×2), and dried over sodium sulfate. Then the mixture was filtered and the filtrate was concentrated to give a residue. The residue was purified by column chromatography on silica gel (eluted with petroleum ether:ethyl acetate=100:1 to 100:7) to give the title compound (2.7 g, 26% yield) as yellow oil. $^1$H NMR (400 MHz, CDCl$_3$) δ=8.02 (s, 4H), 7.82 (d, J=8.4 Hz, 2H), 5.96 (d, J=10.0 Hz, 2H), 4.09 (d, J=2.4 Hz, 2H), 3.57 (t, J=5.2 Hz, 2H), 3.17 (t, J=5.2 Hz, 2H), 2.44 (t, J=2.4 Hz, 1H), 2.23 (d, J=6.4 Hz, 6H)

Step 6—4-((5-Amino-1H-1,2,4-triazol-3-yl)amino)-N-(2-(prop-2-yn-1-yloxy)ethyl)benzene sulfonamide To a solution of 3,5-dimethyl-N-((4-(N-(2-(prop-2-yn-1-yloxy)ethyl)sulfamoyl)phenyl)carbamothioyl)-1H-pyrazole-1-carboximidamide (1 g, 2.30 mmol) in THF (20 mL) was added hydrazine;hydrate (1.29 g, 25.7 mmol) at 20° C. under nitrogen flow. Then the reaction was stirred at 55° C. for 3 h under nitrogen atmosphere. On completion, the reaction was concentrated to give a residue. The solid was reflux in a solvent of EtOAc:PE=1:3 (50 mL) for 5 min. Then the mixture was filtered and the filter cake was washed with EtOAc:PE=1:3 (30 mL) and dried in vacuo to give the title compound (320 mg, 41.34% yield) as yellow solid. $^1$H NMR (400 MHz, DMSO-d$_6$) δ=9.29 (br s, 1H), 9.15-8.84 (m, 1H), 7.71-7.47 (m, 4H), 5.98 (s, 2H), 5.60 (br s, 1H), 4.07 (d, J=2.4 Hz, 2H), 3.43-3.38 (m, 2H), 2.90-2.79 (m, 2H), 1.74 (s, 1H).

Step 7—4-((5-Amino-1-(3-methylthiophene-2-carbonyl)-1H-1,2,4-triazol-3-yl)amino)-N-(2-(prop-2-yn-1-yloxy)ethyl)benzenesulfonamide To a solution of 4-((5-amino-1H-1,2,4-triazol-3-yl)amino)-N-(2-(prop-2-yn-1-yloxy)ethyl) benzenesulfonamide (280 mg, 832 umol) in pyridine (3 mL) and THF (3 mL) was added 3-methylthiophene-2-carbonyl chloride (267 mg, 1.66 mmol, CAS #61341-26-2) at 0° C. under nitrogen flow. Then the reaction was stirred at 20° C. for 10 h under nitrogen atmosphere. On completion, the reaction was poured into saturated ammonium chloride aqueous solution (10 mL) and extracted with ethyl acetate (15 mL×2). The combined organic phase is washed with brine (2×20 mL), and dried over sodium sulfate. Then the mixture was filtered and the filtrate was concentrated to give a residue. The residue was purified by prep-HPLC column: Phenomenex Luna C18 150*25 mm*10 um; mobile phase: [water (0.225% FA)-ACN]; B %: 35%-65%, 10 min) to give the title compound (120 mg, 31% yield) as white solid. $^1$H NMR (400 MHz, DMSO-d$_6$) δ=9.92 (s, 1H), 8.05 (d, J=5.2 Hz, 1H), 7.91-7.78 (m, 4H), 7.77-7.70 (m, 2H), 7.48 (t, J=6.4 Hz, 1H), 7.16 (d, J=5.2 Hz, 1H), 4.08 (d, J=2.4 Hz, 2H), 3.44-3.40 (m, 2H), 2.89 (q, J=6.0 Hz, 2H), 2.63 (s, 3H), 2.57-2.55 (m, 1H).

4-[(8-Cyclopentyl-7-oxo-pyrido[2,3-d]pyrimidin-2-yl)amino]-3-methyl-benzenesulfonyl chloride (Intermediate EF)

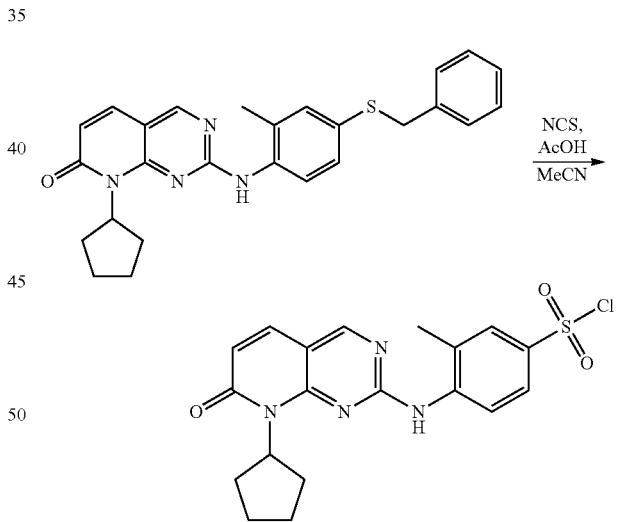

To a solution of 2-(4-benzylsulfanyl-2-methyl-anilino)-8-cyclopentyl-pyrido[2,3-d]pyrimidin-7-one (1.00 g, 2.26 mmol, synthesized via Steps 1-2 of Intermediate CW) in ACN (10 mL), AcOH (1 mL), H$_2$O (0.5 mL) was added NCS (754 mg, 5.65 mmol) in the dark. The mixture was stirred at 25° C. for 0.5 hr in the dark. On completion, the reaction mixture was diluted with H$_2$O (20 mL) and extracted with EA (3×50 mL). The combined organic layers were washed with brine (2×60 mL), dried over with anhydrous Na$_2$SO$_4$, filtered and concentrated in vacuo to give a residue. The residue was purified by prep-TLC (SiO₂, PE:EA=0:1, P1, Rf=0.45) to afford the title compound (900 mg, 95% yield) as a yellow solid. ¹H NMR (400 MHz, DMSO-d₆) δ 9.81 (s, 1H), 8.82 (s, 1H), 7.85 (d, J=9.6 Hz, 1H), 7.60 (s, 1H), 7.54-7.51 (m, 1H), 7.47-7.44 (m, 1H), 7.41-7.35 (m, 1H), 7.32-7.29 (m, 1H), 6.43 (d, J=9.6 Hz, 1H), 5.77-5.63 (m, 1H), 2.31 (s, 3H), 2.16 (d, J=4.8 Hz, 2H), 1.72 (s, 3H), 1.49 (s, 1H). LC-MS (ESI⁺) m/z 419.0 (M+H)⁺.

3-[3-Methyl-4-[4-(methylamino)-1-piperidyl]-2-oxo-benzimidazol-1-yl]piperidine-2,6-dione (Intermediate EG)

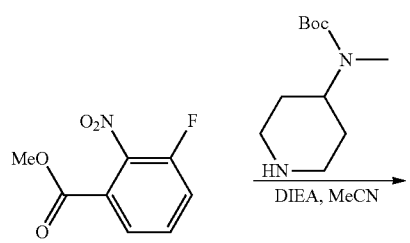

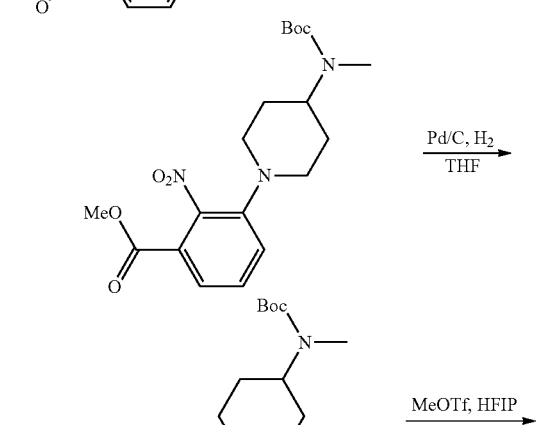

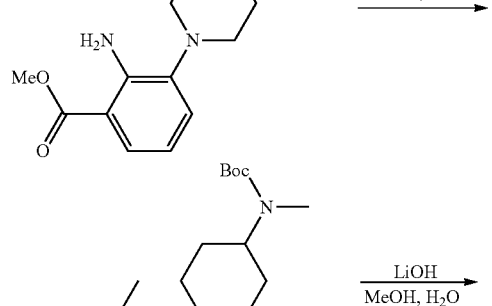

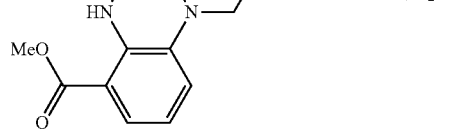

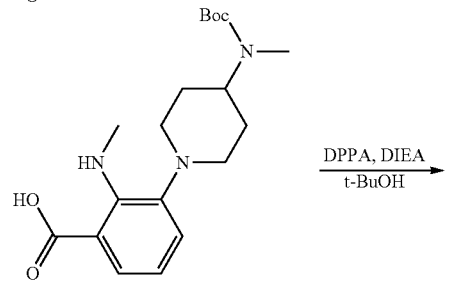

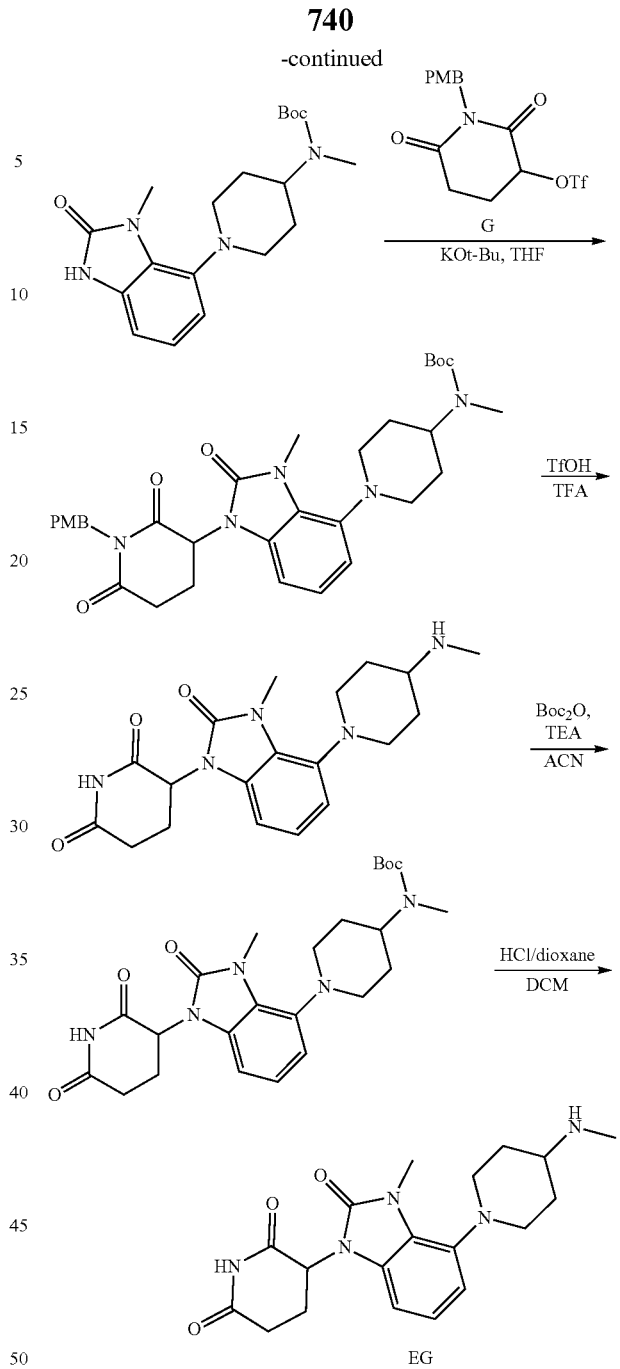

Step 1—Methyl 3-[4-[tert-butoxycarbonyl(methyl)amino]-1-piperidyl]-2-nitro-benzoate To a solution of methyl 3-fluoro-2-nitro-benzoate (10.0 g, 50.2 mmol, CAS #1214353-57-7), tert-butyl N-methyl-N-(4-piperidyl)carbamate (13.9 g, 65.2 mmol, CAS #108612-54-0) in ACN (250 mL) was added DIEA (19.4 g, 150 mmol). The mixture was stirred at 50° C. for 16 hrs. On completion, the mixture was concentrated in vacuo. The mixture was triturated with H₂O (200 mL), filtered and the filtrate was dried in vacuo to give the title compound (19.6 g, 99% yield) as yellow solid. ¹H NMR (400 MHz, DMSO-d₆) δ 7.85 (dd, J=1.2, 8.0 Hz, 1H), 7.79-7.75 (m, 1H), 7.73-7.66 (m, 1H), 3.84 (s, 3H), 4.04-3.68 (m, 1H), 3.11-

3.01 (m, 2H), 2.95-2.82 (m, 2H), 2.70 (s, 3H), 1.79-1.55 (m, 4H), 1.41 (s, 9H), LC-MS (ESI+) m/z 416.1 (M+Na)+.

Step 2—Methyl 2-amino-3-[4-[tert-butoxycarbonyl (methyl)amino]-1-piperidyl]benzoate To a solution of methyl 3-[4-[tert-butoxycarbonyl (methyl)amino]-1-piperidyl]-2-nitro-benzoate (18.6 g, 47.2 mmol) in THF (190 mL) was added Pd/C (2.00 g, 10% wt). The mixture was stirred at 25° C. for 16 hrs under $H_2$ (15 Psi). On completion, the mixture was filtered and concentrated in vacuo to give the title compound (17.1 g, 99% yield) as yellow solid. $^1$H NMR (400 MHz, $CDCl_3$) δ 7.61-7.51 (m, 1H), 7.10-7.01 (m, 1H), 6.52 (t, J=8.0 Hz, 1H), 6.25-6.04 (m, 2H), 4.20-3.88 (m, 1H), 3.79 (s, 3H), 3.15-2.99 (m, 2H), 2.74 (s, 3H), 2.68-2.51 (m, 2H), 1.87-1.66 (m, 4H), 1.41 (s, 9H).

Step 3—Methyl 3-[4-[tert-butoxycarbonyl(methyl) amino]-1-piperidyl]-2-(methylamino)benzoate To a solution of methyl 2-amino-3-[4-[tert-butoxycarbonyl(methyl)amino]-1-piperidyl]benzoate (12.1 g, 33.3 mmol) in 1,1,1,3,3,3-hexafluoropropan-2-ol (45.0 mL) was added methyltrifluoromethane sulfonate (8.21 g, 50.0 mmol). The mixture was stirred at 25° C. for 1 hr. On completion, the mixture was diluted with $H_2O$ (300 mL) and extracted with EA (3×100 mL). The organic layers were washed with brine (3×100 mL), dried over anhydrous $Na_2SO_4$, filtered and concentrated in vacuo to give the title compound (12.5 g, 99% yield) as yellow oil, $^1$H NMR (400 MHz, $CDCl_3$) δ 7.59 (dd, J=1.2, 8.0 Hz, 1H), 7.20-7.12 (m, 1H), 6.72 (t, J=8.0 Hz, 1H), 4.23-3.95 (m, 1H), 3.89 (s, 3H), 3.35-3.23 (m, 2H), 3.01 (s, 3H), 2.82 (s, 3H), 2.70-2.59 (m, 2H), 1.93-1.85 (m, 2H), 1.78-1.71 (m, 2H), 1.50 (s, 9H).

Step 4—3-[4-[Tert-butoxycarbonyl(methyl)amino]-1-piperidyl]-2-(methylamino)benzoic acid To a solution of methyl 3-[4-[tert-butoxycarbonyl (methyl) amino]-1-piperidyl]-2-(methylamino) benzoate (12.5 g, 33.1 mmol) in MeOH (120 mL) and $H_2O$ (20 mL) was added LiOH·$H_2O$ (4.17 g, 99.3 mmol). The mixture was stirred at 60° C. for 12 hrs. On completion, the mixture was concentrated in vacuo. The mixture was diluted with $H_2O$ (150 mL), and extracted with EA (3×50 mL). The aqueous phase was acidified with 1N HCl solution until the pH=5. The mixture was then extracted with EA (3×80 mL), the organic layers were washed with brine (3×80 mL), dried over anhydrous $Na_2SO_4$, filtered and concentrated in vacuo to give the title compound (11.0 g, 91% yield) as yellow solid. $^1$H NMR (400 MHz, $CDCl_3$) δ 7.99-7.87 (m, 1H), 7.41-7.35 (m, 1H), 7.19-7.08 (m, 1H), 4.16-3.81 (m, 1H), 3.15-3.08 (m, 2H), 2.95-2.88 (m, 3H), 2.88-2.79 (m, 5H), 2.00-1.85 (m, 2H), 1.83-1.74 (m, 2H), 1.50 (s, 9H).

Step 5—Tert-butyl N-methyl-N-[1-(3-methyl-2-oxo-1H-benzimidazol-4-yl)-4-piperidyl]carbamate To a solution of 3-[4-[tert-butoxycarbonyl(methyl) amino]-1-piperidyl]-2-(methylamino)benzoic acid (12.5 g, 34.3 mmol) and DIEA (13.3 g, 103 mmol) in t-BuOH (130 mL) was added DPPA (11.3 g, 41.2 mmol) at 0° C. The mixture was stirred at 90° C. for 16 hrs. On completion, the mixture was concentrated in vacuo. The mixture was diluted with $H_2O$ (200 mL), and extracted with EA (3×80 mL). The organic layers were washed with brine (3×50 mL), dried over anhydrous $Na_2SO_4$, filtered and concentrated in vacuo. The mixture was purified by reverse phase: (0.1% $NH_3·H_2O$) to give the title compound (5.4 g, 43% yield) as yellow solid. $^1$H NMR (400 MHz, DMSO-$d_6$) δ 10.80 (s, 1H), 6.95-6.87 (m, 1H), 6.87-6.80 (m, 1H), 6.76-6.70 (m, 1H), 4.01-3.71 (m, 1H), 3.58 (s, 3H), 3.20-3.06 (m, 2H), 2.81-2.69 (m, 5H), 1.96-1.79 (m, 2H), 1.72-1.56 (m, 2H), 1.42 (s, 9H), LC-MS (ESI+) m/z 361.2 (M+H)+.

Step 6—Tert-butyl N-[1-[1-[1-[(4-methoxyphenyl) methyl]-2,6-dioxo-3-piperidyl]-3-methyl-2-oxo-benzimidazol-4-yl]-4-piperidyl]-Nmethyl-carbamate To a solution of tert-butyl N-methyl-N-[1-(3-methyl-2-oxo-1H-benzimidazol-4-yl)-4-piperidyl] carbamate (5.40 g, 14.9 mmol) in THF (60 mL) was added t-BuOK (3.03 g, 26.9 mmol) at −10° C. The mixture was stirred at −10° C. for 0.5 hr. Then a solution of [1-[(4-methoxyphenyl) methyl]-2,6-dioxo-3-piperidyl] trifluoromethanesulfonate (10.2 g, 26.9 mmol, Intermediate G) in THF (50 mL) was added to the above solution. The mixture was stirred at 25° C. for 16 hrs. On completion, the mixture was quenched with saturated $NH_4Cl$ solution (80 mL) and concentrated in vacuo to remove THF. The mixture was then extracted with EA (3×50 mL), and the organic layers were washed with brine (2×50 mL) dried over anhydrous $Na_2SO_4$, filtered and concentrated in vacuo. The mixture was purified by reverse phase (0.1% FA) to give the title compound (6.2 g, 69% yield) as yellow solid. $^1$H NMR (400 MHz, DMSO-$d_6$) δ 7.25-7.18 (m, 2H), 6.97-6.90 (m, 2H), 6.90-6.80 (m, 3H), 5.57-5.45 (m, 1H), 4.89-4.74 (m, 2H), 4.07-3.80 (m, 1H), 3.73 (s, 3H), 3.65 (s, 3H), 3.20-3.12 (m, 2H), 3.10-2.98 (m, 1H), 2.88-2.77 (m, 3H), 2.75 (s, 3H), 2.74-2.68 (m, 1H), 2.09-2.00 (m, 1H), 1.98-1.84 (m, 2H), 1.71-1.60 (m, 2H), 1.43 (s, 9H), LC-MS (ESI+) m/z 592.4 (M+H)+.

Step 7—3-[3-Methyl-4-[4-(methylamino)-1-piperidyl]-2-oxo-benzimidazol-1-yl]piperidine-2,6-dione A solution of tert-butyl N-[1-[1-[1-[(4-methoxyphenyl) methyl]-2,6-dioxo-3-piperidyl]-3-methyl-2-oxo-benzimidazol-4-yl]-4-piperidyl]-N-methyl-carbamate (2.70 g, 4.56 mmol) in TFA (30 mL) and TfOH (3.8 mL) was stirred at 60° C. for 16 hrs. On completion, the mixture was concentrated in vacuo. Then residue was adjusted to pH=3 with saturated $NaHCO_3$ solution. The mixture was purified by reverse phase (0.1% FA) to give the title compound (1.6 g, 94% yield) as blue solid. $^1$H NMR (400 MHz, DMSO-$d_6$) δ 11.09 (s, 1H), 7.04-6.97 (m, 1H), 6.96-6.89 (m, 2H), 5.41-5.33 (m, 1H), 3.64 (s, 3H), 3.23-3.17 (m, 2H), 3.15-2.98 (m, 2H), 2.95-2.85 (m, 1H), 2.82-2.69 (m, 3H), 2.68-2.63 (m, 1H), 2.61 (s, 3H), 2.14-2.05 (m, 2H), 2.04-1.95 (m, 1H), 1.83-1.66 (m, 2H).

Step 8—Tert-butyl N-[1-[1-(2,6-dioxo-3-piperidyl)-3-methyl-2-oxo-benzimidazol-4-yl]-4-piperidyl]-N-methyl-carbamate To a solution of 3-[3-methyl-4-[4-(methylamino)-1-piperidyl]-2-oxo-benzimidazol-1-yl]piperidine-2,6-dione (1.5 g, 4.04 mmol), TEA (817 mg, 8.08 mmol) in ACN (15.0 mL) was added $(Boc)_2O$ (1.32 g, 6.06 mmol). The mixture was stirred at 25° C. for 1 hr. On completion, the mixture was concentrated in vacuo. The mixture was purified by silica gel column (PE:EA=1:1) to give the title compound (700 mg, 36% yield) as yellow solid. $^1$H NMR (400 MHz, DMSO-$d_6$)

δ 11.08 (s, 1H), 7.01-6.91 (m, 2H), 6.90-6.83 (m, 1H), 5.45-5.27 (m, 1H), 3.97-3.76 (m, 1H), 3.64 (s, 3H), 3.20-3.10 (m, 2H), 2.95-2.83 (m, 1H), 2.82-2.76 (m, 2H), 2.74 (s, 3H), 2.73-2.64 (m, 1H), 2.64-2.56 (m, 1H), 2.04-1.98 (m, 1H), 1.95-1.83 (m, 2H), 1.70-1.58 (m, 2H), 1.41 (s, 9H), LC-MS (ESI+) m/z 472.3 (M+H)+.

Step 9—3-[3-Methyl-4-[4-(methylamino)-1-piperidyl]-2-oxo-benzimidazol-1-yl]piperidine-2,6-dione To a solution of tert-butyl N-[1-[1-(2,6-dioxo-3-piperidyl)-3-methyl-2-oxo-benzimidazol-4-yl]-4-piperidyl]-N-methylcarbamate (500 mg, 1.06 mmol) in DCM (10.0 mL) was added HCl/dioxane (4.00 M, 6.00 mL). The mixture was stirred at 25° C. for 0.5 hr. On completion, the mixture was concentrated in vacuo to give the title compound (430 mg, 99% yield, HCl) as white solid. $^1$H NMR (400 MHz, DMSO-$d_6$) δ 11.10 (s, 1H), 8.96 (s, 1H), 7.04-6.97 (m, 1H), 6.97-6.89 (m, 2H), 5.44-5.30 (m, 1H), 3.64 (s, 3H), 3.26-3.14 (m, 2H), 3.14-3.02 (m, 1H), 2.98-2.84 (m, 1H), 2.81-2.72 (m, 2H), 2.70-2.60 (m, 2H), 2.60-2.56 (m, 3H), 2.19-2.08 (m, 2H), 2.05-1.95 (m, 1H), 1.87-1.69 (m, 2H), LC-MS (ESI+) m/z 372.2 (M+H)+

3-[3-Methyl-4-[4-[methyl(4-piperidylmethyl)amino]-1-piperidyl]-2-oxo-benzimidazol-1-yl] piperidine-2,6-dione (Intermediate EH)

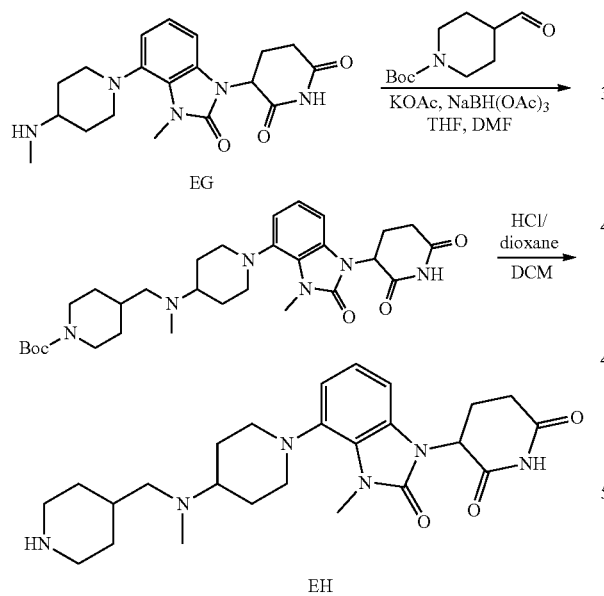

Step 1—Tert-butyl 4-[[[1-[1-(2,6-dioxo-3-piperidyl)-3-methyl-2-oxo-benzimidazol-4-yl]-4-piperidyl]-methyl-amino]methyl]piperidine-1-carboxylate To a solution of 3-[3-methyl-4-[4-(methylamino)-1-piperidyl]-2-oxo-benzimidazol-1-yl]piperidine-2, 6-dione (1.43 g, 3.51 mmol, HCl, Intermediate EG) and tert-butyl 4-formylpiperidine-1-carboxylate (822 mg, 3.86 mmol, CAS #137076-22-3) in mixture solvent of THF (40 mL) and DMF (20 mL) was added KOAc (3.44 g, 35.0 mmol) and NaBH(OAc)$_3$ (1.49 g, 7.01 mmol). The mixture was stirred at 25° C. for 2 hrs. On completion, the mixture was quenched with H$_2$O (1 mL), diluted with H$_2$O (30 mL), and extracted with EA (3×50 mL). The combined organic layer was washed with brine (3×20 mL), dried with anhydrous Na$_2$SO$_4$, filtered and the organic liquor was concentrated in vacuo. The residue was purified by prep-HPLC (column: YMC Triart C18 250*50 mm*7 um; mobile phase: [water(HCl)-ACN]; B %: 10%-40%, 20 min) to give the title compound (1.00 g, 50% yield) as a white solid. $^1$H NMR (400 MHz, CDCl$_3$) δ 10.51 (s, 1H), 8.92-8.82 (m, 1H), 6.94-6.88 (m, 2H), 5.37 (dd, J=5.2, 12.8 Hz, 1H), 3.64 (s, 3H), 3.41-3.32 (m, 2H), 3.26-3.22 (m, 2H), 2.98-2.88 (m, 4H), 2.76 (d, J=4.8 Hz, 3H), 2.68-2.66 (m, 1H), 2.25-2.09 (m, 4H), 2.08-1.97 (m, 3H), 1.96-1.90 (m, 2H), 1.83-1.73 (m, 2H), 1.67-1.61 (m, 2H), 1.51-1.43 (m, 2H), 1.42-1.36 (m, 9H). LC-MS (ESI+) m/z 569.3 (M+H)+.

Step 2—3-[3-Methyl-4-[4-[methyl(4-piperidylmethyl)amino]-1-piperidyl]-2-oxo-benzimidazol-1-yl]piperidine-2,6-dione To a solution of tert-butyl 4-[[[1-[1-(2,6-dioxo-3-piperidyl)-3-methyl-2-oxo-benzimidazol-4-yl]-4-piperidyl]-methyl-amino]methyl]piperidine-1-carboxylate (100 mg, 175 umol) in DCM (2 mL) was added HCl/dioxane (4 M, 1.00 mL). The mixture was stirred at 25° C. for 1 hr. On completion, the mixture was concentrated in vacuo to give the title compound (88 mg, 99% yield, HCl) as a white solid. LC-MS (ESI+) m/z 469.1 (M+H)+.

2-(prop-2-yn-1-yloxy)ethyl 4-methylbenzenesulfonate (Intermediate EI)

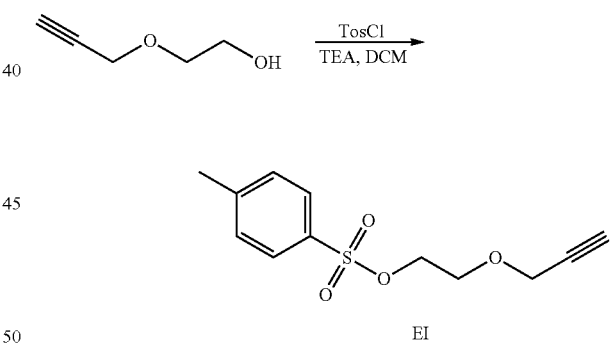

To a solution of 2-prop-2-ynoxyethanol (5 g, 49.9 mmol, CAS #3973-18-0), 4-methylbenzenesulfonyl chloride (11.4 g, 59.9 mmol) in DCM (60 mL) was added TEA (15.1 g, 149 mmol) at 0° C. The mixture was stirred at 25° C. for 12 h. On completion, the mixture was quenched with sat. aq. NH$_4$Cl (60 mL), and extracted with EtOAc (60 mL×2). The combined organic layer was washed with brine (100 mL×3), dried by Na$_2$SO$_4$, concentrated in vacuo. The residue was purified by column chromatography (SiO2, Petroleum ether/Ethyl acetate=8/1 to 3/1) to give the title compound (8.2 g, 58.11% yield) as a yellow oil. $^1$H NMR (400 MHz, DMSO-d6) δ=7.82-7.80 (m, 2H), 7.36-7.34 (m, 2H), 4.21-4.18 (t, 2H), 4.12 (s, 2H), 3.74-3.72 (m, 2H), 2.45 (s, 3H), 2.43 (s, 1H).

(1R,3S)-3-(1-(tert-butyl)-5-(1-(2-(4-(2-(prop-2-yn-1-yloxy)ethyl)piperazin-1-yl)ethyl)-1H-pyrazole-5-carboxamido)-1H-pyrazol-3-yl)cyclopentyl isopropylcarbamate (Intermediate EJ)

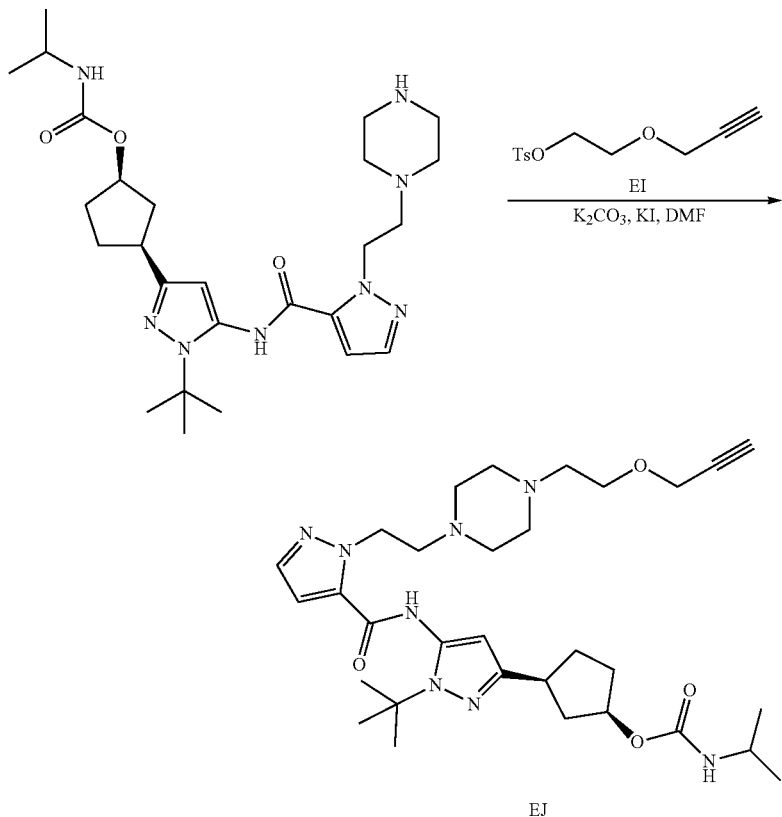

A solution of [(1R,3S)-3-[1-tert-butyl-5-[[2-(2-piperazin-1-ylethyl)pyrazole-3-carbonyl]amino]pyrazol-3-yl]cyclopentyl] N-isopropylcarbamate (0.15 g, 291 umol, synthesized via Steps 1-2 of Intermediate BH), 2-prop-2-ynoxyethyl 4-methylbenzenesulfonate (66.7 mg, 262 umol, Intermediate EI), Cs₂CO₃ (759 mg, 2.33 mmol), and KI (9.68 mg, 58.2 umol) in DMF (6 mL) was stirred at 70° C. for 12 h. On completion, the mixture was quenched with water (10 mL) and extracted with EtOAc (10 mL×2). The combined organic phase was washed with brine (10 mL×3), dried over anhydrous sodium sulfate, filtered and concentrated to give a residue. The residue was purified by column chromatography (SiO2, Petroleum ether/Ethyl acetate=0:1) to give the title compound (0.07 g, 36% yield) as an orange solid. LC-MS (ESI⁺) m/z 597.4 (M+H)⁺.

3-[5-[3-[2-[2-(2-Aminoethoxy)ethoxy]ethoxy]propyl]-3-methyl-2-oxo-benzimidazol-1-yl] piperidine-2,6-dione (Intermediate EK)

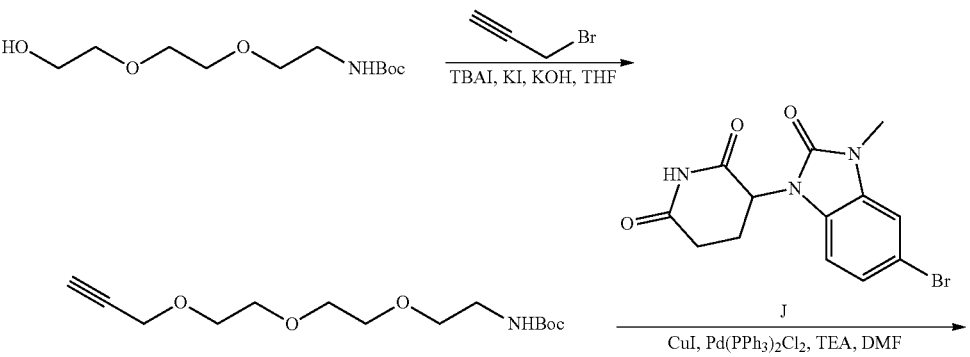

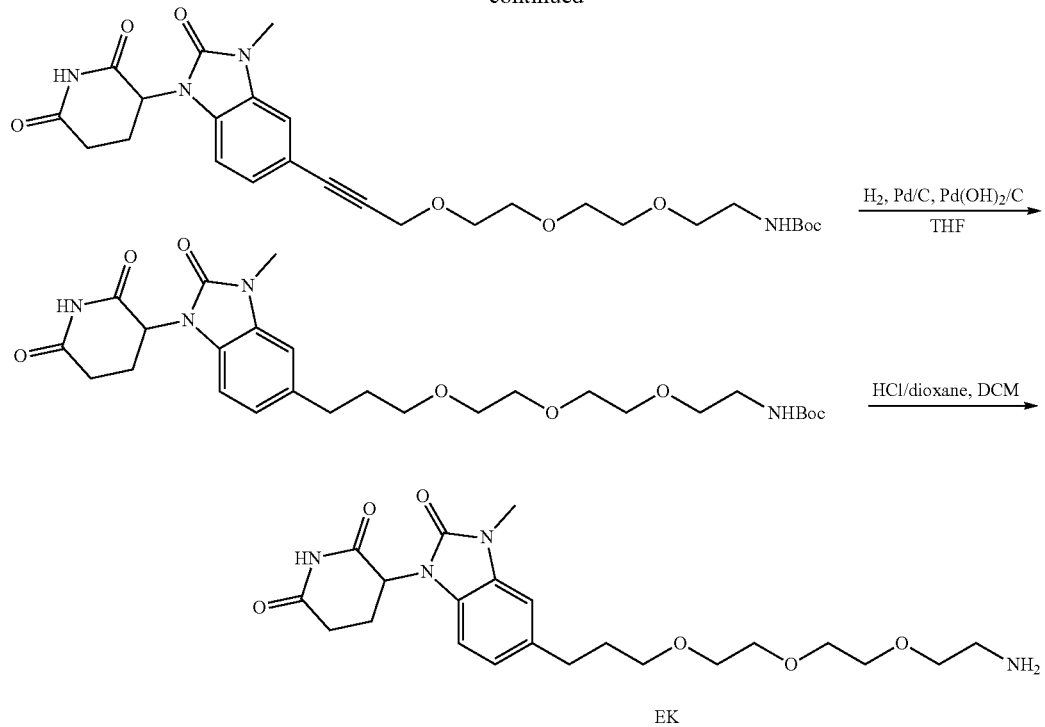

Step 1—Tert-butyl N-[2-[2-(2-prop-2-ynoxyethoxy)ethoxy]ethyl]carbamate

A mixture of tert-butyl N-[2-[2-(2-hydroxyethoxy)ethoxy]ethyl]carbamate (3.00 g, 12.0 mmol), 3-bromoprop-1-yne (1.72 g, 14.4 mmol, 1.24 mL), TBAI (356 mg, 962 umol), KI (299 mg, 1.81 mmol) and KOH (675 mg, 12.0 mmol) in THF (30 mL) was degassed and purged with $N_2$ three times. Then the mixture was stirred at 25° C. for 16 hrs under $N_2$ atmosphere. On completion, the mixture was filtered and the filtrate was concentrated in vacuo. The residue was purified by silica gel chromatography to give the title compound (2.50 g, 72% yield) as light yellow oil. $^1$H NMR (400 MHz, CDCl$_3$) δ 5.05 (s, 1H), 4.22 (d, J=2.4 Hz, 2H), 3.76-3.60 (m, 8H), 3.55 (t, J=5.2 Hz, 2H), 3.35-3.27 (m, 2H), 2.44 (t, J=2.4 Hz, 1H), 1.47 (s, 9H).

Step 2—Tert-butyl N-[2-[2-[2-[3-[1-(2,6-dioxo-3-piperidyl)-3-methyl-2-oxo-benzimidazol-5-yl]prop-2-ynoxy]ethoxy]ethoxy]ethyl]carbamate A mixture of tert-butyl N-[2-[2-(2-prop-2-ynoxyethoxy)ethoxy]ethyl]carbamate (849 mg, 2.96 mmol), 3-(5-bromo-3-methyl-2-oxo-benzimidazol-1-yl)piperidine-2,6-dione (500 mg, 1.48 mmol, Intermediate J), Pd(PPh$_3$)$_2$Cl$_2$ (311 mg, 443 umol), CuI (84 mg, 443 umol) and TEA (2.69 g, 26.6 mmol, 3.70 mL) in DMF (15 mL) was degassed and purged with $N_2$ three times. Then the mixture was stirred at 80° C. for 3 hrs under $N_2$ atmosphere. On completion, the mixture was concentrated in vacuo to give a residue. The residue was purified by reverse phase (0.1% FA) to give the title compound (400 mg, 49% yield) as light yellow solid. $^1$H NMR (400 MHz, DMSO-d$_6$) δ 11.12 (s, 1H), 7.33 (s, 1H), 7.21-7.12 (m, 2H), 6.77-6.71 (m, 1H), 5.39 (dd, J=5.2, 12.8 Hz, 1H), 4.40 (s, 2H), 3.68-3.62 (m, 2H), 3.61-3.56 (m, 2H), 3.55-3.47 (m, 6H), 3.35 (s, 3H), 3.07 (q, J=6.0 Hz, 2H), 2.96-2.80 (m, 1H), 2.72-2.58 (m, 2H), 2.08-1.99 (m, 1H), 1.37 (s, 9H).

Step 3—Tert-butyl N-[2-[2-[2-[3-[1-(2,6-dioxo-3-piperidyl)-3-methyl-2-oxo-benzimidazol-5-yl]propoxy]ethoxy]ethoxy]ethyl]carbamate To a solution of tert-butyl N-[2-[2-[2-[3-[1-(2,6-dioxo-3-piperidyl)-3-methyl-2-oxo-benzimidazol-5-yl]prop-2-ynoxy]ethoxy]ethoxy]ethyl]carbamate (400 mg, 734 umol) in THF (100 mL) was added Pd/C (300 mg, 10 wt %) and Pd(OH)$_2$/C (300 mg, 10 wt %). The mixture was stirred at 20° C. for 4 hrs under H$_2$ (15 psi) atmosphere. On completion, the mixture was filtered and the filtrate was concentrated in vacuo to give the title compound (270 mg, 67% yield) as light yellow solid. $^1$H NMR (400 MHz, DMSO-d$_6$) δ 11.07 (s, 1H), 7.08-6.96 (m, 2H), 6.87 (d, J=7.2 Hz, 1H), 6.73 (s, 1H), 5.34 (dd, J=5.2, 12.4 Hz, 1H), 3.69-3.35 (m, 15H), 3.09-3.01 (m, 2H), 2.97-2.81 (m, 1H), 2.77-2.57 (m, 4H), 2.08-1.94 (m, 1H), 1.89-1.71 (m, 2H), 1.37 (s, 9H).

Step 4—3-[5-[3-[2-[2-(2-Aminoethoxy)ethoxy]ethoxy]propyl]-3-methyl-2-oxo-benzimidazol-1-yl]piperidine-2,6-dione To a solution of tert-butyl N-[2-[2-[2-[3-[1-(2,6-dioxo-3-piperidyl)-3-methyl-2-oxo-benzimidazol-5-yl]propoxy]ethoxy]ethoxy]ethyl]carbamate (270 mg, 492 umol) in DCM (10 mL) was added HCl/dioxane (4 M, 5 mL). The mixture was then stirred at 25° C. for 3 hrs. On completion, the mixture was concentrated in vacuo to give the title compound (220 mg, 92% yield) as light yellow solid. $^1$H NMR (400 MHz, DMSO-d$_6$) δ 11.08 (s, 1H), 7.86 (s, 3H), 7.07-6.97 (m, 2H), 6.91-6.84 (m, 1H), 5.40-5.29 (m, 1H), 3.61 (t, J=5.2 Hz, 2H), 3.59-3.56 (m, 4H), 3.55-3.53 (m, 2H), 3.52-3.48 (m, 2H), 3.43-3.40 (m, 2H), 3.33 (s, 3H), 3.02-2.84 (m, 3H), 2.76-2.58 (m, 4H), 2.05-1.97 (m, 1H), 1.87-1.73 (m, 2H).

(1R,3S)-3-(1-(tert-butyl)-5-(1-(2-(4-(4-(prop-2-yn-1-yloxy)butyl)piperazin-1-yl)ethyl)-1H-pyrazole-5-carboxamido)-1H-pyrazol-3-yl)cyclopentyl isopropylcarbamate (Intermediate EL)

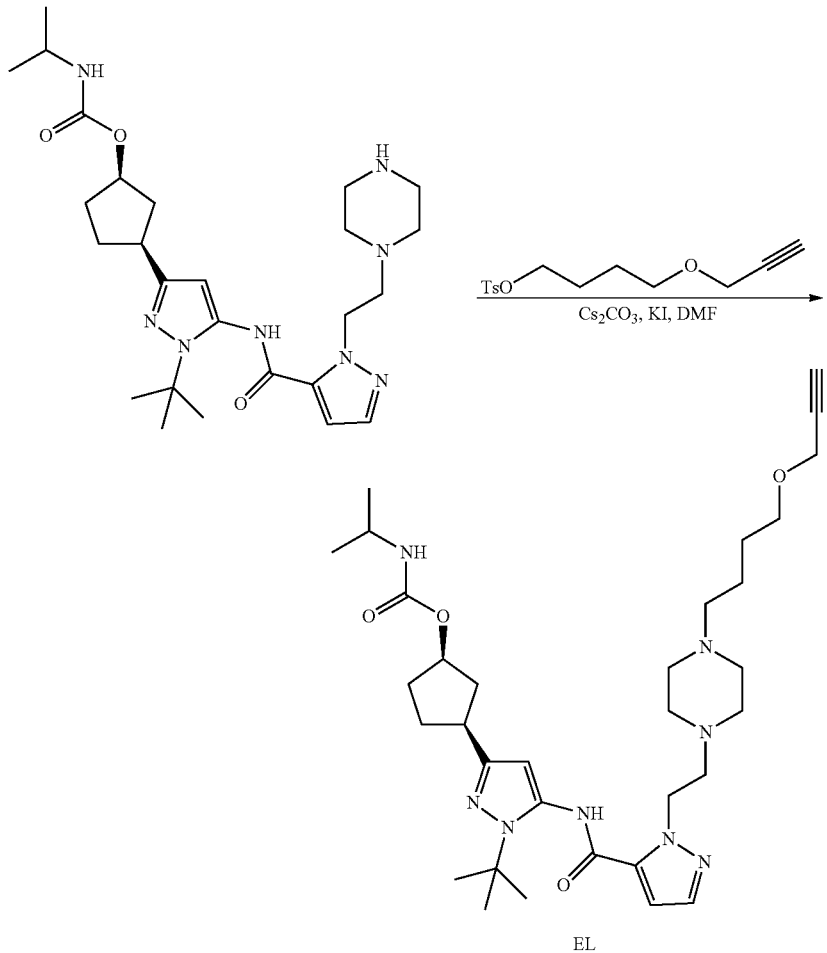

A solution of [(1R,3S)-3-[1-tert-butyl-5-[[2-(2-piperazin-1-ylethyl)pyrazole-3-carbonyl]amino]pyrazol-3-yl]cyclopentyl]N-isopropylcarbamate (0.5 g, 971 umol, synthesized via Steps 1-2 of Intermediate BH), 4-prop-2-ynoxybutyl 4-methylbenzenesulfonate (246 mg, 874 umol, CAS #1125737-76-9), Cs$_2$CO$_3$ (1.58 g, 4.86 mmol), and KI (32.2 mg, 194 umol) in DMF (10 mL) was stirred at 70° C. for 4 h. On completion, the mixture was quenched with sat. NH$_4$Cl (10 mL), and extracted with EtOAc (20 mL×2). The combined organic layer was washed with brine (40 mL×3), dried by Na$_2$SO$_4$, concentrated in vacuo. The residue was purified by column chromatography (SiO$_2$, Petroleum ether/Ethyl acetate=1/1 to 1/2) to give the title compound (180 mg, 27% yield) as a yellow solid. LC-MS (ESI$^+$) m/z 615.8 (M+H)$^+$.

Benzyl (2-(2-(prop-2-yn-1-yloxy)ethoxy)ethyl)carbamate (Intermediate EM)

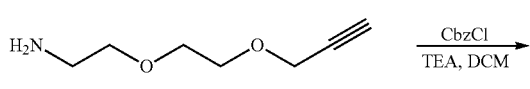

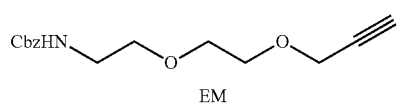

To a solution of 2-(2-prop-2-ynoxyethoxy)ethanamine (0.5 g, 3.49 mmol, CAS #944561-44-8) in DCM (8 mL) was added TEA (389 mg, 3.84 mmol) and benzyl carbonochloridate (655 mg, 3.84 mmol). The mixture was stirred at 25° C. for 12 hrs. On completion, the reaction mixture was poured into water (10 ml), then the solution was extracted with DCM (10 ml×3). The organic layer was washed with brine (10 ml×3), dried with Na$_2$SO$_4$, and concentrated under reduced pressure to give the residue. The residue was purified by column chromatography (SiO$_2$, Petroleum ether/Ethyl acetate=10/1 to 2/1) to give the title compound (850 mg, 82% yield) as a white oil. LC-MS (ESI$^+$) m/z 278.0 (M+H)$^+$.

3-(5-(3-(2-(2-Aminoethoxy)ethoxy)propyl)-3-methyl-2-oxo-2,3-dihydro-1H-benzo[d]imidazol-1-yl)piperidine-2,6-dione (Intermediate EN)

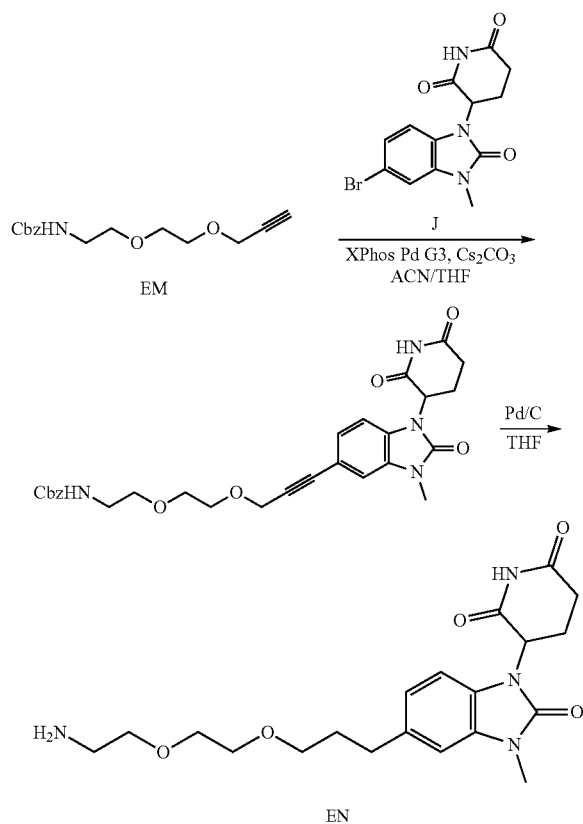

Step 1—Benzyl (2-(2-((3-(1-(2,6-dioxopiperidin-3-yl)-3-methyl-2-oxo-2,3-dihydro-1H-benzo[d]imidazol-5-yl)prop-2-yn-1-yl)oxy)ethoxy)ethyl)carbamate To a solution of benzyl N-[2-(2-prop-2-ynoxyethoxy)ethyl]carbamate (850 mg, 3.07 mmol, Intermediate EM) in THF (7 mL) and ACN (7 mL) was added XPhos Pd G3 (778 mg, 920 umol), Cs$_2$CO$_3$ (5.99 g, 18.4 mmol) and 3-(5-bromo-3-methyl-2-oxo-benzimidazol-1-yl)piperidine-2,6-dione (1.55 g, 4.60 mmol, Intermediate J). The mixture was stirred at 60° C. for 12 hrs under N$_2$ atmosphere. On completion, the reaction mixture was diluted with water and extracted with DCM (10 mL×3). The organic layers was washed with brine (10 mL×3), dried by Na$_2$SO$_4$, concentrated under reduced pressure to give the residue. The residue was purified by column chromatography (SiO2, Petroleum ether/Ethyl acetate=6/1 to 2/1) to give the title compound (1.2 g, 50% yield) as a yellow solid. LC-MS (ESI$^+$) m/z 535.3 (M+H)$^+$.

Step 2—3-(5-(3-(2-(2-Aminoethoxy)ethoxy)propyl)-3-methyl-2-oxo-2,3-dihydro-1H-benzo[d]imidazol-1-yl)piperidine-2,6-dione To a solution of benzyl N-[2-[2-[3-[1-(2,6-dioxo-3-piperidyl)-3-methyl-2-oxo-benzimidazol-5-yl]prop-2-ynoxy]ethoxy]ethyl]carbamate (1.2 g, 2.24 mmol) in THF (30 mL) was added Pd/C (2.38 g, 10 wt %). The mixture was stirred at 25° C. for 4 hrs under H$_2$ atmosphere (15 PSI). On completion, the reaction mixture was filtered and then the solution was concentrated under reduced pressure to give the residue. The residue was purified by prep-HPLC (FA condition) to give the title compound (90 mg, 10% yield) as a white solid. LC-MS (ESI$^+$) m/z 405.2 (M+H)$^+$.

2-[2-[2-(2-prop-2-ynoxyethoxy)ethoxy]ethoxy]ethyl 4-methylbenzenesulfonate (Intermediate EO)

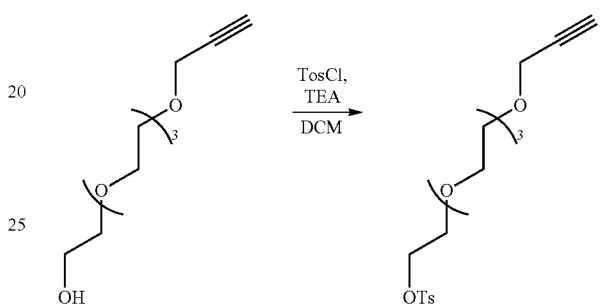

To a solution of 2-[2-[2-(2-prop-2-ynoxyethoxy)ethoxy]ethoxy]ethanol (5 g, 21.5 mmol, CAS #87450-10-0) in DCM (50 mL) was added TEA (6.53 g, 64.6 mmol) and TosCl (4.51 g, 23.7 mmol). The mixture was stirred at 25° C. for 12 hrs. On completion, the reaction mixture was diluted with water (20 ml), and extracted with EtOAc (30 mL×3). The organic layers was dried by Na$_2$SO$_4$ and concentrated under reduced pressure to give the residue. The residue was purified by column chromatography (SiO$_2$, Petroleum ether/Ethyl acetate=4/1 to 1/1) to give the title compound (6.8 g, 60% yield) as a white oil. LC-MS (ESI$^+$) m/z 386.9 (M+H)$^+$.

2-[2-[2-[2-(2-Prop-2-ynoxyethoxy)ethoxy]ethoxy]ethyl]pyrazole-3-carboxylic acid (Intermediate EP)

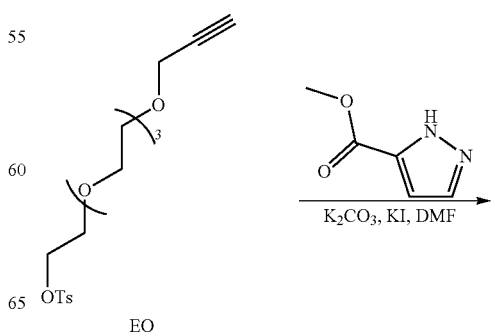

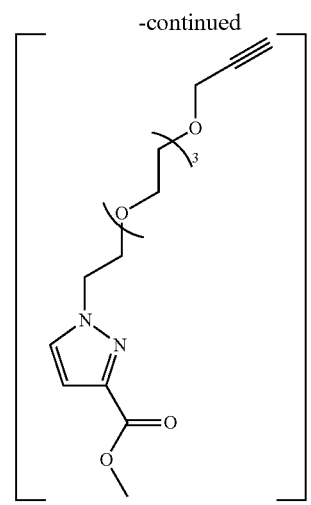
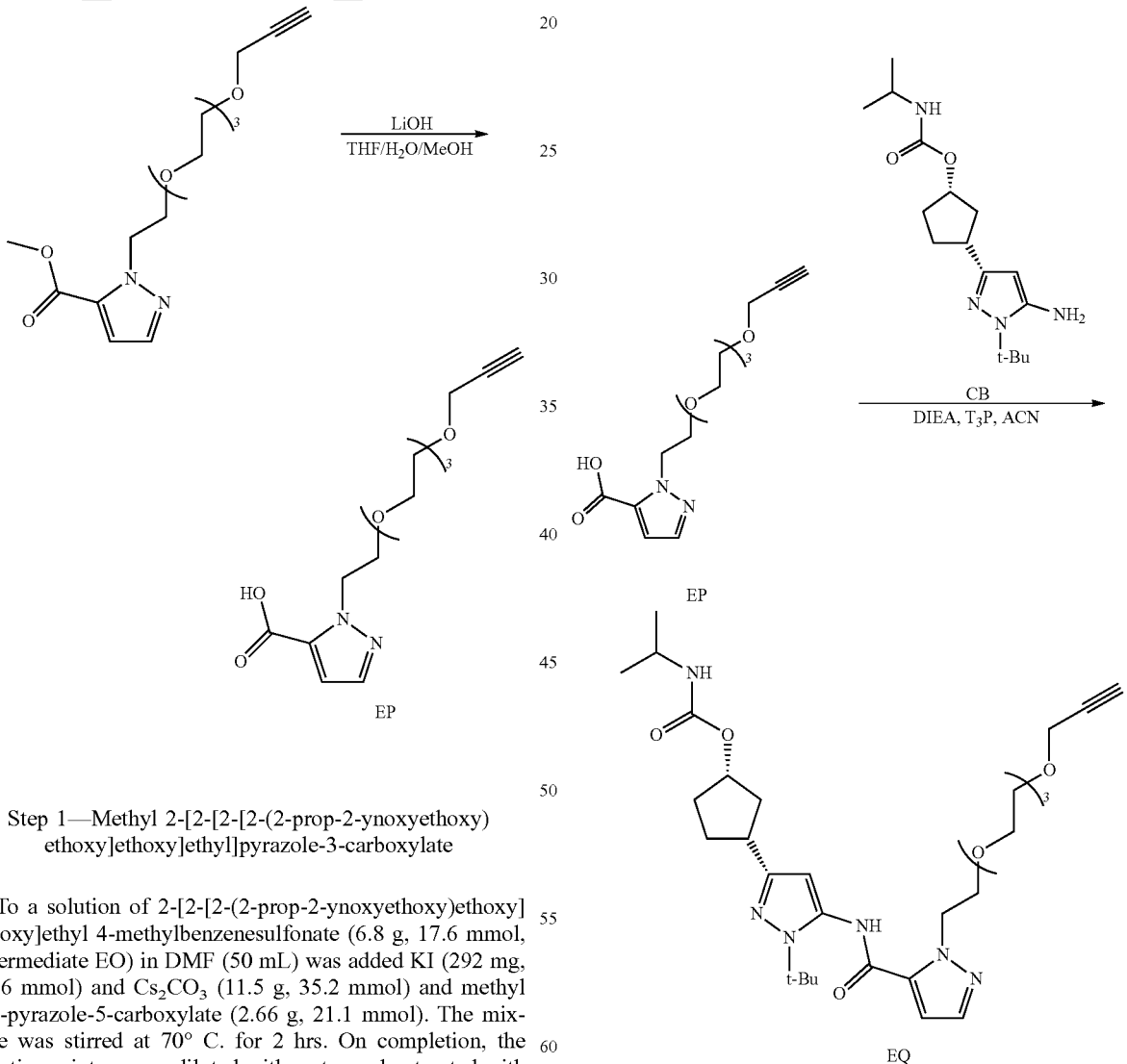

Step 1—Methyl 2-[2-[2-[2-(2-prop-2-ynoxyethoxy)ethoxy]ethoxy]ethyl]pyrazole-3-carboxylate To a solution of 2-[2-[2-(2-prop-2-ynoxyethoxy)ethoxy]ethoxy]ethyl 4-methylbenzenesulfonate (6.8 g, 17.6 mmol, Intermediate EO) in DMF (50 mL) was added KI (292 mg, 1.76 mmol) and $Cs_2CO_3$ (11.5 g, 35.2 mmol) and methyl 1H-pyrazole-5-carboxylate (2.66 g, 21.1 mmol). The mixture was stirred at 70° C. for 2 hrs. On completion, the reaction mixture was diluted with water and extracted with EtOAc (60 mL×3). The organic layer was washed with brine (50 mL×3), dried by $Na_2SO_4$, and concentrated under reduced pressure to give the residue. The residue was purified by column chromatography ($SiO_2$, Petroleum ether/Ethyl acetate=6/1 to 1/1) to give the title compound (3.7 g, 45% yield) as a white oil. LC-MS (ESI$^+$) m/z 341.5 (M+H)$^+$.

Step 2—2-[2-[2-[2-(2-Prop-2-ynoxyethoxy)ethoxy]ethoxy]ethyl]pyrazole-3-carboxylic acid To a solution of methyl 2-[2-[2-[2-(2-prop-2-ynoxyethoxy)ethoxy]ethoxy]ethyl]pyrazole-3-carboxylate (3.7 g, 10.9 mmol) in MeOH (4 mL), THF (4 mL), and $H_2O$ (4 mL) was added LiOH·$H_2O$ (1.82 g, 43.5 mmol). The mixture was stirred at 25° C. for 1 hour. On completion, the pH of the mixture was adjusted to 5 with 1 M HCl, then extracted with EtOAc (10 mL×3). The organic layer was washed with brine (20 mL×3), concentrated under reduced pressure to give the title compound (2.6 g) as a white oil. LC-MS (ESI$^+$) m/z 327.2 (M+H)$^+$.

[(1S,3R)-3-[1-tert-butyl-5-[[2-[2-[2-[2-(2-prop-2-ynoxyethoxy)ethoxy]ethoxy]ethyl]pyrazole-3-carbonyl]amino]pyrazol-3-yl]cyclopentyl] N-isopropylcarbamate (Intermediate EQ)

To a solution of 2-[2-[2-[2-(2-prop-2-ynoxyethoxy)ethoxy]ethoxy]ethyl]pyrazole-3-carboxylic acid (0.6 g, 2 mmol, Intermediate EP) in ACN (6 mL) was added $T_3P$ (3.16 g, 4.96 mmol, 50% solution) and DIEA (1.07 g, 8.27 mmol, 1.44 mL) and [(1S,3R)-3-(5-amino-1-tert-butyl-pyrazol-3-yl)cyclopentyl] N-isopropylcarbamate (510 mg, 1.65 mmol, Intermediate CB). The mixture was stirred at 60° C. for 12 hrs. On completion, the reaction mixture was diluted with water (5 mL), and extracted with EtOAc (6 mL×3). The organic layers was washed brine (6 mL×3), dried over Na₂SO₄, filtered and concentrated under reduced pressure to give the residue. The residue was purified by column chromatography (SiO₂, Petroleum ether/Ethyl acetate=6/1 to 1/2) to give the title compound (240 mg, 23% yield) as a yellow oil. LC-MS (ESI⁺) m/z 617.4 (M+H)⁺.

Tert-butyl((S)-1-(((S)-1-cyclohexyl-2-((S)-2-(4-(3-hydroxybenzoyl)thiazol-2-yl) pyrrolidin-1-yl)-2-oxoethyl)amino)-1-oxopropan-2-yl)(methyl)carbamate (CAS #2095244-42-9) (Intermediate ER)

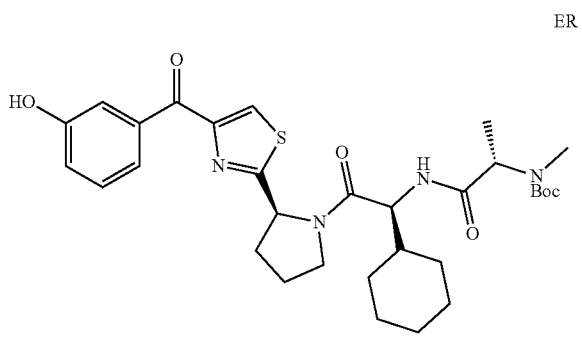 [SMILES: C[C@@H](C(=O)N[C@H](C(=O)N1CCC[C@H]1c1nc(C(=O)c2cccc(O)c2)cs1)C1CCCCC1)N(C)C(=O)OC(C)(C)C]

1-(11-(benzyloxy)undecyl)-1H-pyrazole-4-carboxylic acid (Intermediate ES)

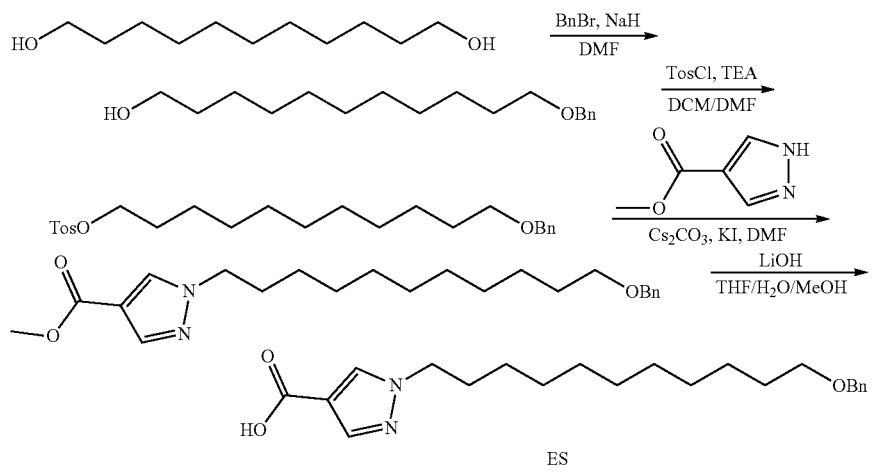

Step 1—11-(benzyloxy)undecan-1-ol

To a suspension of NaH (1.17 g, 29.2 mmol, 60% dispersion in mineral oil) in DMF (30 mL) was slowly added a solution of undecane-1,11-diol (5 g, 26.5 mmol, CAS #765-04-8) in DMF (20 mL) at −10° C. under nitrogen. The reaction mixture was allowed to warm to 25° C. and stirred for 1 h. Next, the reaction mixture was cooled to 0° C., then BnBr (4.09 g, 23.9 mmol, 2.84 mL) was added dropwise. The reaction mixture was warmed to 25° C. and stirred for an additional 16 h. On completion, it was quenched with saturated aqueous NH₄Cl solution (20 mL) at 0° C., and the resulting mixture was extracted with EtOAc (30×3 mL), washed with brine, dried over anhydrous Na₂SO₄, filtered and concentrated in vacuo. The residue was purified by column chromatography (SiO₂, PE:EtOAc=5:1) to give the title compound (3.7 g, 50% yield) as white gum. ¹H NMR (400 MHz, DMSO-d6) δ=7.45-7.17 (m, 5H), 4.44 (s, 2H), 4.32 (t, J=5.2 Hz, 1H), 3.45-3.34 (m, 4H), 1.56-1.48 (m, 2H), 1.40 (br t, J=6.4 Hz, 2H), 1.24 (s, 14H).

Step 2—11-(benzyloxy)undecyl 4-methylbenzenesulfonate

To a solution of 11-(benzyloxy)undecan-1-ol (3.7 g, 10.1 mmol) and TEA (1.43 g, 14.1 mmol, 1.97 mL) in DCM (19 mL) and DMF (19 mL) was added TosCl (2.89 g, 15.2 mmol) at 0° C. under N₂, then the mixture was stirred at 25° C. at 12 h. On completion, the reaction mixture was quenched with saturated NaHCO₃ aqueous (30 mL) at 0° C. and extracted with DCM (10×3 mL). The combined organic layers were washed with brine (10×3 mL), dried over Na₂SO₄, filtered and concentrated in vacuo. The residue was purified by column chromatography (SiO₂, Petroleum ether/Ethyl acetate=25/1 to 5/1) to give the title compound (1.3 g, 30% yield) was a colorless oil. ¹H NMR (400 MHz, DMSO-d6) δ=12.47-12.04 (m, 1H), 8.28-8.18 (m, 1H), 7.77 (s, 1H), 7.43-7.12 (m, 5H), 4.43 (s, 2H), 4.24-4.07 (m, 3H), 3.40 (t, J=6.4 Hz, 2H), 1.75 (quin, J=7.2 Hz, 2H), 1.51 (quin, J=6.8 Hz, 2H), 1.22 (br s, 12H).

Step 3—Methyl 1-(11-(benzyloxy)undecyl)-1H-pyrazole-4-carboxylate

To a solution of methyl 1H-pyrazole-4-carboxylate (395 mg, 3.14 mmol) and 11-(benzyloxy)undecyl 4-methylbenzenesulfonate (1.3 g, 2.61 mmol) in DMF (7.8 mL) was added Cs₂CO₃ (1.70 g, 5.23 mmol) and KI (43.4 mg, 261 umol) at 0° C. under nitrogen flow. Then the reaction was stirred at 70° C. for 16 h under nitrogen atmosphere. On completion, the reaction mixture was with H₂O (20 mL) and extracted with EtOAc (40×3 mL). The organic layer was washed with brine (25×3 mL), dried with Na₂SO₄, filtered and concentrated in vacuo. The residue was purified by column chromatography (SiO₂, Petroleum ether/Ethyl acetate=15/1 to 10/1) to give the title compound (1.3 g) as yellow oil. LC-MS (ESI⁺) m/z 387.7 (M+H)⁺.

Step 4—1-(11-(Benzyloxy)undecyl)-1H-pyrazole-4-carboxylic acid

To a solution of methyl 1-(11-(benzyloxy)undecyl)-1H-pyrazole-4-carboxylate (1.3 g, 3.36 mmol) in THF (18 mL), H₂O (3 mL) and MeOH (3 mL) was added LiOH (161 mg, 6.73 mmol), then the mixture was stirred at 40° C. at 16 h. On completion, the reaction mixture was quenched with H₂O (20 mL) and extracted with EtOAc (10×3 mL). The aqueous phase by addition 2M HCl, the pH was adjusted to 3-4, then the mixture was extracted with EtOAc (10×3 mL). The combined organic layers were washed with brine (10×3 mL), dried over Na₂SO₄ and evaporated to give the title compound (0.7 g) as white solid. LC-MS (ESI⁺) m/z 373.4 (M+H)⁺.

11-(4-((1-(tert-butyl)-3-((1S,3R)-3-((isopropylcarbamoyl)oxy)cyclopentyl)-1H-pyrazol-5-yl)carbamoyl)-1H-pyrazol-1-yl)undecyl-4-methylbenzenesulfonate (Intermediate ET)

Step 1—(1R,3S)-3-(5-(1-(11-(benzyloxy)undecyl)-1H-pyrazole-4-carboxamido)-1-(tert-butyl)-1H-pyrazol-3-yl)cyclopentyl isopropylcarbamate To a solution of 1-(11-(benzyloxy)undecyl)-1H-pyrazole-4-carboxylic acid (650 mg, 1.74 mmol, Intermediate ES) and (1R,3S)-3-(5-amino-1-isopropyl-1H-pyrazol-3-yl)cyclopentyl isopropylcarbamate (357 mg, 1.16 mmol, Intermediate U) in ACN (13 mL) were added DIEA (749 mg, 5.80 mmol) and T₃P (1.48 g, 2.32 mmol, 50% solution), then the mixture was stirred at 80° C. for 16 h. On completion, the reaction mixture was quenched with H₂O (20 mL) and extracted with EtOAc (10×3 mL). The combined organic layers were washed with brine (10×3 mL), dried over sodium sulfate, filtered and concentrated. The crude product was purified by re-MPLC(water (0.225% FA)-ACN) to give the title compound (160 mg, 20% yield) as yellow liquid. LC-MS (ESI⁺) m/z 663.5 (M+H)⁺.

Step 2—(1R,3S)-3-(1-(tert-butyl)-5-(1-(11-hydroxyundecyl)-1H-pyrazole-4-carboxamido)-1H-pyrazol-3-yl)cyclopentyl isopropylcarbamate To a solution of (1R,3S)-3-(5-(1-(11-(benzyloxy)undecyl)-1H-pyrazole-4-carboxamido)-1-(tert-butyl)-1H-pyrazol-3-yl)cyclopentyl isopropylcarbamate (130 mg, 196 umol) in EtOH (2 mL) was added Pd/C (13 mg, 35.3 umol, 10 wt %) under H₂ (15 PSI). Then the mixture was stirred at

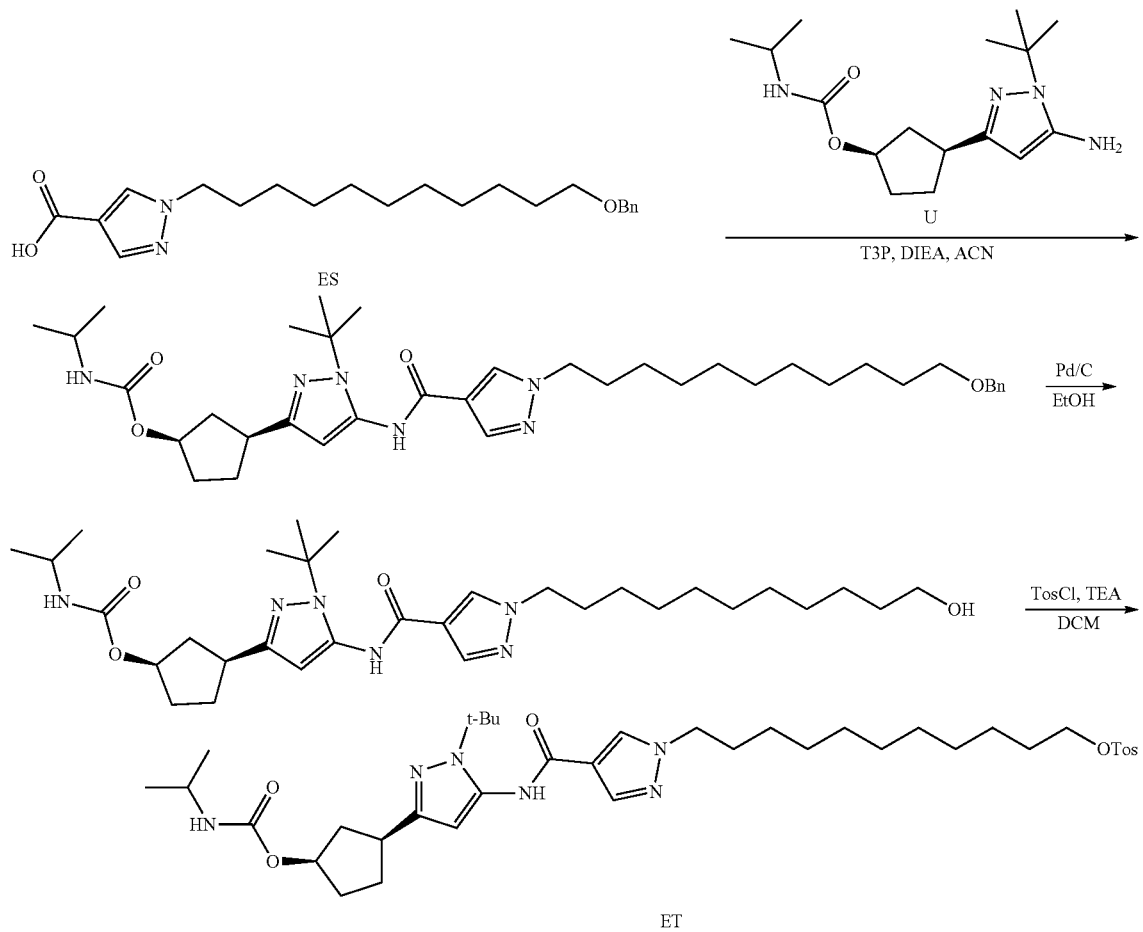

25° C. for 17 h. On completion, filtered and concentrated to give the title compound (75 mg) as a white solid. LC-MS (ESI⁺) m/z 573.9 (M+H)⁺.

Step 3—11-(4-((1-(tert-butyl)-3-((1S,3R)-3-((isopropylcarbamoyl)oxy)cyclopentyl)-1H-pyrazol-5-yl)carbamoyl)-1H-pyrazol-1-yl)undecyl 4-methylbenzenesulfonate To a solution of (1R,3S)-3-(1-(tert-butyl)-5-(1-(11-hydroxyundecyl)-1H-pyrazole-4-carboxamido)-1H-pyrazol-3-yl)cyclopentyl isopropylcarbamate (50 mg, 87.3 umol) in DCM (1 mL) was added TEA (26.5 mg, 261 umol). Then 4-methylbenzenesulfonyl chloride (19.9 mg, 104 umol) was added and the mixture was stirred at 20° C. for 12 h. On completion, the reaction mixture was quenched with NaHCO₃ (aq, 20 mL) at 20° C., and then diluted with EtOAc (10 mL) and extracted with EtOAc (20 mL×3). The combined organic layers were washed with brine (20 mL×2), dried over Na₂SO₄, filtered and concentrated under reduced pressure to give the title compound (120 mg) as yellow solid. LC-MS (ESI⁺) m/z 727.5 (M+H)⁺.

2-(2-(2-(2-(2-(prop-2-yn-1-yloxy)ethoxy)ethoxy)ethoxy)phenyl)acetic acid (Intermediate EU)

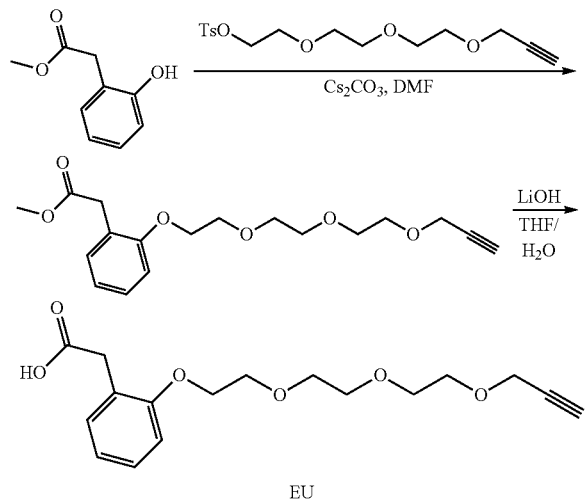

EU

Step 1—Methyl 2-(2-(2-(2-(2-(prop-2-yn-1-yloxy)ethoxy)ethoxy)ethoxy)phenyl)acetate To a solution of 2-[2-(2-prop-2-ynoxyethoxy)ethoxy]ethyl 4-methylbenzenesulfonate (3.7 g, 11 mmol, synthesized via Step 1 of Intermediate BE) and methyl 2-(2-hydroxyphenyl)acetate (1.98 g, 11.8 mmol) in DMF (50 mL) was added Cs₂CO₃ (17.6 g, 54.0 mmol) and KI (179.3 mg, 1.08 mmol) at 0° C. under nitrogen flow. Then the reaction was stirred at 60° C. for 10 h under nitrogen atmosphere. On completion, the reaction was poured into water (70 mL) and extracted with ethyl acetate (100 mL×2). The combined organic phase was washed with brine (50 mL×2), dried over sodium sulfate, filtered to get the filtrate and concentrated to give a residue. The residue was purified by column chromatography on silica gel (eluted with petroleum ether:ethyl acetate=100:1 to 100:25) to give the title compound (2.2 g, 60.5% yield) as colorless oil. LC-MS (ESI⁺) m/z 359.1 (M+Na)⁺.

Step 2—2-(2-(2-(2-(2-(Prop-2-yn-1-yloxy)ethoxy)ethoxy)ethoxy)phenyl)acetic acid

To a solution of methyl 2-[2-[2-[2-(2-prop-2-ynoxyethoxy)ethoxy]ethoxy]phenyl]acetate (2.2 g, 6.54 mmol) in THF (22 mL), methanol (11 mL) and H₂O (11 mL) was added LiOH·H₂O (1.10 g, 26.1 mmol) at 20° C. under nitrogen flow. Then the reaction was stirred at 20° C. for 10 h under nitrogen atmosphere. On completion, the reaction was poured into ice water (50 mL) and acidified by 2 N hydrochloride acid to pH=4. Then the mixture was extracted with ethyl acetate (70 mL×2). The combined organic phase was washed with brine (50 mL×2), dried over sodium sulfate, then filtered to get the filtrate and concentrated to give the title compound (1.5 g) as colorless oil. LC-MS (ESI⁺) m/z 345.1 (M+Na)⁺.

(1S,3R)-3-(1-(tert-butyl)-5-(2-(2-(2-(2-(2-(prop-2-yn-1-yloxy)ethoxy)ethoxy)ethoxy)phenyl)acetamido)-1H-pyrazol-3-yl)cyclopentyl isopropylcarbamate (Intermediate EV)

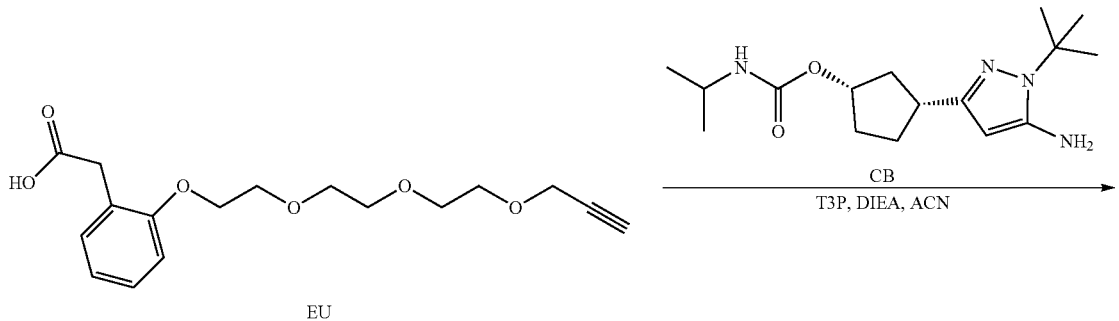

EU

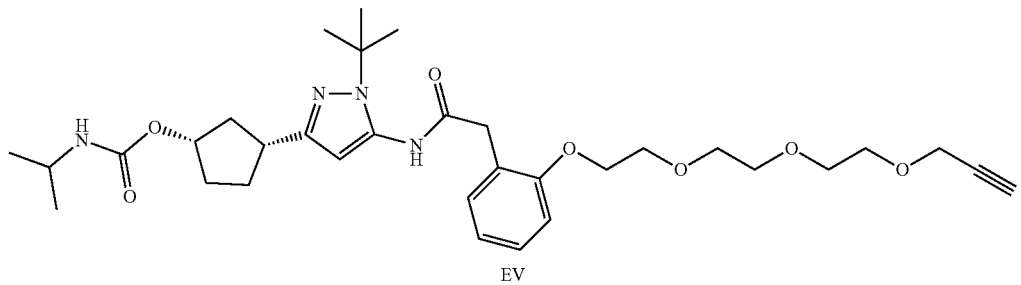

EV

Step 1—(1S,3R)-3-(1-(tert-butyl)-5-(2-(2-(2-(2-(2-(prop-2-yn-1-yloxy)ethoxy)ethoxy)ethoxy)phenyl)acetamido)-1H-pyrazol-3-yl)cyclopentyl isopropylcarbamate To a solution of 2-[2-[2-[2-(2-prop-2-ynoxyethoxy)ethoxy]ethoxy]phenyl]acetic acid (0.5 g, 1.55 mmol, Intermediate EU) and [(1S,3R)-3-(5-amino-1-tert-butyl-pyrazol-3-yl)cyclopentyl] N-isopropylcarbamate (478 mg, 1.55 mmol, Intermediate CB) in ACN (10 mL) was added T3P (2.96 g, 4.65 mmol, 50% solution) and DIEA (1.00 g, 7.76 mmol) at 0° C. under nitrogen flow. Then the reaction was stirred at 20° C. for 10 h under nitrogen atmosphere. On completion, the reaction was poured into water (15 mL) and extracted with ethyl acetate (20 mL×2). The combined organic phase was washed with brine (20 mL×2), and dried over sodium sulfate. Then filtered to get the filtrate and concentrated to give a residue. The residue was purified by column chromatography on silica gel (eluted with petroleum ether:ethyl acetate=100:1 to 100:30) to give the title compound (0.7 g, 74% yield) as colorless oil. $^1$H NMR (400 MHz, CDCl$_3$) δ=7.81 (s, 1H), 7.37-7.29 (m, 2H), 7.02 (t, J=7.3 Hz, 1H), 6.95 (d, J=8.0 Hz, 1H), 6.18 (s, 1H), 5.15 (br s, 1H), 4.65 (br s, 1H), 4.26-4.17 (m, 4H), 3.96-3.87 (m, 2H), 3.86-3.74 (m, 3H), 3.72-3.51 (m, 7H), 3.47-3.39 (m, 2H), 3.08 (quin, J=8.4 Hz, 1H), 2.54-2.36 (m, 2H), 2.03-1.75 (m, 5H), 1.32 (s, 8H), 1.16 (dd, J=3.1, 6.4 Hz, 6H).

(1S,3R)-3-((3S)-5-(1-methyl-3-((non-8-yn-1-yloxy)methyl)-1H-pyrazole-5-carboxamido) pyrazolidin-3-yl)cyclopentyl isopropylcarbamate (Intermediate EW)

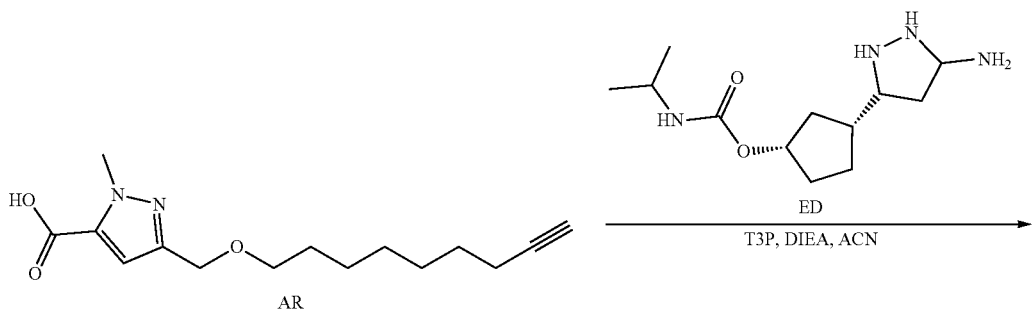

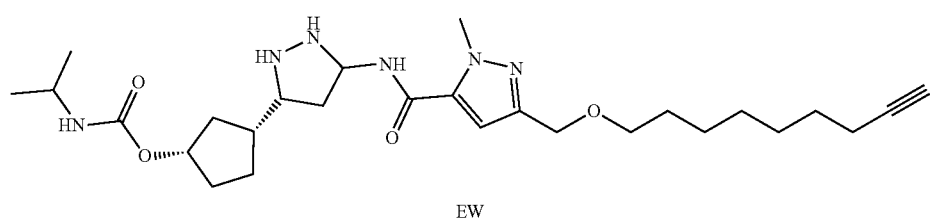

EW

To a solution of 1-methyl-3-((non-8-yn-1-yloxy)methyl)-1H-pyrazole-5-carboxylic acid (150 mg, 539 umol, Intermediate AR) and (1S,3R)-3-((3S)-5-aminopyrazolidin-3-yl)cyclopentylisopropylcarbamate (166 mg, 539 umol, Intermediate ED) in MeCN (3 mL) was added DIEA (348 mg, 2.69 mmol) and T3P (1.03 g, 1.62 mmol, 50% solution). Then the mixture was stirred at 60° C. for 12 h. On completion, the reaction mixture was quenched with H$_2$O (2 mL) at 20° C., and extracted with EtOAc (2 mL×3). The combined organic layers were washed with brine (2 mL×2), dried over Na$_2$SO$_4$, filtered and concentrated under reduced pressure to give a residue. The residue was purified by column chromatography (SiO$_2$, Petroleum ether/Ethyl acetate=1/4 to 1/3) to give the title compound (100 mg, 30% yield) as yellow solid. LC-MS (ESI$^+$) m/z 569.5 (M+H)$^+$.

4-((6-bromo-8-cyclopentyl-5-methyl-7-oxo-7,8-dihydropyrido[2,3-d]pyrimidin-2-yl)amino)-3-methyl-benzene-1-sulfonyl chloride (Intermediate EX)

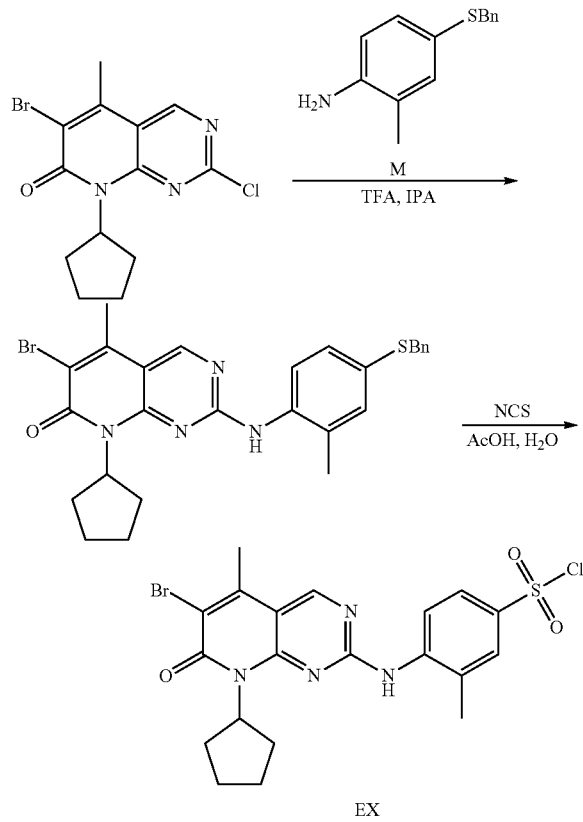

Step 1—2-((4-(Benzylthio)-2-methylphenyl)amino)-6-bromo-8-cyclopentyl-5-methylpyrido[2,3-d]pyrimidin-7(8H)-one To a solution of 6-bromo-2-chloro-8-cyclopentyl-5-methylpyrido[2,3-d]pyrimidin-7(8H)-one (500 mg, 1.46 mmol, CAS #1016636-76-2) and 4-(benzylthio)-2-methylaniline (502 mg, 2.19 mmol, Intermediate M) in IPA (10 mL) was added TFA (1.66 g, 14.6 mmol), then the mixture was stirred at 80° C. for 12 hr. On completion, the reaction mixture was quenched with NaHCO$_3$ solution (20 mL) and extracted with EtOAc (40 mL×3). The organic layer was washed with brine (25 mL×3), dried with anhydrous Na$_2$SO$_4$, filtered and concentrated in vacuo. The residue was purified by column chromatography (SiO$_2$, Petroleum ether/Ethyl acetate=15/1 to 3/1) to give the title compound (440 mg, 56% yield) as a yellow solid. $^1$H NMR (400 MHz, DMSO-d6) δ=9.40 (s, 1H), 8.88 (s, 1H), 7.43-7.20 (m, 8H), 5.82-5.62 (m, 1H), 4.23 (s, 2H), 2.55 (s, 3H), 2.17 (s, 3H), 2.10-2.04 (m, 2H), 1.62 (br s, 4H), 1.40 (br s, 2H) LC-MS (ESI$^+$) m/z 536.9 (M+H)$^+$.

Step 2—4-((6-Bromo-8-cyclopentyl-5-methyl-7-oxo-7,8-dihydropyrido[2,3-d]pyrimidin-2-yl)amino)-3-methylbenzene-1-sulfonyl chloride A solution of 2-((4-(benzylthio)-2-methylphenyl)amino)-6-bromo-8-cyclopentyl-5-methylpyrido[2,3-d]pyrimidin-7(8H)-one (400 mg, 747 umol) in AcOH (10 mL) and HCl (0.3 mL) was added NCS (399 mg, 2.99 mmol) at 0° C., then mixture was stirred at 0-25° C. for 30 min. On completion, the reaction mixture was quenched with water (20 mL) and extracted with DCM (10 mL×3). The organic layer was washed with brine (25 mL×3), dried with anhydrous Na$_2$SO4, filtered and concentrated in vacuo. The residue was purified by column chromatography (SiO$_2$, Petroleum ether/Ethyl acetate=5/1 to 1/1) to afford the title compound (300 mg, 79% yield) as a pink solid. $^1$H NMR (400 MHz, DMSO-d6) δ=9.45 (s, 1H), 8.89 (s, 1H), 7.48 (s, 1H), 7.44-7.35 (m, 2H), 5.83-5.72 (m, 1H), 2.55 (s, 3H), 2.23 (s, 3H), 2.14-2.03 (m, 2H), 1.99 (s, 2H), 1.91 (s, 1H), 1.77-1.62 (m, 4H), 1.51-1.39 (m, 2H), 1.26-1.13 (m, 2H); LC-MS (ESI$^+$) m/z 513.2 (M+H)$^+$.

Benzyl 3,6,9,12-tetraoxapentadec-14-yn-1-ylcarbamate (Intermediate EY)

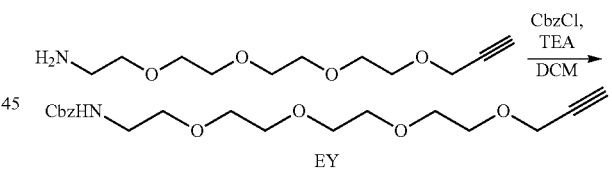

To a solution of 3,6,9,12-tetraoxapentadec-14-yn-1-amine (3 g, 12.97 mmol, CAS #1013921-36-2) in DCM (20 mL) was added TEA (1.44 g, 14.3 mmol). A solution of benzyl carbonochloridate (2.43 g, 14.3 mmol) was added into the mixture at 0° C. The mixture was stirred at 0-20° C. for 12 h. On completion, the reaction mixture was quenched by addition NaHCO$_3$ (sat., aqu, 20 mL) and extracted with EtOAc (30 mL×2). The combined organic layers were washed with brine (20 mL×3), dried over Na$_2$SO$_4$ and evaporated. The crude product was purified by column chromatography (SiO$_2$, Petroleum ether/Ethyl acetate=10/1 to 3/1) to give the title compound (4.4 g, 93% yield) as a white gum. $^1$H NMR (400 MHz, DMSO-d6) δ 7.39-7.28 (m, 5H), 7.24 (br t, J=5.6 Hz, 1H), 5.01 (s, 2H), 4.13 (d, J=2.4 Hz, 2H), 3.55-3.52 (m, 4H), 3.50 (s, 8H), 3.44-3.38 (m, 3H), 3.19-3.08 (m, 2H).

3-(5-(1-amino-3,6,9,12-tetraoxapentadecan-15-yl)-3-methyl-2-oxo-2,3-dihydro-1H-benzo[d]imidazol-1-yl)piperidine-2,6-dione (Intermediate EZ)

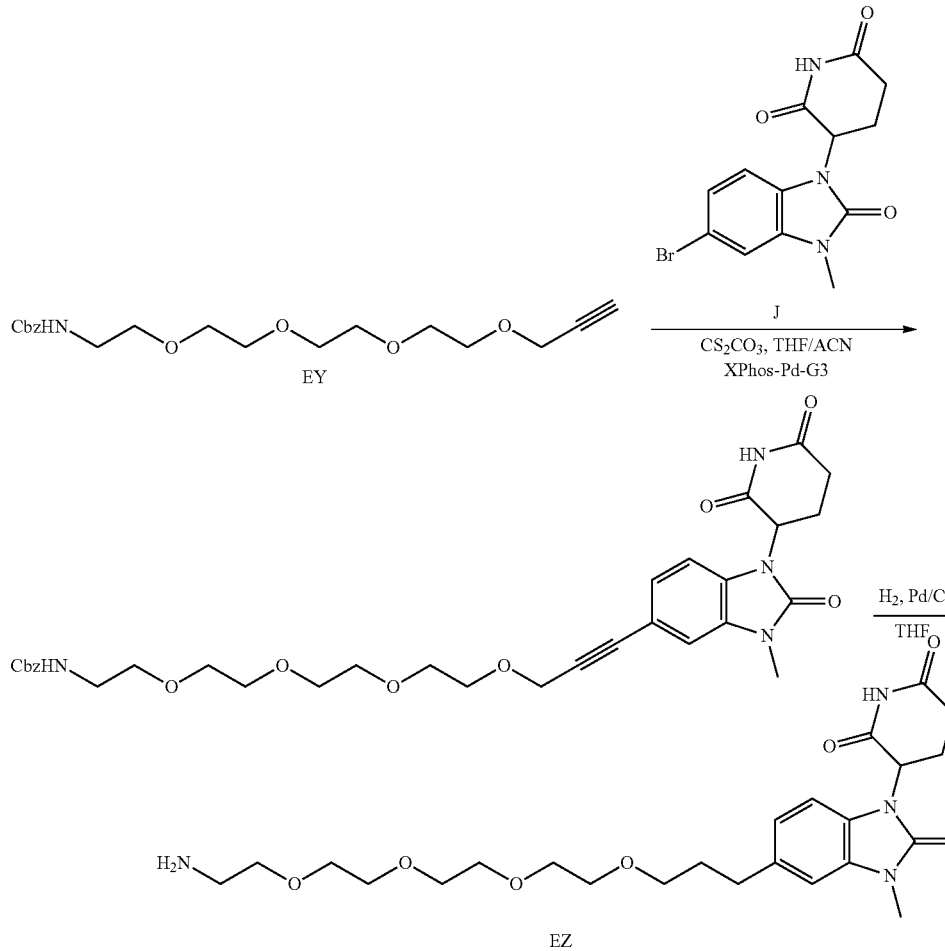

Step 1—Benzyl (15-(1-(2,6-dioxopiperidin-3-yl)-3-methyl-2-oxo-2,3-dihydro-1H-benzo[d]imidazol-5-yl)-3,6,9,12-tetraoxapentadec-14-yn-1-yl)carbamate To a solution of benzyl 3,6,9,12-tetraoxapentadec-14-yn-1-ylcarbamate (2.2 g, 6.02 mmol, Intermediate EY) and 3-(5-bromo-3-methyl-2-oxo-2,3-dihydro-1H-benzo[d]imidazol-1-yl)piperidine-2,6-dione (3.05 g, 9.03 mmol, Intermediate J) in THF (10 mL) and ACN (10 mL) was added XPhos Pd G3 (1.53 g, 1.81 mmol) and $Cs_2CO_3$ (11.8 g, 36.1 mmol) under $N_2$. The mixture was stirred at 20-60° C. for 12 h. On completion, the reaction mixture was quenched with sat. $NH_4Cl$ (20 mL) and extracted with EtOAC (30 mL×2). The combined organic layers were washed with brine (10 mL×3), dried over $Na_2SO_4$ and evaporated. The residue was purified by prep-HPLC (column: Phenomenex luna C18 250*50 mm*10 um; mobile phase: [water (0.225% FA)-ACN]; B %: 28%-55%, 18 min) to give the title compound (2.56 g, 68% yield) as a white gum. $^1$H NMR (400 MHz, DMSO-$d_6$) δ 11.12 (s, 1H), 7.37-7.29 (m, 6H), 7.29-7.25 (m, 1H), 7.19-7.11 (m, 2H), 5.39 (dd, J=5.6, 12.8 Hz, 1H), 5.01 (s, 2H), 4.39 (s, 2H), 3.66-3.61 (m, 2H), 3.60-3.55 (m, 2H), 3.54-3.48 (m, 8H), 3.41 (t, J=6 Hz, 2H), 3.34 (s, 3H), 3.14 (q, J=5.6 Hz, 2H), 2.94-2.83 (m, 1H), 2.76-2.57 (m, 2H), 2.08-2.00 (m, 1H).

Step 2—3-(5-(1-Amino-3,6,9,12-tetraoxapentadecan-15-yl)-3-methyl-2-oxo-2,3-dihydro-1H-benzo[d]imidazol-1-yl)piperidine-2,6-dione To a solution benzyl N-[2-[2-[2-[2-[3-[1-(2,6-dioxo-3-piperidyl)-3-methyl-2-oxo-benzimidazol-5-yl]prop-2-ynoxy]ethoxy]ethoxy]ethoxy]ethyl]carbamate (1 g, 2 mmol) in THF (5 mL) was added Pd/C (400 mg, 642 umol, 10 wt %) under $N_2$. The suspension was degassed under vacuum and purged with $H_2$ several times. The reaction was stirred at 20° C. for 17 h under $H_2$ atmosphere (15 PSI). On completion, the mixture was filtered and concentrated to afford the title compound (690 mg) as a white gum. $^1$H NMR (400 MHz, DMSO-$d_6$) δ 8.11-7.97 (m, 1H), 7.77 (br s, 1H), 7.44 (s, 1H), 7.24 (d, J=7.6 Hz, 1H), 7.21-7.12 (m, 2H), 7.05-6.97 (m, 1H), 6.90-6.80 (m, 1H), 5.33 (br dd, J=5.2, 12.6 Hz, 1H), 4.81 (br dd, J=4.8, 10.8 Hz, 1H), 3.54-3.45 (m, 8H), 3.39 (br d, J=4.4 Hz, 2H), 3.34 (br s, 3H), 2.70-2.58 (m, 3H), 2.18 (s, 1H), 2.04-1.93 (m, 1H), 1.81 (br s, 2H), 1.36 (s, 2H).

(1S,3R)-3-(1-(tert-butyl)-5-(1-(undec-10-yn-1-yl)-1H-pyrazole-4-carboxamido)-1H-pyrazol-3-yl)cyclopentyl isopropylcarbamate (Intermediate FA)

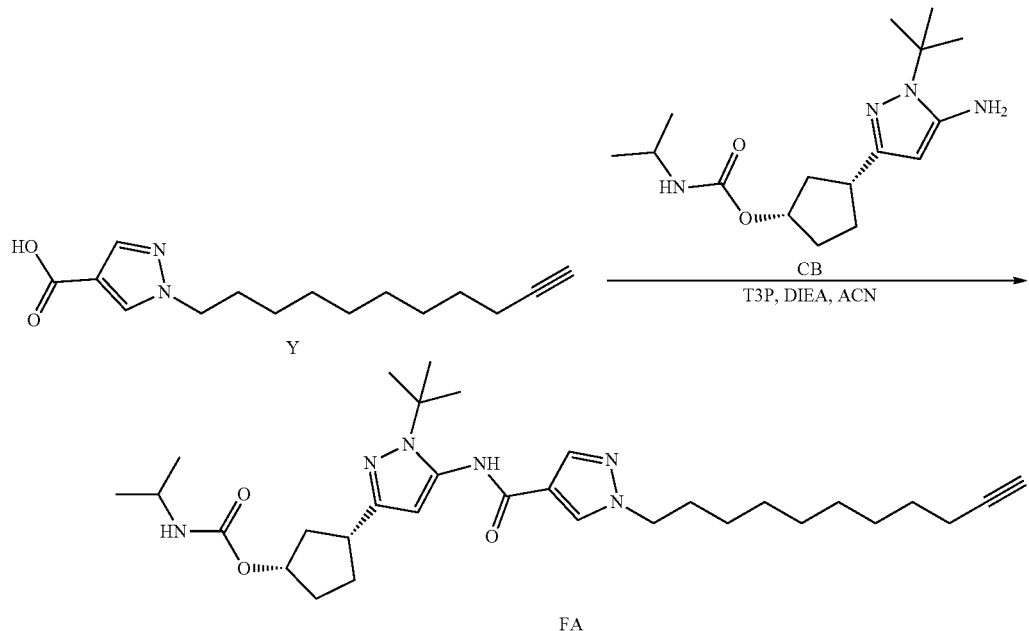

To a solution of 1-undec-10-ynylpyrazole-4-carboxylic acid (500 mg, 1.91 mmol, Intermediate Y) and [(1S,3R)-3-(5-amino-1-tert-butyl-pyrazol-3-yl)cyclopentyl] N-isopropylcarbamate (490 mg, 1.59 mmol, Intermediate CB) in ACN (8 mL) was added DIEA (1.03 g, 7.94 mmol, 1.38 mL) and T3P (3.03 g, 4.76 mmol) dropwise for one portion at 20° C. Then the mixture was stirred at 60° C. for 10 h. On completion, the reaction mixture was poured into ice water (10 mL) and extracted with EtOAc (10 mL×3). The combined organic layers were washed with brine (10 mL×3), dried over anhydrous Na$_2$SO$_4$, filtered and concentrated under reduced pressure to give a residue. The residue was purified by flash silica gel chromatography (ISCO®; 4 g SepaFlash® Silica Flash Column, Eluent of 0~30% Ethyl acetate/Petroleum ether gradient @ 50 mL/min) to give the title compound (325 mg, 37% yield) as a white solid. LC-MS (ESI$^+$) m/z 553.4 (M+H)$^+$.

(2S,4R)-1-((S)-14-amino-2-(tert-butyl)-4-oxo-6,9,12-trioxa-3-azatetradecan-1-oyl)-4-hydroxy-N-(4-(4-methylthiazol-5-yl)benzyl)pyrrolidine-2-carboxamide (Intermediate FB)

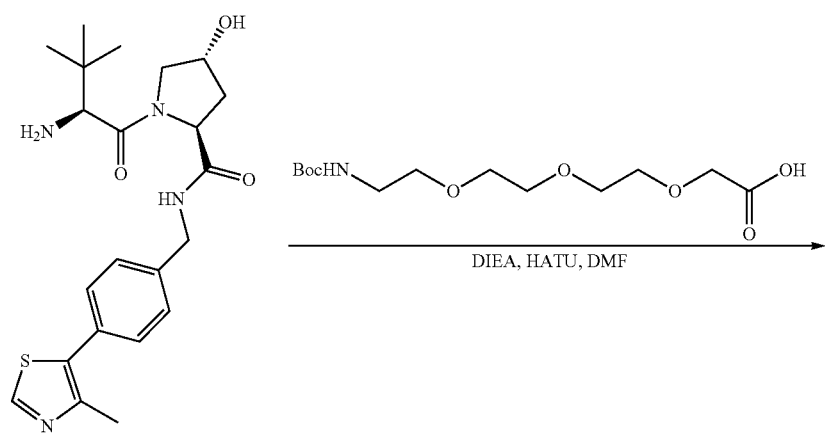

-continued

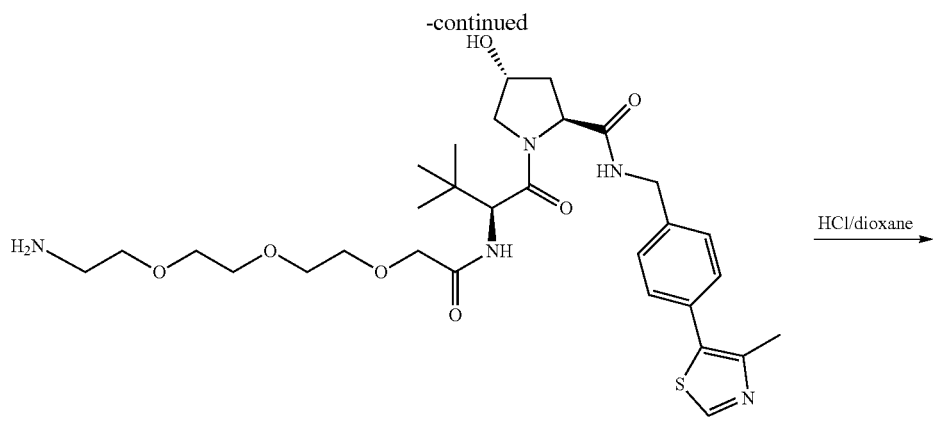

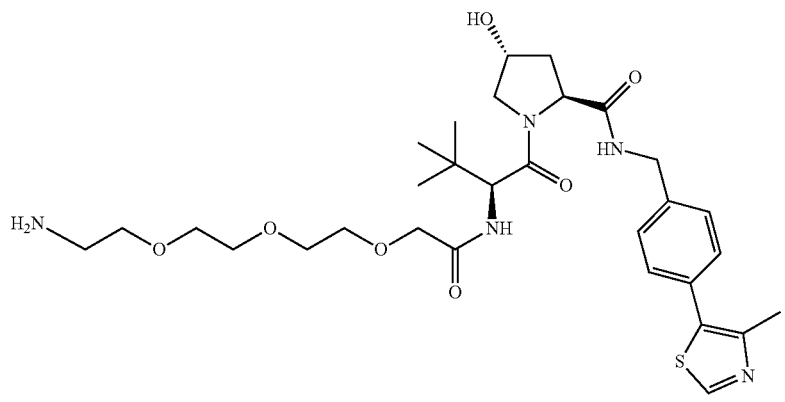

FB

Step 1—Tert-butyl ((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamate (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (233 mg, 542 umol, CAS #1448189-80-7), 2-[2-[2-[2-(tert-butoxycarbonylamino)ethoxy]ethoxy]ethoxy]acetic acid (200 mg, 651 umol, CAS #462100-06-7), DIEA (350 mg, 2.71 mmol), and HATU (247 mg, 651 umol) in DMF (10 mL) was added at 0° C. The mixture was stirred at 25° C. for 12 h. On completion, the mixture was quenched with water (10 mL), and extracted with DCM (10 mL×2). The combined organic layer was washed with brine (10 mL×3), dried by Na$_2$SO$_4$, concentrated in vacuo. The residue was purified by column chromatography (SiO$_2$, DCM/MeOH=10:1 to 2:1) to give the title compound (380 mg, 88% yield) as a yellow solid. LC-MS (ESI$^+$) m/z 620.4 (M+H)$^+$.

Step 2—(2S,4R)-1-((S)-14-amino-2-(tert-butyl)-4-oxo-6,9,12-trioxa-3-azatetradecan-1-oyl)-4-hydroxy-N-(4-(4-methylthiazol-5-yl)benzyl)pyrrolidine-2-carboxamide Tert-butyl ((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamate (0.19 g, 260 umol) in HCl/dioxane (2 mL) was stirred at 25° C. for 10 min. On completion, the mixture was concentrated in vacuo to give the title compound (150 mg, 83% yield) as a white solid. $^1$H NMR (400 MHz, DMSO-d6) δ=11.08-11.04 (m, 1H), 9.51 (s, 1H), 8.73 (s, 1H), 7.77-7.60 (m, 5H), 7.02-6.84 (m, 3H), 6.34-6.31 (d, J=9.2, 1H), 5.69-564 (m, 1H), 5.35-5.30 (m, 1H), 3.50-3.48 (m, 6H), 3.47-3.41 (m, 5H), 3.37-3.30 (m, 6H), 2.90 (s, 2H), 2.63-2.52 (m, 4H), 2.32 (s, 3H), 1.81-1.78 (m, 5H), 1.64-1.43 (m, 6H).

(2S,4R)-1-[(2S)-2-[[2-[2-[2-[2-(2-aminoethoxy)ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide
(Intermediate FC)
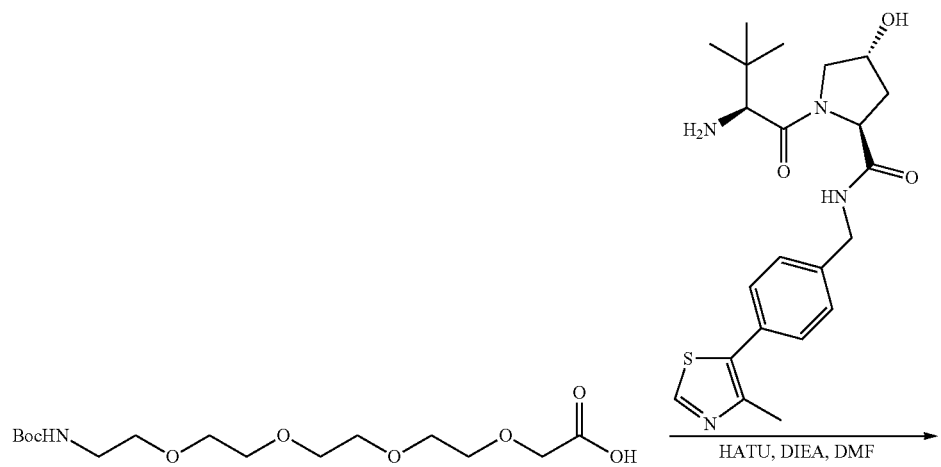
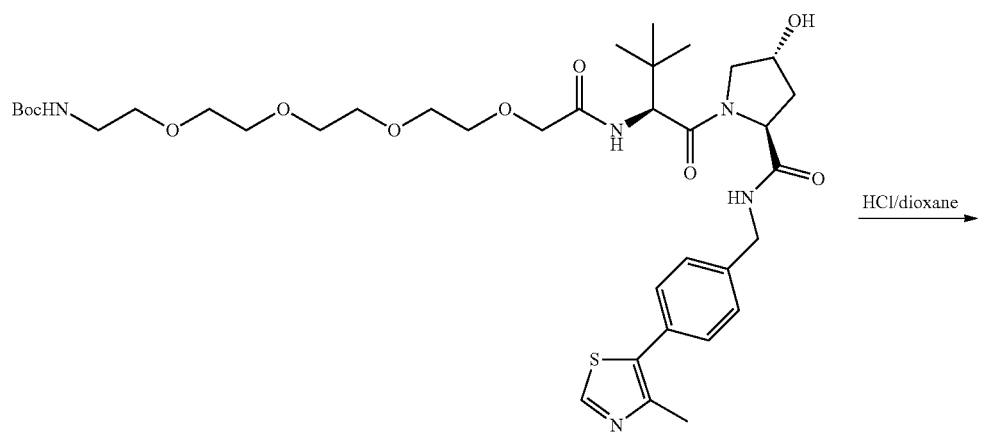
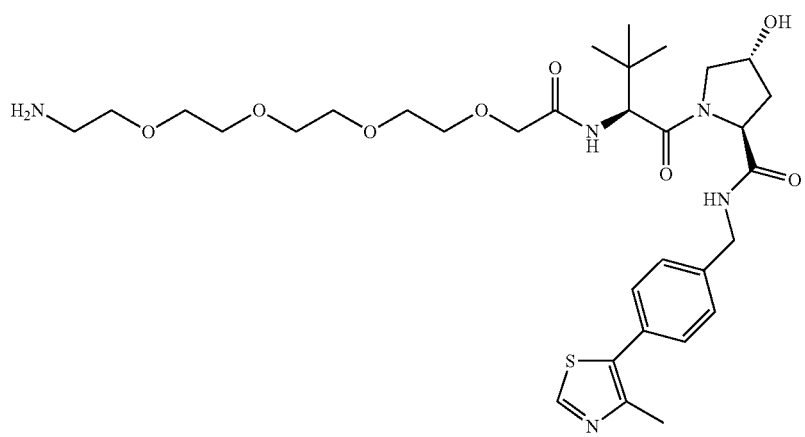
FC

Step 1—Tert-butyl N-[2-[2-[2-[2-[2-[[(1S)-1-[(2S, 4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]ethyl]carbamate To a solution of 2-[2-[2-[2-[2-(tert-butoxycarbonylamino)ethoxy]ethoxy]ethoxy]ethoxy]acetic acid (568 mg, 1.62 mmol, CAS #876345-13-0) (2S, 4R)-1-[(2S)-2-amino-3,3-dimethyl-butanoyl]-4-hydroxy-N-[[4-(4-methylthiazol-5-yl)phenyl]methyl]pyrrolidine-2-carboxamide (580 mg, 1.35 mmol, CAS #1448189-80-7) in DMF (10 mL) was added DIEA (870 mg, 6.74 mmol) and HATU (614.64 mg, 1.62 mmol) at 0° C. The mixture was then stirred at 25° C. for 2 hr. On completion, the reaction mixture was quenched with water 20 mL at 0° C. and extracted with ethyl acetate (10 mL×3). The combined organic layers were washed with salt solution (10 mL×3), dried over sodium sulfate, filtered and concentrated. The residue was purified by column chromatography (SiO$_2$, Petroleum ether/Ethyl acetate=10/1 to 0/1) to give the title compound (800 mg, 78% yield) as a yellow oil. $^1$H NMR (400 MHz, DMSO-d6) δ=9.01-8.96 (m, 1H), 8.59 (br t, J=5.6 Hz, 1H), 7.47-7.42 (m, 1H), 7.42-7.36 (m, 4H), 7.36-7.36 (m, 1H), 6.73 (brt, J=4.8 Hz, 1H), 5.15 (d, J=3.6 Hz, 1H), 4.56 (d, J=9.2 Hz, 1H), 4.37-4.36 (m, 1H), 4.48-4.36 (m, 1H), 4.29-4.20 (m, 1H), 4.01-3.90 (m, 2H), 3.70-3.43 (m, 16H), 3.17 (d, J=5.2 Hz, 1H), 3.04 (q, J=5.6 Hz, 2H), 2.46-2.43 (m, 3H), 2.06 (br dd, J=7.6, 12.8 Hz, 1H), 1.90 (ddd, J=4.0, 8.4, 12.8 Hz, 1H), 1.36 (s, 9H), 0.99-0.89 (m, 9H); LC-MS (ESI$^+$) m/z 764.4 (M+H)$^+$.

Step 2—(2S,4R)-1-[(2S)-2-[[2-[2-[2-[2-(2-aminoethoxy)ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide The solution of tert-butyl N-[2-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]ethyl]carbamate (400 mg, 524 umol) in DCM (2 mL) was added HCl/dioxane (4 mL, 4M), then the mixture was stirred at 25° C. for 1.5 h. On completion, the reaction mixture was concentrated in vacuo to give the title compound (200 mg, 55% yield, HCl) as a yellow solid. $^1$H NMR (400 MHz, DMSO-d6) δ=9.02 (s, 1H), 8.62 (t, J=6.0 Hz, 1H), 8.04-7.75 (m, 3H), 7.52-7.46 (m, 1H), 7.40 (s, 4H), 4.56 (d, J=9.4 Hz, 1H), 4.47-4.37 (m, 2H), 4.36 (br s, 1H), 4.30-4.21 (m, 1H), 3.98 (s, 2H), 3.63-3.57 (m, 8H), 3.56-3.52 (m, 8H), 2.98-2.92 (m, 2H), 2.45 (s, 3H), 2.13-2.01 (m, 1H), 1.90 (ddd, J=4.4, 8.8, 13.2 Hz, 1H), 0.98-0.91 (m, 9H). LC-MS (ESI$^+$) m/z 664.3 (M+H)$^+$.

3-[5-[3-(2-azidoethoxy)propyl]-3-methyl-2-oxo-benzimidazol-1-yl]piperidine-2,6-dione (Intermediate FD)

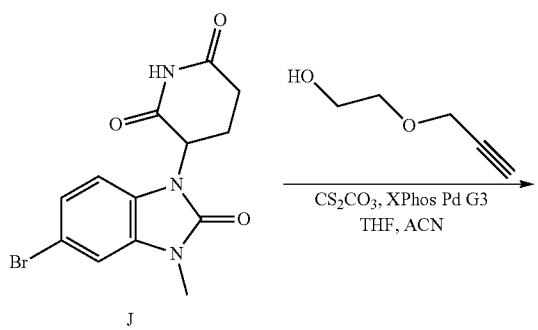

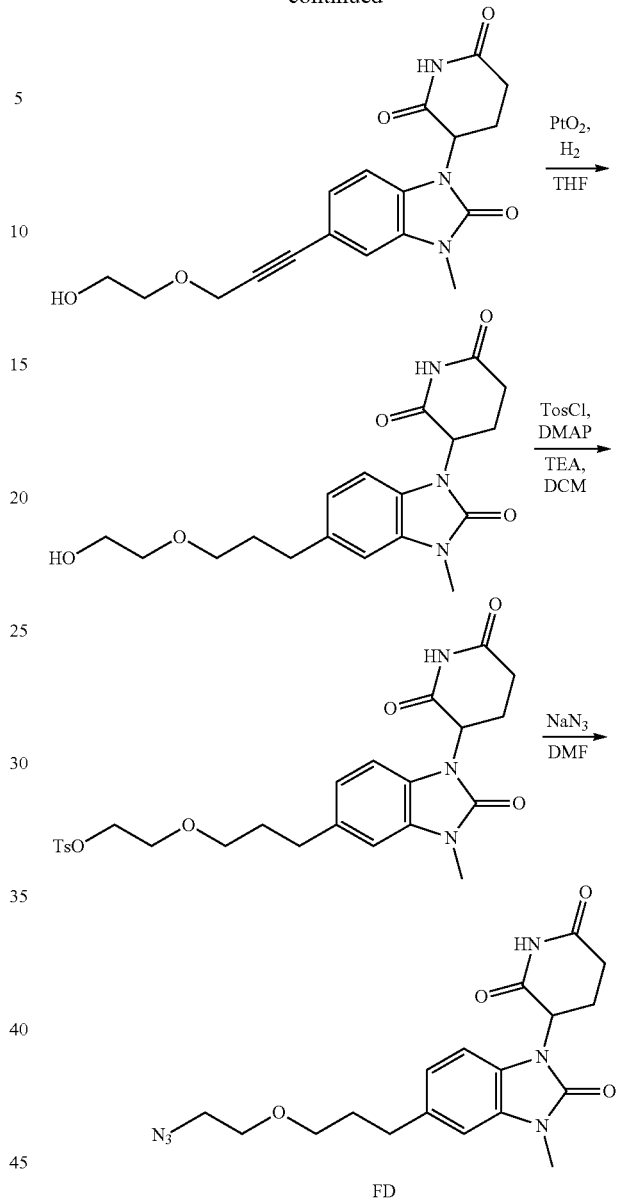

Step 1—3-[5-[3-(2-Hydroxyethoxy)prop-1-ynyl]-3-methyl-2-oxo-benzimidazol-1-yl]piperidine-2,6-dione To a solution of 2-prop-2-ynoxyethanol (500 mg, 4.99 mmol, CAS #3973-18-0) and 3-(5-bromo-3-methyl-2-oxo-benzimidazol-1-yl)piperidine-2,6-dione (2.03 g, 5.99 mmol, Intermediate J) in ACN (10 mL) and THF (10 mL) was added XPhos Pd G3 (845 mg, 999 umol) and Cs$_2$CO$_3$ (4.88 g, 14.9 mmol). The mixture was stirred at 60° C. for 12 h under nitrogen atmosphere. On completion, the reaction mixture was quenched with NH$_4$Cl solution (20 mL) and extracted with ethyl acetate (10 mL×3). The combined organic layer was washed with brine (10 mL×3), dried over Na$_2$SO$_4$, filtered and concentrated. The crude product was purified by column chromatography (SiO$_2$, Petroleum ether/Ethyl acetate=10/1 to 0/1) to give the title compound (550 mg, 31% yield) as a yellow solid. $^1$H NMR (400 MHz, DMSO-d6) δ=11.1 (s, 1H), 7.33 (s, 1H), 7.20-7.09 (m, 2H), 5.39 (dd, J=5.6, 13.2 Hz, 1H), 4.78-4.52 (m, 1H), 4.39 (s, 2H), 4.03 (q, J=7.2 Hz, 1H), 3.56-3.53 (m, 3H), 3.34 (s, 4H), 2.77-2.56 (m, 4H); LC-MS (ESI⁺) m/z 358.1 (M+H)⁺.

Step 2—3-[5-[3-(2-Hydroxyethoxy)propyl]-3-methyl-2-oxo-benzimidazol-1-yl]piperidine-2,6-dione To a solution of 3-[5-[3-(2-hydroxyethoxy) prop-1-ynyl]-3-methyl-2-oxo-benzimidazol-1-yl] piperidine-2, 6-dione (550 mg, 1.5 mmol) in THF (6 mL) was added PtO₂ (69.9 mg, 308 umol) under H₂, the mixture was stirred at 25° C. for 2 h. On completion, the reaction mixture was filtered with diatomite. The organic phase was concentrated under reduced pressure. The crude product was purified by column chromatography (SiO₂, Petroleum ether/Ethyl acetate=10/1 to 0/1) to give the title compound (300 mg, 54% yield) as a yellow solid. ¹H NMR (400 MHz, DMSO-d6) δ=11.08 (s, 1H), 7.04 (d, J=1.2 Hz, 1H), 7.00 (d, J=8.4 Hz, 1H), 6.87 (dd, J=1.6, 8.4 Hz, 1H), 5.33 (dd, J=5.6, 12.8 Hz, 1H), 4.63-4.51 (m, 1H), 3.51 (q, J=5.6 Hz, 2H), 3.44-3.35 (m, 4H), 3.30 (s, 3H), 2.95-2.84 (m, 1H), 2.75-2.57 (m, 4H), 2.05-1.95 (m, 1H), 1.86-1.76 (m, 2H); LC-MS (ESI⁺) m/z 362.0 (M+H)⁺.

Step 3—2-[3-[1-(2,6-Dioxo-3-piperidyl)-3-methyl-2-oxo-benzimidazol-5-yl]propoxy]ethyl 4-methyl-benzenesulfonate To a solution of 3-[5-[3-(2-hydroxyethoxy)propyl]-3-methyl-2-oxo-benzimidazol-1-yl]piperidine-2,6-dione (150 mg, 415 umol) and TEA (126 mg, 1.25 mmol, 173 uL) in DCM (3 mL) was added TosCl (119 mg, 623 umol) and DMAP (10.1 mg, 83.0 umol) at 0° C. under N₂. Then the mixture was stirred at 25° C. for 12 h. On completion, the reaction mixture was quenched with NaHCO₃ solution (30 mL) at 0° C. and extracted with DCM (10 mL×3). The combined organic layer was washed with brine (10 mL×3), dried over Na₂SO4, filtered and concentrated. The residue was purified by column chromatography (SiO₂, Petroleum ether/Ethyl acetate=10/1 to 0/1) to give the title compound (179 mg, 84% yield) as a yellow solid. ¹H NMR (400 MHz, DMSO-d6) δ=11.08 (s, 1H), 7.79 (d, J=8.4 Hz, 2H), 7.47 (d, J=8.4 Hz, 2H), 7.09-6.92 (m, 2H), 6.84 (d, J=8.4 Hz, 1H), 5.33 (dd, J=5.2, 12.8 Hz, 1H), 4.17-4.10 (m, 2H), 3.58-3.50 (m, 2H), 3.30 (br s, 3H), 2.94-2.85 (m, 1H), 2.76-2.62 (m, 2H), 2.60-2.55 (m, 2H), 2.53-2.51 (m, 2H), 2.40 (s, 3H), 2.05-1.99 (m, 1H), 1.79-1.67 (m, 2H); LC-MS (ESI⁺) m/z 516.4 (M+H)⁺.

Step 4—3-[5-[3-(2-azidoethoxy)propyl]-3-methyl-2-oxo-benzimidazol-1-yl]piperidine-2,6-dione To a solution of 2-[3-[1-(2,6-dioxo-3-piperidyl)-3-methyl-2-oxo-benzimidazol-5-yl]propoxy]ethyl 4-methyl-benzenesulfonate (170 mg, 330 umol) in DMF (2 mL) was added NaN₃ (23.6 mg, 362 umol) at 0° C. under N₂. The mixture was then stirred at 40° C. for 12 h. On completion, the reaction was poured into NaHCO₃ solution (10 mL) at 0° C. and extracted with ethyl acetate (10 mL×2). The combined organic phase was washed with brine (10 mL×2), dried over Na₂SO₄, then filtered to get the filtrate and concentrated to give a residue. The residue was purified by prep-HPLC (column: Phenomenex Luna C18 150*25 mm*10 um; mobile phase: [water (0.225% FA)-ACN]; B %: 25%-55%, 10 min) to give the title compound (70 mg, 53% yield) as a yellow oil. LC-MS (ESI⁺) m/z 387.1 (M+H)⁺.

Tert-butyl 6-(2-(tosyloxy)ethoxy)-2-azaspiro[3.3]heptane-2-carboxylate (Intermediate FE)

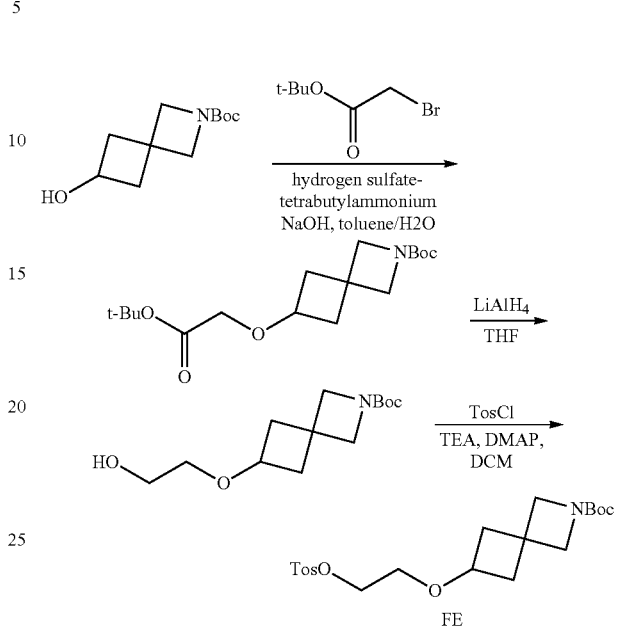

Step 1—Tert-butyl 6-(2-(tert-butoxy)-2-oxoethoxy)-2-azaspiro[3.3]heptane-2-carboxylate To a solution of tert-butyl 6-hydroxy-2-azaspiro[3.3]heptane-2-carboxylate (10 g, 46.8 mmol, CAS #1147557-97-8), tert-butyl 2-bromoacetate (13.7 g, 70.3 mmol) and hydrogen sulfate tetrabutylammonium (1.59 g, 4.69 mmol) in toluene (10 mL) and H₂O (1 mL) was added NaOH (9.38 g, 234 mmol) and the mixture was stirred at rt for 12 hrs. On completion, the reaction mixture was quenched with aqueous NH₄Cl 100 mL at 0° C., and then diluted with H₂O (100 mL) and extracted with EtOAc (150 mL×2). The combined organic layers were dried over Na₂SO₄, filtered and concentrated under reduced pressure to give a residue. The residue was purified by column chromatography (SiO₂, Petroleum ether/Ethyl acetate=10/1 to 3/1) to give the title compound (11 g, 72% yield) as a yellow oil. ¹H NMR (400 MHz, CDCl₃) δ=3.92-3.84 (m, 1H), 3.83-3.77 (m, 6H), 2.47-2.35 (m, 2H), 2.19-2.05 (m, 2H), 1.40 (s, 9H), 1.35 (s, 9H); LC-MS (ESI⁺) m/z 328.2 (M+H)⁺.

Step 2—Tert-butyl 6-(2-hydroxyethoxy)-2-azaspiro[3.3]heptane-2-carboxylate

To a solution of tert-butyl 6-(2-tert-butoxy-2-oxoethoxy)-2-azaspiro[3.3]heptane-2-carboxylate (10 g, 30.5 mmol) in THF (150 mL) was added LiAlH₄ (2.32 g, 61.0 mmol). The mixture was stirred at 0° C. for 2 h. On completion, the reaction mixture was quenched with H₂O (4 mL) and NaOH (15%, 4 mL) at 0° C., and then stirred at 25° C. for 30 min. Then the mixture was filtered and concentrated under reduced pressure to give the title compound (5 g) as a yellow oil. LC-MS (ESI⁺) m/z 258.2 (M+H)⁺.

Step 3—Tert-butyl 6-(2-(tosyloxy)ethoxy)-2-azaspiro[3.3]heptane-2-carboxylate

To a solution of tert-butyl 6-(2-hydroxyethoxy)-2-azaspiro[3.3]heptane-2-carboxylate (5 g, 20 mmol) in DCM (50 mL) was added TEA (5.90 g, 58.2 mmol), TosCl (4.45 g, 23.3 mmol) and DMAP (474 mg, 3.89 mmol). The mixture was stirred at 20° C. for 12 h. On completion, the reaction mixture was quenched with aqueous NH₄Cl (50 mL), and then diluted with H₂O (50 mL) and extracted with DCM (50 mL×3). The combined organic layers were washed dried over Na₂SO₄, filtered and concentrated under reduced pressure to give a residue. The residue was purified by column chromatography (SiO₂, Petroleum ether/Ethyl acetate=10/1 to 4/1) to give the title compound (1.8 g, 22. % yield) as a yellow oil. LC-MS (ESI⁺) m/z 356.2 (M+H)⁺.

3-(5-(1-(2-(2-azaspiro[3.3]heptan-6-yloxy)ethyl)piperidin-4-yl)-3-methyl-2-oxo-2,3-dihydro-1H-benzo[d]imidazol-1-yl)piperidine-2,6-dione (Intermediate FF)

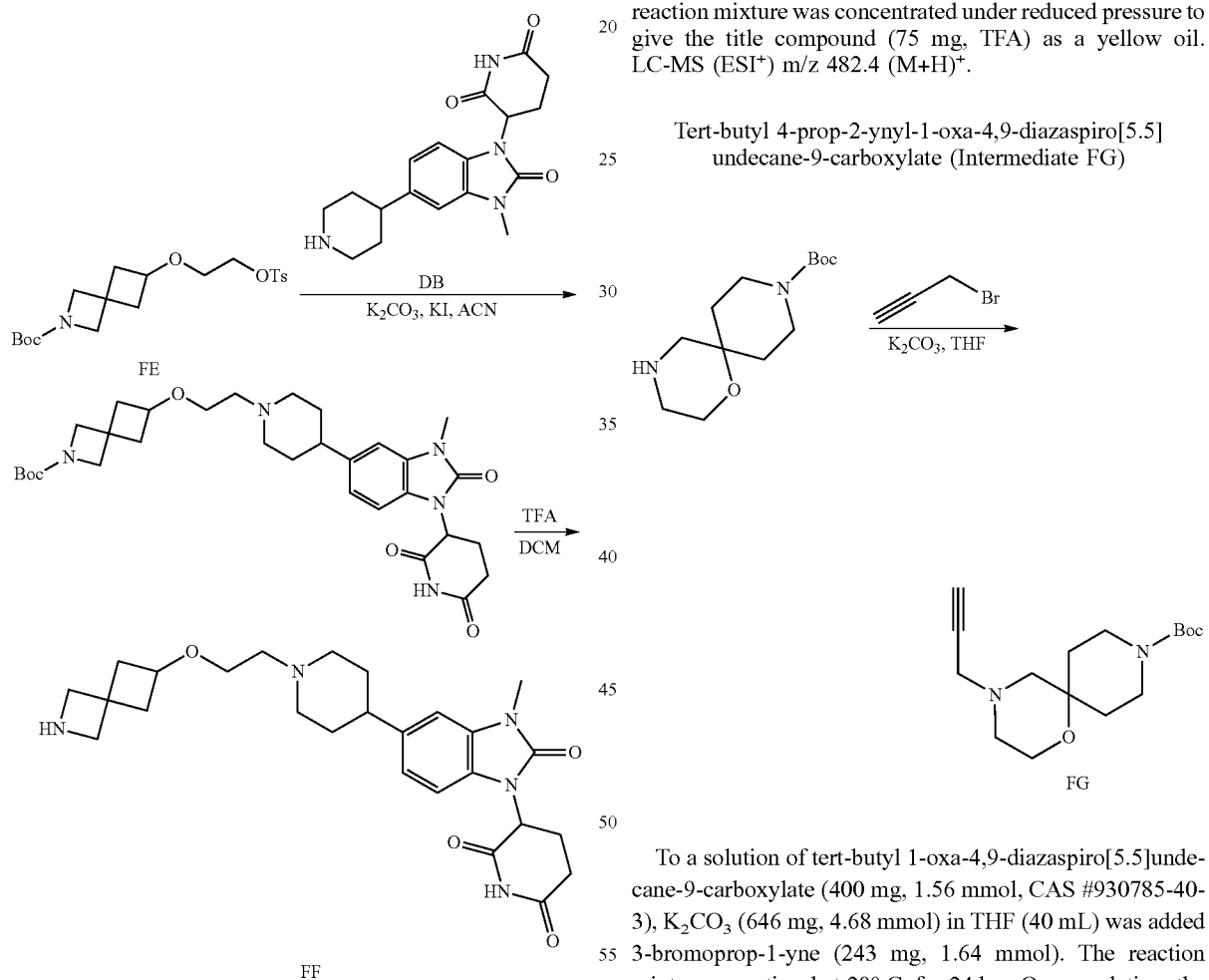

Step 1—Tert-butyl 6-(2-(4-(1-(2,6-dioxopiperidin-3-yl)-3-methyl-2-oxo-2,3-dihydro-1H-benzo[d]imidazol-5-yl)piperidin-1-yl)ethoxy)-2-azaspiro[3.3]heptane-2-carboxylate To a solution of 3-[3-methyl-2-oxo-5-(4-piperidyl)benzimidazol-1-yl]piperidine-2,6-dione (300 mg, 876 umol, Intermediate DB) and tert-butyl 6-[2-(p-tolylsulfonyloxy)ethoxy]-2-azaspiro[3.3]heptane-2-carboxylate (360 mg, 876 umol, Intermediate FE) MACN (3 mL) was added K₂CO₃ (605 mg, 4.38 mmol) and KI (14.5 mg, 87.6 umol). The mixture was stirred at 60° C. for 12 h. On completion, the reaction mixture was concentrated under reduced pressure to give a residue. The residue was purified by prep-HPLC (FA condition) to give the title compound (80 mg, 15% yield) as a white solid. LC-MS (ESI⁺) m/z 582.4 (M+H)⁺.

Step 2—3-(5-(1-(2-(2-Azaspiro[3.3]heptan-6-yloxy)ethyl)piperidin-4-yl)-3-methyl-2-oxo-2,3-dihydro-1H-benzo[d]imidazol-1-yl)piperidine-2,6-dione To a solution of tert-butyl 6-[2-[4-[1-(2,6-dioxo-3-piperidyl)-3-methyl-2-oxo-benzimidazol-5-yl]-1-piperidyl]ethoxy]-2-azaspiro[3.3]heptane-2-carboxylate (80 mg, 140 umol) in DCM (2 mL) was added TFA (15.6 mg, 137 umol). The mixture was stirred at 20° C. for 1 h. On completion, the reaction mixture was concentrated under reduced pressure to give the title compound (75 mg, TFA) as a yellow oil. LC-MS (ESI⁺) m/z 482.4 (M+H)⁺.

Tert-butyl 4-prop-2-ynyl-1-oxa-4,9-diazaspiro[5.5]undecane-9-carboxylate (Intermediate FG)

To a solution of tert-butyl 1-oxa-4,9-diazaspiro[5.5]undecane-9-carboxylate (400 mg, 1.56 mmol, CAS #930785-40-3), K₂CO₃ (646 mg, 4.68 mmol) in THF (40 mL) was added 3-bromoprop-1-yne (243 mg, 1.64 mmol). The reaction mixture was stirred at 20° C. for 24 hrs. On completion, the reaction mixture was concentrated in vacuo. The residue was diluted with H₂O (30 mL), and extracted with EA (3×20 mL). The organic layers were washed with brine (2×15 mL), dried over anhydrous Na₂SO₄, filtered and concentrated in vacuo to give the title compound (450 mg, 97% yield) as yellow oil. ¹H NMR (400 MHz, CDCl₃) δ 3.82-3.65 (m, 4H), 3.27 (d, J=2.4 Hz, 2H), 3.22-3.10 (m, 2H), 2.55-2.50 (m, 2H), 2.37 (s, 2H), 2.29-2.26 (m, 1H), 1.99-1.90 (m, 2H), 1.53-1.45 (m, 11H).

779

3-(4-(Hydroxymethyl)-3-methyl-2-oxo-2,3-dihydro-1H-benzo[d]imidazol-1-yl)piperidine-2,6-dione (Intermediate FH)

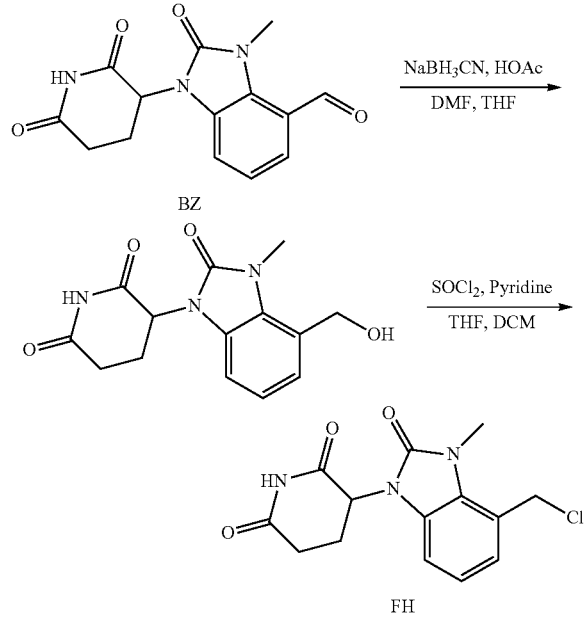

Step 1—3-(4-(Hydroxymethyl)-3-methyl-2-oxo-2,3-dihydro-1H-benzo[d]imidazol-1-yl)piperidine-2,6-dione To a solution of 1-(2,6-dioxo-3-piperidyl)-3-methyl-2-oxo-benzimidazole-4-carbaldehyde (7.00 g, 24.3 mmol, Intermediate BZ) and HOAc (4.39 g, 73.1 mmol) in DMF (50 mL) and THF (50 mL) was added NaBH₃CN (6.13 g, 97.4 mmol) at 60° C. portion-wise, then the mixture was stirred at 60° C. for 2 hours. On completion, the reaction was quenched with 5 mL of water and filtered and the filtrate was concentrated. The residue was purified by reverse phase (FA) to give the title compound (5.00 g, 70% yield) as a white solid. $^1$H NMR (400 MHz, DMSO-$d_6$) δ 11.10 (s, 1H), 7.13-6.89 (m, 3H), 5.38 (d, J=5.4, 12.4 Hz, 1H), 4.74 (s, 2H), 3.62 (s, 3H), 2.95-2.86 (m, 1H), 2.78-2.60 (m, 2H), 2.10-1.95 (m, 1H).

Step 2—3-(4-(Hydroxymethyl)-3-methyl-2-oxo-2,3-dihydro-1H-benzo[d]imidazol-1-yl)piperidine-2,6-dione To a solution of 3-[4-(hydroxymethyl)-3-methyl-2-oxo-benzimidazol-1-yl]piperidine-2,6-dione (5.00 g, 17.2 mmol) and pyridine (273 mg, 3.46 mmol) in THF (30 mL) and DCM (30 mL) was added SOCl₂ (6.17 g, 51.8 mmol), then the mixture was stirred at 20° C. for 12 hrs. On completion, the reaction was concentrated to give the title compound (8.00 g, 90% yield) as a white solid. $^1$H NMR (400 MHz, DMSO-$d_6$) δ 11.08 (s, 1H), 7.19-6.99 (m, 3H), 5.32 (dd, J=5.2, 12.4 Hz, 1H), 5.03 (s, 2H), 3.65 (s, 3H), 2.92-2.80 (m, 1H), 2.73-2.59 (m, 2H), 2.10-1.98 (m, 1H).

780

Benzyl 4-(4-(prop-2-yn-1-yl)piperazin-1-yl)piperidine-1-carboxylate (Intermediate FI)

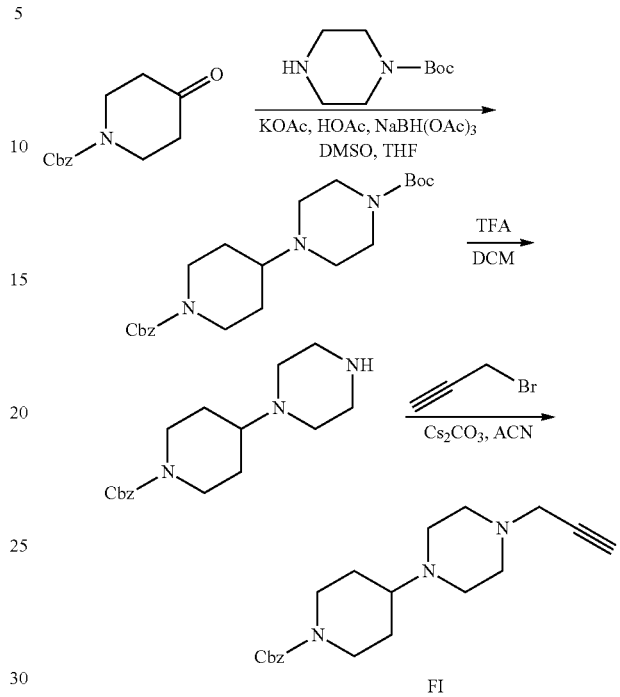

Step 1—Tert-butyl 4-(1-((benzyloxy)carbonyl)piperidin-4-yl)piperazine-1-carboxylate To a solution of benzyl 4-oxopiperidine-1-carboxylate (5 g, 20 mmol, CAS #19099-93-5) and tert-butyl piperazine-1-carboxylate (4.77 g, 21.4 mmol, CAS #57260-71-6) in DMSO (25 mL) and THF (25 mL) was added KOAc (6.31 g, 64.31 mmol) 4A molecular sieves (1 g) and HOAc (3.86 g, 64.3 mmol) and the mixture was stirred at 0° C. for 30 min. Then NaBH(OAc)₃ (13.63 g, 64.31 mmol) was added and the mixture was stirred at 0-20° C. for 12 h. The reaction mixture was quenched with H₂O (50 mL) at 0° C., and then diluted with EtOAc (50 mL) and extracted with EtOAc (50 mL×3). The combined organic layers were washed with sat. NaCl (50 mL×3), dried over Na₂SO₄, filtered and concentrated under reduced pressure to give the title compound (4 g, 46% yield) as a white solid. $^1$H NMR (400 MHz, DMSO-d6) δ=7.45-7.22 (m, 7H), 5.06 (s, 3H), 4.01 (br d, J=13.2 Hz, 2H), 3.78-3.59 (m, 2H), 3.46-3.37 (m, 1H), 3.06 (br s, 1H), 2.92-2.63 (m, 2H), 2.41 (br s, 5H), 1.91 (s, 1H), 1.71 (br d, J=12.2 Hz, 3H), 1.38 (s, 9H), 1.33-1.20 (m, 4H); LC-MS (ESI⁺) m/z 404.5 (M+H)⁺.

Step 2—Benzyl 4-(piperazin-1-yl)piperidine-1-carboxylate

To a solution of tert-butyl 4-(1-((benzyloxy)carbonyl)piperidin-4-yl)piperazine-1-carboxylate (100 mg, 300 umol) in DCM (1 mL) was added TFA (28.2 mg, 247 umol). The mixture was stirred at 25° C. for 4 hr. The reaction mixture was filtered and concentrated under reduced pressure to give the title compound (70 mg) as an orange solid. LC-MS (ESI⁺) m/z 304 (M+H)⁺

Step 3—Benzyl 4-(4-(prop-2-yn-1-yl)piperazin-1-yl)piperidine-1-carboxylate

To a solution of benzyl 4-(piperazin-1-yl)piperidine-1-carboxylate (2.3 g, 7.6 mmol) and 3-bromoprop-1-yne (811.63 mg, 6.82 mmol, CAS #106-96-7) in ACN (25 mL) was added $K_2CO_3$ (10.4 g, 75.8 mmol). The mixture was stirred at 20° C. for 10 h under $N_2$ atmosphere. The reaction mixture was quenched with $H_2O$ (25 mL) at 25° C., and then diluted with EtOAc (25 mL) and extracted with EtOAc (25 mL×3). The combined organic layers were washed with sat. NaCl (25 mL×3), dried over $Na_2SO_4$, filtered and concentrated under reduced pressure to give a residue. The residue was purified by prep-HPLC (column: Phenomenex Gemini 150*25 mm*10 um; mobile phase: [water (0.05% NH3H2O)-ACN]; B %: 25%-55%, 10 min) to give the title compound as a white solid. $^1H$ NMR (400 MHz, DMSO-d6) δ=8.20 (s, 2H), 7.37-7.33 (m, 3H), 5.76 (s, 1H), 5.12-5.00 (m, 2H), 4.62-4.46 (m, 1H), 4.01 (br d, J=13.0 Hz, 2H), 3.53 (br s, 1H), 3.23 (d, J=2.4 Hz, 1H), 2.94-2.71 (m, 3H), 2.45 (br s, 5H), 1.75 (br d, J=10.4 Hz, 3H), 1.29 (dq, J=3.8, 11.8 Hz, 2H); LC-MS (ESI+) m/z 342.4 (M+H)+.

3-(3-methyl-2-oxo-5-(3-(4-(piperidin-4-yl)piperazin-1-yl)propyl)-2,3-dihydro-1H-benzo[d]imidazol-1-yl)piperidine-2,6-dione (Intermediate FJ)

Step 1—Benzyl 4-(4-(3-(1-(2,6-dioxopiperidin-3-yl)-3-methyl-2-oxo-2,3-dihydro-1H-benzo[d]imidazol-5-yl)prop-2-yn-1-yl)piperazin-1-yl)piperidine-1-carboxylate To a solution of benzyl 4-(4-(prop-2-yn-1-yl)piperazin-1-yl)piperidine-1-carboxylate (270 mg, 790 umol, Intermediate FI) and 3-(5-bromo-3-methyl-2-oxo-benzimidazol-1-yl)piperidine-2,6-dione (320 mg, 948 umol, Intermediate J) in THF (1.5 mL) and ACN (1.5 mL) was added XPhos Pd G3 (200 mg, 237 umol) and $Cs_2CO_3$ (1.29 g, 3.95 mmol). The mixture was stirred at 60° C. for 12 h under $N_2$ atmosphere. On completion, the reaction mixture was quenched with $NH_4Cl$ (5 mL) at 0° C., and then diluted with EtOAc (5 mL) and extracted with EtOAc (5 mL×3). The combined organic layers were washed with sat. NaCl (5 mL×3), dried over $Na_2SO_4$, filtered and concentrated under reduced pressure to give a residue. The residue was purified by prep-HPLC (FA condition) to give the title compound (380 mg, 80% yield) as a white solid. $^1H$ NMR (400 MHz, DMSO-d6) δ=11.11 (s, 1H), 8.14 (s, 1H), 7.43-7.27 (m, 6H), 7.19-7.06 (m, 2H), 5.38 (dd, J=5.3, 12.8 Hz, 1H), 5.05 (s, 2H), 4.01 (br d, J=13.0 Hz, 3H), 3.48 (s, 5H), 2.93-2.73 (m, 4H), 2.73-2.58 (m, 3H), 2.44-2.30 (m, 2H), 2.10-1.94 (m, 1H), 1.75 (br d, J=11.2 Hz, 2H), 1.28 (dq, J=4.0, 11.8 Hz, 2H); LC-MS (ESI+) m/z 599.3 (M+H)+.

Step 2—3-(3-methyl-2-oxo-5-(3-(4-(piperidin-4-yl)piperazin-1-yl)propyl)-2,3-dihydro-1H-benzo[d]imidazol-1-yl)piperidine-2,6-dione To a solution of benzyl 4-(4-(3-(1-(2,6-dioxopiperidin-3-yl)-3-methyl-2-oxo-2,3-dihydro-1H-benzo[d]imidazol-5-yl)prop-2-yn-1-yl)piperazin-1-yl)piperidine-1-carboxylate (310 mg, 520 umol) in THF (15 mL) was added Pd/C (548 mg, 517 umol, 10 wt %). The mixture was stirred at 20° C. for 4 h under $H_2$ atmosphere. On completion, the reaction mixture was filtered and concentrated under reduced pressure to give a residue. The residue was purified by prep-HPLC (column: Welch Xtimate C18 150*25 mm*5 um; mobile phase: [water (0.05% HCl)-ACN]; B %: 0%-20%, 10 min) to give the title compound (80 mg, 33% yield) as a white oil. LC-MS (ESI+) m/z 469.4 (M+H)+.

3-(4-(3-(1-oxa-4,9-diazaspiro[5.5]undecan-4-yl)propyl)-3-methyl-2-oxo-2,3-dihydro-1H-benzo[d]imidazol-1-yl)piperidine-2,6-dione (Intermediate FK)

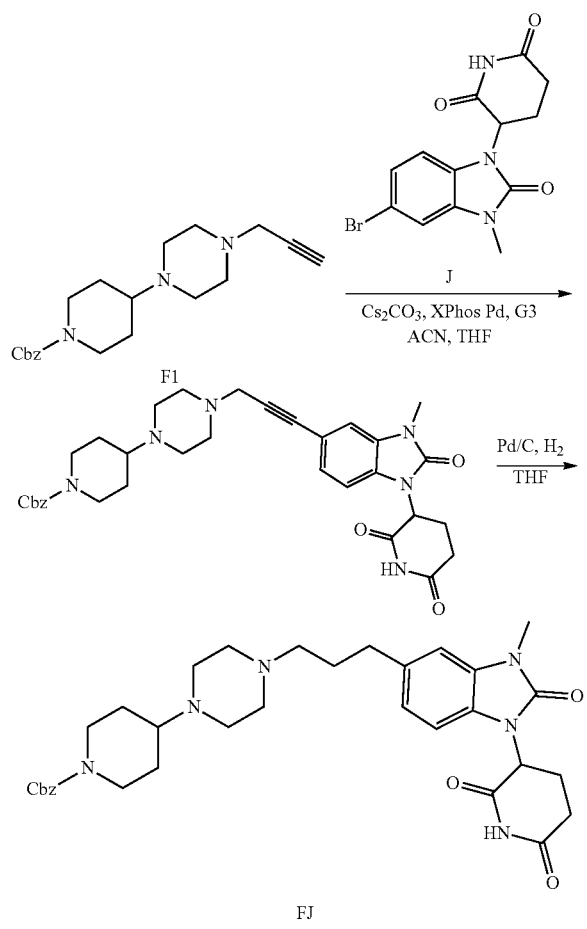

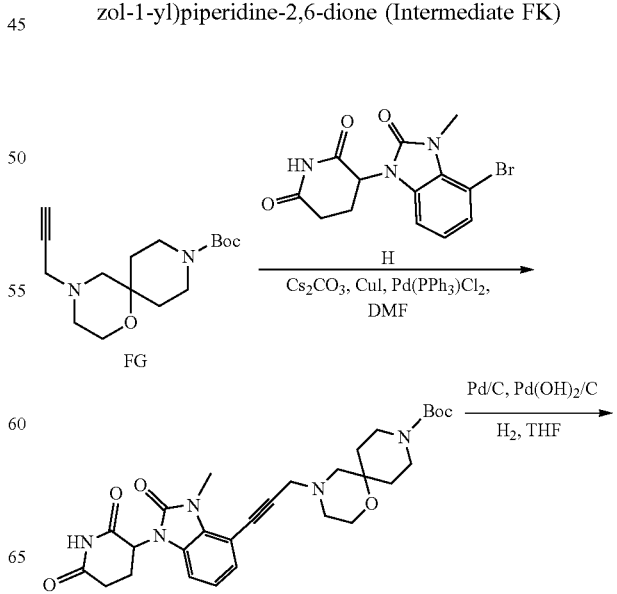

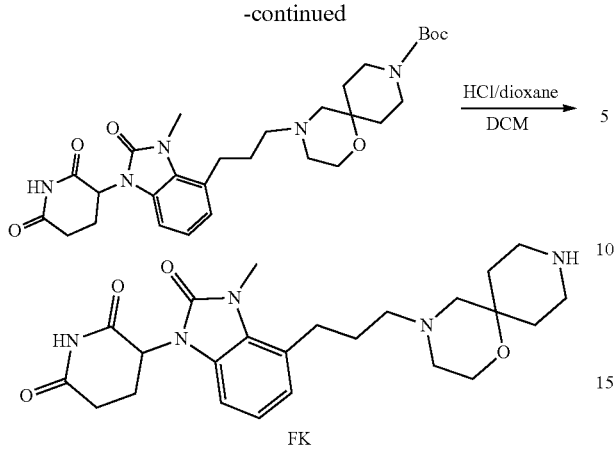

FK

Step 1—Tert-butyl 4-[3-[1-(2,6-dioxo-3-piperidyl)-3-methyl-2-oxo-benzimidazol-4-yl]prop-2-ynyl]-1-oxa-4,9-diazaspiro[5.5]undecane-9-carboxylate To a solution of tert-butyl 4-prop-2-ynyl-1-oxa-4,9-diazaspiro[5.5]undecane-9-carboxylate (450 mg, 1.53 mmol, Intermediate FG), 3-(4-bromo-3-methyl-2-oxo-benzimidazol-1-yl)piperidine-2,6-dione (344 mg, 1.02 mmol, Intermediate H) in DMF (5 mL) was added Pd(PPh$_3$)$_2$Cl$_2$ (143 mg, 203 umol), CuI (38.8 mg, 203 umol) and Cs$_2$CO$_3$ (1.33 g, 4.08 mmol). The reaction mixture was stirred at 80° C. for 3 hrs. On completion, the reaction mixture was filtered and concentrated in vacuo. The residue was purified by reverse phase: (0.1% FA) to give the title compound (400 mg, 71% yield) as yellow solid. $^1$H NMR (400 MHz, DMSO-d$_6$) δ 11.12 (s, 1H), 7.20-7.09 (m, 2H), 7.06-6.99 (m, 1H), 5.47-5.32 (m, 1H), 3.70-3.62 (m, 5H), 3.61-3.54 (m, 4H), 3.11-2.99 (m, 2H), 2.94-2.83 (m, 1H), 2.78-2.68 (m, 1H), 2.66-2.57 (m, 1H), 2.43-2.35 (m, 2H), 2.08-1.98 (m, 1H), 1.89-1.75 (m, 2H), 1.46-1.28 (m, 13H), LC-MS (ESI$^+$) m/z 552.4 (M+H)$^+$.

Step 2—Tert-butyl 4-[3-[1-(2,6-dioxo-3-piperidyl)-3-methyl-2-oxo-benzimidazol-4-yl]propyl]-1-oxa-4,9-diazaspiro[5.5]undecane-9-carboxylate To a solution of tert-butyl 4-[3-[1-(2,6-dioxo-3-piperidyl)-3-methyl-2-oxo-benzimidazol-4-yl] prop-2-ynyl]-1-oxa-4,9-diazaspiro[5.5]undecane-9-carboxylate (100 mg, 181 umol) in THF (10.0 mL) was added Pd/C (50 mg) and Pd(OH)$_2$/C (50 mg). The reaction mixture was stirred at 25° C. for 3 hrs under H$_2$ (15 psi). On completion, the mixture was filtered and the filtrate was concentrated in vacuo to give the title compound (100 mg, 99% yield) as yellow solid. $^1$H NMR (400 MHz, DMSO-d$_6$) δ 11.09 (s, 1H), 7.00-6.93 (m, 2H), 6.92-6.88 (m, 1H), 5.43-5.31 (m, 1H), 3.64-3.59 (m, 3H), 3.57 (s, 3H), 3.55-3.49 (m, 1H), 3.13-2.98 (m, 2H), 2.96-2.83 (m, 3H), 2.76-2.68 (m, 1H), 2.65-2.60 (m, 1H), 2.32-2.25 (m, 3H), 2.24-2.19 (m, 2H), 2.05-1.96 (m, 1H), 1.85-1.68 (m, 5H), 1.45-1.40 (m, 2H), 1.36 (s, 9H).

Step 3—3-[3-Methyl-4-[3-(1-oxa-4,9-diazaspiro [5.5]undecan-4-yl)propyl]-2-oxo-benzimidazol-1-yl] piperidine-2,6-dione To a solution of tert-butyl 4-[3-[1-(2,6-dioxo-3-piperidyl)-3-methyl-2-oxo-benzimidazol-4-yl]propyl]-1-oxa-4, 9-diazaspiro[5.5]undecane-9-carboxylate (100 mg, 179 umol) in DCM (3.00 mL) was added HCl/dioxane (4.00 M, 3.00 mL). The reaction mixture was stirred at 25° C. for 0.5 hr. On completion, the reaction mixture was concentrated in vacuo to give the title compound (88.0 mg, 99% yield, HCl salt) as yellow solid. LC-MS (ESI$^+$) m/z 456.2 (M+H)$^+$.

3-[3-methyl-2-oxo-5-[3-(4-piperidyloxy)propyl]benzimidazol-1-yl]piperidine-2,6-dione (Intermediate FL)

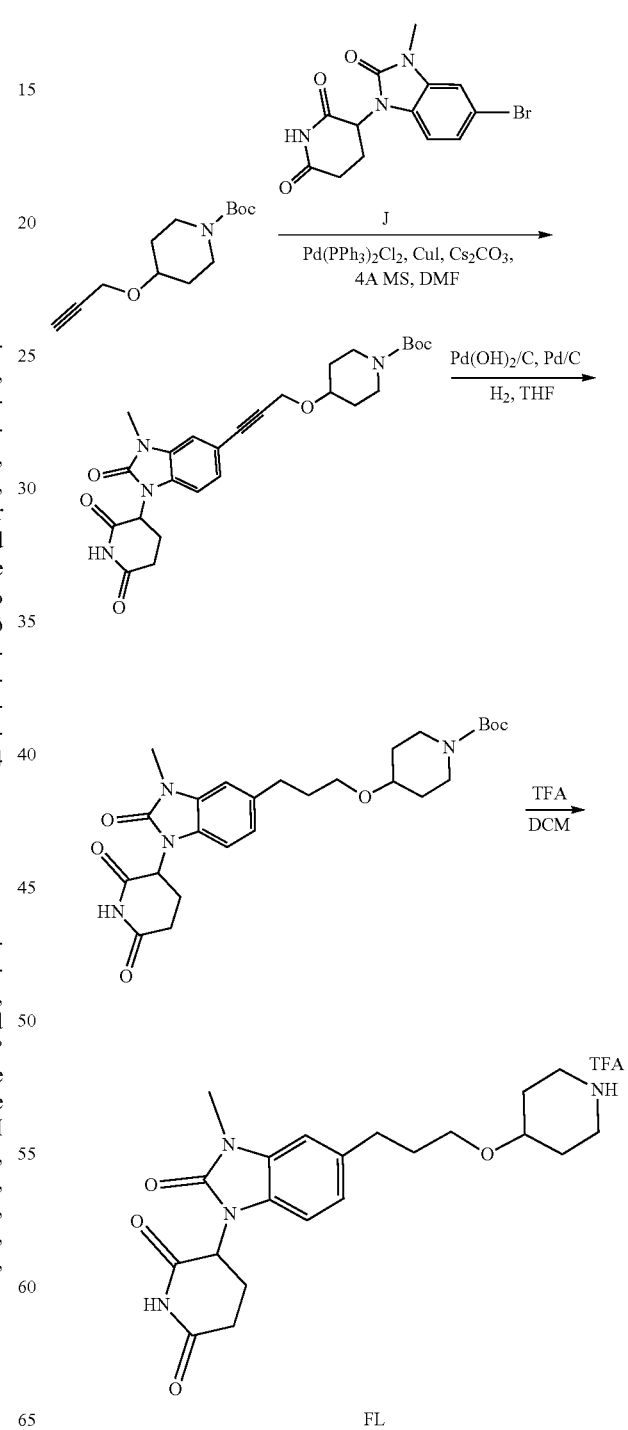

FL

Step 1—Tert-butyl 4-[3-[1-(2,6-dioxo-3-piperidyl)-3-methyl-2-oxo-benzimidazol-5-yl]prop-2-ynoxy]piperidine-1-carboxylate To a mixture of 3-(5-bromo-3-methyl-2-oxo-benzimidazol-1-yl)piperidine-2,6-dione (350 mg, 1.04 mmol, Intermediate J) and tert-butyl 4-prop-2-ynoxypiperidine-1-carboxylate (371 mg, 1.55 mmol, synthesized via Step 1 of Intermediate FW) in DMF (20 mL) was added Pd(PPh$_3$)$_2$Cl$_2$ (72.6 mg, 103 umol), CuI (39.4 mg, 207 umol), Cs$_2$CO$_3$ (1.35 g, 4.14 mmol) and 4A molecular sieves (200 mg, 1.04 mmol) in one portion at 25° C. under N$_2$. The reaction mixture was stirred at 80° C. for 2 hours. On completion, the reaction mixture was quenched by addition water (0.5 mL) at 25° C., and then extracted with EA (3×20 mL). The combined organic layers were washed with brine (20 mL), dried over Na$_2$SO$_4$, filtered and concentrated in vacuo to give a residue. The residue was purified by reverse phase (FA condition) to give the title compound (300 mg, 58% yield) as a yellow solid. $^1$H NMR (400 MHz, CDCl$_3$) δ 8.14 (s, 1H), 7.23-7.17 (m, 1H), 7.12 (d, J=1.2 Hz, 1H), 6.75 (d, J=8.1 Hz, 1H), 5.24-5.17 (m, 1H), 4.43 (s, 2H), 3.85-3.72 (m, 3H), 3.43 (s, 3H), 3.18-3.09 (m, 2H), 3.01-2.92 (m, 1H), 2.90-2.67 (m, 2H), 2.30-2.20 (m, 1H), 1.94-1.86 (m, 2H), 1.64-1.57 (m, 2H), 1.47 (s, 9H); LC-MS (ESI$^+$) m/z 519.3 (M+Na)$^+$.

Step 2—Tert-butyl 4-[3-[1-(2,6-dioxo-3-piperidyl)-3-methyl-2-oxo-benzimidazol-5-yl]propoxy]piperidine-1-carboxylate To a solution of tert-butyl 4-[3-[1-(2,6-dioxo-3-piperidyl)-3-methyl-2-oxo-benzimidazol-5-yl]prop-2-ynoxy]piperidine-1-carboxylate (300 mg, 604 umol) in THF (4 mL) was added Pd/C (50 mg, 10 wt %) and Pd(OH)$_2$/C (50 mg, 10 wt %) under N$_2$. The suspension was degassed under vacuum and purged with H$_2$ three times. The mixture was stirred at 25° C. for 2 hours under H$_2$ (15 psi). On completion, the reaction mixture was filtered and the filtrate was concentrated in vacuo to give a residue. The residue was purified by reverse phase (FA condition) to give the title compound (300 mg, 84% yield) as a yellow solid. $^1$H NMR (400 MHz, CDCl$_3$) δ 8.24 (s, 1H), 6.95-6.85 (m, 2H), 6.73 (d, J=8.2 Hz, 1H), 5.26-5.18 (m, 1H), 3.81-3.73 (m, 2H), 3.49-3.42 (m, 6H), 3.15-3.05 (m, 2H), 2.99-2.82 (m, 2H), 2.75 (t, J=7.6 Hz, 3H), 2.28-2.19 (m, 1H), 1.95-1.77 (m, 4H), 1.53 (d, J=8.8 Hz, 2H), 1.47 (s, 9H); LC-MS (ESI$^+$) m/z 401.0 (M+H-100)$^+$.

Step 3—3-[3-Methyl-2-oxo-5-[3-(4-piperidyloxy)propyl]benzimidazol-1-yl]piperidine-2,6-dione To a mixture of tert-butyl 4-[3-[1-(2, 6-dioxo-3-piperidyl)-3-methyl-2-oxo-benzimidazol-5-yl]propoxy]piperidine-1-carboxylate (270 mg, 539 umol) in DCM (4 mL) was added TFA (1.84 g, 16.2 mmol) at 25° C. The mixture was stirred at 25° C. for 2 hours. On completion, the reaction mixture was concentrated in vacuo to give a residue. The residue was purified by reverse phase (TFA condition) to give the title compound (162 mg, 58% yield, TFA salt) as a yellow solid. LC-MS (ESI$^+$) m/z 401.0 (M+H)$^+$.

Tert-butyl 6-(2-aminoethoxy)-2-azaspiro[3.3]heptane-2-carboxylate (Intermediate FM)

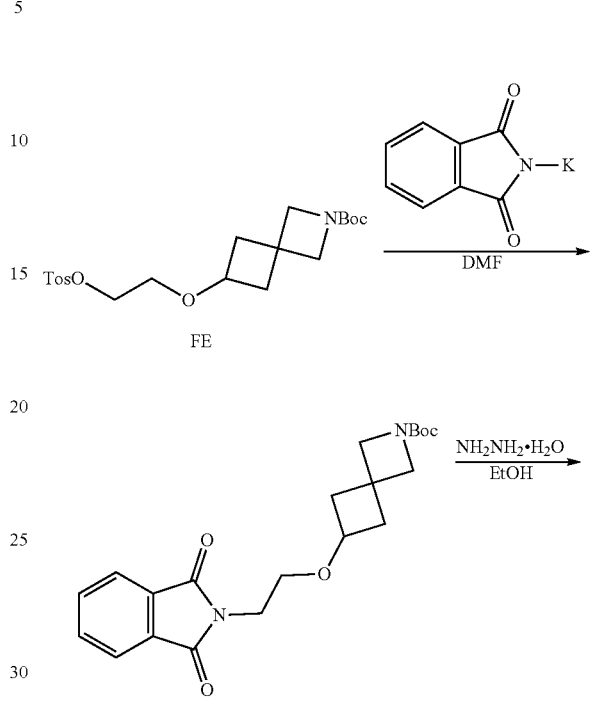

Step 1—Tert-butyl 6-(2-(1,3-dioxoisoindolin-2-yl)ethoxy)-2-azaspiro[3.3]heptane-2-carboxylate To a solution of tert-butyl 6-[2-(p-tolylsulfonyloxy)ethoxy]-2-azaspiro[3.3]heptane-2-carboxylate (1.8 g, 4.4 mmol, Intermediate FE) in DMF (20 mL) was added (1,3-dioxoisoindolin-2-yl)potassium (1.22 g, 6.56 mmol). The mixture was stirred at 80° C. for 12 h. On completion, the reaction mixture was with H$_2$O (20 mL) at 20° C., and then filtered under reduced pressure to give the title compound (1 g) as a white solid. LC-MS (ESI$^+$) m/z 387.1 (M+H)$^+$.

Step 2—Tert-butyl 6-(2-aminoethoxy)-2-azaspiro[3.3]heptane-2-carboxylate

To a solution of tert-butyl 6-[2-(1,3-dioxoisoindolin-2-yl)ethoxy]-2-azaspiro[3.3]heptane-2-carboxylate (400 mg, 1 mmol) in EtOH (6 mL) was added NH$_2$NH$_2$·H$_2$O (259 mg, 5.18 mmol). The mixture was stirred at 50° C. for 2 h. On completion, the residue was purified by re-crystallization from DCM (10 mL) at 20° C., and then filtered and concentrated under reduced pressure to give a residue. The residue was purified by re-crystallization from DCM (10 mL) at 0° C., and then filtered and dried under reduced pressure to give the title compound (240 mg, 90% yield) as a yellow oil. LC-MS (ESI$^+$) m/z 257.1 (M+H)$^+$.

N-(2-(2-azaspiro[3.3]heptan-6-yloxy)ethyl)-4-((8-cyclopentyl-7-oxo-7,8-dihydropyrido[2,3-d]pyrimidin-2-yl)amino)-3-methylbenzenesulfonamide (Intermediate FN)

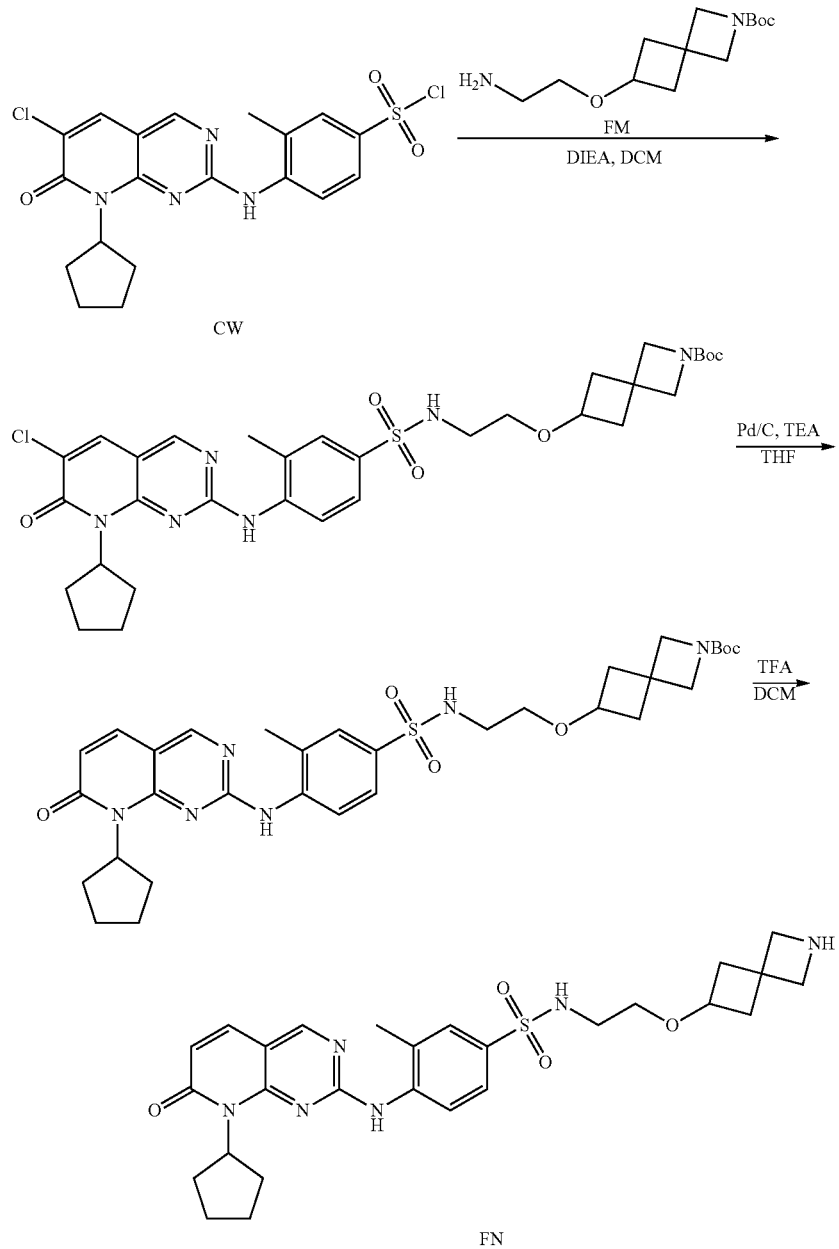

Step 1—Tert-butyl 6-(2-(4-(((6-chloro-8-cyclopentyl-7-oxo-7,8-dihydropyrido[2,3-d]pyrimidin-2-yl)amino)-3-methylphenylsulfonamido)ethoxy)-2-azaspiro[3.3]heptane-2-carboxylate To a solution of tert-butyl 6-(2-aminoethoxy)-2-azaspiro[3.3]heptane-2-carboxylate (200 mg, 800 umol, Intermediate FM) in DCM (5 mL) was added DIEA (302 mg, 2.34 mmol) and 4-[(6-chloro-8-cyclopentyl-7-oxo-pyrido[2,3-d]pyrimidin-2-yl)amino]-3-methyl-benzenesulfonyl chloride (353 mg, 780 umol, Intermediate CW). The mixture was stirred at 20° C. for 10 min. On completion, the reaction mixture was filtered and concentrated under reduced pressure to give the title compound (400 mg) as a yellow oil. LC-MS (ESI$^+$) m/z 673.3 (M+H)$^+$.

Step 2—Tert-butyl 6-(2-(4-((8-cyclopentyl-7-oxo-7,8-dihydropyrido[2,3-d]pyrimidin-2-yl)amino)-3-methylphenylsulfonamido)ethoxy)-2-azaspiro[3.3]heptane-2-carboxylate To a solution of tert-butyl 6-[2-[[4-[(6-chloro-8-cyclopentyl-7-oxo-pyrido[2,3-d]pyrimidin-2-yl)amino]-3-methyl-phenyl]sulfonylamino]ethoxy]-2-azaspiro[3.3]heptane-2- carboxylate (500 mg, 742 umol) and TEA (191 mg, 1.90 mmol) in THF (10 mL) was added TEA (191.98 mg, 1.90 mmol) and Pd/C (10 wt %, 500 mg) under $N_2$. The suspension was degassed under vacuum and purged with $H_2$ several times. The mixture was then stirred under $H_2$ (15 psi) at 20° C. for 0.5 hours. On completion, the reaction mixture was filtered and concentrated under reduced pressure to give the title compound (300 mg) as a yellow solid. LC-MS (ESI+) m/z 639.4 (M+H)+.

Step 3—N-(2-(2-azaspiro[3.3]heptan-6-yloxy)ethyl)-4-((8-cyclopentyl-7-oxo-7,8-dihydropyrido[2,3-d]pyrimidin-2-yl)amino)-3-methylbenzenesulfonamide To a solution of tert-butyl 6-[2-[[4-[(8-cyclopentyl-7-oxo-pyrido[2,3-d]pyrimidin-2-yl)amino]-3-methyl-phenyl]sulfonylamino]ethoxy]-2-azaspiro[3.3]heptane-2-carboxylate (150 mg, 234.82 umol) in DCM (4 mL) was added TFA (693 mg, 6.08 mmol). The mixture was stirred at 20° C. for 0.5 h. On completion the reaction mixture was filtered under reduced pressure to give the title compound (150 mg, TFA salt) as a yellow oil. LC-MS (ESI+) m/z 539.2 (M+H)+.

(3-(1-(2,6-dioxopiperidin-3-yl)-3-methyl-2-oxo-2,3-dihydro-1H-benzo[d]imidazol-5-yl)propiolaldehyde (Intermediate FO)

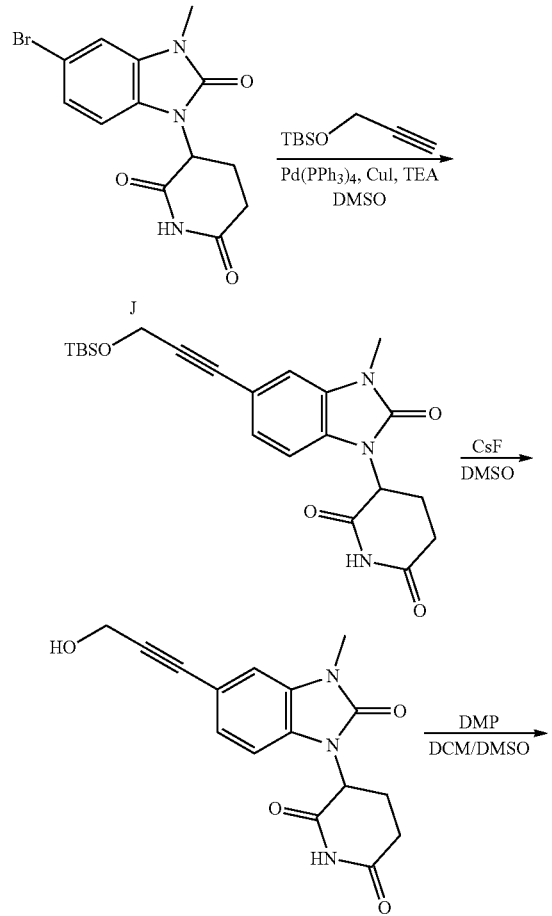

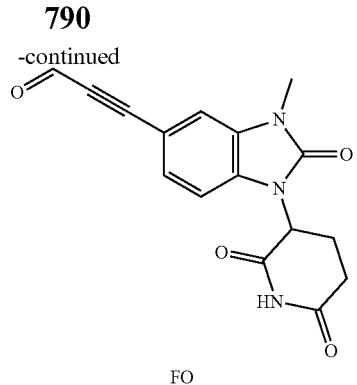

FO

Step 1—3-(5-(3-((Tert-butyldimethylsilyl)oxy)prop-1-yn-1-yl)-3-methyl-2-oxo-2,3-dihydro-1H-benzo[d]imidazol-1-yl)piperidine-2,6-dione A mixture of 3-(5-bromo-3-methyl-2-oxo-benzimidazol-1-yl)piperidine-2,6-dione (3 g, 8.87 mmol, Intermediate J), tert-butyl-dimethyl-prop-2-ynoxy-silane (4.53 g, 26.6 mmol), TEA (4.49 g, 44.3 mmol), Pd(PPh$_3$)$_4$ (1.03 g, 887 umol) and CuI (337 mg, 1.77 mmol) in DMSO (50 mL) was degassed and purged with $N_2$ three times. Then the mixture was stirred at 85° C. for 12 h under $N_2$ atmosphere. On completion, the reaction mixture was diluted with $H_2O$ (200 mL) and extracted with EtOAc (200 mL×2). The combined organic layers were washed with aqueous NaCl (200 mL×2), dried over Na$_2$SO$_4$, filtered and concentrated under reduced pressure to give a residue. The residue was purified by column chromatography (SiO$_2$, Petroleum ether/Ethyl acetate=10/1 to 1/1) to give the title compound (2 g, 50% yield) as a yellow solid. LC-MS (ESI+) m/z 428.2 (M+H)+.

Step 2—3-(5-(3-Hydroxyprop-1-yn-1-yl)-3-methyl-2-oxo-2,3-dihydro-1H-benzo[d]imidazol-1-yl)piperidine-2,6-dione To a solution of 3-[5-[3-[tert-butyl(dimethyl)silyl]oxyprop-1-ynyl]-3-methyl-2-oxo-benzimidazol-1-yl]piperidine-2,6-dione (300 mg, 700 umol) in DMSO (5 mL) was added CsF (532 mg, 3.51 mmol). The mixture was stirred at 20° C. for 2 h. On completion, the reaction mixture was quenched with HCl (1M, 10 mL) at 0° C., and then diluted with $H_2O$ (10 mL) and extracted with EtOAc (20 mL×3). The combined organic layers were washed with aqueous NaCl (10 mL×3), dried over Na$_2$SO$_4$, filtered and concentrated under reduced pressure to give the title compound (200 mg) as a yellow solid. LC-MS (ESI+) m/z 314.1 (M+H)+.

Step 3—(3-(1-(2,6-dioxopiperidin-3-yl)-3-methyl-2-oxo-2,3-dihydro-1H-benzo[d]imidazol-5-yl)propiolaldehyde To a solution of 3-[5-(3-hydroxyprop-1-ynyl)-3-methyl-2-oxo-benzimidazol-1-yl]piperidine-2,6-dione (200 mg, 638 umol) in DCM (5 mL) and DMSO (2 mL) was added DMP (541 mg, 1.28 mmol) at 0° C. The mixture was stirred at 25° C. for 12 hrs. On completion, the reaction mixture was diluted with $H_2O$ (20 mL) and extracted with EA (20 mL×3). The combined organic layers were washed with aqueous NaCl (20 mL×3), dried over Na$_2$SO$_4$, filtered and concentrated under reduced pressure to give the title compound (120 mg) as a yellow solid. LC-MS (ESI⁺) m/z 312.1 (M+H)⁺.

Tert-butyl 9-(2-(tosyloxy)ethoxy)-3-azaspiro[5.5] undecane-3-carboxylate (Intermediate FP)

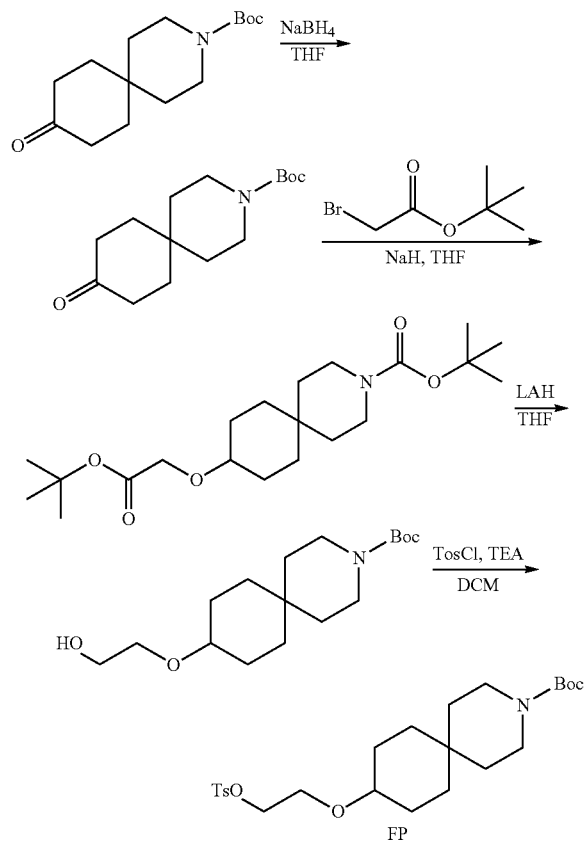

Step 1—Tert-butyl 9-hydroxy-3-azaspiro[5.5]undecane-3-carboxylate

A solution of tert-butyl 9-oxo-3-azaspiro[5.5]undecane-3-carboxylate (3 g, 10 mmol, CAS #873924-08-4) in THF (30 mL) was added NaBH₄ (636 mg, 16.8 mmol) in several portions at 0° C., then the mixture was stirred at 20° C. for 12 h. On completion, the reaction mixture was quenched with NH₄Cl aq. (50 mL) at 20° C., and then diluted with EtOAc (10 mL) and extracted with EtOAc (30 mL×3). The combined organic layers were washed with brine (30 mL×2), dried over Na₂SO₄, filtered and concentrated under reduced pressure to give a residue. The residue was purified by column chromatography (SiO₂, Petroleum ether/Ethyl acetate=10/1 to 3/1) to give the title compound (3 g, 99% yield) as yellow solid.

Step 2—Tert-butyl 9-(2-(tert-butoxy)-2-oxoethoxy)-3-azaspiro[5.5]undecane-3-carboxylate To a solution of tert-butyl 9-hydroxy-3-azaspiro[5.5]undecane-3-carboxylate (3 g, 11.1 mmol) in THF (30 mL) was added NaH (668 mg, 16.7 mmol, 60% dispersion in mineral oil) at 0° C., and the mixture was stirred at 0° C. for 1 h. Then the tert-butyl 2-bromoacetate (3.26 g, 16.7 mmol, 2.47 mL) was added and the mixture was stirred at 0-20° C. for 2 h. On completion, the reaction mixture was quenched with H₂O (20 mL) at 20° C., and then diluted with EtOAc 10 mL and extracted with EtOAc (20 mL×3). The combined organic layers were washed with brine (20 mL×2), dried over Na₂SO₄, filtered and concentrated under reduced pressure to give a residue. The residue was purified by column chromatography (SiO₂, Petroleum ether/Ethyl acetate=5/1 to 1/1) to give the title compound (1.4 g, 33% yield) as colorless gum. ¹H NMR (400 MHz, DMSO-d6) δ=3.95 (s, 2H), 3.26 (br s, 5H), 1.70-1.63 (m, 3H), 1.57 (br dd, J=4.0, 10.0 Hz, 4H), 1.41 (s, 9H), 1.38 (s, 9H), 1.29-1.22 (m, 5H).

Step 3—Tert-butyl 9-(2-hydroxyethoxy)-3-azaspiro[5.5]undecane-3-carboxylate

A solution of tert-butyl 9-(2-(tert-butoxy)-2-oxoethoxy)-3-azaspiro[5.5]undecane-3-carboxylate (1.4 g, 3.7 mmol) in THF (15 mL) was added LiAlH₄ (207 mg, 5.48 mmol) at 0° C., then the mixture was stirred at 0° C. for 2 h under N₂ atmosphere. On completion, the reaction mixture was quenched with H₂O (0.01 mL) at 0° C. and 15% NaOH aq (0.1 mL). The mixture was then filtered and concentrated under reduced pressure to give the title compound (700 mg, 61% yield) as colorless gum. ¹H NMR (400 MHz, DMSO-d6) δ=4.51 (t, J=5.2 Hz, 1H), 3.49-3.46 (m, 1H), 3.48-3.37 (m, 3H), 3.29-3.22 (m, 5H), 1.67 (br dd, J=4.0, 8.8 Hz, 1H), 1.57 (br d, J=10.4 Hz, 3H), 1.38 (s, 9H), 1.36-1.32 (m, 4H), 1.18-1.11 (m, 4H).

Step 4—Tert-butyl 9-(2-(tosyloxy)ethoxy)-3-azaspiro[5.5]undecane-3-carboxylate To a solution of tert-butyl 9-(2-hydroxyethoxy)-3-azaspiro[5.5]undecane-3-carboxylate (700 mg, 2.23 mmol) in DCM (10 mL) was added TEA (677 mg, 6.69 mmol) and 4-methylbenzenesulfonyl chloride (637 mg, 3.35 mmol) at 0° C., then the mixture was stirred at 20° C. for 12 h. On completion, the reaction mixture was quenched with H₂O (20 mL) at 20° C., and then diluted with EtOAc (10 mL) and extracted with EtOAc (20 mL×3). The combined organic layers were washed with brine (20 mL×2), dried over Na₂SO₄, filtered and concentrated under reduced pressure to give a residue. The residue was purified by column chromatography (SiO₂, Petroleum ether/Ethyl acetate=10/1 to 5/1) to give the title compound (430 mg, 29% yield) as white solid. ¹H NMR (400 MHz, DMSO-d6) δ=7.78 (d, J=8.4 Hz, 2H), 7.48 (d, J=8.0 Hz, 2H), 4.11-4.08 (m, 2H), 3.55-3.51 (m, 2H), 3.29-3.21 (m, 5H), 2.42 (s, 3H), 1.63-1.46 (m, 5H), 1.38 (s, 9H), 1.31-1.27 (m, 2H), 1.25-1.21 (m, 3H), 1.11-1.02 (m, 2H).

Tert-butyl 9-(2-aminoethoxy)-3-azaspiro[5.5]undecane-3-carboxylate (Intermediate FQ)

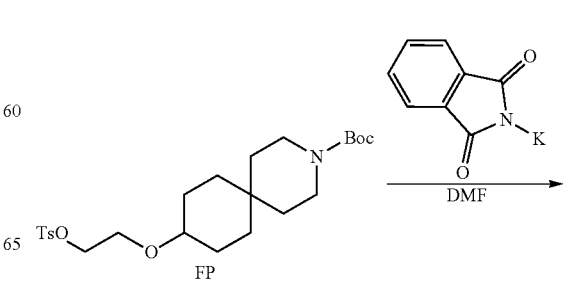

-continued

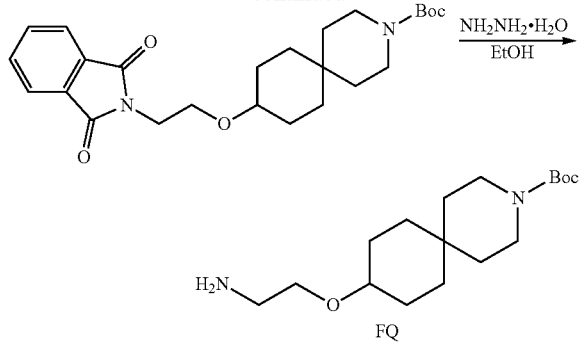

Step 1—Tert-butyl 9-(2-(1,3-dioxoisoindolin-2-yl)ethoxy)-3-azaspiro[5.5]undecane-3-carboxylate A solution of tert-butyl 9-(2-(tosyloxy)ethoxy)-3-azaspiro[5.5]undecane-3-carboxylate (200 mg, 428 umol, Intermediate FP) and potassium 1,3-dioxoisoindolin-2-ide (119 mg, 642 umol) in DMF (1 mL) was stirred at 50° C. for 2 h. On completion, the reaction mixture was quenched with $H_2O$ (20 mL) at 20° C., filtered and washed with $H_2O$ (20 mL) to give the title compound (120 mg, 63% yield) as white solid. LC-MS (ESI$^+$) m/z 465.1 (M+Na)$^+$.

Step 2—Tert-butyl 9-(2-aminoethoxy)-3-azaspiro[5.5]undecane-3-carboxylate

To a solution of tert-butyl 9-(2-(1,3-dioxoisoindolin-2-yl)ethoxy)-3-azaspiro[5.5]undecane-3-carboxylate (120 mg, 270 umol) in EtOH (4 mL) was added $NH_2NH_2 \cdot H_2O$ (102 mg, 2.04 mmol), then the mixture was stirred at 50° C. for 2 h. On completion, mixture was filtered and concentrated in vacuo to give the title compound (130 mg) as white solid. $^1H$ NMR (400 MHz, DMSO-d6) δ=3.36-3.33 (m, 3H), 3.29-3.24 (m, 6H), 2.63 (t, J=5.6 Hz, 2H), 1.72-1.64 (m, 2H), 1.61-1.54 (m, 2H), 1.38 (s, 9H), 1.36-1.32 (m, 3H), 1.28-1.23 (m, 3H), 1.18-1.09 (m, 2H).

N-(2-(3-azaspiro[5.5]undecan-9-yloxy)ethyl)-4-((8-cyclopentyl-7-oxo-7,8-dihydropyrido[2,3-d]pyrimidin-2-yl)amino)-3-methylbenzenesulfonamide (Intermediate FR)

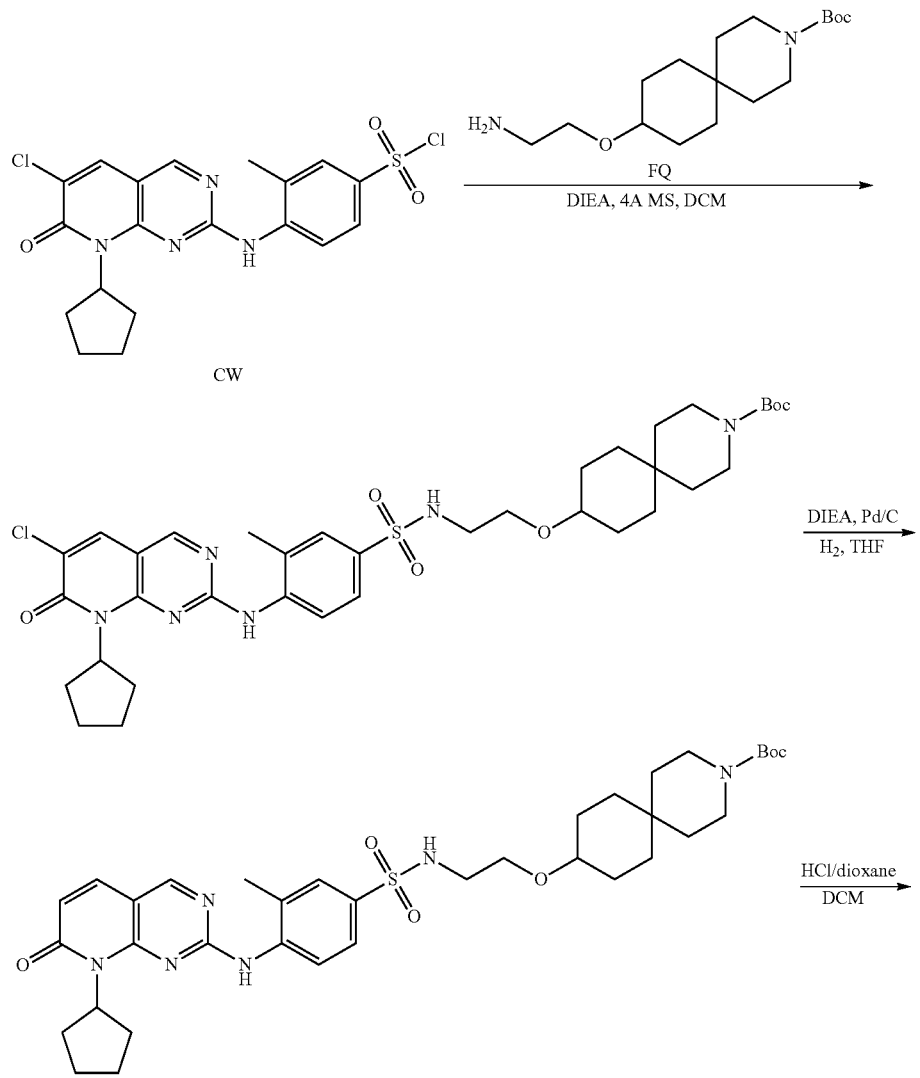

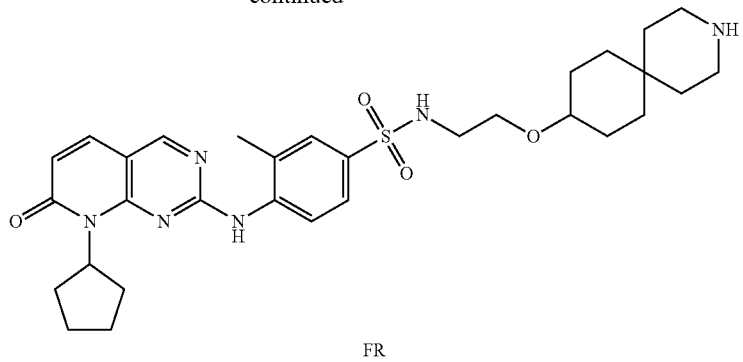

FR

Step 1—Tert-butyl 9-(2-(4-((6-chloro-8-cyclopentyl-7-oxo-7,8-dihydropyrido[2,3-d]pyrimidin-2-yl)amino)-3-methylphenylsulfonamido)ethoxy)-3-azaspiro[5.5]undecane-3-carboxylate To a solution of tert-butyl 9-(2-aminoethoxy)-3-azaspiro[5.5]undecane-3-carboxylate (120 mg, 384 umol, Intermediate FQ) and DIEA (397 mg, 3.07 mmol), 4A MS (100 mg, 384 umol) in DCM (2 mL) was added 4-((6-chloro-8-cyclopentyl-7-oxo-7,8-dihydropyrido[2,3-d]pyrimidin-2-yl)amino)-3-methylbenzene-1-sulfonyl chloride (191 mg, 422 umol, Intermediate CW), then the mixture was stirred 25° C. for 10 min. On completion, the reaction mixture was quenched with $H_2O$ (2 mL) at 20° C., and extracted with DCM mL (2 mL×3). The combined organic layers were washed with brine (2 mL×2), dried over $Na_2SO_4$, filtered and concentrated under reduced pressure to give the title compound (300 mg) as white solid. LC-MS (ESI$^+$) m/z 729.2 (M+H)$^+$.

Step 2—Tert-butyl 9-(2-(4-((8-cyclopentyl-7-oxo-7,8-dihydropyrido[2,3-d]pyrimidin-2-yl)amino)-3-methylphenylsulfonamido)ethoxy)-3-azaspiro[5.5]undecane-3-carboxylate To a solution of Pd/C (500 mg, 471 umol, 10 wt %) in THF (3 mL) was added DIEA (106 mg, 822 umol, 143 uL) and tert-butyl 9-(2-(4-((6-chloro-8-cyclopentyl-7-oxo-7,8-dihydropyrido[2,3-d]pyrimidin-2-yl)amino)-3-methylphenylsulfonamido)ethoxy)-3-azaspiro[5.5]undecane-3-carboxylate (300 mg, 411 umol). Then the mixture was stirred at 20° C. for 2 h under $H_2$ atmosphere (15 PSI). On completion, the reaction mixture was filtered and concentrated in vacuo to give the title compound (120 mg) as brown solid. LC-MS (ESI$^+$) m/z 695.2 (M+H)$^+$.

Step 3—N-(2-(3-azaspiro[5.5]undecan-9-yloxy)ethyl)-4-((8-cyclopentyl-7-oxo-7,8-dihydropyrido[2,3-d]pyrimidin-2-yl)amino)-3-methylbenzenesulfonamide A solution of tert-butyl 9-(2-(4-((8-cyclopentyl-7-oxo-7,8-dihydropyrido[2,3-d]pyrimidin-2-yl)amino)-3-methylphenylsulfonamido)ethoxy)-3-azaspiro[5.5]undecane-3-carboxylate (120 mg, 170 umol) in DCM (5 mL) and HCl/dioxane (4 M, 1 mL) was stirred at 25° C. for 1 h. On completion, the reaction mixture was concentrated under reduced pressure to give the title compound (100 mg) as white solid. LC-MS (ESI$^+$) m/z 595.2 (M+H)$^+$.

3-(1-(2,6-dioxopiperidin-3-yl)-3-methyl-2-oxo-2,3-dihydro-1H-benzo[d]imidazol-5-yl)propanal (Intermediate FS)

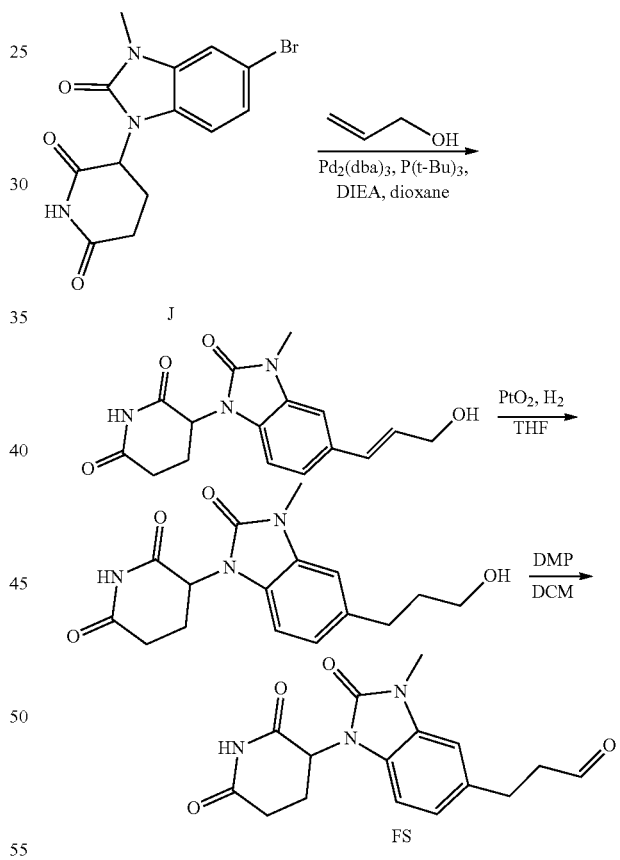

FS

Step 1—3-[5-(3-Hydroxyprop-1-enyl)-3-methyl-2-oxo-benzimidazol-1-yl]piperidine-2,6-dione To a solution of 3-(5-bromo-3-methyl-2-oxo-benzimidazol-1-yl)piperidine-2,6-dione (1.00 g, 2.96 mmol, Intermediate J) and prop-2-en-1-ol (350 mg, 6.03 mmol) in dioxane (10.0 mL) was added P(t-Bu)$_3$ (1.20 g, 591 umol, 10 wt %), Pd$_2$(dba)$_3$ (270 mg, 295 umol) and DIPEA (496 mg, 3.84 mmol). The mixture was stirred at 20° C. for 16 hours under N$_2$. On completion, the mixture was concentrated in vacuo.

The residue was purified by reverse phase chromatography (0.1% FA) to give the title compound (750 mg, 80% yield) as yellow solid. $^1$H NMR (400 MHz, DMSO-$d_6$) δ 12.74 (s, 1H), 11.08 (s, 1H), 9.80-9.62 (m, 1H), 7.11-7.07 (m, 1H), 7.01 (d, J 8.0 Hz, 1H), 6.95-6.93 (m, 1H), 6.96-6.83 (m, 1H), 5.41-5.25 (m, 1H), 3.31 (s, 3H), 2.94-2.89 (m, 2H), 2.81-2.76 (m, 1H), 2.75-2.65 (m, 1H), 2.65-2.54 (m, 1H), 2.04-1.94 (m, 1H).

Step 2—3-[5-(3-Hydroxypropyl)-3-methyl-2-oxo-benzimidazol-1-yl]piperidine-2,6-dione To a solution of 3-[5-[(E)-3-hydroxyprop-1-enyl]-3-methyl-2-oxo-benzimidazol-1-yl]piperidine-2, 6-dione (750 mg, 2.38 mmol) in THF (30.0 mL) was added PtO$_2$ (54.0 mg, 237 umol). The mixture was stirred at 20° C. for 16 hours under H$_2$ (15 psi). On completion, the mixture was filtered and the filtrate was concentrated in vacuo. The residue was purified by reverse phase chromatography (0.1% FA) to give the title compound (220 mg, 29% yield) as white solid. $^1$H NMR (400 MHz, DMSO-$d_6$) δ 11.08 (s, 1H), 7.06-6.96 (m, 2H), 6.90-6.82 (m, 1H), 5.38-5.27 (m, 1H), 3.45-3.42 (m, 2H), 3.33 (s, 3H), 2.98-2.78 (m, 2H), 2.76-2.68 (m, 1H), 2.64-2.60 (m, 1H), 2.59-2.52 (m, 1H), 2.05-1.93 (m, 1H), 1.83-1.66 (m, 2H).

Step 3—3-[1-(2,6-Dioxo-3-piperidyl)-3-methyl-2-oxo-benzimidazol-5-yl]propanal

To a solution of 3-[5-(3-hydroxypropyl)-3-methyl-2-oxo-benzimidazol-1-yl]piperidine-2,6-dione (220 mg, 693 umol) in DCM (10.0 mL) was added DMP (352 mg, 831 umol). The mixture was stirred at 25° C. for 1 hour. On completion, the reaction mixture was quenched with saturated Na$_2$S$_2$O$_3$ (30 mL) and washed with saturated NaHCO$_3$ (2×30 mL). The organic layer was dried over anhydrous Na$_2$SO$_4$, filtered and concentrated in vacuo to give the title compound (200 mg, 91% yield) as yellow solid. LC-MS (ESI$^+$) m/z 316.1 (M+H)$^+$.

8-cyclopentyl-2-((2-methyl-4-(piperazin-1-ylsulfonyl)phenyl)amino)pyrido[2,3-d]pyrimidin-7(8H)-one (Intermediate FT)

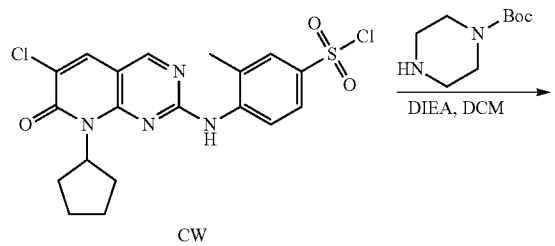

CW

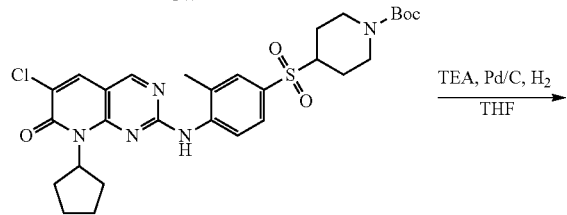

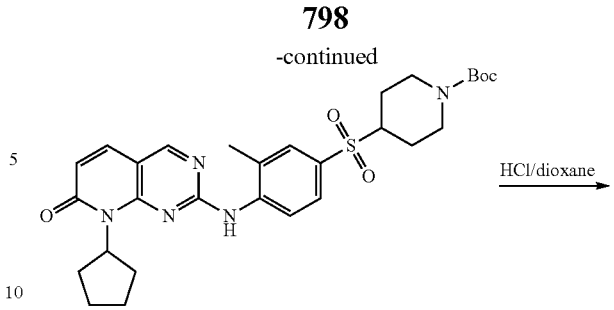

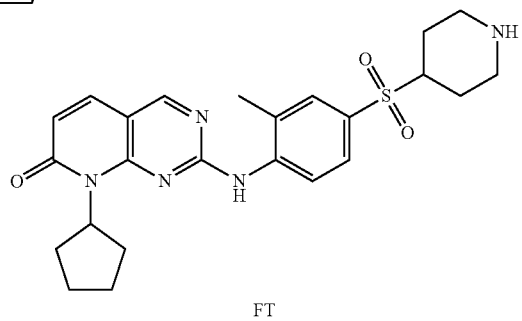

FT

Step 1—Tert-butyl 4-((4-(((6-chloro-8-cyclopentyl-7-oxo-7,8-dihydropyrido[2,3-d]pyrimidin-2-yl)amino)-3-methylphenyl)sulfonyl)piperazine-1-carboxylate To a solution of tert-butyl piperazine-1-carboxylate (90.3 mg, 485 umol, CAS #143238-38-4) in DCM (2 mL) was added DIEA (285 mg, 2.21 mmol) and 4A molecular sieves (200 mg), then 4-((6-chloro-8-cyclopentyl-7-oxo-7,8-dihydropyrido[2,3-d]pyrimidin-2-yl)amino)-3-methylbenzene-1-sulfonyl chloride (200 mg, 441 umol, Intermediate CW) was added and the mixture was stirred at 20° C. for 30 min. The reaction mixture was filtered and concentrated under reduced pressure to give the title compound (100 mg, 38% yield) as a orange solid. LC-MS (ESI$^+$) m/z 603.5 (M+H)$^+$.

Step 2—Tert-butyl 4-((4-((8-cyclopentyl-7-oxo-7,8-dihydropyrido[2,3-d]pyrimidin-2-yl)amino)-3-methylphenyl)sulfonyl)piperazine-1-carboxylate To a solution of tert-butyl 4-((4-(((6-chloro-8-cyclopentyl-7-oxo-7,8-dihydropyrido[2,3-d]pyrimidin-2-yl)amino)-3-methylphenyl)sulfonyl)piperazine-1-carboxylate (180 mg, 298 umol) in THF (2 mL) was added TEA (90.6 mg, 895 umol) and Pd/C (316 mg, 298 umol). The mixture was stirred at 20° C. for 4 h under H$_2$ atmosphere (15 PSI). The reaction mixture was filtered and concentrated under reduced pressure to give the title compound (100 mg, 59% yield) as a white solid. LC-MS (ESI$^+$) m/z 569.3 (M+H)$^+$.

Step 3—8-Cyclopentyl-2-((2-methyl-4-(piperazin-1-ylsulfonyl)phenyl)amino)pyrido[2,3-d]pyrimidin-7(8H)-one A solution of tert-butyl 4-((4-((8-cyclopentyl-7-oxo-7,8-dihydropyrido[2,3-d]pyrimidin-2-yl)amino)-3-methylphenyl)sulfonyl)piperazine-1-carboxylate (100 mg, 175 umol) in HCl/dioxane (1 mL) was stirred at 20° C. for 20 min. On completion, the reaction mixture was filtered and concentrated under reduced pressure to give the title compound (70 mg) as an orange solid. LC-MS (ESI$^+$) m/z 469.2 (M+H)$^+$.

6-(1-(2,6-Dioxopiperidin-3-yl)-3-methyl-2-oxo-2,3-dihydro-1H-benzo[d]imidazol-5-yl)hex-5-ynal (Intermediate FU)

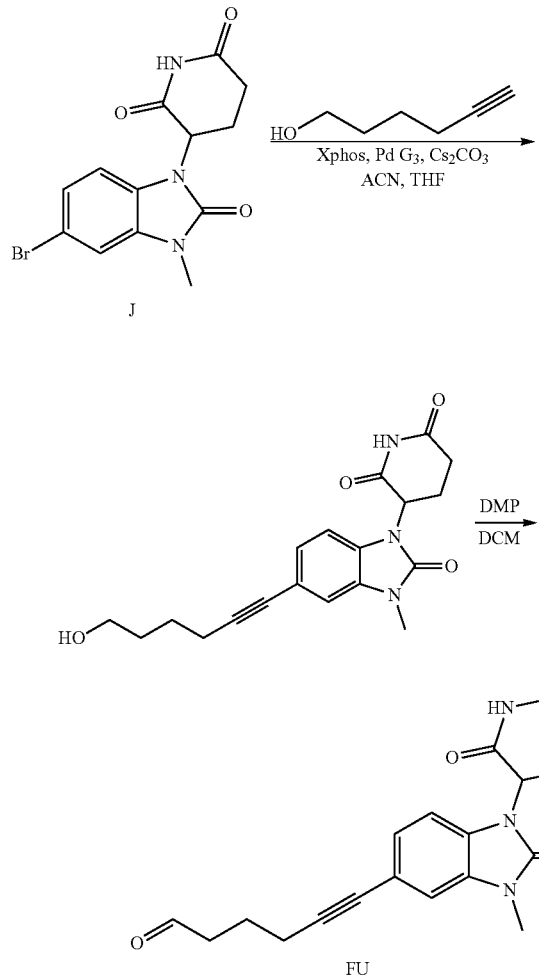

Step 1—3-(5-(6-Hydroxyhex-1-yn-1-yl)-3-methyl-2-oxo-2,3-dihydro-1H-benzo[d]imidazol-1-yl)piperidine-2,6-dione To a solution of hex-5-yn-1-ol (483 mg, 4.93 mmol) (CAS #928-90-5) and 3-(5-bromo-3-methyl-2-oxo-2,3-dihydro-1H-benzo[d]imidazol-1-yl)piperidine-2,6-dione (2 g, 5.91 mmol, Intermediate J) in ACN (10 mL) and THF (10 mL) was added XPhos Pd G3 (1.25 g, 1.48 mmol) and Cs₂CO₃ (8.03 g, 24.6 mmol). Then the mixture was stirred at 60° C. for 12 h under N₂ atmosphere. On completion, the reaction mixture was quenched with sat. NH₄Cl (20 mL) at 0° C., and then diluted with EtOAc (20 mL) and extracted with EtOAc (20 mL×3). The combined organic layers were washed with sat. NaCl (20 mL×3), dried over Na₂SO₄, filtered and concentrated under reduced pressure to give a residue. The residue was purified by column chromatography (SiO₂, Petroleum ether/Ethyl acetate=5/1 to 0/1) to give the title compound (1.3 g, 74% yield) as an orange solid. LC-MS (ESI⁺) m/z 356.2 (M+H)⁺.

Step 2—6-(1-(2,6-Dioxopiperidin-3-yl)-3-methyl-2-oxo-2,3-dihydro-1H-benzo[d]imidazol-5-yl)hex-5-ynal To a solution of 3-(5-(6-hydroxyhex-1-yn-1-yl)-3-methyl-2-oxo-2,3-dihydro-1H-benzo[d]imidazol-1-yl)piperidine-2,6-dione (200 mg, 562 umol) in DCM (2 mL) was added DMP (358 mg, 844 umol) at 0° C. The mixture was stirred at 0-20° C. for 12 hr. On completion, the reaction mixture was quenched with H₂O (10 mL) at 25° C., and then diluted with Na₂SO₃ (10 mL) and extracted with DCM (10 mL×3). The combined organic layers were washed with NaHCO₃ (10 mL×3), dried over Na₂SO₄, filtered and concentrated under reduced pressure to give a residue. The residue was purified by flash silica gel chromatography (ISCO®; 15 g SepaFlash® Silica Flash Column, Eluent of 0~100% Ethyl acetate/Petroleum ether gradient @ 20 mL/min) to give the title compound (80 mg, 40% yield) as a white solid. LC-MS (ESI⁺) m/z 354.2 (M+H)⁺.

(1S,3R)-3-(5-(1-(3,6,9,12-tetraoxapentadec-14-yn-1-yl)-1H-pyrazole-5-carboxamido)-1-(tert-butyl)-1H-pyrazol-3-yl)cyclopentyl pyrrolidine-1-carboxylate (Intermediate FV)

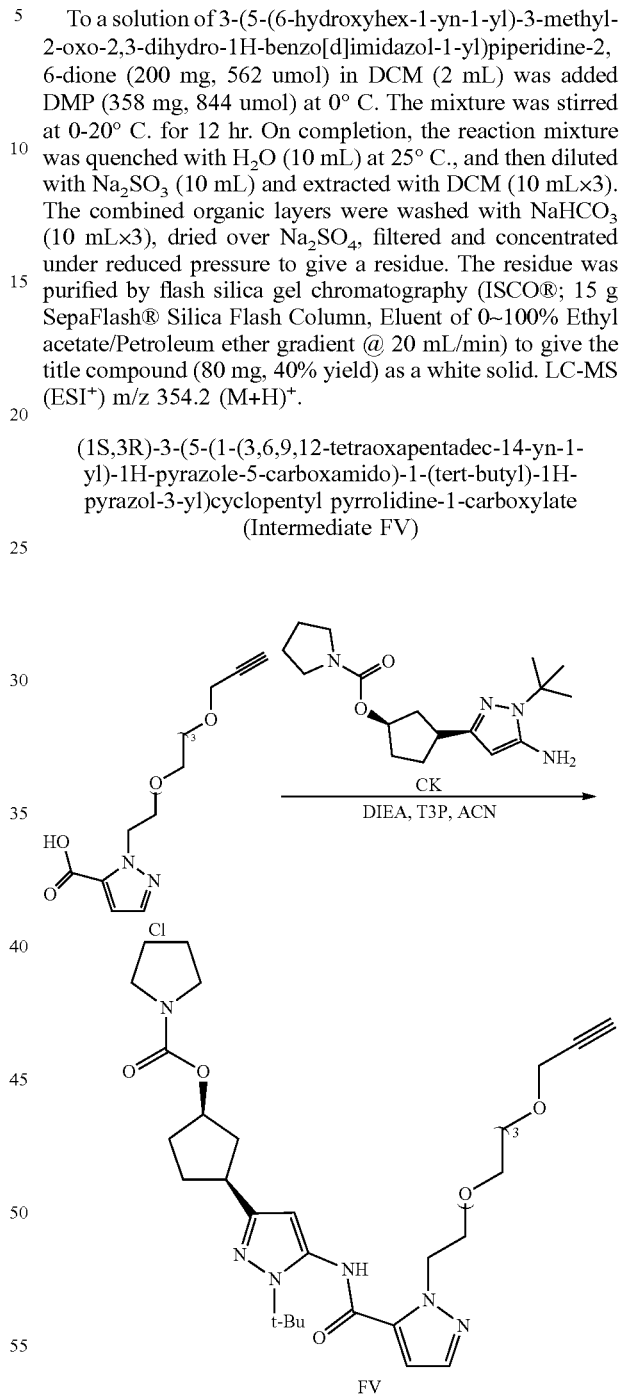

To a solution of (1R,3S)-3-(5-amino-1-(tert-butyl)-1H-pyrazol-3-yl)cyclopentyl pyrrolidine-1-carboxylate (200 mg, 624.16 umol, Intermediate CK) and 1-(3,6,9,12-tetraoxapentadec-14-yn-1-yl)-1H-pyrazole-5-carboxylic acid (185.2 mg, 567.4 umol, Intermediate CI) in ACN (5 mL) were added DIEA (734 mg, 5.67 mmol) and T3P (1.7 g, 2.6 mmol, 50% solution), and the mixture was stirred at 80° C. for 41 h. On completion, the reaction mixture was quenched with H₂O (5 mL) and extracted with EtOAc (7 mL×2). The combined organic layers were washed with brine (5 mL×3), dried over Na$_2$SO$_4$ and evaporated. The residue was purified by column chromatography (SiO$_2$, Petroleum ether/Ethyl acetate=5/1 to 1/1) to give the title compound (200 mg, 56% yield) as a white solid. $^1$H NMR (400 MHz, DMSO-d$_6$) δ 9.93 (s, 1H), 7.58 (d, J=2 Hz, 1H), 7.01 (s, 1H), 6.00 (s, 1H), 5.05-4.97 (m, 1H), 4.66 (t, J=5.6 Hz, 2H), 4.12 (d, J=2.4 Hz, 2H), 3.73 (t, J=5.6 Hz, 2H), 3.54-3.50 (m, 4H), 3.47-3.46 (m, 3H), 3.45 (s, 4H), 3.40 (t, J=2.4 Hz, 1H), 3.22 (br t, J=6.4 Hz, 5H), 3.07-3.01 (m, 1H), 2.39-2.32 (m, 1H), 1.90-1.84 (m, 1H), 1.81-1.69 (m, 8H), 1.51 (s, 9H).

3-(3-methyl-2-oxo-4-(3-(piperidin-4-yloxy)prop-1-yn-1-yl)-2,3-dihydro-1H-benzo[d]imidazol-1-yl) piperidine-2,6-dione (Intermediate FW)

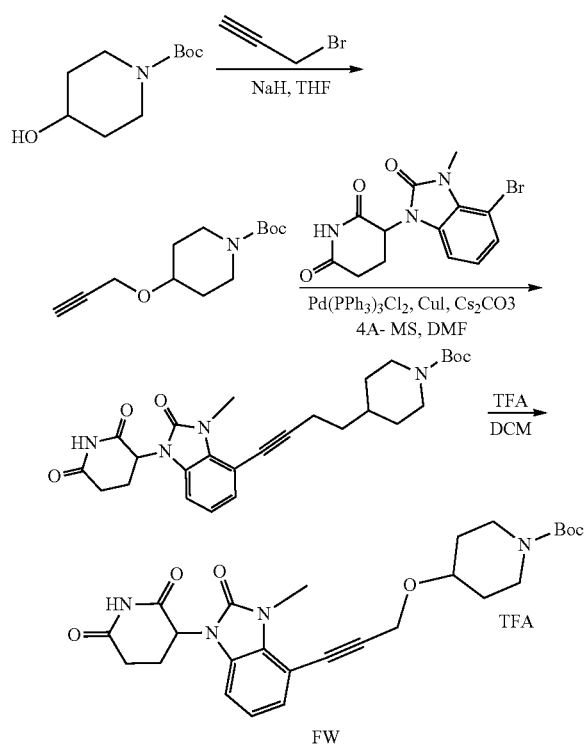

Step 1—Tert-butyl 4-prop-2-ynoxypiperidine-1-carboxylate

To a solution of tert-butyl 4-hydroxypiperidine-1-carboxylate (2.00 g, 9.94 mmol, CAS #109384-19-2) in anhydrous THF (10 mL) was cooled to 0° C., and subsequently NaH (477 mg, 11.9 mmol, 60% oil dispersion) was added. The reaction mixture was stirred at 0° C. for 0.5 hr. Then, 3-bromoprop-1-yne (1.18 g, 9.94 mmol, 856 uL) was added. The resulting reaction mixture was stirred at 25° C. for 12 hrs. On completed, the reaction mixture was quenched with water (1 mL), then diluted with ethyl acetate (100 mL). The organic layers were washed with brine (20 mL), dried over anhydrous sodium sulfate, filtered and the filtrate was concentrated in vacuo. The residue was purified by column chromatography to give the title compound (2.38 g, 100% yield) as yellow oil. $^1$H NMR (400 MHz, CDCl$_3$) δ 4.22 (d, J=2.4 Hz, 2H), 3.84-3.75 (m, 2H), 3.73-3.70 (m, 1H), 3.15-3.09 (m, 2H), 2.43 (t, J=2.4 Hz, 1H), 1.93-1.82 (m, 2H), 1.61-1.50 (m, 2H), 1.47 (s, 9H).

Step 2—Tert-butyl 4-[3-[1-(2,6-dioxo-3-piperidyl)-3-methyl-2-oxo-benzimidazol-4-yl]prop-2-ynoxy] piperidine-1-carboxylate A suspension of 3-(4-bromo-3-methyl-2-oxo-benzimidazol-1-yl)piperidine-2,6-dione (300 mg, 887 umol, Intermediate H), tert-butyl 4-prop-2-ynoxypiperidine-1-carboxylate (318 mg, 1.33 mmol), Pd(PPh$_3$)$_2$Cl$_2$ (124 mg, 177 umol), CuI (33.8 mg, 177 umol), 4A molecular sieves (400 mg) and Cs$_2$CO$_3$ (1.16 g, 3.55 mmol) in DMF (5 mL) was de-gassed under vacuum and purged with N$_2$ several times and then heated to 80° C. for 2 hours under N$_2$. On completion, the reaction mixture was concentrated in vacuo to remove DMF. The residue was diluted with EA (50 mL) and water (20 mL). After, the organic layer was separated and washed with brine (5 mL×2), dried over anhydrous Na$_2$SO$_4$, filtered and the filtrate was concentrated in vacuo to give a residue. The residue was purified by reverse phase to give the title compound (222 mg, 48% yield) as a yellow solid. $^1$H NMR (400 MHz, CDCl$_3$) δ 8.09 (s, 1H), 7.10 (d, J=8.0 Hz, 1H), 6.92 (t, J=8.0 Hz, 1H), 6.69 (d, J=8.0 Hz, 1H), 5.13 (dd, J=5.2, 12.8 Hz, 1H), 4.39 (s, 2H), 3.76-3.66 (m, 6H), 3.09-3.03 (m, 2H), 2.94-2.84 (m, 1H), 2.82-2.71 (m, 1H), 2.71-2.59 (m, 1H), 2.22-2.11 (m, 1H), 1.83-1.78 (m, 2H), 1.57-1.49 (m, 2H), 1.39 (s, 9H), LC-MS (ESI$^+$) m/z 441.2 (M+H-56)$^+$.

Step 3—3-[3-Methyl-2-oxo-4-[3-(4-piperidyloxy) prop-1-ynyl]benzimidazol-1-yl]piperidine-2,6-dione To a mixture of tert-butyl 4-[3-[1-(2,6-dioxo-3-piperidyl)-3-methyl-2-oxo-benzimidazol-4-yl]prop-2-ynoxy]piperidine-1-carboxylate (1.50 g, 3.02 mmol) in DCM (30 mL) was added TFA (23.1 g, 202 mmol, 15 mL). The reaction mixture was stirred at 20° C. for 1 hr. On completion, the reaction mixture was concentrated in vacuo to give the title compound (1.50 g, 97% yield, TFA salt) as yellow oil. LC-MS (ESI$^+$) m/z 397.2 (M+H)$^+$.

3-(3-methyl-2-oxo-4-(piperazin-1-yl)-2,3-dihydro-1H-benzo[d]imidazol-1-yl)piperidine-2,6-dione (Intermediate FY)

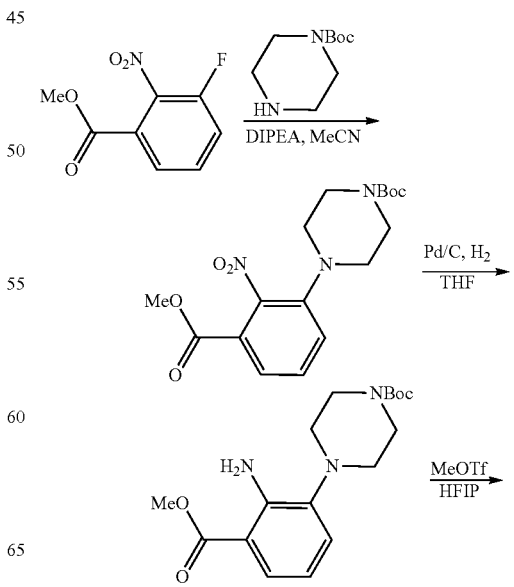

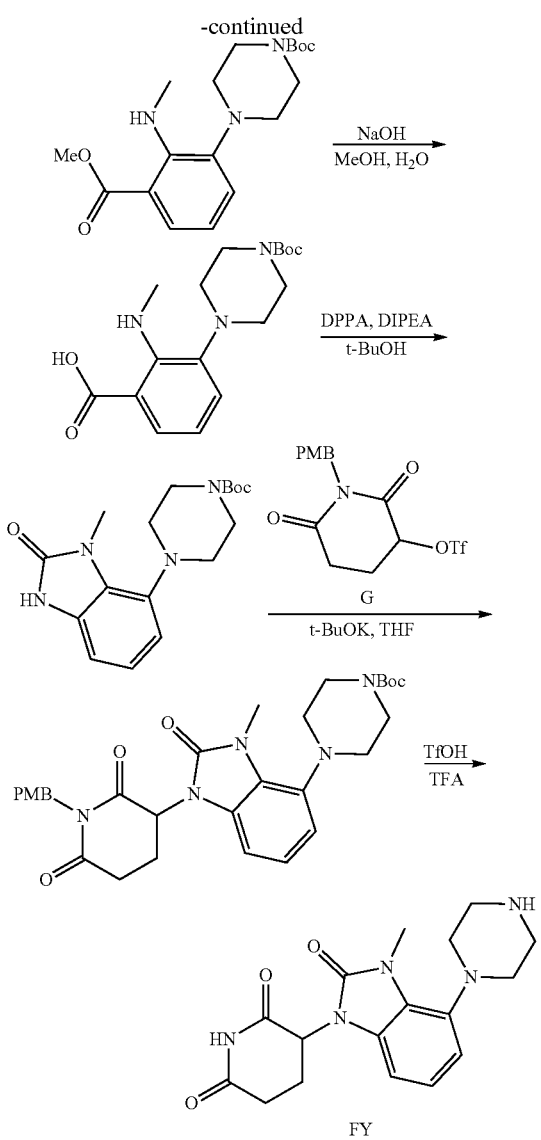

Step 1—Tert-butyl 4-(3-methoxycarbonyl-2-nitrophenyl)piperazine-1-carboxylate

To a solution of methyl 3-fluoro-2-nitro-benzoate (10.0 g, 50.2 mmol, CAS #1214353-57-7) and tert-butyl piperazine-1-carboxylate (11.2 g, 60.3 mmol, CAS #143238-38-4) in ACN (100 mL) was added DIPEA (19.5 g, 151 mmol). The reaction mixture was stirred at 50° C. for 12 hrs. On completion, the mixture was concentrated in vacuo. The residue was dissolved in water (200 mL), then extracted with EA (2×200 mL). The organic layer was washed with brine (2×100 mL), dried with Na$_2$SO$_4$, filtered and the filtrate was concentrated in vacuo to give the title compound (18.3 g, 100% yield) as yellow oil. $^1$H NMR (400 MHz, DMSO-d$_6$) δ 7.86 (dd, J=1.2, 8.0 Hz, 1H), 7.82-7.79 (m, 1H), 7.74-7.68 (m, 1H), 3.83 (s, 3H), 3.40-3.35 (m, 4H), 2.88-2.84 (m, 4H), 1.41 (s, 9H).

Step 2—Tert-butyl 4-(2-amino-3-methoxycarbonylphenyl)piperazine-1-carboxylate

To a solution of tert-butyl 4-(3-methoxycarbonyl-2-nitrophenyl)piperazine-1-carboxylate (17.0 g, 46.5 mmol) in THF (15 mL) was added Pd/C (2.00 g, 10 wt %). The reaction mixture was stirred at 20° C. for 12 hrs under H$_2$ (15 Psi) atmosphere. On completion, the mixture was filtered and the filtrate was concentrated in vacuo to give the title compound (15.2 g, 97% yield) as a yellow solid. $^1$H NMR (400 MHz, CDCl$_3$) δ 7.67 (dd, J=1.2, 8.0 Hz, 1H), 7.10 (dd, J=1.2, 7.6 Hz, 1H), 6.61 (t, J=7.6 Hz, 1H), 6.24 (br s, 2H), 4.28-3.95 (m, 2H), 3.87 (s, 3H), 3.16-2.84 (m, 4H), 2.80-2.55 (m, 2H), 1.49 (s, 9H).

Step 3—Tert-butyl 4-[3-methoxycarbonyl-2-(methylamino)phenyl]piperazine-1-carboxylate To a solution of tert-butyl 4-(2-amino-3-methoxycarbonyl-phenyl)piperazine-1-carboxylate (15.0 g, 44.7 mmol) in 1,1,1,3,3,3-hexafluoropropan-2-ol (40 mL) was added methyl trifluoromethanesulfonate (9.54 g, 58.1 mmol) at 0° C. The reaction mixture was stirred at 0° C. for 0.5 hr. On completion, the mixture was diluted with water (200 mL), then extracted with EA (2×200 mL). The organic layer was washed with brine (2×200 mL), dried with Na$_2$SO$_4$, filtered and the filtrate was concentrated in vacuo to give the title compound (15.0 g, 96% yield) as a yellow solid. $^1$H NMR (400 MHz, DMSO-d$_6$) δ 8.16-7.90 (m, 1H), 7.46 (dd, J=1.2, 8.0 Hz, 1H), 7.23 (d, J=7.6 Hz, 1H), 6.77 (t, J=7.6 Hz, 1H), 3.80 (s, 3H), 3.55-3.45 (m, 4H), 2.87 (s, 3H), 2.80-2.74 (m, 4H), 1.42 (s, 9H).

Step 4—3-(4-Tert-butoxycarbonylpiperazin-1-yl)-2-(methylamino)benzoic acid

To a solution of tert-butyl 4-[3-methoxycarbonyl-2-(methylamino)phenyl]piperazine-1-carboxylate (14.0 g, 40.1 mmol) in a mixed solvent of H$_2$O (20 mL) and MeOH (140 mL) was added NaOH (4.81 g, 120 mmol). The reaction mixture was stirred at 70° C. for 12 hrs. On completion, the mixture was concentrated in vacuo. The residue was diluted with water (200 mL), and extracted with EA (100 mL). The organic layer was discarded. The aqueous phase was acidified with HCl (1N) to pH=3-5, and extracted with EA (2×100 mL). The organic layer was washed with brine (200 mL), dried with Na$_2$SO$_4$, filtered and the filtrate was concentrated in vacuo. The residue was triturated with MeOH/H$_2$O (1:10, 100 mL) and filtered. The filter cake was dried in vacuo to give the title compound (9.60 g, 71% yield) as a white solid. LC-MS (ESI$^+$) m/z 336.1 (M+H)$^+$.

Step 5—Tert-butyl 4-(3-methyl-2-oxo-1H-benzimidazol-4-yl)piperazine-1-carboxylate To a solution of 3-(4-tert-butoxycarbonylpiperazin-1-yl)-2-(methylamino)benzoic acid (9.60 g, 28.6 mmol) and DIPEA (11.1 g, 85.9 mmol) in t-BuOH (200 mL) was added DPPA (7.88 g, 28.6 mmol). The reaction mixture was stirred at 85° C. for 12 hrs. On completion, the mixture was concentrated in vacuo. The residue was diluted with water (200 mL), and extracted with EA (2×200 mL). The organic layer was washed with brine (200 mL) and concentrated in vacuo. The residue was purified by reverse phase (0.1% FA condition) to give the title compound (3.35 g, 35% yield) as a white solid. $^1$H NMR (400 MHz, DMSO-d$_6$) δ 10.84 (s, 1H), 6.94-6.87 (m, 1H), 6.85-6.79 (m, 1H), 6.75 (dd, J=1.2, 7.6 Hz, 1H), 4.06-3.80 (m, 2H), 3.55 (s, 3H), 3.20-2.87 (m, 4H), 2.76-2.56 (m, 2H), 1.42 (s, 9H).

Step 6—Tert-butyl 4-[1-[1-[(4-methoxyphenyl)methyl]-2,6-dioxo-3-piperidyl]-3-methyl-2-oxo-benzimidazol-4-yl]piperazine-1-carboxylate To a solution of tert-butyl 4-(3-methyl-2-oxo-1H-benzimidazol-4-yl)piperazine-1-carboxylate (3.30 g, 9.93 mmol) in THF (50 mL) was added t-BuOK (1.67 g, 14.9 mmol) at 0° C. 1 hr later, and a solution of [1-[(4-methoxyphenyl)methyl]-2,6-dioxo-3-piperidyl] trifluoromethanesulfonate (4.54 g, 11.9 mmol, Intermediate G) in THF (20 mL) was added. The reaction mixture was stirred at 0° C. for 3 hrs. On completion, the mixture was acidified with FA to pH=3-5, diluted with water (300 mL), then extracted with EA (2×300 mL). The organic layer was washed with brine (200 mL) and concentrated in vacuo. The residue was purified by reverse phase flash (0.1% FA condition) to give the title compound (3.90 g, 70% yield) as a white solid. LC-MS (ESI$^+$) m/z 564.3 (M+H)$^+$.

Step 7—3-(3-Methyl-2-oxo-4-piperazin-1-yl-benzimidazol-1-yl)piperidine-2,6-dione To a solution of tert-butyl 4-[1-[1-[(4-methoxyphenyl)methyl]-2,6-dioxo-3-piperidyl]-3-methyl-2-oxo-benzimidazol-4-yl]piperazine-1-carboxylate (3.90 g, 6.92 mmol) in TFA (40 mL) was added TfOH (5 mL). The reaction mixture was stirred at 65° C. for 12 hrs. On completion, the mixture was concentrated in vacuo. The residue was purified by reverse phase flash (0.1% FA condition) to give the title compound (1.70 g, 63% yield, FA salt) as a blue solid. $^1$H NMR (400 MHz, DMSO-d$_6$) δ 11.09 (s, 1H), 7.06-6.99 (m, 1H), 6.96-6.92 (m, 2H), 5.36 (dd, J=5.2, 12.4 Hz, 1H), 3.63 (s, 3H), 3.35-3.25 (m, 4H), 3.16-2.97 (m, 4H), 2.91-2.82 (m, 1H), 2.76-2.57 (m, 2H), 2.05-1.93 (m, 1H).

1-((4-((8-cyclopentyl-7-oxo-7,8-dihydropyrido[2,3-d]pyrimidin-2-yl)amino)-3-methylphenyl)sulfonyl)piperidine-4-carbaldehyde (Intermediate FZ)

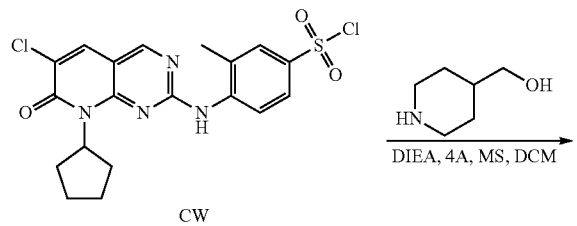

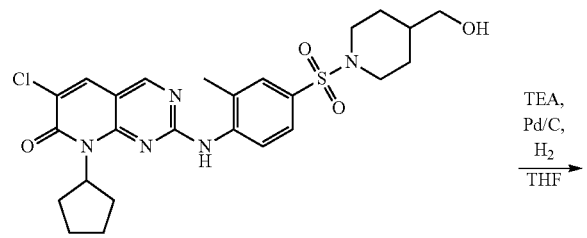

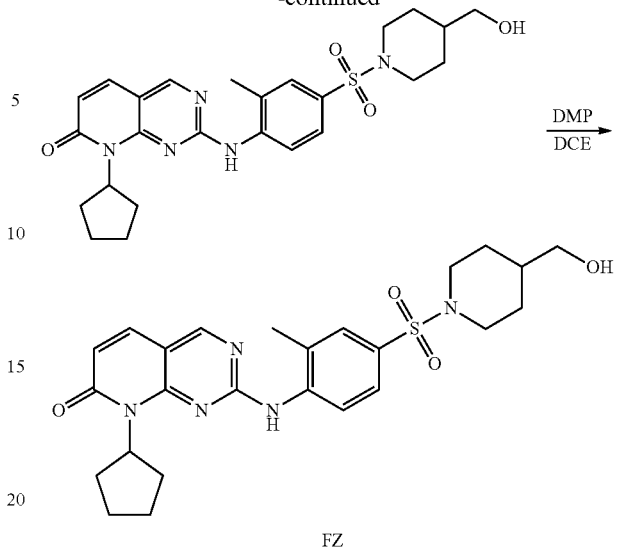

FZ

Step 1—6-Chloro-8-cyclopentyl-2-((4-((4-(hydroxymethyl)piperidin-1-yl)sulfonyl)-2-methylphenyl)amino)pyrido[2,3-d]pyrimidin-7(8H)-one To a solution of 4-piperidylmethanol (530 mg, 4.61 mmol, CAS #6457-49-4) in DCM (20 mL) was added DIEA (2.71 g, 20.9 mmol, 3.65 mL), 4A molecular sieves (2 g) and 4-((6-chloro-8-cyclopentyl-7-oxo-7,8-dihydropyrido[2,3-d]pyrimidin-2-yl)amino)-3-methylbenzene-1-sulfonyl chloride (1.9 g, 4.19 mmol, Intermediate CW). The mixture was stirred at 20° C. for 30 min. On completion, the reaction mixture was filtered and concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 100 mL/min) to give the title compound (2 g, 90% yield) as a white solid. LC-MS (ESI$^+$) m/z 532.1 (M+H)$^+$.

Step 2—8-Cyclopentyl-2-((4-((4-(hydroxymethyl)piperidin-1-yl)sulfonyl)-2-methylphenyl)amino)pyrido[2,3-d]pyrimidin-7(8H)-one To a solution of 6-chloro-8-cyclopentyl-2-((4-((4-(hydroxymethyl)piperidin-1-yl)sulfonyl)-2-methylphenyl)amino)pyrido[2,3-d]pyrimidin-7(8H)-one (100 mg, 200 umol) in THF (20 mL) was added TEA (57.0 mg, 563 umol) and Pd/C (1 g, 943 umol, 10 wt). The mixture was then stirred at 20° C. for 4 h under H$_2$ atmosphere. On completion, the reaction mixture was filtered and concentrated under reduced pressure to give the title compound (50 mg, 54% yield) as a white solid. LC-MS (ESI$^+$) m/z 498.2 (M+H)$^+$.

Step 3—1-((4-((8-cyclopentyl-7-oxo-7,8-dihydropyrido[2,3-d]pyrimidin-2-yl)amino)-3-methylphenyl)sulfonyl)piperidine-4-carbaldehyde To a solution of 8-cyclopentyl-2-((4-((4-(hydroxymethyl)piperidin-1-yl)sulfonyl)-2-methylphenyl)amino)pyrido[2,3-d]pyrimidin-7(8H)-one (500 mg, 1.00 mmol) in DCE (5 mL) was added DMP (639 mg, 1.51 mmol, 466 uL) at 0° C. Then the mixture was stirred at 0-25° C. for 2 h. On completion, the reaction mixture was washed with Na$_2$SO$_3$ (2 mL×2) at 25° C., and then diluted with NaHCO$_3$ (2 mL) and extracted with EtOAc (2 mL×2). The combined organic layers were washed with sat. NaCl (2 mL×2), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 50 mL/min) to give the title compound as a white solid. LC-MS (ESI$^+$) m/z 496.3 (M+H)$^+$.

3-(3-methyl-2-oxo-4-(piperazin-1-ylmethyl)-2,3-dihydro-1H-benzo[d]imidazol-1-yl)piperidine-2,6-dione (Intermediate GA)

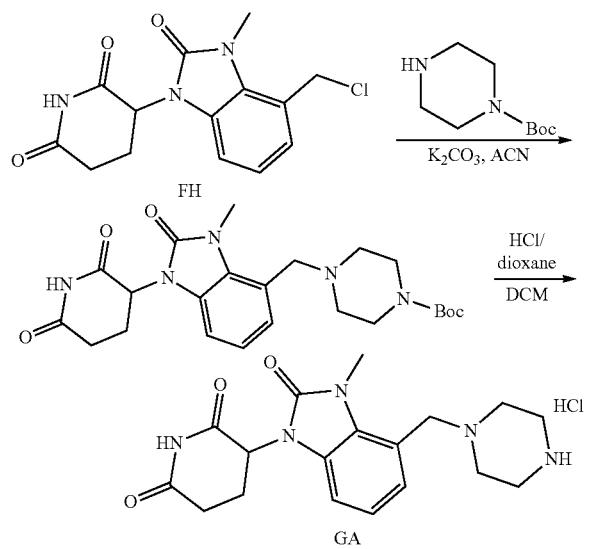

Step 1—Tert-butyl 4-[[1-(2,6-dioxo-3-piperidyl)-3-methyl-2-oxo-benzimidazol-4-yl]methyl] piperazine-1-carboxylate To a solution of 3-[4-(chloromethyl)-3-methyl-2-oxo-benzimidazol-1-yl] piperidine-2,6-dione (400 mg, 1.30 mmol, Intermediate FH) and tert-butyl piperazine-1-carboxylate (200 mg, 1.07 mmol, CAS #143238-38-4) in ACN (5.00 mL) was added K$_2$CO$_3$ (297 mg, 2.15 mmol). The mixture was stirred at 80° C. for 3 hrs. On completion, the reaction mixture was filtered and concentrated in vacuo to give a residue. The residue was purified by reversed phase (0.1% FA condition) to give the title compound (430 mg, 87% yield) as a yellow solid. $^1$H NMR (400 MHz, CDCl$_3$) δ 8.57 (s, 1H), 7.02-6.95 (m, 1H), 6.95-6.89 (m, 1H), 6.81-6.75 (m, 1H), 5.27 (dd, J=5.2, 12.4 Hz, 1H), 3.80 (s, 3H), 3.75-3.67 (m, 2H), 3.47-3.35 (m, 4H), 2.99-2.90 (m, 1H), 2.90-2.80 (m, 1H), 2.80-2.68 (m, 1H), 2.55-2.35 (m, 4H), 2.29-2.17 (m, 1H), 1.46 (s, 9H).

Step 2—3-[3-Methyl-2-oxo-4-(piperazin-1-ylmethyl)benzimidazol-1-yl]piperidine-2,6-dione To a solution of tert-butyl 4-[[1-(2, 6-dioxo-3-piperidyl)-3-methyl-2-oxo-benzimidazol-4-yl] methyl] piperazine-1-carboxylate (60.0 mg, 131 umol) in DCM (5.00 mL) was added HCl/dioxane (4 M, 1.00 mL). The reaction mixture was stirred at 20° C. for 0.5 hr. On completion, the reaction mixture was concentrated in vacuo to give the title compound (50.0 mg, 96% yield, HCl salt) as a white solid. LC-MS (ESI$^+$) m/z 358.1 (M+H)$^+$.

2-(((1r,4r)-4-(((benzyloxy)carbonyl)(methyl)amino)cyclohexyl)oxy)ethyl 4-methylbenzenesulfonate (Intermediate GB)

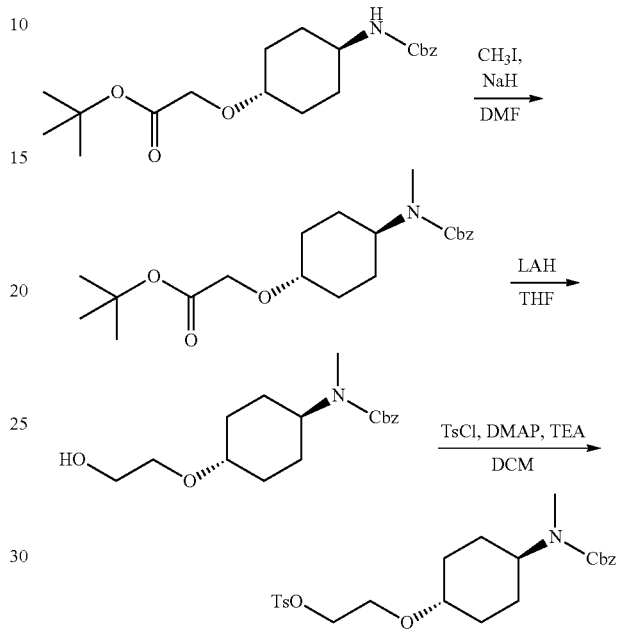

Step 1—Tert-butyl 2-(((1r,4r)-4-(((benzyloxy)carbonyl)(methyl)amino)cyclohexyl)oxy)acetate To a solution of tert-butyl 2-(((1r,4r)-4-(((benzyloxy)carbonyl)amino)cyclohexyl)oxy)acetate (3.50 g, 9.63 mmol, CAS #27489-63-0) in DMF (40 mL) was added NaH (578 mg, 14.5 mmol, 60% dispersion in mineral oil) under N$_2$ at 0° C. and the mixture was stirred for 0.5 h. Then CH$_3$I (2.73 g, 19.3 mmol) was added and the reaction mixture was stirred at 0° C. for 2 h. On completion, the reaction was quenched with sat. NH$_4$Cl (50 mL), then extracted with EtOAc (80 mL×3). The combined organic layers were washed with brine (50 mL×4), dried over Na$_2$SO$_4$ and evaporated. The residue was purified by column chromatography (SiO2, Petroleum ether/Ethyl acetate=10/1 to 9/1) to afford the title compound (2.40 g, 66% yield) as a white solid. $^1$H NMR (400 MHz, CDCl$_3$) δ=7.41-7.28 (m, 5H), 5.14 (s, 2H), 3.99 (d, J=1.6 Hz, 2H), 3.33-3.23 (m, 1H), 2.79 (s, 3H), 2.14 (d, J=10.8 Hz, 2H), 1.76 (d, J=10.4 Hz, 2H), 1.49 (d, J=1.6 Hz, 13H).

Step 2—Benzyl ((1r,4r)-4-(2-hydroxyethoxy)cyclohexyl)(methyl)carbamate

To a solution of tert-butyl 2-(((1r,4r)-4-(((benzyloxy)carbonyl)(methyl)amino)cyclohexyl)oxy)acetate (2.40 g, 6.36 mmol) in THF (30 mL) was added LAH (362 mg, 9.54 mmol) under N$_2$ at 0° C. and the mixture was stirred at 0° C. for 2 h. On completion, the reaction was quenched by addition H$_2$O (2.16 mL), filtered and evaporated to afford the title compound (1.60 g) as a colorless oil. $^1$H NMR (400 MHz, DMSO-d6) δ=7.37-7.34 (m, 3H), 7.33-7.32 (m, 1H), 7.27-7.19 (m, 1H), 5.15 (t, J=5.6 Hz, 1H), 5.07 (s, 2H), 4.55-4.47 (m, 4H), 3.82 (d, J=5.2 Hz, 1H), 3.16-3.13 (m, 1H), 2.73 (s, 3H), 1.99 (d, J=2.8 Hz, 2H), 1.78-1.73 (m, 2H), 1.56 (d, J=8.0 Hz, 2H), 1.14 (d, J=10.8 Hz, 2H).

Step 3—2-(((1r,4r)-4-(((benzyloxy)carbonyl)(methyl)amino)cyclohexyl)oxy)ethyl 4-methylbenzenesulfonate To a solution of benzyl ((1r,4r)-4-(2-hydroxyethoxy)cyclohexyl)(methyl)carbamate (1.60 g, 5.21 mmol) in DCM (16 mL) was added TEA (1.05 g, 10.4 mmol), DMAP (159 mg, 1.30 mmol) and TosCl (1.19 g, 6.25 mmol) under $N_2$ at 0° C. and the mixture was stirred at 20° C. for 2 h. On completion, the reaction mixture was diluted with water (15 mL), and extracted with DCM (15 mL×3). The combined organic layers were washed with brine (8 mL×3), dried over $Na_2SO_4$ and evaporated. The residue was purified by column chromatography ($SiO_2$, Petroleum ether/Ethyl acetate=5/1 to 4/1) to afford the title compound (800 mg, 33% yield) as a yellow oil. $^1$H NMR (400 MHz, DMSO-d6) δ=7.81-7.75 (m, 2H), 7.48 (d, J=8.0 Hz, 2H), 7.41-7.29 (m, 5H), 5.06 (s, 2H), 4.11-4.07 (m, 2H), 3.85-3.72 (m, 1H), 3.57-3.53 (m, 2H), 3.15-3.06 (m, 1H), 2.74-2.69 (m, 3H), 2.41 (s, 3H), 1.89 (d, J=13.2 Hz, 2H), 1.57-1.44 (m, 4H), 1.09 (d, J=12.4 Hz, 2H).

Benzyl ((1r,4r)-4-(2-aminoethoxy)cyclohexyl)(methyl)carbamate (Intermediate GC)

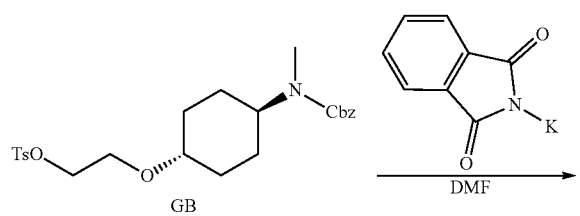

Step 1—Benzyl ((1r,4r)-4-(2-(1,3-dioxoisoindolin-2-yl)ethoxy)cyclohexyl)(methyl)carbamate A solution of 2-(((1r,4r)-4-(((benzyloxy)carbonyl)(methyl)amino)cyclohexyl)oxy)ethyl 4-methylbenzenesulfonate (800 mg, 2 mmol, Intermediate GB) and potassium 1,3-dioxoisoindolin-2-ide (482 mg, 2.60 mmol) in DMF (8 mL) was stirred at 50° C. for 3 h. On completion, the mixture was poured into $H_2O$ (5 mL) and filtered. The filter cake was concentrated in vacuo to afford the title compound (680 mg, 90% yield) as a white solid. $^1$H NMR (400 MHz, DMSO-d$_6$) δ=7.90-7.81 (m, 4H), 7.40-7.26 (m, 5H), 5.05 (s, 2H), 3.84-3.74 (m, 1H), 3.73-3.68 (m, 2H), 3.64-3.58 (m, 2H), 3.26-3.16 (m, 1H), 2.70 (s, 3H), 1.92 (d, J=12.8 Hz, 2H), 1.58-1.47 (m, 4H), 1.12 (dd, J=5.2, 11.2 Hz, 2H).

Step 2—Benzyl ((1r,4r)-4-(2-aminoethoxy)cyclohexyl)(methyl)carbamate

To a solution of benzyl ((1r,4r)-4-(2-(1,3-dioxoisoindolin-2-yl)ethoxy)cyclohexyl)(methyl)carbamate (680 mg, 1.56 mmol) in EtOH (14 mL) was added $N_2H_4 \cdot H_2O$ (398 mg, 7.79 mmol). The mixture was stirred at 50° C. for 2 h. On completion, the mixture was filtered and concentrated in vacuo to afford the title compound (470 mg) as a colorless oil. $^1$H NMR (400 MHz, DMSO-d$_6$) δ=7.43-7.28 (m, 5H), 5.07 (s, 2H), 3.88-3.77 (m, 1H), 3.47-3.41 (m, 2H), 3.19-3.13 (m, 1H), 2.73 (s, 3H), 2.67-2.62 (m, 2H), 2.05-1.97 (m, 2H), 1.56 (d, J=8.0 Hz, 3H), 1.25-1.12 (m, 3H).

4-((8-cyclopentyl-7-oxo-7,8-dihydropyrido[2,3-d]pyrimidin-2-yl)amino)-3-methyl-N-(2-(((1r,4r)-4-(methylamino)cyclohexyl)oxy)ethyl)benzenesulfonamide (Intermediate GD)

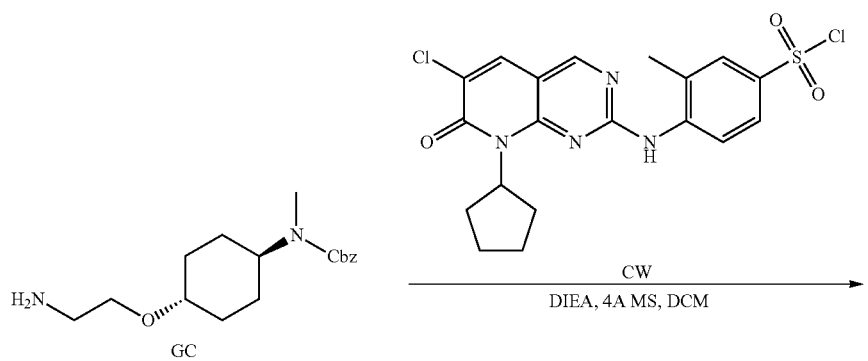

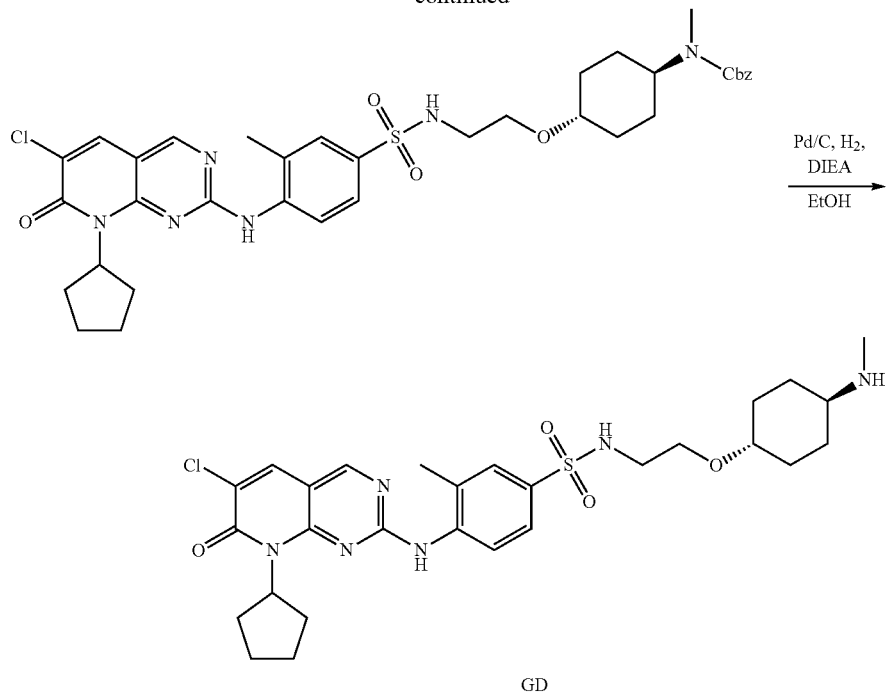

Step 1—Benzyl ((1r,4r)-4-(2-(4-((6-chloro-8-cyclopentyl-7-oxo-7,8-dihydropyrido[2,3-d]pyrimidin-2-yl)amino)-3-methylphenylsulfonamido)ethoxy)cyclohexyl)(methyl)carbamate To a solution of benzyl ((1r,4r)-4-(2-aminoethoxy)cyclohexyl)(methyl)carbamate (446 mg, 1.46 mmol, Intermediate GC) in DCM (6 mL) was added DIEA (855 mg, 6.62 mmol), 4A molecular sieves (600 mg) and 4-((6-chloro-8-cyclopentyl-7-oxo-7,8-dihydropyrido[2,3-d]pyrimidin-2-yl)amino)-3-methylbenzene-1-sulfonyl chloride (600 mg, 1.32 mmol, Intermediate CW). The mixture was stirred at 25° C. for 1 h. On completion, the mixture was filtered and concentrated in vacuo. The residue was purified by column chromatography (SiO$_2$, Petroleum ether/Ethyl acetate=1/1 to 1/2) to afford the title compound (900 mg, 94% yield) as a yellow solid. $^1$H NMR (400 MHz, DMSO-d$_6$) δ=9.68 (s, 1H), 8.76 (s, 1H), 8.18 (s, 1H), 7.74-7.68 (m, 2H), 7.65-7.60 (m, 2H), 7.40-7.30 (m, 5H), 5.76 (s, 1H), 5.06 (s, 2H), 3.86-3.73 (m, 1H), 3.39 (t, J=6.0 Hz, 2H), 3.17-3.04 (m, 1H), 2.89 (q, J=6.0 Hz, 2H), 2.70 (s, 3H), 2.33 (s, 3H), 2.14-2.09 (m, 2H), 1.97-1.92 (m, 2H), 1.76-1.64 (m, 5H), 1.56-1.46 (m, 5H), 1.13 (d, J=3.6 Hz, 2H).

Step 2—4-((8-cyclopentyl-7-oxo-7,8-dihydropyrido[2,3-d]pyrimidin-2-yl)amino)-3-methyl-N-(2-(((1r,4r)-4-(methylamino)cyclohexyl)oxy)ethyl)benzenesulfonamide To a solution of benzyl ((1r,4r)-4-(2-(4-((6-chloro-8-cyclopentyl-7-oxo-7,8-dihydropyrido[2,3-d]pyrimidin-2-yl)amino)-3-methylphenylsulfonamido)ethoxy)cyclohexyl)(methyl)carbamate (300 mg, 0.415 mmol) and DIEA (161 mg, 1.24 mmol) in EtOH (3 mL) was added Pd/C (150 mg, 10 wt %) under N$_2$. The suspension was degassed under vacuum and purged with H$_2$ several times. The mixture was stirred under H$_2$ (15 psi) at 25° C. for 2 hours. Then additional Pd/C (300 mg, 10 wt %) was added to and the mixture was stirred under H$_2$ (15 psi) at 25° C. for 12 hrs. On completion, the mixture was filtered and concentrated in vacuo to afford the title compound (230 mg) as a yellow oil. LC-MS (ESI$^+$) m/z 555.3 (M+H)$^+$.

Tert-butyl 3-(2-(tosyloxy)ethoxy)azetidine-1-carboxylate (Intermediate GE)

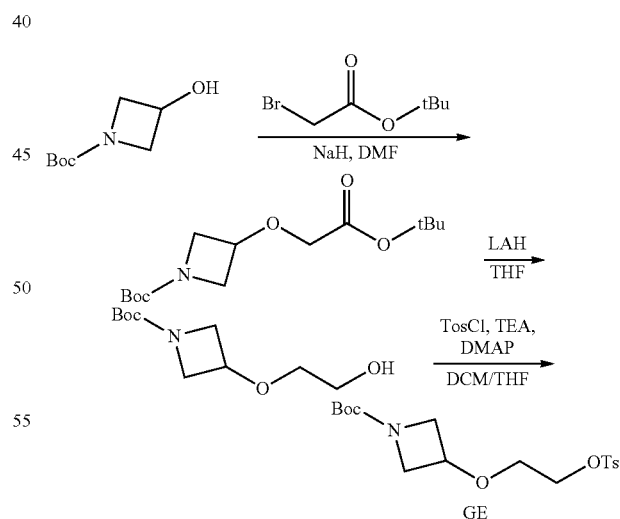

Step 1—Tert-butyl 3-(2-(tert-butoxy)-2-oxoethoxy)azetidine-1-carboxylate

To a solution of tert-butyl 3-hydroxyazetidine-1-carboxylate (10 g, 57.7 mmol, CAS #141699-55-0) in DMF (100 mL) was added NaH (2.77 g, 69.2 mmol, 60% dispersion in mineral oil) at 0° C. The mixture was stirred at 25° C. for 1 h and then tert-butyl 2-bromoacetate (16.9 g, 86.6 mmol) was added and the mixture was stirred at 40° C. for 2 h. On completion, the reaction mixture was quenched with NH₄Cl (100 mL) and extracted with EtOAC (100 mL×3). The combined organic layers were washed with brine (100 mL×3), dried over Na₂SO₄ and evaporated. The residue was purified by silica gel chromatography (Petroleum ether/Ethyl acetate=10/1~3/1) to give the title compound (11 g, 66% yield)) as a yellow solid. ¹H NMR (400 MHz, CDCl₃) δ=4.32 (tt, J=4.4, 6.4 Hz, 1H), 4.08 (dd, J=6.4, 10.0 Hz, 2H), 3.94-3.89 (m, 4H), 1.47 (s, 9H), 1.43 (s, 9H).

Step 2—Tert-butyl 3-(2-hydroxyethoxy)azetidine-1-carboxylate

To a solution of tert-butyl 3-(2-(tert-butoxy)-2-oxoethoxy)azetidine-1-carboxylate (8.8 g, 31 mmol) in THF (90 mL) was added LAH (1.74 g, 45.9 mmol) at 0° C. and the mixture was stirred at 0° C. for 2 h. On completion, the mixture was quenched with H₂O (1.8 mL) and 15% NaOH aqueous solution (1.8 mL), more H₂O (6 mL), and the mixture was stirred at 0° C. for 10 min. Then the mixture was filtered and the filtrate was concentrated to give the title compound (4.4 g) as a yellow oil. ¹H NMR (400 MHz, CDCl₃) δ=4.27-4.16 (m, 1H), 4.16-3.94 (m, 4H), 3.83-3.74 (m, 2H), 3.71-3.64 (m, 4H), 3.58-3.51 (m, 3H), 3.41 (td, J=4.4, 9.2 Hz, 5H), 3.00-2.88 (m, 2H), 2.29 (s, 3H), 1.37 (s, 9H).

Step 3—Tert-butyl 3-(2-(tosyloxy)ethoxy)azetidine-1-carboxylate

To a solution of tert-butyl 3-(2-hydroxyethoxy)azetidine-1-carboxylate (4.4 g, 20.3 mmol) in DCM (80 mL) and THF (20 mL) was added TEA (4.10 g, 40.5 mmol), DMAP (618 mg, 5.06 mmol) and 4-methylbenzenesulfonyl chloride (5.79 g, 30.4 mmol), then the mixture was stirred at 25° C. for 12 h. On completion, the mixture was quenched with water (100 mL) and extracted with EtOAc (100 mL×3). The combined organic layer was washed with brine (100 mL×3) and dried over Na₂SO₄ and concentrated in vacuo. The residue was purified by prep-HPLC (column: YMC Triart C18 250*50 mm*7 um; mobile phase: [water (ammonia hydroxide v/v)-ACN]; B %: 48%-78%, 15 min) to give the title compound (2.1 g, 28% yield) as a yellow oil. ¹H NMR (400 MHz, CDCl₃) δ=7.85-7.79 (m, 2H), 7.39-7.34 (m, 3H), 4.21-4.15 (m, 3H), 4.05-3.98 (m, 2H), 3.76-3.70 (m, 2H), 3.62-3.56 (m, 2H), 2.47 (s, 4H), 1.45 (s, 10H).

3-(5-(1-(2-(azetidin-3-yloxy)ethyl)piperidin-4-yl)-3-methyl-2-oxo-2,3-dihydro-1H-benzo[d]imidazol-1-yl)piperidine-2,6-dione (Intermediate GF)

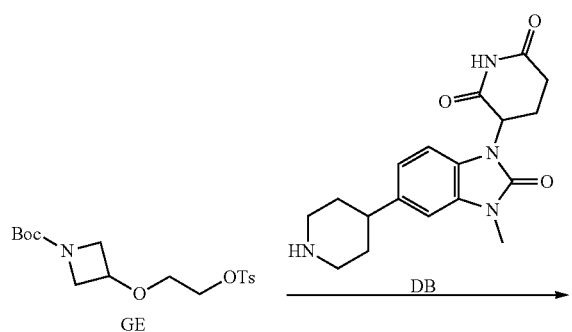

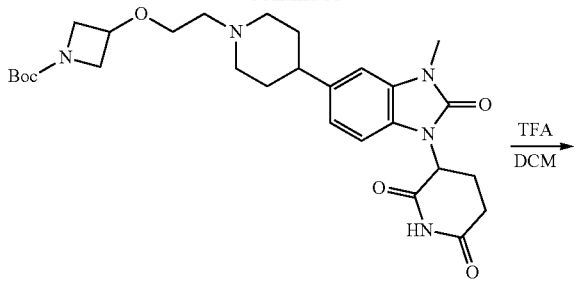

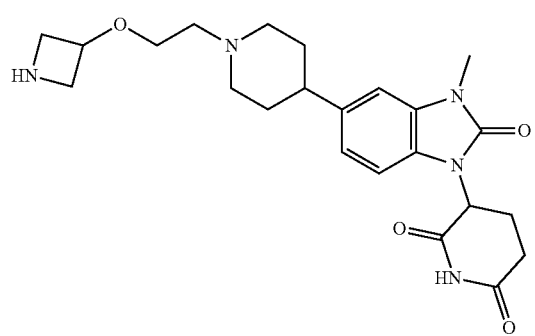

GF

Step 1—Tert-butyl 3-(2-(4-(1-(2,6-dioxopiperidin-3-yl)-3-methyl-2-oxo-2,3-dihydro-1H-benzo[d]imidazol-5-yl)piperidin-1-yl)ethoxy)azetidine-1-carboxylate To a solution of tert-butyl 3-(2-(tosyloxy)ethoxy)azetidine-1-carboxylate (250 mg, 673 umol, Intermediate GE) in DMF (2 mL) was added 3-(3-methyl-2-oxo-5-(piperidin-4-yl)-2,3-dihydro-1H-benzo[d]imidazol-1-yl)piperidine-2,6-dione (192 mg, 560 umol, Intermediate DB from SMA) and DIEA (217.5 mg, 1.68 mmol, 293.08 uL), then the mixture was stirred at 60° C. for 12 hr. On completion, the reaction mixture was quenched with NH₄Cl (5 mL) and extracted with EtOAc (10 mL×2). The combined organic layers were washed with brine (7 mL×3), dried over Na₂SO₄ and evaporated. The crude product was purified by reversed-phase HPLC (0.1% FA condition) to afford the title compound (40 mg, 13% yield) as white solid. LC-MS (ESI⁺) m/z 542.3 (M+H)⁺.

Step 2—3-(5-(1-(2-(azetidin-3-yloxy)ethyl)piperidin-4-yl)-3-methyl-2-oxo-2,3-dihydro-1H-benzo[d]imidazol-1-yl)piperidine-2,6-dione To a solution of tert-butyl 3-(2-(4-(1-(2,6-dioxopiperidin-3-yl)-3-methyl-2-oxo-2,3-dihydro-1H-benzo[d]imidazol-5-yl)piperidin-1-yl)ethoxy)azetidine-1-carboxylate (40 mg, 73.9 umol) in DCM (2 mL) was added TFA (0.4 mL), then the mixture was stirred at 25° C. for 4 h. On completion, the mixture was filtered and concentrated. The crude product was purified by reversed-phase HPLC (0.1% FA condition) to give the title compound (60 mg) as a yellow solid. LC-MS (ESI⁺) m/z 442.2 (M+H)⁺.

Intermediate GG

Tert-butyl ((1r,4r)-4-(2-(prop-2-yn-1-yloxy)ethoxy)cyclohexyl)carbamate (Intermediate GH)

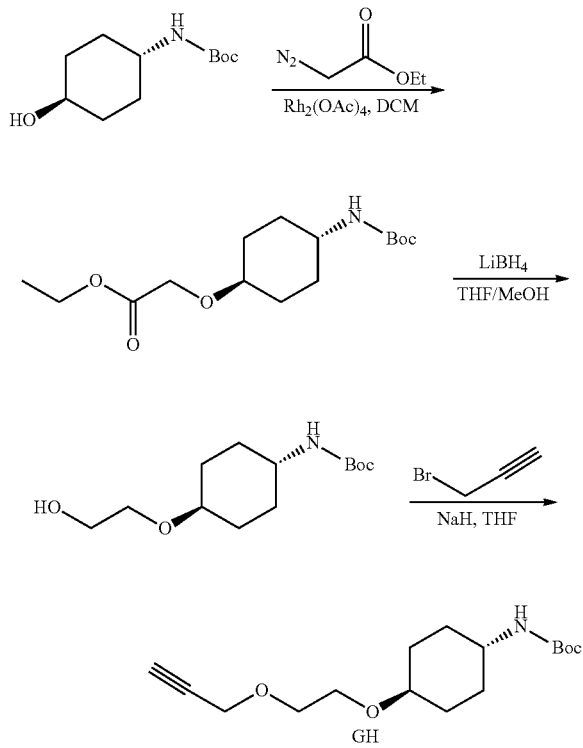

Step 1—Ethyl 2-(((1r,4r)-4-((tert-butoxycarbonyl)amino)cyclohexyl)oxy)acetate To a solution of tert-butyl N-(4-hydroxycyclohexyl)carbamate (12 g, 56 mmol, CAS #111300-06-2) in DCM (100 mL) was added diacetoxyrhodium (1.23 g, 5.57 mmol) and ethyl 2-diazoacetate (47.7 g, 334 mmol) at 0° C. under nitrogen flow. Then the reaction was stirred at 20° C. for 5 h under nitrogen atmosphere. On completion, the reaction was poured into water (150 mL) and extracted with ethyl acetate (2×100 mL). The combined organic phase is washed with brine (2×80 mL), and dried over sodium sulfate. Then the mixture was filtered and the filtrate was concentrated to give a residue. The residue was purified by column chromatography on silica gel (eluted with petroleum ether:ethyl acetate=100:1 to 100:20) to give the title compound (II g, 65% yield) as yellow oil. $^1$H NMR (400 MHz, CDCl$_3$) δ=4.43-4.31 (m, 1H), 3.74-3.68 (m, 2H), 3.59-3.54 (m, 2H), 3.51-3.37 (m, 1H), 3.27 (qt, J=3.6, 10.8 Hz, 1H), 2.02 (br s, 4H), 1.44 (s, 9H), 1.41-1.33 (m, 2H), 1.21-1.11 (m, 2H).

Step 2—Tert-butyl ((1r,4r)-4-(2-hydroxyethoxy)cyclohexyl)carbamate

To a solution of ethyl 2-[4-(tert-butoxycarbonylamino)cyclohexoxy]acetate (11 g, 37 mmol) in THF (110 mL) and MeOH (22 mL) was added LiBH$_4$ (2.87 g, 131 mmol) at 0° C. under nitrogen flow. Then the reaction was stirred at 20° C. for 2 h under nitrogen atmosphere. On completion, the reaction was quenched with saturated citric acid aqueous solution (120 mL) and extracted with ethyl acetate (100 mL×2). The combined organic phase is washed with brine (60 mL×2), and dried over sodium sulfate. The mixture was then filtered and the filtrate was concentrated to give a residue. The residue was purified by column chromatography on silica gel (eluted with petroleum ether:ethyl acetate=100:1 to 100:20) to give the title compound (6.5 g, 69% yield) as yellow gum. $^1$H NMR (400 MHz, CDCl$_3$) δ=4.46-4.27 (m, 1H), 3.73-3.67 (m, 2H), 3.61-3.53 (m, 2H), 3.50-3.37 (m, 1H), 3.33-3.19 (m, 1H), 2.04 (br dd, J=2.1, 10.5 Hz, 4H), 1.50-1.42 (m, 9H), 1.41-1.33 (m, 2H), 1.21-1.08 (m, 2H).

Step 3—Tert-butyl ((1r,4r)-4-(2-(prop-2-yn-1-yloxy)ethoxy)cyclohexyl)carbamate To a solution of tert-butyl N-[4-(2-hydroxyethoxy)cyclohexyl]carbamate (0.4 g, 2 mmol) in THF (10 mL) was added NaH (123 mg, 3.08 mmol, 60% dispersion in mineral oil) and 3-bromoprop-1-yne (366 mg, 3.08 mmol) at 0° C. under nitrogen flow. Then the reaction was stirred at 20° C. for 10 h under nitrogen atmosphere. On completion, the reaction was poured into saturated ammonium chloride aqueous solution (10 mL) and extracted with ethyl acetate (2×15 mL). The combined organic phase was washed with brine (2×10 mL), and dried over sodium sulfate. Then the mixture was filtered and the filtrate was concentrated to give a residue. The residue was purified by column chromatography on silica gel (eluted with petroleum ether:ethyl acetate=100:1 to 100:20) to give the title compound (450 mg, 98% yield) as yellow oil. $^1$H NMR (400 MHz, CDCl$_3$) δ=4.48-4.28 (m, 1H), 4.21 (d, J=2.4 Hz, 2H), 3.73-3.58 (m, 4H), 3.51-3.35 (m, 1H), 3.25 (tt, J=3.6, 10.4 Hz, 1H), 2.42 (t, J=2.4 Hz, 1H), 2.08-1.96 (m, 4H), 1.49-1.41 (m, 8H), 1.40-1.32 (m, 2H), 1.20-1.05 (m, 2H).

3-(5-((Z)-4-(2-(((1r,4r)-4-aminocyclohexyl)oxy)ethoxy)-2-chlorobut-1-en-1-yl)-3-methyl-2-oxo-2,3-dihydro-1H-benzo[d]imidazol-1-yl)piperidine-2,6-dione (Intermediate GI)

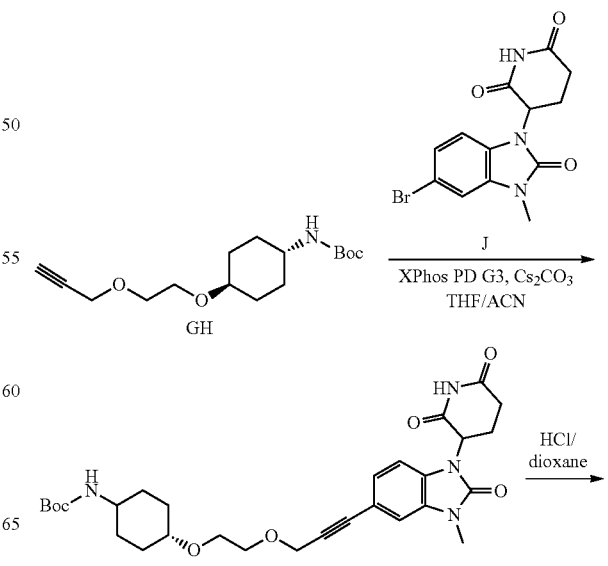

817

-continued

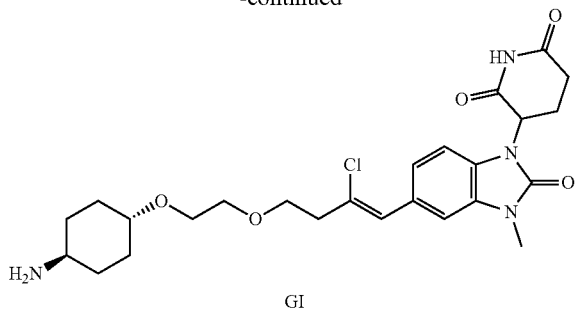

GI

Step 1—Tert-butyl ((1r,4r)-4-(2-((3-(1-(2,6-dioxopiperidin-3-yl)-3-methyl-2-oxo-2,3-dihydro-1H-benzo[d]imidazol-5-yl)prop-2-yn-1-yl)oxy)ethoxy)cyclohexyl)carbamate To a solution of tert-butyl N-[4-(2-prop-2-ynoxyethoxy)cyclohexyl]carbamate (0.45 g, 1.51 mmol, Intermediate GH) and 3-(5-bromo-3-methyl-2-oxo-benzimidazol-1-yl)piperidine-2,6-dione (562 mg, 1.66 mmol, Intermediate J) in THF (4.5 mL) and ACN (4.5 mL) was added $Cs_2CO_3$ (2.47 g, 7.57 mmol) and XPhos Pd G3 (384 mg, 453 umol) at 20° C. under nitrogen flow. Then the reaction was stirred at 60° C. for 10 h under nitrogen atmosphere. On completion, the reaction was poured into water (10 mL) and extracted with ethyl acetate (15 mL×2). The combined organic phase is washed with brine (10 mL×2), dried over sodium sulfate. Then filtered to get the filtrate and concentrated to give a residue. The residue was purified by column chromatography on silica gel (eluted with petroleum ether:ethyl acetate=100:1 to 100:80). Give the title compound (550 mg, 65.5% yield) as yellow solid. $^1$H NMR (400 MHz, $CDCl_3$) δ=7.11 (dd, J=1.2, 8.2 Hz, 1H), 7.04 (s, 1H), 6.68 (d, J=8.4 Hz, 1H), 5.13 (dd, J=5.2, 12.8 Hz, 1H), 4.42-4.25 (m, 3H), 3.70-3.64 (m, 2H), 3.63-3.57 (m, 2H), 3.35 (s, 4H), 3.19 (tt, J=3.6, 10.4 Hz, 1H), 2.92-2.80 (m, 1H), 2.22-2.11 (m, 1H), 2.00-1.85 (m, 4H), 1.62-1.49 (m, 2H), 1.40-1.34 (m, 9H), 1.33-1.26 (m, 2H), 1.11-0.97 (m, 2H).

Step 2—3-(5-((Z)-4-(2-(((1r,4r)-4-aminocyclohexyl)oxy)ethoxy)-2-chlorobut-1-en-1-yl)-3-methyl-2-oxo-2,3-dihydro-1H-benzo[d]imidazol-1-yl)piperidine-2,6-dione A solution of tert-butyl N-[4-[2-[3-[1-(2,6-dioxo-3-piperidyl)-3-methyl-2-oxo-benzimidazol-5-yl]prop-2-ynoxy]ethoxy]cyclohexyl]carbamate (400 mg, 721 umol) in HCl/dioxane (4 M, 5 mL) at 0° C. under nitrogen flow. Then the reaction was stirred at 20° C. for 2 h under nitrogen atmosphere. On completion, the reaction was concentrated to give the title compound (400 mg) as a yellow solid. LC-MS (ESI$^+$) m/z 491.2 (M+H)$^+$.

2-(((1r,4r)-4-(((tert-butyldiphenylsilyl)oxy)methyl)cyclohexyl)oxy)ethanamine (Intermediate GJ)

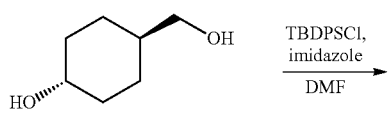

818

-continued

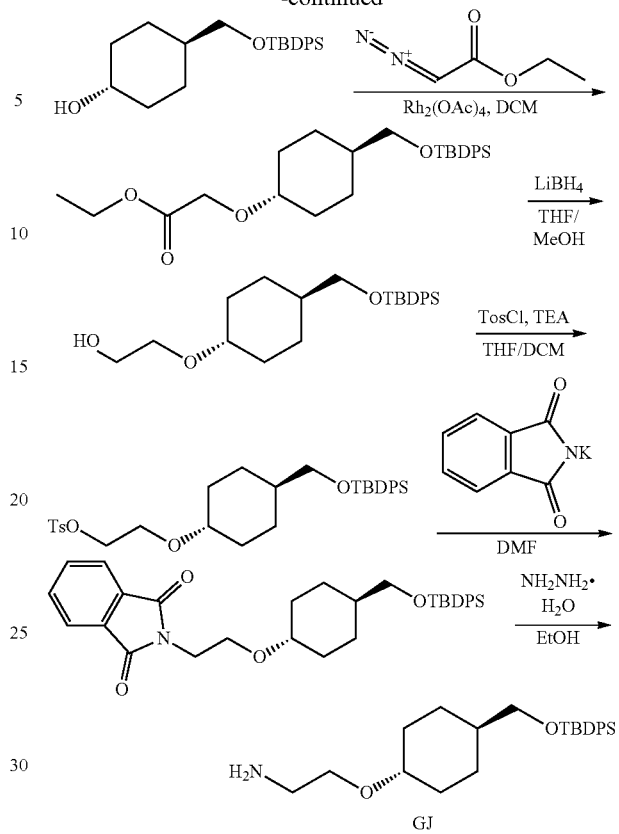

GJ

Step 1—(1r,4r)-4-(((tert-butyldiphenylsilyl)oxy)methyl)cyclohexanol

To a solution of 4-(hydroxymethyl)cyclohexanol (10 g, 76.8 mmol, CAS #3685-27-6) and imidazole (5.75 g, 84.5 mmol) in DMF (300 mL) was added TBDPSCl (22.1 g, 80.6 mmol) at 0° C., then the mixture was stirred at 25° C. for 12 h. On completion, the mixture was quenched with water (300 mL) and extracted with EtOAc (300 mL×3). The combined organic layers was washed with brine (300 mL×3) and dried over $Na_2SO_4$ and concentrated in vacuo. The residue was purified by column chromatography ($SiO_2$, Petroleum ether/Ethyl acetate=10/1 to 3/1) to afford the title compound (19 g, 67% yield) as a yellow oil. $^1$H NMR (400 MHz, $CDCl_3$) δ=7.71-7.63 (m, 4H), 7.48-7.35 (m, 6H), 3.56 (tt, J=4.4, 10.8 Hz, 1H), 3.47 (d, J=6.4 Hz, 2H), 2.05-1.96 (m, 2H), 1.90-1.79 (m, 2H), 1.33-1.20 (m, 3H), 1.06 (m, 11H).

Step 2—Ethyl 2-(((1r,4r)-4-(((tert-butyldiphenylsilyl)oxy)methyl)cyclohexyl)oxy)acetate To a solution of (1r,4r)-4-(((tert-butyldiphenylsilyl)oxy)methyl)cyclohexanol (10 g, 30 mmol) and $Rh_2(OAc)_4$ (1.20 g, 2.71 mmol) in DCM (100 mL) was added ethyl 2-diazoacetate (18.5 g, 162 mmol) dropwise at 0° C., then the mixture was stirred at 25° C. for 12 h under $N_2$ atmosphere. On completion, the mixture was quenched with HOAc (50 mL) and $H_2O$ (100 mL), then extracted with DCM (100 mL×3). The combined organic layer was washed with brine (100 mL×3) and dried over $Na_2SO_4$ and concentrated in vacuo and purified by silica gel chromatography (Petroleum ether/Ethyl acetate=10/1-3/1) to afford the title compound (8 g, 65% yield) as a colorless oil. ¹H NMR (400 MHz, CDCl₃) δ=7.71-7.61 (m, 4H), 7.44-7.34 (m, 6H), 4.31-4.23 (m, 1H), 4.23 (br d, J=7.2 Hz, 2H), 4.12 (s, 2H), 3.46 (d, J=6.1 Hz, 2H), 3.35-3.21 (m, 1H), 2.18-2.02 (m, 2H), 1.92-1.79 (m, 2H), 1.05 (s, 9H).

Step 3—2-(((1r,4r)-4-(((tert-butyldiphenylsilyl)oxy)methyl)cyclohexyl)oxy)ethanol To a solution of ethyl 2-[4-[[tert-butyl(diphenyl)silyl]oxymethyl]cyclohexoxy]acetate (6 g, 10 mmol) in THF (60 mL) and MeOH (12 mL) was added LiBH₄ (862 mg, 39.5 mmol) at 0° C. The mixture was stirred at 0-20° C. for 2 h. On completion, the reaction mixture was quenched with addition saturated citric acid aqueous solution (120 mL) at 0° C., and then diluted with EtOAc (120 mL) and extracted with EtOAc (120 mL×3). The combined organic layers were washed with brine (120 mL×3), dried over Na₂SO₄, filtered and concentrated under reduced pressure to give a residue. The residue was purified by column chromatography (SiO₂, Petroleum ether/Ethyl acetate=5/1 to 1/1) to afford the title compound (5 g, 92% yield) as a white solid. LC-MS (ESI⁺) m/z 413.1 (M+H)⁺.

Step 4—2-(((1r,4r)-4-(((tert-butyldiphenylsilyl)oxy)methyl)cyclohexyl)oxy)ethyl 4-methylbenzenesulfonate To a solution of 2-[4-[[tert-butyl(diphenyl)silyl]oxymethyl]cyclohexoxy]ethanol (5 g, 12.1 mmol) in DCM (80 mL) and THF (20 mL) was added TEA (2.45 g, 24.2 mmol), DMAP (370 mg, 3.03 mmol), and TosCl (3.47 g, 18.1 mmol). The mixture was stirred at 25° C. for 12 h. On completion, the mixture was quenched with water (100 mL) and extracted with EtOAc (100 mL×3). The combined organic layers was washed with brine (100 mL×3) and dried over Na₂SO₄ and concentrated in vacuo. The residue was purified by silica gel chromatography (Petroleum ether/Ethyl acetate=10/1-3/1) to afford the title compound (4 g, 58% yield) as a yellow oil. ¹H NMR (400 MHz, CDCl₃) δ=7.82 (d, J=8.4 Hz, 2H), 7.66 (dd, J=1.2, 7.6 Hz, 4H), 7.47-7.31 (m, 8H), 4.22-4.13 (m, 2H), 3.69-3.64 (m, 2H), 3.46 (d, J=6.0 Hz, 2H), 3.22-3.08 (m, 1H), 2.45 (s, 3H), 1.96 (br d, J=9.6 Hz, 2H), 1.87-1.77 (m, 2H), 1.48 (dt, J=2.4, 6.0 Hz, 1H), 1.27 (t, J=7.2 Hz, 1H), 1.21-1.10 (m, 2H), 1.06 (s, 9H), 1.02-0.85 (m, 3H).

Step 5—2-(2-(((1r,4r)-4-(((tert-butyldiphenylsilyl)oxy)methyl)cyclohexyl)oxy)ethyl)isoindoline-1,3-dione To a solution of 2-[4-[[tert-butyl(diphenyl)silyl]oxymethyl]cyclohexoxy]ethyl 4-methylbenzenesulfonate (2 g, 3.53 mmol) in DMF (10 mL) was added (1,3-dioxoisoindolin-2-yl)potassium (980 mg, 5.29 mmol), then the mixture was stirred at 50° C. for 4 h. On completion, the mixture was quenched with water (10 mL) and filtered. The filter cake was washed with water (10 mL×3) to afford the title compound (2 g) as a yellow solid. ¹H NMR (400 MHz, CDCl₃) δ=7.88 (dd, J=3.2, 5.2 Hz, 2H), 7.74 (dd, J=3.2, 5.2 Hz, 2H), 7.66 (dd, J=1.6, 7.6 Hz, 4H), 7.48-7.32 (m, 6H), 3.95-3.86 (m, 2H), 3.79-3.69 (m, 2H), 3.45 (d, J=6.4 Hz, 2H), 3.28-3.18 (m, 1H), 2.05-1.95 (m, 2H), 1.88-1.79 (m, 2H), 1.56-1.45 (m, 1H), 1.26-1.13 (m, 2H), 1.10-0.91 (m, 11H).

Step 6—2-(((1r,4r)-4-(((tert-butyldiphenylsilyl)oxy)methyl)cyclohexyl)oxy)ethanamine To a solution of 2-[2-[4-[[tert-butyl(diphenyl)silyl]oxymethyl]cyclohexoxy]ethyl]isoindoline-1,3-dione (2 g, 3.69 mmol) in EtOH (80 mL) was added NH₂NH₂·H₂O (1.63 g, 27.6 mmol, 85% solution), and the mixture was stirred at 50° C. for 2 h. On completion, the mixture was filtered and concentrated in vacuo to afford the title compound (1.2 g) as a yellow gum. LC-MS (ESI⁺) m/z 442.3 (M+K)⁺.

4-((6-chloro-8-cyclopentyl-7-oxo-7,8-dihydropyrido[2,3-d]pyrimidin-2-yl)amino)-N-(2-(((1r,4r)-4-formylcyclohexyl)oxy)ethyl)-3-methylbenzenesulfonamide (Intermediate GK)

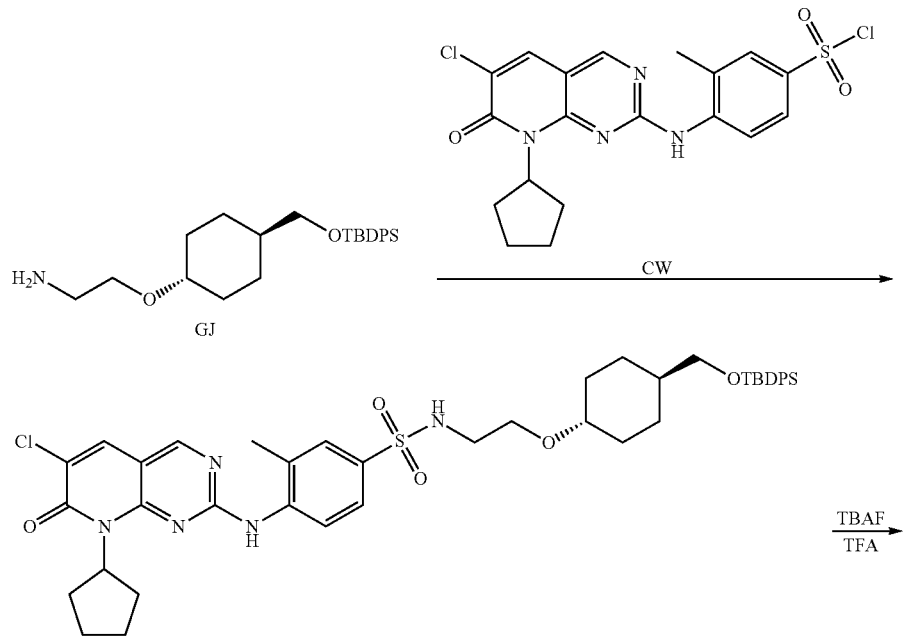

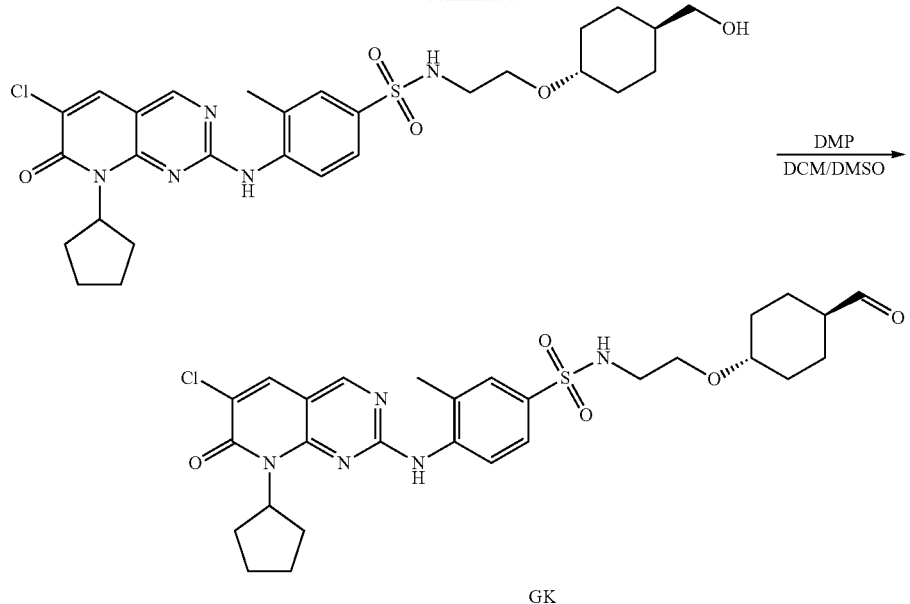

GK

Step 1—N-(2-(((1r,4r)-4-(((tert-butyldiphenylsilyl) oxy)methyl)cyclohexyl)oxy)ethyl)-4-((6-chloro-8-cyclopentyl-7-oxo-7,8-dihydropyrido[2,3-d]pyrimidin-2-yl)amino)-3-methylbenzenesulfonamide To a solution of 4-[(6-chloro-8-cyclopentyl-7-oxo-pyrido[2,3-d]pyrimidin-2-yl)amino]-3-methyl-benzenesulfonyl chloride (500 mg, 1.10 mmol, Intermediate CW) and 2-[4-[[tert-butyl(diphenyl)silyl]oxymethyl]cyclohexoxy] ethanamine (681 mg, 1.65 mmol, Intermediate GJ) in DCM (10 mL) was added DIEA (712 mg, 5.51 mmol) and 4A molecular sieves (500 mg), then the mixture was stirred at 25° C. for 30 min. On completion, the mixture was filtered and concentrated in vacuo to afford the title compound (900 mg) as a yellow oil. LC-MS (ESI$^+$) m/z 828.3 (M+H)$^+$.

Step 2—4-((6-Chloro-8-cyclopentyl-7-oxo-7,8-dihydropyrido[2,3-d]pyrimidin-2-yl)amino)-N-(2-(((1r,4r)-4-(hydroxymethyl)cyclohexyl)oxy)ethyl)-3-methylbenzenesulfonamide A solution of N-[2-[4-[[tert-butyl(diphenyl)silyl]oxymethyl]cyclohexoxy]ethyl]-4-[(6-chloro-8-cyclopentyl-7-oxo-pyrido[2,3-d]pyrimidin-2-yl)amino]-3-methyl-benzenesulfonamide (900 mg, 1.09 mmol) in TBAF (2 M, 10 mL) was stirred at 25° C. for 1 h. On completion, the mixture was concentrated in vacuo and purified by reversed-phase HPLC (0.1% FA condition) to afford the title compound (250 mg, 39% yield) as a yellow oil. $^1$H NMR (400 MHz, CDCl$_3$) δ 8.57 (s, 1H), 8.33 (d, J=8.4 Hz, 1H), 7.79-7.74 (m, 3H), 7.42 (br s, 1H), 5.92 (quin, J=8.8 Hz, 1H), 4.85 (t, J=6.0 Hz, 1H), 3.54 (t, J=5.2 Hz, 2H), 3.46 (d, J=6.4 Hz, 2H), 3.18-3.09 (m, 3H), 2.45 (s, 3H), 2.36-2.25 (m, 2H), 2.13-1.98 (m, 5H), 1.96-1.78 (m, 5H), 1.75-1.66 (m, 3H), 1.50-1.40 (m, 2H), 1.25-1.10 (m, 3H), 1.04-0.90 (m, 2H).

Step 3—4-((6-Chloro-8-cyclopentyl-7-oxo-7,8-dihydropyrido[2,3-d]pyrimidin-2-yl)amino)-N-(2-(((1r,4r)-4-formylcyclohexyl)oxy)ethyl)-3-methylbenzenesulfonamide To a solution of 4-[(6-chloro-8-cyclopentyl-7-oxo-pyrido[2,3-d]pyrimidin-2-yl)amino]-N-[2-[4-(hydroxymethyl)cyclohexoxy]ethyl]-3-methyl-benzenesulfonamide (200 mg, 338 umol) in DCM (4 mL) was added DMP (215 mg, 508 umol), then the mixture was stirred at 25° C. for 12 h. On completion, the mixture was quenched with sat. NaHCO$_3$ (10 mL) and extracted with EtOAc (10 mL×3), The combined organic layers was washed with brine (10 mL×3), dried over Na$_2$SO$_4$ and concentrated in vacuo to afford the title compound (250 mg) as a yellow solid. $^1$H NMR (400 MHz, CDCl$_3$) δ=9.64 (d, J=1.2 Hz, 1H), 8.58 (s, 1H), 8.35 (d, J=8.4 Hz, 1H), 8.27 (dd, J=1.6, 7.6 Hz, 1H), 8.06-8.00 (m, 1H), 7.94 (ddd, J=1.6, 7.2, 8.4 Hz, 1H), 7.78-7.74 (m, 4H), 7.32 (s, 1H), 5.93 (quin, J=8.8 Hz, 1H), 4.83 (t, J=6.0 Hz, 1H), 3.54 (t, J=5.2 Hz, 2H), 3.20-3.10 (m, 3H), 2.45 (s, 3H), 2.38-2.28 (m, 2H), 2.09-1.98 (m, 7H), 1.96-1.85 (m, 3H), 1.76-1.65 (m, 3H), 1.42-1.22 (m, 5H).

3-[4-[4-[Azetidin-3-ylmethyl(methyl)amino]-1-piperidyl]-3-methyl-2-oxo-benzimidazol-1-yl]piperidine-2,6-dione (Intermediate GL)

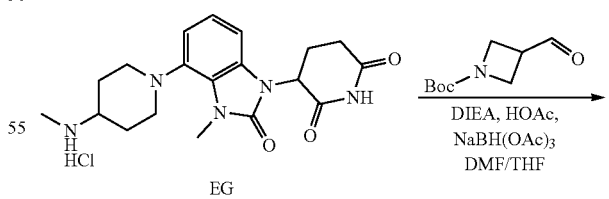

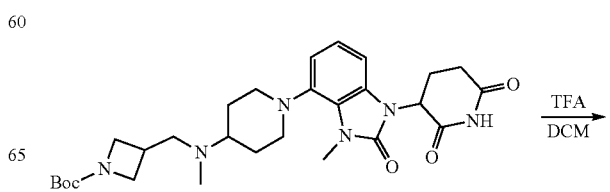

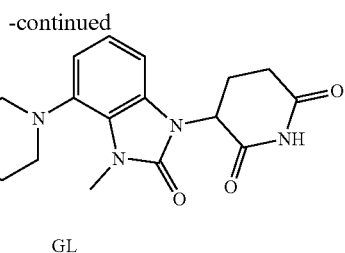

Step 1—Tert-butyl 3-[[[1-[1-(2,6-dioxo-3-piperidyl)-3-methyl-2-oxo-benzimidazol-4-yl]-4-piperidyl]-methyl-amino]methyl]azetidine-1-carboxylate To a mixture of 3-[3-methyl-4-[4-(methylamino)-1-piperidyl]-2-oxo-benzimidazol-1-yl]piperidine-2,6-dione (100 mg, 245 umol, HCl, Intermediate EG) in a mixed solvent of THF (2 mL) and DMF (0.5 mL) was added DIEA (63.3 mg, 490 umol) at −15° C. until the pH=8. Then the mixture was stirred at −15° C. for 10 mins, and HOAc (44.1 mg, 735 umol) was added at −15° C. until the pH=6. The mixture was then stirred at −15° C. for 20 mins. Subsequently, tert-butyl 3-formylazetidine-1-carboxylate (47.6 mg, 257 umol, CAS #177947-96-5) was added and the mixture was stirred at −15° C. for 1 hr. Finally, NaBH(OAc)₃ (103 mg, 490 umol) was added. The resulting reaction mixture was stirred at −15° C. for 1 hr. On completion, the reaction mixture was concentrated in vacuo to afford a residue. The residue was purified by prep-HPLC (column: Phenomenex Luna C18 100*30 mm*5 um; mobile phase: [water(FA)-ACN]; B %: 3%-33%, 8 min) to give the title compound (60 mg, 45% yield) as a white solid. $^1$H NMR (400 MHz, DMSO-d$_6$) δ 11.09 (s, 1H), 6.99-6.84 (m, 3H), 5.38-5.28 (m, 1H), 3.88 (s, 2H), 3.63 (s, 3H), 3.46 (d, J=5.2 Hz, 2H), 3.14 (d, J=11.2 Hz, 2H), 2.89 (s, 1H), 2.71-2.67 (m, 2H), 2.63 (s, 2H), 2.19 (s, 3H), 2.02-1.96 (m, 1H), 1.82-1.74 (m, 2H), 1.71-1.59 (m, 2H), 1.37 (s, 9H), 1.36 (d, J=1.2 Hz, 4H). LCMS (ESI⁺) m/z 541.2 (M+H)⁺.

Step 2—3-[4-[4-[Azetidin-3-ylmethyl(methyl)amino]-1-piperidyl]-3-methyl-2-oxo-benzimidazol-1-yl]piperidine-2,6-dione To a solution of tert-butyl 3-[[[1-[1-(2,6-dioxo-3-piperidyl)-3-methyl-2-oxo-benzimidazol-4-yl]-4-piperidyl]-methyl-amino]methyl]azetidine-1-carboxylate (40.0 mg, 73.9 umol) in DCM (2 mL) was added TFA (616 mg, 5.40 mmol). The mixture was stirred at 25° C. for 1 hour. The reaction mixture was concentrated in vacuo to give the title compound (40.0 mg, 97% yield, TFA) as a white solid. LCMS (ESI⁺) m/z 441.1 (M+H)⁺.

Tert-butyl N-(3-oxopropyl)carbamate (Intermediate GM)

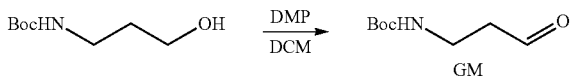

To a solution of tert-butyl N-(3-hydroxypropyl)carbamate (500 mg, 2.85 mmol, CAS #58885-58-8) in DCM (6 mL) was added DMP (1.45 g, 3.42 mmol). The mixture was stirred at 25° C. for 1 hr. The reaction mixture was quenched with Na₂S₂O₃·5H₂O (10 mL), and extracted with DCM (3×20 mL). The combined organic layer was washed with brine (20 mL), dried over anhydrous sodium sulfate, filtered and the filtrate was concentrated in vacuo. The residue was purified by column chromatography (SiO₂, Petroleum ether/Ethyl acetate=10/1 to 5/1) to give the title compound (300 mg, 60% yield) as a colorless oil. $^1$H NMR (400 MHz, CDCl₃) δ 9.82 (s, 1H), 4.91 (d, J=0.8 Hz, 1H), 3.43 (q, J=5.6 Hz, 2H), 2.72 (t, J=5.6 Hz, 2H), 1.44 (s, 9H).

3-[4-[4-[3-Aminopropyl(methyl)amino]-1-piperidyl]-3-methyl-2-oxo-benzimidazol-1-yl]piperidine-2,6-dione (Intermediate GN)

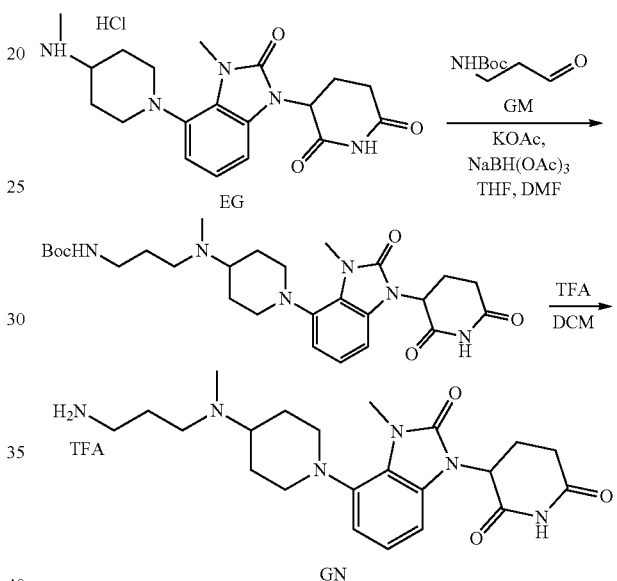

Step 1—Tert-butyl N-[3-[[1-[1-(2,6-dioxo-3-piperidyl)-3-methyl-2-oxo-benzimidazol-4-yl]-4-piperidyl]-methyl-amino]propyl]carbamate3109

To a solution of 3-[3-methyl-4-[4-(methylamino)-1-piperidyl]-2-oxo-benzimidazol-1-yl]piperidine-2,6-dione (100 mg, 269 umol, HCl salt, Intermediate EG) and tert-butyl N-(3-oxopropyl)carbamate (60.6 mg, 350 umol, Intermediate GM) in a mixture solution of THF (2 mL) and DMF (0.5 mL) was added KOAc (264 mg, 2.69 mmol) and NaBH(OAc)₃ (114 mg, 538 umol). The mixture was stirred at 0° C. for 1 hr. On completion, the mixture was quenched with H₂O (0.5 mL) at 0° C. and concentrated in vacuo to afford a residue. The residue was purified by prep-HPLC (column: Phenomenex luna C18 150*25 mm*10 um; mobile phase: [water(FA)-ACN]; B %: 5%-35%, 9 min) to give the title compound (75.0 mg, 52% yield) as a white solid. LCMS (ESI⁺) m/z 529.5 (M+H)⁺.

Step 2—3-[4-[4-[3-Aminopropyl(methyl)amino]-1-piperidyl]-3-methyl-2-oxo-benzimidazol-1-yl] piperidine-2,6-dione To a solution of tert-butyl N-[3-[[1-[1-(2,6-dioxo-3-piperidyl)-3-methyl-2-oxo-benzimidazol-4-yl]-4-piperidyl]- methyl-amino]propyl]carbamate (75.0 mg, 141 umol) in DCM (2 mL) was added TFA (770 mg, 6.75 mmol). The mixture was stirred at 25° C. for 0.5 hour. The reaction mixture was concentrated under reduced pressure to give the title compound (75.0 mg, 97% yield, TFA) as a white solid. LCMS (ESI$^+$) m/z 429.0 (M+H)$^+$.

1-[8-[4-(Methylamino)-1-piperidyl]-4-isoquinolyl] hexahydropyrimidine-2,4-dione (Intermediate GO)

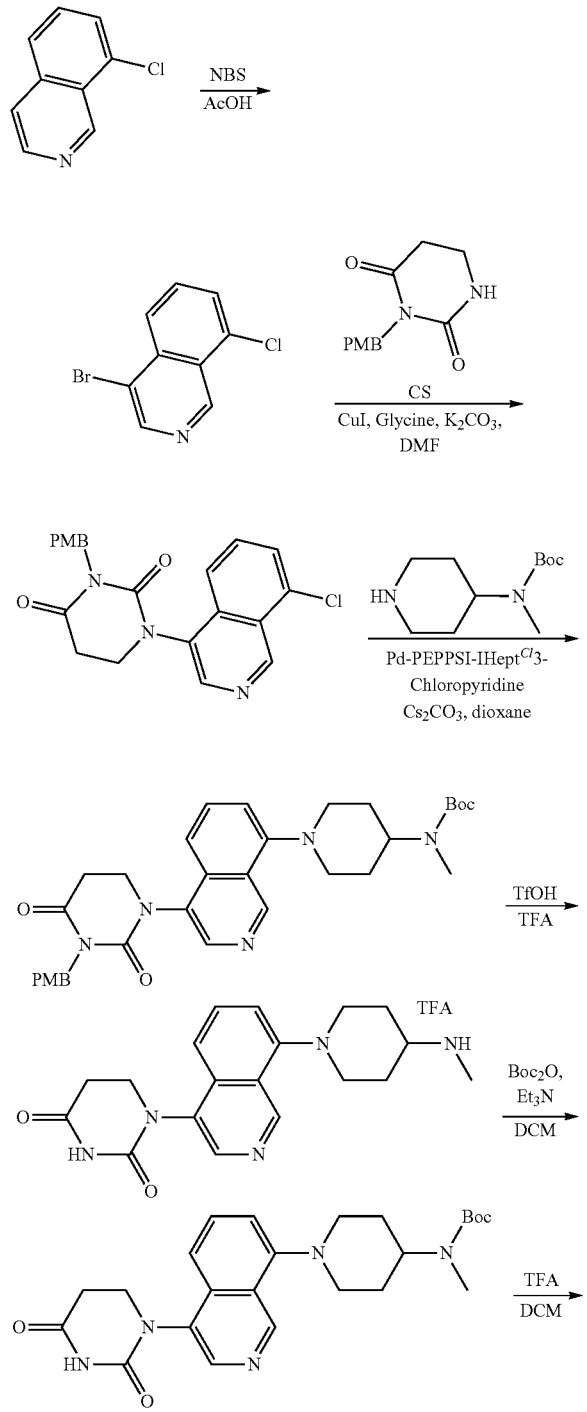

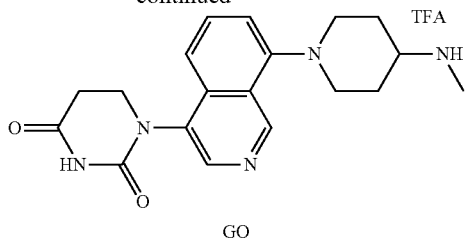

GO

Step 1—4-Bromo-8-chloro-isoquinoline

A mixture of 8-chloroisoquinoline (5.00 g, 30.5 mmol, CAS #34784-07-1), NBS (7.07 g, 39.7 mmol) in HOAc (50 mL) was degassed and purged with N$_2$ three times, and then the mixture was stirred at 50° C. for 40 minutes under N$_2$ atmosphere. On completion, the reaction mixture was neutralized with 15% NaOH (20 mL) and the mixture was extracted with EA (3×20 mL). The combined organic layers were washed with water (50 mL), dried over anhydrous Na$_2$SO$_4$, filtered and concentrated in vacuo to give a residue. Then the residue was purified by column chromatography to give the title compound (400 mg, 73.90% yield) as yellow solid. $^1$H NMR (400 MHz, CDCl$_3$-d) δ 9.58 (s, 1H), 8.79 (s, 1H), 8.12-8.05 (m, 1H), 7.73-7.66 (m, 2H).

Step 2—1-(8-Chloro-4-isoquinolyl)-3-[(4-methoxyphenyl)methyl]hexahydropyrimidine-2A-dione To a solution of 4-bromo-8-chloro-isoquinoline (200 mg, 824 umol) and 3-[(4-methoxyphenyl)methyl] hexahydropyrimidine-2,4-dione (231 mg, 989 umol, Intermediate CS) in DMF (3 mL) was added CuI (47.1 mg, 247 umol), K$_2$CO$_3$ (227 mg, 1.65 mmol) and 2-aminoacetic acid (18.5 mg, 247 umol). Then the mixture was purged with N$_2$ three times and stirred at 140° C. for 8 hours. On completion, the mixture was filtrated, diluted with water (100 mL) and extracted with EA (5×80 mL). The combined organic phase was dried with anhydrous Na$_2$SO$_4$, filtered and concentrated in vacuo to give the residue. Then the residue was purified by reversed-phase HPLC (0.1% FA) to give the title compound (99.2 mg, 30.41% yield) as yellow solid. $^1$H NMR (400 MHz, DMSO-d$_6$) δ 9.56 (s, 1H), 8.72 (s, 1H), 7.98 (d, J=8.4 Hz, 1H), 7.91-7.87 (m, 1H), 7.83-7.77 (m, 1H), 7.29-7.23 (m, 2H), 6.91-6.84 (m, 2H), 4.84 (s, 2H), 4.01-3.94 (m, 1H), 3.80-3.75 (m, 1H), 3.73-3.71 (m, 3H), 3.20-3.12 (m, 1H), 3.01-2.93 (m, 1H). LC-MS (ESI$^+$) m/z 396.0 (M+H)$^+$.

Step 3—Tert-butyl N-[1-[4-[3-[(4-methoxyphenyl)methyl]-2,4-dioxo-hexahydropyrimidin-1-yl]-8-isoquinolyl]-4-piperidyl]-N-methyl-carbamate To a solution of 1-(8-chloro-4-isoquinolyl)-3-[(4-methoxyphenyl)methyl]hexahydropyrimidine-2,4-dione (200 mg, 505 umol) and tert-butyl N-methyl-N-(4-piperidyl) carbamate (119 mg, 555 umol, CAS #108612-54-0) in dioxane (4 mL) was added Cs$_2$CO$_3$ (329 mg, 1.01 mmol) and Pd-PEPPSI-IHept$^{Cl}$3-Chloropyridine (49.1 mg, 50.5 umol), then the mixture was stirred at 80° C. for 8 hours. On completion, the mixture was filtered, diluted with water (20 mL) and extracted with EA (4×10 mL). The extract was dried over anhydrous Na$_2$SO$_4$, filtered and concentrated in vacuo to give the title compound (216 mg, 74.52% yield) as yellow solid. $^1$H NMR (400 MHz, DMSO-d$_6$) δ 9.45 (s, 1H), 8.53 (s, 1H), 7.72-7.66 (m, 1H), 7.54 (d, J=8.4 Hz, 1H), 7.31-7.24 (m, 3H), 6.88 (d, J=8.8 Hz, 2H), 4.83 (s, 2H), 3.93-3.87 (m, 1H), 3.78-3.71 (m, 4H), 3.50-3.42 (m, 2H), 3.17-3.08 (m, 1H), 2.99-2.96 (m, 1H), 2.81 (s, 3H), 2.18-2.03 (m, 2H), 1.75-1.68 (m, 2H), 1.43 (s, 9H), 0.88-0.70 (m, 3H); LC-MS (ESI$^+$) m/z 574.3 (M+H)$^+$.

Step 4—1-[8-[4-(Methylamino)-1-piperidyl]-4-isoquinolyl]hexahydropyrimidine-2,4-dione To a solution of tert-butyl N-[1-[4-[3-[(4-methoxyphenyl)methyl]-2,4-dioxo-hexahydropyrimidin-1-yl]-8-isoquinolyl]-4-piperidyl]-N-methyl-carbamate (206 mg, 359 umol) in TFA (0.5 mL) and TfOH (0.05 mL) was stirred at 70° C. for 1 hour. On completion, the mixture was concentrated in vacuo to give the title compound (100 mg, 78.80% yield, TFA) as yellow solid. LC-MS (ESI$^+$) m/z 354.0 (M+H)$^+$.

Step 5—Tert-butyl N-[1-[4-(2,4-dioxohexahydropyrimidin-1-yl)-8-isoquinolyl]-4-piperidyl]-N-methyl-carbamate To a solution of 1-[8-[4-(methylamino)-1-piperidyl]-4-isoquinolyl]hexahydropyrimidine-2,4-dione (100 mg, 282 umol) in DCM (1 mL) was added Et$_3$N (787 uL, 5.66 mmol) and Boc$_2$O (92.6 mg, 424 umol) at 0° C., then the mixture was stirred at 25° C. for 13 hours. On completion, the mixture was concentrated in vacuo to give the residue, then the residue was purified by reverse-phase (0.1% FA condition) to give the title compound (70.0 mg, 54.55% yield) as yellow solid. $^1$H NMR (400 MHz, DMSO-d$_6$) δ 10.53 (s, 1H), 9.45 (s, 1H), 8.53 (s, 1H), 7.75-7.68 (m, 1H), 7.61 (d, J=8.4 Hz, 1H), 7.28 (d, J=7.2 Hz, 1H), 4.15-3.96 (m, 1H), 3.92-3.86 (m, 1H), 3.72-3.66 (m, 1H), 3.48-3.41 (m, 2H), 3.01-2.84 (m, 3H), 2.81 (s, 3H), 2.78-2.71 (m, 1H), 2.19-2.02 (m, 2H), 1.72-1.70 (m, 2H), 1.43 (s, 9H). LC-MS (ESI$^+$) m/z 454.1 (M+H)$^+$.

Step 6—1-[8-[4-(Methylamino)-1-piperidyl]-4-isoquinolyl]hexahydropyrimidine-2,4-dione To a solution of tert-butyl N-[1-[4-(2,4-dioxohexahydropyrimidin-1-yl)-8-isoquinolyl]-4-piperidyl]-N-methyl-carbamate (60 mg, 132 umol) in DCM (1 mL) was added TFA (0.5 mL, 6.75 mmol), then the mixture was stirred at 25° C. for 1 hour. On completion, the mixture was concentrated in vacuo to give the title compound (58.0 mg, 93.79% yield, TFA) as yellow solid. LC-MS (ESI$^+$) m/z 354.0 (M+H)$^+$.

1-[8-[4-[Methyl(4-piperidylmethyl)amino]-1-piperidyl]-4-isoquinolyl]hexahydropyrimidine-2,4-dione (Intermediate GP)

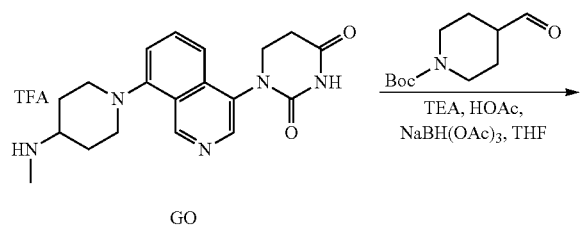

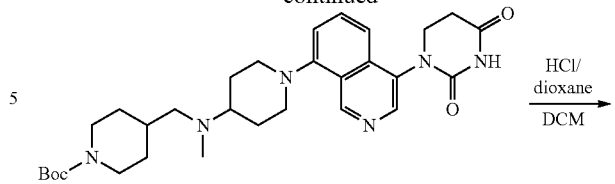

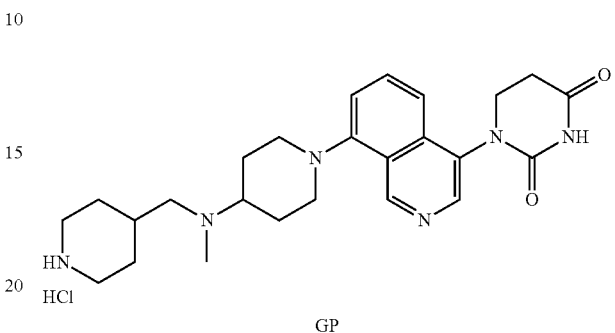

Step 1—Tert-butyl 4-[[[1-[4-(2,4-dioxohexahydropyrimidin-1-yl)-8-isoquinolyl]-4-piperidyl]-methylamino]methyl]piperidine-1-carboxylate To a solution of 1-[8-[4-(methylamino)-1-piperidyl]-4-isoquinolyl]hexahydropyrimidine-2,4-dione (100 mg, 213 umol, TFA, Intermediate GO) in THF (1 mL) was added TEA (29.8 uL, 214 umol). Then tert-butyl 4-formylpiperidine-1-carboxylate (41.0 mg, 192 umol, CAS #137076-22-3) and HOAc (12.2 uL, 214 umol) were added, and the mixture was stirred at −10° C. for 0.5 hr. Then NaBH(OAc)$_3$ (68.0 mg, 321 umol) was added, and the mixture was stirred at −10° C. for 1.5 hrs. On completion, the mixture was quenched with water (1 mL) and concentrated in vacuo to give the residue. The residue was purified by prep-HPLC (column: Phenomenex luna C18 150*25 mm*10 um; mobile phase: [water(FA)-ACN]; B %: 5%-35%, 15 min) to give the title compound (70.0 mg, 59% yield) as a yellow solid. $^1$H NMR (400 MHz, DMSO-d$_6$) δ 10.53 (s, 1H), 9.43 (s, 1H), 8.53 (s, 1H), 7.75-7.68 (m, 1H), 7.61 (d, J=8.4 Hz, 1H), 7.26 (d, J=7.6 Hz, 1H), 4.00-3.85 (m, 3H), 3.72-3.66 (m, 1H), 3.50-3.43 (m, 2H), 3.00-2.92 (m, 2H), 2.88-2.65 (m, 6H), 2.53-2.51 (m, 4H), 2.05-1.87 (m, 4H), 1.75-1.72 (m, 3H), 1.40 (s, 9H), 1.11-0.94 (m, 2H). LC-MS (ESI$^+$) m/z 551.4 (M+H)$^+$.

Step 2—1-[8-[4-[Methyl(4-piperidylmethyl)amino]-1-piperidyl]-4-isoquinolyl]hexahydropyrimidine-2,4-dione To a solution of tert-butyl 4-[[[1-[4-(2,4-dioxohexahydropyrimidin-1-yl)-8-isoquinolyl]-4-piperidyl]-methyl-amino]methyl]piperidine-1-carboxylate (35.0 mg, 63.5 umol) in DCM (0.5 mL) was added HCl/dioxane (3 M, 0.5 mL), then the mixture was stirred at 25° C. for 0.5 hour. On completion, the mixture was concentrated in vacuo to give the title compound (30.0 mg, 97% yield, HCl) as a yellow solid. LC-MS (ESI$^+$) m/z 451.2 (M+H)$^+$.

1-[8-[4-(methylamino)-1-piperidyl]imidazo[1,2-a]pyridin-3-yl]hexahydropyrimidine-2,4-dione (Intermediate GQ)

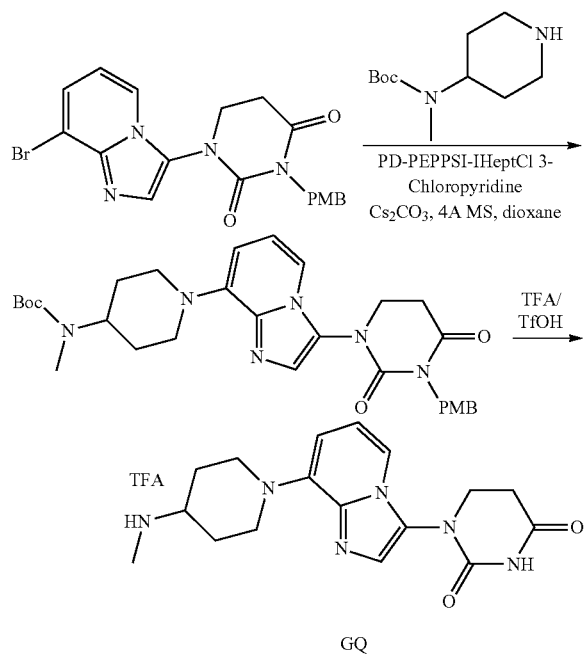

Step 1—Tert-butyl N-[1-[3-[3-[(4-methoxyphenyl)methyl]-2,4-dioxo-hexahydropyrimidin-1-yl] imidazo[1,2-a]pyridin-8-yl]-4-piperidyl]-N-methyl-carbamate A solution of 1-(8-bromoimidazo[1,2-a]pyridin-3-yl)-3-[(4-methoxyphenyl)methyl]hexahydropyrimidine-2,4-dione (600 mg, 1.40 mmol, synthesized via Steps 1-2 of Intermediate BN), tert-butylN-methyl-N-(4-piperidyl)carbamate (449 mg, 2.10 mmol), $Cs_2CO_3$ (1.37 g, 4.19 mmol), PD-PEPPSI-IHeptCl$_3$-Chloropyridine (67.9 mg, 69.8 umol) and 4A molecular sieves (50 mg) in dioxane (15 mL) was stirred at 100° C. under $N_2$ for 16 hrs. On completion, the reaction mixture was diluted with EtOAc (40 mL) and washed with water (30 mL×3). The organic layer was dried over $Na_2SO_4$ and concentrated in vacuo. The residue was triturated with water (20 mL) at 25° C. for 10 min to give the title compound (780 mg, 99% yield) as brown solid. $^1$H NMR (400 MHz, DMSO-d$_6$) δ 7.78 (d, J=6.4 Hz, 1H), 7.47 (s, 1H), 7.24 (d, J=8.8 Hz, 2H), 6.87 (d, J=8.8 Hz, 2H), 6.84-6.79 (m, 1H), 6.54 (d, J=7.2 Hz, 1H), 4.81 (s, 2H), 4.11-3.92 (m, 1H), 3.83-3.75 (m, 2H), 3.72 (s, 3H), 2.93-3.06 (m, 2H), 2.78-2.66 (m, 7H), 1.90-1.81 (m, 2H), 1.65 (d, J=9.6 Hz, 2H), 1.41 (s, 9H).

Step 2—1-[8-[4-(Methylamino)-1-piperidyl]imidazo[1,2-a]pyridin-3-yl]hexahydropyrimidine-2,4-dione A solution of tert-butyl N-[1-[3-[3-[(4-methoxyphenyl)methyl]-2,4-dioxo-hexahydropyrimidin-1-yl] imidazo[1,2-a]pyridin-8-yl]-4-piperidyl]-N-methyl-carbamate (200 mg, 355 umol) and TfOH (680 mg, 4.53 mmol) in TFA (2 mL) was stirred at 70° C. for 1 hr. On completion, the reaction mixture was concentrated in vacuo to give the title compound (162 mg, 99% yield, TFA) as red oil. LC-MS (ESI$^+$) m/z 343.2 (M+H)$^+$.

1-[8-[4-[methyl(4-piperidylmethyl)amino]-1-piperidyl]imidazo[1,2-a]pyridin-3-yl]hexahydropyrimidine-2,4-dione (Intermediate GR)

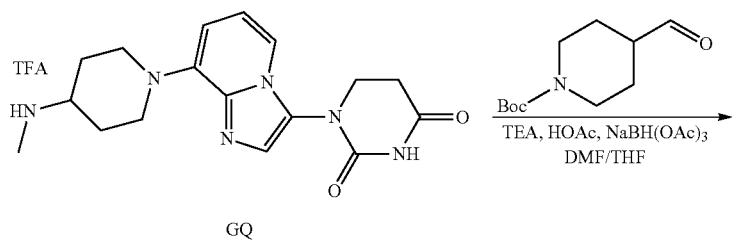

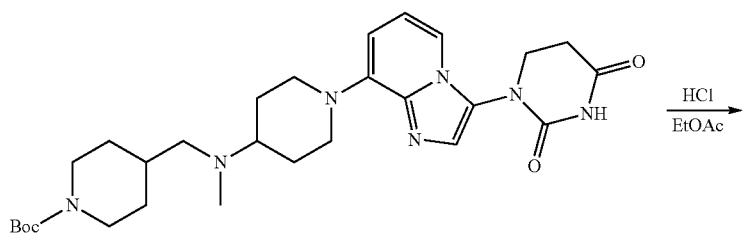

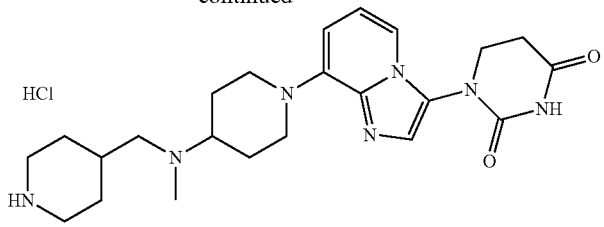

GR

Step 1—Tert-butyl 4-[[[1-[3-(2,4-dioxohexahydro-pyrimidin-1-yl)imidazo[1,2-a]pyridin-8-yl]-4-piperidyl]-methyl-amino]methyl]piperidine-1-carboxylate To a solution of 1-[8-[4-(methylamino)-1-piperidyl]imidazo[1,2-a]pyridin-3-yl]hexahydropyrimidine-2,4-dione (162 mg, 354 umol, TFA, Intermediate GQ), TEA (71.8 mg, 709 umol), HOAc (63.9 mg, 1.06 mmol) in DMF (1 mL) and THF (1.5 mL) was added tert-butyl 4-formylpiperidine-1-carboxylate (113 mg, 532 umol) and the mixture was stirred at 25° C. for 0.5 hr. Then, NaBH(OAc)$_3$ (150 mg, 709 umol) was added into the above mixture and stirred at 25° C. for 1 hr. On completion, the reaction was quenched with water (0.2 mL) and concentrated in vacuo. The residue was purified by reversed-phase (0.1% FA condition) to give the title compound (143 mg, 74% yield) as white solid. $^1$H NMR (400 MHz, DMSO-d$_6$) δ 10.75 (s, 1H), 8.93-8.74 (m, 1H), 8.32-8.00 (m, 1H), 7.98-7.60 (m, 1H), 7.12-6.90 (m, 1H), 4.31-4.07 (m, 1H), 4.00-3.92 (m, 2H), 3.85-3.75 (m, 2H), 3.51-3.46 (s, 2H), 3.22-3.12 (m, 1H), 3.00-2.92 (m, 1H), 2.88-2.69 (m, 9H), 2.19-2.06 (m, 2H), 2.00-1.80 (m, 4H), 1.68 (d, J=11.6 Hz, 1H), 1.40 (s, 9H), 1.19-1.05 (m, 2H).

Step 2—1-[8-[4-[Methyl(4-piperidylmethyl)amino]-1-piperidyl]imidazo[1,2-a]pyridin-3-yl] hexahydropyrimidine-2,4-dione A mixture of tert-butyl 4-[[[1-[3-(2,4-dioxohexahydropyrimidin-1-yl)imidazo[1,2-a]pyridin-8-yl]-4-piperidyl]-methyl-amino]methyl]piperidine-1-carboxylate (76.0 mg, 140 umol) in HCl/EtOAc (2 mL) was stirred at 25° C. for 1 hr. On completion, the reaction mixture was concentrated in vacuo to give the title compound (67 mg, 99% yield, HCl) as yellow solid. LC-MS (ESI$^+$) m/z 440.3 (M+H)$^+$.

3-[3-Methyl-2-oxo-4-[2-(4-piperidyl)ethyl]piperazin-1-yl]benzimidazol-1-yl]piperidine-2,6-dione (Intermediate GS)

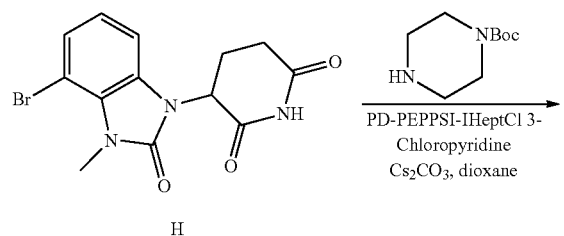

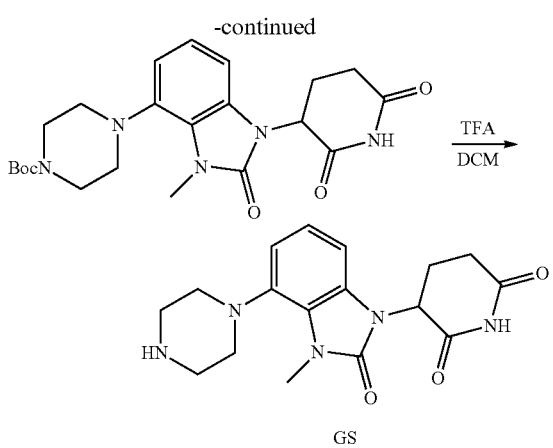

GS

Step 1—Tert-butyl 4-[1-(2,6-dioxo-3-piperidyl)-3-methyl-2-oxo-benzimidazol-4-yl]piperazine-1-carboxylate To a solution of 3-(4-bromo-3-methyl-2-oxo-benzimidazol-1-yl)piperidine-2,6-dione (500 mg, 1.48 mmol, Intermediate H) and tert-butyl piperazine-1-carboxylate (550 mg, 2.96 mmol) in dioxane (10 mL) was added 1,3-bis [2,6-bis (1-ethylpropyl) phenyl]-4,5-dichloro-2H-imidazol-1-ium-2-ide;3-chloropyridine; dichloropalladium (254 mg, 295 umol, CAS #1435347-24-2) and Cs$_2$CO$_3$ (963 mg, 2.96 mmol). The mixture was stirred at 100° C. for 16 hrs under N$_2$ atmosphere. On completion, the reaction mixture was extracted with ethyl acetate (3×20 mL). The combined organic layers were washed with brine (20 mL), dried over anhydrous sodium sulfate, filtered and the filtrate was concentrated in vacuo. The crude product was purified by reversed-phase HPLC (0.1% FA condition) to give the title compound (200 mg, 28% yield) as a white solid. LC-MS (ESI$^+$) m/z 444.2 (M+H)$^+$.

Step 2—3-[3-Methyl-2-oxo-4-[2-(4-piperidyl)ethyl]piperazin-1-yl]benzimidazol-1-yl]piperidine-2,6-dione To a solution of tert-butyl 4-[2-[4-[1-(2, 6-dioxo-3-piperidyl)-3-methyl-2-oxo-benzimidazol-4-yl] piperazin-1-yl] ethyl]piperidine-1-carboxylate (80.0 mg, 144 umol) in DCM (1 mL) was added TFA (16.5 mg, 144 umol). The mixture was stirred at 25° C. for 1 hr. On completion, the mixture was concentrated in vacuo to give the title compound (70 mg, 86% yield) as a white solid. LC-MS (ESI$^+$) m/z 344.0 (M+H)$^+$.

833

3-[3-Methyl-2-oxo-4-[4-[2-(4-piperidyl)ethyl]piperazin-1-yl]benzimidazol-1-yl]piperidine-2,6-dione (Intermediate GT)

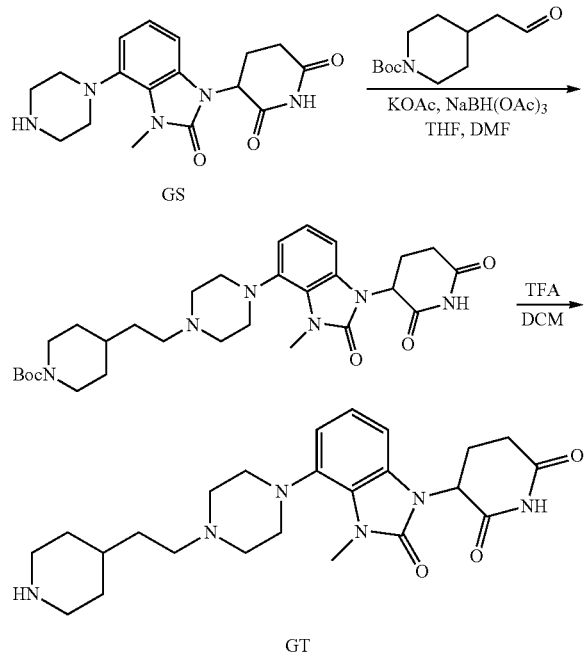

834

Step 1—Tert-butyl 4-[2-[4-[1-(2,6-dioxo-3-piperidyl)-3-methyl-2-oxo-benzimidazol-4-yl]piperazin-1-yl]ethyl]piperidine-1-carboxylate To a solution of 3-(3-methyl-2-oxo-4-piperazin-1-yl-benzimidazol-1-yl)piperidine-2,6-dione (77.0 mg, 224 umol, Intermediate GS) and tert-butyl 4-(2-oxoethyl)piperidine-1-carboxylate (56.1 mg, 246 umol, CAS #142374-19-4) in THF (1 mL) and DMF (0.2 mL) was added KOAc (220 mg, 2.24 mmol). The mixture was stirred at 0° C. for 6 min. Then added the NaBH(OAc)$_3$ (95.1 mg, 448 umol) was added and the mixture was stirred at 0° C. for 1 hr. On completion, the mixture was concentrated in vacuo. The residue was purified by prep-HPLC (column: Phenomenex luna C18 150*25 mm*10 um; mobile phase: [water(FA)-ACN]; B %: 13%-43%, 10 min) to give the title compound (80 mg, 64% yield) as a white solid. LC-MS (ESI$^+$) m/z 555.3 (M+H)$^+$.

Step 2—3-[3-Methyl-2-oxo-4-[4-[2-(4-piperidyl)ethyl]piperazin-1-yl]benzimidazol-1-yl]piperidine-2,6-dione To a solution of tert-butyl 4-[2-[4-[1-(2,6-dioxo-3-piperidyl)-3-methyl-2-oxo-benzimidazol-4-yl] piperazin-1-yl] ethyl]piperidine-1-carboxylate (80.0 mg, 144 umol) in DCM (1 mL) was added TFA (16.4 mg, 144 umol). The mixture was stirred at 25° C. for 1 hr. On completion, the mixture was concentrated in vacuo to give the title compound (70 mg, 85% yield) as a white solid. LC-MS (ESI$^+$) m/z 455.4 (M+H)$^+$.

4-[(6-Chloro-8-cyclopentyl-7-oxo-pyrido[2,3-d]pyrimidin-2-yl)amino]-3-methyl-N-(3-piperazin-1-ylpropyl)benzenesulfonamide (Intermediate GU)

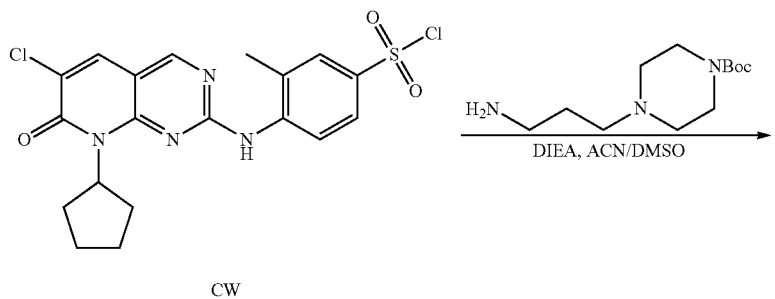

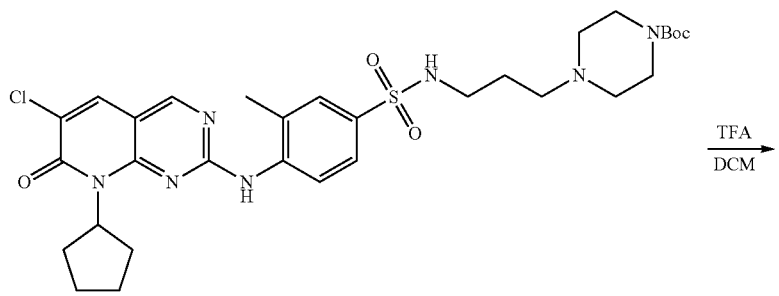

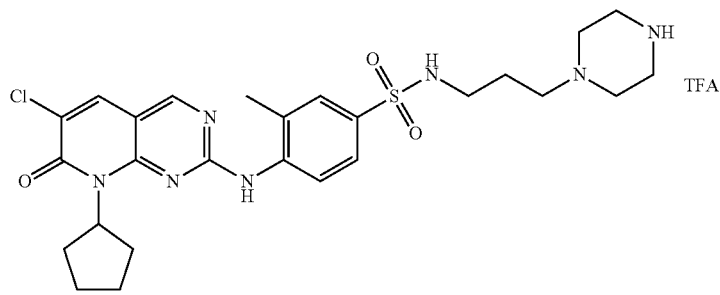

GU

Step 1—Tert-butyl 4-[3-[[4-[(6-chloro-8-cyclopentyl-7-oxo-pyrido[2,3-d]pyrimidin-2-yl)amino]-3-methyl-phenyl]sulfonylamino]propyl]piperazine-1-carboxylate To a solution of tert-butyl 4-(3-aminopropyl)piperazine-1-carboxylate (50.0 mg, 205 umol, CAS #373608-48-1) in a mixture solution of ACN (2 mL) and DMSO (0.5 mL) was added DIEA (53.1 mg, 410 umol) and 4-[(6-chloro-8-cyclopentyl-7-oxo-pyrido[2,3-d]pyrimidin-2-yl)amino]-3-methyl-benzenesulfonyl chloride (139 mg, 308 umol, Intermediate CW). The mixture was stirred at 25° C. for 0.5 hrs. On completion, the reaction mixture was concentrated in vacuo to remove the solvent. The residue was purified by prep-HPLC (column: Waters xbridge 150*25 mm 10 um; mobile phase: [water(NH$_4$HCO$_3$)-ACN]; B %: 46%-76%, 8 min) to give the title compound (130 mg, 95% yield) as a white solid. $^1$H NMR (400 MHz, DMSO-d$_6$) δ 9.68 (s, 1H), 8.75 (s, 1H), 8.18 (s, 1H), 7.72 (d, J=8.4 Hz, 1H), 7.68 (d, J=1.6 Hz, 1H), 7.67-7.59 (m, 1H), 7.53 (t, J=5.6 Hz, 1H), 5.78-5.67 (m, 1H), 3.27-3.19 (m, 4H), 2.78 (q, J=6.4 Hz, 2H), 2.33 (s, 3H), 2.25-2.21 (m, 2H), 2.21-2.16 (m, 4H), 2.15-2.06 (m, 2H), 1.69 (s, 4H), 1.56-1.48 (m, 2H), 1.46 (s, 2H), 1.36 (s, 9H). LCMS (ESI$^+$) m/z 660.1 (M+H)$^+$.

Step 2—4-[(6-Chloro-8-cyclopentyl-7-oxo-pyrido[2,3-d]pyrimidin-2-yl)amino]-3-methyl-N-(3-piperazin-1-ylpropyl)benzenesulfonamide To a solution of tert-butyl 4-[3-[[4-[(6-chloro-8-cyclopentyl-7-oxo-pyrido[2,3-d]pyrimidin-2-yl) amino]-3-methyl-phenyl]sulfonylamino]propyl]piperazine-1-carboxylate (80.0 mg, 121 umol) in DCM (1.5 mL) was added TFA (770 mg, 6.75 mmol). The mixture was stirred at 25° C. for 0.5 hr. The reaction mixture was concentrated in vacuo to give the title compound (80.0 mg, 97% yield, TFA) as a white solid. LCMS (ESI$^+$) m/z 560.2 (M+H)$^+$.

3-(3-Methyl-2-oxo-5-piperazin-1-yl-benzimidazol-1-yl)piperidine-2,6-dione (Intermediate GV)

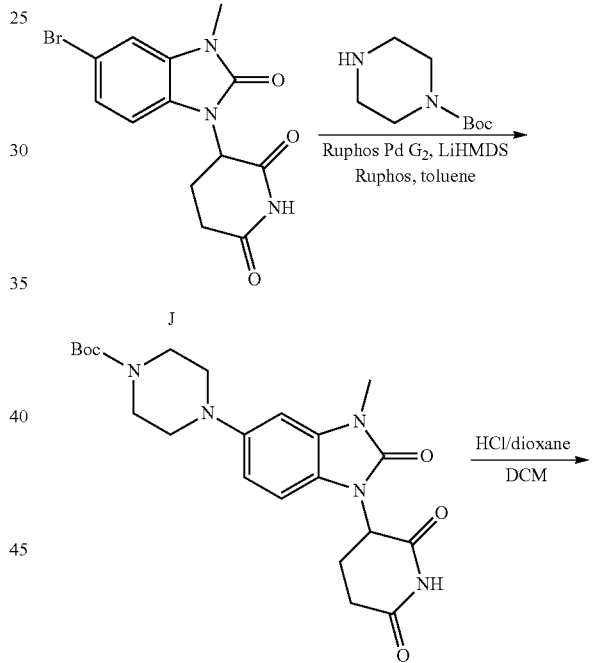

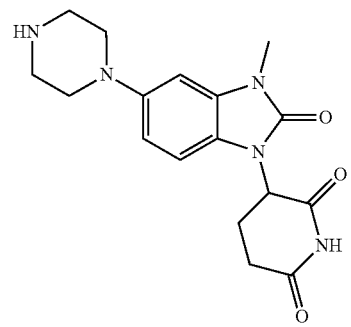

GV

Step 1—Tert-butyl 4-[1-(2,6-dioxo-3-piperidyl)-3-methyl-2-oxo-benzimidazol-5-yl]piperazine-1-carboxylate A mixture of 3-(5-bromo-3-methyl-2-oxo-benzimidazol-1-yl)piperidine-2,6-dione (1.00 g, 2.96 mmol, Intermediate J), tert-butyl piperazine-1-carboxylate (1.32 g, 5.91 mmol, CAS #57260-71-6), 4A molecular sieves, RuPhos (275 mg, 591 umol), and [2-(2-aminophenyl)phenyl]-chloro-palladium;dicyclohexyl-[2-(2,6-diisopropoxyphenyl)phenyl] phosphane (459 mg, 591 umol) in toluene (10 mL) was degassed and purged with $N_2$ three times, and then the mixture was stirred at 25° C. for 30 minutes under $N_2$ atmosphere. Then LiHMDS (1 M, 10.3 mL) was added slowly into the mixture. The mixture was then stirred at 80° C. for 2 hours under $N_2$ atmosphere. On completion, the mixture was diluted with DMF (25 mL), and adjusted pH=5 with FA, then filtered with DCM and concentrated in vacuo. The crude product was triturated with PE:EA=1:1 (10 mL) at 25° C. for 30 minutes, then filtered to give the title compound (820 mg, 57% yield). $^1$H NMR (400 MHz, DMSO-$d_6$) δ 11.07 (s, 1H), 6.97 (d, J=8.4 Hz, 1H), 6.88 (d, J=2.0 Hz, 1H), 6.66 (dd, J=2.0, 8.4 Hz, 1H), 5.30 (dd, J=5.2, 12.8 Hz, 1H), 3.50-3.47 (m, 4H), 3.31 (s, 3H), 3.06-3.02 (m, 4H), 2.90 (s, 1H), 2.63 (s, 1H), 2.53 (d, J=2.0 Hz, 2H), 1.43 (s, 9H). LC-MS (ESI$^+$) m/z 444.1 (M+H)$^+$.

Step 2—3-(3-Methyl-2-oxo-5-piperazin-1-yl-benzimidazol-1-yl)piperidine-2,6-dione To a solution of tert-butyl 4-[1-(2,6-dioxo-3-piperidyl)-3-methyl-2-oxo-benzimidazol-5-yl] piperazine-1-carboxylate (100 mg, 225 umol) in DCM (1 mL) was added HCl/dioxane (4 M, 1 mL). Then the mixture was stirred at 25° C. for 1 hr. On completion, the reaction mixture was concentrated in vacuo to give the desired product (76 mg, 88% yield, HCl) as a white solid. LC-MS (ESI$^+$) m/z 343.9 (M+H)$^+$.

3-[5-[4-[[4-(2-Aminoethoxy)cyclohexyl]methyl] piperazin-1-yl]-3-methyl-2-oxo-benzimidazol-1-yl] piperidine-2,6-dione (Intermediate GW)

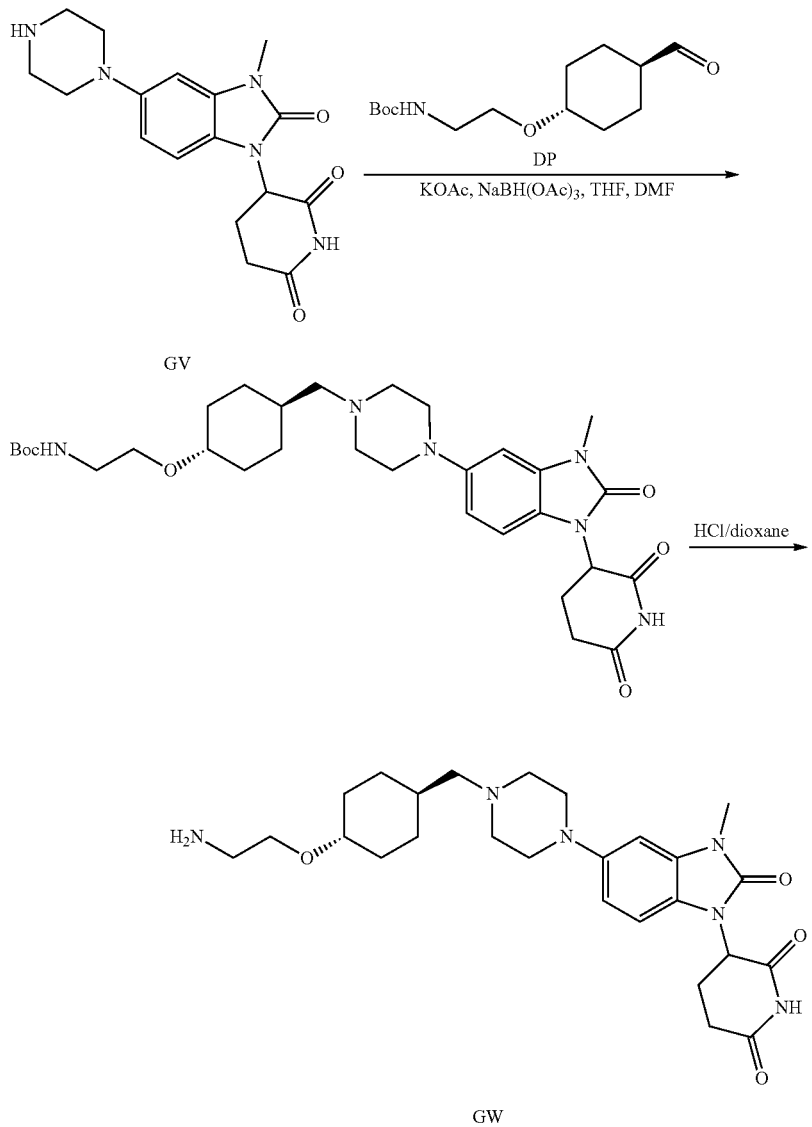

Step 1—Tert-butyl N-[2-[4-[[4-[1-(2,6-dioxo-3-piperidyl)-3-methyl-2-oxo-benzimidazol-5-yl]piperazin-1-yl]methyl]cyclohexoxy]ethyl]carbamate To a solution of 3-(3-methyl-2-oxo-5-piperazin-1-yl-benzimidazol-1-yl)piperidine-2,6-dione (50 mg, 131 umol, HCl, Intermediate GV), and tert-butyl N-[2-(4-formylcyclohexoxy)ethyl]carbamate (35.7 mg, 131 umol, Intermediate DP) in THF (0.5 mL) and DMF (0.5 mL) was added KOAc (129 mg, 1.32 mmol) and NaBH(OAc)$_3$ (55.8 mg, 263 umol). The mixture was then stirred at 25° C. for 1 hr. On completion, the reaction mixture was concentrated in vacuo to give a residue. Then the crude product was purified by prep-HPLC (column: Phenomenex luna C18 150*25 mm*10 um; mobile phase: [water(FA)-ACN]; B %: 7%-37%, 9 min) to afford the title compound (65 mg, 82% yield) as a white solid. LC-MS (ESI$^+$) m/z 599.3 (M+H)$^+$.

Step 2—3-[5-[4-[[4-(2-Aminoethoxy)cyclohexyl]methyl]piperazin-1-yl]-3-methyl-2-oxo-benzimidazol-1-yl]piperidine-2,6-dione To a solution of tert-butyl N-[2-[4-[[4-[1-(2,6-dioxo-3-piperidyl)-3-methyl-2-oxo-benzimidazol-5-yl]piperazin-1-yl]methyl]cyclohexoxy]ethyl]carbamate (55.0 mg, 91.8 umol) in DCM (1 mL) was added TFA (1.54 g, 13.5 mmol). The mixture was then stirred at 25° C. for 0.5 hour. On completion, the reaction mixture was concentrated under reduced pressure to give the title compound (45.0 mg, 79% yield, TFA) as a white solid. LC-MS (ESI$^+$) m/z 499.1 (M+H)$^+$.

3-[5-(Azetidin-3-yl)-3-methyl-2-oxo-benzimidazol-1-yl]piperidine-2,6-dione (Intermediate GX)

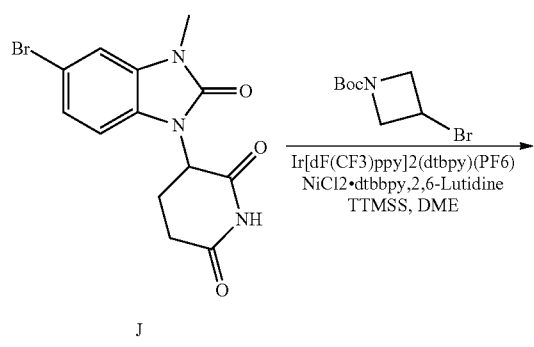

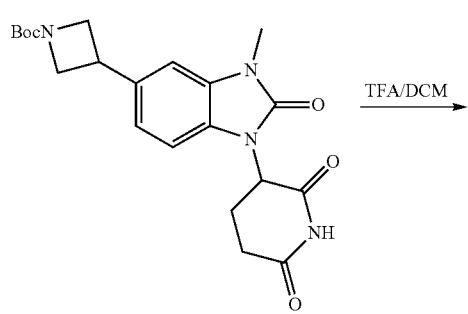

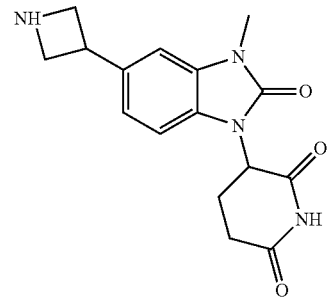

GX

Step 1—Tert-butyl 3-[1-(2,6-dioxo-3-piperidyl)-3-methyl-2-oxo-benzimidazol-5-yl]azetidine-1-carboxylate To a solution of 3-(5-bromo-3-methyl-2-oxo-benzimidazol-1-yl)piperidine-2,6-dione (500 mg, 1.48 mmol, Intermediate J), tert-butyl 3-bromoazetidine-1-carboxylate (453 mg, 1.92 mmol, CAS #1064194-10-0) in DME (2 mL) was added Ir[dF(CF$_3$)ppy]$_2$(dtbpy)(PF$_6$) (16.5 mg, 14.7 umol), TTMSS (367 mg, 1.48 mmol), 2,6-Lutidine (316 mg, 2.96 mmol) and NiCl$_2$·dtbbpy (22 umol). The reaction was stirred and irradiated with a purple 10 W LED lamp (3 cm away), with cooling water to keep the reaction temperature at 25° C. for 14 hrs. On completion, the reaction mixture was purified by prep-HPLC (column: YMC Triart C18 250*50 mm*7 um; mobile phase: [water(FA)-ACN]; B %: 25%-55%, 20 min) to give the title compound (600 mg, 97% yield) as a yellow solid. $^1$H NMR (400 MHz, DMSO-d$_6$) δ 11.10 (s, 1H), 7.21 (d, J=1.2 Hz, 1H), 7.10-7.07 (m, 1H), 6.99 (dd, J=1.2, 8.0 Hz, 1H), 5.36 (dd, J=5.2, 12.8 Hz, 1H), 4.29-4.23 (m, 2H), 3.86 (s, 2H), 3.84-3.78 (m, 1H), 3.36 (s, 3H), 2.96-2.85 (m, 1H), 2.78-2.71 (m, 1H), 2.67-2.62 (m, 1H), 2.04-1.97 (m, 1H), 1.41 (s, 9H). LC-MS (ESI$^+$) m/z 359.6 (M+H)$^+$.

Step 2—3-[5-(Azetidin-3-yl)-3-methyl-2-oxo-benzimidazol-1-yl]piperidine-2,6-dione To a solution of tert-butyl 3-[1-(2,6-dioxo-3-piperidyl)-3-methyl-2-oxo-benzimidazol-5-yl]azetidine-1-carboxylate (100 mg, 241 umol) in DCM (1 mL) was added HCl/dioxane (4 M, 1 mL). The mixture was stirred at 25° C. for 1 hr. On completion, the reaction mixture was concentrated under reduced pressure to give the desired product (84 mg, 99% yield, HCl) as a white solid. LC-MS (ESI$^+$) m/z 314.9 (M+H)$^+$.

3-[5-[1-[[4-(2-Aminoethoxy)cyclohexyl]methyl]azetidin-3-yl]-3-methyl-2-oxo-benzimidazol-1-yl]piperidine-2,6-dione (Intermediate GY)

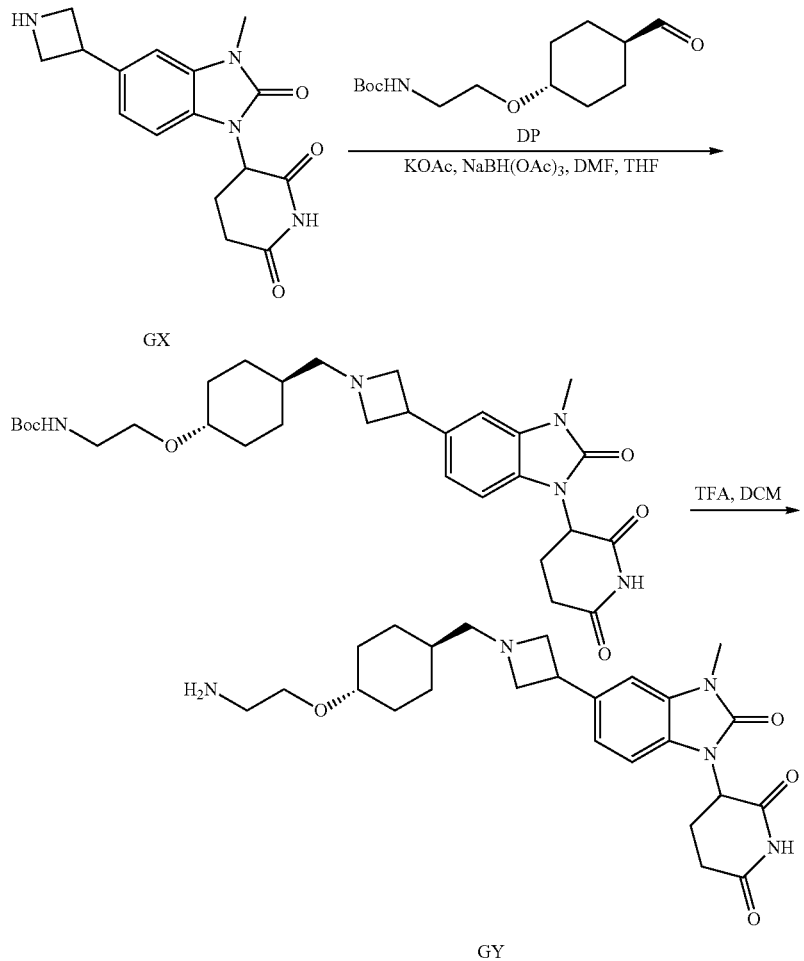

Step 1—Tert-butyl N-[2-[4-[[3-[1-(2,6-dioxo-3-piperidyl)-3-methyl-2-oxo-benzimidazol-5-yl]azetidin-1-yl]methyl]cyclohexoxy]ethyl]carbamate To a solution of 3-[5-(azetidin-3-yl)-3-methyl-2-oxo-benzimidazol-1-yl]piperidine-2,6-dione (55 mg, 156. umol, HCl, Intermediate GX), tert-butyl N-[2-(4-formylcyclohexoxy)ethyl]carbamate (50 mg, 184 umol, Intermediate DP) in DMF (0.5 mL) and THF (0.5 mL) was added KOAc (180 mg, 1.84 mmol) and NaBH(OAc)$_3$ (78.1 mg, 368 umol). The mixture was then stirred at 25° C. for 1 hr. On completion, the reaction mixture was concentrated in vacuo to give a residue. Then the crude was purified by prep-HPLC (column: Phenomenex luna C18 150*25 mm*10 um; mobile phase: [water (FA)-ACN]; B %: 7%-37%, 9 min) to afford the title compound (55 mg, 52% yield) as a white solid. LC-MS (ESI$^+$) m/z 570.3 (M+H)$^+$.

Step 2—3-[5-[1-[[4-(2-Aminoethoxy)cyclohexyl]methyl]azetidin-3-yl]-3-methyl-2-oxo-benzimidazol-1-yl]piperidine-2,6-dione To a solution of tert-butyl N-[2-[4-[[3-[1-(2,6-dioxo-3-piperidyl)-3-methyl-2-oxo-benzimidazol-5-yl]azetidin-1-yl]methyl]cyclohexoxy]ethyl]carbamate (55.0 mg, 96.5 umol) in DCM (0.5 mL) was added TFA (651 mg, 5.71 mmol). The mixture was then stirred at 25° C. for 0.5 hour. On completion, the reaction mixture was concentrated in vacuo to give the title compound (50.0 mg, 89% yield, TFA) as a white solid. LC-MS (ESI$^+$) m/z 470.1 (M+H)$^+$.

3-[3-Methyl-4-[3-(methylamino)azetidin-1-yl]-2-oxo-benzimidazol-1-yl]piperidine-2,6-dione (Intermediate GZ)

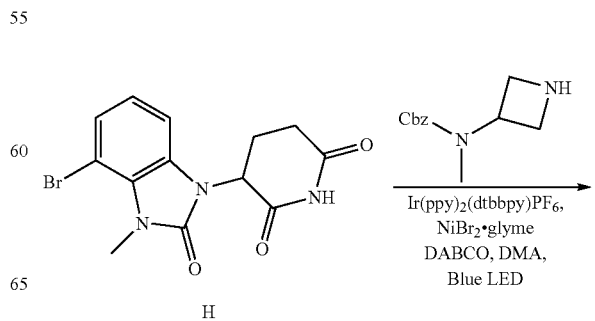

843

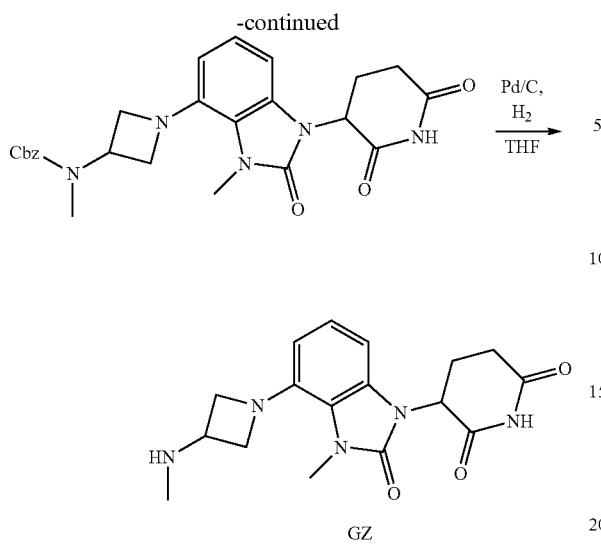

Step 1—Benzyl N-[1-[1-(2,6-dioxo-3-piperidyl)-3-methyl-2-oxo-benzimidazol-4-yl]azetidin-3-yl]-N-methyl-carbamate A mixture of 3-(4-bromo-3-methyl-2-oxo-benzimidazol-1-yl)piperidine-2,6-dione (500 mg, 1.48 mmol, Intermediate H), benzyl N-(azetidin-3-yl)-N-methyl-carbamate (651 mg, 2.96 mmol), DABCO (165 mg, 1.48 mmol, 162 uL), NiBr$_2$·glyme (324 mg, 1.05 mmol) and Ir(ppy)$_2$(dtbbpy)PF$_6$ (1.35 g, 1.48 mmol) in DMA (15 mL) was degassed three times. Then the reaction vial was then sealed with parafilm, placed 2 cm away from one blue LED, and irradiated at 25° C. for 14 hrs. On completion, the mixture was concentrated in vacuo. The residue was purified by column chromatography (SiO$_2$, Petroleum ether/Ethyl acetate=10/1 to 3/1), (Rf=0.50, PE:EA=1:1) to give the title compound (620 mg, 87% yield) as a yellow solid. $^1$H NMR (400 MHz, DMSO-d$_6$) δ 11.08 (d, J=6.0 Hz, 1H), 7.42-7.26 (m, 3H), 7.18 (d, J=7.6 Hz, 1H), 7.14-6.90 (m, 3H), 6.76-6.75 (m, 1H), 5.44-5.26 (m, 1H), 5.09 (s, 1H), 4.02 (t, J=6.8 Hz, 1H), 3.86 (d, J=6.0 Hz, 1H), 3.66-3.52 (m, 2H), 3.34 (s, 3H), 2.99 (s, 2H), 2.94 (s, 3H), 2.74-2.68 (t, 2H), 2.68-2.62 (nm, 2H). LC-MS (ESII) m/z 477.9 (M+H)z Step 2—3-[3-Methyl-4-[3-(methylamino)azetidin-1-yl]-2-oxo-benzimidazol-1-yl]piperidine-2,6-dione A mixture of benzyl N-[1-[1-(2,6-dioxo-3-piperidyl)-3-methyl-2-oxo-benzimidazol-4-yl]azetidin-3-yl]-N-methyl-carbamate (200 mg, 418 umol), Pd/C (20.0 mg, 4.19 umol, 10 wt %) in THF (1.5 mL) was degassed and purged with H$_2$ 3 times. Then the mixture was stirred at 25° C. for 1 hr under H$_2$ atmosphere. On completion, the mixture was filtered and the filtrate was concentrated in vacuo to give the title compound (140 mg, 97% yield) as a white solid. LC-MS (ESI$^+$) m/z 343.8 (M+H)$^+$.

844

3-[3-Methyl-4-[3-[methyl(4-piperidylmethyl)amino]azetidin-1-yl]-2-oxo-benzimidazol-1-yl]piperidine-2,6-dione (Intermediate HA)

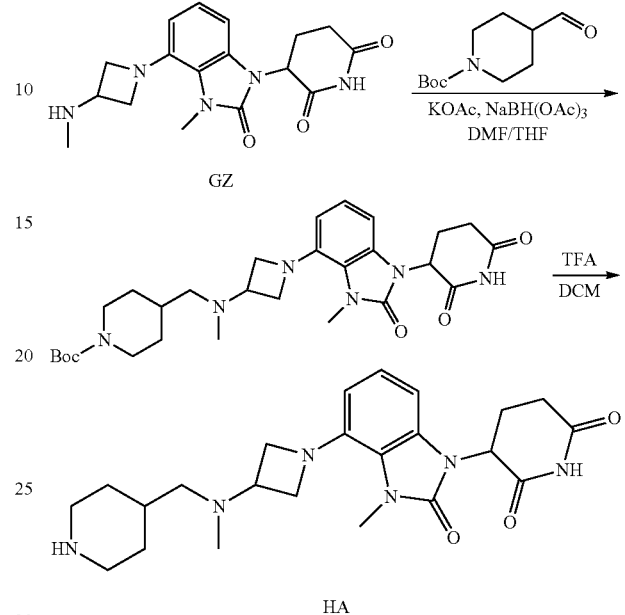

Step 1—Tert-butyl 4-[[[1-[1-(2,6-dioxo-3-piperidyl)-3-methyl-2-oxo-benzimidazol-4-yl]azetidin-3-yl]-methyl-amino]methyl]piperidine-1-carboxylate To a solution of 3-[3-methyl-4-[3-(methylamino)azetidin-1-yl]-2-oxo-benzimidazol-1-yl]piperidine-2,6-dione (140 mg, 407 umol, Intermediate GZ) and tert-butyl 4-formylpiperidine-1-carboxylate (86.9 mg, 407 umol, CAS #137076-22-3) in mixture solvent DMF (1 mL) and THF (1 mL) was added KOAc (400 mg, 4.08 mmol). The mixture was stirred at 0° C. for 6 minutes. After that NaBH(OAc)$_3$ (172 mg, 815 umol) was added to above solution. The mixture was stirred at 0° C. for 2.4 hours. On completion, the mixture was quenched with H$_2$O (0.5 mL), then concentrated in vacuo. The mixture was purified with pre-HPLC (column: Phenomenex C18 150*25 mm*10 um; mobile phase: [water (NH4HCO3)-CAN]; B %: 33%-63%, 8 min) to give the title compound (22 mg, 10% yield) as a white solid. LC-MS (ESI$^+$) m/z 541.2 (M+H)$^+$.

Step 2—3-[3-Methyl-4-[3-[methyl(4-piperidylmethyl)amino]azetidin-1-yl]-2-oxo-benzimidazol-1-yl]piperidine-2,6-dione To a solution of tert-butyl 4-[[[1-[1-(2,6-dioxo-3-piperidyl)-3-methyl-2-oxo-benzimidazol-4-yl] azetidin-3-yl]-methyl-amino]methyl]piperidine-1-carboxylate (22.0 mg, 40.6 umol) in DCM (2 mL) and TFA (2 mL). The mixture was stirred at 25° C. for 1 hr. On completion, the mixture was concentrated in vacuo to give the title compound (17.0 mg, 75% yield, TFA) as a white solid. LC-MS (ESI$^+$) m/z 441.0 (M+H)$^+$.

7'-Cyclopentyl-2'-methylsulfonyl-spiro[cyclopropane-1,5'-pyrrolo[2,3-d]pyrimidine]-6'-one (Intermediate HB)

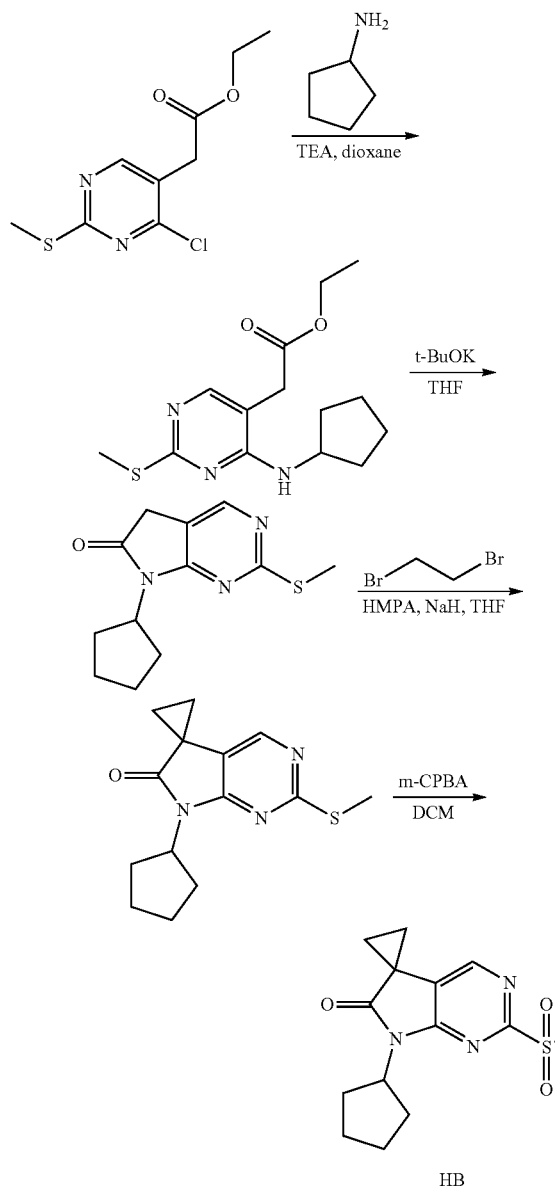

Step 1—Ethyl 2-[4-(cyclopentylamino)-2-methylsulfanyl-pyrimidin-5-yl]acetate To a solution of ethyl 2-(4-chloro-2-methylsulfanyl-pyrimidin-5-yl)acetate (1.00 g, 4.05 mmol, CAS #61727-34-2) in dioxane (10 mL) was added cyclopentanamine (690 mg, 8.11 mmol, CAS #1003-03-8) and TEA (820 mg, 8.11 mmol). The mixture was stirred at 60° C. for 1 hr. On completion, the reaction mixture was quenched with H$_2$O (20 mL) at 25° C., and then extracted with EA (3×10 mL). The combined organic layers were washed with brine (2×20 mL), dried over Na$_2$SO$_4$, filtered and concentrated in vacuo to give the title compound (1.10 g, 91% yield) as a white solid. $^1$H NMR (400 MHz, CDCl$_3$) δ 7.81 (s, 1H), 5.73 (d, J=6.0 Hz, 1H), 4.47-4.39 (m, 1H), 4.14 (q, J=7.2 Hz, 2H), 3.31 (s, 2H), 2.51 (s, 3H), 2.12-2.03 (m, 2H), 1.78-1.71 (m, 2H), 1.68-1.61 (m, 2H), 1.53-1.44 (m, 2H), 1.25 (t, J=7.2 Hz, 3H). LC-MS (ESI$^+$) m/z 296 (M+H)$^+$.

Step 2—7-Cyclopentyl-2-methylsulfanyl-5H-pyrrolo[2,3-d]pyrimidin-6-one

To a solution of ethyl 2-[4-(cyclopentylamino)-2-methylsulfanyl-pyrimidin-5-yl]acetate (1.00 g, 3.39 mmol) in THF (10 mL) was added t-BuOK (1.14 g, 10.1 mmol). The mixture was stirred at 35° C. for 1 hr. On completion, the reaction mixture was quenched with H$_2$O (20 mL) at 25° C., and then extracted with EA (3×20 mL). The combined organic layers were washed with brine (2×20 mL), dried over Na$_2$SO$_4$, filtered and concentrated in vacuo to give a residue. The residue was purified by column chromatography (SiO$_2$, Petroleum ether/Ethyl acetate=100/1 to 10/1) to give the title compound (800 mg, 94% yield) as a white solid. LC-MS (ESI$^+$) m/z 250.0 (M+H)$^+$.

Step 3—7'-Cyclopentyl-2'-methylsulfanyl-spiro[cyclopropane-1,5'-pyrrolo[2,3-d]pyrimidine]-6'-one To a suspension of NaH (5.01 g, 125 mmol, 60% dispersion in mineral oil) in THF (5 mL) N-[bis(dimethylamino)phosphoryl]-N-methylmethanamine (11.2 g, 62.5 mmol) was added a solution of 1,2-dibromoethane (11.7 g, 62.5 mmol, CAS #106-93-4) in THF (5 mL) dropwise and the reaction mixture was stirred at 0° C. for 30 mins. Next, 7-cyclopentyl-2-methylsulfanyl-5-Hpyrrolo[2,3-d]pyrimidin-6-one (7.80 g, 31.2 mmol) was added and the reaction mixture was heated to 50° C. for 1 hr. On completion, the reaction mixture was quenched with 1M HCl aq. (10 mL) at 25° C., and then extracted with EA (3×10 mL). The combined organic layers were washed with brine (2×10 mL), dried over Na$_2$SO$_4$, filtered and concentrated in vacuo to give a residue. Then the residue was purified by column chromatography (SiO$_2$, Petroleum ether/Ethyl acetate=100/1 to 10/1) to give the title compound (7.5 g, 87% yield) as pink oil. LC-MS (ESI$^+$) m/z 276.0 (M+1)$^+$. $^1$H NMR (400 MHz, CDCl$_3$) δ 7.77 (s, 1H), 4.89-4.80 (m, 1H), 2.57 (s, 3H), 2.29-2.20 (m, 2H), 2.02-1.89 (m, 4H), 1.79 (q, J=4.4 Hz, 2H), 1.71-1.63 (m, 2H), 1.58 (q, J=4.0 Hz, 2H).

Step 4—7'-Cyclopentyl-2'-methylsulfonyl-spiro[cyclopropane-1,5'-pyrrolo[2,3-d]pyrimidine]-6'-one To a solution of 7'-cyclopentyl-2'-methylsulfanyl-spiro[cyclopropane-1,5'-pyrrolo[2,3-d]pyrimidine]-6'-one (5.15 g, 18.7 mmol) in DCM (50 mL) was added m-CPBA (11.3 g, 56.1 mmol, 85%) The mixture was stirred at 40° C. for 16 hrs. On completion, the reaction mixture was quenched with H$_2$O (30 mL) at 25° C., and then extracted with EA (3×30 mL). The combined organic layers were washed with brine (2×20 mL), dried over Na$_2$SO$_4$, filtered and concentrated under reduced pressure to give a residue. Then the residue was purified by column chromatography (SiO$_2$, Petroleum ether/Ethyl acetate=100/1 to 0/1) to give the title compound (3.00 g, 52% yield) as a white solid. $^1$H NMR (400 MHz, CDCl$_3$) δ 8.05 (s, 1H), 4.96-488 (m, 1H), 3.34 (s, 3H), 2.23-2.16 (m, 2H), 2.05-2.00 (m, 2H), 2.00-1.95 (m, 4H), 1.82-1.78 (m, 2H), 1.72-1.67 (m, 2H). LC-MS (ESI$^+$) m/z 307.7 (M+1)$^+$.

4-[(7'-Cyclopentyl-6'-oxo-spiro[cyclopropane-1,5'-pyrrolo[2,3-d]pyrimidine]-2'-yl)amino]-3-methyl-benzenesulfonylchloride (Intermediate HC)

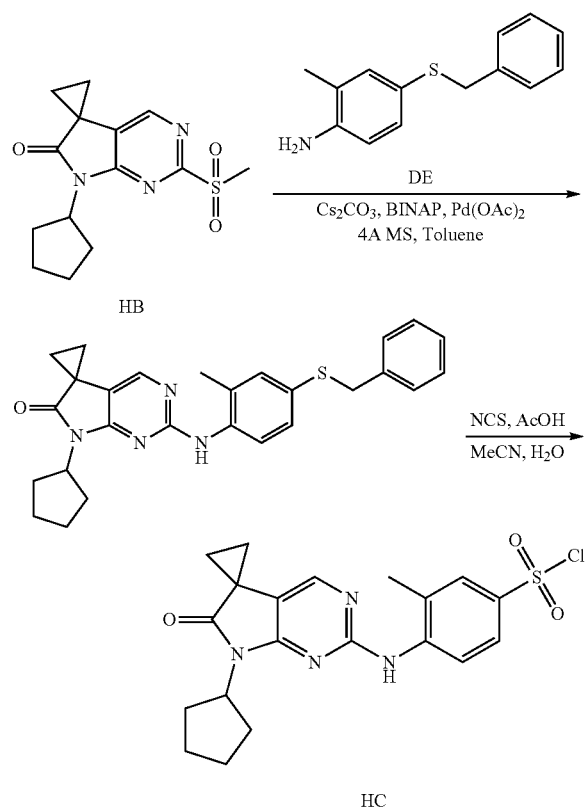

HC

Step 1—2'-(4-Benzylsulfanyl-2-methyl-anilino)-7'-cyclopentyl-spiro[cyclopropane-1,5'-pyrrolo[2,3-d]pyrimidine]-6'-one A mixture of 7'-cyclopentyl-2'-methylsulfonyl-spiro[cyclopropane-1,5'-pyrrolo[2,3-d]pyrimidine]-6'-one (1.00 g, 3.25 mmol, Intermediate HB), 4-benzylsulfanyl-2-methyl-aniline (895 mg, 3.90 mmol, Intermediate DE), 4A molecular sieves (3.25 mmol), Cs$_2$CO$_3$ (3.18 g, 9.76 mmol), Pd(OAc)$_2$ (73.0 mg, 325 umol) and BINAP (405 mg, 650 umol) in toluene (10 mL) was degassed and purged with N$_2$ three times. Then the mixture was stirred at 100° C. for 12 hours under N$_2$ atmosphere. On completion, the reaction mixture was filtered and concentrated in vacuo to give a residue. Then the residue was purified by prep-HPLC (column: Phenomenex luna C18 150*25 mm*10 um; mobile phase: [water(FA)-ACN]; B %: 55%-85%, 17 min) to give the title compound (300 mg, 20% yield) as a white solid. LC-MS (ESI$^+$) m/z 457.2 (M+1)$^+$.

Step 2—4-[(7'-Cyclopentyl-6'-oxo-spiro[cyclopropane-1,5'-pyrrolo[2,3-d]pyrimidine]-2'-yl)amino]-3-methyl-benzenesulfonylchloride To a solution of 2'-(4-benzylsulfanyl-2-methyl-anilino)-7'-cyclopentyl-spiro[cyclopropane-1,5'-pyrrolo [2,3-d]pyrimidine]-6'-one (85.0 mg, 186 umol) in H$_2$O (0.12 mL), ACN (2 mL) and AcOH (0.2 mL) was added NCS (74.5 mg, 558 umol). The mixture was stirred at 25° C. for 1 hr. On completion, the reaction mixture was quenched with H$_2$O (10 mL) at 25° C., and then extracted with EA (3×10 mL). The combined organic layers were washed with brine (2×10 mL), dried over Na$_2$SO$_4$, filtered and concentrated in vacuo to give a residue. Then the residue was purified by column chromatography (SiO$_2$, Petroleum ether/Ethyl acetate=100/1 to 1/1) to give the title compound (80 mg, 99% yield) as a white solid. LC-MS (ESI$^+$) m/z 433.0 (M+1)$^+$.

Tert-butyl N-[4-(2-oxoethoxy)cyclohexyl]carbamate (Intermediate HD)

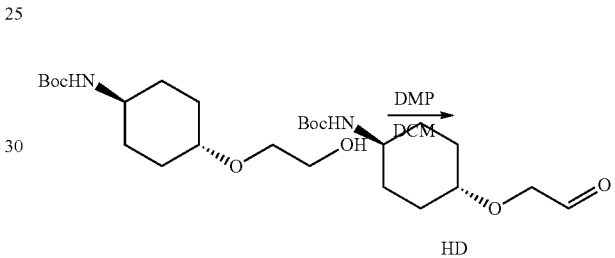

HD

To a solution of tert-butyl N-[4-(2-hydroxyethoxy)cyclohexyl]carbamate (500 mg, 1.93 mmol, synthesized via Steps 1-2 of Intermediate GH) in DCM (5 mL) was added DMP (1.23 g, 2.89 mmol, 895 uL). The mixture was stirred at 25° C. for 1 hr. On completion, the mixture was quenched with Na$_2$S$_2$O$_3$ (20 mL), extracted with DCM (20 mL×3), washed with NaHCO$_3$ (20 mL×3), dried with anhydrous Na$_2$SO$_4$, filtered and the filtrate was concentrated in vacuo. The residue was purified by column chromatography (SiO$_2$, Petroleum ether/Ethyl acetate=10/1 to 2/1) (Rf=0.50, PE:EA=1:1) to give the title compound (490 mg, 98% yield) as a brown oily liquid. $^1$H NMR (400 MHz, DMSO-d$_6$) δ 9.56 (s, 1H), 6.70 (s, 1H), 4.15 (s, 1H), 4.12-3.98 (m, 1H), 3.54-3.38 (m, 2H), 1.98-1.87 (m, 2H), 1.75 (d, J=10.0 Hz, 2H), 1.37 (s, 9H), 1.17 (dd, J=6.0, 12.8 Hz, 4H).

3-[5-[1-[2-(4-Aminocyclohexoxy)ethyl]-4-piperidyl]-3-methyl-2-oxo-benzimidazol-1-yl]piperidine-2,6-dione (Intermediate HE)

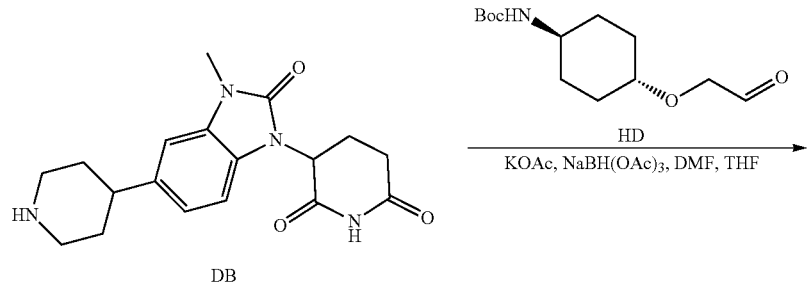

DB

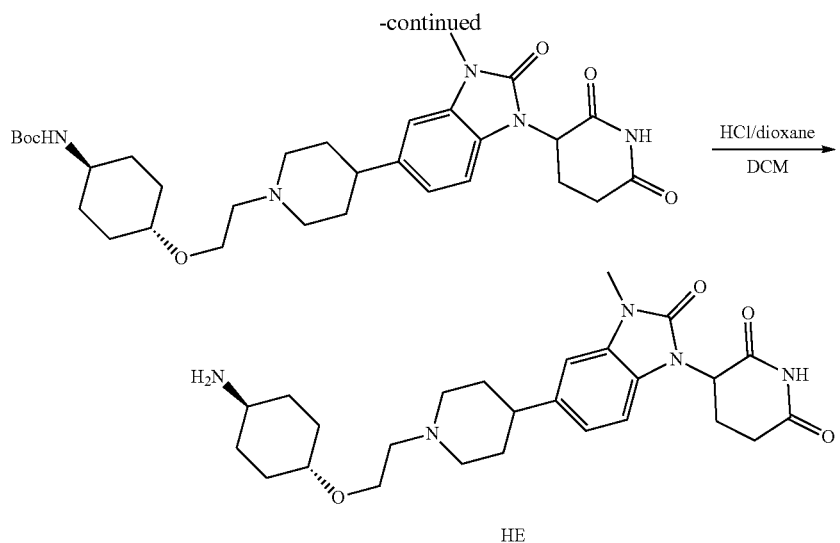

HE

Step 1—Tert-butyl N-[4-[2-[4-[1-(2,6-dioxo-3-piperidyl)-3-methyl-2-oxo-benzimidazol-5-yl]-1-piperidyl]ethoxy]cyclohexyl]carbamate To a solution of tert-butyl N-[4-(2-oxoethoxy)cyclohexyl]carbamate (150 mg, 582 umol, Intermediate HD) and 3-[3-methyl-2-oxo-5-(4-piperidyl)benzimidazol-1-yl]piperidine-2,6-dione (186 mg, 408 umol, TFA, Intermediate DB) in mixture solvent DMF (1 mL) and THF (1 mL) was added KOAc (572 mg, 5.83 mmol). The mixture was stirred at 0° C. for 6 minutes. After that, NaBH(OAc)$_3$ (247 mg, 1.17 mmol) was added to the above solution. The mixture was then stirred at 0° C. for 2.4 hrs. On completion, the mixture was quenched with H$_2$O (0.5 mL), then concentrated in vacuo. The mixture was purified by pre-HPLC (column: Phenomenex luna C18 150*25 mm*10 um; mobile phase: [water (FA)-ACN]; B %: 11%-41%, 9 min) to give the title compound (80.0 mg, 23% yield) as a white solid. LC-MS (ESI$^+$) m/z 584.2 (M+H)$^+$.

Step 2—3-[5-[1-[2-(4-Aminocyclohexoxy)ethyl]-4-piperidyl]-3-methyl-2-oxo-benzimidazol-1-yl]piperidine-2,6-dione To a solution of tert-butyl N-[4-[2-[4-[1-(2,6-dioxo-3-piperidyl)-3-methyl-2-oxo-benzimidazol-5-yl]-1-piperidyl]ethoxy]cyclohexyl]carbamate (100 mg, 171 umol) in DCM (1 mL) was added TFA (1 mL). The mixture was stirred at 25° C. for 1 hr. On completion, the mixture was concentrated in vacuo to give the title compound (20.0 mg, 19% yield, TFA) as a white solid. LC-MS (ESI$^+$) m/z 484.1 (M+H)$^+$.

1-[7-(4-piperidyl)-4-isoquinolyl]hexahydropyrimidine-2,4-dione (Intermediate HF)

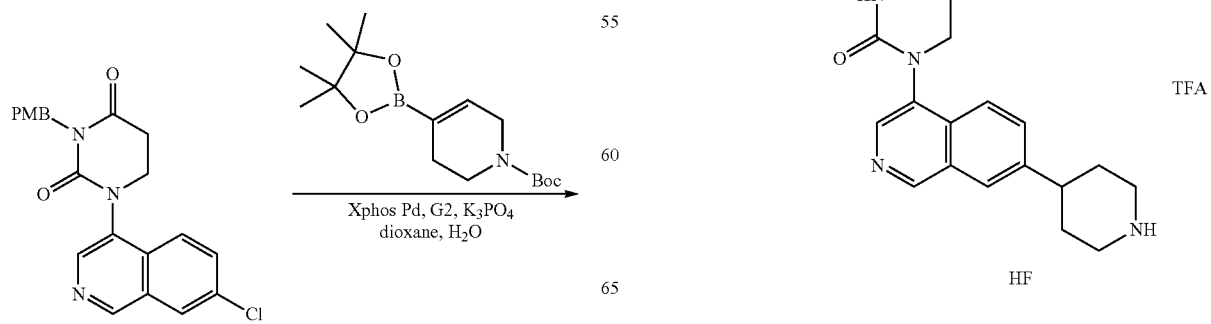

HF

Step 1—Tert-butyl 4-(4-(3-(4-methoxybenzyl)-2,4-dioxotetrahydropyrimidin-1(2H)-yl)isoquinolin-7-yl)-5,6-dihydropyridine-1(2H)-carboxylate To a solution of 1-(7-chloroisoquinolin-4-yl)-3-(4-methoxybenzyl)dihydropyrimidine-2,4(1H,3H)-dione (150 mg, 378 umol, synthesized via Steps 1-2 of Intermediate BM) and tert-butyl 4-(4,4,5,5-tetramethyl-1,3,2-dioxaborolan-2-yl)-5,6-dihydropyridine-1(2H)-carboxylate (140 mg, 454 umol, CAS #286961-14-6) in dioxane (2.0 mL) and water (0.2 mL) was added Xphos Pd G$_2$ (29.8 mg, 37.8 umol) and K$_3$PO$_4$ (160 mg, 757 umol). Then the mixture was stirred at 80° C. for 6 hours. On completion, the reaction solution was diluted with water (20 mL) and then extracted with ethyl acetate (3×10 mL). The combined organic layers were washed with brine (2×10 mL), dried over anhydrous sodium sulfate, filtered and concentrated under vacuum. The residue was purified by prep-TLC to afford the title compound (170 mg, 67% yield) as a brown oil. LC-MS (ESI$^+$) m/z 543.4 (M+H)$^+$.

Step 2—Tert-butyl 4-(4-(3-(4-methoxybenzyl)-2,4-dioxotetrahydropyrimidin-1(2H)-yl)isoquinolin-7-yl)piperidine-1-carboxylate To a solution of tert-butyl 4-(4-(3-(4-methoxybenzyl)-2,4-dioxotetrahydropyrimidin-1(2H)-yl) isoquinolin-7-yl)-5,6-dihydropyridine-1(2H)-carboxylate (160 mg, 294 umol) in THF (20 mL) was added Pd/C (30 mg, 294 umol, 10 wt %) under N$_2$. The mixture was stirred at 20° C. for 1 hour under H$_2$ balloon (15 psi). On completion, the mixture was filtered through celite, then washed with THF (50 mL). The filtrate was concentrated in vacuo to afford the title compound (130 mg, 72% yield) as brown oil. $^1$H NMR (400 MHz, DMSO-d$_6$) δ 9.26 (s, 1H), 8.49 (s, 1H), 8.06 (s, 1H), 7.85 (d, J=8.4 Hz, 1H), 7.75 (dd, J=1.6, 8.8 Hz, 1H), 7.25 (d, J=8.8 Hz, 2H), 6.90-6.86 (m, 2H), 4.83 (s, 2H), 4.13 (d, J=11.0 Hz, 2H), 3.94-3.91 (m, 1H), 3.73 (s, 3H), 3.66-3.54 (m, 4H), 3.15-3.08 (m, 1H), 3.02-2.97 (m, 1H), 1.88-1.85 (m, 2H), 1.68-1.57 (m, 2H), 1.35 (s, 9H); LC-MS (ESI$^+$) m/z 545.2 (M+H)$^+$.

Step 3—1-(7-(Piperidin-4-yl)isoquinolin-4-yl)dihydropyrimidine-2,4(1H,3H)-dione A solution of tert-butyl 4-(4-(3-(4-methoxybenzyl)-2,4-dioxotetrahydropyrimidin-1(2H)-yl) isoquinolin-7-yl)piperidine-1-carboxylate (40.0 mg, 73.4 umol) in TFA (1.0 mL) and TfOH (0.05 mL) was stirred at 70° C. for 3 hours. On completion, the residue was concentrated in vacuo. The residue was purified by prep-HPLC (column: Phenomenex luna C18, 150 mm*25 mm*10 um; mobile phase: [water (0.225% FA)-MeCN]; B %: 1%-15%, 11.5 min), and then further purified by Prep-HPLC (column: Waters xbridge, 150 mm*25 mm*10 um; mobile phase: [water (10 mM NH$_4$HCO$_3$)-MeCN]; B %: 0%-26%, 11 min) to give the title compound (1.03 mg, 4% yield) as a white solid. $^1$H NMR (DMSO-d$_6$, 400 Hz) δ 10.53 (s, 1H), 9.26 (s, 1H), 8.48 (s, 1H), 8.01 (s, 1H), 7.92 (d, J=8.8 Hz, 1H), 7.77-7.74 (m, 1H), 3.96-3.89 (m, 1H), 3.75-3.69 (m, 1H), 3.09 (d, J=12.0 Hz, 2H), 3.00-2.72 (m, 4H), 2.65-2.62 (m, 2H), 1.80 (d, J=12 Hz, 2H), 1.68-1.58 (m, 2H); LC-MS (ESI$^+$) m/z 325.0 (M+H)$^+$.

1-[7-[1-[[4-(2-aminoethoxy)cyclohexyl]methyl]-4-piperidyl]-4-isoquinolyl] hexahydropyr-imidine-2,4-dione (Intermediate HG)

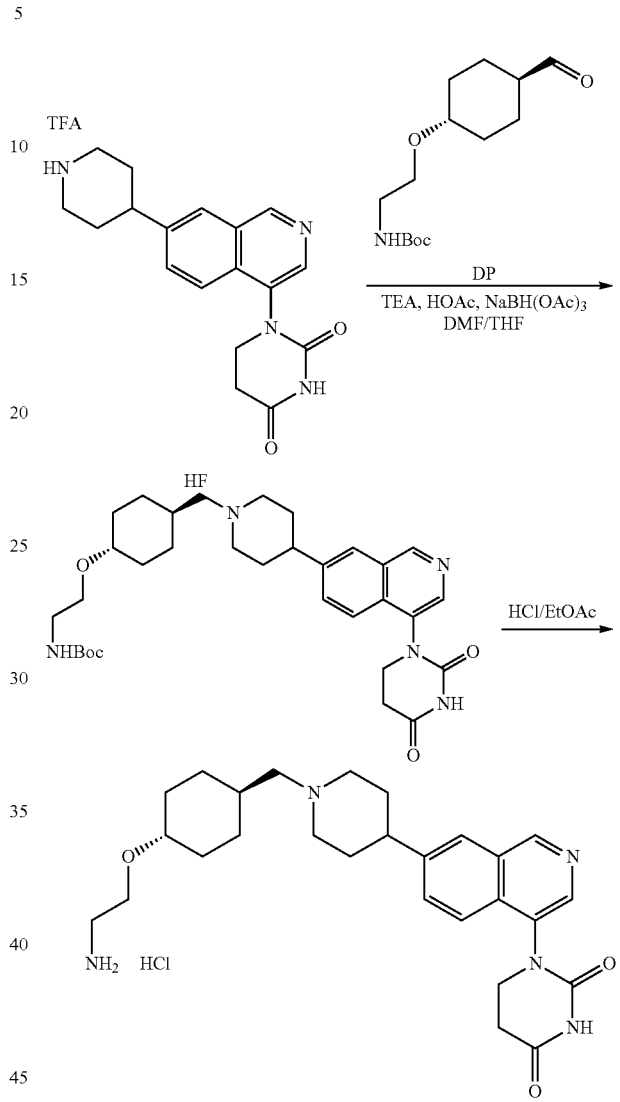

Step 1—Tert-butyl N-[2-[4-[[4-[4-(2,4-dioxohexahydropyrimidin-1-yl)-7-isoquinolyl]-1-piperidyl]methyl]cyclohexoxy]ethyl]carbamate To a solution of 1-[7-(4-piperidyl)-4-isoquinolyl]hexahydropyrimidine-2,4-dione (134 mg, 305 umol, TFA, Intermediate HF), TEA (30.9 mg, 305 umol) and HOAc (36.7 mg, 611 umol) in DMF (1 mL) and THF (1 mL) was added tert-butyl N-[2-(4-formylcyclohexoxy)ethyl]carbamate (82.9 mg, 305 umol, Intermediate DP) at −10° C. The mixture was stirred at −10° C. for 0.5 hr. Then, to the above mixture was added NaBH(OAc)$_3$ (97.1 mg, 458 umol) at −10° C. and the mixture was stirred at −10° C. for 1 hr. On completion, the mixture was quenched with H$_2$O (0.05 mL). The residue was purified by prep-HPLC (column: Phenomenex luna C18 150*25 mm*10 um; mobile phase: [water (FA)-ACN]; B %: 10%-40%, 15 min) to give the title compound (100 mg, 56% yield) as white solid. $^1$H NMR (400 MHz, CDCl$_3$) δ 9.24 (s, 1H), 8.52 (s, 1H), 8.14 (s, 1H), 7.92 (d, J=7.2 Hz, 2H), 7.83-7.78 (m, 1H), 7.76-7.71 (m, 1H), 4.88 (t, J=4.8 Hz, 1H), 4.04-3.97 (m, 1H), 3.89-3.74 (m, 4H), 3.52 (t, J=5.2 Hz, 2H), 3.29 (d, J=5.2 Hz, 2H), 3.25-3.11 (m, 2H), 3.07-2.89 (m, 7H), 2.87-2.70 (m, 3H), 2.63-2.41 (m, 3H), 2.16-2.03 (m, 5H), 1.97 (d, J=13.2 Hz, 2H), 1.89-1.78 (m, 1H), 1.30-1.09 (m, 5H).

Step 2—1-[7-[1-[[4-(2-Aminoethoxy)cyclohexyl]methyl]-4-piperidyl]-4-isoquinolyl]hexahydropyrimidine-2,4-dione A solution of tert-butyl N-[2-[4-[[4-[4-(2,4-dioxohexahydropyrimidin-1-yl)-7-isoquinolyl]-1-piperidyl]methyl]cyclohexoxy]ethyl]carbamate (100 mg, 172 umol) in HCl/EtOAc (3 mL) was stirred at 25° C. for 1 hr. On completion, the mixture was concentrated in vacuo to give the title compound (89 mg, 99% yield, HCl) as white solid. LC-MS (ESI$^+$) m/z 480.1 (M+H)$^+$.

1-[7-(4-piperidyl)imidazo[1,2-a]pyridin-3-yl]hexahydropyrimidine-2,4-dione (Intermediate HH)

Step 1—Tert-butyl 4-[3-(2,4-dioxohexahydropyrimidin-1-yl)imidazo[1,2-a]pyridin-7-yl]piperidine-1-carboxylate To a 40 mL vial equipped with a stir bar was added 1-(7-bromoimidazo[1,2-a]pyridin-3-yl)hexahydropyrimidine-2,4-dione (498 mg, 1.61 mmol, Intermediate AZ), tert-butyl 4-bromopiperidine-1-carboxylate (553 mg, 2.10 mmol, CAS #180695-79-8), Ir[dF(CF3)ppy]$_2$(dtbpy)(PF$_6$) (36.1 mg, 32.2 umol), NiCl$_2$ dtbbpy (19.2 mg, 48.3 umol), TTMSS (400 mg, 1.61 mmol) and 2,6-dimethylpyridine (345 mg, 3.22 mmol) in DME (50 mL). The reaction was stirred and irradiated with a 4×50 W [455 nm] blue LED lamp (3 cm away), with cooling water to keep the reaction temperature at 25° C. for 14 hrs. On completion, the reaction mixture was filtered and the filtered cake was concentrated in vacuo. The crude product was purified by reversed-phase (0.1% FA condition) to give the title compound (220 mg, 33% yield) as white solid. $^1$H NMR (400 MHz, DMSO-d$_6$) δ 10.65 (s, 1H), 8.24 (d, J=7.2 Hz, 1H), 7.51 (s, 1H), 7.38 (s, 1H), 6.98-6.91 (m, 1H), 4.16-4.02 (m, 2H), 3.78 (t, J=6.8 Hz, 2H), 2.87-2.73 (m, 5H), 1.82 (d, J=12.8 Hz, 2H), 1.54 (m, J=4.4, 12.4 Hz, 2H), 1.42 (s, 9H).

Step 2—1-[7-(4-Piperidyl)imidazo[1,2-a]pyridin-3-yl]hexahydropyrimidine-2,4-dione A solution of tert-butyl 4-[3-(2,4-dioxohexahydropyrimidin-1-yl)imidazo[1,2-a]pyridin-7-yl] piperidine-1-carboxylate (220 mg, 532 umol) in HCl/EtOAc (4 mL) was stirred at 25° C. for 1 hr. On completion, the mixture was concentrated in vacuo to give the title compound (186 mg, 99% yield, HCl) as white solid. LCMS (ESI$^+$) m/z 314.0 (M+H)$^+$.

1-[7-[1-[[4-(2-Aminoethoxy)cyclohexyl]methyl]-4-piperidyl]imidazo[1,2-a]pyridin-3-yl]hexahydropyrimidine-2,4-dione (Intermediate HI)

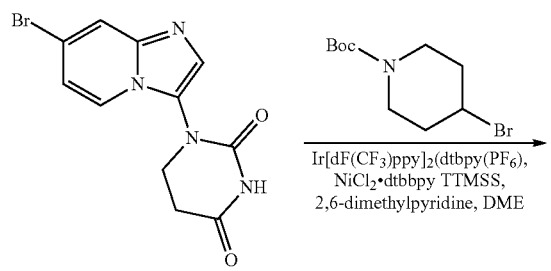

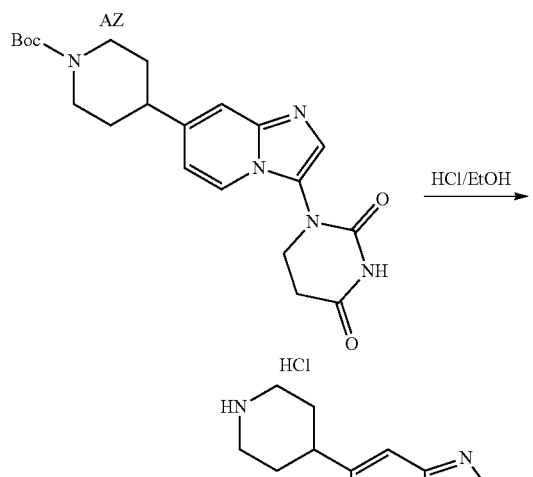

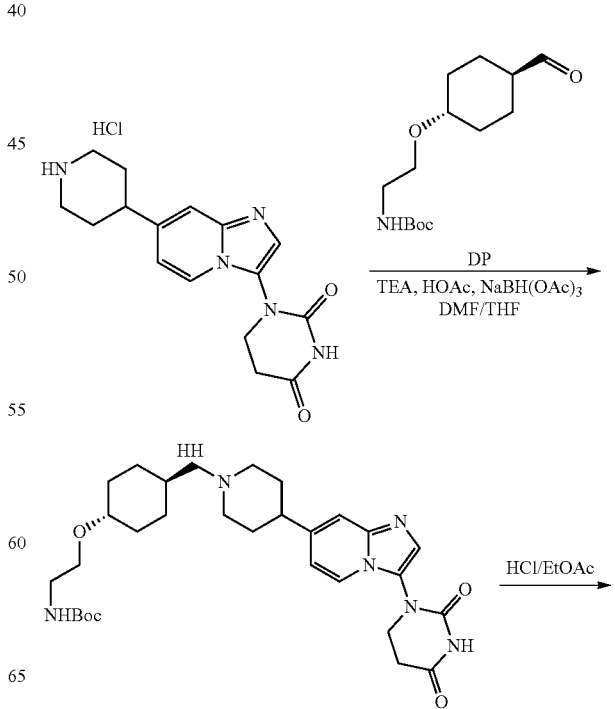

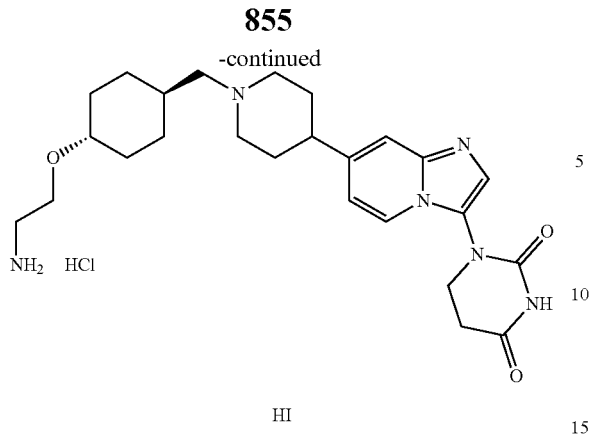

HI

Step 1—Tert-butyl N-[2-[4-[[4-[3-(2,4-dioxohexahydropyrimidin-1-yl)imidazo[1,2-a]pyridin-7-yl]-1-piperidyl]methyl]cyclohexoxy]ethyl]carbamate To a solution of 1-[7-(4-piperidyl)imidazo[1,2-a]pyridin-3-yl]hexahydropyrimidine-2,4-dione (103 mg, 294 umol, HCl, Intermediate HH), TEA (29.8 mg, 294 umol) and HOAc (35.4 mg, 589 umol) in DMF (1 mL) and THF (1 mL) was added tert-butyl N-[2-(4-formylcyclohexoxy)ethyl]carbamate (80 mg, 294 umol, Intermediate DP) at −10° C. The mixture was stirred at −10° C. for 0.5 hr. Then, to the above mixture was added NaBH(OAc)₃ (93.7 mg, 442 umol) at −10° C. and the mixture was stirred at −10° C. for 1 hr. On completion, the mixture was quenched with H₂O (0.05 mL). The residue was purified by prep-HPLC (column: Phenomenex luna C18 150*25 mm*10 um; mobile phase: [water (FA)-ACN]; B %: 1%-30%, 15 min) to give the title compound (70 mg, 41% yield) as white solid. ¹H NMR (400 MHz, CDCl₃) δ 8.40 (s, 1H), 7.79 (d, J=7.2 Hz, 1H), 7.57 (s, 1H), 7.51 (s, 1H), 6.91 (dd, J=1.2, 7.2 Hz, 1H), 5.38-4.84 (m, 1H), 3.89 (t, J=6.8 Hz, 2H), 3.58-3.48 (m, 4H), 3.28 (d, J=5.2 Hz, 2H), 3.24-3.15 (m, 1H), 2.98-2.90 (m, 2H), 2.82-2.68 (m, 3H), 2.62-2.52 (m, 2H), 2.37-2.24 (m, 2H), 2.08 (d, J=10.4 Hz, 2H), 1.95 (d, J=13.2 Hz, 4H), 1.74 (m, 1H), 1.45 (s, 9H), 1.28-1.18 (m, 2H), 1.14-1.03 (m, 2H).

Step 2—1-[7-[1-[[4-(2-Aminoethoxy)cyclohexyl]methyl]-4-piperidyl]imidazo[1,2-a]pyridin-3—yl]hexahydropyrimidine-2,4-dione A solution of tert-butyl N-[2-[4-[[4-[3-(2,4-dioxohexahydropyrimidin-1-yl)imidazo[1,2-a]pyridin-7-yl]-1-piperidyl]methyl]cyclohexoxy]ethyl]carbamate (70.0 mg, 123 umol) in HCl/EtOAc (3 mL) was stirred at 25° C. for 1 hr. On completion, the mixture was concentrated in vacuo to give the title compound (60 mg, 96% yield, HCl) as white solid. LCMS (ESI⁺) m/z 469.4 (M+H)⁺.

Tert-butyl 6-(3-oxopropox)-2-azaspiro[3.3]heptane-2-carboxylate (Intermediate HJ)

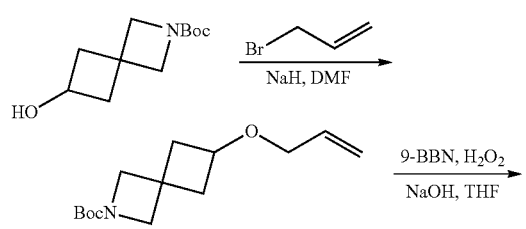

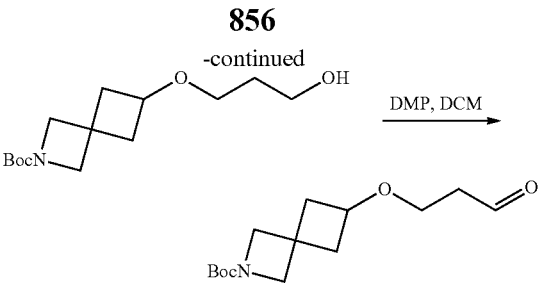

HJ

Step 1—Tert-butyl 6-allyloxy-2-azaspiro[3.3]heptane-2-carboxylate

To a solution of tert-butyl 6-hydroxy-2-azaspiro[3.3]heptane-2-carboxylate (1.00 g, 4.69 mmol, CAS #1147557-97-8) in DMF (20 mL) was added NaH (375 mg, 9.38 mmol, 60% purity) and 3-bromoprop-1-ene (850 mg, 7.03 mmol, CAS #106-95-6). Then the mixture was stirred at 0° C. for 3 hrs. On completion, the reaction mixture was washed with brine (100 mL) and extracted with DCM (50 mL). The organic layer was dried over anhydrous Na₂SO₄ and concentrated in vacuo. The residue was purified by column chromatography (SiO₂, Petroleum ether/Ethyl acetate=20/1 to 5/1) to give the title compound (1.08 g, 90% yield) as a colorless oil. ¹H NMR (400 MHz, CDCl₃) δ 5.99-5.84 (m, 1H), 5.31-5.25 (m, 1H), 5.21-5.17 (m, 1H), 3.91 (s, 2H), 3.90-3.87 (m, 5H), 2.52-2.46 (m, 2H), 2.17-2.10 (m, 2H), 1.45 (s, 9H).

Step 2—Tert-butyl 6-(3-hydroxypropoxy)-2-azaspiro[3.3]heptane-2-carboxylate

To a solution of tert-butyl 6-allyloxy-2-azaspiro[3.3]heptane-2-carboxylate (1.08 g, 4.26 mmol) in THF (12 mL) was added 9-BBN (0.5 M, 25.58 mL) at 0° C. The mixture was then stirred at 25° C. for 16 hrs. The reaction solution was cooled to 0° C., then deionized water (1 mL) and NaOH (3 M, 6 mL) was added. After that, H₂O₂ (4.77 g, 39.2 mmol, 28% solution) was added at 0° C. and the mixture was stirred for 30 min. On completion, the mixture was diluted with water (10 mL) and extracted with EA (10 mL×3). The combined organic layers were washed with brine (10 mL), dried over anhydrous Na₂SO₄, filtered and concentrated in vacuo to give a residue. The residue was purified by column chromatography (SiO₂, Petroleum ether/Ethyl acetate=10/1 to 1/1) to give the title compound (800 mg, 69% yield) as a colorless oil. ¹H NMR (400 MHz, CDCl₃) δ 3.89 (s, 2H), 3.86 (s, 2H), 3.84-3.77 (m, 3H), 3.75 (t, J=5.6 Hz, 2H), 3.49 (t, J=6.0 Hz, 2H), 2.51-2.42 (m, 2H), 2.11-2.03 (m, 2H), 1.42 (s, 9H).

Step 3—Tert-butyl 6-(3-oxopropoxy)-2-azaspiro[3.3]heptane-2-carboxylate

To a solution of tert-butyl 6-(3-hydroxypropoxy)-2-azaspiro[3.3]heptane-2-carboxylate (200 mg, 737 umol) in DCM (4 mL) was added DMP (375 mg, 884 umol). The mixture was stirred at 25° C. for 1 hr. The reaction mixture was quenched with Na₂S₂O₃·5H₂O (10 mL), then extracted with DCM (3×20 mL). The combined organic layer was washed with brine (20 mL), dried over anhydrous sodium sulfate, filtered and the filtrate was concentrated in vacuo. The residue was purified by column chromatography (SiO₂, Petroleum ether/Ethyl acetate=10/1 to 1/1) to give the title compound (90 mg, 45% yield) as a colorless oil. ¹H NMR (400 MHz, CDCl₃) δ 9.79 (s, 1H), 4.35 (t, J=5.2 Hz, 2H), 3.90 (s, 2H), 3.87 (s, 3H), 3.65 (t, J=6.0 Hz, 2H), 2.68-2.62 (m, 2H), 2.47 (d, J=6.4 Hz, 2H), 1.44 (s, 9H).

3-[5-[1-[3-(2-Azaspiro[3.3]heptan-6-yloxy)propyl]-4-piperidyl]-3-methyl-2-oxo-benzimidazol-1-yl]piperidine-2,6-dione (Intermediate HK)

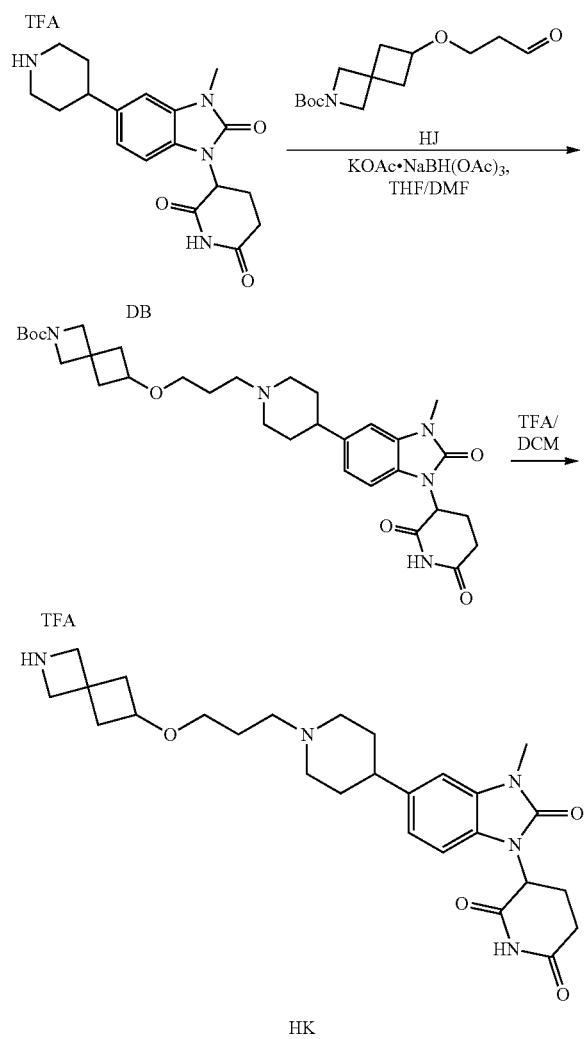

Step 1—Tert-butyl 6-[3-[4-[1-(2,6-dioxo-3-piperidyl)-3-methyl-2-oxo-benzimidazol-5-yl]-1-piperidyl] propoxy]-2-azaspiro[3.3]heptane-2-carboxylate To a solution of 3-[3-methyl-2-oxo-5-(4-piperidyl)benzimidazol-1-yl]piperidine-2,6-dione (60.0 mg, 131 umol, TFA salt, Intermediate DB) and tert-butyl 6-(3-oxopropoxy)-2-azaspiro[3.3] heptane-2-carboxylate (35.4 mg, 131 umol, Intermediate HJ) in a mixture solution of THF (2 mL) and DMF (0.5 mL) was added KOAc (129 mg, 1.31 mmol) and NaBH(OAc)₃ (55.7 mg, 262 umol). The mixture was stirred at 0° C. for 1 hr. On completion, the mixture was quenched with H₂O (0.5 mL) at 0° C. and concentrated in vacuo to afford a residue. The residue was purified by prep-HPLC (column: Phenomenex luna C18 150*25 mm*10 um; mobile phase: [water(FA)-ACN]; B %: 12%-42%, 9 min) to give the title compound (50 mg, 63% yield) as a white solid. LCMS (ESI⁺) m/z 596.5 (M+H)⁺.

Step 2—3-[5-[1-[3-(2-Azaspiro[3.3]heptan-6-yloxy) propyl]-4-piperidyl]-3-methyl-2-oxo-benzimidazol-1-yl]piperidine-2,6-dione To a solution of tert-butyl 6-[3-[4-[1-(2,6-dioxo-3-piperidyl)-3-methyl-2-oxo-benzimidazol-5-yl]-1-piperidyl] propoxy]-2-azaspiro[3.3]heptane-2-carboxylate (50.0 mg, 83.9 umol) in DCM (1 mL) was added TFA (2.31 g, 20.2 mmol). The mixture was stirred at 25° C. for 0.5 hour. On completion, the reaction mixture was concentrated in vacuo to give the title compound (50.0 mg, 97% yield, TFA salt) as a white solid. LCMS (ESI⁺) m/z 496.2 (M+H)⁺.

Benzyl N-[2-(4-piperidyloxy)ethyl]carbamate (Intermediate HL)

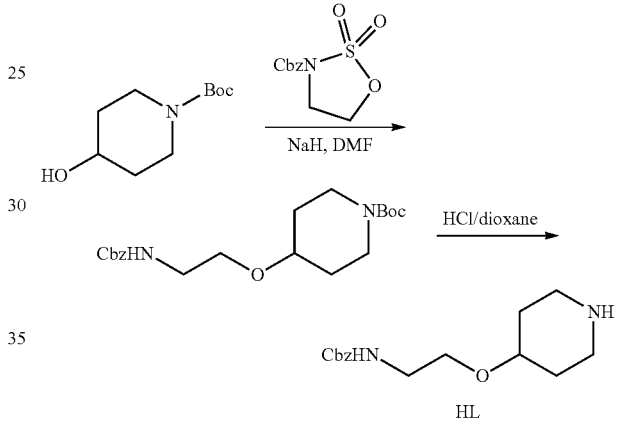

Step 1—Benzyl 4-[2-(tert-butoxycarbonylamino)ethoxy]piperidine-1-carboxylate

To a solution of benzyl 4-hydroxypiperidine-1-carboxylate (400 mg, 1.70 mmol, CAS #95798-23-5) in DMF (8 mL) was added NaH (136 mg, 3.40 mmol, 60% dispersion in mineral oil) in portions at 0° C. The mixture was stirred at 0° C. for 0.5 hr, then benzyl 2,2-dioxooxathiazolidine-3-carboxylate (437 mg, 1.70 mmol, CAS #1215021-54-7) was added. The reaction mixture was stirred at 25° C. for 15.5 hrs. The reaction mixture was washed with brine (30 mL) and extracted with DCM (30 mL). The organic layer was dried over anhydrous Na₂SO₄ and concentrated in vacuo. The residue was purified by column chromatography (SiO₂, Petroleum ether/Ethyl acetate=20/1 to 5/1) to give the title compound (300 mg, 46% yield) as a colorless oil. ¹H NMR (400 MHz, CDCl₃) δ 7.33-7.20 (m, 5H), 5.04 (s, 2H), 3.69-3.65 (m, 2H), 3.46 (s, 2H), 3.16-3.08 (m, 2H), 2.97-2.95 (m, 2H), 2.90-2.80 (m, 1H), 1.64-1.56 (m, 2H), 1.43 (d, J=4.4 Hz, 2H), 1.39 (s, 9H). LCMS (ESI⁺) m/z 401.1 (M+Na)⁺.

Step 2—Benzyl N-[2-(4-piperidyloxy)ethyl]carbamate

To a solution of tert-butyl 4-[2-(benzyloxycarbonylamino)ethoxy]piperidine-1-carboxylate (110 mg, 290 umol) in DCM (1.5 mL) was added TFA (770 mg, 6.75 mmol). The mixture was stirred at 25° C. for 0.5 hr. The reaction mixture was concentrated in vacuo to give the title compound (110 mg, 96% yield, TFA) as a colorless oil. LCMS (ESI$^+$) m/z 279.2 (M+H)$^+$.

3-[5-[4-[[4-(2-Aminoethoxy)-1-piperidyl]methyl]-1-piperidyl]-3-methyl-2-oxo-benzimidazol-1-yl]piperidine-2,6-dione (Intermediate HM)

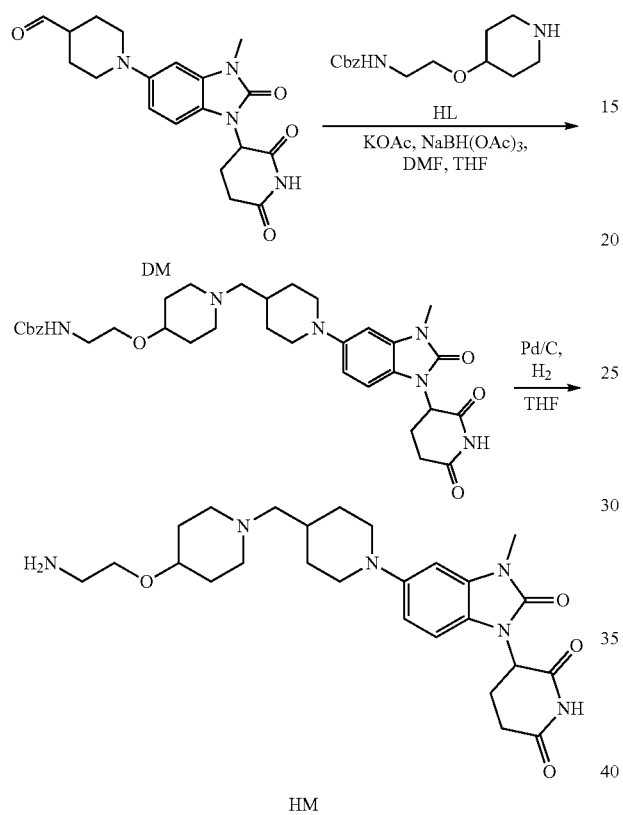

Step 1—Benzyl N-[2-[[1-[[1-[1-(2,6-dioxo-3-piperidyl)-3-methyl-2-oxo-benzimidazol-5-yl]-4-piperidyl] methyl]-4-piperidyl]oxy]ethyl]carbamate To a solution of benzyl N-[2-(4-piperidyloxy)ethyl]carbamate (110 mg, 280 umol, TFA, Intermediate HL) and 1-[1-(2,6-dioxo-3-piperidyl)-3-methyl-2-oxo-benzimidazol-5-yl]piperidine-4-carbaldehyde (103 mg, 280 umol, Intermediate DM) in a mixture solution of THF (2 mL) and DMF (0.5 mL) was added KOAc (275 mg, 2.80 mmol) and NaBH(OAc)$_3$ (118 mg, 560 umol). The mixture was stirred at 0° C. for 1 hr. On completion, the mixture was quenched with H$_2$O (0.5 mL) at 0° C. and concentrated in vacuo to afford a residue. The residue was purified by prep-HPLC (column: Phenomenex luna C18 150*25 mm*10 um; mobile phase: [water(FA)-ACN]; B %: 0%-30%, 9 min) to give the title compound (60.0 mg, 33% yield) as a white solid. LCMS (ESI$^+$) m/z 633.5 (M+H)$^+$.

Step 2—3-[5-[4-[[4-(2-Aminoethoxy)-1-piperidyl]methyl]-1-piperidyl]-3-methyl-2-oxo-benzimidazol-1-yl]piperidine-2,6-dione To a solution of benzyl N-[2-[[1-[[1-[1-(2,6-dioxo-3-piperidyl)-3-methyl-2-oxo-benzimidazol-5-yl]-4-piperidyl] methyl]-4-piperidyl]oxy]ethyl]carbamate (60.0 mg, 94.8 umol) in THF (3 mL) was added Pd/C (40.0 mg, 94.8 umol, 10 wt %) under N$_2$. The suspension was degassed in vacuo and purged with H$_2$ several times. The mixture was stirred at 25° C. for 1 hr under H$_2$ (20 psi). On completion, the reaction was filtered and the filtrate was concentrated in vacuo to give the title compound (30 mg, 63% yield) as a white solid. LCMS (ESI$^+$) m/z 499.2 (M+H)$^+$.

8-Cyclopentyl-2-methylsulfanyl-pyrido[2,3-d]pyrimidin-7-one (Intermediate HN)

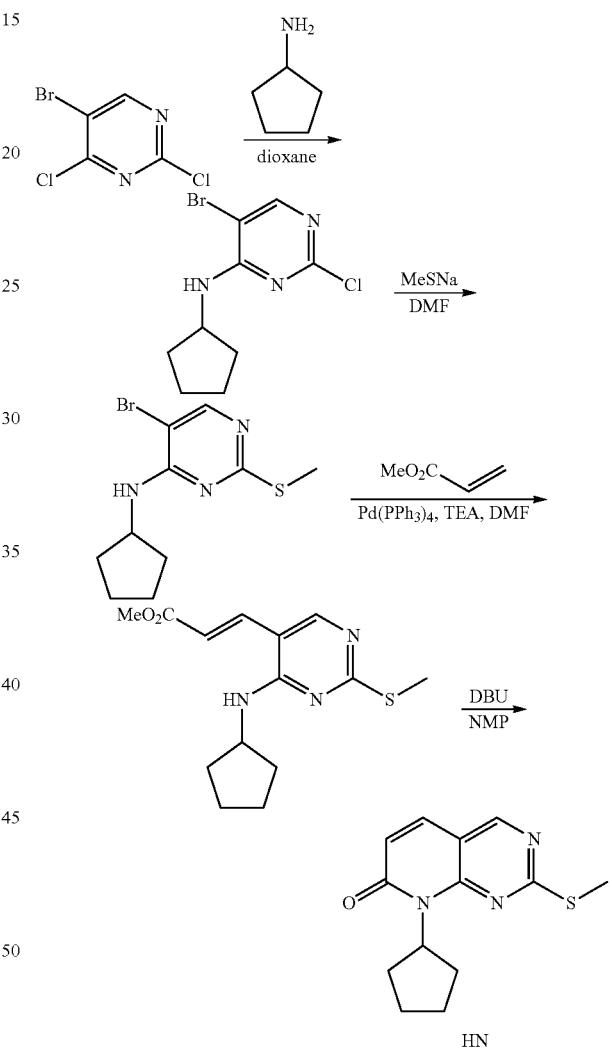

Step 1—5-Bromo-2-chloro-N-cyclopentyl-pyrimidin-4-amine

To a solution of 5-bromo-2,4-dichloro-pyrimidine (5.00 g, 21.9 mmol, CAS #36082-50-5) in dioxane (100 mL) was added cyclopentanamine (2.24 g, 26.3 mmol, CAS #1003-03-8). The mixture was stirred at 25° C. for 6 hrs. On completion, the reaction mixture was with H$_2$O (100 mL) at 25° C., and then extracted with ethyl acetate (3×100 mL). The combined organic layers were washed with brine (2×100 mL), dried over Na$_2$SO$_4$, filtered and concentrated in vacuo to give a residue. Then the residue was purified by column chromatography (SiO₂, Petroleum ether/Ethyl acetate=100/1 to 1/1) to give the title compound (7.50 g, 61% yield) as a white solid. ¹H NMR (400 MHz, DMSO-d₆) δ 8.22 (s, 1H), 7.36 (d, J=7.2 Hz, 1H), 4.35-4.26 (m, 1H), 1.92-1.88 (m, 2H), 1.72-1.65 (m, 2H), 1.63-1.51 (m, 4H).

Step 2—5-Bromo-N-cyclopentyl-2-methylsulfanyl-pyrimidin-4-amine

To a solution of 5-bromo-2-chloro-N-cyclopentyl-pyrimidin-4-amine (2.00 g, 7.23 mmol) in DMF (20 mL) was degassed and purged with N₂ three times, then NaSMe (1.29 g, 18.4 mmol) was added to the mixture. The mixture was stirred at 25° C. for 16 hrs under N₂ atmosphere. On completion, the reaction mixture was quenched with H₂O (20 mL) at 25° C., and then extracted with EA (3×20 mL). The combined organic layers were washed with brine (2×10 mL), dried over Na₂SO₄, filtered and concentrated in vacuo to give a residue. Then the crude product was purified by reversed-phase HPLC (0.1% FA condition) to give the title compound (2.00 g, 95% yield) as off-white oil. ¹H NMR (400 MHz, CDCl₃) δ 8.05 (s, 1H), 5.27 (d, J=4.0 Hz, 1H), 4.44-4.36 (m, 1H), 2.50 (s, 3H), 2.15-2.07 (m, 2H), 1.78-1.63 (m, 4H), 1.53-1.45 (m, 2H).

Step 3—Methyl (E)-3-[4-(cyclopentylamino)-2-methylsulfanyl-pyrimidin-5-yl]prop-2-enoate A mixture of 5-bromo-N-cyclopentyl-2-methylsulfanyl-pyrimidin-4-amine (2.00 g, 6.94 mmol), TEA (2.11 g, 20.8 mmol), Pd(PPh₃)₄ (801 mg, 693 umol) in DMF (20 mL) was degassed and purged with N₂ three times. Then methyl prop-2-enoate (3.11 g, 36.1 mmol, CAS #96-33-3) was added to the mixture, and then the mixture was stirred at 90° C. for 16 hours under N₂ atmosphere. On completion, the reaction mixture was quenched with H₂O (20 mL) at 25° C., and then extracted with EA (3×10 mL). The combined organic layers were washed with brine (2×10 mL), dried over Na₂SO₄ filtered and concentrated under reduced pressure to give a residue. Then the crude product was purified by reversed-phase HPLC (0.1% FA condition) to give the title compound (1.37 g, 67% yield) as a yellow solid. ¹H NMR (400 MHz, CDCl₃) δ 8.14 (s, 1H), 7.49 (d, J=16.0 Hz, 1H), 6.27 (dd, J=1.2, 15.6 Hz, 1H), 5.08 (d, J=6.0 Hz, 1H), 4.52-4.44 (m, 1H), 3.83-3.79 (m, 3H), 2.58-2.51 (m, 3H), 2.19-2.08 (m, 2H), 1.81-1.62 (m, 4H), 1.53-1.45 (m, 2H).

Step 4—8-Cyclopentyl-2-methylsulfanyl-pyrido[2,3-d]pyrimidin-7-one

To a solution of methyl (E)-3-[4-(cyclopentylamino)-2-methylsulfanyl-pyrimidin-5-yl]prop-2-enoate (1.00 g, 3.41 mmol) in NMP (10 mL) was added DBU (2.59 g, 17.0 mmol). The mixture was stirred at 120° C. for 1 hr. On completion, the reaction mixture was quenched with H₂O (20 mL) at 25° C., and then extracted with EA (3×20 mL). The combined organic layers were washed with brine (2×20 mL), dried over Na₂SO₄, filtered and concentrated in vacuo to give a residue. Then the residue was purified by column chromatography (SiO₂, Petroleum ether/Ethyl acetate=100/1 to 10/1) to give the title compound (484 mg, 54% yield) as a yellow solid. LC-MS (ESI⁺) m/z 262.0 (M+1)⁺.

4-[[8-Cyclopentyl-6-(difluoromethyl)-7-oxo-pyrido[2,3-d]pyrimidin-2-yl]amino]-3-methyl-benzene-sulfonyl chloride (Intermediate HO)

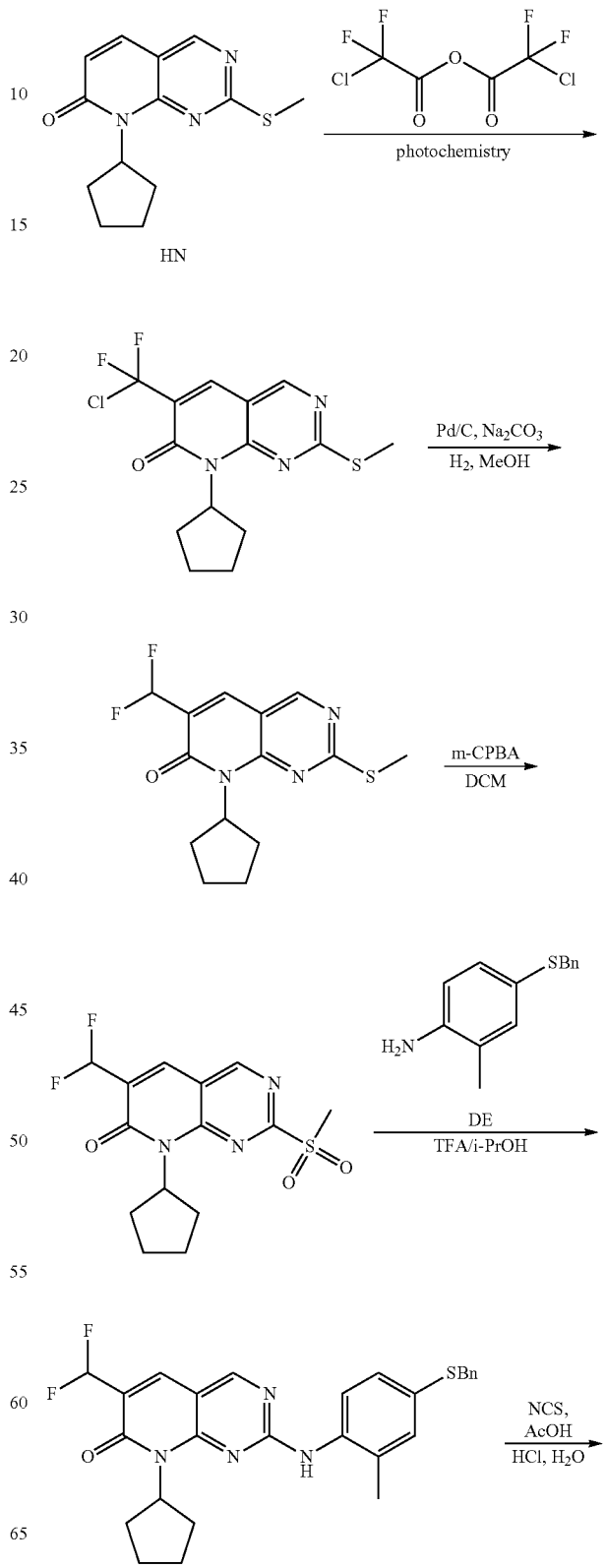

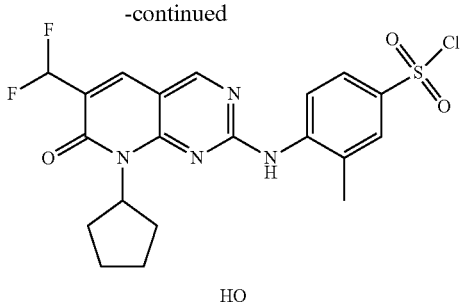

Step 1—6-[Chloro(difluoro)methyl]-8-cyclopentyl-2-methylsulfanyl-pyrido[2,3-d]pyrimidin-7-one To an 40 mL vial equipped with a stir bar was added 8-cyclopentyl-2-methylsulfanyl-pyrido[2,3-d]pyrimidin-7-one (1.00 g, 3.83 mmol, Intermediate HN), (2-chloro-2,2-difluoro-acetyl) 2-chloro-2,2-difluoro-acetate (2.09 g, 8.60 mmol, CAS #2834-23-3), 1-oxido-4-phenyl-pyridin-1-ium (1.31 g, 7.65 mmol), and Ru(bpy)$_3$Cl$_2$.6H$_2$O (28.6 mg, 38.2 umol) in dry ACN (10 mL). The vial was sealed and placed under nitrogen was added. The reaction was stirred and irradiated with a 4×50 W [455 nm] blue LED lamp (3 cm away), with cooling water to keep the reaction temperature at 25° C. for 14 hrs. On completion, the mixture was filtered and concentrated in vacuo. The residue was purified by prep-HPLC (column; mobile phase: [water (TFA)-ACN]; B %: 35%-85%, 30 mins) to give the title compound (1.10 g, 83% yield) as a brown solid. $^1$H NMR (400 MHz, DMSO-d$_6$) δ 9.04 (s, 1H), 8.51 (s, 1H), 5.87 (q, J=8.8 Hz, 1H), 2.61 (s, 3H), 2.27-2.17 (m, 2H), 2.03-1.97 (m, 2H), 1.89-1.82 (m, 2H), 1.70-1.61 (m, 2H). LC-MS (ESI$^+$) m/z 346.0 (M+H)$^+$.

Step 2—8-Cyclopentyl-6-(difluoromethyl)-2-methylsulfanyl-pyrido[2,3-d]pyrimidin-7-one To a solution of 6-[chloro(difluoro)methyl]-8-cyclopentyl-2-methylsulfanyl-pyrido[2,3-d]pyrimidin-7-one (1.10 g, 3.18 mmol) in MeOH (12 mL) was added Na$_2$CO$_3$ (505 mg, 4.77 mmol) and Pd/C (600 mg, 3.18 mmol, 10 wt %). The mixture was stirred at 25° C. for 4 hrs under H$_2$ (15 psi). On completion, the mixture was filtered and concentrated in vacuo to give the title compound (990 mg, 99% yield) as a yellow solid. $^1$H NMR (400 MHz, DMSO-d$_6$) δ 9.02 (d, J=6.0 Hz, 1H), 8.37-8.27 (m, 1H), 5.90-5.81 (m, 1H), 4.12 (s, 1H), 2.61-2.60 (m, 3H), 2.24-2.19 (m, 2H), 2.01-1.97 (m, 2H), 1.86-1.81 (m, 2H), 1.67-1.62 (m, 2H). LC-MS (ESI$^+$) m/z 311.9 (M+H)$^+$.

Step 3—8-Cyclopentyl-6-(difluoromethyl)-2-methylsulfonyl-pyrido[2,3-d]pyrimidin-7-one To a solution of 8-cyclopentyl-6-(difluoromethyl)-2-methylsulfanyl-pyrido[2,3-d]pyrimidin-7-one (990 mg, 3.18 mmol) in DCM (10 mL) was added m-CPBA (968 mg, 4.77 mmol, 85% solution) at 0° C. The mixture was then stirred at 25° C. for 8 hrs. On completion, the mixture was quenched with Na$_2$S$_2$O$_3$ 5H$_2$O (50 mL), washed with NaHCO$_3$ solution (3×50 mL), and extracted with DCM (3×50 mL). The organic layer was then washed with brine (3×50 mL), dried with anhydrous Na$_2$SO$_4$, filtered and concentrated in vacuo. The residue was purified by column chromatography (SiO$_2$, PE/EA=62/38) to give the title compound (500 mg, 4% yield) as a yellow solid. $^1$H NMR (400 MHz, DMSO-d$_6$) δ 9.41 (d, J=4.8 Hz, 1H), 8.58-8.46 (m, 1H), 7.20-6.87 (m, 1H), 5.87-5.76 (m, 1H), 3.48-3.45 (m, 3H), 2.25-2.16 (m, 2H), 2.12-2.05 (m, 2H), 1.93-1.84 (m, 2H), 1.70-1.62 (m, 2H). LC-MS (ESI$^+$) m/z 344.0 (M+H)$^+$.

Step 4—2-(4-Benzylsulfanyl-2-methyl-anilino)-8-cyclopentyl-6-(difluoromethyl)pyrido[2,3-d] pyrimidin-7-one To a solution of 8-cyclopentyl-6-(difluoromethyl)-2-methylsulfonyl-pyrido[2,3-d]pyrimidin-7-one (500 mg, 1.46 mmol) and 4-benzylsulfanyl-2-methyl-aniline (667 mg, 2.91 mmol, Intermediate DE) in i-PrOH (5 mL) was added TFA (1.66 g, 14.56 mmol). The mixture was stirred at 85° C. for 6 hrs. On completion, the mixture was cooled to rt, diluted with H$_2$O (30 mL), and extracted with EA (3×30 mL). The combined organic phases were washed with brine (2×30 mL), dried over anhydrous Na$_2$SO$_4$, filtered and concentrated in vacuo. The residue was purified by column chromatography (SiO$_2$, PE/EA=63/37) to give the title compound (195 mg, 27% yield) as a yellow oil. $^1$H NMR (400 MHz, DMSO-d$_6$) δ 9.63-9.58 (s, 1H), 8.82 (s, 1H), 8.11 (s, 1H), 7.40-7.35 (m, 2H), 7.33-7.25 (m, 5H), 7.22-7.19 (m, 1H), 7.02-6.74 (m, 1H), 5.78-5.48 (m, 1H), 4.24 (s, 2H), 2.17 (s, 3H), 2.11-2.03 (m, 2H), 1.65-1.36 (m, 6H). LC-MS (ESI$^+$) m/z 493.1 (M+H)$^+$.

Step 5—4-[[8-Cyclopentyl-6-(difluoromethyl)-7-oxo-pyrido[2,3-d]pyrimidin-2-yl]amino]-3-methyl-benzenesulfonyl chloride To a solution of 2-(4-benzylsulfanyl-2-methyl-anilino)-8-cyclopentyl-6-(difluoromethyl) pyrido[2,3-d] pyrimidin-7-one (195 mg, 395 umol) in mixture solvent of ACN (2 mL), AcOH (200 uL) and H$_2$O (20 uL) was added NCS (158 mg, 1.19 mmol). The mixture was stirred at 25° C. for 0.5 hr under dark environment. On completion, the mixture was diluted with H$_2$O (5 mL), extracted with EA (3×10 mL). The organic layer was washed with brine (3×10 mL), dried with anhydrous Na$_2$SO$_4$, filtered and the liquor was concentrated in vacuo. The residue was purified by column chromatography (SiO$_2$, PE/EA=85/15) to give the title compound (165 mg, 88% yield) as a yellow solid. $^1$H NMR (400 MHz, DMSO-d$_6$) δ 9.61 (s, 1H), 8.83 (s, 1H), 8.12 (s, 1H), 7.49 (s, 1H), 7.46-7.40 (m, 1H), 7.38-7.32 (m, 1H), 7.04-6.74 (m, 1H), 5.74-5.60 (m, 1H), 2.22 (s, 3H), 2.16-2.07 (m, 2H), 1.74-1.60 (m, 4H), 1.46-1.39 (m, 2H). LC-MS (ESI$^+$) m/z 468.7 (M+H)$^+$.

Tert-butyl N-[2-(3-formylcyclobutoxy)ethyl]carbamate (Intermediate HP)

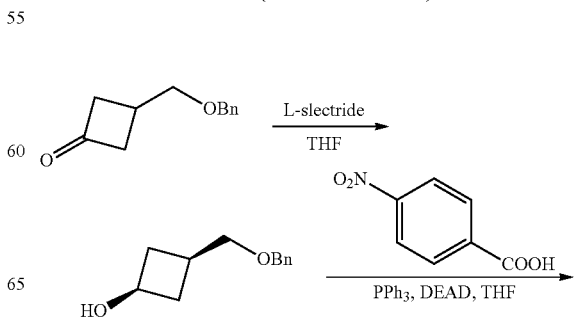

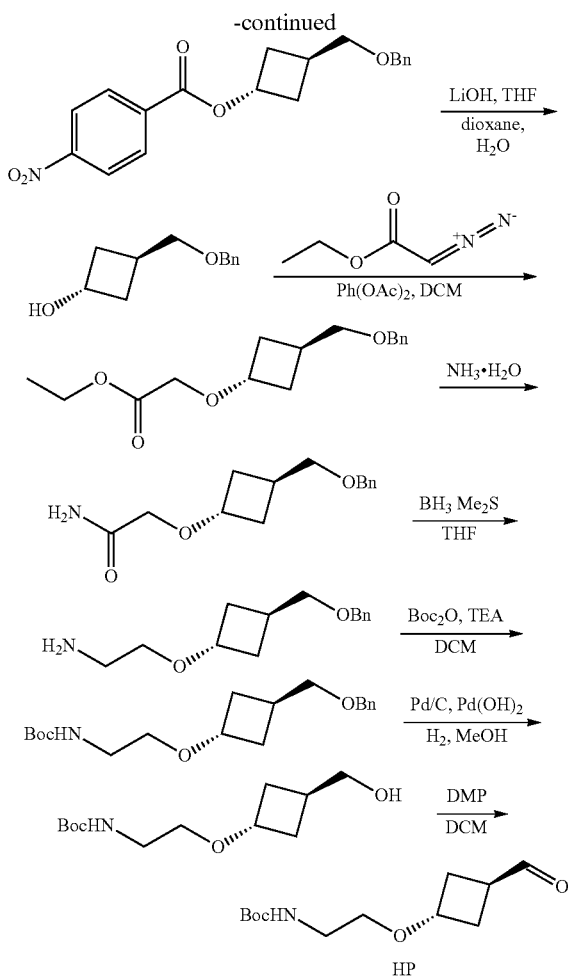

Step 1—3-(Benzyloxymethyl)cyclobutanol

To a solution of 3-(benzyloxymethyl)cyclobutanone (5.00 g, 26.2 mmol, CAS #172324-67-3) in THF (50 mL) with stirring at −70° C., was added dropwise a solution of lithium;trisec-butylboranuide (9.99 g, 52.5 mmol), maintaining the reaction temperature below −65° C. The reaction mixture was allowed to warm to 25° C. for 16 hrs. On completion, the reaction was quenched with saturated sodium bicarbonate (30 mL) and extracted with ethyl acetate (3×50 mL). The combined organic layer was acidified with 2N HCl aqueous (30 mL), and stirred at 25° C. for 3 hrs. Then the organic layer was washed with brine (100 mL), dried over anhydrous $Na_2SO_4$, filtered and concentrated in vacuo. The crude product was purified by column chromatography ($SiO_2$, PE/EA=10/1) to give the title compound (3.50 g, 69% yield) as a yellow oil. $^1$H NMR (400 MHz, $CDCl_3$) δ 7.38-7.28 (m, 5H), 4.55-4.51 (m, 2H), 4.19-4.10 (m, 1H), 3.48-3.43 (m, 2H), 2.53-2.39 (m, 2H), 2.15-2.07 (m, 1H), 1.76-1.65 (m, 2H).

Step 2—[3-(Benzyloxymethyl)cyclobutyl] 4-nitrobenzoate

To a solution of 3-(benzyloxymethyl)cyclobutanol (3.50 g, 18.2 mmol) and 4-nitrobenzoic acid (6.08 g, 36.4 mmol, CAS #1044278-58-1) in THF (100 mL) was added $PPh_3$ (9.55 g, 36.4 mmol). Then a solution of DEAD (6.34 g, 36.4 mmol) in THF (60 mL) was added dropwise into above solution at 0° C. The mixture was degassed and purged with $N_2$ three times and the mixture was stirred at 25° C. for 16 hrs. On completion, the reaction was quenched with water (50 mL), and then extracted with ethyl acetate (3×50 mL). The combined organic layer was washed with brine (3×100 mL), dried over anhydrous sodium sulfate, filtered and the organic liquor was concentrated in vacuo. The residue was purified by column chromatography ($SiO_2$, PE/EA=92/8) to give the title compound (3.00 g, 48% yield) as a white solid. $^1$H NMR (400 MHz, $CDCl_3$) δ 8.32-8.28 (m, 2H), 8.24-8.20 (m, 2H), 7.41-7.28 (m, 5H), 5.37 (q, J=6.8 Hz, 1H), 4.58 (s, 2H), 3.55 (d, J=6.4 Hz, 2H), 2.73-2.62 (m, 1H), 2.46-2.38 (m, 4H).

Step 3—3-(Benzyloxymethyl)cyclobutanol

To a solution of [3-(benzyloxymethyl)cyclobutyl] 4-nitrobenzoate (3 g, 8.79 mmol) in a mixture of dioxane (30 mL) and $H_2O$ (15 mL) was added LiOH·$H_2O$ (737 mg, 17.5 mmol). The mixture was stirred at 25° C. for 1 hr. On completion, the mixture was diluted with $H_2O$ (50 mL), and extracted with EA (3×50 mL). The organic layer was washed with brine (2×50 mL). dried over anhydrous sodium sulfate, filtered and concentrated in vacuo to give the title compound (1.69 g, 100% yield) as a colorless oil. $^1$H NMR (400 MHz, $CDCl_3$) δ 7.39-7.27 (m, 5H), 4.54 (s, 2H), 4.44-4.36 (m, 1H), 3.47 (d, J=7.2 Hz, 2H), 2.58-2.43 (m, 1H), 2.25-2.18 (m, 2H), 2.11-2.03 (m, 2H).

Step 4—Ethyl 2-[3-(benzyloxymethyl)cyclobutoxy]acetate

To a solution of 3-(benzyloxymethyl)cyclobutanol (1.69 g, 8.79 mmol) in DCM (40 mL) was added diacetoxyrhodium (388 mg, 879 umol) and ethyl 2-diazoacetate (4.01 g, 35.1 mmol, CAS #623-73-4). The mixture was degassed and purged with $N_2$ three times and the mixture was stirred at 25° C. for 16 hrs under $N_2$ atmosphere. On completion, the mixture was diluted with $H_2O$ (50 mL), and extracted with DCM (3×50 mL). Then the organic layer was washed with brine (3×50 mL), dried with anhydrous $Na_2SO_4$, filtered and the filtered liquor was concentrated in vacuo. The residue was purified by column chromatography ($SiO_2$, PE/EA=100/1 to 10/1) to give the title compound (2.40 g, 98% yield) as a colorless oil. $^1$H NMR (400 MHz, $CDCl_3$) δ 7.39-7.28 (m, 5H), 4.53 (s, 2H), 4.24 (d, J=3.2 Hz, 2H), 4.17-4.14 (m, 1H), 3.97 (s, 2H), 3.46 (d, J=6.8 Hz, 2H), 2.57-2.46 (m, 1H), 2.24-2.13 (m, 4H), 1.31-1.29 (m, 3H).

Step 5—2-[3-(Benzyloxymethyl)cyclobutoxy]acetamide

To a solution of ethyl 2-[3-(benzyloxymethyl)cyclobutoxy]acetate (2.40 g, 8.62 mmol) in MeOH (20 mL) was added $NH_3·H_2O$ (35.6 g, 284 mmol, 28% solution). The mixture was stirred at 70° C. for 16 hrs. On completion, the mixture was concentrated in vacuo, then dissolved EA (20 mL), diluted with $H_2O$ (30 mL), and extracted with EA (3×20 mL). Then the organic layer was washed with brine (3×20 mL), dried with anhydrous $Na_2SO_4$, filtered and the liquor was concentrated in vacuo to give the title compound (1.60 g, 74% yield) as a brown solid. $^1$H NMR (400 MHz, $CDCl_3$) δ 7.40-7.28 (m, 5H), 6.53 (s, 1H), 5.76 (s, 1H), 4.54 (s, 2H), 4.13 (q, J=6.4 Hz, 1H), 3.84 (s, 2H), 3.47 (d, J=6.4 Hz, 2H), 2.60-2.48 (m, 1H), 2.18-2.11 (m, 4H).

Step 6—2-[3-(Benzyloxymethyl)cyclobutoxy]ethanamine

To a solution of 2-[3-(benzyloxymethyl)cyclobutoxy]acetamide (1.60 g, 6.42 mmol) in THF (18 mL) was added BH$_3$-Me$_2$S (10 M, 6.42 mL) at 25° C. The mixture was then stirred at 60° C. for 16 hrs. On completion, the mixture was quenched with MeOH (3×10 mL), and refluxed for 20 mins (three times), then concentrated in vacuo to give the title compound (1.50 g, 99% yield) as a white solid. LC-MS (ESI$^+$) m/z 236.1 (M+H)$^+$.

Step 7—Tert-butyl N-[2-[3-(benzyloxymethyl)cyclobutoxy]ethyl]carbamate

To a solution of 2-[3-(benzyloxymethyl)cyclobutoxy]ethanamine (1.50 g, 6.37 mmol) in DCM (20 mL) was added TEA (967 mg, 9.56 mmol) and Boc$_2$O (1.53 g, 7.01 mmol). The mixture was stirred at 25° C. for 16 hrs. On completion, the mixture was concentrated in vacuo. The residue was purified by column chromatography (SiO$_2$, PE/EA=40/1) to give the title compound (1.00 g, 46% yield) as a colorless oil. $^1$H NMR (400 MHz, DMSO-d$_6$) δ 7.38-7.25 (m, 5H), 6.76 (t, J=5.2 Hz, 1H), 4.47 (s, 2H), 4.00 (q, J=6.8 Hz, 1H), 3.42 (d, J=6.8 Hz, 2H), 3.23 (t, J=6.0 Hz, 2H), 3.02 (q, J=6.0 Hz, 2H), 2.42-2.33 (m, 1H), 2.00-1.94 (m, 4H), 1.37 (s, 9H).

Step 8—Tert-butyl N-[2-[3-(hydroxymethyl)cyclobutoxy]ethyl]carbamate

To a solution of tert-butyl N-[2-[3-(benzyloxymethyl)cyclobutoxy]ethyl]carbamate (430 mg, 1.28 mmol) in MeOH (5 mL) was added Pd/C (400 mg, 1.28 mmol, 10 wt %) and Pd(OH)$_2$ (430 mg, 612 umol, 20 wt %) under Ar atmosphere. The mixture was then stirred at 50° C. for 16 hrs under H$_2$ (50 psi). On completion, the mixture was filtered and concentrated in vacuo to give the title compound (310 mg, 98% yield) as a colorless oil. $^1$H NMR (400 MHz, CDCl$_3$) δ 4.90 (s, 1H), 4.05 (q, J=6.8 Hz, 1H), 3.64 (d, J=6.8 Hz, 2H), 3.41-3.36 (m, 2H), 3.33-3.27 (m, 2H), 2.41 (q, J=6.8, 13.6 Hz, 1H), 2.12-2.09 (m, 2H), 1.79-1.54 (m, 2H), 1.45 (s, 9H).

Step 9—Tert-butyl N-[2-(3-formylcyclobutoxy)ethyl]carbamate

To a solution of tert-butyl N-[2-[3-(hydroxymethyl)cyclobutoxy]ethyl]carbamate (310 mg, 1.26 mmol) in DCM (5 mL) was added DMP (803 mg, 1.90 mmol). The mixture was stirred at 25° C. for 2 hrs. On completion, the mixture was quenched with Na$_2$S$_2$O$_3$ 5H$_2$O (10 mL), washed with NaHCO$_3$ solution (3×20 mL), and extracted with DCM (3×20 mL). The organic layer was washed with brine (3×20 mL), dried with anhydrous Na$_2$SO$_4$, filtered and the liquor was concentrated in vacuo to give the title compound (307 mg, 99% yield) as a colorless oil. $^1$H NMR (400 MHz, DMSO-d$_6$) δ 9.72 (d, J=2.0 Hz, 1H), 6.82-6.75 (m, 1H), 4.07-3.93 (m, 1H), 3.05-3.00 (t, J=6.0 Hz, 2H), 3.05-3.00 (m, 2H), 2.46-2.39 (m, 3H), 2.09-2.05 (m, 2H), 1.37 (s, 9H).

3-[5-[1-[[3-(2-Aminoethoxy)cyclobutyl]methyl]-4-piperidyl]-3-methyl-2-oxo-benzimidazol-1-yl]piperidine-2,6-dione (Intermediate HQ)

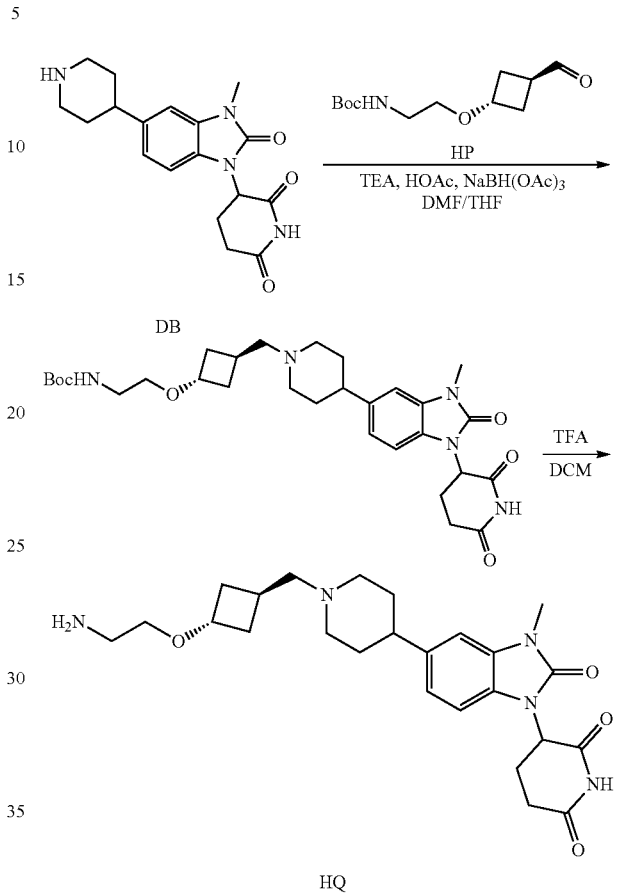

Step 1—Tert-butyl N-[2-[3-[[4-[1-(2,6-dioxo-3-piperidyl)-3-methyl-2-oxo-benzimidazol-S-yl]-1-piperidyl]methyl]cyclobutoxy]ethyl]carbamate To a solution of tert-butyl N-[2-(3-formylcyclobutoxy)ethyl]carbamate (307 mg, 1.26 mmol, Intermediate HP) and 3-[3-methyl-2-oxo-5-(4-piperidyl)benzimidazol-1-yl]piperidine-2,6-dione (575 mg, 1.26 mmol, TFA, Intermediate DB) in a mixture of THF (8 mL) and DMF (2 mL) was added TEA (255 mg, 2.52 mmol). The mixture was stirred at −10° C. for 5 mins. After that AcOH (227 mg, 3.79 mmol) was added to the above solution, then the mixture was stirred at −10° C. for 25 mins. Then NaBH(OAc)$_3$ (534 mg, 2.52 mmol) was added and the mixture was stirred at −10° C. for 3.5 hrs. On completion, the mixture was quenched with H$_2$O (3 mL), then the mixture was concentrated in vacuo. The crude product was purified by reversed phase (0.1% TFA) to give the title compound (187 mg, 27% yield) as a white solid. $^1$H NMR (400 MHz, DMSO-d$_6$) δ 11.09 (s, 1H), 7.06 (d, J=8.0 Hz, 1H), 7.02 (s, 1H), 6.90 (d, J=8.0 Hz, 1H), 6.83-6.74 (m, 1H), 5.40-5.32 (m, 1H), 3.54-3.49 (m, 2H), 3.34 (s, 3H), 3.29-3.26 (m, 2H), 3.21-3.17 (m, 1H), 3.09-3.00 (m, 4H), 2.93-2.82 (m, 2H), 2.73-2.66 (m, 1H), 2.48-2.36 (m, 2H), 2.26-2.18 (m, 1H), 2.17-2.08 (m, 2H), 2.02-1.87 (m, 6H), 1.74-1.60 (m, 2H), 1.37 (s, 9H). LC-MS (ESI$^+$) m/z 570.4 (M+H)$^+$.

Step 2—3-[5-[1-[[3-(2-Aminoethoxy)cyclobutyl]methyl]-4-piperidyl]-3-methyl-2-oxo-benzimidazol-1-yl]piperidine-2,6-dione To a solution of tert-butyl N-[2-[3-[[4-[1-(2,6-dioxo-3-piperidyl)-3-methyl-2-oxo-benzimidazol-5-yl]-1-piperidyl]methyl]cyclobutoxy]ethyl]carbamate (80.0 mg, 140 umol) in DCM (1 mL) was added TFA (308 mg, 2.70 mmol). The mixture was stirred at 25° C. for 0.5 hr. On completion, the mixture was concentrated in vacuo to give the title compound (80.0 mg, 97% yield, TFA) as a yellow oil. LC-MS (ESI$^+$) m/z 470.1 (M+H)$^+$.

3-[3-Methyl-4-[methyl(4-piperidylmethyl)amino]-2-oxo-benzimidazol-1-yl]piperidine-2,6-dione (Intermediate HR)

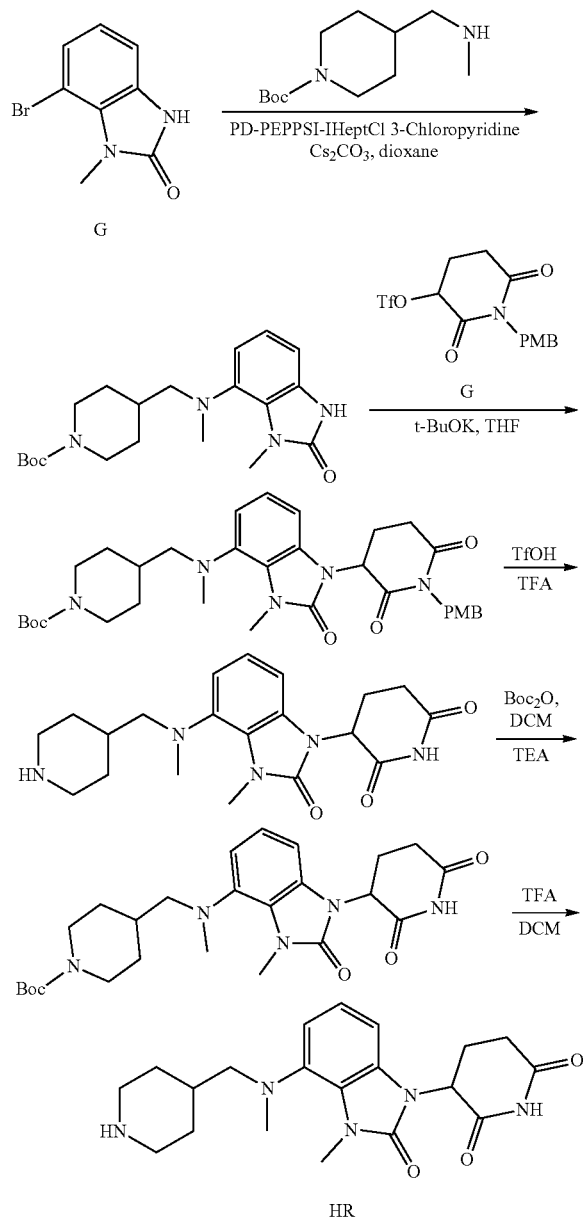

Step 1—Tert-butyl-4-[[methyl-(3-methyl-2-oxo-1H-benzimidazol-4-yl) amino]methyl]piperidine-1-carboxylate A mixture of 4-bromo-3-methyl-1H-benzimidazol-2-one (100 mg, 440 umol, synthesized via Steps 1-3 of Intermediate H), tert-butyl 4-(methylaminomethyl) piperidine-1-carboxylate (100 mg, 440 umol, CAS #138022-02-3), Cs$_2$CO$_3$ (287 mg, 880 umol), 1,3-bis[2,6-bis(1-ethylpropyl)phenyl]-4,5-dichloro-2H-imidazol-1-ium-2-ide;3-chloropyridine;dichloropalladium (38.0 mg, 44.0 umol) and 4A molecular sieves in dioxane (2 mL) was degassed and purged with N$_2$ three times. Then the mixture was stirred at 110° C. for 16 hrs under N$_2$ atmosphere. On completion, the mixture was filtered and concentrated in vacuo to give a residue. The residue was purified by prep-HPLC (column: YMC Triart C18 250*50 mm*7 um; mobile phase: [water (FA)-ACN]; B %: 55%-70%, 26 minutes) to give the title compound (170 mg, 33% yield) as a white solid. $^1$H NMR (400 MHz, DMSO-d$_6$) δ 10.81 (s, 1H), 6.93-6.83 (m, 2H), 6.75-6.68 (m, 1H), 3.90 (d, J=11.2 Hz, 2H), 3.54 (s, 3H), 2.81 (d, J=6.4 Hz, 2H), 2.63 (d, J=3.2 Hz, 1H), 2.57 (s, 3H), 1.65-1.65 (m, 1H), 1.69 (d, J=10.4 Hz, 3H), 1.37 (s, 9H), 1.04-0.95 (m, 2H). LC-MS (ESI$^+$) m/z 374.2 (M+H)$^+$.

Step 2—Tert-butyl 4-[[[1-[1-[(4-methoxyphenyl)methyl]-2,6-dioxo-3-piperidyl]-3-methyl-2-oxo-benzimidazol-4-yl]-methyl-amino]methyl]piperidine-1-carboxylate To a solution of tert-butyl 4-[[methyl-(3-methyl-2-oxo-1H-benzimidazol-4-yl)amino]methyl]piperidine-1-carboxylate (170 mg, 454 umol) in THF (1 mL) was added dropwise t-BuOK (92.0 mg, 817 umol) at –10° C. After addition, the mixture was stirred at this temperature for 30 minutes, and then [1-[(4-methoxyphenyl)methyl]-2,6-dioxo-3-piperidyl] trifluoromethanesulfonate (225 mg, 590 umol, Intermediate G) in THF (1 mL) was added dropwise at –10° C. The resulting mixture was stirred at –10° C. for 12 hours. On completion, the mixture was quenched by NH$_4$Cl (2 mL), diluted with H$_2$O (8 mL), and extracted with EA (2×5 mL). The organic layer was then washed with brine (2×3 mL), dried with anhydrous Na$_2$SO$_4$ and concentrated in vacuo to give the title compound (274 mg, 100% yield) as red oil. LC-MS (ESI$^+$) m/z 606.2 (M+H)$^+$.

Step 3—3-[3-Methyl-4-[methyl (4-piperidylmethyl)amino]-2-oxo-benzimidazol-1-yl]piperidine-2, 6-dione To a solution of tert-butyl 4-[[[1-[1-[(4-methoxyphenyl)methyl]-2,6-dioxo-3-piperidyl]-3-methyl-2-oxo-benzimidazol-4-yl]-methyl-amino]methyl]piperidine-1-carboxylate (270 mg, 446 umol) in TfOH (0.3 mL) was added TFA (3.70 g, 32.4 mmol, 2.4 mL). The mixture was then stirred at 70° C. for 1 hr. On completion, the mixture was concentrated in vacuo to give the title compound (170 mg, 99% yield) as a yellow oil. LC-MS (ESI$^+$) m/z 386.2 (M+H)$^+$.

Step 4—Tert-butyl 4-[[[1-(2, 6-dioxo-3-piperidyl)-3-methyl-2-oxo-benzimidazol-4-yl]-methyl-amino]methyl]piperidine-1-carboxylate To a solution of 3-[3-methyl-4-[methyl(4-piperidylmethyl)amino]-2-oxo-benzimidazol-1-yl] piperidine-2,6-dione (170 mg, 441 umol) in DCM (1 mL) was added TEA (134 mg, 1.32 mmol, 185 uL) and tert-butoxycarbonyl tert-butyl carbonate (106 mg, 485 umol, 112 uL). The mixture was stirred at 25° C. for 3 hrs. On completion, the mixture was concentrated in vacuo to give a residue. The residue was purified by column chromatography (SiO$_2$, Petroleum ether/Ethyl acetate=100/1 to 2/1) to give the title compound (200 mg, 87% yield) as a yellow solid. $^1$H NMR (400 MHz, CDCl$_3$) δ 8.24 (s, 1H), 7.03-6.97 (m, 1H), 6.94-6.88 (m, 1H), 6.58 (d, J=8 Hz, 1H), 5.23 (dd, J=5.2, 12.4 Hz, 1H), 4.13 (d, J=7.2 Hz, 1H), 3.75 (s, 3H), 2.97-2.71 (m, 6H), 2.66 (s, 3H), 2.27-2.19 (m, 1H), 2.05 (s, 1H), 1.75 (d, J=12 Hz, 2H), 1.46 (s, 9H), 1.30-1.24 (m, 2H), 1.17 (s, 2H). LC-MS (ESI$^+$) m/z 486.0 (M+H)$^+$.

Step 5—3-[3-Methyl-4-[methyl(4-piperidylmethyl) amino]-2-oxo-benzimidazol-1-yl]piperidine-2,6-dione To a solution of tert-butyl 4-[[[1-(2,6-dioxo-3-piperidyl)-3-methyl-2-oxo-benzimidazol-4-yl]-methyl-amino]methyl] piperidine-1-carboxylate (90.0 mg, 185 umol) in DCM (0.5 mL) was added TFA (578 mg, 5.06 mmol, 375 uL). The mixture was stirred at 25° C. for 2 hrs. On completion, the mixture was concentrated in vacuo to give the title compound (71 mg, 99% yield) as yellow oil. LC-MS (ESI$^+$) m/z 386.3 (M+H)$^+$.

3-[3-Methyl-4-[methyl-[[1-(4-piperidyl)-4-piperidyl] methyl]amino]-2-oxo-benzimidazol-1-yl] piperidine-2,6-dione (Intermediate HS)

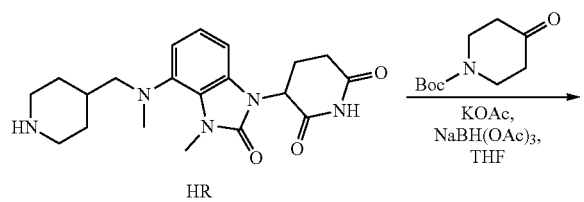

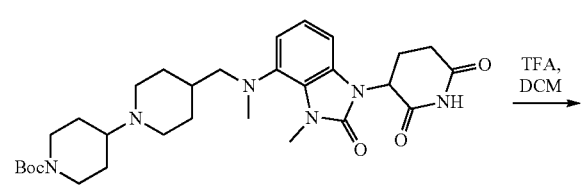

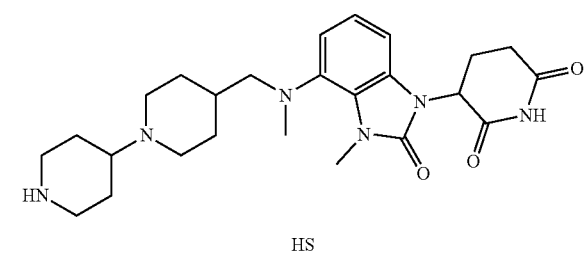

Step 1—Tert-butyl 4-[4-[[[1-(2,6-dioxo-3-piperidyl)-3-methyl-2-oxo-benzimidazol-4-yl]-methylamino]methyl]-1-piperidyl]piperidine-1-carboxylate To a solution of 3-[3-methyl-4-[methyl(4-piperidylmethyl)amino]-2-oxo-benzimidazol-1-yl] piperidine-2,6-dione (71 mg, 184 umol, Intermediate HR) and tert-butyl 4-oxopiperidine-1-carboxylate (367 mg, 1.84 mmol, CAS #79009-07-3) in THF (3 mL) was added KOAc (362 mg, 3.68 mmol) slowly at 0° C. Then NaBH(OAc)$_3$ (390 mg, 1.84 mmol) was added dropwise at 0° C. and the resulting mixture was stirred at 0° C. for 12 hrs. On completion, the mixture was concentrated in vacuo to give a residue. The residue was purified by prep-HPLC (column: Phenomenex luna C18 150*25 mm*10 um; mobile phase: [water (FA)-ACN]; B %: 12%-42%, 10 min) to give the title compound (70.0 mg, 67% yield) as a white solid. $^1$H NMR (400 MHz, CDCl$_3$) δ 8.04 (s, 1H), 7.03-6.98 (m, 1H), 6.90 (d, J=8.0 Hz, 1H), 6.59 (d, J=8.0 Hz, 1H), 5.26-5.18 (m, 1H), 4.33-4.20 (m, 2H), 3.73 (s, 3H), 3.52-3.33 (m, 3H), 3.25-3.18 (m, 1H), 3.00-2.93 (m, 2H), 2.69-2.66 (m, 5H), 2.28-2.22 (m, 1H), 2.15-2.08 (m, 2H), 2.06-1.93 (m, 5H), 1.66-1.58 (m, 6H), 1.45 (s, 9H). LC-MS (ESI$^+$) m/z 569.3 (M+H)$^+$.

Step 2—3-[3-Methyl-4-[methyl-[[1-(4-piperidyl)-4-piperidyl]methyl]amino]-2-oxo-benzimidazol-1-yl] piperidine-2,6-dione To a solution of tert-butyl 4-[4-[[[1-(2,6-dioxo-3-piperidyl)-3-methyl-2-oxo-benzimidazol-4-yl]-methyl-amino] methyl]-1-piperidyl]piperidine-1-carboxylate (30.0 mg, 52.8 umol) in DCM (0.5 mL) was added TFA (770 mg, 6.75 mmol, 0.5 mL). The mixture was stirred at 25° C. for 1 hr. On completion, the mixture was concentrated in vacuo to give the title compound (24 mg, 98% yield) as yellow oil. LC-MS (ESI$^+$) m/z 469.3 (M+H)$^+$.

Tert-butyl 6-(2-oxoethoxy)-2-azaspiro[3.3]heptane-2-carboxylate (Intermediate HT)

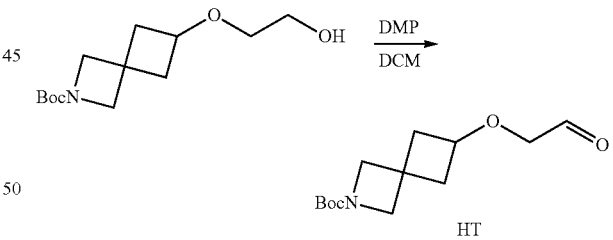

To a solution of tert-butyl 6-(2-hydroxyethoxy)-2-azaspiro [3.3] heptane-2-carboxylate (250 mg, 971 umol, synthesized via Step 1-2 of Intermediate FE) in DCM (3 mL) was added DMP (535 mg, 1.26 mmol). The mixture was stirred at 25° C. for 2 hrs. On completion, the reaction mixture was quenched with H$_2$O (0.1 mL) at 25° C., and then diluted with H$_2$O (5 mL) and extracted with EA (10 mL×3). The combined organic layers were washed with brine (10 mL×2), dried over with Na$_2$SO$_4$, filtered and concentrated under reduced pressure to afford the title compound (248 mg, 99% yield) as colorless oil. $^1$H NMR (400 MHz, DMSO-d$_6$) δ 9.53-9.51 (m, 1H), 4.04-3.98 (m, 1H), 3.76 (d, J=18.6 Hz, 4H), 3.30 (s, 2H), 2.43-2.34 (m, 2H), 2.00-1.91 (m, 2H), 1.33 (s, 9H).

3-[5-[1-[2-(2-Azaspiro[3.3]heptan-6-yloxy)ethyl]-4-piperidyl]-3-methyl-2-oxo-benzimidazol-1-yl]piperidine-2,6-dione (Intermediate HU)

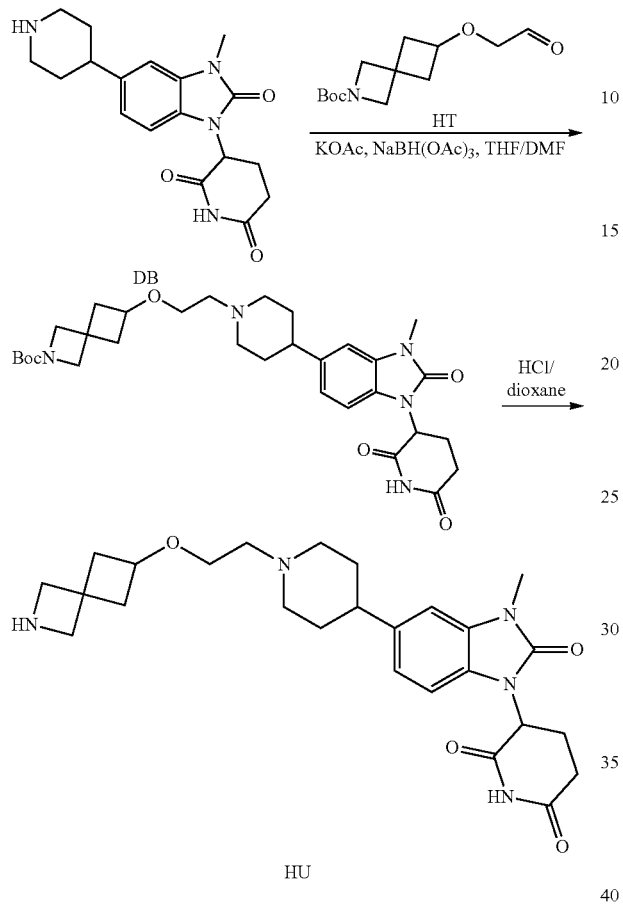

Step 1—Tert-butyl 6-[2-[4-[1-(2,6-dioxo-3-piperidyl)-3-methyl-2-oxo-benzimidazol-5-yl]-1-piperidyl]ethoxy]-2-azaspiro[3.3]heptane-2-carboxylate To a solution of tert-butyl 6-(2-oxoethoxy)-2-azaspiro[3.3]heptane-2-carboxylate (240 mg, 940. μmol, Intermediate HT), 3-[3-methyl-2-oxo-5-(4-piperidyl)benzimidazol-1-yl]piperidine-2,6-dione (284 mg, 752 umol, HCl, Intermediate DB) in THF (0.5 mL), DMF (0.5 mL) was added KOAc (923 mg, 9.40 mmol) and NaBH(OAc)$_3$ (398 mg, 1.88 mmol). The mixture was stirred at 0° C. for 2 hrs. On completion, the reaction mixture was concentrated under reduced pressure and purified by prep-HPLC (column: Phenomenex luna C18 150*25 mm*10 um; mobile phase: [water(FA)-ACN]; B %: 23%-53%, 9 min) to give the title compound (100 mg, 12% yield) as a white solid LC-MS (ESI$^+$) m/z 583.0 (M+H)$^+$.

Step 2—3-[5-[1-[2-(2-Azaspiro[3.3]heptan-6-yloxy)ethyl]-4-piperidyl]-3-methyl-2-oxo-benzimidazol-1-yl]piperidine-2,6-dione To a solution of tert-butyl 6-[2-[4-[1-(2,6-dioxo-3-piperidyl)-3-methyl-2-oxo-benzimidazol-5-yl]-1-piperidyl]ethoxy]-2-azaspiro[3.3]heptane-2-carboxylate (80 mg, 137 umol) in DCM (0.4 mL) was added TFA (616 mg, 5.40 mmol). The mixture was stirred at 25° C. for 0.2 hr. On completion, the reaction mixture was concentrated under reduced pressure to give the title compound (65 mg, 79% yield, TFA) as a yellow oil. LC-MS (ESI$^+$) m/z 482.7 (M+H)$^+$.

1-[4-[4-(2-Aminoethyl)-1-piperidyl]phenyl]hexahydropyrimidine-2,4-dione (Intermediate HV)

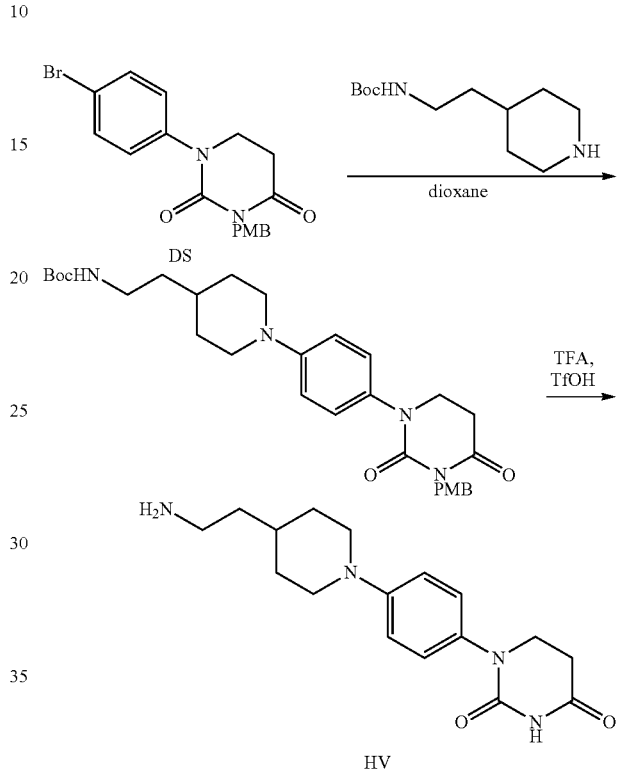

Step 1—Tert-butyl N-[2-[1-[4-[3-[(4-methoxyphenyl)methyl]-2,4-dioxo-hexahydropyrimidin-1-yl]phenyl]-4-piperidyl]ethyl]carbamate A mixture of 1-(4-bromophenyl)-3-[(4-methoxyphenyl)methyl]hexahydropyrimidine-2,4-dione (500 mg, 1.28 mmol, Intermediate DS), tert-butyl N-[2-(4-piperidyl)ethyl]carbamate (293 mg, 1.28 mmol, CAS #165528-81-4), 1,3-bis [2,6-bis (1-ethylpropyl)phenyl]-4,5-dichloro-2H-imidazol-1-ium-2-ide;3-chloropyridine;dichloropalladium (165 mg, 192 umol, CAS #1435347-24-2), and Cs$_2$CO$_3$ (837 mg, 2.57 mmol) in dioxane (5 mL) was degassed and purged with N$_2$ three times. Then the mixture was stirred at 100° C. for 16 hrs under N$_2$ atmosphere. On completion, the reaction mixture was extracted with ethyl acetate (3×10 mL). The combined organic layers were washed with brine (5 mL), dried over anhydrous sodium sulfate, filtered and the filtrate was concentrated in vacuo. The crude product was purified by reversed-phase HPLC (0.1% FA condition) to give the title compound (200 mg, 29% yield) as a faint yellow solid. LC-MS (ESI$^+$) m/z 537.4 (M+H)$^+$.

Step 2—1-[4-[4-(2-Aminoethyl)-1-piperidyl]phenyl] hexahydropyrimidine-2,4-dione To a solution of tert-butyl N-[2-[1-[4-[3-[(4-methoxyphenyl)methyl]-2,4-dioxo-hexahydropyrimidin-1-yl] phenyl]-

4-piperidyl]ethyl]carbamate (50 mg, 93.1 umol) in TFA (0.8 mL) and TfOH (0.1 mL). The mixture was stirred at 70° C. for 1 hr. On completion, the mixture was concentrated in vacuo and DMSO (1 mL) and DIEA was added until the pH=8. The mixture was then diluted with water and lyophilized to give the title compound (30 mg, 17% yield) as a faint yellow solid. LC-MS (ESI$^+$) m/z 317.0 (M+H)$^+$.

Spiro[2.4]heptan-7-amine (Intermediate HW)

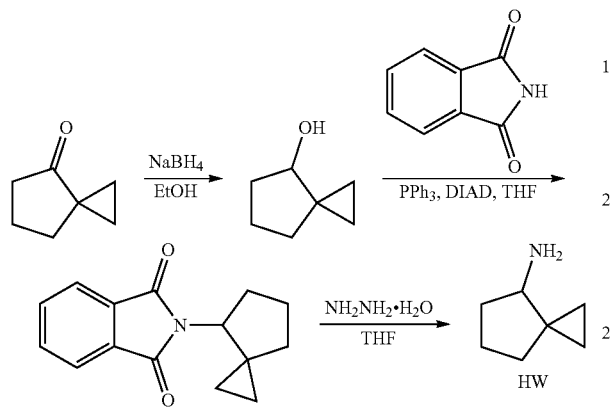

Step 1-Spiro[2.4]heptan-7-ol

To a solution of spiro[2.4]heptan-7-one (4.50 g, 40.8 mmol, CAS #5771-32-4) in EtOH (40 mL) was added NaBH$_4$ (3.91 g, 103 mmol) at 0° C. The reaction was then stirred at 25° C. for 2 hrs. On completion, the reaction was quenched with NH$_4$Cl (10 mL). The mixture was diluted with EA (400 mL), washed with water (200 mL×3), dried over Na$_2$SO$_4$ and filtered. The filtrate was concentrated in vacuo to give the title compound (2.91 g, 63% yield) as yellow oil. $^1$H NMR (400 MHz, DMSO-d$_6$) δ 4.28 (d, J=4.4 Hz, 1H), 3.51-3.45 (m, 1H), 1.93-1.83 (m, 1H), 1.81-1.70 (m, 2H), 1.66-1.49 (m, 2H), 1.43-1.33 (m, 1H), 0.77-0.69 (m, 1H), 0.43-0.29 (m, 3H).

Step 2—2-Spiro[2.4]heptan-7-ylisoindoline-1,3-dione

To a solution of spiro[2.4]heptan-7-ol (2.40 g, 21.4 mmol), isoindoline-1,3-dione (3.78 g, 25.6 mmol, CAS #85-41-6), and PPh$_3$ (8.42 g, 32.0 mmol) in THF (60 mL) was added DIAD (6.49 g, 32.0 mmol) at 25° C. under N$_2$. The reaction was stirred at 60° C. for 16 hrs. On completion, the reaction was added ice water (100 mL). The mixture was extracted with EA (200 mL) and concentrated in vacuo. The residue was purified by column chromatography (SiO$_2$, Petroleum ether/Ethyl acetate=20/1 to 10/1) to give the title compound (1.7 g, 32% yield) as yellow solid. $^1$H NMR (400 MHz, DMSO-d$_6$) δ 7.83 (s, 4H), 4.32 (t, J=8.0 Hz, 1H), 2.26-2.10 (m, 3H), 2.02-1.93 (m, 1H), 1.80-1.67 (m, 1H), 1.49-1.34 (m, 1H), 0.63-0.54 (m, 1H), 0.51-0.41 (m, 2H), 0.32-0.24 (m, 1H).

Step 3-Spiro[2.4]heptan-7-amine

To a solution of 2-spiro[2.4]heptan-7-ylisoindoline-1,3-dione (1.4 g, 5.8 mmol) in THF (30 mL) was added NH$_2$NH$_2$H$_2$O (1.66 g, 33.1 mmol). The reaction was stirred at 60° C. for 3 hrs. On completion, the reaction was diluted with THF (30 mL) and filtered. The filtrate was concentrated in vacuo to give the title compound (550 mg, 85% yield) as yellow oil. $^1$H NMR (400 MHz, CDCl$_3$) δ 2.84 (t, J=5.6 Hz, 1H), 2.13-2.02 (m, 1H), 1.88-1.78 (m, 2H), 1.76-1.64 (m, 1H), 1.48-1.42 (m, 2H), 1.28 (s, 2H), 0.64-0.57 (m, 1H), 0.49-0.29 (m, 3H).

4-[(6-chloro-7-oxo-8-spiro[2.4]heptan-7-yl-pyrido[2,3-d]pyrimidin-2-yl)amino]-3-methyl-benzenesulfonyl chloride (Intermediate HX)

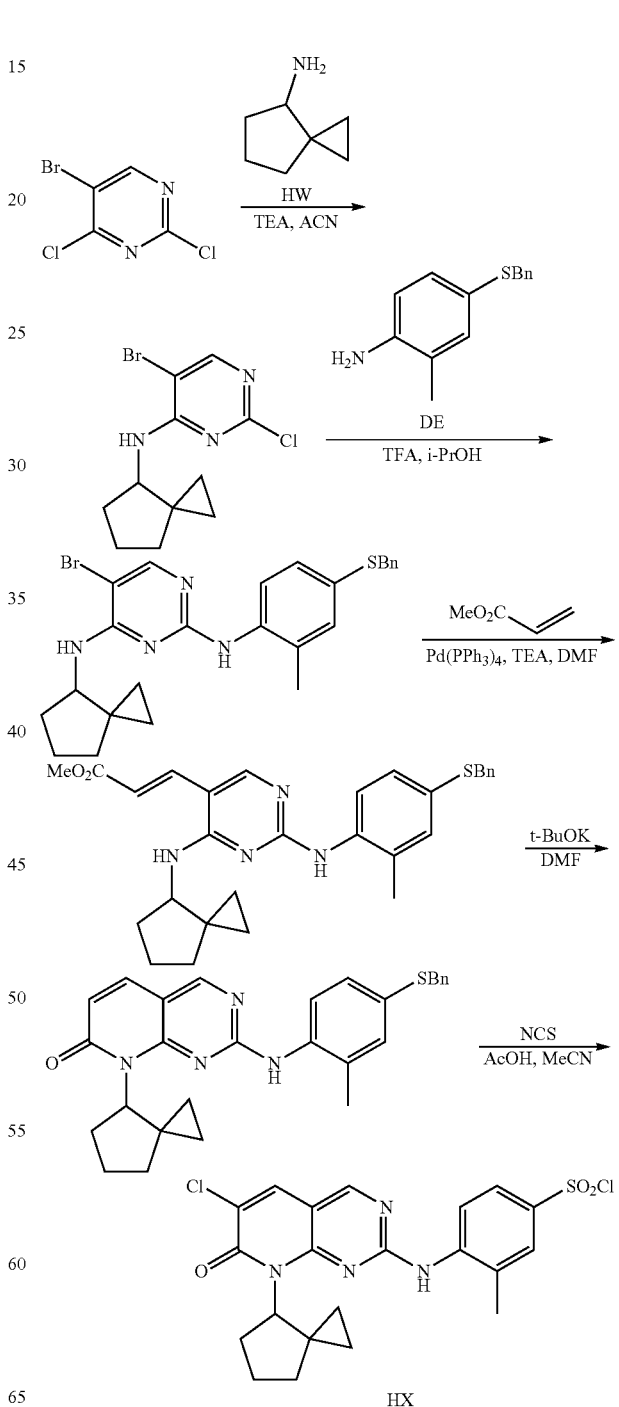

HX

Step 1—5-Bromo-2-chloro-N-spiro[2.4]heptan-7-ylpyrimidin-4-amine

To a solution of 5-bromo-2,4-dichloro-pyrimidine (983 mg, 4.32 mmol, CAS #36082-50-5) and TEA (567 mg, 5.61 mmol) in ACN (15 mL) was added spiro[2.4]heptan-7-amine (480 mg, 4.32 mmol, Intermediate HW) at 0° C. The reaction was then stirred at 25° C. for 16 hrs. On completion, the reaction was diluted with EA (100 mL). The organic layer was washed with water (50 mL×2), dried over $Na_2SO_4$ and filtered. The filtrate was concentrated in vacuo. The residue was purified by column chromatography ($SiO_2$, Petroleum ether/Ethyl acetate=1/0 to 30/1) to give the title compound (505 mg, 38% yield) as yellow oil. LC-MS (ESI$^+$) m/z 303.7 (M+H)$^+$.

Step 2—N2-(4-benzylsulfanyl-2-methyl-phenyl)-5-bromo-N4-spiro[2.4]heptan-7-yl-pyrimidine-2,4-diamine To a solution of 5-bromo-2-chloro-N-spiro[2.4]heptan-7-yl-pyrimidin-4-amine (450 mg, 1.49 mmol) and 4-benzylsulfanyl-2-methyl-aniline (375 mg, 1.64 mmol, Intermediate DE) in IPA (10 mL) was added TFA (3.39 g, 29.7 mmol) under $N_2$. The reaction was stirred at 80° C. for 16 hrs under $N_2$. On completion, the reaction was diluted with EA (100 mL). The organic layer was washed with water (70 mL) and concentrated in vacuo. The residue was purified by reverse phase (0.1% FA condition) to give the title compound (400 mg, 54% yield) as red solid. LC-MS (ESI$^+$) m/z 496.9 (M+H)$^+$.

Step 3—Methyl (E)-3-[2-(4-benzylsulfanyl-2-methyl-anilino)-4-(spiro[2.4]heptan-7-ylamino)pyrimidin-5-yl]prop-2-enoate To a mixture of N2-(4-benzylsulfanyl-2-methyl-phenyl)-5-bromo-N4-spiro[2.4]heptan-7-yl-pyrimidine-2,4-diamine (340 mg, 686 umol), TEA (208 mg, 2.06 mmol) and Pd(PPh$_3$)$_4$ (158 mg, 137 umol) in DMF (3.5 mL) was added methyl prop-2-enoate (0.54 g, 6.27 mmol). The reaction was then stirred at 90° C. for 16 hrs under $N_2$. On completion, the reaction was diluted with water (50 mL) and extracted with EA (70 mL×2). The organic layer was washed with water (50 mL×3), dried over $Na_2SO_4$ and filtered. The filtrate was concentrated in vacuo. The residue was purified by column chromatography ($SiO_2$, Petroleum ether/Ethyl acetate=10/1 to 3/1) to give the title compound (200 mg, 58% yield) as brown oil. LC-MS (ESI$^+$) m/z 501.3 (M+H)$^+$.

Step 4—2-(4-Benzylsulfanyl-2-methyl-anilino)-8-spiro[2.4]heptan-7-yl-pyrido[2,3-d]pyrimidin-7-one To a solution of methyl (E)-3-[2-(4-benzylsulfanyl-2-methyl-anilino)-4-(spiro[2.4]heptan-7-ylamino) pyrimidin-5-yl]prop-2-enoate (180 mg, 359 umol) in DMF (3 mL) was added t-BuOK (121 mg, 1.08 mmol) at 25° C. and stirred for 0.5 hr. Then, the reaction was stirred at 120° C. for 2 hrs. On completion, the reaction was diluted with EA (40 mL). The organic layer was washed with water (30 mL×3), dried over $Na_2SO_4$ and filtered. The filtrate was concentrated in vacuo. The residue was purified by column chromatography ($SiO_2$, Petroleum ether/Ethyl acetate=5/1 to 1/1) to give the title compound (80 mg, 47% yield) as yellow oil. LC-MS (ESI$^+$) m/z 469.6 (M+H)$^+$.

Step 5—4-[(6-Chloro-7-oxo-8-spiro[2.4]heptan-7-yl-pyrido[2,3-d]pyrimidin-2-yl)amino]-3-methyl-benzenesulfonyl chloride To a solution of 2-(4-benzylsulfanyl-2-methyl-anilino)-8-spiro[2.4]heptan-7-yl-pyrido[2,3-d] pyrimidin-7-one (80.0 mg, 170 umol) in HOAc (0.1 mL) and ACN (1 mL) was added NCS (91.1 mg, 682 umol) and $H_2O$ (30.7 ug, 1.71 umol) in the dark. The reaction was stirred at 25° C. for 0.5 hr in the dark. On completion, the reaction was diluted with EA (50 mL). The organic layer washed with water (50 mL), dried over $Na_2SO_4$ and filtered. The filtrate was concentrated in vacuo. The residue was purified by column chromatography ($SiO_2$, Petroleum ether/Ethyl acetate=5/1 to 2/1) to give the title compound (60 mg, 73% yield) as yellow solid. LC-MS (ESI$^+$) m/z 479.0 (M+H)$^+$.

Tert-butyl 4-(4-piperidyloxymethyl)piperidine-1-carboxylate (Intermediate HY)

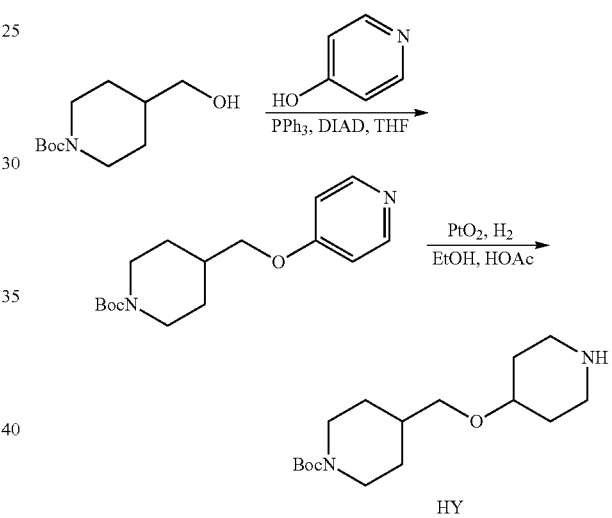

Step 1—Tert-butyl 4-(4-pyridyloxymethyl)piperidine-1-carboxylate

A mixture of tert-butyl 4-(hydroxymethyl)piperidine-1-carboxylate (10 g, 46.5 mmol, CAS #123855-51-6), pyridin-4-ol (4.42 g, 46.5 mmol, CAS #626-64-2), PPh$_3$ (25.0 g, 93.0 mmol), DIAD (19.0 g, 93.0 mmol, 18.0 mL) in THF (50 mL) was degassed and purged with $N_2$ three times, and then the mixture was stirred at 25° C. for 16 hrs under $N_2$ atmosphere. On completion, the mixture was diluted with $H_2O$ (50 mL) and extracted with DCM (3×100 mL). The combined organic layers were washed with brine (2×30 mL), dried over anhydrous $Na_2SO_4$, filtered and concentrated in vacuo to give a residue. The crude product was purified by reversed-phase HPLC (0.1% FA condition) to give the title compound (4.9 g, 37% yield) as a white solid. $^1$H NMR (400 MHz, CDCl$_3$) δ 8.44 (d, J=6.0 Hz, 2H), 6.82 (d, J=6.0 Hz, 2H), 4.18 (d, J=4.0 Hz, 2H), 3.87 (d, J=6.4 Hz, 2H), 2.76 (t, J=12.4 Hz, 2H), 2.09-1.90 (m, 1H), 1.82 (d, J=12.8 Hz, 2H), 1.48 (s, 9H), 1.35-1.23 (m, 2H). LC-MS (ESI$^+$) m/z 293.3 (M+H)$^+$.

Step 2—Tert-butyl 4-(4-piperidyloxymethyl)piperidine-1-carboxylate

A mixture of tert-butyl 4-(4-pyridyloxymethyl)piperidine-1-carboxylate (2 g, 6.84 mmol), PtO$_2$ (1.55 g, 6.84 mmol), HOAc (8.40 g, 140 mmol, 8.00 mL) in EtOH (20 mL) was degassed and purged with H$_2$ three times. Then the mixture was stirred at 40° C. for 16 hrs under H$_2$ atmosphere. On completion, the mixture was filtered and concentrated in vacuo to give the title compound (2.00 g, 82% yield, HOAc salt) as white oil. $^1$H NMR (400 MHz, DMSO-d$_6$) δ 5.35-4.85 (m, 1H), 3.92 (d, J=12.0 Hz, 2H), 3.41-3.32 (m, 1H), 3.27-3.20 (m, 2H), 3.00-2.87 (m, 2H), 2.66 (t, J=9.2 Hz, 3H), 2.34-2.19 (m, 1H), 1.88-1.76 (m, 1H), 1.63 (d, J=12.0 Hz, 3H), 1.49-1.41 (m, 2H), 1.38 (s, 9H), 1.09-0.93 (m, 3H). LC-MS (ESI$^+$) m/z 299.1 (M+H)$^+$.

3-[3-Methyl-2-oxo-4-[4-(4-piperidylmethoxy)-1-piperidyl]benzimidazol-1-yl]piperidine-2,6-dione (Intermediate HZ)

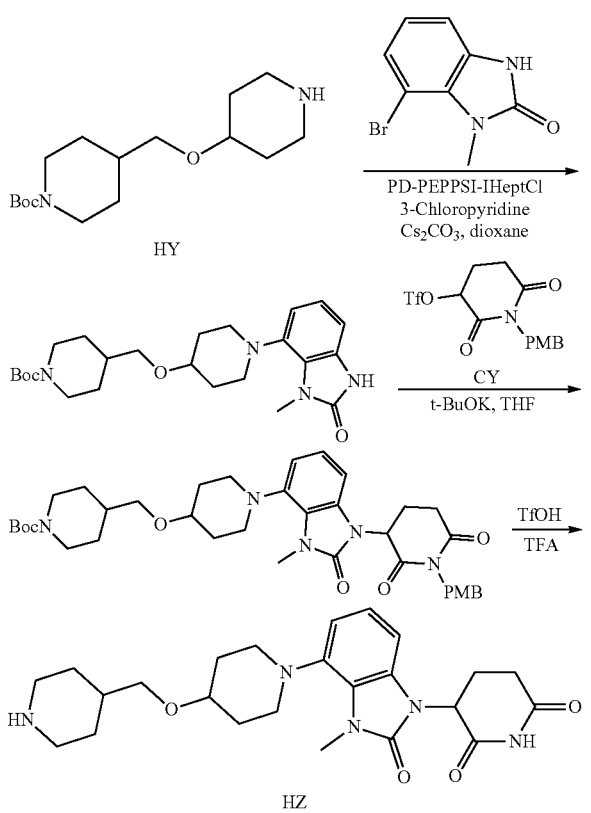

Step 1—Tert-butyl 4-[[1-(3-methyl-2-oxo-1H-benzimidazol-4-yl)-4-piperidyl]oxymethyl]piperidine-1-carboxylate A mixture of tert-butyl 4-(4-piperidyloxymethyl)piperidine-1-carboxylate (50 mg, 168 umol, Intermediate HY), 4-bromo-3-methyl-1H-benzimidazol-2-one (150 mg, 661 umol, synthesized via Steps 1-3 of Intermediate H), Cs$_2$CO$_3$ (1.35 g, 4.13 mmol), 1,3-bis[2,6-bis(1-ethylpropyl)phenyl]-4,5-dichloro-2H-imidazol-1-ium-2-ide;3-chloropyridine;dichloropalladium (71.0 mg, 83.0 umol) and 4A molecular sieves in dioxane (1 mL) was degassed and purged with N$_2$ three times. Then the mixture was stirred at 100° C. for 12 hrs under N$_2$ atmosphere. On completion, the mixture was filtered and concentrated in vacuo to give a residue. The residue was purified by prep-HPLC (column: Phenomenex Luna C18 200*40 mm*10 um; mobile phase: [water (FA)-ACN]; B %: 65%-95%, 10 minutes) to give the title compound (70 mg, 9% yield) as a white solid. LC-MS (ESI$^+$) m/z 445.3 (M+H)$^+$.

Step 2—Tert-butyl 4-[[1-[1-[1-[(4-methoxyphenyl)methyl]-2,6-dioxo-3-piperidyl]-3-methyl-2-oxo-benzimidazol-4-yl]-4-piperidyl]oxymethyl]piperidine-1-carboxylate To a solution of tert-butyl 4-[[1-(3-methyl-2-oxo-1H-benzimidazol-4-yl)-4-piperidyl]oxymethyl] piperidine-1-carboxylate (100 mg, 225 umol) in THF (1 mL) was added t-BuOK (46 mg, 405 umol) and 1-[(4-methoxyphenyl)methyl]-2,6-dioxo-3-piperidyl]trifluoromethanesulfonate (112 mg, 293 umol, Intermediate CY). The mixture was stirred at −10° C. for 6 hrs. On completion, the mixture was quenched with NH$_4$Cl (1 mL), diluted with H$_2$O (8 mL), and extracted with EA (2×5 mL). The organic layer was then washed with brine (2×3 mL), dried with anhydrous Na$_2$SO$_4$ and concentrated in vacuo to give a residue. The residue was purified by prep-TLC (SiO$_2$, Petroleum ether:Ethyl acetate=0:1) to give the title compound (130 mg, 77% yield) as red oil. $^1$H NMR (400 MHz, DMSO-d$_6$) δ 7.21 (d, J=8.8 Hz, 2H), 6.95-6.88 (m, 2H), 6.85 (d, J=8.8 Hz, 2H), 6.75 (d, J=5.6 Hz, 1H), 5.53-5.46 (m, 1H), 4.86-4.70 (m, 2H), 3.98-3.89 (m, 2H), 3.72 (s, 3H), 3.71 (d, J=1.6 Hz, 1H), 3.62 (s, 3H), 3.12-3.00 (m, 2H), 2.84-2.69 (m, 5H), 2.06-1.98 (m, 3H), 1.88-1.81 (m, 1H), 1.74-1.60 (m, 4H), 1.59-1.51 (m, 1H), 1.39 (s, 9H), 1.24 (s, 3H), 1.09-0.99 (m, 2H). LC-MS (ESI$^+$) m/z 676.4 (M+H)$^+$.

Step 3—3-[3-Methyl-2-oxo-4-[4-(4-piperidylmethoxy)-1-piperidyl]benzimidazol-1-yl]piperidine-2,6-dione To a solution of tert-butyl 4-[[1-[1-[1-[(4-methoxyphenyl)methyl]-2,6-dioxo-3-piperidyl]-3-methyl-2-oxo-benzimidazol-4-yl]-4-piperidyl]oxymethyl]piperidine-1-carboxylate (30 mg, 44.4 umol) in TFA (0.8 mL) was added TfOH (170 mg, 1.13 mmol, 100 uL). The mixture was stirred at 70° C. for 2 hrs. On completion, the mixture was concentrated in vacuo to give a residue. The residue was purified by prep-TLC (SiO$_2$, PE:EA=0:1) to give the title compound (20 mg, 97% yield) as a yellow oil. LC-MS (ESI$^+$) m/z 456.1 (M+H)$^+$.

Tert-butyl N-[2-(4-formylcyclohexoxy)ethyl]-N-methyl-carbamate (Intermediate IA)

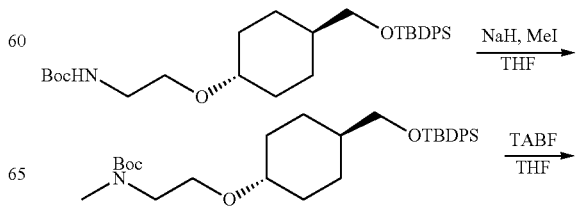

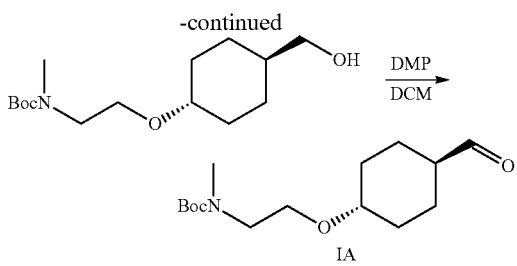

Step 1—Tert-butyl N-[2-[4-[[tert-butyl(diphenyl) silyl]oxymethyl]cyclohexoxy]ethyl]-N-methyl-carbamate To a solution of tert-butyl N-[2-[4-[[tert-butyl(diphenyl) silyl]oxymethyl]cyclohexoxy]ethyl]carbamate (400 mg, 781 umol, synthesized via Steps 1-6 of Intermediate DP) in THF (4 mL) was added NaH (93.8 mg, 2.34 mmol, 60% dispersion in mineral oil) and MeI (389 uL, 6.25 mmol) at 0° C., then the mixture was stirred at 25° C. for 10 hrs. On completion, the mixture was quenched with sat. NH₄Cl (3 mL), then washed with water (50 mL) and extracted with EA (50 mL×3). The combined organic layers were dried over anhydrous Na₂SO₄, and concentrated in vacuo to give the residue. The residue was purified by column chromatography (SiO₂, PE:EA=100:3 to 20:1) to give the title compound (300 mg, 73% yield) as a yellow oil. ¹H NMR (400 MHz, CDCl₃) δ 7.67-7.65 (m, 4H), 7.47-7.33 (m, 6H), 3.57-3.56 (m, 2H), 3.47-3.45 (m, 2H), 3.37 (s, 2H), 3.19-3.14 (m, 1H), 2.93 (s, 3H), 2.09-2.00 (m, 2H), 1.85-1.82 (m, 2H), 1.58-1.51 (m, 1H), 1.47 (s, 9H), 1.24-1.16 (m, 2H), 1.06 (s, 9H), 1.03-0.94 (m, 2H).

Step 2—Tert-butyl N-[2-[4-(hydroxymethyl)cyclohexoxy]ethyl]-N-methyl-carbamate To a solution of tert-butyl N-[2-[4-[[tert-butyl(diphenyl) silyl]oxymethyl]cyclohexoxy]ethyl]-N-methyl-carbamate (300 mg, 570 umol) in THF (3 mL) was added TBAF (1 M, 855 uL), then the mixture was stirred at 25° C. for 2 hrs. On completion, the mixture was concentrated in vacuo to give a residue. The residue was purified by column chromatography (SiO₂, PE:EA=20:1 to 2:1) to give the title compound (150 mg, 91% yield) as a yellow oil. ¹H NMR (400 MHz, CDCl₃) δ 3.58 (s, 2H), 3.46-3.45 (m, 2H), 3.36-3.35 (m, 2H), 3.25-3.15 (m, 1H), 2.92 (s, 3H), 2.07-2.04 (m, 2H), 1.85-1.82 (m, 2H), 1.64-1.53 (m, 1H), 1.46 (s, 9H), 1.27-1.17 (m, 2H), 1.05-0.91 (m, 2H).

Step 3—Tert-butyl N-[2-(4-formylcyclohexoxy) ethyl]-N-methyl-carbamate

To a solution of tert-butyl N-[2-[4-(hydroxymethyl)cyclohexoxy]ethyl]-N-methyl-carbamate (50.0 mg, 174 umol) in DCM (1 mL) was added DMP (110 mg, 261 umol) at 0° C., then the mixture was stirred at 25° C. for 2 hrs. On completion, the mixture was quenched with sodium thiosulfate pentahydrate (5 mL) and NaHCO₃ (5 mL), then extracted with DCM (10 mL×3). The combined organic layers were dried over anhydrous Na₂SO₄, then concentrated in vacuo to give the title compound (30.0 mg, 60% yield) as a yellow oil.

3-[3-Methyl-5-[1-[[4-[2-(methylamino)ethoxy]cyclohexyl]methyl]-4-piperidyl]-2-oxo-benzimidazol-1-yl]piperidine-2,6-dione (Intermediate IB)

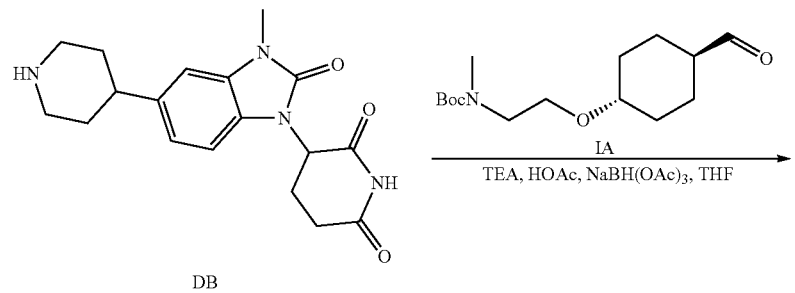

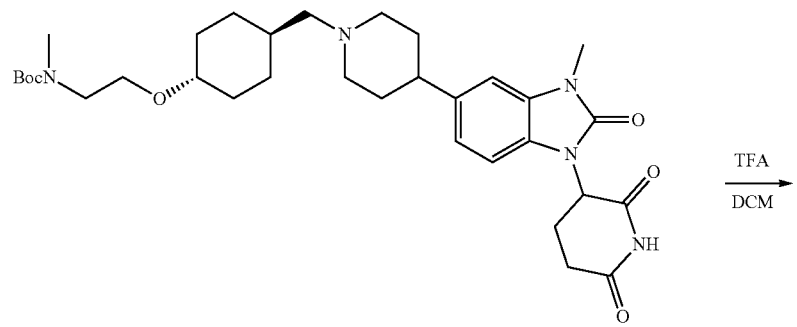

-continued

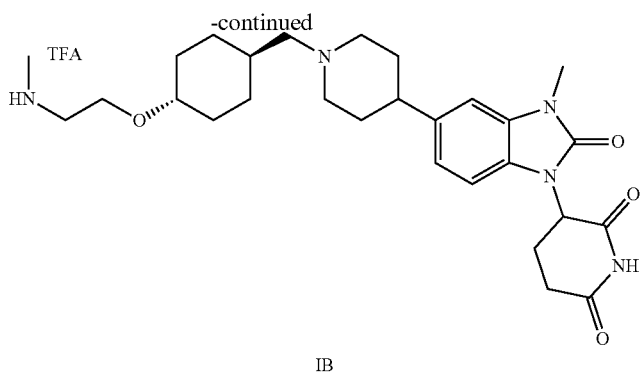

IB

Step 1—Tert-butyl N-[2-[4-[[4-[1-(2,6-dioxo-3-piperidyl)-3-methyl-2-oxo-benzimidazol-5-yl]-1-piperidyl]methyl]cyclohexoxy]ethyl]-N-methyl-carbamate To a solution of 3-[3-methyl-2-oxo-5-(4-piperidyl)benzimidazol-1-yl]piperidine-2,6-dione (38.4 mg, 84.1 umol, TFA, Intermediate DB) in THF (1 mL) was added TEA (14.6 uL, 105 umol). Then tert-butyl N-[2-(4-formylcyclohexoxy)ethyl]-N-methyl-carbamate (30.0 mg, 105 umol, Intermediate IA) and HOAc (6.01 uL, 105 umol) were added, and the mixture was stirred at −10° C. for 0.5 hr. Next, NaBH(OAc)$_3$ (33.4 mg, 158 umol) was added, and the mixture was stirred at −10° C. for 1.5 hrs. On completion, the mixture was concentrated in vacuo to give the residue. The residue was purified by prep-HPLC (column: Phenomenex luna C18 150*25 mm*10 um; mobile phase: [water(FA)-ACN]; B %: 15%-45%, 8 min) to give the title compound (10.0 mg, 16% yield) as a colorless gum. LC-MS (ESI$^+$) m/z 612.4 (M+H)$^+$.

Step 2—3-[3-Methyl-5-[1-[[4-[2-(methylamino)ethoxy]cyclohexyl]methyl]-4-piperidyl]-2-oxo-benzimidazol-1-yl]piperidine-2,6-dione To a solution of tert-butyl N-[2-[4-[[4-[1-(2,6-dioxo-3-piperidyl)-3-methyl-2-oxo-benzimidazol-5-yl]-1-piperidyl]methyl]cyclohexoxy]ethyl]-N-methyl-carbamate (10.0 mg, 16.3 umol) in DCM (0.5 mL) was added TFA (0.2 mL, 2.70 mmol), then the mixture was stirred 25° C. for 1 hr. On completion, the mixture was concentrated in vacuo to give the title compound (10.0 mg, 97% yield, TFA) as a colorless oil. LC-MS (ESI$^+$) m/z 512.2 (M+H)$^+$.

Tert-butyl N-[5-[(2-chloroacetyl)amino]pentyl]carbamate (Intermediate IC)

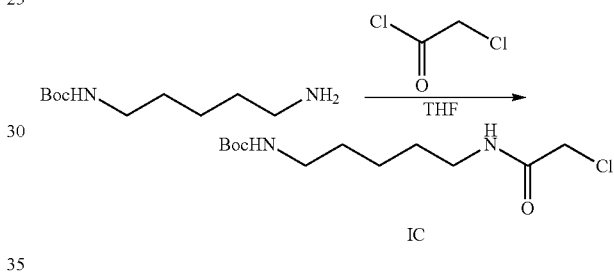

To a solution of tert-butyl N-(5-aminopentyl)carbamate (500 mg, 2.47 mmol, 514 ul, CAS #51644-96-3) in THF (5 mL) was added 2-chloroacetyl chloride (418 mg, 3.71 mmol, 29.0 uL, CAS #79-04-9) and mixture was stirred at 25° C. for 1 hour. On completion, the mixture was concentrated in vacuo to give the title compound (500 mg, 72% yield) as a white solid. LC-MS (ESI$^+$) m/z 178.9 (M+H)$^+$.

N-(5-aminopentyl)-2-[4-(2,6-dioxo-3-piperidyl)phenoxy]acetamide (Intermediate ID)

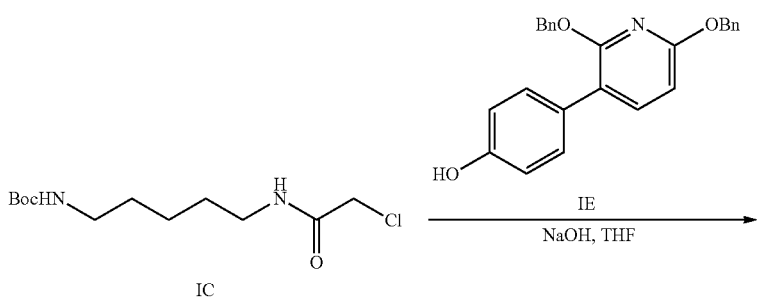

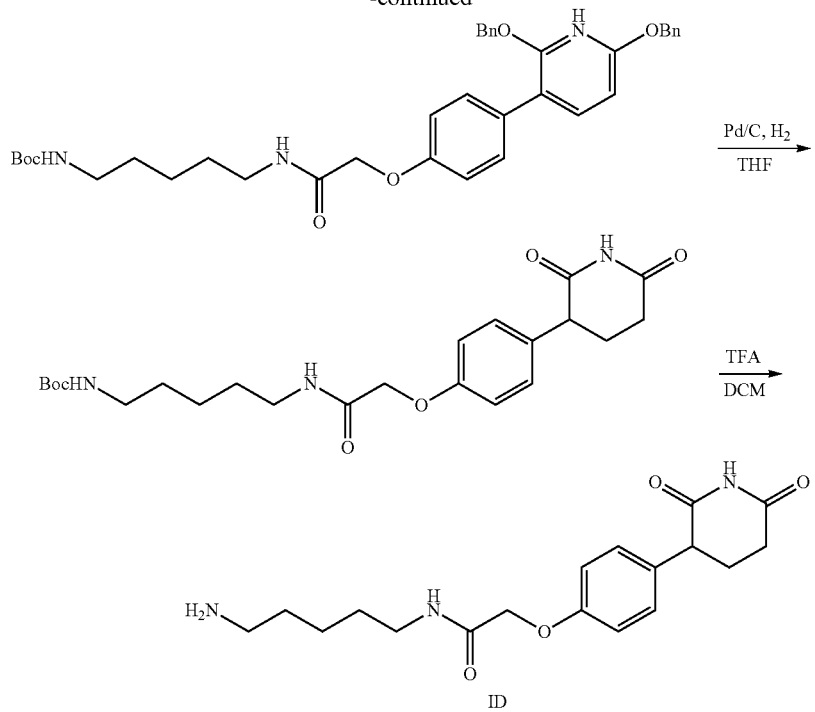

Step 1—Tert-butyl N-[5-[[2-[4-(2,6-dibenzyloxy-3-pyridyl)phenoxy]acetyl]amino]pentyl]carbamate To a solution of tert-butyl N-[5-[(2-chloroacetyl)amino]pentyl]carbamate (500 mg, 1.79 mmol, Intermediate IC) and 4-(2,6-dibenzyloxy-3-pyridyl)phenol (206 mg, 538 umol, Intermediate IE) in THF (5 mL) was added NaOH (322 mg, 8.07 mmol). The mixture was then stirred at 25° C. for 1 hr. On completion, the mixture was diluted with $H_2O$ (0.5 mL), then concentrated in vacuo to give the title compound (183 mg, 16% yield) as a yellow solid. $^1$H NMR (400 MHz, DMSO-$d_6$) δ 8.05 (t, J=5.6 Hz, 1H), 7.70 (d, J=8.0 Hz, 1H), 7.50-7.29 (m, 12H), 6.97 (d, J=8.4 Hz, 2H), 6.79-6.71 (m, 1H), 6.53 (d, J=8.0 Hz, 1H), 5.38 (d, J=12.8 Hz, 4H), 4.47 (s, 2H), 3.13-3.08 (m, 2H), 2.93-2.83 (m, 4H), 2.07 (s, 2H), 1.36 (s, 9H), 1.25-1.19 (m, 2H). LC-MS (ESI$^+$) m/z 626.3 (M+H)$^+$.

Step 2—Tert-butyl N-[5-[[2-[4-(2,6-dioxo-3-piperidyl)phenoxy]acetyl]amino]pentyl]carbamate To a solution of tert-butyl N-[5-[[2-[4-(2,6-dibenzyloxy-3-pyridyl)phenoxy]acetyl]amino]pentyl] carbamate (173 mg, 276 umol) in THF (2.00 mL) was added Pd/C (2.00 mg, 2.76 umol, 10 wt %). The mixture was then stirred at 25° C. for 1 hr under $H_2$. On completion, the mixture was filtered and the filtrate was concentrated in vacuo. The mixture was purified by reversed phase (0.1% FA) to give the title compound (48.0 mg, 38% yield) as a white solid. LC-MS (ESI$^+$) m/z 347.9 (M-100)$^+$.

Step 3—N-(5-aminopentyl)-2-[4-(2,6-dioxo-3-piperidyl)phenoxy]acetamide

To a solution of tert-butyl N-[5-[[2-[4-(2,6-dioxo-3-piperidyl)phenoxy]acetyl]amino]pentyl]carbamate (48.0 mg, 107 umol) in TFA (1 mL) and DCM (2 mL). The mixture was stirred at 25° C. for 1 hr. On completion, the mixture was concentrated in vacuo to give the title compound (37.0 mg, 74% yield, TFA) as a colorless oily liquid. LC-MS (ESI$^+$) m/z 347.9 (M+H)$^+$.

4-(2,6-Bis(benzyloxy)pyridin-3-yl)phenol (Intermediate IE)

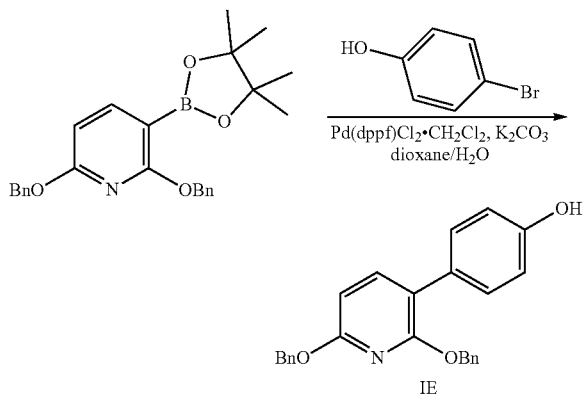

A mixture of 2,6-bis(benzyloxy)-3-(4,4,5,5-tetramethyl-1,3,2-dioxaborolan-2-yl)pyridine (9.50 g, 22.8 mmol, CAS #2152673-80-6), 4-bromophenol (3.94 g, 22.8 mmol, CAS #106-41-2), $K_2CO_3$ (9.44 g, 68.3 mmol), and Pd(dppf)Cl$_2$·CH$_2$Cl$_2$ (1.86 g, 2.28 mmol) in dioxane (150 mL) and $H_2O$ (30 mL) was degassed and purged with $N_2$ three times. Then the mixture was stirred at 80° C. for 12 hrs under $N_2$ atmosphere. On completion, the reaction mixture was diluted with $H_2O$ (200 mL) and extracted with EA (200 mL×2). The combined organic layers were washed with aqueous NaCl (200 mL×2), dried over Na$_2$SO$_4$, filtered and concentrated in vacuo to give a residue. The residue was purified by column chromatography (SiO$_2$, Petroleum ether/Ethyl acetate=10/1 to 5/1) to give the title compound (7 g, 79% yield) as an off-white solid. $^1$H NMR (400 MHz, DMSO-d$_6$) δ 9.45 (s, 1H), 7.66 (d, J=8.0 Hz, 1H), 7.49-7.24 (m, 12H), 6.78 (d, J=8.4 Hz, 2H), 6.51 (d, J=8.0 Hz, 1H), 5.38 (d, J=13.2 Hz, 4H); LC-MS (ESI$^+$) m/z 384.2 (M+H)$^+$.

Tert-butyl N-[2-[2-[(2-chloroacetyl)amino]ethoxy]ethyl]carbamate (Intermediate IF)

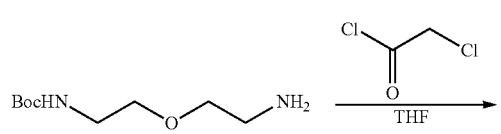

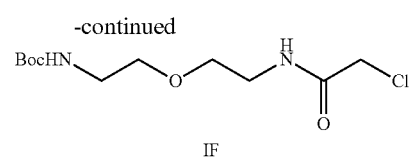

To a solution of tert-butyl N-[2-(2-aminoethoxy)ethyl]carbamate (500 mg, 2.45 mmol, CAS #127828-22-2) in DCM (5 mL) was added TEA (743 mg, 7.34 mmol). Then 2-chloroacetyl chloride (331.75 mg, 2.94 mmol, CAS #79-04-9) in DCM (3 mL) was added to the mixture at 0° C. The reaction was stirred at 25° C. for 1 hr. On completion, the mixture was diluted with DCM (60 mL) and washed with water (50 mL×3). The organic layer was dried over Na$_2$SO$_4$, filtered and the filtrate was concentrated in vacuo to give the title compound (610 mg, 88% yield) as yellow oil.

N-[2-(2-aminoethoxy)ethyl]-2-[4-(2,6-dioxo-3-piperidyl)phenoxy]acetamide (Intermediate IG)

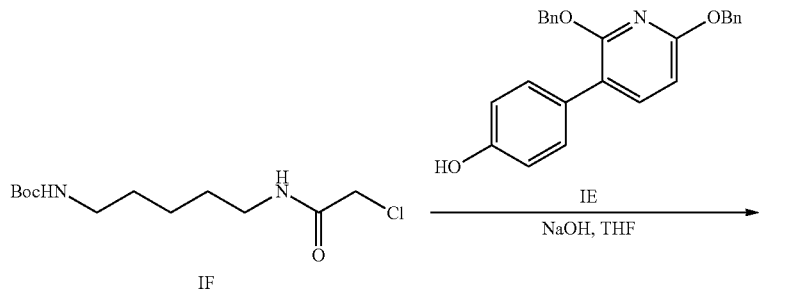

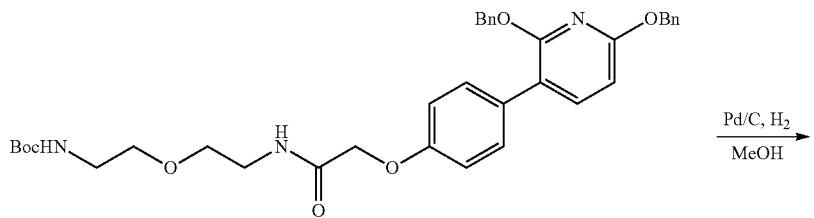

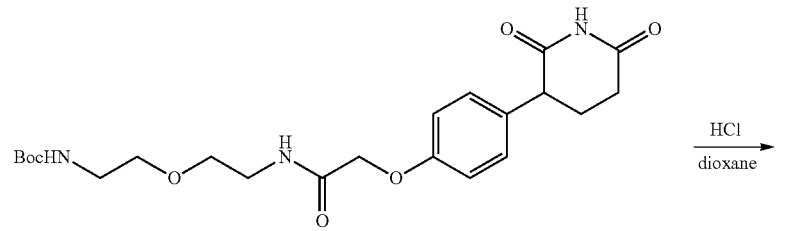

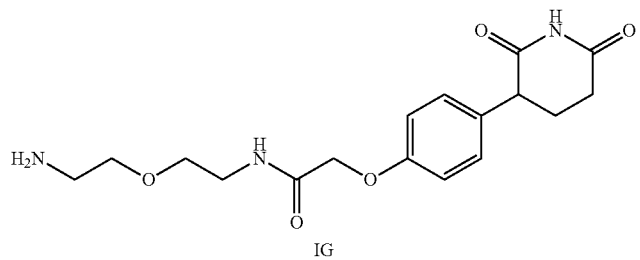

Step 1—Tert-butyl N-[2-[2-[[2-[4-(2,6-dibenzyloxy-3-pyridyl)phenoxy]acetyl]amino]ethoxy]ethyl] carbamate To a solution of tert-butyl N-[2-[2-[(2-chloroacetyl)amino]ethoxy]ethyl]carbamate (246 mg, 876 umol, Intermediate IF) and 4-(2,6-dibenzyloxy-3-pyridyl)phenol (120 mg, 312 umol, Intermediate IE) in DMF (4 mL) was added $Cs_2CO_3$ (305 mg, 938 umol). The reaction was then stirred at 50° C. for 4 hrs. On completion, the mixture was diluted with EA (50 mL) and washed with water (30 mL×3). The organic layer was dried over $Na_2SO_4$, filtered and the filtrate was concentrated in vacuo. The residue was purified by column chromatography ($SiO_2$, Petroleum ether/Ethyl acetate=3/1 to 1/1). Then, the crude product was further purified by prep-HPLC (column: Phenomenex luna C18 150*25 mm*10 um; mobile phase: [water (FA)-ACN]; B %: 66%-96%, 10 min) to give the title compound (196 mg, 99% yield) as colorless oil. $^1$H NMR (400 MHz, DMSO-$d_6$) δ 8.08 (m, J=5.6 Hz, 1H), 7.69 (d, J=8.0 Hz, 1H), 7.51-7.46 (m, 2H), 7.45-7.41 (m, 2H), 7.40-7.23 (m, 8H), 6.97 (d, J=8.8 Hz, 2H), 6.81-6.69 (m, 1H), 6.52 (d, J=8.0 Hz, 1H), 5.39 (s, 2H), 5.36 (s, 2H), 4.49 (s, 2H), 3.45-3.39 (m, 2H), 3.36 (t, J=6.0 Hz, 2H), 3.27 (s, 1H), 3.05 (m, J=5.6 Hz, 2H), 1.42-1.42 (m, 1H), 1.35 (s, 9H).

Step 2—Tert-butyl N-[2-[2-[[2-[4-(2,6-dioxo-3-piperidyl)phenoxy]acetyl]amino]ethoxy]ethyl] carbamate To a solution of tert-butyl N-[2-[2-[[2-[4-(2,6-dibenzyloxy-3-pyridyl)phenoxy]acetyl]amino] ethoxy]ethyl]carbamate (100 mg, 159 umol) in MeOH (4 mL) was added Pd/C (50 mg, 159 umol, 10 wt %) under $N_2$ atmosphere. The suspension was degassed and purged with $H_2$ three times. Then the mixture was stirred at 25° C. for 2 hrs under $H_2$ (15 Psi) atmosphere. On completion, the mixture was diluted with MeOH (10 mL), filtered and the filtrate was concentrated in vacuo to give the title compound (59 mg, 82% yield) as colorless solid. LC-MS (ESI$^+$) m/z 350.0 (M+H)$^+$.

Step 3—N-[2-(2-aminoethoxy)ethyl]-2-[4-(2,6-dioxo-3-piperidyl)phenoxy]acetamide A mixture of tert-butyl N-[2-[2-[[2-[4-(2,6-dioxo-3-piperidyl)phenoxy]acetyl]amino]ethoxy] ethyl]carbamate (59 mg, 131 umol) in HCl/EtOAc (4 M, 4 mL) was stirred at 25° C. for 0.5 hr. On completion, the mixture was concentrated in vacuo to give the title compound (45 mg, 98% yield) as white solid. LC-MS (ESI$^+$) m/z 350.0 (M+H)$^+$.

Tert-butyl N-[2-[2-[2-[(2-chloroacetyl)amino]ethoxy]ethoxy]ethyl]carbamate (Intermediate IH)

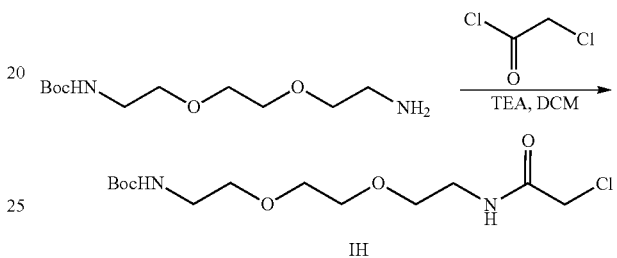

To a solution of tert-butyl N-[2-[2-(2-aminoethoxy)ethoxy]ethyl]carbamate (500 mg, 2.01 mmol, CAS #153086-78-3) in DCM (3 mL) was added TEA (840 uL, 6.04 mmol). Then a solution of 2-chloroacetyl chloride (192 uL, 2.42 mmol, CAS #79-04-9) in DCM (2 mL) was dropwise added at 0° C., and the mixture was stirred at 25° C. for 1 hr. On completion, the mixture was diluted with DCM (50 mL) and washed with water (40 mL×3). The combined organic layers were dried over anhydrous $Na_2SO_4$, then concentrated in vacuo to give the title compound (550 mg, 84% yield) as a yellow oil.

N-[2-[2-(2-aminoethoxy)ethoxy]ethyl]-2-[4-(2,6-dioxo-3-piperidyl)phenoxy]acetamide (Intermediate II)

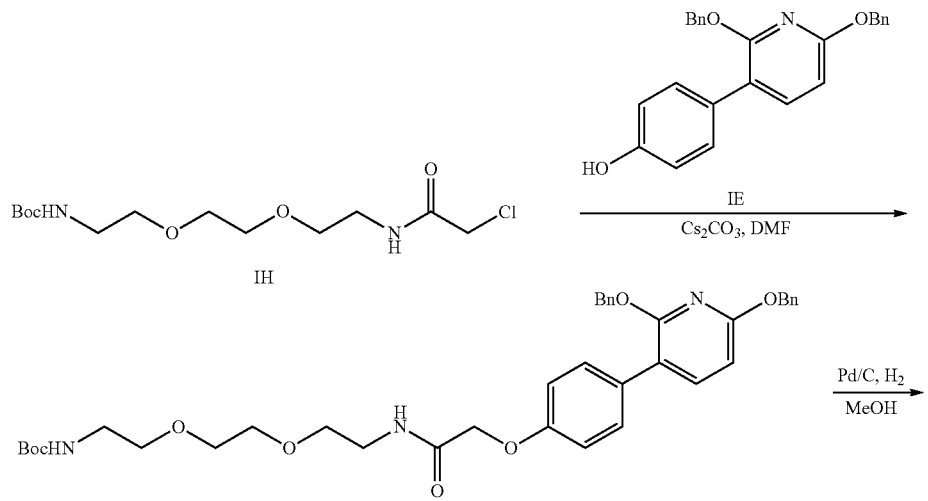

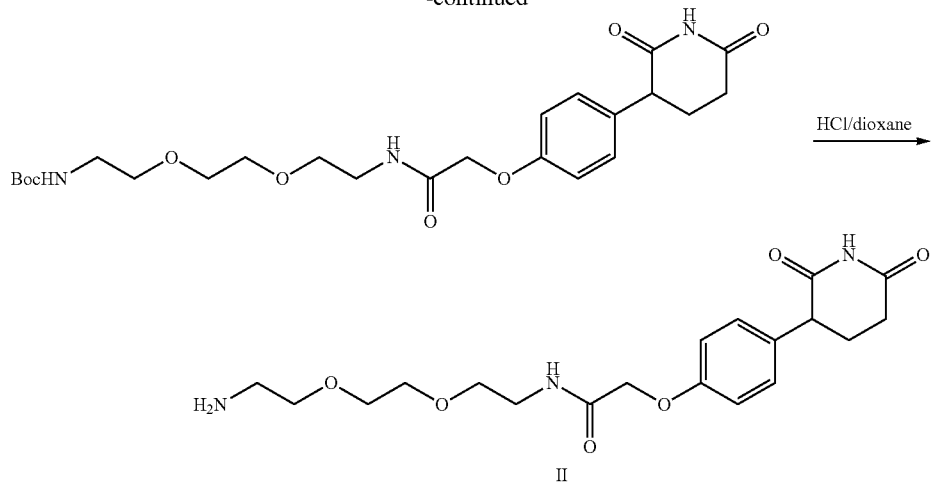

Step 1—Tert-butyl N-[2-[2-[2-[[2-[4-(2,6-dibenzyloxy-3-pyridyl)phenoxy]acetyl]amino]ethoxy]ethoxy] ethyl]carbamate To a solution of tert-butyl N-[2-[2-[2-[(2-chloroacetyl)amino]ethoxy]ethoxy]ethyl]carbamate (474 mg, 1.46 mmol, Intermediate IH) and 4-(2,6-dibenzyloxy-3-pyridyl)phenol (280 mg, 730 umol, Intermediate IE) in DMF (5 mL) was added $Cs_2CO_3$ (713 mg, 2.19 mmol), then the mixture was stirred at 50° C. for 2 hours. On completion, the mixture was filtered and the filtrate was diluted with EA (40 mL) and washed with water (30 mL×3). The combined organic layers were dried over anhydrous $Na_2SO_4$, then concentrated in vacuo to give the residue. The residue was purified by column chromatography ($SiO_2$, PE:EA=20:1 to 1:2) to give the title compound (480 mg, 97% yield) as a yellow oil. $^1$H NMR (400 MHz, DMSO-$d_6$) δ 8.24 (s, 1H), 8.07 (t, J=5.6 Hz, 1H), 7.70 (d, J=8.0 Hz, 1H), 7.49 (d, J=8.8 Hz, 2H), 7.46-7.41 (m, 2H), 7.40-7.32 (m, 7H), 6.97 (d, J=8.8 Hz, 2H), 6.74 (s, 1H), 6.53 (d, J=8.0 Hz, 1H), 5.75 (s, 1H), 5.38 (d, J=13.6 Hz, 4H), 4.49 (s, 2H), 4.06 (s, 1H), 3.49-3.47 (m, 4H), 3.44-3.43 (m, 2H), 3.37-3.36 (m, 2H), 3.06-3.04 (m, 2H), 1.36 (s, 9H). LC-MS (ESI$^+$) m/z 672.5 (M+H)$^+$.

Step 2—Tert-butyl N-[2-[2-[2-[[2-[4-(2,6-dioxo-3-piperidyl)phenoxy]acetyl]amino]ethoxy]ethoxy] ethyl]carbamate To a solution of tert-butyl N-[2-[2-[2-[[2-[4-(2,6-dibenzyloxy-3-pyridyl)phenoxy]acetyl]amino]ethoxy] ethoxy] ethyl]carbamate (150 mg, 223 umol) in MeOH (1 mL) was added Pd/C (50.0 mg, 10 wt %) under $N_2$ atmosphere. Then the mixture was degassed and charged with $H_2$ three times and then stirred at 25° C. under $H_2$ (15 psi) for 2 hrs. On completion, the mixture was filtered and the filtrate was concentrated in vacuo to give the title compound (100 mg, 90% yield) as a white gum. LC-MS (ESI$^+$) m/z 494.0 (M+H)$^+$.

Step 3—N-[2-[2-(2-aminoethoxy)ethoxy]ethyl]-2-[4-(2,6-dioxo-3-piperidyl)phenoxy]acetamide A solution of tert-butyl N-[2-[2-[2-[[2-[4-(2,6-dioxo-3-piperidyl)phenoxy]acetyl]amino]ethoxy]ethoxy] ethyl]carbamate (50.0 mg, 101 umol) in HCl/dioxane (1 mL) was stirred at 25° C. for 0.5 hr. On completion, the mixture was concentrated in vacuo to give the title compound (40.0 mg, 91% yield, HCl) as a white solid. LC-MS (ESI$^+$) m/z 394.0 (M+H)$^+$.

3-[3-methyl-2-oxo-5-[4-(4-piperidyloxy)-1-piperidyl]benzimidazol-1-yl]piperidine-2,6-dione (Intermediate IJ)

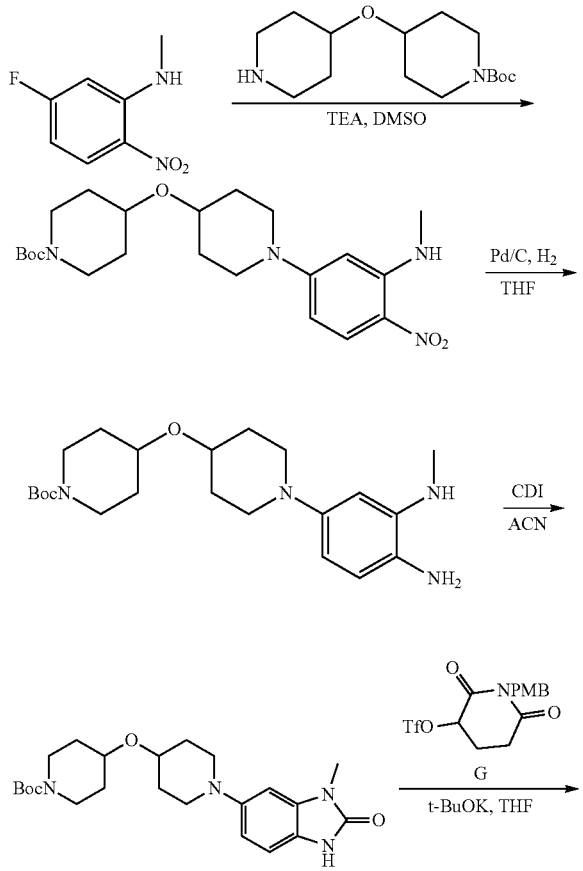

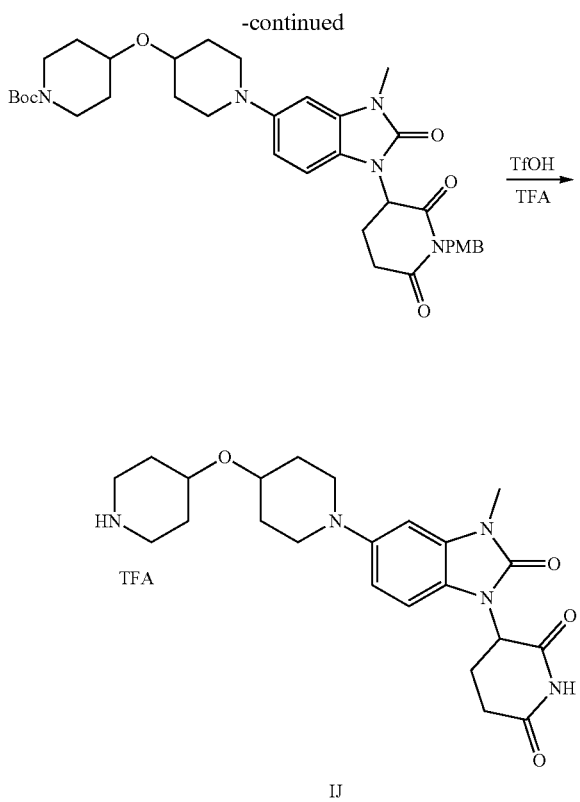

Step 1—Tert-butyl 4-[[1-[3-(methylamino)-4-nitro-phenyl]-4-piperidyl]oxy]piperidine-1-carboxylate A mixture of 5-fluoro-N-methyl-2-nitro-aniline (498 mg, 2.93 mmol, CAS #120381-42-2), TEA (889 mg, 8.79 mmol, 1.22 mL) and tert-butyl 4-(4-piperidyloxy)piperidine-1-carboxylate (1.00 g, 3.52 mmol, CAS #845305-83-1) in DMSO (12 mL) was stirred at 50° C. for 2 hrs. On completion, the reaction mixture was diluted with EA (90 mL) and washed with water (30 mL×3). The organic layer was dried over Na$_2$SO$_4$, filtered and concentrated in vacuo. The residue was purified by column chromatography (SiO$_2$, PE:EA=3:1 to 1:1) to give the title compound (1.05 g, 82% yield) as yellow solid. $^1$H NMR (400 MHz, DMSO-d$_6$) δ 8.35 (d, J=4.8 Hz, 1H), 7.88 (d, J=9.6 Hz, 1H), 6.47-6.36 (m, 1H), 5.92 (d, J=2.4 Hz, 1H), 3.82-3.69 (m, 3H), 3.68-3.59 (m, 3H), 3.27-3.15 (m, 2H), 3.09-2.96 (m, 2H), 2.93 (d, J=4.8 Hz, 3H), 1.92-1.82 (m, 2H), 1.79-1.69 (m, 2H), 1.51-1.42 (m, 2H), 1.39 (s, 9H), 1.36-1.27 (in, 2H)

Step 2—Tert-butyl 4-[[1-[4-amino-3-(methylamino) phenyl]-4-piperidyl]oxy]piperidine-1-carboxylate To a solution of tert-butyl 4-[[1-[3-(methylamino)-4-nitro-phenyl]-4-piperidyl]oxy]piperidine-1-carboxylate (1 g, 2.30 mmol) in THF (20 mL) was added Pd/C (500 mg, 2.30 mmol, 10 wt %) under Ar. The suspension was degassed under vacuum and purged with H$_2$ several times. The mixture was then stirred under H$_2$ (15 psi) at 25° C. for 5 hrs. On completion, the reaction mixture was filtered and concentrated in vacuo to give the title compound (853 mg, 91% yield) as yellow oil. $^1$H NMR (400 MHz, DMSO-d$_6$) δ 6.40 (d, J=8.0 Hz, 1H), 6.08-5.97 (m, 2H), 4.55-4.47 (m, 1H), 3.98 (s, 2H), 3.68-3.58 (m, 3H), 3.54-3.46 (m, 1H), 3.28-3.20 (m, 2H), 3.00 (s, 2H), 2.68 (d, J=5.2 Hz, 3H), 2.67-2.60 (m, 2H), 1.92-1.82 (m, 2H), 1.81-1.71 (m, 2H), 1.57-1.47 (m, 2H), 1.39 (s, 9H), 1.35-1.25 (m, 2H).

Step 3—Tert-butyl 4-[[1-(3-methyl-2-oxo-1H-benz-imidazol-5-yl)-4-piperidyl]oxy]piperidine-1-carboxylate A mixture of tert-butyl 4-[[1-[4-amino-3-(methylamino) phenyl]-4-piperidyl]oxy]piperidine-1-carboxylate (800 mg, 1.98 mmol) and CDI (480 mg, 2.97 mmol) in ACN (10 mL) was stirred at 80° C. for 4 hrs. On completion, the reaction mixture was concentrated in vacuo to remove ACN (5 mL). Then, the mixture was added dropwise into water (80 mL) and filtered. The filtered cake was dried in vacuo to give the title compound (680 mg, 79% yield) as purple solid. $^1$H NMR (400 MHz, DMSO-d$_6$) δ 10.48 (s, 1H), 6.79 (d, J=8.4 Hz, 1H), 6.73 (d, J=1.6 Hz, 1H), 6.59-6.55 (m, 1H), 3.68-3.53 (m, 4H), 3.42-3.35 (m, 2H), 3.23 (s, 3H), 3.01 (t, J=9.6 Hz, 2H), 2.86-2.73 (m, 2H), 1.94-1.86 (m, 2H), 1.80-1.72 (m, 2H), 1.60-1.49 (m, 2H), 1.39 (s, 9H), 1.35-1.26 (m, 2H).

Step 4—Tert-butyl 4-[[1-[1-[1-[(4-methoxyphenyl) methyl]-2,6-dioxo-3-piperidyl]-3-methyl-2-oxo-benzimidazol-5-yl]-4-piperidyl]oxy]piperidine-1-carboxylate A mixture of tert-butyl 4-[[1-(3-methyl-2-oxo-1H-benz-imidazol-5-yl)-4-piperidyl]oxy]piperidine-1-carboxylate (600 mg, 1.39 mmol) and tBuOK (234 mg, 2.09 mmol) in THF (7 mL) was stirred at 0° C. for 0.5 hr. Then, a mixture of [1-[(4-methoxyphenyl)methyl]-2,6-dioxo-3-piperidyl]tri-fluoromethanesulfonate (797 mg, 2.09 mmol, Intermediate G) in THF (5 mL) was added dropwise into the above mixture and the mixture was stirred for 0.5 hr at 0° C. On completion, the reaction mixture was diluted with EA (80 mL) and the organic layer was washed with water (50 mL×3). The organic layer was dried over Na$_2$SO$_4$, filtered and concentrated in vacuo. The residue was purified by column chromatography (SiO$_2$, PE:EA=1:1 to 1:3 to 0:1) to give the title compound (900 mg, 97% yield) as green solid. $^1$H NMR (400 MHz, DMSO-d$_6$) δ 7.20 (d, J=8.8 Hz, 2H), 6.88-6.82 (m, 3H), 6.80 (d, J=8.4 Hz, 1H), 6.59-6.53 (m, 1H), 5.47-5.38 (m, 1H), 4.85-4.73 (m, 2H), 3.74-3.71 (m, 3H), 3.68-3.56 (m, 4H), 3.46-3.38 (m, 2H), 3.30 (s, 3H), 3.09-2.97 (m, 3H), 2.86-2.77 (m, 3H), 2.73-2.63 (m, 1H), 2.06-2.00 (m, 1H), 1.95-1.87 (m, 2H), 1.80-1.71 (m, 2H), 1.62-1.51 (m, 2H), 1.39 (s, 9H), 1.35-1.27 (m, 2H).

Step 5—3-[3-Methyl-2-oxo-5-[4-(4-piperidyloxy)-1-piperidyl]benzimidazol-1-yl]piperidine-2,6-dione A mixture of tert-butyl 4-[[1-[1-[1-[(4-methoxyphenyl) methyl]-2,6-dioxo-3-piperidyl]-3-methyl-2-oxo-benzimida-zol-5-yl]-4-piperidyl]oxy]piperidine-1-carboxylate (300 mg, 453 umol) and TfOH (1.02 g, 6.80 mmol, 0.6 mL) in TFA (3 mL) was stirred at 70° C. for 2.5 hrs. On completion, the reaction mixture was concentrated in vacuo to give the title compound (251 mg, 99% yield, TFA) as red oil. LC-MS (ESI$^+$) m/z 441.9 (M+H)$^+$.

3-[5-[4-[[1-(3-aminopropyl)-4-piperidyl]oxy]-1-piperidyl]-3-methyl-2-oxo-benzimidazol-1-yl] piperidine-2,6-dione (Intermediate IK)

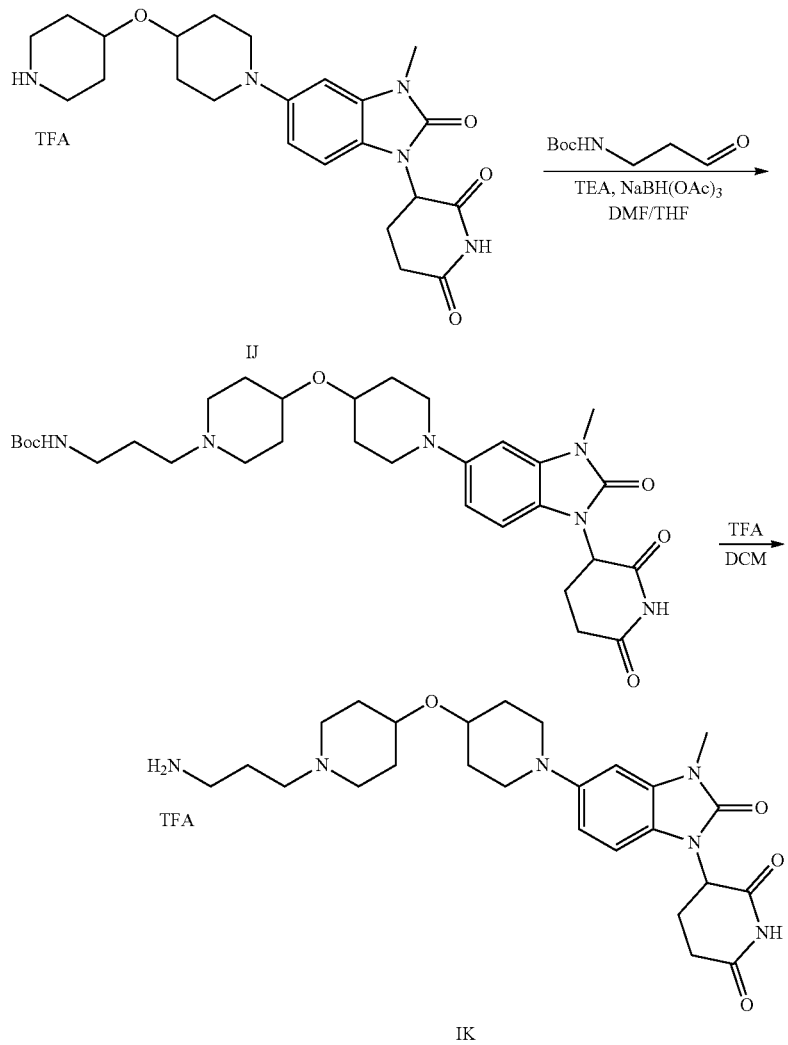

Step 1—Tert-butyl N-[3-[4-[[1-[1-(2,6-dioxo-3-piperidyl)-3-methyl-2-oxo-benzimidazol-5-yl]-4-piperidyl]oxy]-1-piperidyl]propyl]carbamate To a solution of 3-[3-methyl-2-oxo-5-[4-(4-piperidyloxy)-1-piperidyl]benzimidazol-1-yl]piperidine-2,6-dione (250 mg, 450 umol, TFA, Intermediate IJ), TEA (136 mg, 1.35 mmol) and HOAc (108 mg, 1.80 mmol) in DMF (2 mL) and THF (2 mL) was added tert-butyl N-(3-oxopropyl) carbamate (169 mg, 975 umol, Intermediate GM). The mixture was stirred at 25° C. for 0.5 hr. Then, NaBH(OAc)$_3$ (143 mg, 675 umol) was added and the mixture was stirred at 25° C. for 1.5 hrs. On completion, the reaction mixture was quenched with water (0.2 mL) and concentrated in vacuo. The residue was purified by prep-HPLC (column: Phenomenex C18 250*50 mm*10 um; mobile phase: [water (NH$_4$HCO$_3$)-ACN]; B %: 20%-50%, 8 min) to give the title compound (140 mg, 51% yield) as white solid. $^1$H NMR (400 MHz, DMSO-d$_6$) δ 11.05 (s, 1H), 6.92 (d, J=8.4 Hz, 1H), 6.83 (d, J=2.0 Hz, 1H), 6.79-6.74 (m, 1H), 6.65-6.60 (m, 1H), 5.39-5.16 (m, 1H), 3.58-3.51 (m, 1H), 3.44-3.39 (m, 3H), 3.30 (s, 3H), 2.94-2.88 (m, 3H), 2.86-2.77 (m, 3H), 2.64-2.60 (m, 1H), 2.24 (t, J=7.2 Hz, 3H), 2.06-1.94 (m, 4H), 1.94-1.85 (m, 3H), 1.83-1.73 (m, 3H), 1.54-1.47 (m, 4H), 1.37 (s, 9H).

Step 2—3-[5-[4-[[1-(3-Aminopropyl)-4-piperidyl]oxy]-1-piperidyl]-3-methyl-2-oxo-benzimidazol-1-yl] piperidine-2,6-dione A mixture of tert-butyl N-[3-[4-[[1-[1-(2,6-dioxo-3-piperidyl)-3-methyl-2-oxo-benzimidazol-5-yl]-4-piperidyl]oxy]-1-piperidyl]propyl]carbamate (35.0 mg, 58.4 umol) and TFA (359 mg, 3.15 mmol) in DCM (1 mL) was stirred at 25° C. for 1 hr. On completion, the reaction mixture was concentrated in vacuo to give the title compound (35.8 mg, 99% yield, TFA) as colorless oil. LC-MS (ESI$^+$) m/z 498.9 (M+H)$^+$.

Tert-butyl N-[2-[2-[2-(4-piperidylmethoxy)ethoxy]ethoxy]ethyl]carbamate (Intermediate IL)

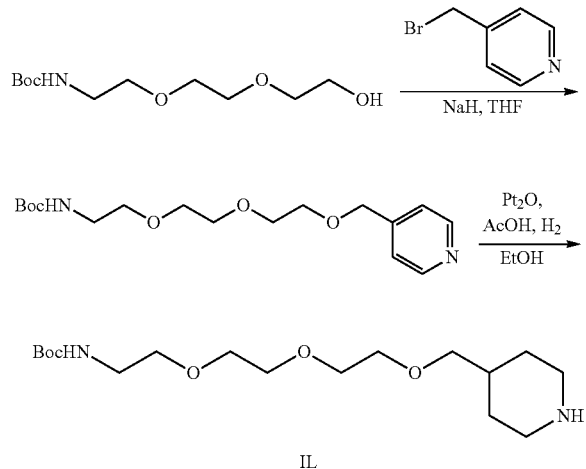

Step 1—Tert-butyl N-[2-[2-[2-(4-pyridylmethoxy)ethoxy]ethoxy]ethyl]carbamate A mixture of tert-butyl N-[2-[2-(2-hydroxyethoxy)ethoxy]ethyl]carbamate (500 mg, 2.01 mmol, CAS #139115-92-7) in THF (5 mL) was degassed and purged with $N_2$ three times. Then NaH (160 mg, 4.01 mmol, 60% dispersion in mineral oil) was added to the mixture at 0° C. and the mixture was stirred for 1 hour. Then 4-(bromomethyl)pyridine (345 mg, 2.01 mmol, CAS #54751-01-8) was added and the mixture was stirred at 25° C. for 2 hrs under $N_2$ atmosphere. On completion, the reaction mixture was with $H_2O$ (10 mL) at 25° C., and then extracted with EA (3×10 mL). The combined organic layers were washed with brine (2×10 mL), dried over $Na_2SO_4$, filtered and concentrated in vacuo to give a residue. The residue was then purified by prep-HPLC (column: Phenomenex C18 250*50 mm*10 um; mobile phase: [water (ammonia hydroxide v/v)-ACN]; B %: 18%-48%, 8 min) to give the title compound (200 mg, 28% yield) as colorless oil. LC-MS (ESI$^+$) m/z 341.2 (M+1)$^+$. $^1$H NMR (400 MHz, CDCl$_3$) δ 8.58 (d, J=6.0 Hz, 2H), 7.29 (d, J=6.0 Hz, 2H), 5.01 (s, 1H), 4.60 (s, 2H), 3.73-3.68 (m, 4H), 3.68-3.63 (m, 4H), 3.55 (t, J=4.8 Hz, 2H), 3.32-3.31 (m, 2H), 1.44 (s, 9H).

Step 2—Tert-butyl N-[2-[2-[2-(4-piperidylmethoxy)ethoxy]ethoxy]ethyl]carbamate To a solution of tert-butyl N-[2-[2-[2-(4-pyridylmethoxy)ethoxy]ethoxy]ethyl]carbamate (170 mg, 499 umol) in EtOH (5 mL) and AcOH (525 mg, 8.74 mmol) was added PtO$_2$ (113 mg, 499 umol) under $N_2$ atmosphere. The suspension was degassed and purged with $H_2$ three times. The mixture was stirred under $H_2$ (15 Psi) at 40° C. for 16 hrs. On completion, the reaction mixture was filtered and concentrated in vacuo to give the title compound (150 mg, 86% yield) as a white solid. $^1$H NMR (400 MHz, CDCl$_3$) δ 5.33-4.94 (m, 1H), 3.65-3.58 (m, 8H), 3.56-3.52 (m, 2H), 3.44-3.29 (m, 6H), 2.86-2.80 (m, 2H), 1.95-1.76 (m, 4H), 1.44 (s, 9H), 1.33-1.23 (m, 1H).

1-[4-[4-[2-[2-(2-Aminoethoxy)ethoxy]ethoxymethyl]-1-piperidyl]phenyl]hexahydropyrimidine-2,4-dione (Intermediate IM)

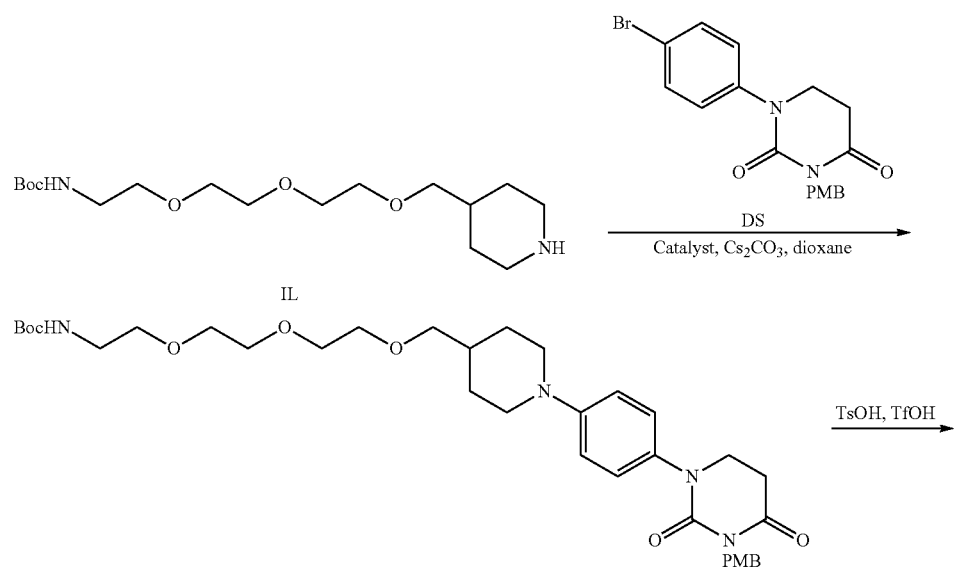

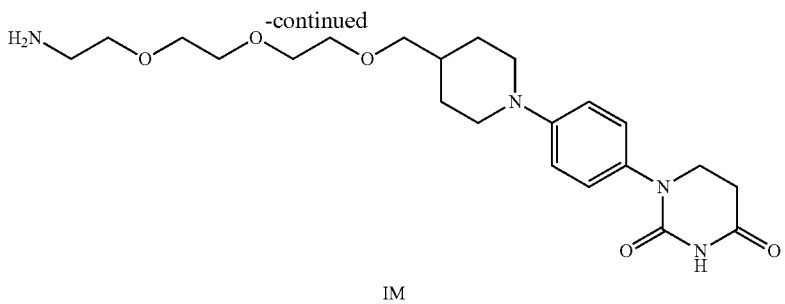

IM

Step 1—Tert-butyl N-[2-[2-[2-[[1-[4-[3-[(4-methoxyphenyl)methyl]-2,4-dioxo-hexahydropyrimidin-1-yl]phenyl]-4-piperidyl]methoxy]ethoxy]ethoxy]ethyl]carbamate A mixture of tert-butyl N-[2-[2-[2-(4-piperidylmethoxy)ethoxy]ethoxy]ethyl]carbamate (150 mg, 432 umol, Intermediate IL), 1-(4-bromophenyl)-3-[(4-methoxyphenyl)methyl]hexahydropyrimidine-2,4-dione (134 mg, 346 umol, Intermediate DS), Cs$_2$CO$_3$ (564 mg, 1.73 mmol) and 1,3-bis[2,6-bis(1-ethylpropyl)phenyl]-4,5-dichloro-2H-imidazol-1-ium-2-ide;3-chloropyridine;dichloropalladium (37.2 mg, 43.2 umol) in dioxane (2 mL) was degassed and purged with N$_2$ three times. Then the mixture was stirred at 100° C. for 16 hrs under N$_2$ atmosphere. On completion, the reaction mixture was filtered and concentrated in vacuo to give a residue. Then the residue was purified by prep-HPLC (column: Phenomenex luna C18 150*25 mm*10 um; mobile phase: [water(FA)-ACN]; B %: 29%-59%, 15 min) to give the title compound (70.0 mg, 24% yield) as a white solid. LC-MS (ESI$^+$) m/z 655.2 (M+1)$^+$.

Step 2—1-[4-[4-[2-[2-(2-Aminoethoxy)ethoxy]ethoxymethyl]-1-piperidyl]phenyl]hexahydropyrimidine-2,4-dione To a solution of tert-butyl N-[2-[2-[2-[[1-[4-[3-[(4-methoxyphenyl)methyl]-2,4-dioxo-hexahydropyr-imidin-1-yl]phenyl]-4-piperidyl]methoxy]ethoxy]ethoxy]ethyl]carbamate (70.0 mg, 106 umol) in TFA (1.2 mL) was added TfOH (0.396 mg, 2.64 umol). The mixture was stirred at 70° C. for 1 hr. On completion, the reaction mixture was concentrated in vacuo to give the title compound (45.0 mg, 96% yield) as a yellow solid. LC-MS (ESI$^+$) m/z 435.1 (M+1)$^+$.

Tert-butyl N-[3-[(2-chloroacetyl)amino]propyl]carbamate (Intermediate IN)

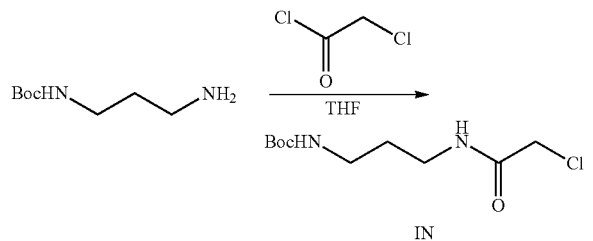

To a solution of tert-butyl N-(3-aminopropyl)carbamate (1.00 g, 5.74 mmol, CAS #75178-96-0) in THF (10 mL) was added 2-chloroacetyl chloride (1.30 g, 11.4 mmol). The mixture was stirred at 25° C. for 1 hr. On completion, the reaction mixture was diluted with H$_2$O (5 mL) and extracted with EA (3×5 mL). The combined organic layers were washed with brine (2×5 mL), dried over anhydrous Na$_2$SO$_4$, filtered and concentrated in vacuo to give the title compound (1.00 g, 70% yield) as a white solid. $^1$H NMR (400 MHz, CDCl$_3$) δ 7.43-7.29 (m, 1H) 4.16-4.08 (m, 6H) 3.38 (d, J=6.4 Hz, 2H) 3.19 (s, 2H) 1.80-1.63 (m, 2H) 1.45 (s, 9H).

N-(3-aminopropyl)-2-[4-(2,6-dioxo-3-piperidyl)phenoxy]acetamide (Intermediate 10)

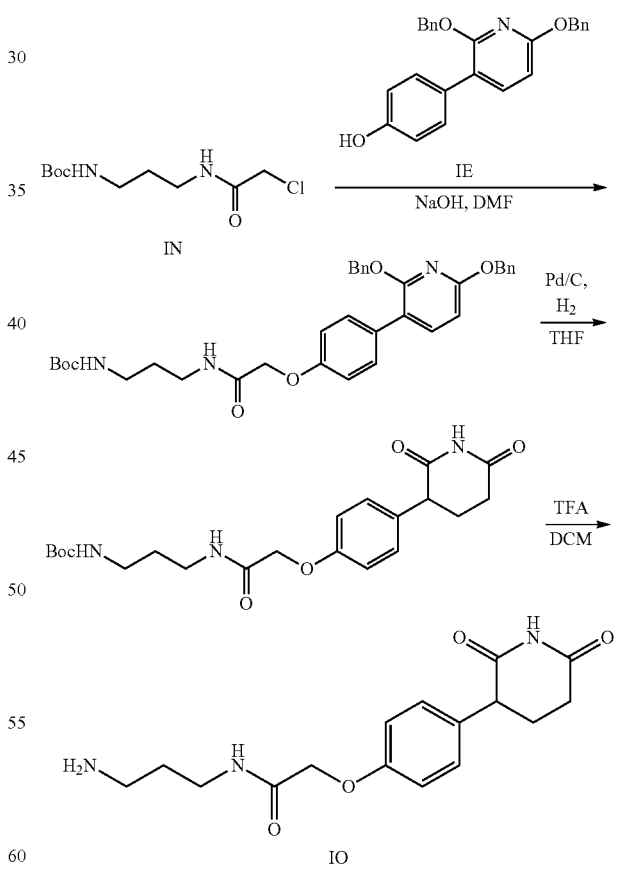

Step 1—Tert-butyl N-[3-[[2-[4-(2,6-dibenzyloxy-3-pyridyl)phenoxy]acetyl]amino]propyl]carbamate To a solution of tert-butyl N-[3-[(2-chloroacetyl)amino]propyl]carbamate (5×100 mg, 5×398 umol, Intermediate IN)

in DMF (5×2 mL) was added NaOH (5×63.8 mg, 5×1.60 mmol) and 4-(2,6-dibenzyloxy-3-pyridyl)phenol (5×45.8 mg, 5×119 umol, Intermediate IE). The mixture was stirred at 25° C. for 16 hrs. On completion, the reaction mixture was diluted with H$_2$O (10 mL) and extracted with EA (3×5 mL). The combined organic layers were washed with brine (2×5 mL), dried over anhydrous Na$_2$SO$_4$, filtered and concentrated in vacuo to give a residue. The crude product was purified by reversed-phase HPLC (0.1% FA condition) to give the title compound (170 mg, 14% yield) as a white solid. $^1$H NMR (400 MHz, CDCl$_3$) δ 7.58 (d, J=8.4 Hz, 1H) 7.52 (d, J=8.8 Hz, 2H) 7.46-7.42 (m, 2H) 7.41-7.28 (m, 10H) 6.97 (d, J=8.8 Hz, 2H) 6.48 (d, J=8 Hz, 1H) 5.44-5.36 (m, 4H) 4.54 (s, 2H) 3.42 (d, J=6.4 Hz, 2H) 3.16 (d, J=6.4 Hz, 2H) 1.69-1.66 (m, 2H) 1.46-1.43 (m, 9H). LC-MS (ESI$^+$) m/z 598.1 (M+H)$^+$.

Step 2—Tert-butyl N-[3-[[2-[4-(2,6-dioxo-3-piperidyl)phenoxy]acetyl]amino]propyl]carbamate To a solution of tert-butyl N-[3-[[2-[4-(2,6-dibenzyloxy-3-pyridyl)phenoxy]acetyl]amino]propyl] carbamate (115 mg, 192 umol) in THF (2 mL) was added Pd/C (227 mg, 193 umol) under N$_2$ atmosphere. The suspension was degassed and purged with H$_2$ three times. The mixture was stirred under H$_2$ at 25° C. for 2 hrs. On completion, the reaction mixture was filtered and concentrated in vacuo to give the title compound (80.0 mg, 99% yield) as colorless oil. LC-MS (ESI$^+$) m/z 319.9 (M+H)$^+$.

Step 3—N-(3-aminopropyl)-2-[4-(2,6-dioxo-3-piperidyl)phenoxy]acetamide

To a solution of tert-butyl N-[3-[[2-[4-(2,6-dioxo-3-piperidyl)phenoxy]acetyl]amino]propyl]carbamate (80.0 mg, 190 umol) in DCM (1 mL) was added TFA (1.31 g, 11.4 mmol). The mixture was stirred at 25° C. for 1 hr. On completion, the reaction mixture was filtered and concentrated in vacuo to give the title compound (60.0 mg, 99% yield) as colorless oil. LC-MS (ESI$^+$) m/z 319.9 (M+H)$^+$.

Tert-butyl N-[7-[(2-chloroacetyl)amino]heptyl]carbamate (Intermediate IP)

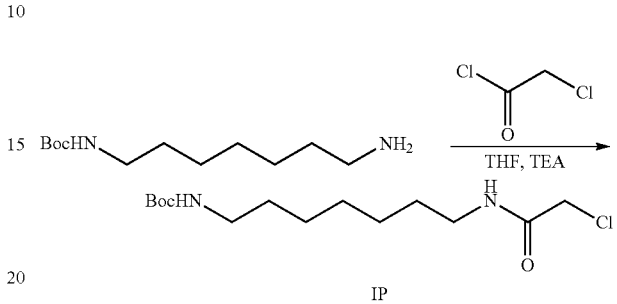

To a solution of tert-butyl N-(7-aminoheptyl)carbamate (600 mg, 2.60 mmol, CAS #99733-18-3) in THF (1 mL) was added TEA (264 mg, 2.60 mmol, 363 uL) and 2-chloroacetyl chloride (353 mg, 3.13 mmol, 249 uL, CAS #79-04-9). The mixture was stirred at 25° C. for 12 hrs. On completion, the mixture was concentrated in vacuo to give the title compound (799 mg, 100% yield) as a yellow solid. LC-MS (ESI$^+$) m/z 329.1 (M+H)$^+$.

N-(7-aminoheptyl)-2-[4-(2,6-dioxo-3-piperidyl)phenoxy]acetamide (Intermediate IQ)

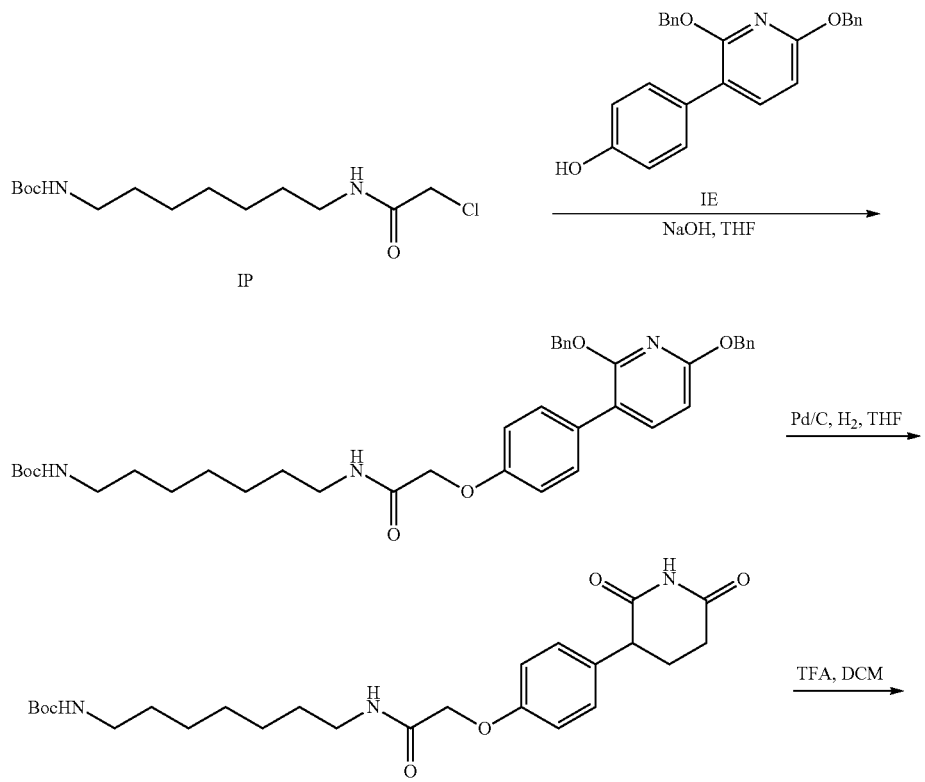

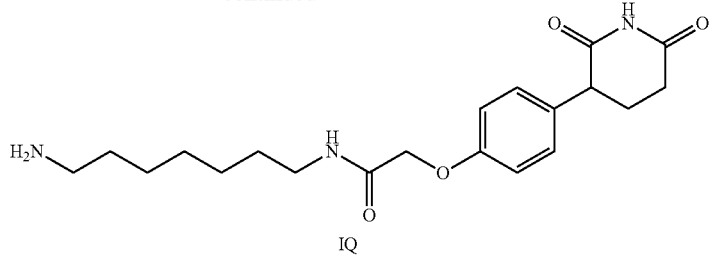

IQ

Step 1—Tert-butyl N-[7-[[2-[4-(2,6-dibenzyloxy-3-pyridyl)phenoxy]acetyl]amino]heptyl]carbamate To a solution of tert-butyl N-[7-[(2-chloroacetyl)amino]heptyl]carbamate (799 mg, 2.60 mmol, Intermediate IP) in THF (1 mL) was added NaOH (469 mg, 11.7 mmol) and 4-(2,6-dibenzyloxy-3-pyridyl)phenol (200 mg, Intermediate IE). The mixture was stirred at 25° C. for 12 hrs. On completion, the mixture was diluted with H₂O (15 mL) and extracted with EA (3×15 mL). The combined organic layers were washed with brine (2×10 mL), dried over anhydrous Na₂SO₄, filtered and concentrated in vacuo to give a residue. The residue was purified by prep-HPLC (column: YMC Triart C18 250*50 mm*7 um; mobile phase: [water (FA)-ACN]; B %: 56%-86%, 20 minutes) to give the title compound (360 mg, 21% yield) as yellow oil. ¹H NMR (400 MHz, CDCl₃) δ 7.58 (d, J=8.0 Hz, 1H), 7.55-7.50 (m, 2H), 7.46-7.41 (m, 2H), 7.40-7.29 (m, 7H), 6.97-6.93 (m, 2H), 6.61 (t, J=5.6 Hz, 1H), 6.48 (d, J=8.0 Hz, 1H), 5.47-5.35 (m, 4H), 4.53 (s, 2H), 3.40-3.32 (m, 2H), 3.10 (d, J=6.0 Hz, 2H), 1.61-1.47 (m, 4H), 1.45 (s, 10H), 1.33 (s, 7H). LC-MS (ESI⁺) m/z 654.2 (M+H)⁺.

Step 2—Tert-butyl N-[7-[[2-[4-(2,6-dioxo-3-piperidyl)phenoxy]acetyl]amino]heptyl]carbamate To a solution of tert-butyl N-[7-[[2-[4-(2,6-dibenzyloxy-3-pyridyl)phenoxy]acetyl]amino]heptyl]carbamate (257 mg, 393 umol) in THF (2 mL) was added Pd/C (47 mg, 39.2 umol, 10 wt %) under N₂. The suspension was degassed under vacuum and purged with H₂ several times. The mixture was then stirred under H₂ (15 psi) at 25° C. for 12 hrs. On completion, the mixture was filtered and concentrated in vacuo to give the title compound (150 mg, 81% yield) as yellow oil. ¹H NMR (400 MHz, CDCl₃) δ 8.02 (d, J=1.2 Hz, 1H), 7.18 (d, J=8.8 Hz, 2H), 6.97-6.91 (m, 2H), 6.52 (s, 1H), 4.50 (s, 2H), 3.75 (dd, J=5.2, 10.0 Hz, 1H), 3.39-3.30 (m, 2H), 3.10 (d, J=6.0 Hz, 2H), 2.80-2.62 (m, 2H), 2.39-2.12 (m, 3H), 1.45 (s, 9H), 1.44 (s, 3H), 1.31 (s, 6H). LC-MS (ESI⁺) m/z 476.0 (M+H)⁺.

Step 3—N-(7-aminoheptyl)-2-[4-(2,6-dioxo-3-piperidyl)phenoxy]acetamide

To a solution of tert-butyl N-[7-[[2-[4-(2,6-dioxo-3-piperidyl)phenoxy]acetyl]amino]heptyl]carbamate (90 mg, 189 umol) in DCM (0.5 mL) was added TFA (770 mg, 6.75 mmol). The mixture was then stirred at 25° C. for 1 hr. On completion, the mixture was concentrated in vacuo to give the title compound (70 mg, 99% yield) as yellow oil. LC-MS (ESI⁺) m/z 375.7 (M+H)⁺.

4-[(6-Chloro-8-isopropyl-7-oxo-pyrido[2,3-d]pyrimidin-2-yl)amino]-3-methyl-N-(2-piperazin-1-ylethyl)benzenesulfonamide (Intermediate IR)

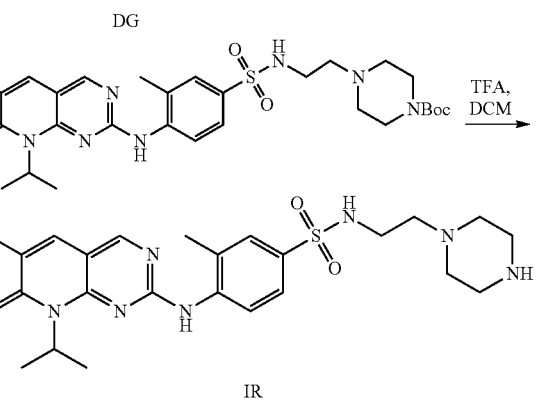

Step 1—Tert-butyl 4-[2-[[4-[(6-chloro-8-isopropyl-7-oxo-pyrido[2,3-d]pyrimidin-2-yl)amino]-3-methyl-phenyl]sulfonylamino]ethyl]piperazine-1-carboxylate To a solution of 4-[(6-chloro-8-isopropyl-7-oxo-pyrido[2,3-d]pyrimidin-2-yl)amino]-3-methyl-benzenesulfonyl chloride (100 mg, 234 umol, Intermediate DG) in ACN (1.00 mL) and DMF (1 m L) was added DIEA (30.2 mg, 234 umol, 40.7 uL), 4A molecular sieves (5.00 mg, 234 umol) and tert-butyl 4-(2-aminoethyl) piperazine-1-carboxylate (53.0 mg, 234 umol, CAS #192130-34-0). The mixture was then stirred at 25° C. for 10 min. On completion, the mixture was concentrated in vacuo. The mixture was purified by pre-HPLC (column: Phenomenex luna C18 150*25 mm*10 um; mobile phase: [water(FA)-ACN]; B %: 19%-49%, 9 min) to give the title compound (130 mg, 89% yield) as a white solid. LC-MS (ESI⁺) m/z 620.3 (M+H)⁺.

Step 2—4-[(6-Chloro-8-isopropyl-7-oxo-pyrido[2,3-d]pyrimidin-2-yl)amino]-3-methyl-N-(2-piperazin-1-ylethyl)benzenesulfonamide To a solution of tert-butyl 4-[2-[[4-[(6-chloro-8-isopropyl-7-oxo-pyrido [2,3-d] pyrimidin-2-yl) amino]-3-methylphenyl]sulfonylamino]ethyl]piperazine-1-carboxylate (89.0 mg, 143 umol) in DC M (1.00 mL), TFA (1.00 mL). The mixture was stirred at 25° C. for 1 hr. On completion, the mixture was concentrated in vacuo to give the title compound (80.0 mg, 87% yield, TFA) as a brown oily liquid. LC-MS (ESI$^+$) m/z 520.1 (M+H)$^+$.

Benzyl 4-(4-piperidylmethoxy)piperidine-1-carboxylate (Intermediate IS)

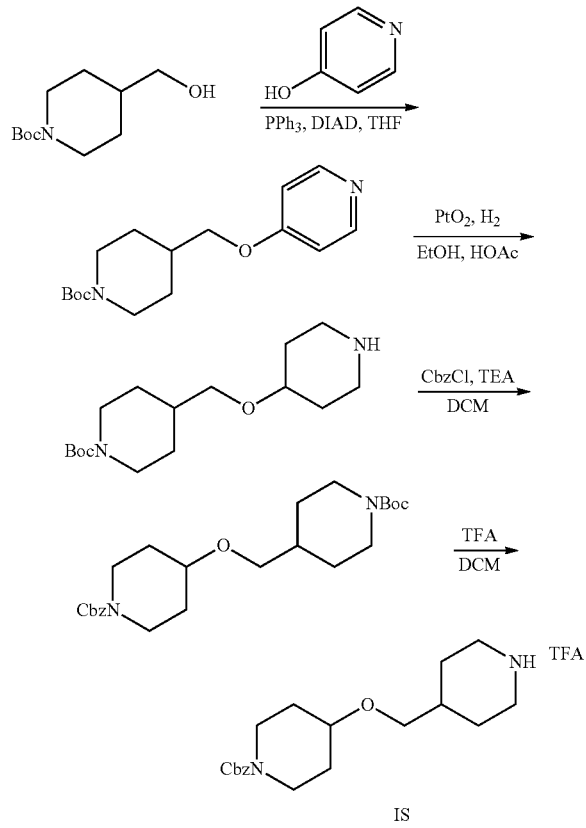

Step 1—Tert-butyl 4-(4-pyridyloxymethyl)piperidine-1-carboxylate

A mixture of tert-butyl 4-(hydroxymethyl)piperidine-1-carboxylate (10 g, 46.5 mmol, CAS #123855-51-6), pyridin-4-ol (4.42 g, 46.5 mmol, CAS #626-64-2), PPh$_3$ (25.0 g, 93.0 mmol), and DIAD (19.0 g, 93.0 mmol, 18.0 mL) in THF (50 mL) was degassed and purged with N$_2$ three times. Then the mixture was stirred at 25° C. for 16 hrs under N$_2$ atmosphere. On completion, the mixture was diluted with H$_2$O (50 mL) and extracted with DCM (100 mL×3). The combined organic layers were washed with brine (2×30 mL), dried anhydrous Na$_2$SO$_4$ and concentrated in vacuo to give a residue. The crude product was purified by reversed-phase HPLC (0.1% FA condition) to give the title compound (4.90 g, 37% yield) was obtained as a white solid. $^1$H NMR (400 MHz, CDCl$_3$) δ 8.44 (d, J=6.0 Hz, 2H), 6.82 (d, J=6.0 Hz, 2H), 4.18 (d, J=4.0 Hz, 2H), 3.87 (d, J=6.4 Hz, 2H), 2.80-2.74 (m, 2H), 2.09-1.90 (m, 1H), 1.82 (d, J=12.8 Hz, 2H), 1.48 (s, 9H), 1.35-1.23 (m, 2H). LC-MS (ESI$^+$) m/z 293.3 (M+H)$^+$.

Step 2 Tert-butyl 4-(4-piperidyloxymethyl)piperidine-1-carboxylate

A mixture of tert-butyl 4-(4-pyridyloxymethyl)piperidine-1-carboxylate (2.8 g, 9.58 mmol), PtO$_2$ (2.17 g, 9.58 mmol), and HOAc (10.50 g, 174.85 mmol, 10 mL) in EtOH (28 mL) was degassed and purged with H$_2$ three times. Then the mixture was stirred at 40° C. for 16 hrs under H$_2$ atmosphere. On completion, the mixture was filtered and concentrated in vacuo to give the title compound (2.5 g, 73% yield, HOAc salt) as white oil. $^1$H NMR (400 MHz, CDCl$_3$) δ 4.12 (d, J=2.0 Hz, 2H), 3.57 (s, 1H), 3.28-3.18 (m, 3H), 3.13-3.05 (m, 2H), 3.03-2.92 (m, 1H), 2.73-2.69 (m, 2H), 2.05 (s, 9H), 2.00 (s, 1H), 1.89-1.79 (m, 2H), 1.77-1.63 (m, 4H), 1.31-1.24 (m, 1H), 1.20-1.09 (m, 2H).

Step 3 Tert-butyl 4-[(1-benzyloxycarbonyl-4-piperidyl)oxymethyl]piperidine-1-carboxylate To a solution of tert-butyl 4-(4-piperidyloxymethyl)piperidine-1-carboxylate (2.60 g, 7.25 mmol, HOAC) in DCM (30 mL) was added TEA (1.47 g, 14.5 mmol, 2.02 mL) and CbzCl (990 mg, 5.80 mmol, 825 uL, CAS #501-53-1). The mixture was stirred at 25° C. for 3 hrs. On completion, the reaction mixture was filtered and concentrated in vacuo to give a residue. The residue was purified by prep-HPLC (column: Phenomenex luna C18 250*50 mm*15 um; mobile phase: [water (FA)-ACN]; B %: 60%-85%, 22 minutes) to give the title compound (760 mg, 24% yield) as yellow oil. $^1$H NMR (400 MHz, CDCl$_3$) δ 7.39-7.34 (m, 4H), 7.34-7.29 (m, 1H), 5.13 (s, 2H), 4.11 (d, J=13.2 Hz, 2H), 3.79 (s, 2H), 3.47-3.41 (m, 1H), 3.30-3.22 (m, 4H), 2.75-2.65 (m, 2H), 1.80 (s, 2H), 1.72 (dd, J=3.2, 8.8 Hz, 3H), 1.60-1.56 (m, 2H), 1.46 (s, 9H), 1.19-1.08 (m, 2H). LC-MS (ESI$^+$) m/z 433.1 (M+H)$^+$.

Step 4 Benzyl 4-(4-piperidylmethoxy)piperidine-1-carboxylate

To a solution of tert-butyl 4-[(1-benzyloxycarbonyl-4-piperidyl)oxymethyl]piperidine-1-carboxylate (650 mg, 1.50 mmol) in DCM (3 mL) was added TFA (4.62 g, 40.5 mmol, 3 mL). The mixture was stirred at 25° C. for 1 hr. On completion, the reaction mixture was concentrated in vacuo to give the title compound (600 mg, 90% yield, TFA salt) as yellow oil. LC-MS (ESI$^+$) m/z 333.1 (M+H)$^+$.

3-[3-methyl-2-oxo-4-[4-(4-piperidyloxymethyl)-1-piperidyl]benzimidazol-1-yl]piperidine-2,6-dione (Intermediate IT)

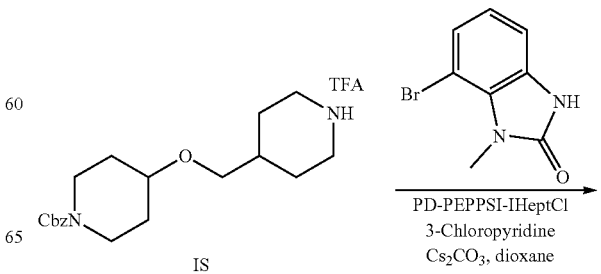

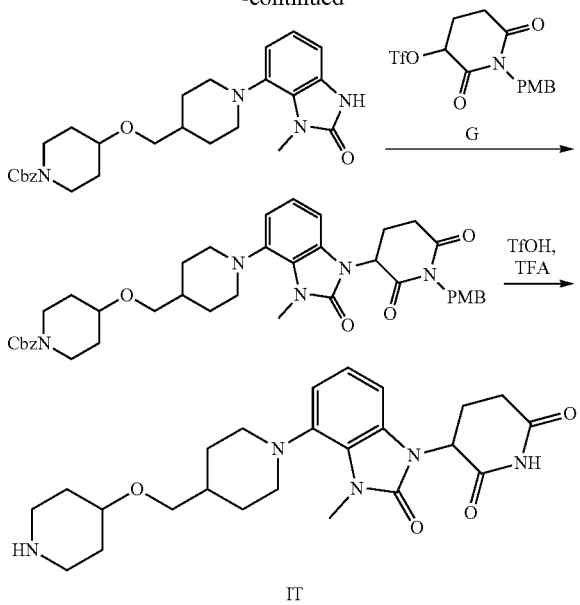

Step 1—Benzyl 4-[[1-(3-methyl-2-oxo-1H-benzimidazol-4-yl)-4-piperidyl]methoxy] piperidine-1-carboxylate A mixture of benzyl 4-(4-piperidylmethoxy)piperidine-1-carboxylate (250 mg, 752 umol, Intermediate IS), 4-bromo-3-methyl-1H-benzimidazol-2-one (239 mg, 1.05 mmol, synthesized via Steps 1-3 of Intermediate H), $Cs_2CO_3$ (1.47 g, 4.51 mmol), and 1,3-bis[2,6-bis(1-ethylpropyl)phenyl]-4,5-dichloro-2H-imidazol-1-ium-2-ide;3-chloropyridine; dichloropalladium (64.7 mg, 75.2 umol) in dioxane (3 mL) was degassed and purged with $N_2$ three times. Then the mixture was stirred at 100° C. for 12 hrs under $N_2$ atmosphere. On completion, the mixture was filtered and concentrated in vacuo to give a residue. The residue was purified by prep-HPLC (column: YMC Triart C18 250*50 mm*7 um; mobile phase: [water (FA)-A CN]; B %: 70%-80%, 23 minutes) to give the title compound (170 mg, 24% yield) as yellow oil. $^1$H NMR (400 MHz, $CDCl_3$) δ 9.29 (s, 1H), 7.41-7.29 (m, 5H), 7.02-6.96 (m, 1H), 6.87 (dd, J=8.0, 12.0 Hz, 2H), 5.14 (s, 2H), 3.78 (s, 2H), 3.75 (s, 3H), 3.53-3.45 (m, 1H), 3.38 (d, J=4.8 Hz, 2H), 3.31-3.24 (m, 2H), 3.20 (d, J=10.0 Hz, 2H), 2.79-2.67 (m, 2H), 1.88 (d, J=12.0 Hz, 5H), 1.74-1.59 (m, 2H), 1.51-1.39 (m, 2H). LC-MS ($ESI^+$) m/z 479.4 $(M+H)^+$.

Step 2—Benzyl 4-[[1-[1-[1-[(4-methoxyphenyl)methyl]-2, 6-dioxo-3-piperidyl]-3-methyl-2-oxo-benzimidazol-4-yl]-4-piperidyl]methoxy]piperidine-1-carboxylate To a solution of benzyl 4-[[1-(3-methyl-2-oxo-1H-benzimidazol-4-yl)-4-piperidyl]methoxy] piperidine-1-carboxylate (70 mg, 146 umol) in THF (1 mL) was added t-BuOK (29.5 mg, 263 umol) and [1-[(4-methoxyphenyl)methyl]-2, 6-dioxo-3-piperidyl] trifluoromethanesulfonate (72.5 mg, 190 umol, Intermediate G). The mixture was stirred at −10° C. for 12 hrs. On completion, the mixture was quenched with $NH_4Cl$ (1 mL), diluted with $H_2O$ (8 mL), and extracted with EA (2×5 mL). The combined organic layer was washed with brine (2×3 mL), dried over anhydrous $Na_2SO_4$, filtered and concentrated in vacuo to give the title compound (100 mg, 97% yield) as a green solid. LC-MS ($ESI^+$) m/z 710.4 $(M+H)^+$.

Step 3—3-[3-Methyl-2-oxo-4-[4-(4-piperidyloxymethyl)-1-piperidyl]benzimidazol-1-yl]piperidine-2,6-dione To a solution of benzyl 4-[[1-[1-[1-[(4-methoxyphenyl)methyl]-2, 6-dioxo-3-piperidyl]-3-methyl-2-oxo-benzimidazol-4-yl]-4-piperidyl]methoxy]piperidine-1-carboxylate (100 mg, 141 umol) in TFA (1 mL) was added TfOH (21.1 mg, 141 umol, 12.5 uL). The mixture was stirred at 70° C. for 2 hrs. On completion, the reaction mixture was filtered and concentrated in vacuo to give a residue. The residue was purified by prep-HPLC (column: Phenomenex Luna C18 200*40 mm*10 um; mobile phase: [water (FA)-ACN]; B %: 5%-35%, 10 minutes) to give the title compound (20 mg, 32% yield) as a white solid. L C-MS ($ESI^+$) m/z 456.2 $(M+H)^+$.

Tert-butyl N-[2-(4-piperidylmethoxy)ethyl]carbamate (Intermediate IU)

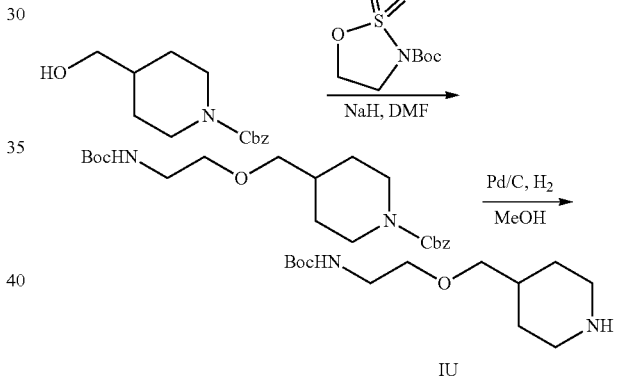

Step 1—Benzyl 4-[2-(tert-butoxycarbonylamino) ethoxymethyl]piperidine-1-carboxylate A mixture of benzyl 4-(hydroxymethyl)piperidine-1-carboxylate (2.00 g, 8.02 mmol, CAS #122860-33-7), NaH (641 mg, 16.0 mmol) in DMF (10 mL) was degassed and purged with $N_2$ three times. Then the mixture was stirred at 25° C. for 0.5 hour under $N_2$ atmosphere, then tert-butyl 2,2-dioxooxathiazolidine-3-carboxylate (3.94 g, 17.6 mmol, CAS #459817-82-4) was added into the mixture. The mixture was stirred at 25° C. for 2.5 hours under $N_2$. On completion, the reaction mixture was quenched with $H_2O$ (10 mL) at 25° C., and then extracted with EA (3×10 mL). The combined organic layers were washed with brine (2×10 mL), dried over anhydrous $Na_2SO_4$, filtered and concentrated in vacuo to give a residue. The residue was purified by column chromatography ($SiO_2$, Petroleum ether/Ethyl acetate=100/1 to 3/1) to give the title compound (1.20 g, 38.1% yield) as yellow oil. $^1$H NMR (400 MHz, DMSO-$d_6$) δ 7.40-7.26 (m, 5H) 6.74 (d, J=5.2 Hz, 1H) 5.06 (s, 2H) 4.00 (d, J=13.2 Hz, 2H) 3.37-3.30 (m, 3H) 3.22 (d, J=6.4 Hz, 2H)

3.06 (d, J=6.0 Hz, 2H) 2.81-2.75 (m, 1H) 1.69 (s, 1H) 1.64 (d, J=12.8 Hz, 2H) 1.37 (s, 9H) 1.09-0.99 (m, 2H).

Step 2—Tert-butyl N-[2-(4-piperidylmethoxy)ethyl]carbamate

To a solution of benzyl 4-[2-(tert-butoxycarbonylamino)ethoxymethyl]piperidine-1-carboxylate (1.20 g, 3.06 mmol) in MeOH (2 mL) was added Pd/C (361 mg, 305 umol) under N₂ atmosphere. The suspension was degassed and purged with H₂ three times. The mixture was stirred under H₂ at 25° C. for 12 hrs. On completion, the reaction mixture was filtered and concentrated in vacuo to give the title compound (780 mg, 99% yield) as colorless oil. ¹H NMR (400 MHz, CDCl₃) 4.86 (s, 1H) 3.46 (d, J=4.8 Hz, 3H) 3.34-3.22 (m, 4H) 3.09 (d, J=12.4 Hz, 1H) 2.61 (d, J=1.6 Hz, 1H) 1.99-1.77 (m, 1H) 1.74-1.69 (m, 4H) 1.45 (s, 9H) 1.30-1.11 (m, 2H).

1-[4-[4-(2-Aminoethoxymethyl)-1-piperidyl]phenyl] hexahydropyrimidine-2,4-dione (Intermediate IV)

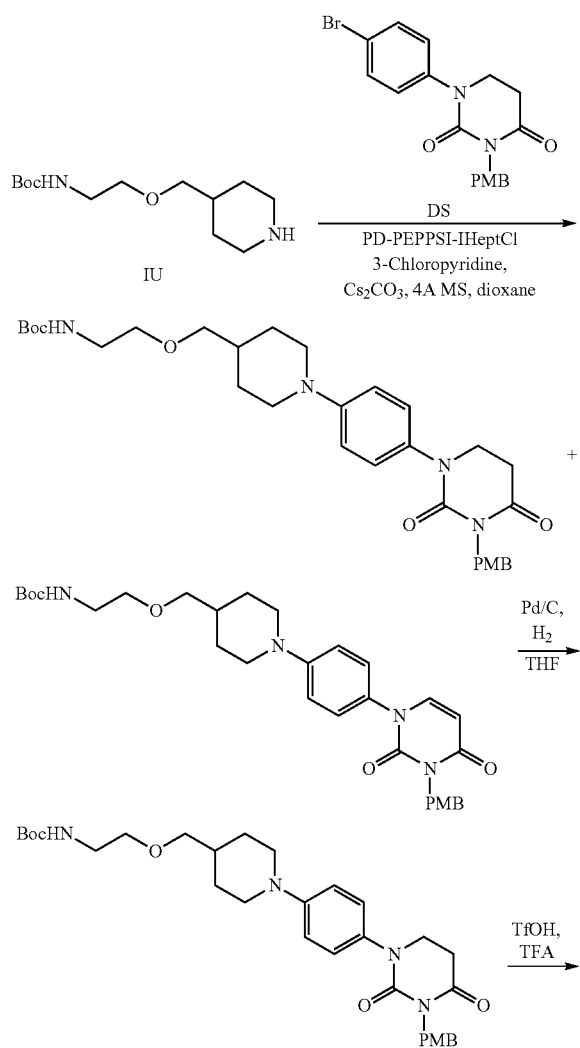

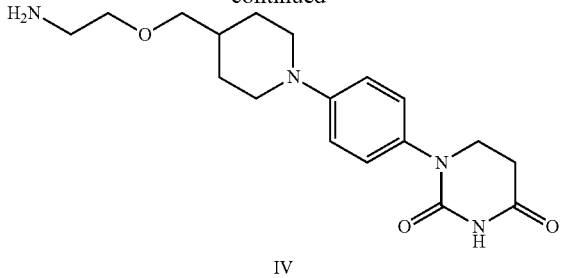

Step 1—Tert-butyl N-[2-[[1-[4-[3-[(4-methoxyphenyl)methyl]-2,4-dioxo-hexahydropyrimidin-1-yl]phenyl]-4-piperidyl]methoxy]ethyl]carbamate and tert-butyl N-[2-[[1-[4-[3-[(4-methoxyphenyl)methyl]-2,4-dioxo-pyrimidin-1-yl]phenyl]-4-piperidyl]methoxy]ethyl]carbamate A mixture of 1-(4-bromophenyl)-3-[(4-methoxyphenyl)methyl]hexahydropyrimidine-2,4-dione (607 mg, 1.56 mmol, Intermediate DS), tert-butyl N-[2-(4-piperidylmethoxy)ethyl]carbamate (310 mg, 1.20 mmol, Intermediate IU), 1,3-bis[2,6-bis(1-propylbutyl)phenyl]-4,5-dichloro-2H-imidazol-1-ium-2-ide;3-chloropyridine;dichloropalladium (116 mg, 119 umol), Cs₂CO₃ (781 mg, 2.40 mmol) and 4 Å molecular sieves (2.00 mg) in dioxane (5 mL) was degassed and purged with N₂ three times. Then the mixture was stirred at 100° C. for 16 hrs under N₂ atmosphere. On completion, the reaction mixture was filtered and concentrated in vacuo to give a residue. Then the residue was purified by prep-HPLC (column: Phenomenex C18 150*25 mm*10 um; mobile phase: [water(NH₄HCO₃)-ACN]; B %: 40%-70%, 8 min) to give the cru de product as a mixture of the title compounds (260 mg, 38% yield) as a white solid. LC-MS (ESI⁺) m/z (565.4 and 567.4) (M+H)⁺.

Step 2—Tert-butyl N-[2-[[1-[4-[3-[(4-methoxyphenyl)methyl]-2,4-dioxo-hexahydropyrimidin-1-yl]phenyl]-4-piperidyl]methoxy]ethyl]carbamate To a solution of tert-butyl N-[2-[[1-[4-[3-[(4-methoxyphenyl)methyl]-2,4-dioxo-pyrimidin-1-yl]phenyl]-4-piperidyl]methoxy]ethyl]carbamate (260 mg, 460 umol) in THF (2 mL) was added Pd/C (542 mg, 460 umol) under N₂. The suspension was degassed under vacuum and purged with H₂ three times. The mixture was stirred under H₂ at 25° C. for 16 hrs. On completion, the reaction mixture was filtered and concentrated in vacuo to give a residue. Then the residue was purified by prep-HPLC (column: Welch Ultimate C18 150*25 mm*5 um; mobile phase: [water(TFA)-ACN]; B %: 25%-55%, 10 min) to give the title compound (200 mg, 74% yield) as colorless oil. LC-MS (ESI⁺) m/z 567.3 (M+H)⁺.

Step 3—1-[4-[4-(2-Aminoethoxymethyl)-1-piperidyl]phenyl]hexahydropyrimidine-2,4-di one To a solution of tert-butyl N-[2-[[1-[4-[3-[(4-methoxyphenyl)methyl]-2,4-dioxo-hexahydropyrimidin-1-yl]phenyl]-4-piperidyl]methoxy]ethyl]carbamate (200 mg, 352 umol) in TFA (2 mL) was added TfOH (680 mg, 4.53 mmol). The mixture was stirred at 70° C. for 1 hour. On completion, the reaction mixture was filtered and concentrated in vacuo to give the title compound (122 mg, quant. yield) as colorless oil. LC-MS (ESI+) m/z 346.9 (M+H)+.

Tert-butyl N-[2-[2-(4-piperidylmethoxy)ethoxy]ethyl]carbamate (Intermediate IW)

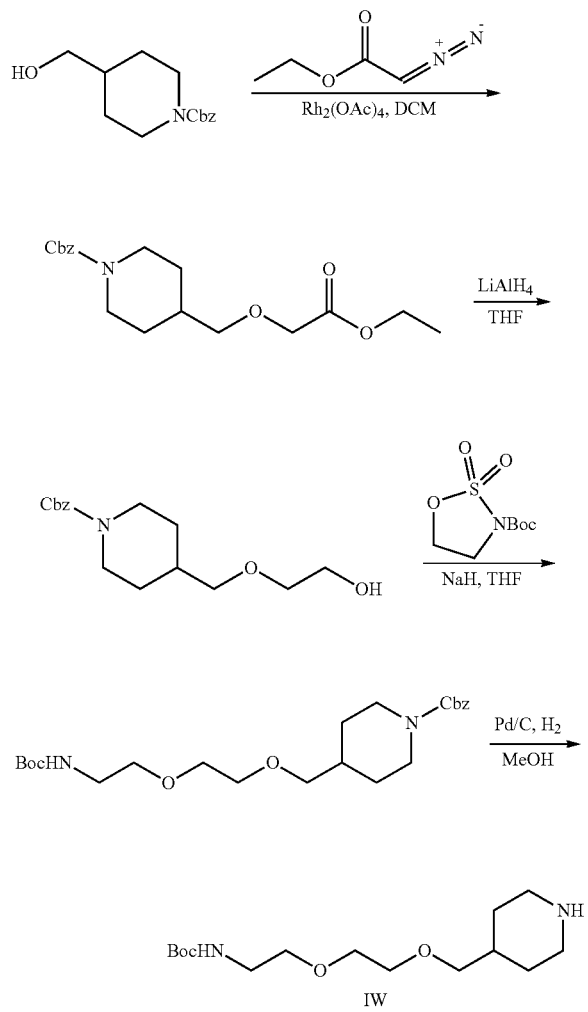

Step 1—Benzyl 4-[(2-ethoxy-2-oxo-ethoxy)methyl]piperidine-1-carboxylate

To a solution of ethyl 2-diazoacetate (1.37 g, 12.0 mmol) and benzyl 4-(hydroxymethyl)piperidine-1-carboxylate (1 g, 4.01 mmol, CAS #122860-33-7) in DCM (10 mL) was added Rh$_2$(OAc)$_4$ (178 mg, 401 umol). The mixture was stirred at 25° C. for 16 hrs. On completion, the mixture was diluted with H$_2$O (20 mL) and extracted with DCM (20 mL×3). The combined organic layers were washed with brine (2×10 mL), dried over anhydrous Na$_2$SO$_4$, filtered and concentrated in vacuo to give a residue. The residue was purified by column chromatography (SiO$_2$, PE/EA=100/1 to 8/1) to give a crude product. The crude product was purified by reversed-phase (0.1% FA condition) to give the title compound (1.00 g, 64% yield) as colorless oil. $^1$H NMR (400 MHz, DMSO-d$_6$) δ 7.40-7.28 (m, 5H), 5.06 (s, 2H), 4.13-4.07 (m, 2H), 3.99 (d, J=13.2 Hz, 2H), 3.31 (d, J=6.4 Hz, 2H), 2.79 (s, 2H), 1.80-1.70 (m, 1H), 1.66 (d, J=13.6 Hz, 2H), 1.19 (t, J=7.2 Hz, 3H), 1.10-1.00 (m, 2H).

Step 2—Benzyl 4-(2-hydroxyethoxymethyl)piperidine-1-carboxylate

A mixture of benzyl 4-[(2-ethoxy-2-oxo-ethoxy)methyl]piperidine-1-carboxylate (900 mg, 2.68 mmol) in THF (10 mL) and LiAlH$_4$ (153 mg, 4.03 mmol) was added the mixture at 0° C. After 10 minutes, the cooling bath was removed and after stirring at 25° C. for 20 minutes. Then the mixture was stirred at 25° C. for 2 hrs under N$_2$ atmosphere. On completion, the mixture was quenched with H$_2$O (1 mL) at 0° C., then diluted with solution of 15% NaOH (1 mL). The mixture was dried with anhydrous Na$_2$SO$_4$, filtered and the filtered liquor was concentrated in vacuo to give a residue (800 mg, 87% yield) as colorless oil. $^1$H NMR (400 MHz, DMSO-d$_6$) δ 7.41-7.28 (m, 5H), 5.06 (s, 2H), 4.60-4.46 (m, 1H), 4.00 (d, J=13.2 Hz, 2H), 3.48 (d, J=4.4 Hz, 1H), 3.40-3.34 (m, 2H), 3.33 (s, 1H), 3.24 (d, J=6.4 Hz, 2H), 2.87-2.67 (m, 2H), 1.77-1.69 (m, 1H), 1.66 (d, J=12.8 Hz, 2H), 1.10-1.02 (m, 2H).

Step 3—Benzyl 4-[2-[2-(tert-butoxycarbonylamino)ethoxy]ethoxymethyl]piperidine-1-carboxylate To a solution of benzyl 4-(2-hydroxyethoxymethyl)piperidine-1-carboxylate (800 mg, 2.73 mmol) and tert-butyl 2,2-dioxooxathiazolidine-3-carboxylate (1.03 g, 4.64 mmol, CAS #459817-82-4) in THF (8 mL) was added NaH (219 mg, 5.45 mmol, 60% dispersion in mineral oil). The mixture was stirred at 25° C. for 3 hrs. On completion, the mixture was quenched with H$_2$O (1 mL) at 0° C., and then diluted with H$_2$O (10 mL) and extracted with EA (3×15 mL). The combined organic layers were washed with brine (2×10 mL), dried over anhydrous Na$_2$SO$_4$, filtered and concentrated in vacuo to give a residue. The residue was purified by prep-HPLC (column: Phenomenex luna C18 250*50 mm*15 um; mobile phase: [water (FA)-ACN]; B %: 55%-75%, 28 minutes) to give the title compound (300 mg, 26% yield) as a white solid. $^1$H NMR (400 MHz, CDCl$_3$) δ 7.38-7.35 (m, 4H), 7.32 (dd, J=4.0, 4.8 Hz, 1H), 7.27 (s, 1H), 5.13 (s, 2H), 4.20 (d, J=7.2 Hz, 2H), 3.61-3.53 (m, 6H), 3.32 (d, J=6.0 Hz, 4H), 2.83-2.74 (m, 2H), 1.80 (dd, J=6.8, 3.6 Hz, 1H), 1.75 (d, J=13.2 Hz, 2H), 1.45 (s, 9H), 1.21-1.10 (m, 2H). LC-MS (ESI+) m/z 437.4 (M+H)+.

Step 4—Tert-butyl N-[2-[2-(4-piperidylmethoxy)ethoxy]ethyl]carbamate

To a solution of benzyl 4-[2-[2-(tert-butoxycarbonylamino)ethoxy]ethoxymethyl]piperidine-1-carboxylate (300 mg, 687 umol) in MeOH (3 mL) was added Pd/C (407 mg, 344 umol, 10 wt %) under N$_2$. The suspension was degassed under vacuum and purged with H$_2$ several times. The mixture was stirred under H$_2$ (15 psi) at 25° C. for 12 hrs. On completion, the mixture was filtered and concentrated under reduced pressure to give the title compound (200 mg, 96% yield) as yellow oil. $^1$H NMR (400 MHz, CDCl$_3$) δ 5.07-4.89 (m, 1H), 3.64-3.59 (m, 2H), 3.58-3.54 (m, 4H), 3.36-3.30 (m, 4H), 3.09 (dd, J=12.4, 2.8 Hz, 1H), 2.76-2.58 (m, 1H), 1.99-1.84 (m, 1H), 1.76-1.71 (m, 2H), 1.61 (d, J=2.0 Hz, 1H), 1.45 (s, 9H), 1.34-1.22 (m, 1H), 1.22-1.08 (m, 2H).

1-[4-[4-[2-(2-Aminoethoxy)ethoxymethyl]-1-piperidyl]phenyl]hexahydropyrimidine-2,4-dione (Intermediate IX)

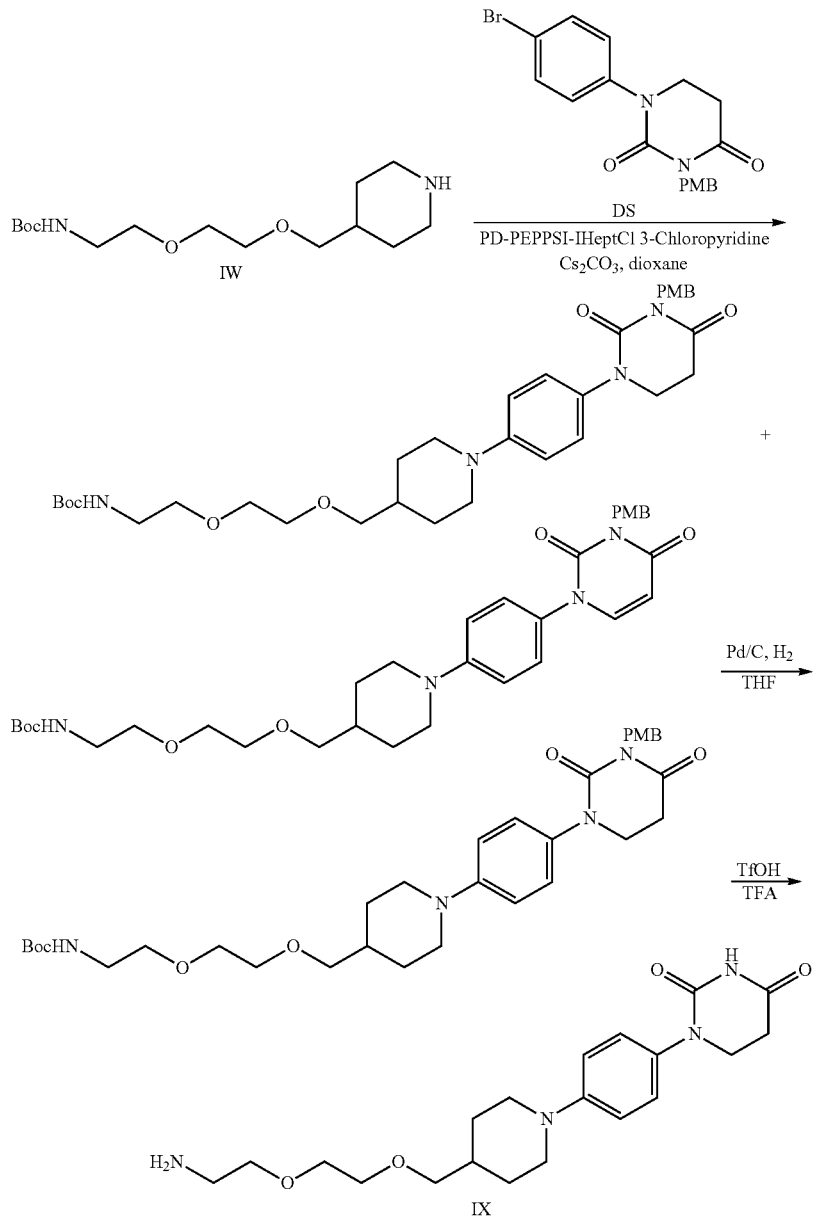

Step 1—Tert-butylN-[2-[2-[[1-[4-[3-[(4-methoxyphenyl)methyl]-2,4-dioxo-hexahydropyrimidin-1-yl]phenyl]-4-piperidyl]methoxy]ethoxy]ethyl]carbamate and tert-butylN-[2-[2-[[1-[4-[3-[(4-methoxyphenyl)methyl]-2,4-dioxo-pyrimidin-1-yl]phenyl]-4-piperidyl]methoxy]ethoxy]ethyl]carbamate A mixture of tert-butyl N-[2-[2-(4-piperidylmethoxy)ethoxy]ethyl]carbamate (150 mg, 496 umol, Intermediate IW), 1-(4-bromophenyl)-3-[(4-methoxyphenyl)methyl]hexahydropyrimidine-2,4-dione (232 mg, 595 umol, Intermediate DS), 1,3-bis[2,6-bis(1-ethylpropyl)phenyl]-4,5-dichloro-2H-imidazol-1-ium-2-ide; 3-chloropyridine;dichloropalladium (42.7 mg, 49.6 umol), and $Cs_2CO_3$ (323 mg, 992 umol) in dioxane (1 mL) was degassed and purged with $N_2$ three times. Then the mixture was stirred at 100° C. for 12 hrs under $N_2$ atmosphere. On completion, the mixture was filtered and concentrated in vacuo to give a residue. The residue was purified by prep-HPLC (column: Phenomenex C18 250*50 mm*10 um; mobile phase: [water ($NH_4HCO_3$)-ACN]; B %: 41%-71%, 8 minutes) to give the crude product as a mixture of the title compounds (140 mg, 47% yield) as a yellow solid. LC-MS (ESI$^+$) m/z (609.4 and 611.3) (M+H)$^+$.

915

Step 2—Tert-butyl N-[2-[2-[[1-[4-[3-[(4-methoxy-phenyl)methyl]-2,4-dioxo-hexahydropyrimidin-1-yl]phenyl]-4-piperidyl]methoxy]ethoxy]ethyl]carbamate To a solution of tert-butyl N-[2-[2-[[1-[4-[3-[(4-methoxy-phenyl) methyl]-2,4-dioxo-pyrimidin-1-yl]phenyl]-4-piperidyl]methoxy]ethoxy]ethyl]carbamate (140 mg, 230 umol) in THF (1 mL) was added Pd/C (272 mg, 10 wt %) under $N_2$. The suspension was degassed under vacuum and purged with $H_2$ several times. The mixture was stirred under $H_2$ (15 psi) at 25° C. for 12 hrs. On completion, the mixture was filtered and concentrated in vacuo to give a residue. The residue was purified by prep-HPLC (column: Welch Xtimate C18 150*25 mm*5 um; mobile phase: [water (TFA)-ACN]; B %: 22%-52%, 10 minutes) to give the title compound (80.0 mg, 55% yield) as a white solid. LC-MS (ESI$^+$) m/z 611.4 (M+H)$^+$ Step 3—1-[4-[4-[2-(2-Aminoethoxy)ethoxymethyl]-1-piperidyl]phenyl]hexahydropyrimidine-2,4-dione To a solution of tert-butyl N-[2-[2-[[1-[4-[3-[(4-methoxy-phenyl) methyl]-2,4-dioxo-hexahydropyrimidin-1-yl]phenyl]-4-piperidyl]methoxy]ethoxy]ethyl]carbamate (80 mg, 131 umol) in TFA (1 mL) was added TfOH (20 mg, 131 umol, 12.0 uL). The mixture was stirred at 70° C. for 2 hrs. On completion, the mixture was concentrated in vacuo to give the title compound (51 mg, 99% yield) as yellow oil. LC-MS (ESI$^+$) m/z 391.1 (M+H)$^+$.

4-[[6-(Cyclohexoxy)-9H-purin-2-yl]amino]-N,3-dimethyl-benzenesulfonamide (Intermediate IY)

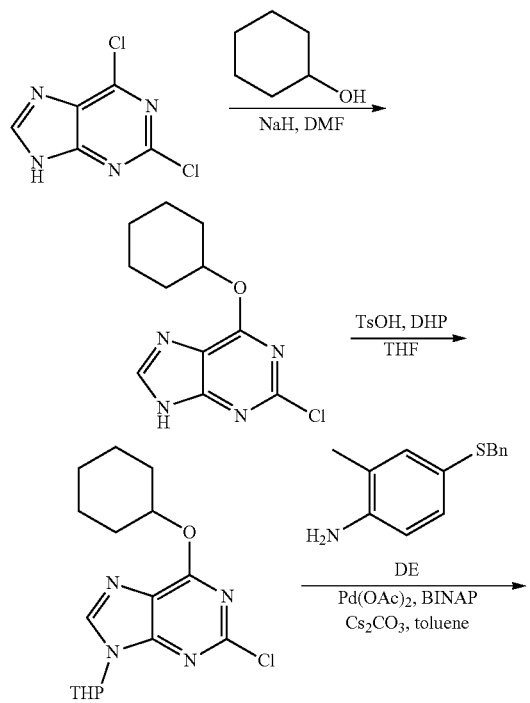

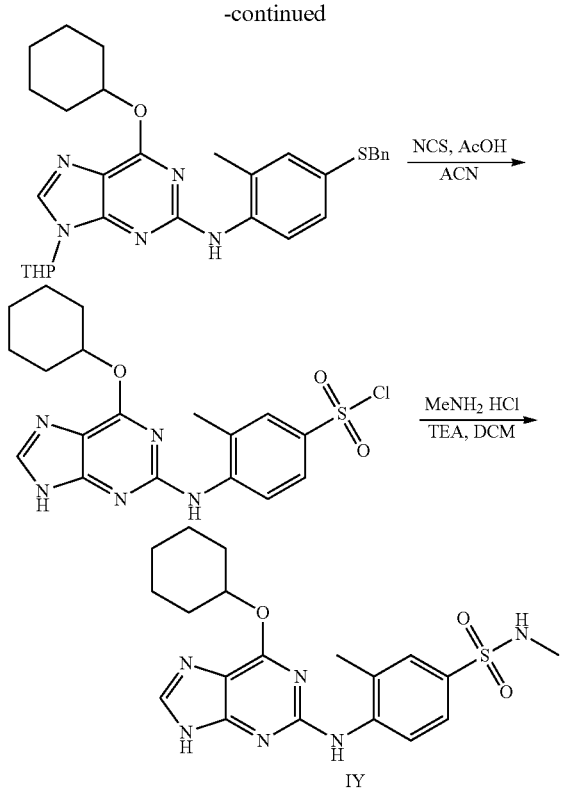

Step 1—2-Chloro-6-(cyclohexoxy)-9H-purine

To a solution of cyclohexanol (1.06 g, 10.5 mmol) in DMF (30 mL) was added NaH (846 mg, 21.1 mmol, 60% dispersion in mineral oil) 0° C. The reaction was stirred at 0° C. for 0.5 hr. Then, 2,6-dichloro-9H-purine (2.00 g, 10.58 mmol, CAS #5451-40-1) was added and the mixture was stirred at 25° C. for 16 hrs. On completion, the reaction was quenched with water (2 mL) at 0° C. The mixture was diluted with EA (100 mL) and washed with water (70 mL). Then, the water phase was filtered. The filtered cake was dried in vacuo to give the title compound (1.56 g, 58% yield) as white solid. LC-MS (ESI$^+$) m/z 252.8 (M+H)$^+$.

Step 2—2-chloro-6-(cyclohexoxy)-9-tetrahydropyran-2-yl-purine

A mixture of 2-chloro-6-(cyclohexoxy)-9H-purine (1.56 g, 6.17 mmol), DHP (1.04 g, 12.3 mmol) and TsOH (106 mg, 617 umol) in THF (22 mL) was stirred at 70° C. for 16 hrs. On completion, the reaction was diluted with EA (100 mL). The organic layer was washed with water (100 mL×3), dried over $Na_2SO_4$ and filtered. The filtrate was concentrated in vacuo. The residue was purified by column chromatography (SiO$_2$, Petroleum ether/Ethyl acetate=10/1 to 3/1) to give the title compound (1.6 g, 76% yield) as white solid. $^1$H NMR (400 MHz, DMSO-d$_6$) δ 8.61 (s, 1H), 5.74-5.60 (m, 1H), 5.37-5.24 (m, 1H), 4.01 (d, J=11.2 Hz, 1H), 3.83-3.63 (m, 1H), 2.30-2.18 (m, 1H), 2.08-1.91 (m, 4H), 1.81-1.69 (m, 3H), 1.64-1.52 (m, 5H), 1.49-1.37 (m, 2H), 1.36-1.25 (m, 1H).

Step 3—N-(4-benzylsulfanyl-2-methyl-phenyl)-6-(cyclohexoxy)-9-tetrahydropyran-2-yl-purin-2-amine A solution of 2-chloro-6-(cyclohexoxy)-9-tetrahydropyran-2-yl-purine (1.60 g, 4.75 mmol), 4-benzylsulfanyl-2- methyl-aniline (980 mg, 4.28 mmol, Intermediate DE), Pd(OAc)$_2$ (106 mg, 475 umol), BINAP (295 mg, 475 umol) and Cs$_2$CO$_3$ (4.64 g, 14.2 mmol) in toluene (25 mL) was stirred at 100° C. for 4 hrs under N$_2$. On completion, the reaction was diluted with EA (100 mL). The organic layer was washed with water (100 mL×2), dried over Na$_2$SO$_4$ and filtered. The filtrate was concentrated in vacuo. The residue was purified by column chromatography (SiO$_2$, Petroleum ether/Ethyl acetate=3/1 to 1/1) to give the title compound (1.6 g, 63% yield) as red solid. LC-MS (ESI$^+$) m/z 530.1 (M+H)$^+$.

Step 4—4-[[6-(Cyclohexoxy)-9H-purin-2-yl]amino]-3-methyl-benzenesulfonyl chloride To a solution of N-(4-benzylsulfanyl-2-methyl-phenyl)-6-(cyclohexoxy)-9-tetrahydropyran-2-yl-purin-2-amine (100 mg, 188 umol), H$_2$O (34.0 ug, 1.89 umol) in HOAc (0.3 mL) and ACN (0.9 mL) was added NCS (75.6 mg, 566 umol). The reaction was stirred at 25° C. for 1 hr under dark. On completion, the reaction was concentrated in vacuo to give the title compound (79.0 mg, 187 umol, 99% yield) as green oil. LC-MS (ESI$^+$) m/z 422.2 (M+H)$^+$.

Step 5—4-[[6-(cyclohexoxy)-9H-purin-2-yl]amino]-N,3-dimethyl-benzenesulfonamide

To a solution of methanamine;hydrochloride (18.9 mg, 280 umol) and TEA (94.7 mg, 936 umol) in DCM (2 mL) was added 4-[[6-(cyclohexoxy)-9H-purin-2-yl]amino]-3-methyl-benzenesulfonyl chloride (79.0 mg, 187 umol) at 0° C. The reaction was then stirred at 25° C. for 1 hr. On completion, the reaction was concentrated in vacuo. The residue was purified by prep-HPLC (column: Waters xbridge 150*25 mm 10 um; mobile phase: [water (NH$_4$HCO$_3$)-ACN]; B %: 26%-56%, 8 min) to give the title compound (14.0 mg, 18% yield) as white solid. $^1$H NMR (400 MHz, DMSO-d$_6$) δ 12.92-12.66 (m, 1H), 8.54 (s, 1H), 8.15-7.92 (m, 2H), 7.64-7.50 (m, 2H), 7.27 (q, J=5.2 Hz, 1H), 5.33-5.17 (m, 1H), 2.41 (d, J=5.2 Hz, 3H), 2.36 (s, 3H), 2.11-2.00 (m, 2H), 1.81-1.75 (m, 2H), 1.62-1.49 (m, 3H), 1.46-1.20 (m, 3H); LC-MS (ESI$^+$) m/z 417.0 (M+H)$^+$.

3-Methyl-4-[[4-(1-methylpyrazol-4-yl)-5-(trifluoromethyl)pyrimidin-2-yl]amino]benzenesulfonyl chloride (Intermediate IZ)

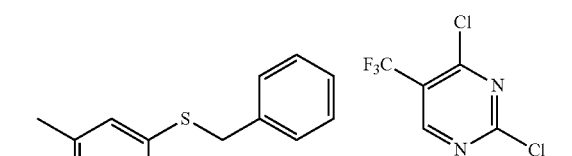

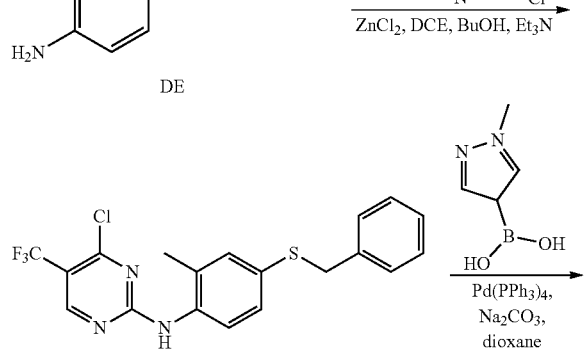

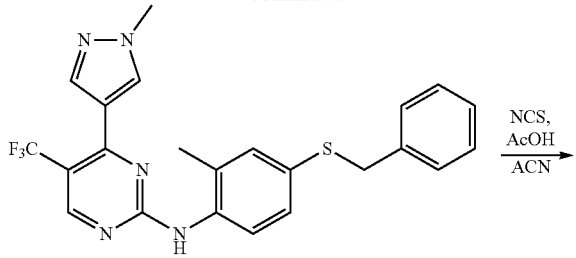

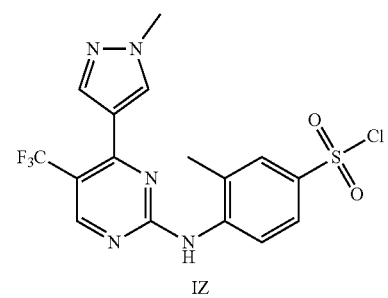

Step 1—N-(4-benzylsulfanyl-2-methyl-phenyl)-4-chloro-5-(trifluoromethyl)pyrimidin-2-amine To a solution of 2,4-dichloro-5-(trifluoromethyl)pyrimidine (1 g, 4.61 mmol, CAS #3932-97-6) in mixture solvent of t-BuOH (30 mL) and DCE (30 mL) was added ZnCl$_2$ (1 M, 5.53 mL) at 0° C. After 1 hour, a solution of 4-benzylsulfanyl-2-methyl-aniline (1.06 g, 4.61 mmol, Intermediate DE) and TEA (513 mg, 5.07 mmol) in mixture solvent of t-BuOH (15 mL) and DCE (15 mL) was added dropwise into the above solution. The mixture was stirred at 25° C. for 16 hrs. On completion, the mixture was quenched with ice water (100 ml) and extracted with DCM (90 ml×3). The combined organic phase was washed with H$_2$O (300 mL), dried over anhydrous sodium sulfate, filtered and concentrated to give a residue. The residue was purified by column chromatography (SiO$_2$, PE/EA=30/1 to 15/1) to give the title compound (1.7 g, 81% yield) as a white solid. $^1$H NMR (400 MHz, DMSO-d$_6$) δ 10.05 (s, 1H), 8.65 (s, 1H), 7.40-7.34 (m, 2H), 7.33-7.27 (m, 3H), 7.26-7.19 (m, 3H), 4.24 (s, 2H), 2.15 (s, 3H); LC-MS (ESI$^+$) m/z 409.8 (M+H)$^+$.

Step 2—N-(4-benzylsulfanyl-2-methyl-phenyl)-4-(1-methylpyrazol-4-yl)-5-(trifluoromethyl) pyrimidin-2-amine A mixture of N-(4-benzylsulfanyl-2-methyl-phenyl)-4-chloro-5-(trifluoromethyl)pyrimidin-2-amine (0.8 g, 1.95 mmol), (1-methylpyrazol-4-yl)boronic acid (491 mg, 3.90 mmol, CAS #847818-55-7), Pd(PPh$_3$)$_2$Cl$_2$ (137 mg, 195 umol) and Na$_2$CO$_3$ (2M, 2.73 mL) in dioxane (23 mL) was degassed and purged with N$_2$ three times. Then the mixture was stirred at 100° C. for 12 hrs under N$_2$ atmosphere. On completion, the mixture was quenched with ice water (100 ml) and extracted with DCM (50 ml×3). The combined organic phase was washed with H$_2$O (300 mL), dried over anhydrous sodium sulfate, filtered and concentrated to give a residue. The residue was purified by column chromatography (SiO$_2$, PE/EA=20/1 to 1/1) to give the title compound (0.8 g, 83% yield) as yellow solid. $^1$H NMR (400 MHz, DMSO-d$_6$) δ 9.43 (s, 1H), 8.62 (s, 1H), 8.15 (s, 1H), 7.86 (s, 1H), 7.42-7.35 (m, 3H), 7.33-7.27 (m, 2H), 7.26-7.17 (m, 3H), 4.23 (s, 2H), 3.92 (s, 3H), 2.18 (s, 3H); LC-MS (ESI$^+$) m/z 456.3 (M+H)$^+$.

Step 3—3-Methyl-4-[[4-(1-methylpyrazol-4-yl)-5-(trifluoromethyl)pyrimidin-2-yl]amino]benzenesulfonyl chloride To a solution of N-(4-benzylsulfanyl-2-methyl-phenyl)-4-(1-methylpyrazol-4-yl)-5-(trifluoromethyl) pyrimidin-2-amine (100 mg, 219 umol) in HOAc (0.4 mL) and ACN (1.2 mL) was added NCS (87.9 mg, 658 umol). The mixture was stirred at 25° C. for 1 hr. On completion, the mixture was concentrated to give the title compound (100 mg, 92% yield, HOAc) as a yellow oil. LC-MS (ESI$^+$) m/z 431.9 (M+H)$^+$.

4-[[4-Cyclohexyl-5-(trifluoromethyl) pyrimidin-2-yl]amino]-3-methyl-benzenesulfonyl chloride (Intermediate JA)

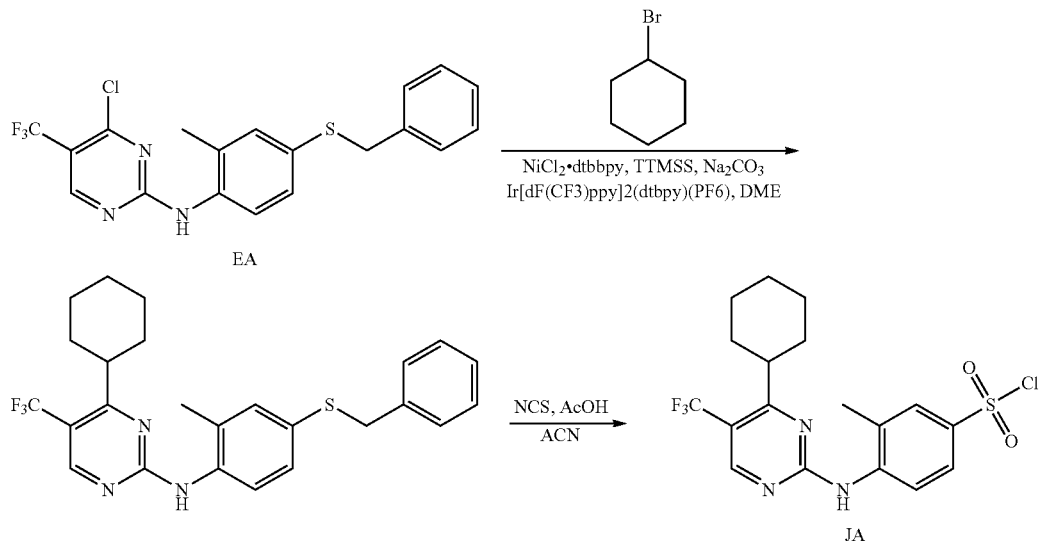

Step 1—N-(4-benzylsulfanyl-2-methyl-phenyl)-4-cyclohexyl-5-(trifluoromethyl) pyrimidin-2-amine To an 40 mL vial equipped with a stir bar was added N-(4-benzylsulfanyl-2-methyl-phenyl)-4-chloro-5-(trifluoromethyl)pyrimidin-2-amine (500 mg, 1.22 mmol, Intermediate EA) bromocyclohexane (258 mg, 1.59 mmol), TTMSS (303 mg, 1.22 mmol), NiCl$_2$·dtbbpy (7.28 mg, 18.3 umol), Ir[dF(CF$_3$)ppy]$_2$(dtbpy)(PF$_6$) (13.6 mg, 12.2 umol), and Na$_2$CO$_3$ (258 mg, 2.44 mmol) in DME (10 mL). The vial was sealed and placed under nitrogen. The reaction was stirred and irradiated with a 10 W blue LED lamp (3 cm away), with cooling water to keep the reaction temperature at 25° C. for 14 hr. On completion, the reaction mixture was concentrated in vacuo. The mixture was diluted with H$_2$O (20 mL) and extracted with DCM (20 mL×3). The combined organic layers were washed with saturated NaCl with H$_2$O (10 mL), dried over anhydrous Na$_2$SO$_4$, filtered and concentrated in vacuo to give a residue. The residue was purified by column chromatography (SiO$_2$, PE:EA=50:1 to 30:1) and reverse phase (0.1% FA condition) to give the title compound (215 mg, 38% yield) as a white solid. $^1$H NMR (400 MHz, DMSO-d$_6$) δ 9.40 (s, 1H), 8.53 (s, 1H), 7.37-7.33 (m, 2H), 7.32-7.26 (m, 2H), 7.26-7.19 (m, 2H), 7.15 (dd, J=2.0, 8.4 Hz, 1H), 4.22 (s, 2H), 3.30 (s, 1H), 2.74-2.71 (m, 1H), 2.16 (s, 3H), 1.78-1.75 (m, 2H), 1.70-1.65 (m, 3H), 1.62-1.48 (m, 2H), 1.37-1.13 (m, 3H). LC-MS (ESI$^+$) m/z 458.1 (M+H)$^+$.

Step 2—4-[[4-Cyclohexyl-5-(trifluoromethyl)pyrimidin-2-yl]amino]-3-methyl-benzenesulfonyl chloride To a solution of N-(4-benzylsulfanyl-2-methyl-phenyl)-4-cyclohexyl-5-(trifluoromethyl) pyrimidin-2-amine (60 mg, 131 umol) in HOAc (0.5 mL) and ACN (1.5 mL) was added NCS (52.5 mg, 393 umol). The mixture was stirred at 25° C. for 1 hr. On completion, the reaction mixture was concentrated in vacuo to give the title compound (60 mg, 98% yield) as a white solid. LC-MS (ESI$^+$) m/z 434.1 (M+H)$^+$.

Benzyl 4-[2-(4-piperidyl)ethyl]piperazine-1-carboxylate (Intermediate JB)

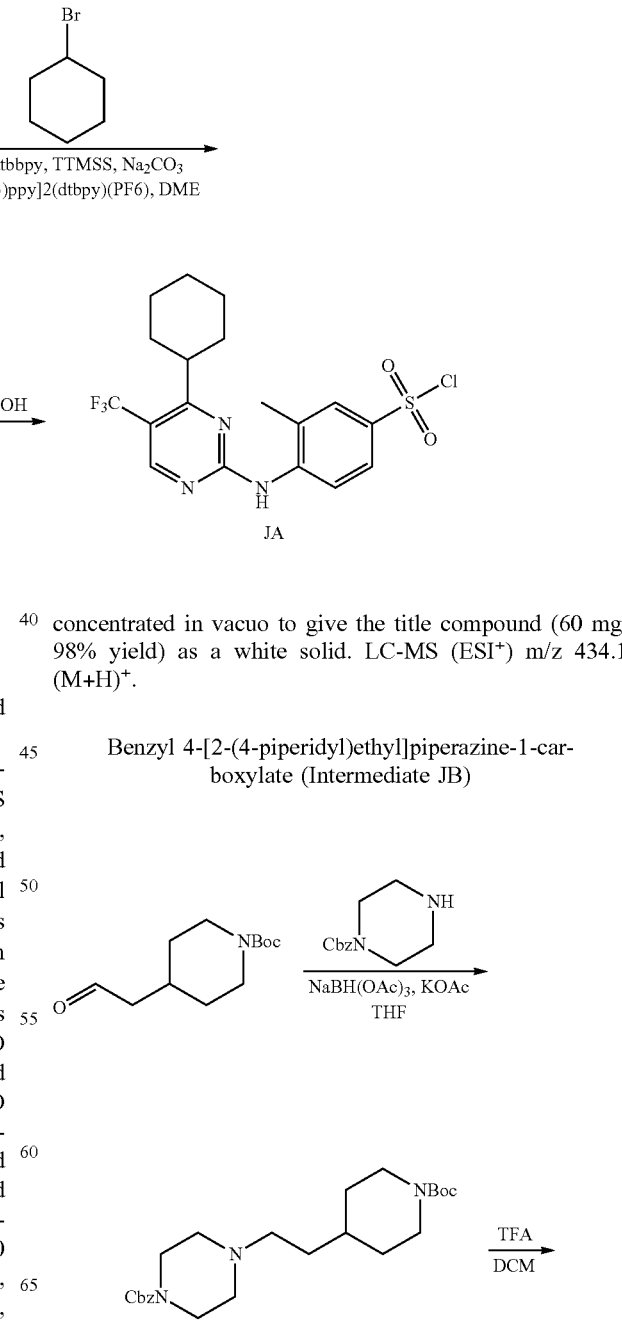

-continued

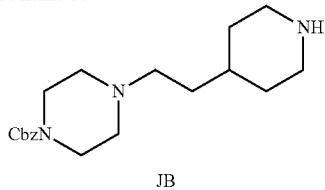

JB

Step 1—Tert-butyl 4-[2-(1-benzyloxycarbonyl-4-piperidyl)ethyl]piperazine-1-carboxylate To a solution of benzyl piperazine-1-carboxylate (1.02 g, 4.62 mmol, 893 uL, CAS #31166-44-6) in THF (10 mL) was added KOAc (4.32 g, 44.0 mmol) dropwise, and then tert-butyl 4-(2-oxoethyl) piperidine-1-carboxylate (1 g, 4.40 mmol, CAS #142374-19-4) was added at 0° C. After addition, the mixture was stirred at this temperature for 30 minutes, and then NaBH(OAc)$_3$ (1.86 g, 8.80 mmol) was added dropwise at 0° C. The resulting mixture was stirred at 0° C. for 1.5 hours. On completion, the mixture was diluted with H$_2$O (20 mL) and extracted with EA (20 mL×3). The combined organic layers were washed with brine (2×10 mL), dried over anhydrous Na$_2$SO$_4$, filtered and concentrated in vacuo to give a residue. The residue was purified by column chromatography (SiO$_2$, Petroleum ether/Ethyl acetate=100/1 to 5/1) to give the title compound (2.0 g, 88% yield, HOAc salt) as a colorless oil. $^1$H NMR (400 MHz, CDCl$_3$) δ 7.38-7.31 (m, 5H), 5.13 (s, 2H), 4.08 (d, J=12.0 Hz, 2H), 3.59 (t, J=4.8 Hz, 4H), 2.67 (t, J=12.0 Hz, 2H), 2.58-2.48 (m, 6H), 1.63 (d, J=12.4 Hz, 2H), 1.47 (s, 3H), 1.45 (s, 9H), 1.17-1.05 (m, 2H). LC-MS (ESI$^+$) m/z 432.5 (M+H)$^+$.

Step 2—Benzyl 4-[2-(4-piperidyl)ethyl]piperazine-1-carboxylate

To a solution of benzyl 4-[2-(1-tert-butoxycarbonyl-4-piperidyl)ethyl]piperazine-1-carboxylate (2 g, 4.07 mmol, HOAc) in DCM (10 mL) was added TFA (13.5 g, 119 mmol, 8.80 mL). The mixture was stirred at 25° C. for 1 hr. On completion, the mixture was concentrated in vacuo to give the title compound (1.8 g, 99% yield, TFA salt) as a white solid. LC-MS (ESI$^+$) m/z 332.4 (M+H)$^+$.

3-[3-Methyl-2-oxo-4-[4-(2-piperazin-1-ylethyl)-1-piperidyl]benzimidazol-1-yl]piperidine-2,6-dione (Intermediate JC)

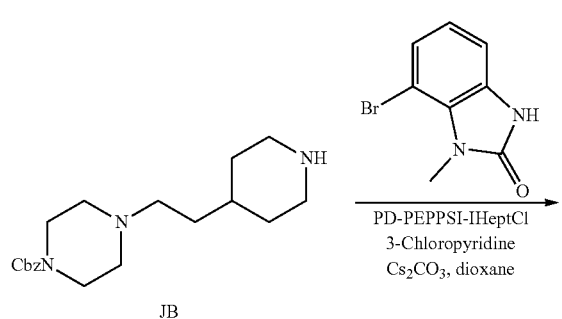

-continued

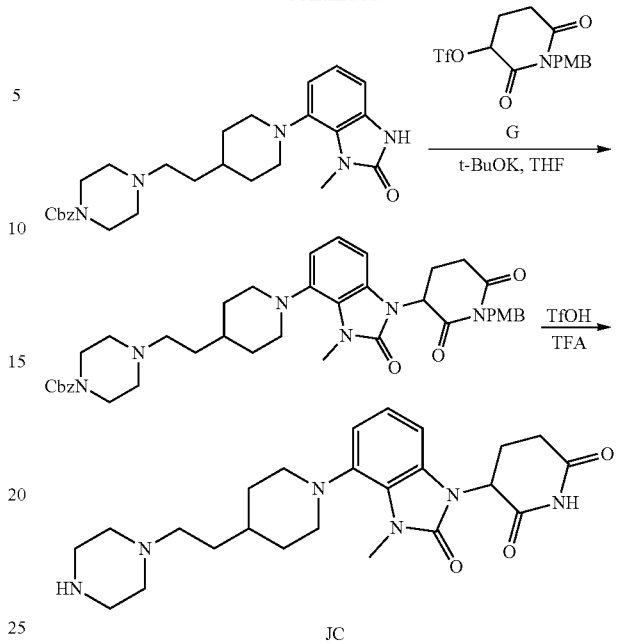

JC

Step 1—Benzyl 4-[2-[1-(3-methyl-2-oxo-1H-benzimidazol-4-yl)-4-piperidyl]ethyl]piperazine-1-carboxylate A mixture of benzyl 4-[2-(4-piperidyl)ethyl]piperazine-1-carboxylate (100 mg, 225 umol, TFA, Intermediate JB), 4-bromo-3-methyl-1H-benzimidazol-2-one (51.0 mg, 225 umol, synthesized via Steps 1-3 of Intermediate H), Cs$_2$CO$_3$ (439 mg, 1.35 mmol, 1,3-bis[2,6-bis(1-ethylpropyl)phenyl]-4,5-dichloro-2H-imidazol-1-ium-2-ide;3-chloropyridine;dichloropalladium (9.66 mg, 11.2 umol, CAS #1435347-24-2) in dioxane (4 mL) was degassed and purged with N$_2$ three times. Then the mixture was stirred at 110° C. for 12 hrs under N$_2$ atmosphere. On completion, the mixture was filtered and concentrated in vacuo to give a residue. The residue was purified by prep-HPLC (column: Phenomenex luna C18 250*50 mm*15 um; mobile phase: [water (FA)-ACN]; B %: 20%-60%, 25 minutes) to give the title compound (50 mg, 43% yield) as a yellow solid. $^1$H NMR (400 MHz, DMSO-d$_6$) δ 10.68 (s, 1H), 8.04 (s, 1H), 7.32-7.12 (m, 5H), 6.81-6.74 (m, 1H), 6.66 (d, J=7.6 Hz, 1H), 6.60 (dd, J=0.8, 7.6 Hz, 1H), 4.96 (s, 2H), 3.43 (s, 3H), 3.31 (s, 4H), 2.94 (d, J=11.2 Hz, 2H), 2.41-2.36 (m, 2H), 2.36-2.27 (m, 6H), 1.62 (d, J=10.0 Hz, 2H), 1.36-1.23 (m, 4H). LC-MS (ESI$^+$) m/z 478.2 (M+H)$^+$.

Step 2—Benzyl 4-[2-[1-[1-[1-[(4-methoxyphenyl)methyl]-2,6-dioxo-3-piperidyl]-3-methyl-2-oxo-benzimidazol-4-yl]-4-piperidyl]ethyl]piperazine-1-carboxylate To a solution of benzyl 4-[2-[1-(3-methyl-2-oxo-1H-benzimidazol-4-yl)-4-piperidyl]ethyl] piperazine-1-carboxylate (300 mg, 628 umol) in THF (5 mL) was added t-BuOK (127 mg, 1.13 mmol). After addition, the mixture was stirred at this temperature for 30 minutes, and then [1-[(4-methoxyphenyl) methyl]-2,6-dioxo-3-piperidyl] trifluoromethanesulfonate (431 mg, 1.13 mmol, Intermediate G) was added dropwise at −10° C. The mixture was then stirred at −10° C.

for 12 hrs. On completion, the mixture was quenched with NH₄Cl (1 mL), diluted with H₂O (8 mL), and extracted with EA (2×5 mL). Then the organic layer was washed with brine (2×3 mL), dried with anhydrous Na₂SO₄ and concentrated in vacuo to give a residue. The crude product was purified by reversed-phase HPLC (0.1% FA condition) to give the title compound (350 mg, 77% yield) as a yellow solid. ¹H NMR (400 MHz, DMSO-d₆) δ 7.42-7.28 (m, 5H), 7.21 (d, J=8.8 Hz, 2H), 6.95-6.89 (m, 2H), 6.89-6.84 (m, 2H), 6.76 (s, 1H), 5.50 (dd, J=5.2, 12.8 Hz, 1H), 5.08 (s, 2H), 4.88-4.73 (m, 2H), 3.73 (s, 3H), 3.62 (s, 3H), 3.40 (s, 4H), 3.08 (d, J=11.6 Hz, 2H), 2.86-2.75 (m, 2H), 2.74-2.62 (m, 4H), 2.35 (d, J=4.0 Hz, 6H), 2.08-1.98 (m, 1H), 1.77 (d, J=10.4 Hz, 2H), 1.50-1.37 (m, 4H). LC-MS (ESI⁺) m/z 709.4 (M+H)⁺.

Step 3—3-[3-Methyl-2-oxo-4-[4-(2-piperazin-1-ylethyl)-1-piperidyl]benzimidazol-1-yl]piperidine-2,6-dione To a solution of benzyl 4-[2-[1-[1-[1-[(4-methoxyphenyl)methyl]-2,6-dioxo-3-piperidyl]-3-methyl-2-oxo-benzimidazol-4-yl]-4-piperidyl]ethyl]piperazine-1-carboxylate (350 mg, 494 umol) in TFA (2 mL) was added TfOH (578 mg, 3.85 mmol, 0.34 mL). The mixture was stirred at 70° C. for 2 hrs. On completion, the mixture was concentrated in vacuo to give the title compound (224 mg, 99% yield) as yellow solid. LC-MS (ESI⁺) m/z 455.0.0 (M+H)⁺.

N-[2-(2-aminoethoxy)ethyl]-4-[(6-chloro-8-cyclopentyl-7-oxo-pyrido[2,3-d]pyrimidin-2-yl) amino]-3-methyl-benzenesulfonamide (Intermediate JD)

Step 1—Tert-butyl N-[2-[2-[[4-[(6-chloro-8-cyclopentyl-7-oxo-pyrido[2,3-d]pyrimidin-2-yl)amino]-3-methyl-phenyl]sulfonylamino]ethoxy]ethyl]carbamate To a solution of tert-butyl N-[2-(2-aminoethoxy)ethyl]carbamate (112 mg, 551 umol, CAS #127828-22-2) in DCM (3 mL) was added TEA (1.65 mmol, 230 uL) and 4-[(6-chloro-8-cyclopentyl-7-oxo-pyrido[2,3-d]pyrimidin-2-yl)amino]-3-methyl-benzenesulfonyl chloride (250 mg, 551 umol, Intermediate CW), then the mixture was stirred at 25° C. for 1 hour. On completion, the mixture was filtered to give the residue. The residue was purified by prep-HPLC (column: Phenomenex luna C18 (column: Phenomenex C18 150*25 mm*10 um; mobile phase: [water(NH4HCO3)-ACN]; B %: 42%-72%, 8 min) to give the title compound (150 mg, 43% yield) as a white solid. ¹H NMR (400 MHz, DMSO-d₆) δ 8.75 (s, 1H), 8.17 (s, 1H), 7.74-7.68 (m, 2H), 7.66-7.59 (m, 2H), 6.85-6.75 (m, 1H), 5.80-5.67 (m, 1H), 3.35 (t, J=5.6 Hz, 2H), 3.28-3.24 (m, 3H), 3.07-3.01 (m, 2H), 2.95-2.89 (m, 2H), 2.32 (s, 3H), 2.18-2.04 (m, 2H), 1.76-1.63 (m, 4H), 1.50-1.42 (m, 2H), 1.36 (s, 9H). LC-MS (ESI⁺) m/z 620.8 (M+H)⁺.

Step 2—N-[2-(2-aminoethoxy)ethyl]-4-[(6-chloro-8-cyclopentyl-7-oxo-pyrido[2,3-d]pyrimidin-2-yl)amino]-3-methyl-benzenesulfonamide To a solution of tert-butyl N-[2-[2-[[4-[(6-chloro-8-cyclopentyl-7-oxo-pyrido[2,3-d]pyrimidin-2-yl) amino]-3-methyl-phenyl]sulfonylamino]ethoxy]ethyl]carbamate (140 mg, 225 umol) was added HCl/dioxane (4 mL), then the

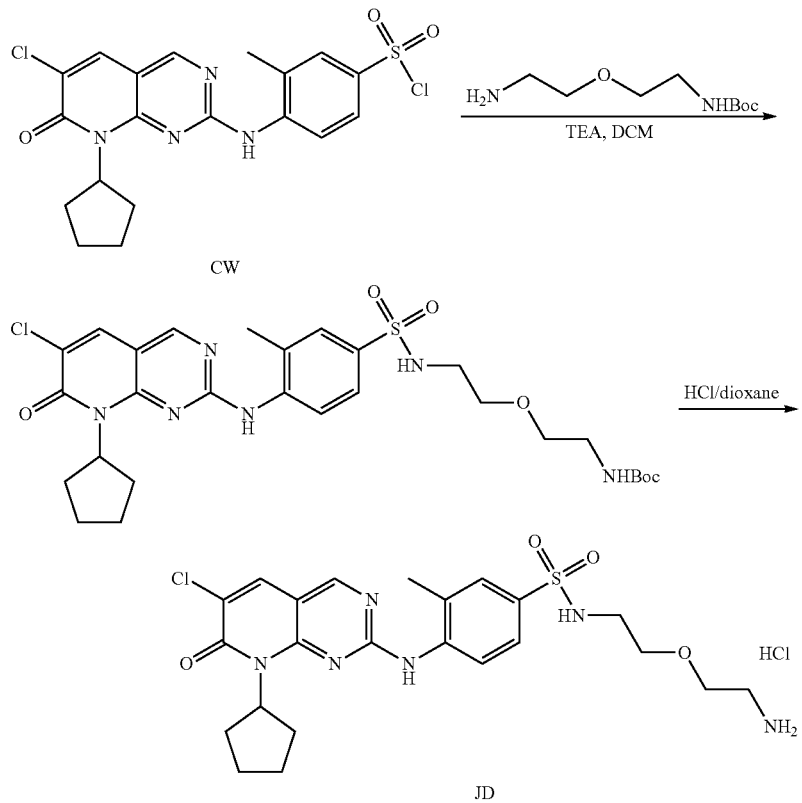

mixture was stirred at 25° C. for 1 hour. On completion, the mixture was concentrated in vacuo to give the title compound (123 mg, 97% yield, HCl) as a white solid. LC-MS (ESI$^+$) m/z 520.8 (M+H)$^+$.

2-[3-(2,4-dioxohexahydropyrimidin-1-yl)-4-methyl-phenoxy]acetic acid (Intermediate JE)

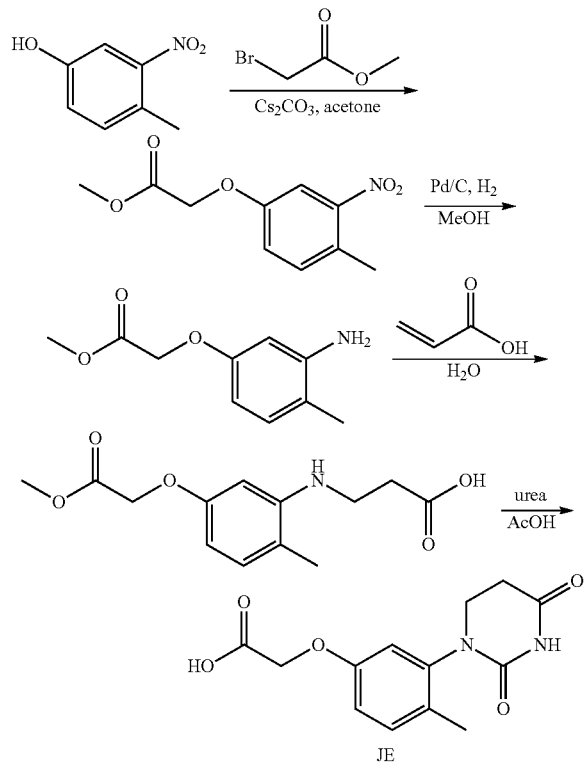

Step 1—Methyl 2-(4-methyl-3-nitro-phenoxy)acetate

To a solution of 4-methyl-3-nitro-phenol (5 g, 30 mmol, CAS #2042-14-0) in acetone (100 mL) was added methyl 2-bromoacetate (7.49 g, 50 mmol, 4.62 mL) and Cs$_2$CO$_3$ (21.28 g, 65.30 mmol), then the mixture was heated to 60° C. for 16 hrs. On completion, the reaction was cooled to 20° C. and then poured into water (700 mL), where solid precipitated. The mixture was filtered and the filter cake was washed with water (100 ml), then dried in vacuo to give the title compound (5 g, 6% yield) as gray solid.

Step 2—Methyl 2-(3-amino-4-methyl-phenoxy)acetate

To a solution of methyl 2-(4-methyl-3-nitro-phenoxy) acetate (5 g, 20 mmol) in MeOH (100 mL) was added Pd/C (0.5 g, 20 mmol, 5 wt %), the resulting suspension was degassed and then purged with H$_2$ gas (15 psi). The reaction was stirred at 20° C. for 2 hrs. On completion, the reaction mixture was filtered, and the filtrate was concentrated in vacuo to give the title compound (4 g, 20.49 mmol, 92% yield) as colorless oil.

Step 3—3-[5-(2-Methoxy-2-oxo-ethoxy)-2-methyl-anilino]propanoic acid

To a solution of methyl 2-(3-amino-4-methyl-phenoxy) acetate (4 g, 20 mmol) in H$_2$O (2 mL) was added acrylic acid (4.43 g, 61.5 mmol, 4.22 mL) and the mixture was stirred at 80° C. for 3 hrs. On completion, the reaction was concentrated in vacuo to give the title compound (14 g) as yellow gum.

Step 4—2-[3-(2,4-Dioxohexahydropyrimidin-1-yl)-4-methyl-phenoxy]acetic acid

To a solution of 3-[5-(2-methoxy-2-oxo-ethoxy)-2-methyl-anilino]propanoic acid (13.33 g, 29.93 mmol) in AcOH (30 mL) was added urea (5.39 g, 89.79 mmol, 4.81 mL), and the mixture was heated to 130° C. for 16 hrs. On completion, the reaction was cooled to 20° C., then HCl (60 ml, 2N) was added and the mixture was stirred for 10 mins. The resulting mixture was poured into water (70 ml), where solid precipitated. The suspension was filtered and the filter cake was washed with water (20 ml). The filter cake was triturated with MeOH (10 ml) and then filtered. The filter cake was dried in vacuo to give the title compound (1.30 g, 16% yield) as white solid. $^1$H NMR (400 MHz, DMSO-d$_6$) δ=12.97 (br s, 1H), 10.33 (s, 1H), 7.16 (d, J=8.4 Hz, 1H), 6.89 (t, J=6.8 Hz, 1H), 6.81-6.78 (m, 1H), 4.64 (s, 2H), 3.79-3.73 (m, 1H), 3.51-3.46 (m, 1H), 2.81-2.60 (m, 2H), 2.01 (s, 3H). LC-MS (ESI$^+$) m/z 279.2 (M+H)$^+$.

2-(4-chloro-3-(2,4-dioxotetrahydropyrimidin-1(2H)-yl)phenoxy)acetic acid (Intermediate JF)

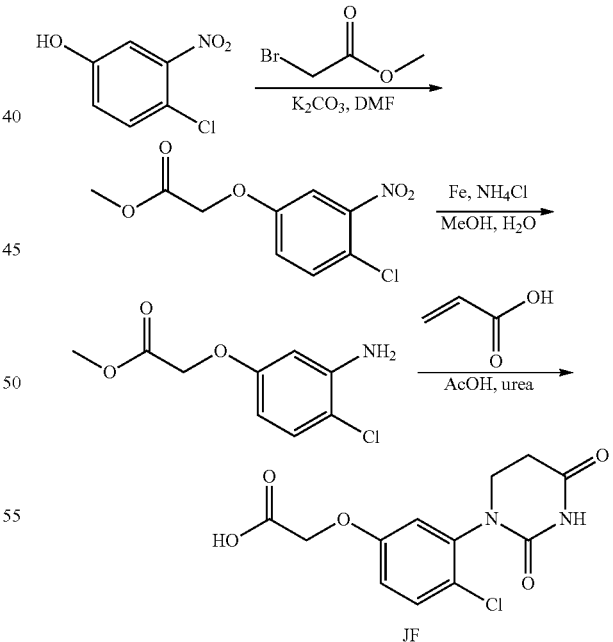

Step 1—Methyl 2-(4-chloro-3-nitro-phenoxy)acetate

To solution of 4-chloro-3-nitro-phenol (10 g, 60 mmol, CAS #610-78-6) in DMF (100 mL) was added methyl 2-bromoacetate (10.58 g, 69.14 mmol, 6.53 mL, CAS #96-

32-2), and K$_2$CO$_3$ (15.93 g, 115.2 mmol). The mixture was stirred at 25° C. for 2 hr. On completion, the reaction mixture was partitioned between water (50 mL) and EtOAc (35 mL). The organic phase was separated, washed with water (20 mL×3), dried over Na$_2$SO$_4$, filtered and concentrated under reduced pressure to give the title compound (10 g, 71% yield) as white solid. $^1$H NMR (400 MHz, CDCl$_3$) δ=7.47-7.29 (m, 2H), 7.02 (dd, J=3.0, 8.9 Hz, 1H), 4.62 (s, 2H), 3.75 (s, 3H). LC-MS (ESI$^+$) m/z 215.0 (M-30)$^+$.

Step 2—Methyl 2-(3-amino-4-chloro-phenoxy) acetate

To a solution of methyl 2-(4-chloro-3-nitro-phenoxy) acetate (10 g, 40 mmol) in MeOH (40 mL) was added iron powder (6.82 g, 122.14 mmol), NH$_4$Cl (10.89 g, 203.6 mmol) and water (130 mL) at 25° C. The mixture was stirred at 60° C. for 4 hr. On completion, the reaction mixture was partitioned between water (100 mL) and EtOAc (30 mL). The organic phase was separated, washed with water (20 mL×3), dried over Na$_2$SO$_4$, filtered and concentrated under reduced pressure to give a residue. The residue was purified by column chromatography (SiO$_2$, Petroleum ether/Ethyl acetate=5:1, R$_f$=0.6) to give the title compound (8 g, 89% yield) as a yellow solid. $^1$H NMR (400 MHz) δ=7.14 (s, 1H), 7.12 (s, 1H), 7.17-7.09 (m, 1H), 6.35 (d, J=2.8 Hz, 1H), 6.25 (dd, J=2.8, 8.7 Hz, 1H), 4.58 (s, 2H), 4.16-4.02 (m, 2H), 3.84-3.78 (m, 1H), 3.80 (s, 2H), 2.05 (s, 1H), 1.26 (t, J=7.2 Hz, 1H). LC-MS (ESI$^+$) m/z 216.0 (M+H)$^+$.

Step 3—2-[4-Chloro-3-(2,4-dioxohexahydropyrimidin-1-yl)phenoxy]acetic acid

A mixture of methyl 2-(3-amino-4-chloro-phenoxy) acetate (4 g, 19 mmol) and acrylic acid (5.35 g, 74.2 mmol, 5.09 mL) was stirred at 120° C. for 4 hr. Then AcOH (40 mL) and urea (5.57 g, 92.8 mmol, 4.97 mL) was added at 20° C. The resulting mixture was stirred at 120° C. for 12 hr. On completion, the reaction mixture was poured into a mixture of water (100 mL) and HCl (12 M, 1.55 mL), and the mixture was stirred at 20° C. for 0.5 hr. The mixture was then filtered and the filtrate was concentrated in vacuo. The residue was purified by combi-flash (0.1% TFA) to give the title compound (358.67 mg, 6% yield) as white solid. $^1$H NMR (400 MHz, DMSO-d$_6$) δ=13.34-12.83 (m, 1H), 10.46 (s, 1H), 7.50-7.41 (m, 1H), 7.14 (d, J=2.8 Hz, 1H), 6.99-6.89 (m, 1H), 4.71 (s, 2H), 3.81-3.50 (m, 2H), 2.82-2.63 (m, 2H) LC-MS (ESI$^+$) m/z 299.0 (M+H)$^+$.

N-[2-[2-(2-aminoethoxy)ethoxy]ethyl]-4-[(6-chloro-8-cyclopentyl-7-oxo-pyrido[2,3-d]pyrimidin-2-yl) amino]-3-methyl-benzenesulfonamide (Intermediate JG)

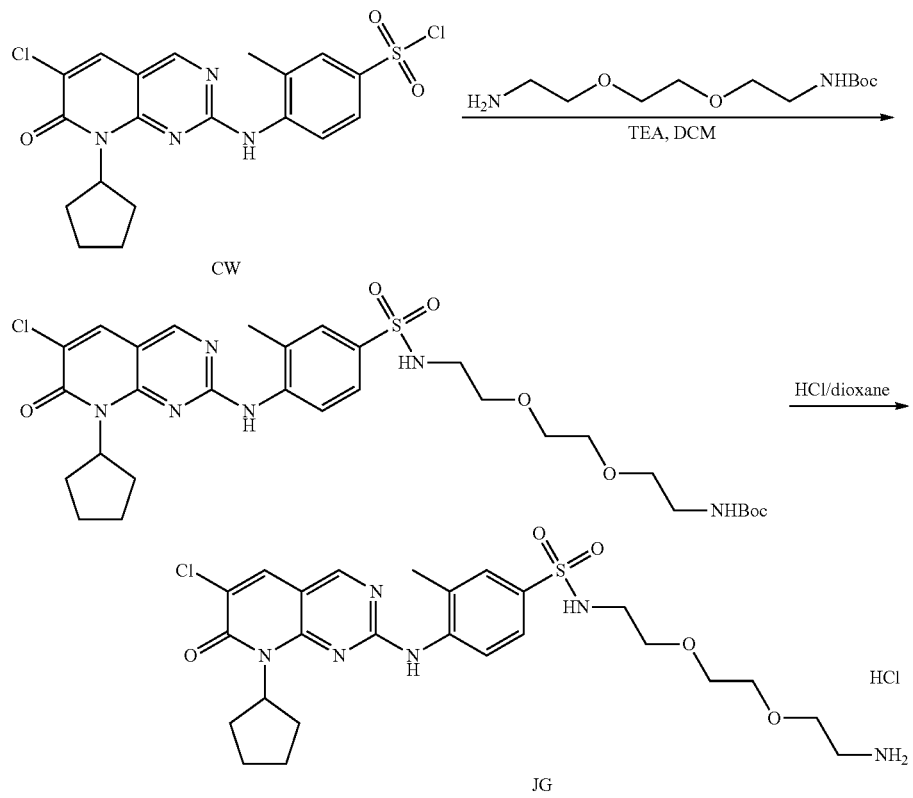

Step 1—Tert-butyl N-[2-[2-[2-[[4-[(6-chloro-8-cyclopentyl-7-oxo-pyrido[2,3-d]pyrimidin-2-yl) amino]-3-methyl-phenyl]sulfonylamino]ethoxy]ethoxy]ethyl]carbamate To a solution of tert-butyl N-[2-[2-(2-aminoethoxy) ethoxy]ethyl]carbamate (137 mg, 551 umol, CAS #153086-78-3) in DCM (4 mL) was added TEA (167 mg, 1.65 mmol) until the pH=7-8, then 4-[(6-chloro-8-cyclopentyl-7-oxo-pyrido[2,3-d]pyrimidin-2-yl)amino]-3-methyl-benzenesulfonylchloride (250 mg, 551 umol, Intermediate CW) was added. Then the mixture was stirred at 25° C. for 0.5 hr. On completion, the mixture was concentrated in vacuo to give the residue. The residue was purified by prep-HPLC (column: Phenomenex C18 150*25 mm*10 um; mobile phase: [water (NH$_4$HCO$_3$)-ACN]; B %: 42%-72%, 8 min) to give the title compound (90.0 mg, 24% yield) as a white solid. $^1$H NMR (400 MHz, DMSO-d$_6$) δ 9.66 (s, 1H), 8.75 (s, 1H), 8.17 (s, 1H), 7.72-7.68 (m, 2H), 7.67-7.60 (m, 2H), 6.74 (t, J=5.4 Hz, 1H), 5.79-5.68 (m, 1H), 3.47-3.38 (m, 7H), 3.09-3.02 (m, 2H), 2.92-2.87 (m, 2H), 2.32 (s, 3H), 2.17-2.03 (m, 2H), 1.69 (s, 4H), 1.45 (s, 3H), 1.35 (s, 9H). LC-MS (ESI$^+$) m/z 664.8 (M+H)$^+$.

Step 2—N-[2-[2-(2-aminoethoxy)ethoxy]ethyl]-4-[(6-chloro-8-cyclopentyl-7-oxo-pyrido[2,3-d]pyrimidin-2-yl)amino]-3-methyl-benzenesulfonamide A solution of tert-butyl N-[2-[2-[2-[[4-[(6-chloro-8-cyclopentyl-7-oxo-pyrido[2,3-d]pyrimidin-2-yl) amino]-3-methyl-phenyl]sulfonylamino]ethoxy]ethoxy]ethyl]carbamate (70.0 mg, 105 umol) in HCl/dioxane (2 mL) and the mixture was stirred at 25° C. for 0.5 hr. On completion, the mixture was concentrated in vacuo to give the title compound (62.0 mg, 97% yield, HCl) as a white solid. LC-MS (ESI$^+$) m/z 565.0 (M+H)$^+$.

4-chloro-3-(2,4-dioxohexahydropyrimidin-1-yl)benzoic acid (Intermediate JH)

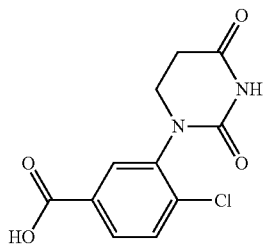 [SMILES: O=C1CCN(c2cc(C(=O)O)ccc2Cl)C(=O)N1]

Tert-butyl N-[3-(4-piperidyl)propyl]carbamate (Intermediate JI)

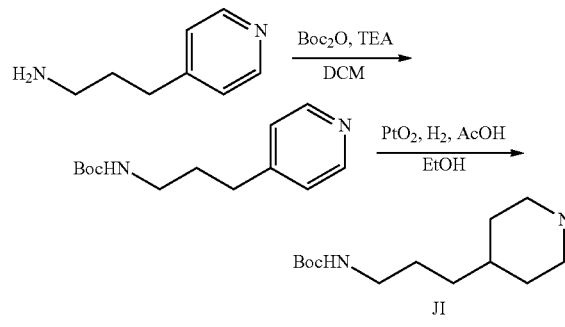

Step-1—Tert-butyl N-[3-(4-pyridyl)propyl]carbamate

To a solution of 3-(4-pyridyl)propan-1-amine (1.00 g, 7.34 mmol, CAS #30532-36-6) in DCM (10 mL) was added Boc$_2$O (1.92 g, 8.81 mmol) and Et$_3$N (1.49 g, 14.6 mmol). The mixture was stirred at 25° C. for 2 hrs. On completion, the residue was diluted with H$_2$O (5 mL) and extracted with DCM (3×10 mL). The combined organic layers were washed with brine (2×6 mL), dried over anhydrous Na$_2$SO$_4$, filtered and concentrated in vacuo to give a residue. The residue was purified by column chromatography (SiO$_2$, Petroleum ether/Ethyl acetate=100/1 to 1/1) to give the title compound (1.50 g, 85% yield) as colorless oil. $^1$H NMR (400 MHz, CDCl$_3$) δ 8.49 (d, J=6.0 Hz, 2H) 7.12 (d, J=5.6 Hz, 2H) 4.63 (s, 1H) 3.16 (d, J=6.4 Hz, 2H) 2.66-2.61 (m, 2H) 1.86-1.78 (m, 2H) 1.44 (s, 9H). LC-MS (ESI$^+$) m/z 237.1 (M+H)$^+$.

Step 2—Tert-butyl N-[3-(4-piperidyl)propyl]carbamate

To a solution of tert-butyl N-[3-(4-pyridyl)propyl]carbamate (1.50 g, 6.35 mmol) in EtOH (12 mL) was added PtO$_2$ (1.44 g, 6.35 mmol) and AcOH (6.30 g, 104 mmol) under N$_2$ atmosphere. The suspension was degassed and purged with H$_2$ three times. The mixture was stirred under H$_2$ at 40° C. for 16 hrs. On completion, the reaction mixture was filtered and concentrated in vacuo to give the title compound (1.50 g, 98% yield) as colorless oil. $^1$H NMR (400 MHz, CDCl$_3$) δ 3.37 (d, J=12.8 Hz, 2H) 3.09 (d, J=5.2 Hz, 2H) 2.81 (t, J=12.4 Hz, 2H) 1.82 (d, J=11.6 Hz, 2H) 1.69-1.56 (m, 1H) 1.52-1.46 (m, 5H) 1.43 (s, 9H) 1.31 (d, J=5.6 Hz, 2H) 1.28-1.22 (m, 1H).

1-[4-[4-(3-Aminopropyl)-1-piperidyl]phenyl]hexahydropyrimidine-2,4-dione (Intermediate JJ)

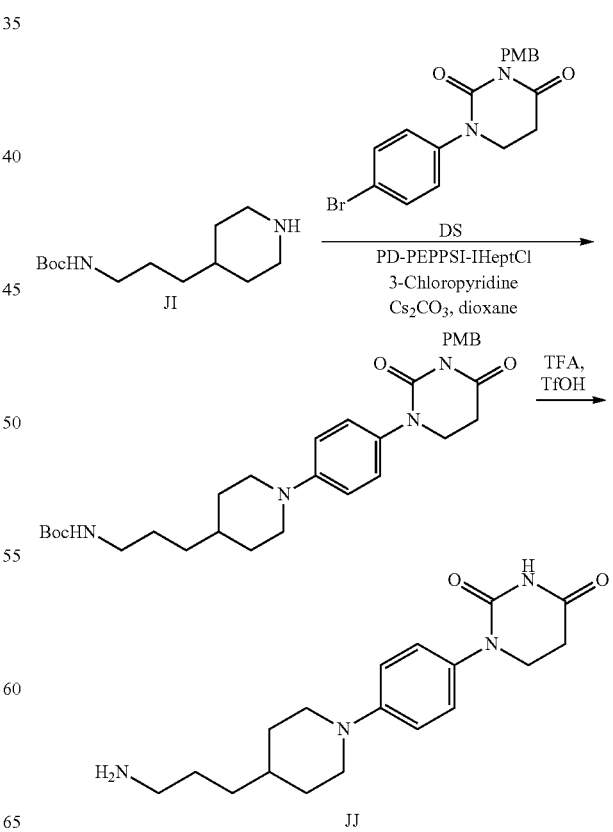

Step 1—Tert-butyl N-[3-[1-[4-[3-[(4-methoxyphenyl)methyl]-2,4-dioxo-hexahydropyrimidin-1-yl]phenyl]-4-piperidyl]propyl]carbamate A mixture of tert-butyl N-[3-(4-piperidyl)propyl]carbamate (233 mg, 963 umol, Intermediate JI), 1-(4-bromophenyl)-3-[(4-methoxyphenyl)methyl]hexahydropyrimidine-2,4-dione (150 mg, 385 umol, Intermediate DS), 1,3-bis[2,6-bis(1-propylbutyl)phenyl]-4,5-dichloro-2H-imidazol-1-ium-2-ide;3-chloropyridine;dichloropalladium (37.4 mg, 38.5 umol), and $Cs_2CO_3$ (502 mg, 1.54 mmol) in dioxane (3 mL) was degassed and purged with $N_2$ three times. Then the mixture was stirred at 100° C. for 16 hrs under $N_2$ atmosphere. On completion, the reaction mixture was filtered and concentrated in vacuo to give a residue. Then the residue was purified by prep-HPLC (column: Phenomenex C18 150*25 mm*10 um; mobile phase: [water($NH_4HCO_3$)-ACN]; B %: 46%-76%, 8 min) to give the title compound (130 mg, 60% yield) as a white solid. $^1$H NMR (400 MHz, $CDCl_3$) δ 7.43 (d, J=8.8 Hz, 2H) 7.12 (d, J=8.8 Hz, 2H) 6.92 (d, J=8.8 Hz, 2H) 6.83 (d, J=8.4 Hz, 2H) 4.95 (s, 2H) 3.79 (s, 3H) 3.72 (t, J=6.8 Hz, 2H) 3.65 (d, J=12.4 Hz, 2H) 3.17-3.08 (m, 2H) 2.85 (t, J=6.8 Hz, 2H) 2.74-2.64 (m, 2H) 1.78 (d, J=11.2 Hz, 2H) 1.51 (d, J=7.6 Hz, 3H) 1.46 (s, 9H) 1.35 (d, J=12.0 Hz, 2H) 1.33-1.26 (m, 3H). LC-MS (ESI$^+$) m/z 551.0 (M+H)$^+$.

Step 2—1-[4-[4-(3-Aminopropyl)-1-piperidyl]phenyl]hexahydropyrimidine-2,4-dione To a solution of tert-butyl N-[3-[1-[4-[3-[(4-methoxyphenyl)methyl]-2,4-dioxo-hexahydropyrimidin-1-yl]phenyl]-4-piperidyl]propyl]carbamate (70.0 mg, 127 umol) in TFA (1 mL) was added TfOH (340 mg, 2.27 mmol). The mixture was stirred at 70° C. for 1 hr. On completion, the reaction mixture was filtered and concentrated in vacuo to give the title compound (42.0 mg, 100% yield) as colorless oil. LC-MS (ESI$^+$) m/z 330.9 (M+H)$^+$.

3-[3-methyl-4-[4-(methylaminomethyl)-1-piperidyl]-2-oxo-benzimidazol-1-yl]piperidine-2,6-dione (Intermediate JK)

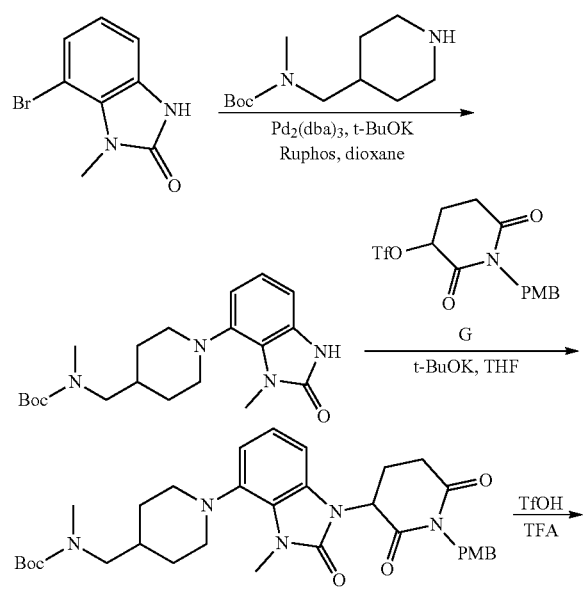

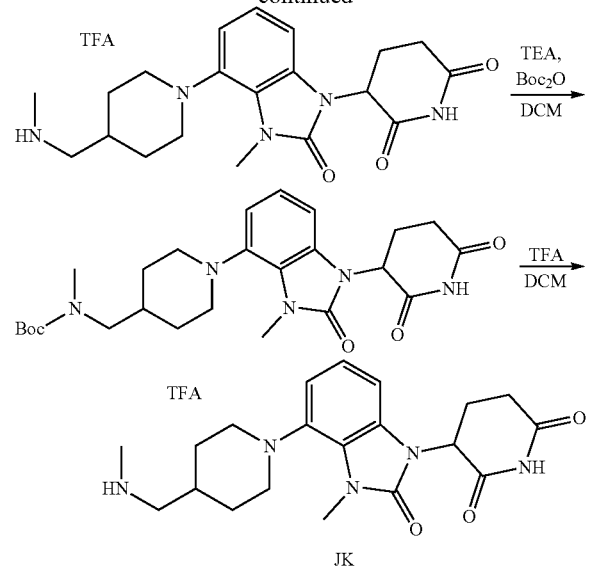

Step 1—Tert-butyl N-methyl-N-[[i-(3-methyl-2-oxo-1H-benzimidazol-4-yl)-4-piperidyl]methyl]carbamate A mixture of 4-bromo-3-methyl-1H-benzimidazol-2-one (0.85 g, 3.74 mmol, synthesized via Steps 1-3 of Intermediate H), tert-butyl N-methyl-N-(4-piperidylmethyl)carbamate (940 mg, 4.12 mmol, CAS #138022-04-5), RuPhos (174 mg, 374 umol), $Pd_2(dba)_3$ (342 mg, 374 umol) and t-BuOK (1.26 g, 11.2 mmol) in dioxane (20 mL) was stirred at 90° C. for 16 hrs under $N_2$. On completion, the reaction was diluted with EA (100 mL). The organic layer was washed with water (70 mL×3), dried over $Na_2SO_4$ and filtered. The filtrate was concentrated in vacuo. The residue was purified by column chromatography ($SiO_2$, DCM/Ethyl acetate=0% to 35%) to give the title compound (800 mg, 57% yield) as brown solid. LC-MS (ESI$^+$) m/z 375.3 (M+H)$^+$.

Step 2—Tert-butyl N-[[1-[1-[1-[(4-methoxyphenyl)methyl]-2,6-dioxo-3-piperidyl]-3-methyl-2-oxo-benzimidazol-4-yl]-4-piperidyl]methyl]-N-methyl-carbamate To a solution of tert-butyl N-methyl-N-[[1-(3-methyl-2-oxo-1H-benzimidazol-4-yl)-4-piperidyl]methyl]carbamate (460 mg, 1.23 mmol) in THF (10 mL) was added t-BuOK (413 mg, 3.69 mmol) at 0° C. The reaction was stirred at 0° C. for 0.5 hr. Then, the above mixture was added [1-[(4-methoxyphenyl)methyl]-2,6-dioxo-3-piperidyl] trifluoromethanesulfonate (702 mg, 1.84 mmol, Intermediate G) at 0° C. The reaction was stirred at 25° C. for 1.5 hrs. On completion, the reaction was diluted with EA (100 mL). The organic layer was washed with water (100 mL×2) and concentrated in vacuo. The residue was purified by column chromatography ($SiO_2$, DCM/Ethyl acetate=100/0 to 50/50) to give the title compound (400 mg, 53% yield) as brown solid. LC-MS (ESI$^+$) m/z 606.4 (M+H)$^+$.

Step 3—3-[3-methyl-4-[4-(methylaminomethyl)-1-piperidyl]-2-oxo-benzimidazol-1-yl]piperidine-2,6-dione A mixture of tert-butyl N-[[1-[1-[1-[(4-methoxyphenyl)methyl]-2,6-dioxo-3-piperidyl]-3-methyl-2-oxo-benzimidazol-4-yl]-4-piperidyl]methyl]-N-methyl-carbamate (270 mg, 445 umol) and TfOH (1.38 g, 9.18 mmol) in TFA (1 mL) was stirred at 70° C. for 1 hr. On completion, the reaction was concentrated in vacuo to give the title compound (222 mg, 99% yield, TFA) as brown oil. LC-MS (ESI$^+$) m/z 386.0 (M+H)$^+$.

Step 4—Tert-butyl N-[[1-[1-(2,6-dioxo-3-piperidyl)-3-methyl-2-oxo-benzimidazol-4-yl]-4-piperidyl]methyl]-N-methyl-carbamate To a mixture of 3-[3-methyl-4-[4-(methylaminomethyl)-1-piperidyl]-2-oxo-benzimidazol-1-yl] piperidine-2,6-dione (222 mg, 444 umol, TFA) and TEA (134 mg, 1.33 mmol) in DCM (2 mL) was added Boc$_2$O (145 mg, 666 umol). The reaction was stirred at 25° C. for 1 hr. On completion, the reaction was diluted with EA (100 mL). The organic layer was washed with water (70 mL×2), dried over Na$_2$SO$_4$ and filtered. The filtrate was concentrated in vacuo. The crude product was triturated with PE:EA=10:1 (10 mL) at 25° C. for 30 min to give the title compound (200 mg, 92% yield) as brown solid. LC-MS (ESI$^+$) m/z 486.4 (M+H)$^+$.

Step 5—3-[3-Methyl-4-[4-(methylaminomethyl)-1-piperidyl]-2-oxo-benzimidazol-1-yl]piperidine-2,6-dione A mixture of tert-butyl N-[[1-[1-(2,6-dioxo-3-piperidyl)-3-methyl-2-oxo-benzimidazol-4-yl]-4-piperidyl]methyl]-N-methyl-carbamate (200 mg, 411 umol) and TFA (770 mg, 6.75 mmol, 0.5 mL) in DCM (2 mL) was stirred at 25° C. for 1 hr. On completion, the reaction was concentrated in vacuo to give the title compound (205 mg, 99% yield, TFA) as brown oil. LC-MS (ESI$^+$) m/z 386.1 (M+H)$^+$.

3-[3-methyl-4-[4-[[methyl(4-piperidyl)amino]methyl]-1-piperidyl]-2-oxo-benzimidazol-1-yl] piperidine-2,6-dione (Intermediate JL)

Step 1—Tert-butyl 4-[[1-[1-(2,6-dioxo-3-piperidyl)-3-methyl-2-oxo-benzimidazol-4-yl]-4-piperidyl]methyl-methyl-amino]piperidine-1-carboxylate To a solution of 3-[3-methyl-4-[4-(methylaminomethyl)-1-piperidyl]-2-oxo-benzimidazol-1-yl]piperidine-2,6-dione (202 mg, 404 umol, TFA, Intermediate CL), TEA (40.9 mg, 404 umol) and HOAc (48.5 mg, 808 umol) in DMF (1 mL) and THF (3 mL) was added tert-butyl 4-oxopiperidine-1-carboxylate (241 mg, 1.21 mmol, CAS #79099-07-3). The reaction was stirred at 25° C. for 0.5 hr. Then NaBH(OAc)$_3$ (128 mg, 606 umol) was added and the mixture was stirred at 40° C. for 1.5 hrs. On completion, the reaction was quenched with water (0.05 mL) and diluted with EA (70 mL). The organic layer was washed with water (70 mL) and concentrated in vacuo. The residue was purified by prep-HPLC (column: Phenomenex luna C18 150*25 mm*10 um; mobile phase: [water (FA)-ACN]; B %: 12%-42%, 10 min) to give the title compound (130 mg, 56% yield) as brown solid. $^1$H NMR (400 MHz, DMSO-d$_6$) δ 11.08 (s, 1H), 7.02-6.96 (m, 1H), 6.94-6.86 (m, 2H), 5.42-5.37 (m, 1H), 4.68 (d, J=3.6 Hz, 2H), 4.17-4.02 (m, 2H), 3.63 (s, 3H), 3.15 (d, J=10.0 Hz, 2H), 2.94 (s, 4H), 2.78 (s, 3H), 2.02-1.90 (m, 4H), 1.72-1.62 (m, 5H), 1.41 (s, 9H), 1.30-1.16 (m, 5H); LC-MS (ESI$^+$) m/z 569.3 (M+H)$^+$.

Step 2—3-[3-Methyl-4-[4-[[methyl(4-piperidyl)amino]methyl]-1-piperidyl]-2-oxo-benzimidazol-1-yl] piperidine-2,6-dione A mixture of tert-butyl 4-[[1-[1-(2,6-dioxo-3-piperidyl)-3-methyl-2-oxo-benzimidazol-4-yl]-4-piperidyl]methyl-methyl-amino]piperidine-1-carboxylate (50.0 mg, 87.9 umol) in HCl/dioxane (4 M, 2 mL) was stirred at 25° C. for 1 hr. On completion, the residue was concentrated in vacuo to give the title compound (44 mg, 99% yield, HCl) as white solid. LC-MS (ESI$^+$) m/z 469.2 (M+H)$^+$.

3-[4-(2,7-Biazaspiro[3.5]nonan-7-yl)-3-methyl-2-oxo-benzimidazol-1-yl]piperidine-2,6-dione (Intermediate JM)

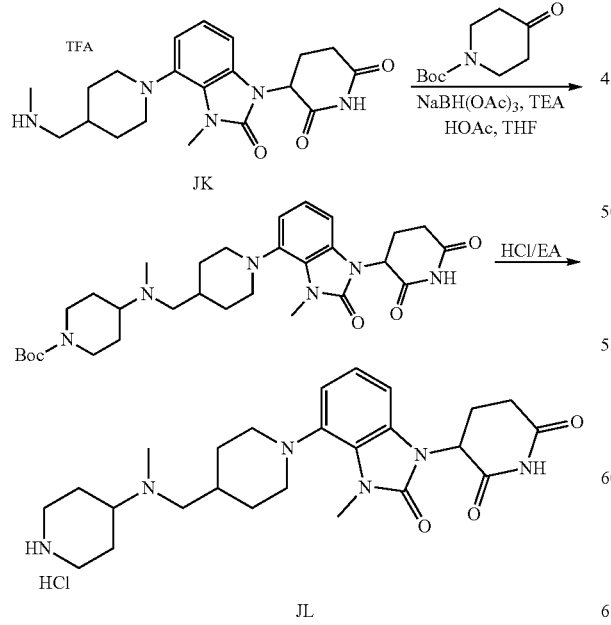

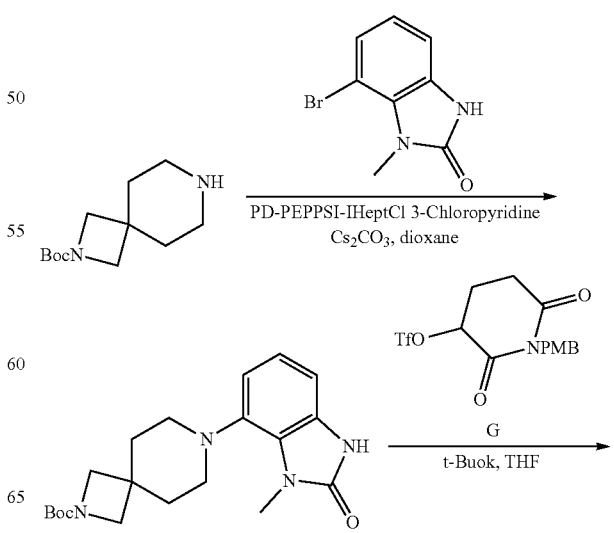

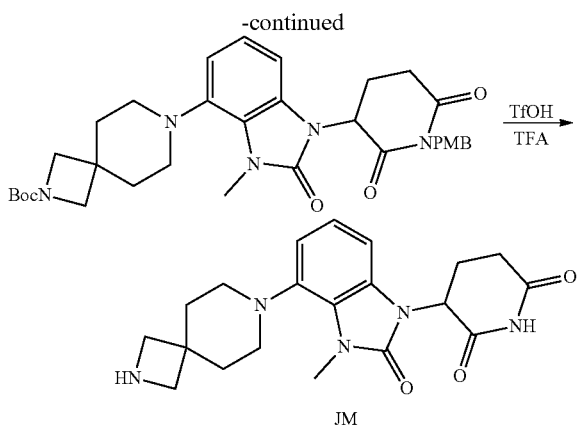

Step 1—Tert-butyl 7-(3-methyl-2-oxo-1H-benzimidazol-4-yl)-2,7-diazaspiro[3.5]nonane-2-carboxylate To a solution of tert-butyl 2,7-diazaspiro[3.5]nonane-2-carboxylate (2.00 g, 8.84 mmol, CAS #236406-55-6), 4-bromo-3-methyl-1H-benzimidazol-2-one (2.21 g, 9.72 mmol, synthesized via Steps 1-3 of Intermediate H) in dioxane (20 mL) was added Cs$_2$CO$_3$ (5.76 g, 17.6 mmol), 4A molecular sieves and 1,3-bis[2,6-bis(1-ethylpropyl)phenyl]-4,5-dichloro-2H-imidazol-1-ium-2-ide;3-chloropyridine;dichloropalladium (380 mg, 441 umol) and the mixture was purged with N$_2$ three times. Then the mixture was stirred at 110° C. for 16 hours under N$_2$ atmosphere. On completion, the reaction mixture was filtered and concentrated in vacuo to give a residue. Then the residue was purified by prep-HPLC (column: Phenomenex luna C18 250*50 mm*15 um; mobile phase: [water(FA)-ACN]; B %: 55%-65%, 22 min) to give the title compound (1.4 g, 41% yield) as a yellow solid. $^1$H NMR (400 MHz, DMSO-d$_6$) δ 10.77 (s, 1H), 6.90-6.84 (m, 1H), 6.79-6.75 (m, 1H), 6.70 (d, J=7.6 Hz, 1H), 3.62 (d, J=2.0 Hz, 2H), 3.52 (s, 3H), 2.95 (d, J=2.0 Hz, 2H), 2.63-2.56 (m, 2H), 1.83 (s, 6H), 1.37 (s, 9H).

Step 2—Tert-butyl 7-[1-[1-[(4-methoxyphenyl)methyl]-2,6-dioxo-3-piperidyl]-3-methyl-2-oxo-benzimidazol-4-yl]-2,7-diazaspiro[3.5]nonane-2-carboxylate To a solution of tert-butyl 7-(3-methyl-2-oxo-1H-benzimidazol-4-yl)-2,7-diazaspiro[3.5]nonane-2-carboxylate (900 mg, 2.42 mmol) in THF (5 mL) was added t-BuOK (488 mg, 4.35 mmol) and stirred for 30 mins at −10° C. Then [1-[(4-methoxyphenyl)methyl]-2,6-dioxo-3-piperidyl]trifluoromethanesulfonate (921 mg, 2.42 mmol, Intermediate G) was dissolved in THF (5 mL) and added to the mixture and which was then stirred for 3 hrs at −10° C. On completion, the reaction mixture was quenched with NH$_4$Cl (10 mL) at 25° C., and then diluted with H$_2$O (50 mL) and extracted with EA (3×100 mL). The combined organic layers were washed with brine (2×100 mL), dried over anhydrous Na$_2$SO$_4$, filtered and concentrated in vacuo to give a residue. The residue was purified by prep-HPLC (column: YMC Triart C18 250*50 mm*7 um; mobile phase: [water(FA)-ACN]; B %: 49%-79%, 22 min) to give the title compound (647 mg, 44% yield) as a gray solid. $^1$H NMR (400 MHz, DMSO-d$_6$) δ 7.19 (d, J=8.8 Hz, 2H), 6.92-6.82 (m, 4H), 6.76 (s, 1H), 5.50-5.45 (m, 1H), 4.86-4.69 (m, 2H), 3.71 (s, 3H), 3.66 (s, 2H), 3.60 (s, 3H), 3.58-3.52 (m, 2H), 3.02-2.95 (m, 2H), 2.81-2.80 (m, 1H), 2.75 (s, 1H), 2.69-2.61 (m, 2H), 2.05-1.98 (m, 1H), 1.85 (s, 4H), 1.38 (s, 9H).

Step 3—3-[4-(2,7-Biazaspiro[3.5]nonan-7-yl)-3-methyl-2-oxo-benzimidazol-1-yl]piperidine-2,6-dione To a solution of tert-butyl 7-[1-[1-[(4-methoxyphenyl)methyl]-2,6-dioxo-3-piperidyl]-3-methyl-2-oxo-benzimidazol-4-yl]-2,7-diazaspiro[3.5]nonane-2-carboxylate (200 mg, 331 umol) in TFA (1.2 mL) was added TfOH (340 mg, 2.27 mmol). The mixture was then stirred at 70° C. for 2 hrs. On completion, the reaction mixture was filtered and concentrated in vacuo to give the title compound (160 mg, 97% yield, TFA salt) as a white solid. LC-MS (ESI$^+$) m/z 384.1 (M+H)$^+$.

3-[3-Methyl-2-oxo-4-[2-(4-piperidyl)-2,7-diazaspiro[3.5]nonan-7-yl]benzimidazol-1-yl]piperidine-2,6-dione (Intermediate JN)

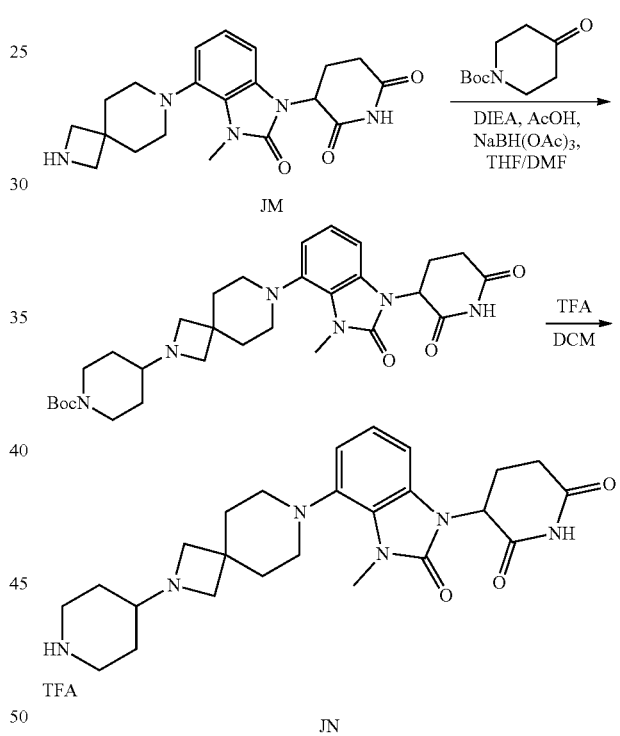

Step 1—5-Bromo-N-cyclopentyl-2-methylsulfanyl-pyrimidin-4-amine

To a solution of 3-[4-(2,7-diazaspiro[3.5]nonan-7-yl)-3-methyl-2-oxo-benzimidazol-1-yl]piperidine-2,6-dione (160 mg, 321 umol, TFA salt, Intermediate JM) in THF (1 mL) and DMF (0.5 mL) was added AcOK (315 mg, 3.22 mmol) and tert-butyl 4-oxopiperidine-1-carboxylate (76.9 mg, 385 umol, CAS #79099-07-3) at −10° C. for 1 hr. Then NaBH(OAc)$_3$ (136 mg, 643 umol) was added and the mixture at −10° C. The mixture was then stirred at −10° C. for 1 hr. On completion, the reaction mixture was quenched with H$_2$O (1 mL) at 25° C., and then filtered and concentrated in vacuo to give a residue. Then the residue was purified by prep- HPLC (column: Welch Xtimate C18 150*25 mm*5 um; mobile phase: [water(FA)-ACN]; B %: 5%-35%, 10 min) to give the title compound (90 mg, 49% yield)) as a white solid. $^1$H NMR (400 MHz, DMSO-d$_6$) δ 11.08 (s, 1H), 7.00-6.95 (m, 1H), 6.88-6.86 (m, 2H), 5.36-5.32 (m, 1H), 3.90 (d, J=12.4 Hz, 2H), 3.62 (s, 4H), 3.49 (d, J=2.8 Hz, 2H), 3.01 (s, 2H), 2.92-2.84 (m, 2H), 2.77 (s, 1H), 2.70-2.63 (m, 3H), 2.37-2.31 (m, 1H), 2.03-1.74 (m, 8H), 1.43 (s, 1H), 1.40 (s, 9H), 1.17-1.04 (m, 2H).

Step 2—3-[3-Methyl-2-oxo-4-[2-(4-piperidyl)-2,7-diazaspiro[3.5]nonan-7-yl]benzimidazol-1-yl] piperidine-2,6-dione To a solution of tert-butyl 4-[7-[1-(2,6-dioxo-3-piperidyl)-3-methyl-2-oxo-benzimidazol-4-yl]-2,7-diazaspiro[3.5]nonan-2-yl]piperidine-1-carboxylate (50.0 mg, 88.2 umol) in DCM (2 mL) was added TFA (770 mg, 6.75 mmol). The mixture was stirred at 25° C. for 1 hr. On completion, the reaction mixture was concentrated in vacuo to give the title compound (40 mg, 97% yield, TFA salt) as a red solid. LC-MS (ESI$^+$) m/z 467.2 (M+1)$^+$.

6-chloro-8-isopropyl-2-[2-methyl-4-[(4-piperazin-1-yl-1-piperidyl)sulfonyl]anilino]pyrido[2,3-d]pyrimidin-7-one (Intermediate JO)

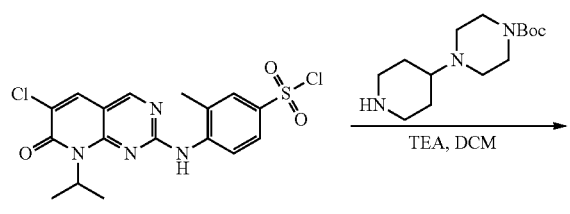

Step 1—Tert-butyl 4-[1-[4-[(6-chloro-8-isopropyl-7-oxo-pyrido[2,3-d]pyrimidin-2-yl)amino]-3-methyl-phenyl]sulfonyl-4-piperidyl]piperazine-1-carboxylate To a solution of tert-butyl 4-(4-piperidyl)piperazine-1-carboxylate (69.3 mg, 257 umol, CAS #205059-24-1) and TEA (118 mg, 1.17 mmol) in DCM (1 mL) was added the solution of 4-[(6-chloro-8-isopropyl-7-oxo-pyrido [2,3-d]pyrimidin-2-yl)amino]-3-methyl-benzenesulfonyl chloride (100 mg, 234 umol, Intermediate DG) in DCM (1 mL) at 0° C. The reaction mixture was stirred at 25° C. for 1 hr. On completion, the reaction mixture was diluted with DCM (20 mL) and washed with H$_2$O (10 mL×3). The organic layer was dried over Na$_2$SO$_4$, filtered and concentrated in vacuo to give the title compound (150 mg, 97% yield) as yellow solid. $^1$H NMR (400 MHz, DMSO-d$_6$) δ 9.69 (s, 1H), 8.75 (s, 1H), 8.17 (s, 1H), 7.80 (d, J=7.6 Hz, 1H), 7.64 (d, J=1.6 Hz, 1H), 7.57 (dd, J=2.0, 8.4 Hz, 1H), 5.61 (d, J=3.2 Hz, 1H), 3.68 (d, J=11.6 Hz, 2H), 3.24 (s, 4H), 2.39-2.31 (m, 7H), 2.26-2.17 (m, 3H), 1.77 (d, J=10.4 Hz, 2H), 1.44-1.35 (m, 17H).

Step 2—6-Chloro-8-isopropyl-2-[2-methyl-4-[(4-piperazin-1-yl-1-piperidyl)sulfonyl]anilino]pyrido[2,3-d]pyrimidin-7-one A solution of tert-butyl 4-[1-[4-[(6-chloro-8-isopropyl-7-oxo-pyrido[2,3-d]pyrimidin-2-yl)amino]-3-methyl-phenyl]sulfonyl-4-piperidyl]piperazine-1-carboxylate (100 mg, 151 umol) in HCl/dioxane (2 mL) was stirred at 25° C. for 1 hr. On completion, the reaction mixture was concentrated in vacuo to give the title compound (90 mg, 99% yield) as yellow solid. LCMS (ESI$^+$) m/z 560.0 (M+H)$^+$.

3-[4-(3,9-Diazaspiro[5.5]undecan-3-yl)-3-methyl-2-oxo-benzimidazol-1-yl]piperidine-2,6-dione (Intermediate JP)

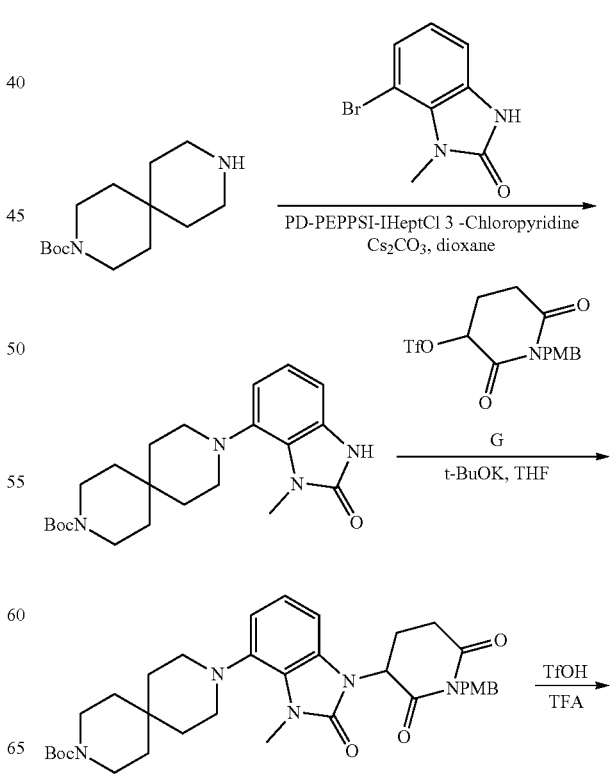

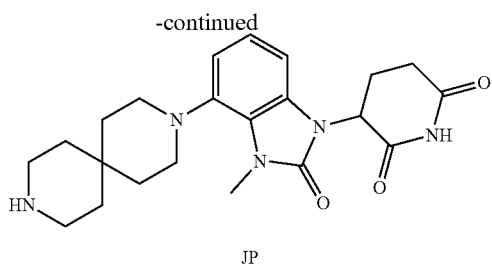

JP

Step 1—Tert-butyl 9-(3-methyl-2-oxo-1H-benzimidazol-4-yl)-3,9-diazaspiro[5.5]undecane-3-carboxylate A mixture of tert-butyl 3,9-diazaspiro[5.5]undecane-3-carboxylate (1.00 g, 3.93 mmol, CAS #173405-78-2), 4-bromo-3-methyl-1H-benzimidazol-2-one (892 mg, 3.93 mmol, synthesized via Steps 1-3 of Intermediate H), Cs₂CO₃ (2.56 g, 7.86 mmol), and 1,3-bis[2,6-bis(1-propylbutyl)phenyl]-4,5-dichloro-2H-imidazol-1-ium-2-ide;3-chloropyridine; dichloropalladium (382 mg, 393 umol) in dioxane (20 mL) was degassed and purged with N₂ three times. Then the mixture was stirred at 100° C. for 12 hrs under N₂ atmosphere. On completion, the reaction mixture was diluted with H₂O (20 mL) and extracted with EA (3×20 mL). The combined organic layers were washed with brine (2×10 mL), dried over anhydrous Na₂SO₄, filtered and concentrated in vacuo to give a residue. The residue was purified by prep-HPLC (column: Phenomenex luna C18 250*50 mm*15 um; mobile phase: [water(FA)-ACN]; B %: 60%-70%, 25 min) to give the title compound (1.17 g, 36% yield) as a white solid. ¹H NMR (400 MHz, CDCl₃) δ 9.86 (s, 1H) 7.02-6.96 (m, 1H) 6.93-6.84 (m, 2H) 3.76 (s, 3H) 3.47-3.39 (m, 4H) 2.96 (s, 4H) 1.74 (s, 2H) 1.65 (d, J=10.0 Hz, 4H) 1.48 (s, 9H) 1.45-1.35 (m, 2H). LC-MS (ESI⁺) m/z 401.1 (M+H)⁺.

Step 2—Tert-butyl 9-[1-[1-[(4-methoxyphenyl)methyl]-2,6-dioxo-3-piperidyl]-3-methyl-2-oxo-benzimidazol-4-yl]-3,9-diazaspiro[5.5]undecane-3-carboxylate To a solution of tert-butyl 9-(3-methyl-2-oxo-1H-benzimidazol-4-yl)-3,9-diazaspiro[5.5]undecane-3-carboxylate (500 mg, 1.25 mmol) in THF (5 mL) was added t-BuOK (252 mg, 2.25 mmol) and [1-[(4-methoxyphenyl)methyl]-2,6-dioxo-3-piperidyl] trifluoromethanesulfonate (714 mg, 1.87 mmol, Intermediate G). The mixture was stirred at −10° C. for 12 hrs. On completion, the reaction mixture was quenched with NH₄Cl aq. (2 mL) at 25° C., and was diluted with H₂O (5 mL) and extracted with EA (3×5 mL). The combined organic layers were washed with brine (2×5 mL), dried over anhydrous Na₂SO₄, filtered and concentrated in vacuo to give a residue. The residue was purified by prep-HPLC (column: Phenomenex Luna C18 200*40 mm*10 um; mobile phase: [water(FA)-ACN]; B %: 65%-95%, 10 min) to give the title compound (350 mg, 44% yield) as a white solid. ¹H NMR (400 MHz, CDCl₃) δ 7.39-7.35 (m, 2H) 6.95-6.87 (m, 2H) 6.85-6.81 (m, 2H) 6.28 (d, J=7.2 Hz, 1H) 5.21 (d, J=5.2 Hz, 1H) 5.02-4.92 (m, 2H) 3.80 (s, 3H) 3.77 (s, 3H) 3.46-3.40 (m, 4H) 3.04-2.98 (m, 1H) 2.95 (s, 4H) 2.87-2.77 (m, 1H) 2.61 (d, J=4.0 Hz, 1H) 2.15 (d, J=2.4 Hz, 1H) 1.56-1.80 (m, 8H) 1.48 (s, 9H). LC-MS (ESI⁺) m/z 632.4 (M+H)⁺.

Step 3—3-[4-(3,9-Diazaspiro[5.5]undecan-3-yl)-3-methyl-2-oxo-benzimidazol-1-yl]piperidine-2,6-dione To a solution of tert-butyl 9-[1-[1-[(4-methoxyphenyl)methyl]-2,6-dioxo-3-piperidyl]-3-m ethyl-2-oxo-benzimidazol-4-yl]-3,9-diazaspiro[5.5]undecane-3-carboxylate (200 mg, 316 umol) in TfOH (0.3 mL) was added TFA (3.08 g, 27.0 mmol). The mixture was stirred at 70° C. for 1 hr. On completion, the reaction mixture was filtered and concentrated in vacuo to give the title compound (130 mg, quant. yield) as yellow oil. LC-MS (ESI⁺) m/z 412.3 (M+H)⁺.

3-[3-Methyl-2-oxo-4-[3-(4-piperidyl)-3,9-diazaspiro[5.5]undecan-9-yl]benzimidazol-1-yl]piperidine-2,6-dione (Intermediate JQ)

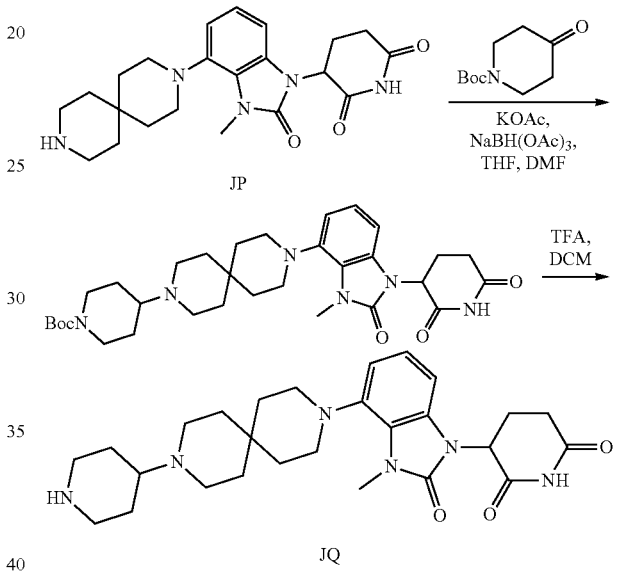

Step 1—Tert-butyl 4-[9-[1-(2,6-dioxo-3-piperidyl)-3-methyl-2-oxo-benzimidazol-4-yl]-3, 9-diazaspiro[5.5]undecan-3-yl]piperidine-1-carboxylate To a solution of 3-[4-(3,9-diazaspiro[5.5]undecan-3-yl)-3-methyl-2-oxo-benzimidazol-1-yl]piperidine-2,6-dione (30.0 mg, 72.9 umol, Intermediate JP) in THF (0.5 mL) and DMF (0.5 mL) was added tert-butyl 4-oxopiperidine-1-carboxylate (217 mg, 1.09 mmol) and KOAc (35.7 mg, 364 umol). After 0.5 hr, NaBH(OAc)₃ (30.9 mg, 145 umol) was added into the mixture then the mixture was stirred at 25° C. for 12 hrs. On completion, the reaction mixture was filtered and concentrated in vacuo to give a residue. Then the residue was purified by prep-HPLC (column: Phenomenex C18 150*25 mm*10 um; mobile phase [water(NH₄HCO₃)-ACN]; B %: 30%-60%, 8 min) to give the title compound (35.0 mg, 79% yield) as a white solid. LC-MS (ESI⁺) m/z 595.7 (M+H)⁺.

Step 2—3-[3-Methyl-2-oxo-4-[3-(4-piperidyl)-3,9-diazaspiro[5.5]undecan-9-yl]benzimidazol-1-yl]piperidine-2,6-dione To a solution of tert-butyl 4-[9-[1-(2,6-dioxo-3-piperidyl)-3-methyl-2-oxo-benzimidazol-4-yl]-3,9-diazaspiro

[5.5]undecan-3-yl]piperidine-1-carboxylate (35.0 mg, 58.8 umol) in DCM (1 mL) was added TFA (770 mg, 6.75 mmol). The mixture was stirred at 25° C. for 1 hr. On completion, the reaction mixture was filtered and concentrated in vacuo to give the title compound (29.0 mg, quant. yield) as yellow oil. LC-MS (ESI$^+$) m/z 495.4 (M+H)$^+$.

Tert-butyl N-(3-piperazin-1-ylcyclobutyl)carbamate (Intermediate JR)

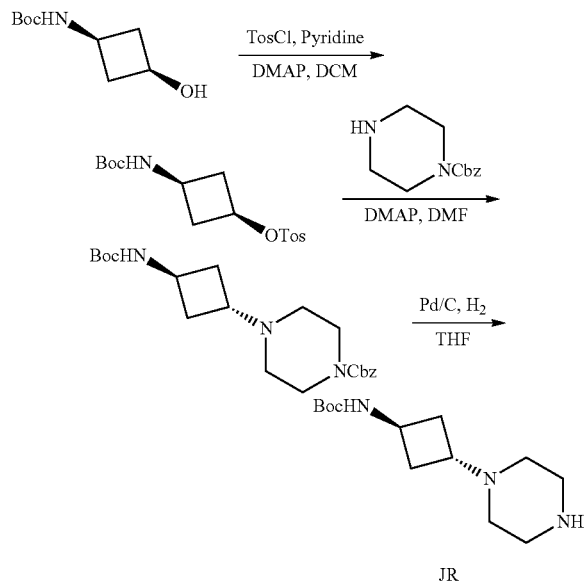

Step 1—[3-(Tert-butoxycarbonylamino)cyclobutyl] 4-methylbenzenesulfonate

To a solution of tert-butyl N-(3-hydroxycyclobutyl)carbamate (4.0 g, 21.4 mmol, CAS #389890-43-1), pyridine (10.1 g, 128 mmol), and DMAP (2.61 g, 21.4 mmol) in DCM (80 mL) was added TosCl (7.74 g, 40.6 mmol) at 0° C., then the mixture was stirred at 20° C. for 16 hrs. On completion, the reaction was washed with 20% of citric acid (45 ml×3) and brine (50 ml). The organic layer was dried over anhydrous Na$_2$SO$_4$, filtered and concentrated in vacuo to give a residue. The residue was purified by column chromatography (SiO$_2$, PE/EA=10/1 to 1/1) to give the title compound (6.26 g, 85% yield) as off-white solid. $^1$H NMR (400 MHz, DMSO-d$_6$) δ 7.81-7.73 (m, 2H), 7.47 (d, J=8.0 Hz, 2H), 7.13 (d, J=8.0 Hz, 1H), 4.53-4.46 (m, 1H), 3.62-3.48 (m, 1H), 2.42 (s, 3H), 2.02-1.92 (m, 2H), 1.36 (s, 2H), 1.33 (s, 9H), LC-MS (ESI$^+$) m/z 242.0 (M-100+H)$^+$.

Step 2—Benzyl 4-[3-(tert-butoxycarbonylamino)cyclobutyl]piperazine-1-carboxylate The solution of [3-(tert-butoxycarbonylamino)cyclobutyl] 4-methylbenzenesulfonate (3.0 g, 8.79 mmol), benzyl piperazine-1-carboxylate (4.84 g, 21.8 mmol, CAS #31166-44-6), and DMAP (107 mg, 879 umol) in DMF (40 mL) was degassed and purged with N$_2$ three times. Then the mixture was stirred at 100° C. for 16 hrs under N$_2$ atmosphere. On completion, the reaction mixture was cooled to rt, diluted with water (200 ml), and extracted with EA (50 ml×4). The organic layers were combined, washed with brine, dried over anhydrous Na$_2$SO$_4$, filtered and concentrated in vacuo to give a residue. The residue was purified by reverse phase (0.1% FA condition) to give the title compound (970 mg, 25% yield, FA) as yellow oil. $^1$H NMR (400 MHz, DMSO-d$_6$) δ 8.16 (s, 1H), 7.43-7.21 (m, 5H), 5.12-5.05 (m, 2H), 4.25-4.13 (m, 1H), 4.07-3.80 (m, 2H), 2.77-2.65 (m, 1H), 2.28-2.15 (m, 4H), 2.15-1.85 (m, 6H), 1.36 (s, 9H), LC-MS (ESI$^+$) m/z 390.2 (M+H)$^+$.

Step 3—Tert-butyl N-(3-piperazin-1-ylcyclobutyl)carbamate

A solution of benzyl 4-[3-(tert-butoxycarbonylamino)cyclobutyl]piperazine-1-carboxylate (300 mg, 770 umol, FA) in THF (5 mL) was added Pd/C (100 mg, 10 wt %) under Ar. The suspension was degassed under vacuum and purged with H$_2$ three times. Then stirred under at 20° C. for 4 hrs under H$_2$ (15 psi) atmosphere. On completion, the reaction was filtered to give a filtrate, then concentrated in vacuo to give the title compound (190 mg, 96% yield) as yellow oil. $^1$H NMR (400 MHz, CDCl$_3$) δ 6.98 (s, 1H), 5.20-4.60 (m, 1H), 4.28-3.93 (m, 1H), 2.89 (t, J=4.8 Hz, 2H), 2.42-2.17 (m, 5H), 2.00-1.95 (m, 2H), 1.44 (s, 9H), 1.32-1.21 (m, 3H), 0.89 (s, 1H).

3-[5-[4-[[4-(3-Aminocyclobutyl)piperazin-1-yl]methyl]-1-piperidyl]-3-methyl-2-oxo-benzimidazol-1-yl]piperidine-2,6-dione (Intermediate JS)

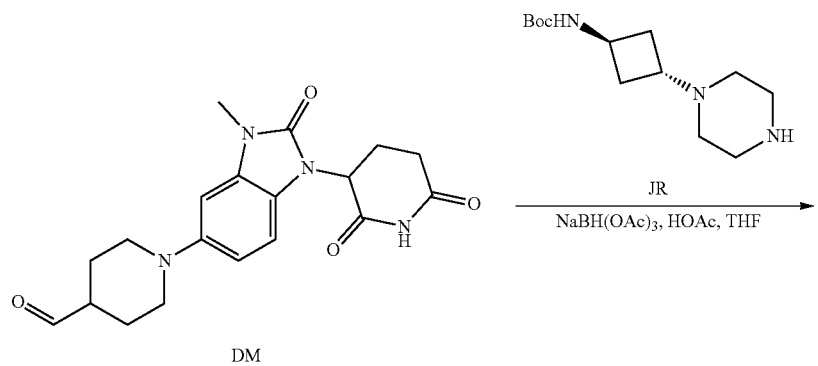

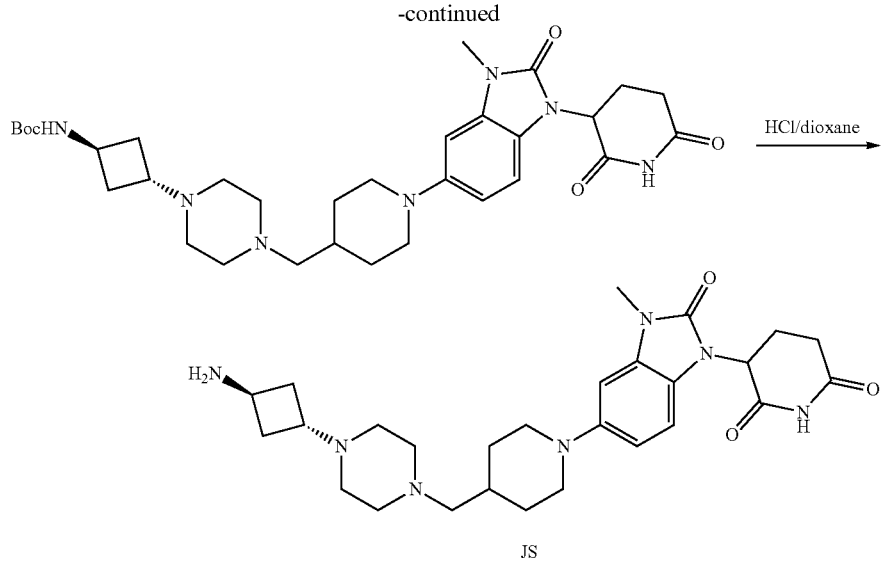

Step 1—Tert-butyl N-[3-[4-[[1-[1-(2,6-dioxo-3-piperidyl)-3-methyl-2-oxo-benzimidazol-5-yl]-4-piperidyl]methyl]piperazin-1-yl]cyclobutyl]carbamate To a solution of 1-[1-(2,6-dioxo-3-piperidyl)-3-methyl-2-oxo-benzimidazol-5-yl]piperidine-4-carbaldehyde (228 mg, 548 umol, FA, Intermediate DM) in THF (4 mL) was added TEA (55.5 mg, 548 umol), then the mixture was stirred at −10° C. for 15 mins. Next, tert-butyl N-(3-piperazin-1-ylcyclobutyl) carbamate (140 mg, 548 umol, Intermediate JR) and HOAc (32.9 mg, 548 umol) was added and the mixture was stirred at −10° C. for 15 mins. Finally, NaBH(OAc)$_3$ (151 mg, 713 umol) was added and the mixture was stirred at −10° C. for 1 hr. On completion, the reaction was quenched with water (0.3 ml) and concentrated in vacuo to give a residue. The residue was purified by prep-HPLC (column: Phenomenex luna C18 150*25 mm*10 um; mobile phase: [water (FA)-ACN]) to give the title compound (80 mg, 22% yield, FA) as off-white solid. $^1$H NMR (400 MHz, CDCl$_3$) δ 8.35 (s, 1H), 6.72-6.62 (m, 3H), 6.44-5.67 (m, 3H), 5.19 (dd, J=5.2, 12.4 Hz, 1H), 4.83 (s, 1H), 4.05 (s, 1H), 3.54 (d, J=10.8 Hz, 2H), 3.40 (s, 3H), 3.28-3.17 (m, 1H), 2.97-2.45 (m, 16H), 2.29-2.07 (m, 3H), 1.89 (d, J=12.4 Hz, 2H), 1.74 (s, 1H), 1.45 (s, 9H), LC-MS (ESI$^+$) m/z 610.2 (M+H)$^+$.

Step 2—3-[5-[4-[[4-(3-Aminocyclobutyl)piperazin-1-yl]methyl]-1-piperidyl]-3-methyl-2-oxo-benzimidazol-1-yl]piperidine-2,6-dione A solution of tert-butyl N-[3-[4-[[1-[1-(2,6-dioxo-3-piperidyl)-3-methyl-2-oxo-benzimidazol-5-yl]-4-piperidyl]methyl]piperazin-1-yl]cyclobutyl]carbamate (60 mg, 91.5 umol, FA) in HCl/dioxan e (2.0 mL) was stirred at 20° C. for 1 hr. On completion, the reaction was concentrated in vacuo to give the title compound (48 mg, 96% yield, HCl) as off-white solid. LC-MS (ESI$^+$) m/z 510.4 (M+H)$^+$.

Tert-butyl N-(3-piperazin-1-ylcyclobutyl)carbamate (Intermediate JT)

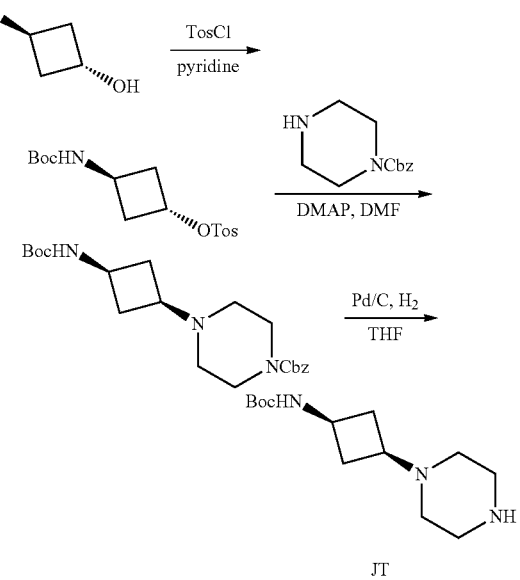

Step 1—[3-(Tert-butoxycarbonylamino)cyclobutyl] 4-methylbenzenesulfonate

To a solution of tert-butyl N-(3-hydroxycyclobutyl)carbamate (2 g, 10.68 mmol, CAS #98-59-9) in pyridine (15 mL) was added 4-methylbenzenesulfonyl chloride (3.05 g, 16.0 mmol), then the reaction mixture was stirred at 50° C. for 12 hrs. On completion, the reaction mixture was quenched with H$_2$O (30 mL) and extracted with EA (2×20 mL). The combined organic phase was washed with brine (2×20 mL), dried with anhydrous Na$_2$SO$_4$, filtered and the filtrate was concentrated in vacuo to give a residue. The residue was purified by column chromatography (SiO$_2$, PE:EA=50:1 to PE:EA=3:1,PE:EA=3:1, P1: Rf=0.32) to give the title compound (3.3 g, 90% yield) as a white solid. ¹H NMR (400 MHz, DMSO-d₆) δ 7.76 (d, J=8.4 Hz, 2H), 7.48 (d, J=8.0 Hz, 2H), 5.03-4.76 (m, 1H), 3.88-3.68 (m, 1H), 2.42 (s, 3H), 2.32-2.24 (m, 2H), 2.19-2.08 (m, 2H), 1.34 (s, 9H).

Step 2—Benzyl 4-[3-(tert-butoxycarbonylamino)cyclobutyl]piperazine-1-carboxylate To a solution of [3-(tert-butoxycarbonylamino)cyclobutyl] 4-methylbenzenesulfonate (2.80 g, 8.20 mmol) and benzyl piperazine-1-carboxylate (2.71 g, 12.3 mmol, 2.38 mL) in DMF (15 mL) was added DMAP (50.1 mg, 410 umol). The mixture was stirred at 100° C. for 16 hrs. On completion, the residue was diluted with water (60 mL) and extracted with EA (2×20 mL). The combined organic layer was washed with brine (20 mL) and dried over Na₂SO₄, filtered and the filtrate was concentrated in vacuo to give a residue. The residue was purified by reverse phase (0.1% FA condition) to give the title compound (2 g 62% yield) as brown oil. ¹H NMR (400 MHz, DMSO-d₆) δ 7.35 (s, 5H), 5.13 (s, 2H), 4.82-4.67 (m, 1H), 3.97-3.79 (m, 1H), 3.55 (s, 4H), 2.58-2.31 (m, 6H), 1.80-1.78 (m, 2H), 1.43 (s, 9H), LC-MS (ESI⁺) m/z 390.3 (M+H)⁺.

Step 3—Tert-butyl N-(3-piperazin-1-ylcyclobutyl)carbamate

To a solution of benzyl 4-[3-(tert-butoxycarbonylamino)cyclobutyl]piperazine-1-carboxylate (500 mg, 1.28 mmol) in THF (10 mL) was added Pd/C (500 mg, 1.28 mmol, 10 wt %), then the reaction mixture was stirred at 25° C. for 1 hr under H₂. On completion, the reaction mixture was filtered and the filtrate was concentrated in vacuo to give the title compound (327 mg, 99% yield) as a white solid, LC-MS (ESI⁺) m/z 255.8 (M+H)⁺.

3-[5-[4-[[4-(3-Aminocyclobutyl)piperazin-1-yl]methyl]-1-piperidyl]-3-methyl-2-oxo-benzimidazol-1-yl]piperidine-2,6-dione (Intermediate JU)

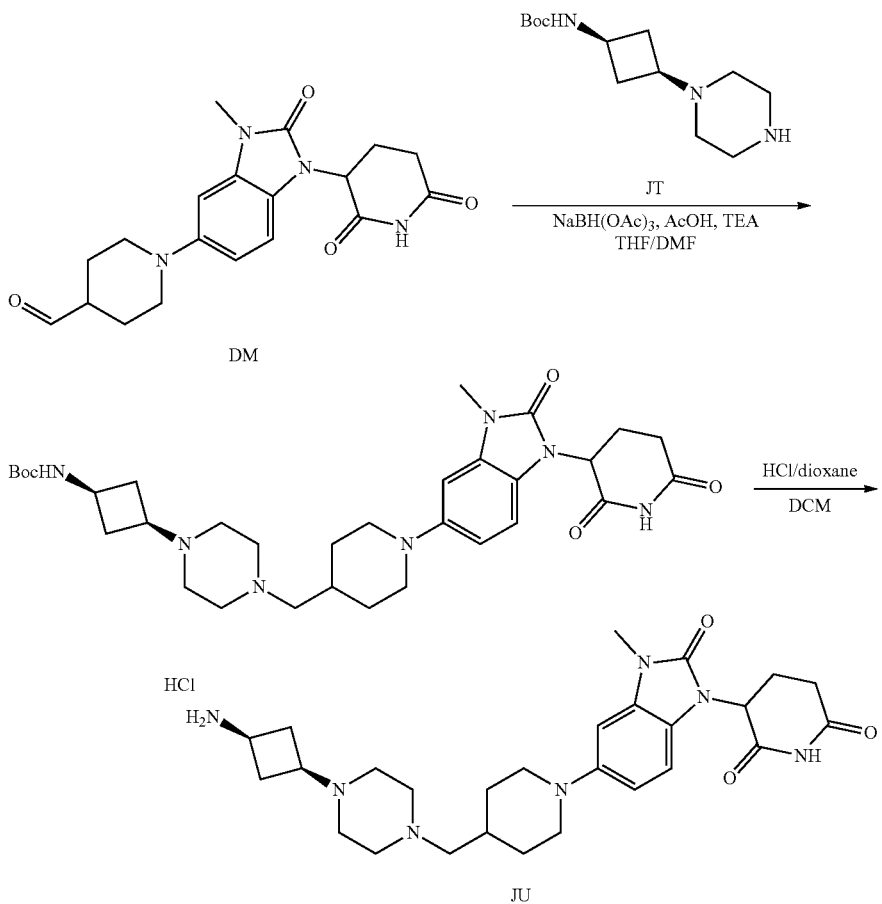

Step 1—Tert-butyl N-[3-[4-[[1-[1-(2,6-dioxo-3-piperidyl)-3-methyl-2-oxo-benzimidazol-5-yl]-4-piperidyl]methyl]piperazin-1-yl]cyclobutyl]carbamate To a solution of tert-butyl N-(3-piperazin-1-ylcyclobutyl)carbamate (293 mg, 1.15 mmol, Intermediate JT) and 1-[1-(2,6-dioxo-3-piperidyl)-3-methyl-2-oxo-benzimidazol-5-yl]piperidine-4-carbaldehyde (425 mg, 1.15 mmol, Intermediate DM) in DMF (2 mL) and THF (10 mL) was added TEA (116 mg, 1.15 mmol, 159 uL). The mixture was stirred at −10° C. for 10 mins, then AcOH (137 mg, 2.29 mmol, 131 uL) was added to the mixture, and the mixture was stirred at −10° C. for 20 mins. Then NaBH(OAc)₃ (316 mg, 1.49 mmol) was added to the mixture, and the mixture was stirred at −10° C. for 1 hr. On completion the reaction mixture was quenched with water (0.5 mL) and concentrated in vacuo to give a residue. The residue was purified by reverse phase (0.1% FA condition) to give the title compound (450 mg, 64% yield) as a purple solid. $^1$H NMR (400 MHz, DMSO-$d_6$) δ 11.06 (s, 1H), 8.16 (s, 1H), 7.04 (d, J=8.0 Hz, 1H), 6.92 (d, J=8.4 Hz, 1H), 6.81 (d, J=2.0 Hz, 1H), 6.62 (dd, J=2.0, 8.4 Hz, 1H), 5.28 (dd, J=5.2, 13.2 Hz 1H), 3.67-3.60 (m, 1H), 3.57-3.54 (m, 2H), 3.29 (s, 3H), 2.95-2.83 (m, 1H), 2.74-2.65 (m, 1H), 2.64-2.52 (m, 4H), 2.43-2.20 (m, 9H), 2.18-2.16 (m, 2H), 2.02-1.93 (m, 1H), 1.78-1.75 (m, 2H), 1.70-1.56 (m, 3H), 1.36 (s, 9H), 1.30-1.15 (m, 2H), LC-MS (ESI$^+$) m/z 610.4 (M+H)$^+$.

Step 2—3-[5-4-[[4-(3-Aminocyclobutyl)piperazin-1-yl]methyl]-1-piperidyl]-3-methyl-2-oxo-benzimidazol-1-yl]piperidine-2,6-dione To a solution of tert-butyl N-[3-[4-[[1-[1-(2,6-dioxo-3-piperidyl)-3-methyl-2-oxo-benzimidazol-5-yl]-4-piperidyl]methyl]piperazin-1-yl]cyclobutyl]carbamate (100 mg, 164 umol) in DCM (1 mL) was added HCl/dioxane (3 M, 2 mL). The mixture was then stirred at 25° C. for 2 hrs. On completion, the reaction mixture was filtered and the filtrate was concentrated in vacuo to give the title compound (89 mg, 99% yield, HCl) as a gray solid. LC-MS (ESI$^+$) m/z 510.4 (M+H)$^+$.

3-[5-[4-(3,9-diazaspiro[5.5]undecan-3-ylmethyl)-1-piperidyl]-3-methyl-2-oxo-benzimidazol-1-yl]piperidine-2,6-dione (Intermediate JV)

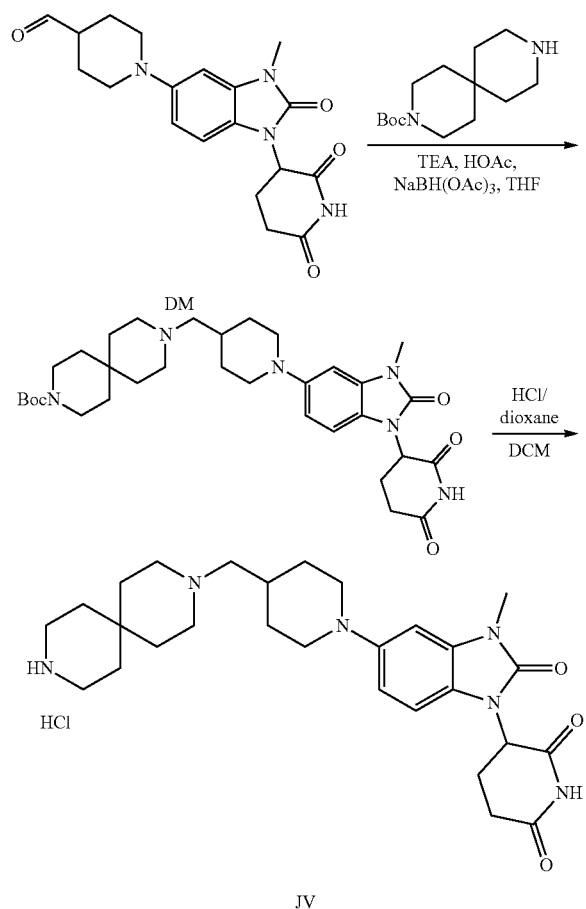

Step 1—Tert-butyl 9-[[1-[1-(2,6-dioxo-3-piperidyl)-3-methyl-2-oxo-benzimidazol-5-yl]-4-piperidyl]methyl]-3,9-diazaspiro[5.5]undecane-3-carboxylate To a solution of 1-[1-(2,6-dioxo-3-piperidyl)-3-methyl-2-oxo-benzimidazol-5-yl]piperidine-4-carbaldehyde (210 mg, 567 umol, Intermediate DM) and tert-butyl 3,9-diazaspiro[5.5]undecane-3-carboxylate (158 mg, 623 umol, CAS #173405-78-2) in THF (2 mL) and DMF (2 mL) was added HOAc (34.0 mg, 567 umol) and TEA (57.3 mg, 567 umol) at −10° C. and the mixture was stirred at −10° C. for 20 min. Then, NaBH(OAc)$_3$ (180 mg, 850 umol) was added at −10° C., and the reaction mixture was stirred at −10° C. for 2 hrs. On completion, the reaction mixture was quenched with H$_2$O (0.5 mL). The residue was purified by prep-HPLC (column: Phenomenex luna C18 150*25 mm*10 um; mobile phase: [water (FA)-ACN]; B %: 3%-33%, 15 min) to give the title compound (250 mg, 72% yield) as a brown solid. $^1$H NMR (400 MHz, DMSO-$d_6$) δ 11.05 (s, 1H), 6.92 (d, J=8.4 Hz, 1H), 6.81 (d, J=2.0 Hz, 1H), 6.62 (dd, J=2.0, 8.4 Hz, 1H), 5.28 (dd, J=5.2, 12.8 Hz, 1H), 3.57 (d, J=12.0 Hz, 2H), 3.27 (s, 4H), 2.95-2.83 (m, 1H), 2.73-2.58 (m, 4H), 2.55-2.51 (m, 3H), 2.38 (d, J=6.8 Hz, 2H), 2.02-1.95 (m, 1H), 1.78 (d, J=12.8 Hz, 2H), 1.69 (dd, J=3.6, 7.2 Hz, 1H), 1.54-1.47 (m, 4H), 1.40-1.32 (m, 15H), 1.32-1.19 (m, 4H).

Step 2—3-[5-[4-(3,9-diazaspiro[5.5]undecan-3-ylmethyl)-1-piperidyl]-3-methyl-2-oxo-benzimidazol-1-yl]piperidine-2,6-dione To a solution of tert-butyl 9-[[1-[1-(2,6-dioxo-3-piperidyl)-3-methyl-2-oxo-benzimidazol-5-yl]-4-piperidyl]methyl]-3,9-diazaspiro[5.5]undecane-3-carboxylate (100 mg, 164 umol) in DCM (0.2 mL) was added HCl/dioxane (4 M, 1.00 mL), then the reaction mixture was stirred at 25° C. for 1 hr. On completion, the reaction mixture was concentrated in vacuo to give the title compound (89 mg, 99% yield) as a yellow solid. LCMS (ESI$^+$) m/z 509.4 (M+H)$^+$.

7-Bromoheptanal (Intermediate JW)

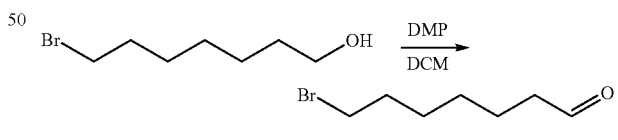

To a solution of 7-bromoheptan-1-ol (100 mg, 512 umol, CAS #10160-24-4) in DCM (3 m L) was added DMP (260 mg, 615 umol). The mixture was stirred at 25° C. for 1 hr. On complete, the reaction mixture was quenched with Na$_2$S$_2$O$_3$.5H$_2$O (10 mL), and extracted with DCM (3×20 mL). The combined organic layer was washed with brine (20 mL), dried over anhydrous sodium sulfate, filtered and the filtrate was concentrated in vacuo to give the title compound (95 mg, 95% yield) as a white solid.

3-(4-amino-3-methyl-2-oxo-benzimidazol-1-yl)piperidine-2,6-dione (Intermediate JX)

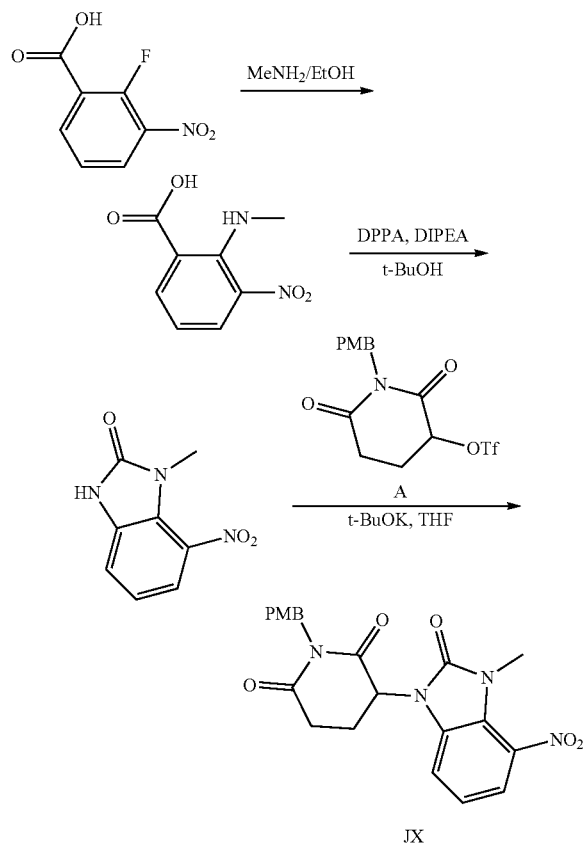

Step 1—2-(Methylamino)-3-nitro-benzoic acid

To a solution of MeNH$_2$/EtOH (54.0 mmol, 200 mL, 30% solution) was added 2-fluoro-3-nitro-benzoic acid (10.0 g, 54.0 mmol) in portions at 0° C. Then the reaction mixture was stirred at 20° C. for 2 hrs. On completion, the mixture was concentrated in vacuo. The residue was diluted with water (100 mL), acidified with citric acid to pH=3-5, stirred and filtered. The filter cake was dried in vacuo to give the title compound (9.60 g, 91% yield) as a yellow solid. $^1$H NMR (400 MHz, DMSO-d$_6$) δ 13.41 (s, 1H), 8.62 (s, 1H), 8.04 (dd, J=1.6, 8.0 Hz, 1H), 7.97 (dd, J=1.6, 8.0 Hz, 1H), 6.72 (t, J=8.0 Hz, 1H), 2.70 (s, 3H).

Step 2—3-Methyl-4-nitro-1H-benzimidazol-2-one

To a solution of 2-(methylamino)-3-nitro-benzoic acid (8.60 g, 43.8 mmol) and DIPEA (17.0 g, 132 mmol) in t-BuOH (200 mL) was added DPPA (12.1 g, 43.8 mmol) dropwise at 0° C. Then the reaction mixture was stirred at 85° C. for 12 hours. On completion, the mixture was diluted with MeOH (100 mL), cooled to 10-20° C., filtered and the filter cake was dried in vacuo to give the title compound (6.80 g, 80% yield) as a yellow solid. $^1$H NMR (400 MHz, DMSO-d$_6$) δ 11.61 (s, 1H), 7.58 (dd, J=0.8, 8.0 Hz, 1H), 7.30 (dd, J=0.8, 8.0 Hz, 1H), 7.18-7.07 (m, 1H), 3.34 (s, 3H).

Step 3—1-[(4-Methoxyphenyl)methyl]-3-(3-methyl-4-nitro-2-oxo-benzimidazol-1-yl)piperidine-2,6-dione To a solution of 3-methyl-4-nitro-1H-benzimidazol-2-one (7.20 g, 37.3 mmol) in THF (70 mL) was added t-BuOK (8.37 g, 74.6 mmol) at −10-0° C. One hour later, a solution of [1-[(4-methoxyphenyl)methyl]-2,6-dioxo-3-piperidyl] trifluoromethanesulfonate (21.3 g, 55.9 mmol, Intermediate H) in THF (50 mL) was added into the above mixture and the reaction mixture was stirred at 0-20° C. for 12 hrs. On completion, the mixture was acidified with FA to pH=3-5, diluted with water (300 mL), and extracted with EA (2×300 mL). The organic layer was washed with brine (200 mL), then concentrated in vacuo. The residue was purified by reverse phase (0.1% FA condition) to give the title compound (5.80 g, 37% yield) as a yellow solid. $^1$H NMR (400 MHz, DMSO-d$_6$) δ 7.69 (dd, J=0.8, 8.0 Hz, 1H), 7.46 (d, J=8.0 Hz, 1H), 7.27-7.17 (m, 3H), 6.93-6.78 (m, 2H), 5.67 (dd, J=5.2, 12.8 Hz, 1H), 4.94-4.62 (m, 2H), 3.72 (s, 3H), 3.41 (s, 3H), 3.11-2.98 (m, 1H), 2.89-2.70 (m, 2H), 2.17-2.08 (m, 1H).

Step 4—3-(3-Methyl-4-nitro-2-oxo-benzimidazol-1-yl)piperidine-2,6-dione

To a solution of 1-[(4-methoxyphenyl)methyl]-3-(3-methyl-4-nitro-2-oxo-benzimidazol-1-yl) piperidine-2,6-dione (2.00 g, 4.71 mmol) in TFA (20 mL) was added TfOH (2 mL). The reaction mixture was stirred at 60° C. for 12 hours. On completion, the mixture was concentrated in vacuo. The residue was purified by reverse phase (0.1% FA condition) to give the title compound (900 mg, 63% yield) as a yellow solid. $^1$H NMR (400 MHz, DMSO-d$_6$) δ 11.19 (s, 1H), 7.68 (dd, J=0.8, 8.0 Hz, 1H), 7.55 (d, J=8.0 Hz, 1H), 7.23 (t, J=8.0 Hz, 1H), 5.51 (dd, J=5.2, 12.8 Hz, 1H), 3.41 (s, 3H), 2.95-2.85 (m, 1H), 2.80-2.60 (m, 2H), 2.13-2.06 (m, 1H).

Step 5—3-(4-Amino-3-methyl-2-oxo-benzimidazol-1-yl)piperidine-2,6-dione

To a solution of 3-(3-methyl-4-nitro-2-oxo-benzimidazol-1-yl)piperidine-2,6-dione (850 mg, 2.79 mmol) in THF (50 mL) was added Pd/C (200 mg, 10% wt). The reaction mixture was stirred at 20° C. for 12 hrs under H$_2$ (15 Psi) atmosphere. On completion, the mixture was filtered and the filtrate was concentrated in vacuo to give the title compound (0.70 g, 91% yield) as a pink solid. LC-MS (ESI$^+$) m/z 275.1 (M+H)$^+$.

3-(4-Amino-3-methyl-2-oxo-benzimidazol-1-yl)-1-[(4-methoxyphenyl)methyl]piperidine-2,6-dione (Intermediate JY)

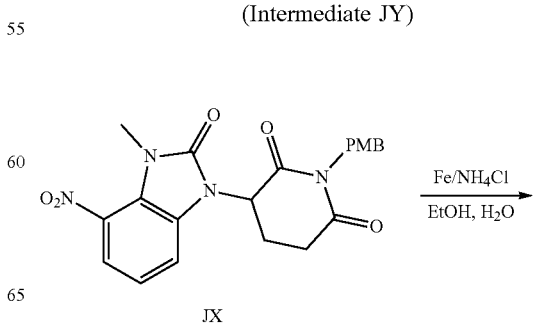

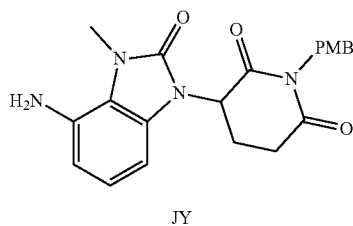

To a solution of 1-[(4-methoxyphenyl)methyl]-3-(3-methyl-4-nitro-2-oxo-benzimidazol-1-yl)piperidine-2,6-dione (310 mg, 730 umol, Intermediate JX) in a mixture solution of EtOH (5 mL) and H₂O (5 mL) was added Fe (203 mg, 3.65 mmol) and NH₄Cl (390 mg, 7.30 mmol). The mixture was stirred a t 80° C. for 2 hrs. The reaction mixture was filtered and the filtrate concentrated in vacuo to give a residue. Then the residue was partitioned between EA (10 ml) and water (10 ml). The organic layer was collected, and the aqueous layer was extracted with EA (2×8 ml). The combined organic layers were washed with brine (10 ml), dried over anhydrous sodium sulfate, and concentrated in vacuo to give the title compound (285 mg, 98% yield) as a yellow solid. LCMS (ESI⁺) m/z 394.9 (M+H)⁺.

3-[4-(7-bromoheptylamino)-3-methyl-2-oxo-benzimidazol-1-yl]-1-[(4-methoxyphenyl) m ethyl]piperidine-2,6-dione (Intermediate JZ)

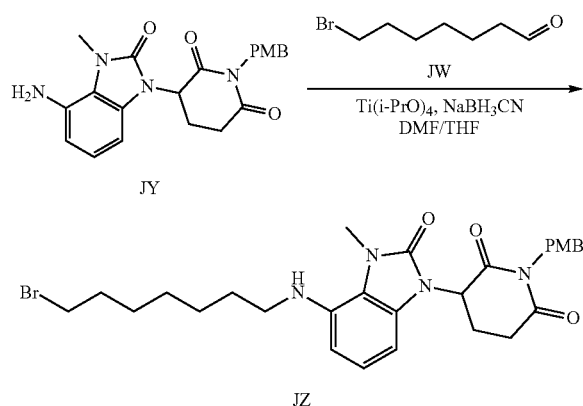

To a solution of 3-(4-amino-3-methyl-2-oxo-benzimidazol-1-yl)-1-[(4-methoxyphenyl)methyl] piperidine-2,6-dione (50.0 mg, 126 umol, Intermediate JY) in a mixed solvent of THF (2 mL) and D MF (0.5 mL) was added 7-bromoheptanal (25.7 mg, 133 umol, Intermediate JW) and tetraisopropoxytitanium (72.0 mg, 253 umol) at 25° C. for 16 hrs. Then, NaBH₃CN (15.9 mg, 253 umol) was added into the mixture and the reaction mixture was stirred at 25° C. for 1 hr. The reaction mixture was partitioned between H₂O (20 mL) and EA (20 mL). The organic phase was separated, washed with brine (20 mL), dried over anhydrous Na₂SO₄, filtered and concentrated in vacuo to give a residue. The residue was purified by prep-T LC (SiO₂, PE:EA=1:1) to give the title compound (25 mg, 34% yield) as a white solid. LCMS (ESI⁺) m/z 573.1 (M+H)⁺.

6-Chloro-8-isopropyl-2-(4-piperidylamino)pyrido[2,3-d]pyrimidin-7-one (Intermediate K

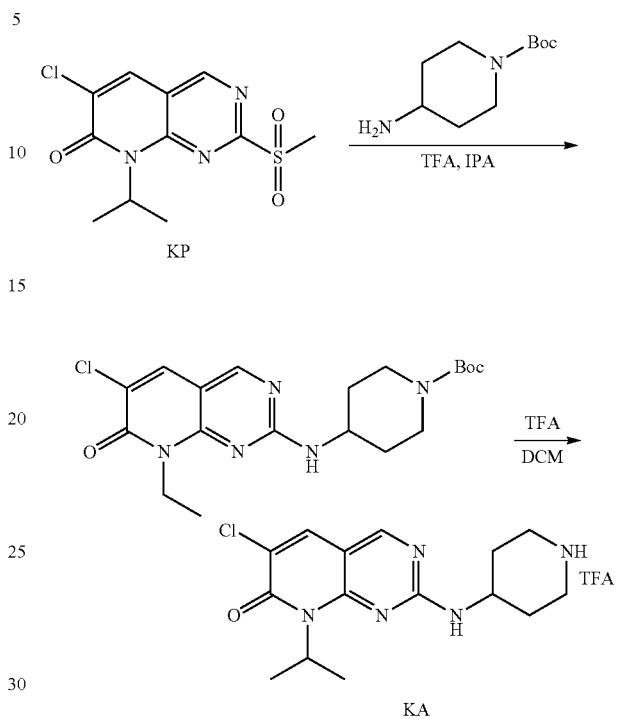

Step 1—Tert-butyl 4-[(6-chloro-8-isopropyl-7-oxopyrido[2,3-d]pyrimidin-2-yl)amino]piperidine-1-carboxylate To a solution of 6-chloro-8-isopropyl-2-methylsulfonyl-pyrido[2,3-d]pyrimidin-7-one (450 mg, 1.49 mmol, Intermediate KP) in DMSO (1 mL) was added DIEA (192 mg, 1.49 mmol), tert-butyl 4-aminopiperidine-1-carboxylate (358 mg, 1.79 mmol, CAS #502482-34-0). The mixture was stirred at 90° C. for 1 hr. On completion, the reaction mixture was filtered and concentrated in vacuo to give a residue. The residue was purified by prep-HPLC (column: YMC Triart C18 250*50 mm*7 um; mobile phase: [water (FA)-ACN]; B %: 65%-75%, 22 min) to give the title compound (800 mg, 63% yield) as a white solid. ¹H NM R (400 MHz, DMSO-d₆) δ 8.62-8.56 (m, 1H), 8.05 (s, 1H), 7.97 (d, J=7.2 Hz, 1H), 7.81 (d, J=6.4 Hz, 1H), 5.86-5.61 (m, 1H), 4.09-3.98 (m, 1H), 3.92 (d, J=12.4 Hz, 2H), 2.97-2.82 (m, 2H), 1.90-1.80 (m, 2H), 1.54-1.48 (m, 6H), 1.40 (s, 12H). LCMS (ESI⁺) m/z 422.0 (M+H)⁺.

Step 2—6-Chloro-8-isopropyl-2-(4-piperidylamino)pyrido[2,3-d]pyrimidin-7-one

To a solution of tert-butyl 4-[(6-chloro-8-isopropyl-7-oxo-pyrido[2,3-d]pyrimidin-2-yl)amino] piperidine-1-carboxylate (170 mg, 402 umol) in DCM (3 mL) was added TFA (1.54 g, 13.5 mmol). The mixture was stirred at 25° C. for 0.5 hr. The reaction mixture was concentrated in vacuo to give the title compound (175 mg, 99% yield, TFA) as a white solid. LCMS (ESI⁺) m/z 321.9 (M+H)⁺.

6-Chloro-8-isopropyl-2-[[1-(1H-pyrazol-4-ylsulfonyl)-4-piperidyl]amino]pyrido[2,3-d]pyrimidin-7-one (Intermediate KB)

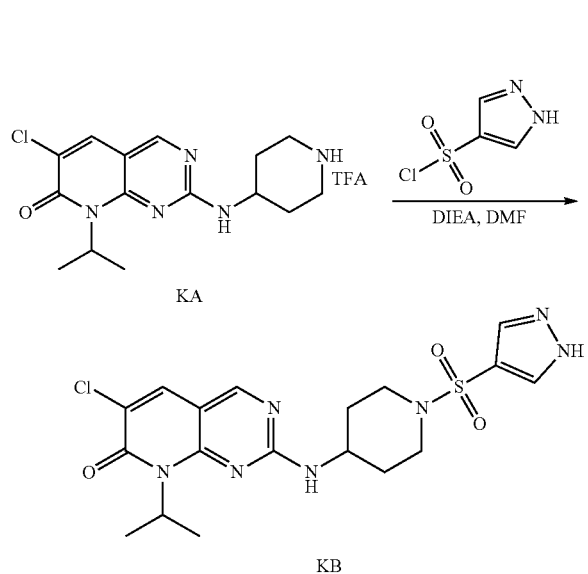

To a solution of 6-chloro-8-isopropyl-2-(4-piperidylamino)pyrido[2,3-d]pyrimidin-7-one (175 mg, 401 umol, TFA, Intermediate KA) in DMF (4 mL) was added DIEA (155 mg, 1.20 mmol) and 1H-pyrazole-4-sulfonyl chloride (93.6 mg, 562 umol, CAS #438630-64-9). The mixture was stirred at 25° C. for 0.5 hr. The reaction mixture was concentrated in vacuo to give a residue. The residue was purified by prep-HPLC (column: Phenomenex luna C18 150*25 mm*10 um; mobile phase: [water(FA)-ACN]; B %: 28%-58%, 9 min) to give the title compound (100 mg, 55% yield) as a white solid. $^1$H NMR (400 MHz, DMSO-$d_6$) δ 13.76 (s, 1H), 8.57 (s, 1H), 8.40-8.10 (m, 1H), 8.04 (s, 1H), 8.01 (d, J=7.2 Hz, 1H), 7.86 (d, J=7.2 Hz, 1H), 5.86-5.51 (m, 1H), 3.81 (d, J=15.2 Hz, 1H), 3.47 (d, J=12.0 Hz, 2H), 2.49-2.46 (m, 1H), 2.45-2.35 (m, 1H), 2.03-1.89 (m, 2H), 1.70-1.57 (m, 2H), 1.48 (d, J=6.8 Hz, 6H). LCMS (ESI$^+$) m/z 452.0 (M+H)$^+$.

6-(Difluoromethyl)-2-methylsulfonyl-8-spiro[2.4]heptan-7-yl-pyrido[2,3-d]pyrimidin-7-one (Intermediate KC)

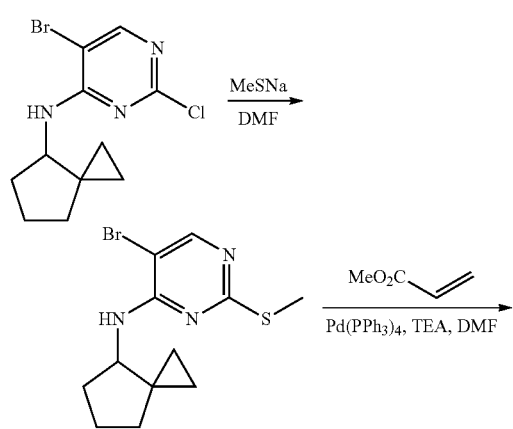

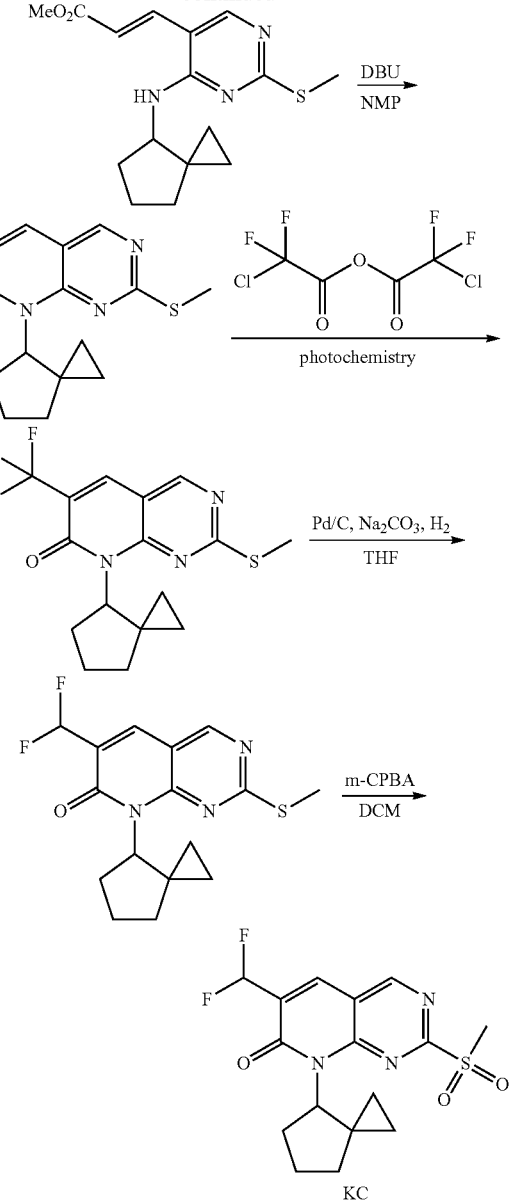

Step 1—5-Bromo-2-methylsulfanyl-N-spiro[2.4]heptan-7-yl-pyrimidin-4-amine

To a solution of 5-bromo-2-chloro-N-spiro[2.4]heptan-7-yl-pyrimidin-4-amine (6.70 g, 22.1 mmol, synthesized via Step 1 of Intermediate HX) in DMF (70 mL) was added NaSMe (2.54 g, 36.2 m mol, 2.31 mL) at 0° C. The reaction was stirred at 25° C. for 16 hrs. On completion, the reaction was diluted with EA (150 mL). The organic layer was washed with water (2×100 mL), dried over anhydrous Na$_2$SO$_4$ and filtered. The filtrate was concentrated in vacuo to give the title compound (6.2 g, 89% yield) as a yellow solid. LC-MS (ESI$^+$) m/z 315.8 (M+1)$^+$.

Step 2—Methyl (E)-3-[2-methylsulfanyl-4-(spiro[2.4]heptan-7-ylamino)pyrimidin-5-yl]prop-2-enoate To a solution of 5-bromo-2-methylsulfanyl-N-spiro[2.4]heptan-7-yl-pyrimidin-4-amine (6.20 g, 19.7 mmol), TEA (2.00 g, 19.7 mmol, 2.75 mL), and Pd(PPh$_3$)$_4$ (2.28 g, 1.97 mmol) in DMF (100 m L) was added methyl prop-2-enoate (13.0 g, 151 mmol, 13.6 mL, CAS #96-33-3). The reaction was then stirred at 90° C. for 32 hrs under N$_2$. On completion, the reaction was diluted with EA (200 mL). The organic layer was washed with water (2×100 mL), dried over anhydrous Na$_2$SO$_4$ and filtered. The filtrate was concentrated in vacuo and then the residue was purified by column chromatography (SiO$_2$, Petroleum ether/Ethyl acetate=1/4) to give the title compound (3.9 g, 61% yield) as a yellow solid. LC-MS (ESI$^+$) m/z 320.3 (M+1)$^+$.

Step 3—2-Methylsulfanyl-8-spiro[2.4]heptan-7-yl-pyrido[2,3-d]pyrimidin-7-one

To a solution of methyl (E)-3-[2-methylsulfanyl-4-(spiro [2.4]heptan-7-ylamino)pyrimidin-5-yl] prop-2-enoate (2.80 g, 8.77 mmol) in NMP (30 mL) was added DBU (6.67 g, 43.8 mmol, 6.61 mL). The reaction was stirred at 150° C. for 2 hrs under N$_2$. On completion, the reaction was diluted with EA (300 mL). The organic layer was washed with water (3×100 mL), dried over anhydrous Na$_2$SO$_4$ and filtered. The filtrate was concentrated in vacuo and then the residue was purified by column chromatography (Si O$_2$, Petroleum ether/ Ethyl acetate=5/1) to give the title compound (2.3 g, 91% yield) as a brown solid. L C-MS (ESI$^+$) m/z 288.0 (M+1)$^+$.

Step 4—6-[Chloro(difluoro)methyl]-2-methylsulfanyl-8-spiro[2.4]heptan-7-yl-pyrido[2,3-d]pyrimidin-7-one To an 15 mL vial equipped with a stir bar was added 4-phenylpyridine N-Oxide (2.38 g, 13.9 mmol), 2-methylsulfanyl-8-spiro[2.4]heptan-7-yl-pyrido[2,3-d]pyrimidin-7-one (2.00 g, 6.96 mmol), Ru(bpy)$_3$Cl$_2$.6H$_2$O (52.1 mg, 69.5 umol) in dry ACN (2 mL). Then (2-chloro-2,2-difluoro-acetyl) 2-chloro-2,2-difluoro-acetate (4.23 g, 17.40 mmol, CAS #2834-23-3) was added. The vial was sealed and placed under nitrogen was added. The reaction was stirred and irradiated with a 34 W blue LED lamp (2 cm away) with cooling water to keep the reaction temperature at 25° C. for 16 hrs. On completion, the reaction was concentrated in vacuo. Then the residue was purified by column chromatography (SiO$_2$, Petroleum ether/Ethyl acetate=10/1 to 3/1) to give the title compound (2.59 g, 100% yield) as a yellow solid. LC-MS (ESI$^+$) m/z 372.0 (M+1)$^+$.

Step 5—N-[5-isopropoxy-6-(1H-pyrazol-4-yl)-[1,2,4]triazolo[1,5-a]pyrazin-2-yl]acetamide A mixture of 6-[chloro(difluoro)methyl]-2-methylsulfanyl-8-spiro[2.4]heptan-7-yl-pyrido [2,3-d] pyrimidin-7-one (1.00 g, 2.69 mmol), Pd/C (318 mg, 268 umol, 10 wt %), Na$_2$CO$_3$ (427 mg, 4.03 m mol) in THF (20 mL) was degassed and purged with H$_2$ three times. Then the mixture was stirred under H$_2$ (30 Psi) at 25° C. for 1 hr under H$_2$ atmosphere. On completion, the reaction mixture was filtered and concentrated in vacuo to give a residue. Then the residue was purified by prep-HPLC (column: YMC Triart C 18 250*50 mm*7 um; mobile phase: [water(FA)-ACN]; B %: 60%-70%, 20 min) to give a title compound (107 mg, 11% yield). LC-MS (ESI$^+$) m/z 338.0 (M+1)$^+$.

Step 6—6-(Difluoromethyl)-2-methylsulfonyl-8-spiro[2.4]heptan-7-yl-pyrido[2,3-d]pyrimidin-7-one To a solution of 6-(difluoromethyl)-2-methylsulfanyl-8-spiro[2.4]heptan-7-yl-pyrido[2,3-d]pyrimidin-7-one (100 mg, 296 umol) in DCM (2 mL) was added m-CPBA (240 mg, 1.19 mmol, 85% solution). The mixture was stirred at 40° C. for 16 hrs. On completion, the reaction mixture was quenched with H$_2$O (5 mL) at 25° C., and then extracted with EA (3×5 mL). The combined organic layers were washed with brine (2×5 mL), dried over anhydrous Na$_2$SO$_4$, filtered and concentrated in vacuo to give a residue. Then the residue was purified by prep-TLC (SiO$_2$, PE:EA=1:1) to give a title compound (50 mg, 40% yield). $^1$H NMR (400 MHz, CDCl$_3$) δ 9.04 (s, 1H), 8.07 (s, 1H), 7.02-6.69 (m, 1H), 6.01-5.69 (m, 1H), 3.40 (s, 3H), 2.59-2.49 (m, 1H), 2.25-2.13 (m, 2H), 1.97-1.85 (m, 1H), 1.56 (s, 1H), 1.47-1.42 (m, 1H), 0.75-0.59 (m, 3H), 0.03-0.01 (m, 1H). LC-MS (ESI$^+$) m/z 370.0 (M+1)$^+$.

4-[[6-(Difluoromethyl)-7-oxo-8-spiro[2.4]heptan-7-yl-pyrido[2,3-d]pyrimidin-2-yl]amino]-3-methyl-benzenesulfonyl chloride (Intermediate KD)

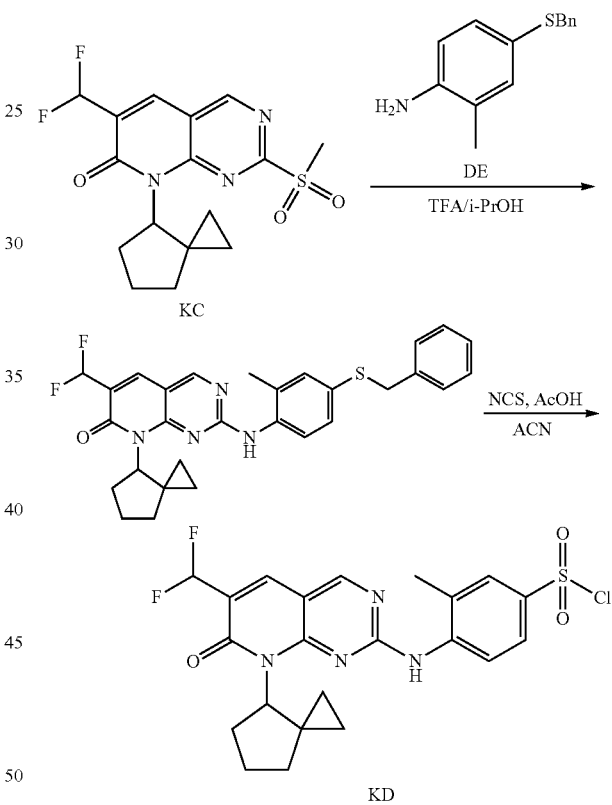

Step 1—2-(4-Benzylsulfanyl-2-methyl-anilino)-6-(difluoromethyl)-8-spiro[2.4]heptan-7-v 1-pyrido [2,3-d]pyrimidin-7-one A mixture of 6-(difluoromethyl)-2-methylsulfonyl-8-spiro[2.4]heptan-7-yl-pyrido[2,3-d]pyrimidin-7-one (45.0 mg, 121 umol, Intermediate KC), 4-benzylsulfanyl-2-methyl-aniline (83.8 mg, 365 umol, Intermediate DE), and TFA (138 mg, 1.22 mmol, 90.2 uL) in IPA (2 mL) was stirred at 90° C. for 32 hrs. On completion, the reaction mixture was concentrated in vacuo to give a residue. Then the residue was purified by prep-TLC (SiO$_2$, PE:EA=1:1) to give the title compound (35 mg, 55% yield) as a white solid. LC-MS (ESI$^+$) m/z 519.4 (M+1)$^+$.

Step 2—4-[[6-(Difluoromethyl)-7-oxo-8-spiro[2.4]heptan-7-yl-pyrido[2,3-d]pyrimidin-2-yl]amino]-3-methyl-benzenesulfonyl chloride To a solution of 2-(4-benzylsulfanyl-2-methyl-anilino)-6-(difluoromethyl)-8-spiro[2.4]heptan-7-yl-pyrido[2,3-d]pyrimidin-7-one (26.9 mg, 51.9 umol) in $H_2O$ (0.06 mL), ACN (1 mL) and AcOH (0.1 mL) was added NCS (17.3 mg, 129 umol). The mixture was stirred at 25° C. for 0.5 hr. On completion the reaction mixture was quenched with $H_2O$ (10 mL) at 25° C., and then extracted with EA (3×10 mL). The combined organic layers were washed with brine (2×10 mL), dried over anhydrous $Na_2SO_4$, filtered and concentrated under reduced pressure to give a residue. Then the residue was purified by prep-TLC ($SiO_2$, PE/EA=1/1) to give the title compound (20 mg, 77% yield) as a white solid. LC-MS (ESI$^+$) m/z 495.1 (M+1)$^+$.

4-Bromo-5-methoxy-3-methyl-1H-benzimidazol-2-one (Intermediate KE)

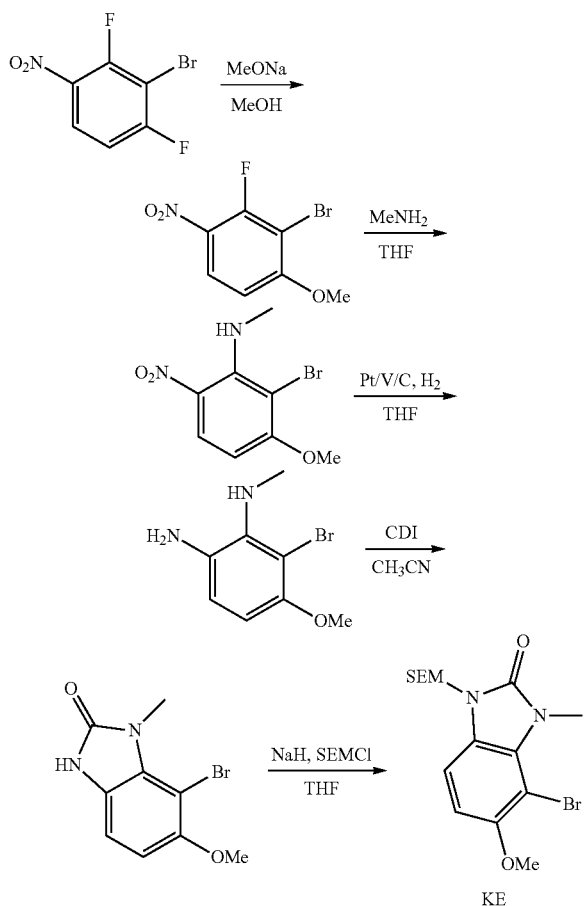

Step 1—2-Bromo-3-fluoro-1-methoxy-4-nitro-benzene

To a mixture of 2-bromo-1,3-difluoro-4-nitro-benzene (5.00 g, 21.01 mmol, from CAS #103977-78-2) in MeOH (50 mL) was added NaOMe (1.14 g, 21.0 mmol) at 0° C. The mixture was warmed to 20° C. and stirred for 2 hours. On completion, the mixture was poured into the water (60 mL) and the aqueous phase was extracted with ethyl acetate (2×40 mL). The combined organic phase was washed with brine (2×40 mL), dried with anhydrous $Na_2SO_4$, filtered and concentrated in vacuo to give the crude product. The crude product was triturated with PE:EA=20:1 (10 mL) to give the title compound (1.80 g, 34% yield) as white solid. $^1$H NMR (400 MHz, CDCl$_3$) δ 8.14 (dd, J=8.4, 9.2 Hz, 1H), 6.81 (dd, J=1.6, 9.2 Hz, 1H), 4.04 (s, 3H).

Step 2—2-Bromo-3-methoxy-N-methyl-6-nitro-aniline

To a mixture of 2-bromo-3-fluoro-1-methoxy-4-nitro-benzene (1.60 g, 6.40 mmol) in THF (20 mL) was added MeNH$_2$ (2 M, 4.80 mL) and the mixture was stirred at 20° C. for 2 hours. On completion, the mixture was concentrated in vacuo to give the residue. The residue was purified by column chromatography ($SiO_2$, petroleum ether/ethyl acetate=50:1 to 10:1) to give the title compound (1.40 g, 83% yield) as brown solid. $^1$H NMR (400 MHz, CDCl$_3$) δ 8.06 (d, J=9.6 Hz, 1H), 6.73 (s, 1H), 6.44 (d, J=9.2 Hz, 1H), 3.97 (s, 3H), 3.09 (d, J=5.2 Hz, 3H).

Step 3—3-Bromo-4-methoxy-N2-methyl-benzene-1,2-diamine

To a mixture of 2-bromo-3-methoxy-N-methyl-6-nitro-aniline (1.40 g, 5.36 mmol) in THF (10 mL) and MeOH (10 mL) was added platinum (104 mg, 53.6 umol, 10 wt %) under H$_2$ (15 psi) and stirred at 20° C. for 2 hours. On completion, the mixture was filtered and concentrated to give the title compound (1.20 g, 96% yield) as a yellow solid.

Step 4—4-Bromo-5-methoxy-3-methyl-1H-benzimidazol-2-one

To a mixture 3-bromo-4-methoxy-N2-methyl-benzene-1,2-diamine (1.1 g, 4.76 mmol) in CH$_3$CN (20 mL) was added CDI (1.16 g, 7.14 mmol) and the mixture was stirred at 90° C. for 3 hours. On completion, the mixture was concentrated to remove the CH$_3$CN, then H$_2$O (10 mL) was added into the mixture. The mixture was filtered to give the filter cake which was dried to give the title compound (1.00 g, 81% yield) as brown solid. $^1$H NMR (400 MHz, CDCl$_3$) δ 6.89 (d, J=8.4 Hz, 1H), 6.59 (d, J=8.8 Hz, 1H), 3.81 (s, 3H), 3.71 (s, 3H), 2.72 (d, J=2.4 Hz, 1H).

Step 5—4-Bromo-5-methoxy-3-methyl-1-((2-(trimethylsilyl)ethoxy)methyl)-1H-benzo[d]imidazol-2(3H)-one To a solution of 7-bromo-6-methoxy-1-methyl-1H-benzo[d]imidazol-2(3H)-one (1.00 g, 3.90 mmol) in THF (30 mL) was added NaH (234 mg, 5.85 mmol, 60% dispersion in mineral oil) at 0° C. and the mixture was stirred at 0° C. for 0.5 hr. Then SEM-Cl (0.98 g, 5.85 mmol) was added to above solution and the mixture was stirred at 65° C. for 10 hrs. On completion, the mixture was quenched with H$_2$O (30 mL), and extracted with EA (2×30 mL). The organic layers were washed with brine (2×30 mL), dried over anhydrous Na$_2$SO$_4$, filtered and concentrated in vacuo. The mixture was purified by silica gel column (PE:EA=20:1) to give the title compound (1.30 g, 86% yield) as yellow oil. LC-MS (ESI$^+$) m/z 387.0 (M+H)$^+$.

3-(5-methoxy-3-methyl-4-(4-(methylamino)piperidin-1-yl)-2-oxo-2,3-dihydro-1H-benzo[d] imidazol-1-yl)piperidine-2,6-dione (Intermediate KF)

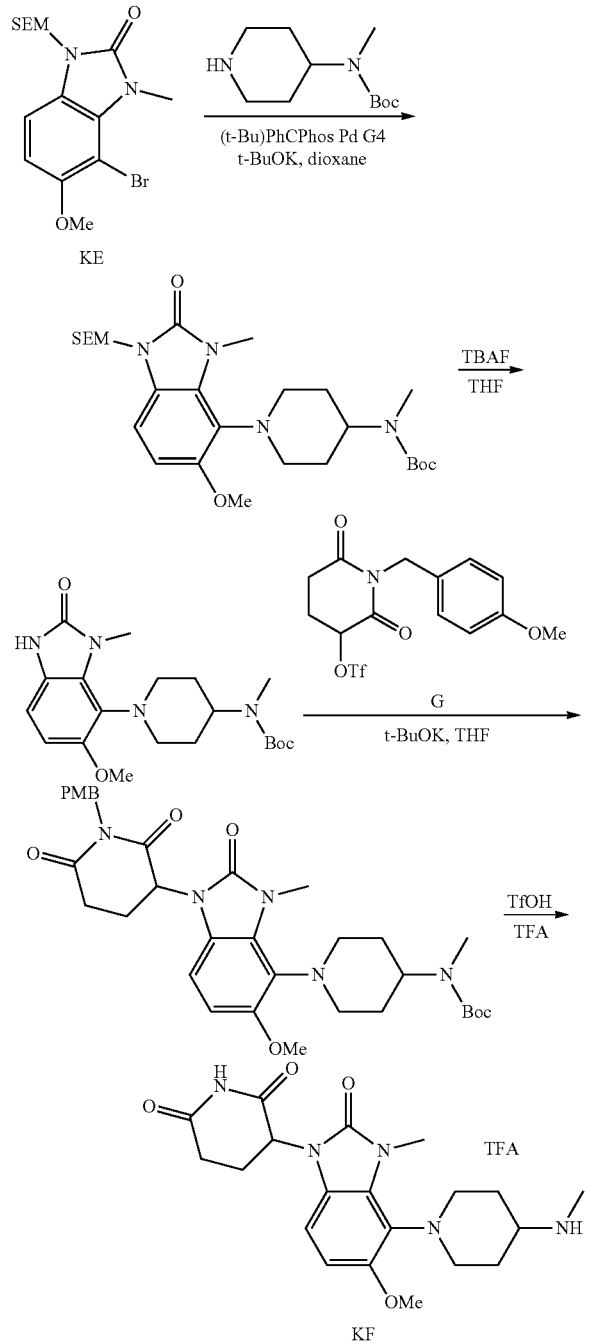

Step 1—Tert-butyl N-[1-[5-methoxy-3-methyl-2-oxo-1-(2-trimethylsilylethoxymethyl)benzimidazol-4-yl]-4-piperidyl]-N-methyl-carbamate A solution of 4-bromo-5-methoxy-3-methyl-1-(2-trimethylsilylethoxymethyl)benzimidazol-2-one (250 mg, 645 umol, Intermediate KE) tert-butyl N-methyl-N-(4-piperidyl)carbamate (276 mg, 1.29 mmol, CAS #108612-54-0), (t-Bu) PhCPhos Pd G4 (35 mg, 64.5 umol) and t-BuOK (217 mg, 1.94 mmol) in dioxane (8 mL) was stirred at 85° C. under $N_2$ for 16 hrs. On completion, the reaction mixture was diluted with EtOAC (40 mL), and washed with brine (2×20 mL). The organic layer was separated and dried over $Na_2SO_4$ and concentrated in vacuo. The residue was purified by reverse phase (FA condition) to give the title compound (35.0 mg, 10% yield). $^1$H NMR (400 MHz, MeOD) δ 7.04 (d, J=8.8 Hz, 1H), 6.79 (d, J=8.8 Hz, 1H), 5.31 (s, 2H), 3.89 (s, 3H), 3.81 (s, 3H), 3.67-3.53 (m, 4H), 3.39 (s, 1H), 3.06-2.99 (m, 2H), 2.87 (s, 3H), 2.09-1.92 (m, 2H), 1.68 (d, J=12 Hz, 2H), 1.53 (s, 9H), 1.39-1.31 (m, 2H), 0.98-0.89 (m, 2H), 0.00 (s, 9H).

Step 2—Tert-butyl (1-(5-methoxy-3-methyl-2-oxo-2,3-dihydro-1H-benzo[d]imidazol-4-yl)piperidin-4-yl)(methyl)carbamate To a solution of tert-butyl N-[1-[5-methoxy-3-methyl-2-oxo-1-(2-trimethylsilylethoxymethyl) benzimidazol-4-yl]-4-piperidyl]-N-methyl-carbamate (40.0 mg, 76.8 umol) in THF (5 mL) was added TBAF (200 mg, 768 umol) at 25° C. The reaction was warmed to 70° C. and stirred for 16 hrs. On completion, the reaction mixture was diluted with EtOAc (60 mL), and washed with brine (4×30 mL). The organic layer was separated, dried over $Na_2SO_4$ and concentrated in vacuo to give the title compound (29.0 mg, 96% yield) as brown solid. $^1$H NMR (400 MHz, DMSO-$d_6$) δ 6.78 (d, J=8.4 Hz, 1H), 6.67 (d, J=8.4 Hz, 1H), 3.82 (s, 3H), 3.61 (s, 3H), 3.38-3.20 (m, 2H), 3.01-2.90 (m, 2H), 2.79 (s, 3H), 1.97-1.82 (m, 2H), 1.64-1.51 (m, 2H), 1.48 (s, 9H).

Step 3—Tert-butyl (1-(5-methoxy-1-(1-(4-methoxybenzyl)-2,6-dioxopiperidin-3-yl)-3-methyl-2-oxo-2,3-dihydro-1H-benzo[d]imidazol-4-yl)piperidin-4-yl)(methyl)carbamate To a solution of tert-butyl N-[1-(5-methoxy-3-methyl-2-oxo-1H-benzimidazol-4-yl)-4-piperidyl]-N-methyl-carbamate (24.0 mg, 61.4 umol) in THF (3 mL) was added tBuOK (13.8 mg, 122 umol) at 0° C. and the mixture was stirred at 0° C. for 30 min. Then, a solution of [1-[(4-methoxyphenyl)methyl]-2,6-dioxo-3-piperidyl] trifluoromethanesulfonate (37.5 mg, 98.3 umol, Intermediate G) in THF (0.5 mL) was added into the mixture slowly and the reaction was stirred at 0° C. for 2 hrs. On completion, the reaction mixture was quenched with saturated $NH_4Cl$ solution (1 mL), and diluted with water (10 mL). The mixture was then extracted with EtOAc (2×40 mL). The organic layer was separated, dried over $Na_2SO_4$ and concentrated in vacuo. The residue was purified by prep-TLC (DCM:EtOAc=3:1, Rf=0.5) to give the title compound (36 mg, 94% yield) as yellow solid. LC-MS (ESI$^+$) m/z 622.2 (M+H)$^+$.

Step 4—3-(5-methoxy-3-methyl-4-(4-(methylamino) piperidin-1-yl)-2-oxo-2,3-dihydro-1H-benzo[d] imidazol-1-yl)piperidine-2,6-dione To a solution of tert-butyl N-[1-[5-methoxy-1-[1-[(4-methoxyphenyl)methyl]-2,6-dioxo-3-piperidyl]-3-methyl-2-oxo-benzimidazol-4-yl]-4-piperidyl]-N-methyl-carbamate (30.0 mg, 48.2 umol) in TFA (0.4 mL) was added TfOH (0.08 mL) at 25° C. The reaction mixture was warmed to 70° C. and stirred for 3 hrs. On completion, the reaction mixture was concentrated in vacuo. The residue was purified by prep-HPLC (column: Phenomenex luna C18 150*25 mm*10 um; mobile phase: [water (0.225% FA)-ACN]; B %:

3%-33%, 11 min) to give the title compound (11.0 mg, 56% yield) as white solid. LC-MS (ESI⁺) m/z 402.1 (M+H)⁺.

3-[5-Methoxy-3-methyl-4-[4-[methyl(4-piperidylmethyl)amino]-1-piperidyl]-2-oxo-benz imidazol-1-yl]piperidine-2,6-dione (Intermediate KG)

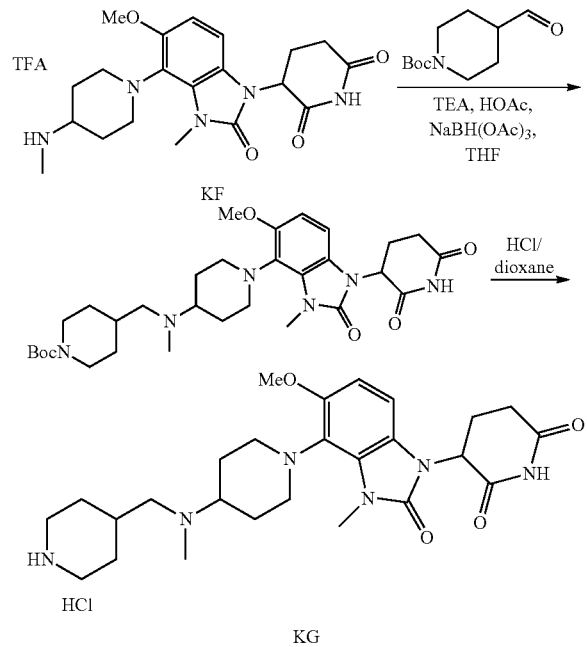

Step 1—Tert-butyl 4-[[[1-[1-(2,6-dioxo-3-piperidyl)-5-methoxy-3-methyl-2-oxo-benzimidazol-4-yl]-4-piperidyl]-methyl-amino]methyl]piperidine-1-carboxylate To a solution of 3-[5-methoxy-3-methyl-4-[4-(methylamino)-1-piperidyl]-2-oxo-benzimidazol-1-yl] piperidine-2,6-dione (110 mg, 213 umol, TFA, Intermediate KF) in THF (1 mL) was added TEA (59.4 uL, 426 umol). Then tert-butyl 4-formylpiperidine-1-carboxylate (40.9 mg, 192 umol, CAS #137076-22-3) and HOAc (12.2 uL, 213 umol) were added, the mixture was stirred at −10° C. for 0.5 hour. The n NaBH(OAc)₃ (67.8 mg, 320 umol) was added and the mixture was stirred at −10° C. for 1.5 hrs. On completion, the mixture was quenched with water (1 mL), filtered and the filtrate was concentrated in vacuo to give the residue. The residue was purified by prep-HPLC (column: Phenomenex luna C18 150*25 mm*10 um; mobile phase: [water (FA)-ACN]; B %: 10%-40%, 10 min) to give the title compound (80.0 mg, 62% yield) as yellow solid. ¹H NMR (400 MHz, DMSO-$d_6$) δ 11.06 (s, 1H), 6.87 (d, J=8.4 Hz, 1H), 6.68 (d, J=8.8 Hz, 1H), 5.32-5.27 (m, 1H), 3.96-3.93 (m, 2H), 3.77 (s, 3H), 3.60 (s, 3H), 3.38-3.33 (m, 2H), 2.99-2.97 (m, 2H), 2.93-2.81 (m, 2H), 2.78-2.57 (m, 7H), 2.53-2.51 (m, 2H), 2.01-1.66 (m, 8H), 1.40 (s, 9H), 1.11-0.95 (m, 2H). LC-MS (ESI⁺) m/z 599.2 (M+H)⁺.

Step 2—3-[5-Methoxy-3-methyl-4-[4-[methyl(4-piperidylmethyl)amino]-1-piperidyl]-2-oxo-benzimidazol-1-yl]piperidine-2,6-dione A solution of tert-butyl 4-[[[1-[1-(2,6-dioxo-3-piperidyl)-5-methoxy-3-methyl-2-oxo-benz imidazol-4-yl]-4-piperidyl]-methyl-amino]methyl]piperidine-1-carboxylate (50.0 mg, 83.4 umol) in HCl/dioxane (1 mL) was stirred at 25° C. for 1 hr. On completion, the mixture was concentrated in vacuo to give the title compound (40.0 mg, 89% yield, HCl) as yellow solid. LC-MS (ESI⁺) m/z 499.1 (M+H)⁺.

3-[5-[4-[[4-(3-Aminopropyl)piperazin-1-yl]methyl]-1-piperidyl]-3-methyl-2-oxo-benzimidazol-1-yl]piperidine-2,6-dione (Intermediate KH)

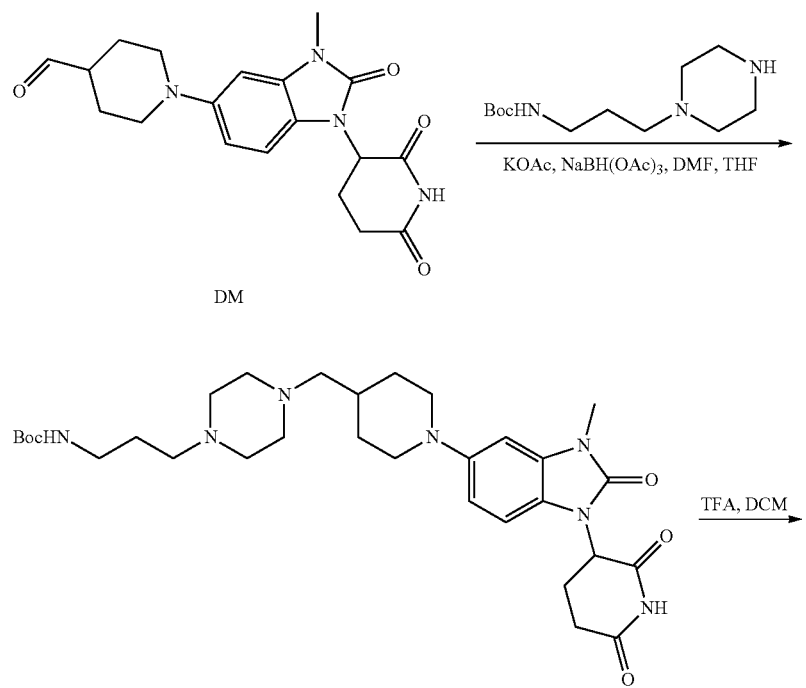

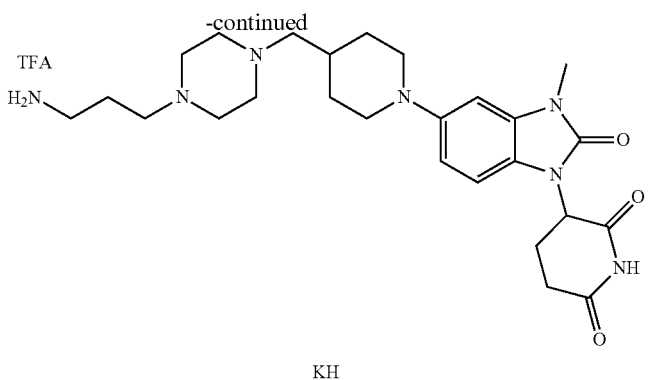

KH

Step 1—Tert-butyl N-[3-[4-[[1-[1-(2,6-dioxo-3-piperidyl)-3-methyl-2-oxo-benzimidazol-5-yl]-4-piperidyl]methyl]piperazin-1-yl]propyl]carbamate To a solution of tert-butyl N-(3-piperazin-1-ylpropyl)carbamate (50.0 mg, 205 umol, CAS #874831-60-4) and 1-[1-(2,6-dioxo-3-piperidyl)-3-methyl-2-oxo-benzimidazol-5-yl]piperidine-4-carbaldehyde (85.5 mg, 205 umol, FA, Intermediate DM) in mixture solvent THF (1 mL) and DMF (1 mL) was added KOAc (201 mg, 2.05 mmol). The mixture was stirred at 0° C. for 5 minutes. Then NaBH(OAc)$_3$ (87.0 mg, 410 umol) was added and the mixture was stirred at 0° C. for 30 min. On completion, the mixture was quenched with H$_2$O (0.5 mL), then concentrated in vacuo to give a residue. The residue was purified by pre-HPLC (column: Phenomenex luna C18 150*25 mm*10 um; mobile phase: [water(FA)-ACN]; B %: 0%-23%, 9 min) to give the title compound (88 mg, 71% yield) as a colorless oily liquid. $^1$H NMR (400 MHz, DMSO-d$_6$) δ 11.05 (s, 1H), 6.92 (d, J=8.4 Hz, 1H), 6.85-6.76 (m, 2H), 6.62 (dd, J=1.6, 8.4 Hz, 1H), 5.28 (dd, J=5.2, 12.8 Hz, 2H), 3.57 (d, J=11.6 Hz, 8H), 2.96-2.88 (m, 6H), 2.74-2.70 (m, 2H), 2.42 (s, 3H), 2.33 (t, J=7.2 Hz, 3H), 2.19 (d, J=7.2 Hz, 2H), 2.01-1.94 (m, 1H), 1.78 (d, J=11.2 Hz, 2H), 1.57-1.50 (m, 2H), 1.37 (s, 9H), 1.29-1.18 (m, 2H). LC-MS (ESI$^+$) m/z 598.2 (M+H)$^+$.

Step 2—3-[5-[4-[[4-(3-Aminopropyl)piperazin-1-yl]methyl]-1-piperidyl]-3-methyl-2-oxo-benzimidazol-1-yl]piperidine-2,6-dione To a solution of tert-butyl N-[3-[4-[[1-[1-(2,6-dioxo-3-piperidyl)-3-methyl-2-oxo-benzimidazol-5-yl]-4-piperidyl]methyl]piperazin-1-yl]propyl]carbamate (60.0 mg, 100 umol) in DCM (2 mL) was added TFA (1 mL). The mixture was stirred at 25° C. for 1 hr. On completion, the mixture was concentrated in vacuo to give the title compound (45.0 mg, 90% yield) as a colorless oily liquid. LC-MS (ESI$^+$) m/z 498.1 (M+H)$^+$.

Tributyl-(3-isopropyl-2-methyl-imidazol-4-yl)stannane (Intermediate KI)

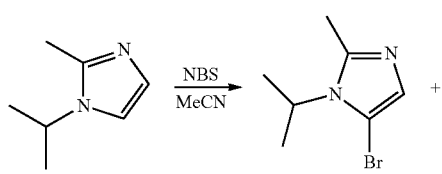

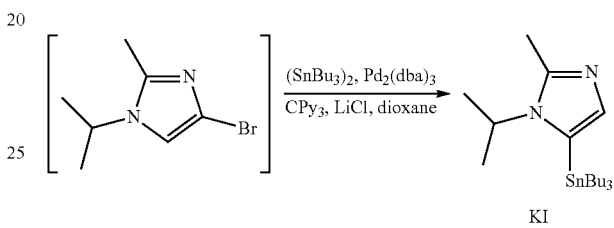

Step 1—5-Bromo-1-isopropyl-2-methyl-imidazole and 4-bromo-1-isopropyl-2-methyl-imidazole To a mixture of 1-isopropyl-2-methyl-imidazole (10.0 g, 80.5 mmol, CAS #87606-45-1) in ACN (100 mL) was added NBS (14.3 g, 80.5 mmol) at 0° C., then the reaction mixture was stirred at 25° C. for 16 hours. On completion, the residue was diluted with water (80 mL), and extracted with EA (3×100 mL). The combined organic layer was dried over Na$_2$SO$_4$, filtered and concentrated in vacuo to give 5-bromo-1-isopropyl-2-methyl-imidazole (8.00 g, 49% yield, $^1$H NMR (400 MHz, DMSO-d$_6$) δ 6.79 (s, 1H), 4.57 (d, J=7.0, 14.0 Hz, 1H), 2.37 (s, 3H), 1.46 (d, J=7.2 Hz, 6H) as white oil and 4-bromo-1-isopropyl-2-methyl-imidazole (2.00 g, 12% yield, $^1$H NMR (400 MHz, DMSO-d$_6$) δ=7.29 (s, 1H), 4.34 (td, J=6.4, 13.2 Hz, 1H), 2.27 (s, 3H), 1.32 (d, J=6.4 Hz, 6H) as white oil.

Step 2—Tributyl-(3-isopropyl-2-methyl-imidazol-4-yl)stannane

To a mixture of 5-bromo-1-isopropyl-2-methyl-imidazole (1.50 g, 7.39 mmol) in dioxane (30 mL) was added Pd$_2$(dba)$_3$ (676 mg, 738 umol) and LiCl (939 mg, 22.1 mmol) and tricyclohexylphosphane (2.07 g, 7.39 mmol) and tributyl(tributylstannyl)stannane (42.8 g, 73.8 mmol), then the reaction mixture was stirred at 100° C. for 12 hrs. On completion, the reaction mixture was quenched with CsF (aq) (50 mL) and concentrated in vacuo to give the title compound (3 g, 98% yield) as brown oil. LC-MS (ESI$^+$) m/z 412.6 (M+H)$^+$.

4-[[4-(3-isopropyl-2-methyl-imidazol-4-yl)-5-(trifluoromethyl)pyrimidin-2-yl]amino]-3-methyl-benzenesulfonyl chloride (Intermediate KJ)

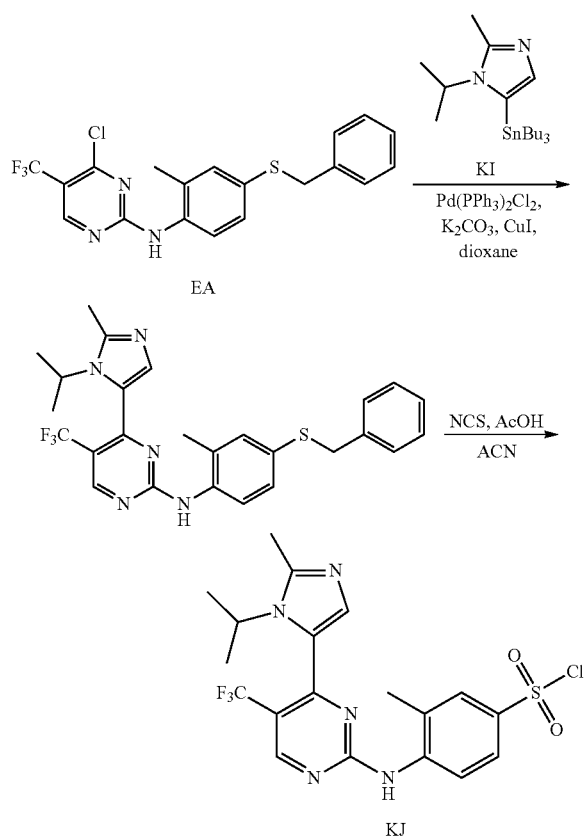

Step 1—N-(4-benzylsulfanyl-2-methyl-phenyl)-4-(3-isopropyl-2-methyl-imidazol-4-yl)-5-(trifluoromethyl)-pyrimidin-2-amine To a mixture of tributyl-(3-isopropyl-2-methyl-imidazol-4-yl)stannane (3.00 g, 7.26 mmol, Intermediate KI) and N-(4-benzylsulfanyl-2-methyl-phenyl)-4-chloro-5-(trifluoromethyl)pyrimidin-2-amine (2.98 g, 7.26 mmol, Intermediate EA) in dioxane (2 mL) was added $K_2CO_3$ (3.01 g, 21.7 mmol), CuI (138 mg, 725 umol) and $Pd(PPh_3)_2Cl_2$ (509 mg, 725 umol). Then the reaction mixture was stirred at 110° C. for 12 hrs. On completion, the residue was diluted with water (30 mL), and extracted with EA (3×60 mL). The combined organic layer was dried over $Na_2SO_4$, filtered and concentrated in vacuo to give a residue. The residue was purified by column chromatography ($SiO_2$, PE:EA=50:1 to PE:EA=1:1). Then the residue was purified by prep-HPLC (column: Phenomenex luna C18 150*25 mm*10 um; mobile phase: [water(FA)-ACN]; B %: 27%-57%, 10 min) to give the title compound (2 g, 55% yield) as a white solid. LC-MS (ESI$^+$) m/z 498.4 (M+H)$^+$.

Step 2—4-[[4-(3-Isopropyl-2-methyl-imidazol-4-yl)-5-(trifluoromethyl)pyrimidin-2-yl]amino]-3-methyl-benzenesulfonyl chloride To a mixture of N-(4-benzylsulfanyl-2-methyl-phenyl)-4-(3-isopropyl-2-methyl-imidazol-4-yl)-5-(trifluoromethyl) pyrimidin-2-amine (65.0 mg, 130 umol) in ACN (1 mL), HOAc (0.3 mL), and $H_2O$ (0.1 mL) was added NCS (52.3 mg, 391 umol). Then the reaction mixture was stirred at 25° C. for 0.5 hour. On completion, the mixture was concentrated in vacuo to give the title compound (60 mg, 86.0% yield, HOAC) as a yellow oil. LC-MS (ESI$^+$) m/z 474.2 (M+H)$^+$.

3-(3-Methyl-2-oxo-4-(piperidin-4-yl)-2,3-dihydro-1H-benzo[d]imidazol-1-yl)piperidine-2,6-dione (Intermediate KL)

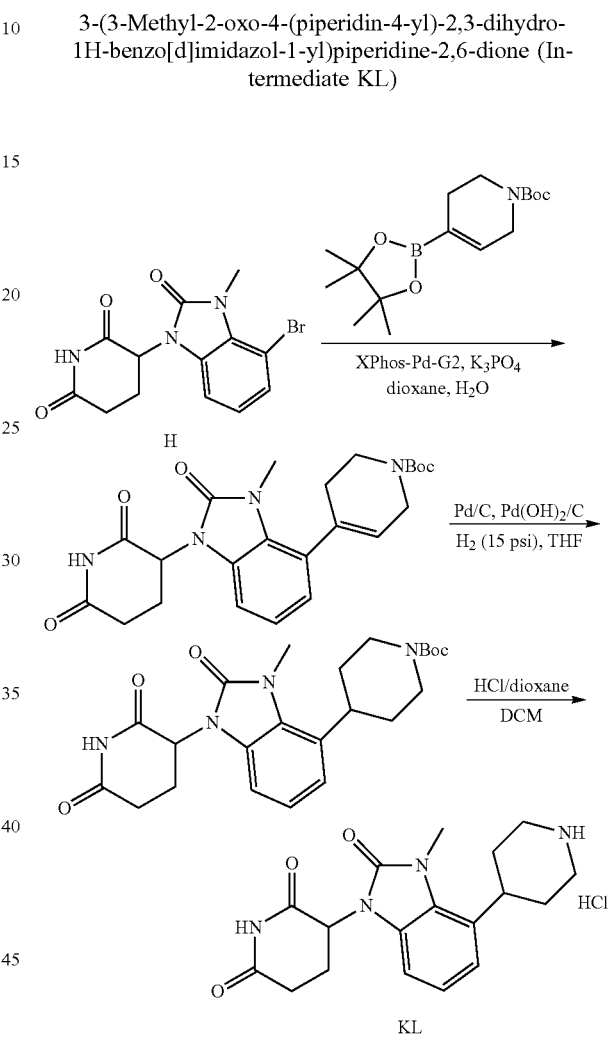

Step 1—Tert-butyl 4-(1-(2,6-dioxopiperidin-3-yl)-3-methyl-2-oxo-2,3-dihydro-1H-benzo[d]imidazol-4-yl)-5,6-dihydropyridine-1(2H)-carboxylate To a solution of 3-(4-bromo-3-methyl-2-oxo-benzimidazol-1-yl)piperidine-2,6-dione (9.00 g, 26.6 mmol, Intermediate H), tert-butyl 4-(4,4,5,5-tetramethyl-1,3,2-dioxaborolan-2-yl)-3,6-dihydro-2H-pyridine-1-carboxylate (12.3 g, 39.9 mmol, CAS #286961-14-6) and XPhos-Pd-G2 (2.09 g, 2.66 mmol) in dioxane (150 mL) and $H_2O$ (15 mL) was added $K_3PO_4$ (11.3 g, 53.2 mmol). The reaction mixture was stirred at 80° C. for 4 hours under $N_2$. On completion, the reaction mixture was filtered. The filtrate was dried with anhydrous $Na_2SO_4$ and filtered. The filtrate was concentrated in vacuo. The residue was triturated with sat. $NH_4Cl$ (2×50 mL), water (2×50 mL) and EA (2×50 mL) and filtered. The solid was dried in vacuo to give the title compound (8.00 g, 68% yield) as an off-white solid. LC-MS (ESI⁺) m/z 441.1 (M+H)⁺

Step 2—Tert-butyl 4-(1-(2,6-dioxopiperidin-3-yl)-3-methyl-2-oxo-2,3-dihydro-1H-benzo[d]imidazol-4-yl)piperidine-1-carboxylate To a solution of tert-butyl 4-[1-(2,6-dioxo-3-piperidyl)-3-methyl-2-oxo-benzimidazol-4-yl]-3,6-dihydro-2H-pyridine-1-carboxylate (8.00 g, 18.2 mmol) in DMF (20 mL) and THF (60 mL) was added H₂, Pd/C (1.00 g, 10 wt %) and Pd(OH)₂ (1.00 g, 3.56 mmol, 50 wt %). The mixture was degassed and purged with nitrogen 3 times, then degassed and purged with hydrogen 3 times. The mixture was stirred at 25° C. for 16 hrs under hydrogen (15 psi) atmosphere. On completion, the reaction mixture was filtered and the combined filtrates were concentrated in vacuo to give the title compound (5.60 g, 70% yield) as a white solid. $^1$H NMR (400 MHz, DMSO-d₆) δ 11.10 (s, 1H), 7.06-6.92 (m, 3H), 5.38 (m, 1H), 4.18-3.96 (m, 2H), 3.60 (s, 3H), 3.48-3.39 (m, 1H), 2.97-2.81 (m, 3H), 2.76-2.61 (m, 2H), 2.05-1.94 (m, 1H), 1.81 (m, 2H), 1.65-1.50 (m, 2H), 1.47-1.40 (m, 9H). LC-MS (ESI⁺) m/z 287.4 (387.3)⁺.

Step 3—3-(3-Methyl-2-oxo-4-(piperidin-4-yl)-2,3-dihydro-1H-benzo[d]imidazol-1-yl)piperidine-2,6-dione To a solution of tert-butyl 4-[1-(2,6-dioxo-3-piperidyl)-3-methyl-2-oxo-benzimidazol-4-yl]piperidine-1-carboxylate (100 mg, 226 umol) in DCM (1 mL) was added HCl/dioxane (1 mL). The reaction mixture was stirred at 25° C. for 0.5 hr. On completion, the reaction mixture was concentrated in vacuo to give the title compound (85.0 mg, 99% yield) as a yellow solid. LC-MS (ESI⁺) m/z 343.3 (M+H)⁺.

6-Chloro-8-cyclopentyl-2-methylsulfonyl-pyrido[2,3-d]pyrimidin-7-one (Intermediate KM)

Step 1—8-Cyclopentyl-2-methylsulfonyl-pyrido[2,3-d]pyrimidin-7-one

To a solution of 8-cyclopentyl-2-methylsulfanyl-pyrido[2,3-d]pyrimidin-7-one (2.00 g, 7.65 mmol, Intermediate HN) in DCM (20 mL) was added m-CPBA (6.21 g, 30.6 mmol, 85% solution). The mixture was stirred at 40° C. for 3 hrs. On completion, the reaction mixture was quenched with Na₂CO₃ aq. (10 mL) at 25° C., and then extracted with EA (3×30 mL). The combined organic layers were washed with brine (2×20 mL), dried over Na₂SO₄, filtered and concentrated in vacuo to give the title compound (2.00 g, 89% yield) as a yellow oil. LC-MS (ESI⁺) m/z 293.9 (M+1)⁺.

Step 2—6-Chloro-8-cyclopentyl-2-methylsulfonyl-pyrido[2,3-d]pyrimidin-7-one

To a solution of 8-cyclopentyl-2-methylsulfonyl-pyrido[2,3-d]pyrimidin-7-one (100 mg, 340.9 umol) in DMF (1 mL) was added NCS (500 mg, 3.75 mmol). The mixture was stirred at 70° C. for 16 hrs. On completion, the reaction mixture was filtered and concentrated in vacuo to give a residue. Then the crude product was purified by reversed-phase HPLC (0.1% FA condition) to give the title compound (280 mg, 24% yield) as a brown solid. LC-MS (ESI⁺) m/z 327.9 (M+1)⁺. $^1$H NMR (400 MHz, CDCl₃) δ 8.94 (s, 1H), 7.96 (s, 1H), 6.08-5.92 (m, 1H), 3.40 (s, 3H), 2.32-2.23 (m, 2H), 2.22-2.13 (m, 2H), 2.04-1.96 (m, 2H), 1.77-1.70 (m, 2H).

6-Chloro-8-cyclopentyl-2-[2-methyl-4-(2-oxopiperazin-1-yl)anilino]pyrido[2,3-d]pyrimidin-7-one (Intermediate KN)

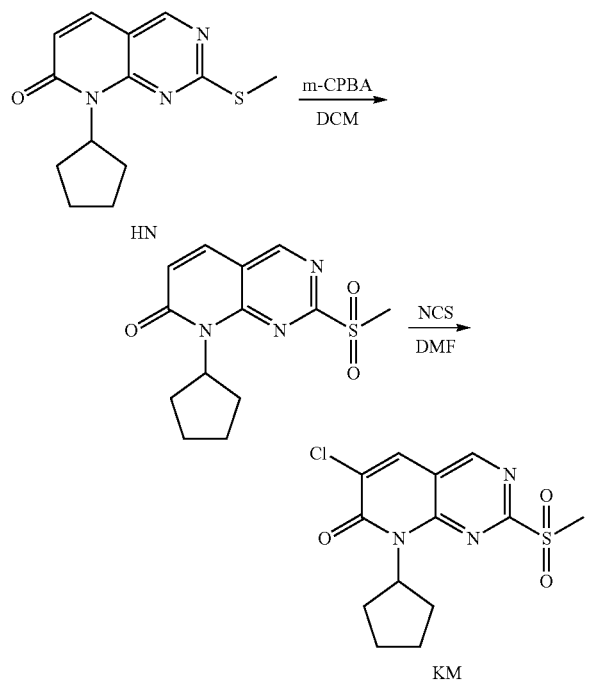

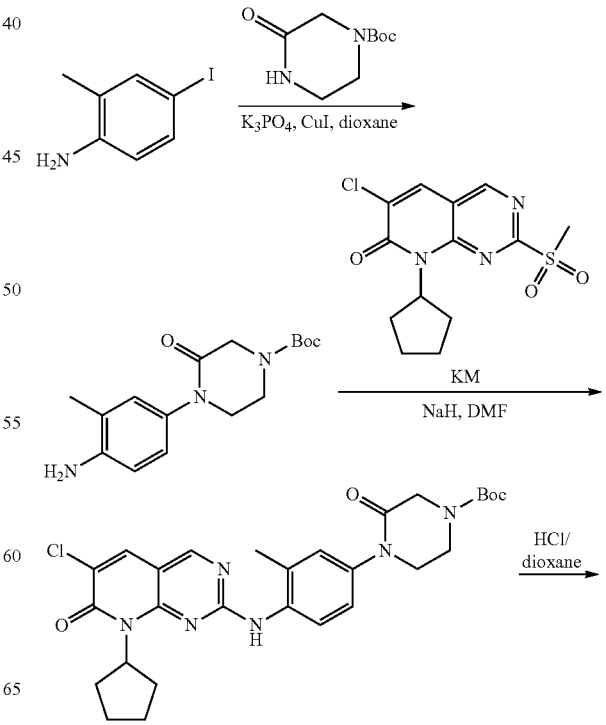

969

-continued

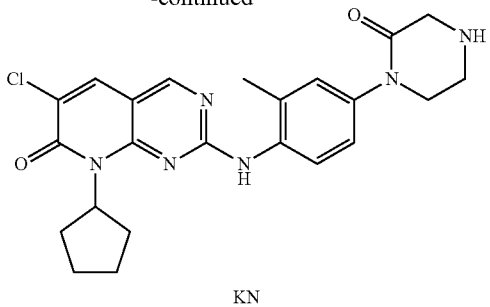

KN

Step 1—Tert-butyl 4-(4-amino-3-methyl-phenyl)-3-oxo-piperazine-1-carboxylate To a solution of tert-butyl 3-oxopiperazine-1-carboxylate (2.00 g, 9.99 mmol, CAS #76003-29-7) and 4-iodo-2-methyl-aniline (2.79 g, 11.9 mmol, CAS #13194-68-8) in dioxane (35 mL) was added CuI (1.90 g, 9.99 mmol), $K_3PO_4$ (5.30 g, 24.9 mmol) and $N_1,N_2$-dimethylcyclohexane-1,2-diamine (2.84 g, 19.9 mmol). Then the mixture was purged with $N_2$ three times and stirred at 110° C. for 10 hrs. On completion, the mixture was filtered and concentrated in vacuo to give the residue. The residue was purified by column chromatography ($SiO_2$, PE:EA=10:1 to 1:5) to give the title compound (2.50 g, 81% yield) as a yellow solid. $^1$H NMR (400 MHz, DMSO-$d_6$) δ 6.83 (d, J=2.0 Hz, 1H), 6.79 (d, J=2.4, 8.4 Hz, 1H), 6.57 (d, J=8.4 Hz, 1H), 4.88 (s, 2H), 4.03-3.96 (m, 2H), 3.66-3.54 (m, 4H), 2.03 (s, 3H), 1.44 (s, 9H). LC-MS (ESI$^+$) m/z 306.0 (M+H)$^+$.

Step 2—Tert-butyl 4-[4-[(6-chloro-8-cyclopentyl-7-oxo-pyrido[2,3-d]pyrimidin-2-yl)amino]-3-methyl-phenyl]-3-oxo-piperazine-1-carboxylate To a solution of tert-butyl 4-(4-amino-3-methyl-phenyl)-3-oxo-piperazine-1-carboxylate (400 mg, 1.31 mmol) and 6-chloro-8-cyclopentyl-2-methylsulfonyl-pyrido[2,3-d]pyrimidin-7-one (429 mg, 1.31 mmol, Intermediate KM) in dioxane (10 mL) was added $Cs_2CO_3$ (853 mg, 2.62 mmol) and Pd-PEPPSI-IHeptCl3-Chloropyridine (127 mg, 130 umol). Then the mixture was purged with $N_2$ three times and stirred at 80° C. for 12 hrs. On completion, the mixture was filtered to give the residue. The residue was purified by prep-HPLC (column: Phenomenex luna C18 150*25 mm*10 um; mobile phase: [water(FA)-ACN]; B %: 55%-85%, 10 min) to give the title compound (85.0 mg, 11% yield) as a yellow solid. LC-MS (ESI$^+$) m/z 553.3 (M+H)$^+$.

Step 3—6-Chloro-8-cyclopentyl-2-[2-methyl-4-(2-oxopiperazin-1-yl)anilino]pyrido[2,3-d]pyrimidin-7-one To a solution of tert-butyl 4-[4-[(6-chloro-8-cyclopentyl-7-oxo-pyrido[2,3-d]pyrimidin-2-yl)amino]-3-methyl-phenyl]-3-oxo-piperazine-1-carboxylate (80.0 mg, 144 umol) was added HCl/dioxane (2 mL), then the mixture was stirred at 25° C. for 1 hr. On completion, the mixture was concentrated in vacuo to give the title compound (70.0 mg, 98% yield, HCl) as a white solid. LC-MS (ESI$^+$) m/z 452.9 (M+H)$^+$.

970

4-[4-[4-[(6-Chloro-8-cyclopentyl-7-oxo-pyrido[2,3-d]pyrimidin-2-yl)amino]-3-methyl-phenyl]-3-oxo-piperazin-1-yl]cyclohexanecarbaldehyde (Intermediate KO)

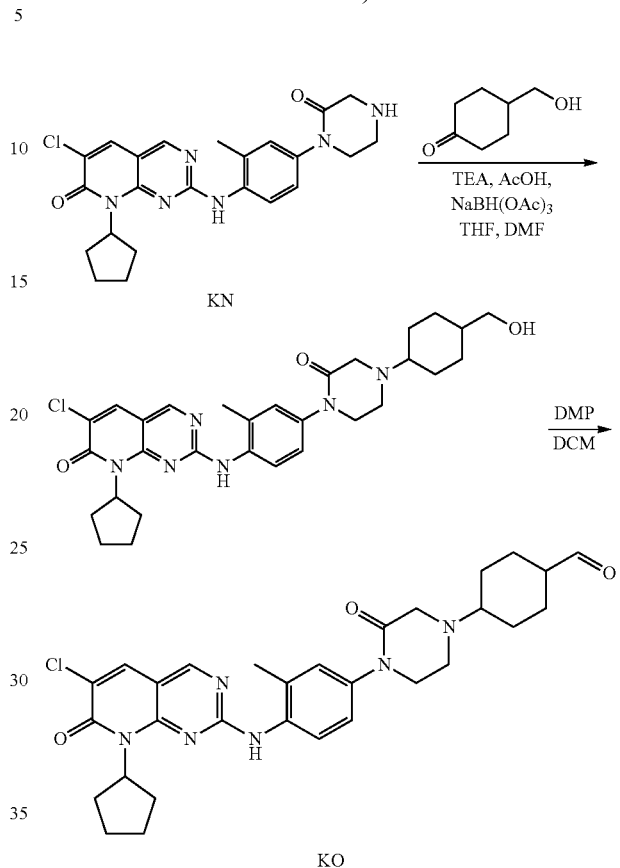

Step 1—6-Chloro-8-cyclopentyl-2-[4-[4-[4-(hydroxymethyl)cyclohexyl]-2-oxo-piperazin-1-yl]-2-methyl-anilino]pyrido[2,3-d]pyrimidin-7-one To a solution of 6-chloro-8-cyclopentyl-2-[2-methyl-4-(2-oxopiperazin-1-yl)anilino]pyrido[2,3-d] pyrimidin-7-one (70.0 mg, 154 umol, HCl, Intermediate KN) in DMF (0.5 mL) and THF (1 mL) was added TEA (718.45 umol, 0.1 mL). Then 4-(hydroxymethyl)cyclohexanone (29.7 mg, 231 umol, CAS #38580-68-6) and AcOH (1.75 mmol, 0.1 mL) was added and the mixture was stirred at 25° C. for 0.2 hour. Then NaBH(OAc)$_3$ (65.5 mg, 309 umol) was added and the mixture was stirred 25° C. for 1 hr. On completion, the mixture was filtered to give the residue. The residue was purified by prep-HPLC (column: Phenomenex luna C18 150*25 mm*10 um; mobile phase: [water (FA)-ACN]; B %: 10%-40%, 15 min) to give the title compound (55.0 mg, 62% yield) as a yellow solid. $^1$H NMR (400 MHz, DMSO-$d_6$) δ 9.49 (s, 1H), 8.70 (s, 1H), 8.20-8.10 (m, 1H), 7.41-7.33 (m, 1H), 7.29-7.10 (m, 2H), 5.81-5.62 (m, 1H), 4.33 (s, 1H), 3.66-3.56 (m, 2H), 3.28 (s, 2H), 3.22 (s, 2H), 2.89-2.80 (m, 2H), 2.20 (s, 3H), 2.17-2.06 (m, 2H), 1.91-1.77 (m, 2H), 1.72-1.15 (m, 12H), 0.97-0.84 (m, 1H), LC-MS (ESI$^+$) m/z 565.2 (M+H)$^+$.

Step 2—4-[4-[4-[(6-Chloro-8-cyclopentyl-7-oxo-pyrido[2,3-d]pyrimidin-2-yl)amino]-3-methyl-phenyl]-3-oxo-piperazin-1-yl]cyclohexanecarbaldehyde To a solution of 6-chloro-8-cyclopentyl-2-[4-[4-[4-(hydroxymethyl)cyclohexyl]-2-oxo-piperazin-1-yl]-2-methyl-anilino]pyrido[2,3-d]pyrimidin-7-one (50.0 mg, 88.4 umol) in DCM (1.5 mL) was added DMP (56.2 mg, 132 umol) at 0° C., then the mixture was stirred at 25° C. for 1 hr. On completion, the mixture was diluted with DCM (2 mL), then quenched with saturated $Na_2S_2O_3$ (3 mL) and saturated $NaHCO_3$ (3 mL), and stirred at 25° C. for 10 minutes. After that, the mixture was extracted with DCM (3 mL×3). Then the combined organic layers were dried over anhydrous $Na_2SO_4$, filtered and concentrated in vacuo to give the title compound (47.0 mg, 94% yield) as a yellow solid. LC-MS (ESI$^+$) m/z 563.3 (M+H)$^+$.

6-Chloro-8-isopropyl-2-methylsulfonyl-pyrido[2,3-d]pyrimidin-7-one (Intermediate KP)

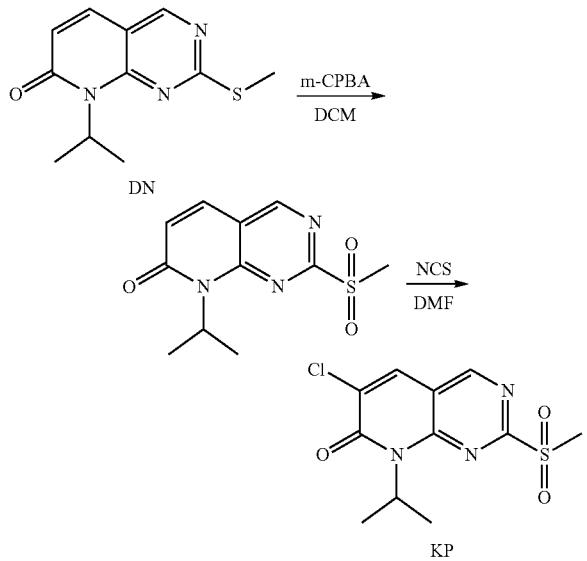

Step 1—8-Isopropyl-2-methylsulfonyl-pyrido[2,3-d]pyrimidin-7-one

To a solution of 8-isopropyl-2-methylsulfanyl-pyrido[2,3-d]pyrimidin-7-one (2.20 g, 9.35 mmol, Intermediate DN) in DCM (20.0 mL) was added m-CPBA (7.59 g, 37.0 mmol, 85% solution). The mixture was stirred at 40° C. for 3 hrs. On completion, the reaction mixture was quenched with $Na_2CO_3$ aq. (100 mL) at 25° C., and then extracted with EA (3×100 mL). The combined organic layers were washed with brine (2×100 mL), dried over anhydrous $Na_2SO_4$, filtered and concentrated in vacuo to give the title compound (2.10 g, 84% yield) as a yellow solid. $^1$H NMR (400 MHz, DMSO-d$_6$) δ 9.27 (s, 1H), 8.07 (d, J=9.6 Hz, 1H), 6.87 (d, J=9.6 Hz, 1H), 5.65 (td, J=6.8, 13.6 Hz, 1H), 3.46 (s, 3H), 1.56 (d, J=7.2 Hz, 6H). LC-MS (ESI$^+$) m/z 267.9 (M+H)$^+$.

Step 2—6-Chloro-8-isopropyl-2-methylsulfonyl-pyrido[2,3-d]pyrimidin-7-one

To a solution of 8-isopropyl-2-methylsulfonyl-pyrido[2,3-d]pyrimidin-7-one (100 mg, 374 umol) in DMF (1.50 mL) was added NCS (149 mg, 1.12 mmol). The mixture was stirred at 70° C. for 16 hrs. On completion, the mixture was concentrated in vacuo. The mixture was purified by reversed phase (0.1% FA) to give the title compound (74.0 mg, 65% yield) as a yellow solid. $^1$H NMR (400 MHz, DMSO-d$_6$) δ 9.27-9.25 (m, 1H), 8.68-8.37 (m, 1H), 5.90-5.58 (m, 1H), 3.48 (d, J=2.4 Hz, 3H), 1.58 (s, 6H). LC-MS (ESI$^+$) m/z 301.8 (M+H)$^+$.

1-(2,6-dioxo-3-piperidyl)-3-methyl-2-oxo-benzimidazole-5-carbaldehyde (Intermediate KQ)

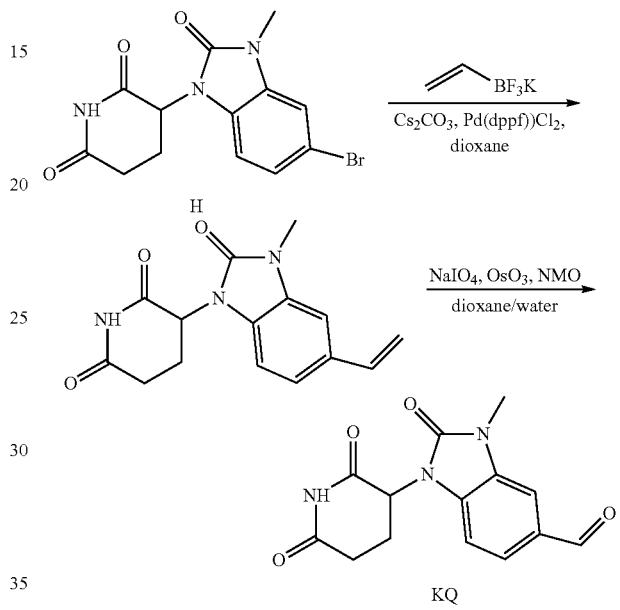

Step 1—3-(3-Methyl-2-oxo-5-vinyl-benzimidazol-1-yl)piperidine-2,6-dione

A mixture of 3-(5-bromo-3-methyl-2-oxo-benzimidazol-1-yl)piperidine-2,6-dione (3.00 g, 8.87 mmol, Intermediate J), potassium hydride, trifluoro (vinyl)boron (3.57 g, 26.6 mmol), $Cs_2CO_3$ (2 M, 8.87 mL), Pd(dppf)Cl$_2$—CH$_2$Cl$_2$ (724 mg, 887 umol) and in dioxane (30 mL) was degassed and purged with $N_2$ for 3 times, and then the mixture was stirred at 80° C. for 3 hours under $N_2$ atmosphere. On completion, the reaction mixture was concentrated in vacuo to give a residue. The residue was purified by reverse phase (TFA condition) to give the title compound (1.60 g, 58% yield) as a yellow solid. LC-MS (ESI$^+$) m/z 286.0 (M+H)$^+$.

Step 2—1-(2,6-Dioxo-3-piperidyl)-3-methyl-2-oxo-benzimidazole-5-carbaldehyde

To a solution of 3-(3-methyl-2-oxo-5-vinyl-benzimidazol-1-yl)piperidine-2,6-dione (0.30 g, 1.05 mmol) in a mixed solvent of dioxane (20 mL) and H$_2$O (2 mL) was added NaIO$_4$ (449 mg, 2.10 mmol), OsO$_4$ (267 mg, 1.00 mmol) and NMO (61.0 mg, 525 umol). The mixture was stirred at 25° C. for 0.5 hr. On completion, the residue was diluted with water (10 mL) and extracted with ethyl acetate (2×20 mL). The combined organic layers were washed with brine (20 mL), dried over $Na_2SO_4$, filtered and concentrated in vacuo to give a residue. The residue was purified by prep-HPLC (TFA condition) to give the title compound (0.1 g, 32% yield) as a gray solid. LC-MS (ESI$^+$) m/z 288.0 (M+H)$^+$.

Example 1 (Method 1): Synthesis of 2-((5-Bromo-2-((4-(N-(15-(1-(2,6-dioxopiperidin-3-yl)-3-methyl-2-oxo-2,3-dihydro-1H-benzo[d]imidazol-4-yl)-3,6,9,12-tetraoxapentadecyl)sulfamoyl)-2-methylphenyl)amino)pyrimidin-4-yl)amino)-6-fluorobenzamide (I-37)

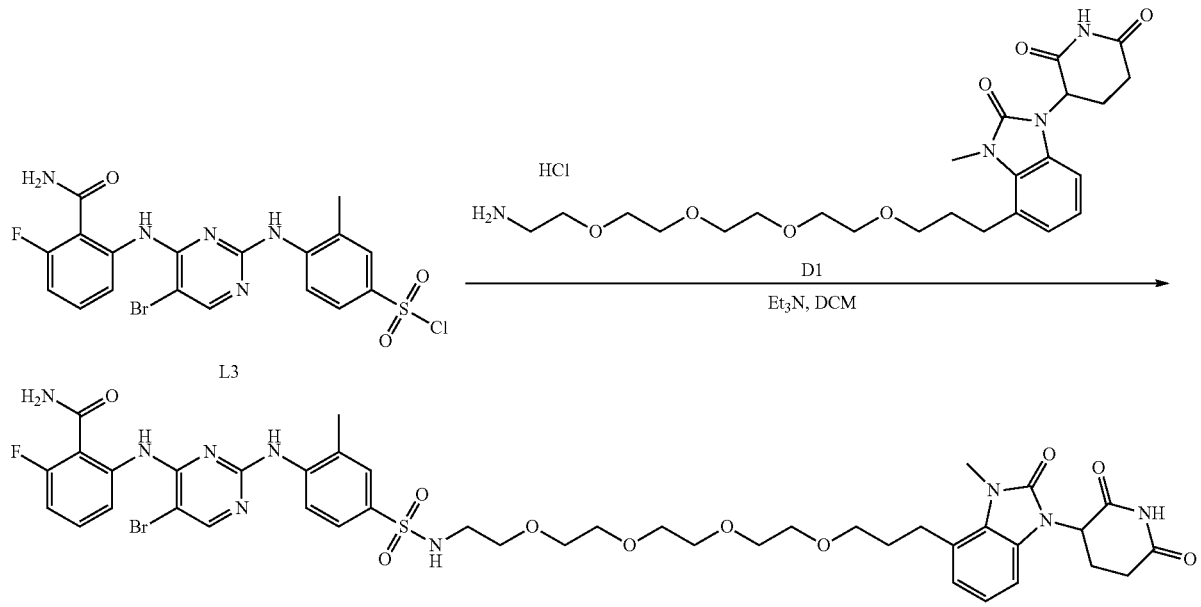

To a solution of 3-(4-(1-amino-3,6,9,12-tetraoxapentadecan-15-yl)-3-methyl-2-oxo-2,3-dihydro-1H-benzo[d]imidazol-1-yl)piperidine-2,6-dione hydrochloride (51.3 mg, 0.097 mmol, Intermediate D1) in DCM (5.0 mL) was added Et$_3$N (0.2 mL) and 4-((5-bromo-4-((2-carbamoyl-3-fluorophenyl)amino)pyrimidin-2-yl)amino)-3-methylbenzenesulfonyl chloride (50 mg, 0.097 mmol, Intermediate L3) and the mixture was stirred at rt for 4 h. The mixture was diluted with water (15 mL), and extracted with DCM (30 mL×3). The combined organic extracts were dried over Na$_2$SO$_4$ and concentrated under reduced pressure. The residue was purified by prep-TLC (DCM/MeOH=10/1, v/v) to afford the title compound (25.5 mg, 27% yield) as a white solid. LCMS m/z=970.4 & 972.4 [M+H]; $^1$H NMR (400 MHz, DMSO-d$_6$) δ 11.1 (s, 1H), 10.2 (s, 1H), 9.00 (s, 1H), 8.28 (s, 1H), 8.18-8.03 (m, 3H), 7.73 (d, J=8.4 Hz, 1H), 7.67-7.54 (m, 3H), 7.32-7.23 (m, 1H), 7.02-6.92 (m, 3H), 6.91-6.83 (m, 1H), 5.35 (dd, J=12.4, 5.4 Hz, 1H), 3.55 (s, 3H), 3.53-3.39 (m, 16H), 2.97-2.84 (m, 5H), 2.73-2.57 (m, 2H), 2.29 (s, 3H), 2.03-1.95 (m, 1H), 1.86-1.76 (m, 2H).

TABLE 4

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-d$_6$) δ |
|---|---|---|---|---|
| I-1[e,f] | CP | CO | 831.3 | 9.51 (s, 1H), 8.73 (s, 1H), 7.87-7.46 (m, 5H), 7.07-6.89 (m, 2H), 6.85 (d, J = 7.2Hz, 1H), 6.33 (d, J = 9.2Hz, 1H), 5.72-5.62 (m, 1H), 5.33 (dd, J = 5.2, 12.8Hz, 1H), 3.54-3.45 (m, 8H), 3.39 (td, J = 6.4, 15.2Hz, 4H), 3.00-2.84 (m, 3H), 2.73-2.57 (m, 5H), 2.32 (s, 5H), 2.21-1.91 (m, 4H), 1.86-1.75 (m, 2H), 1.64 (br s, 4H), 1.50-1.37 (m, 2H) |
| I-2[e,f] | E1 | CO | 875.4 | 11.07 (br d, J = 1.4Hz, 1H), 9.51 (s, 1H), 8.73 (s, 1H), 7.81-7.56 (m, 6H), 7.07-6.95 (m, 2H), 6.85 (d, J = 7.2Hz, 1H), 6.33 (d, J = 9.2Hz, 1H), 5.75-5.59 (m, 1H), 5.33 (dd, J = 5.6, 12.8Hz, 1H), 3.56-3.43 (m, 16H), 2.95-2.82 (m, 4H), 2.70-2.60 (m, 8H), 2.36-2.29 (m, 6H), 2.18-2.08 (m, 3H), 2.03-1.95 (m, 2H), 1.83-1.76 (m, 2H), 1.69-1.60 (m, 4H), 1.47-1.38 (m, 3H), 1.23 (br s, 2H) |
| I-3[e] | E1 | CH | 889.4 | 11.07 (s, 1H), 8.83 (s, 1H), 7.93 (s, 1H), 7.84 (d, J = 8.4Hz, 1H), 7.62 (s, 1H), 7.50-7.59 (m, 2H), 6.95-7.05 (m, 2H), 6.85 (d, J = 8.4Hz, 1H), 5.33 (dd, J = 12.8, 5.6Hz, 1H), 4.70 (t, J = 8.4Hz, 1H), 3.44-3.53 (m, 11H), 3.38 (d, J = 5.2Hz, 3 |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-$d_6$) δ |
|---|---|---|---|---|
| | | | | H), 2.87 (q, J = 5.6Hz, 3H), 2.60-2.68 (m, 6H), 2.33 (s, 3H), 1.97-2.09 (m, 4H), 1.72-1.83 (m, 6H), 1.64-1.68 (m, 2H), 1.48-1.55 (m, 4H), 1.23 (s, 2H) |
| I-4[e] | F1 | CH | 889.5 | 10.81-11.27 (m, 1H), 8.83 (s, 1H), 7.93 (s, 1H), 7.85 (d, J = 8.4Hz, 1H), 7.51-7.63 (m, 4H), 7.13 (d, J = 8.80 Hz, 1H), 7.03 (d, J = 7.2Hz, 1H), 6.59 (t, J = 5.6Hz, 1H), 5.05 (dd, J = 12.80, 5.60 Hz, 1H), 4.70 (quin, J = 8.40 Hz, 1H), 3.57-3.67 (m, 2H), 3.41-3.53 (m, 14H), 3.30 (s, 3H), 2.82-2.91 (m, 3H), 2.32 (s, 3H), 1.93-2.16 (m, 4H), 1.73-1.83 (m, 4 H), 1.63-1.69 (m, 2H), 1.48-1.54 (m, 4H) |
| I-5 | E4 | L2 | 865.2[b] | 10.8 (br s, 1H), 9.51 (br s, 1H), 8.89 (s, 1H), 8.16 (s, 1H), 7.94 (d, J = 8.4Hz, 1H), 7.68 (s, 1H), 7.63 (d, J = 8.2Hz, 1H), 7.43 (br s, 1H), 7.04-6.71 (m, 4H), 5.75 (t, J = 8.6Hz, 1H), 5.30 (dd, J = 12.8, 5.4Hz, 1H), 4.26 (s, 1H), 3.60-3.36 (m, 8H), 3.31 (s, 3H), 2.98-2.83 (m, 3H), 2.74-2.60 (m, 4H), 2.45-2.37 (m, 1H), 2.35 (s, 3H), 2.08-1.97 (m, 1H), 1.95-1.64 (m, 6H), 1.64-1.52 (m, 1H), 0.98 (s, 3H) |
| I-6 | E3 | L2 | 863.4 | 11.0 (br s, 1H), 9.53 (br s, 1H), 8.89 (s, 1H), 8.16 (s, 1H), 7.94 (d, J = 8.4Hz, 1H), 7.66 (s, 1H), 7.62 (d, J = 8.4Hz, 1H), 7.34 (s, 1H), 7.03-6.71 (m, 4H), 5.81-5.70 (m, 1H), 5.36-5.25 (m, 1H), 4.26 (s, 1H), 3.31 (s, 3H), 2.94-2.83 (m, 1H), 2.80-2.72 (m, 2H), 2.70-2.63 (m, 2H), 2.62-2.54 (m, 3H), 2.36 (s, 3H), 2.07-1.99 (m, 1H), 1.93-1.82 (m, 2H), 1.81-1.65 (m, 2H), 1.62-1.50 (m, 3H), 1.45-1.33 (m, 2H), 1.33-1.14 (m, 10H), 0.98 (s, 3H). |
| I-7 | E1 | L2 | 955.3 | 11.0 (br s, 1H), 9.52 (br s, 1H), 8.89 (s, 1H), 8.16 (s, 1H), 7.94 (d, J = 8.4Hz, 1H), 7.70 (s, 1H), 7.63 (dd, J = 8.4, 2.3Hz, 1H), 7.50-7.41 (m, 1H), 7.03-6.73 (m, 4H), 5.75 (t, J = 8.6Hz, 1H), 5.30 (dd, J = 12.7, 5.4Hz, 1H), 4.26 (s, 1H), 3.55-3.45 (m, 12H), 3.44-3.38 (m, 4H), 3.32 (s, 3H), 2.97-2.84 (m, 3H), 2.75-2.59 (m, 4H), 2.46-2.38 (m, 1H), 2.36 (s, 3H), 2.05-1.98 (m, 1H), 1.94-1.66 (m, 6H), 1.62-1.52 (m, 1H), 0.98 (s, 3H) |
| I-8 | D4 | L2 | 865.2[b] | 11.0 (br s, 1H), 9.52 (br s, 1H), 8.88 (s, 1H), 8.15 (s, 1H), 7.94 (d, J = 8.4Hz, 1H), 7.68 (s, 1H), 7.64 (d J = 8.4Hz, 1H), 7.55-7.45 (m, 1H), 7.03-6.72 (m, 4H), 5.75 (t, J = 8.6Hz, 1H), 5.33 (dd, J = 12.6, 5.4Hz, 1H), 4.26 (s, 1H), 3.54 (s, 3H), 3.52-3.41 (m, 8H), 2.99-2.84 (m, 5H), 2.80-2.58 (m, 4H), 2.46-2.37 (m, 1H), 2.36 (s, 3H), 2.07-1.98 (m, 1H), 1.94-1.66 (m, 6H), 1.63-1.53 (m, 1H), 0.98 (s, 3H) |
| I-9 | D3 | L2 | 863.3 | 11.0 (br s, 1H), 9.53 (br s, 1H), 8.89 (s, 1H), 8.15 (s, 1H), 7.94 (d, J = 8.4Hz, 1H), 7.66 (s, 1H), 7.62 (d, J = 8.4Hz, 1H), 7.34 (s, 1H), 7.10-6.73 (m, 4H), 5.75 (t, J = 8.6Hz, 1H), 5.32 (dd, J = 12.6, 5.4Hz, 1H), 4.26 (s, 1H), 3.53 (s, 3H), 2.97-2.59 (m, 7H), 2.48-2.39 (m, 1H), 2.36 (s, 3H), 2.08-1.97 (m, 1H), 1.95-1.82 (m, 2H), 1.81-1.65 (m, 2H), 1.63-1.52 (m, 3H), 1.45-1.19 (m, 12H), 0.98 (s, 3H) |
| I-10 | D2 | L2 | 887.4[c] | 11.0 (br s, 1H), 9.54 (br s, 1H), 8.89 (s, 1H), 8.16 (s, 1H), 7.94 (d, J = 8.4Hz, 1H), 7.66 (s, 1H), 7.61 (d, J = 8.4Hz, 1H), 7.34 (s, 1H), 7.03-6.72 (m, 4H), 5.80-5.72 (m, 1H), 5.33 (dd, J = 12.6, 5.4Hz, 1H), 4.26 (s, 1H), 3.54 (s, 3H), 2.93-2.84 (m, 3H), 2.80-2.73 (m, 2H), 2.73-2.61 (m, 2H), 2.46-2.40 (m, 1H), 2.36 (s, 3H), 2.07-1.98 (m, 1H), 1.92-1.83 (m, 2H), 1.80-1.66 (m, 2H), 1.63-1.54 (m, 3H), 1.44-1.15 (m, 18H), 0.98 (s, 3H) |
| I-11 | D1 | L2 | 977.3[d] | 11.0 (br s, 1H), 9.53 (br s, 1H), 8.89 (s, 1H), 8.16 (s, 1H), 7.94 (d, J = 8.6Hz, 1H), 9.68 (s, 1H), 7.63 (d, J = 8.8Hz, 1H), 7.46 (s, 1H), 7.04-6.74 (m, 4H), 5.79-5.71 (m, 1H), 5.33 (dd, J = 12.7, 5.3Hz, 1H), 4.27 (s, 1H), 3.59-3.38 (m, 19H), 3.02-2.83 (m, 5H), 2.73-2.56 (m, 2H), 2.46-2.37 (m, 1H), 2.36 (s, 3H), 2.09-1.95 (m, 2H), 1.94-1.67 (m, 5H), 1.62-1.53 (m, 1H), 0.98 (s, 3H) |
| I-12[g] | G3 | K | 925.4 | 11.0 (s, 1H), 8.73 (s, 1H), 8.05 (s, 2H), 7.57 (dd, J = 8.6, 7.2 Hz, 1H), 7.07 (d, J = 8.6Hz, 1H), 7.01 (d, J = 7.0 Hz, 1H), 6.84 (t, J = 55.2Hz, 1H), 6.45 (t, J = 5.8Hz, 1H), 5.85 (t, J = 8.2Hz, 1H), 5.02 (dd, J = 12.8, 5.6Hz, 1H), 4.27 (s, 1H), 4.12-3.87 (m, 1H), 3.62 (t, J = 14.2Hz, 2H), 3.33-3.24 (m, 3H), 3.06-2.81 (m, 5H), 2.68-2.45 (m, 2H), 2.25-1.79 (m, 7H), 1.72-1.54 (m, 6H), 1.44-1.19 (m, 22H), 0.99 (s, 3H) |
| I-13 | F5 | L2 | 875.4[b] | 11.0 (br s, H), 9.51 (br s, 1H), 8.89 (s, 1H), 8.15 (s, 1H), 7.94 (d, J = 8.4Hz, 1H), 7.66 (s, 1H), 7.62 (d, J = 8.5Hz, 1H), 7.57 (t, J = 7.7Hz, 1H), 7.33 (t, J = 5.2Hz, 1H), 7.06 (d, J = 8.7 |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-$d_6$) δ |
|---|---|---|---|---|
| | | | | Hz, 1H), 7.01 (d, J = 6.7Hz, 1H), 6.88 (t, J = 54.8Hz, 1H), 6.48-6.38 (m, 1H), 5.75 (t, J = 8.6Hz, 1H), 5.02 (dd, J = 12.8, 5.4Hz, 1H), 4.24 (s, 1H), 3.32-3.22 (m, 2H), 2.93-2.81 (m, 1H), 2.80-2.70 (m, 2H), 2.69-2.53 (m, 2H), 2.47-2.40 (m, 1H), 2.36 (s, 3H), 2.09-1.98 (m, 1H), 1.98-1.82 (m, 2H), 1.82-1.64 (m, 2H), 1.61-1.52 (m, 3H), 1.45-1.18 (m, 12H), 0.98 (s, 3H) |
| I-14 | D5 | L2 | 819.3[b] | 11.0 (br s, 1H), 9.53 (br s, 1H), 8.89 (s, 1H), 8.16 (s, 1H), 7.94 (d, J = 8.4Hz, 1H), 7.67 (s, 1H), 7.62 (d, J = 8.4Hz, 1H), 7.36 (t, J = 5.4Hz, 1H), 6.96-6.92 (m, 2H), 6.89 (t, J = 55.2Hz, 1H), 6.86-6.81 (m, 1H), 5.75 (t, J = 8.6Hz, 1H), 5.32 (dd, J = 12.8, 5.4Hz, 1H), 4.26 (s, 1H), 3.53 (s, 3H), 2.94-2.83 (m, 3H), 2.82-2.75 (m, 2H), 2.71-2.60 (m, 2H), 2.46-2.38 (m, 1H), 2.36 (s, 3H), 2.07-1.96 (m, 2H), 1.96-1.83 (m, 2H), 1.80-1.68 (m, 2H), 1.61-1.52 (m, 2H), 1.44-1.40 (m, 2H), 1.36-1.26 (m, 4H), 0.98 (s, 3H) |
| I-15[g] | G2 | K | 869.4 | 11.0 (s, 1H), 8.74 (s, 1H), 8.06 (s, 2H), 7.58 (t, J = 7.8Hz, 1H), 7.08 (d, J = 8.6Hz, 1H), 7.01 (d, J = 7.0 Hz, 1H), 6.85 (t, J = 55.2Hz, 1H), 6.46 (t, J = 5.8Hz, 1H), 5.86 (t, J = 8.4Hz, 1H), 5.03 (dd, J = 12.8, 5.4Hz, 1H), 4.29 (s, 1H), 4.12-3.89 (m, 1H), 3.62 (t, J = 13.8Hz, 2H), 3.34-3.25 (m, 2H), 3.06-2.83 (m, 6H), 2.66-2.54 (m, 2H), 2.24-2.09 (m, 2H), 2.08-1.81 (m, 6H), 1.72-1.56 (m, 7H), 1.44-1.23 (m, 11H), 0.99 (s, 3H) |
| I-16 | F6 | L2 | 821.4 | 11.1 (br s, 1H), 9.63 (br s, 1H), 8.90 (s, 1H), 8.18 (s, 1H), 7.95 (br s, 1H), 7.66 (s, 1H), 7.61 (d, J = 9.3Hz, 1H), 7.57-7.53 (m, 1H), 7.49 (t, J = 5.0 Hz, 1H), 7.05 (d, J = 8.5Hz, 1H), 6.99 (d, J = 7.0 Hz, 1H), 6.90 (t, J = 54.8Hz, 1H), 6.57-6.45 (m, 1H), 5.80-5.66 (m, 1H), 5.04 (dd, J = 12.9, 5.3Hz, 1H), 4.40 (s, 1H), 3.27-3.19 (m, 2H), 2.95-2.81 (m, 1H), 2.81-2.71 (m, 2H), 2.64-2.53 (m, 2H), 2.44-2.35 (m, 1H), 2.35 (s, 3H), 2.07-1.64 (m, 5H), 1.59-1.39 (m, 5H), 1.36-1.26 (m, 2H), 0.97 (s, 3H) |
| I-17 | F1 | L2 | 937.5[c] | 11.0 (br s, 1H), 9.53 (br s, 1H), 8.90 (s, 1H), 8.16 (s, 1H), 7.94 (d, J = 8.6Hz, 1H), 7.68 (s, 1H), 7.63 (d, J = 8.6Hz, 1H), 7.57 (t, J = 7.7Hz, 1H), 7.47 (br s, 1H), 7.13 (d, J = 8.6Hz, 1H), 7.03 (d, J = 7.0 Hz, 1H), 6.89 (t, J = 55.2Hz, 1H), 6.56 (t, J = 5.8Hz, 1H), 5.78-5.71 (m, 1H), 5.03 (dd, J = 12.8, 5.6Hz, 1H), 4.27 (s, 1H), 3.63 (t, J = 5.6Hz, 2H), 3.60-3.40 (m, 15H), 2.97-2.82 (m, 3H), 2.69-2.56 (m, 3H), 2.45-2.37 (m, 1H), 2.36 (s, 3H), 2.08-2.01 (m, 1H), 1.97-1.83 (m, 2H), 1.81-1.67 (m, 2H), 1.62-1.53 (m, 1H), 0.98 (s, 3H) |
| I-18[g] | G1 | K | 813.4 | 11.0 (s, 1H), 8.73 (s, 1H), 8.05 (s, 2H), 7.58 (t, J = 7.8Hz, 1H), 7.09 (d, J = 8.6Hz, 1H), 7.02 (d, J = 7.2Hz, 1H), 6.84 (t, J = 55.2Hz, 1H), 6.48 (t, J = 6.0 Hz, 1H), 5.86 (t, J = 8.4Hz, 1H), 5.03 (dd, J = 12.8, 5.4Hz, 1H), 4.27 (s, 1H), 4.09-3.90 (m, 1H), 3.63 (t, J = 13.8Hz, 2H), 3.38-3.27 (m, 2H), 3.08-3.00 (m, 2H), 2.99-2.82 (m, 3H), 2.65-2.53 (m, 2H), 2.22-2.15 (m, 1H), 2.07-1.83 (m, 5H), 1.74-1.56 (m, 6H), 1.52-1.35 (m, 5H), 1.27-1.22 (m, 2H), 1.00 (s, 3H) |
| I-31 | F4 | L3 | 878.3 & 880.3 | 10.9 (s, 1H), 10.2 (s, 1H), 8.85 (s, 1H), 8.26 (s, 1H), 8.11 (d, J = 8.4Hz, 1H), 8.00 (s, 1H), 7.93 (s, 1H), 7.74 (d, J = 8.4Hz, 1H), 7.63 (s, 1H), 7.61-7.52 (m, 2H), 7.38-7.20 (m, 2H), 7.08-6.99 (m, 2H), 6.93 (t, J = 9.2Hz, 1H), 6.42 (t, J = 5.8 Hz, 1H), 5.02 (dd, J = 12.8, 5.4Hz, 1H), 3.28 (q, J = 6.8Hz, 2H), 2.93-2.81 (m, 1H), 2.80-2.72 (m, 2H), 2.67-2.55 (m, 2H), 2.30 (s, 3H), 2.09-2.00 (m, 1H), 1.61-1.50 (m, 2H), 1.44-1.36 (m, 2H), 1.34-1.20 (m, 8H) |
| I-32 | E4 | L3 | 882.3 & 884.3 | 11.1 (s, 1H), 10.2 (s, 1H), 9.00 (s, 1H), 8.28 (s, 1H), 8.20-8.00 (m, 3H), 7.73 (d, J = 8.4Hz, 1H), 7.64 (s, 1H), 7.62-7.56 (m, 2H), 7.32-7.24 (m, 1H), 7.05-6.93 (m, 3H), 6.85 (d, J = 8.0 Hz, 1H), 5.33 (dd, J = 12.8, 5.2Hz, 1H), 3.51-3.40 (m, 6H), 3.37 (t, J = 6.4Hz, 2H), 3.31 (s, 3H), 2.96-2.84 (m, 3H), 2.74-2.58 (m, 4H), 2.28 (s, 3H), 2.05-1.95 (m, 1H), 1.85-1.74 (m, 2H) |
| I-34 | D4 | L3 | 882.4 & 884.3 | 11.1 (s, 1H), 10.2 (s, 1H), 9.00 (s, 1H), 8.28 (s, 1H), 8.19-8.01 (m, 3H), 7.73 (d, J = 8.4Hz, 1H), 7.71-7.54 (m, 3H), 7.31-7.21 (m, 1H), 7.03-6.89 (m, 3H), 6.89-6.81 (m, 1H), 5.35 (dd, J = 12.4, 5.2Hz, 1H), 3.54 (s, 3H), 3.47 (s, 4H), 3.43 (t, J = 5.2Hz, 4H), 3.01-2.83 (m, 5H), 2.76-2.57 (m, 2H), 2.28 (s, 3H), 2.03-1.95 (m, 1H), 1.87-1.75 (m, 2H) |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-$d_6$) δ |
|---|---|---|---|---|
| I-35 | E2 | L3 | 920.4 & 922.40 | 11.1 (s, 1H), 10.2 (s, 1H), 9.00 (s, 1H), 8.28 (s, 1H), 8.18-8.04 (m, 3H), 7.74 (d, J = 8.4Hz, 1H), 7.64-7.55 (m, 2H), 7.44 (t, J = 5.8Hz, 1H), 7.31-7.23 (m, 1H), 7.02-6.91 (m, 3H), 6.84 (dd, J = 8.0, 1.6Hz, 1H), 5.33 (dd, J = 12.7, 5.3Hz, 1H), 3.32 (s, 3H), 2.96-2.83 (m, 1H), 2.77-2.54 (m, 6H), 2.29 (s, 3H), 2.04-1.95 (m, 1H), 1.60-1.50 (m, 2H), 1.39-1.30 (m, 2H), 1.26-1.22 (m, 4H), 1.21-1.10 (m, 12H) |
| I-36 | D2 | L3 | 920.4 & 922.4 | 11.1 (s, 1H), 10.2 (s, 1H), 9.00 (s, 1H), 8.28 (s, 1H), 8.18-8.03 (m, 3H), 7.74 (d, J = 8.4Hz, 1H), 7.65-7.53 (m, 2H), 7.44 (t, J = 5.8Hz, 1H), 7.32-7.22 (m, 1H), 6.99-6.90 (m, 3H), 6.84 (dd, J = 5.6, 3.4Hz, 1H), 5.35 (dd, J = 12.6, 5.4Hz, 1H), 3.54 (s, 3H), 2.92-2.82 (m, 3H), 2.77-2.66 (m, 3H), 2.65-2.59 (m, 1H), 2.29 (s, 3H), 2.04-1.96 (m, 1H), 1.61-1.51 (m, 2H), 1.38-1.31 (m, 4H), 1.30-1.09 (m, 14H) |
| I-107 | EH | CW | 885.4 | 11.08 (s, 1H), 9.73 (s, 1H), 8.76 (s, 1H), 8.17 (s, 1H), 7.77 (d, J = 8.4Hz, 1H), 7.63 (s, 1H), 7.57 (d, J = 8.4Hz, 1H), 6.99-6.92 (m, 1H), 6.86 (d, J = 8.0 Hz, 2H), 5.73 (t, J = 8.8Hz, 1H), 5.38-5.30 (m, 1H), 3.66 (d, J = 11.2Hz, 2H), 3.60 (s, 3H), 3.11 (d, J = 11.2Hz, 2H), 2.94-2.83 (m, 1H), 2.73-2.61 (m, 4H), 2.35 (s, 3H), 2.26-2.18 (m, 4H), 2.15 (s, 3H), 2.14-2.07 (m, 2H), 2.02-1.95 (m, 1H), 1.80-1.68 (m, 8H), 1.65-1.54 (m, 2H), 1.53-1.31 (m, 4H), 1.19-1.10 (m, 2H) |
| I-110[f] | GI | CW | 841.4 | 11.07 (br s, 1H), 9.51 (s, 1H), 7.77 (d, J = 9.2Hz, 1H), 7.73-7.67 (m, 2H), 7.66-7.61 (m, 1H), 7.59 (d, J = 6.8Hz, 1H), 7.05-6.97 (m, 2H), 6.85 (d, J = 1.2, 8.0 Hz, 1H), 6.34 (d, J = 9.2Hz, 1H), 5.72-5.60 (m, 1H), 5.33 (dd, J = 5.2, 12.8Hz, 1H), 3.50-3.41 (m, 4H), 3.37 (t, J = 6.4Hz, 2H), 3.32 (br s, 3H), 3.22-3.11 (m, 1H), 3.02-2.83 (m, 2H), 2.78-2.56 (m, 4H), 2.53-2.52 (m, 1H), 2.33 (s, 3H), 2.19-2.07 (m, 2H), 2.05-1.95 (m, 1H), 1.92-1.74 (m, 4H), 1.73-1.58 (m, 6H), 1.50-1.34 (m, 2H), 1.29-1.00 (m, 4H) |
| I-114 | EH | EF | 851.4 | 11.09 (s, 1H), 9.59 (s, 1H), 8.75 (s, 1H), 7.77 (dd, J = 4.8, 8.8 Hz, 2H), 7.64 (s, 1H), 7.57 (dd, J = 1.6, 8.4Hz, 1H), 6.99-6.93 (m, 1H), 6.86 (d, J = 8.0 Hz, 2H), 6.37-6.31 (m, 1H), 5.73-5.62 (m, 1H), 5.40-5.29 (m, 1H), 3.67 (d, J = 10.8Hz, 3H), 3.61 (s, 3H), 3.11 (d, J = 11.0 Hz, 4H), 2.96-2.80 (m, 3H), 2.72-2.60 (m, 5H), 2.36 (s, 3H), 2.28-2.22 (m, 4H), 2.18 (s, 3H), 2.12-2.08 (m, 2H), 2.03-1.95 (m, 1H), 1.68 (d, J = 2.0 Hz, 4H), 1.48-1.41 (m, 3H), 1.19-1.11 (m, 2H) |
| I-116[f] | GF | CW | 824.2 | 11.08 (br s, 1H), 9.55 (s, 1H), 8.71 (s, 1H), 8.25 (s, 1H), 7.91 (d, J = 8.4Hz, 1H), 7.77-7.70 (m, 2H), 7.65 (dd, J = 2.0, 8.4 Hz, 1H), 7.01 (d, J = 1.2Hz, 1H), 6.95 (d, J = 8.0 Hz, 1H), 6.82 (dd, J = 1.2, 8.2Hz, 1H), 6.34 (d, J = 9.6Hz, 1H), 5.70 (br t, J = 8.8Hz, 1H), 5.32 (dd, J = 5.6, 12.8Hz, 1H), 4.16 (t, J = 6.0 Hz, 1H), 3.99-3.93 (m, 2H), 3.48 (br dd, J = 5.2, 8.8 Hz, 4H), 3.30 (s, 3H), 2.85 (br d, J = 11.2Hz, 3H), 2.74-2.58 (m, 3H), 2.40 (s, 3H), 2.38-2.35 (m, 2H), 2.18-2.10 (m, 2H), 2.02-1.92 (m, 3H), 1.74-1.58 (m, 8H), 1.47 (br d, J = 4.4Hz, 2H) |
| I-118 | FW | FX | 779.3 | 11.21-10.99 (m, 1H), 9.53 (s, 1H), 8.74 (s, 1H), 7.81-7.73 (m, 2H), 7.64 (d, J = 1.6Hz, 1H), 7.57 (dd, J = 2.4, 8.4Hz, 1H), 7.19-7.13 (m, 1H), 7.10-7.05 (m, 1H), 7.03-6.95 (m, 1H), 6.33 (d, J = 9.2Hz, 1H), 5.69-5.59 (m, 1H), 5.37 (dd, J = 5.6, 12.8Hz, 1H), 4.42 (s, 2H), 3.66 (dt, J = 3.6, 6.8Hz, 1H), 3.56 (s, 3H), 3.18-3.06 (m, 2H), 2.93-2.80 (m, 3H), 2.73-2.62 (m, 2H), 2.35 (s, 3H), 2.17-2.04 (m, 2H), 2.02-1.86 (m, 3H), 1.70-1.57 (m, 6H), 1.48-1.35 (m, 2H) |
| I-120[f] | FW | CW | 783.3 | 11.27-10.84 (m, 1H), 9.56-9.39 (m, 1H), 8.68 (s, 1H), 7.84-7.71 (m, 2H), 7.64 (d, J = 1.6Hz, 1H), 7.57 (dd, J = 2.0, 8.4 Hz, 1H), 6.96-6.85 (m, 2H), 6.78 (dd, J = 1.6, 7.2Hz, 1H), 6.33 (d, J = 9.2Hz, 1H), 5.72-5.62 (m, 1H), 5.32 (br dd, J = 5.2, 12.8Hz, 1H), 3.44 (s, 3H), 3.42-3.39 (m, 3H), 3.14-3.05 (m, 2H), 2.86 (br dd, J = 6.4, 8.8Hz, 4H), 2.70-2.57 (m, 2H), 2.36 (s, 3H), 2.11 (dt, J = 8.2, 9.8Hz, 2H), 1.94-1.78 (m, 3H), 1.77-1.54 (m, 8H), 1.51-1.39 (m, 2H), 1.23 (br s, 2H) |
| I-121 | FW | CW | 813.3 | 11.17-11.03 (m, 1H), 9.68 (s, 1H), 8.75 (s, 1H), 8.17 (s, 1H), 7.76 (d, J = 8.4Hz, 1H), 7.65 (d, J = 1.6Hz, 1H), 7.58 (dd, J = 2.0, 8.4Hz, 1H), 7.15 (d, J = 7.6Hz, 1H), 7.10-7.04 (m, 1H), 7.03-6.97 (m, 1H), 5.75-5.63 (m, 1H), 5.38 (dd, J = 5.4, 12.8Hz, 1H), 4.42 (s, 2H), 3.66 (dt, J = 3.6, 7.2Hz, 1H), 3.56 (s, 3H), 3.13 (br t, J = 7.6Hz, 2H), 2.92-2.82 (m, 3H), |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | 1H NMR (400 MHz, DMSO-d6) δ |
|---|---|---|---|---|
| | | | | 2.75-2.61 (m, 2H), 2.35 (s, 3H), 2.15-2.03 (m, 2H), 2.03-1.96 (m, 1H), 1.95-1.86 (m, 2H), 1.66 (br s, 6H), 1.44 (br s, 2H) |
| I-127[f] | FL | CW | 783.3 | 11.07 (s, 1H), 9.55 (s, 1H), 8.73 (s, 1H), 7.79-7.74 (m, 2H), 7.64-7.55 (m, 2H), 6.95-6.76 (m, 3H), 6.35-6.32 (d, J = 9.2, 1H), 5.66-5.64 (m, 1H), 5.30-5.28 (m, 1H), 3.35-3.28 (m, 6H), 3.21-3.08 (m, 2H), 2.80-2.63 (m, 5H), 2.58-2.54 (m, 2H), 2.35 (s, 3H), 2.12-2.08 (m, 2H), 1.75-1.65 (m, 5H), 1.57-1.43 (m, 8H) |
| I-128[f] | DD | CW | 794.4 | 11.08 (br s, 1H), 9.56 (s, 1H), 8.76 (s, 1H), 7.83-7.75 (m, 2H), 7.66 (s, 1H), 7.62-7.56 (m, 1H), 6.99-6.90 (m, 2H), 6.85 (br d, J = 7.6Hz, 1H), 6.35 (d, J = 9.2Hz, 1H), 5.68 (br t, J = 8.4 Hz, 1H), 5.42-5.25 (m, 1H), 3.59 (s, 3H), 2.99 (br s, 4H), 2.83 (br d, J = 3.6Hz, 4H), 2.70-2.65 (m, 2H), 2.63 (br s, 2H), 2.37 (s, 3H), 2.17-2.09 (m, 2H), 2.01-1.95 (m, 1H), 1.76 (br d, J = 2.4Hz, 2H), 1.67 (br s, 5H), 1.54-1.43 (m, 7H) |
| I-129[f] | FK | CW | 838.4 | 11.09 (s, 1H), 9.55 (s, 1H), 8.75 (s, 1H), 7.78-7.54 (m, 4H), 6.95-6.87 (m, 3H), 6.35-6.33 (d, J = 9.2, 1H), 5.69-5.65 (m, 1H), 5.38-5.34 (m, 1H), 3.55 (s, 3H), 3.47-3.40 (m, 4H), 2.90-2.89 (m, 2H), 2.65-2.50 (m, 2H), 2.47-2.45 (m, 4H), 2.35 (s, 3H), 2.28-2.17 (m, 6H), 1.98-1.44 (m, 10H) |
| I-130[f] | CA | CW | 808.3 | 11.08 (s, 1H), 9.54 (s, 1H), 8.75 (s, 1H), 7.77 (dd, J = 2.0, 8.4 Hz, 2H), 7.63 (s, 1H), 7.56 (dd, J = 1.6, 8.4Hz, 1H), 7.04 (br d, J = 7.6Hz, 1H), 6.92 (t, J = 7.6Hz, 1H), 6.83 (d, J = 7.6Hz, 1H), 6.34 (d, J = 9.6Hz, 1H), 5.76-5.53 (m, 1H), 5.35 (br dd, J = 5.6, 12.4Hz, 1H), 3.62 (s, 3H), 3.58 (br d, J = 5.2Hz, 1H), 2.92 (br s, 4H), 2.76-2.54 (m, 4H), 2.35 (s, 3H), 2.32-2.26 (m, 4H), 2.17-2.08 (m, 2H), 2.03-1.96 (m, 1H), 1.65 (br s, 4H), 1.50 (br s, 4H), 1.41 (br s, 2H), 1.28 (br s, 4H) |
| I-131[f] | CF | CW | 840.5 | 11.08 (s, 1H), 9.60 (s, 1H), 8.76 (s, 1H), 7.77 (dd, J = 4.8, 8.8 Hz, 2H), 7.63 (d, J = 2.0 Hz, 1H), 7.56 (dd, J = 2.0, 8.4Hz, 1H), 7.02-6.95 (m, 2H), 6.83 (dd, J = 1.2, 8.4Hz, 1H), 6.34 (d, J = 9.6Hz, 1H), 5.65 (quin, J = 8.8Hz, 1H), 5.33 (dd, J = 5.6, 12.4Hz, 1H), 3.32 (br s, 5H), 3.30 (s, 3H), 2.89 (br d, J = 3.2.0 Hz, 4H), 2.75-2.59 (m, 4H), 2.42 (br s, 4H), 2.36 (s, 3H), 2.27 (br t, J = 6.4Hz, 2H), 2.17-2.06 (m, 2H), 2.04-1.94 (m, 1H), 1.83-1.73 (m, 2H), 1.66 (br d, J = 2.4Hz, 4H), 1.43 (br d, J = 2.4Hz, 6H) |
| I-132[f] | FJ | CW | 851.4 | 11.07 (s, 1H), 9.57 (s, 1H), 8.76 (s, 1H), 7.80-7.75 (m, 2H), 7.64 (d, J = 1.6Hz, 1H), 7.57 (dd, J = 1.9, 8.4Hz, 1H), 7.04-6.97 (m, 2H), 6.89-6.83 (m, 1H), 6.35 (d, J = 9.4Hz, 1H), 5.68 (quin, J = 8.6Hz, 1H), 5.33 (dd, J = 5.3, 12.8Hz, 1H), 3.67 (br d, J = 11.4Hz, 2H), 3.32 (s, 3H), 2.95-2.85 (m, 1H), 2.73-2.63 (m, 2H), 2.62-2.59 (m, 2H), 2.43 (br s, 5H), 2.37-2.33 (m, 5H), 2.28-2.20 (m, 5H), 2.12 (br d, J = 6.8Hz, 3H), 2.03-1.98 (m, 1H), 1.79 (br d, J = 11.0 Hz, 2H), 1.73-1.65 (m, 6H), 1.49-1.41 (m, 4H) |
| I-134[f] | FF | CW | 864.5 | 11.09 (s, 1H), 9.58 (s, 1H), 8.78 (s, 1H), 8.89-8.86 (m, 1H), 8.78 (d, J = 9.2Hz, 1H), 7.70 (s, 1H), 7.64 (d, J = 6.4Hz, 1H), 7.08 (s, 1H), 6.99 (d, J = 8.0 Hz, 1H), 6.89 (d, J = 8.4Hz, 1H), 6.35 (d, J = 9.2Hz, 1H), 5.73-5.71 (m, 1H), 5.35-5.31 (m, 1H), 3.74-3.67 (m, 5H), 3.30-3.29 (m, 2H), 2.94-2.91 (m, 3H), 2.68-2.67 (m, 4H), 2.45-2.40 (m, 3H), 2.39 (s, 3H), 2.20-2.00 (m, 7H), 1.96-1.70 (m, 2H), 1.70-1.69 (m, 9H), 1.50-1.47 (m, 2H) |
| I-135 | EK | CW | 865.2 | 9.51 (s, 1H), 11.07 (s, 1H), 9.66 (s, 1H), 8.74 (s, 1H), 8.16 (s, 1H), 7.70-7.61 (m, 4H), 7.01-6.84 (m, 3H), 5.75-5.70 (m, 1H), 5.35-5.30 (m, 1H), 3.50-3.47 (m, 6H), 3.46-3.36 (m, 9H), 2.89-2.52 (m, 8H), 2.32 (s, 3H), 1.81-1.79 (m, 3H), 1.68-1.45 (m, 8H) |
| I-138[f] | EZ | EX | 889.4 | 11.07 (s, 1H), 9.48 (s, 1H), 8.79 (s, 1H), 7.73-7.67 (m, 2H), 7.64-7.55 (m, 2H), 7.05-6.95 (m, 2H), 6.85 (d, J = 8.0 Hz, 1H), 6.20 (s, 1H), 5.72-5.59 (m, 1H), 5.33 (dd, J = 5.2, 12.6 Hz, 1H), 3.50 (s, 6H), 3.48-3.44 (m, 6H), 3.39 (br d, J = 5.6 Hz, 4H), 3.31 (br s, 3H), 2.89 (q, J = 6.0 Hz, 3H), 2.75-2.68 (m, 1H), 2.68-2.63 (m, 3H), 2.60 (br d, J = 9.2Hz, 3H), 2.32 (s, 3H), 2.11 (br d, J = 2.4Hz, 2H), 2.04-1.95 (m, 1H), 1.85-1.74 (m, 2H), 1.63 (br s, 4H), 1.42 (br s, 2H) |
| I-139[f] | FC | CO | 1046.5 | 9.51 (s, 1H), 9.00-8.95 (m, 1H), 8.73 (s, 1H), 8.62-8.56 (m, 1H), 7.76 (d, J = 9.6Hz, 1H), 7.72-7.66 (m, 2H), 7.66-7.59 (m, 2H), 7.44-7.35 (m, 4H), 6.33 (d, J = 9.2Hz, 1H), 5.73-5.60 (m, 1H), 5.18-5.11 (m, 1H), 4.56 (d, J = 9.6Hz, 1H), |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | 1H NMR (400 MHz, DMSO-$d_6$) δ |
|---|---|---|---|---|
| | | | | 4.46-4.34 (m, 2H), 4.29-4.19 (m, 1H), 3.95 (s, 2H), 3.72-3.64 (m, 1H), 3.63-3.47 (m, 10H), 3.47-3.37 (m, 8H), 2.89 (br d, J = 5.6Hz, 2H), 2.69-2.65 (m, 1H), 2.46-2.41 (m, 3H), 2.32 (s, 3H), 2.17-2.08 (m, 2H), 1.64 (br s, 4H), 1.49-1.37 (m, 2H), 1.00-0.86 (m, 9H) |
| I-140[f] | FB | CO | 1002.4 | 9.51 (s, 1H), 8.97 (s, 1H), 8.73 (s, 1H), 8.59-8.57 (s, 1H), 7.77-7.69 (m, 5H), 7.63-7.39 (m, 5H), 6.34-6.32 (d, J = 9.2Hz, 2H), 5.69-5.65 (m, 1H), 5.15(s, 1H), 4.57-4.35 (m, 5H), 3.95 (s, 2H), 3.59-3.51 (m, 6H), 3.47-3.30 (m, 8H), 2.90-2.88 (m, 2H), 2.43 (s, 3H), 2.33-3.32 (m, 3H), 2.33-2.07(m, 2H), 1.90-1.43 (m, 7H), 0.93 (m, 9H) |
| I-143 | EZ | EX | 969.2 | 11.07 (br s, 1H), 9.63 (s, 1H), 8.95 (s, 1H), 7.74-7.67 (m, 2H), 7.62 (dd, J = 2.0, 8.4Hz, 2H), 7.05-6.95 (m, 2H), 6.87-6.82 (m, 1H), 5.76 (br t, J = 8.4Hz, 1H), 5.32 (dd, J = 5.2, 12.8Hz, 1H), 3.50 (s, 6H), 3.48-3.43 (m, 6H), 3.42-3.36 (m, 4H), 3.31 (s, 3H), 2.93-2.84 (m, 3H), 2.73-2.66 (m, 1H), 2.63 (br t, J = 7.6Hz, 3H), 2.56 (s, 3H), 2.32 (s, 3H), 2.14-2.03 (m, 2H), 2.03-1.96 (m, 1H), 1.84-1.75 (m, 2H), 1.68 (br s, 4H), 1.44 (br s, 2H) |
| I-144[f] | EN | EX | 801.4 | 11.07 (s, 1H), 9.48 (s, 1H), 8.79 (s, 1H), 7.74-7.66 (m, 2H), 7.66-7.58 (m, 2H), 7.05-6.95 (m, 2H), 6.85 (d, J = 8.0 Hz, 1H), 6.20 (s, 1H), 5.74-5.58 (m, 1H), 5.33 (dd, J = 5.2, 12.8 Hz, 1H), 3.52-3.40 (m, 6H), 3.37 (br t, J = 6.4Hz, 2H), 3.30 (d, J = 3.6Hz, 6H), 2.91 (q, J = 6.0 Hz, 2H), 2.75-2.65 (m, 2H), 2.63 (br d, J = 6.8Hz, 2H), 2.32 (s, 3H), 2.20-1.92 (m, 4H), 1.84-1.76 (m, 2H), 1.63 (br s, 4H), 1.43 (br d, J = 5.6 Hz, 2H) |
| I-146[f] | EN | CW | 787.1 | 11.07 (br d, J = 5.5Hz, 1H), 9.51 (s, 1H), 8.73 (s, 1H), 7.75 (d, J = 9.4Hz, 1H), 7.72-7.67 (m, 2H), 7.66-7.59 (m, 2H), 7.05-6.94 (m, 2H), 6.85 (d, J = 8.3Hz, 1H), 6.33 (d, J = 9.3 Hz, 1H), 5.66 (quin, J = 8.7Hz, 1H), 5.32 (dd, J = 5.3, 12.8 Hz, 1H), 3.48-3.35 (m, 8H), 3.31 (br s, 3H), 2.95-2.83 (m, 3H), 2.76-2.57 (m, 4H), 2.35-2.30 (m, 3H), 2.12 (br s, 2H), 2.03-1.92 (m, 1H), 1.84-1.73 (m, 2H), 1.64 (br s, 4H), 1.42 (br d, J = 4.3Hz, 2H) |
| I-150 | EN | CH | 801.4 | 11.07 (s, 1H), 8.83 (s, 1H), 7.93 (s, 1H), 7.84 (d, J = 8.4Hz, 1H), 7.62 (s, 1H), 7.58-7.50 (m, 2H), 7.07-7.02 (m, 2H), 6.96 (d, J = 8.8Hz, 1H), 5.35-5.30 (m, 1H), 4.72-4.67 (m, 1H), 3.50-3.32 (m, 11H), 2.90-2.88 (m, 3H), 2.70-2.50 (m, 4H), 2.32 (s, 3H), 2.20-2.00 (m, 3H), 1.79-1.50 (m, 12H) |
| I-159 | DQ | KJ | 935.6 | 11.08 (s, 1H), 9.86 (s, 1H), 8.82 (s, 1H), 7.68 (s, 1H), 7.65-7.62 (m, 1H), 7.61-7.57 (m, 2H), 7.09 (s, 1H), 6.99 (d, J = 8.4 Hz, 1H), 6.94 (s, 1H), 6.90 (d, J = 7.4Hz, 1H), 5.33 (d, J = 5.4, 12.8Hz, 1H), 4.50 (d, J = 7.2, 14.0 Hz, 1H), 3.40-3.36 (m, 3H), 3.13-3.01 (m, 1H), 2.94-2.81 (m, 6H), 2.71 (d, J = 4.4 Hz, 1H), 2.63 (d, J = 5.6Hz, 1H), 2.60-2.57 (m, 2H), 2.41 (s, 3H), 2.29 (s, 3H), 2.06 (d, J = 6.8Hz, 2H), 2.01-1.96 (m, 1H), 1.94-1.86 (m, 4H), 1.78-1.67 (m, 6H), 1.46-1.36 (m, 1H), 1.21 (d, J = 6.8Hz, 6H), 1.10-0.99 (m, 2H), 0.86-0.75 (m, 2H) |
| I-160 | EH | KJ | 906.3 | 11.08 (s, 1H), 9.90 (s, 1H), 8.85 (s, 1H), 7.70 (d, J = 8.8Hz, 1H), 7.61 (s, 1H), 7.56-7.51 (m, 1H), 6.95 (t, J = 3.8Hz, 2H), 6.89-6.84 (m, 2H), 5.42-5.26 (m, 1H), 4.57-4.41 (m, 1H), 3.65 (d, J = 1.2Hz, 1H), 3.61 (s, 3H), 3.15-3.09 (m, 2H), 2.92-2.83 (m, 2H), 2.69 (s, 4H), 2.40 (s, 3H), 2.32 (s, 3H), 2.23 (d, J = 6.4Hz, 2H), 2.16 (s, 3H), 2.03-1.93 (m, 2H), 1.79-1.72 (m, 3H), 1.67-1.57 (m, 2H), 1.48-1.32 (m, 2H), 1.23 (s, 2H), 1.21 (s, 3H), 1.19 (s, 3H), 1.15-1.08 (m, 2H) |
| I-161 | KH | DO | 904.2 | 11.05 (s, 1H), 9.79 (s, 1H), 8.88 (s, 1H), 8.15 (s, 1H), 7.74 (d, J = 8.4Hz, 1H), 7.68 (s, 1H), 7.65-7.61 (m, 1H), 7.53 (t, J = 5.6Hz, 1H), 7.05-6.78 (m, 3H), 6.65-6.56 (m, 1H), 5.65-5.49 (m, 1H), 5.28 (dd, J = 5.2, 12.8Hz, 1H), 3.59-3.50 (m, 2H), 2.82-2.73 (m, 3H), 2.70-2.64 (m, 3H), 2.36-2.31 (m, 6H), 2.30-2.18 (m, 8H), 2.11 (d, J = 6.8Hz, 2H), 2.07-1.91 (m, 2H), 1.74 (d, J = 11.6Hz, 2H), 1.62-1.47 (m, 4H), 1.39 (d, J = 6.0 Hz, 6H), 1.28-1.14 (m, 3H) |
| I-162 | HS | KD | 927.3 | 11.09 (s, 1H), 9.81-9.80 (m, 1H), 8.89 (s, 1H), 8.16 (s, 1H), 7.64 (s, 1H), 7.56 (s, 1H), 7.04-6.82 (m, 4H), 5.71-5.45 (m, 1H), 5.41-5.28 (m, 1H), 3.68 (d, J = 10.8Hz, 2H), 3.59 (s, 3H), 2.90-2.84 (m, 1H), 2.80-2.73 (m, 4H), 2.63-2.62 (m, 2H), 2.57 (s, 3H), 2.32 (s, 3H), 2.25-2.10 (m, 4H), 2.07-1.82 (m, 6H), 1.77-1.66 (m, 4H), 1.53-1.40 (m, 4H), 1.23 (s, 2H), |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-$d_6$) δ |
|---|---|---|---|---|
| | | | | 1.14-1.06 (m, 2H), 0.54-0.37 (m, 2H), 0.35-0.25 (m, 1H), 0.17-0.06 (m, 1H) |
| I-163 | EH | DG | 859.6 | 11.08 (s, 1H), 9.70 (s, 1H), 8.74 (s, 1H), 8.16 (s, 1H), 7.83-7.75 (m, 1H), 7.63 (s, 1H), 7.60-7.53 (m, 1H), 6.94 (d, J = 8.0 Hz, 1H), 6.90-6.83 (m, 2H), 5.69-5.52 (m, 1H), 5.37-5.30 (m, 1H), 3.15-3.06 (m, 4H), 2.93-2.83 (m, 2H), 2.73-2.62 (m, 6H), 2.35 (s, 3H), 2.26-2.18 (m, 4H), 2.16 (s, 3H), 2.04-1.94 (m, 2H), 1.81-1.69 (m, 4H), 1.65-1.55 (m, 2H), 1.39 (d, J = 6.0 Hz, 6H), 1.25-1.10 (m, 3H) |
| I-164 | KG | DG | 889.5 | 11.07 (s, 1H), 9.70 (s, 1H), 8.75 (s, 1H), 8.16 (s, 1H), 7.80 (d, J = 6.8Hz, 1H), 7.63 (s, 1H), 7.58 (d, J = 8.4Hz, 1H), 6.84 (d, J = 8.8Hz, 1H), 6.65 (d, J = 8.8Hz, 1H), 5.67-5.52 (m, 1H), 5.31-5.26 (m, 1H), 3.73 (s, 3H), 3.65 (d, J = 11.2Hz, 2H), 3.58 (s, 3H), 3.30-3.24 (m, 2H), 2.89-2.87 (m, 2H), 2.65-2.58 (m, 2H), 2.36 (s, 3H), 2.22-2.20 (m, 4H), 2.15 (s, 3H), 2.07 (s, 2H), 1.98-1.95 (m, 1H), 1.79-1.76 (m, 2H), 1.65-1.59 (m, 2H), 1.58-1.49 (m, 2H), 1.40 (d, J = 6.4Hz, 7H), 1.18-1.06 (m, 2H) |
| I-166 | GL | CW | 857.2 | 11.09 (s, 1H), 9.70 (s, 1H), 8.70 (s, 1H), 8.09 (s, 1H), 8.03 (d, J = 8.4Hz, 1H), 7.74 (s, 1H), 7.69 (d, J = 8.4Hz, 1H), 6.89-6.79 (m, 2H), 6.67 (d, J = 7.2Hz, 1H), 5.85-5.73 (m, 1H), 5.37-5.29 (m, 1H), 4.40-4.28 (m, 1H), 3.84 (t, J = 8.4Hz, 2H), 3.51 (s, 3H), 3.44 (d, J = 6.8Hz, 2H), 2.97 (d, J = 9.2Hz, 2H), 2.89 (s, 1H), 2.67 (s, 1H), 2.59 (s, 2H), 2.43 (s, 3H), 2.20-2.16 (m, 1H), 2.15 (d, J = 7.6Hz, 3H), 2.04 (s, 3H), 2.01-1.96 (m, 1H), 1.84-1.72 (m, 4H), 1.59-1.50 (m, 4H), 1.45-1.36 (m, 2H), 1.07-1.04 (m, 2H) |
| I-167 | GN | CW | 845.3 | 11.08 (s, 1H), 9.67 (s, 1H), 8.74 (s, 1H), 8.16 (s, 1H), 7.74 (d, J = 8.4Hz, 1H), 7.69 (d, J = 1.6Hz, 1H), 7.65-7.60 (m, 1H), 7.55 (s, 1H), 6.92 (d, J = 8.0 Hz, 1H), 6.84 (t, J = 7.2Hz, 2H), 5.78-5.70 (m, 1H), 5.36-5.31 (m, 1H), 3.60 (s, 3H), 3.10 (d, J = 11.6Hz, 2H), 2.92-2.85 (m, 1H), 2.84-2.79 (m, 2H), 2.63 (s, 2H), 2.59 (d, J = 1.2Hz, 1H), 2.41 (t, J = 6.4Hz, 3H), 2.33 (s, 3H), 2.16 (s, 3H), 2.13-2.06 (m, 2H), 2.01-1.95 (m, 1H), 1.70 (s, 6H), 1.64-1.49 (m, 5H), 1.49-1.42 (m, 2H) |
| I-168 | GP | CW | 867.4 | 10.52 (s, 1H), 9.74 (s, 1H), 9.37 (s, 1H), 8.74 (s, 1H), 8.51 (s, 1H), 8.16 (s, 1H), 7.77 (d, J = 8.4Hz, 1H), 7.72-7.63 (m, 2H), 7.58-7.56 (m, 2H), 7.20 (d, J = 7.6Hz, 1H), 5.78-5.69 (m, 1H), 3.95-3.83 (m, 1H), 3.72-3.61 (m, 3H), 3.49-3.36 (m, 2H), 3.01-2.90 (m, 1H), 2.83-2.69 (m, 3H), 2.36 (s, 3H), 2.31-2.19 (m, 7H), 2.14-2.07 (m, 2H), 1.81-1.79 (m, 6H), 1.72 (s, 4H), 1.50-1.39 (m, 3H), 1.25-1.13 (m, 3H) |
| I-169 | GR | CW | 856.1 | 10.63 (s, 1H), 9.73 (s, 1H), 8.75 (s, 1H), 8.17 (s, 1H), 7.82-7.74 (m, 2H), 7.65-7.62 (m, 1H), 7.58-7.54 (m, 1H), 7.44 (s, 1H), 6.82-6.76 (m, 1H), 6.48 (d, J = 7.2Hz, 1H), 5.77-5.67 (m, 1H), 4.39-4.28 (m, 2H), 3.79-3.71 (m, 2H), 3.65 (d, J = 11.6Hz, 2H), 2.86-2.77 (m, 2H), 2.69-2.65 (m, 2H), 2.35 (s, 3H), 2.25-2.18 (m, 4H), 2.16-2.08 (m, 5H), 1.81-1.66 (m, 9H), 1.63-1.53 (m, 2H), 1.49-1.36 (m, 3H), 1.19-1.08 (m, 2H) |
| I-170 | GT | CW | 871.6 | 11.08 (s, 1H), 9.73 (s, 1H), 8.77 (s, 1H), 8.18 (s, 1H), 7.76 (d, J = 8.4Hz, 1H), 7.64 (d, J = 1.6Hz, 1H), 7.57 (dd, J = 1.6, 8.4 Hz, 1H), 7.05-6.95 (m, 1H), 6.89 (d, J = 8.4Hz, 2H), 5.73 (m, J = 8.8Hz, 1H), 5.34 (dd, J = 5.2, 12.4Hz, 1H), 3.65 (d, J = 11.2Hz, 2H), 3.60 (s, 3H), 3.01-2.81 (m, 6H), 2.76-2.67 (m, 2H), 2.61 (d, J = 17.6Hz, 3H), 2.54 (s, 2H), 2.35 (s, 3H), 2.20 (t, J = 11.2Hz, 2H), 2.12 (dd, J = 7.6, 11.2Hz, 2H), 2.02-1.95 (m, 1H), 1.78-1.66 (m, 6H), 1.50-1.37 (m, 4H), 1.28-1.17 (m, 3H) |
| I-171 | GW | CW | 915.4 | 11.06 (s, 1H), 9.67 (s, 1H), 8.76 (s, 1H), 8.19-8.17 (m, 1H), 7.75-7.69 (m, 2H), 7.65-7.59 (m, 2H), 6.94 (d, J = 8.4Hz, 1H), 6.82 (d, J = 1.6Hz, 1H), 6.63-6.58 (m, 1H), 5.79-5.70 (m, 1H), 5.33-5.25 (m, 1H), 3.39 (t, J = 5.6Hz, 2H), 3.30 (s, 3H), 3.09-3.02 (m, 5H), 2.89 (d, J = 5.6Hz, 2H), 2.70-2.65 (m, 1H), 2.59 (s, 1H), 2.45 (s, 3H), 2.34 (s, 3H), 2.09 (d, J = 6.8Hz, 5H), 2.01-1.96 (m, 1H), 1.90 (d, J = 11.2Hz, 2H), 1.79-1.67 (m, 7H), 1.46 (d, J = 4.0 Hz, 3H), 1.12-1.01 (m, 2H), 0.88-0.77 (m, 2H) |
| I-172 | GY | CW | 886.2 | 11.09 (s, 1H), 9.67 (s, 1H), 8.75 (s, 1H), 8.17 (s, 1H), 7.74-7.69 (m, 2H), 7.65-7.59 (m, 2H), 7.13 (s, 1H), 7.05-7.01 (m, 1H), 6.99-6.95 (m, 1H), 5.78-5.70 (m, 1H), 5.38-5.31 (m, 1H), 3.61-3.55 (m, 3H), 3.39 (t, J = 6.0 Hz, 2H), 3.34 (s, 3H), |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-$d_6$) δ |
|---|---|---|---|---|
| | | | | 3.04-2.99 (m, 2H), 2.92-2.86 (m, 3H), 2.70-2.66 (m, 1H), 2.33 (s, 3H), 2.25-2.22 (m, 2H), 2.16-2.07 (m, 3H), 1.93-1.85 (m, 3H), 1.77-1.67 (m, 7H), 1.50-1.43 (m, 2H), 1.08-0.98 (m, 2H), 0.91-0.79 (m, 3H) |
| I-173 | HA | CW | 857.6 | 11.07 (s, 1H), 9.72 (s, 1H), 8.76 (s, 1H), 8.18 (s, 1H), 7.75 (d, J = 8.4Hz, 1H), 7.65-7.52 (m, 2H), 6.98-6.90 (m, 1H), 6.73 (d, J = 8.0 Hz, 1H), 6.64 (d, J = 8.4Hz, 1H), 5.81-5.66 (m, 1H), 5.69-5.28 (m, 1H), 3.87 (d, J = 4.0 Hz, 2H), 3.65 (d, J = 11.2Hz, 2H), 3.54 (s, 3H), 3.53-3.45 (m, 2H), 3.20 (t, J = 6.4 Hz, 1H), 2.97-2.81 (m, 1H), 2.70-2.57 (m, 2H), 2.54 (s, 1H), 2.34 (s, 3H), 2.21 (t, J = 11.2Hz, 2H), 2.15-2.06 (m, 2H), 2.02 (s, 3H), 1.80-1.66 (m, 6H), 1.44 (s, 4H), 1.19-1.02 (m, 3H) |
| I-174 | DQ | DG | 888.6 | 11.09 (s, 1H), 9.66 (s, 1H), 8.74 (s, 1H), 8.16 (s, 1H), 7.75 (d, J = 8.4Hz, 1H), 7.69 (d, J = 1.6Hz, 1H), 7.63 (dd, J = 2.0, 8.4 Hz, 1H), 7.59 (t, J = 6.0 Hz, 1H), 7.07 (s, 1H), 7.01 (d, J = 8.0 Hz, 1H), 6.90 (d, J = 8.0 Hz, 1H), 5.70-5.53 (m, 1H), 5.34 (dd, J = 5.6, 12.8Hz, 1H), 3.43-3.40 (m, 2H), 3.40-3.38 (m, 3H), 3.14-2.98 (m, 4H), 2.95-2.84 (m, 4H), 2.66-2.62 (m, 2H), 2.61-2.57 (m, 2H), 2.33 (s, 3H), 2.31-2.23 (m, 2H), 2.04-1.87 (m, 4H), 1.79-1.73 (m, 5H), 1.41 (d, J = 6.8Hz, 6H), 1.14-1.01 (m, 2H), 0.91-0.79 (m, 2H) |
| I-175 | EH | HC | 865.4 | 11.08 (s, 1H), 8.91 (s, 1H), 7.95 (s, 1H), 7.91 (d, J = 8.4Hz, 1H), 7.56 (s, 1H), 7.50 (d, J = 7.6Hz, 1H), 6.98-6.92 (m, 1H), 6.90-6.81 (m, 2H), 5.41-5.29 (m, 1H), 4.71 (t, J = 8.8Hz, 1H), 3.65-3.62 (m, 2H), 3.60 (s, 3H), 3.14-3.08 (m, 2H), 2.92-2.83 (m, 1H), 2.71-2.62 (m, 4H), 2.35 (s, 3H), 2.22 (d, J = 7.6Hz, 2H), 2.15 (s, 3H), 2.12-1.92 (m, 4H), 1.84-1.65 (m, 11H), 1.63-1.56 (m, 2H), 1.52-1.51 (m, 4H), 1.43-1.34 (m, 2H), 1.23 (s, 1H), 1.17-1.06 (m, 2H) |
| I-176 | HE | CW | 900.6 | 11.08 (s, 1H), 9.67 (s, 1H), 8.76 (s, 1H), 8.18 (s, 1H), 7.72-7.69 (m, 1H), 7.67-7.66 (m, 1H), 7.66-7.58 (m, 2H), 7.08 (s, 1H), 6.98 (s, 1H), 6.92-6.87 (m, 1H), 5.86-5.60 (m, 1H), 5.45-5.26 (m, 1H), 3.47 (d, J = 5.2Hz, 2H), 3.25 (s, 3H), 2.99-2.84 (m, 5H), 2.73-2.60 (m, 4H), 2.32 (s, 3H), 2.15-2.04 (m, 4H), 1.91-1.83 (m, 2H), 1.75-1.63 (m, 10H), 1.44 (s, 2H), 1.29-1.03 (m, 6H) |
| I-177 | HG | CW | 896.1 | 10.56-10.49 (m, 1H), 9.67 (s, 1H), 9.24 (s, 1H), 8.75 (s, 1H), 8.48 (s, 1H), 8.17 (s, 1H), 8.03 (s, 1H), 7.90 (d, J = 8.0 Hz, 1H), 7.77-7.73 (m, 1H), 7.70 (d, J = 6.8Hz, 1H), 7.65-7.59 (m, 2H), 5.81-5.67 (m, 1H), 3.99-3.86 (m, 1H), 3.78-3.68 (m, 1H), 3.38 (d, J = 6.4Hz, 2H), 3.11-3.03 (m, 1H), 2.99-2.86 (m, 5H), 2.79-2.68 (m, 2H), 2.33 (s, 3H), 2.14-2.05 (m, 4H), 2.01-1.89 (m, 4H), 1.84-1.65 (m, 11H), 1.49-1.40 (m, 3H), 1.11-1.01 (m, 2H), 0.88-0.78 (m, 2H) |
| I-178 | HI | CW | 885.5 | 10.63 (s, 1H), 9.67 (s, 1H), 8.75 (s, 1H), 8.28 (s, 1H), 8.23-8.14 (m, 2H), 7.75-7.67 (m, 2H), 7.65-7.57 (m, 2H), 7.48 (s, 1H), 7.34 (s, 1H), 6.91 (d, J = 7.2Hz, 1H), 5.74 (t, J = 8.8Hz, 1H), 3.78 (t, J = 6.4Hz, 2H), 3.41-3.39 (m, 2H), 3.13-3.00 (m, 2H), 2.92-2.85 (m, 4H), 2.84-2.76 (m, 2H), 2.33 (s, 3H), 2.14-2.08 (m, 2H), 2.05 (d, J = 7.6Hz, 2H), 1.96-1.87 (m, 4H), 1.80-1.73 (m, 4H), 1.71-1.60 (m, 5H), 1.50-1.39 (m, 3H), 1.23 (s, 1H), 1.11-1.00 (m, 2H), 0.86-0.76 (m, 2H) |
| I-179 | HK | CW | 912.2 | 11.08 (s, 1H), 9.73 (s, 1H), 8.77 (s, 1H), 8.18 (s, 1H), 7.86 (d, J = 8.4Hz, 1H), 7.70 (d, J = 1.6Hz, 1H), 7.66-7.61 (m, 1H), 7.07 (d, J = 1.2Hz, 1H), 6.99 (d, J = 8.0 Hz, 1H), 6.90-6.86 (m, 1H), 5.76 (t, J = 8.4Hz, 1H), 5.36-5.30 (m, 1H), 3.71 (s, 2H), 3.69 (d, J = 7.2Hz, 1H), 3.66 (s, 2H), 3.33-3.32 (m, 3H), 3.24-3.19 (m, 2H), 2.95-2.85 (m, 3H), 2.75-2.67 (m, 1H), 2.67-2.57 (m, 2H), 2.39 (s, 3H), 2.29 (t, J = 6.4Hz, 2H), 2.20-2.15 (m, 2H), 2.14-2.06 (m, 2H), 2.02-1.91 (m, 3H), 1.86-1.80 (m, 2H), 1.77-1.69 (m, 6H), 1.68-1.62 (m, 2H), 1.61-1.56 (m, 2H), 1.52-1.45 (m, 2H) |
| I-180 | HM | CW | 915.4 | 11.05 (s, 1H), 9.67 (s, 1H), 8.75 (s, 1H), 8.17 (s, 1H), 7.74-7.59 (m, 4H), 6.91 (d, J = 9.2Hz, 1H), 6.79 (s, 1H), 6.60 (d, J = 8.0 Hz, 1H), 5.74 (t, J = 8.8Hz, 1H), 5.31-5.24 (m, 1H), 3.54 (d, J = 11.6Hz, 2H), 3.38 (t, J = 5.6Hz, 2H), 3.30 (s, 3H), 3.23-3.16 (m, 1H), 2.90 (d, J = 5.6Hz, 3H), 2.68 (d, J = 3.2 Hz, 1H), 2.65 (s, 4H), 2.57 (s, 2H), 2.33 (s, 3H), 2.12 (d, J = 5.6Hz, 4H), 2.01-1.96 (m, 2H), 1.79-1.67 (m, 8H), 1.55 (s, 1H), 1.46 (d, J = 2.4Hz, 2H), 1.41-1.31 (m, 2H), 1.26-1.17 (m, 2H) |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | 1H NMR (400 MHz, DMSO-d6) δ |
|---|---|---|---|---|
| I-181 | EH | HO | 901.4 | 11.08 (s, 1H), 9.86 (s, 1H), 8.90 (s, 1H), 8.16 (s, 1H), 7.74 (d, J = 8.4Hz, 1H), 7.67-7.64 (m, 1H), 7.61-7.55 (m, 1H), 7.05-6.89 (m, 2H), 6.88-6.84 (m, 2H), 5.72-5.62 (m, 1H), 5.36-5.30 (m, 1H), 3.71-3.64 (m, 2H), 3.61 (s, 3H), 3.11 (d, J = 10.8Hz, 2H), 2.91-2.82 (m, 1H), 2.71-2.62 (m, 4H), 2.35 (s, 3H), 2.26-2.19 (m, 4H), 2.16 (s, 3H), 2.14-2.07 (m, 2H), 2.01-1.96 (m, 1H), 1.83-1.70 (m, 6H), 1.69-1.53 (m, 6H), 1.46-1.40 (m, 2H), 1.19-1.08 (m, 2H) |
| I-182 | HQ | CW | 886.5 | 11.07 (s, 1H), 9.66 (s, 1H), 8.75 (s, 1H), 8.17 (s, 1H), 7.75-7.69 (m, 2H), 7.65-7.61 (m, 2H), 7.07 (s, 1H), 6.98 (d, J = 8.4 Hz, 1H), 6.90-6.85 (m, 1H), 5.79-5.70 (m, 1H), 5.33 (dd, J = 5.2, 12.4Hz, 1H), 3.77-3.67 (m, 1H), 3.29 (s, 3H), 3.26 (t, J = 6.0 Hz, 2H), 2.89 (d, J = 5.6Hz, 2H), 2.75-2.69 (m, 1H), 2.65-2.58 (m, 2H), 2.45-2.40 (m, 2H), 2.33 (s, 3H), 2.33-2.31 (m, 2H), 2.29-2.23 (m, 2H), 2.16-2.06 (m, 3H), 2.03-1.85 (m, 6H), 1.71-1.66 (m, 6H), 1.49-1.39 (m, 4H) |
| I-183 | HS | CW | 885.7 | 11.08 (s, 1H), 9.71 (s, 1H), 8.76 (s, 1H), 8.18 (s, 1H), 7.76 (d, J = 8.4Hz, 1H), 7.62 (d, J = 1.6Hz, 1H), 7.56 (dd, J = 2.0, 8.0 Hz, 1H), 6.99-6.84 (m, 3H), 5.78-5.66 (m, 1H), 5.38-5.30 (m, 1H), 3.67 (d, J = 12.0 Hz, 2H), 3.59 (s, 3H), 3.29 (s, 1H), 2.90-2.83 (m, 2H), 2.80-2.72 (m, 6H), 2.57 (s, 3H), 2.37-2.31 (m, 5H), 2.19 (d, J = 11.2Hz, 3H), 2.13-2.09 (m, 2H), 2.04-1.99 (m, 2H), 1.74-1.67 (m, 8H), 1.45 (d, J = 8.0 Hz, 2H), 1.13-1.04 (m, 2H) |
| I-184 | HU | CW | 899.1 | 11.06 (s, 1H), 9.71 (s, 1H), 8.76 (s, 1H), 8.17 (s, 1H), 7.88-7.83 (m, 1H), 7.70-7.67 (m, 1H), 7.62 (d, J = 8.4Hz, 1H), 7.05 (s, 1H), 6.97 (d, J = 8.4Hz, 1H), 6.87 (d, J = 7.6Hz, 1H), 5.82-5.70 (m, 1H), 5.35-5.27 (m, 1H), 3.74-3.63 (m, 5H), 3.28 (s, 3H), 2.96-2.83 (m, 3H), 2.65 (s, 2H), 2.37 (s, 3H), 2.31 (s, 2H), 2.22-2.08 (m, 5H), 2.05-1.96 (m, 3H), 1.89-1.80 (m, 3H), 1.78-1.61 (m, 9H), 1.51-1.44 (m, 2H) |
| I-185 | HV | CW | 733.5 | 10.24 (s, 1H), 9.67 (s, 1H), 8.75 (s, 1H), 8.17 (s, 1H), 7.74-7.67 (m, 2H), 7.65-7.60 (m, 1H), 7.52 (t, J = 5.6Hz, 1H), 7.10 (d, J = 9.2Hz, 2H), 6.88 (d, J = 9.2Hz, 2H), 5.79-5.67 (m, 1H), 3.70-3.58 (m, 4H), 2.81 (m, J = 6.4Hz, 2H), 2.67 (t, J = 6.8Hz, 2H), 2.61-2.53 (m, 2H), 2.33 (s, 3H), 2.17-2.05 (m, 2H), 1.75-1.58 (m, 6H), 1.50-1.40 (m, 3H), 1.40-1.34 (m, 2H), 1.21-1.08 (m, 2H) |
| I-186 | DQ | HC | 894.2 | 11.15-10.97 (m, 1H), 8.83 (s, 1H), 7.94 (s, 1H), 7.88 (d, J = 8.6Hz, 1H), 7.62 (s, 1H), 7.59-7.55 (m, 1H), 7.50 (s, 1H), 7.08 (d, J = 0.8Hz, 1H), 7.02-6.97 (m, 1H), 6.93-6.87 (m, 1H), 5.37--5.29 (m, 1H), 4.75-4.67 (m, 1H), 3.39-3.35 (m, 4H), 3.33 (s, 3H), 3.29 (s, 4H), 2.88-2.85 (m, 4H), 2.33 (s, 3H), 2.12-2.06 (m, 2H), 2.04 (d, J = 7.6Hz, 2H), 2.00 (d, J = 6.8Hz, 1H), 1.92-1.85 (m, 4H), 1.78-1.72 (m, 5H), 1.71-1.65 (m, 6H), 1.53-1.49 (m, 3H), 1.23 (s, 2H), 1.07-0.98 (m, 2H), 0.84-0.76 (m, 2H) |
| I-187 | DQ | HO | 930.5 | 11.08 (s, 1H), 9.80 (s, 1H), 8.90 (s, 1H), 8.16 (s, 1H), 7.72-7.67 (m, 2H), 7.67-7.60 (m, 2H), 7.07-6.76 (m, 4H), 5.72-5.60 (m, 1H), 5.39-5.30 (m, 1H), 3.42 (t, J = 6.0 Hz, 2H), 3.33 (s, 3H), 3.27-3.17 (m, 2H), 3.17-3.06 (m, 2H), 2.93-2.85 (m, 3H), 2.73-2.65 (m, 3H), 2.33 (s, 3H), 2.19-2.05 (m, 3H), 2.04-1.90 (m, 4H), 1.87-1.75 (m, 6H), 1.73-1.52 (m, 6H), 1.48-1.40 (m, 2H), 1.15-1.04 (m, 2H), 0.97-0.84 (m, 2H) |
| I-188 | DQ | HX | 940.2 | 11.07 (s, 1H), 9.62 (s, 1H), 8.74 (s, 1H), 8.16 (s, 1H), 7.79-7.66 (m, 2H), 7.62 (d, J = 8.4Hz, 2H), 7.08 (s, 1H), 6.99 (d, J = 8.0 Hz, 1H), 6.89 (d, J = 8.4Hz, 1H), 5.79-5.58 (m, 1H), 5.33 (dd, J = 5.2, 12.4Hz, 1H), 3.40 (s, 2H), 3.33 (s, 3H), 3.10-3.06 (m, 2H), 2.89 (s, 4H), 2.71 (d, J = 2.8Hz, 2H), 2.32 (s, 3H), 2.09 (s, 4H), 2.01-1.89 (m, 8H), 1.80-1.77 (m, 1H), 1.73-1.65 (m, 5H), 1.47-1.37 (m, 2H), 1.32-1.26 (m, 1H), 1.11-1.03 (m, 2H), 0.87-0.78 (m, 2H), 0.56-0.27 (m, 4H) |
| I-189 | HZ | CW | 872.1 | 11.08 (br s, 1H), 9.72 (s, 1H), 8.76 (s, 1H), 8.18 (s, 1H), 7.77 (br d, J = 8.1Hz, 1H), 7.64 (s, 1H), 7.57 (br d, J = 8.1Hz, 1H), 7.00-6.92 (m, 1H), 6.89-6.84 (m, 2H), 5.78-5.66 (m, 1H), 5.36-5.31 (m, 1H), 3.68 (br d, J = 10.0 Hz, 2H), 3.60 (s, 3H), 3.02 (br s, 2H), 2.95-2.82 (m, 2H), 2.75-2.65 (m, 4H), 2.35 (s, 3H), 2.28-2.21 (m, 2H), 2.14-2.07 (m, 2H), 2.02-1.96 (m, 2H), 1.80-1.66 (m, 8H), 1.61-1.35 (m, 6H), 1.29-1.21 (m, 2H) |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-d$_6$) δ |
|---|---|---|---|---|
| I-190 | EH | HX | 911.5 | 11.07 (s, 1H), 9.70 (s, 1H), 8.73 (s, 1H), 8.16 (s, 1H), 7.81-7.72 (m, 1H), 7.63 (s, 1H), 7.55 (d, J = 8.0 Hz, 1H), 6.99-6.90 (m, 1H), 6.85 (d, J = 8.0 Hz, 2H), 5.75-5.52 (m, 1H), 5.33 (dd, J = 5.2, 12.4Hz, 1H), 3.67 (d, J = 11.1Hz, 2H), 3.60 (s, 3H), 3.10 (d, J = 10.8Hz, 2H), 2.93-2.84 (m, 1H), 2.75-2.54 (m, 8H), 2.45-2.41 (m, 1H), 2.33 (s, 3H), 2.26 (d, J = 6.4Hz, 2H), 2.20-2.14 (m, 4H), 2.00-1.93 (m, 2H), 1.81-1.69 (m, 4H), 1.60 (d, J = 10.4Hz, 3H), 1.46-1.34 (m, 1H), 1.31-1.21 (m, 1H), 1.18-1.06 (m, 2H), 0.56-0.25 (m, 3H), 0.04 (d, J = 2.0 Hz, 1H) |
| I-191 | IB | CW | 929.8 | 11.08 (s, 1H), 9.69 (s, 1H), 8.76 (s, 1H), 8.18 (s, 1H), 7.79-7.75 (m, 1H), 7.68 (d, J = 1.6Hz, 1H), 7.62-7.59 (m, 1H), 7.08 (s, 1H), 7.02-6.98 (m, 1H), 6.90 (d, J = 8.0 Hz, 1H), 5.80-5.67 (m, 1H), 5.35-5.30 (m, 1H), 3.55-3.52 (m, 2H), 3.33 (s, 3H), 3.15-3.12 (m, 2H), 2.96-2.84 (m, 3H), 2.76 (s, 3H), 2.65-2.61 (m, 1H), 2.59-2.58 (m, 1H), 2.54 (s, 2H), 2.35 (s, 3H), 2.15-2.05 (m, 4H), 2.03-1.90 (m, 5H), 1.80-1.66 (m, 10H), 1.51-1.40 (m, 3H), 1.11-1.00 (m, 2H), 0.91-0.76 (m, 2H) |
| I-192 | ID | CW | 764.4 | 10.89-10.63 (m, 1H), 9.65 (s, 1H), 8.75 (s, 1H), 8.17 (s, 1H), 8.02 (t, J = 5.2Hz, 1H), 7.73-7.67 (m, 2H), 7.63-7.59 (m, 1H), 7.56-7.43 (m, 1H), 7.13 (d, J = 8.8Hz, 2H), 6.90 (d, J = 8.4Hz, 2H), 5.80-5.63 (m, 1H), 4.42 (s, 2H), 3.81-3.74 (m, 1H), 3.28 (s, 6H), 3.10-3.05 (m, 2H), 2.32 (s, 3H), 2.19-2.06 (m, 4H), 1.72-1.64 (m, 4H), 1.41-1.36 (m, 4H), 1.25-1.19 (m, 2H) |
| I-193 | IG | CW | 766.1 | 10.78 (s, 1H), 9.65 (s, 1H), 8.74 (s, 1H), 8.17 (s, 1H), 8.04 (t, J = 5.6Hz, 1H), 7.73-7.67 (m, 2H), 7.67-7.45 (m, 2H), 7.13 (d, J = 8.8Hz, 2H), 6.90 (d, J = 8.4Hz, 2H), 5.73 (t, J = 8.4 Hz, 1H), 4.45 (s, 2H), 3.77 (m, J = 4.8, 11.6Hz, 1H), 3.39 (m, J = 5.6Hz, 4H), 3.27 (d, J = 5.6Hz, 3H), 2.94-2.87 (m, 2H), 2.62 (m, J = 5.2, 11.6Hz, 1H), 2.32 (s, 3H), 2.18-2.07 (m, 3H), 1.97 (s, 1H), 1.68 (s, 4H), 1.51-1.41 (m, 2H) |
| I-194 | IK | CW | 915.1 | 11.05 (s, 1H), 9.67 (s, 1H), 8.75 (s, 1H), 8.17 (s, 1H), 7.75-7.70 (m, 1H), 7.67 (s, 1H), 7.64-7.58 (m, 1H), 7.55 (t, J = 5.2 Hz, 1H), 6.91 (d, J = 8.4Hz, 1H), 6.81 (d, J = 2.0 Hz, 1H), 6.65-6.53 (m, 1H), 5.80-5.66 (m, 1H), 5.35-5.21 (m, 1H), 3.55-3.47 (m, 1H), 3.41-3.36 (m, 2H), 3.29 (s, 3H), 2.93-2.84 (m, 1H), 2.83-2.74 (m, 4H), 2.64-2.55 (m, 5H), 2.33 (s, 3H), 2.23-2.17 (m, 2H), 2.15-2.07 (m, 2H), 2.01-1.90 (m, 3H), 1.89-1.82 (m, 2H), 1.77-1.66 (m, 6H), 1.56-1.44 (m, 6H), 1.39-1.30 (m, 2H) |
| I-195 | IM | CW | 851.1 | 10.24 (s, 1H), 9.66 (s, 1H), 8.74 (s, 1H), 8.17 (s, 1H), 7.71-7.68 (m, 2H), 7.65-7.61 (m, 2H), 7.11 (d, J = 8.8Hz, 2H), 6.90 (d, J = 8.8Hz, 2H), 5.77-5.70 (m, 1H), 3.70-3.66 (m, 3H), 3.63 (s, 1H), 3.49-3.47 (m, 4H), 3.46-3.45 (m, 2H), 3.41 (t, J = 6.0 Hz, 2H), 3.29 (s, 1H), 3.26 (d, J = 6.4Hz, 2H), 2.91 (q, J = 5.6Hz, 2H), 2.67 (t, J = 6.8Hz, 4H), 2.60 (d, J = 11.6Hz, 3H), 2.32 (s, 3H), 2.10-2.08 (m, 2H), 1.73-1.65 (m, 7H), 1.45 (s, 2H), 1.29-1.22 (m, 2H) |
| I-196 | IO | CW | 736.2 | 10.78 (s, 1H) 9.66 (s, 1H) 8.75 (s, 1H) 8.17 (s, 1H) 8.07 (d, J = 5.6Hz, 1H) 7.72-7.69 (m, 1H) 7.63-7.59 (m, 1H) 7.55 (d, J = 5.2Hz, 1H) 7.13 (d, J = 8.8Hz, 2H) 6.89 (d, J = 8.8 Hz, 2H) 5.73 (d, J = 8Hz, 1H) 4.43 (s, 2H) 3.77 (d, J = 4.8 Hz, 1H) 3.14 (d, J = 6.8Hz, 2H) 2.75 (d, J = 6.8Hz, 2H) 2.67 (d, J = 2Hz, 1H) 2.62 (d, J = 5.2Hz, 1H) 2.32 (s, 3H) 2.17-2.07 (m, 4H) 1.99 (d, J = 4.4Hz, 1H) 1.68 (s, 4H) 1.61-1.56 (m, 2H) 1.45 (s, 2H) |
| I-197 | IQ | CW | 792.0 | 10.79 (s, 1H), 9.66 (s, 1H), 8.75 (s, 1H), 8.17 (s, 1H), 8.02 (t, J = 5.6Hz, 1H), 7.73-7.64 (m, 2H), 7.61 (d, J = 9.2Hz, 1H), 7.49 (t, J = 5.6Hz, 1H), 7.13 (d, J = 8.4Hz, 2H), 6.90 (d, J = 8.0 Hz, 2H), 5.77-5.66 (m, 1H), 4.43 (s, 2H), 3.78 (dd, J = 4.8, 11.2Hz, 1H), 3.12-3.05 (m, 2H), 2.76-2.69 (m, 2H), 2.68-2.60 (m, 2H), 2.32 (s, 3H), 2.18-2.07 (m, 3H), 2.04-1.95 (m, 1H), 1.68 (s, 4H), 1.45-1.34 (m, 6H), 1.19 (s, 6H) |
| I-198 | II | CW | 809.8 | 10.79 (s, 1H), 9.66 (s, 1H), 8.74 (s, 1H), 8.17 (s, 1H), 8.05 (t, J = 6.0 Hz, 1H), 7.73-7.67 (m, 2H), 7.66-7.59 (m, 2H), 7.13 (d, J = 8.8Hz, 2H), 6.90 (d, J = 8.8Hz, 2H), 5.80-5.66 (m, 1H), 4.45 (s, 2H), 3.80-3.77 (m, 1H), 3.48-3.44 (m, 4H), 3.43-3.38 (m, 4H), 3.29-3.25 (m, 2H), 2.92-2.87 (m, 2H), 2.69-2.65 (m, 1H), 2.52 (s, 1H), 2.46-2.45 (m, 1H), 2.32 (s, |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-$d_6$) δ |
|---|---|---|---|---|
| | | | | 3H), 2.16-2.06 (m, 3H), 2.03-1.95 (m, 1H), 1.69-1.68 (m, 4H), 1.48-1.40 (m, 2H) |
| I-199 | IT | CW | 872.6 | 11.05 (s, 1H), 9.93-9.37 (m, 1H), 8.69 (s, 1H), 8.11 (s, 1H), 7.82 (d, J = 8.4Hz, 1H), 7.64 (s, 1H), 7.57 (d, J = 8.4Hz, 1H), 6.95-6.79 (m, 2H), 6.71 (d, J = 7.6Hz, 1H), 5.80-5.64 (m, 1H), 5.33 (dd, J = 4.8, 12.8Hz, 1H), 3.53 (s, 3H), 3.39 (s, 1H), 3.20 (d, J = 4.4Hz, 2H), 3.02-2.84 (m, 7H), 2.77-2.57 (m, 3H), 2.36 (s, 3H), 2.33 (s, 1H), 2.12 (d, J = 4.0 Hz, 2H), 2.01-1.96 (m, 1H), 1.88-1.78 (m, 2H), 1.73 (s, 4H), 1.61 (d, J = 6.0 Hz, 4H), 1.47 (s, 3H), 1.24 (s, 2H) |
| I-200 | IV | CW | 763.4 | 10.24 (s, 1H) 9.66 (s, 1H) 8.74 (s, 1H) 8.16 (s, 1H) 7.74-7.69 (m, 2H) 7.63 (d, J = 6.8Hz, 2H) 7.11 (d, J = 8.0 Hz, 2H) 6.88 (d, J = 8.0 Hz, 2H) 5.73 (d, J = 8.4Hz, 1H) 3.70-3.62 (m, 4H) 3.37 (d, J = 5.6Hz, 2H) 3.21 (d, J = 5.6Hz, 2H) 2.93 (d, J = 5.6Hz, 2H) 2.67 (d, J = 6.0 Hz, 2H) 2.64-2.59 (m, 2H) 2.33 (s, 3H) 2.18-2.04 (m, 3H) 1.70 (d, J = 6.0 Hz, 6H) 1.46 (s, 2H) 1.22 (d, J = 12.0 Hz, 2H) |
| I-201 | IX | CW | 807.3 | 10.25 (s, 1H), 9.66 (s, 1H), 8.74 (s, 1H), 8.16 (s, 1H), 7.75-7.68 (m, 2H), 7.63 (d, J = 10.0 Hz, 1H), 7.11 (d, J = 8.8Hz, 2H), 6.89 (d, J = 8.8Hz, 2H), 5.73 (t, J = 8.4Hz, 1H), 3.71-3.62 (m, 4H), 3.45-3.44 (m, 2H), 3.42 (t, J = 6.0 Hz, 2H), 3.25 (d, J = 6.0 Hz, 2H), 2.90 (t, J = 6.0 Hz, 2H), 2.67 (t, J = 6.8Hz, 3H), 2.64-2.57 (m, 3H), 2.33 (s, 3H), 2.10 (s, 2H), 1.76-1.61 (m, 8H), 1.45 (s, 2H), 1.28-1.21 (m, 2H) |
| I-202 | DQ | IY | 883.6 | 12.75 (s, 1H), 11.07 (s, 1H), 8.53 (s, 1H), 8.08-7.94 (m, 2H), 7.66-7.55 (m, 2H), 7.52-7.43 (m, 1H), 7.08 (s, 1H), 6.99 (d, J = 8.0 Hz, 1H), 6.89 (d, J = 8.4Hz, 1H), 5.32 (dd, J = 5.2, 12.8Hz, 1H), 5.27-5.17 (m, 1H), 3.35 (d, J = 6.0 Hz, 2H), 3.32 (s, 3H), 3.06-2.96 (m, 1H), 2.92-2.80 (m, 5H), 2.75-2.61 (m, 3H), 2.35 (s, 3H), 2.07-1.96 (m, 5H), 1.92-1.83 (m, 4H), 1.81-1.73 (m, 3H), 1.71-1.65 (m, 4H), 1.61-1.47 (m, 4H), 1.42-1.26 (m, 4H), 1.10-0.94 (m, 2H), 0.85-0.67 (m, 2H) |
| I-203 | EH | IZ | 864.2 | 11.08 (s, 1H), 9.68 (s, 1H), 8.73 (s, 1H), 8.28-8.19 (m, 2H), 7.94-7.88 (m, 2H), 7.66-7.58 (m, 2H), 6.99-6.92 (m, 1H), 6.88-6.84 (m, 2H), 5.38-5.30 (m, 1H), 3.93 (s, 3H), 3.70-3.63 (m, 2H), 3.61 (s, 3H), 3.11 (d, J = 11.2Hz, 2H), 2.94-2.85 (m, 1H), 2.69-2.65 (m, 3H), 2.63 (s, 1H), 2.38 (s, 3H), 2.34-2.32 (m, 1H), 2.29-2.25 (m, 1H), 2.22 (d, J = 7.2Hz, 2H), 2.16 (s, 3H), 2.04-1.94 (m, 1H), 1.83-1.68 (m, 4H), 1.66-1.53 (m, 2H), 1.50-1.38 (m, 1H), 1.18-1.06 (m, 2H) |
| I-204 | EH | IY | 854.4 | 12.77 (d, J = 2.0 Hz, 1H), 11.07 (s, 1H), 8.60 (s, 1H), 8.08 (d, J = 7.2Hz, 1H), 7.99 (s, 1H), 7.57-7.46 (m, 2H), 6.99-6.89 (m, 1H), 6.85 (d, J = 8.0 Hz, 2H), 5.33 (dd, J = 5.2, 12.4Hz, 1H), 5.25-5.16 (m, 1H), 3.66-3.60 (m, 4H), 3.10 (d, J = 10.4 Hz, 2H), 2.95-2.81 (m, 1H), 2.73-2.62 (m, 4H), 2.37 (s, 4H), 2.34-2.29 (m, 1H), 2.22 (d, J = 7.6Hz, 3H), 2.15 (s, 3H), 2.06-1.95 (m, 3H), 1.81-1.69 (m, 6H), 1.63-1.48 (m, 5H), 1.44-1.22 (m, 5H), 1.19-1.06 (m, 2H) |
| I-205 | DQ | JA | 895.6 | 11.07 (s, 1H), 9.64 (s, 1H), 8.62 (s, 1H), 7.76 (d, J = 8.4Hz, 1H), 7.66 (s, 1H), 7.64-7.53 (m, 2H), 7.09 (s, 1H), 6.99 (d, J = 8.4Hz, 1H), 6.90 (d, J = 8.8Hz, 1H), 5.36-5.27 (m, 1H), 3.10-3.01 (m, 1H), 2.94-2.87 (m, 4H), 2.85 (s, 3H), 2.80-2.73 (m, 1H), 2.62-2.59 (m, 1H), 2.34-2.32 (m, 5H), 2.16 (d, J = 2.4Hz, 1H), 2.04-2.01 (m, 2H), 2.02-1.93 (m, 2H), 1.92-1.85 (m, 4H), 1.77-1.75 (m, 3H), 1.75-1.66 (m, 8H), 1.58-1.56 (m, 3H), 1.37-1.35 (m, 2H), 1.34-1.27 (m, 2H), 1.23 (s, 2H), 1.20-1.18 (m, 1H), 1.10-0.97 (m, 2H), 0.87-0.77 (m, 2H) |
| I-206 | EH | JA | 866.6 | 11.07 (s, 1H), 9.68 (s, 1H), 8.64 (s, 1H), 7.88-7.78 (m, 1H), 7.64-7.52 (m, 2H), 7.00-6.92 (m, 1H), 6.89-6.82 (m, 2H), 5.34-5.32 (m, 1H), 3.66-3.64 (m, 2H), 3.60 (s, 3H), 3.11-3.29 (m, 2H), 2.78 (s, 2H), 2.59-2.57 (m, 1H), 2.46-2.44 (m, 1H), 2.35 (s, 4H), 2.34-2.31 (m, 1H), 2.15 (s, 3H), 2.06-1.90 (m, 2H), 1.85-1.65 (m, 11H), 1.64-1.53 (m, 4H), 1.32-1.30 (m, 4H), 1.24-1.05 (m, 4H) |
| I-207 | JC | DG | 846.5 | 11.06 (s, 1H), 9.74 (s, 1H), 8.75 (s, 1H), 8.16 (s, 1H), 7.81-7.71 (m, 1H), 7.65 (s, 1H), 7.59 (d, J = 8.4Hz, 1H), 6.97-6.90 (m, 2H), 6.84 (d, J = 7.2Hz, 1H), 5.63-5.50 (m, 1H), 5.33 (dd, J = 5.2, 12.8Hz, 1H), 3.59 (s, 3H), 3.05 (d, J = 10.4Hz, 2H), 2.88 (s, 6H), 2.73-2.59 (m, 5H), 2.45 (s, 4H), 2.35 (s, 3H), 2.02-1.94 (m, 1H), 1.77-1.69 (m, 2H), 1.37 (s, 11H) |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | $^1$H NMR (400 MHz, DMSO-$d_6$) δ |
|---|---|---|---|---|
| I-208 | JJ | CW | 747.0 | 8.75 (s, 1H) 8.17 (s, 1H) 7.74-7.67 (m, 2H) 7.62 (d, J = 8.0 Hz, 1H) 7.42-7.34 (m, 1H) 7.10 (d, J = 8.8Hz, 2H) 6.87 (d, J = 9.2Hz, 2H) 5.79-5.67 (m, 1H) 3.68 (t, J = 6.8Hz, 2H) 3.61 (d, J = 12.4Hz, 2H) 2.75 (t, J = 7.2Hz, 2H) 2.61-2.56 (m, 2H) 2.33 (s, 3H) 2.13-2.08 (m, 2H) 1.72-1.60 (m, 7H) 1.43 (d, J = 6.8Hz, 5H) 1.23 (s, 1H) 1.21-1.13 (m, 4H) |
| I-209 | EH | DZ | 838.2 | 11.07 (s, 1H), 9.05-8.98 (m, 1H), 8.41-8.34 (m, 1H), 7.81-7.74 (m, 1H), 7.60 (s, 1H), 7.54 (d, J = 8.4Hz, 1H), 7.45 (s, 1H), 7.09 (d, J = 5.2Hz, 1H), 6.98-6.92 (m, 1H), 6.90-6.83 (m, 2H), 5.53-5.44 (m, 1H), 5.37-5.30 (m, 1H), 3.68-3.63 (m, 2H), 3.61 (s, 3H), 3.17-3.06 (m, 4H), 2.92-2.84 (m, 1H), 2.63 (s, 2H), 2.43 (s, 3H), 2.34 (s, 3H), 2.32-2.32 (m, 2H), 2.29 (s, 2H), 2.23 (d, J = 4.4Hz, 2H), 2.04-1.94 (m, 2H), 1.80-1.70 (m, 4H), 1.65-1.57 (m, 2H), 1.48-1.34 (m, 2H), 1.26 (d, J = 7.2Hz, 6H), 1.13 (d, J = 11.2Hz, 2H) |
| I-210 | DQ | IZ | 893.2 | 11.07 (s, 1H), 9.66 (s, 1H), 8.71 (s, 1H), 8.21 (s, 1H), 7.91 (s, 1H), 7.84-7.77 (m, 1H), 7.71-7.62 (m, 2H), 7.57 (t, J = 6.0 Hz, 1H), 7.08 (s, 1H), 7.00 (d, J = 8.0 Hz, 1H), 6.90 (d, J = 8.8 Hz, 1H), 5.37-5.30 (m, 1H), 3.93 (s, 3H), 3.66-3.52 (m, 1H), 3.08-2.98 (m, 2H), 2.97-2.84 (m, 5H), 2.71 (d, J = 3.6Hz, 1H), 2.64 (s, 2H), 2.34 (s, 3H), 1.99 (m, 2H), 1.88 (d, J = 10.4 Hz, 2H), 1.78-1.67 (m, 6H), 1.47-1.41 (m, 1H), 1.31-1.18 (m, 6H), 1.08-0.99 (m, 2H), 0.87-0.81 (m, 2H) |
| I-211 | JL | DG | 859.1 | 11.08 (s, 1H), 9.70 (s, 1H), 8.74 (s, 1H), 8.16 (s, 1H), 7.86-7.76 (m, 1H), 7.68-7.62 (m, 1H), 7.61-7.55 (m, 1H), 6.99-6.91 (m, 1H), 6.85 (t, J = 6.8Hz, 2H), 5.67-5.55 (m, 1H), 5.38-5.29 (m, 1H), 3.68 (d, J = 11.2Hz, 2H), 3.59 (s, 3H), 3.11-2.99 (m, 2H), 2.94-2.83 (m, 1H), 2.65 (d, J = 14.4Hz, 4H), 2.36 (s, 3H), 2.33-2.27 (m, 4H), 2.24-2.18 (m, 2H), 2.14 (s, 3H), 2.02-1.95 (m, 1H), 1.76-1.66 (m, 4H), 1.52-1.46 (m, 2H), 1.41 (d, J = 6.4Hz, 6H), 1.29-1.16 (m, 2H) |
| I-212 | JN | DG | 857.0 | 11.07 (s, 1H), 9.69 (s, 1H), 8.74 (s, 1H), 8.15 (s, 1H), 7.79 (d, J = 8.0 Hz, 1H), 7.64 (d, J = 1.6Hz, 1H), 7.59-7.56 (m, 1H), 6.97-6.92 (m, 1H), 6.87-6.81 (m, 2H), 5.60 (d, J = 3.2Hz, 1H), 5.35-5.30 (m, 1H), 3.59 (s, 3H), 2.99-2.83 (m, 8H), 2.74-2.66 (m, 2H), 2.62-2.58 (m, 4H), 2.35 (s, 3H), 2.07 (s, 1H), 2.01-1.96 (m, 1H), 1.78 (s, 4H), 1.72-1.66 (m, 2H), 1.40 (d, J = 6.0 Hz, 6H), 1.31-1.18 (m, 3H) |
| I-213 | JQ | DG | 885.1 | 11.06 (s, 1H) 9.68 (s, 1H) 8.75 (s, 1H) 8.17 (s, 1H) 7.80 (d, J = 8.0 Hz, 1H) 7.64 (s, 1H) 7.58 (d, J = 8.4Hz, 1H) 6.98-6.90 (m, 2H) 6.85 (d, J = 6.0 Hz, 1H) 5.72-5.47 (m, 1H) 5.33 (m, 1H) 3.70-3.66 (m, 2H) 3.61 (s, 3H) 2.84 (s, 4H) 2.68-2.61 (m, 4H) 2.42 (s, 4H) 2.35 (s, 3H) 2.28-2.15 (m, 4H) 1.99 (m, 1H) 1.79 (d, J = 11.6Hz, 2H) 1.66-1.56 (m, 4H) 1.52-1.46 (m, 4H) 1.40 (d, J = 6.8Hz, 6H) |
| I-214 | EH | DO | 875.3 | 11.08 (s, 1H), 9.84 (s, 1H), 8.89 (s, 1H), 8.17 (d, J = 14.4Hz, 2H), 7.82-7.72 (m, 1H), 7.71-7.51 (m, 2H), 6.99-6.92 (m, 1H), 6.91-6.82 (m, 2H), 5.64-5.47 (m, 1H), 5.35-5.31 (m, 1H), 3.68-3.64 (m, 2H), 3.61 (s, 3H), 2.91-2.82 (m, 2H), 2.70-2.61 (m, 8H), 2.35 (s, 3H), 2.27-2.18 (m, 4H), 2.16 (s, 3H), 1.82-1.69 (m, 4H), 1.66-1.55 (m, 2H), 1.38 (d, J = 5.2 Hz, 6H), 1.19-1.08 (m, 2H) |
| I-215 | JS | DG | 900.5 | 11.05 (s, 1H), 9.65 (s, 1H), 8.74 (s, 1H), 8.16 (s, 1H), 7.90 (d, J = 6.8Hz, 1H), 7.72 (d, J = 8.4Hz, 1H), 7.66 (s, 1H), 7.60 (d, J = 8.8Hz, 1H), 6.91 (d, J = 8.4Hz, 1H), 6.80 (s, 1H), 6.61 (d, J = 8.8Hz, 1H), 5.66-5.50 (m, 1H), 5.27 (dd, J = 5.6, 13.2 Hz, 1H), 3.67-3.46 (m, 3H), 3.29 (s, 3H), 2.95-2.81 (m, 1H), 2.74-2.55 (m, 6H), 2.33 (s, 6H), 2.27-2.06 (m, 6H), 2.05-1.93 (m, 3H), 1.91-1.79 (m, 2H), 1.75 (d, J = 12.4Hz, 2H), 1.66-1.52 (m, 1H), 1.39 (d, J = 6.8Hz, 6H), 1.27-1.15 (m, 2H) |
| I-216 | JU | DG | 900.1 | 11.05 (s, 1H), 9.65 (s, 1H), 8.74 (s, 1H), 8.17 (s, 1H), 7.80 (d, J = 9.2Hz, 1H), 7.74 (d, J = 8.4Hz, 1H), 7.67 (s, 1H), 7.62 (d, J = 8.0 Hz, 1H), 6.91 (d, J = 8.4Hz, 1H), 6.79 (s, 1H), 6.61 (d, J = 7.6Hz, 1H), 5.67-5.49 (m, 1H), 5.27 (dd, J = 5.6, 12.6 Hz, 1H), 3.54 (d, J = 11.2Hz, 2H), 3.29 (s, 3H), 2.94-2.82 (m, 1H), 2.72-2.60 (m, 3H), 2.59-2.53 (m, 3H), 2.33 (s, 3H), 2.32-2.19 (m, 5H), 2.18-2.00 (m, 7H), 2.01-1.92 (m, 1H), 1.76-1.70 (m, 2H), 1.64-1.49 (m, 3H), 1.41 (d, J = 6.8Hz, 6H), 1.26-1.14 (m, 2H) |
| I-217 | JV | CW | 925.4 | 11.05 (s, 1H), 9.71 (s, 1H), 8.77 (s, 1H), 8.20-8.17 (m, 2H), 7.78 (d, J = 8.4Hz, 1H), 7.64 (d, J = 1.6Hz, 1H), 7.57 (dd, |

TABLE 4-continued

Compounds synthesized via Method 1, coupling the corresponding amines with benzenesulfonyl chlorides.

| I-#[a] | Amine | Sulfonyl Chloride | LCMS (ESI+) m/z (M + H)+ | 1H NMR (400 MHz, DMSO-d6) δ |
|---|---|---|---|---|
| | | | | J = 2.0, 8.4Hz, 1H), 6.91 (d, J = 8.4Hz, 1H), 6.79 (d, J = 2.0 Hz, 1H), 6.60 (dd, J = 2.0, 8.8Hz, 1H), 5.73 (t, J = 8.4Hz, 1H), 5.27 (dd, J = 5.2, 12.8Hz, 1H), 3.53 (d, J = 11.6Hz, 2H), 3.29 (s, 3H), 2.95-2.84 (m, 5H), 2.72-2.60 (m, 2H), 2.57 (s, 1H), 2.54 (d, J = 1.2Hz, 1H), 2.36 (s, 3H), 2.26 (s, 4H), 2.16-2.07 (m, 4H), 2.00-1.94 (m, 1H), 1.77-1.66 (m, 6H), 1.60-1.54 (m, 1H), 1.49 (s, 4H), 1.45 (d, J = 7.2Hz, 2H), 1.31 (s, 4H), 1.24-1.15 (m, 2H) |

[a]The reaction was run anywhere from 1-24 hrs at rt. Purification of the coupled product via standard techniques including prep-HPLC and reverse phase chromatography.
[b]LCMS m/z reported as [M − H]−.
[c]LCMS m/z reported as [M − H2O + H]+.
[d]LCMS m/z reported as [M + Na]+.
[e]DIEA was used as the base in ACN and the reaction was run for 10 min to 2 hr at rt.
[f]The product of the coupling was then hydrogenated over Pd/C, with DIEA or TEA in THF under hydrogen atmosphere for 0.5-40 h at rt.
[g]2-Me—THF used as the solvent, reaction stirred at rt overnight.

Example 2 (Method 2): Synthesis of 3-(4-(1-(4-((6-(Difluoromethyl)-8-((1R,2R)-2-hydroxy-2-methylcyclopentyl)-7-oxo-7,8-dihydropyrido[2,3-d]pyrimidin-2-yl)amino)piperidin-1-yl)-1-oxo-3,6,9,12-tetraoxapentadecan-15-yl)-3-methyl-2-oxo-2,3-dihydro-1H-benzo[d]imidazol-1-yl)piperidine-2,6-dione (I-21)

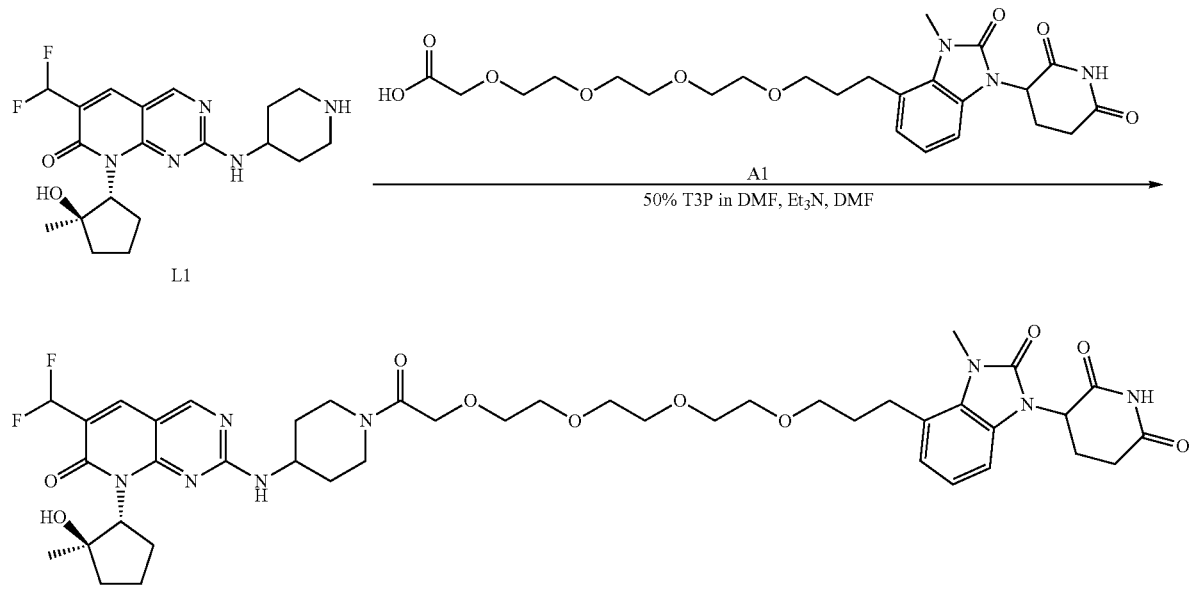 [SMILES: C[C@@]1(O)CCC[C@H]1n1c(=O)c(C(F)F)cc2cnc(NC3CCNCC3)nc21 ; Cn1c(=O)n(C2CCC(=O)NC2=O)c2cccc(CCCOCCOCCOCCOCC(=O)O)c21 ; "A1" ; Cn1c(=O)n(C2CCC(=O)NC2=O)c2cccc(CCCOCCOCCOCCOCC(=O)N3CCC(Nc4ncc5cc(C(F)F)c(=O)n([C@@H]6CCC[C@@]6(C)O)c5n4)CC3)c21]

To a solution of 6-(difluoromethyl)-8-((1R,2R)-2-hydroxy-2-methylcyclopentyl)-2-(piperidin-4-ylamino)pyrido[2,3-d]pyrimidin-7(8H)-one (55.8 mg, 0.142 mmol, Intermediate L1) and 15-(1-(2,6-dioxopiperidin-3-yl)-3-methyl-2-oxo-2,3-dihydro-1H-benzo[d]imidazol-4-yl)-3,6,9,12-tetraoxapentadecanoic acid (60 mg, 0.118 mmol, Intermediate A1) in DMF (5 mL) was added Et3N (119.4 mg, 1.18 mmol) and the mixture was cooled to −20° C. Next, a 50% solution of T3P in DMF (90.1 mg, 0.142 mmol) was added and the mixture was stirred at −20° C. for 2 h, then allowed to warm to rt and stirred overnight. On completion, the mixture was diluted with water (20 mL), and extracted with EtOAc (30 mL×3). The combined organic layers washed with brine, dried over Na2SO4 and concentrated under reduced pressure. The residue was purified by prep-HPLC (Model: SHIMADZU Preparative HPLC System-including a LC-20AP Pump, a SPD-20A Detector and Labsolutions (version 5.90) software; Column: Agilent 10, Prep-C18, 250×21.2 mm. Solvent/Gradient: 5-80% Acetonitrile in water containing 0.100 HCOOH. Flow Rate: 20 mL/min) to give the title compound (21.4 mg, 21% yield) as a white solid. LCMS: m/z=883.5 [M+H]; 1H(NMR (400 MHz, DMSO-d6) δ 10.9 (s, 1H), 8.76 (s, 1H), 8.10 (s, 2H), 7.05-6.68 (m, 4H), 5.69 (s, 1H), 5.32 (dd, J=12.6, 5.4 Hz, 1H), 4.49-3.83 (m, 5H), 3.60-3.49 (m, 16H), 3.46 (t, J=6.0 Hz, 2H), 3.15-3.02 (m, 1H), 3.01-2.78 (m, 4H), 2.75-2.59 (m, 3H), 2.07-1.42 (m, 12H), 1.26 (s, 3H).

TABLE 5

Compounds synthesized via Method 2, coupling the corresponding amines with acids.

| I-#[a] | Amine | Acid | LCMS (ESI+) m/z (M + H)+ | $^1$H NMR (400 MHz, DMSO-d$_6$) δ |
|---|---|---|---|---|
| I-19 | L1 | B4 | 795.5 | 10.9 (s, 1H), 8.76 (s, 1H), 8.10 (s, 2H), 7.06-6.70 (m, 4H), 5.68 (s, 1H), 5.30 (dd, J = 12.6, 5.5 Hz, 1H), 4.65 (s, 1H), 4.48-3.71 (m, 5H), 3.62-3.57 (m, 2H), 3.56-3.51 (m, 2H), 3.43 (t, J = 6.4 Hz, 2H), 3.25-3.05 (m, 5H), 2.94-2.84 (m, 1H), 2.74-2.57 (m, 5H), 2.07-1.88 (m, 5H), 1.87-1.77 (m, 3H), 1.72-1.37 (m, 4H), 1.25 (s, 3H) |
| I-20 | L1 | B1 | 883.6 | 10.9 (s, 1H), 8.76 (s, 1H), 8.11 (s, 2H), 7.11-6.70 (m, 4H), 5.69 (s, 1H), 5.30 (dd, J = 12.6, 5.4 Hz, 1H), 4.66 (s, 1H), 4.34-3.83 (m, 5H), 3.60-3.51 (m, 10H), 3.51-3.46 (m, 2H), 3.40 (t, J = 6.4 Hz, 2H), 3.10 (s, 1H), 3.32 (s, 3H), 2.95-2.68 (m, 1H), 2.67-2.58 (m, 3H), 2.05-1.77 (m, 8H), 1.75-1.33 (m, 4H), 1.26 (s, 3H) |
| I-22 | L1 | B3 | 791.5 | 10.8 (s, 1H), 8.76 (s, 1H), 8.11 (s, 2H), 7.01-6.73 (m, 4H), 5.69 (s, 1H), 5.30 (dd, J = 12.8, 5.5 Hz, 1H), 4.65 (s, 1H), 4.35 (s, 1H), 4.12-3.80 (m, 2H), 3.32 (s, 3H), 3.10 (s, 1H), 2.92-2.85 (m, 1H), 2.76-2.58 (m, 6H), 2.30 (t, J = 7.4 Hz, 2H), 2.07-1.84 (m, 6H), 1.79-1.69 (m, 1H), 1.65-1.56 (m, 3H), 1.54-1.45 (m, 3H), 1.34-1.24 (m, 12H) |
| I-23 | L1 | A3 | 791.5 | 10.9 (s, 1H), 8.76 (s, 1H), 8.11 (s, 2H), 7.06-6.73 (m, 4H), 5.68 (s, 1H), 5.40-5.25 (m, 1H), 4.66 (s, 1H), 4.34 (s, 1H), 4.08-4.82 (m, 2H), 3.55 (s, 3H), 3.08 (s, 1H), 2.94-2.83 (m, 3H), 2.77-2.58 (m, 4H), 2.35-2.27 (m, 2H), 2.08-1.82 (m, 6H), 1.74 (s, 1H), 1.66-1.57 (m, 3H), 1.55-1.46 (m, 3H), 1.43-1.23 (m, 12H) |
| I-24 | L1 | C1 | 883.5 | 10.9 (s, 1H), 8.76 (s, 1H), 8.10 (s, 2H), 7.57 (dd, J = 8.5, 7.1 Hz, 1H), 7.12 (d, J = 8.6 Hz, 1H), 7.03 (d, J = 7.0 Hz, 1H), 6.87 (t, J = 55.2 Hz, 1H), 6.56 (t, J = 5.8 Hz, 1H), 5.68 (s, 1H), 5.03 (dd, J = 12.8, 5.5 Hz, 1H), 4.65 (s, 1H), 4.34-3.80 (m, 5H), 3.63 (t, J = 5.4 Hz, 2H), 3.60-3.51 (m, 13H), 3.49-3.44 (m, 2H), 3.10 (s, 1H), 2.96-2.78 (m, 1H), 2.64-2.52 (m, 2H), 2.08-1.38 (m, 10H), 1.25 (s, 4H) |
| I-25 | L1 | B2 | 833.6 | 10.9 (s, 1H), 8.76 (s, 1H), 8.11 (s, 2H), 7.04-6.71 (m, 4H), 5.69 (s, 1H), 5.30 (dd, J = 12.8, 5.6 Hz, 1H), 4.65 (s, 1H), 4.34 (s, 1H), 4.14-3.77 (m, 2H), 3.32 (s, 3H), 3.14 (s, 1H), 2.96-2.57 (m, 7H), 2.30 (t, J = 7.4 Hz, 2H), 2.09-1.82 (m, 6H), 1.74 (q, J = 7.2 Hz, 1H), 1.61 (q, J = 7.8, 7.3 Hz, 3H), 1.49 (q, J = 7.2 Hz, 3H), 1.31-1.27 (m, 18H) |
| I-26 | L1 | A2 | 833.6 | 10.9 (s, 1H), 8.76 (s, 1H), 8.11 (s, 2H), 7.09-6.70 (m, 4H), 5.69 (s, 1H), 5.40-5.28 (m, 1H), 4.66 (s, 1H), 4.34 (s, 1H), 4.09-4.82 (m, 2H), 3.55 (s, 3H), 3.16-3.05 (m, 1H), 2.94-2.84 (m, 3H), 2.79-2.59 (m, 4H), 2.31 (t, J = 7.4 Hz, 2H), 2.08-1.83 (m, 6H), 1.75 (d, J = 11.4 Hz, 1H), 1.62 (q, J = 7.6 Hz, 3H), 1.55-1.45 (m, 3H), 1.40-1.21 (m, 18H) |
| I-27 | L1 | C4 | 795.4 | 10.8 (s, 1H), 8.76 (s, 1H), 8.10 (s, 2H), 7.57 (t, J = 7.8 Hz, 1H), 7.13 (d, J = 8.6 Hz, 1H), 7.02 (d, J = 7.2 Hz, 1H), 6.88 (t, J = 55.2 Hz, 1H), 6.57 (t, J = 5.9 Hz, 1H), 5.83-5.54 (m, 1H), 5.03 (dd, J = 12.8, 5.4 Hz, 1H), 4.65 (s, 1H), 4.40-3.75 (m, 5H), 3.66 (t, J = 5.2 Hz, 2H), 3.64-3.56 (m, 4H), 3.52-3.44 (m, 2H), 2.94-2.65 (m, 3H), 2.65-2.52 (m, 2H), 2.11-1.38 (m, 11H), 1.25 (s, 3H) |
| I-28 | L1 | C3 | 791.5 | 10.9 (s, 1H), 8.77 (s, 1H), 8.11 (s, 2H), 7.58 (t, J = 8.4, 7.1 Hz, 1H), 7.09 (d, J = 8.6 Hz, 1H), 7.02 (d, J = 6.8 Hz, 1H), 6.88 (t, J = 55.2 Hz, 1H), 6.46 (t, J = 5.8 Hz, 1H), 5.69 (s, 1H), 5.03 (dd, J = 12.8, 5.4 Hz, 1H), 4.65 (s, 1H), 4.34 (s, 1H), 4.22-3.77 (m, 2H), 3.36-3.27 (m, 2H), 3.16-3.02 (m, 1H), 2.96-2.82 (m, 1H), 2.79-2.51 (m, 4H), 2.31 (t, J = 7.4 Hz, 2H), 2.07-1.80 (m, 6H), 1.78-1.68 (m, 1H), 1.65-1.30 (m, 13H), 1.28-1.23 (m, 3H) |
| I-29 | L1 | A4 | 795.3 | 10.9 (s, 1H), 8.75 (s, 1H), 8.22-7.74 (m, 2H), 7.06-6.69 (m, 4H), 5.68 (s, 1H), 5.32 (dd, J = 12.6, 5.4 Hz, 1H), 4.65 (s, 1H), 4.38-3.82 (m, 5H), 3.63-3.54 (m, 7H), 3.49 (t, J = 6.2 Hz, 2H), 3.10 (s, 1H), 3.01-2.82 (m, 4H), 2.76-2.59 (m, 3H), 2.07-1.82 (m, 8H), 1.74-1.41 (m, 4H), 1.25 (s, 3H) |
| I-30 | L1 | C2 | 847.7 | 10.9 (s, 1H), 8.76 (s, 1H), 8.11 (s, 2H), 7.57 (t, J = 7.6 Hz, 1H), 7.08 (d, J = 8.6 Hz, 1H), 7.01 (d, J = 6.8 Hz, 1H), 6.87 (t, J = 55.1 Hz, 1H), 6.45 (t, J = 5.8 Hz, 1H), 5.69 (s, 1H), 5.03 (dd, J = 12.7, 5.4 Hz, 1H), 4.80-4.56 (m, 1H), 4.48-4.26 (m, 1H), 4.22-3.77 (m, 2H), 3.35-3.25 (m, 2H), 3.15-3.02 (m, 1H), 2.95-2.82 (m, 1H), 2.81-2.53 (m, 3H), 2.30 (t, J = 7.4 Hz, 2H), 2.11-1.38 (m, 14H), 1.40-1.11 (m, 18H) |
| I-218[b] | JD | JE | 781.5 | 10.30 (s, 1H), 9.64 (s, 1H), 8.75 (s, 1H), 8.18 (s, 1H), 8.06 (t, 1H), 7.72-7.67 (m, 2H), 7.66-7.60 (m, 2H), 7.14 (d, 1H), 6.92 (d, 1H), 6.88-6.80 (m, 1H), 5.80-5.65 (m, 1H), 4.44 (s, 2H), 3.80-3.69 (m, 1H), 3.54-3.44 (m, 1H), 3.42-3.35 (m, 4H), 3.30-3.24 (m, 3H), 2.94-2.87 (m, 2H), 2.78-2.65 (m, 2H), 2.32 (s, 3H), |

TABLE 5-continued

Compounds synthesized via Method 2, coupling the corresponding amines with acids.

| I-#[a] | Amine | Acid | LCMS (ESI+) m/z (M + H)+ | 1H NMR (400 MHz, DMSO-d6) δ |
|---|---|---|---|---|
| | | | | 2.14-2.11 (m, 1H), 2.10-2.06 (m, 3H), 1.70-1.66 (m, 4H), 1.50-1.40 (m, 2H) |
| I-219[b] | JD | JF | 772.6 | 10.50 (s, 1H), 9.64 (s, 1H), 8.75 (s, 1H), 8.60 (t, 1H), 8.16 (s, 1H), 7.95 (d, 1H), 7.87-7.79 (m, 1H), 7.72-7.59 (m, 5H), 5.79-5.65 (m, 1H), 3.80-3.70 (m, 1H), 3.67-3.57 (m, 1H), 3.51-3.36 (m, 6H), 2.96-2.92 (m, 2H), 2.78-2.71 (m, 2H), 2.32 (s, 3H), 2.15-2.06 (m, 2H), 1.72-1.66 (m, 4H), 1.48-1.40 (m, 2H) |
| I-220[b] | JG | JE | 825.4 | 10.34 (s, 1H), 9.66 (s, 1H), 8.74 (s, 1H), 8.17 (s, 1H), 8.05 (t, J = 5.6 Hz, 1H), 7.74-7.67 (m, 2H), 7.67-7.58 (m, 2H), 7.17 (d, J = 8.4 Hz, 1H), 6.91 (d, J = 2.8 Hz, 1H), 6.84-6.81 (m, 1H), 5.80-5.65 (m, 1H), 4.43 (s, 2H), 3.80-3.69 (m, 1H), 3.50-3.38 (m, 9H), 3.29-3.25 (m, 2H), 2.91-2.87 (m, 2H), 2.78-2.65 (m, 2H), 2.32 (s, 3H), 2.09 (s, 5H), 1.68 (s, 4H), 1.45 (s, 2H) |
| I-221[b] | JG | JH | 814.9 | 10.52 (s, 1H), 9.65 (s, 1H), 8.74 (s, 1H), 8.64 (t, J = 5.6 Hz, 1H), 8.17 (s, 1H), 7.95 (d, J = 2.0 Hz, 1H), 7.85-7.81 (m, 1H), 7.73-7.67 (m, 2H), 7.66-7.59 (m, 2H), 5.77-5.70 (m, 1H), 3.78-3.71 (m, 1H), 3.67-3.56 (m, 1H), 3.54-3.48 (m, 4H), 3.48-3.44 (m, 2H), 3.41-3.39 (m, 4H), 2.91-2.87 (m, 2H), 2.76-2.72 (m, 2H), 2.32 (s, 3H), 2.16-2.03 (m, 2H), 1.68 (s, 4H), 1.52-1.38 (m, 2H) |

[a]Coupling under standard conditions, Purification of the coupled product via standard techniques including prep-HPLC and reverse phase chromatography.
[b]CMPI, DIEA, in DMF at rt for 1.5 hrs was used for the coupling.

Example 3 (Method 3): Synthesis of [(1R,3S)-3-[1-tert-butyl-5-[[5-(methoxymethyl)-2-methyl-pyrazole-3-carbonyl]amino]pyrazol-3-yl]cyclopentyl] N-[7-[1-(2,6-dioxo-3-piperidyl)-3-methyl-2-oxo-benzimidazol-5-yl]heptyl]carbamate (I-81)

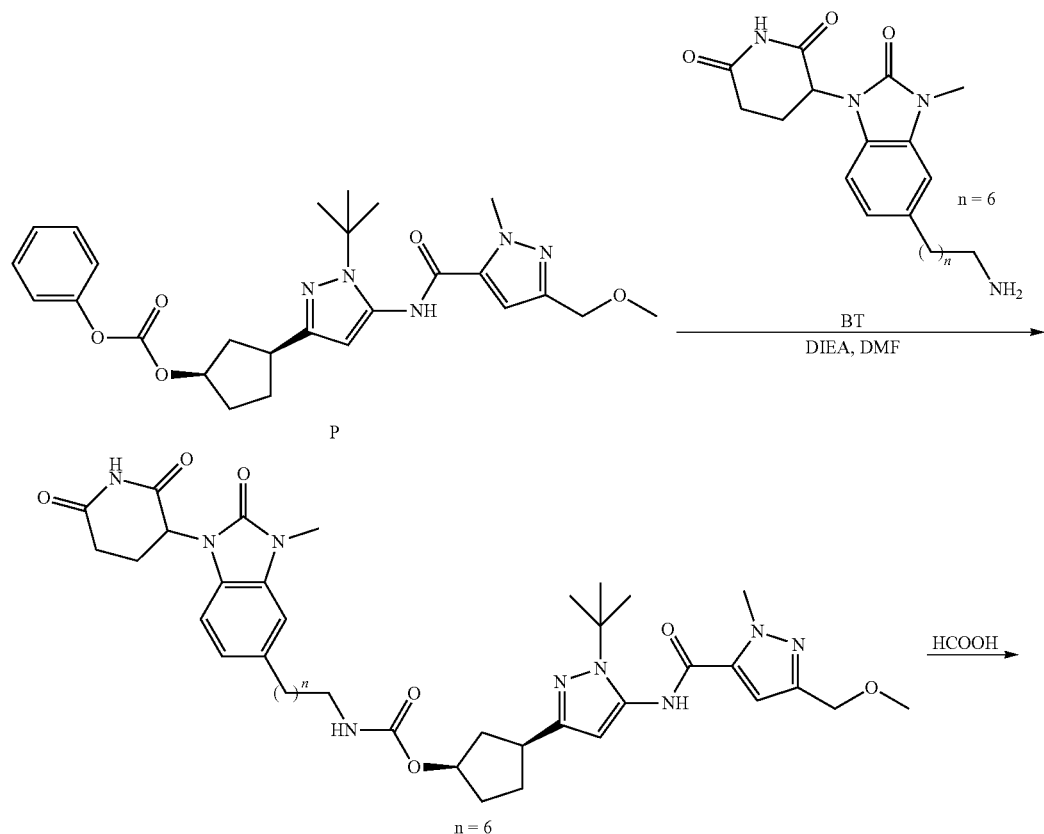

-continued

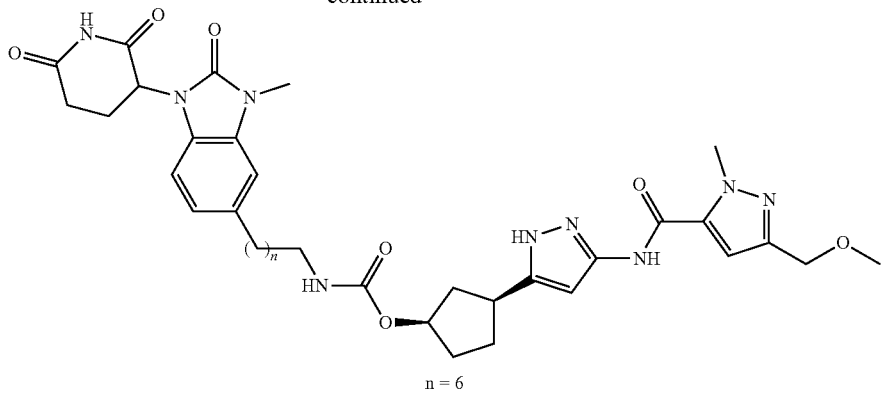

n = 6

Step 1—[(1R,3S)-3-[1-tert-butyl-5-[[5-(methoxymethyl)-2-methyl-pyrazole-3-carbonyl]amino]pyrazol-3-yl]cyclopentyl] N-[9-[1-(2,6-dioxo-3-piperidyl)-3-methyl-2-oxo-benzimidazol-5-yl]nonyl]carbamate. A solution of (1R,3S)-3-(1-(tert-butyl)-5-(3-(methoxymethyl)-1-methyl-1H-pyrazole-5-carboxamido)-1H-pyrazol-3-yl)cyclopentyl phenyl carbonate (50 mg, 101 umol, Intermediate P), 3-[5-(7-aminoheptyl)-3-methyl-2-oxo-benzimidazol-1-yl]piperidine-2,6-dione (56.4 mg, 151 umol, Intermediate BT) and DIEA (65.2 mg, 504 umol) in DMF (0.5 mL) was stirred at 80° C. for 12 h. On completion, the mixture was quenched with sat. NH$_4$Cl (5 mL), and extracted with EtOAc (5 mL×2). The combined organic layer was washed with brine (10 mL×2), dried by Na$_2$SO$_4$, and concentrated in vacuo. The residue was purified by column chromatography (SiO$_2$, Petroleum ether/Ethyl acetate=0/1) to give the title compound (0.04 g, 21% yield, 40% purity) as an orange solid. LCMS: tR=0.680 min., (ES$^+$) m/z (M+H)$^+$=774.4.

Step 2—[(1R,3S)-3-[1-tert-butyl-5-[[5-(methoxymethyl)-2-methyl-pyrazole-3-carbonyl]amino]pyrazol-3-yl]cyclopentyl] N-[7-[1-(2,6-dioxo-3-piperidyl)-3-methyl-2-oxo-benzimidazol-5-yl]heptyl]carbamate. A solution of [(1R,3S)-3-[1-tert-butyl-5-[[5-(methoxymethyl)-2-methyl-pyrazole-3-carbonyl]amino]pyrazol-3-yl]cyclopentyl] N-[7-[1-(2,6-dioxo-3-piperidyl)-3-methyl-2-oxo-benzimidazol-5-yl]heptyl]carbamate (0.03 g, 38.8 umol, 40% purity) in HCOOH (1 mL) was stirred at 80° C. for 2 h. On completion, the mixture was concentrated in vacuo. The residue was purified by prep-HPLC (FA condition, column: Phenomenex luna C18 150*25 mm*10 um; mobile phase: [water (0.225%₀FA)-ACN]; B %: 35%-65%, 10 min) to give the title compound (15 mg, 20.3 umol, 52% yield) as white solid. LCMS: tR=0.620 min., (ES) m/z (M+H)$^+$=718.3. $^1$H NMR (400 MHz, DMSO-d6) δ=12.41-12.09 (br, 1H), 11.07 (s, 1H), 10.90-10.56 (br, 1H), 7.11 (s, 1H), 7.04-6.99 (m, 2H), 6.97 (s, 1H), 6.84 (br d, J=8.8 Hz, 1H), 6.40 (br s, 1H), 5.32 (br dd, 3=5.2, 12.4 Hz, 1H), 5.02-4.94 (m, 1H), 4.33 (s, 2H), 4.04 (s, 3H), 3.31 (br s, 3H), 3.26 (s, 3H), 3.10-3.04 (i, 1H), 2.96-2.87 (m, 3H), 2.71-2.66 (m, 1H), 2.66-2.55 (m, 4H), 2.54 (br s, 1H), 2.03-1.97 (m, 2H), 1.89 (br dd, =3.6, 6.4 Hz, 1H), 1.77-1.69 (m, 2H), 1.57 (br s, 2H), 1.40-1.34 (m, 2H), 1.25 (br d, =13.2 Hz, 6H).

TABLE 6

Compounds synthesized via Method 3, coupling the corresponding amines with carbamates in Step 1.

| I-# | Amine | Carbamate | LCMS (ESI+) m/z (M + H)$^+$ | $^1$H NMR (400 MHz, DMSO-d$_6$) δ |
|---|---|---|---|---|
| I-60 | F1 | P | 838.4 | 12.26-12.15 (m, 1H), 10.71 (br s, 1H), 7.57 (t, J = 8.0 Hz, 1H), 7.18-7.10 (m, 2H), 7.03 (d, J = 6.8 Hz, 2H), 6.59 (br t, J = 5.6 Hz, 1H), 6.45-6.36 (m, 1H), 5.09-4.93 (m, 2H), 4.33 (s, 2H), 4.04 (s, 3H), 3.61 (br t, J = 5.6 Hz, 2H), 3.58-3.50 (m, 6H), 3.50-3.47 (m, 7H), 3.26 (s, 3H), 3.14-3.03 (m, 4H), 2.94-2.79 (m, 2H), 2.07 (s, 2H), 2.04-1.99 (m, 2H), 1.93-1.86 (m, 1H), 1.79-1.54 (m, 4H) |
| I-69 | CG | P | 778.4 | 12.22 (br s, 1H), 11.08 (br s, 1H), 10.71 (s, 1H), 7.11 (s, 1H), 7.03 (br t, J = 4.4 Hz, 1H), 6.95 (br d, J = 4.4 Hz, 2H), 6.87-6.83 (m, 1H), 6.41 (br s, 1H), 5.35 (br dd, J = 5.2, 12.8 Hz, 1H), 5.02-4.96 (m, 1H), 4.33 (s, 2H), 4.04 (s, 3H), 3.55 (s, 3H), 3.43 (br s, 1H), 3.42 (br s, 2H), 3.30 (br s, 2H), 3.26 (s, 3H), 3.12-3.06 (m, 1H), 3.05-2.90 (m, 6H), 2.89-2.84 (m, 1H), 2.76-2.69 (m, 1H), 2.68-2.62 (m, 2H), 2.03-1.96 (m, 2H), 1.91-1.86 (m, 1H), 1.84-1.79 (m, 2H), 1.75-1.69 (m, 4H), 1.67-1.54 (m, 4H) |
| I-70 | CF | P | 803.4 | 11.07 (s, 1H), 10.73 (s, 1H), 8.22 (br d, J = 2.8 Hz, 1H), 7.12 (s, 1H), 7.02 (s, 1H), 6.99 (d, J = 8.0 Hz, 1H), 6.85 (br d, J = 8.0 Hz, 1H), 6.41 (s, 1H), 5.33 (br dd, J = 5.2, 12.8 Hz, 1H), 5.07-5.01 (m, 1H), 4.32 (s, 2H), 4.05 (s, 3H), 3.36-3.35 (m, 1H), 3.34 (br s, 4H), 3.32 (br s, 3H), 3.26 (s, 3H), 3.18-3.12 (m, 2H), 2.91-2.83 (m, 1H), 2.71-2.62 (m, 4H), 2.43-2.36 |

TABLE 6-continued

Compounds synthesized via Method 3, coupling the
corresponding amines with carbamates in Step 1.

| I-# | Amine | Carbamate | LCMS (ESI+) m/z (M + H)+ | $^1$H NMR (400 MHz, DMSO-$d_6$) δ |
|---|---|---|---|---|
| | | | | (m, 2H), 2.25 (br d, J = 5.2 Hz, 4H), 2.23-2.20 (m, 2H), 2.06-1.97 (m, 2H), 1.93-1.86 (m, 1H), 1.85-1.70 (m, 6H), 1.49-1.40 (m, 4H) |
| I-71 | D3 | P | 746.2 | 12.25-12.15 (m, 1H), 11.09 (br s, 1H), 10.72 (br s, 1H), 7.12 (s, 1H), 7.03 (br t, J = 5.8 Hz, 1H), 6.95 (br d, J = 4.8 Hz, 2H), 6.88-6.82 (m, 1H), 6.41 (br s, 1H), 5.36 (dd, J = 5.4, 12.4 Hz, 1H), 5.03-4.95 (m, 1H), 4.33 (s, 2H), 4.05 (s, 3H), 3.54 (s, 3H), 3.27 (s, 3H), 3.14-3.02 (m, 1H), 3.00-2.78 (m, 6H), 2.76-2.62 (m, 2H), 2.08-1.96 (m, 2H), 1.94-1.84 (m, 1H), 1.79-1.69 (m, 2H), 1.66-1.51 (m, 3H), 1.37 (br s, 4H), 1.33-1.28 (m, 2H), 1.25 (br s, 6H) |
| I-79 | E3 | P | 746.3 | 12.22 (br s, 1H), 11.07 (s, 1H), 10.71 (br s, 1H), 7.11 (s, 1H), 7.02-6.99 (m, 2H), 6.97 (s, 1H), 6.84 (br d, J = 8.0 Hz, 1H), 6.41 (br s, 1H), 5.32 (br dd, J = 5.3, 12.7 Hz, 1H), 5.03-4.96 (m, 1H), 4.33 (s, 2H), 4.04 (s, 3H), 3.31 (br s, 3H), 3.26 (s, 3H), 3.10-3.04 (m, 1H), 2.98-2.92 (m, 2H), 2.90-2.85 (m, 1H), 2.71-2.62 (m, 2H), 2.61-2.52 (m, 4H), 2.04-1.97 (m, 2H), 1.92-1.85 (m, 1H), 1.76-1.69 (m, 2H), 1.56 (br d, J = 6.1 Hz, 2H), 1.36 (br s, 2H), 1.28-1.20 (m, 10H) |
| I-94 | D3 | P | 746.2 | 12.23 (br d, J = 6.4 Hz, 1H), 11.20-10.98 (m, 1H), 10.82-10.65 (m, 1H), 7.11 (s, 1H), 7.02 (br t, J = 5.6 Hz, 1H), 6.97-6.90 (m, 2H), 6.88-6.81 (m, 1H), 6.40 (br d, J = 1.2 Hz, 1H), 5.35 (br dd, J = 5.2, 12.4 Hz, 1H), 5.07-4.93 (m, 1H), 4.33 (s, 2H), 4.04 (s, 3H), 3.54 (s, 3H), 3.26 (s, 3H), 3.15-3.01 (m, 1H), 2.98-2.81 (m, 5H), 2.75-2.58 (m, 2H), 2.07-1.94 (m, 2H), 1.92-1.82 (m, 1H), 1.76-1.66 (m, 2H), 1.66-1.49 (m, 3H), 1.43-1.15 (m, 13H) |
| I-95 | AN | P | 718.3 | 12.23 (br s, 1H), 11.08 (br s, 1H), 10.72 (br s, 1H), 7.11 (s, 1H), 7.07-6.81 (m, 4H), 6.41 (br s, 1H), 5.35 (br dd, J = 5.2, 12.4 Hz, 1H), 5.00 (br d, J = 4.0 Hz, 1H), 4.33 (s, 2H), 4.04 (s, 3H), 3.54 (s, 3H), 3.26 (s, 3H), 3.13-3.00 (m, 1H), 2.98-2.84 (m, 5H), 2.75-2.56 (m, 2H), 2.06-1.95 (m, 2H), 1.94-1.83 (m, 1H), 1.78-1.67 (m, 2H), 1.65-1.52 (m, 3H), 1.43-1.21 (m, 9H) |

$^a$Step 1 was run anywhere from 60-80° C. for 12-27 hrs. Step 2 was run anywhere from 70-80° C. for 2-24 hrs.

Example 4 (Method 4): Synthesis of (1R,3S)-3-(5-(1-(4-(((1-((1-(2,6-dioxopiperidin-3-yl)-3-methyl-2-oxo-2,3-dihydro-1H-benzo[d]imidazol-4-yl)methyl)piperidin-4-yl)(methyl)amino)methyl)cyclohexyl)-1H-pyrazole-4-carboxamido)-1H-pyrazol-3-yl)cyclopentyl isopropylcarbamate (I-84)

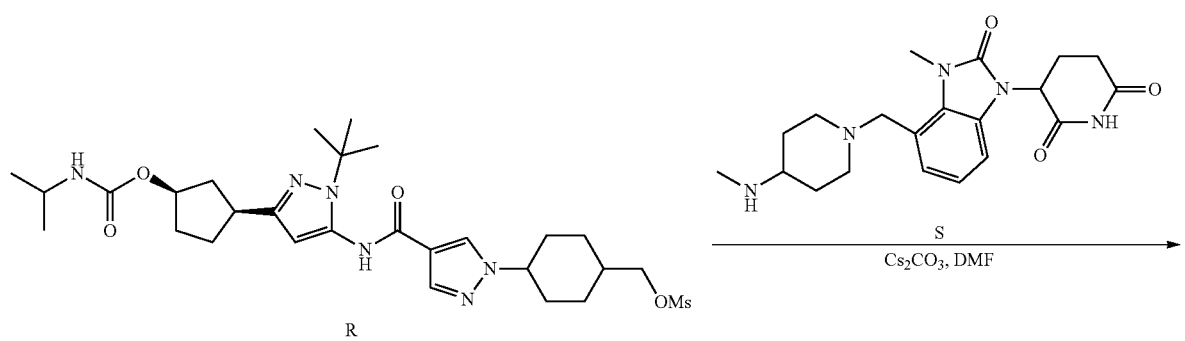

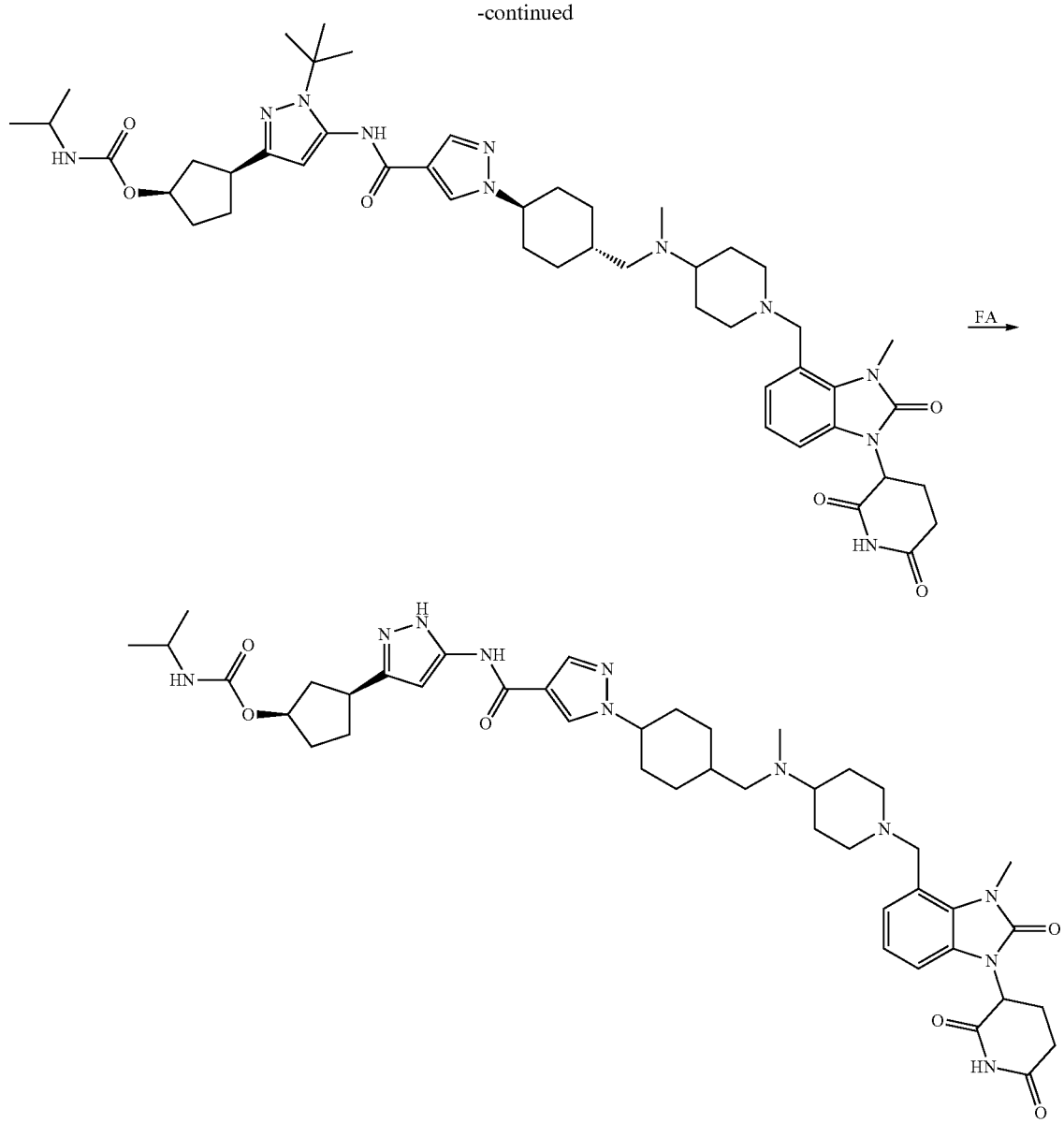

Step 1—(1R,3S)-3-(1-(tert-butyl)-5-(1-((1r,4S)-4-(((1-((1-(2,6-dioxopiperidin-3-yl)-3-methyl-2-oxo-2,3-dihydro-1H-benzo[d]imidazol-4-yl)methyl)piperidin-4-yl)(methyl)amino)methyl)cyclohexyl)-1H-pyrazole-4-carboxamido)-1H-pyrazol-3-yl)cyclopentyl isopropylcarbamate. To a solution of [4-[4-[[2-tert-butyl-5-[(1S,3R)-3-(isopropylcarbamoyloxy)cyclopentyl]pyrazol-3-yl]carbamoyl]pyrazol-1-yl]cyclohexyl]methyl methanesulfonate (40.0 mg, 67.5 umol, Intermediate R) and 3-[3-methyl-4-[[4-(methylamino)-1-piperidyl]methyl]-2-oxo-benzimidazol-1-yl]piperidine-2,6-dione (78.0 mg, 202.44 umol, Intermediate S) in DMF (1 mL) was added Cs$_2$CO$_3$ (110 mg, 337 umol) at 20° C. under nitrogen flow. Then the reaction was stirred at 20-60° C. for 10 h under nitrogen atmosphere. On completion, the reaction was filtered to get the filtrate. The filtrate was purified by prep-HPLC (0.1% FA condition) to give the title compound (10 mg, 17% yield) as colorless oil. LC-MS (ESI$^+$) m/z 882.5 (M+H)$^+$.

Step 2—(1R,3S)-3-(5-(1-(4-(((1-((1-(2,6-dioxopiperidin-3-yl)-3-methyl-2-oxo-2,3-dihydro-1H-benzo[d]imidazol-4-yl)methyl)piperidin-4-yl)(methyl)amino)methyl)cyclohexyl)-1H-pyrazole-4-carboxamido)-1H-pyrazol-3-yl)cyclopentyl isopropylcarbamate. To a solution of [(1R,3S)-3-[2-tert-butyl-5-[[1-[4-[[[1-[[1-(2,6-dioxo-3-piperidyl)-3-methyl-2-oxo-benzimidazol-4-yl]methyl]-4-piperidyl]-methyl-amino]pyrazol-3-yl]cyclopentyl] N-isopropylcarbamate (10.0 mg, 11.3 umol) in formic acid (0.2 mL) at 20° C. under nitrogen flow. Then the reaction was stirred at 70° C. for 10 h under nitrogen atmosphere. On completion, the reaction was concentrated to give a residue. The residue was purified by prep-HPLC (0.1% FA condition) to give the title compound (5 mg, 50% yield) as colorless oil. $^1$H NMR (400 MHz, DMSO-d$_6$) δ=10.43-10.26 (br s, 1H), 8.37 (br d, J=5.2 Hz, 2H), 8.12-7.96 (m, 1H), 7.09-6.85 (m, 3H), 6.36 (s, 1H), 5.63-5.43 (m, 1H), 5.00 (br d, J=4.0 Hz, 1H), 4.29-3.98 (m, 2H), 3.68-3.60 (m, 8H), 3.11-2.93 (m, 3H), 2.90-2.72 (m, 4H), 2.65-2.55 (m, 1H), 2.41-2.34 (m, 3H), 2.17-1.54 (m, 18H), 1.38-1.22 (m, 2H), 1.20-1.09 (m, 2H), 1.03 (br d, J=6.4 Hz, 6H). LC-MS (ESI$^+$) m/z 826.3 (M+H)$^+$.

TABLE 7

Compounds synthesized via Method 4, coupling the corresponding amines with mesylates in Step 1.

| I-# | Amine | Mesylate | LCMS (ESI+) m/z (M + H)+ | 1H NMR (400 MHz, DMSO-d6) δ |
|---|---|---|---|---|
| I-50[a] | BS | BR | 797.3 | 11.11 (s, 1H), 10.37 (s, 1H), 8.33 (s, 1H), 8.21 (s, 1H), 8.05 (s, 1H), 7.10 (d, J = 7.8 Hz, 1H), 7.06-7.02 (m, 1H), 6.99 (d, J = 8 Hz, 1H), 6.96-6.92 (m, 1H), 6.37 (s, 1H), 5.37 (br dd, J = 5.2, 12.8 Hz, 1H), 4.99 (br d, J = 3.2 Hz, 1H), 4.27 (br t, J = 5.2 Hz, 2H), 3.74 (br t, J = 5.2 Hz, 3H), 3.61 (s, 3H), 3.49 (br s, 3H), 3.03 (br d, J = 8.0 Hz, 1H), 2.92-2.74 (m, 4H), 2.73-2.58 (m, 3H), 2.39 (br d, J = 6.4 Hz, 2H), 2.05-1.94 (m, 4H), 1.88 (dt, J = 3.2, 6.8 Hz, 1H), 1.70 (br d, J = 9.2 Hz, 4H), 1.63-1.46 (m, 2H), 1.36-1.23 (m, 2H), 1.02 (br d, J = 6.4 Hz, 6H) |
| I-62[a] | BP | BR | 805.7 | 10.37 (br s, 1H), 8.35-8.23 (m, 2H), 8.05 (s, 1H), 6.98-6.90 (m, 2H), 6.87-6.81 (m, 1H), 6.36 (br d, J = 6.0 Hz, 1H), 5.49-5.29 (m, 1H), 4.99 (br d, J = 2.4 Hz, 1H), 4.32-4.20 (m, 2H), 3.90-3.69 (m, 4H), 3.55 (br d, J = 8.0 Hz, 5H), 3.46-3.43 (m, 3H), 3.38-3.34 (m, 3H), 3.15-3.00 (m, 2H), 2.98-2.88 (m, 3H), 2.86-2.77 (m, 1H), 2.74-2.61 (m, 1H), 2.37-2.29 (m, 3H), 2.11 (s, 2H), 2.05-1.56 (m, 11H), 1.02 (br d, J = 6.4 Hz, 6H) |
| I-93[b] | S | V | 840.4 | 12.0 (br s, 1H), 10.43-10.26 (br s, 1H), 8.37 (br d, J = 5.2 Hz, 2H), 7.58 (s, 1H), 7.30 (S, 1H), 7.06-7.04 (m, 1H), 6.97-6.86 (m, 3H), 6.27 (s, 1H), 5.52-5.48 (m, 1H), 5.00 (br d, J = 2.4 Hz, 1H), 4.08-3.55 (m, 8H), 3.38 (s, 3H), 3.11-2.93 (m, 3H), 2.90-2.72 (m, 4H), 2.35 (m, 1H), 2.00-1.60 (m, 17H), 1.12-1.00 (m, 11H) |

[a]K2CO3 was used as the base in Step 1, which was run in MeCN at 40° C. for 12 hr.
[b]Step 1 was run at 60° C. 12 hr, Step 2 was run at 75° C. for 12 hr.

Example 5 (Method 5): [(1R,3S)-3-[5-[[2-[2-[2-[3-[1-(2,6-dioxo-3-piperidyl)-3-methyl-2-oxo-benzimidazol-4-yl]propoxy]ethoxy]ethyl]pyrazole-3-carbonyl]amino]-1H-pyrazol-3-yl]cyclopentyl]N-isopropylcarbamate (I-78)

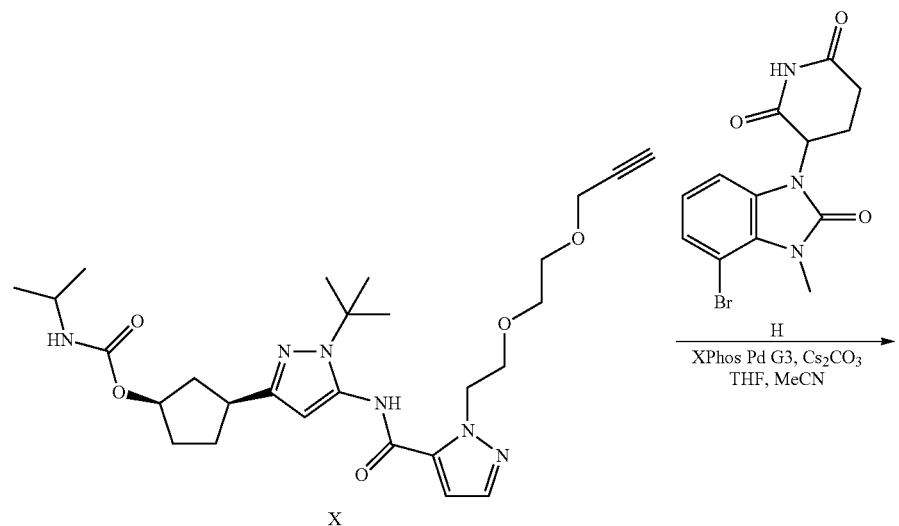

1011
-continued
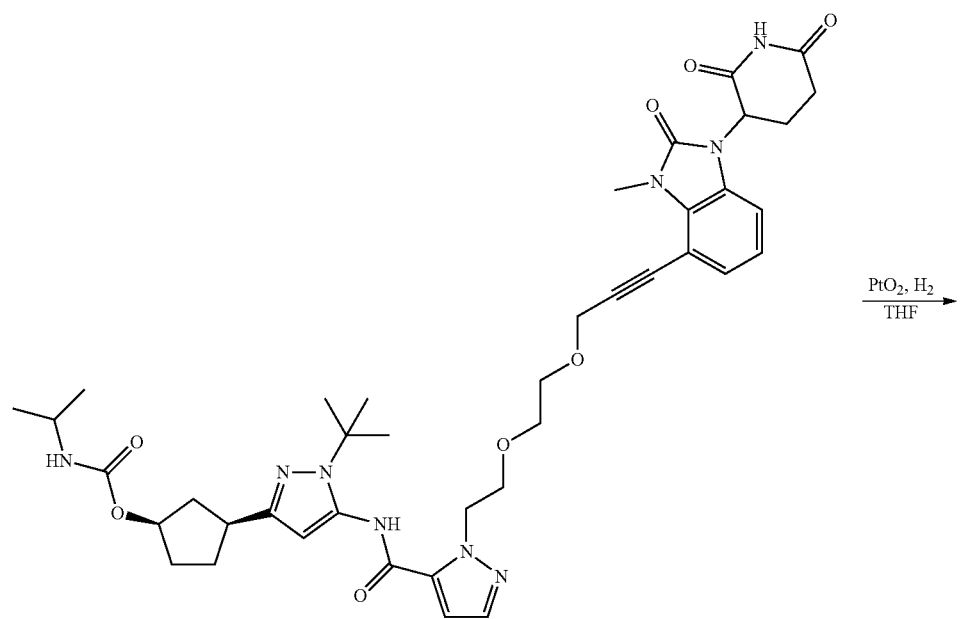
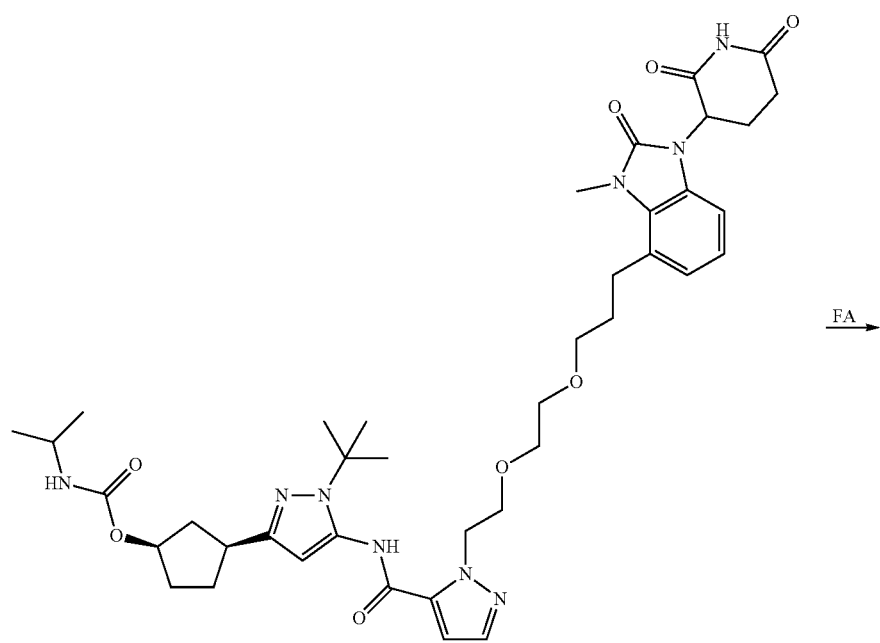

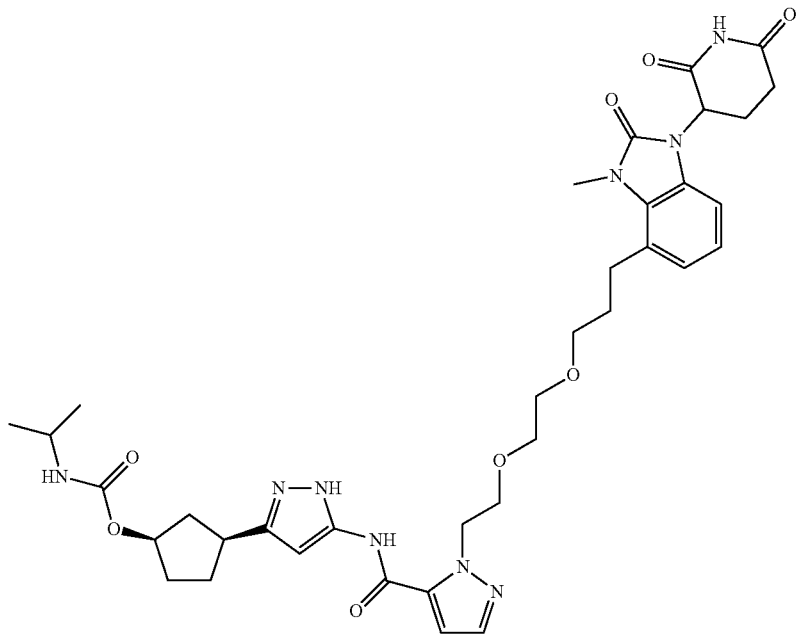 [SMILES: CC(C)NC(=O)O[C@@H]1CC[C@H](c2cc(NC(=O)c3ccnn3CCOCCOCCCc3cccc4c3n(C)c(=O)n4C3CCC(=O)NC3=O)[nH]n2)C1]

Step 1—(1R,3S)-3-(1-(tert-butyl)-5-(1-(2-(2-((3-(1-(2,6-dioxopiperidin-3-yl)-3-methyl-2-oxo-2,3-dihydro-1H-benzol[d]imidazol-4-yl)prop-2-yn-1-yl)oxy)ethoxy)ethyl)-1H-pyrazole-5-carboxamido)-1H-pyrazol-3-yl)cyclopentyl isopropylcarbamate. To a solution of [(1R,3S)-3-[1-tert-butyl-5-[[2-[2-(2-prop-2-ynoxyethoxy)ethyl]pyrazole-3-carbonyl]amino]pyrazol-3-yl]cyclopentyl] N-isopropylcarbamate (200 mg, 378 umol, Intermediate X) and 3-(4-bromo-3-methyl-2-oxo-benzimidazol-1-yl)piperidine-2,6-dione (153 mg, 454 umol, Intermediate H) in THF (1 mL) and ACN (1 mL) was added XPhos Pd G3 (96.1 mg, 113 umol) and Cs$_2$CO$_3$ (616 mg, 1.89 mmol). The mixture was stirred at 60° C. for 4 h under nitrogen atmosphere. On completion, the reaction mixture was quenched with NH$_4$Cl (sat. aq, 5 mL) at 0° C., then extracted with EtOAc (5 mL×3). The combined organic layers was washed with brine (5 mL×3), dried over Na$_2$SO$_4$, filtered and concentrated under reduced pressure to give a residue. The residue was purified by prep-HPLC (column: Phenomenex luna C18 150*25 mm*10 um; mobile phase: [water (0.225% FA)-ACN]; B %: 38%-68%, 10 min) to give the title compound (70 mg, 24% yield) as a white solid. LCMS: tR=0.642 min., (ES+) m/z (M+H)$^+$=786.3.

Step 2—[(1R,3S)-3-[1-tert-butyl-5-[[2-[2-[2-[3-[1-(2,6-dioxo-3-piperidyl)-3-methyl-2-oxo-benzimidazol-4-yl]propoxy]ethoxy]ethyl]pyrazole-3-carbonyl]amino]pyrazol-3-yl]cyclopentyl]N-isopropylcarbamate. A solution of (1R,3S)-3-(1-(tert-butyl)-5-(1-(2-(2-((3-(1-(2,6-dioxopiperidin-3-yl)-3-methyl-2-oxo-2,3-dihydro-1H-benzo[d]imidazol-4-yl)prop-2-yn-1-yl)oxy)ethoxy)ethyl)-1H-pyrazole-5-carboxamido)-1H-pyrazol-3-yl)cyclopentyl isopropylcarbamate (100 mg, 127 umol) and PtO$_2$ (14.0 mg, 61.7 umol) in THF (2 mL) was placed under H$_2$ atmosphere and was stirred at 25° C. for 1 h. On completion, the mixture was filtered and the filtration was concentrated in vacuo to give the title compound (100 mg) as brown solid.

Step 3—[(1R,3S)-3-[5-[[2-[2-[2-[3-[1-(2,6-dioxo-3-piperidyl)-3-methyl-2-oxo-benzimidazol-4-yl]propoxy]ethoxy]ethyl]pyrazole-3-carbonyl]amino]-1H-pyrazol-3-yl]cyclopentyl] N-isopropylcarbamate. A solution of [(1R,3S)-3-[1-tert-butyl-5-[[2-[2-[2-[3-[1-(2,6-dioxo-3-piperidyl)-3-methyl-2-oxo-benzimidazol-4-yl]propoxy]ethoxy]ethyl]pyrazole-3-carbonyl]amino]pyrazol-3-yl]cyclopentyl]N-isopropylcarbamate (70 mg, 88.6 umol) in HCOOH (1 mL) was stirred at 80° C. for 2 h. On completion, the mixture was concentrated in vacuo. The residue was purified by prep-HPLC (FA condition, column: Phenomenex luna C18 150*25 mm*10 um; mobile phase: [water (0.225% FA)-ACN]; B %: 28%-58%, 10 min) to give the title compound (20 mg, 30% yield) as a white solid. $^1$H NMR (400 MHz, DMSO-d$_6$) δ=12.20 (br s, 1H), 11.08 (s, 1H), 10.73 (br s, 1H), 7.51 (d, J=2.0 Hz, 1H), 7.12 (d, J=1.6 Hz, 1H), 6.95 (br d, J=5.2 Hz, 3H), 6.85-6.81 (m, 1H), 6.41 (br s, 1H), 5.35 (br dd, J=5.2, 12.5 Hz, 1H), 5.04-4.95 (m, 1H), 4.70 (t, J=5.6 Hz, 2H), 3.76 (t, J=5.6 Hz, 2H), 3.61-3.54 (m, 1H), 3.52 (s, 3H), 3.50-3.42 (m, 4H), 3.38 (br t, J=6.0 Hz, 2H), 3.09-3.00 (m, 1H), 2.92-2.87 (m, 2H), 2.85 (br d, J=5.6 Hz, 1H), 2.75-2.61 (m, 2H), 2.46-2.41 (m, 1H), 2.04-1.96 (m, 2H), 1.91-1.84 (m, 1H), 1.80-1.70 (m, 4H), 1.64-1.57 (m, 1H), 1.02 (d, J=6.4 Hz, 6H); LC-MS (ESI$^+$) m/z 734.3 (M+H)$^+$.

Table 8. Compounds synthesized via Method 5, coupling the corresponding alkynes with bromides in Step 1.

TABLE 8

Compounds synthesized via Method 5, coupling the corresponding alkynes with bromides in Step 1.

| I-#[a] | Alkyne | Bromide | LCMS (ESI+) m/z (M + H)+ | 1H NMR (400 MHz, DMSO-d$_6$) δ |
|---|---|---|---|---|
| I-47 | CN | J | 822.4 | 12.22 (br s, 1H), 11.11-11.02 (m, 1H), 10.71 (br s, 1H), 7.08 (s, 1H), 7.02 (s, 1H), 6.99 (d, J = 8.0 Hz, 1H), 6.94 (br d, J = 6.8 Hz, 1H), 6.85 (d, J = 8.0 Hz, 1H), 6.41 (br s, 1H), 5.33 (dd, J = 5.6, 12.8 Hz, 1H), 5.02-4.96 (m, 1H), 4.64 (t, J = 5.6 Hz, 2H), 4.34 (s, 2H), 3.73 (t, J = 5.6 Hz, 2H), 3.60-3.54 (m, 1H), 3.45 (br d, J = 2.0 Hz, 2H), 3.43 (d, J = 4.0 Hz, 4H), 3.42-3.41 (m, 1H), 3.38-3.34 (m, 4H), 3.31 (br s, 3H), 3.26 (s, 3H), 3.10-3.02 (m, 1H), 2.93-2.85 (m, 1H), 2.69-2.60 (m, 4H), 2.03-1.96 (m, 2H), 1.93-1.86 (m, 1H), 1.81-1.76 (m, 2H), 1.76-1.70 (m, 2H), 1.65-1.57 (m, 1H), 1.02 (d, J = 6.4 Hz, 6H) |
| I-48[b] | CD | H | 818.4 | 12.01 (br s, 1H), 11.09 (s, 1H), 10.22 (br s, 1H), 7.24-7.12 (m, 2H), 7.05-6.78 (m, 5H), 6.29 (br s, 1H), 5.36 (br dd, J = 5.6, 12.4 Hz, 1H), 4.97 (br d, J = 2.0 Hz, 1H), 4.06 (br t, J = 4.4 Hz, 2H), 3.72 (br t, J = 4.4 Hz, 2H), 3.65-3.39 (m, 15H), 3.13-2.81 (m, 5H), 2.78-2.63 (m, 3H), 2.06-1.46 (m, 9H), 1.01 (br d, J = 6.4 Hz, 6H) |
| I-49 | CQ | J | 778.4 | 12.25-12.20 (m, 1H), 11.07 (s, 1H), 10.71 (s, 1H), 7.51 (d, J = 2.0 Hz, 1H), 7.12 (s, 1H), 7.02 (s, 1H), 6.99 (d, J = 8.0 Hz, 1H), 6.96-6.92 (m, 1H), 6.86 (d, J = 8.0 Hz, 1H), 6.42 (br s, 1H), 5.33 (dd, J = 5.2, 12.8 Hz, 1H), 5.02-4.97 (m, 1H), 4.68 (t, J = 6.0 Hz, 2H), 3.73 (t, J = 6.0 Hz, 2H), 3.60-3.54 (m, 1H), 3.49-3.46 (m, 1H), 3.45 (br s, 3H), 3.44 (br d, J = 3.6 Hz, 4H), 3.43-3.40 (m, 2H), 3.39-3.34 (m, 4H), 3.30 (br s, 3H), 2.92-2.85 (m, 1H), 2.65-2.57 (m, 4H), 2.00 (br dd, J = 4.8, 10.3 Hz, 2H), 1.78 (br t, J = 7.2 Hz, 2H), 1.74 (br s, 2H), 1.02 (d, J = 6.4 Hz, 6H) |
| I-51 | CL | J | 790.4 | 12.44-11.99 (m, 1H), 11.07 (s, 1H), 10.72 (s, 1H), 7.51 (d, J = 2.0 Hz, 1H), 7.12 (d, J = 1.6 Hz, 1H), 7.03-6.97 (m, 2H), 6.85 (dd, J = 1.2, 8.4 Hz, 1H), 6.44 (br s, 1H), 5.33 (dd, J = 5.6, 12.8 Hz, 1H), 5.08-4.98 (m, 1H), 4.68 (t, J = 5.6 Hz, 2H), 3.73 (t, J = 5.6 Hz, 2H), 3.46-3.42 (m, 7H), 3.36 (s, 2H), 3.31 (s, 4H), 3.26-3.20 (m, 4H), 3.12 (br t, J = 8.4 Hz, 1H), 2.94-2.84 (m, 1H), 2.68-2.61 (m, 3H), 2.44-2.39 (m, 1H), 2.06-1.96 (m, 2H), 1.88 (ddd, J = 3.6, 6.4, 12.8 Hz, 1H), 1.83-1.68 (m, 10H) |
| I-52 | AS | CE | 788.5 | 12.41-12.02 (m, 1H), 10.73 (br s, 1H), 8.38 (s, 1H), 7.11 (s, 1H), 7.04-6.92 (m, 3H), 6.83 (d, J = 8.4 Hz, 1H), 6.40 (br s, 1H), 5.39 (dd, J = 5.2, 12.9 Hz, 1H), 5.09-4.97 (m, 1H), 4.36 (s, 2H), 4.04 (s, 3H), 3.84 (s, 1H), 3.57 (qd, J = 6.8, 13.6 Hz, 1H), 3.42-3.40 (m, 2H), 3.32 (br s, 3H), 3.02 (s, 3H), 2.98-2.92 (m, 1H), 2.82-2.69 (m, 2H), 2.58 (br t, J = 7.6 Hz, 2H), 2.05-1.98 (m, 2H), 1.92-1.85 (m, 1H), 1.76-1.69 (m, 2H), 1.60-1.55 (m, 2H), 1.51-1.46 (m, 2H), 1.26 (br d, J = 9 Hz, 12H), 1.03 (d, J = 6.4 Hz, 6H) |
| I-55 | CJ | H | 822.4 | 12.23 (br s, 1H), 11.07 (br s, 1H), 10.71 (br s, 1H), 8.47 (s, 1H), 7.50 (d, J = 2.0 Hz, 1H), 7.12 (d, J = 1.2 Hz, 1H), 6.95 (d, J = 5.2 Hz, 2H), 6.88-6.84 (m, 1H), 6.42 (br s, 1H), 5.36 (dd, J = 5.2, 12.6 Hz, 1H), 5.00 (br d, J = 3.6 Hz, 1H), 4.67 (t, J = 5.6 Hz, 2H), 3.72 (t, J = 6.0 Hz, 2H), 3.62-3.56 (m, 1H), 3.55 (s, 3H), 3.51-3.48 (m, 4H), 3.48 (br s, 4H), 3.45 (br d, J = 4.8 Hz, 4H), 3.44 (br s, 4H), 3.43 (br s, 3H), 3.11-3.03 (m, 1H), 2.96-2.92 (m, 2H), 2.90-2.83 (m, 1H), 2.72-2.62 (m, 2H), 2.52 (d, J = 2.0 Hz, 2H), 2.04-1.96 (m, 2H), 1.93-1.86 (m, 1H), 1.84-1.79 (m, 2H), 1.77-1.69 (m, 2H), 1.66-1.57 (m, 1H), 1.03 (d, J = 6.4 Hz, 6H) |
| I-57[b] | BH | H | 758.4 | 11.09 (s, 1H), 10.75 (s, 1H), 7.51 (d, J = 2.0 Hz, 1H), 7.09 (d, J = 2.0 Hz, 1H), 6.95 (br d, J = 4.8 Hz, 2H), 6.89-6.83 (m, 1H), 6.40 (s, 1H), 5.36 (br dd, J = 5.6, 12.6 Hz, 1H), 5.01 (br s, 1H), 4.63 (br t, J = 6.8 Hz, 2H), 3.62-3.53 (m, 6H), 3.15-2.99 (m, 2H), 2.96-2.83 (m, 3H), 2.77-2.55 (m, 5H), 2.44-2.24 (m, 8H), 2.09-1.96 (m, 2H), 1.95-1.84 (m, 1H), 1.81-1.55 (m, 5H), 1.03 (d, J = 6.4 Hz, 6H) |
| I-58[b] | BH | J | 758.4 | 11.08 (s, 1H), 10.75 (s, 1H), 8.20 (s, 1H), 7.51 (d, J = 2.0 Hz, 1H), 7.09 (d, J = 1.6 Hz, 1H), 7.03 (s, 1H), 6.99 (d, J = 8.0 Hz, 1H), 6.95 (br d, J = 7.6 Hz, 1H), 6.86 (d, J = 8.4 Hz, 1H), 6.40 (s, 1H), 5.33 (dd, J = 5.2, 12.7 Hz, 1H), 5.00 (br d, J = 3.2 Hz, 1H), 4.63 (br t, J = 6.4 Hz, 2H), 3.58 (br dd, J = 7.2, 13.7 Hz, 3H), 3.32 (s, 3H), 3.14-3.00 (m, 2H), 2.95-2.84 (m, 1H), 2.69-2.62 (m, 3H), 2.59 (br t, J = 7.2 Hz, 2H), 2.47-2.26 (m, 8H), 2.23 (br t, J = 7.2 Hz, 2H), 2.10-1.97 (m, 2H), 1.95-1.84 (m, 1H), 1.81-1.55 (m, 5H), 1.03 (d, J = 6.4 Hz, 6H) |

TABLE 8-continued

Compounds synthesized via Method 5, coupling the corresponding alkynes with bromides in Step 1.

| I-#[a] | Alkyne | Bromide | LCMS (ESI+) m/z (M + H)+ | 1H NMR (400 MHz, DMSO-d$_6$) δ |
|---|---|---|---|---|
| I-59 | CJ | J | 822.4 | 12.26-12.18 (m, 1H), 11.07 (br s, 1H), 10.70 (s, 1H), 7.51 (d, J = 1.6 Hz, 1H), 7.12 (s, 1H), 7.02 (s, 1H), 6.99 (d, J = 8.0 Hz, 1H), 6.97-6.90 (m, 1H), 6.85 (d, J = 8.0 Hz, 1H), 6.42 (br s, 1H), 5.32 (dd, J = 5.2, 12.8 Hz, 1H), 5.00 (br dd, J = 1.6, 3.5 Hz, 1H), 4.67 (t, J = 5.6 Hz, 2H), 3.72 (t, J = 5.6 Hz, 2H), 3.57 (dd, J = 6.8, 13.6 Hz, 1H), 3.50-3.48 (m, 2H), 3.47 (d, J = 2.4 Hz, 2H), 3.46 (d, J = 2.4 Hz, 2H), 3.45-3.43 (m, 5H), 3.40-3.35 (m, 4H), 3.10-3.03 (m, 1H), 2.93-2.85 (m, 1H), 2.67-2.61 (m, 4H), 2.52 (br d, J = 2.0 Hz, 2H), 2.04-1.96 (m, 2H), 1.92-1.85 (m, 1H), 1.82-1.77 (m, 2H), 1.76-1.69 (m, 2H), 1.65-1.56 (m, 1H), 1.03 (d, J = 6.4 Hz, 6H) |
| I-61 | Z | CE | 772.4 | 12.09 (br d, J = 1.6 Hz, 1H), 10.33 (br s, 1H), 8.33 (s, 1H), 8.04 (s, 1H), 7.06-6.91 (m, 3H), 6.84 (d, J = 8.0 Hz, 1H), 6.38 (br s, 1H), 5.40 (dd, J = 5.2, 12.8 Hz, 1H), 5.00 (br d, J = 4.4 Hz, 1H), 4.11 (br t, J = 6.8 Hz, 3H), 3.63-3.53 (m, 4H), 3.18-2.99 (m, 8H), 2.79 (br d, J = 2.8 Hz, 2H), 2.77-2.65 (m, 8H), 2.62-2.56 (m, 9H), 2.06-1.95 (m, 3H), 1.95-1.84 (m, 2H), 1.82-1.67 (m, 6H), 1.59 (br dd, J = 4.8, 7.2 Hz, 4H), 1.33-1.18 (m, 18H), 1.03 (br d, J = 6.4 Hz, 7H) |
| I-63[b] | Z | BO | 740.7 | 12.34-11.82 (m, 1H), 10.53 (s, 1H), 10.32 (s, 1H), 9.48 (s, 1H), 8.55 (s, 1H), 8.36-8.28 (m, 1H), 8.03 (s, 1H), 7.83 (d, J = 8.4 Hz, 1H), 7.72 (dd, J = 7.2, 8.4 Hz, 1H), 7.53 (d, J = 6.4 Hz, 1H), 6.95 (br d, J = 7.2 Hz, 1H), 6.37 (br d, J = 1.2 Hz, 1H), 5.00 (br s, 1H), 4.10 (t, J = 7.2 Hz, 2H), 3.91 (qd, J = 4.8, 12.4 Hz, 1H), 3.76-3.66 (m, 1H), 3.62-3.49 (m, 1H), 3.06-2.94 (m, 2H), 2.75 (td, J = 5.6, 16.4 Hz, 1H), 2.70-2.64 (m, 1H), 2.05-1.82 (m, 3H), 1.81-1.64 (m, 7H), 1.35-1.16 (m, 14H), 1.03 (d, J = 6.4 Hz, 6H) |
| I-64[b] | Z | BN | 729.8 | 10.65 (s, 1H), 10.34 (br s, 1H), 8.39-8.28 (m, 1H), 8.14 (d, J = 6.6 Hz, 1H), 8.04 (s, 1H), 7.52 (s, 1H), 7.09 (d, J = 6.8 Hz, 1H), 6.88 (t, J = 6.8 Hz, 1H), 6.38 (br s, 1H), 5.08-4.92 (m, 1H), 4.11 (t, J = 6.8 Hz, 2H), 3.79 (br t, J = 6.4 Hz, 2H), 2.95-2.76 (m, 5H), 2.10-1.96 (m, 2H), 1.95-1.84 (m, 1H), 1.82-1.66 (m, 7H), 1.65-1.56 (m, 1H), 1.43-1.13 (m, 18H), 1.03 (d, J = 6.4 Hz, 6H) |
| I-65[b,c] | BJ | BO | 760.4 | 12.19-12.00 (m, 1H), 10.54 (s, 1H), 10.35 (br s, 1H), 9.50 (s, 1H), 8.56 (s, 1H), 8.33 (s, 1H), 8.05 (s, 1H), 7.85 (d, J = 8.4 Hz, 1H), 7.78-7.71 (m, 1H), 7.53 (d, J = 7.0 Hz, 1H), 7.02-6.86 (m, 1H), 6.40 (br d, J = 0.8 Hz, 1H), 5.06-4.93 (m, 1H), 4.27 (t, J = 5.1 Hz, 2H), 3.92 (ddd, J = 5.2, 9.6, 12.0 Hz, 1H), 3.79 (t, J = 5.2 Hz, 2H), 3.71 (td, J = 5.6, 12.0 Hz, 1H), 3.55-3.49 (m, 9H), 3.46 (t, J = 6.4 Hz, 3H), 3.23 (br dd, J = 5.6, 8.4 Hz, 3H), 3.09-2.92 (m, 3H), 2.76 (td, J = 5.2, 16.8 Hz, 1H), 2.06-1.97 (m, 1H), 1.96-1.85 (m, 4H), 1.77-1.67 (m, 2H), 1.65-1.56 (m, 1H), 1.03 (br d, J = 6.4 Hz, 6H) |
| I-66[b] | BJ | BN | 749.3 | 12.22-11.85 (m, 1H), 10.64 (br s, 1H), 10.36 (br s, 1H), 8.32 (s, 1H), 8.14 (d, J = 6.4 Hz, 1H), 8.05 (s, 1H), 7.51 (s, 1H), 7.08 (d, J = 6.8 Hz, 1H), 6.95 (br d, J = 7.2 Hz, 1H), 6.87 (t, J = 6.8 Hz, 1H), 6.73 (s, 1H), 6.37 (br s, 1H), 4.99 (br d, J = 4.0 Hz, 1H), 4.27 (t, J = 5.2 Hz, 2H), 3.78 (br t, J = 5.2 Hz, 4H), 3.58-3.54 (m, 1H), 3.51 (br d, J = 1.2 Hz, 4H), 3.49 (br s, 1H), 3.48 (br d, J = 1.2 Hz, 4H), 3.43 (s, 2H), 3.07-3.02 (m, 1H), 2.92 (br t, J = 7.6 Hz, 2H), 2.82 (br s, 2H), 2.04-1.98 (m, 2H), 1.97-1.93 (m, 2H), 1.72 (br d, J = 8.4 Hz, 2H), 1.67-1.53 (m, 2H), 1.02 (br d, J = 6.4 Hz, 6H) |
| I-67[c,d] | Z | BO | 736.3 | 10.57 (s, 1H), 10.32 (s, 1H), 9.54 (s, 1H), 8.62 (s, 1H), 8.32 (s, 1H), 8.03 (s, 1H), 7.98 (dd, J = 3.2, 6.4 Hz, 1H), 7.82-7.74 (m, 2H), 6.95 (br d, J = 8.4 Hz, 1H), 6.37 (br s, 1H), 4.99 (br d, J = 3.2 Hz, 1H), 4.09 (t, J = 6.8 Hz, 2H), 3.94 (ddd, J = 5.2, 10.0, 12.4 Hz, 1H), 3.71 (td, J = 6.0, 12.4 Hz, 1H), 3.63-3.49 (m, 1H), 3.07-2.94 (m, 2H), 2.80-2.69 (m, 1H), 2.62 (t, J = 6.8 Hz, 2H), 2.04-1.98 (m, 1H), 1.95-1.83 (m, 1H), 1.81-1.56 (m, 8H), 1.52-1.46 (m, 2H), 1.36-1.27 (m, 6H), 1.23 (br s, 3H), 1.02 (d, J = 6.4 Hz, 6H) |
| I-68[d] | Z | BN | 725.4 | 12.25-11.96 (m, 1H), 10.67 (s, 1H), 10.32 (br s, 1H), 8.33 (s, 1H), 8.03 (s, 1H), 7.56 (s, 1H), 7.37 (d, J = 6.4 Hz, 1H), 7.02-6.86 (m, 2H), 6.46-6.29 (m, 1H), 5.10-4.89 (m, 1H), 4.10 (t, J = 7.2 Hz, 2H), 3.79 (br t, J = 6.4 Hz, 2H), 3.64-3.50 (m, 1H), 3.10-3.01 (m, 1H), 2.89-2.76 (m, 2H), 2.71-2.64 (m, 1H), 2.04-1.97 (m, 1H), 1.92-1.85 (m, 1H), 1.79-1.69 (m, 4H), 1.65-1.40 (m, 6H), 1.36-1.11 (m, 10H), 1.03 (d, J = 6.4 Hz, 6H) |

TABLE 8-continued

Compounds synthesized via Method 5, coupling the corresponding alkynes with bromides in Step 1.

| I-#[a] | Alkyne | Bromide | LCMS (ESI+) m/z (M + H)+ | 1H NMR (400 MHz, DMSO-d$_6$) δ |
|---|---|---|---|---|
| I-72 | BJ | H | 778.2 | 11.09 (br s, 1H), 10.35 (s, 1H), 8.32 (s, 1H), 8.05 (s, 1H), 7.03-6.89 (m, 3H), 6.85 (dd, J = 3.2, 5.6 Hz, 1H), 6.37 (s, 1H), 5.35 (dd, J = 5.6, 12.4 Hz, 1H), 5.00 (br s, 1H), 4.27 (t, J = 5.2 Hz, 2H), 3.78 (t, J = 5.2 Hz, 2H), 3.54 (s, 3H), 3.52-3.47 (m, 8H), 3.44-3.42 (m, 3H), 3.15-2.97 (m, 2H), 2.95-2.90 (m, 2H), 2.88 (br d, J = 1.2 Hz, 1H), 2.72-2.60 (m, 2H), 2.07-1.95 (m, 2H), 1.93-1.84 (m, 1H), 1.84-1.77 (m, 2H), 1.76-1.67 (m, 2H), 1.65-1.55 (m, 1H), 1.02 (br d, J = 6.4 Hz, 6H) |
| I-73[b,c] | BJ | BM | 760.5 | 12.30-11.85 (m, 1H), 10.53 (s, 1H), 10.36 (br s, 1H), 9.22 (s, 1H), 8.47 (s, 1H), 8.32 (s, 1H), 8.05 (s, 1H), 7.97 (s, 1H), 7.90 (d, J = 8.4 Hz, 1H), 7.69 (d, J = 8.4 Hz, 1H), 6.95 (br d, J = 7.2 Hz, 1H), 6.38 (br s, 1H), 4.99 (br d, J = 4.0 Hz, 1H), 4.27 (t, J = 5.2 Hz, 2H), 3.92 (ddd, J = 5.2, 9.9, 12.1 Hz, 1H), 3.83-3.66 (m, 3H), 3.62-3.44 (m, 9H), 3.39 (br d, J = 6.4 Hz, 3H), 3.08-2.90 (m, 2H), 2.82 (br t, J = 7.6 Hz, 2H), 2.48-2.40 (m, 1H), 2.08-1.54 (m, 7H), 1.02 (br d, J = 6.4 Hz, 6H) |
| I-74[b] | BJ | AZ | 749.5 | 10.67-10.56 (m, 1H), 10.33 (s, 1H), 8.32 (s, 1H), 8.18 (d, J = 7.2 Hz, 1H), 8.05 (s, 1H), 7.47 (s, 1H), 7.33 (s, 1H), 6.96-6.88 (m, 1H), 6.83 (dd, J = 1.2, 7.2 Hz, 1H), 6.37 (s, 1H), 5.00 (br d, J = 3.2 Hz, 1H), 4.31-4.24 (m, 2H), 3.84-3.74 (m, 4H), 3.62-3.56 (m, 1H), 3.54-3.44 (m, 9H), 3.39 (br t, J = 6.4 Hz, 3H), 3.09-3.01 (m, 1H), 2.82 (br t, J = 6.4 Hz, 2H), 2.66 (br t, J = 7.6 Hz, 2H), 2.46 (br d, J = 7.2 Hz, 1H), 2.06-1.55 (m, 7H), 1.03 (d, J = 6.4 Hz, 6H) |
| I-75 | BJ | J | 778.3 | 12.10 (br s, 1H), 11.08 (s, 1H), 10.36 (br s, 1H), 8.33 (s, 1H), 8.06 (s, 1H), 7.03-6.93 (m, 3H), 6.85 (d, J = 8.0 Hz, 1H), 6.38 (br s, 1H), 5.34 (dd, J = 5.2, 12.8 Hz, 1H), 5.00 (br d, J = 3.6 Hz, 1H), 4.28 (t, J = 5.2 Hz, 2H), 3.79 (t, J = 5.2 Hz, 2H), 3.62-3.54 (m, 1H), 3.54-3.50 (m, 4H), 3.50-3.46 (m, 4H), 3.39-3.36 (m, 2H), 3.33 (br s, 3H), 3.09-3.00 (m, 1H), 2.95-2.85 (m, 1H), 2.76-2.67 (m, 1H), 2.64 (br d, J = 6.8 Hz, 2H), 2.61 (s, 1H), 2.48-2.43 (m, 1H), 2.03-1.96 (m, 2H), 1.93-1.85 (m, 1H), 1.82-1.70 (m, 4H), 1.65-1.56 (m, 1H), 1.03 (br d, J = 6.4 Hz, 6H) |
| I-76[d] | AD | H | 768.2 | 12.49-11.87 (m, 1H), 11.55-10.60 (m, 1H), 9.87-9.42 (m, 1H), 7.85 (d, J = 2.4 Hz, 1H), 7.17-6.89 (m, 4H), 6.77 (d, J = 2.4 Hz, 1H), 6.36 (br s, 1H), 5.38 (dd, J = 5.2, 12.8 Hz, 1H), 5.06-4.94 (m, 1H), 4.16 (br t, J = 7.2 Hz, 2H), 3.67-3.50 (m, 4H), 3.05 (br d, J = 6.8 Hz, 1H), 2.95-2.83 (m, 1H), 2.73-2.58 (m, 2H), 2.45 (br s, 1H), 2.06-1.96 (m, 2H), 1.95-1.48 (m, 9H), 1.45-1.35 (m, 2H), 1.26 (br s, 11H), 1.03 (d, J = 6.6 Hz, 6H) |
| I-77 | BL | J | 822.7 | 12.11 (br s, 1H), 11.09 (s, 1H), 10.35 (s, 1H), 8.33 (s, 1H), 8.06 (s, 1H), 7.08-6.91 (m, 3H), 6.86 (dd, J = 1.2, 8.0 Hz, 1H), 6.38 (br s, 1H), 5.34 (dd, J = 5.2, 12.8 Hz, 1H), 5.00 (br d, J = 3.2 Hz, 1H), 4.27 (t, J = 5.2 Hz, 2H), 3.77 (t, J = 5.2 Hz, 2H), 3.57-3.43 (m, 13H), 3.38 (br t, J = 6.4 Hz, 2H), 3.32 (s, 4H), 3.12-3.01 (m, 1H), 2.95-2.84 (m, 1H), 2.77-2.58 (m, 4H), 2.09-1.58 (m, 8H), 1.03 (br d, J = 6.4 Hz, 6H) |
| I-82 | X | J | 734.4 | 12.22 (br s, 1H), 11.07 (s, 1H), 10.72 (br s, 1H), 7.51 (d, J = 2.0 Hz, 1H), 7.12 (s, 1H), 7.03-6.88 (m, 3H), 6.84 (br d, J = 7.6 Hz, 1H), 6.42 (br s, 1H), 5.32 (dd, J = 5.2, 12.8 Hz, 1H), 4.98 (br d, J = 2.4 Hz, 1H), 4.69 (br t, J = 5.6 Hz, 2H), 3.75 (t, J = 5.6 Hz, 2H), 3.64-3.51 (m, 1H), 3.51-3.37 (m, 5H), 3.08-3.04 (m, 1H), 2.95-2.84 (m, 2H), 2.77-2.58 (m, 5H), 2.04-1.82 (m, 5H), 1.77-1.57 (m, 6H), 1.02 (d, J = 6.4 Hz, 6H) |
| I-83 | BF | J | 778.4 | 12.23 (br s, 1H), 11.07 (s, 1H), 10.72 (s, 1H), 7.51 (d, J = 2.0 Hz, 1H), 7.12 (s, 1H), 7.04-6.97 (m, 2H), 6.85 (d, J = 8.4 Hz, 1H), 6.41 (br s, 1H), 5.33 (dd, J = 5.2, 12.4 Hz, 1H), 4.68 (t, J = 5.6 Hz, 2H), 3.73 (t, J = 5.6 Hz, 2H), 3.57 (br dd, J = 6.8, 13.2 Hz, 1H), 3.50-3.40 (m, 8H), 3.31-3.26 (m, 6H), 3.14-2.99 (m, 1H), 2.97-2.83 (m, 1H), 2.76-2.60 (m, 4H), 2.47-2.42 (m, 2H), 2.09-1.95 (m, 2H), 1.88 (ddd, J = 4.0, 6.4, 12.8 Hz, 1H), 1.83-1.67 (m, 4H), 1.66-1.55 (m, 1H), 1.03 (d, J = 6.4 Hz, 6H) |
| I-85 | AF | J | 734.4 | 12.10 (br d, J = 2.6 Hz, 1H), 11.14-10.99 (m, 1H), 10.35 (br s, 1H), 8.37-8.31 (m, 1H), 8.07 (s, 1H), 7.03-6.94 (m, 2H), 6.85 (d, J = 8.6 Hz, 1H), 6.39 (br s, 1H), 5.33 (dd, J = 5.2, 12.9 Hz, 1H), 5.06-4.94 (m, 1H), 4.34-4.25 (m, 2H), 3.80 (t, J = 5.32 Hz, 2H), 3.64-3.56 (m, 1H), 3.56-3.50 (m, 2H), |

TABLE 8-continued

Compounds synthesized via Method 5, coupling the corresponding alkynes with bromides in Step 1.

| I-#[a] | Alkyne | Bromide | LCMS (ESI+) m/z (M + H)+ | ¹H NMR (400 MHz, DMSO-d$_6$) δ |
|---|---|---|---|---|
| | | | | 3.49-3.44 (m, 2H), 3.39-3.35 (m, 2H), 3.31 (s, 3H), 3.12-2.99 (m, 1H), 2.97-2.84 (m, 1H), 2.64-2.59 (m, 2H), 2.55-2.53 (m, 1H), 2.07-1.53 (m, 10H), 1.03 (br d, J = 6.4 Hz, 6H) |
| I-87 | AB | J | 730.5 | 12.23 (br d, J = 2.1 Hz, 1H), 11.15-11.01 (m, 1H), 10.70 (br s, 1H), 7.49 (d, J = 2.0 Hz, 1H), 7.13 (d, J = 1.4 Hz, 1H), 6.99-6.90 (m, 3H), 6.84 (br dd, J = 3.6, 5.2 Hz, 1H), 6.41 (br s, 1H), 5.35 (dd, J = 5.2, 12.4 Hz, 1H), 4.99 (br d, J = 2.8 Hz, 1H), 4.50 (br t, J = 7.2 Hz, 2H), 3.62-3.55 (m, 1H), 3.53 (s, 3H), 3.12-3.01 (m, 1H), 2.95-2.81 (m, 3H), 2.74-2.58 (m, 2H), 2.04-1.85 (m, 3H), 1.75-1.51 (m, 7H), 1.37-1.18 (m, 10H), 1.03 (d, J = 6.5 Hz, 6H) |
| I-89 | AM | H | 772.8 | 12.39-12.07 (m, 1H), 11.25-10.95 (m, 1H), 10.71 (br s, 1H), 7.48 (d, J = 1.6 Hz, 1H), 7.12 (d, J = 1.2 Hz, 1H), 6.94 (br d, J = 5.2 Hz, 3H), 6.87-6.82 (m, 1H), 6.40 (br s, 1H), 5.35 (br dd, J = 5.2, 12.5 Hz, 1H), 5.09-4.93 (m, 1H), 4.50 (br t, J = 6.8 Hz, 2H), 3.63-3.50 (m, 4H), 3.17-3.02 (m, 1H), 2.91-2.82 (m, 3H), 2.78-2.58 (m, 2H), 2.08-1.95 (m, 2H), 1.94-1.83 (m, 1H), 1.78-1.52 (m, 7H), 1.41-1.14 (m, 17H), 1.03 (d, J = 6.4 Hz, 6H) |
| I-90 | BF | H | 778.4 | 12.29-12.15 (m, 1H), 11.15-11.01 (m, 1H), 10.76-10.65 (m, 1H), 7.50 (d, J = 2.0 Hz, 1H), 7.11 (s, 1H), 6.95 (br d, J = 5.2 Hz, 3H), 6.89-6.82 (m, 1H), 6.42 (br s, 1H), 5.36 (dd, J = 5.2, 12.6 Hz, 1H), 5.07-4.92 (m, 1H), 4.68 (t, J = 5.6 Hz, 2H), 3.73 (t, J = 5.6 Hz, 2H), 3.54 (s, 3H), 3.49-3.38 (m, 10H), 3.14-2.99 (m, 1H), 2.97-2.81 (m, 3H), 2.77-2.61 (m, 2H), 2.45-2.36 (m, 2H), 2.07-1.96 (m, 2H), 1.93-1.69 (m, 5H), 1.66-1.56 (m, 1H), 1.02 (d, J = 6.4 Hz, 6H) |
| I-91[b,c] | BD | J | 730.6 | 12.22-11.95 (m, 1H), 11.07 (br s, 1H), 10.44-10.23 (m, 1H), 8.33 (s, 1H), 8.03 (s, 1H), 7.02-6.94 (m, 3H), 6.84 (d, J = 7.2 Hz, 1H), 6.37 (br s, 1H), 5.32 (dd, J1 = 12.8 Hz, J2 = 5.6 Hz, 1H), 5.00 (br d, J = 4.4 Hz, 1H), 4.10 (t, J = 6.8 Hz, 2H), 3.61-3.52 (m, 1H), 3.31 (s, 3H), 3.05 (br dd, J1 = 8.8 Hz, J2 = 7.6 Hz, 1H), 2.95-2.83 (m, 1H), 2.68-2.56 (m, 4H), 2.00 (br dd, J1 = 10.8 Hz, J2 = 5.6 Hz, 2H), 1.93-1.85 (m, 1H), 1.78-1.70 (m, 4H), 1.58 (br d, J = 6.4 Hz, 3H), 1.25 (br d, J = 5.2 Hz, 11H), 1.03 (d, J = 6.4 Hz, 6H) |
| I-92[b] | BD | H | 730.7 | 12.09 (br s, 1H), 11.08 (s, 1H), 10.32 (br s, 1H), 8.33 (s, 1H), 8.03 (s, 1H), 7.00-6.89 (m, 3H), 6.88-6.80 (m, 1H), 6.39 (br s, 1H), 5.35 (br dd, J$_1$ = 12.4 Hz, J$_2$ = 5.6 Hz, 1H), 5.05-4.94 (m, 1H), 4.10 (t, J = 6.8 Hz, 2H), 3.64-3.46 (m, 4H), 3.11-2.99 (m, 1H), 2.90-2.85 (m, 2H), 2.73-2.60 (m, 2H), 2.03-1.96 (m, 2H), 1.93-1.85 (m, 1H), 1.80-1.67 (m, 4H), 1.63-1.52 (m, 3H), 1.41-1.18 (m, 12H), 1.03 (d, J = 6.4 Hz, 6H) |
| I-96[b] | Z | J | 758.4 | 12.17-12.00 (m, 1H), 11.07 (br s, 1H), 10.40-10.26 (m, 1H), 8.33 (s, 1H), 8.03 (s, 1H), 7.06-6.91 (m, 3H), 6.84 (d, J = 8.4 Hz, 1H), 6.44-6.32 (m, 1H), 5.41-5.23 (m, 1H), 5.09-4.92 (m, 1H), 4.10 (t, J = 6.8 Hz, 2H), 3.65-3.51 (m, 1H), 3.29 (br s, 3H), 3.14-2.80 (m, 2H), 2.70 (s, 1H), 2.58 (br t, J = 7.6 Hz, 2H), 2.10-1.82 (m, 4H), 1.82-1.50 (m, 8H), 1.30-1.18 (m, 14H), 1.03 (d, J = 6.4 Hz, 6H) |
| I-97[b] | Z | H | 758.4 | 12.17-12.00 (m, 1H), 11.18-11.01 (m, 1H), 10.41-10.25 (m, 1H), 8.33 (s, 1H), 8.03 (s, 1H), 6.95 (m, 3H), 6.88-6.81 (m, 1H), 6.44-6.32 (m, 1H), 5.36 (dd, J = 5.2, 12.8 Hz, 1H), 5.05-4.95 (m, 1H), 4.10 (t, J = 6.8 Hz, 2H), 3.62-3.50 (m, 4H), 3.15-2.97 (m, 1H), 2.96-2.82 (m, 3H), 2.67-2.61 (m, 1H), 2.07-1.82 (m, 4H), 1.82-1.69 (m, 4H), 1.64-1.54 (m, 3H), 1.42-1.17 (m, 15H), 1.03 (d, J = 6.4 Hz, 6H) |
| I-99 | AS | J | 774.3 | CD3Cl) δ 10.04-9.67 (m, 1H), 7.08-6.57 (m, 5H), 5.61-5.42 (m, 1H), 5.38-5.13 (m, 2H), 4.54-4.36 (m, 2H), 4.25-4.15 (m, 3H), 3.95-3.72 (m, 1H), 3.53-3.45 (m, 2H), 3.44-3.41 (m, 3H), 3.40-3.18 (m, 1H), 2.98-2.70 (m, 3H), 2.69-2.61 (m, 2H), 2.54-2.38 (m, 1H), 2.30-2.15 (m, 2H), 2.05-1.89 (m, 4H), 1.64-1.52 (m, 4H), 1.38-1.21 (m, 11H), 1.15 (br d, J = 6.8 Hz, 6H), 0.93-0.75 (m, 1H) |
| I-100 | AS | H | 774.3 | CDCl$_3$) δ 10.61 (s, 1H), 7.17-7.05 (m, 1H), 7.03-6.85 (m, 3H), 6.71-6.59 (m, 1H), 5.69-5.52 (m, 1H), 5.36-5.27 (m, 1H), 5.25-5.17 (m, 1H), 4.77 (br d, J = 5.2 Hz, 1H), 4.50-4.44 (m, 2H), 4.20 (d, J = 2.4 Hz, 3H), 3.85-3.77 (m, 1H), 3.67 (d, J = 16.0 Hz, 3H), 3.55-3.46 (m, 2H), 3.44-3.22 (m, 1H), 2.93-2.86 (m, 3H), 2.83-2.70 (m, 2H), 2.53-2.42 (m, 1H), 2.28-2.18 (m, 2H), 2.07-1.91 (m, 5H), 1.67-1.31 (m, 14H), 1.15 (br d, J = 6.4 Hz, 6H) |

TABLE 8-continued

Compounds synthesized via Method 5, coupling the corresponding alkynes with bromides in Step 1.

| I-#[a] | Alkyne | Bromide | LCMS (ESI+) m/z (M + H)+ | 1H NMR (400 MHz, DMSO-d$_6$) δ |
|---|---|---|---|---|
| I-101 | AP | H | 746.2 | 12.22 (br s, 1H), 11.08 (br s, 1H), 10.71 (br s, 1H), 7.12 (s, 1H), 6.97-6.91 (m, 3H), 6.85 (dd, J = 3.6, 5.6 Hz, 1H), 6.42 (br s, 1H), 5.35 (dd, J = 5.2, 12.8 Hz, 1H), 5.07-4.95 (m, 1H), 4.36 (s, 2H), 4.04 (s, 3H), 3.62-3.56 (m, 1H), 3.54 (s, 3H), 3.41 (t, J = 6.4 Hz, 2H), 3.13-3.02 (m, 1H), 2.93-2.81 (m, 3H), 2.74-2.58 (m, 2H), 2.52 (d, J = 2.0 Hz, 1H), 2.08-1.95 (m, 2H), 1.93-1.83 (m, 1H), 1.79-1.67 (m, 2H), 1.64-1.47 (m, 5H), 1.41-1.29 (m, 6H), 1.03 (d, J = 6.4 Hz, 6H) |
| I-102 | AX | J | 744.1 | 12.22-11.82 (m, 1H), 11.08 (br s, 1H), 10.34 (br s, 1H), 7.56 (s, 1H), 7.30 (s, 1H), 7.05-6.97 (m, 2H), 6.93 (br d, J = 7.6 Hz, 1H), 6.85 (br d, J = 7.6 Hz, 1H), 6.28 (br s, 1H), 5.33 (br dd, J = 5.2, 12.5 Hz, 1H), 4.98 (br d, J = 1.6 Hz, 1H), 4.01 (br t, J = 6.8 Hz, 2H), 3.67-3.48 (m, 1H), 3.39 (s, 2H), 3.02 (td, J = 8.0, 15.3 Hz, 1H), 2.96-2.81 (m, 1H), 2.77-2.56 (m, 4H), 2.47-2.39 (m, 1H), 2.06-1.94 (m, 2H), 1.93-1.81 (m, 1H), 1.79-1.49 (m, 6H), 1.25 (br d, J = 9.2 Hz, 10H), 1.02 (br d, J = 6.0 Hz, 6H) |
| I-104 | AX | H | 744.4 | 12.23-11.75 (m, 1H), 11.09 (br s, 1H), 10.34 (s, 1H), 7.56 (s, 1H), 7.30 (s, 1H), 6.99-6.91 (m, 3H), 6.89-6.83 (m, 1H), 6.28 (br s, 1H), 5.36 (dd, J = 5.2, 12.6 Hz, 1H), 4.98 (br d, J = 2.0 Hz, 1H), 4.02 (t, J = 7.2 Hz, 2H), 3.62-3.51 (m, 4H), 3.44-3.38 (m, 2H), 3.09-2.97 (m, 1H), 2.95-2.81 (m, 3H), 2.77-2.58 (m, 2H), 2.47-2.38 (m, 1H), 2.06-1.95 (m, 2H), 1.93-1.80 (m, 1H), 1.79-1.49 (m, 7H), 1.45-1.13 (m, 10H), 1.02 (br d, J = 6.2 Hz, 6H) |
| I-106 | AP | J | 774.3 (M − H) | 12.22 (br s, 1H), 11.07 (br s, 1H), 10.71 (br s, 1H), 7.11 (s, 1H), 7.03-6.93 (m, 3H), 6.84 (br d, J = 7.6 Hz, 1H), 6.42 (br s, 1H), 5.32 (br dd, J = 5.2, 12.6 Hz, 1H), 5.00 (br d, J = 2.0 Hz, 1H), 4.36 (s, 2H), 4.04 (s, 3H), 3.63-3.51 (m, 1H), 3.41 (t, J = 6.4 Hz, 2H), 3.31 (br s, 3H), 3.12-3.01 (m, 1H), 2.94-2.83 (m, 1H), 2.74-2.55 (m, 4H), 2.08-1.83 (m, 3H), 1.83-1.43 (m, 8H), 1.29 (br s, 6H), 1.03 (d, J = 6.4 Hz, 6H) |
| I-122 | FV | J | 834.4 | 12.23 (br s, 1H), 11.07 (br s, 1H), 10.80-10.61 (m, 1H), 7.51 (d, J = 2.0 Hz, 1H), 7.12 (d, J = 1.6 Hz, 1H), 7.05-6.95 (m, 2H), 6.85 (d, J = 8.0 Hz, 1H), 6.44 (br s, 1H), 5.37-5.26 (m, 1H), 5.07-5.00 (m, 1H), 4.68 (t, J = 5.6 Hz, 2H), 3.72 (t, J = 5.6 Hz, 2H), 3.49-3.42 (m, 12H), 3.31 (br s, 3H), 3.27-3.21 (m, 5H), 3.16-3.05 (m, 2H), 2.96-2.82 (m, 2H), 2.68-2.57 (m, 5H), 2.06-1.97 (m, 2H), 1.92-1.86 (m, 1H), 1.81-1.73 (m, 8H) |
| I-137 | AS | AZ | 745.4 | 12.35-12.05 (m, 1H), 10.71-10.67 (m, 1H), 10.80-10.50 (m, 2H), 8.18 (d, J = 7.2 Hz, 1H), 7.46 (s, 1H), 7.33 (s, 1H), 7.11 (s, 1H), 6.95 (br d, J = 7.2 Hz, 1H), 6.83 (dd, J = 1.6, 7.1 Hz, 1H), 6.47-6.39 (m, 1H), 5.00 (br d, J = 2.0 Hz, 1H), 4.36 (s, 2H), 4.04 (s, 3H), 3.77 (t, J = 6.8 Hz, 2H), 3.57 (qd, J = 6.8, 13.7 Hz, 1H), 3.46-3.35 (m, 3H), 3.13-3.00 (m, 1H), 2.81 (br t, J = 6.4 Hz, 2H), 2.62 (br t, J = 7.2 Hz, 2H), 2.02 (qd, J = 7.2, 15.2 Hz, 1H), 1.94-1.84 (m, 1H), 1.77-1.68 (m, 2H), 1.60 (br s, 3H), 1.52-1.46 (m, 2H), 1.27 (br d, J = 12.8 Hz, 10H), 1.03 (d, J = 6.4 Hz, 6H) |
| I-141 | FA | AZ | 729.5 | 12.57-11.46 (m, 1H), 10.63 (s, 1H), 10.34 (br s, 1H), 8.33 (s, 1H), 8.18 (d, J = 7.2 Hz, 1H), 8.03 (s, 1H), 7.47 (s, 1H), 7.32 (s, 1H), 6.95 (br d, J = 7.2 Hz, 1H), 6.83 (d, J = 7.2 Hz, 1H), 6.37 (br s, 1H), 5.00 (br d, J = 4.0 Hz, 1H), 4.10 (br t, J = 6.8 Hz, 2H), 3.77 (t, J = 6.4 Hz, 2H), 3.56 (td, J = 6.4, 13.2 Hz, 1H), 3.36 (br s, 19H), 3.05 (td, J = 8.0, 16.0 Hz, 1H), 2.81 (br t, J = 6.4 Hz, 2H), 2.62 (br t, J = 7.2 Hz, 2H), 2.48-2.40 (m, 1H), 2.06-1.95 (m, 1H), 1.95-1.82 (m, 1H), 1.82-1.66 (m, 4H), 1.60 (br s, 3H), 1.33-1.14 (m, 14H), 1.03 (br d, J = 6.4 Hz, 6H) |
| I-142 | Z | AZ | 729.4 | 12.48-11.67 (m, 1H), 10.63 (br s, 1H), 10.38-10.26 (m, 1H), 8.33 (s, 1H), 8.18 (d, J = 7.2 Hz, 1H), 8.03 (s, 1H), 7.46 (s, 1H), 7.32 (s, 1H), 6.94 (br d, J = 8.0 Hz, 1H), 6.92-6.91 (m, 1H), 6.83 (dd, J = 1.2, 7.2 Hz, 1H), 6.40-6.35 (m, 1H), 5.03-4.96 (m, 1H), 4.10 (t, J = 6.8 Hz, 2H), 3.77 (t, J = 6.8 Hz, 2H), 3.63-3.53 (m, 1H), 3.09-3.01 (m, 1H), 2.81 (br t, J = 6.4 Hz, 2H), 2.68-2.66 (m, 1H), 2.62 (t, J = 7.2 Hz, 2H), 2.34-2.31 (m, 1H), 2.04-1.97 (m, 1H), 1.92-1.83 (m, 1H), 1.80-1.67 (m, 5H), 1.60 (br s, 3H), 1.33-1.16 (m, 16H), 1.03 (d, J = 6.4 Hz, 6H) |
| I-145 | EW | AZ | 745.4 | 12.44-12.01 (m, 1H), 10.84-10.33 (m, 2H), 8.32-8.12 (m, 1H), 7.46 (s, 1H), 7.33 (s, 1H), 7.11 (s, 1H), 6.99-6.87 (m, 1H), 6.83 (d, J = 6.8 Hz, 1H), 6.41 (br s, 1H), 5.00 (br d, J = |

TABLE 8-continued

Compounds synthesized via Method 5, coupling the corresponding alkynes with bromides in Step 1.

| I-#[a] | Alkyne | Bromide | LCMS (ESI+) m/z (M + H)+ | 1H NMR (400 MHz, DMSO-d6) δ |
|---|---|---|---|---|
| | | | | 2.0 Hz, 1H), 4.36 (s, 2H), 4.04 (s, 3H), 3.77 (br t, J = 6.8 Hz, 2H), 3.66-3.52 (m, 1H), 3.40 (br t, J = 6.4 Hz, 3H), 3.15-3.00 (m, 1H), 2.90-2.73 (m, 2H), 2.62 (br t, J = 7.2 Hz, 2H), 2.39-2.29 (m, 1H), 2.08-1.97 (m, 1H), 1.95-1.84 (m, 1H), 1.80-1.68 (m, 2H), 1.60 (br s, 2H), 1.54-1.43 (m, 3H), 1.27 (br d, J = 12.4 Hz, 9H), 1.03 (d, J = 6.4 Hz, 6H) |
| I-147 | EV | J | 818.3 | 12.19-11.80 (m, 1H), 11.08 (br s, 1H), 10.23 (br s, 1H), 7.23-7.14 (m, 2H), 7.05-6.82 (m, 6H), 6.27 (br s, 1H), 5.33 (dd, J = 5.3, 12.8 Hz, 1H), 4.97 (br d, J = 2.1 Hz, 1H), 4.06 (t, J = 4.7 Hz, 2H), 3.76-3.69 (m, 2H), 3.63-3.53 (m, 5H), 3.51-3.44 (m, 6H), 3.40-3.36 (m, 3H), 3.32 (s, 3H), 3.10-2.97 (m, 1H), 2.96-2.82 (m, 1H), 2.75-2.57 (m, 4H), 2.47-2.40 (m, 1H), 2.06-1.93 (m, 2H), 1.91-1.75 (m, 3H), 1.75-1.62 (m, 2H), 1.61-1.48 (m, 1H), 1.01 (br d, J = 6.4 Hz, 6H) |
| I-149 | EQ | J | 822.5 | 12.23 (s, 1 H), 11.07 (s, 1 H), 10.71 (s, 1H), 7.51 (s, 1H), 7.12 (s, 1H), 7.03-6.98 (m, 3H), 6.85 (d, J = 8.0 Hz, 1H), 6.42 (s, 1H), 5.35-5.30 (m, 1H), 5.00 (s, 1H), 6.68 (t, J = 5.6 Hz, 1H), 3.73 (t, J = 6.0 Hz, 1H), 3.70-3.32 (m, 19H), 3.32-3.31 (m, 1H), 3.30-2.90 (m, 1H), 3.50-3.60 (m, 4H), 2.02-2.02 (m, 2H), 1.90-1.50 (m, 6H), 1.02 (d, J = 6.4 Hz, 6H) |
| I-151 | EJ | J | 802.4 | 11.07 (s, 1H), 10.74 (s, 1H), 8.20 (s, 1H), 7.50-6.84 (m, 5H), 6.39 (s, 1H), 5.35-5.30 (m, 1H), 5.01-4.95 (m, 1H), 4.62-4.59 (m, 2H), 3.56-3.40 (m, 6H), 3.36-3.33(m, 5H), 3.12-2.85(m, 2H), 2.62-2.60 (m, 4H), 2.41-2.37 (m, 8H), 2.01-1.77 (m, 9H), 1.03 (d, J = 6.4 Hz, 6H) |
| I-152 | EL | J | 830.5 | 11.07 (s, 1H), 10.74 (s, 1H), 8.22 (s, 1H), 7.50-6.84 (m, 5H), 6.39 (s, 1H), 5.35-5.30 (m, 1H), 5.00 (s, 1H), 4.62-4.00 (d, J = 6.8 Hz, 2H), 3.60-3.54 (m, 4H), 3.41-3.31(m, 9H), 2.63-2.61(m, 5H), 2.38-2.20 (m, 10H), 1.80-1.44 (m, 9H), 1.02 (d, J = 6.4 Hz, 6H) |

[a]Step 1 was run at 60° C. for 4-12 hr. Step 3 was run at 70-80° C. for 2-12 hrs. Purification by standard techniquest including prep HPLC with various conditions.
[b]Step 2 utilized Pd/C with hydrogenation (15 psi) at rt in THF for 10 min-12 hr.
[c]Chloride not bromide used for Step 1.
[d]Step 2 hydrogenation was skipped.
[e]Step 1 utilized CuI, Pd(PPh3)2Cl2 and TEA for the coupling and the mixture was stirred at 60° C. for 2 hours.

Example 6 (Method 6): Synthesis of (1R,3S)-3-(3-(2-(1-(7-(1-(2,6-dioxopiperidin-3-yl)-3-methyl-2-oxo-2,3-dihydro-1H-benzo[d]imidazol-4-yl)heptyl)-1H-pyrazol-4-yl)acetamido)-1H-pyrazol-5-yl)cyclopentyl isopropylcarbamate (I-247)

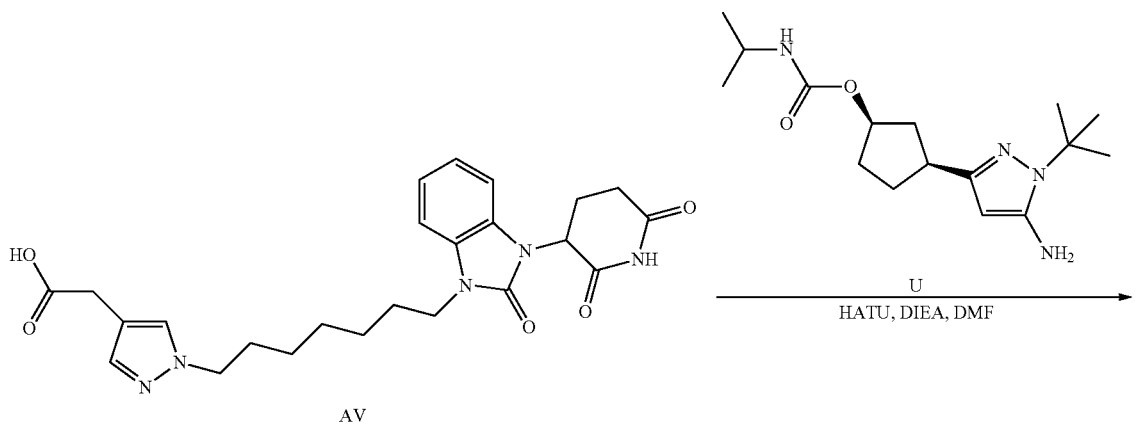

-continued

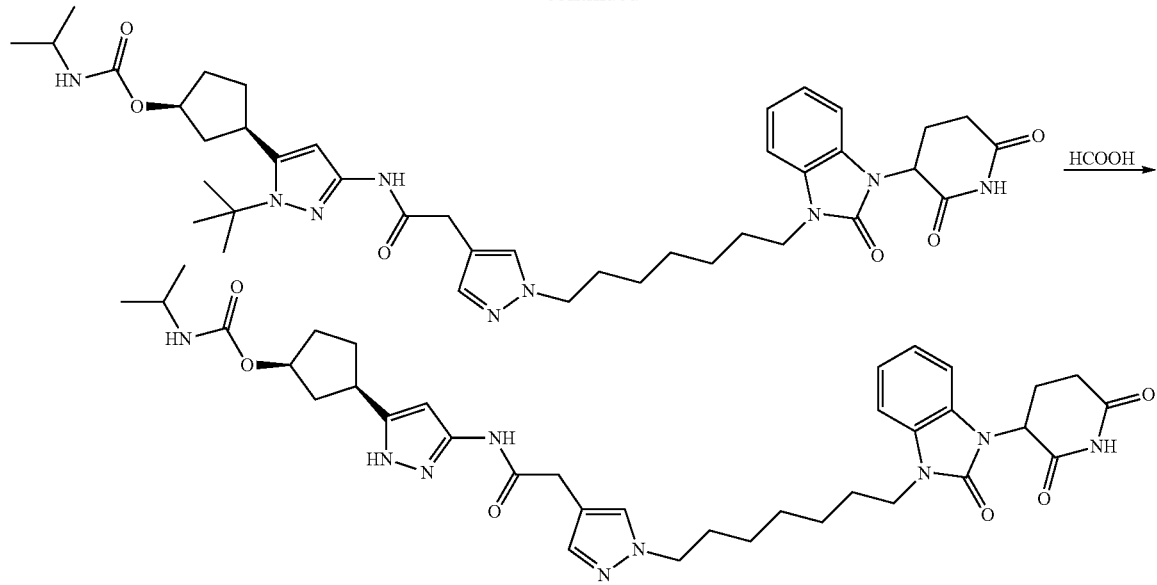

Step 1—(1R,3S)-3-(1-(tert-butyl)-3-(2-(1-(7-(1-(2,6-dioxopiperidin-3-yl)-3-methyl-2-oxo-2,3-dihydro-1H-benzo[d]imidazol-4-yl)heptyl)-1H-pyrazol-4-yl)acetamido)-1H-pyrazol-5-yl)cyclopentyl isopropylcarbamate. To a solution of 2-[1-[7-[1-(2,6-dioxo-3-piperidyl)-3-methyl-2-oxo-benzimidazol-4-yl]heptyl]pyrazol-4-yl]acetic acid (34 mg, 0.07 mmol, Intermediate AV) and (1R,3S)-3-(5-amino-1-(tert-butyl)-1H-pyrazol-3-yl)cyclopentyl isopropylcarbamate (26 mg, 0.08 mmol, Intermediate U) in DMF (1 mL) was added HATU (40 mg, 0.11 mmol) in one portion, followed by DIEA (27 mg, 0.21 mmol). The mixture was stirred at 50° C. for 5 h. On completion, HCOOH (0.2 mL) was added to the mixture and the mixture stirred at 20° C. for 0.5 hour. The solution was purified by prep-HPLC (column: Phenomenex Luna C18 150*25 mm*10 um; mobile phase: [water (0.225% FA)-ACN]; B %: 38%-68%, 11.5 min) and lyophilized to give the title compound (25 mg, 46% yield) as a yellow solid. LC-MS (ESI⁺) m/z 772.7 (M+H)⁺.

Step 2—(1R,3S)-3-(3-(2-(1-(7-(1-(2,6-dioxopiperidin-3-yl)-3-methyl-2-oxo-2,3-dihydro-1H-benzo[d]imidazol-4-yl)heptyl)-1H-pyrazol-4-yl)acetamido)-1H-pyrazol-5-yl)cyclopentyl isopropylcarbamate. The solution of (1R,3S)-3-(1-(tert-butyl)-5-(2-(1-(7-(1-(2,6-dioxopiperidin-3-yl)-3-methyl-2-oxo-2,3-dihydro-1H-benzo[d]imidazol-4-yl) heptyl)-1H-pyrazol-4-yl)acetamido)-1H-pyrazol-3-yl) cyclopentyl isopropylcarbamate (25 mg, 0.03 mmol) in HCOOH (2.00 g, 41.63 mmol) was stirred at 80° C. for 12 hours. On completion, the mixture was concentrated in vacuo. The residue was purified by prep-HPLC (column: Phenomenex luna C18 150*25 mm*10 um; mobile phase: [water (0.225% FA)-ACN]; B %: 30%-60%, 11.5 min) and lyophilized to give the title compound (3 mg, 11% yield) as a yellow gum. LC-MS (ESI⁺) m/z 716.6 (M+H)⁺. ¹H NMR (400 MHz, DMSO-d₆) δ=12.11-11.95 (m, 1H), 11.09 (br s, 1H), 10.34 (d, J=3.2 Hz, 1H), 7.56 (s, 1H), 7.30 (s, 1H), 6.99-6.90 (m, 3H), 6.88-6.83 (m, 1H), 6.37-6.21 (m, 1H), 5.36 (dd, J₁=12.4 Hz, J₂=4.8 Hz, 1H), 5.03-4.93 (m, 1H), 4.03 (t, J=7.2 Hz, 2H), 3.54 (s, 3H), 3.39 (s, 2H), 3.07-2.97 (m, 1H), 2.91-2.82 (m, 3H), 2.76-2.68 (m, 1H), 2.66-2.58 (m, 1H), 2.04-1.96 (m, 2H), 1.90-1.83 (m, 1H), 1.77-1.67 (m, 4H), 1.64-1.51 (m, 4H), 1.41-1.29 (m, 5H), 1.25-1.20 (m, 2H), 1.02 (d, J=6.4 Hz, 6H).

Example 7. Synthesis of (1R,3S)-3-(3-(2-(1-(7-(1-(2,6-dioxopiperidin-3-yl)-3-methyl-2-oxo-2,3-dihydro-1H-benzo[d]imidazol-5-yl)heptyl)-1H-pyrazol-4-yl)acetamido)-1H-pyrazol-5-yl)cyclopentyl isopropylcarbamate (I-103)

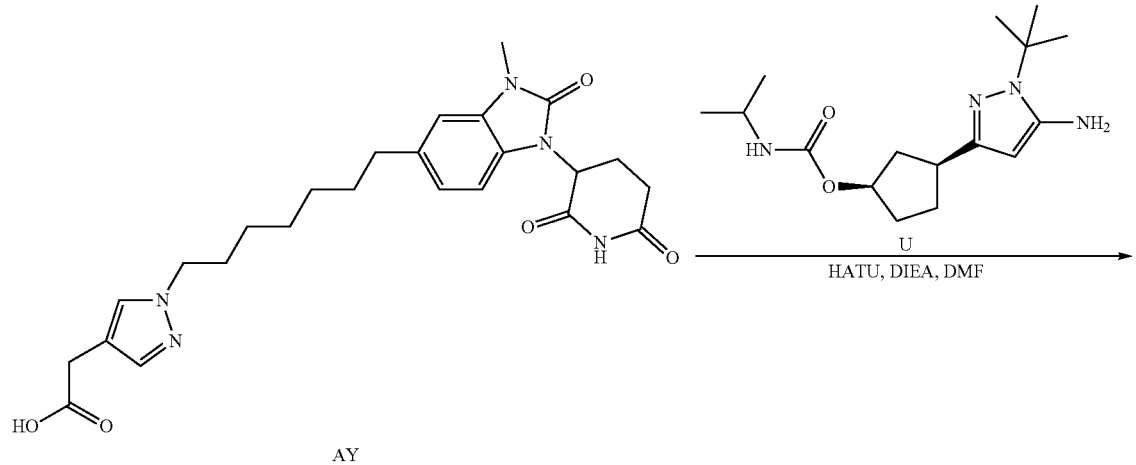

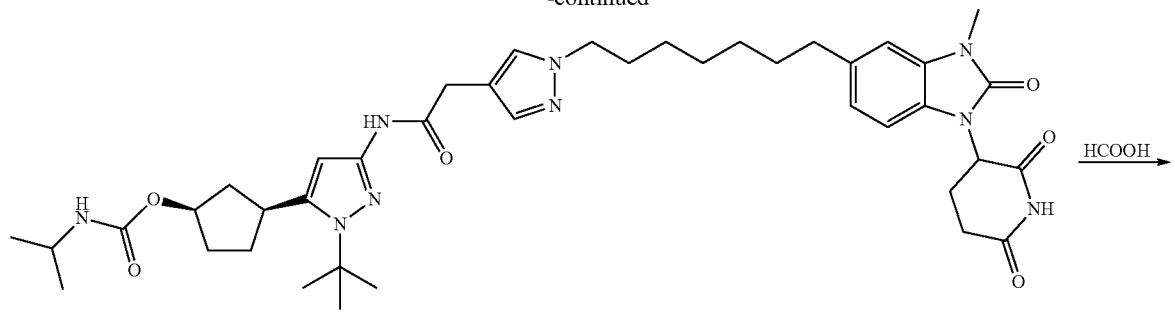

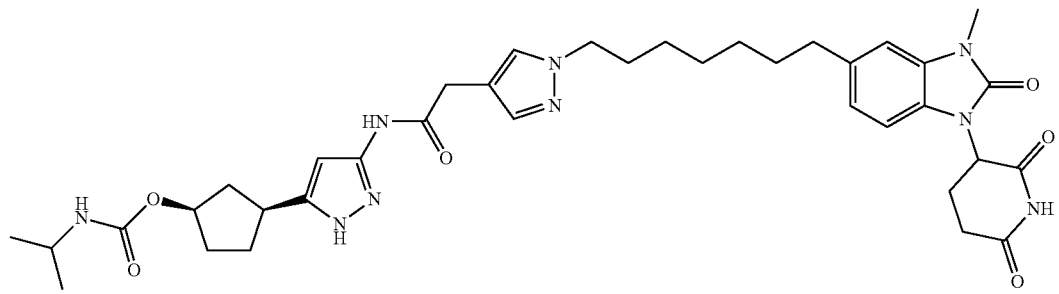

(1R,3S)-3-(3-(2-(1-(7-(1-(2,6-dioxopiperidin-3-yl)-3-methyl-2-oxo-2,3-dihydro-1H-benzo[d]imidazol-5-yl)heptyl)-1H-pyrazol-4-yl)acetamido)-1H-pyrazol-5-yl)cyclopentyl isopropylcarbamate was synthesized as described in Method 6, coupling 2-(1-(7-(1-(2,6-dioxopiperidin-3-yl)-3-methyl-2-oxo-2,3-dihydro-1H-benzo[d]imidazol-5-yl)heptyl)-1H-pyrazol-4-yl)acetic acid (Intermediate AY) and (1R,3S)-3-(5-amino-1-(tert-butyl)-1H-pyrazol-3-yl)cyclopentyl isopropylcarbamate (Intermediate U) in Step 1. The final compound was purified by prep-HPLC (column: Phenomenex Luna C18 150*25 mm*10 um; mobile phase: [water (0.225% FA)-ACN]; B %: 30%-60%, 11.5 min) and lyophilized to give the title compound (11 mg, 34% yield) as a yellow gum. LC-MS (ESI+) m/z 716.6 (M+H)+; $^1$H NMR (400 MHz, DMSO-$d_6$) δ=12.17-11.89 (m, 1H), 11.08 (s, 1H), 10.34 (s, 1H), 7.56 (s, 1H), 7.30 (s, 1H), 7.03-6.97 (m, 2H), 6.93 (d, J=7.6 Hz, 1H), 6.85 (dd, $J_1$=8.0 Hz, $J_2$=1.2 Hz, 1H), 6.28 (br s, 1H), 5.33 (dd, $J_1$=12.8 Hz, $J_2$=5.2 Hz, 1H), 4.98 (d, J=2.0 Hz, 1H), 4.02 (t, J=7.2 Hz, 2H), 3.56 (td, $J_1$=13.6 Hz, $J_2$=6.8 Hz, 1H), 3.39 (s, 2H), 3.32 (s, 1H), 3.09-2.97 (m, 1H), 2.96-2.84 (m, 1H), 2.77-2.66 (m, 1H), 2.66-2.56 (m, 3H), 2.49-2.39 (m, 2H), 2.05-1.93 (m, 2H), 1.92-1.81 (m, 1H), 1.77-1.63 (m, 4H), 1.62-1.51 (m, 3H), 1.36-1.15 (m, 7H), 1.02 (d, J=6.4 Hz, 6H).

Example 8 (Method 7): Synthesis of 4-[(6-chloro-8-isopropyl-7-oxo-pyrido[2,3-d]pyrimidin-2-yl)amino]-3-methyl-N-(3-piperazin-1-ylpropyl)benzenesulfonamide (I-157)

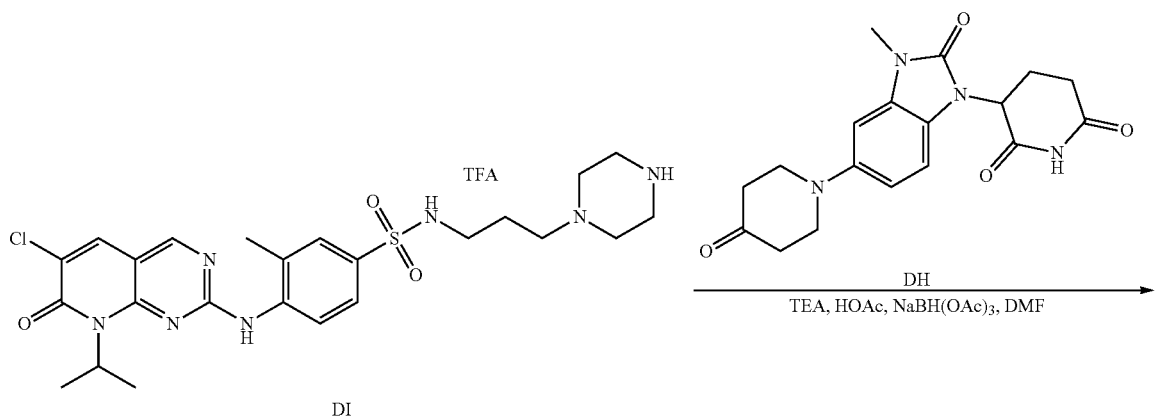

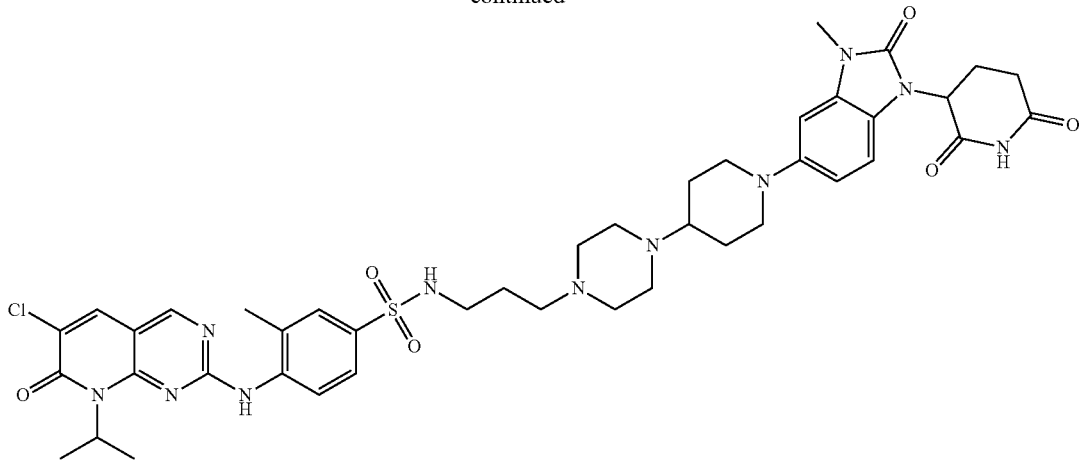

To a solution of 4-[(6-chloro-8-isopropyl-7-oxo-pyrido[2,3-d]pyrimidin-2-yl)amino]-3-methyl-N-(3-piperazin-1-yl-propyl)benzenesulfonamide (50 mg, 77.1 umol, TFA, Intermediate DI) in DMF (2 mL) was added TEA (7.81 mg, 77.1 umol) at −10° C. Then 3-[3-methyl-2-oxo-5-(4-oxo-1-piperidyl)benzimidazol-1-yl]piperidine-2,6-dione (27.4 mg, 77.1 umol, Intermediate DH) and HOAc (4.63 mg, 77.1 umol) was added at −10° C. and the mixture was stirred for 30 mins. Next, NaBH(OAc)$_3$ (32.7 mg, 154 umol) was added and the mixture was stirred at −10° C. for 2 hrs. On completion, the reaction mixture was quenched with water (0.05 mL) and concentrated in vacuo to give a residue. The residue was purified by prep-HPLC (column: Waters xbridge 150*25 mm 10 um; mobile phase: [water (NH$_4$HCO$_3$)-ACN]; B %: 27%-57%, 8 min) to give the title compound (3.9 mg, 6% yield) as a light white solid. $^1$H NMR (400 MHz, DMSO-d$_6$) δ 11.06 (s, 1H), 9.65 (s, 1H), 8.74 (s, 1H), 8.16 (s, 1H), 7.77 (d, J=7.2 Hz, 1H), 7.68 (s, 1H), 7.65-7.60 (m, 1H), 7.56-7.50 (m, 1H), 6.97-6.87 (m, 1H), 6.81 (s, 1H), 6.61 (d, J=8.4 Hz, 1H), 5.69-5.56 (m, 1H), 5.28 (dd, J=4.4, 13.2 Hz, 1H), 3.59 (td, J=4.0, 6.4 Hz, 2H), 2.87-2.74 (m, 4H), 2.71-2.64 (m, 3H), 2.63 (s, 2H), 2.59 (s, 3H), 2.34 (s, 6H), 2.29-2.13 (m, 5H), 2.04-1.92 (m, 2H), 1.88-1.75 (m, 2H), 1.61-1.48 (m, 4H), 1.41 (d, J=6.4 Hz, 6H), LC-MS (ESI$^+$) m/z 874.3 (M+H)$^+$.

TABLE 9

Compounds synthesized via Method 7, reductive amination of the corresponding amines and ketones/aldehydes.

| I-# | Amine | Aldehyde/Ketone | LCMS (ESI+) m/z (M + H)$^+$ | $^1$H NMR (400 MHz, DMSO-d$_6$) δ |
|---|---|---|---|---|
| I-108 | DB | GK | 914.3 | 11.10 (s, 1H), 9.69 (s, 1H), 8.78-8.74 (m, 1H), 8.19 (s, 1H), 7.75-7.68 (m, 2H), 7.67-7.58 (m, 2H), 7.08 (br d, J = 7.6 Hz, 1H), 7.03 (br s, 1H), 6.92 (br d, J = 8.1 Hz, 1H), 5.80-5.67 (m, 1H), 5.42-5.29 (m, 1H), 3.59 (br d, J = 10.5 Hz, 2H), 3.44 (br d, J = 5.0 Hz, 2H), 3.35 (s, 3H), 3.20-3.15 (m, 1H), 3.08-2.79 (m, 8H), 2.72-2.59 (m, 2H), 2.34 (br s, 3H), 2.17-2.09 (m, 2H), 1.99 (br s, 7H), 1.87-1.77 (m, 3H), 1.75-1.66 (m, 4H), 1.52-1.42 (m, 2H), 1.23-1.11 (m, 2H), 1.07-0.90 (m, 2H) |
| I-109$^b$ | DB | GK | 880.4 | 11.09 (br s, 1H), 9.53 (br s, 1H), 8.74 (br s, 1H), 7.81-7.74 (m, 1H), 7.73-7.66 (m, 2H), 7.65-7.57 (m, 2H), 7.12-6.99 (m, 2H), 6.91 (br d, J = 8.4 Hz, 1H), 6.34 (br d, J = 8.9 Hz, 1H), 5.74-5.61 (m, 1H), 5.44-5.26 (m, 1H), 3.65-3.55 (m, 4H), 3.34 (br s, 3H), 3.16 (br d, J = 1.3 Hz, 1H), 3.08-2.82 (m, 8H), 2.72-2.61 (m, 2H), 2.33 (br s, 3H), 2.20-2.10 (m, 2H), 1.98 (br s, 7H), 1.80 (br d, J = 12.0 Hz, 3H), 1.71-1.60 (m, 4H), 1.50-1.35 (m, 2H), 1.20-1.10 (m, 2H), 1.06-0.94 (m, 2H) |
| I-111 | FN | KQ | 810.3 | 11.08 (s, 1H), 9.52 (s, 1H), 8.73 (s, 1H), 7.75 (d, J = 9.6 Hz, 1H), 7.70-7.67 (m, 2H), 7.62-7.60 (m, 2H), 7.04-7.02 (m, 2H), 7.00-6.90 (s, 1H), 6.33 (d, J = 9.2 Hz, 1H), 5.65 (br t, J = 8.8 Hz, 1H), 5.36-5.34 (m, 1H), 3.75-3.72 (m, 1H), 3.38 (s, 2H), 3.50 (s, 3H), 3.25-3.22 (m, 4H), 3.11 (s, 2H), 3.06 (s, 2H), 2.87-2.85 (m, 3H), 2.70-2.61 (m, 2H), 2.33-2.31 (m, 4H), 2.30-2.29 (s, 1H), 2.18-2.09 (m, 2H), 2.07-2.00 (m, 1H), 1.87-1.86 (m, 2H), 1.65 (br s, 4H), 1.44 (br s, 2H) |

TABLE 9-continued

Compounds synthesized via Method 7, reductive amination
of the corresponding amines and ketones/aldehydes.

| I-# | Amine | Aldehyde/ Ketone | LCMS (ESI+) m/z (M + H)+ | $^1$H NMR (400 MHz, DMSO-d$_6$) δ |
|---|---|---|---|---|
| I-112 | DB | FZ | 822.3 | 11.07 (br s, 1H), 9.58 (s, 1H), 8.75 (s, 1H), 8.23 (s, 1H), 7.80-7.72 (m, 2H), 7.65-7.60 (m, 1H), 7.56 (dd, J = 2.0, 8.4 Hz, 1H), 7.07 (s, 1H), 7.02-6.95 (m, 1H), 6.88 (br d, J = 8.0 Hz, 1H), 6.38-6.24 (m, 1H), 5.79-5.57 (m, 1H), 5.32 (dd, J = 5.6, 12.8 Hz, 1H), 3.72-3.61 (m, 3H), 2.88 (br d, J = 10.8 Hz, 3H), 2.71-2.59 (m, 2H), 2.37-2.28 (m, 4H), 2.23 (br d, J = 12.8 Hz, 1H), 2.12 (br d, J = 6.8 Hz, 5H), 2.01-1.88 (m, 3H), 1.78 (br d, J = 10.8 Hz, 2H), 1.67 (br s, 9H), 1.53-1.38 (m, 4H), 1.23-1.09 (m, 2H) |
| I-113 | S | FZ | 865.3 | 11.10 (s, 1H), 9.58 (s, 1H), 8.76 (s, 1H), 8.14 (s, 1H), 7.81-7.75 (m, 2H), 7.63 (d, J = 2.0 Hz, 1H), 7.56 (dd, J = 2.0, 8.4 Hz, 1H), 7.08 (br d, J = 8.0 Hz, 1H), 6.96 (t, J = 7.6 Hz, 1H), 6.86 (d, J = 7.6 Hz, 1H), 6.35 (d, J = 9.6 Hz, 1H), 5.68 (br t, J = 8.8 Hz, 1H), 5.37 (br dd, J = 5.6, 12.4 Hz, 1H), 3.65 (s, 6H), 2.92-2.84 (m, 3H), 2.73-2.57 (m, 4H), 2.38-2.31 (m, 5H), 2.25-2.07 (m, 5H), 2.04-1.94 (m, 3H), 1.82-1.60 (m, 9H), 1.55-1.38 (m, 5H), 1.25-1.14 (m, 2H) |
| I-115 | GA | FZ | 837.5 | 11.09 (br s, 1H), 9.58 (s, 1H), 8.76 (s, 1H), 7.80-7.73 (m, 2H), 7.62 (d, J = 1.8 Hz, 1H), 7.55 (dd, J = 2.0, 8.4 Hz, 1H), 7.06 (br d, J = 7.8 Hz, 1H), 6.97-6.92 (m, 1H), 6.86 (d, J = 7.2 Hz, 1H), 6.35 (d, J = 9.4 Hz, 1H), 5.72-5.61 (m, 1H), 5.37 (br dd, J = 5.2, 12.4 Hz, 1H), 3.66-3.61 (m, 7H), 2.92-2.84 (m, 1H), 2.77-2.58 (m, 5H), 2.36-2.33 (m, 5H), 2.23-2.10 (m, 6H), 2.06 (br d, J = 7.2 Hz, 2H), 2.00 (br d, J = 5.2 Hz, 1H), 1.78-1.63 (m, 7H), 1.42 (br d, J = 2.4 Hz, 3H), 1.17-1.08 (m, 2H) |
| I-117 | GD | DM | 909.2 | 11.05 (s, 1H), 9.52 (s, 1H), 8.74 (s, 1H), 8.21 (s, 1H), 7.77-7.68 (m, 3H), 7.63-7.58 (m, 2H), 6.91 (d, J = 8.4 Hz, 1H), 6.80 (d, J = 2.0 Hz, 1H), 6.61 (dd, J = 2.0, 8.4 Hz, 1H), 6.33 (d, J = 9.6 Hz, 1H), 5.68 (t, J = 8.8 Hz, 1H), 5.28 (dd, J = 5.2, 12.8 Hz, 1H), 3.54 (d, J = 12.0 Hz, 2H), 3.36 (t, J = 6.0 Hz, 2H), 3.30 (s, 3H), 3.06-3.01 (m, 1H), 2.91-2.84 (m, 3H), 2.68-2.55 (m, 4H), 2.33 (s, 3H), 2.19 (d, J = 7.2 Hz, 2H), 2.13 (s, 5H), 2.01-1.96 (m, 1H), 1.90 (d, J = 10.4 Hz, 2H), 1.78-1.72 (m, 2H), 1.66 (s, 6H), 1.45 (d, J = 6.8 Hz, 3H), 1.22-1.00 (m, 7H) |
| I-119 | FY | FZ | 823.4 | 11.21-10.97 (m, 1H), 9.58 (s, 1H), 8.75 (s, 1H), 7.77 (d, J = 9.2 Hz, 2H), 7.63 (d, J = 1.6 Hz, 1H), 7.56 (dd, J = 2.0, 8.4 Hz, 1H), 7.01-6.94 (m, 1H), 6.93-6.85 (m, 2H), 6.34 (d, J = 9.2 Hz, 1H), 5.67 (quin, J = 8.4 Hz, 1H), 5.34 (dd, J = 5.6, 12.8 Hz, 1H), 3.67 (br d, J = 11.2 Hz, 2H), 3.59 (s, 3H), 2.97-2.78 (m, 6H), 2.69-2.65 (m, 1H), 2.64-2.61 (m, 3H), 2.58 (br s, 1H), 2.35 (s, 3H), 2.26-2.10 (m, 8H), 2.01-1.95 (m, 1H), 1.79 (br d, J = 11.2 Hz, 2H), 1.67 (br s, 4H), 1.51-1.39 (m, 3H), 1.21-1.12 (m, 2H) |
| I-123 | FT | FU | 806.4 | 11.17 (s, 1H), 9.66 (s, 1H), 8.89-8.75 (m, 1H), 7.88-7.76 (m, 2H), 7.69 (d, J = 1.6 Hz, 1H), 7.62 (dd, J = 2.0, 8.4 Hz, 1H), 7.24 (d, J = 0.8 Hz, 1H), 7.17-7.06 (m, 2H), 6.39 (d, J = 9.2 Hz, 1H), 5.70 (br t, J = 8.4 Hz, 1H), 5.42 (dd, J = 5.4, 12.8 Hz, 1H), 3.37 (s, 3H), 3.03-2.86 (m, 5H), 2.82-2.60 (m, 3H), 2.50 (br s, 3H), 2.46-2.41 (m, 5H), 2.39-2.33 (m, 2H), 2.23-2.13 (m, 2H), 2.11-2.04 (m, 1H), 1.71 (br s, 4H), 1.61-1.45 (m, 6H) |
| I-124 | FR | FS | 894.2 | 11.08 (br s, 1H), 9.51 (s, 1H), 8.73 (s, 1H), 8.27 (s, 1H), 7.77-7.71 (m, 1H), 7.68 (d, J = 1.6 Hz, 1H), 7.64-7.57 (m, 2H), 7.04-6.96 (m, 2H), 6.85 (d, J = 8.0 Hz, 1H), 6.33 (d, J = 9.2 Hz, 1H), 5.68 (br t, J = 8.4 Hz, 1H), 5.33 (dd, J = 5.2, 12.8 Hz, 1H), 3.35 (br t, J = 6.0 Hz, 2H), 3.32 (s, 3H), 3.16-3.11 (m, 1H), 2.89 (d, J = 5.2 Hz, 2H), 2.77-2.55 (m, 5H), 2.35-2.27 (m, 10H), 2.12 (br d, J = 8.4 Hz, 2H), 2.01-1.94 (m, 1H), 1.66 (br s, 5H), 1.51-1.38 (m, 6H), 1.34-1.17 (m, 5H), 1.06-0.99 (m, 2H) |
| I-125 | FR | FO | 890.3 | 11.11 (br s, 1H), 9.51 (s, 1H), 8.74 (s, 1H), 8.27 (s, 1H), 7.79-7.55 (m, 5H), 7.27 (s, 1H), 7.11 (s, 2H), 6.33 (d, J = 9.2 Hz, 1H), 5.67 (br t, J = 8.4 Hz, 1H), 5.38 (dd, J = 5.2, 12.4 Hz, 1H), 3.43 (br s, 3H), 3.36 (br s, 2H), 3.34 (s, 3H), 3.18-3.15 (m, 1H), 2.92-2.84 (m, 3H), 2.72-2.60 (m, 2H), 2.44 (br d, J = 4.8 Hz, 4H), 2.32 (s, 3H), 2.20-1.96 (m, 4H), 1.64 (br d, J = 8.4 Hz, 5H), 1.46-1.38 (m, 4H), 1.35-1.23 (m, 4H), 1.06 (br t, J = 10.4 Hz, 2H) |
| I-126 | FN | FO | 834.2 | 11.12 (s, 1H), 9.52 (s, 1H), 8.74 (s, 1H), 7.76 (d, J = 9.6 Hz, 1H), 7.71 (d, J = 8.4 Hz, 1H), 7.68 (d, J = 1.6 Hz, 1H), 7.64- |

TABLE 9-continued

Compounds synthesized via Method 7, reductive amination of the corresponding amines and ketones/aldehydes.

| I-# | Amine | Aldehyde/ Ketone | LCMS (ESI+) m/z (M + H)+ | 1H NMR (400 MHz, DMSO-d6) δ |
|---|---|---|---|---|
| | | | | 7.60 (m, 2H), 7.28 (s, 1H), 7.12 (s, 2H), 6.33 (d, J = 9.2 Hz, 1H), 5.68 (br t, J = 8.8 Hz, 1H), 5.42-5.34 (m, 1H), 3.81-3.72 (m, 1H), 3.38 (s, 2H), 3.34 (s, 3H), 3.26 (br t, J = 6.0 Hz, 2H), 3.22 (s, 2H), 3.18 (s, 2H), 2.92-2.85 (m, 3H), 2.73-2.61 (m, 2H), 2.53 (br s, 1H), 2.33 (s, 3H), 2.31-2.28 (m, 1H), 2.18-2.09 (m, 2H), 2.07-2.00 (m, 1H), 1.93-1.87 (m, 2H), 1.65 (br s, 4H), 1.44 (br s, 2H) |
| I-133 | FN | FS | 838.4 | 11.08 (s, 1H), 9.53 (s, 1H), 8.73 (s, 1H), 7.78-7.67 (m, 3H), 7.64-7.59 (m, 2H), 7.02-6.96 (m, 2H), 6.83 (d, J = 8.0 Hz, 1H), 6.33 (d, J = 9.3 Hz, 1H), 5.67 (br t, J = 8.6 Hz, 1H), 5.33 (dd, J = 5.4, 12.9 Hz, 1H), 3.77-3.70 (m, 1H), 3.31 (s, 3H), 3.24 (br t, J = 5.9 Hz, 3H), 3.18-3.13 (m, 3H), 2.90-2.82 (m, 3H), 2.72-2.62 (m, 2H), 2.59-2.53 (m, 3H), 2.42-2.38 (m, 2H), 2.32 (s, 3H), 2.28 (br d, J = 7.1 Hz, 1H), 2.16-2.09 (m, 2H), 2.02-1.96 (m, 1H), 1.90-1.84 (m, 2H), 1.65 (br s, 4H), 1.57-1.50 (m, 2H), 1.43 (br d, J = 4.0 Hz, 2H) |
| I-222 | GU | DM | 914.3 | 11.05 (s, 1H), 9.67 (s, 1H), 8.76 (s, 1H), 8.17 (s, 1H), 7.73 (d, J = 8.4 Hz, 1H), 7.67 (s, 1H), 7.61 (d, J = 8.0 Hz, 1H), 7.53 (t, J = 5.6 Hz, 1H), 6.91 (d, J = 8.4 Hz, 1H), 6.79 (d, J = 1.6 Hz, 1H), 6.62-6.58 (m, 1H), 5.73 (s, 1H), 5.32-5.25 (m, 1H), 3.54 (d, J = 11.6 Hz, 2H), 3.30 (s, 3H), 2.95-2.84 (m, 1H), 2.78 (d, J = 6.8 Hz, 2H), 2.63 (s, 2H), 2.58 (s, 2H), 2.33 (s, 3H), 2.27 (d, J = 2.0 Hz, 4H), 2.23-2.19 (m, 3H), 2.10 (d, J = 6.4 Hz, 4H), 2.01-1.95 (m, 1H), 1.76-1.66 (m, 7H), 1.57-1.44 (m, 6H), 1.25-1.13 (m, 3H) |
| I-223 | DI | DM | 888.3 | 11.05 (s, 1H), 9.66 (s, 1H), 8.74 (s, 1H), 8.17 (s, 1H), 7.88-7.50 (m, 4H), 6.92 (d, J = 8.4 Hz, 1H), 6.81 (s, 1H), 6.62 (d, J = 8.0 Hz, 1H), 5.81-5.49 (m, 1H), 5.42-5.13 (m, 1H), 3.62-3.55 (m, 2H), 3.30 (s, 2H), 2.84-2.77 (m, 4H), 2.71-2.62 (m, 8H), 2.34 (s, 3H), 2.33-2.30 (m, 2H), 2.29-2.16 (m, 4H), 2.05-1.92 (m, 2H), 1.79-1.78 (m, 4H), 1.65-1.50 (m, 2H), 1.42 (d, J = 6.4 Hz, 6H), 1.30-1.18 (m, 2H) |
| I-224 | IR | DM | 874.0 | 11.05 (s, 1H), 9.65 (s, 1H), 8.74 (s, 1H), 8.16 (s, 1H), 7.75 (br d, J = 8.0 Hz, 1H), 7.70 (s, 1H), 7.64 (br d, J = 8.4 Hz, 1H), 7.51-7.39 (m, 1H), 6.91 (br d, J = 8.4 Hz, 1H), 6.80 (s, 1H), 6.61 (d, J = 8.4 Hz, 1H), 5.69-5.55 (m, 1H), 5.28 (dd, J = 5.2, 12.4 Hz, 1H), 3.57-3.54 (m, 4H), 3.02-3.01 (m, 2H), 2.87-2.85 (m, 4H), 2.68-2.67 (m, 2H), 2.62 (br s, 2H), 2.58 (br s, 3H), 2.57-2.53 (m, 4H), 2.41-2.39 (m, 4H), 2.34 (s, 3H), 2.04-1.94 (m, 1H), 1.76-1.73 (m, 2H), 1.42-1.40 (m, 6H), 1.29-1.18 (m, 2H) |
| I-225 | JO | DM | 914.3 | 11.14 (s, 1H), 9.70 (s, 1H), 8.77 (s, 1H), 8.18 (s, 1H), 7.93-7.75 (m, 2H), 7.67 (s, 1H), 7.61 (d, J = 8.4 Hz, 2H), 7.30 (d, J = 8.4 Hz, 1H), 5.74-5.57 (m, 1H), 5.44 (dd, J = 5.2, 12.8 Hz, 1H), 3.97 (s, 6H), 3.82 (d, J = 9.2 Hz, 2H), 3.70 (s, 3H), 3.63-3.54 (m, 4H), 3.38 (s, 3H), 3.19 (d, J = 4.4 Hz, 1H), 2.96-2.86 (m, 1H), 2.79-2.62 (m, 2H), 2.37 (s, 3H), 2.25 (d, J = 10.4 Hz, 8H), 2.07-1.95 (m, 3H), 1.89-1.78 (m, 2H), 1.44 (d, J = 6.4 Hz, 6H) |
| I-226 | KL | KO | 889.8 | 11.10 (s, 1H), 9.55 (s, 1H), 8.70 (s, 1H), 8.14 (s, 1H), 7.51-7.41 (m, 1H), 7.28-7.15 (m, 2H), 7.11-7.01 (m, 2H), 6.95 (d, J = 7.6 Hz, 1H), 5.78-5.65 (m, 1H), 5.45-5.34 (m, 1H), 4.12-3.97 (m, 2H), 3.88-3.80 (m, 2H), 3.63 (s, 3H), 3.46-3.37 (m, 2H), 3.24-3.13 (m, 3H), 3.04-2.97 (m, 1H), 2.96-2.82 (m, 2H), 2.78-2.68 (m, 2H), 2.64 (s, 1H), 2.61 (d, J = 1.2 Hz, 1H), 2.24 (s, 3H), 2.19-1.95 (m, 10H), 1.88-1.39 (m, 12H), 1.18-1.05 (m, 1H) |
| I-227 | DB | KO | 889.6 | 11.10 (s, 1H), 9.55 (s, 1H), 8.70 (s, 1H), 8.12 (s, 1H), 7.49-7.41 (m, 1H), 7.27-7.16 (m, 2H), 7.08 (d, J = 8.0 Hz, 1H), 7.04 (s, 1H), 6.96-6.90 (m, 1H), 5.83-5.65 (m, 1H), 5.42-5.31 (m, 1H), 3.94-3.84 (m, 2H), 3.61 (s, 4H), 3.35 (s, 3H), 3.27-3.13 (m, 2H), 3.11-2.98 (m, 3H), 2.95-2.83 (m, 2H), 2.76-2.68 (m, 1H), 2.66-2.63 (m, 1H), 2.63-2.59 (m, 1H), 2.26-2.21 (m, 3H), 1.98-1.90 (m, 10H), 1.91-1.37 (m, 12H), 1.18-1.02 (m, 1H) |

[a]Reductive amination performed under standard conditions, including using KOAc as a base used, as well as adding 4 Å molecular sieves. The reaction run anywhere from −10 to rt, and the final products were purified by standard techniques including prep-HPCl and silica gel chromatography.
[b]The product of the reductive amination was further hydrogenated over Pd/C, and DIEA, in THF under H$_2$ (15 PSI) for 12 hr at rt.

Example 9. Synthesis of (1R,3S)-3-(5-(1-(4-((9-((1-(2,6-dioxopiperidin-3-yl)-3-methyl-2-oxo-2,3-dihydro-1H-benzo[d]imidazol-4-yl)methyl)-3,9-diazaspiro[5.5]undecan-3-yl)methyl)phenyl)-1H-pyrazole-4-carboxamido)-1H-pyrazol-3-yl) cyclopentyl isopropylcarbamate (I-53)

brine (2×3 mL), and dried over sodium sulfate. The mixture was then filtered and the filtrate was concentrated to give a residue. The residue was purified by prep-HPLC [column: Phenomenex Luna C18 150*25 mm*10 um; mobile phase: [water (0.225% FA)-ACN]; B %: 9%-39%, 10 min] to give the title compound (10 mg, 10.9 umol, 12% yield) as yellow oil. LC-MS (ESI+) m/z 458.9 (M+H)+.

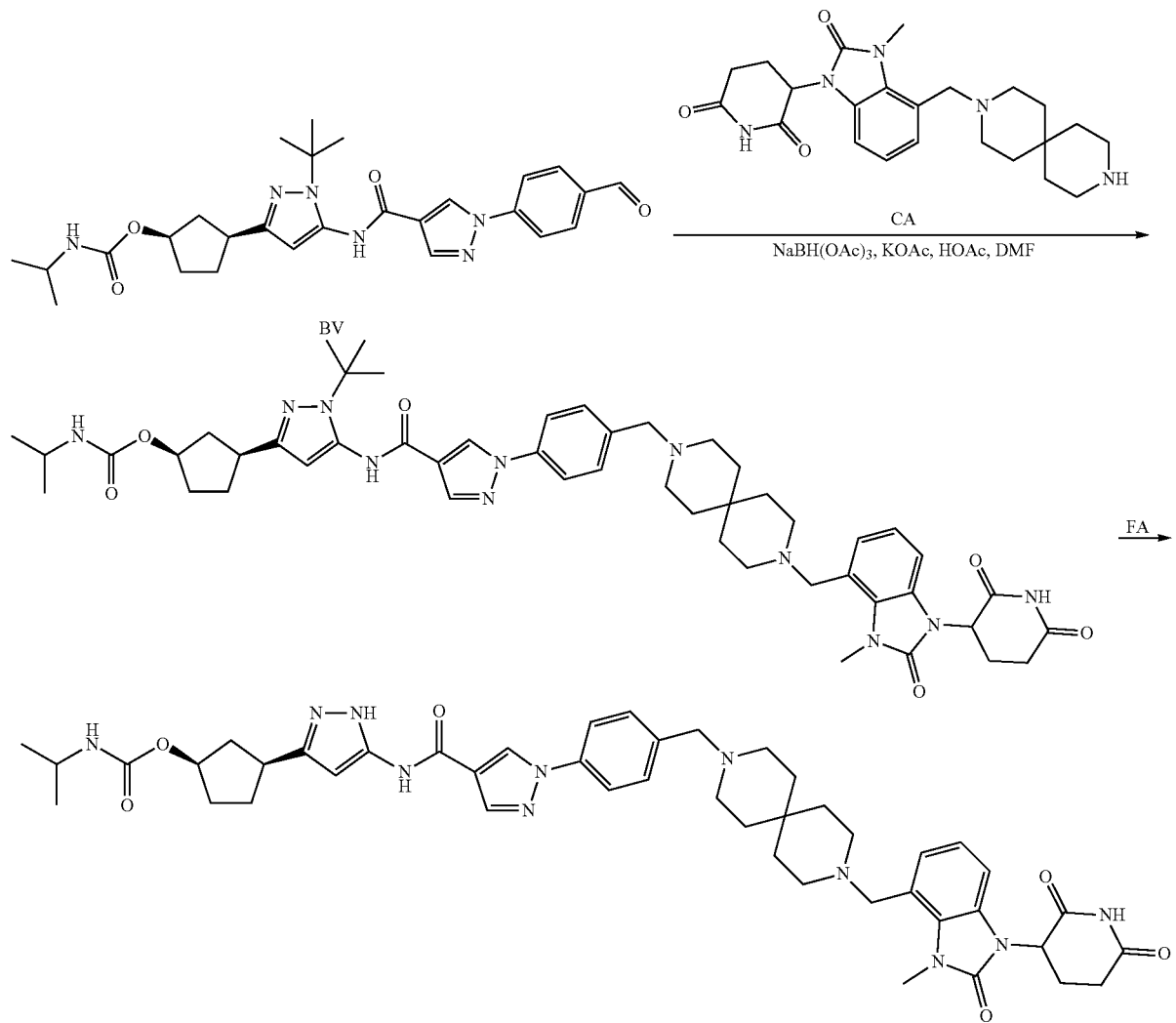

Step 1—(1R,3S)-3-(1-(tert-butyl)-5-(1-(4-((9-((1-(2,6-dioxopiperidin-3-yl)-3-methyl-2-oxo-2,3-dihydro-1H-benzo[d]imidazol-4-yl)methyl)-3,9-diazaspiro[5.5]undecan-3-yl)methyl)phenyl)-1H-pyrazole-4-carboxamido)-1H-pyrazol-3-yl)cyclopentyl isopropylcarbamate. To a solution of 3-(4-(3,9-diazaspiro[5.5]undecan-3-ylmethyl)-3-methyl-2-oxo-2,3-dihydro-1H-benzo[d]imidazol-1-yl)piperidine-2,6-dione (37.8 mg, 88.8 umol, Intermediate CA) and (1R,3S)-3-(1-(tert-butyl)-5-(1-(4-formylphenyl)-1H-pyrazole-4-carboxamido)-1H-pyrazol-3-yl)cyclopentyl isopropylcarbamate (45 mg, 88.8 umol, Intermediate BV) in DMF (1 mL) and THF (1 mL) was added AcOH (16.0 mg, 266 umol), NaBH(OAc)$_3$ (37.6 mg, 177 umol) and AcOK (26.1 mg, 266 umol) in one portion. The mixture was stirred at 25° C. for 10 h. On completion, the resulting mixture was poured into ice water (3 mL) and extracted with ethyl acetate (2×3 mL). The combined organic phase was washed with Step 2—(1R,3S)-3-(5-(1-(4-((9-((1-(2,6-dioxopiperidin-3-yl)-3-methyl-2-oxo-2,3-dihydro-1H-benzo[d]imidazol-4-yl)methyl)-3,9-diazaspiro[5.5]undecan-3-yl)methyl)phenyl)-1H-pyrazole-4-carboxamido)-1H-pyrazol-3-yl) cyclopentyl isopropylcarbamate. A solution of (1R,3S)-3-(1-(tert-butyl)-5-(1-(4-((9-((1-(2,6-dioxopiperidin-3-yl)-3-methyl-2-oxo-2,3-dihydro-1H-benzo[d]imidazol-4-yl) methyl)-3,9-diazaspiro[5.5]undecan-3-yl)methyl)phenyl)-1H-pyrazole-4-carboxamido)-1H-pyrazol-3-yl)cyclopentyl isopropylcarbamate (10 mg, 10.9 umol) in HCOOH (1 mL) was stirred at 20-80° C. for 1 h. On completion, the mixture was concentrated to give a residue. The residue was purified by prep-HPLC (column: Phenomenex Luna C18 150*25 mm*10 um; mobile phase: [water (0.225% FA)-ACN]; B %: 29%-59%, 10 min) to give the title compound (0.59 mg, 6% yield) as a off-white solid. $^1$H NMR (400 MHz, DMSO-d$_6$) δ=11.24-10.94 (m, 1H), 10.52 (br s, 1H), 9.08 (s, 1H), 8.30

(d, J=3.6 Hz, 2H), 7.78 (d, J=8.5 Hz, 2H), 7.43 (d, J=8.4 Hz, 2H), 7.06 (br d, J=7.5 Hz, 1H), 7.00-6.90 (m, 2H), 6.90-6.83 (m, 1H), 6.46-6.37 (m, 1H), 5.41-5.31 (m, 1H), 5.05-4.95 (m, 1H), 3.66 (s, 3H), 3.63-3.55 (m, 4H), 2.94-2.83 (m, 2H), 2.76-2.57 (m, 4H), 2.37-2.32 (m, 8H), 2.08-1.84 (m, 4H), 1.80-1.56 (m, 4H), 1.41 (br d, J=15.5 Hz, 6H), 1.03 (d, J=6.6 Hz, 6H). LC-MS (ESI$^+$) m/z 860.5 (M+H)$^+$.

Example 10. Synthesis of (1R,3S)-3-(3-(1-(4-(((3-(1-(2,6-dioxopiperidin-3-yl)-3-methyl-2-oxo-2,3-dihydro-1H-benzo[d]imidazol-4-yl)prop-2-yn-1-yl)(methyl)amino)methyl)phenyl)-1H-pyrazole-4-carboxamido)-1H-pyrazol-5-yl)cyclopentyl isopropylcarbamate (I-54)

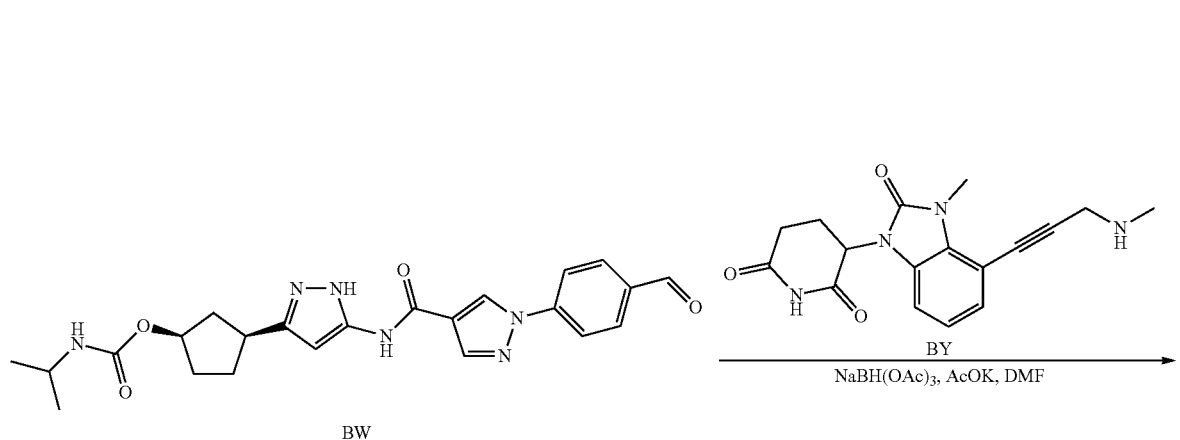

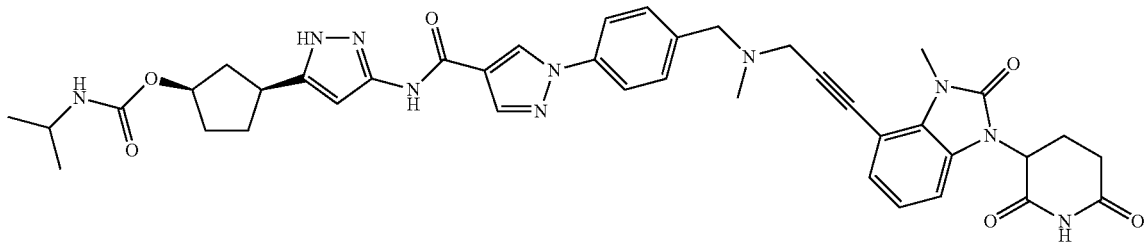

To a solution of 3-(3-methyl-4-(3-(methylamino)prop-1-yn-1-yl)-2-oxo-2,3-dihydro-1H-benzo[d]imidazol-1-yl)piperidine-2,6-dione (38.0 mg, 116 umol, Intermediate BY) in DMF (0.3 mL) and THF (0.3 mL) was added KOAc (30.5 mg, 310 umol), (1R,3S)-3-(5-(1-(4-formylphenyl)-1H-pyrazole-4-carboxamido)-1H-pyrazol-3-yl)cyclopentyl isopropylcarbamate (35 mg, 77.7 umol, Intermediate BW) and NaBH(OAc)$_3$ (32.9 mg, 155 umol) at 0° C. for one portion. The mixture was stirred at 0-25° C. for 10 h. The mixture was poured into ice water (3 mL) and extracted with ethyl acetate (2×3 mL). The combined organic phase was washed with brine (2×3 mL), then dried over sodium sulfate. Then the mixture was filtered and the filtrate was concentrated to give a residue. The residue was purified by prep-HPLC (column: Phenomenex Luna C18 150*25 mm*10 um; mobile phase: [water (0.225% FA)-ACN]; B %: 15%-45%, 10 min) to give the title compound (8.17 mg, 10.7 umol, 14% yield) as a white solid. $^1$H NMR (400 MHz, DMSO-d$_6$) δ=12.21-12.11 (m, 1H), 11.12-11.08 (m, 1H), 10.52 (s, 1H), 9.11-9.07 (m, 1H), 8.30 (s, 1H), 7.83-7.81 (m, 2H), 7.51-7.49 (m, 2H), 7.17-6.95 (m, 4H), 6.42 (s, 1H), 5.42-5.36 (m, 1H), 5.01-4.99 (m, 1H), 3.69 (s, 3H), 3.67-3.60 (m, 4H), 3.20-2.65 (m, 6H), 2.33 (s, 3H), 2.13 (s, 1H), 2.04-1.72 (m, 6H), 1.03 (d, J=6.4 Hz, 6H). LC-MS (ESI$^+$) m/z 761.4 (M+H)$^+$.

Example 11. Synthesis of (1R,3S)-3-(5-(1-(2-(4-(3-(1-(2,6-dioxopiperidin-3-yl)-3-methyl-2-oxo-2,3-dihydro-1H-benzo[d]imidazol-4-yl)prop-2-yn-1-yl)piperazin-1-yl)ethyl)-1H-pyrazole-5-carboxamido)-1H-pyrazol-3-yl)cyclopentyl isopropylcarbamate (I-56)

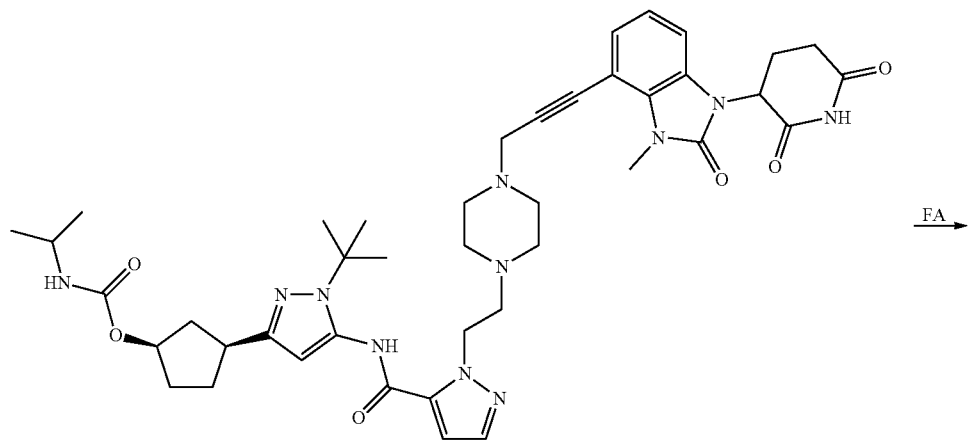

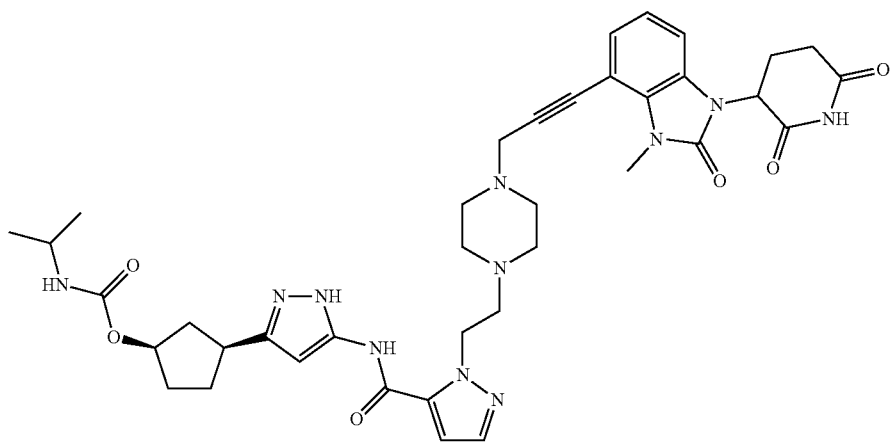

A solution of (1R,3S)-3-(1-(tert-butyl)-5-(1-(2-(4-(3-(1-(2,6-dioxopiperidin-3-yl)-3-methyl-2-oxo-2,3-dihydro-1H-benzo[d]imidazol-4-yl)prop-2-yn-1-yl)piperazin-1-yl)ethyl)-1H-pyrazole-5-carboxamido)-1H-pyrazol-3-yl) cyclopentyl isopropylcarbamate (25 mg, 30.8 umol, synthesized via step 1 of Method 5) in formic acid (0.5 mL) was stirred at 70° C. for 10 h under nitrogen atmosphere. On completion, the reaction was concentrated to give a residue. The residue was purified by prep-HPLC (column: Phenomenex Luna C18 150*25 mm*10 um; mobile phase: [water (0.225% FA)-ACN]; B %: 11%-41%, 10 min) and lyophilized to give the title compound (1.56 mg, 7% yield) as a yellow gum. $^1$H NMR (400 MHz, DMSO-$d_6$) δ=12.36-12.15 (m, 1H), 11.11 (br d, J=4.8 Hz, 1H), 10.75 (br s, 1H), 7.50 (d, J=2.0 Hz, 1H), 7.14 (d, J=8.0 Hz, 1H), 7.11-7.05 (m, 2H), 7.03-6.97 (m, 1H), 6.94 (br d, J=6.8 Hz, 1H), 6.44-6.36 (m, 1H), 5.38 (dd, J=5.2, 12.5 Hz, 1H), 4.99 (br d, J=5.6 Hz, 1H), 4.62 (brt, J=6.4 Hz, 2H), 3.64-3.53 (m, 4H), 3.49 (s, 2H), 3.17-2.83 (m, 6H), 2.77-2.56 (m, 6H), 2.35-2.29 (m, 2H), 2.06-1.97 (m, 2H), 1.89 (br d, J=6.8 Hz, 5H), 1.02 (d, J=6.4 Hz, 6H). LC-MS (ESI$^+$) m/z 754.4 (M+H)$^+$.

Example 12. Synthesis of (1R,3S)-3-(5-(1-(9-(1-(2,6-dioxopiperidin-3-yl)-3-methyl-2-oxo-2,3-dihydro-1H-benzo[d]imidazol-5-yl)non-8-yn-1-yl)-1H-pyrazole-5-carboxamido)-1H-pyrazol-3-yl)cyclopentyl isopropylcarbamate (I-86)

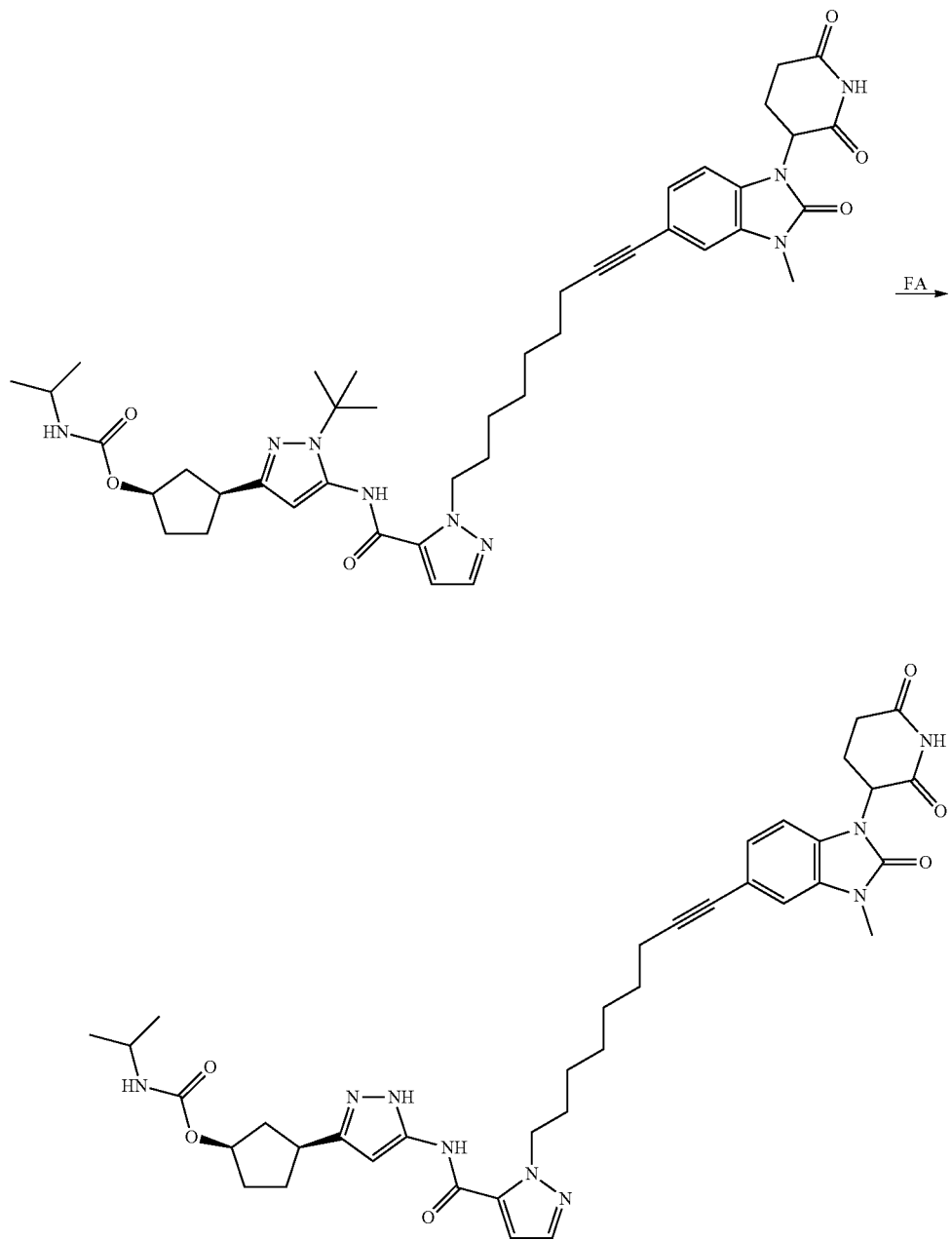

The solution of [(1R,3S)-3-[1-tert-butyl-5-[[2-[9-[1-(2,6-dioxo-3-piperidyl)-3-methyl-2-oxo-benzimidazol-5-yl]non-8-ynyl]pyrazole-3-carbonyl]amino]pyrazol-3-yl]cyclopentyl] N-isopropylcarbamate (0.07 g, 89.5 umol, synthesized via Step 1 of Method 5) in HCOOH (0.5 mL) was stirred at 80° C. for 2 h. On completion, the mixture was concentrated in vacuo and purified by prep-HPLC (FA condition, column: 3_Phenomenex Luna C18 75*30 mm*3 um; mobile phase: [water (0.225% FA)-ACN]; B %: 42%-72%, 10 min) to give the title compound (12 mg, 17% yield) as a white solid. $^1$H NMR (400 MHz, DMSO-d6) δ=7.50 (d, J=2.0 Hz, 1H), 7.13 (br s, 1H), 7.11 (d, J=8.0 Hz, 1H), 7.06-7.03 (m, 1H), 6.99 (d, J=8.0 Hz, 1H), 6.97-6.92 (m, 1H), 6.42 (br s, 1H), 5.39 (dd, J=5.2, 12.8 Hz, 1H), 5.03-4.97 (m, 1H), 4.52 (br t, J=7.2 Hz, 2H), 3.63 (s, 3H), 3.58 (br dd, J=6.4, 14.0 Hz, 1H), 3.12-3.04 (m, 1H), 2.93-2.84 (m, 1H), 2.76-2.65 (m, 2H), 2.35-2.31 (m, 1H), 2.05-2.00 (m, 2H), 1.89 (dt, J=2.8, 6.8 Hz, 1H), 1.77-1.70 (m, 4H), 1.67-1.61 (m, 1H), 1.58-1.51 (m, 2H), 1.41-1.23 (m, 7H), 1.03 (d, J=6.5 Hz, 6H).

1045

Example 13. Synthesis of (1R,3S)-3-(5-(1-(12-(1-(2,6-dioxopiperidin-3-yl)-3-methyl-2-oxo-2,3-dihydro-1H-benzo[d]imidazol-4-yl)dodec-11-yn-1-yl)-1H-pyrazole-5-carboxamido)-1H-pyrazol-3-yl)cyclopentyl isopropylcarbamate (I-88)

1046

A solution of (1R,3S)-3-(1-(tert-butyl)-5-(1-(12-(1-(2,6-dioxopiperidin-3-yl)-3-methyl-2-oxo-2,3-dihydro-1H-benzo[d]imidazol-4-yl)dodec-11-yn-1-yl)-1H-pyrazole-5-carboxamido)-1H-pyrazol-3-yl)cyclopentyl isopropylcarbamate (50 mg, 60.7 umol, synthesized via Step 1 of Method 5) in HCOOH (2 mL) was stirred at 70° C. for

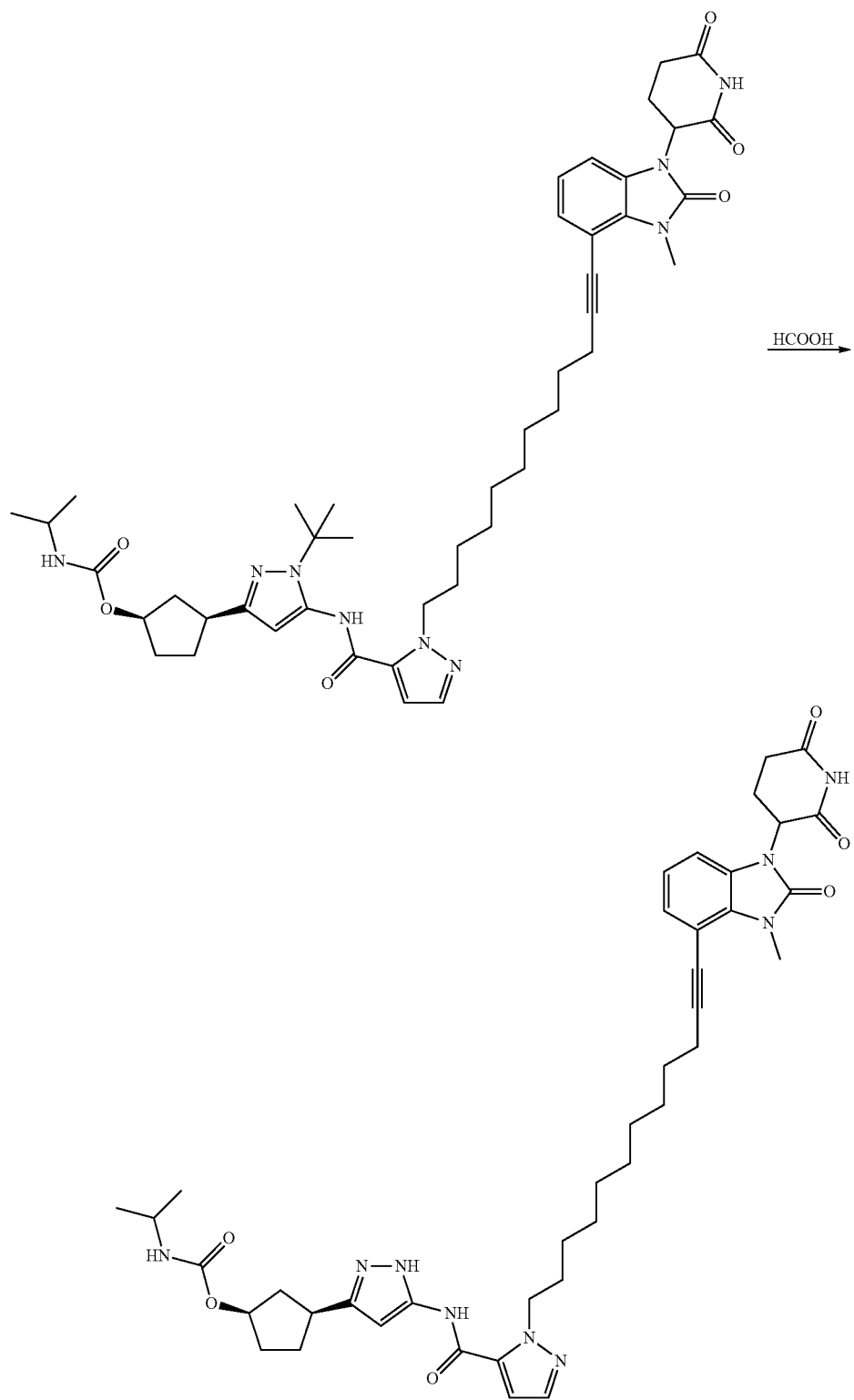 [SMILES: CC(C)NC(=O)O[C@@H]1CC[C@H](c2cc(NC(=O)c3ccnn3CCCCCCCCCCC#Cc3cccc4c3n(C)c(=O)n4C3CCC(=O)NC3=O)n(C(C)(C)C)n2)C1 ; "HCOOH" ; CC(C)NC(=O)O[C@@H]1CC[C@H](c2cc(NC(=O)c3ccnn3CCCCCCCCCCC#Cc3cccc4c3n(C)c(=O)n4C3CCC(=O)NC3=O)[nH]n2)C1]

12 h. On completion, the mixture was concentrated under reduced pressure to give a residue. The residue was purified by prep-HPLC (column: Phenomenex luna C18 150*25 mm*10 um; mobile phase: [water (0.225% FA)-ACN]; B %: 62%-92%, 11.5 min) and lyophilized to give the title compound (12.7 mg, 25% yield) as off-white solid. $^1$H NMR (400 MHz, DMSO-d6) δ 12.23 (br s, 1H), 11.10 (br s, 1H), 10.69 (br s, 1H), 7.48 (s, 1H), 7.25-6.81 (m, 5H), 6.41 (br s, 1H), 5.38 (br dd, J=5.2, 12.6 Hz, 1H), 5.00 (br d, J=3.6 Hz, 1H), 4.49 (br t, J=6.8 Hz, 2H), 3.72-3.49 (m, 3H), 3.14-3.02 (m, 1H), 2.96-2.82 (m, 1H), 2.77-2.57 (m, 2H), 2.47-2.40 (m, 4H), 2.08-1.96 (m, 3H), 1.93-1.84 (m, 1H), 1.78-1.65 (m, 4H), 1.60-1.51 (m, 2H), 1.46-1.35 (m, 2H), 1.34-1.17 (m, 10H), 1.03 (br d, J=6.4 Hz, 6H). LC-MS (ESI$^+$) m/z 768.4 (M+H)$^+$.

Example 14. Synthesis of (1R,3S)-3-(5-(1-(11-(3-(2-((S)-1-((S)-2-cyclohexyl-2-((S)-2-(methylamino)propanamido)acetyl)pyrrolidin-2-yl)thiazole-4-carbonyl)phenoxy)undecyl)-1H-pyrazole-4-carboxamido)-1H-pyrazol-3-yl)cyclopentyl isopropylcarbamate (I-148)

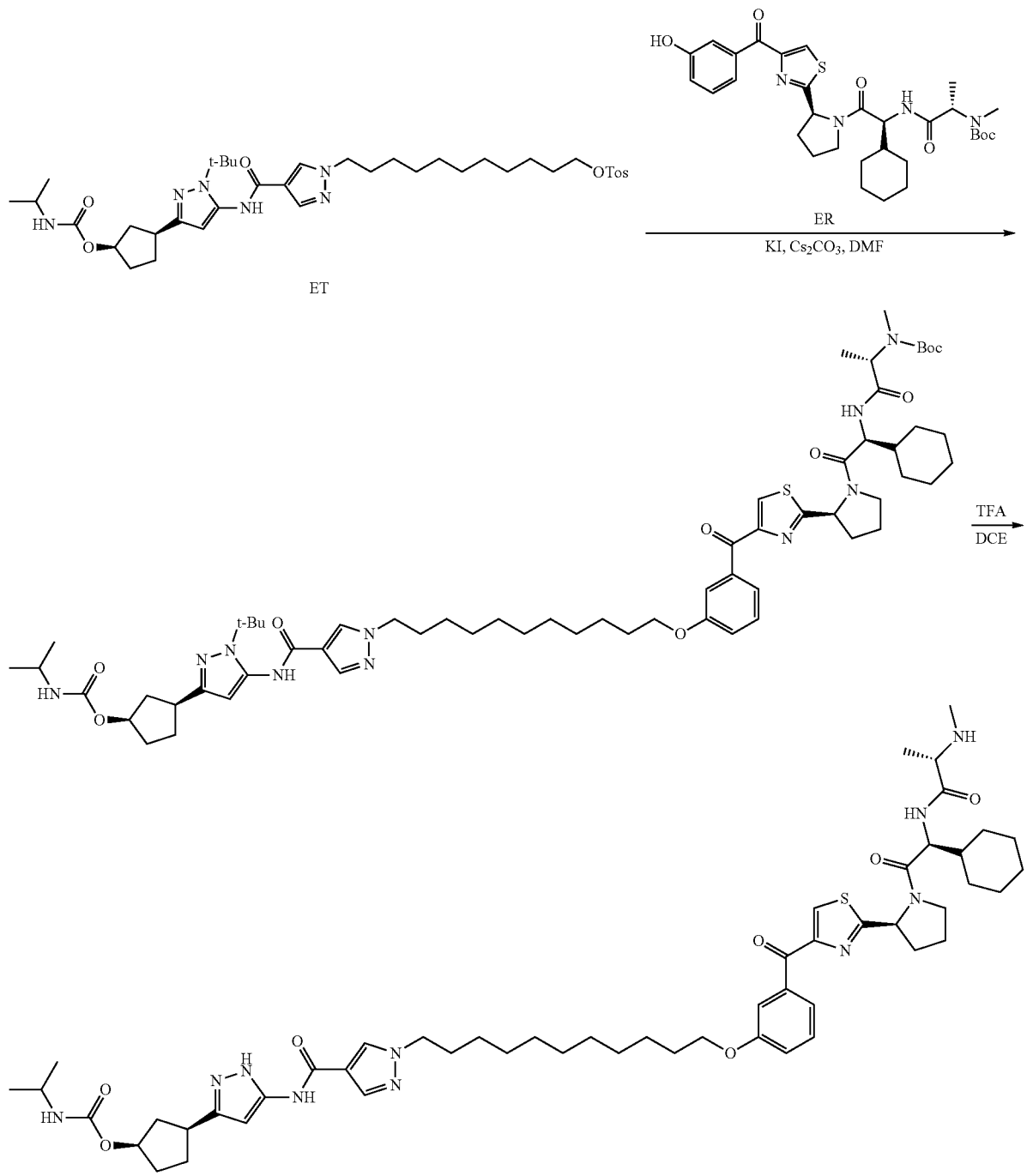

Step 1—Tert-butyl ((S)-1-(((S)-2-((S)-2-(4-(3-((11-(4-((1-(tert-butyl)-3-((1S,3R)-3-((isopropylcarbamoyl)oxy)cyclopentyl)-1H-pyrazol-5-yl)carbamoyl)-1H-pyrazol-1-yl)undecyl)oxy)benzoyl)thiazol-2-yl)pyrrolidin-1-yl)-1-cyclohexyl-2-oxoethyl)amino)-1-oxopropan-2-yl)(methyl)carbamate. To a solution of 11-(4-((1-(tert-butyl)-3-((1S,3R)-3-((isopropylcarbamoyl)oxy)cyclopentyl)-1H-pyrazol-5-yl)carbamoyl)-1H-pyrazol-1-yl)undecyl 4-methylbenzenesulfonate (100 mg, 68.7 umol, Intermediate ET) and tert-butyl((S)-1-(((S)-1-cyclohexyl-2-((S)-2-(4-(3-hydroxybenzoyl)thiazol-2-yl) pyrrolidin-1-yl)-2-oxoethyl)amino)-1-oxopropan-2-yl)(methyl)carbamate (49.4 mg, 82.5 umol, Intermediate ER) in DMF (2 mL) was added KI (1.14 mg, 6.88 umol) and Cs$_2$CO$_3$ (67.2 mg, 206 umol). Then the mixture was stirred at 70° C. for 2 h. On completion, the reaction mixture was quenched with aqueous NaHCO$_3$ (2 mL) at 20° C., then diluted with 1 mL EtOAc and extracted with EtOAc (2 mL×3). The combined organic layers were washed with brine (2 mL×2), dried over Na$_2$SO$_4$, filtered and concentrated under reduced pressure to give a residue. The residue was purified by prep-TLC (SiO$_2$, Petroleum ether:Ethyl acetate=0:1) to give the title compound (20 mg, 25% yield) as brown solid.

Step 2—(1R,3S)-3-(5-(1-(11-(3-(2-((S)-1-((S)-2-cyclohexyl-2-((S)-2-(methylamino)propanamido)acetyl)pyrrolidin-2-yl)thiazole-4-carbonyl)phenoxy)undecyl)-1H-pyrazole-4-carboxamido)-1H-pyrazol-3-yl)cyclopentyl isopropylcarbamate. A solution of tert-butyl ((S)-1-(((S)-2-((S)-2-(4-(3-((11-(4-((1-(tert-butyl)-3-((1S,3R)-3-((isopropylcarbamoyl)oxy)cyclopentyl)-1H-pyrazol-5-yl)carbamoyl)-1H-pyrazol-1-yl)undecyl)oxy)benzoyl)thiazol-2-yl) pyrrolidin-1-yl)-1-cyclohexyl-2-oxoethyl)amino)-1-oxopropan-2-yl)(methyl)carbamate (20 mg, 17.3 umol) in DCE (0.5 mL) was added TFA (154 mg, 1.35 mmol, 0.1 mL), then the mixture was stirred at 80° C. for 12 h. On completion, filtered and concentrated under reduced pressure to give a residue, the residue was purified by prep-HPLC (column: Phenomenex Luna C18 150*25 mm*10 um; mobile phase: [water (0.225% FA)-ACN]; B %: 34%-64%, 10 min) to give the title compound (3.89 mg, 23% yield) as off-white solid. $^1$H NMR (400 MHz, DMSO-d6) δ=12.32-11.83 (m, 1H), 10.33 (br s, 1H), 8.51-8.43 (m, 1H), 8.33 (s, 1H), 8.03 (s, 1H), 7.98-7.88 (m, 1H), 7.68-7.58 (m, 2H), 7.48-7.42 (m, 1H), 7.25-7.19 (m, 1H), 6.95 (br d, J=6.8 Hz, 1H), 6.36 (br s, 1H), 5.42-5.34 (m, 1H), 4.99 (br d, J=2.8 Hz, 1H), 4.52-4.42 (m, 1H), 4.10 (t, J=6.8 Hz, 2H), 4.01 (br t, J=6.4 Hz, 3H), 3.84-3.76 (m, 1H), 3.71-3.63 (m, 1H), 3.55 (br dd, J=7.6, 14.0 Hz, 2H), 3.09-2.99 (m, 2H), 2.99-2.92 (m, 1H), 2.29-2.23 (m, 1H), 2.22-2.12 (m, 3H), 2.09 (s, 2H), 2.05-1.96 (m, 3H), 1.92-1.85 (m, 1H), 1.73 (br dd, J=6.4, 13.1 Hz, 8H), 1.60 (br s, 4H), 1.55-1.48 (m, 1H), 1.45-1.38 (m, 2H), 1.24 (br s, 10H), 1.20-1.12 (m, 3H), 1.11-1.05 (m, 4H), 1.02 (br d, J=6.4 Hz, 6H), 0.96-0.89 (m, 1H). LC-MS (ESI$^+$) m/z 997.6 (M+H)$^+$.

Example 15. Synthesis of 4-[[5-amino-1-(3-methyl-thiophene-2-carbonyl)-1,2,4-triazol-3-yl]amino]-N-[2-[[1-[2-[3-[1-(2,6-dioxo-3-piperidyl)-3-methyl-2-oxo-benzimidazol-5-yl]propoxy]ethyl]triazol-4-yl]methoxy]ethyl]benzenesulfonamide (I-136)

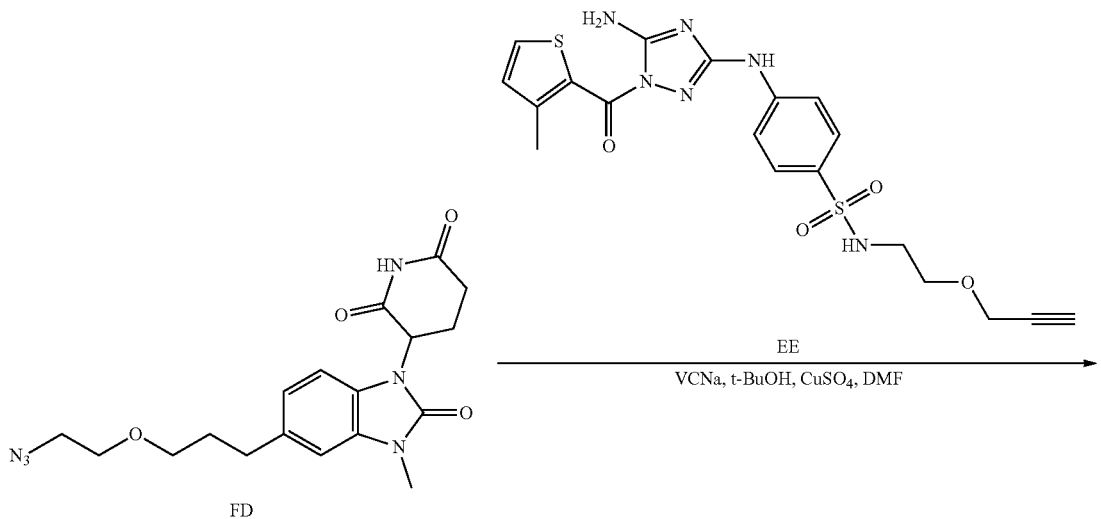

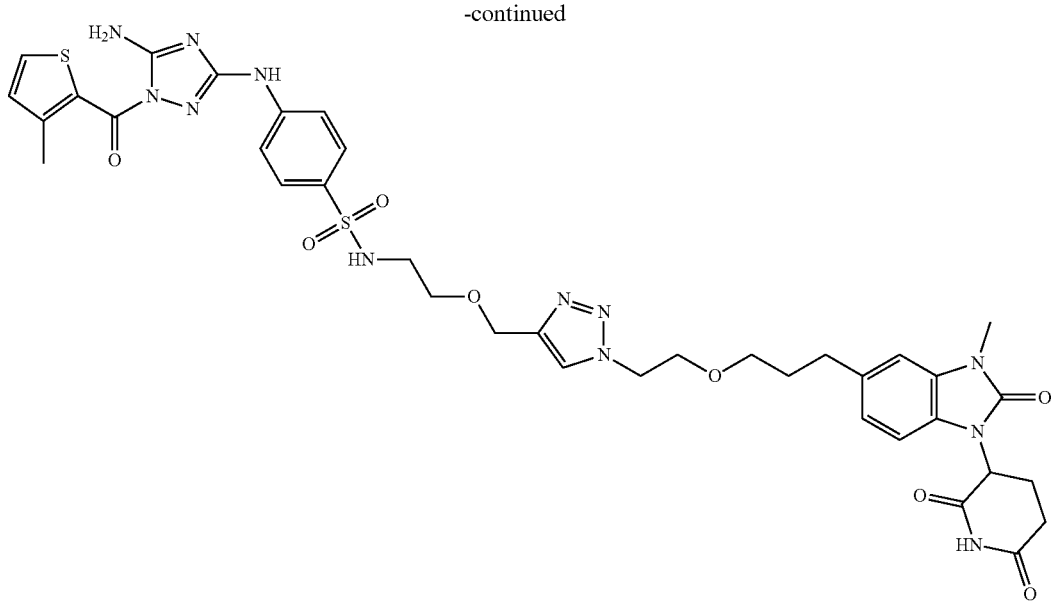

To a solution of 3-[5-[3-(2-azidoethoxy)propyl]-3-methyl-2-oxo-benzimidazol-1-yl]piperidine-2,6-dione (70 mg, 200 umol, Intermediate FD) and 4-[[5-amino-1-(3-methylthiophene-2-carbonyl)-1,2,4-triazol-3-yl]amino]-N-(2-prop-2-ynoxyethyl)benzenesulfonamide (83.4 mg, 181 umol, Intermediate EE) in DMF (1 mL) and was added CuSO$_4$ (14.5 mg, 90.6 umol), sodium (2R)-2-[(2R)-3,4-dihydroxy-5-oxo-2H-furan-2-yl]-2-hydroxy-ethanolate (108 mg, 543 umol, VCNa), t-BuOH (0.9 mL) and H$_2$O (0.1 mL) at 20° C. under nitrogen flow. Then the reaction was stirred at 70° C. for 2 h under nitrogen atmosphere. On completion, the mixture was filtered, the filter liquor was concentrated under reduced pressure to give a residue. The crude product was purified by reversed-phase HPLC (column: Phenomenex Luna C18 100*30 mm*5 um; mobile phase: [water (0.225% FA)-ACN]; B %: 30%-60%, 8 min) to give the title compound (58 mg, 37% yield) as a white solid. $^1$H NMR (400 MHz, DMSO-d6) δ=11.08 (br s, 1H), 9.94 (s, 1H), 8.06-8.02 (m, 2H), 7.91-7.79 (m, 4H), 7.76-7.70 (m, 2H), 7.51-7.43 (m, 1H), 7.16 (d, J=5.2 Hz, 1H), 7.01-6.91 (m, 2H), 6.79 (dd, J=1.6, 8.0 Hz, 1H), 5.33 (dd, J=5.2, 12.8 Hz, 1H), 4.54-4.49 (m, 2H), 4.47 (s, 2H), 3.75 (t, J=5.2 Hz, 2H), 3.45-3.40 (m, 2H), 3.38 (br s, 4H), 3.31 (s, 3H), 2.91-2.86 (m, 2H), 2.76-2.65 (m, 1H), 2.63 (s, 3H), 2.57-2.52 (m, 2H), 2.04-1.95 (m, 1H), 1.81-1.68 (m, 2H); LC-MS (ESI$^+$) m/z 847.4 (M+H)$^+$.

Example 16. Synthesis of 3-[4-[7-[4-[[4-[(6-Chloro-8-isopropyl-7-oxo-pyrido[2,3-d]pyrimidin-2-yl)amino]-1-piperidyl] sulfonyl]pyrazol-1-yl]heptylamino]-3-methyl-2-oxo-benzimidazol-1-yl]piperidine-2,6-dione (I-165)

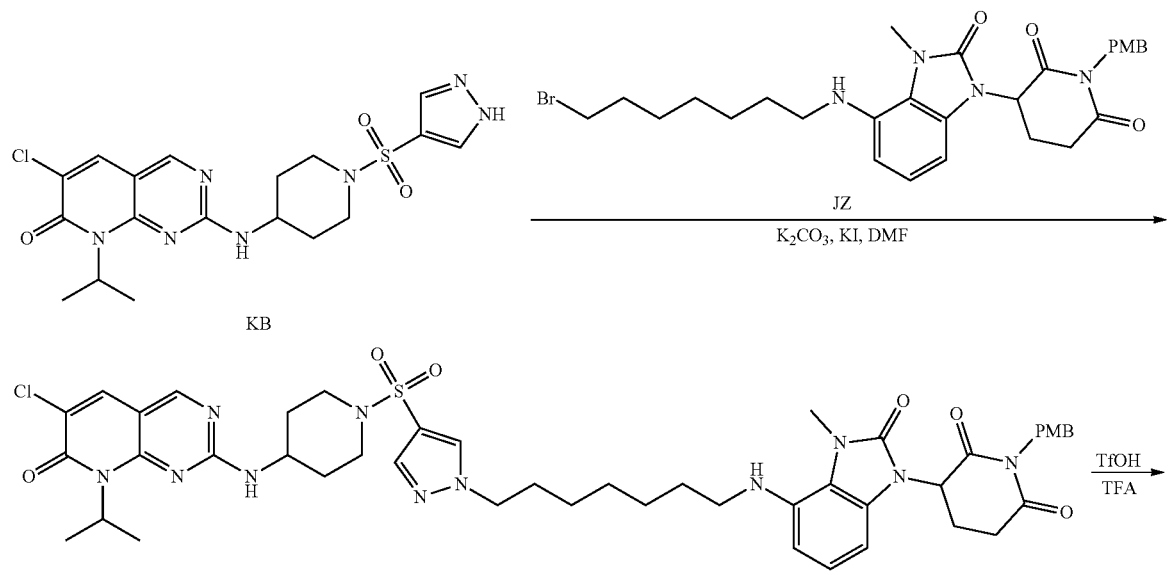

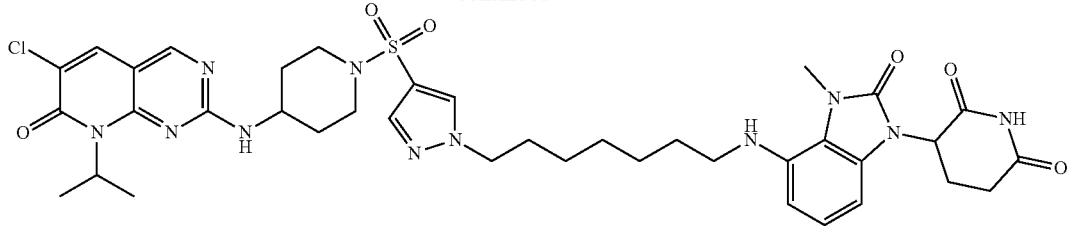

Step 1—3-[4-(7-Bromoheptylamino)-3-methyl-2-oxo-benzimidazol-1-yl]-1-[(4-methoxyphenyl) methyl]piperidine-2,6-dione. To a solution of 3-[4-(7-bromoheptylamino)-3-methyl-2-oxo-benzimidazol-1-yl]-1-[(4-methoxyphenyl)methyl]piperidine-2,6-dione (24.0 mg, 41.9 umol, Intermediate JZ) and 6-chloro-8-isopropyl-2-[[1-(1H-pyrazol-4-ylsulfonyl)-4-piperidyl]amino]pyrido[2,3-d]pyrimidin-7-one (18.9 mg, 41.9 umol, Intermediate KB) in DMF (2 mL) was added $K_2CO_3$ (29.0 mg, 209 umol) and KI (6.97 mg, 41.9 umol). The mixture was stirred at 25° C. for 2 hrs. On completion, the reaction mixture was quenched with $H_2O$ (1 mL) at 25° C. Then the mixture was filtered and partitioned between EA (10 mL) and water (10 mL). The organic layer was collected, and the aqueous layer was extracted with EA (2×8 mL). The combined organic layers were washed with brine (10 mL), dried over anhydrous sodium sulfate, and concentrated in vacuo to give the title compound (35 mg, 88% yield) as a white solid. LCMS ($ESI^+$) m/z 942.5 $(M+H)^+$.

Step 2—3-[4-[7-[4-[[4-[(6-Chloro-8-isopropyl-7-oxo-pyrido[2,3-d]pyrimidin-2-yl)amino]-1-piperidyl] sulfonyl]pyrazol-1-yl]heptylamino]-3-methyl-2-oxo-benzimidazol-1-yl]piperidine-2,6-dione. To a solution of 3-[4-[7-[4-[[4-[(6-chloro-8-isopropyl-7-oxo-pyrido[2,3-d]pyrimidin-2-yl)amino]-1-piperidyl]sulfonyl]pyrazol-1-yl]heptylamino]-3-methyl-2-oxo-benzimidazol-1-yl]-1-[(4-methoxyphenyl)methyl]piperidine-2,6-dione (30.0 mg, 31.8 umol) in TFA (1.6 mL) was added TfOH (0.2 mL). The mixture was stirred at 70° C. for 2 hrs. On completion, the mixture was concentrated in vacuo to afford a residue. To the residue was added ACN (1 mL) and TEA at 25° C. until the pH=6. The mixture was concentrated in vacuo to afford a residue. The residue was purified by prep-HPLC (column: Phenomenex luna C18 150*25 mm*10 um; mobile phase: [water(FA)-ACN]; B %: 45%-75%, 9 min) to give the title compound (19.2 mg, 69% yield) as a yellow solid. $^1$H NMR (400 MHz, DMSO-$d_6$) δ 11.06 (s, 1H), 8.57 (s, 1H), 8.45-8.36 (m, 1H), 8.11-7.74 (m, 3H), 6.84 (t, J=8.0 Hz, 1H), 6.50 (d, J=7.6 Hz, 1H), 6.38 (d, J=8.4 Hz, 1H), 5.83-5.58 (m, 1H), 5.28 (dd, J=5.2, 12.4 Hz, 1H), 4.20 (t, J=6.8 Hz, 2H), 3.89-3.67 (m, 2H), 3.59 (s, 3H), 3.01 (t, J=7.2 Hz, 2H), 2.94-2.82 (m, 1H), 2.75-2.67 (m, 1H), 2.66-2.58 (m, 2H), 2.46 (s, 2H), 2.40 (d, J=12.4 Hz, 1H), 2.02-1.91 (m, 3H), 1.87-1.79 (m, 2H), 1.73-1.53 (m, 5H), 1.48 (d, J=6.8 Hz, 6H), 1.35 (d, J=2.4 Hz, 4H), 1.25-1.19 (m, 2H). LCMS ($ESI^+$) m/z 822.4 $(M+H)^+$.

Example 17. Degradation Assays

CDK2 and CDK1 Degradation by Immunoblotting

Ovarian cancer cell line OVCAR-8 were cultured in 12-well plates in complete growth medium. A serial dilution of each compound was added to individual wells from a 2× stock solution, and cells were cultured for 24 hours. Cells were collected by centrifugation, and cell pellets lysed with addition of chilled RIPA buffer supplemented with protease/phosphatase inhibitors followed by incubation for 20 minutes on ice. Lysates were clarified by centrifugation and 5×SDS loading buffer was added to the supernatant followed by heating to 100° C. for 10 minutes. An aliquot of the samples were separated by SDS-PAGE and transferred to a nitrocellulose membrane. Immunoblotting was performed according to standard procedures using anti-CDK2 primary antibody (Abcam ab32147) at 1:1000 dilution and IRDye 800CW goat anti-Rabbit secondary antibody (LICOR) and imaged using a LICOR Odyssey instrument. Blots were stained with anti-beta-Actin primary antibody (Cell Signaling Technology mAb #4970) for normalization. The normalized CDK2/Actin values were calculated as a percent of DMSO treated cells and plotted to determine the concentration at which 50% of CDK2 signal is decreased (DC50). The determination of CDK1 degradation was determined similarly using anti-CDK1 primary antibody (Abcam ab131450).

CCNE1 Degradation in MKN-1 Cells

Gastric cancer cell line MKN-1 were cultured in 6-well plates in complete growth medium. A serial dilution of each compound was added to individual wells from a 2× stock solution, and cells were cultured for 24 hours. Following 24-hr incubation, cells were lysed with addition of chilled RIPA buffer supplemented with protease/phosphatase inhibitors followed by incubation for 20 minutes on ice. Lysates were clarified by centrifugation and 5×SDS loading buffer was added to the supernatant followed by heating to 100° C. for 10 minutes. An aliquot of the samples were separated by SDS-PAGE and transferred to a nitrocellulose membrane. Immunoblotting was performed according to standard procedures using anti-CCNE1 primary antibody (Abcam #ab33911) at 1:1000 dilution and IRDye 800CW goat anti-Rabbit secondary antibody (LICOR) and imaged using a LICOR Odyssey instrument. Blots were stained with anti-beta-Actin primary antibody (Cell Signaling Technology mAb 43700) for normalization. The normalized CCNE1/Actin values were calculated as a percent of DMSO treated cells and plotted to determine the concentration at which 50% of CCNE1 signal is decreased.

CDK2, CDK1, and CCNE1 DC50 results for compounds of the invention are reported in Table 10. The letter codes for DC50 and IC50 include: A (<0.01 μM), B (0.01-0.1 μM), C (>0.1-1.0 μM), D (>1.0-5.0 μM), and E (>5.0 μM).

TABLE 10

| I-# | CDK2 DC50, (OVCAR-8, 24 h) | CDK1 DC50, (OVCAR-8, 24 h) | Cyclin E1 DC50, (MKN-1 by WB) |
|---|---|---|---|
| I-5 | A | E | — |
| I-7 | A | E | — |
| I-8 | B | E | — |
| I-11 | B | E | — |
| I-15 | B | C | — |
| I-17 | B | E | — |

TABLE 10-continued

| I-# | CDK2 DC50, (OVCAR-8, 24 h) | CDK1 DC50, (OVCAR-8, 24 h) | Cyclin E1 DC50, (MKN-1 by WB) |
|---|---|---|---|
| I-19 | inactive | — | — |
| I-20 | inactive | — | — |
| I-21 | inactive | — | — |
| I-22 | inactive | — | — |
| I-23 | inactive | — | — |
| I-24 | inactive | — | — |
| I-25 | inactive | — | — |
| I-26 | inactive | — | — |
| I-27 | inactive | — | — |
| I-28 | inactive | — | — |
| I-29 | inactive | — | — |
| I-30 | inactive | — | — |
| I-37 | B | D | — |
| I-55 | B | E | — |
| I-59 | B | E | — |
| I-64 | B | D | — |
| I-67 | C | D | — |
| I-68 | B | E | — |
| I-72 | B | E | — |
| I-73 | C | E | — |
| I-74 | C | E | — |
| I-75 | B | E | — |
| I-77 | C | E | — |
| I-83 | B | E | — |
| I-84 | D | — | — |
| I-85 | inactive | — | — |
| I-87 | inactive | — | — |
| I-89 | inactive | — | — |
| I-91 | B | E | — |
| I-92 | B | D | — |
| I-93 | inactive | — | — |
| I-96 | B | E | — |
| I-97 | B | D | — |
| I-99 | A | E | — |
| I-100 | A | C | — |
| I-101 | A | C | — |
| I-102 | B | C | — |
| I-103 | B | E | — |
| I-104 | B | D | — |
| I-106 | B | D | — |
| I-108 | A | C | A |
| I-109 | A | C | A |
| I-110 | A | D | — |
| I-111 | B | D | — |
| I-114 | A | D | — |
| I-117 | A | C | A |
| I-124 | A | D | — |
| I-126 | A | D | — |
| I-138 | E | E | — |
| I-139 | E | E | — |
| I-142 | B | E | — |
| I-145 | A | C | — |
| I-146 | A | D | — |
| I-148 | D | D | — |
| I-149 | B | E | — |
| I-150 | E | E | — |
| I-151 | D | E | — |
| I-152 | — | E | — |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of the following formula:

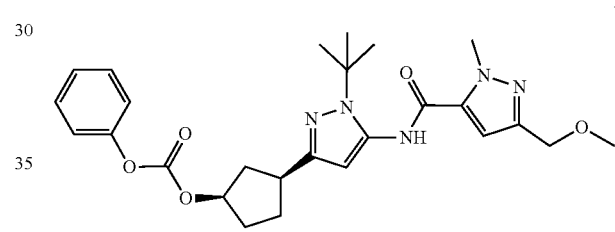

P or a salt thereof.

2. A compound of any one of the following formulae:

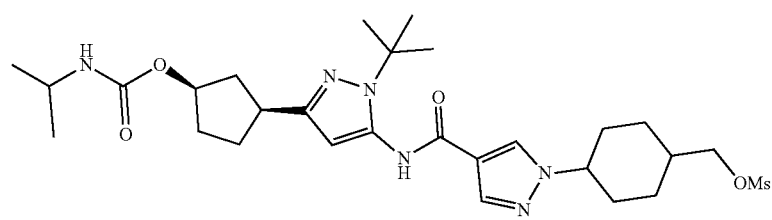

R

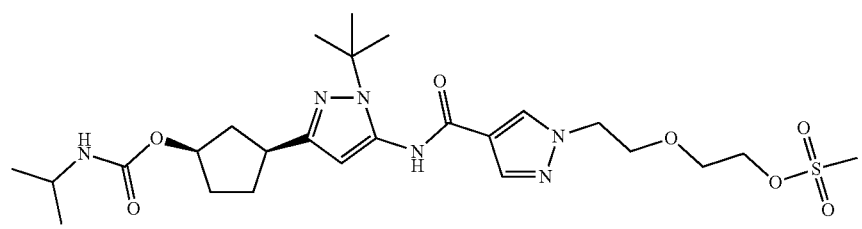

BR

1057
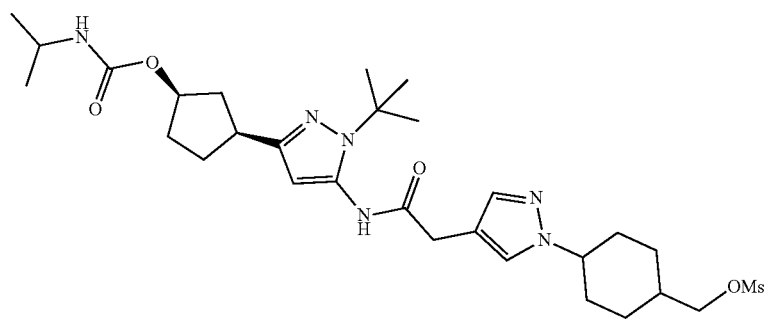
or a salt thereof.
3. A compound of any one of the following formulae:
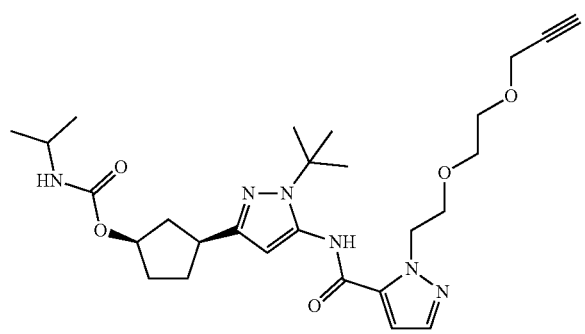
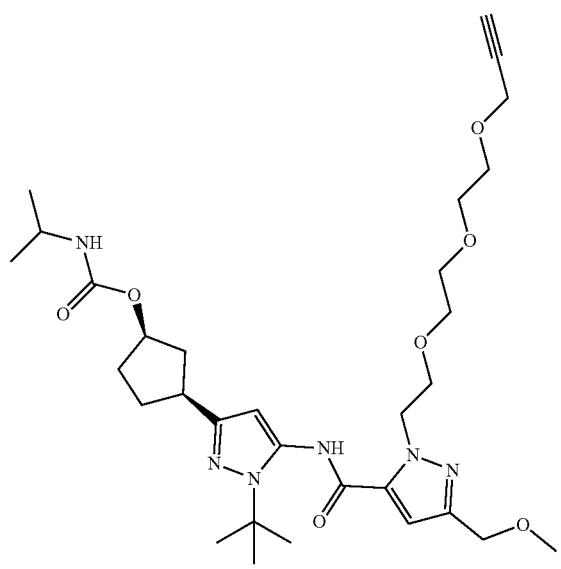
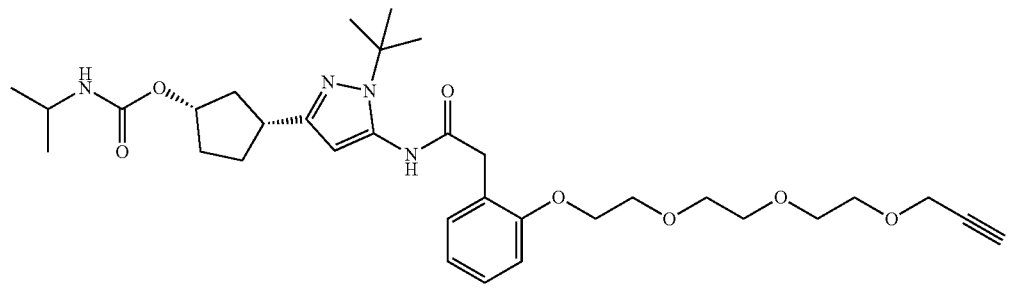

-continued
1059
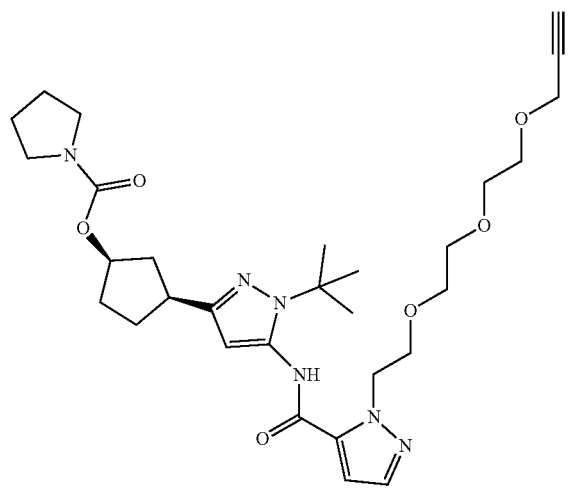
1060
CL
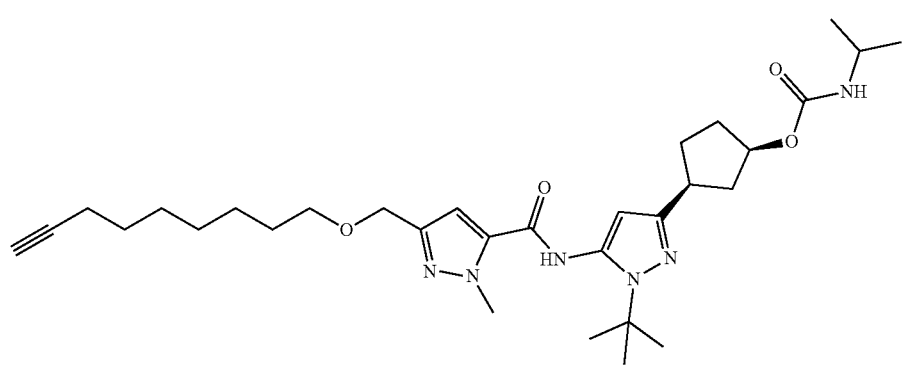
AS
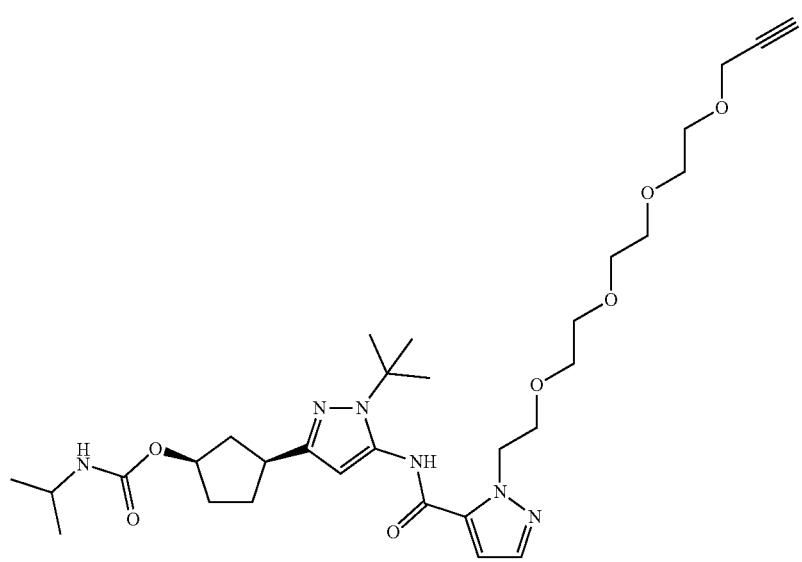
CJ

-continued
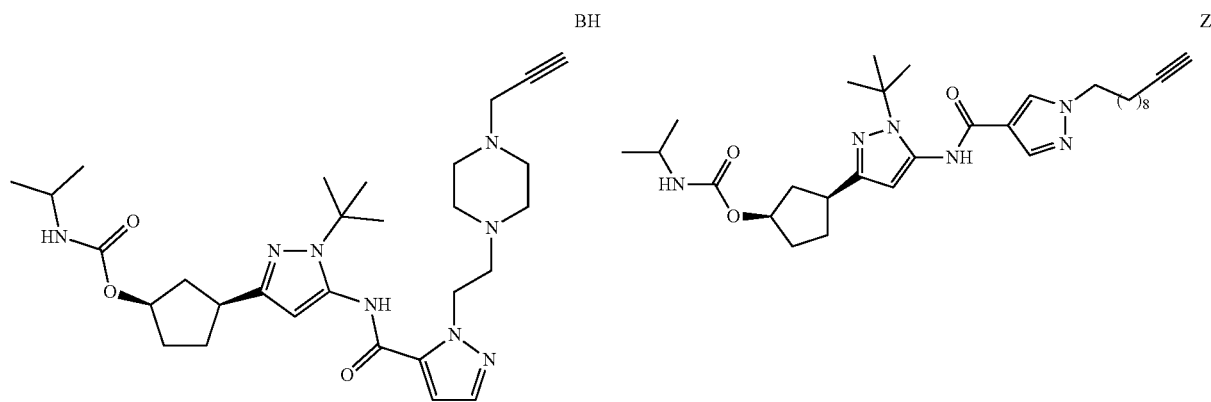
BH
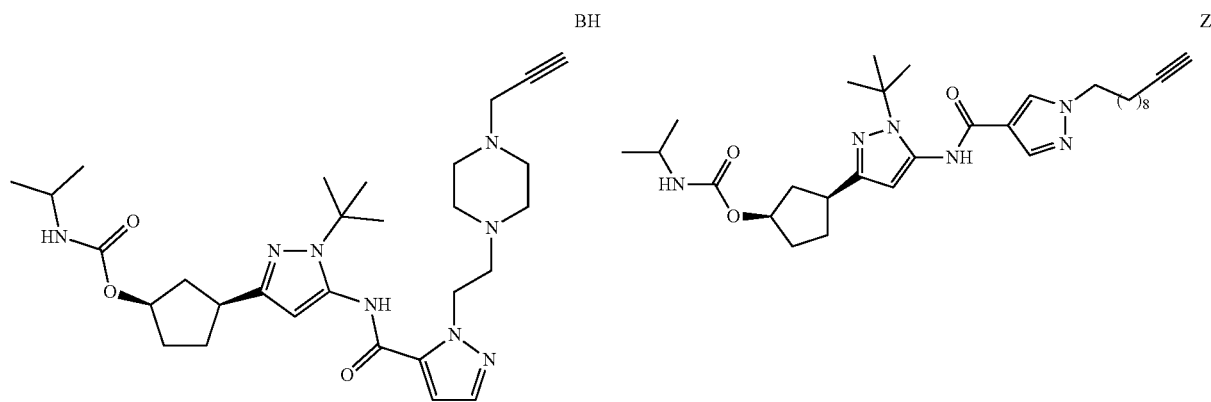
Z
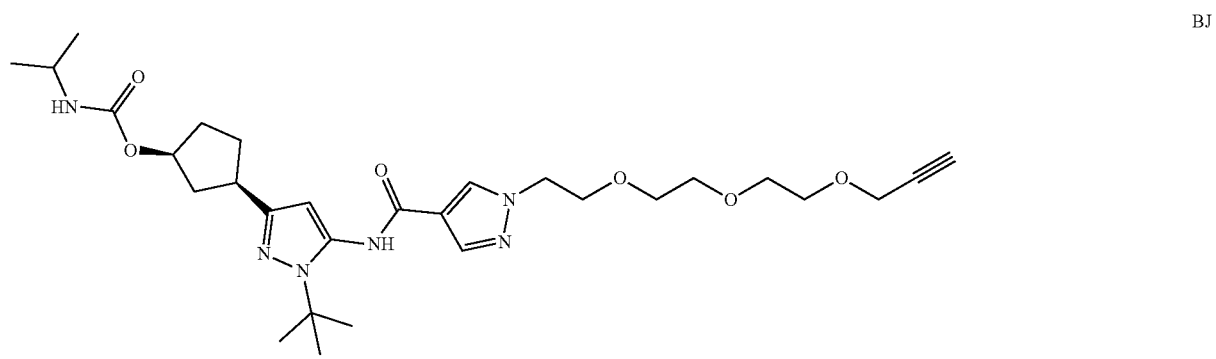
BJ
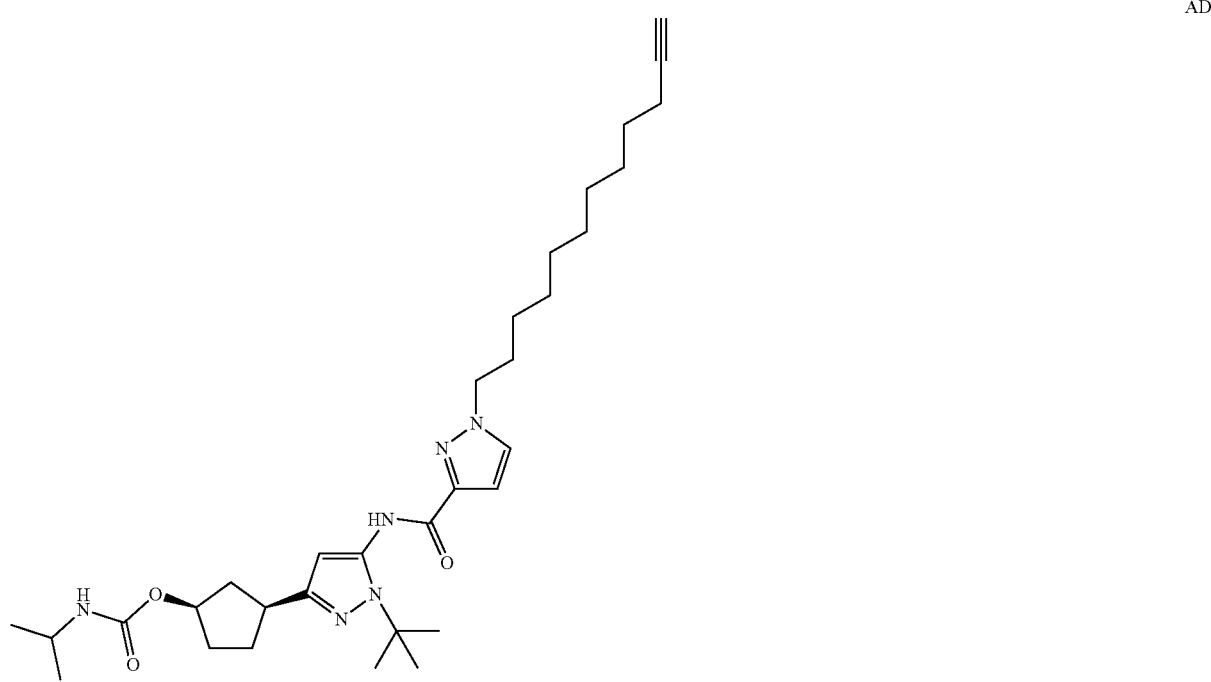
AD

-continued
1063          1064
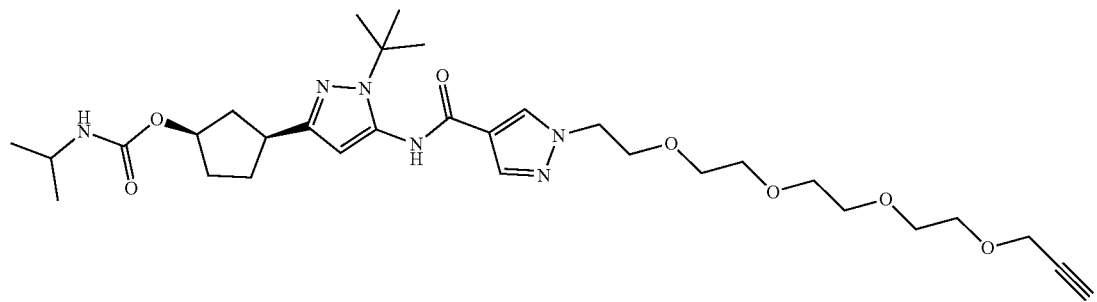
BL
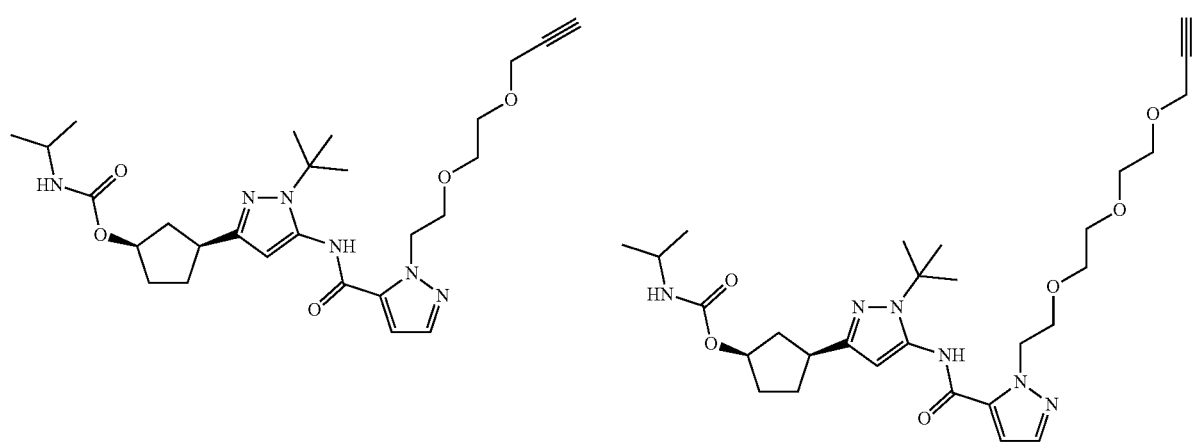
X          BF
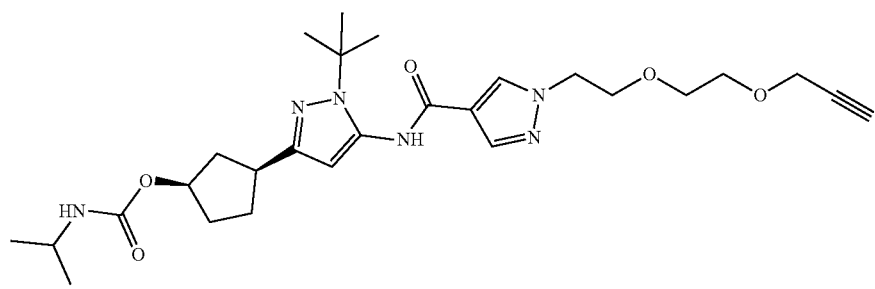
AF
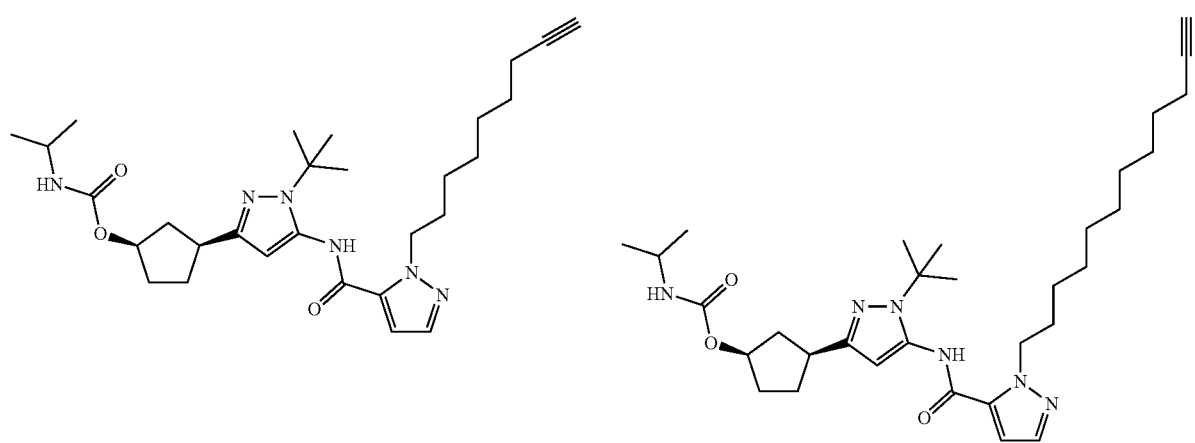
AB          AM 1065                               1066
-continued
BD
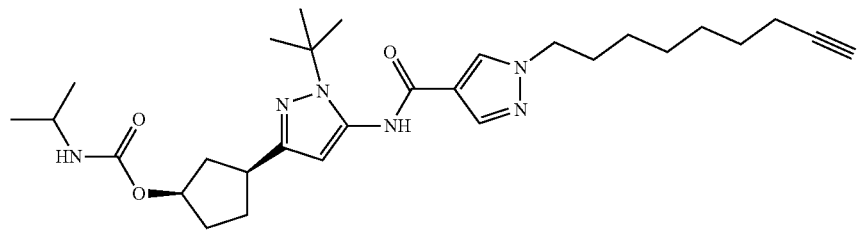
AP
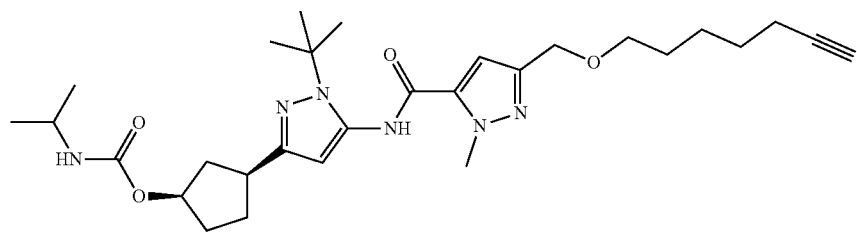
AX                               FV
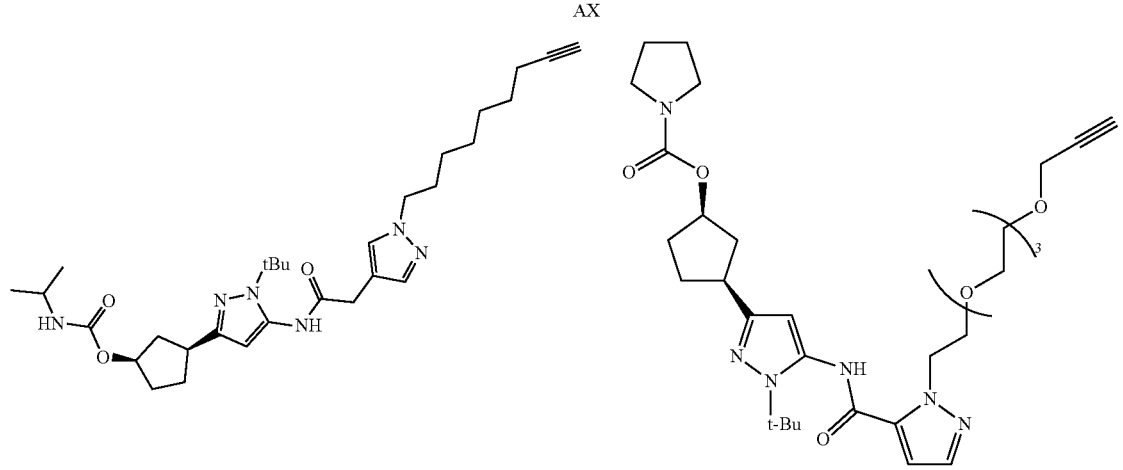
FA
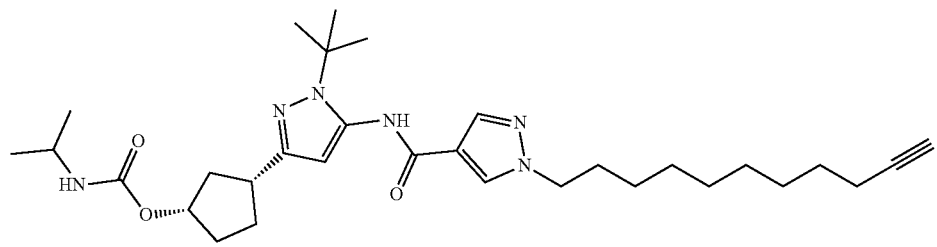
EW
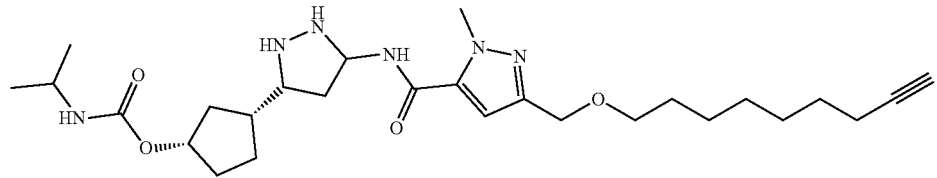
EV
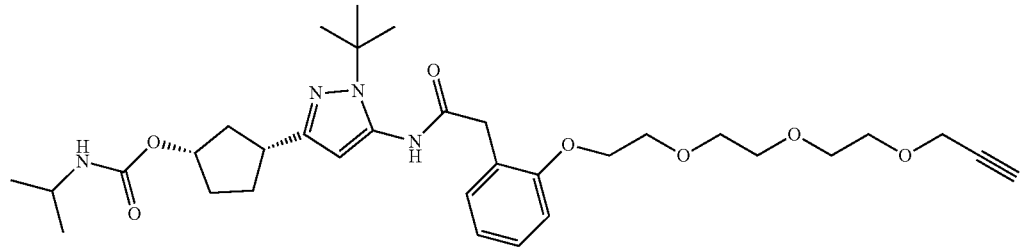

1067
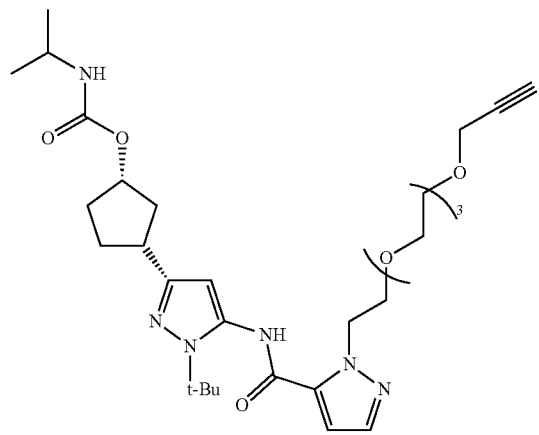
EQ
1068
-continued
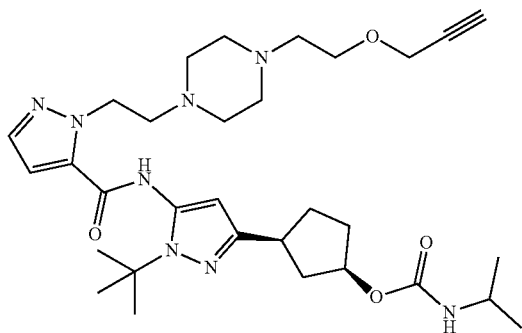
EJ
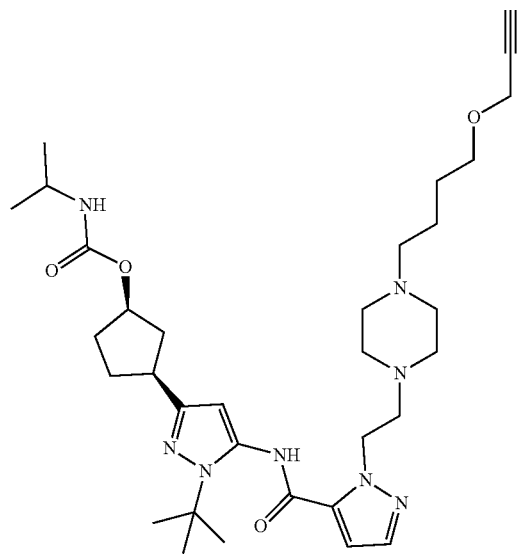
EL
or a salt thereof.
4. The compound of claim 2, wherein the compound is of the following formula:
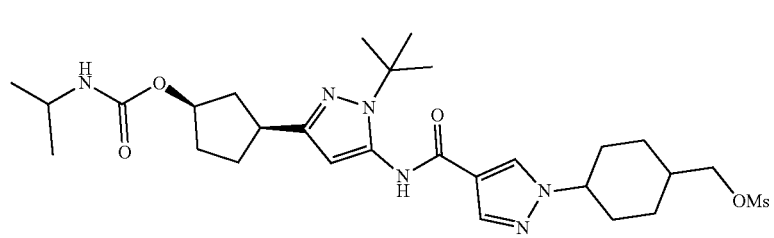
R
or a salt thereof.

5. The compound of claim 2, wherein the compound is of the following formula:
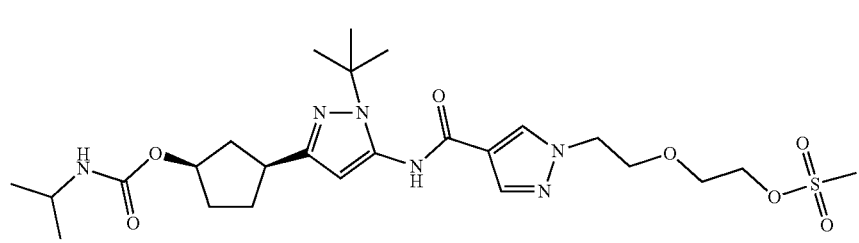
BR
or a salt thereof.
6. The compound of claim 2, wherein the compound is of the following formula:
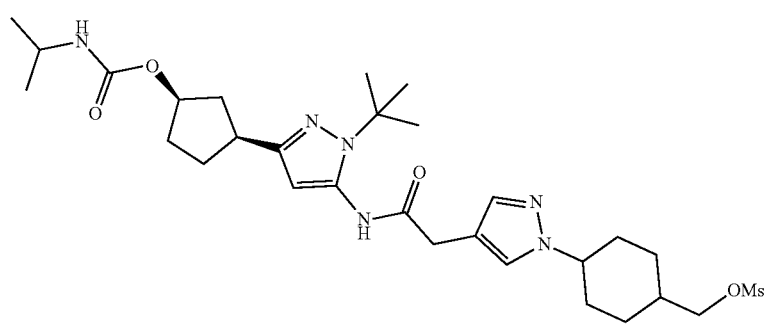
V
or a salt thereof.
7. The compound of claim 3, wherein the compound is of any one of the following formulae:
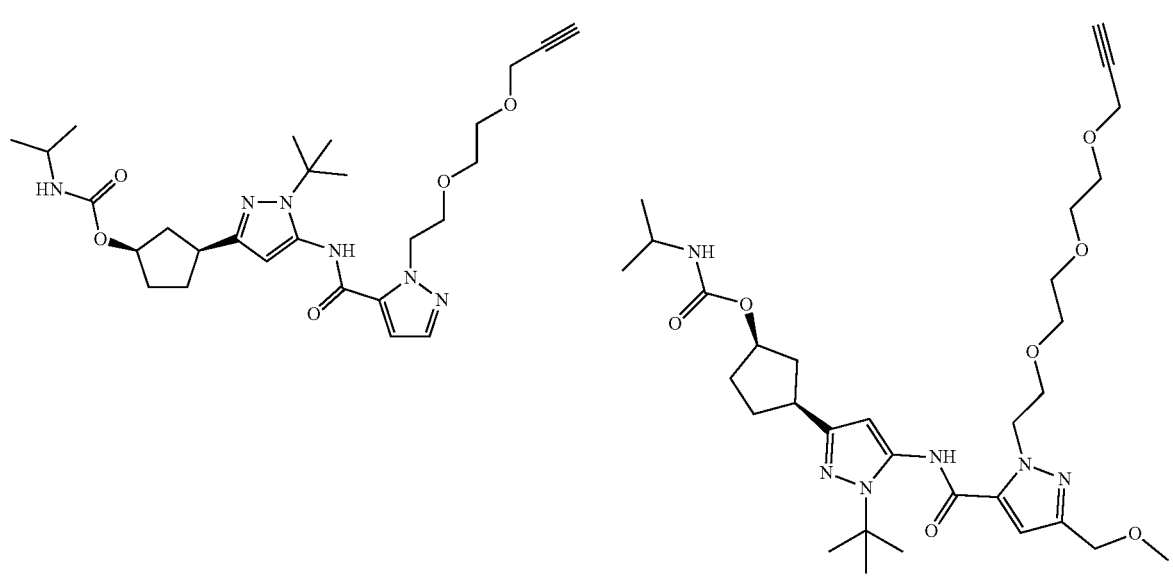
X
CN

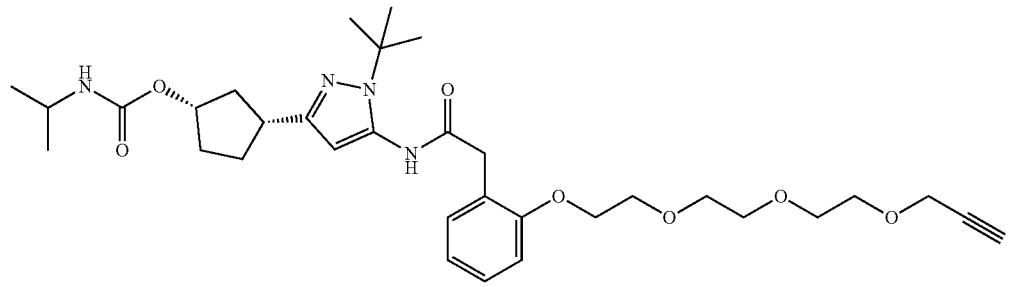
CD
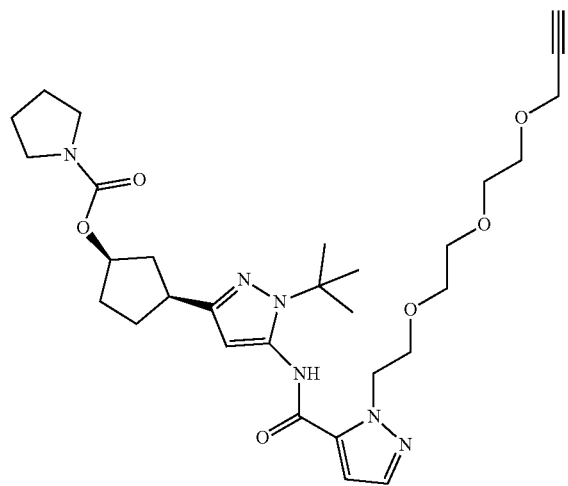
CL
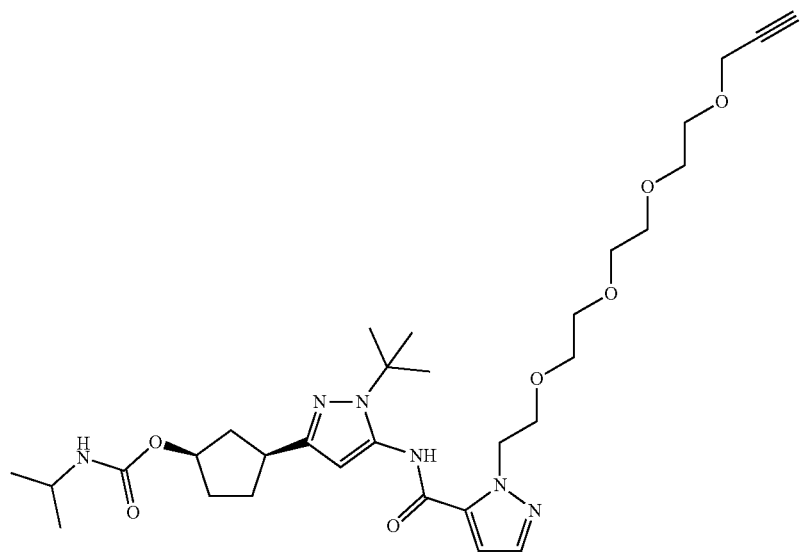
CJ

-continued
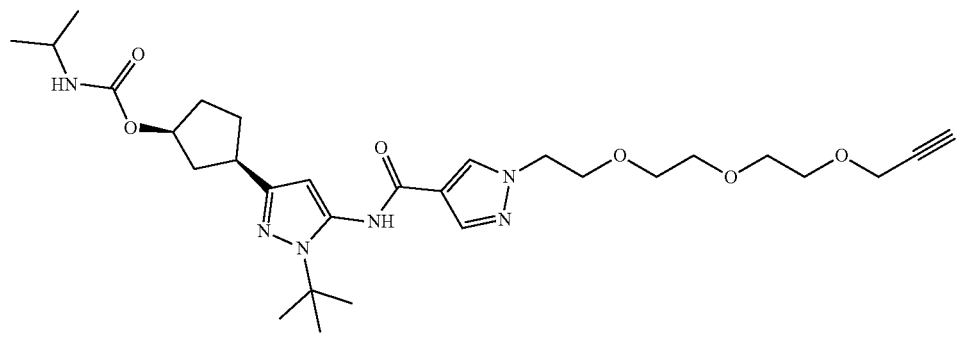
BJ
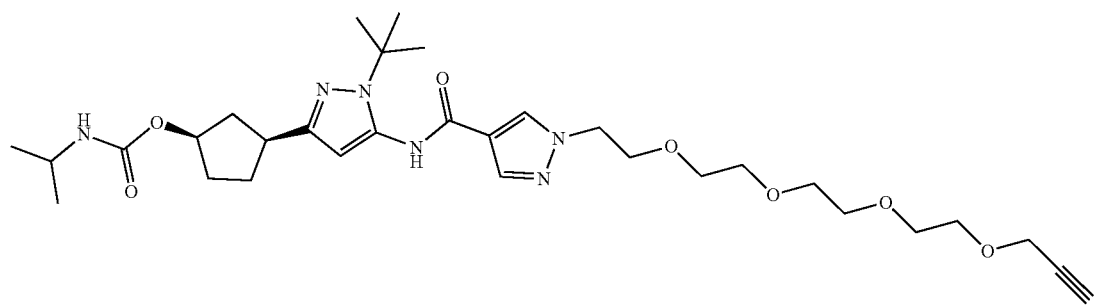
BL
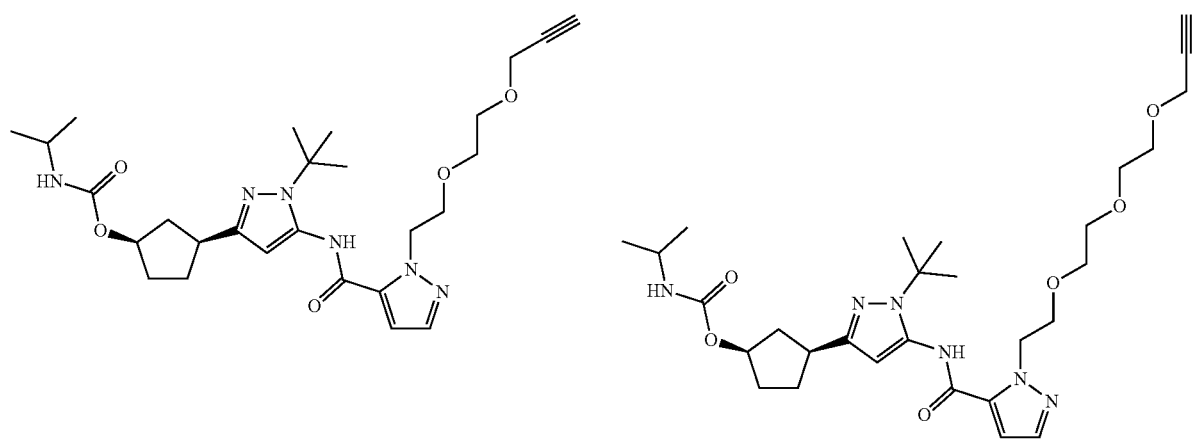
X
BF
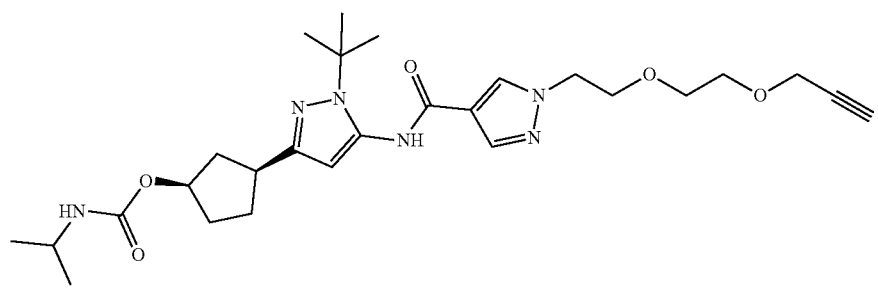
AF

FV
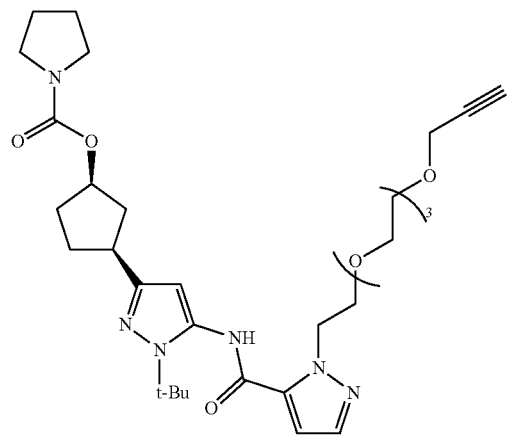
EV
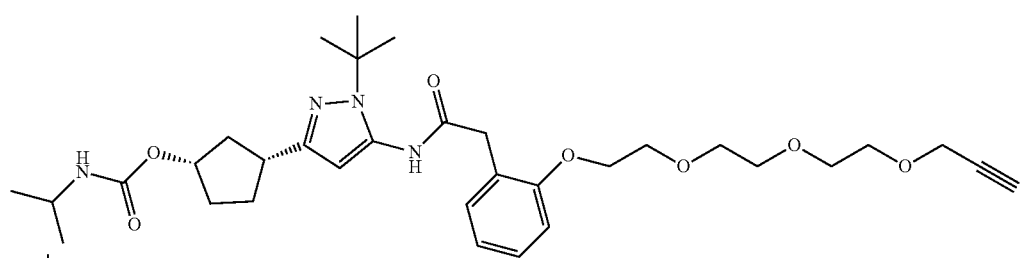
EQ
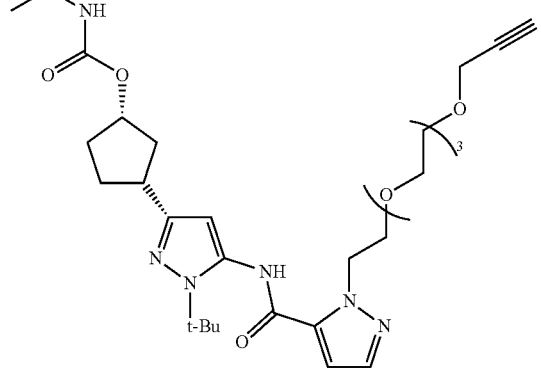
or a salt thereof.
8. The compound of claim 3, wherein the compound is of any one of the following formulae:
AS
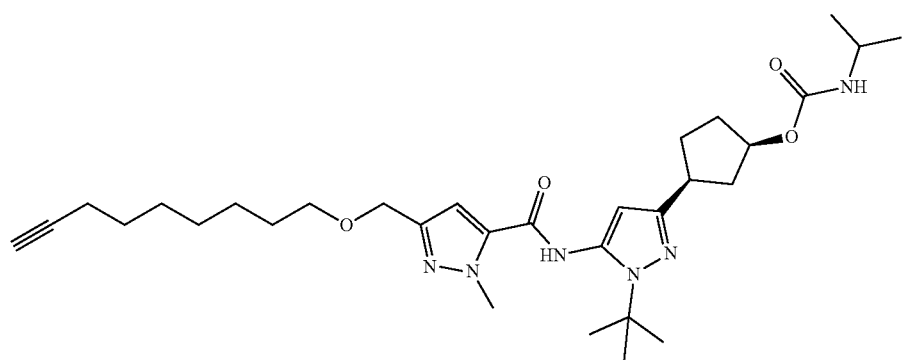

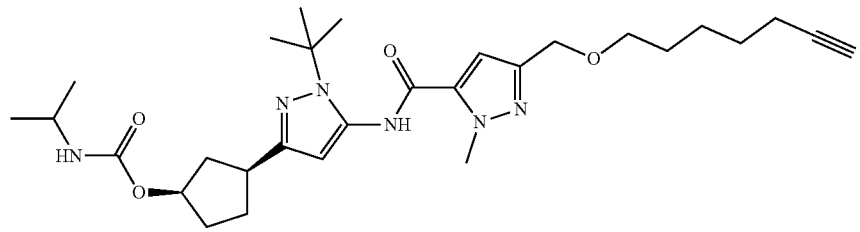
AP
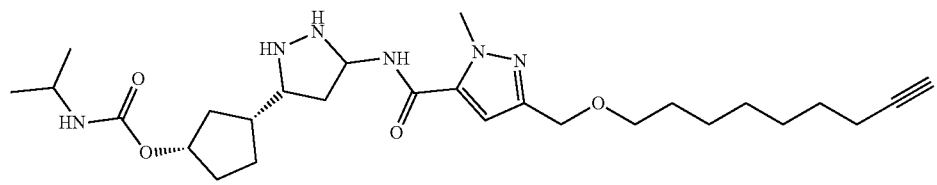
EW
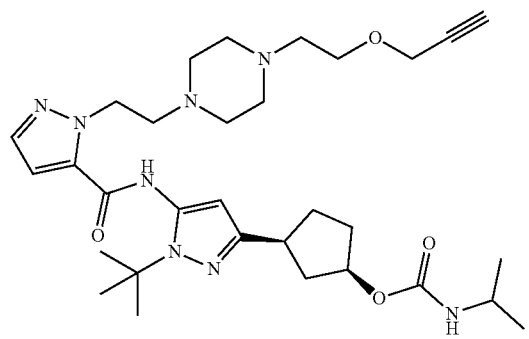
EJ
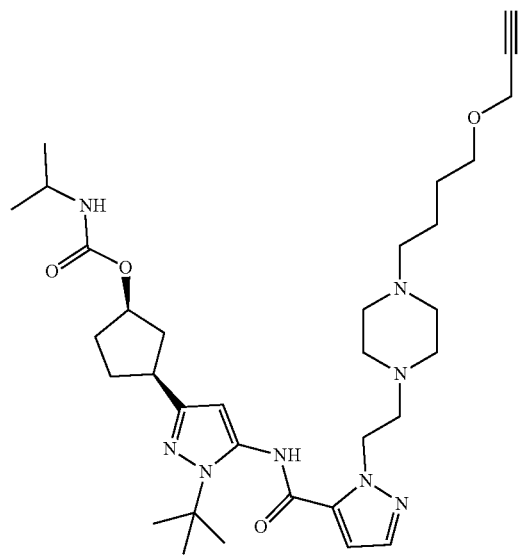
EL
or a salt thereof.
9. The compound of claim 3, wherein the compound is of any one of the following formulae:
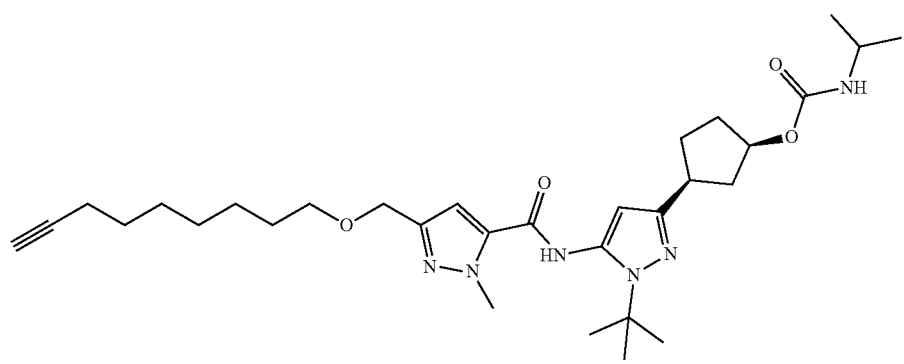
AS -continued
1079
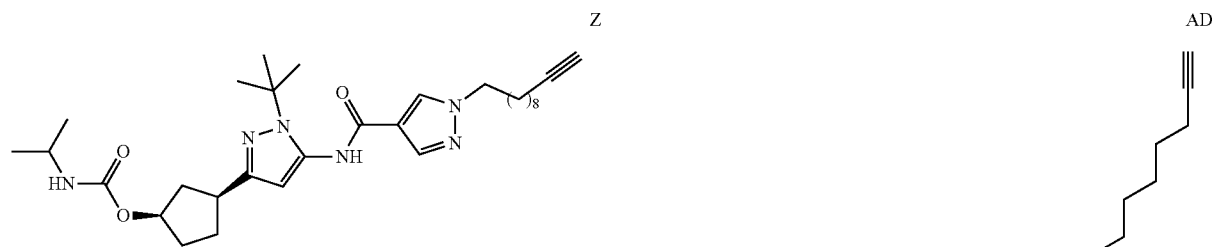
Z
1080
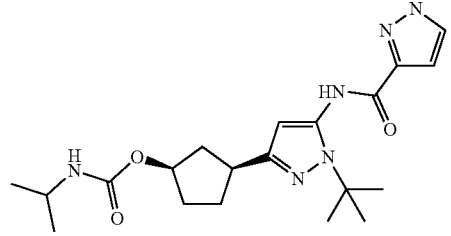
AD
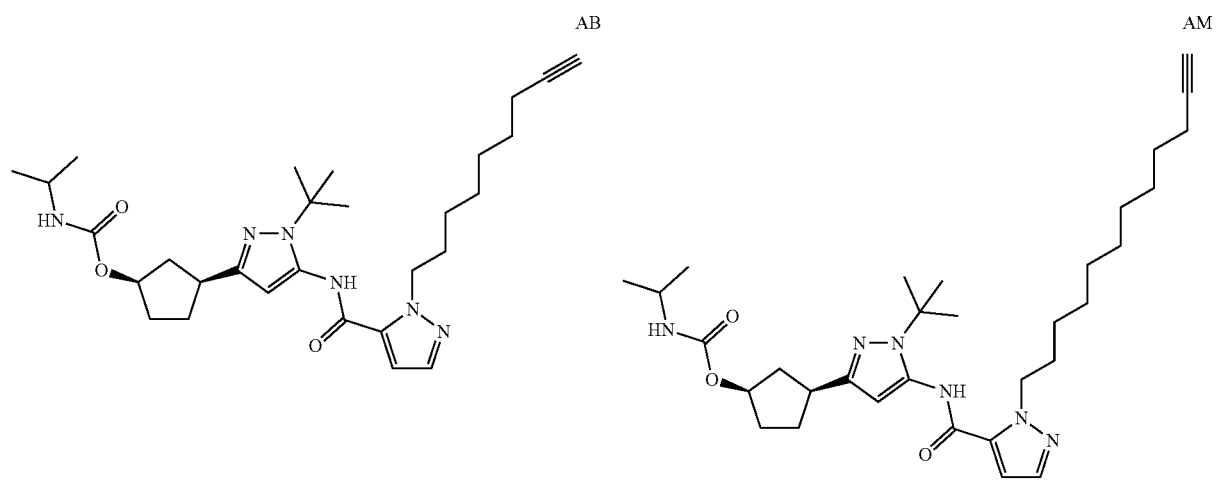
AB
AM
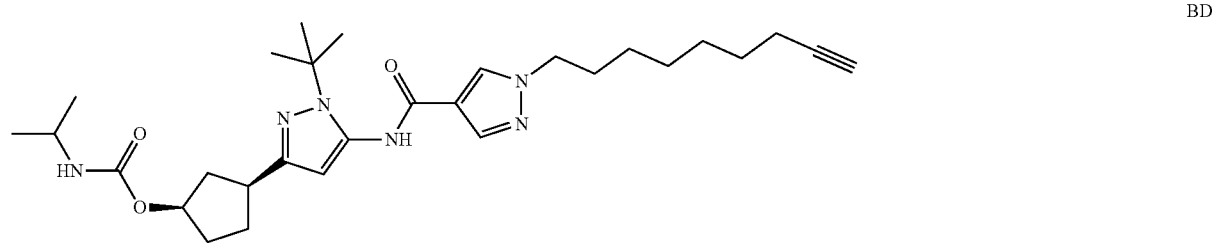
BD

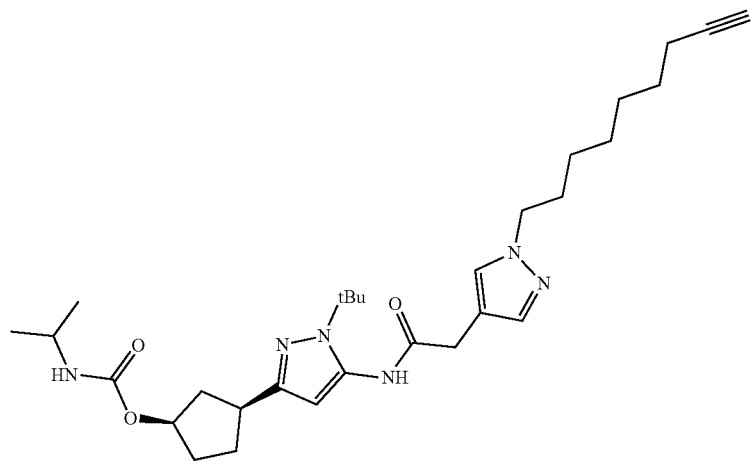
AX
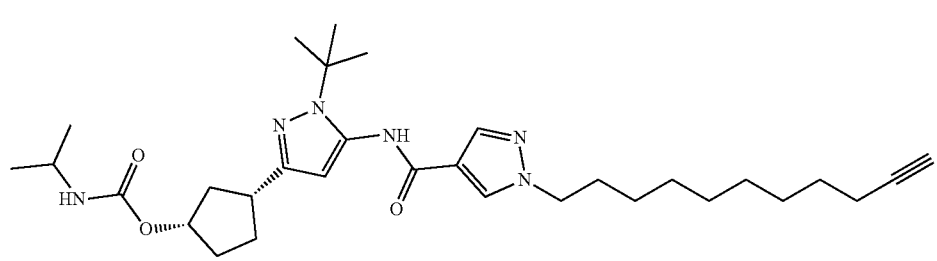
FA
or a salt thereof.
10. The compound of claim 3, wherein the compound is of the following formula:
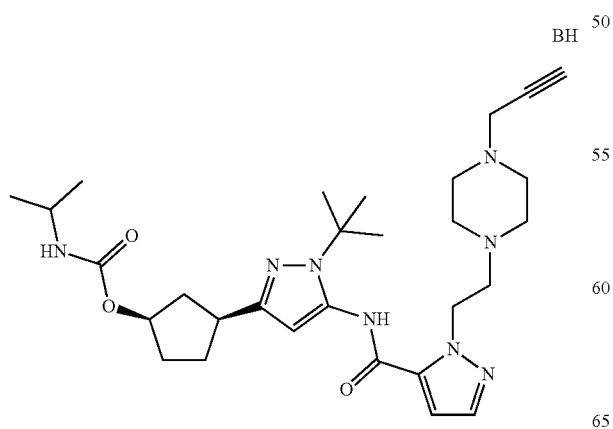
BH
or a salt thereof.

11. The compound of claim 3, wherein the compound is of any one of the following formulae:
X
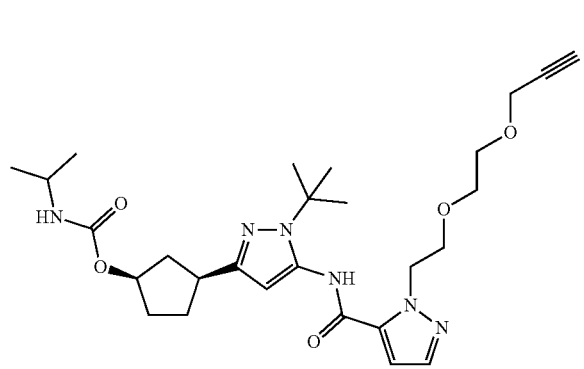
CN
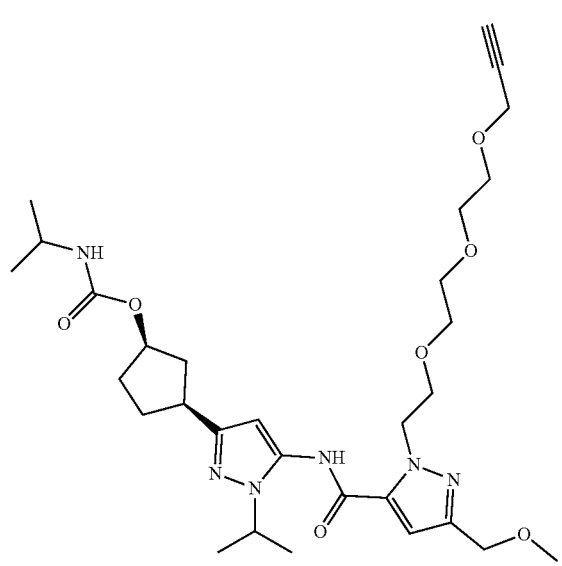
CL
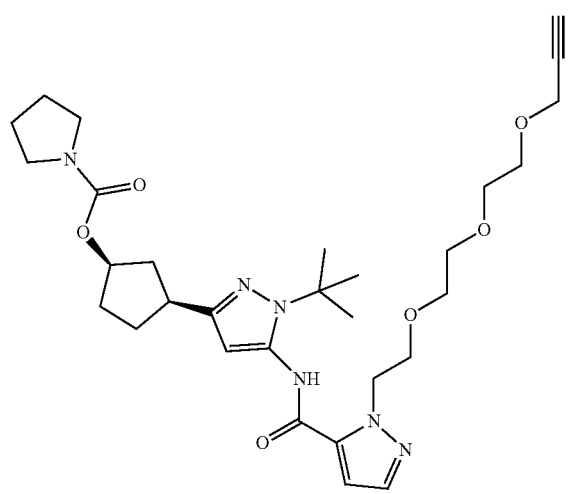
AS
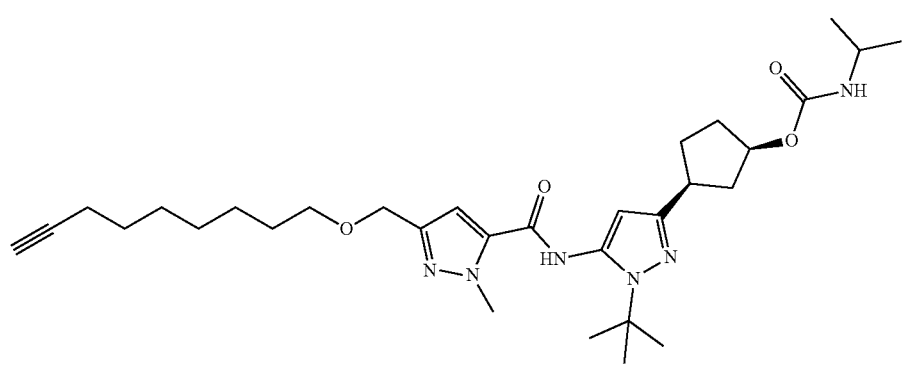

-continued
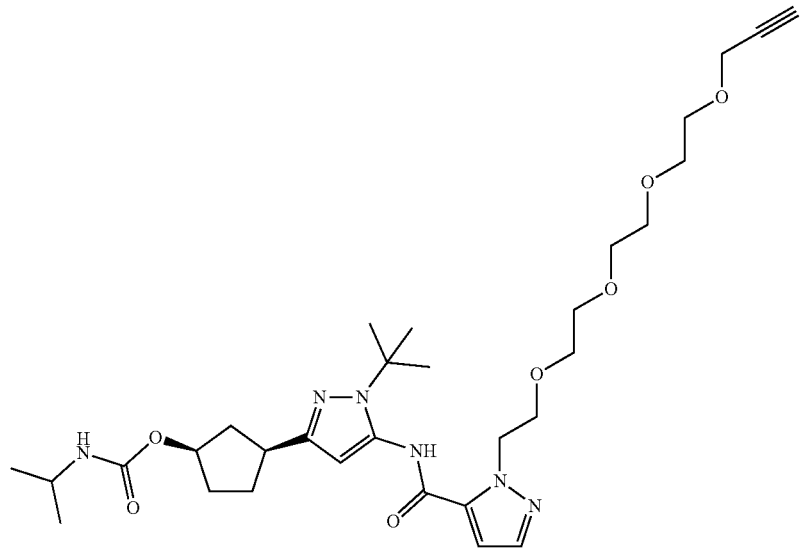
CJ
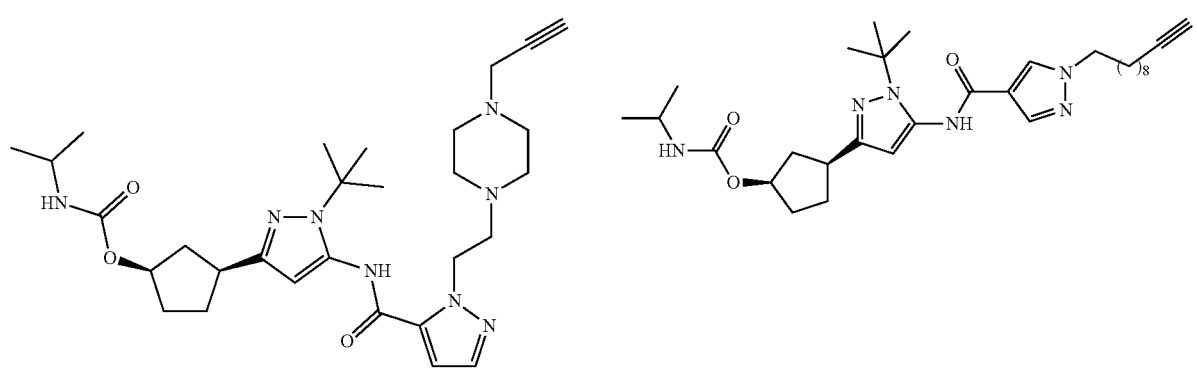
BH
Z
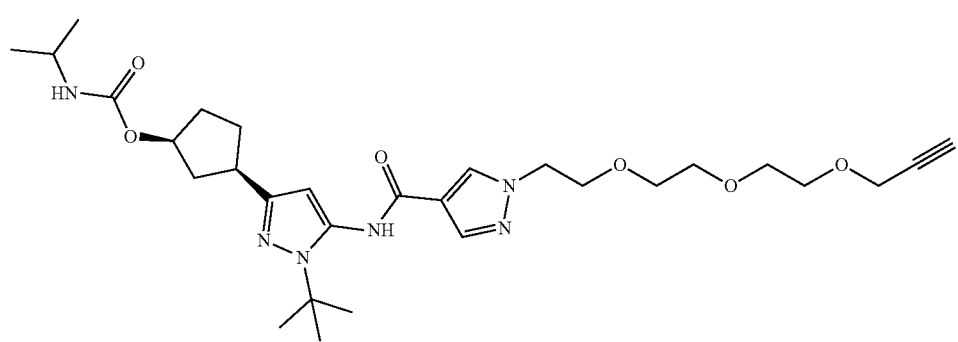
BJ 1087 1088
-continued
AD
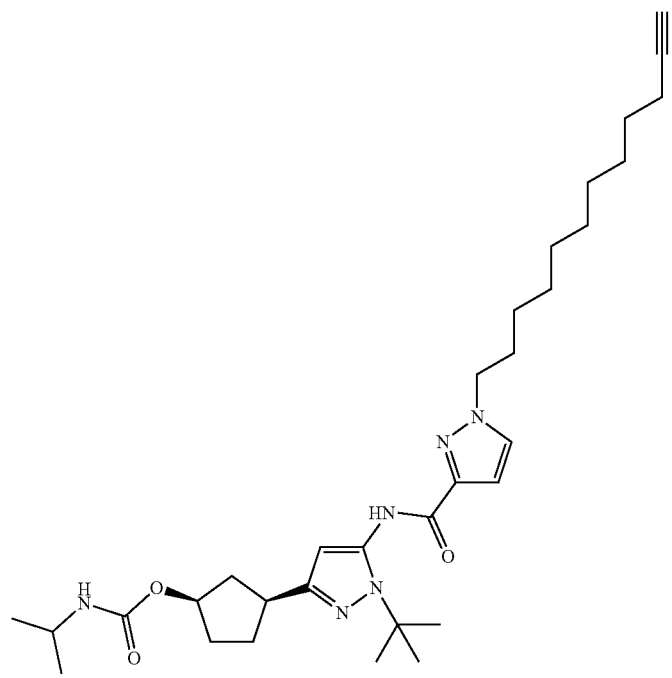
BL
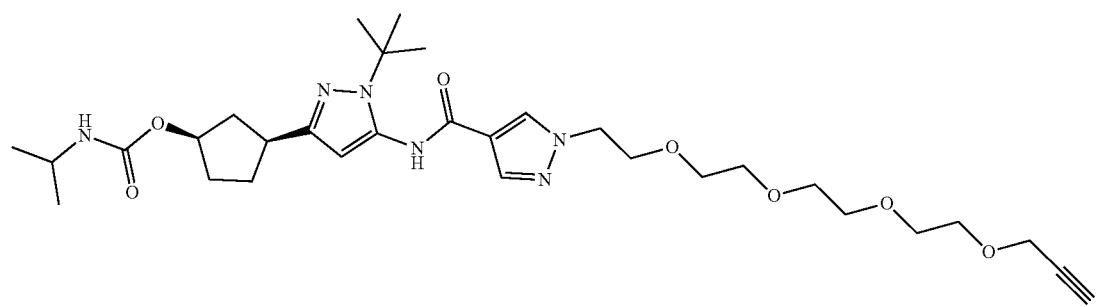
X
BF
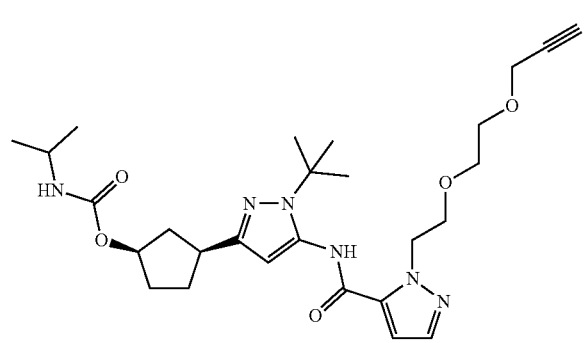
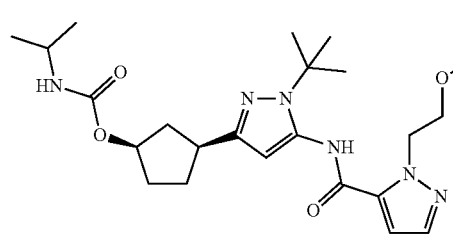

-continued
1089        1090
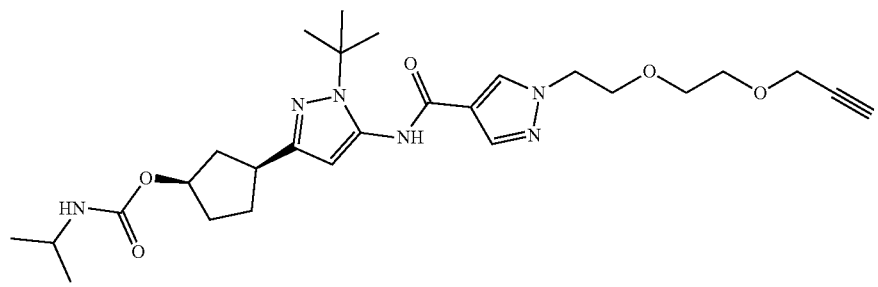
AF
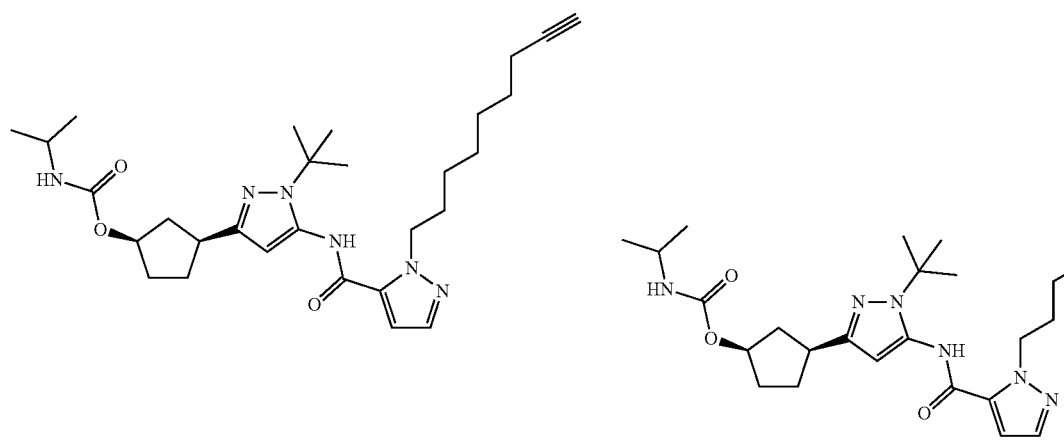
AB
AM
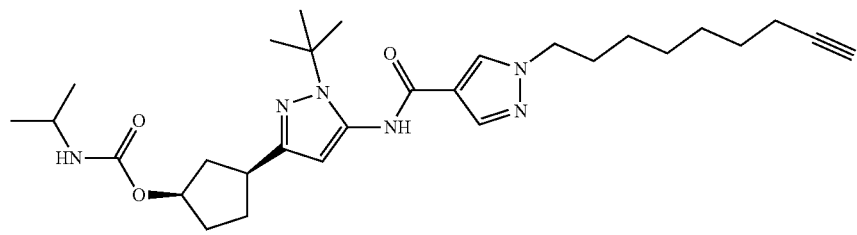
BD
AP
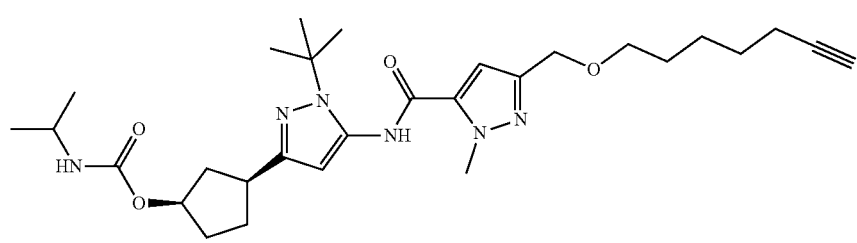

1091 1092
-continued
AX                                           FV
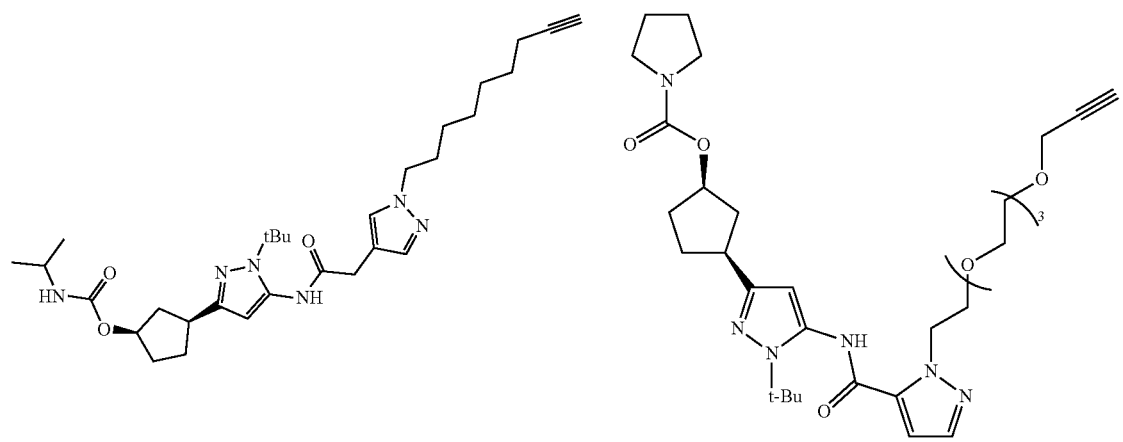
                                             FA
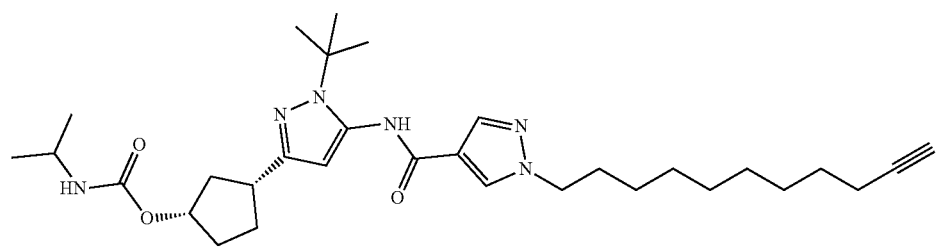
                                             EW
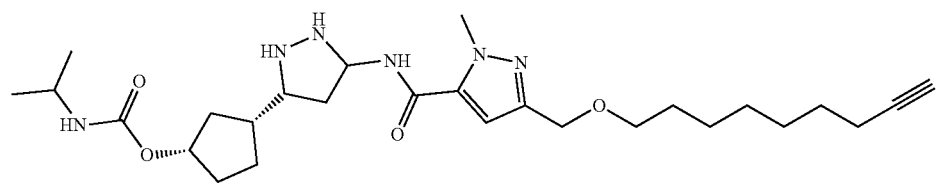
EQ                                           EJ
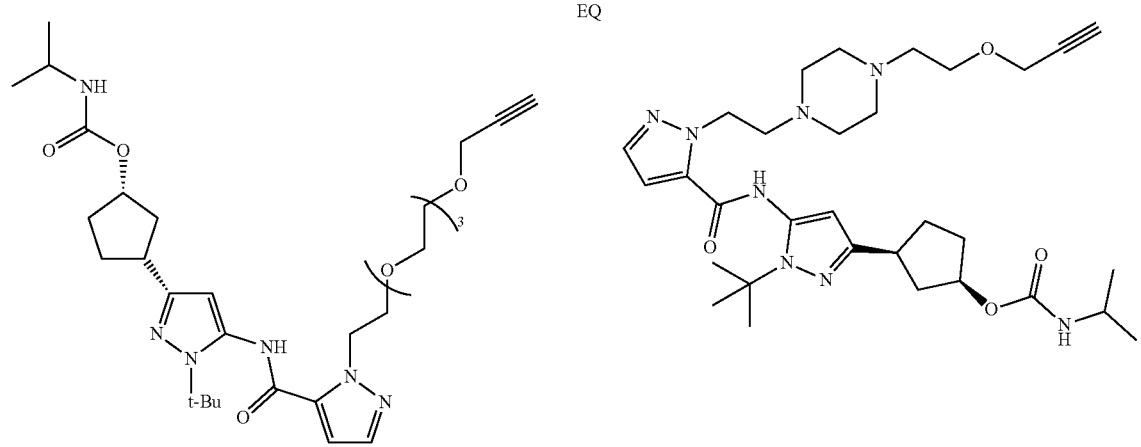

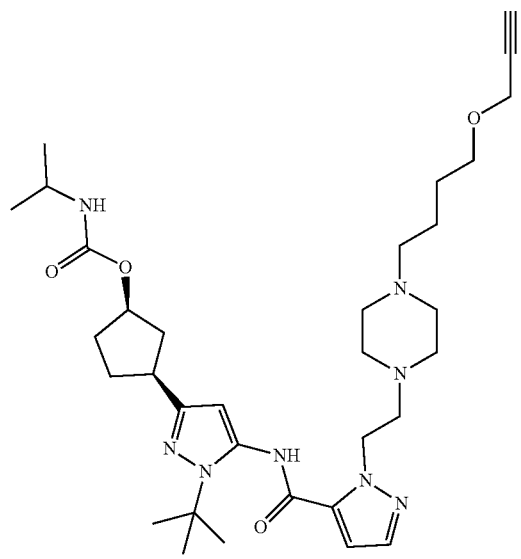
EL
or a salt thereof.
12. The compound of claim 3, wherein the compound is of any one of the following formulae:
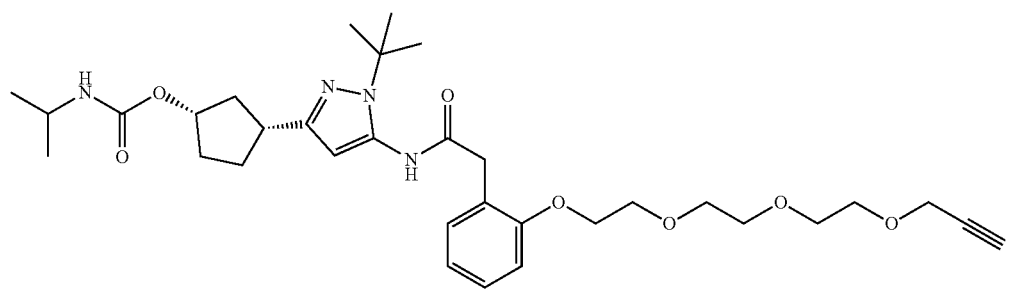
CD
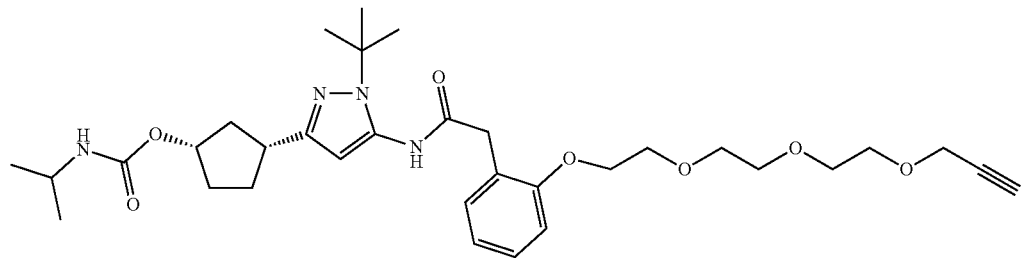
EV
or a salt thereof.
* * * * *